(12) United States Patent
Wu et al.

(10) Patent No.: US 12,187,722 B2
(45) Date of Patent: Jan. 7, 2025

(54) SMALL MOLECULE INHIBITORS OF TEAD TRANSCRIPTION FACTORS

(71) Applicant: The General Hospital Corporation, Boston, MA (US)

(72) Inventors: Xu Wu, Lexington, MA (US); Pranab Maiti, Hyderabad (IN); Chandrasekhar Abbineni, Hyderabad (IN); Krishna Chaitanya Talluri, Hyderabad (IN); Sunil Kumar Panigrahi, Boudh (IN); Gopala Krishna Jarugumilli, Malden, MA (US); Yang Sun, Quincy, MA (US)

(73) Assignee: The General Hospital Corporation, Boston, MA (US)

( * ) Notice: Subject to any disclaimer, the term of this patent is extended or adjusted under 35 U.S.C. 154(b) by 199 days.

(21) Appl. No.: 17/439,735

(22) PCT Filed: Mar. 13, 2020

(86) PCT No.: PCT/US2020/022757
§ 371 (c)(1),
(2) Date: Sep. 15, 2021

(87) PCT Pub. No.: WO2020/190774
PCT Pub. Date: Sep. 24, 2020

(65) Prior Publication Data
US 2023/0113085 A1    Apr. 13, 2023

Related U.S. Application Data

(60) Provisional application No. 62/819,347, filed on Mar. 15, 2019.

(51) Int. Cl.
*A61P 35/00* (2006.01)
*A61K 31/165* (2006.01)
(Continued)

(52) U.S. Cl.
CPC .......... *C07D 471/04* (2013.01); *C07C 211/55* (2013.01); *C07C 211/56* (2013.01); *C07C 229/44* (2013.01); *C07C 229/48* (2013.01); *C07C 229/58* (2013.01); *C07C 237/40* (2013.01); *C07C 255/58* (2013.01); *C07C 311/44* (2013.01); *C07D 205/04* (2013.01); *C07D 207/16* (2013.01); *C07D 209/08* (2013.01); *C07D 211/62* (2013.01); *C07D 213/74* (2013.01); *C07D 213/80* (2013.01); *C07D 215/227* (2013.01); *C07D 231/56* (2013.01); *C07D 233/61* (2013.01); *C07D 235/18* (2013.01); *C07D 239/42* (2013.01); *C07D 241/28* (2013.01);
(Continued)

(58) Field of Classification Search
CPC ...... A61P 35/00; A61P 31/136; C07D 471/04;
C07D 205/04; C07D 207/16; C07D 209/08; C07D 211/62; C07D 213/74; C07D 213/80; C07D 213/82; C07D 215/227; C07D 231/56; C07D 233/61; C07D 233/64; C07D 235/18; C07D 235/06; C07D 235/08; C07D 239/42; C07D 239/88; C07D 239/48; C07D 241/28; C07D 241/20; C07D 249/08; C07D 249/10; C07D 275/06; C07D 295/135; C07D 317/32; C07D 401/06; C07D 401/12; C07D 257/04; C07D 277/28; C07D 295/88; C07D 295/155; C07D 207/34; C07D 213/79; C07D 231/14; C07C 211/55; C07C 211/56; C07C 211/26; C07C 211/60; C07C 229/44; C07C 229/48; C07C 229/58; C07C 234/40; C07C 255/58; C07C 311/44; C07C 2601/04; C07C 2601/08; C07C 2601/10; C07C 2601/14; C07C 2601/16; C07C 2601/18; C07C 2601/02; C07C 2603/66; C07C 2603/74; C07C 225/22; C07C 225/61; C07C 237/24; C07C 317/28; C07C 323/63; A61K 31/165; A61K 31/18; A61K 31/195; A61K 31/196; A61K 31/24; A61K 31/397; A61K 31/401; A61K 31/405; A61K 31/41; A61K 31/416; A61K 31/4184; A61K 31/4196; A61K 31/428; A61K 31/44; A61K 31/4439; A61K 31/4704; A61K 31/496; A61K 31/4965; A61K 31/505
See application file for complete search history.

(56) References Cited

U.S. PATENT DOCUMENTS 5,200,550 A    4/1993  Shroot et al.
5,939,462 A    8/1999  Connell et al.
(Continued)

FOREIGN PATENT DOCUMENTS

CN    1187185      7/1998
CN    108524511    9/2018
(Continued)

OTHER PUBLICATIONS

Extended European Search Report in European Appln. No. 20773621.6, dated Nov. 9, 2022, 17 pages.
(Continued)

*Primary Examiner* — Sun Jae Yoo
(74) *Attorney, Agent, or Firm* — Fish & Richardson P.C.

(57) ABSTRACT

The present disclosure compounds, as well as their compositions and methods of use. The compounds inhibit the activity of the TEAD transcription factor, and are useful in the treatment of diseases related to the activity of TEAD transcription factor including, e.g., cancer and other diseases.

23 Claims, 10 Drawing Sheets

| (51) | Int. Cl. | | (52) | U.S. Cl. |
|---|---|---|---|---|
| | A61K 31/18 | (2006.01) | | CPC ......... C07D 249/08 (2013.01); C07D 275/06 |
| | A61K 31/195 | (2006.01) | | (2013.01); C07D 295/135 (2013.01); C07D |
| | A61K 31/196 | (2006.01) | | 317/32 (2013.01); C07D 401/06 (2013.01); |
| | A61K 31/24 | (2006.01) | | C07D 401/12 (2013.01) |
| | A61K 31/397 | (2006.01) | | |
| | A61K 31/401 | (2006.01) | | |
| | A61K 31/405 | (2006.01) | (56) | References Cited |
| | A61K 31/41 | (2006.01) | | |
| | A61K 31/416 | (2006.01) | | U.S. PATENT DOCUMENTS |
| | A61K 31/4184 | (2006.01) | | |
| | A61K 31/4196 | (2006.01) | | 6,346,532 B1   2/2002 Maruyama et al. |
| | A61K 31/428 | (2006.01) | | 7,723,369 B2   5/2010 Mjalli et al. |
| | A61K 31/44 | (2006.01) | | 7,897,605 B2   3/2011 Wang et al. |
| | A61K 31/4439 | (2006.01) | | 8,883,888 B2  11/2014 Sakamoto et al. |
| | A61K 31/4704 | (2006.01) | | 10,696,642 B2   6/2020 Wu |
| | A61K 31/496 | (2006.01) | | |
| | A61K 31/4965 | (2006.01) | | FOREIGN PATENT DOCUMENTS |
| | C07C 211/26 | (2006.01) | | |
| | C07C 211/55 | (2006.01) | EP | 0776881   6/1997 |
| | C07C 211/56 | (2006.01) | EP | 1256341   11/2002 |
| | C07C 211/60 | (2006.01) | EP | 1344525   9/2003 |
| | C07C 225/22 | (2006.01) | EP | 2415755   2/2012 |
| | C07C 229/44 | (2006.01) | EP | 2990057   3/2016 |
| | C07C 229/48 | (2006.01) | JP | 2002-249473   9/2002 |
| | C07C 229/58 | (2006.01) | JP | 2005-527529   9/2005 |
| | C07C 237/40 | (2006.01) | JP | 2007-502260   2/2007 |
| | C07C 255/58 | (2006.01) | JP | 2007-538092   12/2007 |
| | C07C 311/44 | (2006.01) | JP | 2010-538004   12/2010 |
| | C07C 317/28 | (2006.01) | JP | 2011-512413   4/2011 |
| | C07C 323/63 | (2006.01) | JP | 2011-524411   9/2011 |
| | C07D 205/04 | (2006.01) | JP | 2012-506876   3/2012 |
| | C07D 207/16 | (2006.01) | JP | 2013-501785   1/2013 |
| | C07D 207/34 | (2006.01) | JP | 2013-056930   3/2013 |
| | C07D 209/08 | (2006.01) | JP | 2018-528246   9/2018 |
| | C07D 211/62 | (2006.01) | WO | WO 1998/001132   1/1998 |
| | C07D 213/74 | (2006.01) | WO | WO 2002/000196   1/2002 |
| | C07D 213/79 | (2006.01) | WO | WO 2003/078404   9/2003 |
| | C07D 213/80 | (2006.01) | WO | WO 2005/118544   12/2005 |
| | C07D 215/227 | (2006.01) | WO | WO 2008/082003   7/2008 |
| | C07D 231/14 | (2006.01) | WO | WO 2008/147831   12/2008 |
| | C07D 231/56 | (2006.01) | WO | WO 2010/125390   11/2010 |
| | C07D 233/61 | (2006.01) | WO | WO 2011/002038   1/2011 |
| | C07D 233/64 | (2006.01) | WO | WO 2011/019405   2/2011 |
| | C07D 235/06 | (2006.01) | WO | WO 2015/014944   2/2012 |
| | C07D 235/08 | (2006.01) | WO | WO 2012/130159   10/2012 |
| | C07D 235/18 | (2006.01) | WO | WO 2012/135641   10/2012 |
| | C07D 239/42 | (2006.01) | WO | WO 2012/137181   10/2012 |
| | C07D 239/48 | (2006.01) | WO | WO 2015/026990   2/2015 |
| | C07D 239/88 | (2006.01) | WO | WO 2015/051149   4/2015 |
| | C07D 241/20 | (2006.01) | WO | WO 2017/053706   3/2017 |
| | C07D 241/28 | (2006.01) | WO | WO 2017/158190   9/2017 |
| | C07D 249/08 | (2006.01) | WO | WO 2018/154118   8/2018 |
| | C07D 249/10 | (2006.01) | WO | WO 2018/157843   9/2018 |
| | C07D 257/04 | (2006.01) | WO | WO 2018/160138   9/2018 |
| | C07D 275/06 | (2006.01) | WO | WO 2019/027855   2/2019 |
| | C07D 277/28 | (2006.01) | WO | WO 2019/165032   8/2019 |
| | C07D 295/135 | (2006.01) | | |
| | C07D 295/155 | (2006.01) | | OTHER PUBLICATIONS |
| | C07D 317/32 | (2006.01) | | |
| | C07D 401/06 | (2006.01) | | |
| | C07D 401/12 | (2006.01) | | |
| | C07D 471/04 | (2006.01) | | |

Féau et al., "Novel flufenamic acid analogues as inhibitors of androgen receptor mediated transcription," ACS Chem Biol., Oct. 2009, 4(10):834-43.

Kagechika et al., "Retinobenzoic acids. 1. Structure-activity relationships of aromatic amides with retinoidal activity," J Med Chem., Nov. 1988, 31(11):2182-92.

Stepanov et al., "Synthesis and biological activity of several derivatives of N-[(1-adamantyl)phenyl] anthranilic acid," Pharmaceutical Chemistry Journal, Oct. 1971, 5(10):588-589.

Tian et al., "Abstract: Effects of niflumic acid on the proliferation of human hepatoma cells," Sheng Li Xue Bao, Apr. 2003, 55(2):160-4, 1 page (English Abstract).

Umemiya et al., "Regulation of retinoidal actions by diazepinylbenzoic acids. Retinoid synergists which activate the RXR-RAR heterodimers," J Med Chem., Dec. 1997, 40(26):4222-34.

(56) References Cited

OTHER PUBLICATIONS

PubChem CID No. 407452, "([1,1'-Biphenyl]-2-yl)(phenyl)methanone," Create date Mar. 26, 2005, modified Dec. 3, 2022, 15 pages.
Yamaoka et al., "Identification of novel plasminogen activator inhibitor-1 inhibitors with improved or al bioavailability: Structure optimization of N-acylanthranilic acid derivatives," Bioorganic & Medicinal Chemistry Letters, Feb. 2018, 28(4):809-813.
Bedadurge & Shaikh, "Designing Hypothesis of 2-Substituted-N-[4-(1-methyl-4,5-diphenyl1H-imidazole-2-yl)phenyl]Acetamide Analogs as Anticancer Agents: QSAR Approach," Journal of the Korean Chemical Society, Dec. 2013, 57(6):744-754.
Benhaddou et al., Transcription factor TEA.D4 regulates expression of myogenin and the unfolded protein response genes during C2C12 cell differentiation. Cell Death Differ, 2012, 19:220-231.
Berge et al., "Pharmaceutical Salts," J. Pharm. Sci., Jan. 1977, 66(1):1-19.
Birch et al., "Rationally Designing Safe Anilines: The Challenging Case of 4-Aminobiphenyls," Journal of Medicinal Chemistry, 2012, 55(8):3923-3933.
Burns et al., "Simple Palladium(II) Precatalyst for Suzuki-Miyaura Couplings: Efficient Reactions of Benzylic, Aryl, Heteroaryl, and Vinyl Coupling Partners," Organic Letters, 2007, 9(26):5397-5400.
Chan et al., "A role for TAZ in migration, invasion, and tumorigenesis of breast cancer cells," Cancer Res, 2008, 68:2592-2598.
Chan et al., "Autopalmitoylation of TEAD Proteins Regulates Transcriptional Output of Hippo Pathway," Nat Chem Biol, Apr. 2016, 12:282-289.
Chan et al., "Supplemental Information: Autopalmitoylation of TEAD Proteins Regulates Transcriptional Output of Hippo Pathway," Nat Chem Biol, Apr. 2016, 12:282-289.
Chandra et al., "The GDI-like solubilizing factor PDEdelta sustains the spatial organization and signalling of Ras family proteins," Nat Cell Biol, 2012, 14:148-158.
Chen et al., "Structural basis of YAP recognition by TEAD4 in the hippo pathway," Genes Dev, 2010, 24:290-300.
Cheng et al., "An Efficient and Practical Method for Highly Chemoselective Hydrogenation of Nitrobenzylamines to Aminobenzylamine Hydrochlorides," Advanced Synthesis and Catalysis, 2007, 349(10):1775-1780.
Davies et al., "Structure-Based Design, Synthesis, and Characterization of Inhibitors of Human and Plasmodium falciparum Dihydroorotate Dehydrogenases," Journal of Medicinal Chemistry, 2009, 52(9):2683-2693.
Dong et al., "Exploration of the linkage elements of porcupine antagonists led to potent Wnt signaling pathway inhibitors," Bioorganic & Medicinal Chemistry, 2015, 23(21):6855-6868.
Duncan and Gilman, "Autoacylation of G protein alpha subunits," J Biol Chem, 1996, 271: 23594-23600.
Dupont et al., "Role of YAP/TAZ in mechanotransduction," Nature, 2011, 474:179-183.
EP Extended European Search Report in EP Appln. No. 16849687.5, dated Jul. 22, 2019, 15 pages.
EP Office Action in European U.S. Appl. No. 16/849,687, dated Mar. 26, 2020, 3 pages.
Faergeman and Knudsen, "Role of long-chain fatty acyl-CoA esters in the regulation of metabolism and in cell signaling," Biochem J, 1997, 323(1):1-12.
Fitamant et al., "YAP Inhibition Restores Hepatocyte Differentiation in Advanced HCC, Leading to Tumor Regression," Cell Reports, 2015, 10(10):1692-1707.
Fukata and Fukata, "Protein palmitoylation in neuronal development and synaptic Plasticity," Nat Rev Neurosci, Mar. 2010, 11:161-175.
Gamage et al., "Structure—Activity Relationships for the Antileishmanial and Antitrypanosomal Activities of 1'-Substituted 9-Anilinoacridines," Journal of Medicinal Chemistry, 1997, 40(16):2634-2642.
Greaves and Chamberlain, "DHHC palmitoyl transferases: substrate interactions and (patho)physiology," Trends Biochem Sci, 2011, 36(5): 245-253.

Hang and Linder, "Exploring protein lipidation with chemical biology," Chem Rev, 2011, 111(10):6341-6358.
Hannoush, "Profiling cellular myristoylation and palmitoylation using omega-alkynyl fatty acids," Methods Mol Biol, 2012, 800:85-94.
Hantschel et al., "A myristoy l/phosphotyrosine switch regulates c-Abl," Cell, 2003, 112:845-857.
Harvey et al., "The Hippo pathway and human cancer," Nature Reviews Cancer, 2013, 13:246-257.
International Preliminary Report on Patentability in International Application No. PCT/US2016/053318, mailed on Apr. 5, 2018.
International Preliminary Report on Patentability in International Application No. PCT/US2020/22757, mailed on Sep. 20, 2021, 8 pages.
International Search Report and Written Opinion in International Application No. PCT/US2016/053318, mailed Feb. 16, 2017, 10 pages.
International Search Report and Written Opinion in International Application No. PCT/US2020/22757, mailed on Aug. 11, 2020, 10 pages.
Ismail et al., "Arl2-GTP and Arl3-GTP regulate a GDI-like transport system for farnesylated cargo," Nat Chem Biol, 2011, 7:942-949.
Jennings and Linder, "DHHC protein S-acyltransferases use similar ping-pong kinetic mechanisms but display different acyl-CoA specificities," J Biol Chem, 2012, 287:7236-7245.
Jiao et al., "A peptide mimicking VGLL4 function acts as a YAP antagonist therapy against gastric cancer," Cancer Cell, 2014, 25:166-180.
Johnson and Halder, "The two faces of Hippo: targeting the Hippo pathway for regenerative medicine and cancer treatment," Nature Reviews. Drug Discovery, 2014, 13:63-79.
Kim et al., "cAMP/PKA signalling reinforces the LATS-YAP pathway to fully suppress YAP in response to actin cytoskeletal changes," Embo J, 2013, 32: 1543-1555.
Kloetzel et al., "Tuberculostatic Properties of Some Diphenylamines," Antibiotics Chemotherapy, 1954, 4(2):150-154.
Koontz et al., "The Hippo effector Yorkie controls normal tissue growth by antagonizing scalloped-mediated default repression," Dev Cell, 2013, 25:388-401.
Koperniku et al., "4-(1-Adamantyl)phenylalkylamines with Potential Antiproliferative Activity," Letters in Organic Chemistry, 2016,13(3):171-176.
Kummel et al., "Unique self-palmitoylation activity of the transport protein particle component Bet3: a mechanism required for protein stability," PNAS, 2006, 103:12701-12706.
Li et al., "Structural insights into the YAP and TEAD complex," Genes & Development, 2010, 24:235-240.
Littke et al., "Versatile Catalysts for the Suzuki Cross-Coupling of Arylboronic Acids with Aryl and Vinyl Halides and Triflates under Mild Conditions," Journal of the American Chemical Society, 2000, 122(17):4020-4028.
Liu-Chittenden et al., "Genetic and pharmacological disruption of the TEAD-YAP complex suppresses the oncogenic activity of YAP," Genes & Development, 2012, 26:1300-1305.
Manikrao et al., "Rapid, Economical and Green Solid Oxidation of Sulfides to Sulfones and Their Antimicrobial Evaluation—Part 2," Der Pharma Chennica, 2010, 2(5):76-83.
Martin and Cravatt, "Large-scale profiling of protein palmitoylation in mammalian cells," Nat Methods, 2009, 6, 135-138.
Menendez and Lupu, "Fatty acid synthase and the lipogenic phenotype in cancer pathogenesis," Nat Rev Cancer, 2007, 7:763-777.
Mohseni et al.. "A genetic screen identifies an LKB1-MARK signaling axis controlling the Hippo-YAP pathway," Nat Cell Biol, 2014, 16:108-117.
Nagar et al., "Structural basis for the autoinhibition of c-Abl tyrosine kinase," Cell, 2003, 112:859-871.
NCBI Accession No. 2513683, Database PubChem Compound [Online] Jul. 16, 2005 (Jul. 16, 2005), retrieved from NCBI Database, retrieved from URL <https://pubchem.ncbi.nlm.nih.gov/compound/2513683#section=Substances-by-Category>, 10 pages.

(56) References Cited

OTHER PUBLICATIONS

NCBI Accession No. 41931789, DATABASE PubChem Compound [Online] May 30, 2009 (May 30, 2009), retrieved from NCBI Database, retrieved from URL <https://pubchem.ncbi.nlm.nih.gov/compound/41931789>, 9 pages.
Nguyen et al., "LKB1 tumor suppressor regulates AMP kinase/mTOR-independent cell growth and proliferation via the phosphorylation of Yap," Oncogene, 2013, 32(35):4100-4109.
Noland et al., "Palmitoylation of TEAD Transcription Factors is Required for Their Stability and Function in Hippo Pathway Signaling," Structure, 2016, 24:1-8.
Ota and Sasaki "Mammalian Tead proteins regulate cell proliferation and contact inhibition as transcriptional mediators of Hippo signaling," Development, 2008, 135:4059-4069.
Pan, "Hippo signaling in organ size control," Genes Dev, 2007, 21:886-897.
Pan, "The hippo signaling pathway in development and cancer," Dev Cell, 2010, 19:491-505.
Park et al., "Novel TAZ modulators enhance myogenic differentiation and muscle regeneration," Br J Pharmacol, 2014, 171: 4051-4061.
Petursson et al., "Protecting Groups in Carbohydrate Chemistry," J. Chem. Educ., 1997, 74(11):1297-1303.
Pobbati et al., "Targeting the Central Pocket in Human Transcription Factor TEAD as a Potential Cancer Therapeutic Strategy," Structure, 2015, 23:2076-2086.
PubChem CID No. 133453607, "3-fluoro-4-morpholin-4-yl-N-(4-nitrophenyl)aniline," Create Date May 25, 2015, 8 pages.
PubChem CID No. 407452, "([1,1'-Biphenyl]-2-yl)(phenyl)methanone," Create Date Mar. 26, 2005, 13 pages.
PubChem CID No. 61827415, "2-Methyl-4-(4-nitroanilino)benzoic acid," Create Date Oct. 22, 2012, 7 pages.
*Remington's Pharmaceutical Sciences*, 17th Ed., Mack Publishing Company, Easton, 1985, Chapter 76, p. 1418.
Resh, "Trafficking and signaling by fatty-acylated and prenylated proteins," Nat Chem Biol, 2006, 2(11):584-590.
Resh, "Use of analogs and inhibitors to study the functional significance of protein palmitoylation," Methods, 2006, 40(2):191-197.
Roth et al., "Global analysis of protein palmitoylation in yeast," Cell, 2006, 125(5):1003-1013.
SID 47645506, PUBCHEM: Substance Record, Feb. 20, 2008, retrieved on Oct. 24, 2016, retrieved from URL :<https://pubchem.ncbi.nlm.nih.gov/substance/47645506>, 10 pages.
Skorobogatyi et al., "5-Arylethynyl-2'-deoxyuridines, compounds active against HSV-1," Organic and Biomolecular Chemistry, 2006, 4(6):1091-1096.
Smotrys and Linder, "Palmitoylation of intracellular signaling proteins: regulation and function," Annu Rev Biochem, 2004, 73:559-587.
Sorrentino et al., "Metabolic control of YAP and TAZ by the mevalonate pathway," Nat. Cell, Biol., 2014, 16:357-366.
Stahl et al., "Handbook of Pharmaceutical Salts: Properties, Selection, and Use," Wiley, 2002, p. 329-350.
STN Accession No. 717130-47-7, Database Registry [Online] Chemical Abstracts Service, Columbus, Ohio, US; Jul. 27, 2004 (Jul. 27, 2004), retrieved from STN Database, 1 page.
STN Accession No. 831247-17-7, Database Registry [Online] Chemical Abstracts Service, Columbus, Ohio, US; Feb. 15, 2005 (Feb. 15, 2005), retrieved from STN Database, 1 page.
STN Accession No. 832687-05-5, Database Registry [Online] Chemical Abstracts Service, Columbus, Ohio, US; Feb. 17, 2005 (Feb. 17, 2005), retrieved from STN Database, 1 page.
STN Accession No. 838812-50-3, Database Registry [Online] Chemical Abstracts Service, Columbus, Ohio, US; Feb. 27, 2005 (Feb. 27, 2005), retrieved from STN Database, 1 page.
STN Accession No. 896657-58-2, Database Registry [Online] Chemical Abstracts Service, Columbus, Ohio, US; Jul. 28, 2006 (Jul. 28, 2006), retrieved from STN Database, 1 page.
STN Accession No. 948157-71-9, Database Registry [Online] Chemical Abstracts Service, Columbus, Ohio, US; Sep. 26, 2007 (Sep. 26, 2007), retrieved from STN Database, 1 page.
STN Accession No. 955199-09-4, Database Registry [Online] Chemical Abstracts Service, Columbus, Ohio, US; Nov. 21, 2007 (Nov. 21, 2007), retrieved from STN Database.
STN Accession No. 380572-22-5, Database Registry [Online] Chemical Abstracts Service, Columbus, Ohio, US; Jan. 7, 2002 (Jan. 7, 2002), retrieved from STN Database, 1 page.
Testaferri et al., "Structural Effects on the Reactivity of Carbon Radicals in Homolytic Aromatic Substitutions, Part III. Reaction of the 1-Adamantyl Radical with Benzene Derivatives," Journal of the Chemical Society, Perkin Transactions 2: Physical Organic Chemistry, 1976, 6:662-668.
Tian et al., "Structural and functional analysis of the YAP-binding domain of human TEAD2," PNAS, 2010, 107: 7293-7298.
Tseng et al., "N-[(Aryl Substitue Adamantane)Alkyl] 2-Mercaptoacetamidines, Their Corresponding Disulfies and S-Phosphorothioates," Tetrahedron, 1988, 44(7):1893-1904.
Turnbull et al., "Structure of palmitoylated BET3: insights into TRAPP complex assembly and membrane localization," Embo J, 2005, 24(5):875-884.
Wagner et al., "Kovalente Bindung von 1-Aminoadamantanderivaten an Proteinantigene nach dem Isothiocyanat-und dem Imidsaureesterverfahren," Pharmazie, 1981, 36(6):400-402 (English Abstract).
Wan et al., "Palmitoylated proteins: purification and identification," Nat Protoc, 2007, 2(7):1573-1584.
Wang et al., "Potent, Orally Active Heterocycle-Based Combretastatin A-4 Analogues: Synthesis, Structure-Activity Relationship, Pharmacokinetics, and In Vivo Antitumor Activity Evaluation," Journal of Medicinal Chemistry, 2002, 45(8):1697-1711.
Wu et al., "Intramolecular Direct C—H Bond Arylation from Aryl Chlorides: a Translation-Metal-Fee Approach for Facile Access of Phenanthridines," Organic Letters, 2012, 14(20):5306-5309.
Wu et al., "The TEAD/TEF family protein Scalloped mediates transcriptional output of the Hippo growth-regulatory pathway," Dev Cell, 2008, 14:388-398.
Yang et al., "Screening with a novel cell-based assay for TAZ activators identifies a compound that enhances myogenesis in C2C12 cells and facilitates muscle repair in a muscle injury model," Mol Cell Biol, 2014, 34(9):1607-1621.
Yang et al., "Submicromolar concentrations of palmitoyl-CoA specifically thioesterify cysteine 244 in glyceraldehyde-3-phosphate dehydrogenase inhibiting enzyme activity: a novel mechanism potentially underlying fatty acid induced insulin resistance," Biochemistry, 2005, 44(35):11903-11912.
Yount et al., "Palmitoylome profiling reveals S-palmitoylation-dependent antiviral activity of IFITM3," Nat Chem Biol, 2010, 6(8):610-614.
Yurttas et al., "Synthesis and antitumor activity evaluation of new 2-(4-aminophenyl) benzothiazole derivatives bearing different heterocyclic rings," Journal of Enzyme Inhibition and Medicinal Chemistry, Sep. 2014, 30(3):458-465.
Yurttas et al., "Synthesis and anticancer activity evaluation of N-[4-(2-methylthiazol-4-yl) phenyl] acetamide derivatives containing (benz) azole moiety," Journal of Enzyme Inhibition and Medicinal Chemistry, Apr. 2014, 29(2):175-184.
Zhang et al., "Photoreceptor cGMP phosphodiesterase delta subunit (PDEdelta)functions as a prenyl-binding protein," J Biol Chem, 2004, 279:407-413.
Zhang et al., "VGLL4 functions as a new tumor suppressor in lung cancer by negatively regulating the YAP-TEAD transcriptional complex," Cell Res, 2014, 24:331-343.
Zhao et al., "TEAD mediates YAP-dependent gene induction and growth control," Genes & Development, 2008, 22:1962-1971.
Zheng et al., "2-Bromopalmitate Analogues as Activity-Based Probes to Explore Palmitoyl Acyltransferases," J. Am. Chem. Soc., 2013, 135(19):7082-7085.
Zheng et al., "Clickable analogue of cerulenin as chemical probe to explore protein palmitoylation," ACS Chem Biol, 2015, 10:115-121.

(56) References Cited

OTHER PUBLICATIONS

Zhou et al., "Mst1 and Mst2 maintain hepatocyte quiescence and suppress hepatocellular carcinoma development through inactivation of the Yap1 oncogene," Cancer Cell, 2009, 16(5):425-438.

Zhou et al., "Targeting Hippo pathway by specific interruption of YAP-TEAD interaction using cyclic YAP-like peptides," Faseb J, 2015, 29:724-732.

Zou et al., "Group 4 Dimethylsilylenebisamido Complexes Bearing the 6-[2-(Diethylboryl)phenyl]pyrid-2-yl Motif: Synthesis and Use in Tandem Ring Opening Metathesis/Vinyl-Insertion Copolymerization of Cyclic Olefins with Ethylene," Chemistry-A European Journal, 2011, 17(49)13832-13846.

Marighetti et al., "Scaffold Identification of a New Class of Potent and Selective BCRP Inhibitors," ChemMedChem, Apr. 2015, 10(4):742-751.

Office Action in Korean Appln. No. 10-2021-7032688, dated Feb. 15, 2024, 21 pages (with English translation).

Luo et al., "Design and Synthesis of New Imatinib Analogs Containing Thiazolyl Moiety," Journal of Heterocyclic Chemistry, Nov. 2013, 50(6):1357-1362.

Office Action in Japanese Appln. No. 2023-076091, dated Jun. 4, 2024, 11 pages (with English translation).

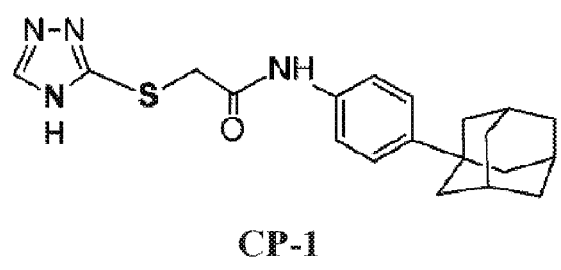
CP-1
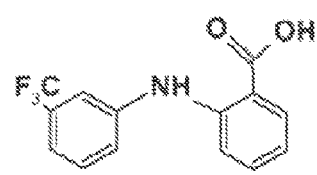
Flufenamic Acid
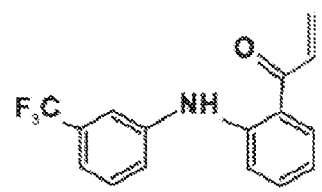
CP-42
FIG. 2

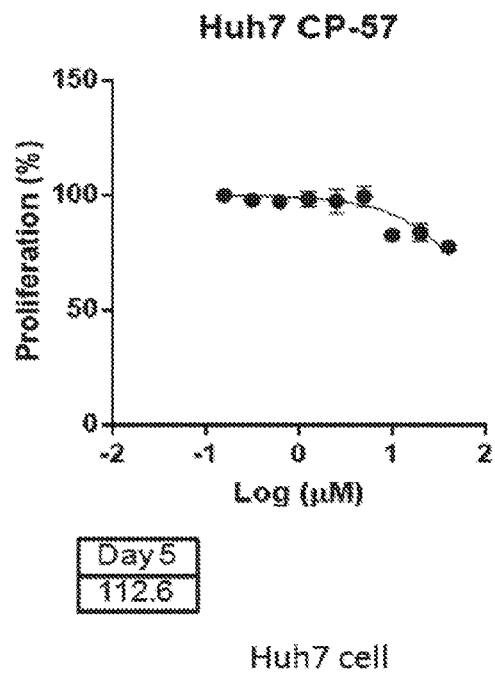
Huh7 cell	FIG. 9
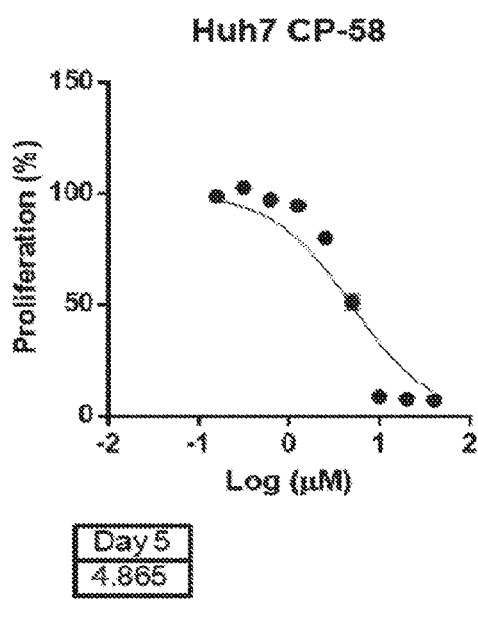
Huh7 cell	FIG. 10

SMALL MOLECULE INHIBITORS OF TEAD TRANSCRIPTION FACTORS

CLAIM OF PRIORITY

This application is a national stage application under 35 USC § 371 of International Application No. PCT/US2020/022757, filed on Mar. 13, 2020, which claims priority to U.S. Patent Application Ser. No. 62/819,347, filed on Mar. 15, 2019, the entire contents of which are hereby incorporated by reference.

GOVERNMENT SUPPORT

This invention was made with government support under Grant Nos. 1R01CA181537 and R01DK107651 awarded by the National Institutes of Health. The government has certain rights in the invention.

TECHNICAL FIELD

The present application is concerned with pharmaceutically useful compounds. The disclosure provides new compounds as well as their compositions and methods of use. The compounds inhibit the autopalmitoylation of TEAD-transcription factors and are therefore useful in the treatment of diseases related to the activity of TEAD-transcription factors including, e.g., cancers and other diseases.

BACKGROUND

Hippo signaling plays key roles in organ size control and tumor suppression. The signal transduction involves a core kinase cascade, including MST1/2 and Lats1/2 kinases, leading to YAP/TAZ phosphorylation, cytoplasmic retention and inhibition[3]. Physiological or pathological inactivation of these kinases leads to YAP/TAZ dephosphorylation and nuclear accumulation. Subsequently, nuclear YAP/TAZ binds to the TEA domain transcription factors (TEAD1-4 in mammals, and Scalloped in *Drosophila*) to mediate the target genes expression. The TEAD-YAP complex regulates normal development of skin, muscle, lung and liver, and are also oncogenic factor amplified in many human cancers. TEADs can also bind to Vgll4, which has been implicated as a tumor suppressor by competing with YAP/TAZ for TEADs binding. Therefore, TEADs are essential in regulating the transcriptional output of Hippo pathway. Although targeting TEAD-YAP could be a promising therapeutic approach for diseases with deregulated Hippo pathway, it remains challenging to directly inhibit transcription factors with small molecules. Therefore, understanding the regulation of TEADs might reveal new therapeutic opportunities for drug discovery.

Post-translational S-palmitoylation attaches a 16-carbon palmitate to the cysteine residue through a reversible thioester bond. A large number of palmitoylated proteins have been identified through proteomic studies. Dynamic S-palmitoylation plays critical roles regulating the trafficking, membrane localization and functions of many proteins, including Src-family kinases, GTPases, and synaptic adhesion molecules. Asp-His-His-Cys (DHHC) family proteins are evolutionarily conserved protein palmitoyl acyltransferases (PATs), mediating enzymatic S-palmitoylation. In addition, some proteins could bind to palmitoyl-Coenzyme A (CoA) directly, and undergo PAT-independent autopalmitoylation. However, autopalmitoylation is poorly characterized. Most of the reported examples of autopalmitoylation are observed under non-physiological, high concentration of palmitoyl-CoA (>100 µM). To date, only a few proteins, including yeast transporter protein Bet3, are autopalmitoylated under physiological concentrations of palmitoyl-CoA (1-10 µM). Therefore, it is important to reveal additional autopalmitoylated proteins and to understand their regulations and functions.

SUMMARY

The present disclosure provides, inter alia, a compound of Formula (I):

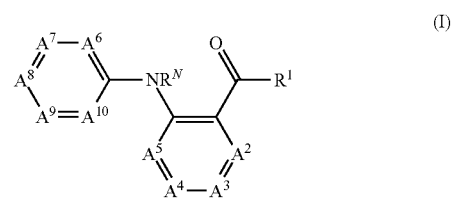

or a pharmaceutically acceptable salt thereof; wherein the variables are as defined below.

The present disclosure also provides a composition comprising a compound of Formula (I), or a pharmaceutically acceptable salt thereof, and at least one pharmaceutically acceptable carrier.

The present disclosure also provides methods of treating cancer and other diseases comprising administering to a patient a therapeutically effective amount of a compound of Formula (I), or a pharmaceutically acceptable salt thereof.

The details of one or more embodiments are set forth in the description below. Other features, objects and advantages will be apparent from the description and from the claims.

BRIEF DESCRIPTION OF THE DRAWINGS

FIG. 2 is a scheme showing the structures of some reference compounds.

FIG. 9 is a plot showing inhibition of cell proliferation in the huh7 human hepatoma cell line by the compound CP-57 at various concentrations.

FIG. 10 is a plot showing inhibition of cell proliferation in the huh7 human hepatoma cell line by the compound CP-58 at various concentrations.

DETAILED DESCRIPTION

Figure 1:
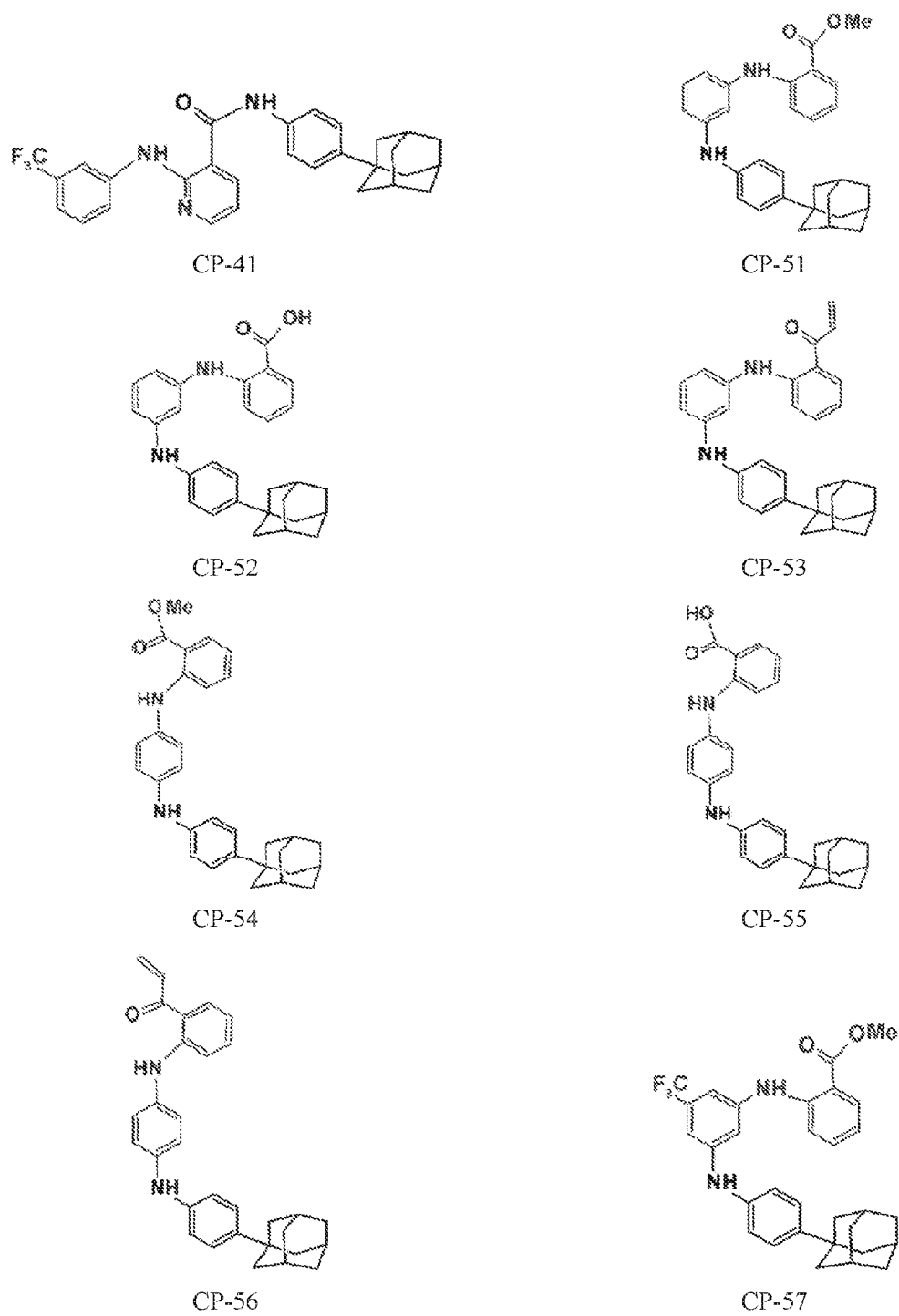
FIG. 1 scheme showing the structures of examples of compounds within the scope of the invention.
Figure 1:
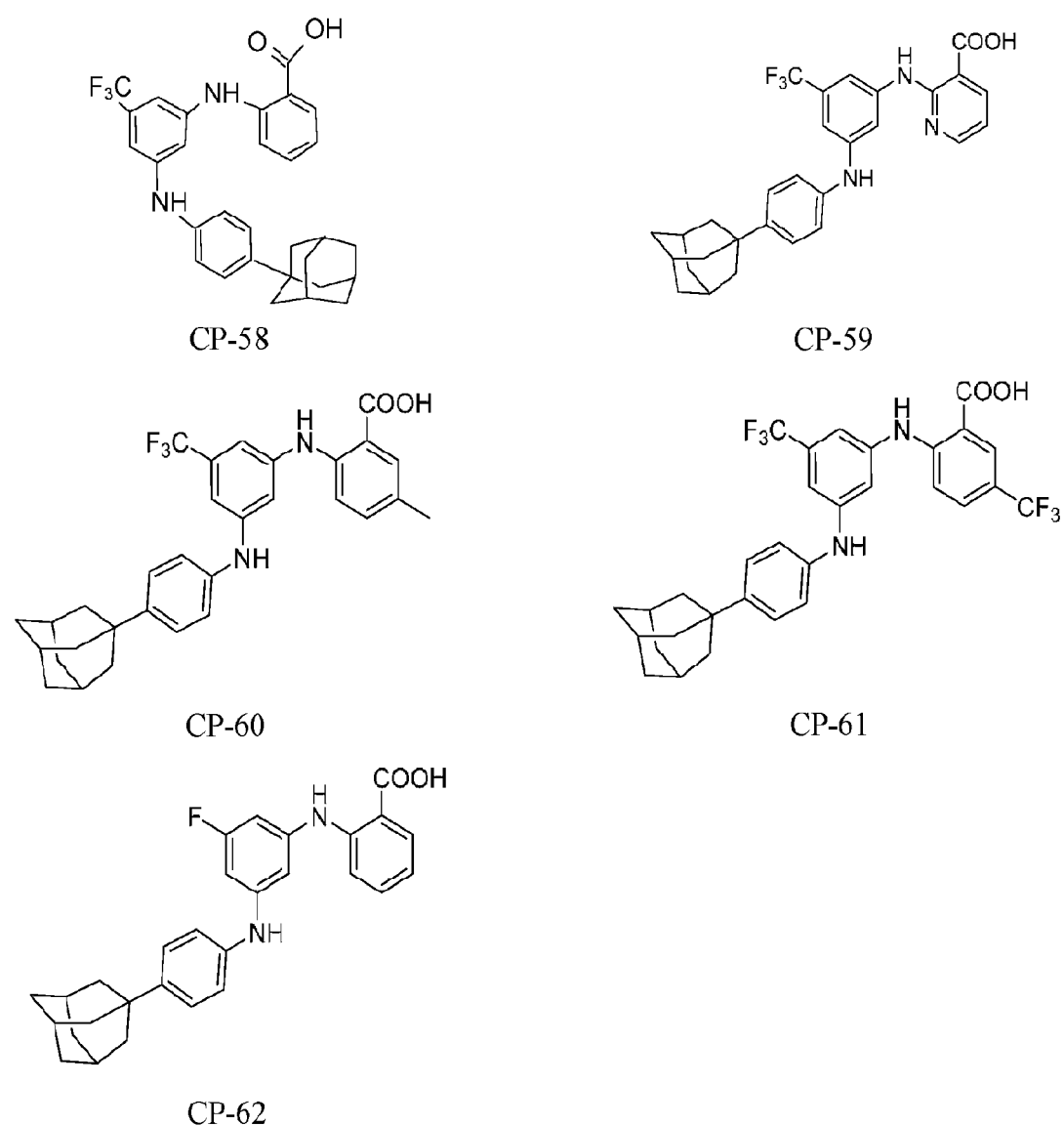

For the terms "e.g." and "such as," and grammatical equivalents thereof, the phrase "and without limitation" is understood to follow unless explicitly stated otherwise.

The singular forms "a," "an," and "the" include plural referents unless the context clearly dictates otherwise.

The term "about" means "approximately" (e.g., plus or minus approximately 10% of the indicated value).

The expressions, "ambient temperature" and "room temperature" (abbreviated "r.t.") refer generally to a temperature, e.g., a reaction temperature, that is about the temperature of the room in which the reaction is carried out, e.g., a temperature from about 20° C. to about 30° C., typically about 25° C.

Through proteomic and biochemical studies, it has been identified that the TEAD transcription factors are palmitoylated at evolutionarily conserved cysteine residues. It has been found that TEADs undergo PAT-independent autopalmitoylation, under physiological concentrations of palmitoyl-CoA. The crystal structures of the lipid-bound TEADs, and revealed a new ligand-binding site in TEADs. Furthermore, autopalmitoylation plays critical roles in regulating TEAD-YAP association and their physiological functions in vitro and in vivo. Therefore, palmitoylation of TEADs plays important roles in regulating Hippo pathway transcriptional complexes.

The discovery of a new ligand-binding site in TEADs has allowed the discovery of small molecule inhibitors of TEAD autopalmitoylation. While not being bound by any theory, it is understood that the ligands bind to the palmitate-binding pocket, and inhibit TEAD-YAP interaction, cancer cell proliferation and migration. Therefore, direct inhibition of TEAD autopalmitoylation activities is useful to inhibit these oncogenic transcription factors.

I. Compounds

The present disclosure provides, inter alia, a compound of Formula (I):

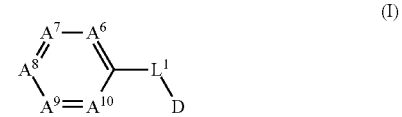
(I)

or a pharmaceutically acceptable salt thereof, wherein:
$L^1$ is absent, or a group of formula $N(R^N)$ or $C(O)$;
D is a group of formula (D1), (D2), (D3), (D4), (D5), (D6) or (D7):

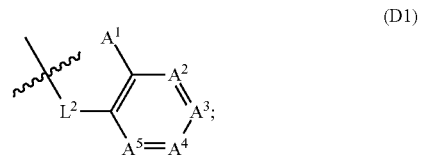
(D1)

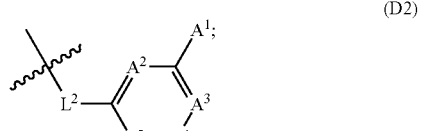
(D2)

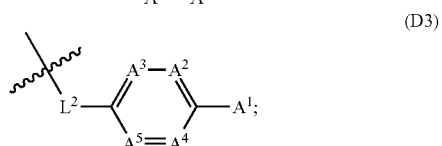
(D3)

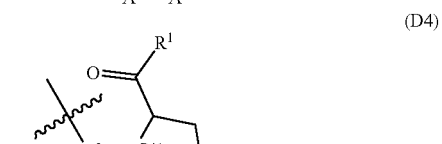
(D4)

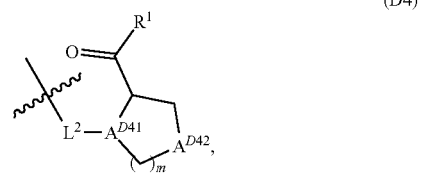
(D5)

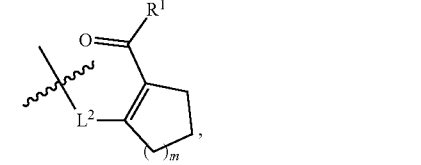
(D6)

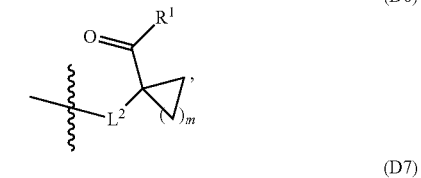
(D7)

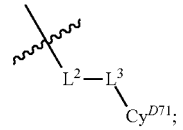

m is 1, 2 or 3;
$A^1$ is $C(O)R^1$, $S(O)_2R^1$, $NHC(O)R^1$, $(C_{1-3}$ alkylene)-$C(O)R^1$, $NH(C_{1-3}$ alkylene)-$C(O)R^1$, CN, $NO_2$, 5-10 membered heteroaryl, 4-10 membered heterocycloalkyl, ($C_{1-3}$ alkylene)-5-10 membered heteroaryl, or ($C_{1-3}$ alkylene)-4-10 membered heterocycloalkyl, wherein the ($C_{1-3}$ alkylene) group of the ($C_{1-3}$ alkylene)-C(O)R$^1$ group forming A$^1$ is unsubstituted or substituted by 1, 2, 3, 4 or 5 substituents each independently selected from halogen, OR$^{a1}$, NR$^{c1}$R$^{d1}$, NR$^{a1}$(CO)(C$_{1-6}$ alkyl), and NR$^{a1}$(CO)O(C$_{1-6}$ alkyl); and wherein the 5-10 membered heteroaryl, 4-10 membered heterocycloalkyl, ($C_{1-3}$ alkylene)-5-10 membered heteroaryl, or ($C_{1-3}$ alkylene)-4-10 membered heterocycloalkyl forming A$^1$ is unsubstituted or substituted by 1, 2, 3, 4 or 5 substituents each independently selected from halogen, OR$^{a1}$, SR$^{a1}$, C(O)OR$^{a1}$, NR$^{c1}$R$^{d1}$, and C(O)NR$^{c1}$R$^{d1}$;

L$^2$ is absent, or a group of formula N(R$^N$), O, or C(O);

L$^3$ is absent or a group of formula CH$_2$, C≡C, N(R$^N$) or C(O);

each R$^N$ is independently H, C$_{1-6}$ alkyl, C(O)C$_{1-6}$ alkyl, or C(O)OC$_{1-6}$ alkyl;

R$^1$ is H, C$_{1-6}$ alkyl, C$_{2-6}$ alkenyl, C$_{2-6}$ alkynyl, Cy$^{1A}$, OH, OC$_{1-6}$ alkyl, OCy$^{1A}$O(C$_{1-3}$ alkylenyl)Cy$^{1A}$, NH$_2$, NHC$_{1-6}$ alkyl, N(C$_{1-6}$ alkyl)$_2$, NHCy$^{1A}$, NH(C$_{1-3}$ alkylenyl)Cy$^{1A}$, N(C$_{1-6}$ alkyl)Cy$^{1A}$, or N(C$_{1-6}$ alkyl)(C$_{1-3}$ alkylenyl)Cy$^{1A}$, wherein each of the C$_{1-6}$ alkyl forming R$^1$ is unsubstituted or substituted by 1, 2, 3, 4 or 5 substituents each independently selected from halogen, OR$^{a1}$, SR$^{a1}$, and NR$^{c1}$R$^{d1}$;

Cy$^{1A}$ is C$_{6-10}$ aryl, C$_{3-15}$ cycloalkyl, 5-10 membered heteroaryl, or 4-10 membered heterocycloalkyl, wherein each of the C$_{6-10}$ aryl, C$_{3-15}$ cycloalkyl, 5-10 membered heteroaryl, or 4-10 membered heterocycloalkyl forming Cy$^{1A}$ is unsubstituted or substituted by 0, 1 or 2 Cy$^{1B}$ and 0, 1, 2, 3, 4 or 5 substituents each independently selected from unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, and C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

each Cy$^{1B}$ is C$_{6-10}$ aryl, C$_{3-15}$ cycloalkyl, 5-10 membered heteroaryl, or 4-10 membered heterocycloalkyl, wherein each of the C$_{6-10}$ aryl, C$_{3-15}$ cycloalkyl, 5-10 membered heteroaryl, or 4-10 membered heterocycloalkyl forming Cy$^{1B}$ is unsubstituted or substituted by 1, 2, 3, 4 or 5 substituents each independently selected from unsubstituted C$_{1-6}$ alkyl, C$_{2-6}$ alkenyl, C$_{2-6}$ alkynyl, halogen, C$_{1-6}$ haloalkyl, CN, OR$^{a1}$ SR$^{a1}$, and NR$^{c1}$R$^{d1}$; and C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

A$^2$ is CR$^2$ or N;
A$^3$ is CR$^3$ or N;
A$^4$ is CR$^4$ or N;
A$^5$ is CR$^5$ or N;
A$^6$ is CR$^6$ or N;
A$^7$ is CR$^7$ or N;
A$^8$ is CR$^8$ or N;
A$^9$ is CR$^9$ or N;
A$^{10}$ is CR$^{10}$ or N;
A$^{D41}$ is CH, C(C$_{1-6}$ alkyl) or N;
A$^{D42}$ is CH$_2$, NH or NC$_{1-6}$ alkyl;

R$^2$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, C(O)OR$^{a1}$, C(O)NR$^{c1}$R$^{d1}$ or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

R$^3$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, C(O)OR$^{a1}$, C(O)NR$^{c1}$R$^{d1}$ or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

R$^4$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, C(O)OR$^{a1}$, C(O)NR$^{c1}$R$^{d1}$ or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

R$^5$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, C(O)OR$^{a1}$, C(O)NR$^{c1}$R$^{d1}$ or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

R$^6$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, S(O)$_2$R$^{b1}$, S(O)$_2$NR$^{c1}$R$^{d1}$, NR$^{c1}$R$^{d1}$, C(O)OR$^{a1}$, C(O)NR$^{c1}$R$^{d1}$, Cy$^{7A}$, OCy$^{7A}$, O(C$_{1-3}$ alkylenyl)Cy$^{7A}$, C(O)OCy$^{7A}$, C(O)O(C$_{1-3}$ alkylenyl)Cy$^{7A}$, NHCy$^{7A}$NH(C$_{1-3}$ alkylenyl)Cy$^{7A}$, N(C$_{1-6}$ alkyl)Cy$^{7A}$, N(C(O)C$_{1-6}$ alkyl)Cy$^{7A}$, N(C$_{1-6}$ alkyl)(C$_{1-3}$ alkylenyl)Cy$^{7A}$, C(O)NHCy$^{7A}$, C(O)NH(C$_{1-3}$ alkylenyl)Cy$^{7A}$, C(O)N(C$_{1-6}$ alkyl)Cy$^{7A}$, C(O)N(C$_{1-6}$ alkyl)(C$_{1-3}$ alkylenyl)Cy$^{7A}$, or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

R$^7$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, C(O)OR$^{a1}$, S(O)$_2$NR$^{c1}$R$^{d1}$, C(O)NR$^{c1}$R$^{d1}$, Cy$^{7A}$, OCy$^{7A}$, O(C$_{1-3}$ alkylenyl)Cy$^{7A}$, C(O)OCy$^{7A}$, C(O)O(C$_{1-3}$ alkylenyl)Cy$^{7A}$, NHCy$^{7A}$, NH(C$_{1-3}$ alkylenyl)Cy$^{7A}$, N(C$_{1-6}$ alkyl)Cy$^{7A}$, N(C(O)C$_{1-6}$ alkyl)Cy$^{7A}$, N(C$_{1-6}$ alkyl)(C$_{1-3}$ alkylenyl)Cy$^{7A}$, C(O)NHCy$^{7A}$, C(O)NH(C$_{1-3}$ alkylenyl)Cy$^{7A}$, C(O)N(C$_{1-6}$ alkyl)Cy$^{7A}$, C(O)N(C$_{1-6}$ alkyl)(C$_{1-3}$ alkylenyl)Cy$^{7A}$ or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

Cy$^{7A}$ is C$_{6-10}$ aryl, C$_{3-15}$ cycloalkyl, 5-10 membered heteroaryl, or 4-10 membered heterocycloalkyl, wherein each of the C$_{6-10}$ aryl, C$_{3-15}$ cycloalkyl, 5-10 membered heteroaryl, or 4-10 membered heterocycloalkyl forming Cy$^{7A}$ is unsubstituted or substituted by 0, 1 or 2 substituents selected from Cy$^{7B}$, OCy$^{7B}$, NHCy$^{7B}$, and C(O)NHCy$^{7B}$, and 0, 1, 2, 3, 4 or 5 substituents each independently selected from unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, C(O)OR$^{a1}$, C(O)NR$^{c1}$R$^{d1}$, and C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

each Cy$^{7B}$ is C$_{6-10}$ aryl, C$_{3-15}$ cycloalkyl, 5-10 membered heteroaryl, or 4-10 membered heterocycloalkyl, wherein each of the C$_{6-10}$ aryl, C$_{3-15}$ cycloalkyl, 5-10 membered heteroaryl, or 4-10 membered heterocycloalkyl forming Cy$^{7B}$ is unsubstituted or substituted by 1, 2, 3, 4 or 5 substituents each independently selected from unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, C(O)OR$^{a1}$, C(O)NR$^{c1}$R$^{d1}$, and C$_{1-6}$ alkyl that is substituted by 1, 2, or 3 substituents each independently selected from halogen, C$_{1-6}$ haloalkyl, CN, OR$^{a1}$, SR$^{a1}$, NR$^{c1}$R$^{d1}$;

R$^8$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, S(O)$_2$NR$^{c1}$R$^{d1}$, SR$^{a1}$, NR$^{c1}$R$^{d1}$, NR$^{c1}$S(O)$_2$R$^{b1}$, C(O)OR$^{a1}$, C(O)NR$^{c1}$R$^{d1}$, Cy$^{8A}$, OH, OCy$^{8A}$, O(C$_{1-3}$ alkylenyl)Cy$^{8A}$, C(O)OCy$^{8A}$, C(O)O(C$_{1-3}$ alkylenyl)Cy$^{8A}$, NHCy$^{8A}$, N(Cy$^{8A}$)$_2$, NH(C$_{1-3}$ alkylenyl)Cy$^{8A}$, N(C$_{1-6}$ alkyl)Cy$^{8A}$, N(C(O)C$_{1-6}$ alkyl)Cy$^{8A}$, SO$_2$NHCy$^{8A}$, N(C$_{1-6}$ alkyl)(C$_{1-3}$ alkylenyl)Cy$^{8A}$, C(O)NHCy$^{8A}$, C$_{1-3}$ alkylene-C(O)NHCy$^{8A}$, C(O)NH(C$_{1-3}$ alkylenyl)Cy$^{8A}$, C(O)N(C$_{1-6}$ alkyl)Cy$^{8A}$, C(O)N(C$_{1-6}$ alkyl)(C$_{1-3}$ alkylenyl)Cy$^{8A}$, or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

Cy$^{8A}$ is C$_{6-10}$ aryl, C$_{3-15}$ cycloalkyl, 5-10 membered heteroaryl, or 4-10 membered heterocycloalkyl, wherein each of the C$_{6-10}$ aryl, C$_{3-15}$ cycloalkyl, 5-10 membered heteroaryl, or 4-10 membered heterocycloalkyl forming Cy$^{8A}$ is unsubstituted or substituted by 0, 1 or 2 substituents selected from Cy$^{8B}$, OCy$^{8B}$, NHCy$^{8B}$, and C(O)NHCy$^{8B}$, and 0, 1, 2, 3, 4 or 5 substituents each independently selected from unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, C(O)OR$^{a1}$, C(O)NR$^{c1}$R$^{d1}$, and C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

each Cy$^{8B}$ is C$_{6-10}$ aryl, C$_{3-15}$ cycloalkyl, 5-10 membered heteroaryl, or 4-10 membered heterocycloalkyl, wherein each of the C$_{6-10}$ aryl, C$_{3-15}$ cycloalkyl, 5-10 membered heteroaryl, or 4-10 membered heterocycloalkyl forming Cy$^{8B}$ is unsubstituted or substituted by 1, 2, 3, 4 or 5 substituents each independently selected from unsubstituted C$_{1-6}$ alkyl, C$_{2-6}$ alkenyl, C$_{2-6}$ alkynyl, halogen, C$_{1-6}$ haloalkyl, CN, OR$^{a1}$ SR$^{a1}$, NR$^{c1}$R$^{d1}$, C(O)OR$^{a1}$, C(O)NR$^{c1}$R$^{d1}$, and C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

R$^9$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, NR$^{c1}$C(O)R$^{b1}$, C(O)OR$^{a1}$, C(O)NR$^{c1}$R$^{d1}$, or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

R$^{10}$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, C(O)OR$^{a1}$, C(O)NR$^{c1}$R$^{d1}$, or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

Cy$^{D71}$ is C$_{6-10}$ aryl, C$_{3-15}$ cycloalkyl, 5-14 membered heteroaryl, or 4-10 membered heterocycloalkyl, wherein each of the C$_{6-10}$ aryl, C$_{3-15}$ cycloalkyl, 5-10 membered heteroaryl, or 4-10 membered heterocycloalkyl forming Cy$^{D71}$ is unsubstituted or substituted by 0, 1 or 2 substituents selected from Cy$^{D72}$, CH$_2$Cy$^{D72}$, OCy$^{D72}$, NHCy$^{D72}$, O—C$_{1-6}$ alkylene-Cy$^{D72}$, N(C$_{1-6}$ alkyl)Cy$^{D72}$, N(C(O)C$_{1-6}$ alkyl)Cy$^{D72}$, and C(O)NHCy$^{D72}$, and 0, 1, 2, 3, 4 or 5 substituents each independently selected from unsubstituted C$_{1-6}$ alkyl, C$_{2-6}$ alkenyl, C$_{2-6}$ alkynyl, halogen, C$_{1-6}$ haloalkyl, CN, OR$^{a1}$, S(hal)$_5$, SR$^{a1}$, NR$^{c1}$R$^{d1}$, C(O)OR$^{a1}$, C(O)NR$^{c1}$R$^{d1}$, and C$_{1-6}$ alkyl or C$_{2-6}$ alkenyl that is substituted by 1, 2, or 3 substituents each independently selected from halogen, C$_{1-6}$ haloalkyl, CN, OR$^{a1}$, SR$^{a1}$, C(O)OR$^{a1}$, and NR$^{c1}$R$^{d1}$;

each Cy$^{D72}$ is C$_{6-10}$ aryl, C$_{3-15}$ cycloalkyl, 5-10 membered heteroaryl, or 4-10 membered heterocycloalkyl, wherein each of the C$_{6-10}$ aryl, C$_{3-15}$ cycloalkyl, 5-10 membered heteroaryl, or 4-10 membered heterocycloalkyl forming Cy$^{D72}$ is unsubstituted or substituted by 1, 2, 3, 4 or 5 substituents each independently selected from unsubstituted C$_{1-6}$ alkyl, C$_{2-6}$ alkenyl, C$_{2-6}$ alkynyl, C$_{6-10}$ aryl, C$_{3-15}$ cycloalkyl, 4-10 membered heterocycloalkyl, halogen, C$_{1-6}$ haloalkyl, CN, OR$^{a1}$, SR$^{a1}$, NR$^{c1}$R$^{d1}$, C(O)OR$^{a1}$, C(O)NR$^{c1}$R$^{d1}$, and C$_{1-6}$ alkyl that is substituted by 1, 2, or 3 substituents each independently selected from C$_{6-10}$ aryl, C$_{3-15}$ cycloalkyl, 4-10 membered heterocycloalkyl, halogen, C$_{1-6}$ haloalkyl, CN, OR$^{a1}$, SR$^{a1}$, C(O)OR$^{a1}$, and NR$^{c1}$R$^{d1}$, wherein said C$_{6-10}$ aryl, C$_{3-15}$ cycloalkyl, and 4-10 membered heterocycloalkyl are each optionally substituted with 1, 2, or 3 substituents independently selected from C$_{1-6}$ alkyl, halogen, C$_{1-6}$ haloalkyl, CN, OR$^{a1}$, SR$^{a1}$, NR$^{c1}$R$^{d1}$, C(O)OR$^{a1}$, and C(O)NR$^{c1}$R$^{d1}$; and R$^{a1}$, R$^{b1}$, R$^{c1}$ and R$^{d1}$ are each independently selected from H, C$_{1-6}$ alkyl, C$_{1-6}$ haloalkyl, HO—C$_{1-6}$ alkylene, amino-C$_{1-6}$ alkylene, C$_{1-6}$ alkylamino-C$_{1-6}$ alkylene, di(C$_{1-6}$ alkyl)amino-C$_{1-6}$ alkylene, C$_{1-6}$ alkoxy-C$_{1-6}$ alkylene, C$_{6-10}$ aryl, C$_{2-6}$ alkenyl and C$_{2-6}$ alkynyl; or R$^{c1}$ and R$^{d1}$ together with the nitrogen atom to which they are both attached together form a 4-10 membered unsubstituted heterocycloalkyl ring or a heterocyclic ring that is substituted with 1, 2, or 3 substituents independently selected from C$_{1-6}$ alkyl, halogen, C$_{1-6}$ haloalkyl, CN, OR$^{a1}$, SR$^{a1}$, NR$^{c1}$R$^{d1}$, C(O)OR$^{a1}$, and C(O)NR$^{c1}$R$^{d1}$;

provided:

L$^1$ is a group of formula N(R$^N$) when L$^2$ is C(O);
L$^1$ is a group of formula C(O) when L$^2$ is N(R$^N$);
L$^2$ is absent, or a group of formula N(R$^N$) when L$^1$ is C(O);
L$^2$ is absent, or a group of formula C(O) when L$^1$ is N(R$^N$);
A$^{D41}$ is CH, C(C$_{1-6}$ alkyl) when A$^{D42}$ is NH or NC$_{1-6}$ alkyl;
A$^{D42}$ is CH$_2$ when A$^{D41}$ is NH or NC$_{1-6}$ alkyl;
no more than two of A$^2$, A$^3$, A$^4$ and A$^5$ is N;
no more than two of A$^6$, A$^7$, A$^8$, A$^9$ and A$^{10}$ is N; and
either R$^1$ is present and is Cy$^{1A}$, OCy$^{1A}$, O(C$_{1-3}$ alkylenyl)Cy$^{1A}$, NHCy$^{1A}$ NH(C$_{1-3}$ alkylenyl)Cy$^{1A}$, N(C$_{1-6}$ alkyl)Cy$^{1A}$, or N(C$_{1-6}$ alkyl)(C$_{1-3}$ alkylenyl)Cy$^{1A}$; or R$^7$ is Cy$^{7A}$, OCy$^{7A}$, O(C$_{1-3}$ alkylenyl)Cy$^{7A}$, C(O)OCy$^{7A}$, C(O)O(C$_{1-3}$ alkylenyl)Cy$^{7A}$, NHCy$^{7A}$, NH(C$_{1-3}$ alkylenyl)Cy$^{7A}$, N(C$_{1-6}$ alkyl)Cy$^{7A}$, N(C$_{1-6}$ alkyl)(C$_{1-3}$ alkylenyl)Cy$^{7A}$; C(O)NHCy$^{7A}$, C(O)NH(C$_{1-3}$ alkylenyl)Cy$^{7A}$, C(O)N(C$_{1-6}$ alkyl)Cy$^{7A}$, or C(O)N(C$_{1-6}$ alkyl)(C$_{1-3}$ alkylenyl)Cy$^{7A}$, or R$^8$ is Cy$^{8A}$, OCy$^{8A}$, O(C$_{1-3}$ alkylenyl)Cy$^{8A}$, C(O)OCy$^{8A}$, C(O)O(C$_{1-3}$ alkylenyl)Cy$^{8A}$, NHCy$^{8A}$, NH(C$_{1-3}$ alkylenyl)Cy$^{8A}$, N(C$_{1-6}$ alkyl)Cy$^{8A}$, N(C$_{1-6}$ alkyl)(C$_{1-3}$ alkylenyl)Cy$^{8A}$, C(O)NHCy$^{8A}$, C(O)NH(C$_{1-3}$ alkylenyl)Cy$^{8A}$, C(O)N(C$_{1-6}$ alkyl)Cy$^{8A}$, or C(O)N(C$_{1-6}$ alkyl)(C$_{1-3}$ alkylenyl)Cy$^{8A}$.

The present disclosure provides, inter alia, a compound of Formula (I):

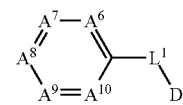

(I)

or a pharmaceutically acceptable salt thereof, wherein:

$L^1$ is absent, or a group of formula $N(R^N)$ or $C(O)$;

D is a group of formula (D1), (D2), (D3), (D4), (D5), (D6), or (D7):

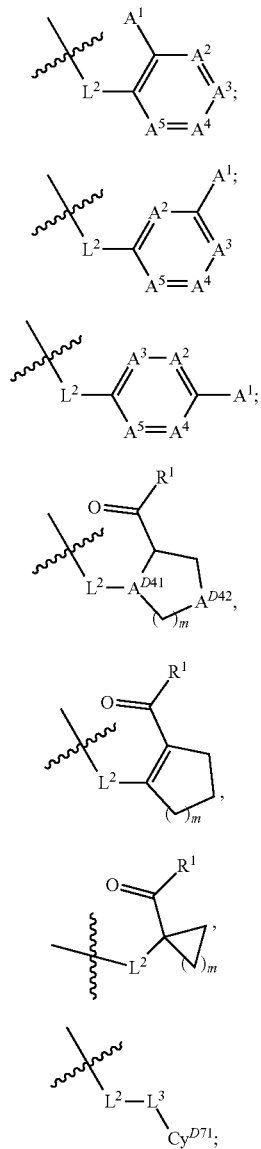

m is 1, 2 or 3;

$A^1$ is $C(O)R^1$, $S(O)_2R^1$, $NHC(O)R^1$, $(C_{1-3}$ alkylene$)$-$C(O)R^1$, $NH(C_{1-3}$ alkylene$)$-$C(O)R^1$, CN, $NO_2$, 5-10 membered heteroaryl, 4-10 membered heterocycloalkyl, $(C_{1-3}$ alkylene$)$-5-10 membered heteroaryl, or $(C_{1-3}$ alkylene$)$-4-10 membered heterocycloalkyl, wherein the $(C_{1-3}$ alkylene$)$ group of the $(C_{1-3}$ alkylene$)$-$C(O)R^1$ group forming $A^1$ is unsubstituted or substituted by 1, 2, 3, 4 or 5 substituents each independently selected from halogen, $OR^{a1}$, $NR^{c1}R^{d1}$, $NR^{a1}(CO)(C_{1-6}$ alkyl$)$, and $NR^{a1}(CO)O(C_{1-6}$ alkyl$)$; and wherein the 5-10 membered heteroaryl, 4-10 membered heterocycloalkyl, $(C_{1-3}$ alkylene$)$-5-10 membered heteroaryl, or $(C_{1-3}$ alkylene$)$-4-10 membered heterocycloalkyl forming $A^1$ is unsubstituted or substituted by 1, 2, 3, 4 or 5 substituents each independently selected from halogen, $OR^{a1}$, $SR^{a1}$, $C(O)OR^{a1}$, $NR^{c1}R^{d1}$ and $C(O)NR^{c1}R^{d1}$;

$L^2$ is absent, or a group of formula $N(R^N)$, O, or $C(O)$;

$L^3$ is absent or a group of formula $CH_2$, $C\equiv C$, $N(R^N)$ or $C(O)$;

each $R^N$ is independently H, $C_{1-6}$ alkyl, $C(O)C_{1-6}$ alkyl, or $C(O)OC_{1-6}$ alkyl;

$R^1$ is H, $C_{1-6}$ alkyl, $C_{2-6}$ alkenyl, $C_{2-6}$ alkynyl, $Cy^{1A}$, OH, $OC_{1-6}$ alkyl, $OCy^{1A}$, $O(C_{1-3}$ alkylenyl$)Cy^{1A}$, $NH_2$, $NHC_{1-6}$ alkyl, $N(C_{1-6}$ alkyl$)_2$, $NHCy^{1A}$, $NH(C_{1-3}$ alkylenyl$)Cy^{1A}$, $N(C_{1-6}$ alkyl$)Cy^{1A}$, or $N(C_{1-6}$ alkyl$)(C_{1-3}$ alkylenyl$)Cy^{1A}$, wherein each of the $C_{1-6}$ alkyl forming $R^1$ is unsubstituted or substituted by 1, 2, 3, 4 or 5 substituents each independently selected from halogen, $OR^{a1}$, $SR^{a1}$, and $NR^{c1}R^{d1}$;

$Cy^{1A}$ is $C_{6-10}$ aryl, $C_{3-15}$ cycloalkyl, 5-10 membered heteroaryl, or 4-10 membered heterocycloalkyl, wherein each of the $C_{6-10}$ aryl, $C_{3-15}$ cycloalkyl, 5-10 membered heteroaryl, or 4-10 membered heterocycloalkyl forming $Cy^{1A}$ is unsubstituted or substituted by 0, 1 or 2 $Cy^{1B}$ and 0, 1, 2, 3, 4 or 5 substituents each independently selected from unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$ and $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

each $Cy^{1B}$ is $C_{6-10}$ aryl, $C_{3-15}$ cycloalkyl, 5-10 membered heteroaryl, or 4-10 membered heterocycloalkyl, wherein each of the $C_{6-10}$ aryl, $C_{3-15}$ cycloalkyl, 5-10 membered heteroaryl, or 4-10 membered heterocycloalkyl forming $Cy^{1B}$ is unsubstituted or substituted by 1, 2, 3, 4 or 5 substituents each independently selected from unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, and $NR^{c1}R^{d1}$; and $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$A^2$ is $CR^2$ or N;
$A^3$ is $CR^3$ or N;
$A^4$ is $CR^4$ or N;
$A^5$ is $CR^5$ or N;
$A^6$ is $CR^6$ or N;
$A^7$ is $CR^7$ or N;
$A^8$ is $CR^8$ or N;
$A^9$ is $CR^9$ or N;
$A^{10}$ is $CR^{10}$ or N;
$A^{D41}$ is CH, $C(C_{1-6}$ alkyl$)$ or N;
$A^{D42}$ is $CH_2$, NH or $NC_{1-6}$ alkyl;

$R^2$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $C(O)OR^{a1}$, $C(O)NR^{c1}R^{d1}$ or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^3$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $C(O)OR^{a1}$, $C(O)NR^{c1}R^{d1}$ or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^4$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $C(O)OR^{a1}$, $C(O)NR^{c1}R^{d1}$ or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^5$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $C(O)OR^{a1}$, $C(O)NR^{c1}R^{d1}$ or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^6$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $C(O)OR^{a1}$, $C(O)NR^{c1}R^{d1}$ or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^7$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $C(O)OR^{a1}$, $C(O)NR^{c1}R^{d1}$, $Cy^{7A}$, $OCy^{7A}$, $O(C_{1-3}$ alkylenyl$)Cy^{7A}$, $C(O)OCy^{7A}$, $C(O)O(C_{1-3}$ alkylenyl$)Cy^{7A}$, $NHCy^{7A}$, $NH(C_{1-3}$ alkylenyl$)Cy^{7A}$, $N(C_{1-6}$ alkyl$)Cy^{7A}$, $N(C(O)C_{1-6}$ alkyl$)Cy^{7A}$, $N(C_{1-6}$ alkyl$)(C_{1-3}$ alkylenyl$)Cy^{7A}$, $C(O)NHCy^{7A}$, $C(O)NH(C_{1-3}$ alkylenyl$)Cy^{7A}$, $C(O)N(C_{1-6}$ alkyl$)Cy^{7A}$, $C(O)N(C_{1-6}$ alkyl$)(C_{1-3}$ alkylenyl$)Cy^{7A}$ or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$Cy^{7A}$ is $C_{6-10}$ aryl, $C_{3-15}$ cycloalkyl, 5-10 membered heteroaryl, or 4-10 membered heterocycloalkyl, wherein each of the $C_{6-10}$ aryl, $C_{3-15}$ cycloalkyl, 5-10 membered heteroaryl, or 4-10 membered heterocycloalkyl forming $Cy^{7A}$ is unsubstituted or substituted by 0, 1 or 2 substituents selected from $Cy^{7B}$, $OCy^{7B}$, $NHCy^{7B}$, and $C(O)NHCy^{7B}$, and 0, 1, 2, 3, 4 or 5 substituents each independently selected from unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $C(O)OR^{a1}$, $C(O)NR^{c1}R^{d1}$, and $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

each $Cy^{7B}$ is $C_{6-10}$ aryl, $C_{3-15}$ cycloalkyl, 5-10 membered heteroaryl, or 4-10 membered heterocycloalkyl, wherein each of the $C_{6-10}$ aryl, $C_{3-15}$ cycloalkyl, 5-10 membered heteroaryl, or 4-10 membered heterocycloalkyl forming $Cy^{7B}$ is unsubstituted or substituted by 1, 2, 3, 4 or 5 substituents each independently selected from unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $C(O)OR^{a1}$, $C(O)NR^{c1}R^{d1}$, and $C_{1-6}$ alkyl that is substituted by 1, 2, or 3 substituents each independently selected from halogen, $C_{1-6}$ haloalkyl, CN, $OR^{a1}$, $SR^{a1}$, $NR^{c1}R^{d1}$;

$R^8$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $C(O)OR^{a1}$, $C(O)NR^{c1}R^{d1}$, $Cy^{8A}$, OH, $OCy^{8A}$, $O(C_{1-3}$ alkylenyl$)Cy^{8A}$, $C(O)OCy^{8A}$, $C(O)O(C_{1-3}$ alkylenyl$)Cy^{8A}$, $NHCy^{8A}$, $N(Cy^{8A})_2$, $NH(C_{1-3}$ alkylenyl$)Cy^{8A}$, $N(C_{1-6}$ alkyl$)Cy^{8A}$, $N(C(O)C_{1-6}$ alkyl$)Cy^{8A}$, $SO_2NHCy^{8A}$, $N(C_{1-6}$ alkyl$)(C_{1-3}$ alkylenyl$)Cy^{8A}$, $C(O)NHCy^{8A}$, $C_{1-3}$ alkylene-$C(O)NHCy^{8A}$, $C(O)NH(C_{1-3}$ alkylenyl$)Cy^{8A}$, $C(O)N(C_{1-6}$ alkyl$)Cy^{8A}$, $C(O)N(C_{1-6}$ alkyl$)(C_{1-3}$ alkylenyl$)Cy^{8A}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$Cy^{8A}$ is $C_{6-10}$ aryl, $C_{3-15}$ cycloalkyl, 5-10 membered heteroaryl, or 4-10 membered heterocycloalkyl, wherein each of the $C_{6-10}$ aryl, $C_{3-15}$ cycloalkyl, 5-10 membered heteroaryl, or 4-10 membered heterocycloalkyl forming $Cy^{8A}$ is unsubstituted or substituted by 0, 1 or 2 substituents selected from $Cy^{8B}$, $OCy^{8B}$, $NHCy^{8B}$, and $C(O)NHCy^{8B}$, and 0, 1, 2, 3, 4 or 5 substituents each independently selected from unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $C(O)OR^{a1}$, $C(O)NR^{c1}R^{d1}$, and $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

each $Cy^{8B}$ is $C_{6-10}$ aryl, $C_{3-15}$ cycloalkyl, 5-10 membered heteroaryl, or 4-10 membered heterocycloalkyl, wherein each of the $C_{6-10}$ aryl, $C_{3-15}$ cycloalkyl, 5-10 membered heteroaryl, or 4-10 membered heterocycloalkyl forming $Cy^{8B}$ is unsubstituted or substituted by 1, 2, 3, 4 or 5 substituents each independently selected from unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $C(O)OR^{a1}$, $C(O)NR^{c1}R^{d1}$, and $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^9$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $C(O)OR^{a1}$, $C(O)NR^{c1}R^{d1}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{10}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $C(O)OR^{a1}$, $C(O)NR^{c1}R^{d1}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$Cy^{D71}$ is $C_{6-10}$ aryl, $C_{3-15}$ cycloalkyl, 5-14 membered heteroaryl, or 4-10 membered heterocycloalkyl, wherein each of the $C_{6-10}$ aryl, $C_{3-15}$ cycloalkyl, 5-10 membered heteroaryl, or 4-10 membered heterocycloalkyl forming $Cy^{D71}$ is unsubstituted or substituted by 0, 1 or 2 substituents selected from $Cy^{D72}$, $CH_2Cy^{D72}$, $OCy^{D72}$, $NHCy^{D72}$, $O-C_{1-6}$ alkylene-$Cy^{D72}$, $N(C_{1-6}$ alkyl$)Cy^{D72}$, $N(C(O)C_{1-6}$ alkyl$)Cy^{D72}$, and $C(O)NHCy^{D72}$, and 0, 1, 2, 3, 4 or 5 substituents each independently selected from unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $C(O)OR^{a1}$, $C(O)NR^{c1}R^{d1}$, and $C_{1-6}$ alkyl or $C_{2-6}$ alkenyl that is substituted by 1, 2, or 3 substituents each independently selected from halogen, $C_{1-6}$ haloalkyl, CN, $OR^{a1}$, $SR^{a1}$, $C(O)OR^{a1}$, and $NR^{c1}R^{d1}$;

each $Cy^{D72}$ is $C_{6-10}$ aryl, $C_{3-15}$ cycloalkyl, 5-10 membered heteroaryl, or 4-10 membered heterocycloalkyl, wherein each of the $C_{6-10}$ aryl, $C_{3-15}$ cycloalkyl, 5-10 membered heteroaryl, or 4-10 membered heterocycloalkyl forming $Cy^{D72}$ is unsubstituted or substituted by 1, 2, 3, 4 or 5 substituents each independently selected from unsubstituted $C_{1-6}$ alkyl, $C_{2-6}$ alkenyl, $C_{2-6}$ alkynyl, $C_{3-15}$ cycloalkyl, halogen, $C_{1-6}$ haloalkyl, CN, $OR^{a1}$, $SR^{a1}$, $NR^{c1}R^{d1}$, $C(O)OR^{a1}$, $C(O)NR^{c1}R^{d1}$, and $C_{1-6}$ alkyl that is substituted by 1, 2, or 3 substituents each independently selected from halogen, $C_{1-6}$ haloalkyl, CN, $OR^{a1}$, $SR^{a1}$, $C(O)OR^{a1}$, and $NR^{c1}R^{d1}$; and $R^{a1}$, $R^{b1}$, $R^{c1}$ and $R^{d1}$ are each independently selected from H, $C_{1-6}$ alkyl, $HO-C_{1-6}$ alkylene, $C_{1-6}$ alkoxy-$C_{1-6}$ alkylene, $C_{6-10}$ aryl, $C_{2-6}$ alkenyl and $C_{2-6}$ alkynyl; or $R^{c1}$ and $R^{d1}$ together with the nitrogen atom to which they are both attached together form a 4-10 membered unsubstituted heterocycloalkyl ring;

In some embodiments:
$L^1$ is a group of formula $N(R^N)$ when $L^2$ is C(O);
$L^1$ is a group of formula C(O) when $L^2$ is $N(R^N)$;
$L^2$ is absent, or a group of formula $N(R^N)$ when $L^1$ is C(O);
$L^2$ is absent, or a group of formula C(O) when $L^1$ is $N(R^N)$;
$A^{D41}$ is CH, $C(C_{1-6}$ alkyl) when $A^{D42}$ is NH or $NC_{1-6}$ alkyl;
$A^{D42}$ is $CH_2$ when $A^{D41}$ is NH or $NC_{1-6}$ alkyl;
no more than two of $A^2$, $A^3$, $A^4$ and $A^5$ is N;
no more than two of $A^6$, $A^7$, $A^8$, $A^9$ and $A^{10}$ is N; and
either $R^1$ is present and is $Cy^{1A}$, $OCy^{1A}$, $O(C_{1-3}$ alkylenyl)$Cy^{1A}$, $NHCy^{1A}$ $NH(C_{1-3}$ alkylenyl)$Cy^{1A}$, $N(C_{1-6}$ alkyl)$Cy^{1A}$, or $N(C_{1-6}$ alkyl)$(C_{1-3}$ alkylenyl)$Cy^{1A}$; or
$R^7$ is $Cy^{7A}$, $OCy^{7A}$, $O(C_{1-3}$ alkylenyl)$Cy^{7A}$ C(O)O$Cy^{7A}$, $C(O)O(C_{1-3}$ alkylenyl)$Cy^{7A}$, $NHCy^{7A}$, $NH(C_{1-3}$ alkylenyl)$Cy^{7A}$, $N(C_{1-6}$ alkyl)$Cy^{7A}$, $N(C_{1-6}$ alkyl)$(C_{1-3}$ alkylenyl)$Cy^{7A}$; $C(O)NHCy^{7A}$, $C(O)NH(C_{1-3}$ alkylenyl)$Cy^{7A}$, $C(O)N(C_{1-6}$ alkyl)$Cy^{7A}$, or $C(O)N(C_{1-6}$ alkyl)$(C_{1-3}$ alkylenyl)$Cy^{7A}$, or
$R^8$ is $Cy^{8A}$, $OCy^{8A}$, $O(C_{1-3}$ alkylenyl)$Cy^{8A}$, $C(O)OCy^{8A}$, $C(O)O(C_{1-3}$ alkylenyl)$Cy^{8A}$, $NHCy^{8A}$, $NH(C_{1-3}$ alkylenyl)$Cy^{8A}$, $N(C_{1-6}$ alkyl)$Cy^{8A}$, $N(C_{1-6}$ alkyl)$(C_{1-3}$ alkylenyl)$Cy^{8A}$, $C(O)NHCy^{8A}$, $C(O)NH(C_{1-3}$ alkylenyl)$Cy^{8A}$, $C(O)N(C_{1-6}$ alkyl)$Cy^{8A}$, or $C(O)N(C_{1-6}$ alkyl)$(C_{1-3}$ alkylenyl)$Cy^{8A}$.

In some embodiments, $L^1$ is absent.
In some embodiments, $L^1$ is $N(R^N)$, e.g., NH or NMe.
In some embodiments, $L^1$ is C(O).
In some embodiments, D is a group of formula (D1).
In some embodiments, D is a group of formula (D2).
In some embodiments, D is a group of formula (D3).
In some embodiments, D is a group of formula (D4).
In some embodiments, D is a group of formula (D5).
In some embodiments, D is a group of formula (D6).
In some embodiments, D is a group of formula (D7).
In some embodiments, $A^1$ is $C(O)R^1$, e.g., C(O)OH.
In some embodiments, $A^1$ is $S(O)_2R^1$.
In some embodiments, $A^1$ is $NHC(O)R^1$.
In some embodiments, $A^1$ is $NH(C_{1-3}$ alkylene)-$C(O)R^1$.
In some embodiments, wherein $A^1$ is $(C_{1-3}$ alkylene)-$C(O)R^1$, wherein the $(C_{1-3}$ alkylene) group of the $(C_{1-3}$ alkylene)-$C(O)R^1$ group forming $A^1$ is unsubstituted or substituted by 0, 1, 2, 3, 4 or 5 substituents each independently selected from halogen, $OR^{a1}$, $NR^{c1}R^{d1}$, $NR^{a1}(CO)(C_{1-6}$ alkyl), and $NR^{a1}(CO)O(C_{1-6}$ alkyl).
In some embodiments, $A^1$ is $(C_{1-3}$ alkylene)-$C(O)R^1$, wherein the $(C_{1-3}$ alkylene) group of the $(C_{1-3}$ alkylene)-$C(O)R^1$ group forming $A^1$ is substituted by $NR^{c1}R^{d1}$, $NR^{a1}(CO)(C_{1-6}$ alkyl), or $NR^{a1}(CO)O(C_{1-6}$ alkyl), e.g., $CH_2CH(NH_2)C(O)OH$.
In some embodiments, $A^1$ is CN.
In some embodiments, $A^1$ is $NO_2$.
In some embodiments, $A^1$ is 5-10 membered heteroaryl, 4-10 membered heterocycloalkyl, $(C_{1-3}$ alkylene)-5-10 membered heteroaryl, or $(C_{1-3}$ alkylene)-4-10 membered heterocycloalkyl that is unsubstituted or substituted by 0, 1, 2, 3, 4 or 5 substituents each independently selected from halogen, $OR^{a1}$, $SR^{a1}$, $C(O)OR^{a1}$, $NR^{c1}R^{d1}$ and $C(O)NR^{c1}R^{d1}$.
In some embodiments, $A^1$ is 5-10 membered heteroaryl, 4-10 membered heterocycloalkyl, $CH_2$(5-10 membered heteroaryl), or $CH_2$(4-10 membered heterocycloalkyl) that is unsubstituted or substituted by 1, 2, 3, 4 or 5 substituents each independently selected from halogen, $OR^{a1}$, $SR^{a1}$, $C(O)OR^{a1}$, $NR^{c1}R^{d1}$ and $C(O)NR^{c1}R^{d1}$.

In some embodiments, $A^2$ is $CR^2$.
In some embodiments, $R^2$ is H.
In some embodiments, $A^2$ is N.
In some embodiments, $A^3$ is $CR^3$.
In some embodiments, $R^3$ is H, $C_{1-6}$ alkyl or $C_{1-6}$ haloalkyl.
In some embodiments, $R^3$ is H, methyl or trifluoroethyl.
In some embodiments, $R^3$ is H.
In some embodiments, $A^3$ is N.
In some embodiments, $A^4$ is $CR^4$.
In some embodiments, $R^4$ is H.
In some embodiments, $A^4$ is N.
In some embodiments, $A^5$ is $CR^5$.
In some embodiments, $R^5$ is H.
In some embodiments, $A^5$ is N.
In some embodiments, $A^2$ is $CR^2$, $A^3$ is $CR^3$, $A^4$ is $CR^4$, and $A^5$ is $CR^5$.
In some embodiments, $A^2$ is $CR^2$, $A^3$ is $CR^3$, $A^4$ is $CR^4$, and $A^5$ is N.
In some embodiments, D is a group of formula (D4).
In some embodiments, $A^{D41}$ is CH.
In some embodiments, $A^{D41}$ is $C(C_{1-6}$ alkyl).
In some embodiments, $A^{D41}$ is N.
In some embodiments, $A^{D42}$ is NH.
In some embodiments, $A^{D42}$ is $NC_{1-6}$ alkyl, e.g., NMe.
In some embodiments, $A^{D42}$ is $CH_2$.
In some embodiments, D is a group of formula (D4) and m is 1.
In some embodiments, D is a group of formula (D4) and m is 2.
In some embodiments, D is a group of formula (D4) and m is 3.
In some embodiments, D is a group of formula (D5).
In some embodiments, D is a group of formula (D5) and m is 1.
In some embodiments, D is a group of formula (D5) and m is 2.
In some embodiments, D is a group of formula (D5) and m is 3.
In some embodiments, D is a group of formula (D6).
In some embodiments, D is a group of formula (D6) and m is 1.
In some embodiments, D is a group of formula (D6) and m is 2.
In some embodiments, D is a group of formula (D6) and m is 3.
In some embodiments, D is a group of formula (D7).
In some embodiments, $L^2$ is absent.
In some embodiments, $L^2$ is a group of formula O.
In some embodiments, $L^2$ is a group of formula $N(R^N)$.
In some embodiments, $L^2$ is a group of formula C(O).
In some embodiments, $L^3$ is absent.
In some embodiments, $L^3$ is a group of formula $CH_2$.
In some embodiments, $L^3$ is a group of formula $N(R^N)$.
In some embodiments, $L^3$ is a group of formula C(O).
In some embodiments, $L^3$ is a group of formula C≡C.
In some embodiments, $Cy^{D71}$ is $C_{6-10}$ aryl (e.g., phenyl).
In some embodiments, $Cy^{D71}$ is $C_{3-15}$ cycloalkyl (e.g., cyclopropyl).
In some embodiments, $Cy^{D71}$ is 5-10 membered heteroaryl (e.g., triazol, pyridine, dihydropyrido[2,1-b]pyrimidin-2-one, 3,4-dihydroquinolin-2-one, benzo[d]isothiazole-1,1-dioxide, 2H-indazole, pyrazole, dioxolane, pyrrole, indole, imidazole, benzimidazole).

In some embodiments, Cy$^{D71}$ is 4-10 membered heterocycloalkyl (e.g., piperidine, 1,3-dioxolane, indoline, pyrrolidine).

In some embodiments, the C$_{6-10}$ aryl, C$_{3-15}$ cycloalkyl, 5-10 membered heteroaryl, or 4-10 membered heterocycloalkyl forming Cy$^{D71}$ is unsubstituted.

In some embodiments, the C$_{6-10}$ aryl, C$_{3-15}$ cycloalkyl, 5-10 membered heteroaryl, or 4-10 membered heterocycloalkyl forming Cy$^{D71}$ is substituted.

In some embodiments, the C$_{6-10}$ aryl, C$_{3-15}$ cycloalkyl, 5-10 membered heteroaryl, or 4-10 membered heterocycloalkyl forming Cy$^{D71}$ is substituted by 1, 2, 3, 4 or 5 substituents each independently selected from unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, C(O)OR$^{a1}$, C(O)NR$^{c1}$R$^{d1}$, and C$_{1-6}$ alkyl or C$_{2-6}$ alkenyl that is substituted by 1, 2, or 3 substituents each independently selected from halogen, C$_{1-6}$ haloalkyl, CN, OR$^{a1}$, SR$^{a1}$, C(O)OR$^{a1}$, and NR$^{c1}$R$^{d1}$.

In some embodiments, the C$_{6-10}$ aryl, C$_{3-15}$ cycloalkyl, 5-10 membered heteroaryl, or 4-10 membered heterocycloalkyl forming Cy$^{D71}$ is substituted by 0, 1 or 2 substituents selected from Cy$^{D72}$, CH$_2$Cy$^{D72}$, OCy$^{D72}$, NHCy$^{D72}$, O—C$_{1-6}$ alkylene-Cy$^{D72}$, N(C$_{1-6}$ alkyl)Cy$^{D72}$, N(C(O)C$_{1-6}$ alkyl)Cy$^{D72}$, and C(O)NHCy$^{D72}$.

In some embodiments, Cy$^{D72}$ is C$_{6-10}$ aryl (e.g., phenyl).

In some embodiments, Cy$^{D72}$ is C$_{3-15}$ cycloalkyl (e.g., cyclopropyl).

In some embodiments, Cy$^{D72}$ is 5-10 membered heteroaryl (e.g., triazol, pyridine, dihydropyrido[2,1-b]pyrimidin-2-one, 3,4-dihydroquinolin-2-one, benzo[d]isothiazole-1,1-dioxide, 2H-indazole, pyrazole, dioxolane, pyrrole, indole, imidazole, benzimidazole).

In some embodiments, Cy$^{D72}$ is 4-10 membered heterocycloalkyl (e.g., piperidine, 1,3-dioxolane, indoline, pyrrolidine).

In some embodiments, the C$_{6-10}$ aryl, C$_{3-15}$ cycloalkyl, 5-10 membered heteroaryl, or 4-10 membered heterocycloalkyl forming Cy$^{D72}$ is unsubstituted.

In some embodiments, the C$_{6-10}$ aryl, C$_{3-15}$ cycloalkyl, 5-10 membered heteroaryl, or 4-10 membered heterocycloalkyl forming Cy$^{D72}$ is substituted.

In some embodiments, the C$_{6-10}$ aryl, C$_{3-15}$ cycloalkyl, 5-10 membered heteroaryl, or 4-10 membered heterocycloalkyl forming Cy$^{D72}$ is substituted by 0, 1 or 2 substituents selected from C$_{1-6}$ alkyl, C$_{2-6}$ alkenyl, C$_{2-6}$ alkynyl, C$_{3-15}$ cycloalkyl, halogen, C$_{1-6}$ haloalkyl, CN, OR$^{a1}$, SR$^{a1}$, NR$^{c1}$R$^{d1}$, C(O)OR$^{a1}$, C(O)NR$^{c1}$R$^{d1}$, and C$_{1-6}$ alkyl that is substituted by 1, 2, or 3 substituents each independently selected from halogen, C$_{1-6}$ haloalkyl, CN, OR$^{a1}$, SR$^{a1}$, C(O)OR$^{a1}$, and NR$^{c1}$R$^{d1}$.

In some embodiments, R$^1$ is H, C$_{1-6}$ alkyl, C$_{2-6}$ alkenyl, C$_{2-6}$ alkynyl, Cy$^{1A}$, OH, OC$_{1-6}$ alkyl, OCy$^{1A}$, O(C$_{1-3}$ alkylenyl)Cy$^{1A}$, NH$_2$, NHC$_{1-6}$ alkyl, N(C$_{1-6}$ alkyl)$_2$, NHCy$^{1A}$, NH(C$_{1-3}$ alkylenyl)Cy$^{1A}$, N(C$_{1-6}$ alkyl)Cy$^{1A}$, or N(C$_{1-6}$ alkyl)(C$_{1-3}$ alkylenyl)Cy$^{1A}$.

In some embodiments, R$^1$ is Cy$^{1A}$, OCy$^{1A}$, O(C$_{1-3}$ alkylenyl)Cy$^{1A}$, NHCy$^{1A}$ NH(C$_{1-3}$ alkylenyl)Cy$^{1A}$, N(C$_{1-6}$ alkyl)Cy$^{1A}$, or N(C$_{1-6}$ alkyl)(C$_{1-3}$ alkylenyl)Cy$^{1A}$.

In some embodiments, R$^1$ is NHCy$^{1A}$.

In some embodiments, R$^1$ is C$_{1-6}$ alkyl (e.g., methyl), C$_{2-6}$ alkenyl, C$_{2-6}$ alkynyl, Cy$^{1A}$OH, or OC$_{1-6}$ alkyl (e.g., OMe).

In some embodiments, R$^1$ is OH.

In some embodiments, R$^1$ is a group of one of the following formulae:

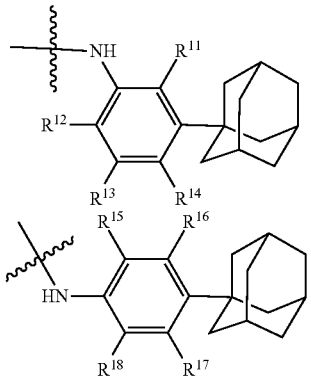

wherein:

R$^{11}$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, Cy$^{1B}$, OH, OCy$^{1B}$, O(C$_{1-3}$ alkylenyl)Cy$^{1B}$, NHCy$^{1B}$, NH(C$_{1-3}$ alkylenyl)Cy$^{1B}$, N(C$_{1-6}$ alkyl)Cy$^{1B}$, or N(C$_{1-6}$ alkyl)(C$_{1-3}$ alkylenyl)Cy$^{1B}$, or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

R$^{12}$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, Cy$^{1B}$, OH, OCy$^{1B}$, O(C$_{1-3}$ alkylenyl)Cy$^{1B}$, NHCy$^{1B}$, NH(C$_{1-3}$ alkylenyl)Cy$^{1B}$, N(C$_{1-6}$ alkyl)Cy$^{1B}$, or N(C$_{1-6}$ alkyl)(C$_{1-3}$ alkylenyl)Cy$^{1B}$, or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

R$^{13}$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, Cy$^{1B}$, OH, OCy$^{1B}$, O(C$_{1-3}$ alkylenyl)Cy$^{1B}$, NHCy$^{1B}$, NH(C$_{1-3}$ alkylenyl)Cy$^{1B}$, N(C$_{1-6}$ alkyl)Cy$^{1B}$, or N(C$_{1-6}$ alkyl)(C$_{1-3}$ alkylenyl)Cy$^{1B}$, or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

R$^{14}$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, Cy$^{1B}$, OH, OCy$^{1B}$, O(C$_{1-3}$ alkylenyl)Cy$^{1B}$, NHCy$^{1B}$, NH(C$_{1-3}$ alkylenyl)Cy$^{1B}$, N(C$_{1-6}$ alkyl)Cy$^{1B}$, or N(C$_{1-6}$ alkyl)(C$_{1-3}$ alkylenyl)Cy$^{1B}$, or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

R$^{15}$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, Cy$^{1B}$, OH, OCy$^{1B}$, O(C$_{1-3}$ alkylenyl)Cy$^{1B}$, NHCy$^{1B}$, NH(C$_{1-3}$ alkylenyl)Cy$^{1B}$, N(C$_{1-6}$ alkyl)Cy$^{1B}$, or N(C$_{1-6}$ alkyl)(C$_{1-3}$ alkylenyl)Cy$^{1B}$, or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

R$^{16}$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, Cy$^{1B}$, OH, OCy$^{1B}$, O(C$_{1-3}$ alkylenyl)Cy$^{1B}$, NHCy$^{1B}$, NH(C$_{1-3}$ alkylenyl)Cy$^{1B}$, N(C$_{1-6}$ alkyl)Cy$^{1B}$, or N(C$_{1-6}$ alkyl)(C$_{1-3}$ alkylenyl)Cy$^{1B}$, or C$_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{17}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{1B}$, OH, $OCy^{1B}$, $O(C_{1-3}$ alkylenyl)$Cy^{1B}$, $NHCy^{1B}$, $NH(C_{1-3}$ alkylenyl)$Cy^{1B}$, $N(C_{1-6}$ alkyl)$Cy^{1B}$, or $N(C_{1-6}$ alkyl)$(C_{1-3}$ alkylenyl)$Cy^{1B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$; and $R^{18}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{1B}$, OH, $OCy^{1B}$, $O(C_{1-3}$ alkylenyl)$Cy^{1B}$, $NHCy^{1B}$, $NH(C_{1-3}$ alkylenyl)$Cy^{1B}$, $N(C_{1-6}$ alkyl)$Cy^{1B}$, or $N(C_{1-6}$ alkyl)$(C_{1-3}$ alkylenyl)$Cy^{1B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$.

In some embodiments, $R^1$ is a group of one of the following formulae:

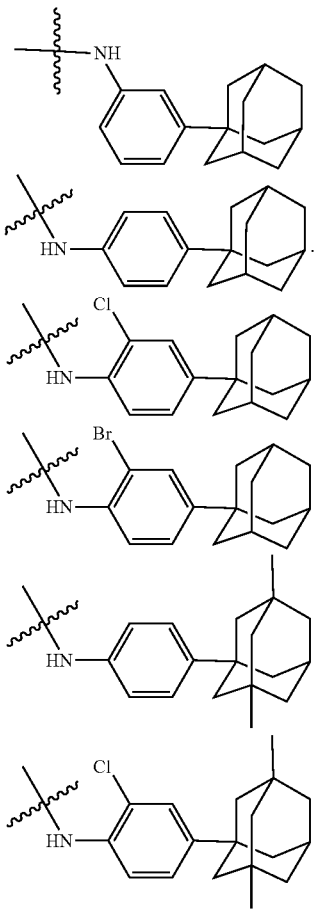

In some embodiments, $Cy^{1A}$ is $C_{6-10}$ aryl, e.g., phenyl that is unsubstituted or substituted by 0, 1 or 2 $Cy^{1B}$ and 0, 1, 2, 3, 4 or 5 substituents each independently selected from unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$ and $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$.

In some embodiments, $Cy^{1A}$ is $C_{6-10}$ aryl, e.g., phenyl that is unsubstituted or substituted by 1 $Cy^{1B}$ and 0, 1, 2, 3, 4 or 5 substituents each independently selected from unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$ and $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$.

In some embodiments, $Cy^{1A}$ is $C_{6-10}$ aryl, e.g., phenyl that is unsubstituted or substituted by 1 $Cy^{1B}$.

In some embodiments, each $Cy^{1B}$ is $C_{3-15}$ cycloalkyl (e.g., $C_{3-10}$ cycloalkyl, e.g., adamantyl, e.g., adamant-1-yl) that is unsubstituted or substituted by 1, 2, 3, 4 or 5 substituents each independently selected from unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$ and $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$.

In some embodiments, each $Cy^{1B}$ is unsubstituted $C_{3-15}$ cycloalkyl (e.g., $C_{3-10}$ cycloalkyl, e.g., adamantyl, e.g., adamant-1-yl).

In some embodiments, $Cy^{1A}$ is a group of one of the following formulae:

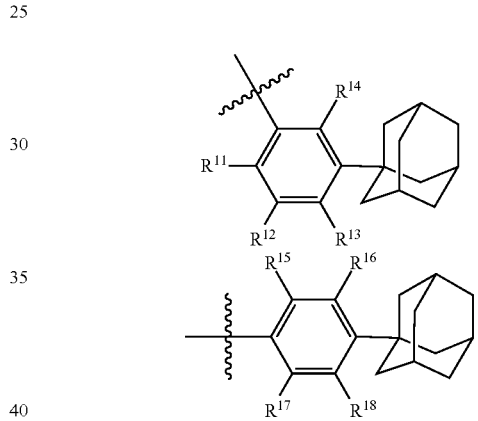

wherein $R^{11}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{1B}$, OH, $OCy^{1B}$, $O(C_{1-3}$ alkylenyl)$Cy^{1B}$, $NHCy^{1B}$, $NH(C_{1-3}$ alkylenyl)$Cy^{1B}$, $N(C_{1-6}$ alkyl)$Cy^{1B}$, or $N(C_{1-6}$ alkyl)$(C_{1-3}$ alkylenyl)$Cy^{1B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{12}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{1B}$, OH, $OCy^{1B}$, $O(C_{1-3}$ alkylenyl)$Cy^{1B}$, $NHCy^{1B}$, $NH(C_{1-3}$ alkylenyl)$Cy^{1B}$, $N(C_{1-6}$ alkyl)$Cy^{1B}$, or $N(C_{1-6}$ alkyl)$(C_{1-3}$ alkylenyl)$Cy^{1B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{13}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{1B}$, OH, $OCy^{1B}$, $O(C_{1-3}$ alkylenyl)$Cy^{1B}$, $NHCy^{1B}$, $NH(C_{1-3}$ alkylenyl)$Cy^{1B}$, $N(C_{1-6}$ alkyl)$Cy^{1B}$, or $N(C_{1-6}$ alkyl)$(C_{1-3}$ alkylenyl)$Cy^{1B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{14}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{1B}$, OH, $OCy^{1B}$, $O(C_{1-3}$ alkylenyl)$Cy^{1B}$, $NHCy^{1B}$, $NH(C_{1-3}$ alkylenyl)$Cy^{1B}$, $N(C_{1-6}$ alkyl)$Cy^{1B}$, or $N(C_{1-6}$ alkyl)($C_{1-3}$ alkylenyl)$Cy^{1B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{15}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{1B}$, OH, $OCy^{1B}$, $O(C_{1-3}$ alkylenyl)$Cy^{1B}$, $NHCy^{1B}$, $NH(C_{1-3}$ alkylenyl)$Cy^{1B}$, $N(C_{1-6}$ alkyl)$Cy^{1B}$, or $N(C_{1-6}$ alkyl)($C_{1-3}$ alkylenyl)$Cy^{1B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{16}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{1B}$, OH, $OCy^{1B}$, $O(C_{1-3}$ alkylenyl)$Cy^{1B}$, $NHCy^{1B}$, $NH(C_{1-3}$ alkylenyl)$Cy^{1B}$, $N(C_{1-6}$ alkyl)$Cy^{1B}$, or $N(C_{1-6}$ alkyl)($C_{1-3}$ alkylenyl)$Cy^{1B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{17}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{1B}$, OH, $OCy^{1B}$, $O(C_{1-3}$ alkylenyl)$Cy^{1B}$, $NHCy^{1B}$, $NH(C_{1-3}$ alkylenyl)$Cy^{1B}$, $N(C_{1-6}$ alkyl)$Cy^{1B}$, or $N(C_{1-6}$ alkyl)($C_{1-3}$ alkylenyl)$Cy^{1B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$; and $R^{18}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{1B}$, OH, $OCy^{1B}$, $O(C_{1-3}$ alkylenyl)$Cy^{1B}$, $NHCy^{1B}$, $NH(C_{1-3}$ alkylenyl)$Cy^{1B}$, $N(C_{1-6}$ alkyl)$Cy^{1B}$, or $N(C_{1-6}$ alkyl)($C_{1-3}$ alkylenyl)$Cy^{1B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$.

In some embodiments, $Cy^{1A}$ is a group of one of the following formulae:

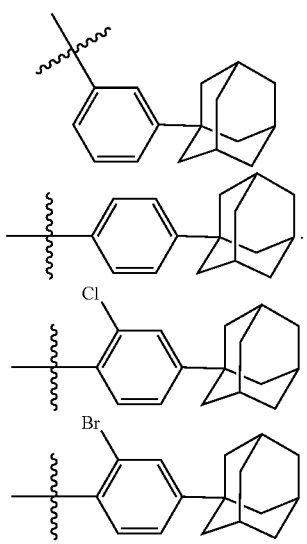

-continued

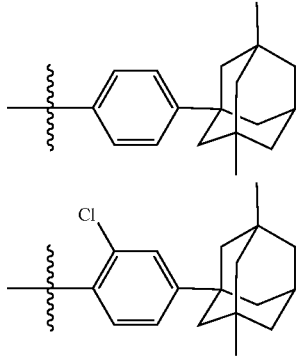

In some embodiments, $Cy^{1A}$ is $C_{3-15}$ cycloalkyl (e.g., $C_{3-10}$ cycloalkyl, e.g., adamantyl, e.g., adamant-1-yl) that is unsubstituted or substituted by 0, 1 or 2 $Cy^{1B}$ and 0, 1, 2, 3, 4 or 5 substituents each independently selected from unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$ and $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$. In some embodiments, $Cy^{1A}$ is $C_{3-15}$ cycloalkyl (e.g., $C_{3-10}$ cycloalkyl, e.g., adamantyl, e.g., adamant-1-yl) that is unsubstituted or substituted by 1, 2, 3, 4 or 5 substituents each independently selected from unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$ and $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$ In some embodiments, $Cy^{1A}$ is unsubstituted $C_{3-15}$ cycloalkyl (e.g., $C_{3-10}$ cycloalkyl, e.g., adamantyl, e.g., adamant-1-yl). In some embodiments, $Cy^{1A}$ is adamantyl, e.g., adamant-1-yl that is unsubstituted or substituted. In some embodiments, $Cy^{1A}$ is unsubstituted adamantyl, e.g., adamant-1-yl.

In some embodiments:

$R^7$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$ or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$; and $R^8$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$ or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$.

In some embodiments, $R^7$ is H and $R^8$ is H.
In some embodiments, $L^2$ is absent.
In some embodiments, $L^2$ is $N(R^N)$.
In some embodiments, $L^2$ is $C(O)$.
In some embodiments, $R^N$ is H.
In some embodiments, $A^6$ is $CR^6$.
In some embodiments, $R^6$ is H.
In some embodiments, $A^6$ is N.
In some embodiments, $A^7$ is $CR^7$.
In some embodiments, $R^7$ is H.
In some embodiments, $R^7$ is $Cy^{7A}$, $OCy^{7A}$, $O(C_{1-3}$ alkylenyl)$Cy^{7A}$, $C(O)OCy^{7A}$, $C(O)O(C_{1-3}$ alkylenyl)$Cy^{7A}$, $NHCy^{7A}$, $NH(C_{1-3}$ alkylenyl)$Cy^{7A}$, $N(C_{1-6}$ alkyl)$Cy^{7A}$, $N(C_{1-6}$ alkyl)($C_{1-3}$ alkylenyl)$Cy^{7A}$; $C(O)NHCy^{7A}$, $C(O)NH(C_{1-3}$ alkylenyl)$Cy^{7A}$, $C(O)N(C_{1-6}$ alkyl)$Cy^{7A}$, or $C(O)N(C_{1-6}$ alkyl)($C_{1-3}$ alkylenyl)$Cy^{7A}$.

In some embodiments, $R^7$ is $Cy^{7A}$, $OCy^{7A}$, $O(C_{1-3}$ alkylenyl)$Cy^{7A}$, $NHCy^{7A}$, $NH(C_{1-3}$ alkylenyl)$Cy^{7A}$, $N(C_{1-6}$ alkyl)$Cy^{7A}$, or $N(C_{1-6}$ alkyl)$(C_{1-3}$ alkylenyl)$Cy^{7A}$.

In some embodiments, $R^7$ is $N(C(O)C_{1-6}$ alkyl)$Cy^{7A}$.

In some embodiments, $R^7$ is $NHCy^{7A}$.

In some embodiments, $R^7$ is a group of one of the following formulae:

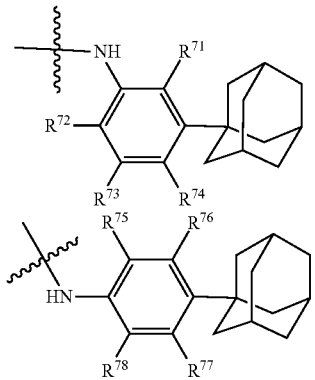

wherein:

$R^{71}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{7B}$, OH, $OCy^{7B}$, $O(C_{1-3}$ alkylenyl)$Cy^{7B}$, $NHCy^{7B}$, $NH(C_{1-3}$ alkylenyl)$Cy^{7B}$, $N(C_{1-6}$ alkyl)$Cy^{7B}$, or $N(C_{1-6}$ alkyl)$(C_{1-3}$ alkylenyl)$Cy^{7B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{72}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{7B}$, OH, $OCy^{7B}$, $O(C_{1-3}$ alkylenyl)$Cy^{7B}$, $NHCy^{7B}$, $NH(C_{1-3}$ alkylenyl)$Cy^{7B}$, $N(C_{1-6}$ alkyl)$Cy^{7B}$, or $N(C_{1-6}$ alkyl)$(C_{1-3}$ alkylenyl)$Cy^{7B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{73}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{7B}$, OH, $OCy^{7B}$, $O(C_{1-3}$ alkylenyl)$Cy^{7B}$, $NHCy^{7B}$, $NH(C_{1-3}$ alkylenyl)$Cy^{7B}$, $N(C_{1-6}$ alkyl)$Cy^{7B}$, or $N(C_{1-6}$ alkyl)$(C_{1-3}$ alkylenyl)$Cy^{7B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{74}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{7B}$, OH, $OCy^{7B}$, $O(C_{1-3}$ alkylenyl)$Cy^{7B}$, $NHCy^{7B}$, $NH(C_{1-3}$ alkylenyl)$Cy^{7B}$, $N(C_{1-6}$ alkyl)$Cy^{7B}$, or $N(C_{1-6}$ alkyl)$(C_{1-3}$ alkylenyl)$Cy^{7B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{75}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{7B}$, OH, $OCy^{7B}$, $O(C_{1-3}$ alkylenyl)$Cy^{7B}$, $NHCy^{7B}$, $NH(C_{1-3}$ alkylenyl)$Cy^{7B}$, $N(C_{1-6}$ alkyl)$Cy^{7B}$, or $N(C_{1-6}$ alkyl)$(C_{1-3}$ alkylenyl)$Cy^{7B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{76}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{7B}$, OH, $OCy^{7B}$, $O(C_{1-3}$ alkylenyl)$Cy^{7B}$, $NHCy^{7B}$, $NH(C_{1-3}$ alkylenyl)$Cy^{7B}$, $N(C_{1-6}$ alkyl)$Cy^{7B}$, or $N(C_{1-6}$ alkyl)$(C_{1-3}$ alkylenyl)$Cy^{7B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{77}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{7B}$, OH, $OCy^{7B}$, $O(C_{1-3}$ alkylenyl)$Cy^{7B}$, $NHCy^{7B}$, $NH(C_{1-3}$ alkylenyl)$Cy^{7B}$, $N(C_{1-6}$ alkyl)$Cy^{7B}$, or $N(C_{1-6}$ alkyl)$(C_{1-3}$ alkylenyl)$Cy^{7B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$; and $R^{78}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{7B}$, OH, $OCy^{7B}$, $O(C_{1-3}$ alkylenyl)$Cy^{7B}$, $NHCy^{7B}$, $NH(C_{1-3}$ alkylenyl)$Cy^{7B}$, $N(C_{1-6}$ alkyl)$Cy^{7B}$, or $N(C_{1-6}$ alkyl)$(C_{1-3}$ alkylenyl)$Cy^{7B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$.

In some embodiments, $R^7$ is a group of one of the following formulae:

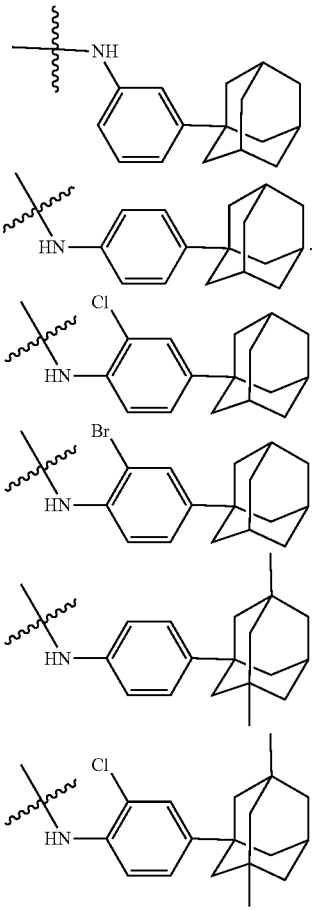

In some embodiments, $Cy^{7A}$ is $C_{6-10}$ aryl, e.g., phenyl that is unsubstituted or substituted by 0, 1 or 2 $Cy^{7B}$ and 0, 1, 2, 3, 4 or 5 substituents each independently selected from unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, and $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$.

In some embodiments, $Cy^{7A}$ is $C_{6-10}$ aryl, e.g., phenyl that is unsubstituted or substituted by 1 $Cy^{7B}$ and 0, 1, 2, 3, 4 or 5 substituents each independently selected from unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, and $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$.

In some embodiments, $Cy^{7A}$ is $C_{6-10}$ aryl, e.g., phenyl that is unsubstituted or substituted by 1 $Cy^{7B}$.

In some embodiments, each $Cy^{7B}$ is $C_{3-15}$ cycloalkyl (e.g., $C_{3-10}$ cycloalkyl, e.g., adamantyl, e.g., adamant-1-yl) that is unsubstituted or substituted by 1, 2, 3, 4 or 5 substituents each independently selected from unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, and $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$.

In some embodiments, each $Cy^{7B}$ is unsubstituted $C_{3-15}$ cycloalkyl (e.g., $C_{3-10}$ cycloalkyl, e.g., adamantyl, e.g., adamant-1-yl).

In some embodiments, $Cy^{7A}$ is a group of one of the following formulae:

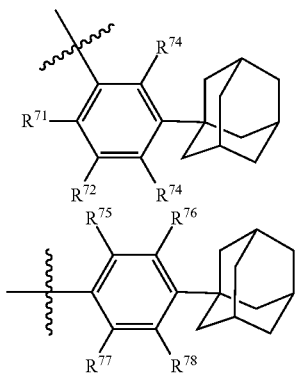

wherein:
$R^{71}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{8B}$, OH, $OCy^{8B}$, $O(C_{1-3}$ alkylenyl)$Cy^{8B}$, $NHCy^{8B}$, $NH(C_{1-3}$ alkylenyl)$Cy^{8B}$, $N(C_{1-6}$ alkyl)$Cy^{8B}$, or $N(C_{1-6}$ alkyl)$(C_{1-3}$ alkylenyl)$Cy^{8B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{72}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{8B}$, OH, $OCy^{8B}$, $O(C_{1-3}$ alkylenyl)$Cy^{8B}$, $NHCy^{8B}$, $NH(C_{1-3}$ alkylenyl)$Cy^{8B}$, $N(C_{1-6}$ alkyl)$Cy^{8B}$, or $N(C_{1-6}$ alkyl)$(C_{1-3}$ alkylenyl)$Cy^{8B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{73}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{8B}$, OH, $OCy^{8B}$, $O(C_{1-3}$ alkylenyl)$Cy^{8B}$, $NHCy^{8B}$, $NH(C_{1-3}$ alkylenyl)$Cy^{8B}$, $N(C_{1-6}$ alkyl)$Cy^{8B}$, or $N(C_{1-6}$ alkyl)$(C_{1-3}$ alkylenyl)$Cy^{8B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{74}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{8B}$, OH, $OCy^{8B}$, $O(C_{1-3}$ alkylenyl)$Cy^{8B}$, $NHCy^{8B}$, $NH(C_{1-3}$ alkylenyl)$Cy^{8B}$, $N(C_{1-6}$ alkyl)$Cy^{8B}$, or $N(C_{1-6}$ alkyl)$(C_{1-3}$ alkylenyl)$Cy^{8B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{75}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{8B}$, OH, $OCy^{8B}$, $O(C_{1-3}$ alkylenyl)$Cy^{8B}$, $NHCy^{8B}$, $NH(C_{1-3}$ alkylenyl)$Cy^{8B}$, $N(C_{1-6}$ alkyl)$Cy^{8B}$, or $N(C_{1-6}$ alkyl)$(C_{1-3}$ alkylenyl)$Cy^{8B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{76}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{8B}$, OH, $OCy^{8B}$, $O(C_{1-3}$ alkylenyl)$Cy^{8B}$, $NHCy^{8B}$, $NH(C_{1-3}$ alkylenyl)$Cy^{8B}$, $N(C_{1-6}$ alkyl)$Cy^{8B}$, or $N(C_{1-6}$ alkyl)$(C_{1-3}$ alkylenyl)$Cy^{8B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{77}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{8B}$, OH, $OCy^{8B}$, $O(C_{1-3}$ alkylenyl)$Cy^{8B}$, $NHCy^{8B}$, $NH(C_{1-3}$ alkylenyl)$Cy^{8B}$, $N(C_{1-6}$ alkyl)$Cy^{8B}$, or $N(C_{1-6}$ alkyl)$(C_{1-3}$ alkylenyl)$Cy^{8B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$; and $R^{78}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{8B}$, OH, $OCy^{8B}$, $O(C_{1-3}$ alkylenyl)$Cy^{8B}$, $NHCy^{8B}$, $NH(C_{1-3}$ alkylenyl)$Cy^{8B}$, $N(C_{1-6}$ alkyl)$Cy^{8B}$, or $N(C_{1-6}$ alkyl)$(C_{1-3}$ alkylenyl)$Cy^{8B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$.

In some embodiments, $Cy^{7A}$ is a group of one of the following formulae:

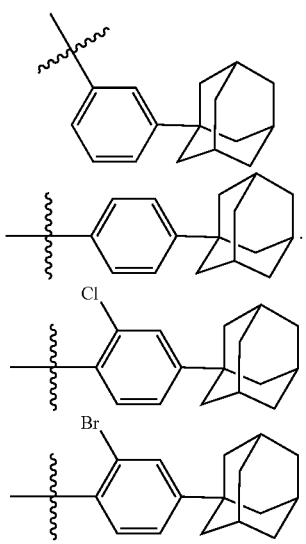

-continued

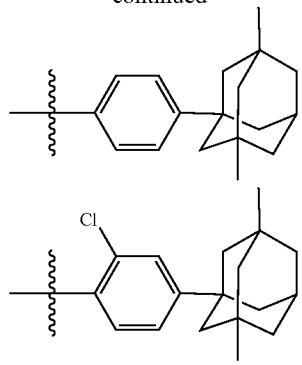

In some embodiments, Cy$^{7A}$ is C$_{3-15}$ cycloalkyl (e.g., C$_{3-10}$ cycloalkyl, e.g., adamantyl, e.g., adamant-1-yl) that is unsubstituted or substituted by 0, 1 or 2 Cy$^{7B}$ and 0, 1, 2, 3, 4 or 5 substituents each independently selected from unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$ and C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$. In some embodiments, Cy$^{7A}$ is C$_{3-15}$ cycloalkyl (e.g., C$_{3-10}$ cycloalkyl, e.g., adamantyl, e.g., adamant-1-yl) that is unsubstituted or substituted by 01, 2, 3, 4 or 5 substituents each independently selected from unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$ and C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$ In some embodiments, Cy$^{7A}$ is unsubstituted C$_{3-15}$ cycloalkyl (e.g., C$_{3-10}$ cycloalkyl, e.g., adamantyl, e.g., adamant-1-yl). In some embodiments, Cy$^{7A}$ is adamantyl, e.g., adamant-1-yl that is unsubstituted or substituted. In some embodiments, Cy$^{7A}$ is unsubstituted adamantyl, e.g., adamant-1-yl.

In some embodiments:
  R$^1$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$ or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$; and
  R$^8$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$ or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$.

In some embodiments, A$^1$ is CR$^1$, A$^2$ is CR$^2$, A$^3$ is CR$^3$, A$^4$ is CR$^4$, A$^5$ is CR$^5$, A$^6$ is CR$^6$, A$^8$ is CR$^8$, A$^9$ is CR$^9$, and A$^{10}$ is CR$^{10}$.

In some embodiments, A$^1$ is CR$^1$, A$^3$ is CR$^3$, A$^4$ is CR$^4$, A$^5$ is N, A$^6$ is CR$^6$, A$^8$ is CR$^8$, A$^9$ is CR$^9$, and A$^{10}$ is CR$^{10}$.

In some embodiments, A$^7$ is N.
In some embodiments, A$^8$ is CR$^8$.
In some embodiments, R$^8$ is H.
In some embodiments, R$^8$ is Cy$^{8A}$, OCy$^{8A}$, O(C$_{1-3}$ alkylenyl)Cy$^{8A}$, C(O)OCy$^{8A}$, C(O)O(C$_{1-3}$ alkylenyl)Cy$^{8A}$, NHCy$^{8A}$, NH(C$_{1-3}$ alkylenyl)Cy$^{8A}$, N(C$_{1-6}$ alkyl)Cy$^{8A}$, N(C$_{1-6}$ alkyl)(C$_{1-3}$ alkylenyl)Cy$^{8A}$, C(O)NHCy$^{8A}$, C(O)NH(C$_{1-3}$ alkylenyl)Cy$^{8A}$, C(O)N(C$_{1-6}$ alkyl)Cy$^{8A}$, or C(O)N(C$_{1-6}$ alkyl)(C$_{1-3}$ alkylenyl)Cy$^{8A}$.

In some embodiments, R$^8$ is Cy$^{8A}$, OCy$^{8A}$, O(C$_{1-3}$ alkylenyl)Cy$^{8A}$, NHCy$^{8A}$, NH(C$_{1-3}$ alkylenyl)Cy$^{8A}$, N(C$_{1-6}$ alkyl)Cy$^{8A}$, or N(C$_{1-6}$ alkyl)(C$_{1-3}$ alkylenyl)Cy$^{8A}$.

In some embodiments, R$^8$ is N(Cy$^{8A}$)$_2$.
In some embodiments, R$^8$ is N(C(O)C$_{1-6}$ alkyl)Cy$^{8A}$.
In some embodiments, R$^8$ is SO$_2$NHCy$^{8A}$.
In some embodiments, R$^8$ is C$_{1-3}$ alkylene-C(O)NHCy$^{8A}$.
In some embodiments, R$^8$ is NHCy$^{8A}$.
In some embodiments, R$^8$ is a group of one of the following formulae:

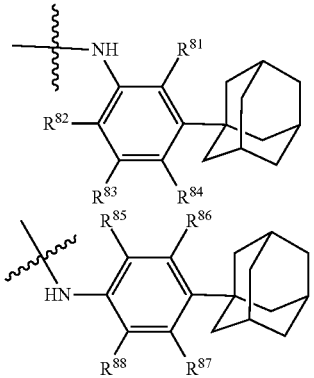

wherein:
R$^{81}$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, Cy$^{8A}$, OH, OCy$^{8A}$, O(C$_{1-3}$ alkylenyl)Cy$^{8A}$, NHCy$^{8A}$, NH(C$_{1-3}$ alkylenyl)Cy$^{8A}$, N(C$_{1-6}$ alkyl)Cy$^{8A}$, or N(C$_{1-6}$ alkyl)(C$_{1-3}$ alkylenyl)Cy$^{8A}$, or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

R$^{82}$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, Cy$^{8A}$, OH, OCy$^{8A}$, O(C$_{1-3}$ alkylenyl)Cy$^{8A}$, NHCy$^{8A}$, NH(C$_{1-3}$ alkylenyl)Cy$^{8A}$, N(C$_{1-6}$ alkyl)Cy$^{8A}$, or N(C$_{1-6}$ alkyl)(C$_{1-3}$ alkylenyl)Cy$^{8A}$, or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

R$^{83}$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, Cy$^{8A}$, OH, OCy$^{8A}$, O(C$_{1-3}$ alkylenyl)Cy$^{8A}$, NHCy$^{8A}$, NH(C$_{1-3}$ alkylenyl)Cy$^{8A}$, N(C$_{1-6}$ alkyl)Cy$^{8A}$, or N(C$_{1-6}$ alkyl)(C$_{1-3}$ alkylenyl)Cy$^{8A}$, or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

R$^{84}$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, Cy$^{8A}$, OH, OCy$^{8A}$, O(C$_{1-3}$ alkylenyl)Cy$^{8A}$, NHCy$^{8A}$, NH(C$_{1-3}$ alkylenyl)Cy$^{8A}$, N(C$_{1-6}$ alkyl)Cy$^{8A}$, or N(C$_{1-6}$ alkyl)(C$_{1-3}$ alkylenyl)Cy$^{8A}$, or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

R$^{85}$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, Cy$^{8A}$, OH, OCy$^{8A}$, O(C$_{1-3}$ alkylenyl)Cy$^{8A}$, NHCy$^{8A}$, NH(C$_{1-3}$ alkylenyl)Cy$^{8A}$, N(C$_{1-6}$ alkyl)Cy$^{8A}$, or N(C$_{1-6}$ alkyl)(C$_{1-3}$ alkylenyl)Cy$^{8A}$, or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

$R^{86}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{8A}$, OH, $OCy^{8A}$, $O(C_{1-3}$ alkylenyl)$Cy^{8A}$, $NHCy^{8A}$, $NH(C_{1-3}$ alkylenyl)$Cy^{8A}$, $N(C_{1-6}$ alkyl)$Cy^{8A}$, or $N(C_{1-6}$ alkyl)($C_{1-3}$ alkylenyl)$Cy^{8A}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{87}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{8A}$, OH, $OCy^{8A}$, $O(C_{1-3}$ alkylenyl)$Cy^{8A}$, $NHCy^{8A}$, $NH(C_{1-3}$ alkylenyl)$Cy^{8A}$, $N(C_{1-6}$ alkyl)$Cy^{8A}$, or $N(C_{1-6}$ alkyl)($C_{1-3}$ alkylenyl)$Cy^{8A}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$; and $R^{88}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{8A}$, OH, $OCy^{8A}$, $O(C_{1-3}$ alkylenyl)$Cy^{8A}$, $NHCy^{8A}$, $NH(C_{1-3}$ alkylenyl)$Cy^{8A}$, $N(C_{1-6}$ alkyl)$Cy^{8A}$, or $N(C_{1-6}$ alkyl)($C_{1-3}$ alkylenyl)$Cy^{8A}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$.

In some embodiments, $R^8$ is a group of one of the following formulae:

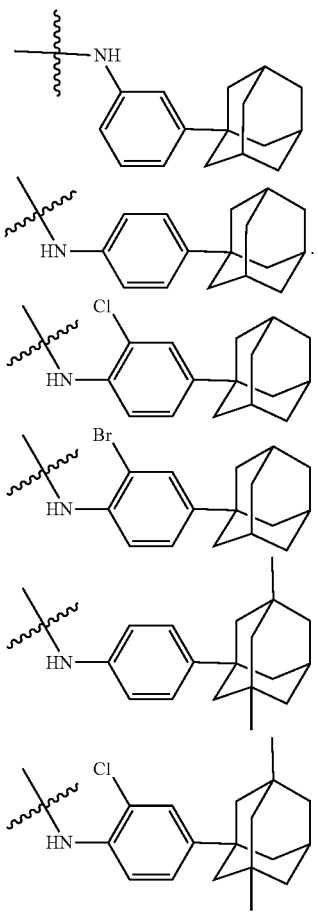

In some embodiments, $Cy^{8A}$ is $C_{6-10}$ aryl, e.g., phenyl that is unsubstituted or substituted by 0, 1 or 2 $Cy^{8B}$ and 0, 1, 2, 3, 4 or 5 substituents each independently selected from unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$ and $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$.

In some embodiments, $Cy^{8A}$ is $C_{6-10}$ aryl, e.g., phenyl that is unsubstituted or substituted by 1 $Cy^{8B}$ and 0, 1, 2, 3, 4 or 5 substituents each independently selected from unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, and $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$.

In some embodiments, $Cy^{8A}$ is $C_{6-10}$ aryl, e.g., phenyl that is unsubstituted or substituted by 1 $Cy^{8B}$.

In some embodiments, each $Cy^{8B}$ is $C_{3-15}$ cycloalkyl (e.g., $C_{3-10}$ cycloalkyl, e.g., adamantyl, e.g., adamant-1-yl) that is unsubstituted or substituted by 1, 2, 3, 4 or 5 substituents each independently selected from unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$ and $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$.

In some embodiments, each $Cy^{8B}$ is unsubstituted $C_{3-15}$ cycloalkyl (e.g., $C_{3-10}$ cycloalkyl, e.g., adamantyl, e.g., adamant-1-yl).

In some embodiments, $Cy^{8A}$ is a group of one of the following formulae:

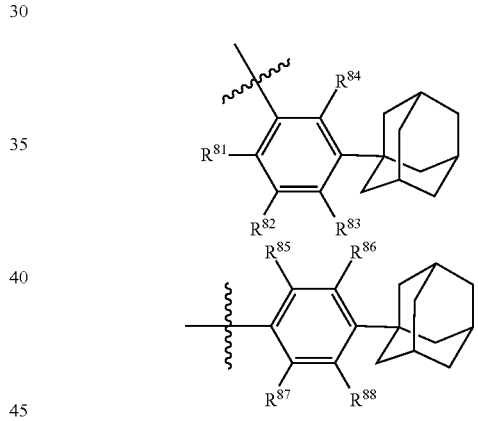

wherein:

$R^{81}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{8A}$, OH, $OCy^{8A}$, $O(C_{1-3}$ alkylenyl)$Cy^{8A}$, $NHCy^{8A}$, $NH(C_{1-3}$ alkylenyl)$Cy^{8A}$, $N(C_{1-6}$ alkyl)$Cy^{8A}$, or $N(C_{1-6}$ alkyl)($C_{1-3}$ alkylenyl)$Cy^{8A}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{82}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{8A}$, OH, $OCy^{8A}$, $O(C_{1-3}$ alkylenyl)$Cy^{8A}$, $NHCy^{8A}$, $NH(C_{1-3}$ alkylenyl)$Cy^{8A}$, $N(C_{1-6}$ alkyl)$Cy^{8A}$, or $N(C_{1-6}$ alkyl)($C_{1-3}$ alkylenyl)$Cy^{8A}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{83}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{8A}$, OH, $OCy^{8A}$, $O(C_{1-3}$ alkylenyl)$Cy^{8A}$, $NHCy^{8A}$, $NH(C_{1-3}$ alkylenyl)$Cy^{8A}$, $N(C_{1-6}$ alkyl)$Cy^{8A}$, or N(C$_{1-6}$ alkyl)(C$_{1-3}$ alkylenyl)Cy$^{8A}$, or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

R$^{84}$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, Cy$^{8A}$, OH, OCy$^{8A}$, O(C$_{1-3}$ alkylenyl)Cy$^{8A}$, NHCy$^{8A}$, NH(C$_{1-3}$ alkylenyl)Cy$^{8A}$, N(C$_{1-6}$ alkyl)Cy$^{8A}$, or N(C$_{1-6}$ alkyl)(C$_{1-3}$ alkylenyl)Cy$^{8A}$, or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

R$^{85}$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, Cy$^{8A}$, OH, OCy$^{8A}$, O(C$_{1-3}$ alkylenyl)Cy$^{8A}$, NHCy$^{8A}$, NH(C$_{1-3}$ alkylenyl)Cy$^{8A}$, N(C$_{1-6}$ alkyl)Cy$^{8A}$, or N(C$_{1-6}$ alkyl)(C$_{1-3}$ alkylenyl)Cy$^{8A}$, or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

R$^{86}$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, Cy$^{8A}$, OH, OCy$^{8A}$, O(C$_{1-3}$ alkylenyl)Cy$^{8A}$, NHCy$^{8A}$, NH(C$_{1-3}$ alkylenyl)Cy$^{8A}$, N(C$_{1-6}$ alkyl)Cy$^{8A}$, or N(C$_{1-6}$ alkyl)(C$_{1-3}$ alkylenyl)Cy$^{8A}$, or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

R$^{87}$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, Cy$^{8A}$, OH, OCy$^{8A}$, O(C$_{1-3}$ alkylenyl)Cy$^{8A}$, NHCy$^{8A}$, NH(C$_{1-3}$ alkylenyl)Cy$^{8A}$, N(C$_{1-6}$ alkyl)Cy$^{8A}$, or N(C$_{1-6}$ alkyl)(C$_{1-3}$ alkylenyl)Cy$^{8A}$, or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$; and R$^{88}$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, Cy$^{8A}$, OH, OCy$^{8A}$, O(C$_{1-3}$ alkylenyl)Cy$^{8A}$, NHCy$^{8A}$, NH(C$_{1-3}$ alkylenyl)Cy$^{8A}$, N(C$_{1-6}$ alkyl)Cy$^{8A}$, or N(C$_{1-6}$ alkyl)(C$_{1-3}$ alkylenyl)Cy$^{8A}$, or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$.

In some embodiments, Cy$^{8A}$ is a group of one of the following formulae:

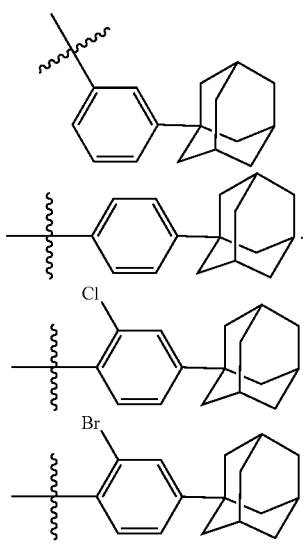

-continued

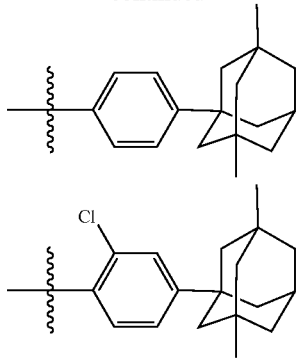

In some embodiments, Cy$^{8A}$ is C$_{3-15}$ cycloalkyl (e.g., C$_{3-10}$ cycloalkyl, e.g., adamantyl, e.g., adamant-1-yl) that is unsubstituted or substituted by 0, 1 or 2 Cy$^{8B}$ and 0, 1, 2, 3, 4 or 5 substituents each independently selected from unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$ and C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$. In some embodiments, Cy$^{8A}$ is C$_{3-15}$ cycloalkyl (e.g., C$_{3-10}$ cycloalkyl, e.g., adamantyl, e.g., adamant-1-yl) that is unsubstituted or substituted by 01, 2, 3, 4 or 5 substituents each independently selected from unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$ and C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$ In some embodiments, Cy$^{8A}$ is unsubstituted C$_{3-15}$ cycloalkyl (e.g., C$_{3-10}$ cycloalkyl, e.g., adamantyl, e.g., adamant-1-yl). In some embodiments, Cy$^{8A}$ is adamantyl, e.g., adamant-1-yl that is unsubstituted or substituted. In some embodiments, Cy$^{8A}$ is unsubstituted adamantyl, e.g., adamant-1-yl.

In some embodiments:
R$^1$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$ or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$; and R$^7$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$ or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$.

In some embodiments, A$^1$ is CR$^1$, A$^2$ is CR$^2$, A$^3$ is CR$^3$, A$^4$ is CR$^4$, A$^5$ is CR$^5$, A$^6$ is CR$^6$, A$^7$ is CR$^7$, A$^8$ is CR$^8$, A$^9$ is CR$^9$, and A$^{10}$ is CR$^{10}$.

In some embodiments, A$^1$ is CR$^1$, A$^3$ is CR$^3$, A$^4$ is CR$^4$, A$^5$ is N, A$^6$ is CR$^6$, A$^7$ is CR$^7$, A$^8$ is CR$^8$, A$^9$ is CR$^9$, and A$^{10}$ is CR$^{10}$.

In some embodiments, A$^8$ is N.
In some embodiments, A$^9$ is CR$^9$.
In some embodiments, R$^9$ is H, C$_{1-6}$ alkyl or C$_{1-6}$ haloalkyl.
In some embodiments, R$^9$ is H, methyl or trifluoroethyl.
In some embodiments, R$^9$ is H.
In some embodiments, A$^9$ is N.
In some embodiments, A$^{10}$ is CR$^{10}$.
In some embodiments, R$^{10}$ is H.
In some embodiments, A$^{10}$ is N.

In some embodiments, the compound is a compound of one of the following formulae (I-1) to (I-60):
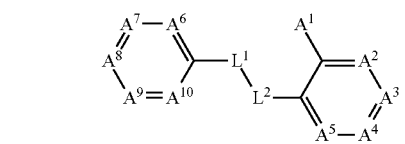
(I-1)
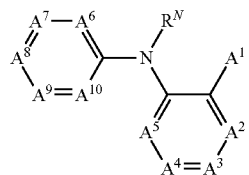
(I-2)
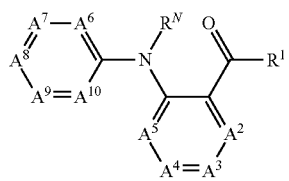
(I-3)
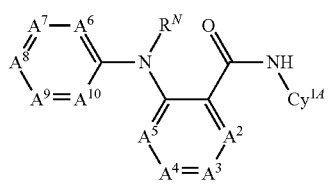
(I-4)
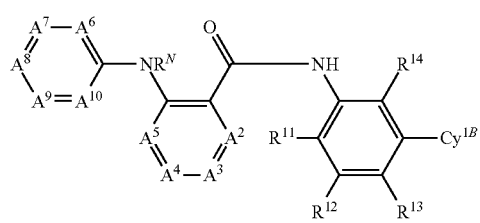
(I-5)
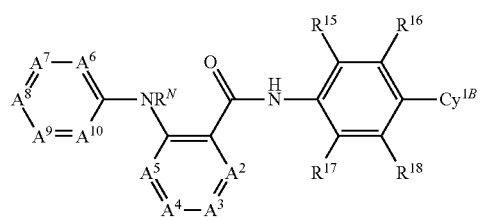
(I-6)
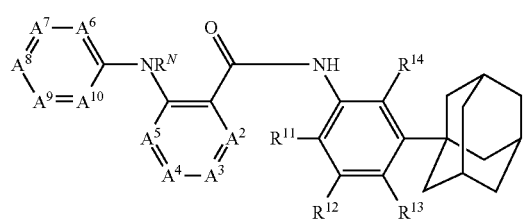
(I-7)
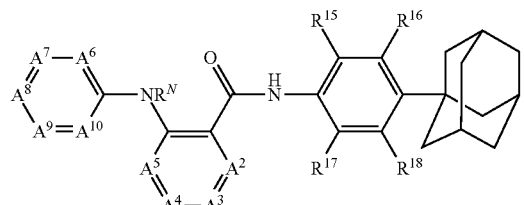
(I-8)
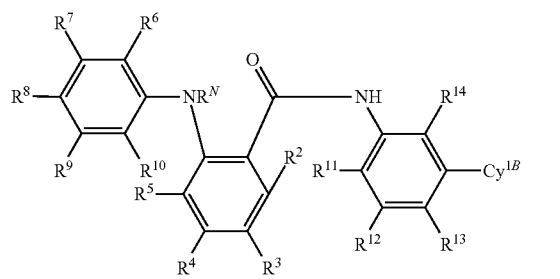
(I-9)
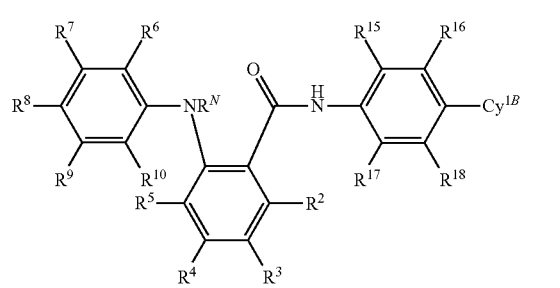
(I-10)
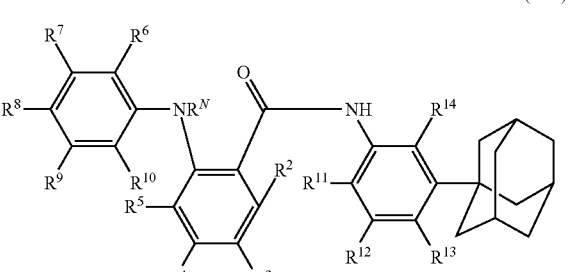
(I-11)
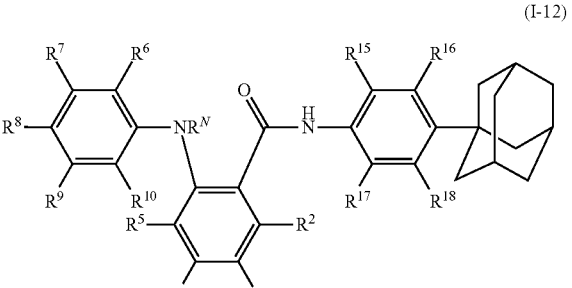
(I-12)
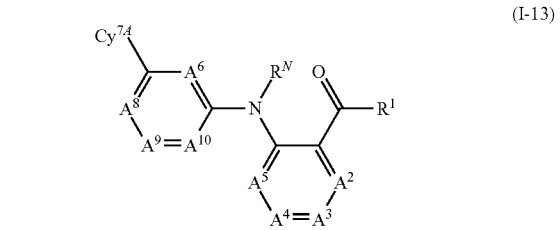
(I-13)

(I-14) 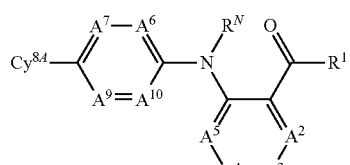
(I-15) 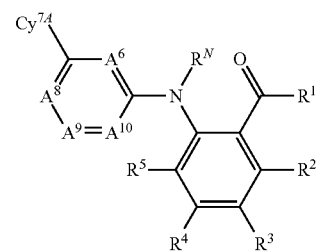
(I-16) 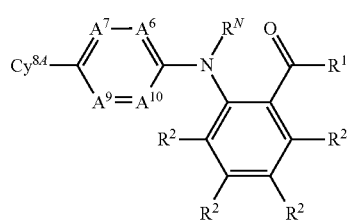
(I-17) 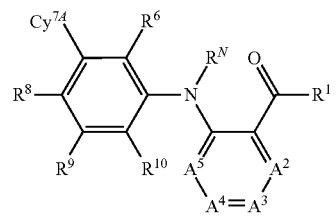
(I-18) 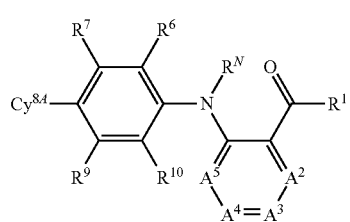
(I-19) 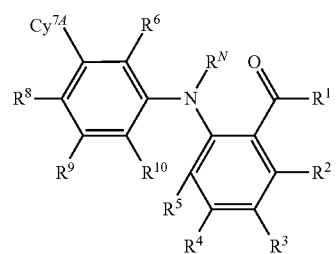
(I-20) 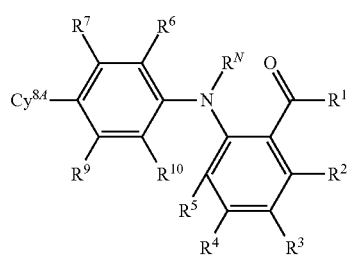
(I-21) 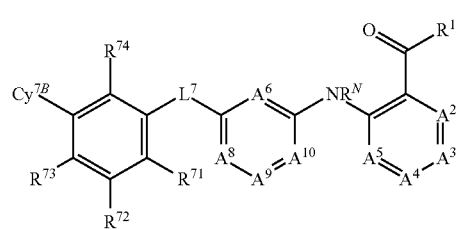
(I-22) 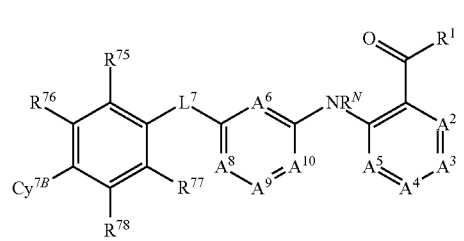
(I-23) 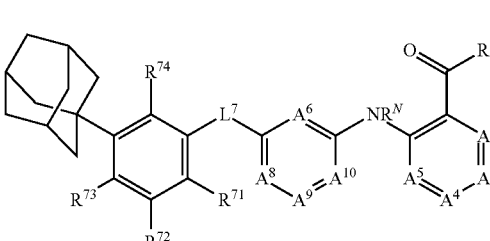
(I-24) 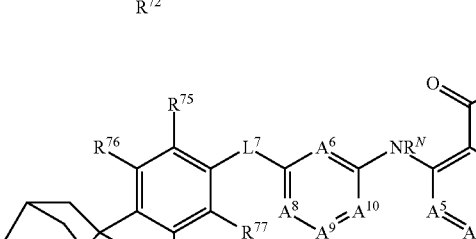
(I-25) 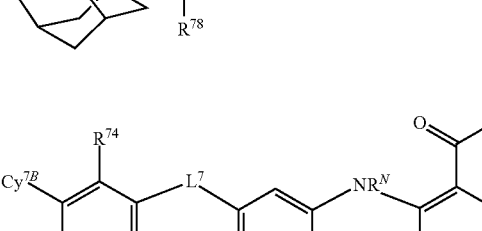
(I-26) 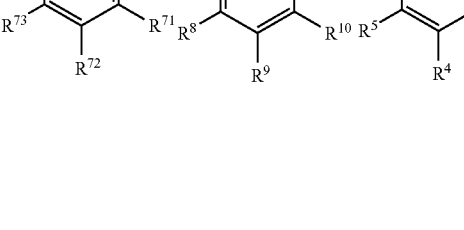

(I-27)
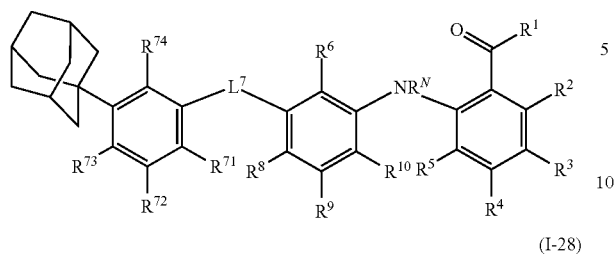
(I-28)
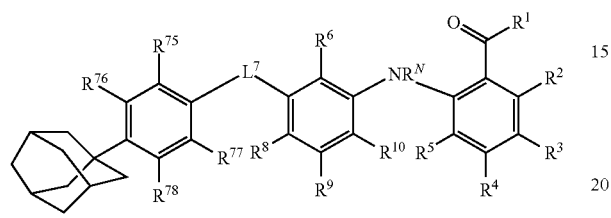
(I-29)
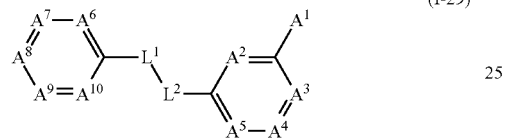
(I-30)
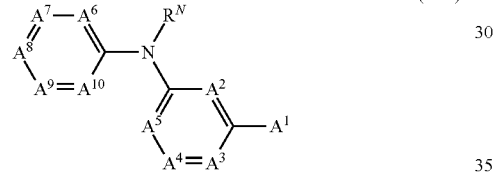
(I-31)
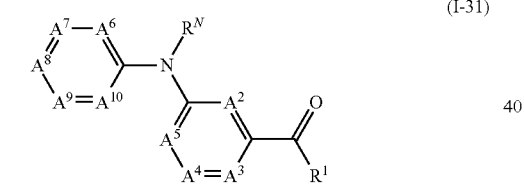
(I-32)
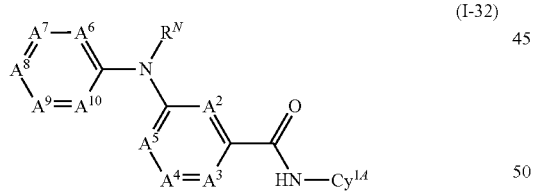
(I-33)
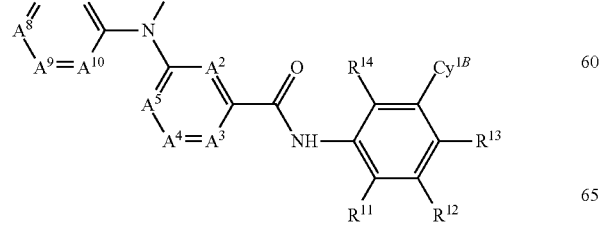
(I-34)
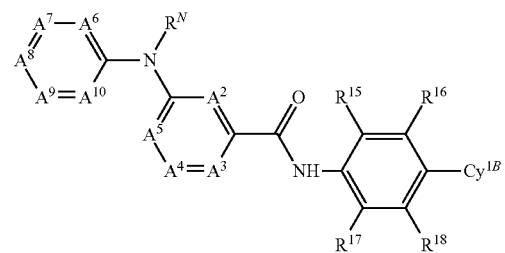
(I-35)
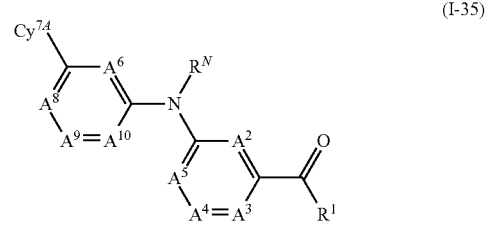
(I-36)
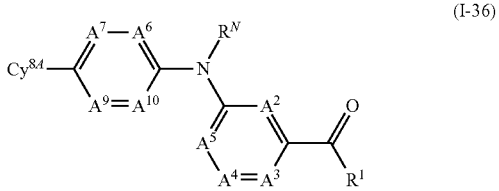
(I-37)
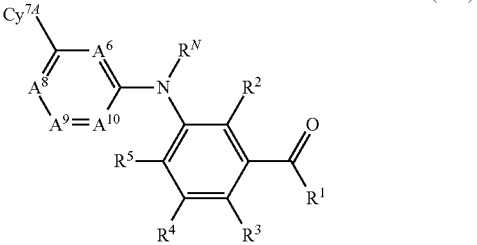
(I-38)
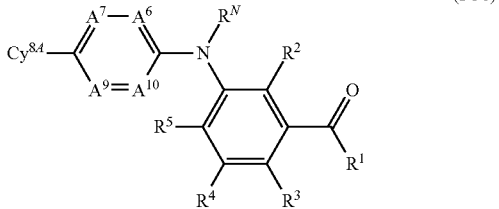
(I-39)
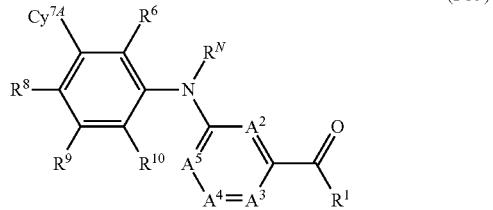
(I-40)
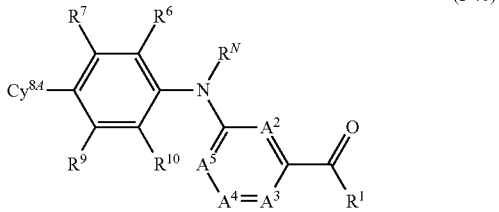

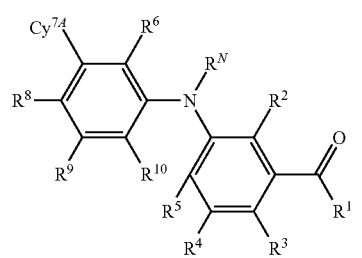
(I-41)
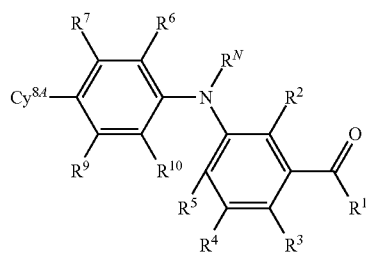
(I-42)
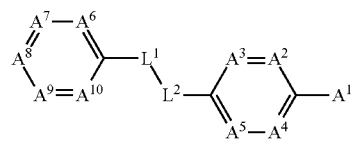
(I-43)
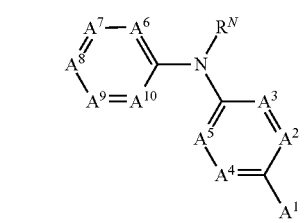
(I-44)
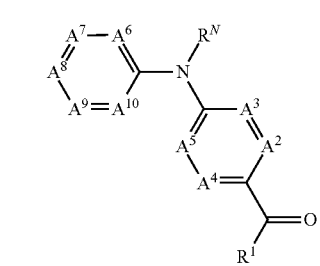
(I-45)
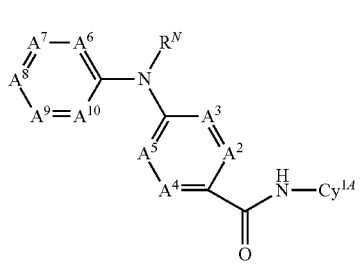
(I-46)
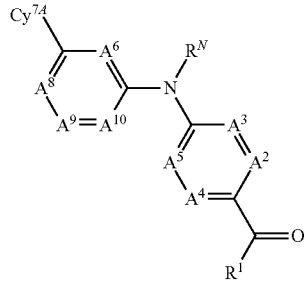
(I-47)
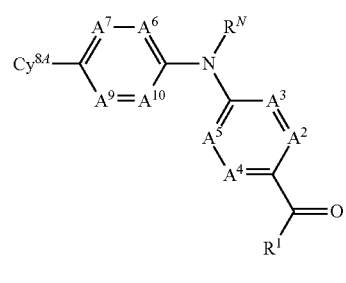
(I-48)
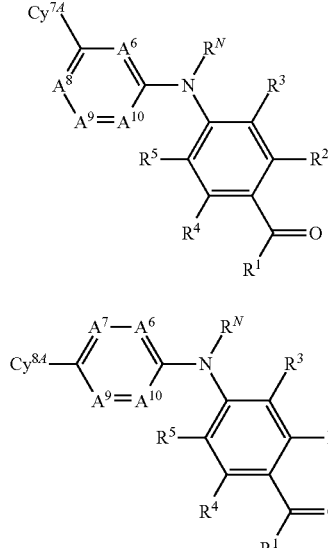
(I-49)
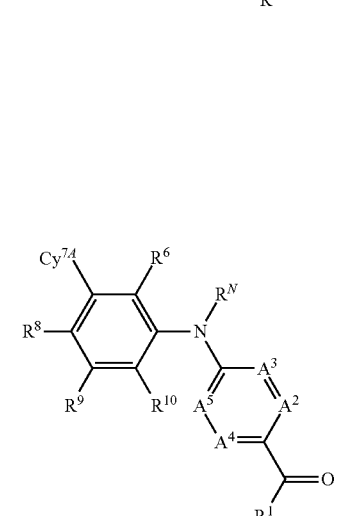
(I-50)
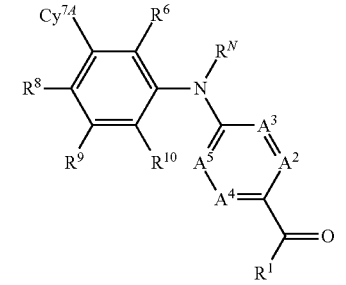
(I-51)

wherein:

R$^1$, R$^2$, R$^3$, R$^4$, R$^5$, R$^6$, R$^7$, R$^8$, R$^9$, R$^{10}$, R$^N$, A$^1$, A$^2$, A$^3$, A$^4$, A$^5$, A$^6$, A$^7$, A$^8$, A$^9$, A$^{10}$, Cy$^{1A}$, Cy$^{1B}$, Cy$^{7A}$, Cy$^{7B}$, Cy$^{8A}$, Cy$^{8B}$, L$^1$ and L$^2$, are as defined above for the compounds of formula (I), or any of the embodiments thereof;

L$^7$ is absent, O, NH or N(C$_{1-6}$ alkyl);

L$^8$ is absent, O, NH or N(C$_{1-6}$ alkyl);

R$^{11}$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, Cy$^{1B}$, OH, OCy$^{1B}$, O(C$_{1-3}$ alkylenyl)Cy$^{1B}$, NHCy$^{1B}$, NH(C$_{1-3}$ alkylenyl)Cy$^{1B}$, N(C$_{1-6}$ alkyl)Cy$^{1B}$, or N(C$_{1-6}$ alkyl)(C$_{1-3}$ alkylenyl)Cy$^{1B}$, or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

R$^{12}$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, Cy$^{1B}$, OH, OCy$^{1B}$, O(C$_{1-3}$ alkylenyl)Cy$^{1B}$, NHCy$^{1B}$, NH(C$_{1-3}$ alkylenyl)Cy$^{1B}$, N(C$_{1-6}$ alkyl)Cy$^{1B}$, or N(C$_{1-6}$ alkyl)(C$_{1-3}$ alkylenyl)Cy$^{1B}$, or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

R$^{13}$ is H, unsubstituted C$_{1-6}$ alkyl, C$_{2-6}$ alkenyl, C$_{2-6}$ alkynyl, halogen, C$_{1-6}$ haloalkyl, CN, OR$^{a1}$, SR$^{a1}$, NR$^{c1}$R$^{d1}$, Cy$^{1B}$, OH, OCy$^{1B}$, O(C$_{1-3}$ alkylenyl)Cy$^{1B}$, NHCy$^{1B}$, NH(C$_{1-3}$ alkylenyl)Cy$^{1B}$, N(C$_{1-6}$ alkyl)Cy$^{1B}$, or N(C$_{1-6}$ alkyl)(C$_{1-3}$ alkylenyl)Cy$^{1B}$, or C$_{1-6}$ alkyl that is substituted by 1, 2, or 3 substituents each independently selected from halogen, C$_{1-6}$ haloalkyl, CN, OR$^{a1}$, SR$^{a1}$, and NR$^{c1}$R$^{d1}$;

$R^{14}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{1B}$, OH, $OCy^{1B}$, $O(C_{1-3}$ alkylenyl)$Cy^{1B}$, $NHCy^{1B}$, $NH(C_{1-3}$ alkylenyl)$Cy^{1B}$, $N(C_{1-6}$ alkyl)$Cy^{1B}$, or $N(C_{1-6}$ alkyl)$(C_{1-3}$ alkylenyl)$Cy^{1B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{15}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{1B}$, OH, $OCy^{1B}$, $O(C_{1-3}$ alkylenyl)$Cy^{1B}$, $NHCy^{1B}$, $NH(C_{1-3}$ alkylenyl)$Cy^{1B}$, $N(C_{1-6}$ alkyl)$Cy^{1B}$, or $N(C_{1-6}$ alkyl)$(C_{1-3}$ alkylenyl)$Cy^{1B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{16}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{1B}$, OH, $OCy^{1B}$, $O(C_{1-3}$ alkylenyl)$Cy^{1B}$, $NHCy^{1B}$, $NH(C_{1-3}$ alkylenyl)$Cy^{1B}$, $N(C_{1-6}$ alkyl)$Cy^{1B}$, or $N(C_{1-6}$ alkyl)$(C_{1-3}$ alkylenyl)$Cy^{1B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{17}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{1B}$, OH, $OCy^{1B}$, $O(C_{1-3}$ alkylenyl)$Cy^{1B}$, $NHCy^{1B}$, $NH(C_{1-3}$ alkylenyl)$Cy^{1B}$, $N(C_{1-6}$ alkyl)$Cy^{1B}$, or $N(C_{1-6}$ alkyl)$(C_{1-3}$ alkylenyl)$Cy^{1B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{18}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{1B}$, OH, $OCy^{1B}$, $O(C_{1-3}$ alkylenyl)$Cy^{1B}$, $NHCy^{1B}$, $NH(C_{1-3}$ alkylenyl)$Cy^{1B}$, $N(C_{1-6}$ alkyl)$Cy^{1B}$, or $N(C_{1-6}$ alkyl)$(C_{1-3}$ alkylenyl)$Cy^{1B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{71}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{7B}$, OH, $OCy^{7B}$, $O(C_{1-3}$ alkylenyl)$Cy^{7B}$, $NHCy^{7B}$, $NH(C_{1-3}$ alkylenyl)$Cy^{7B}$, $N(C_{1-6}$ alkyl)$Cy^{7B}$, or $N(C_{1-6}$ alkyl)$(C_{1-3}$ alkylenyl)$Cy^{7B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{72}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{7B}$, OH, $OCy^{7B}$, $O(C_{1-3}$ alkylenyl)$Cy^{7B}$, $NHCy^{7B}$, $NH(C_{1-3}$ alkylenyl)$Cy^{7B}$, $N(C_{1-6}$ alkyl)$Cy^{7B}$, or $N(C_{1-6}$ alkyl)$(C_{1-3}$ alkylenyl)$Cy^{7B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{73}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{7B}$, OH, $OCy^{7B}$, $O(C_{1-3}$ alkylenyl)$Cy^{7B}$, $NHCy^{7B}$, $NH(C_{1-3}$ alkylenyl)$Cy^{7B}$, $N(C_{1-6}$ alkyl)$Cy^{7B}$, or $N(C_{1-6}$ alkyl)$(C_{1-3}$ alkylenyl)$Cy^{7B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{74}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{7B}$, OH, $OCy^{7B}$, $O(C_{1-3}$ alkylenyl)$Cy^{7B}$, $NHCy^{7B}$, $NH(C_{1-3}$ alkylenyl)$Cy^{7B}$, $N(C_{1-6}$ alkyl)$Cy^{7B}$, or $N(C_{1-6}$ alkyl)$(C_{1-3}$ alkylenyl)$Cy^{7B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{75}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{7B}$, OH, $OCy^{7B}$, $O(C_{1-3}$ alkylenyl)$Cy^{7B}$, $NHCy^{7B}$, $NH(C_{1-3}$ alkylenyl)$Cy^{7B}$, $N(C_{1-6}$ alkyl)$Cy^{7B}$, or $N(C_{1-6}$ alkyl)$(C_{1-3}$ alkylenyl)$Cy^{7B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{76}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{7B}$, OH, $OCy^{7B}$, $O(C_{1-3}$ alkylenyl)$Cy^{7B}$, $NHCy^{7B}$, $NH(C_{1-3}$ alkylenyl)$Cy^{7B}$, $N(C_{1-6}$ alkyl)$Cy^{7B}$, or $N(C_{1-6}$ alkyl)$(C_{1-3}$ alkylenyl)$Cy^{7B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{77}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{7B}$, OH, $OCy^{7B}$, $O(C_{1-3}$ alkylenyl)$Cy^{7B}$, $NHCy^{7B}$, $NH(C_{1-3}$ alkylenyl)$Cy^{7B}$, $N(C_{1-6}$ alkyl)$Cy^{7B}$, or $N(C_{1-6}$ alkyl)$(C_{1-3}$ alkylenyl)$Cy^{7B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$; and $R^{78}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{7B}$, OH, $OCy^{7B}$, $O(C_{1-3}$ alkylenyl)$Cy^{7B}$, $NHCy^{7B}$, $NH(C_{1-3}$ alkylenyl)$Cy^{7B}$, $N(C_{1-6}$ alkyl)$Cy^{7B}$, or $N(C_{1-6}$ alkyl)$(C_{1-3}$ alkylenyl)$Cy^{7B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{81}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{8B}$, OH, $OCy^{8B}$, $O(C_{1-3}$ alkylenyl)$Cy^{8B}$, $NHCy^{8B}$, $NH(C_{1-3}$ alkylenyl)$Cy^{8B}$, $N(C_{1-6}$ alkyl)$Cy^{8B}$, or $N(C_{1-6}$ alkyl)$(C_{1-3}$ alkylenyl)$Cy^{8B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{82}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{8B}$, OH, $OCy^{8B}$, $O(C_{1-3}$ alkylenyl)$Cy^{8B}$, $NHCy^{8B}$, $NH(C_{1-3}$ alkylenyl)$Cy^{8B}$, $N(C_{1-6}$ alkyl)$Cy^{8B}$, or $N(C_{1-6}$ alkyl)$(C_{1-3}$ alkylenyl)$Cy^{8B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{83}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{8B}$, OH, $OCy^{8B}$, $O(C_{1-3}$ alkylenyl)$Cy^{8B}$, $NHCy^{8B}$, $NH(C_{1-3}$ alkylenyl)$Cy^{8B}$, $N(C_{1-6}$ alkyl)$Cy^{8B}$, or $N(C_{1-6}$ alkyl)$(C_{1-3}$ alkylenyl)$Cy^{8B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{84}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{8B}$, OH, $OCy^{8B}$, $O(C_{1-3}$ alkylenyl)$Cy^{8B}$, $NHCy^{8B}$, $NH(C_{1-3}$ alkylenyl)$Cy^{8B}$, $N(C_{1-6}$ alkyl)$Cy^{8B}$, or $N(C_{1-6}$ alkyl)$(C_{1-3}$ alkylenyl)$Cy^{8B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{85}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{8B}$, OH, $OCy^{8B}$, $O(C_{1-3}$ alkylenyl)$Cy^{8B}$, $NHCy^{8B}$, $NH(C_{1-3}$ alkylenyl)$Cy^{8B}$, $N(C_{1-6}$ alkyl)$Cy^{8B}$, or $N(C_{1-6}$ alkyl)$(C_{1-3}$ alkylenyl)$Cy^{8B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{86}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{8B}$, OH, $OCy^{8B}$, $O(C_{1-3}$ alkylenyl)$Cy^{8B}$, $NHCy^{8B}$, $NH(C_{1-3}$ alkylenyl)$Cy^{8B}$, $N(C_{1-6}$ alkyl)$Cy^{8B}$, or $N(C_{1-6}$ alkyl)$(C_{1-3}$ alkylenyl)$Cy^{8B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$;

$R^{87}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{8B}$, OH, $OCy^{8B}$, $O(C_{1-3}$ alkylenyl)$Cy^{8B}$, $NHCy^{8B}$, $NH(C_{1-3}$ alkylenyl)$Cy^{8B}$, $N(C_{1-6}$ alkyl)$Cy^{8B}$, or $N(C_{1-6}$ alkyl)$(C_{1-3}$ alkylenyl)$Cy^{8B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$; and $R^{88}$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $Cy^{8B}$, OH, $OCy^{8B}$, $O(C_{1-3}$ alkylenyl)$Cy^{8B}$, $NHCy^{8B}$, $NH(C_{1-3}$ alkylenyl)$Cy^{8B}$, $N(C_{1-6}$ alkyl)$Cy^{8B}$, or $N(C_{1-6}$ alkyl)$(C_{1-3}$ alkylenyl)$Cy^{8B}$, or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$.

In some embodiments, $R^1$ is OH.
In some embodiments, $R^1$ is $OC_{1-6}$ alkyl (e.g., OMe).
In some embodiments, $R^1$ is $C_{2-6}$ alkenyl (e.g., vinyl).
In some embodiments, $L^7$ is NH.
In some embodiments, $L^8$ is NH.
In some embodiments, $R^{a1}$, $R^{b1}$, $R^{c1}$ and $R^{d1}$ are each independently selected from H, $C_{1-6}$ alkyl, HO—$C_{1-6}$ alkylene, $C_{1-6}$ alkoxy-$C_{1-6}$ alkylene, $C_{6-10}$ aryl, $C_{2-6}$ alkenyl and $C_{2-6}$ alkynyl.

In some embodiments, the compound is a compound of one of the following formulae, or a pharmaceutically acceptable salt thereof:

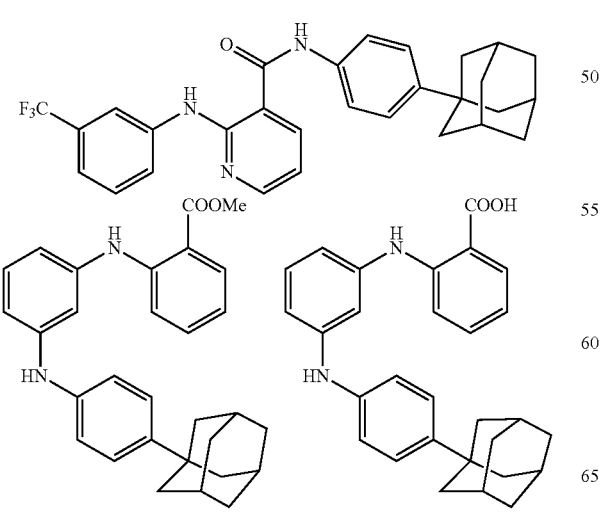

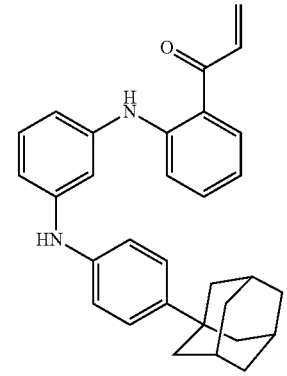

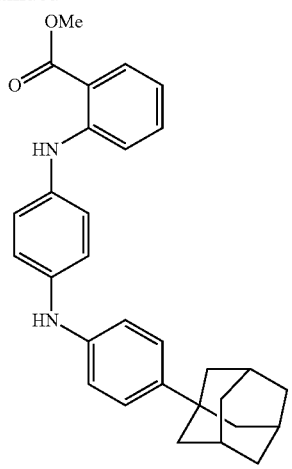

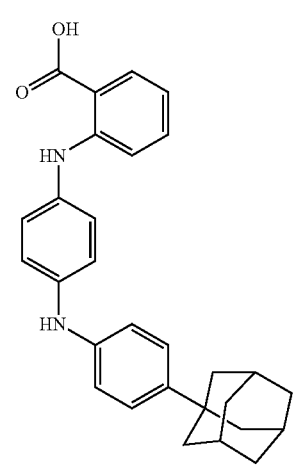

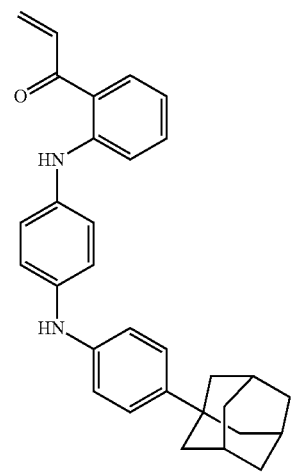

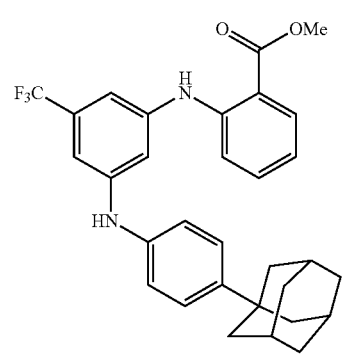

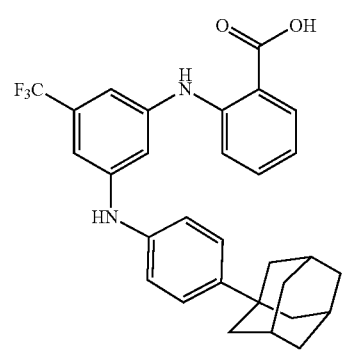

-continued
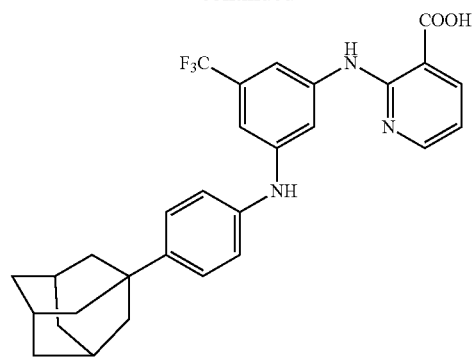
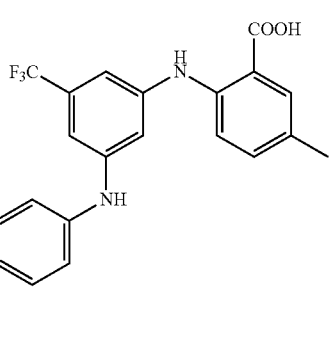
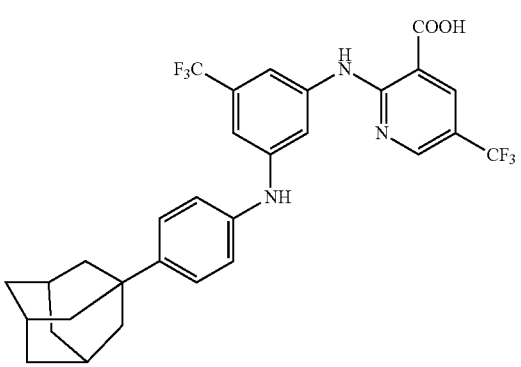
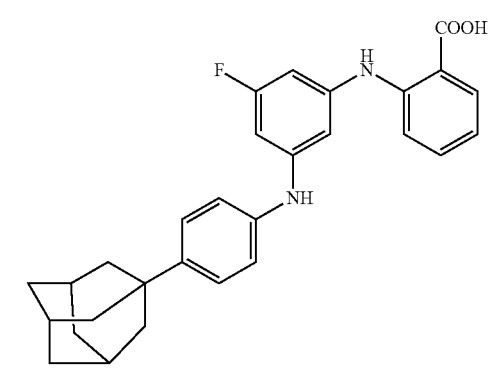
-continued
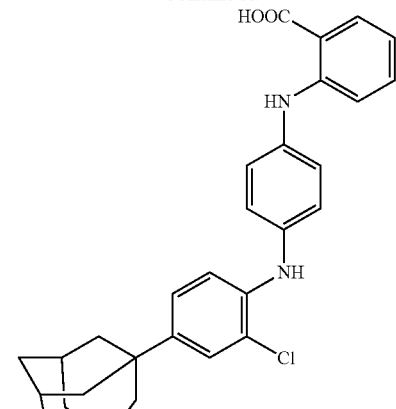
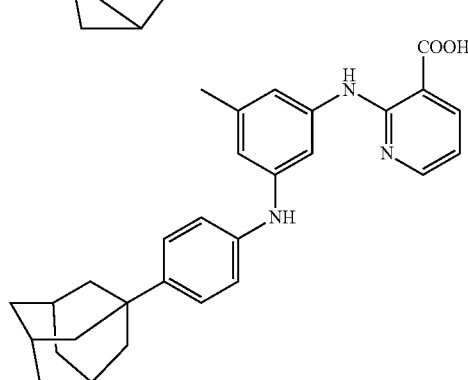
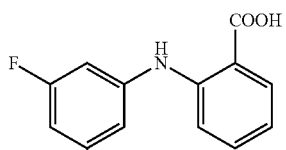
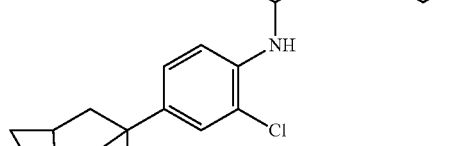
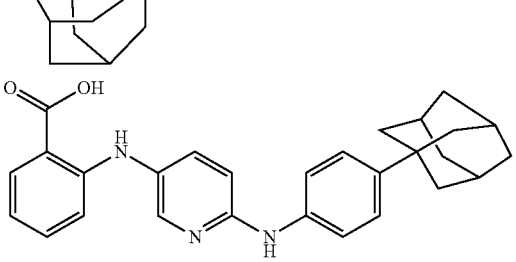
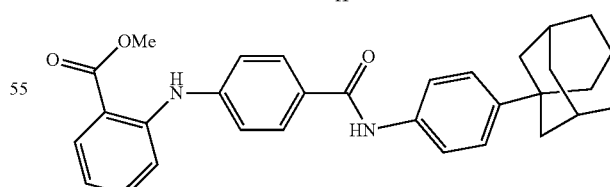
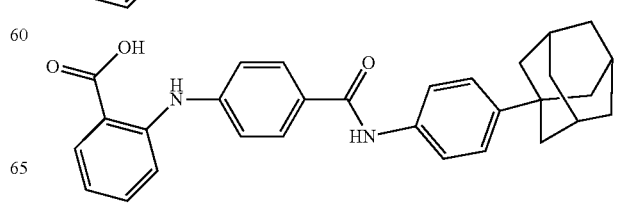

47
-continued
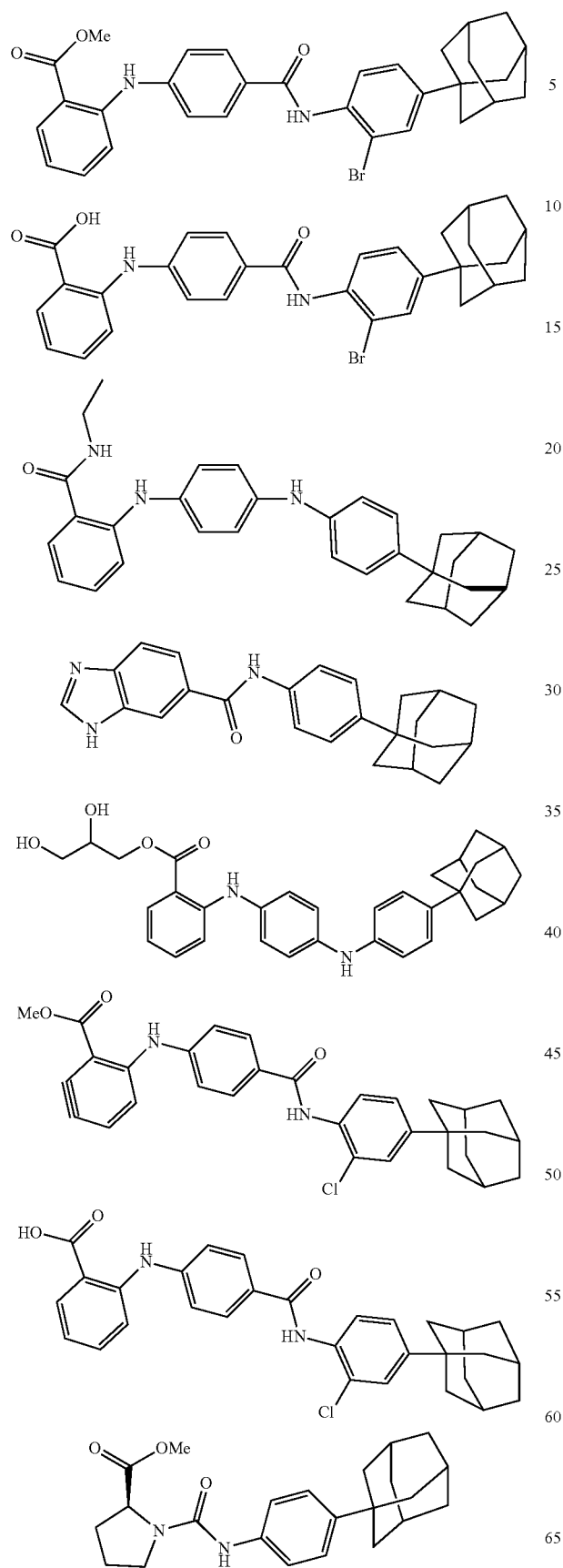
48
-continued
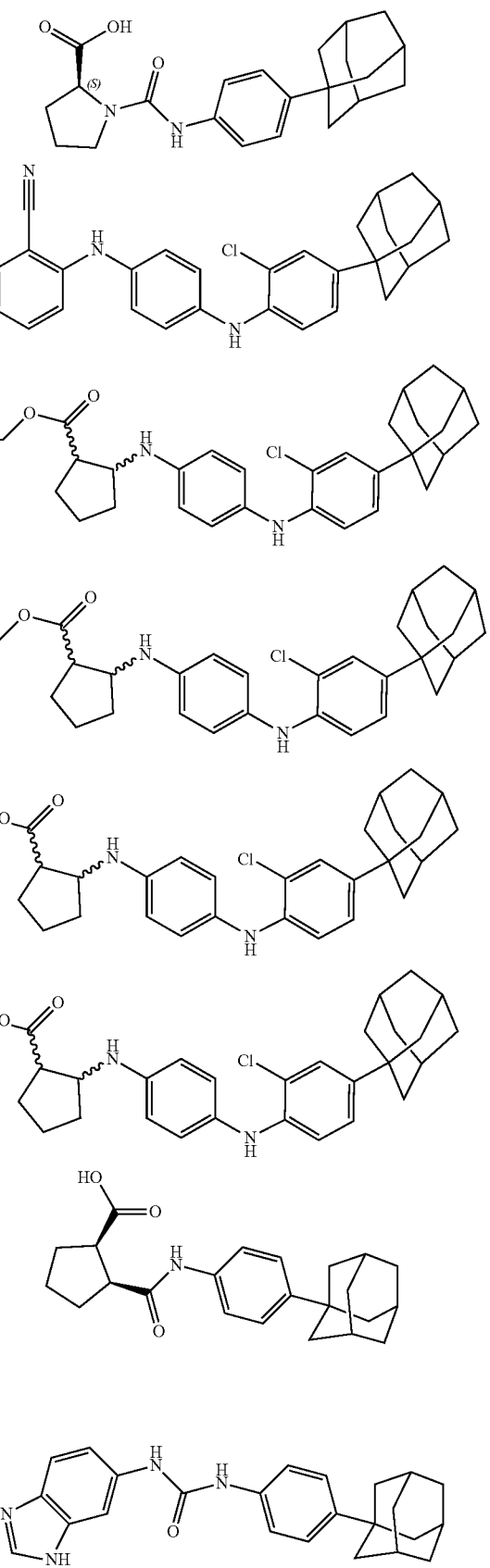

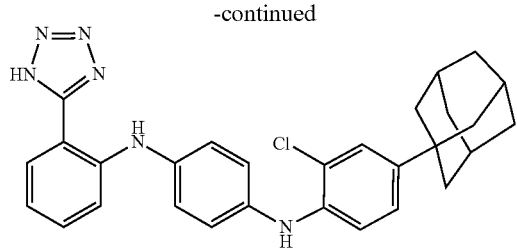
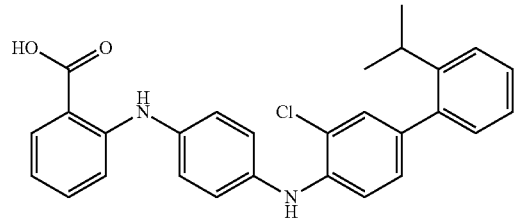
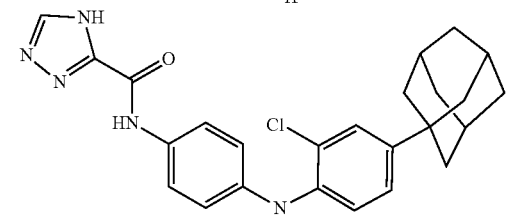
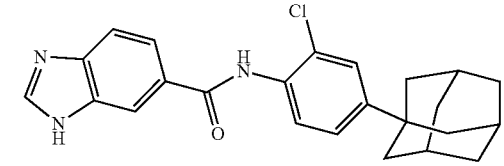
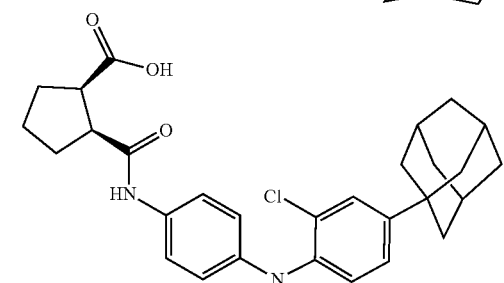
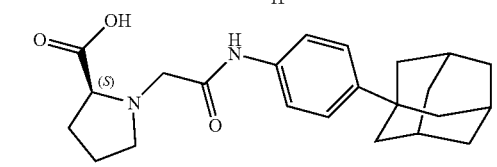
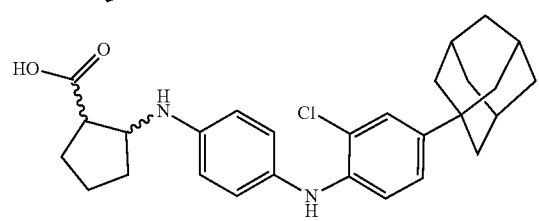
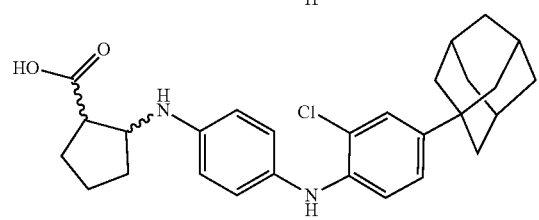
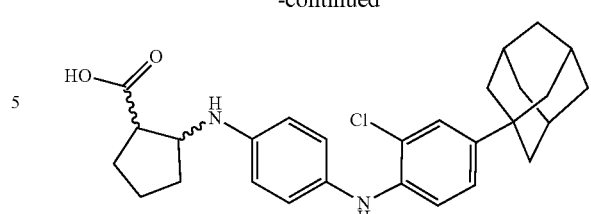
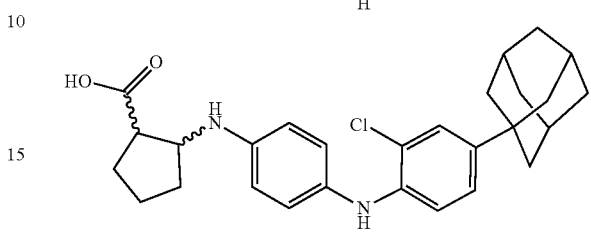
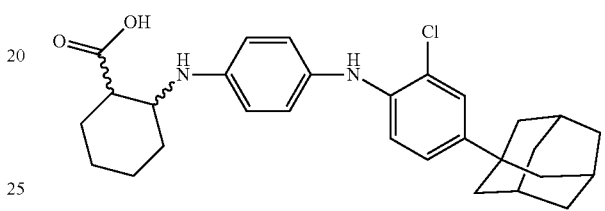
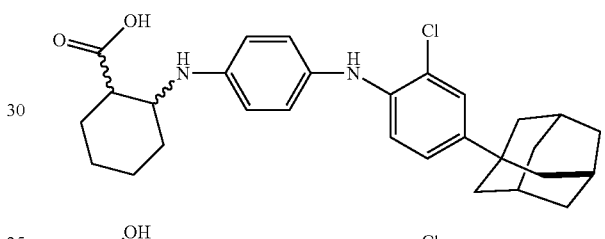
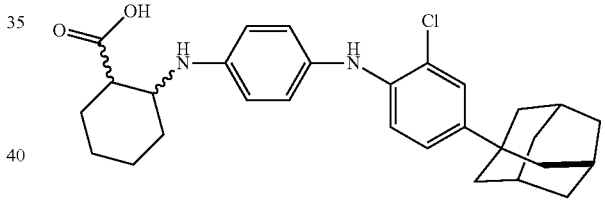
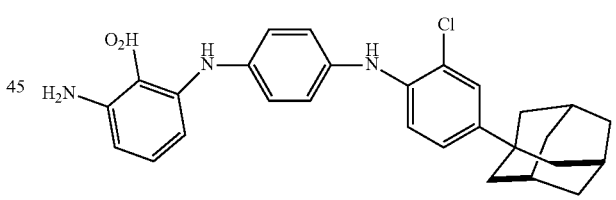
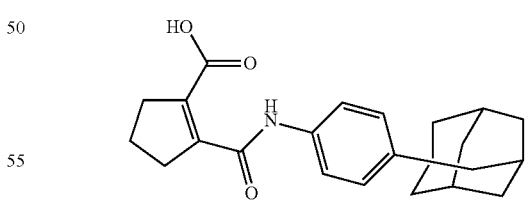
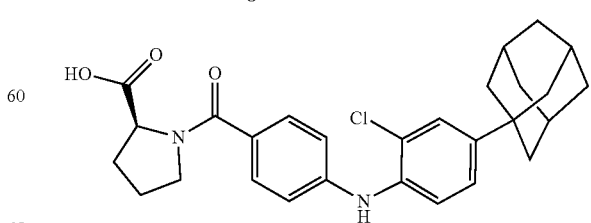

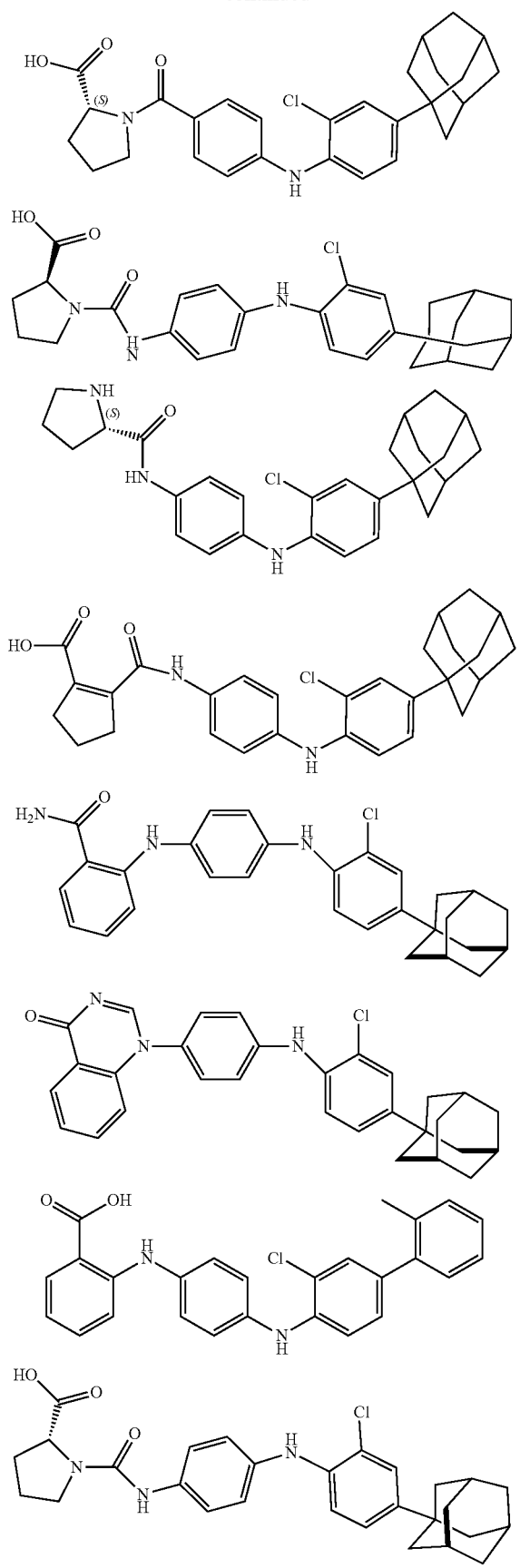
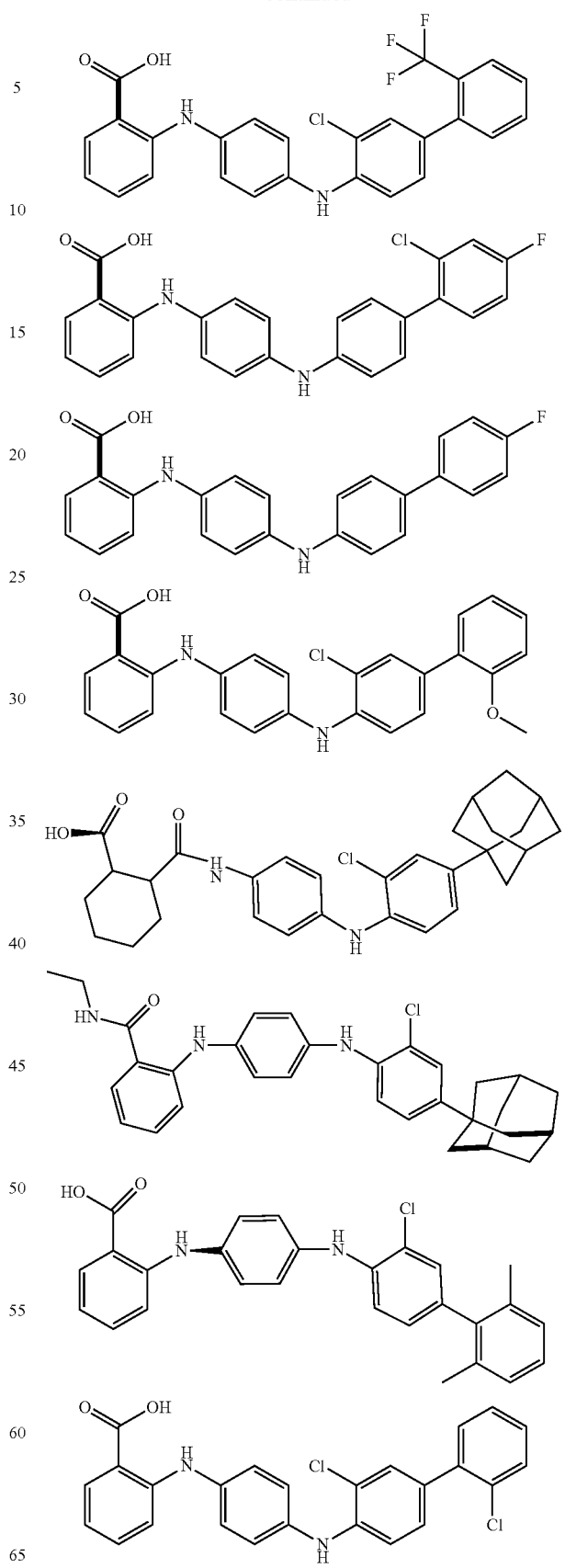

53
-continued
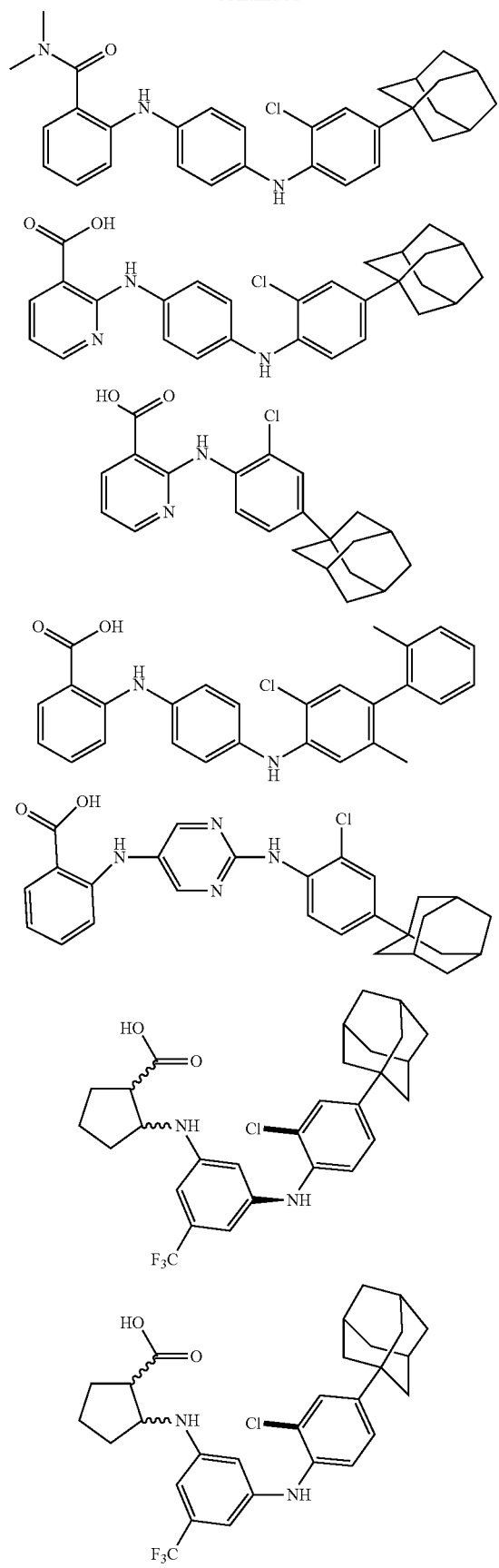
54
-continued
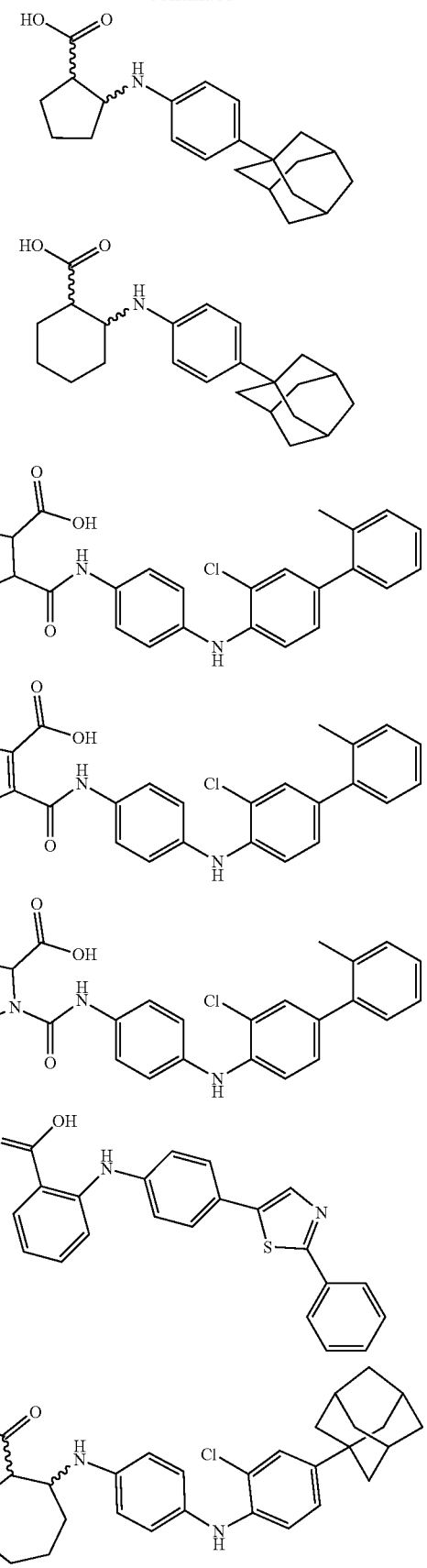

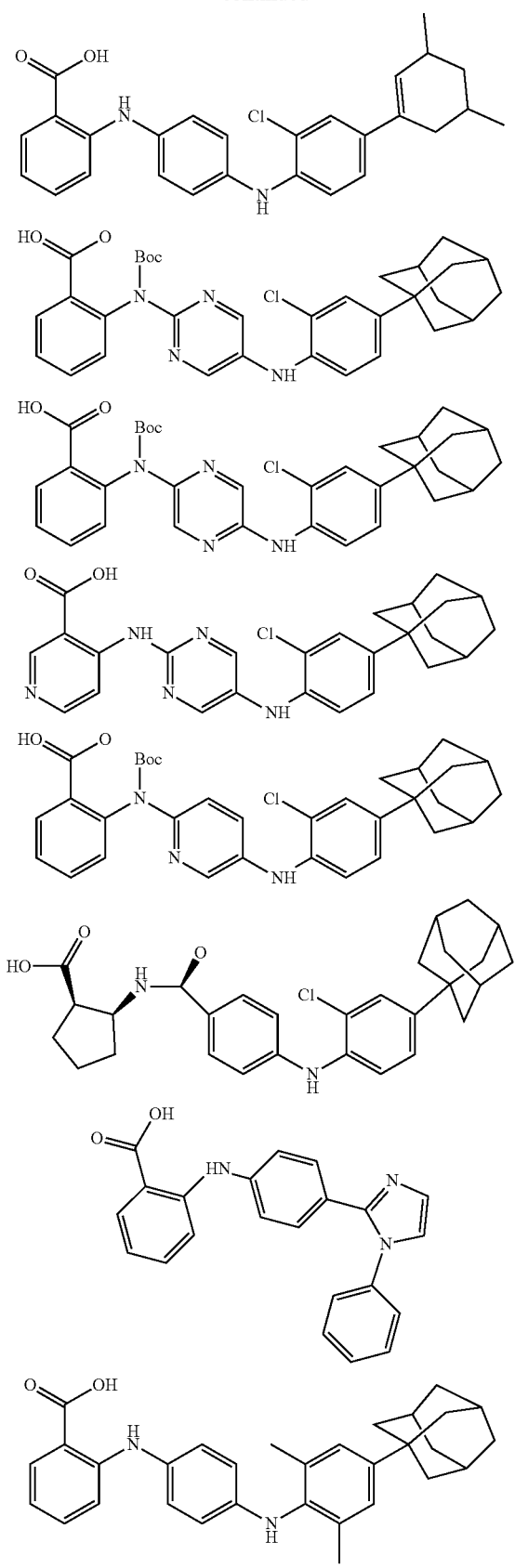
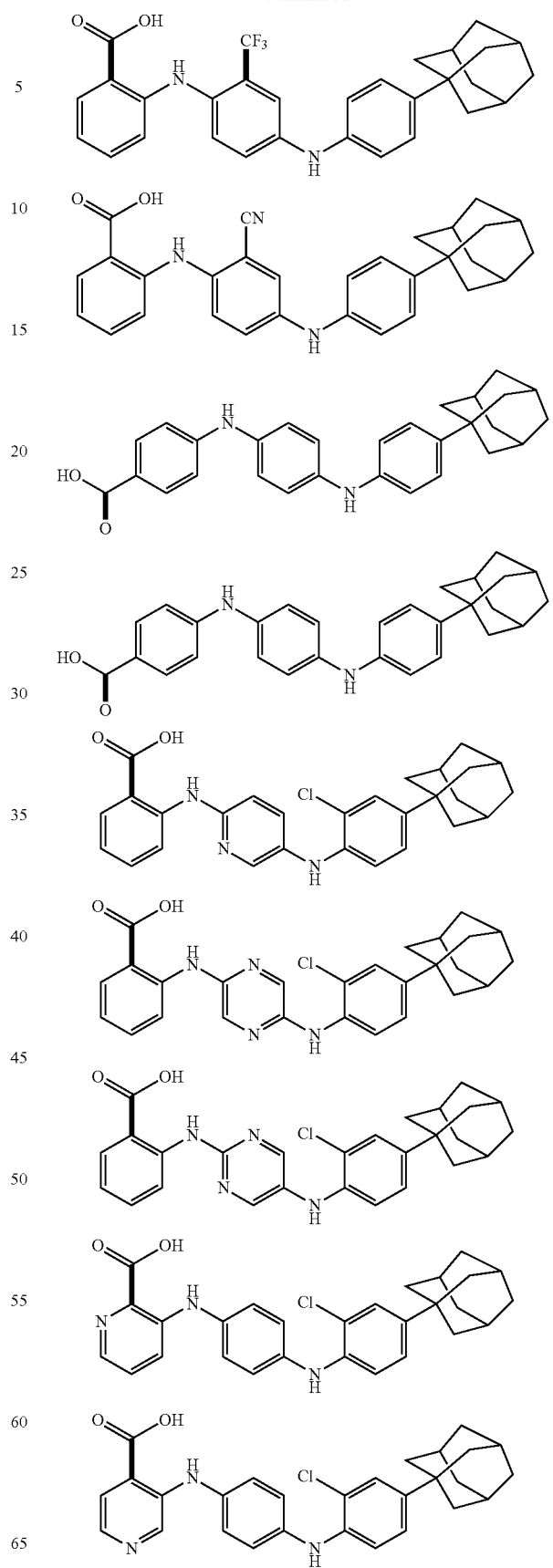

-continued
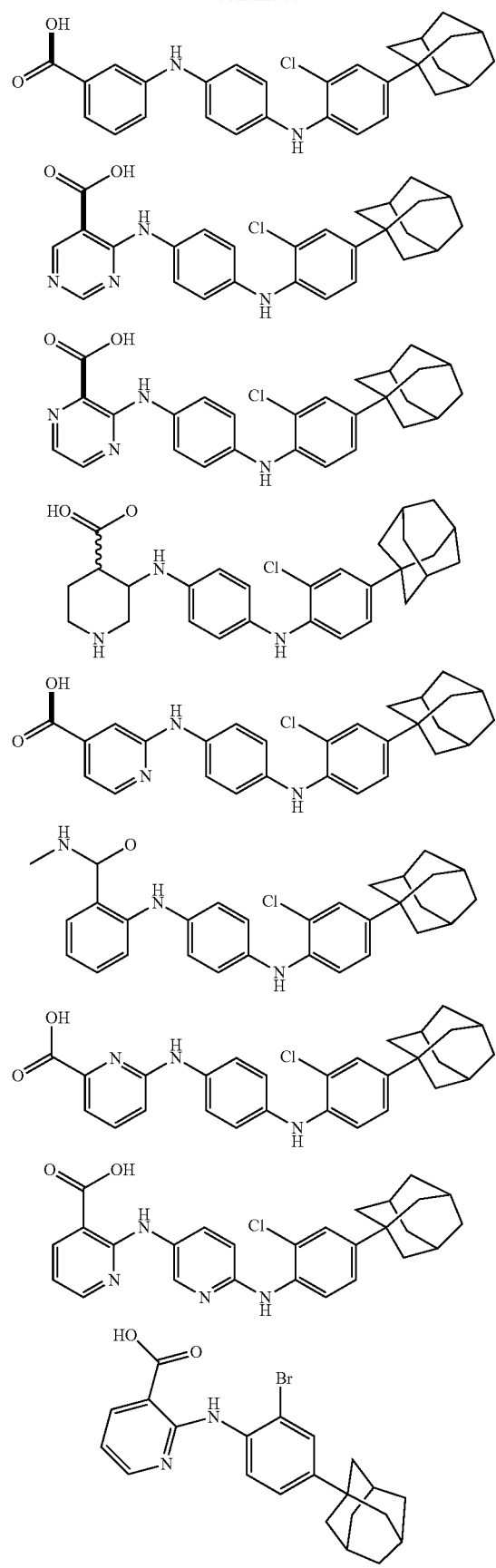
-continued
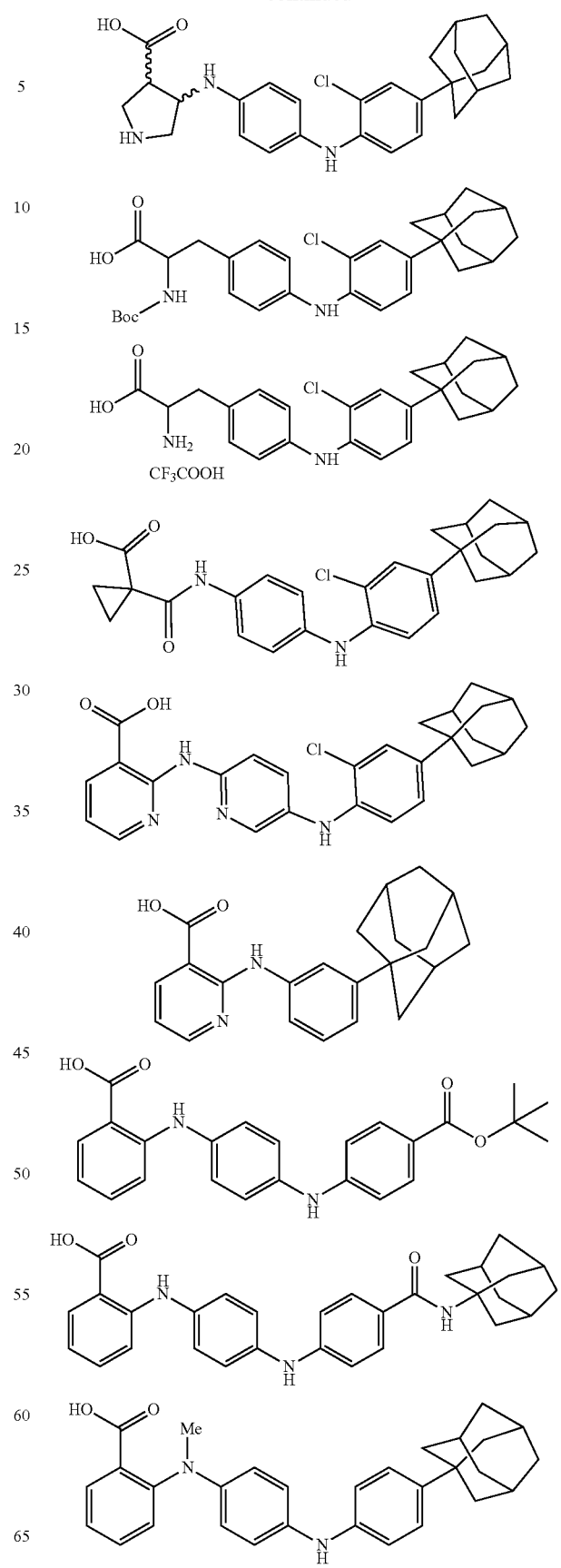

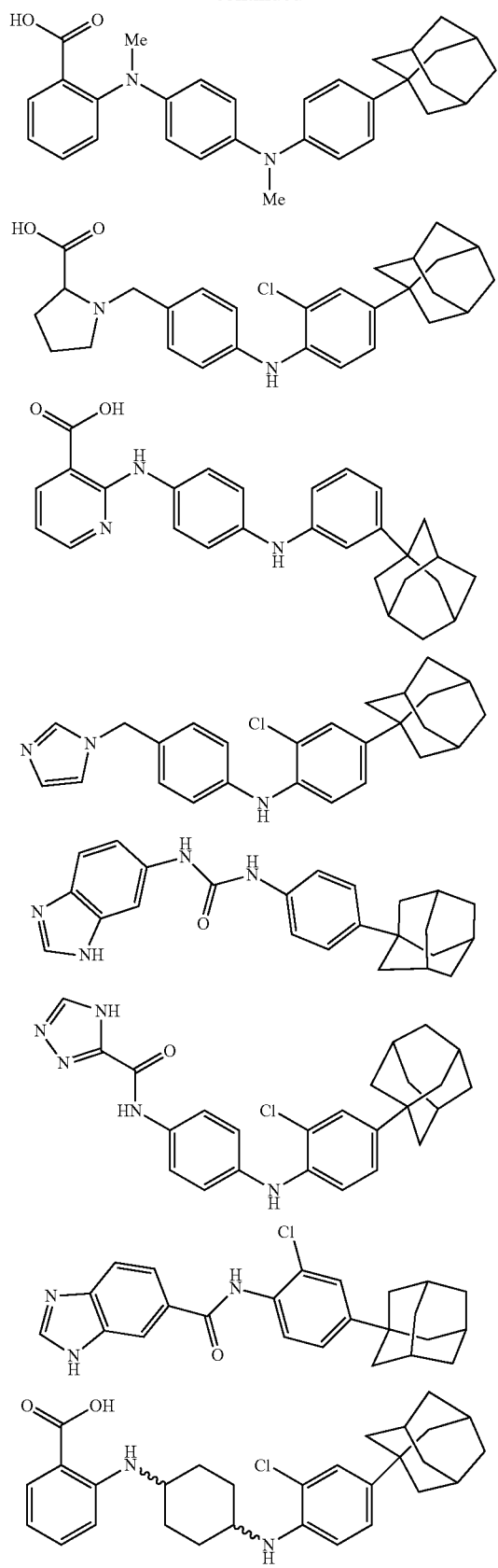
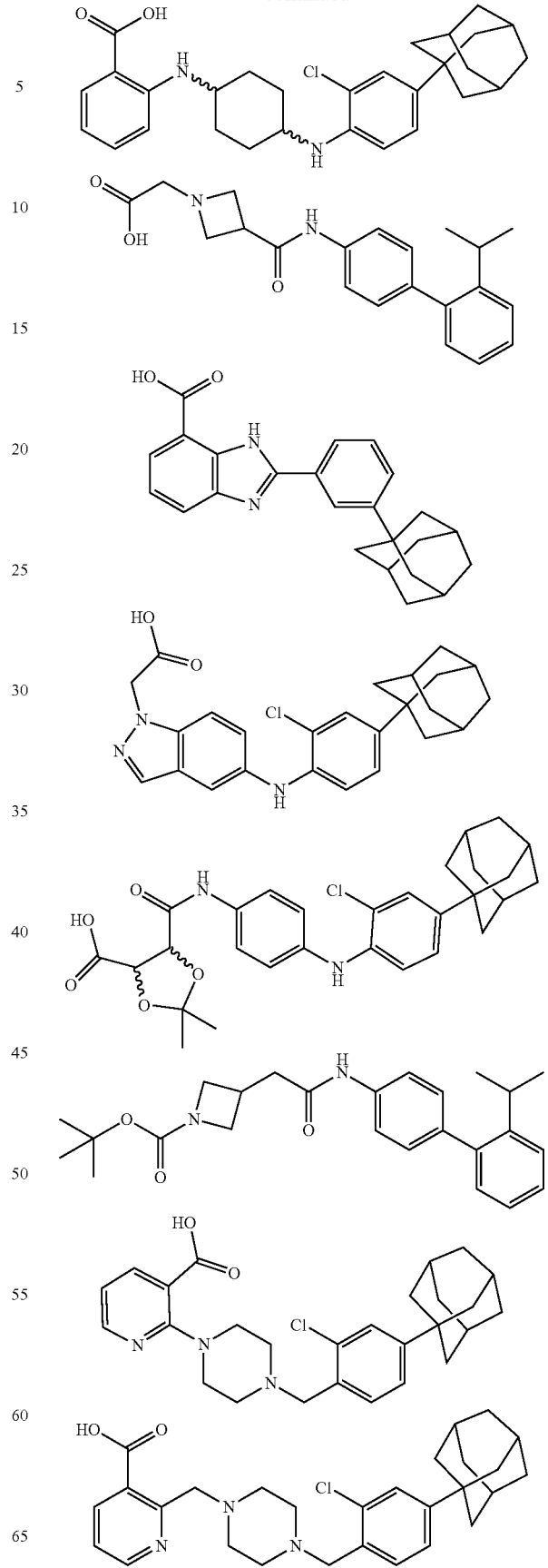

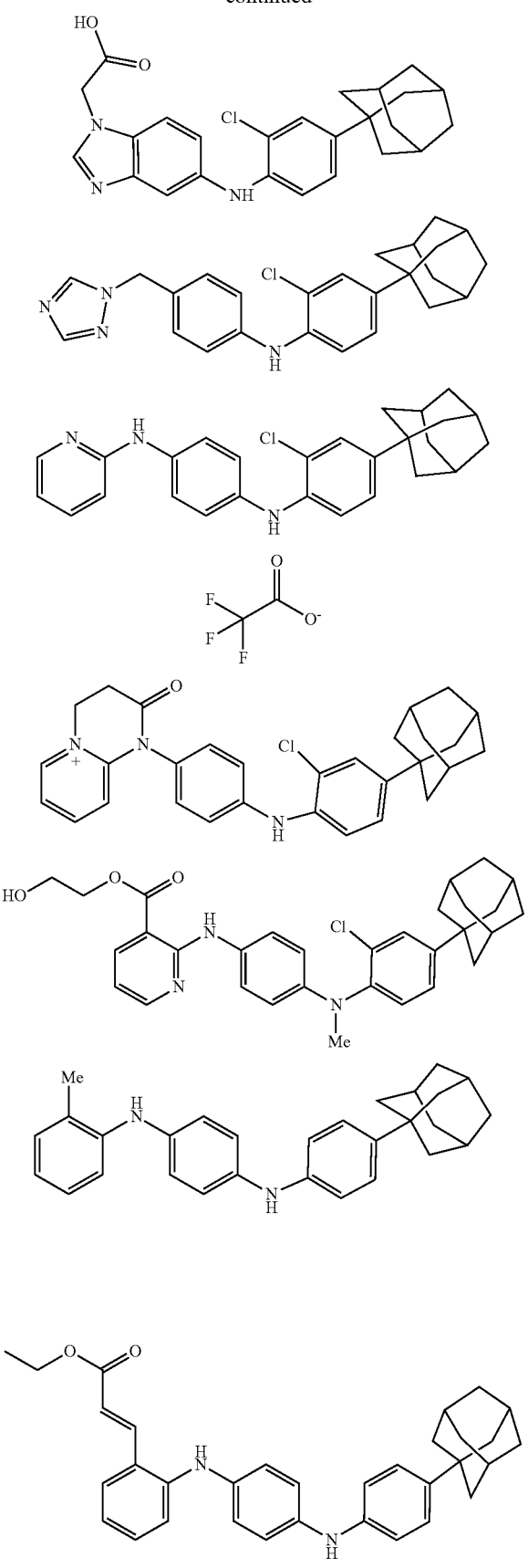
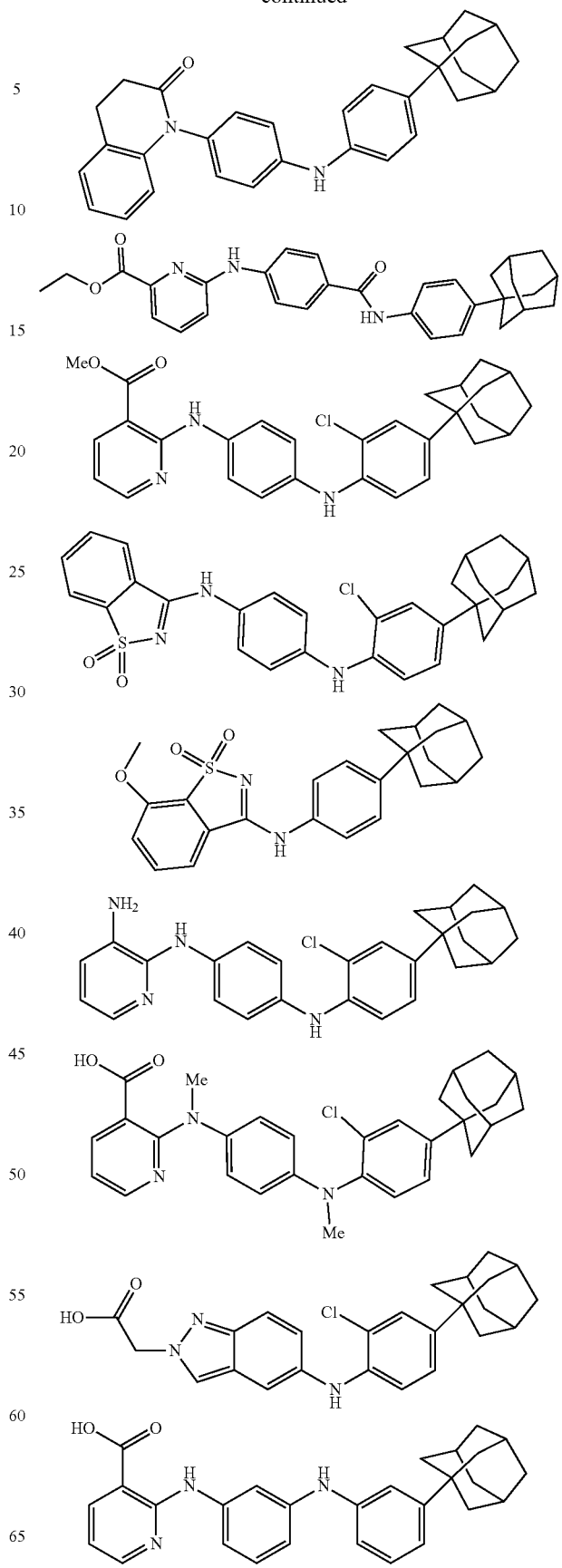

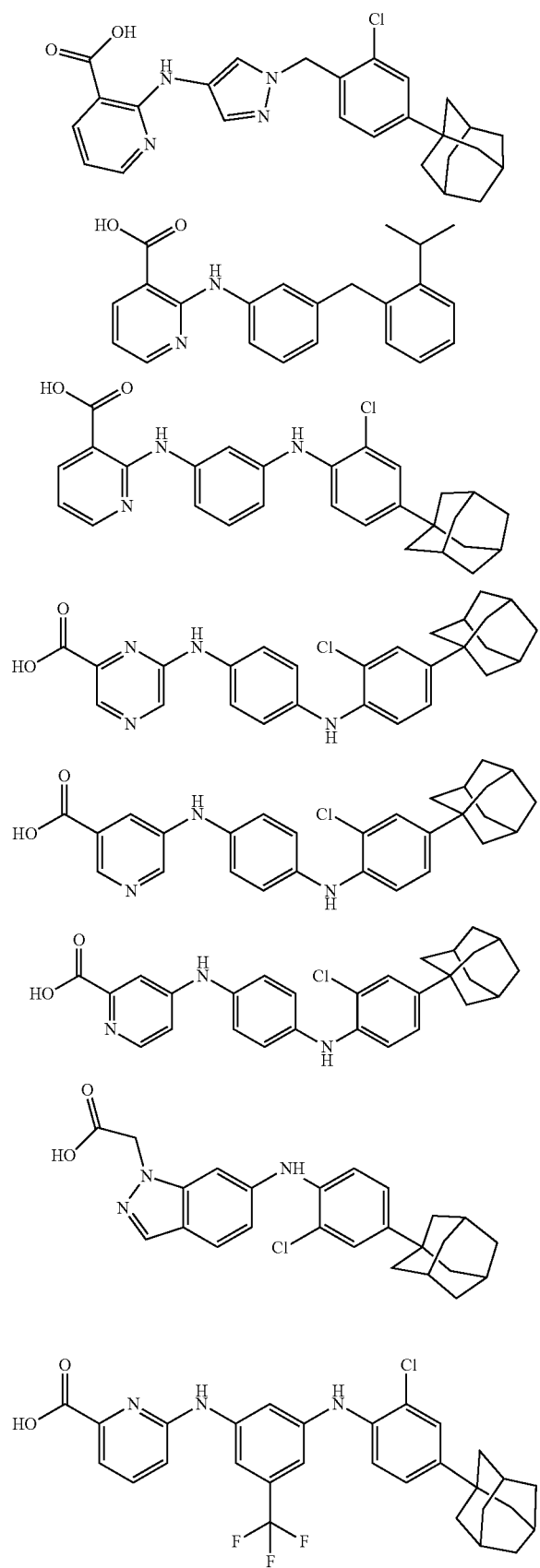
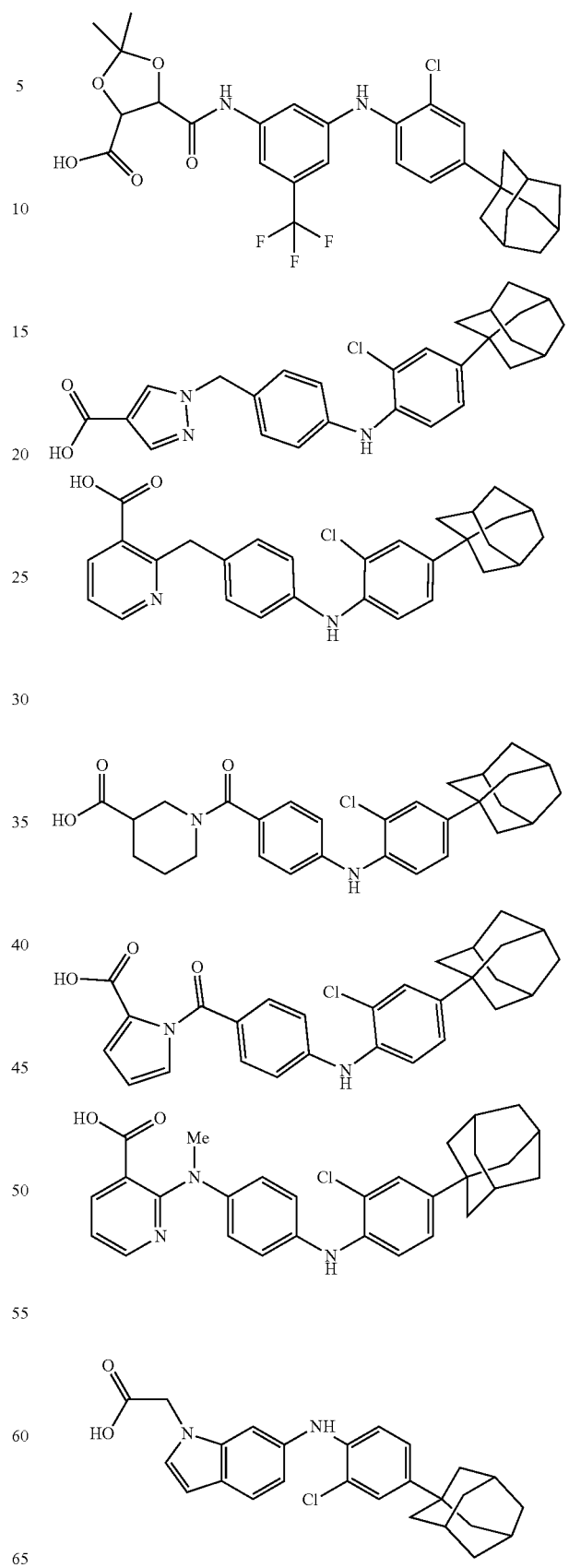

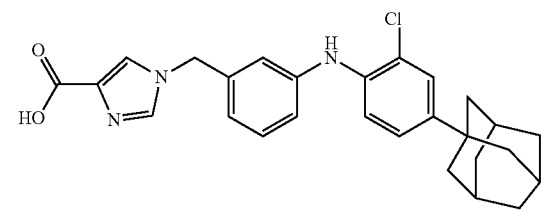
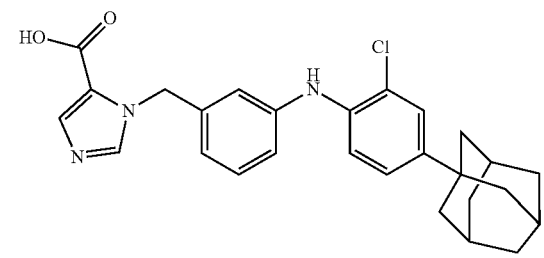
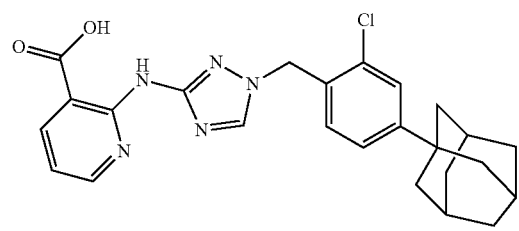
CF₃COOH
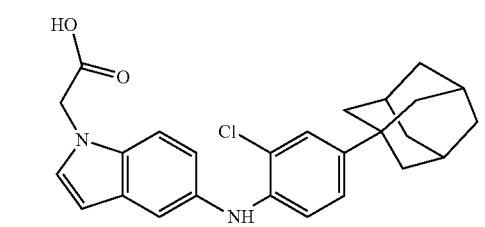
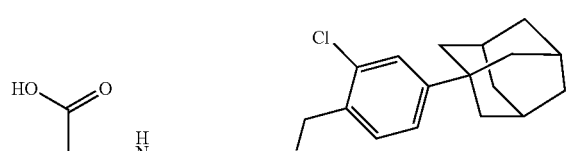
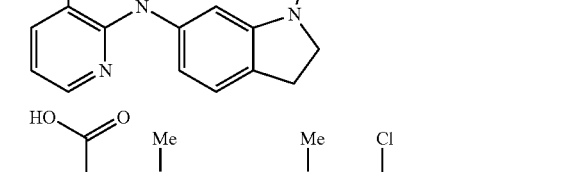
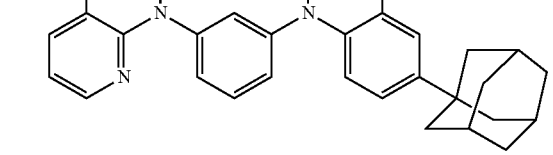
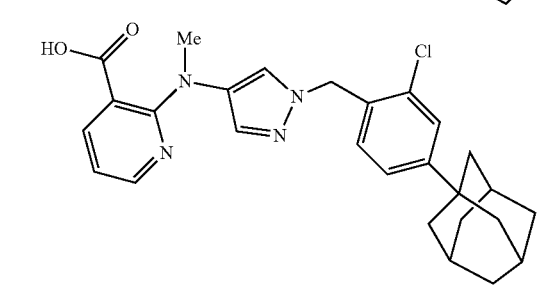
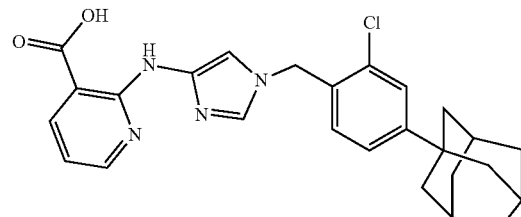
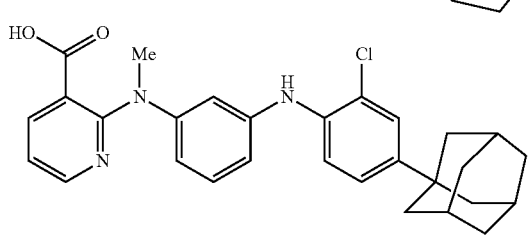
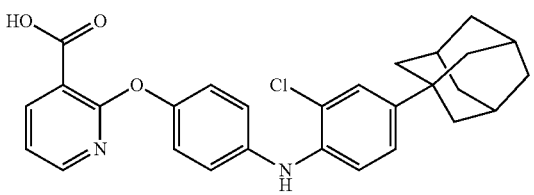
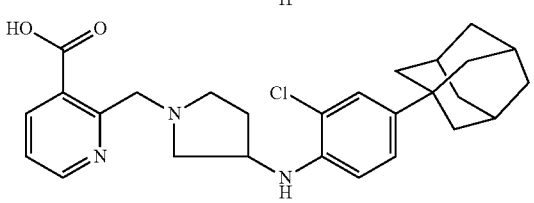
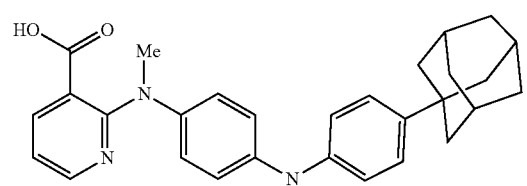
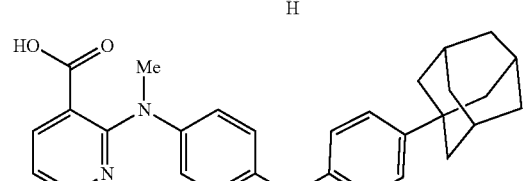
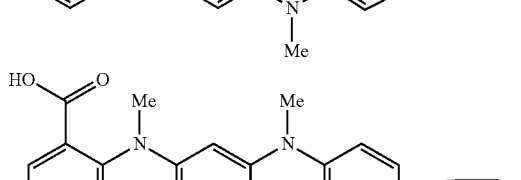
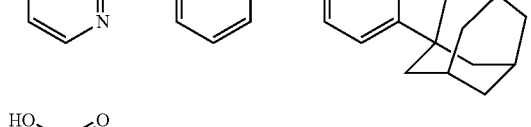
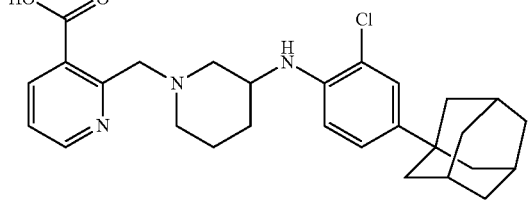

67
-continued
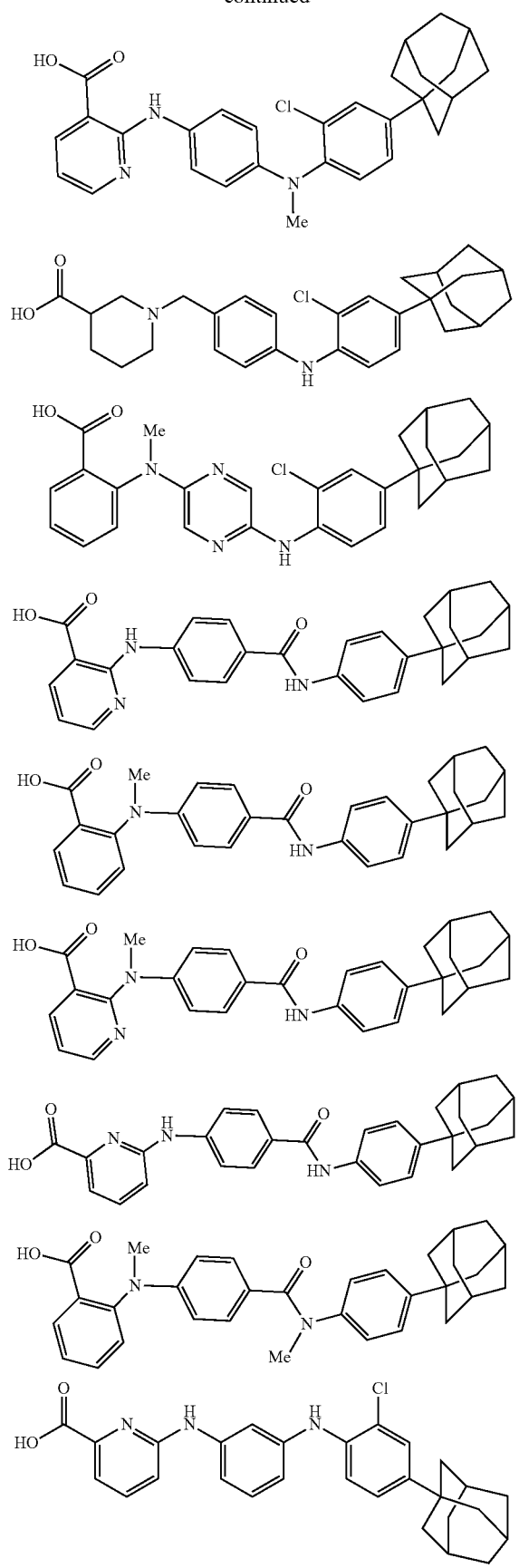
68
-continued
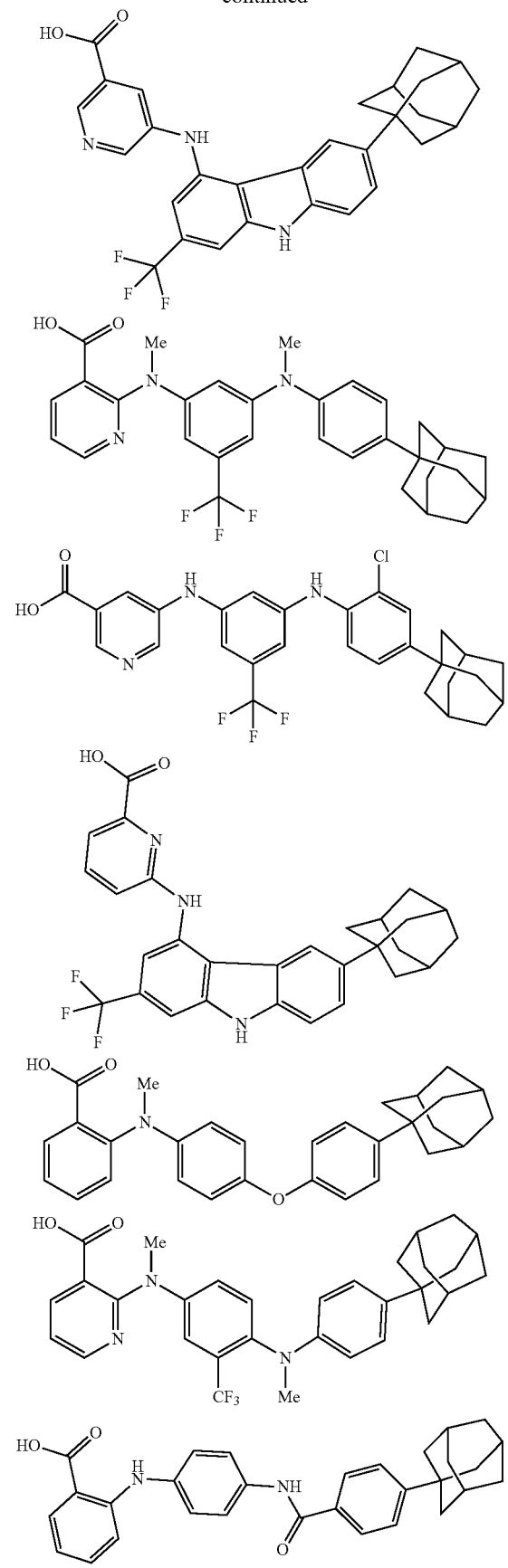

69
-continued
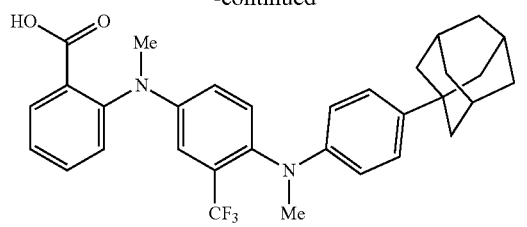
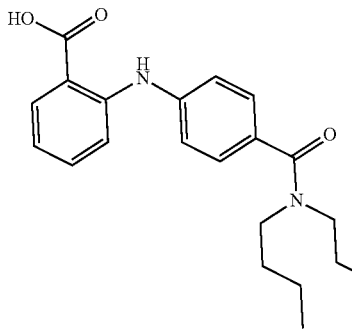
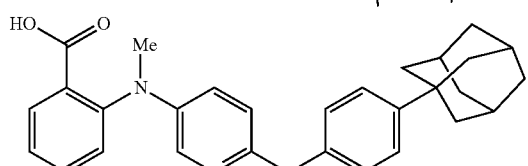
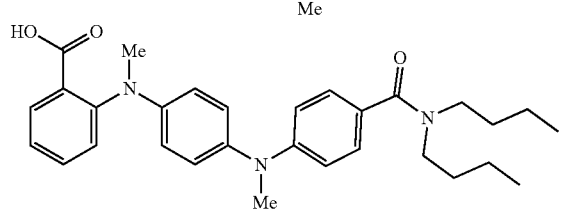
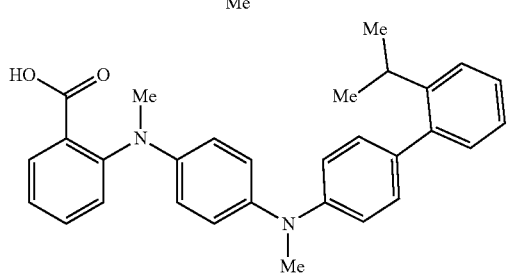
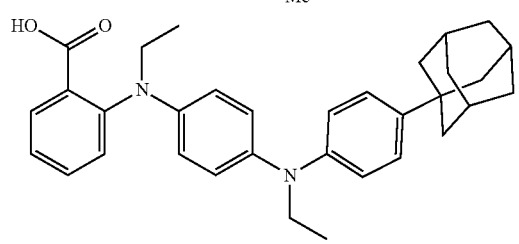
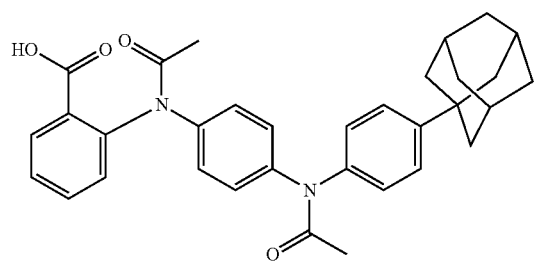
70
-continued
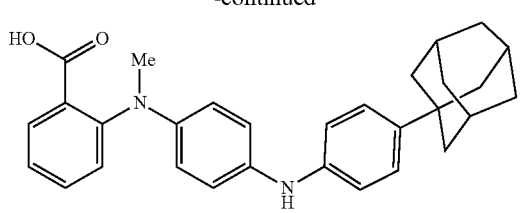
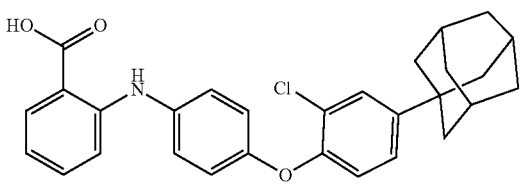
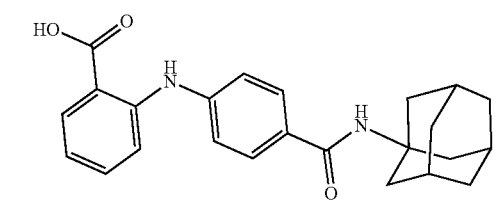
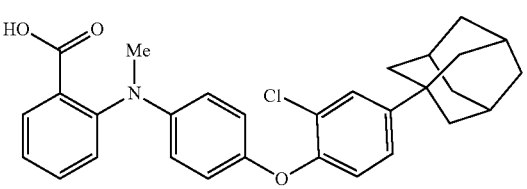
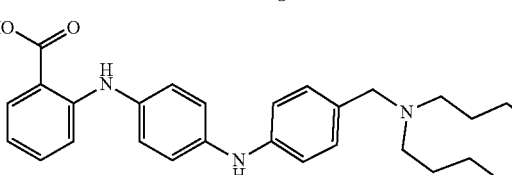
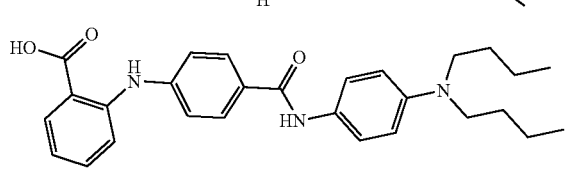
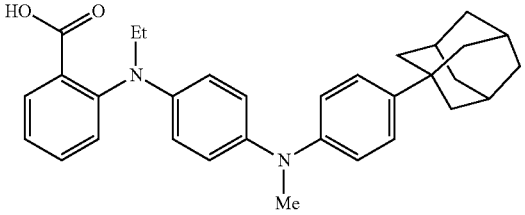
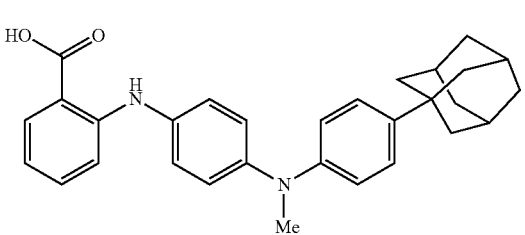

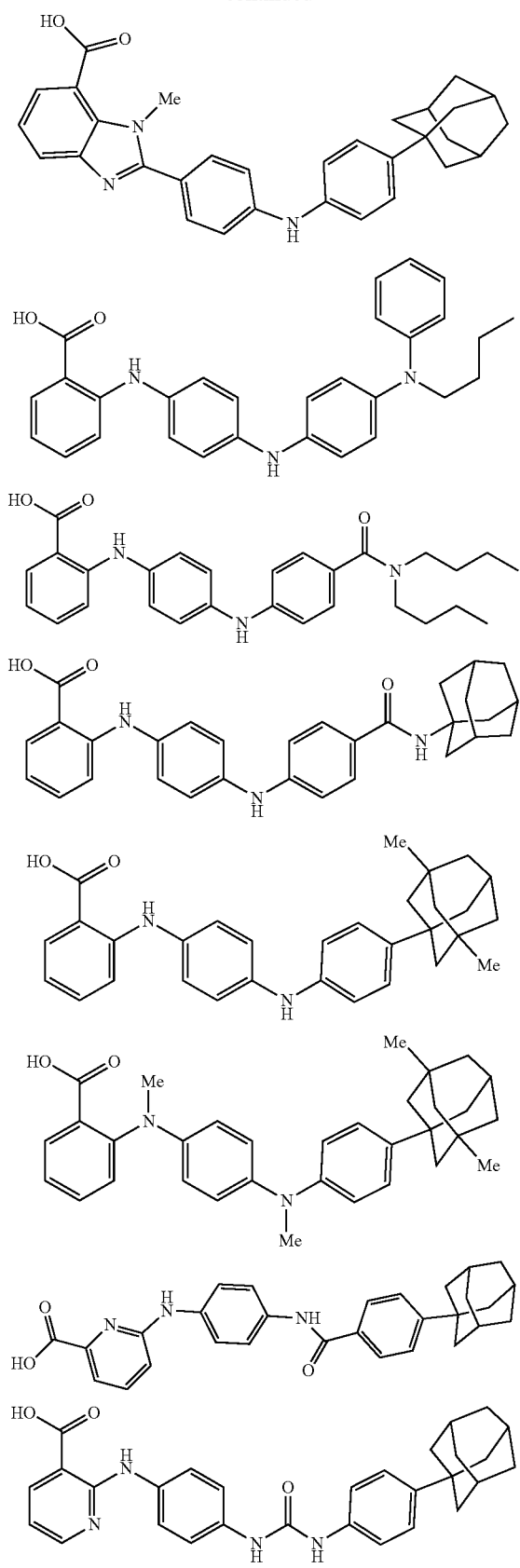
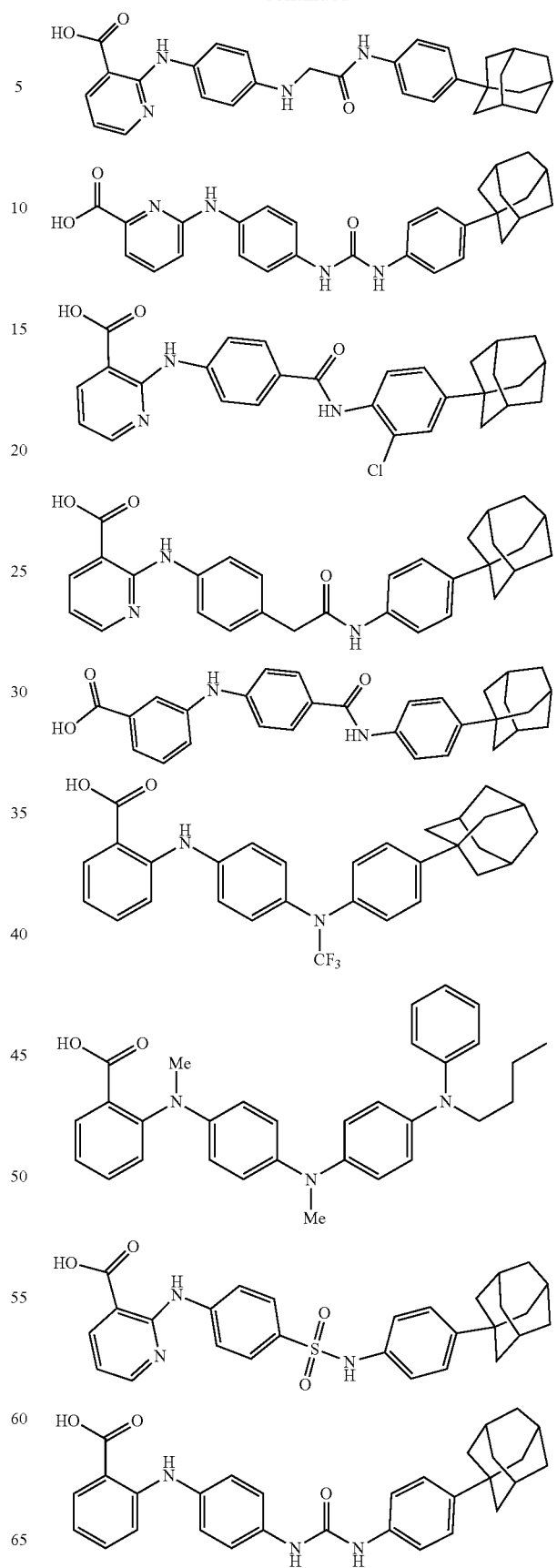

73
-continued
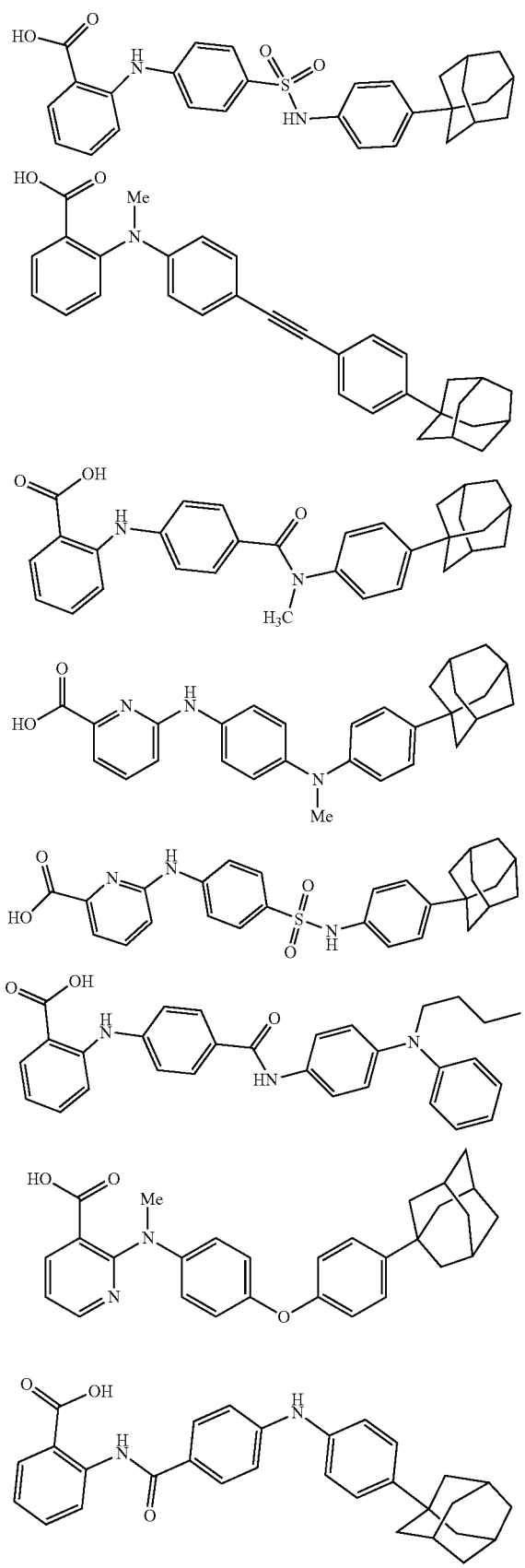
74
-continued
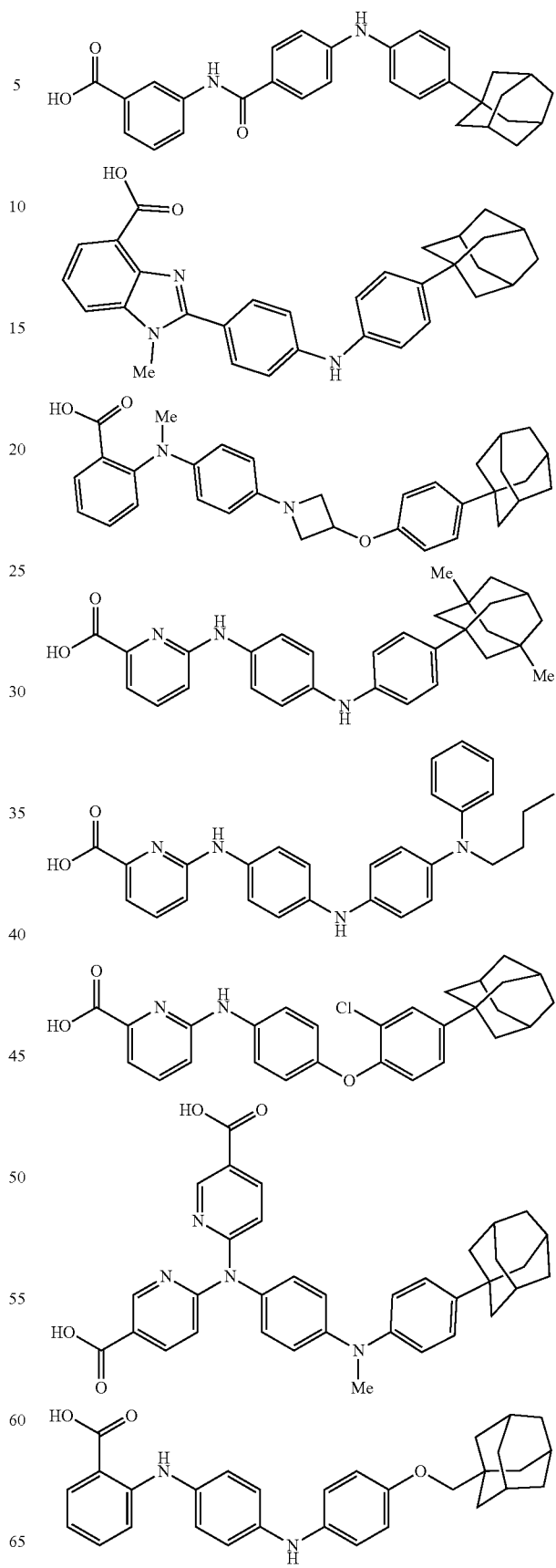

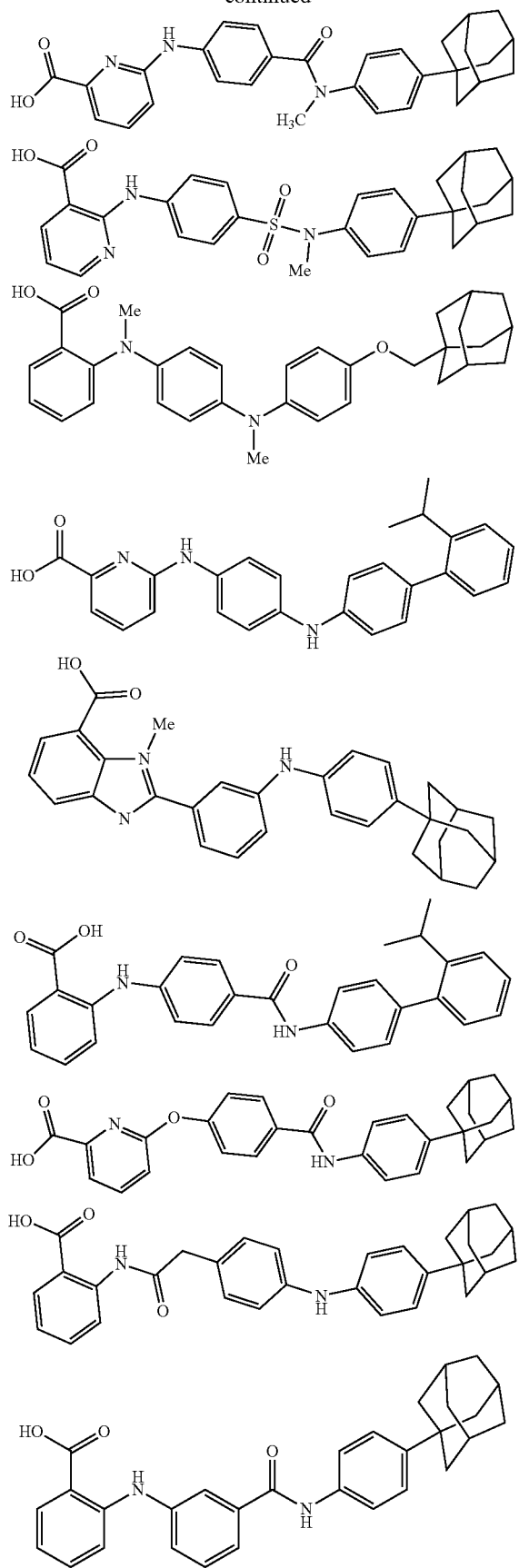
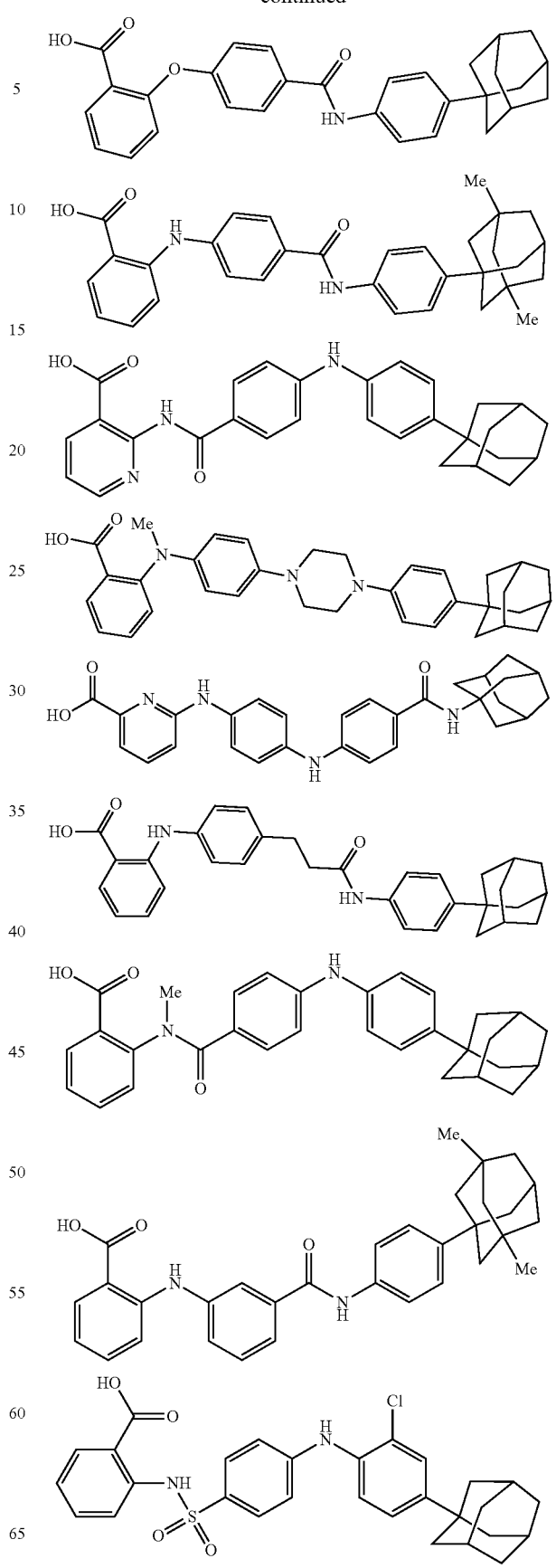

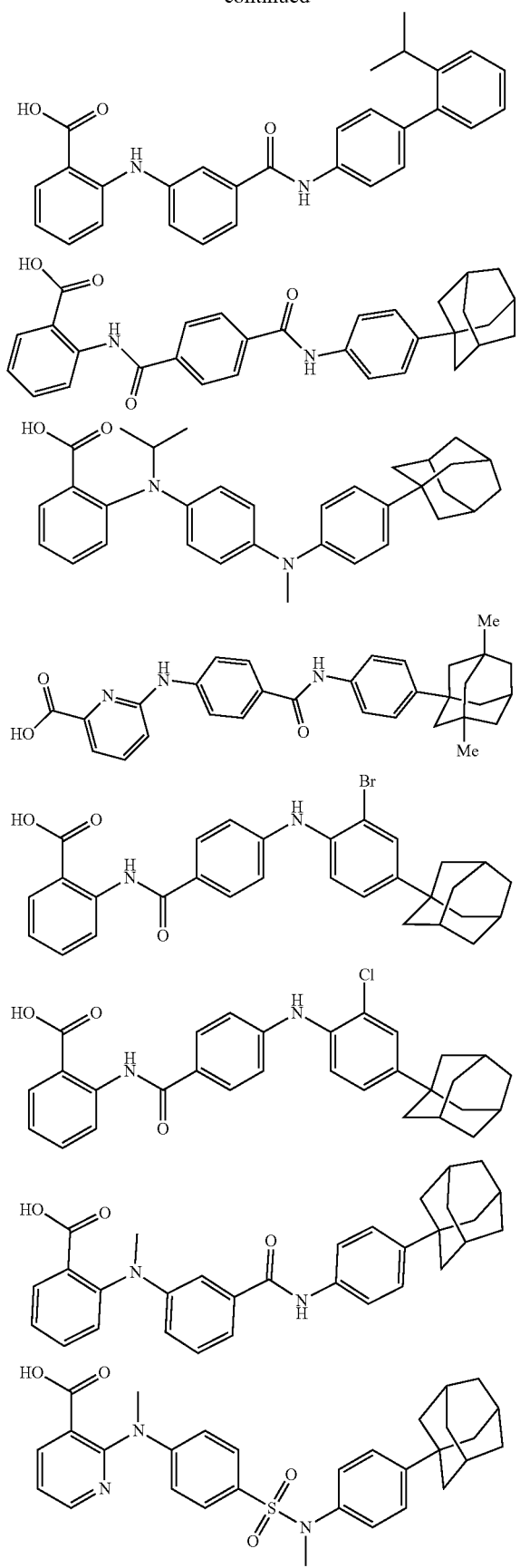
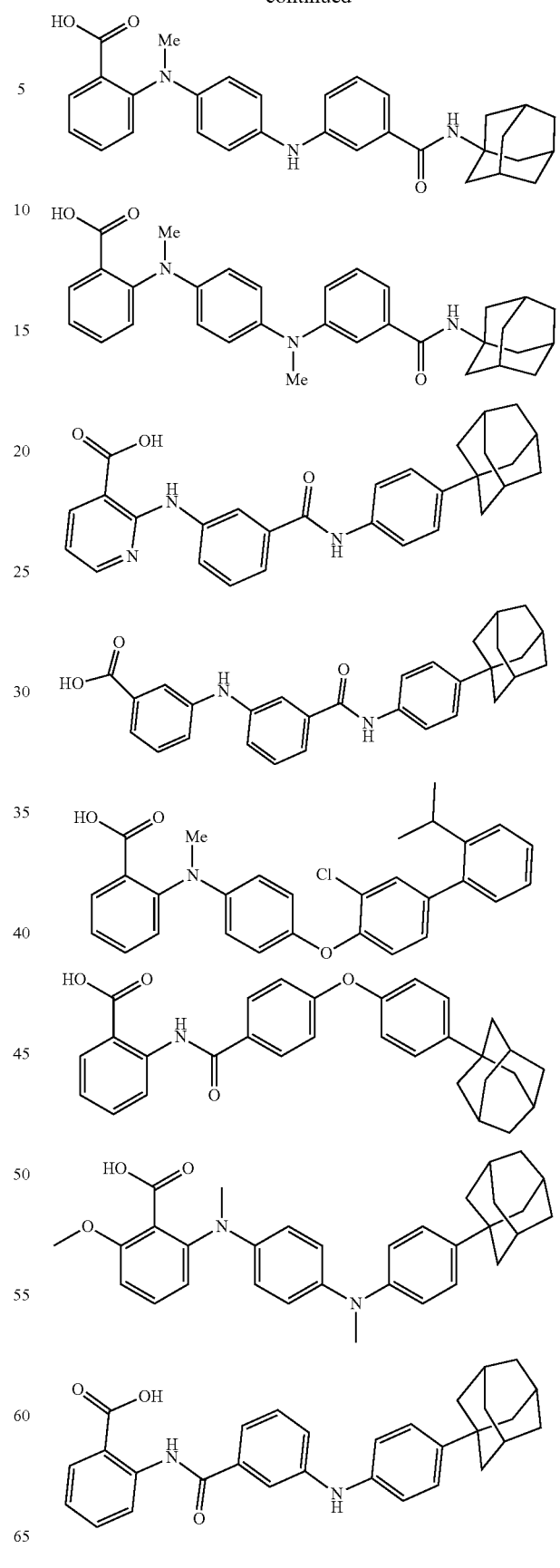

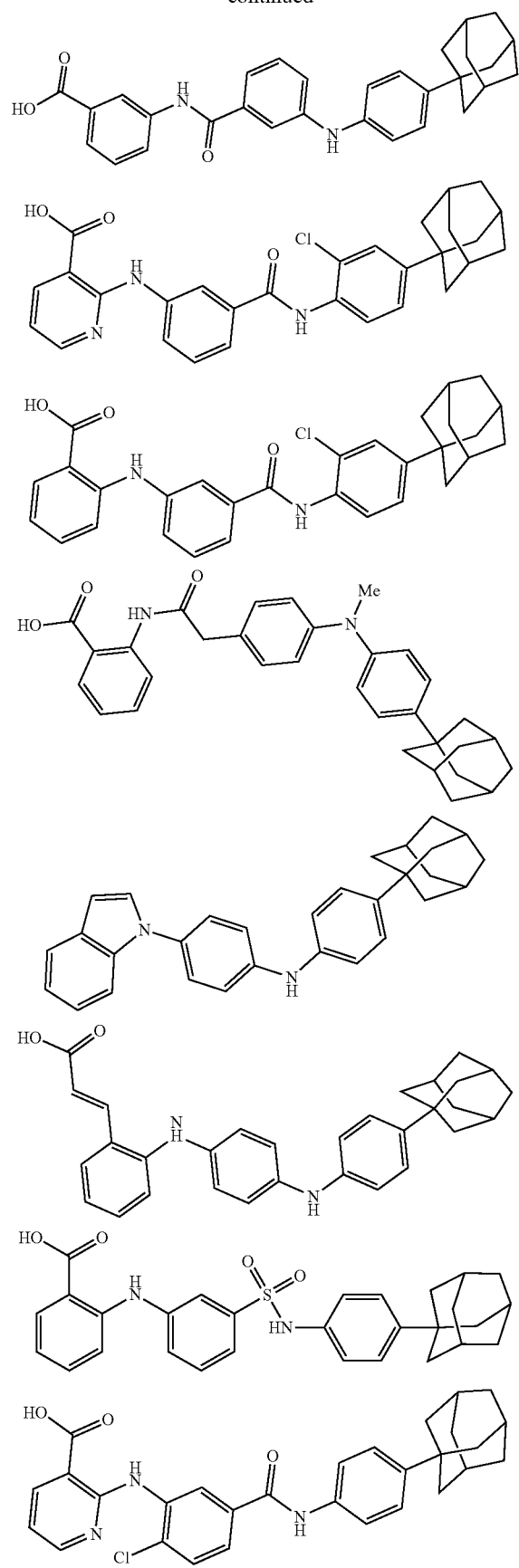
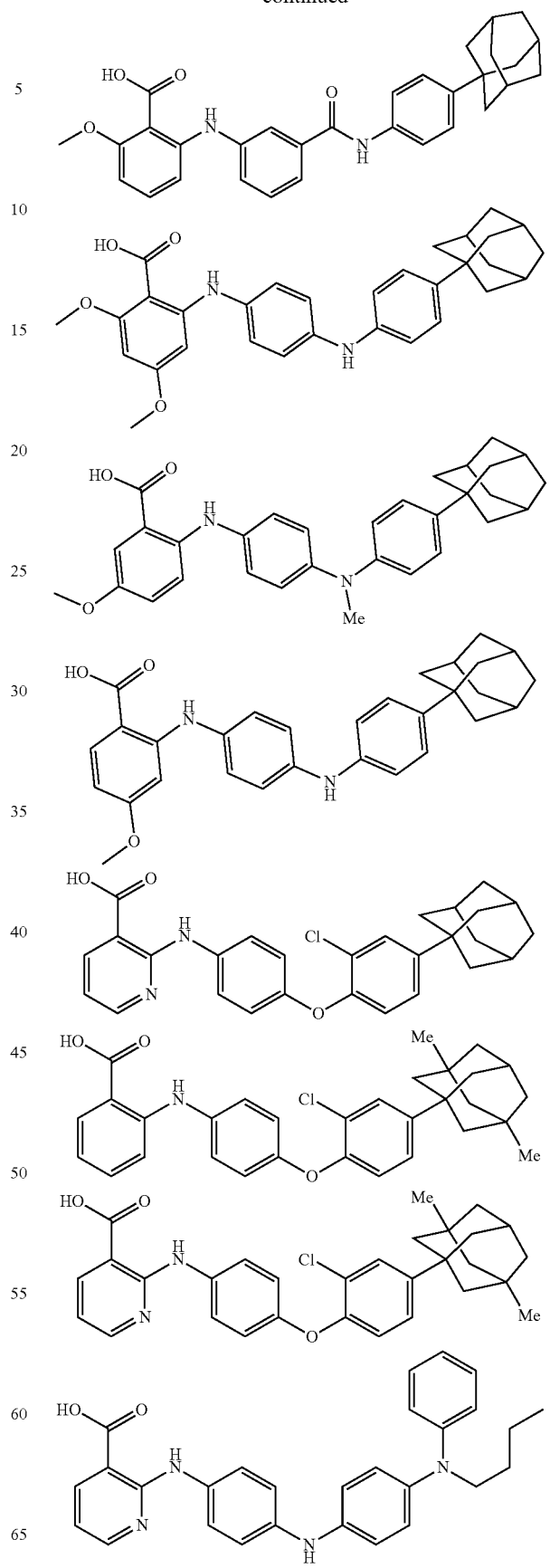

-continued
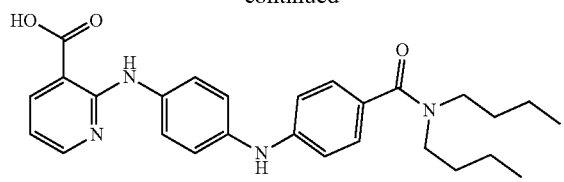
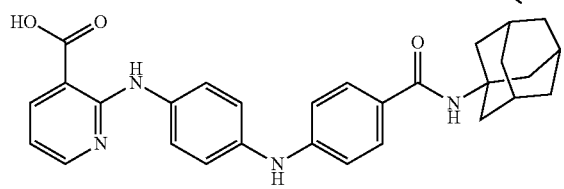
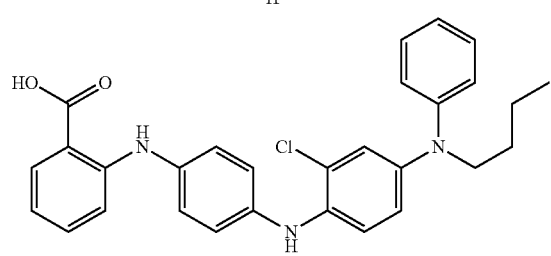
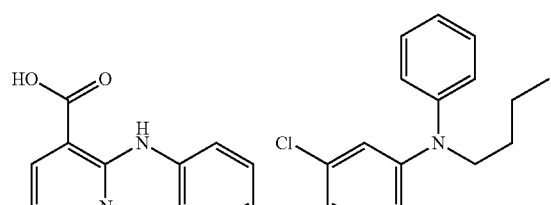
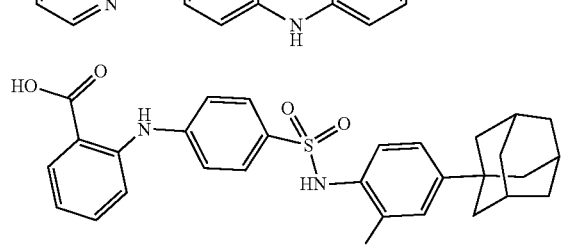
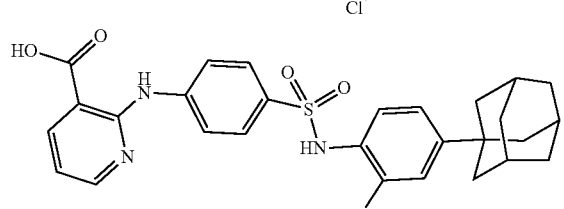
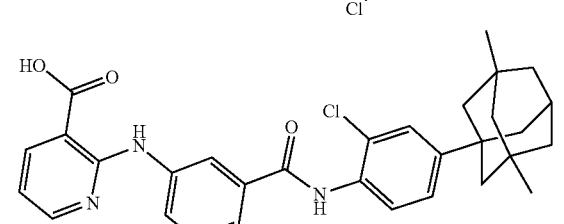
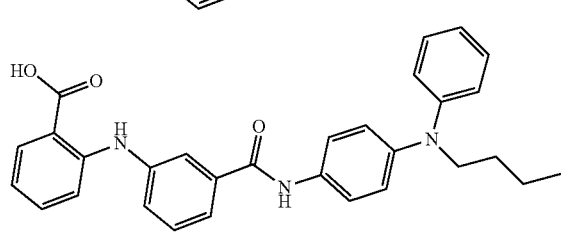
-continued
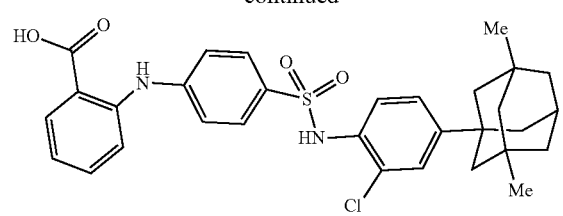
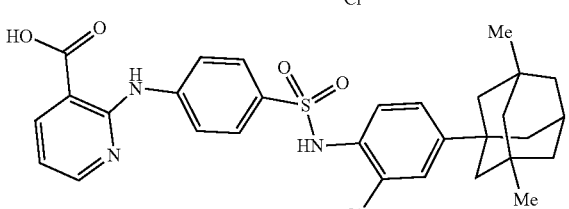
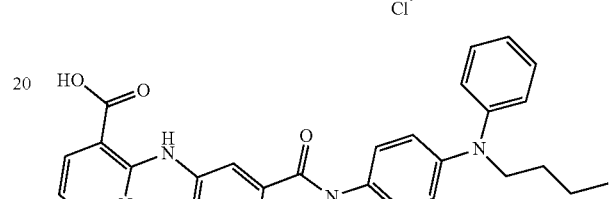
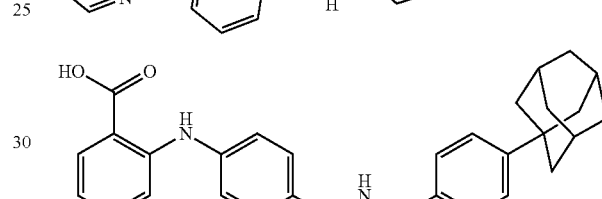
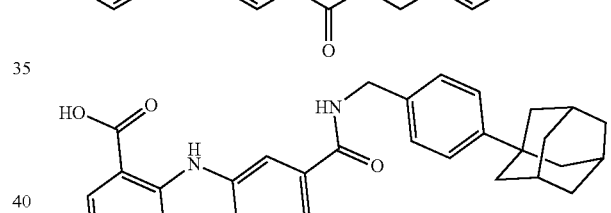
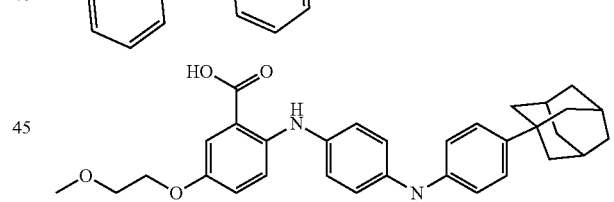
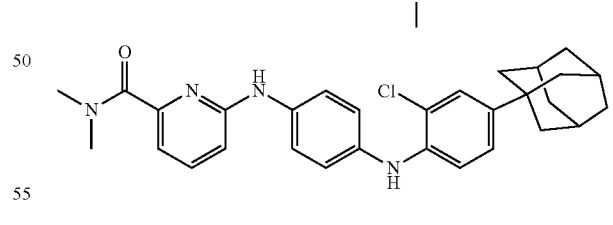
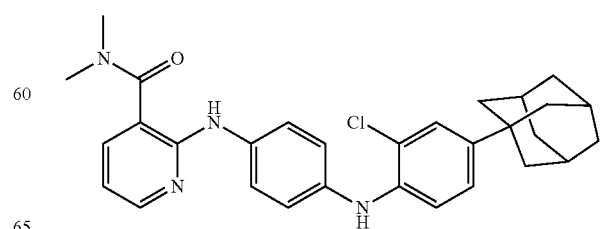

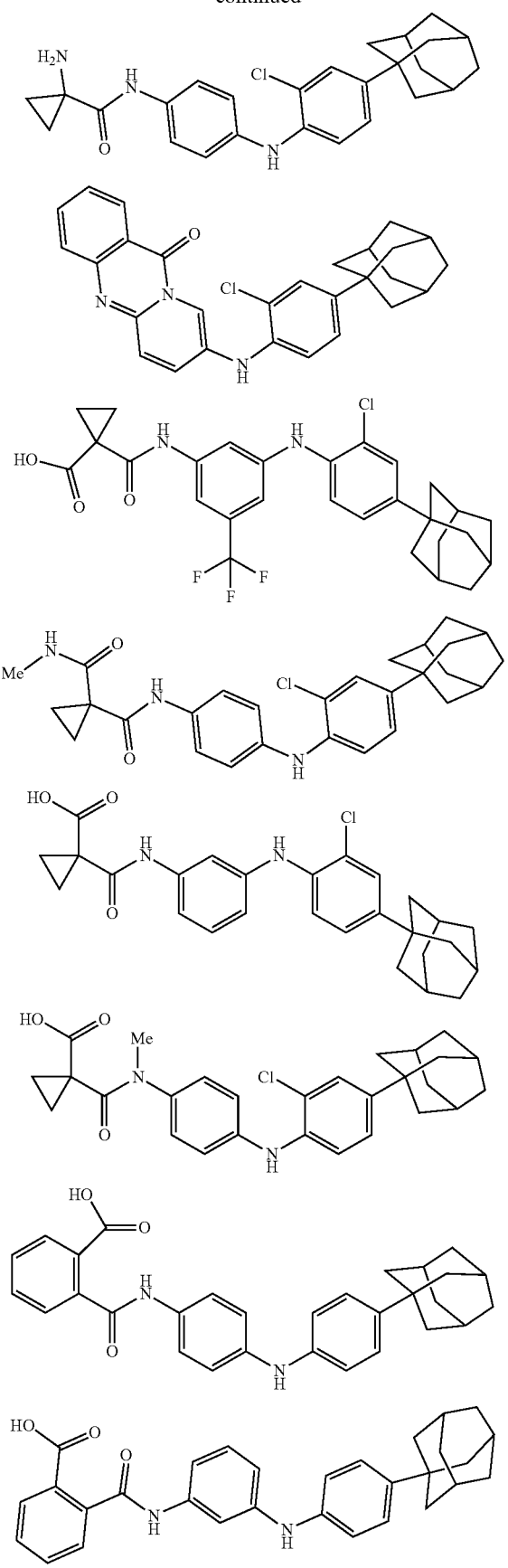
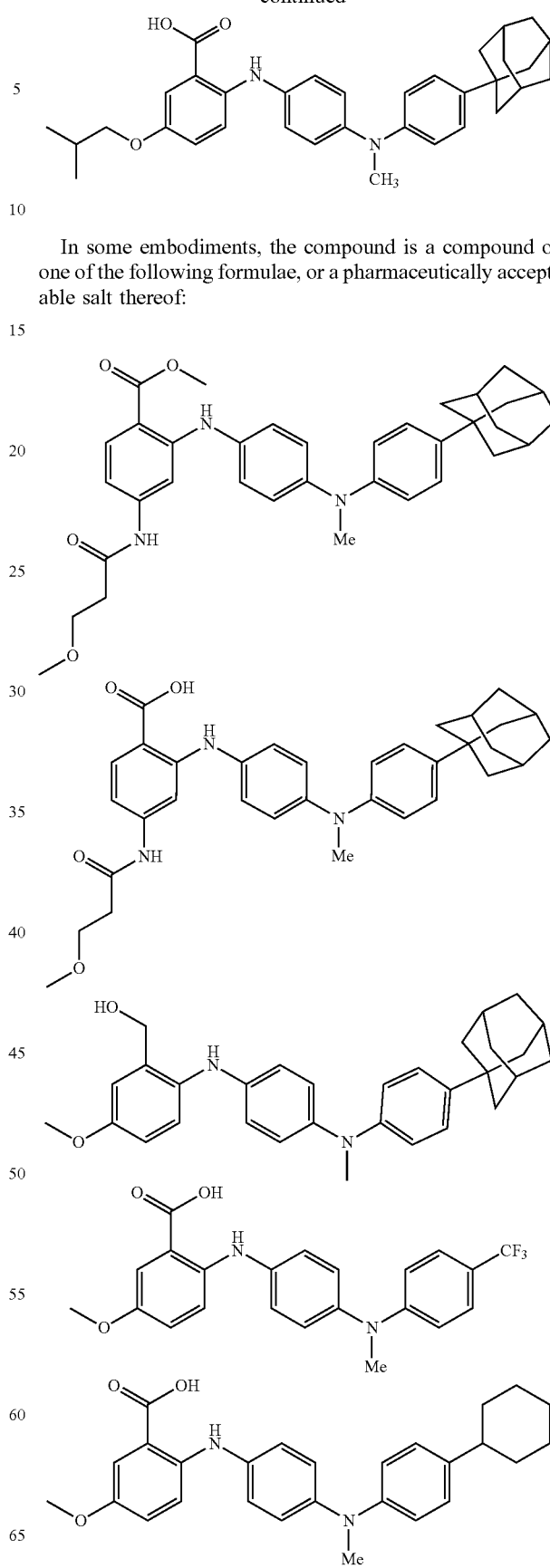
In some embodiments, the compound is a compound of one of the following formulae, or a pharmaceutically acceptable salt thereof:

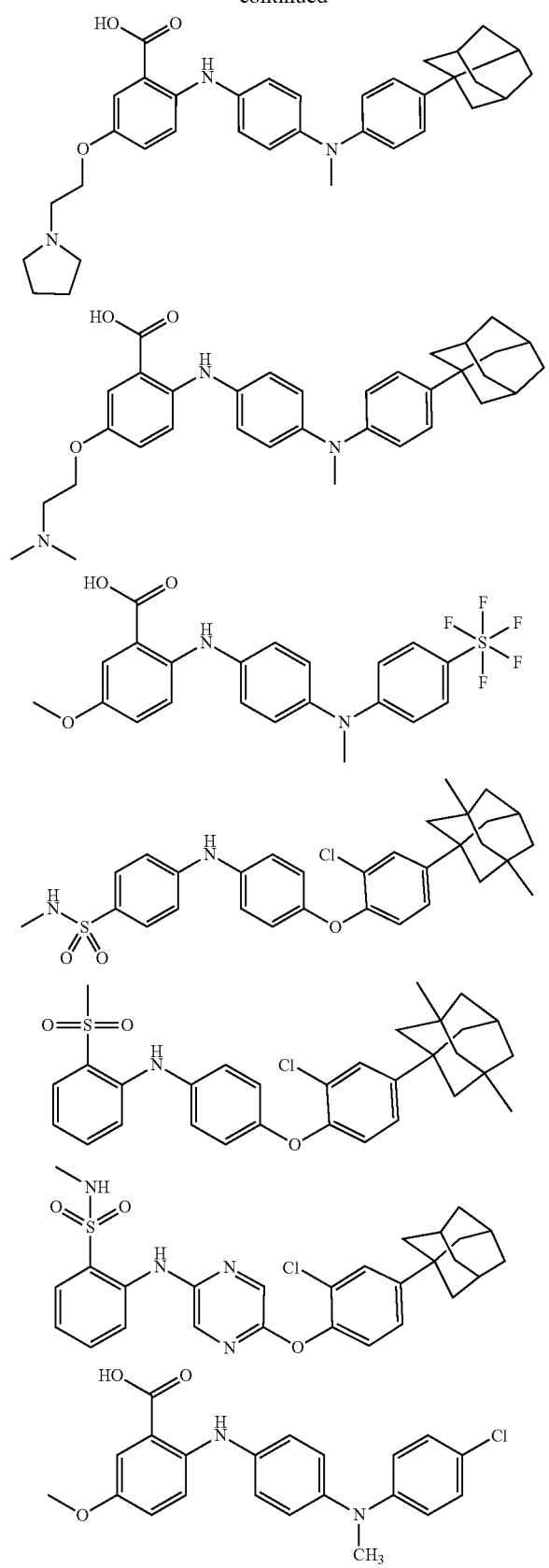
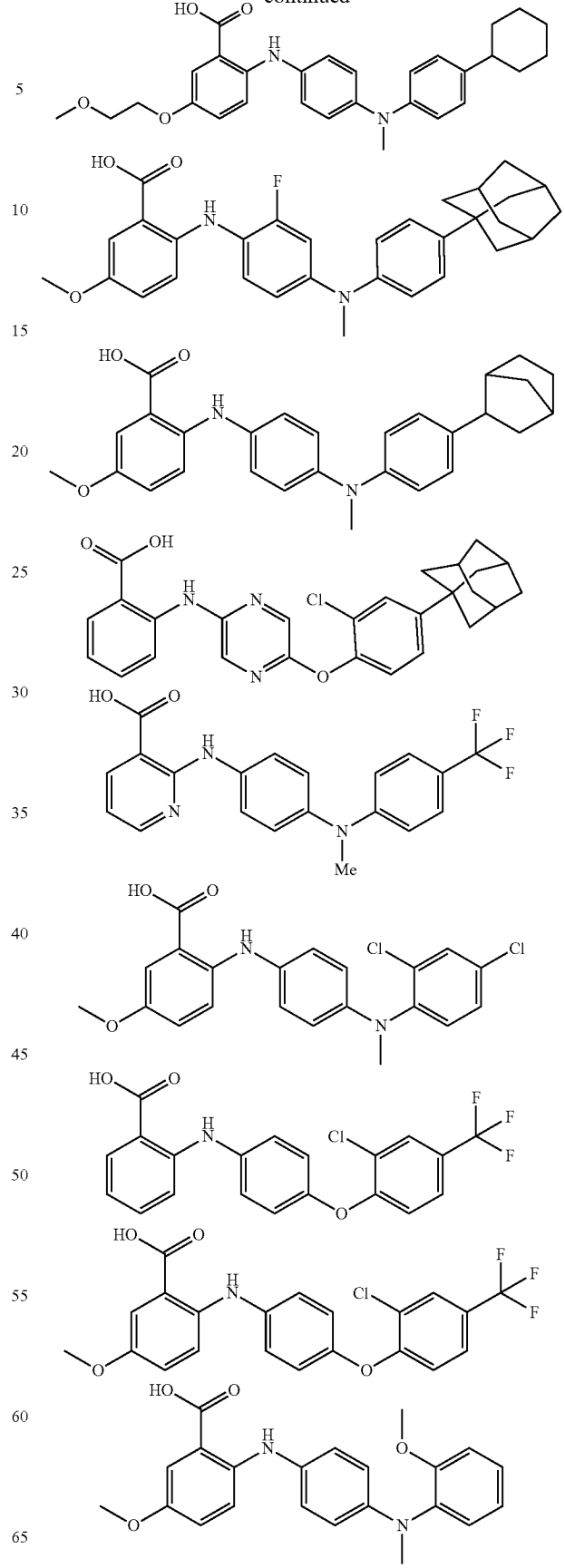

87
-continued
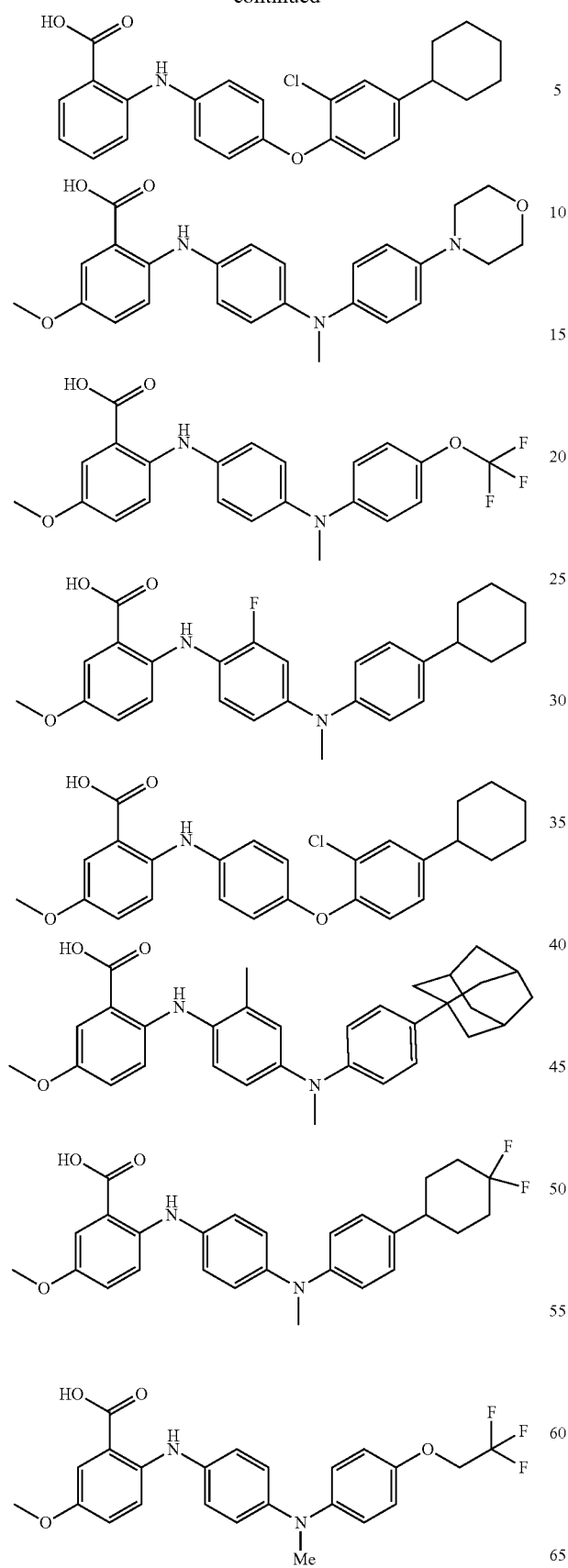
88
-continued
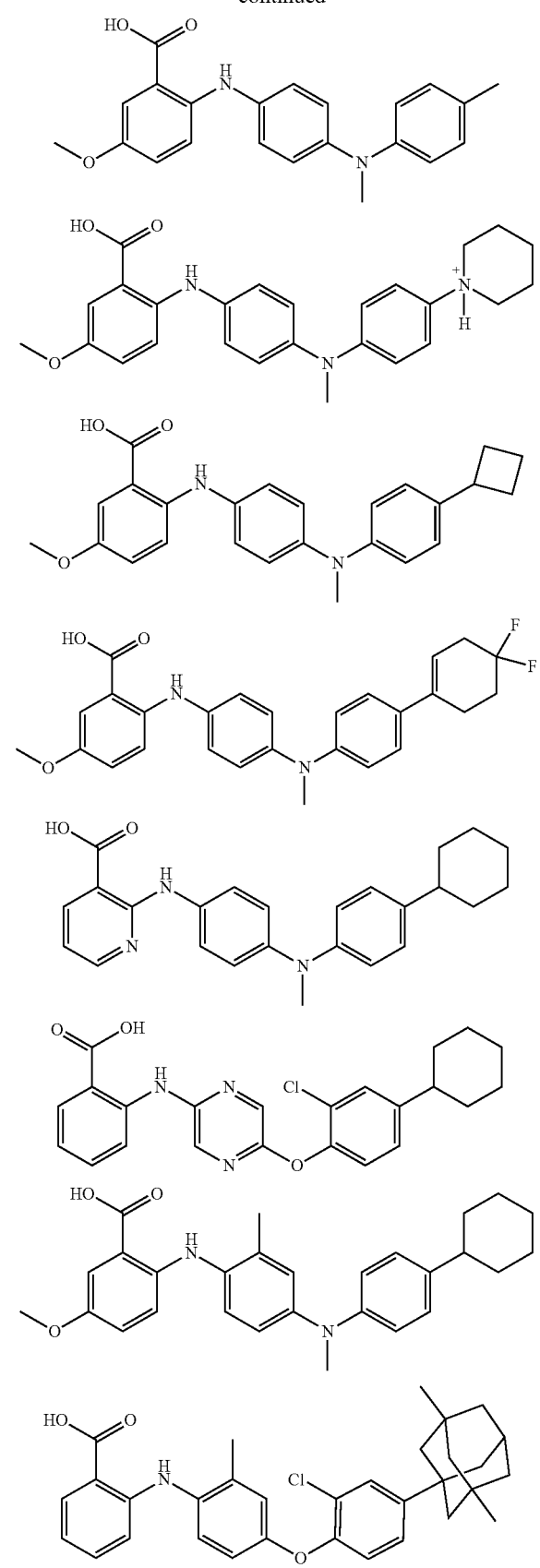

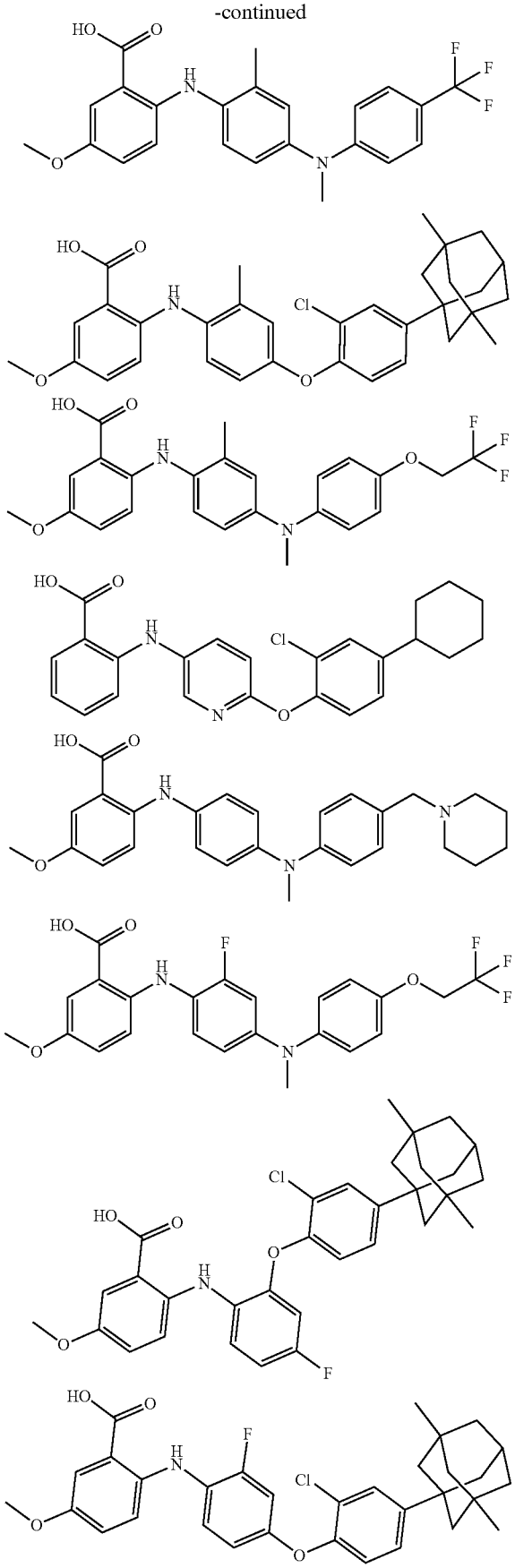
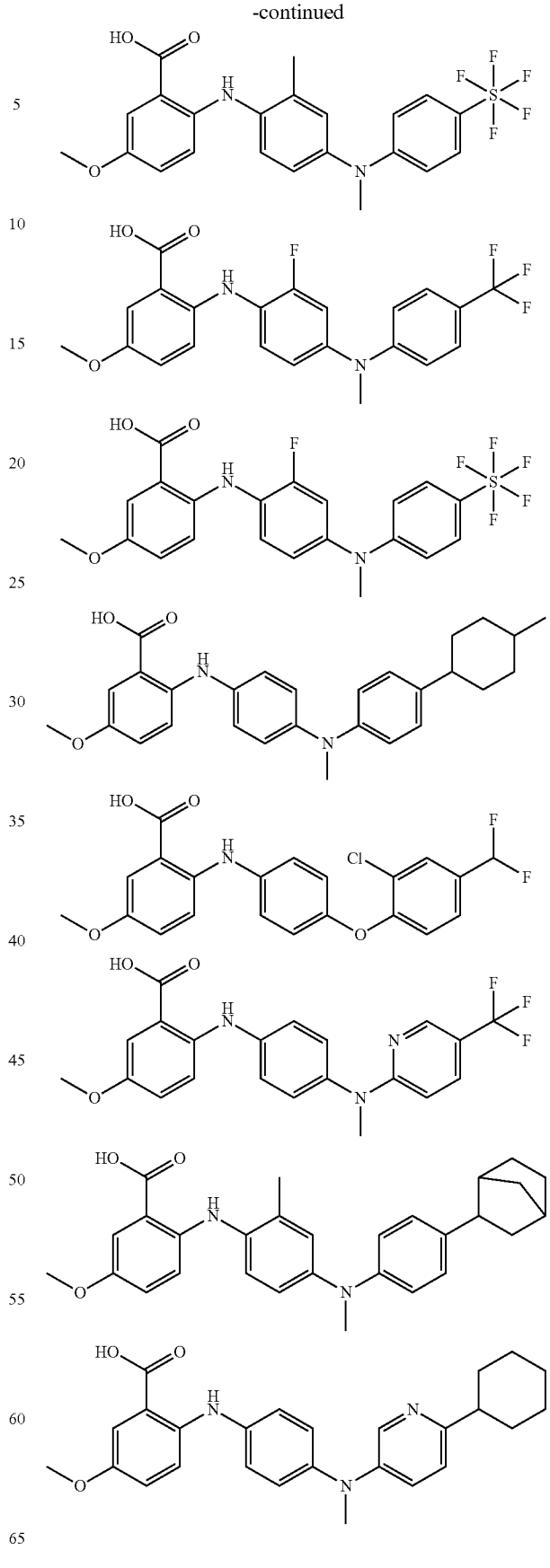

-continued
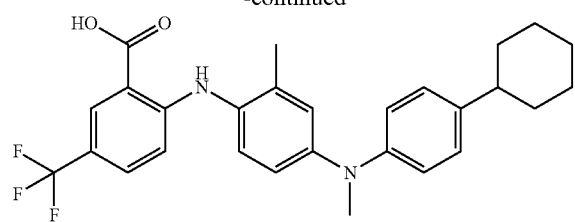
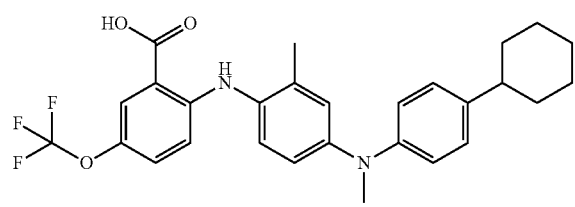
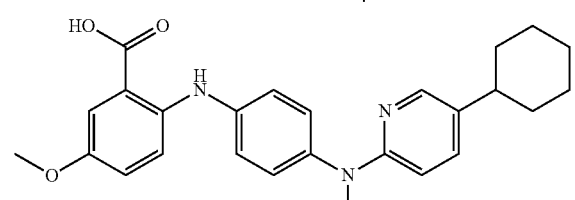
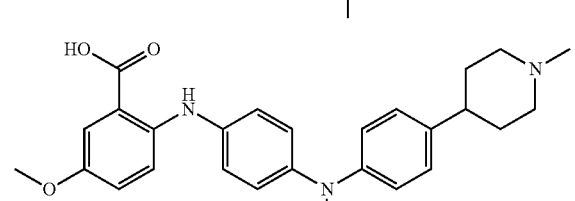
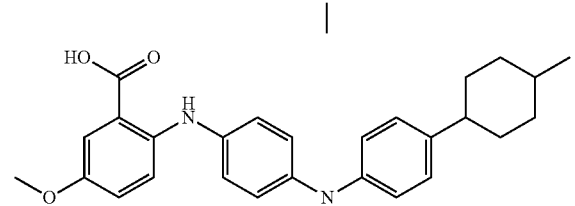
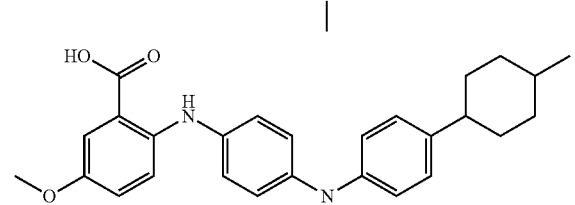
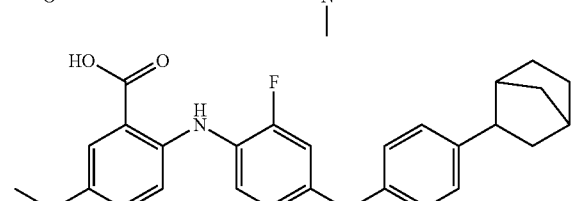
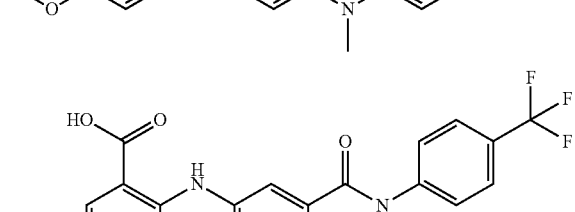
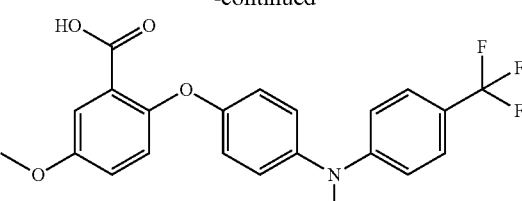
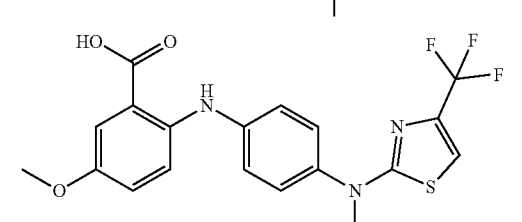
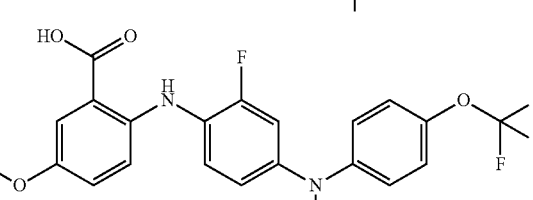
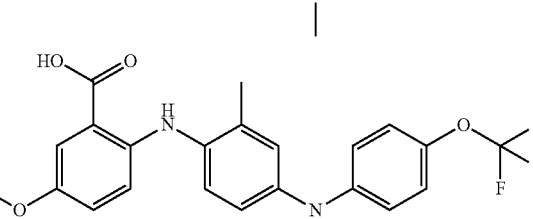
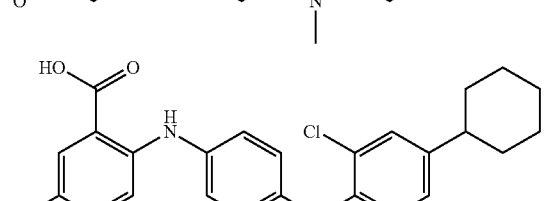
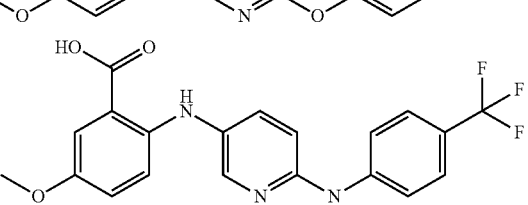
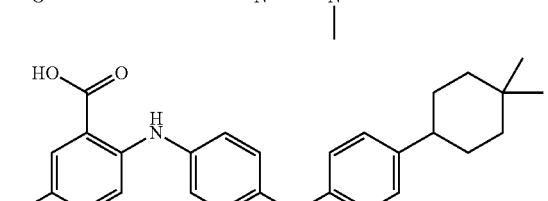
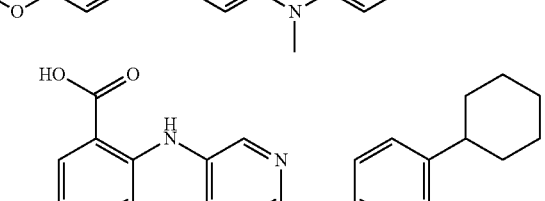

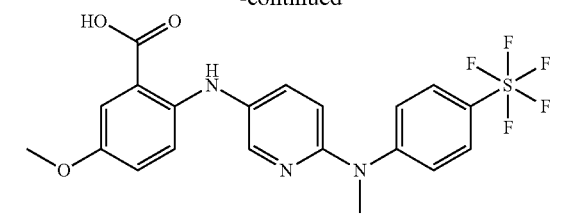
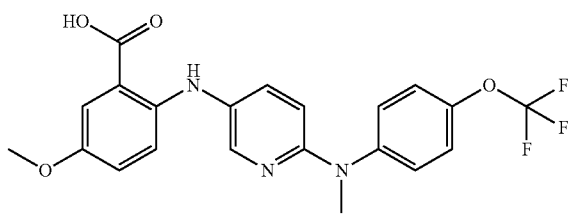
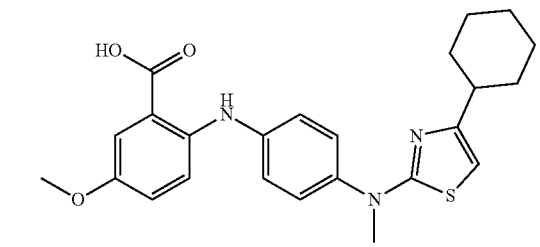
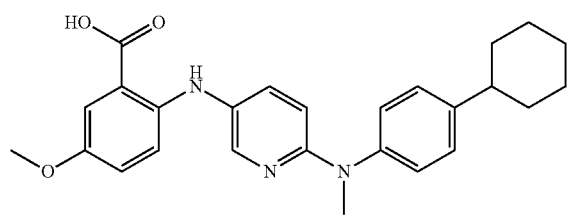
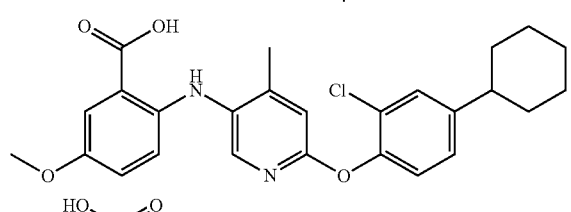
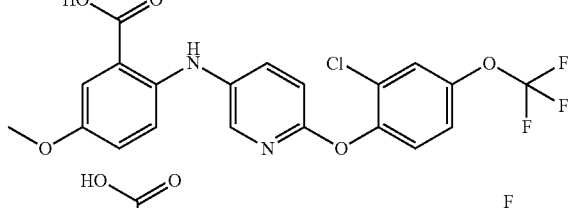
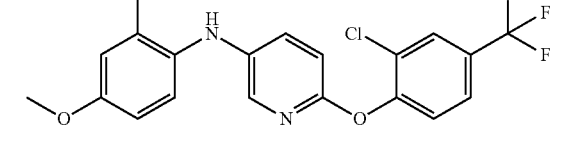
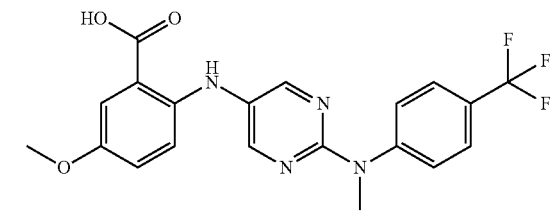
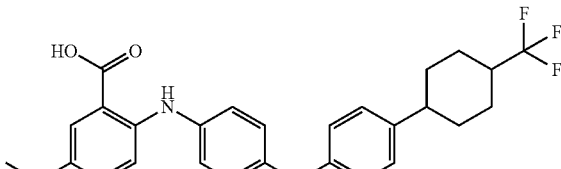
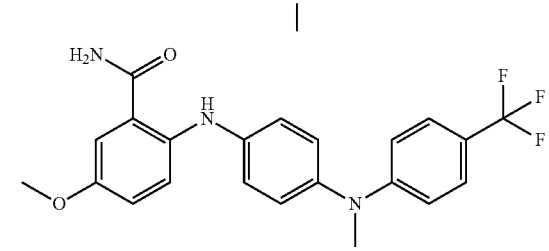
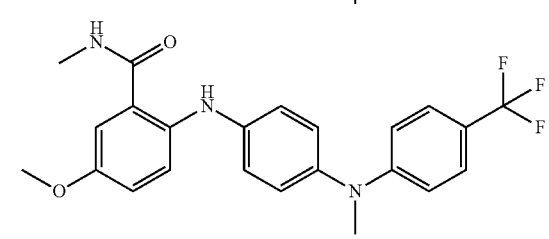
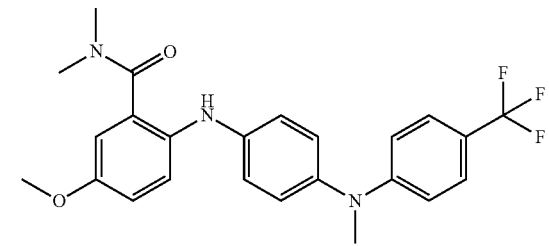
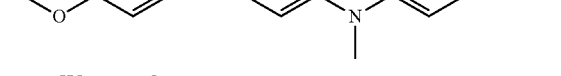
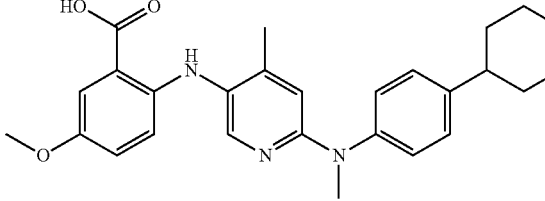
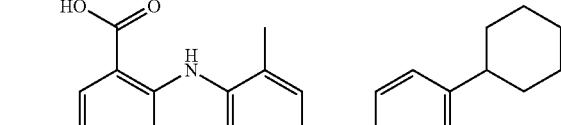
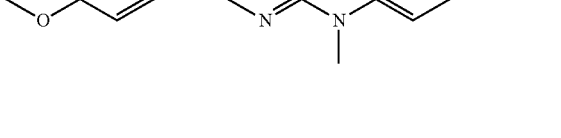
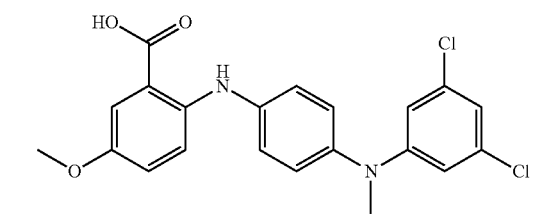

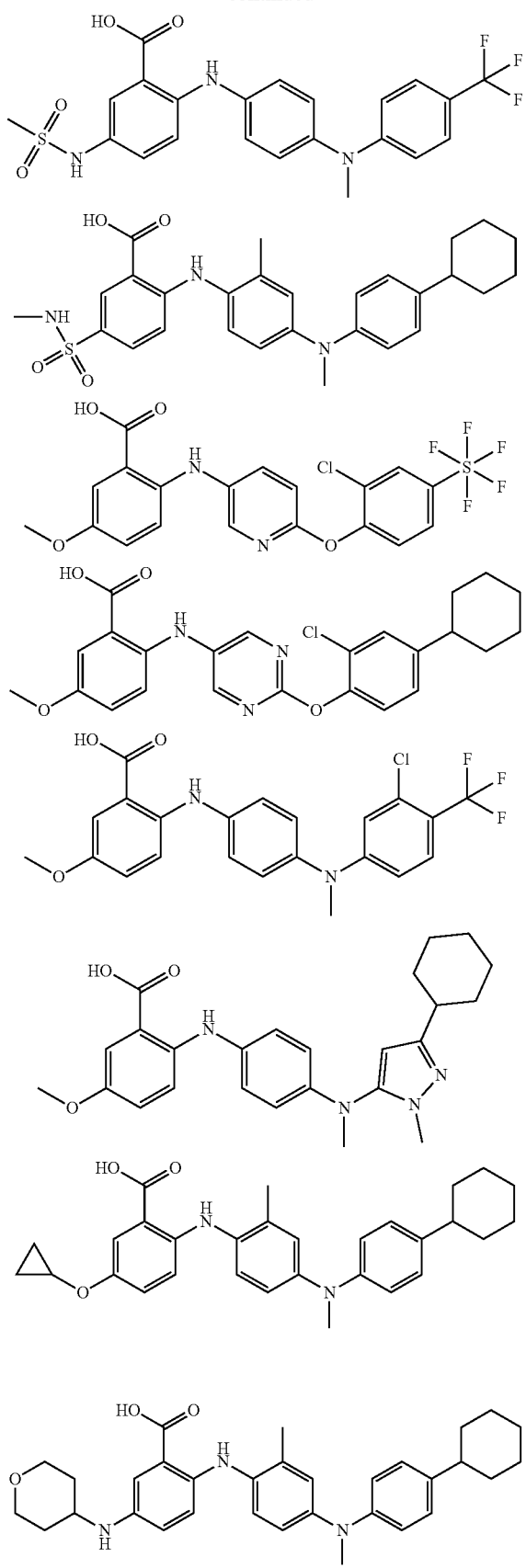
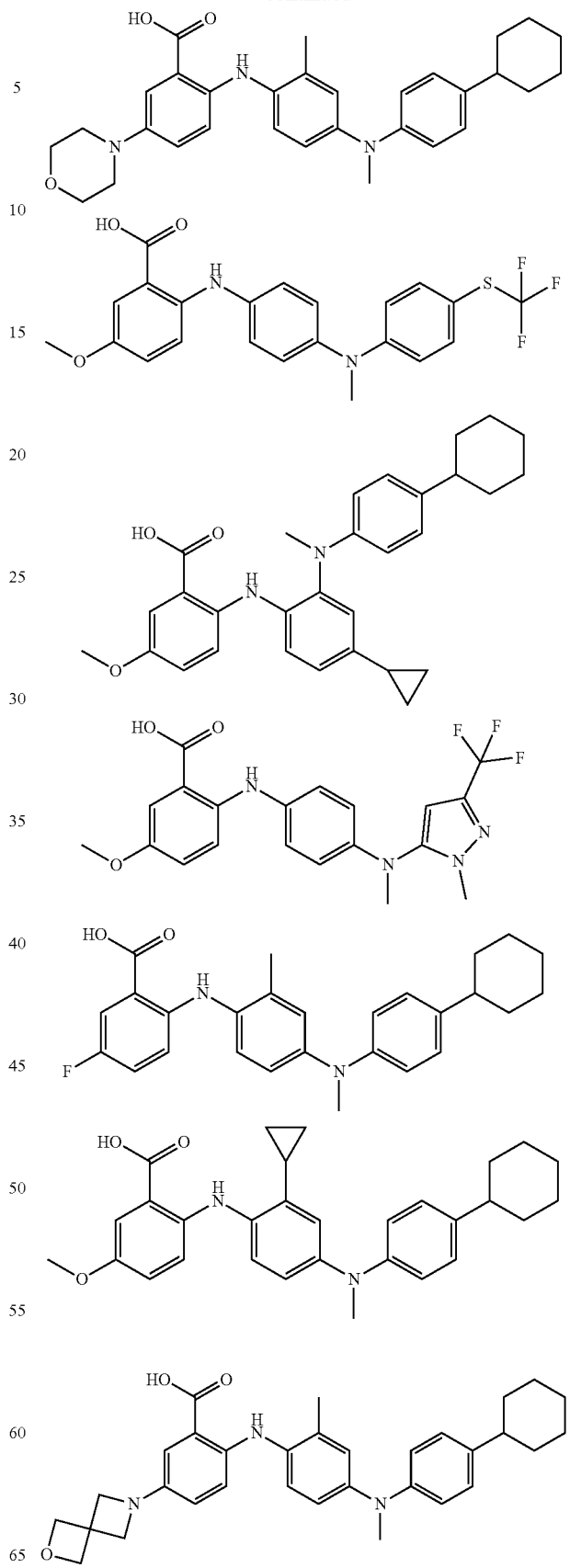

-continued
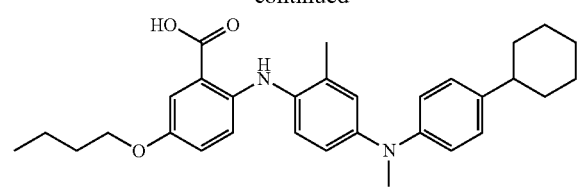
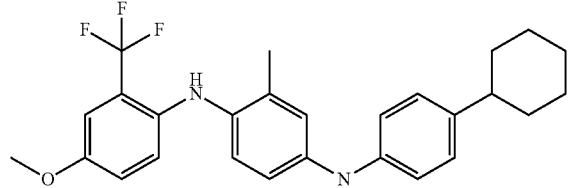
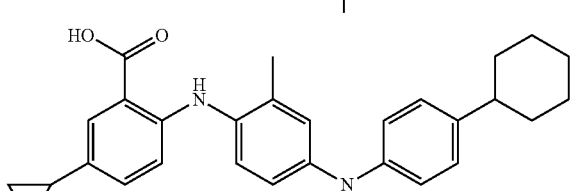
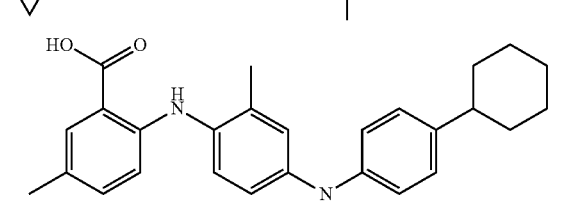
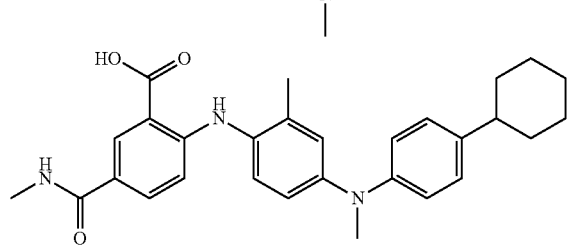
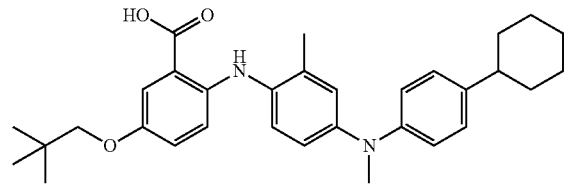
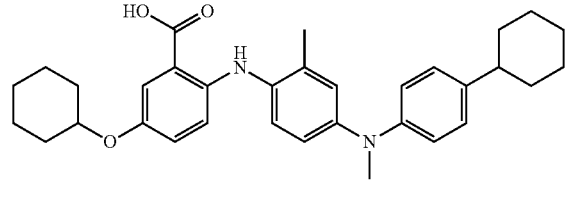
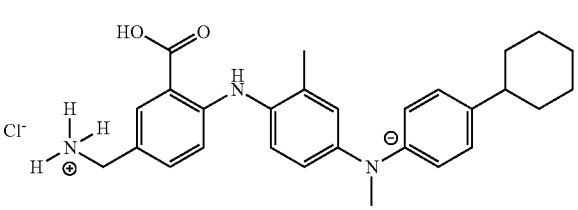
-continued
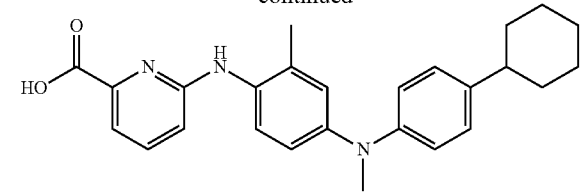
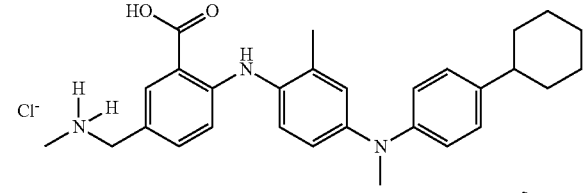
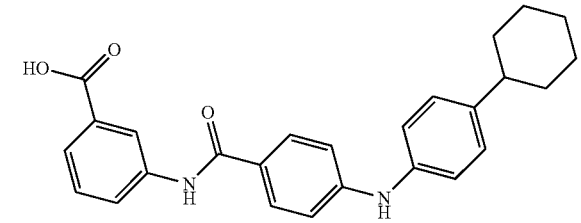
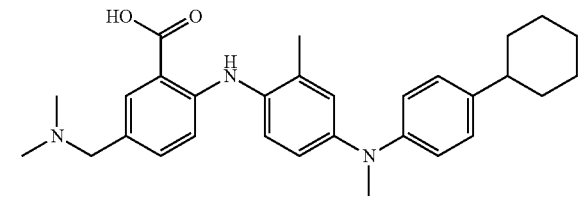
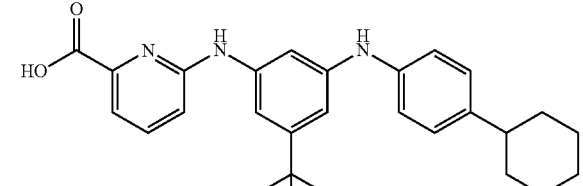
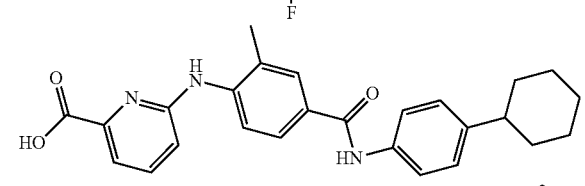
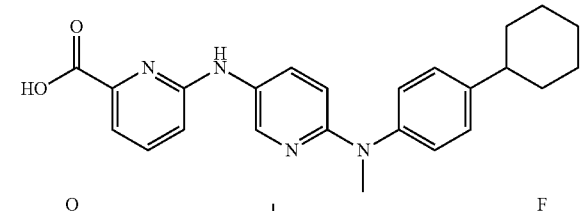
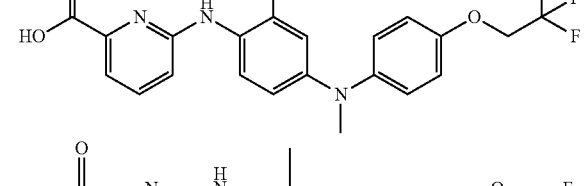
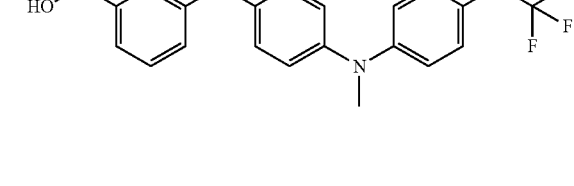

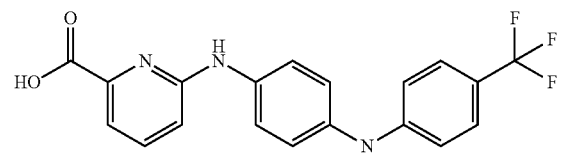
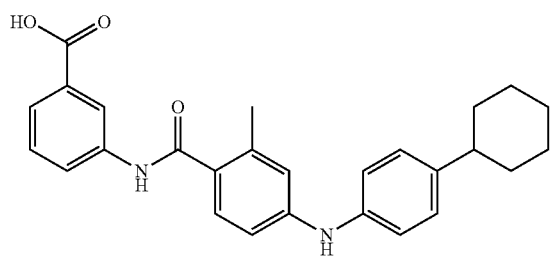
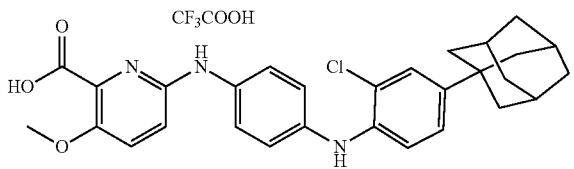
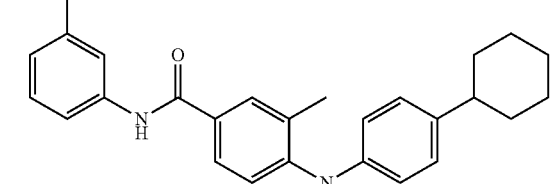
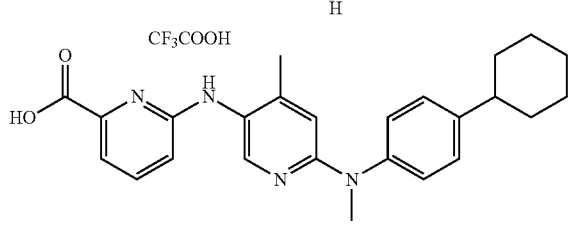
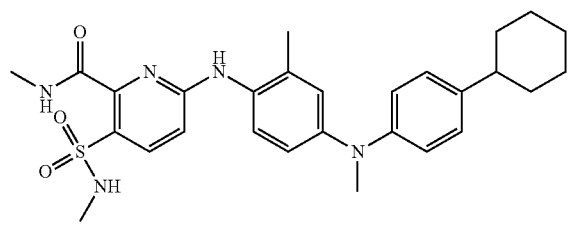
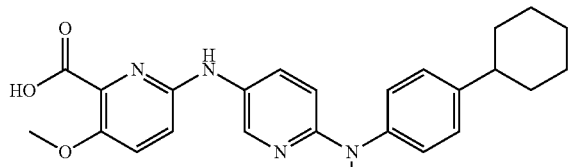
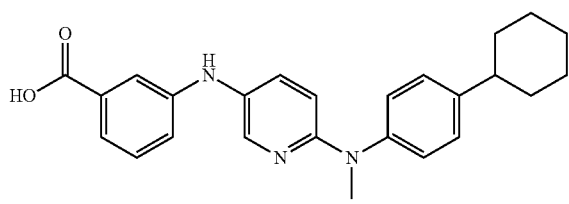
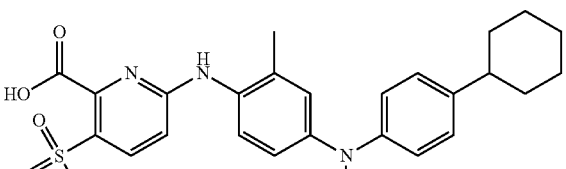
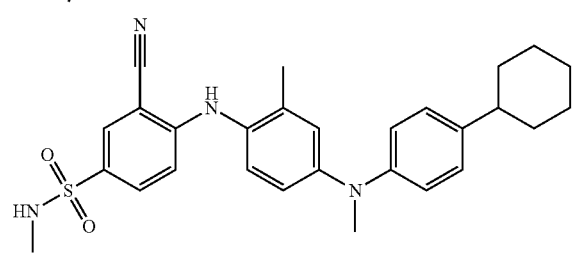
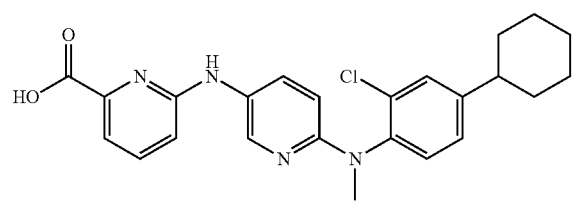
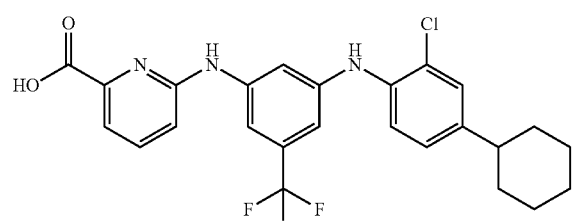
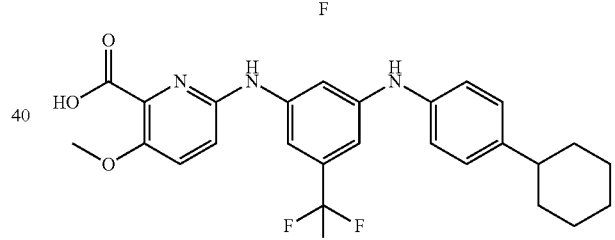
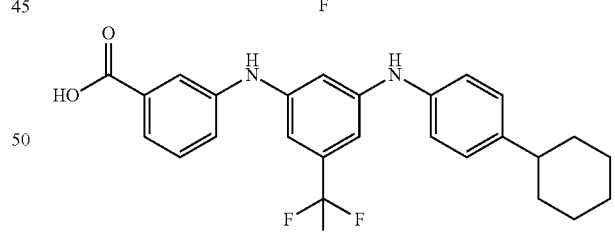
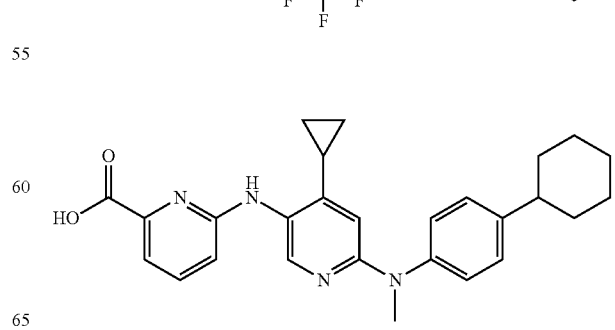

101
-continued
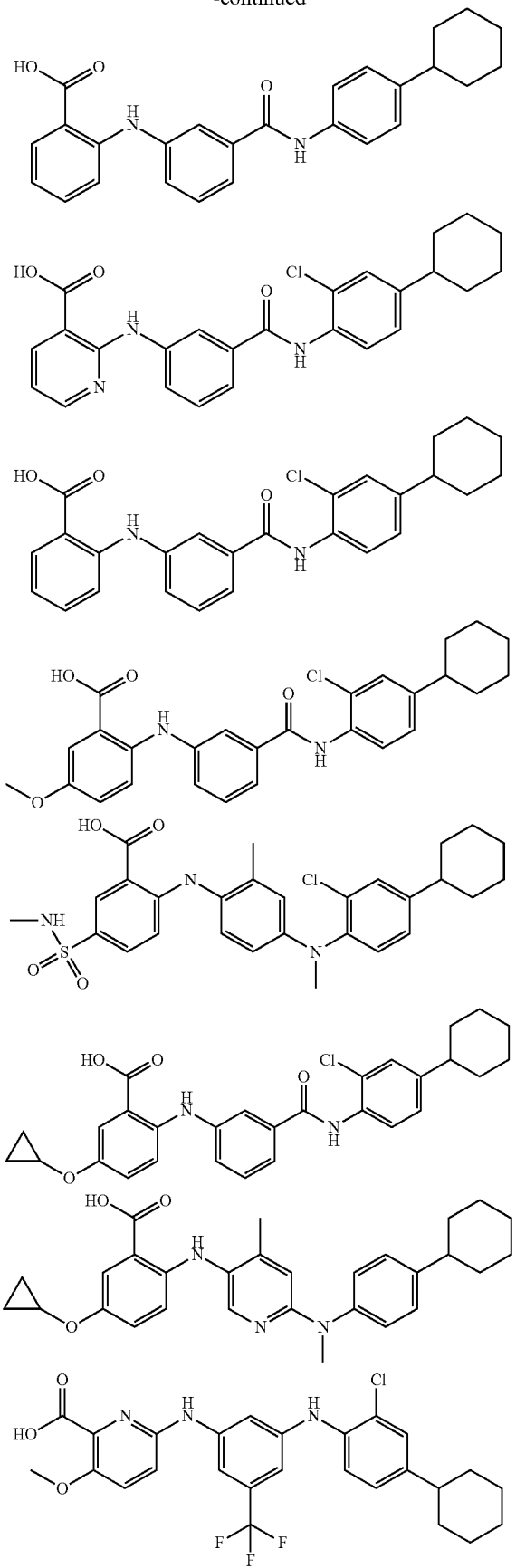
102
-continued
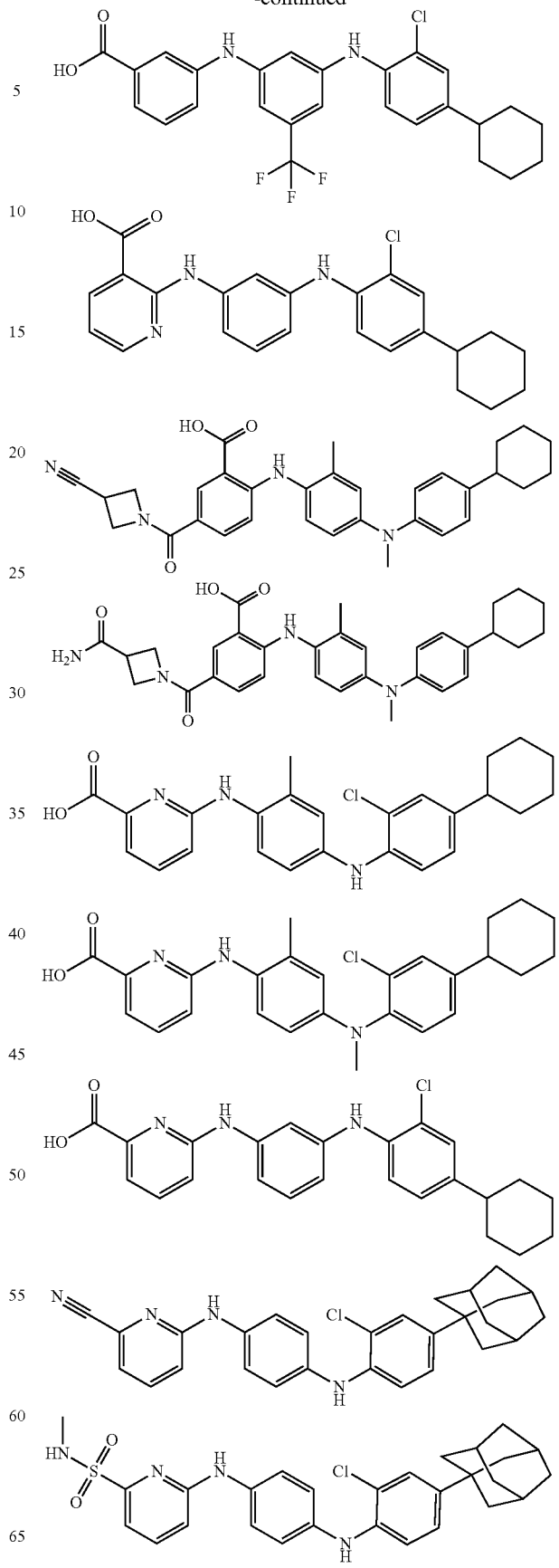

-continued

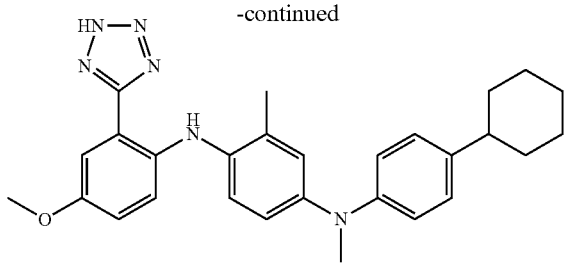

The compounds, or any of the embodiments thereof, can be provided in the form of a composition such as a pharmaceutical composition that includes the compound, or a salt such as a pharmaceutically acceptable salt thereof, and at least one additional agent such as a pharmaceutically acceptable carrier.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated that features described as embodiments of the compounds of Formula (I) can be combined in any suitable combination.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group. When the term is used to refer to a carbocyclic ring (e.g., aryl or cycloalkyl), all of the ring atoms are carbon atoms. When the term is used to refer to a heterocyclic ring (e.g., heteroaryl or heterocycloalkyl), one or more of the ring atoms (e.g., 1, 2, 3, or 4) are heteroatoms (e.g., nitrogen, oxygen or sulfur) and the remainder (e.g., n–1, n–2, n–3, or n–4) are carbon atoms.

At various places in the present specification, variables defining divalent linking groups are described. It is specifically intended that each linking substituent include both the forward and backward forms of the linking substituent. For example, —NR(CR'R")$_n$— includes both —NR(CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. The term "optionally substituted" means unsubstituted or substituted. The term "substituted" means that a hydrogen atom is removed and replaced by a substituent. A single divalent substituent, e.g., oxo, can replace two hydrogen atoms.

The term "Cn-m" indicates a range which includes the endpoints, wherein n and m are integers and indicate the number of carbons. Examples include $C_{1-4}$, $C_{1-6}$ and the like. Whenever the term is used intended to describe each member included in the group, $C_n$ through $C_m$ as if each had been explicitly set forth. For example, the term $C_{1-6}$ is intended to describe each of the members $C_1$, $C_2$, $C_3$, $C_4$, $C_5$ and $C_6$.

The term "alkyl" employed alone or in combination with other terms, refers to a saturated hydrocarbon group that may be straight-chain or branched. The term "Cn-m alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "Cn-m alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "Cn-m alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene", employed alone or in combination with other terms, refers to a divalent alkyl linking group. An alkylene group formally corresponds to an alkane with two C—H bond replaced by points of attachment of the alkylene group to the remainder of the compound.

The term "Cn-m alkylene" refers to an alkylene group having n to m carbon atoms. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl and the like.

The term "alkoxy", employed alone or in combination with other terms, refers to a group of formula —O-alkyl, wherein the alkyl group is as defined above. The term "Cn-m alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms.

The terms "halo" or "halogen", used alone or in combination with other terms, refers to fluoro, chloro, bromo and iodo.

The term "haloalkyl" refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CCl_3$, $CHCl_2$, $C_2Cl_5$ and the like. In some embodiments, the haloalkyl group is a fluoroalkyl group.

The term "haloalkoxy", employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "amino" refers to a group of formula —$NH_2$.

The term "carbamyl" refers to a group of formula —C(=O)$NH_2$.

The term "carbonyl", employed alone or in combination with other terms, refers to a —C(=O)— group, which also may be written as C(O).

The term "carbonyl", employed alone or in combination with other terms, refers to a —C(=O)— group.

The term "carboxy" refers to a group of formula —C(=O)OH.

The term "oxo" refers to oxygen as a divalent substituent, forming a carbonyl group, or attached to a heteroatom forming a sulfoxide or sulfone group, or an N-oxide group.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2, 3 or 4 fused rings). The term "Cn-m aryl" refers to an aryl group having from n to m ring carbon atoms. Aryl groups include, e.g., phenyl, naphthyl, indenyl and the like. In some embodiments, aryl groups have from 6 to 10 carbon atoms. In some embodiments, the aryl group is phenyl.

The term "arylalkylenyl," employed alone or in combination with other terms, refers to an aryl group, as defined herein, attached to an alkylene group, as defined herein. The term "$C_{n-m}$ aryl $C_{o-p}$ alkylenyl" refers to an arylalkylenyl group with an aryl group having from n to m ring carbon atoms attached to an alkylene group having from o to p carbon atoms. Arylalkylenyl groups include, e.g., benzyl, phenethyl and the like.

The term "heteroaryl" or "heteroaromatic" employed alone or in combination with other terms, refers to a monocyclic or polycyclic aromatic heterocycle having at least one heteroatom ring member selected from sulfur, oxygen and nitrogen. In some embodiments, the heteroaryl is a 5- or 6-membered monocyclic heteroaryl ring. In some embodiments, the heteroaryl is 5- to 10-membered $C_{1-9}$ heteroaryl, which is monocyclic or bicyclic and which has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1, 2, 3, or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. Example heteroaryl groups include, but are not limited to, pyridine, pyrimidine, pyrazine, pyridazine, pyrrole, pyrazole, azolyl, oxazole, thiazole, imidazole, furan, thiophene, quinoline, isoquinoline, indole, benzothiophene, benzofuran, benzisoxazole, imidazo[1,2-b]thiazole, imidazo[1,2-b]pyridazine, purine, furopyridine (e.g., furo[3,2-b]pyridine), thienopyridine (e.g. thieno[3,2-b]pyridine) or the like.

A five-membered heteroaryl ring is a heteroaryl group having five ring atoms wherein one or more (e.g., 1, 2, 3 or 4) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl and pyridazinyl.

The term "heteroarylalkylenyl," employed alone or in combination with other terms, refers to heteroaryl group, as defined herein, attached to an alkylene group, as defined herein. The term "n-m membered heteroaryl $C_{o-p}$ alkylenyl" refers to a heteroaryl group having from n to m ring atoms attached to an alkylene group having from o to p carbon atoms. Heteroarylalkylenyl groups include, e.g., pyridylmethyl, pyridylethyl and the like.

The term "cycloalkyl", employed alone or in combination with other terms, refers to a non-aromatic, saturated, monocyclic, bicyclic or polycyclic hydrocarbon ring system, including cyclized alkyl and alkenyl groups. The term "Cn-m cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have, e.g., 3, 4, 5, 6, 7, 8, 9 or 10 ring-forming carbons ($C_{3-10}$) or 3, 4, 5, 6 or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally substituted by oxo or sulfido. Cycloalkyl groups also include cycloalkylidenes. Example cycloalkyl groups include cyclopropyl, cyclobutyl, cyclopentyl, cyclohexyl, cyclopentenyl, cyclohexenyl, cyclohexadienyl, norbornyl, norpinyl, bicyclo[2.1.1]hexanyl, bicyclo[1.1.1]pentanyl, adamantyl and the like. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like, for example indanyl or tetrahydronaphthyl. A cycloalkyl group containing a fused aromatic ring can be attached through any ring-forming atom including a ring-forming atom of the fused aromatic ring.

The term "arylalkylenyl," employed alone or in combination with other terms, refers to a cycloalkyl group, as defined herein, attached to an alkylene group, as defined herein. The term "Cn-m cycloalkyl $C_{o-p}$ alkylenyl" refers to an cycloalkylalkylenyl group with a cycloalkyl group having from n to m ring carbon atoms attached to an alkylene group having from o to p carbon atoms. Cycloalkylalkylenyl groups include, e.g., cyclopropylmethyl, cyclopropylethyl, cyclobutylmethyl, cyclohexylmethyl, and the like.

The term "heterocycloalkyl", employed alone or in combination with other terms, refers to non-aromatic ring or ring system, which may optionally contain one or more alkenylene groups as part of the ring structure, which has at least one heteroatom ring member independently selected from nitrogen, sulfur oxygen and phosphorus, and which has 4-10 ring members, 4-7 ring members or 4-6 ring members. Included in heterocycloalkyl are monocyclic 4-, 5-, 6- and 7-membered heterocycloalkyl groups. Heterocycloalkyl groups can include mono- or bicyclic (e.g., having two fused or bridged rings) ring systems. In some embodiments, the heterocycloalkyl group is a monocyclic group having 1, 2 or 3 heteroatoms independently selected from nitrogen, sulfur and oxygen. Examples of heterocycloalkyl groups include azetidine, pyrrolidine, piperidine, piperazine, morpholine, thiomorpholine, pyran, azepane, tetrahydropyran, tetrahydrofuran, dihydropyran, dihydrofuran and the like. Ring-forming carbon atoms and heteroatoms of a heterocycloalkyl group can be optionally substituted by oxo or sulfido (e.g., C(=O), S(=O), C(S) or S(=O)$_2$, etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include 1, 2, 3, 4-tetrahydroquinoline, dihydrobenzofuran, azetidine, azepane, diazepan (e.g., 1,4-diazepan), pyrrolidine, piperidine, piperazine, morpholine, thiomorpholine, pyran, tetrahydrofuran and di- and tetra-hydropyran.

The term "heterocycloalkylalkylenyl," employed alone or in combination with other terms, refers to heterocycloalkyl group, as defined herein, attached to an alkylene group, as defined herein. The term "n-m membered heterocycloalkyl $C_{o-p}$ alkylenyl" refers to a heterocycloalkyl group having from n to m ring atoms attached to an alkylene group having from o to p carbon atoms. Heteroarylalkylenyl groups include, e.g., tetrahydrofurylmethyl.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereoisomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereoisomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

The term, "compound," is meant to include all stereoisomers, geometric isomers, tautomers and isotopes of the structures depicted.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature" are understood in the art, and refer generally to a temperature, e.g., a reaction temperature, that is about the temperature of the room in which the reaction is carried out, e.g., a temperature from about 20° C. to about 30° C.

The present invention also includes salts, particularly pharmaceutically acceptable salts, of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences*, 17$^{th}$ Ed., (Mack Publishing Company, Easton, 1985), p. 1418, Berge et al., *J. Pharm. Sci.*, 1977, 66(1), 1-19 and in Stahl et al., *Handbook of Pharmaceutical Salts: Properties, Selection, and Use*, (Wiley, 2002). In some embodiments, the compounds described herein include the N-oxide forms.

The following abbreviations may be used herein: AcOH (acetic acid); Ac$_2$O (acetic anhydride); Al$_2$O$_3$ (aluminium oxide); aq. (aqueous); atm. (atmosphere(s)); Boc (t-butoxycarbonyl); Boc$_2$O (di-tert-butyldicarbonate); BOP ((benzotriazol-1-yloxy)tris(dimethylamino)phosphonium hexafluorophosphate); br (broad); c-Pr (cyclopropyl); Cbz (carboxybenzyl); calc. (calculated); CeCl$_3$.7H$_2$O (cerium (III) chloride heptahydrate); Cs$_2$CO$_3$ (cesium carbonate); CuI (copper (I) iodide); d (doublet); dd (doublet of doublets); DCM (dichloromethane); DIPEA (N,N-diisopropylethylamine); DMAP (4-dimethylaminopyridine); DMF (N,N-dimethylformamide); DMSO (dimethylsulfoxide); Et (ethyl); EtOAc (ethyl acetate); EtOH (ethanol); Fmoc (9-fluorenylmethylmethoxycarbonyl); g (gram(s)); h (hour (s)); H$_2$ (hydrogen gas); H$_2$O$_2$ (hydrogen peroxide); HATU (N,N,N',N'-tetramethyl-O-(7-azabenzotriazol-1-yl)uronium hexafluorophosphate); HBr (hydrogen bromide); HCl (hydrochloric acid or hydrogen chloride); HPLC (high performance liquid chromatography); Hz (hertz); i-Pr (isopropyl); i-PrOH (isopropyl alcohol); J (coupling constant); KOAc (potassium acetate); K$_3$PO$_4$ (potassium phosphate); K$_3$PO$_4$.H$_2$O (tripotassium phosphate hydrate); LCMS (liquid chromatography-mass spectrometry); LiAlH$_4$ (lithium tetrahydroaluminate); LiBH$_4$ (lithium tetrahydroborate); LiOH (lithium hydroxide); LiOH.H$_2$O (lithium hydroxide monohydrate); m (multiplet); M (molar); mCPBA (m-chloroperbenzoic acid); Me (methyl); MeCN (acetonitrile); MeOH (methanol); MgSO$_4$ (magnesium sulfate); MS (mass spectrometry); mg (milligram(s)); min. (minutes(s)); mL (milliliter(s)); mmol (millimole(s)); N (normal); N$_2$ (nitrogen gas); NaHCO$_3$ (sodium bicarbonate); NaIO$_4$ (sodium metaperiodate); NaN$_3$ (sodium azide); NaOH (sodium hydroxide); Na$_2$SO$_4$ (sodium sulfate); n-Bu (n-butyl); n-BuLi (n-butyllithium); NH$_4$Cl (ammonium chloride); NH$_4$OH (ammonium hydroxide); nM (nanomolar); NMR (nuclear magnetic resonance spectroscopy); Pd (palladium); Pd(dppf)Cl$_2$ ([1,1'-bis(diphenylphosphino)ferrocene]palladium(II) dichloride); Pd(OAc)$_2$ (palladium acetate); Pd(tBu$_3$P)$_2$ (bis(tri-tert-butylphosphine)palladium); pM (picomolar); Pd(PPh$_3$)$_4$ (tetrakis(triphenylphosphine)palladium(O)); PPh$_3$ (triphenylphosphine); psi (pounds per square inch); PTFE (polytetrafluoroethylene); RP-HPLC (reverse phase high performance liquid chromatography); r.t. (room temperature); s (singlet); t (triplet or tertiary); tert (tertiary); tt (triplet of triplets); TBAF (tetra-n-butylammoniumfluoride); t-Bu (tert-butyl); TEA (triethylamine); TFA (trifluoroacetic acid); THF (tetrahydrofuran); µg (microgram (s)); µL (microliter(s)); m (micromolar); wt % (weight percent).

II. SYNTHESIS

Compounds of the invention, including salts thereof, can be prepared using known organic synthesis techniques and can be synthesized according to any of numerous possible synthetic routes, such as shown in the Scheme below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure*, 6th Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry or by chromatographic methods such as high performance liquid chromatography (HPLC) or thin layer chromatography (TLC).

The Schemes below provide general guidance in connection with preparing the compounds of the invention. One skilled in the art would understand that the preparations shown in the Schemes can be modified or optimized using general knowledge of organic chemistry to prepare various compounds of the invention.

Compounds of Formula (I) can be prepared as shown in Scheme 1 by coupling an aniline of Formula (II) with a compound of formula III, wherein L is a suitable leaving group, which can include halogen, such as bromine or iodine, or a sulfonate group (alkyl or aryl sulfonate, such as methanesulfonate, trifluoromethanesulfonate, benzenesulfonate, p-toluenesulfonate, or naphthalenesulfonate). The reaction can be carried out in the presence of a base such as potassium carbonate and a copper salt such as copper (I) iodide or copper (I) oxide. The reaction can also be carried out in the presence of a suitable organometallic catalyst, e.g., using Buchwald-Hartwig cross-coupling conditions. Suitable solvents for the reaction include tetrahydrofuran, 1,4-dioxane, tolune, or 1,2-dichlorobenzene. The preferred solvent is 1,2-dichlorobenzene. The reaction can typically be performed at a temperature of 0-200° C., e.g., a temperature of 100-150° C.

The present disclosure provides, inter alia, a methods of making certain compounds of Formula (I) according to Formula (Ia) by the route shown in Scheme 1:

SCHEME 1

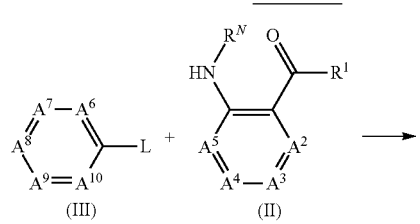

-continued

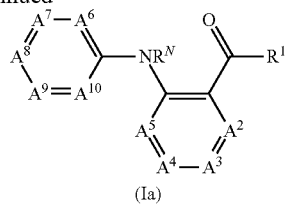

(Ia)

Compounds of Formula (II) and (III) are either commercially available, known in the literature, or may be prepared by methods known to one skilled in the art.

Certain compounds of formula (I) may be useful as intermediates in the synthesis of other compounds of formula (I). For example, compounds of formula (I) wherein $R^1$ is $OC_{1-6}$ alkyl, $OCy^{1A}$, $O(C_{1-3}$ alkylenyl)$Cy^{1A}$, $NHCy^{1A}$ $NH(C_{1-3}$ alkylenyl)$Cy^{1A}$, $N(C_{1-6}$ alkyl)$Cy^{1A}$, or $N(C_{1-6}$ alkyl)$(C_{1-3}$ alkylenyl)$Cy^{1A}$ can be used to synthesize compounds of formula (I) wherein $R^1$ is OH via hydrolysis of the ester or amide group.

It will be appreciated by one skilled in the art that the processes described are not the exclusive means by which compounds of the invention may be synthesized and that a broad repertoire of synthetic organic reactions is available to be potentially employed in synthesizing compounds of the invention. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, 2nd Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, 6th Ed. (Wiley, 2007); Trost et al. (Ed.), *Comprehensive Organic Synthesis* (Pergamon Press, 1991).

III. USES OF THE COMPOUNDS

Compounds of the invention can inhibit the autopalmitoylation of TEAD-transcription factors and, thus, are useful in treating diseases and disorders associated with activity of TEAD-transcription factors. For the uses described herein, any of the compounds of the invention, including any of the embodiments thereof, may be used.

Thus, the present disclosure provides methods of treating a TEAD-transcription factor-associated disease or disorder in an individual (e.g., patient) by administering to the individual in need of such treatment a therapeutically effective amount or dose of a compound of Formula (I), or any of the embodiments thereof, or a pharmaceutical composition thereof. The present disclosure also provides a compound of Formula (I), or any of the embodiments thereof, or a pharmaceutical composition thereof, for use in treating a TEAD-transcription factor associated disease or disorder. Also provided is the use of a compound of Formula (I), or any of the embodiments thereof, or a pharmaceutical composition thereof, in the manufacture of a medicament for treating a TEAD-transcription factor-associated disease or disorder. The disease or disorder can be one that is associated with TEAD1, TEAD2, TEAD3, or TEAD4.

A TEAD-transcription factor-associated disease can include any disease, disorder or condition that is directly or indirectly linked to expression or activity of TEAD-transcription factors, including over-expression and/or abnormal activity levels. Abnormal activity levels can be determined by comparing activity level in normal, healthy tissue or cells with activity level in diseased cells. A TEAD-transcription factor-associated disease can also include any disease, disorder or condition that can be prevented, ameliorated, inhibited or cured by modulating TEAD-transcription factor activity. In some embodiments, the disease is characterized by the abnormal activity or expression (e.g., overexpression) of TEAD-transcription factor. A TEAD-transcription factor-associated disease can also refer to any disease, disorder or condition wherein modulating the expression or activity TEAD-transcription factor is beneficial.

TEAD-transcription factor associated diseases that can be treated using the compounds of the invention include cancer. The cancers include solid tumors, e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head or neck, thyroid cancer, glioblastoma, sarcoma, bladder cancer, etc. Other TEAD-transcription factor associated diseases include hepatocellular carcinoma, medulloblastoma, cutaneous squamous cell carcinoma, lung cancer, pancreatic cancer, esophagus cancer, liver cancer, colon cancer, melanoma, or uveal melanoma. TEAD-transcription factor associated diseases also include hematological cancers, e.g., lymphoma, leukemia such as acute lymphoblastic leukemia (ALL), acute myelogenous leukemia (AML), chronic lymphocytic leukemia (CLL), chronic myelogenous leukemia (CML), diffuse large B-cell lymphoma (DLBCL), mantle cell lymphoma, non-Hodgkin lymphoma (including relapsed non-Hodgkin lymphoma, refractory non-Hodgkin lymphoma and recurrent follicular non-Hodgkin lymphoma), Hodgkin lymphoma and multiple myeloma.

The cancer can be a cancer in which abnormally proliferating cells of the cancer express one or more TEADs, for example, a cancer that expresses one or more of TEAD1, TEAD2, TEAD3, and/or TEAD4. The method can include testing cancer cells of the individual for expression of one or more TEADs, e.g., one or more of TEAD1, TEAD2, TEAD3, and/or TEAD4, and treating the cancer according to the methods described herein based on the determination that the cancer expresses TEAD1, TEAD2, TEAD3, and/or TEAD4.

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

The term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease. In one embodiment, treating or treatment includes preventing or reducing the risk of developing the disease; e.g., preventing or reducing the risk of developing a disease, condition or disorder in an individual who may be predisposed to the disease, condition or disorder but does not yet experience or display the pathology or symptomatology of the disease.

Combination Therapies

Cancer cell growth and survival can be impacted by multiple signaling pathways. Thus, it is useful to combine different chemotherapeutic agents treat such conditions. Use of combination therapy may reduce the likelihood of drug-resistance arising in a cell population, and/or reduce the toxicity of treatment.

The compounds can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

When more than one pharmaceutical agent is administered to a patient, they can be administered simultaneously, sequentially, or in combination (e.g., for more than two agents).

VI. Formulation, Dosage Forms and Administration

When employed as pharmaceuticals, the compounds of the invention can be administered in the form of pharmaceutical compositions. Thus the present disclosure provides a composition comprising a compound Formula (I), or a pharmaceutically acceptable salt thereof, or any of the embodiments thereof, and at least one pharmaceutically acceptable carrier. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel KOOLV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the compound of the invention. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

IV. Labeled Compounds and Assay Methods

The compounds of the invention can further be useful in investigations of biological processes in normal and abnormal tissues. Thus, another aspect of the present invention relates to labeled compounds of the invention (radio-labeled, fluorescent-labeled, etc.) that would be useful not only in imaging techniques but also in assays, both in vitro and in vivo, for localizing and quantitating TEAD transcription factor in tissue samples, including human, and for identifying TEAD transcription factor ligands by inhibition binding of a labeled compound. Accordingly, the present invention includes assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^3H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro labeling and competition assays, compounds that incorporate $^3H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is to be understood that a "radio-labeled" or "labeled compound" is a compound that has incorporated at least one radionuclide. In some embodiments the radionuclide is selected from the group consisting of $^3H$, $^{14}C$, $^{125}I$, $^{35}S$ and $^{82}Br$. In some embodiments, the compound incorporates 1, 2 or 3 deuterium atoms. Synthetic methods for incorporating radio-isotopes into organic compounds are known in the art.

Specifically, a labeled compound of the invention can be used in a screening assay to identify and/or evaluate compounds. For example, a newly synthesized or identified compound (i.e., test compound) which is labeled can be evaluated for its ability to bind a TEAD transcription factor by monitoring its concentration variation when contacting with the TEAD transcription factor, through tracking of the labeling. For example, a test compound (labeled) can be evaluated for its ability to reduce binding of another compound which is known to bind to a TEAD transcription factor (i.e., standard compound). Accordingly, the ability of a test compound to compete with the standard compound for binding to the TEAD transcription factor directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

V. Kits

The present disclosure also includes pharmaceutical kits useful, e.g., in the treatment or prevention of TEAD transcription factor-associated diseases or disorders, such as cancer, which include one or more containers containing a pharmaceutical composition comprising a therapeutically effective amount of a compound of Formula (I), or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

EXAMPLES

Compound Synthesis

Experimental:

The MS (Mass Spectral) data provided in the examples were obtained using the following equipment: API 2000 LC/MS/MS/Triple quad; Agilent (1260 infinity) LCMS-SQD 6120/Single quad and Shimadzu LCMS-2020/Single quad.

The NMR data provided in the examples were obtained using the equipment-$^1HNMR$: $^1HNMR$: Varian –400 MHz, JEOL –400 MHz.

The abbreviations used in the entire specification may be summarized herein below with their particular meaning.

° C. (degree Celsius); δ (delta); % (percentage); $(BOC)_2O$ (Boc anhydride); bs (Broad singlet); $CDCl_3$ (Deuterated chloroform); DCM (Dichloromethane); DMF (Dimethyl formamide); DIPEA (N, N-Diisopropyl ethylamine); DMAP (Dimethyl aminopyridine); (DMSO-d6 (Deuterated DMSO); d (Doublet); dd (Doublet of doublet); Fe (Iron powder); g or gm (gram); HATU (1-[bis(dimethylamino) methylene]-1H-1,2,3-triazolo[4,5-b]pyridinium 3-oxid hexafluorophosphate); H or $H_2$ (Hydrogen); $H_2O$ (Water); HCl (Hydrochloric acid); h or hr (Hours); Hz (Hertz); HPLC (High-performance liquid chromatography); J (Coupling constant); LiOH (Lithium hydroxide); MeOH (Methanol); mmol (Millimol); M (Molar); mL (Millilitre); mg (Milligram); m (Multiplet); mm (Millimeter); MHz (Megahertz); min (Minutes); NaH (Sodium hydride); $NaHCO_3$ (Sodium bicarbonate); $Na_2SO_4$ (Sodium sulphate); $N_2$ (Nitrogen); NMR (Nuclear magnetic resonance spectroscopy); Pd/C (palladium carbon); RT (Room Temperature); s (Singlet); TEA (Triethylamine); TFA (Trifluoroacetic acid); TLC (Thin Layer Chromatography); THF (Tetrahydrofuran); t (Triplet); rac.BINAP ((±)-2,2'-Bis(diphenylphosphino)-1,1'-binaphthalene); $Pd_2dba_3$ (Tris(dibenzylideneacetone) dipalladium(0)); XPhos (2-Dicyclohexylphosphino-2',4',6'-triisopropylbiphenyl); in vacuo (under vacuum); eq. (equivalents); ppt (precipitate); NA (not available).

A general procedure for the synthesis of certain exemplified compounds is shown in Scheme II below:

SCHEME 2

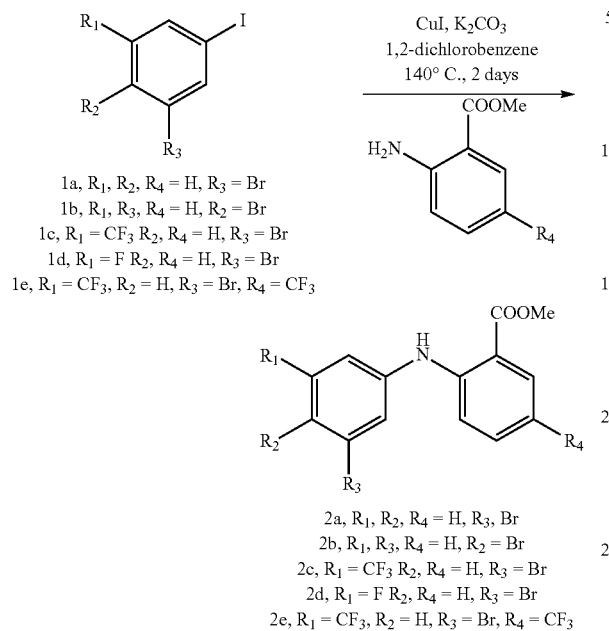

1a, $R_1, R_2, R_4 = H, R_3 = Br$
1b, $R_1, R_3, R_4 = H, R_2 = Br$
1c, $R_1 = CF_3$ $R_2, R_4 = H, R_3 = Br$
1d, $R_1 = F$ $R_2, R_4 = H, R_3 = Br$
1e, $R_1 = CF_3, R_2 = H, R_3 = Br, R_4 = CF_3$

2a, $R_1, R_2, R_4 = H, R_3, Br$
2b, $R_1, R_3, R_4 = H, R_2 = Br$
2c, $R_1 = CF_3$ $R_2, R_4 = H, R_3 = Br$
2d, $R_1 = F$ $R_2, R_4 = H, R_3 = Br$
2e, $R_1 = CF_3, R_2 = H, R_3 = Br, R_4 = CF_3$

To a solution of iodide (1 mmol) and amine (1 mmol) in 1,2-dichlorobenzene was added potassium carbonate (1.5 mmol) under nitrogen atmosphere followed by copper iodide (0.05 mmol). Resulting mixture was stirred at r.t. for 1 h and then heated at 180° C. for 2 days. After completion of the reaction resulting mixture was diluted with dichloromethane (50 mL) and filtered through bed of diatomaceous earth. The organic solution was dried with MgSO₄, concentrated in vacuo and purified by flash column chromatography with hexane/ethyl acetate (gradient of pure hexane to 20/1 hexane/ethyl acetate) as eluent Yield 40-69%.

Compound 2a was confirmed with proton NMR and Mass spectroscopy (ESI) and ($R_f$ of 0.3 with pure hexane as eluent TLC).

For Compound 2a ¹H NMR (500 MHz, CDCl₃): δ 9.46 (s, 1H), 7.98-7.94 (m, 1H), 7.40 (s, 1H), 7.35 (m, 1H), 7.28 (d, 1H), 7.19-7.13 (m, 3H), 6.79 (m, 1H), 3.90 (s, 3H) ppm. Mass (M+H, 307.1) Yield 56%.

Compound 2b (M+H 306.1), 2c (M+H 375.1), 2d (M+H 325.1), 2e (M+H 443.1) were confirmed with Mass spectroscopy (LC-MS/ESI) and also consistent on TLC with retention factor ($R_f$ of 0.3 with pure hexane as eluent).

A general procedure for synthesis of starting material for compounds CP-59 and CP-65 is shown in Scheme 3 below:

SCHEME 3

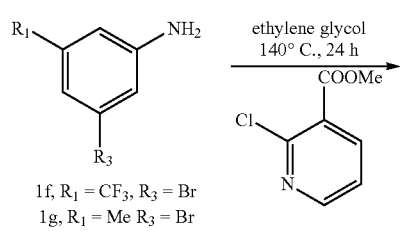

1f, $R_1 = CF_3, R_3 = Br$
1g, $R_1 = Me$ $R_3 = Br$

-continued

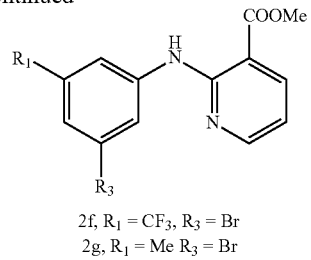

2f, $R_1 = CF_3, R_3 = Br$
2g, $R_1 = Me$ $R_3 = Br$

The requisite amine (1 mmol) and chloro-nicotinate (1 mmol) were dissolved in ethylene glycol and then heated at 140° C. for 24 h. After completion of the reaction resulting mixture was diluted with ethyl acetate (50 mL) and washed three times with 20 mL of water. The organic solution was dried with MgSO₄, concentrated in vacuo and purified by flash column chromatography with hexane/ethyl acetate (gradient of pure hexane to 15/1 hexane/ethyl acetate) as eluent. Yield 55-59%

Compound 2f (M+H, 376.1) and 2g (M+H, 322.1) were confirmed with spectroscopy (ESI) and ($R_f$ of 0.1 with pure hexane as eluent TLC)

A cross-coupling procedure used in the preparation of several example compounds is shown in Scheme 4 below.

SCHEME 4

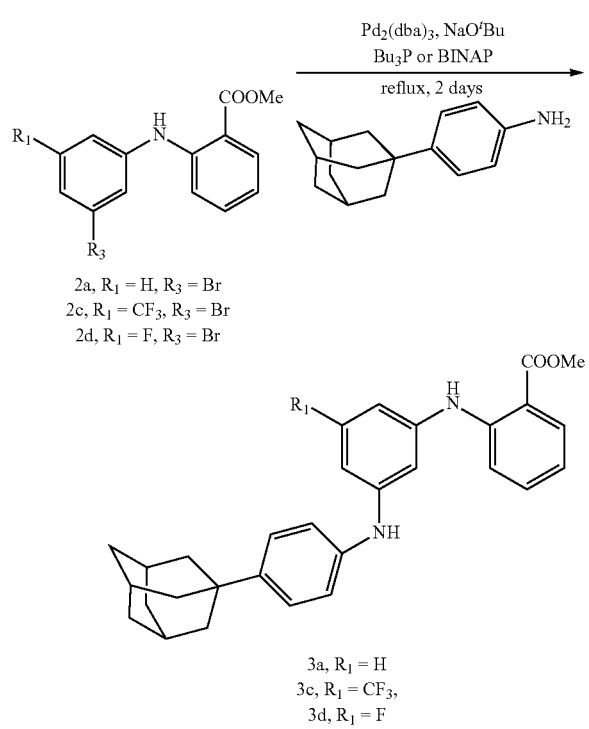

2a, $R_1 = H, R_3 = Br$
2c, $R_1 = CF_3, R_3 = Br$
2d, $R_1 = F, R_3 = Br$

3a, $R_1 = H$
3c, $R_1 = CF_3$,
3d, $R_1 = F$

To an oven-dried Schlenk tube was added amine (1 mmol) and bromide (1 mmol) and toluene (3 mL). To the above homogeneous solution t-BuONa (1.5 mmol) was added. After stirring for 5 minutes, Pd₂(dba)₃ (0.05 mmol) and Bu₃P (0.075 mmol), were added under nitrogen atmosphere. The mixture was stirred for 24 h at 110° C. After cooling to r.t., the reaction mixture was diluted with ethyl acetate (50 mL) and filtered through bed of diatomaceous earth. The organic solution was dried with MgSO$_4$, concentrated in vacuo and purified by flash column chromatography with hexane/ethyl acetate (gradient of pure hexane to 10/1 hexane/ethyl acetate) as eluent to give desired product. Yield 42-55%

For Compound 3a $^1$H NMR (500 MHz, CDCl$_3$): δ 9.45 (s, 1H), 8.01 (s, 1H), 7.5-7.7.30 (m, 2H), 7.2-7.1 (m, 2H), 6.98 (s, 1H), 6.8 (s, 1H) 6.78-6.26 (m, 4H), 5.99 (s, 1H) 3.90 (s, 3H), 2.23-1.97 (m, 15H) ppm For Compound 3c $^1$H NMR (500 MHz, CDCl$_3$): δ 9.45 (s, 1H), 8.01 (s, 1H), 7.45-7.23. (d, 2H), 7.23-7.01 (m, 6H), 6.98-7.01 (d, 2H), 6.94 (s, 1H), 3.93 (s, 3H), 5.99 (s, 1H) 2.21-1.98 (m, 15H) ppm For Compound 3d $^1$H NMR (500 MHz, CDCl$_3$): δ 9.45 (s, 1H), 8.01 (s, 1H), 7.45-7.01 (m, 4H), 6.94 (s, 1H), 6.63 (s, 1H) 6.65-6.20 (m, 4H), 5.98 (s, 1H) 3.92 (s, 3H), 2.21-1.98 (m, 15H) ppm A cross-coupling procedure used in the preparation of several example compounds is shown in Scheme 5 below.

Compound 3g confirmed with LC-MS/ESI (M+H 468.57)

A cross-coupling procedure used in the preparation of several example compounds is shown in Scheme 6 below.

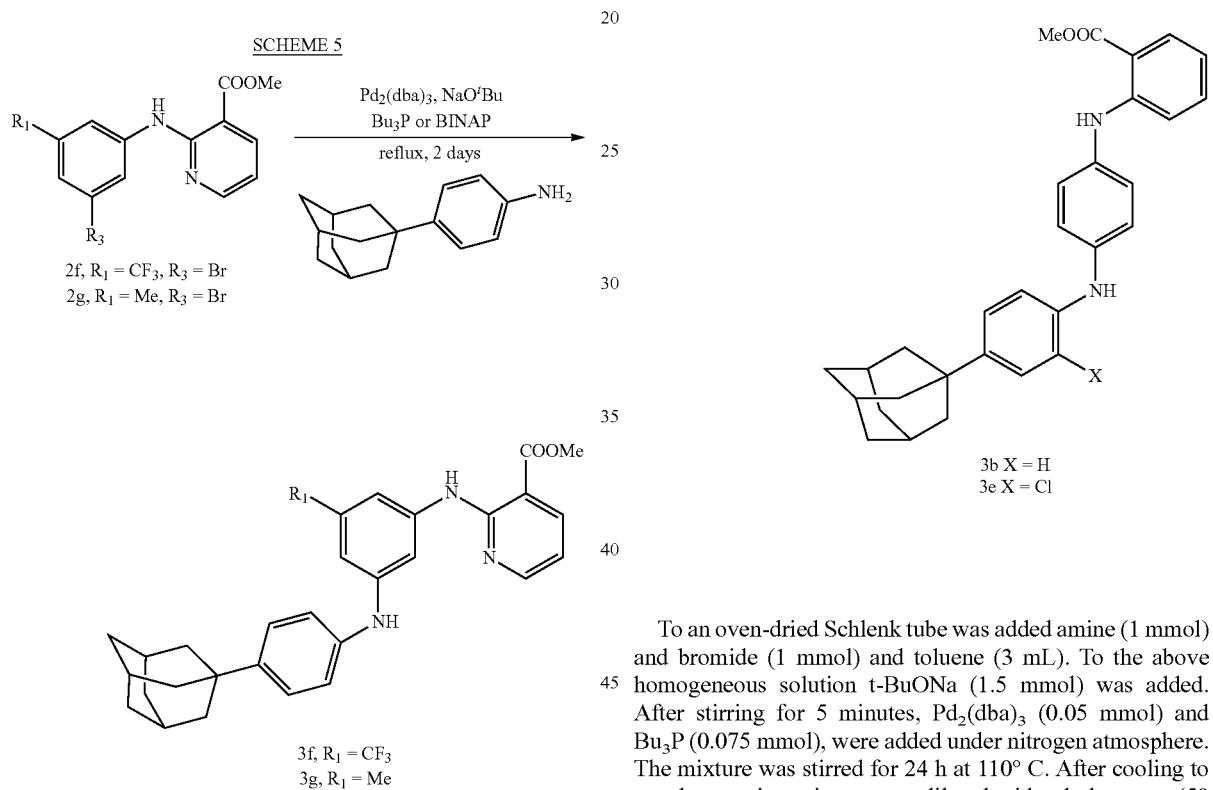

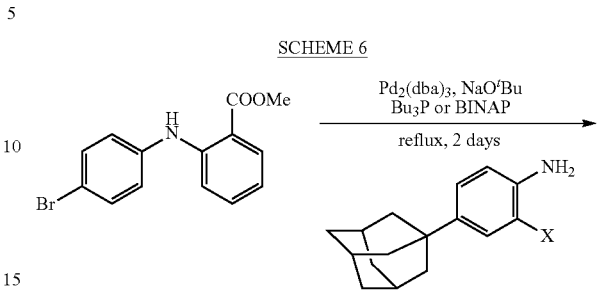

To an oven-dried Schlenk tube was added amine (1 mmol) and bromide (1 mmol) and toluene (3 mL). To the above homogeneous solution t-BuONa (1.5 mmol) was added. After stirring for 5 minutes, Pd$_2$(dba)$_3$ (0.05 mmol) and Bu$_3$P (0.075 mmol), were added under nitrogen atmosphere. The mixture was stirred for 24 h at 110° C. After cooling to r.t., the reaction mixture was diluted with ethyl acetate (50 mL) and filtered through bed of diatomaceous earth. The organic solution was dried with MgSO$_4$, concentrated in vacuo and purified by flash column chromatography with hexane/ethyl acetate (gradient of pure hexane to 10/1 hexane/ethyl acetate) as eluent to give desired product. Yield 50-54%

For Compound 3f $^1$H NMR (500 MHz, CDCl$_3$): δ 9.45 (s, 1H), 8.01 (s, 1H), 7.49-7.33. (d, 2H), 7.23-7.01 (m, 5H), 6.91-7.04 (d, 2H), 6.94 (s, 1H), 3.93 (s, 3H), 5.99 (s, 1H) 2.21-1.98 (m, 15H) ppm To an oven-dried Schlenk tube was added amine (1 mmol) and bromide (1 mmol) and toluene (3 mL). To the above homogeneous solution t-BuONa (1.5 mmol) was added. After stirring for 5 minutes, Pd$_2$(dba)$_3$ (0.05 mmol) and Bu$_3$P (0.075 mmol), were added under nitrogen atmosphere. The mixture was stirred for 24 h at 110° C. After cooling to r.t., the reaction mixture was diluted with ethyl acetate (50 mL) and filtered through bed of diatomaceous earth. The organic solution was dried with MgSO$_4$, concentrated in vacuo and purified by flash column chromatography with hexane/ethyl acetate (gradient of pure hexane to 10/1 hexane/ethyl acetate) as eluent to give desired product (39-55% yield).

For Compound 3b $^1$H NMR (500 MHz, CDCl$_3$): δ 9.45 (s, 1H), 8.01 (s, 1H), 7.67-7.56 (d, 2H), 7.2-7.1 (m, 2H), 6.98 (s, 1H), 6.82 (s, 1H) 6.78-6.26 (m, 2H), 5.99 (s, 1H) 3.92 (s, 3H), 2.23-1.97 (m, 15H) ppm For Compound 3e $^1$H NMR (500 MHz, CDCl$_3$): δ 9.46 (s, 1H), 8.05 (s, 1H), 7.79-7.56 (m, 4H), 7.2-6.99 (m, 4H), 6.98 (s, 1H, 5.99 (s, 1H) 3.94 (s, 3H), 2.23-1.97 (m, 15H) ppm Carboxylic acid compounds were prepared by hydrolysis reactions as shown in Schemes 7, 8, 9 and 10, and the experimental procedures described below.

SCHEME 7

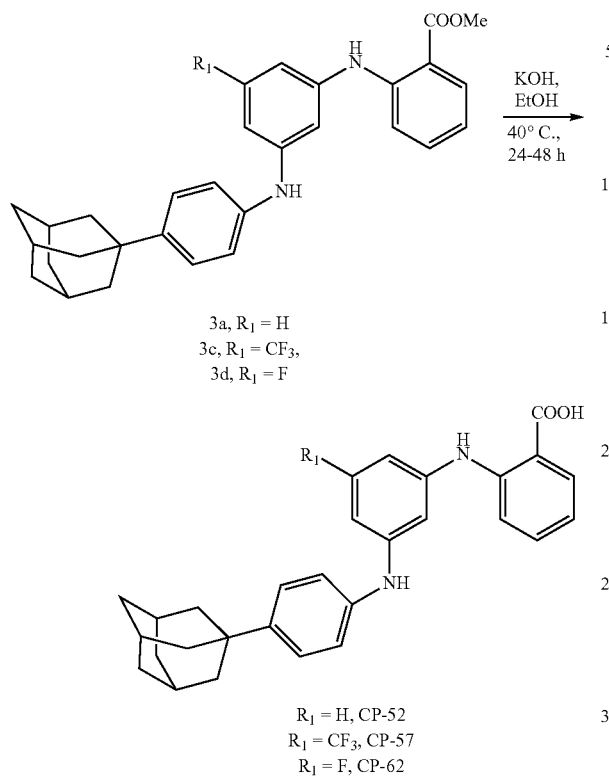

3a, R₁ = H
3c, R₁ = CF₃,
3d, R₁ = F

R₁ = H, CP-52
R₁ = CF₃, CP-57
R₁ = F, CP-62

To a solution of ester (1 mmol) in ethanol (10 mL) was added 2 mmol of 2N NaOH solution and heated at 40° C. for 24-48 h. Upon completion of the reaction, reaction was cooled on ice and acidified with 2N Hydrochloride solution and extracted three times with 10 mL of ethyl acetate. The organic solution was dried with MgSO₄, concentrated in vacuo and purified by flash column chromatography with hexane/ethyl acetate (gradient of pure hexane to 5/1 hexane/ethyl acetate) as eluent to give desired product. Yield 70-79%

CP-52 was confirmed by LC-MS (ESI, M+H 439.1).
CP-57 was confirmed by LC-MS (ESI M+H 521.1).
CP-62 was confirmed by LC-MS (ESI M+H 457.1).

SCHEME 8

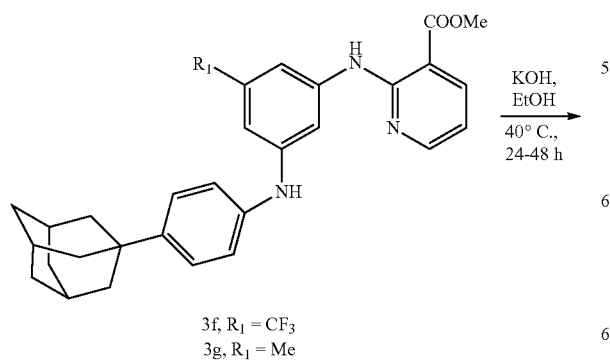

3f, R₁ = CF₃
3g, R₁ = Me

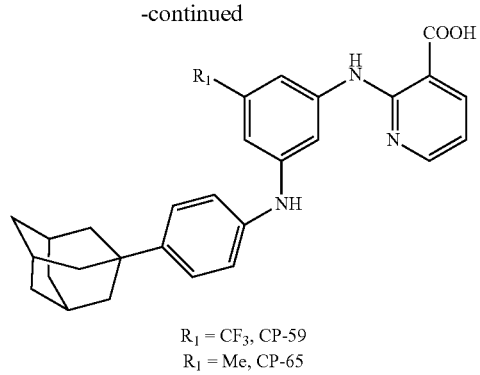

R₁ = CF₃, CP-59
R₁ = Me, CP-65

To a solution of ester (1 mmol) in ethanol (10 mL) was added 2 mmol of 2N NaOH solution and heated at 40° C. for 24-48 h. Upon completion of the reaction, reaction was cooled on ice and acidified with 2N Hydrochloride solution and extracted three times with 10 mL of ethyl acetate. The organic solution was dried with MgSO₄, concentrated in vacuo and purified by flash column chromatography with hexane/ethyl acetate (gradient of pure hexane to 5/1 hexane/ethyl acetate) as eluent to give desired product. Yield 80-83%

CP-59 was confirmed by LC-MS (ESI, M+H 509.1).
CP-65 was confirmed by LC-MS (ESI, M+H 454.1).

SCHEME 9

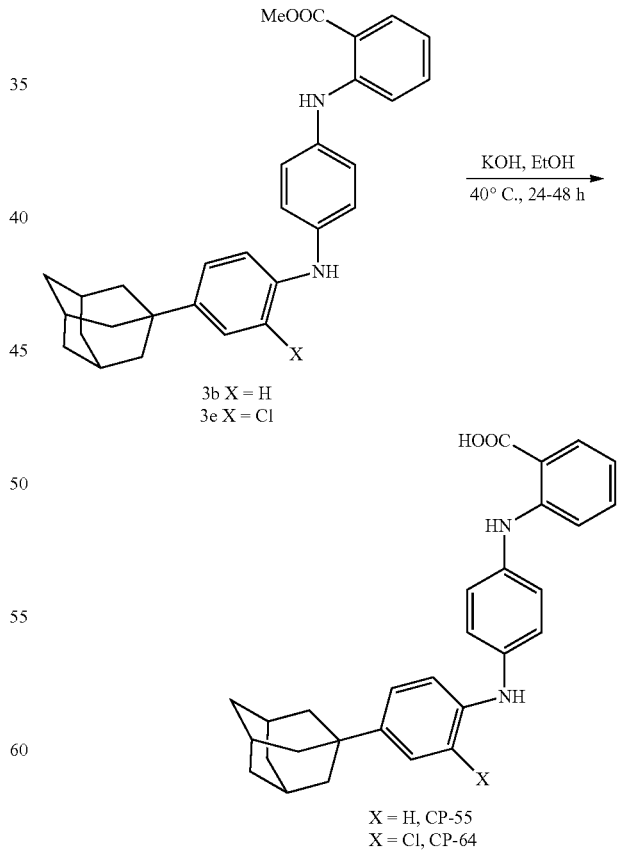

3b X = H
3e X = Cl

X = H, CP-55
X = Cl, CP-64

CP-55 was confirmed by LC-MS (ESI, M+H 439.12).
CP-64 was confirmed by LC-MS (ESI, M+H 474.1).

SCHEME 10

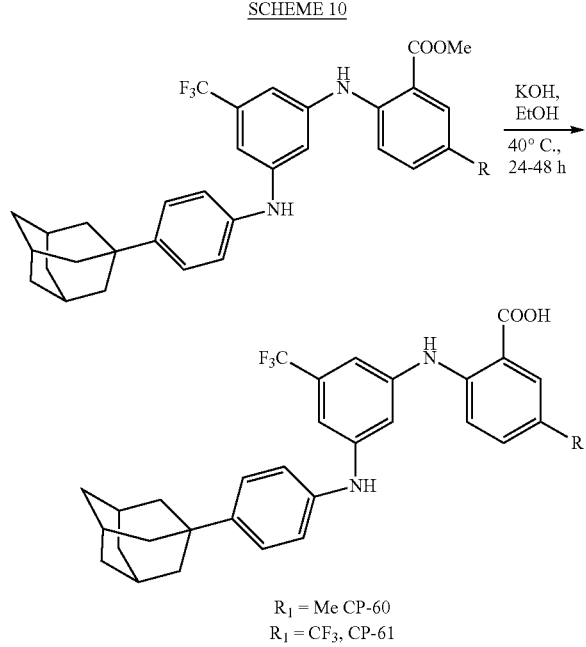

R₁ = Me CP-60
R₁ = CF₃, CP-61

To a solution of ester (1 mmol) in ethanol (10 mL) was added 2 mmol of 2N NaOH solution and heated at 40° C. for 24-48 h. Upon completion of the reaction, reaction was cooled on ice and acidified with 2N Hydrochloride solution and extracted three times with 10 mL of ethyl acetate. The organic solution was dried with MgSO₄, concentrated in vacuo and purified by flash column chromatography with hexane/ethyl acetate (gradient of pure hexane to 5/1 hexane/ethyl acetate) as eluent to give desired product. Yield 73-87%

CP-55 was confirmed by LC-MS (ESI, M+H 521.1).

CP-64 was confirmed by LC-MS (ESI, M+H 575.1).

Carboxylic acid compounds were converted to vinyl ketone compounds as shown in Scheme 11, and the experimental procedures described below.

SCHEME 11

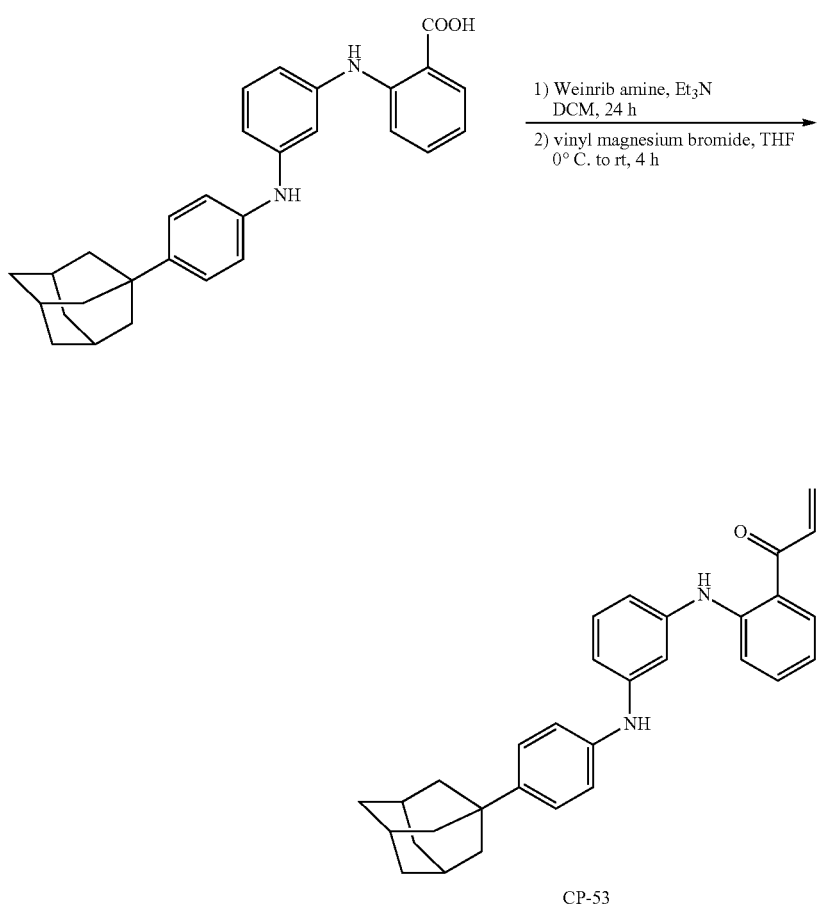

CP-53

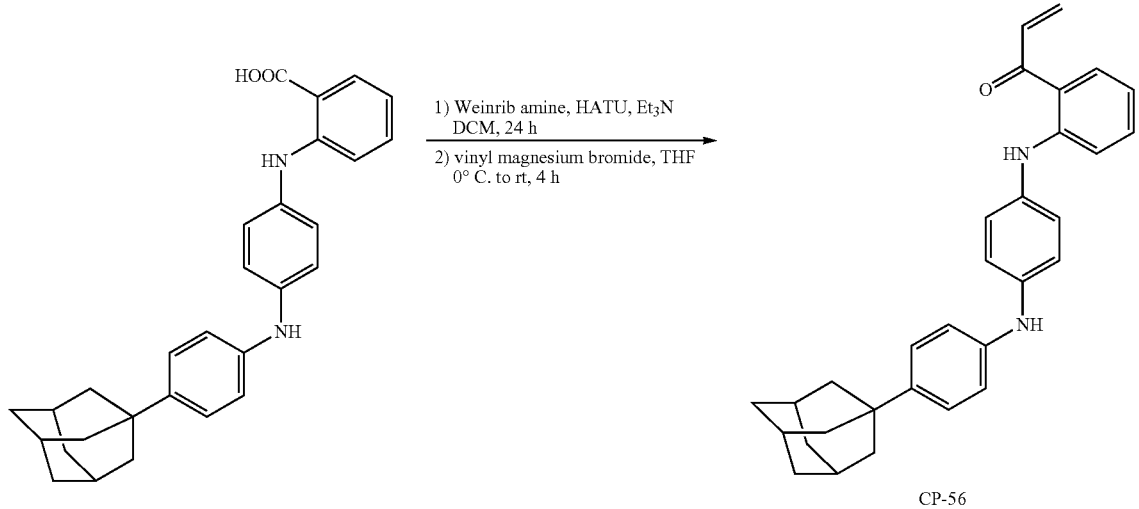

The acid was converted to Weinreb amide. To a solution of acid (0.1 mmol) in dichloromethane (1 mL) was added triethylamine (0.25 mmol) followed by Weinreb amine salt (0.2 mmol), HATU (0.2 mmol) and stirred at r.t. for 16 h. After completion of the reaction, water was and added and extracted three times with 10 mL of ethyl acetate. The organic solution was dried with MgSO$_4$, concentrated in vacuo and purified by flash column chromatography with hexane/ethyl acetate (gradient of pure hexane to 5/1 hexane/ethyl acetate) as eluent to give desired product.

An ice cooled solution of Weinreb amide (1 mmol) in anhydrous THF (10 mL) was added 4 mL of 1M solution of vinyl magnesium bromide in THF and warmed to r.t. and stirred for 4 h after completion of the reaction, quenched with 1N hydrochloride solution at 0° C. and extracted three times with 10 mL of ethyl acetate. The organic solution was dried with MgSO$_4$, concentrated in vacuo and purified by flash column chromatography with hexane/ethyl acetate (gradient of pure hexane to 5/1 hexane/ethyl acetate) as eluent to give desired product. Yield 42-57%.

CP-55 was confirmed by LC-MS (ESI, M+H 449.14).
CP-64 was confirmed by LC-MS (ESI, M+H 449.16).
Certain exemplified compound can be synthesized and characterized as discussed below.

Intermediate-I

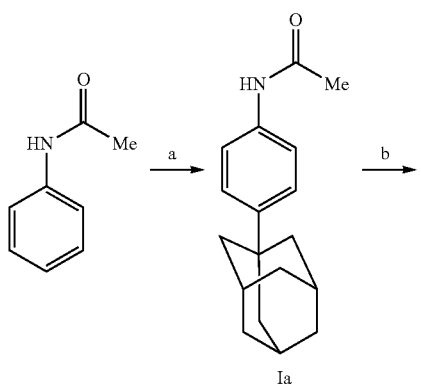

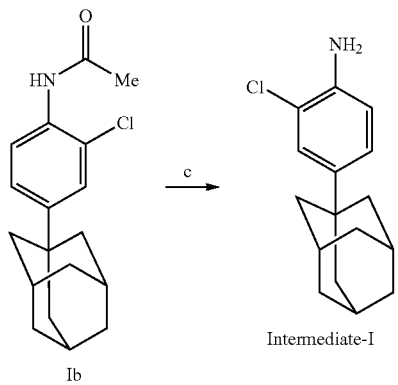

Step-a: Synthesis of N-(4-((3r,5r,7r)-adamantan-1-yl)phenyl) acetamide (Ia)

To a solution of acetanilide (50 g, 369 mmol, 1.0 eq.) in 1,1,2,2-tetrachloroethane (300 mL) was added 1-bromoadamantane (87.5 g, 406 mmol, 1.1 eq.) and stirred for 5 minutes. Zinc chloride anhydrous (25.1 g, 184 mmol, 0.5 eq.) was added and stirred at 100° C. for 36 h. Reaction mixture was cooled to RT and excess tetrachloroethane was removed by concentrating in vacuo. The residue was dissolved in ethyl acetate, washed with water and brine. The organic layer was dried over anhydrous Sodium sulfate, adsorbed over silica and purified by flash column chromatography to afford title product as a white solid (58 g, 58%).

$^1$H NMR (400 MHz, DMSO-d6) δ 9.81 (s, 1H), 7.47 (d, J=8.8 Hz, 2H), 7.25 (d, J=8.8 Hz, 2H), 2.04 (bs, 2H), 2.00 (s, 3H), 1.82 (s, 6H), 1.72 (s, 6H); LC-MS: m/z 270.1 (M+H)$^+$

The below intermediates were prepared by a procedure similar to Intermediate-Ia using appropriate reactants and reagents in presence of suitable solvents and appropriate reaction conditions.

| CP | Intermediate No. | Structure | Analytical data |
|---|---|---|---|
| 396 | Ia.1 | (structure: N-(4-(3,5-dimethyladamantan-1-yl)phenyl)acetamide) | ¹H NMR (400 MHz, DMSO-d6) δ 9.80 (s, 1H), 7.47 (d, J = 8.8 Hz, 2H), 7.24 (d, J = 8.8 Hz, 2H), 2.13-2.11 (m, 1H), 2.00 (s, 3H), 1.65 (s, 2H), 1.49-1.32 (m, 8H), 1.17 (s, 2H), 0.84 (s, 6H). LC-MS: m/z 298.2 (M + H)⁺ |

Step-b: Synthesis of N-(4-((3r,5r,7r)-adamantan-1-yl)-2-chlorophenyl)acetamide (Ib)

A solution of N-(4-((3r,5r,7r)-adamantan-1-yl)phenyl)acetamide (25 g, 92.8 mmol, 1.0 eq.) in DMF (500 mL) at 0° C. was added with N-chlorosuccinimide (13.6 g, 101 mmol, 1.1 eq.). The reaction mixture was allowed to RT and stirred for 16 h. Excess DMF was removed by concentrating in vacuo. The residue was dissolved in ethyl acetate, washed with water and brine. The organic layer was dried over anhydrous Sodium sulfate and concentrated in vacuo. The crude solid (22 g, 780%) obtained was used in next step without further purification.

¹H NM/R (400 MHz, DMSO-d6) δ 9.42 (s, 1H), 7.58 (d, J=8.3 Hz, 1H), 7.37 (d, J=2.5 Hz, 1H), 7.29 (dd, J₁=2.85 Hz, J₂=8.8 Hz, 1H), 2.06 (bs, 6H), 1.75 (s, 6H), 1.69 (s, 6H); LC-MS: m/z 304.10 (M+H)⁺

The below intermediates were prepared by a procedure similar to Intermediate-Ib using appropriate reactants and reagents in presence of suitable solvents and appropriate reaction conditions.

| CP | Intermediate No. | Structure | Analytical data |
|---|---|---|---|
| 170 | Ib.1 | (structure with Br) | ¹H NMR (400 MHz, DMSO-d6) δ 8.21-8.19 (m, 1H), 7.53-7.48 (m, 2H), 7.31-7.29 (m, 1H), 2.22 (s, 3H), 2.09 (s, 3H), 1.86 (s, 6H), 1.80-1.60 (m, 6H). LC-MS: m/z 348.0 M + H)⁺ |
| 396 | Ib.2 | (structure with Cl) | ¹H NMR (400 MHz, DMSO-d6) δ 9.42 (s, 1H), 7.58 (d, J = 8.8 Hz, 1H), 7.37 (d, J = 1.6 Hz, 1H), 7.28 (dd, J₁ = 2.0 Hz, J₂ = 8.4 Hz, 1H), 2.14-2.12 (m, 1H), 2.06 (s, 3H), 1.67 (s, 2H), 1.51-1.32 (m, 8H), 1.18 (s, 2H), 0.85 (s, 6H). LC-MS: m/z 332.2 (M + H)⁺ |

Step-c: Synthesis of 4-((3r,5r,7r)-adamantan-1-yl)-2-chloroaniline (Intermediate-1)

To a solution of N-(4-((3r,5r,7r)-adamantan-1-yl)-2-chlorophenyl)acetamide (17 g, 56 mmol, 1.0 eq.) in methanol (150 mL), conc. HCl (150 mL) was added and refluxed at 100° C. for 8 h. Excess methanol was removed in vacuo. The white ppt. obtained was filtered off. The filtered solid was washed with a solution of Sodium bicarbonate followed by water and dried under vacuum. Desired product was obtained as a white solid (13 g, 880).

$^1$H NMR (400 MHz, DMSO-d6) δ 7.08 (d, $J_1$=2.4 Hz, 1H), 7.02 (dd, $J_1$=1.9 Hz, $J_2$=8.3 Hz, 1H), 6.73 (d, J=8.3 Hz, 1H), 5.09 (bs, 2H), 2.01 (s, 3H), 1.76 (s, 6H), 1.66 (s, 6H); LC-MS: m/z 262.2 (M+H)$^+$

The below intermediates were prepared by a procedure similar to Intermediate-I using appropriate reactants and reagents in presence of suitable solvents and appropriate reaction conditions.

| CP | Intermediate No. | Structure | Analytical data |
|---|---|---|---|
|  | I.1 |  | $^1$H NMR (400 MHz, DMSO-d6) δ 6.99 (d, J = 8.3 Hz, 2H), 6.50 (d, J = 8.3 Hz, 1H), 4.76 (s, 2H), 2.01 (bs, 3H), 1.77 (s, 6H), 1.70 (s, 6H). LC-MS: m/z 228.1 (M + H)$^+$ |
| 295 | I.2 | 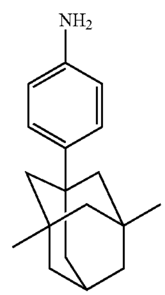 | $^1$H NMR (400 MHz, DMSO-d6) δ 7.06 (d, J = 8.4 Hz, 2H), 6.63 (d, J = 7.6 Hz, 2H), 6.10-6.00 (bs, 2H), 2.10 (s, 1H), 1.61 (s, 2H), 1.45-1.30 (m, 8H), 1.15 (s, 2H), 0.84 (s, 6H). LC-MS: m/z 256.2 (M + H)$^+$ |
| 396 | I.3 | 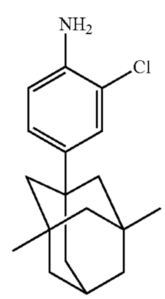 | $^1$H NMR (400 MHz, DMSO-d6) δ 7.19 (d, J = 2.0 Hz, 1H), 7.11 (dd, $J_1$ = 2.0 Hz, $J_2$ = 8.4 Hz, 1H), 6.91 (d, J = 8.4 Hz, 1H), 2.11-2.10 (m, 1H), 1.61 (s, 2H), 1.46-1.30 (m, 8H), 1.15 (s, 2H), 0.84 (s, 6H). LC-MS: m/z 290.2 (M + H)$^+$ |
| 170 | I.4 | 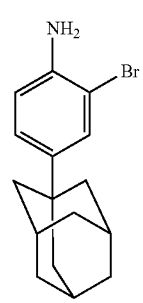 [SMILES: Nc1ccc(C23CC4CC(CC(C4)C2)C3)cc1Br] | $^1$H NMR (400 MHz, DMSO-d6) δ 7.39-7.38 (m, 1H), 7.12-7.09 (m, 1H), 6.74-6.72 (m, 1H), 3.94 (s, 2H), 2.09 (s, 3H), 1.86 (s, 6H), 1.80-1.69 (m, 6H). |

The below intermediates were prepared by a procedure similar to the ones described in literature using appropriate reactants and reagents in presence of suitable solvents and appropriate reaction conditions.

| CP | Intermediate No. | Structure | Literature report | Analytical data |
|---|---|---|---|---|
| 113, 132, 133 | I.5 | (4-amino-3-chloro-2'-methylbiphenyl) | Journal of the American Chemical Society, 2000, vol. 122, 17, p. 4020-4028 | $^1$H NMR (400 MHz, DMSO-d6) δ 7.21 (d, J = 3.5 Hz, 1H), 7.19 (t, J = 3.4 Hz, 2H), 7.13 (d, J = 1.9 Hz, 2H), 7.10 (dd, $J_1$ = 2.0 Hz, $J_2$ = 8.3 Hz, 1H), 6.84 (d, J = 8.3 Hz, 1H), 5.40 (s, 2H), 2.23 (s, 3H). LC-MS: m/z 218.0 (M + H)$^+$ |
| 115 | I.6 | (4-amino-3-chloro-2'-trifluoromethylbiphenyl) | Organic Letters, 2012, vol. 14, 20, p. 5306-5309 | $^1$H NMR (400 MHz, DMSO-d6) δ 7.73-7.69 (m, 1H), 7.50 (t, J = 7.3 Hz, 1H), 7.49 (t, J = 7.9 Hz, 1H), 7.30 (d, J = 5.3 Hz, 1H), 7.22 (d, J = 1.4 Hz, 1H), 7.03 (d, J = 1.0 Hz, 1H), 6.77 (d, J = 8.3 Hz, 1H), 4.11 (s, 2H). LC-MS: m/z 271.9 (M + H)$^+$ |
| 116 | I.7 | (4'-amino-2-chloro-4-fluorobiphenyl) | Journal of Medicinal Chemistry, 2012, vol. 55, 8, p. 3923-3933 | $^1$H NMR (400 MHz, DMSO-d6) δ 7.46 (dd, $J_1$ = 3.0 Hz, $J_2$ = 8.8 Hz, 1H), 7.38-7.34 (m, 1H), 7.24-7.22 (m, 1H), 7.07 (d, J = 2.0 Hz, 2H), 6.61 (d, J = 4.4 Hz, 2H), 5.25 (s, 2H). LC-MS: m/z 221.9 (M + H)$^+$ |
| 118 | I.8 | (4-amino-3-chloro-2'-methoxybiphenyl) | Journal of Medicinal Chemistry, 2009, vol. 52, 9, p. 2683-2693 | $^1$H NMR (400 MHz, DMSO-d6) δ 7.31 (d, J = 1.9 Hz, 1H), 7.28-7.22 (m, 2H), 7.16 (dd, $J_1$ = 2.5 Hz, $J_2$ = 8.4 Hz, 1H), 7.05 (d, J = 8.3 Hz, 1H), 6.99-6.95 (dt, $J_1$ = 1.0 Hz, $J_2$ = 6.3 Hz, 1H), 6.81 (d, J = 8.3 Hz, 1H), 5.38 (s, 2H), 3.75 (s, 3H). LC-MS: m/z 233.9 (M + H)$^+$ |
| 121 | I.9 | (4-amino-3-chloro-2',6'-dimethylbiphenyl) | WO2015/14944, 2015, A1 | $^1$H NMR (400 MHz, DMSO-d6) δ 7.10-7.05 (m, 3H), 6.93 (d, J = 2.0 Hz, 1H), 6.86 (d, J = 8.3 Hz, 1H), 6.77 (dd, $J_1$ = 1.4 Hz, $J_2$ = 7.8 Hz, 1H), 5.34 (s, 2H), 1.99 (s, 6H). |

-continued

| CP | Intermediate No. | Structure | Literature report | Analytical data |
|---|---|---|---|---|
| 122 | I.10 | 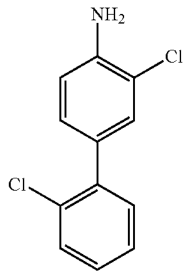 [SMILES: Nc1ccc(-c2ccccc2Cl)cc1Cl] | Journal of Medicinal Chemistry, 2009, vol. 52, 9, p. 2683-2693 | $^1$H NMR (400 MHz, DMSO-d6) δ 7.51 (d, J = 7.3 Hz, 1H), 7.38-7.32 (m, 3H), 7.26 (d, J = 2.0 Hz, 1H), 7.12 (dd, J$_1$ = 1.9 Hz, J$_2$ = 8.3 Hz, 1H), 6.85 (d, J = 8.4 Hz, 1H), 5.53 (s, 2H). LC-MS: m/z 238.1 (M + H)$^+$ |
| 126 | I.11 | 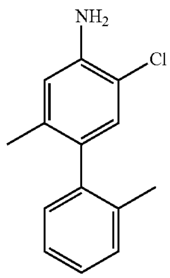 | Journal of Medicinal Chemistry, 2009, vol. 52, 9, p. 2683-2693 | LC-MS: m/z 232.0 (M + H)$^+$ |
| 140 | I.12 | 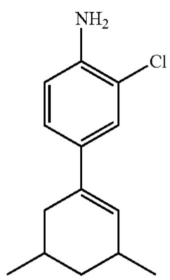 | WO2012/137181, 2012, A1 | $^1$H NMR (400 MHz, DMSO-d6) δ 7.19 (t, J = 2.0 Hz, 1H), 7.10 (dd, J1 = 2.0 Hz, J2 = 8.3 Hz, 1H), 6.72 (d, J = 8.3 Hz, 1H), 5.78 (s, 1H), 5.28 (s, 2H), 2.33 (m, 2H), 1.82-1.71 (m, 4H), 0.77-0.74 (m, 6H). |
| 146 | I.13 | 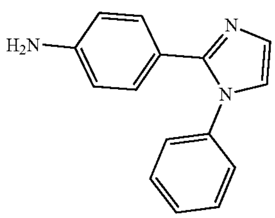 [SMILES: Nc1ccc(-c2nccn2-c2ccccc2)cc1] | Journal of Medicinal Chemistry, 2002, vol. 45, 8, p. 1697-1711 | $^1$H NMR (400 MHz, DMSO-d6) δ 7.47-7.40 (m, 4H), 7.32 (d, J = 1.6 Hz, 1H), 7.25 (d, J = 7.2 Hz, 2H), 7.05 (d, J = 1.2 Hz, 1H), 6.94 (d, J = 8.4 Hz, 2H), 6.41 (d, J = 8.8 Hz, 2H). LC-MS: m/z 236.1 (M + H)$^+$ |
| 178 | I.14 | 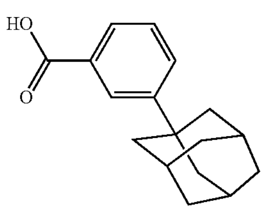 [SMILES: O=C(O)c1cccc(C23CC4CC(CC(C4)C2)C3)c1] | U.S. Pat. No. 5,200,550 A1 | $^1$H NMR (400 MHz, DMSO-d6) δ 12.91 (bs, 1H), 7.93 (t, J = 1.2 Hz, 1H), 7.76 (d, J = 8.0 Hz, 1H), 7.64 (d, J = 8.0 Hz, 1H), 7.44 (t, J = 8.0 Hz, 1H), 2.07 (s, 3H), 1.88 (s, 6H), 1.75 (s, 6H). |
| 177, 191, 200, | I.15 | 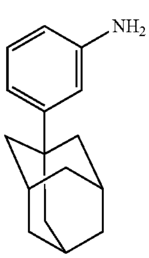 [SMILES: Nc1cccc(C23CC4CC(CC(C4)C2)C3)c1] | Journal of the Chemical Society, Perkin Transactions 2: Physical Organic Chemistry (1972-1999), 1976, p. 662-668 | $^1$H NMR (400 MHz, DMSO-d6) δ 7.92 (t, J = 7.8 Hz, 1H), 6.56 (t, J = 2.0 Hz, 1H), 6.49 (d, J = 7.9 Hz, 1H), 6.35 (dd, J$_1$ = 0.9 Hz, J$_2$ = 7.9 Hz, 1H), 4.86 (s, 2H), 2.03 (s, 3H), 1.75 (s, 6H), 1.71 (s, 6H). |

-continued

| CP | Intermediate No. | Structure | Literature report | Analytical data |
|---|---|---|---|---|
| 193 | I.16 | 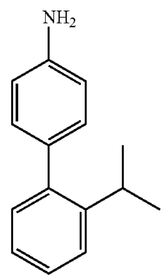 [SMILES: CC(C)c1ccccc1-c1ccc(N)cc1] | Chemistry-A European Journal, 2011, vol. 17, 49, p. 13832-13846 | ¹H NMR (400 MHz, DMSO-d6) δ 7.34 (d, J = 7.8 Hz, 1H), 7.24 (t, J = 0.9 Hz, 1H), 7.14 (t, J = 1.0 Hz, 1H), 7.05 (d, J = 1.0 Hz, 1H), 6.91 (d, J = 9.0 Hz, 2H), 6.60 (d, J = 8.3 Hz, 2H), 5.08 (s, 2H), 3.08 (m, 1H), 1.10 (d, J = 6.9 Hz, 6H). |
| 287 | I.17 | 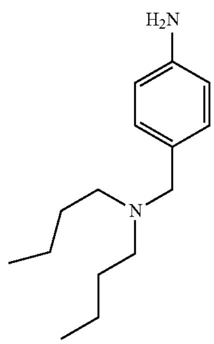 [SMILES: CCCCN(CCCC)Cc1ccc(N)cc1] | Advanced Synthesis and Catalysis, 2007, vol. 349, 10, p. 1775-1780 | LC-MS: m/z 235.2 (M + H)⁺ |
| 288 | I.18 | 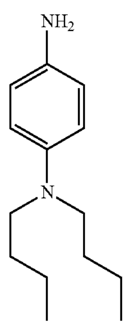 [SMILES: CCCCN(CCCC)c1ccc(N)cc1] | Journal of Medicinal Chemistry, 1997, vol. 40, 16, p. 2634-2642 | ¹H NMR (400 MHz, CDCl3) δ 6.65-6.63 (m, 4H), 3.14 (s, 2H), 3.12 (m, 4H), 1.48 (m, 4H), 1.32 (m, 4H), 0.91 (m, 6H). |
| 292 | I.19 | 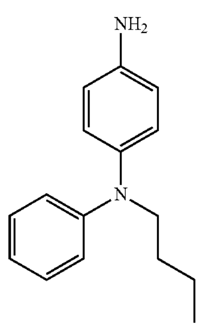 [SMILES: CCCCN(c1ccccc1)c1ccc(N)cc1] | Antibiotics Chemotherapy, 1954, vol. 4, p. 150, 152 | ¹H NMR (400 MHz, DMSO-d6) δ 7.05 (t, J = 7.3 Hz, 2H), 6.81 (d, J = 6.8 Hz, 2H), 6.60-6.52 (m, 5H), 5.02 (s, 2H), 3.48 (t, J = 7.8 Hz, 2H), 1.52-1.46 (m, 2H), 1.33-1.27 (m, 2H), 0.86 (t, J = 3.9 Hz, 3H). |
| 291, 328 | I.20 | 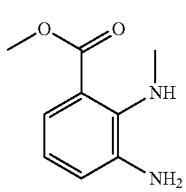 | WO2008/82003, 2008, A1 | LC-MS: m/z 181.10 (M + H)⁺ |

-continued

| CP | Intermediate No. | Structure | Literature report | Analytical data |
|---|---|---|---|---|
| 309 | I.21 | 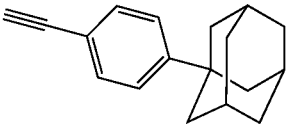 [SMILES: C#Cc1ccc(C23CC4CC(CC(C4)C2)C3)cc1] | Organic and Biomolecular Chemistry, 2006, vol. 4, 6, p. 1091-1096 | $^1$H NMR (400 MHz, DMSO-d6) δ 7.42-7.35 (m, 4H), 2.05 (s, 3H), 1.84 (s, 6H), 1.73 (s, 6H). LC-MS: m/z 237.1 (M + H)$^+$ |
| 318 | I.22 | 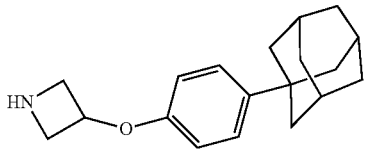 [SMILES: c1cc(C23CC4CC(CC(C4)C2)C3)ccc1OC1CNC1] | WO2010/125390, 2010, A1 | LC-MS: m/z 284.2 (M-113)$^+$ Azetidine fragment |
| 338 | I.23 | 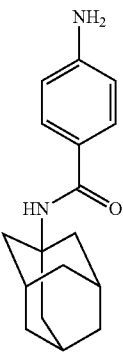 [SMILES: Nc1ccc(C(=O)NC23CC4CC(CC(C4)C2)C3)cc1] | Pharmazie, 1981, vol. 36, 6, p. 400-402 | $^1$H NMR (400 MHz, DMSO-d6) δ 7.50 (d, J = 8.0 Hz, 2H), 7.02 (s, 1H), 6.49 (d, J = 8.4 Hz, 2H), 5.50 (s, 2H), 2.03 (s, 9H), 1.64 (s, 6H). LC-MS: m/z 271.15 (M + H)$^+$ |
| 203 | I.24 | 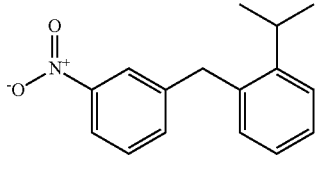 | Organic Letters, 2007, vol. 9, 26, p. 5397-5400 | $^1$H NMR (400 MHz, DMSO-d6) δ 8.07-8.05 (m, 1H), 7.94 (s, 1H), 7.61-7.57 (m, 2H), 7.30 (d, J = 7.2 Hz, 1H), 7.28-7.24 (m, 1H), 7.20-7.16 (m, 2H), 4.20 (s, 2H), 3.11-3.07 (m, 1H), 1.06 (d, J = 6.8 Hz, 6H). |
| 321 | I.25 | 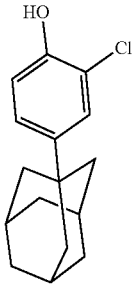 [SMILES: Oc1ccc(C23CC4CC(CC(C4)C2)C3)cc1Cl] | Letters in Organic Chemistry, 2016, vol. 13, 3, p. 171-176 | $^1$H NMR (400 MHz, DMSO-d6) δ 9.83 (s, 1H), 7.22-7.21 (m, 1H), 7.12-7.10 (m, 1H), 6.90-6.88 (m, 1H), 2.03 (s, 3H), 1.79 (s, 6H), 1.71 (s, 6H). |
| 323 | I.26 | 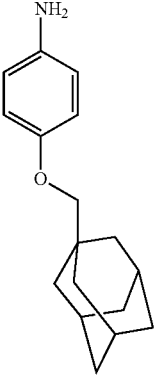 | WO2015/51149, 2015, A1 | $^1$H NMR (400 MHz, DMSO-d6) δ 6.62 (d, J = 8.8 Hz, 2H), 6.48 (d, J = 8.8 Hz, 2H), 4.54 (s, 2H), 3.37 (s, 2H), 1.96 (s, 3H), 1.69-1.59 (m, 12H). |

-continued

| CP | Intermediate No. | Structure | Literature report | Analytical data |
|---|---|---|---|---|
| 337 | I.27 | 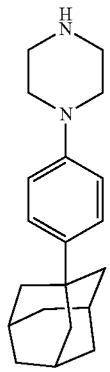 [SMILES: c1cc(C23CC4CC(CC(C4)C2)C3)ccc1N1CCNCC1] | Letters in Organic Chemistry, 2016, vol. 13, 3, p. 171-176 | ¹H NMR (400 MHz, DMSO-d6) δ 7.17 (d, J = 8.8 Hz, 2H), 6.83 (d, J = 8.4 Hz, 2H), 2.98-2.96 (m, 4H), 2.92-2.88 (m, 1H), 2.81-2.80 (m, 4H), 2.03 (s, 3H), 1.81 (s, 6H), 1.71 (s, 6H). LC-MS: m/z 297.3 (M + H)⁺ |
| 388 | I.28 | 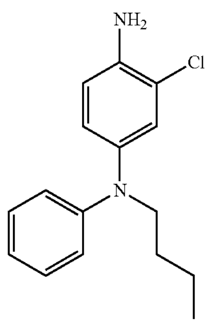 [SMILES: CCCCN(c1ccccc1)c1ccc(N)c(Cl)c1] | Antibiotics Chemotherapy, 1954, vol. 4, p. 150, 152 | ¹H NMR (400 MHz, DMSO-d6) δ 7.12-7.08 (m, 2H), 6.96 (d, J = 2.0 Hz, 1H), 6.86-6.80 (m, 2H), 6.64-6.58 (m, 3H), 5.30 (s, 2H), 3.50 (t, J = 7.2 Hz, 2H), 1.51-1.46 (m, 2H), 1.35-1.28 (m, 2H), 0.87 (t, J = 7.2 Hz, 3H). LC-MS: m/z 275.1 (M + H)⁺ |
| 407, 408 | I.29 | 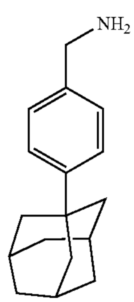 [SMILES: NCc1ccc(C23CC4CC(CC(C4)C2)C3)cc1] | Tetrahedron, 1988, vol. 44, 7, p. 1893-1904 | ¹H NMR (400 MHz, DMSO-d6) δ 7.26-7.24 (m, 4H), 3.66 (s, 2H), 2.05 (s, 3H), 1.84 (s, 6H), 1.73 (s, 6H). LC-MS: m/z 242.2 (M + H)⁺ |
| 314 | I.30 | 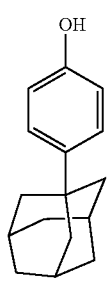 [SMILES: Oc1ccc(C23CC4CC(CC(C4)C2)C3)cc1] | Letters in Organic Chemistry, 2016, vol. 13, 3, p. 171-176 | ¹H NMR (400 MHz, DMSO-d6) δ 9.07 (s, 1H), 7.13-7.11 (m, 2H), 6.68-6.66 (m, 2H), 2.03 (s, 3H), 1.80 (s, 6H), 1.71 (s, 6H). LC-MS: m/z 228.0 (M + H)⁺ |
| 383 | I.31 | 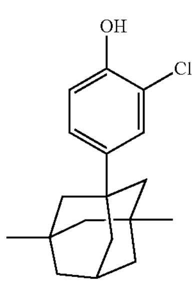 [SMILES: CC12CC3CC(C)(C1)CC(c1ccc(O)c(Cl)c1)(C3)C2] | Letters in Organic Chemistry, 2016, vol. 13, 3, p. 171-176 | ¹H NMR (400 MHz, DMSO-d6) δ 6.87-6.83 (m, 1H), 6.65 (dd, J₁ = 2.8 Hz, J₂ = 8.8 Hz, 1H), 6.15 (d, J = 8.4 Hz, 1H), 2.08-2.05 (m, 1H), 1.54 (s, 2H), 1.38-1.29 (m, 8H), 1.11 (s, 2H), 0.82 (s, 6H). LC-MS: m/z 289.05 (M − H)⁻. |

| CP | Intermediate No. | Structure | Literature report | Analytical data |
|---|---|---|---|---|
| 360 | I.32 | (structure: 2-chloro-4-(2-isopropylphenyl)phenol) | Chemistry-A European Journal, 2011, vol. 17, 49, p. 13832-13846 | $^1$H NMR (400 MHz, DMSO-d6) δ 10.20 (s, 1H), 7.39 (d, J = 7.9 Hz, 1H), 7.32 (t, J = 7.4 Hz, 1H), 7.19 (t, J = 6.3 Hz, 2H), 7.09 (d, J = 7.3 Hz, 1H), 7.03 (t, J = 8.3 Hz, 2H), 2.99-2.96 (m, 1H), 1.11 (d, J = 6.9 Hz, 6H). LC-MS: m/z 245.1 (M − H)$^-$. |
| 93 | I.33 | (structure: 2-chloro-4-(2-isopropylphenyl)aniline) | Chemistry-A European Journal, 2011, vol. 17, 49, p. 13832-13846 | LC-MS: m/z 246.0 (M + H)$^+$ |

Step-a: Synthesis of methyl 2-((4-bromophenyl)amino)benzoate (Intermediate-II)

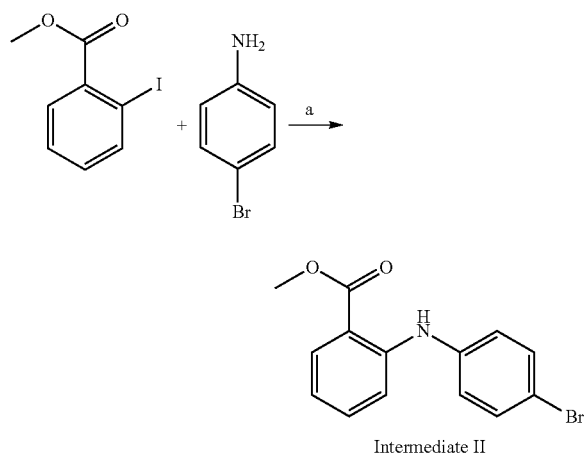

Intermediate II

A solution of methyl 2-iodobenzoate (30 g, 114.5 mmol, 1.0 eq.) and 4-bromoaniline (19.3 g, 114.5 mmol, 1.0 eq.) in toluene (500 mL) was added with cesium carbonate (49 g, 150 mmol, 1.3 eq.) and de-gassed with N$_2$ gas for 15 min. Palladium acetate (1.28 g, 5.7 mmol, 0.05 eq.) and rac. BINAP (3.56 g, 5.7 mmol, 0.05 eq.) were added and de-gassed for 5 min. Reaction mass was heated at 110° C. for 16 h. Reaction mass was filtered through celite, concentrated in vacuo and purified by combi-flash to afford the title product as pale brown liquid (33 g, 940%).

$^1$H NMR (400 MHz, DMSO-d6) δ 9.25 (s, 1H), 7.89 (dd, J$_1$=2.0 Hz, J$_2$=8.3 Hz, 1H), 7.51 (d, J=2.9 Hz, 2H), 7.48 (t, J=1.9 Hz, 1H), 7.26 (d, J=7.8 Hz, 1H), 7.21 (d, J=4.9 Hz, 2H), 6.87 (t, J=1.0 Hz, 1H), 3.84 (s, 3H); LC-MS: m/z 307.9 (M+H)$^{2+}$

The below intermediates were prepared by a procedure similar to Intermediate-II using appropriate reactants and reagents employing suitable Pd & Fe catalysts and ligands and in presence of suitable solvents and appropriate reaction conditions.

| CP | Intermediate No. | Structure | Analytical data |
|---|---|---|---|
| 52 | II.1 | (structure: methyl 2-((3-bromophenyl)amino)benzoate) | LC-MS: m/z 308 (M + H)$^{2+}$ |

| CP | Intermediate No. | Structure | Analytical data |
|---|---|---|---|
| 127 | II.2 | (methyl 2-((2-chloropyrimidin-4-yl)amino)benzoate) | ¹H NMR (400 MHz, DMSO-d6) δ 10.24 (s, 1H), 8.20 (d, J = 5.6 Hz, 1H), 7.89-7.82 (m, 2H), 7.64 (t, J = 8.4 Hz, 1H), 7.27 (t, J = 7.6 Hz, 1H), 6.84 (d, J = 6.0 Hz, 1H), 3.77 (s, 3H). LC-MS: m/z 263.9 (M + H)⁺ |
| 141, 154 | II.3 | (methyl 2-((5-bromopyrimidin-2-yl)amino)benzoate) | ¹H NMR (400 MHz, DMSO-d6) δ 10.83 (s, 1H), 8.69 (s, 2H), 8.57 (d, J = 8.4 Hz, 1H), 7.98 (dd, J₁ = 1.6 Hz, J₂ = 8.0 Hz, 1H), 7.66-7.61 (m, 1H), 7.11 (t, J = 7.6 Hz, 1H), 3.86 (s, 3H). LC-MS: m/z 309.9 (M + H)²⁺ |
| 142, 252 | II.4 | (methyl 2-((5-bromopyrazin-2-yl)amino)benzoate) | ¹H NMR (400 MHz, DMSO-d6) δ 10.34 (s, 1H), 8.35 (d, J = 1.6 Hz, 1H), 8.29-8.26 (m, 2H), 7.94 (dd, J₁ = 1.6 Hz, J₂ = 7.6 Hz, 1H), 7.60 (t, J = 8.0 Hz, 1H), 7.11 (t, J = 8.0 Hz, 1H), 3.84 (s, 3H). LC-MS: m/z 309.9 (M + H)²⁺ |
| 144, 152, 155 | II.5 | (methyl 2-((5-bromopyridin-2-yl)amino)benzoate) | ¹H NMR (400 MHz, DMSO-d6) δ 10.18 (s, 1H), 8.39 (d, J = 8.8 Hz, 1H), 8.30 (d, J = 2.4 Hz, 1H), 7.92 (dd, J₁ = 1.2 Hz, J2 = 7.6 Hz, 1H), 7.83 (dd, J₁ = 2.4 Hz, J₂ = 8.8 Hz, 1H), 7.56 (t, J = 7.2 Hz, 1H), 7.04-6.98 (m, 2H), 3.84 (s, 3H). LC-MS: m/z 308.9 (M + H)²⁺ |
| 158 | II.6 | (methyl 3-((4-bromophenyl)amino)benzoate) | ¹H NMR (400 MHz, DMSO-d6) δ 8.57 (s, 1H), 7.63 (t, J = 1.5 Hz, 1H), 7.44-7.40 (m, 4H), 7.33-7.30 (m, 1H), 7.06-7.02 (m, 2H), 3.83 (s, 3H). LC-MS: m/z 307.9 (M + H)²⁺ |
| 175 | II.7 | (methyl 2-((5-bromopyridin-2-yl)amino)nicotinate) | ¹H NMR (400 MHz, DMSO-d6) δ 10.72 (s, 1H), 8.52 (dd, J₁ = 2.0 Hz, J₂ = 4.8 Hz, 1H), 8.49 (d, J = 9.0 Hz, 1H), 8.39 (d, J =0 2.4 Hz, 1H), 8.34 (dd, J₁ = 2.0 Hz, J₂ = 8.0 Hz, 1H), 8.0 (dd, J₁ = 2.4 Hz, J₂ = 8.8 Hz, 1H), 7.06 (dd, J₁ = 5.2 Hz, J₂ = 8.0 Hz, 1H), 3.91 (s, 3H). LC-MS: m/z 310 (M + H)²⁺ |
| 194 | II.8 | (methyl 2-(4-Boc-piperazin-1-yl)nicotinate) | ¹H NMR (400 MHz, DMSO-d6) δ 8.29 (dd, J₁ = 1.6 Hz, J₂ = 4.4 Hz, 1H), 7.95 (dd, J₁ = 2.0 Hz, J₂ = 7.2 Hz, 1H), 6.86 (dd, J₁ = 5.2 Hz, J₂ = 8.0 Hz, 1H), 3.82 (s, 3H), 3.42 (s, 4H), 3.29-3.25 (m, 4H). |
| 200, 233, 241, 247 | II.9 | (methyl 2-((3-bromophenyl)amino)nicotinate) | ¹H NMR (400 MHz, DMSO-d6) δ 10.15 (s, 1H), 8.46 (dd, J₁ = 1.4 Hz, J₂ = 4.9 Hz, 1H), 8.28 (dd, J₁ = 1.4 Hz, J₂ = 7.8 Hz, 1H), 8.20 (s, 1H), 7.56 (d, J = 7.8 Hz, 1H), 7.27 (t, J = 8.3 Hz, 1H), 7.19 (d, J = 7.8 Hz, 1H), 6.97-6.94 (m, 1H), 3.91 (s, 3H). LC-MS: m/z 306.9 (M + H)⁺ |

| CP | Intermediate No. | Structure | Analytical data |
|---|---|---|---|
| 218, 385, 386, 389 | II.10 | 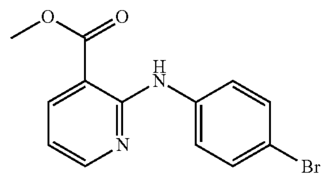 [SMILES: COC(=O)c1cccnc1Nc1ccc(Br)cc1] | ¹H NMR (400 MHz, DMSO-d6) δ 10.13 (s, 1H), 8.44 (dd, J₁ = 1.6 Hz, J₂ = 4.8 Hz, 1H), 8.28 (dd, J₁ = 2.0 Hz, J₂ = 8.0 Hz, 1H), 7.72 (d, J = 9.2 Hz, 2H), 7.49 (d, J = 8.8 Hz, 2H), 6.95-6.92 (m, 1H), 3.91 (s, 3H). LC-MS: m/z 307.1 (M + H)⁺ |
| 223 | II.11 | 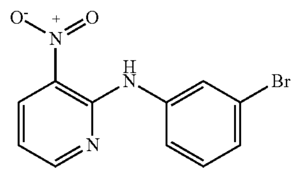 | ¹H NMR (400 MHz, DMSO-d6) δ 9.96 (s, 1H), 8.56 (d, J = 1.0 Hz, 2H), 8.01 (s, 1H), 7.66-7.60 (m, 1H), 7.34-7.29 (m, 2H), 7.06-7.03 (m, 1H). LC-MS: m/z 294.0 (M + H)⁺ |
| 242 | II.12 | 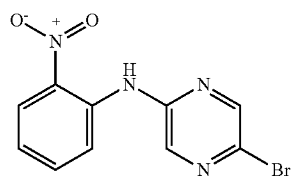 | ¹H NMR (400 MHz, DMSO-d6) δ 9.98 (s, 1H), 8.28-8.26 (m, 2H), 8.06-8.04 (m, 1H), 7.92-7.89 (m, 1H), 7.72-7.68 (m, 1H), 7.28 (t, J = 0.8 Hz, 1H). LC-MS: m/z 295.0 (M + H)⁺ |
| 243 | II.13 | 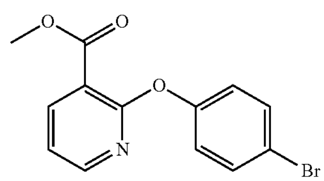 [SMILES: COC(=O)c1cccnc1Oc1ccc(Br)cc1] | ¹H NMR (400 MHz, DMSO-d6) δ 9.67 (s, 1H), 8.3 (m, 2H), 7.59 (d, J = 8.8 Hz, 2H), 7.30 (m, 3H), 7.11 (d, J =8.8 Hz, 2H), 6.72 (d, J = 8.9 Hz, 2H), 3.85 (s, 3H). |
| 251 | II.14 | 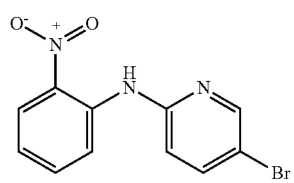 | ¹H NMR (400 MHz, DMSO-d6) δ 10.17 (s, 1H), 8.70 (d, J = 1.0 Hz, 1H), 8.38 (d, J = 2.4 Hz, 1H), 8.24 (dd, J₁ = 1.9 Hz, J₂ = 8.8 Hz, 1H), 7.73 (dd, J₁ = 2.4 Hz, J₂ = 8.3 Hz, 1H), 7.62-7.56 (m, 1H), 7.01 (t, J = 1.5 Hz, 1H), 6.88 (d, J = 8.8 Hz, 1H). LC-MS: m/z 295.9 (M + H)²⁺ |
| 254 | II.15 | 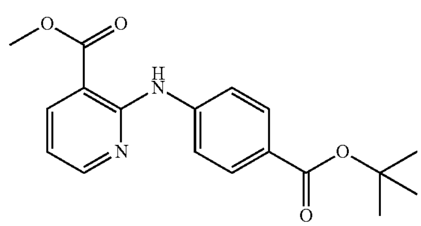 [SMILES: COC(=O)c1cccnc1Nc1ccc(C(=O)OC(C)(C)C)cc1] | ¹H NMR (400 MHz, DMSO-d6) δ 10.38 (s, 1H), 8.49 (dd, J₁ = 1.5 Hz, J₂ = 4.4 Hz, 1H), 8.31 (dd, J₁ = 1.9 Hz, J₂ = 7.8 Hz, 1H), 7.89-7.84 (m, 4H), 7.02-6.99 (m, 1H), 3.92 (s, 3H), 1.54 (s, 9H). |
| 259, 346 | II.16 | 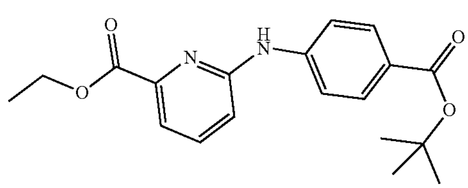 [SMILES: CCOC(=O)c1cccc(Nc2ccc(C(=O)OC(C)(C)C)cc2)n1] | ¹H NMR (400 MHz, DMSO-d6) δ 9.76 (s, 1H), 7.97 (d, J = 8.8 Hz, 2H), 7.83-7.78 (m, 3H), 7.52 (d, J = 7.3 Hz, 1H), 7.13 (d, J = 8.3 Hz, 1H), 4.37-4.32 (m, 2H), 1.54 (s, 9H), 1.36 (t, J = 6.8 Hz, 3H). |
| 264 | II.17 | 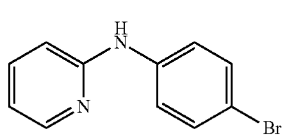 [SMILES: Brc1ccc(Nc2ccccn2)cc1] | ¹H NMR (400 MHz, DMSO-d6) δ 9.16 (s, 1H), 8.15 (dd, J₁ = 1.2 Hz, J₂ = 5.6 Hz, 1H), 7.69-7.66 (m, 2H), 7.59-7.55 (m, 1H), 7.42-7.39 (m, 2H), 6.82 (d, J = 8.0 Hz, 1H), 6.78-6.75 (m, 1H). LC-MS: m/z 249.0 (M + H)⁺ |

-continued

| CP | Intermediate No. | Structure | Analytical data |
|---|---|---|---|
| 265 | II.18 | 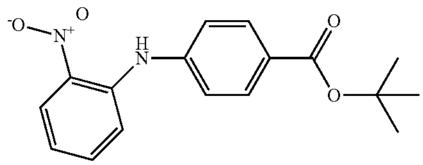 | ¹H NMR (400 MHz, DMSO-d6) δ 9.30 (s, 1H), 8.11 (dd, J₁ = 1.2 Hz, J₂ = 8.0 Hz, 1H), 7.85 (d, J = 8.8 Hz, 2H), 7.58 (t, J = 6.8 Hz, 1H), 7.47 (d, J = 8.0 Hz, 1H), 7.30 (d, J = 8.8 Hz, 2H), 7.09-7.05 (m, 1H), 1.54 (s, 9H). LC-MS: m/z 313.0 (M − H)⁻ |
| 269 | II.19 | 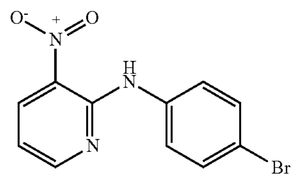 | ¹H NMR (400 MHz, DMSO-d6) δ 9.95 (s, 1H), 8.56-8.51 (m, 2H), 7.66-7.64 (m, 2H), 7.54-7.52 (m, 2H), 7.02 (dd J₁ = 5.2 Hz, J₂ = 8.4 Hz, 1H). |
| 274, 285, | II.20 | 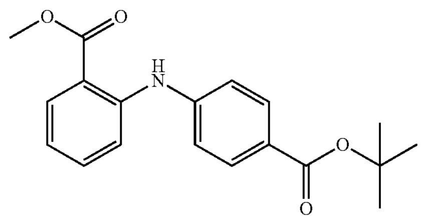 [SMILES: COC(=O)c1ccccc1Nc1ccc(C(=O)OC(C)(C)C)cc1] | ¹H NMR (400 MHz, DMSO-d6) δ 9.40 (s, 1H), 7.93 (d, J = 7.8 Hz, 1H), 7.83 (d, J = 8.3 Hz, 2H), 7.53-7.44 (m, 2H), 7.26 (d, J = 8.8 Hz, 2H), 6.98 (t, J = 7.8 Hz, 1H), 3.84 (s, 3H), 1.53 (s, 9H). LC-MS: m/z 328.0 (M + H)⁺ |
| 302 | II.21 | 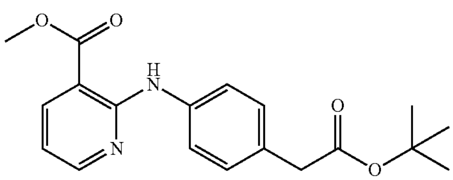 [SMILES: COC(=O)c1cccnc1Nc1ccc(CC(=O)OC(C)(C)C)cc1] | ¹H NMR (400 MHz, DMSO-d6) δ 10.06 (s, 1H), 8.41 (dd, J₁ = 2.0 Hz, J₂ = 4.9 Hz, 1H), 8.26 (dd, J₁ = 1.9 Hz, J₂ = 7.8 Hz, 1H), 7.66 (d, J = 8.8 Hz, 2H), 7.21 (d, J = 8.4 Hz, 2H), 6.88 (m, 1H), 3.90 (s, 3H), 3.50 (s, 2H), 1.42 (s, 9H). LC-MS: m/z 343.0 (M + H)⁺ |
| 303 | II.22 | 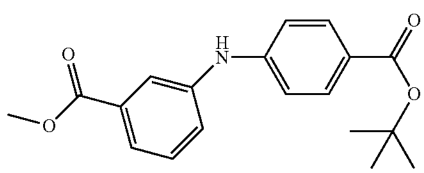 [SMILES: COC(=O)c1cccc(Nc2ccc(C(=O)OC(C)(C)C)cc2)c1] | ¹H NMR (400 MHz, DMSO-d6) δ 8.93 (s, 1H), 7.78 (d, J = 8.8 Hz, 2H), 7.73 (s, 1H), 7.55-7.50 (m, 1H), 7.44 (d, J = 4.4 Hz, 2H), 7.09 (d, J = 8.8 Hz, 2H), 3.84 (s, 3H), 1.53 (s, 9H). LC-MS: m/z 328.0 (M + H)⁺ |
| 327 | II.23 | 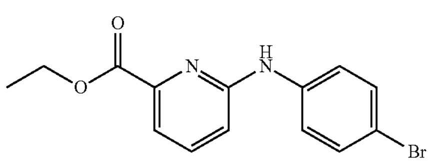 [SMILES: CCOC(=O)c1cccc(Nc2ccc(Br)cc2)n1] | ¹H NMR (400 MHz, DMSO-d6) δ 9.48 (s, 1H), 7.85 (d, J = 8.8 Hz, 2H), 7.74 (t, J = 7.6 Hz, 1H), 7.47-7.42 (m, 3H), 7.05 (d, J = 8.4 Hz, 1H), 4.35-4.30 (m, 2H), 1.35 (t, J = 7.2 Hz, 3H). LC-MS: m/z 321.0 (M + H)⁺ |
| 330 | II.24 | 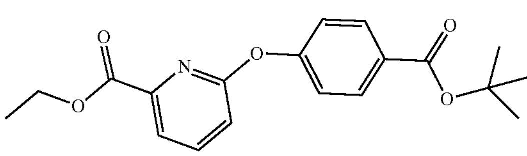 [SMILES: CCOC(=O)c1cccc(Oc2ccc(C(=O)OC(C)(C)C)cc2)n1] | LC-MS: m/z 288.0 (M − 56H)⁺; t-butyl fragment |
| 333, 408 | II.25 | 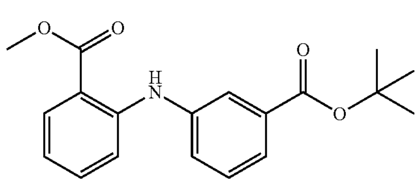 [SMILES: COC(=O)c1ccccc1Nc1cccc(C(=O)OC(C)(C)C)c1] | ¹H NMR (400 MHz, DMSO-d6) δ 9.31 (s, 1H), 7.96-7.90 (m, 1H), 7.72 (s, 1H), 7.59-7.57 (m, 1H), 7.50-7.44 (m, 3H), 7.25 (d, J = 8.4 Hz, 1H), 3.82 (s, 3H), 1.50 (s, 9H). LC-MS: m/z 328.2 (M + H)⁺ |

-continued
| CP | Intermediate No. | Structure | Analytical data |
|---|---|---|---|
| 334 | II.26 | 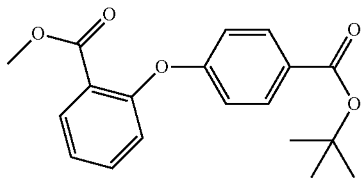 [SMILES: COC(=O)c1ccccc1Oc1ccc(C(=O)OC(C)(C)C)cc1] | ¹H NMR (400 MHz, DMSO-d6) δ 7.91 (d, J = 9.3 Hz, 1H), 7.88 (d, J = 8.8 Hz, 2H), 7.69 (t, J = 7.8 Hz, 1H), 7.40 (t, J = 7.8 Hz, 1H), 7.20 (d, J = 8.3 Hz, 1H), 6.93 (d, J = 8.8 Hz, 2H), 3.67 (s, 3H), 1.53 (s, 9H). |
| 347 | II.27 | 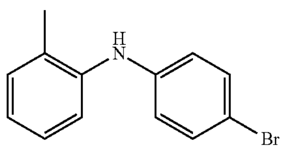 | ¹H NMR (400 MHz, DMSO-d6) δ 7.57 (s, 1H), 7.29 (d, J = 8.8 Hz, 2H), 7.21 (d, J = 7.6 Hz, 1H), 7.15-7.12 (m, 2H), 6.97-6.94 (m, 1H), 6.77 (d, J = 8.8 Hz, 2H), 2.17 (s, 3H). LC-MS: m/z 262.0 (M + H)⁺ |
| 651 | II.28 | 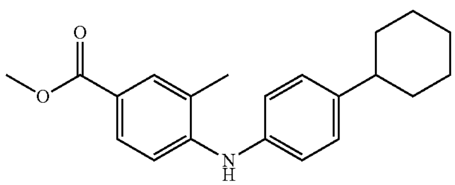 [SMILES: COC(=O)c1ccc(Nc2ccc(C3CCCCC3)cc2)c(C)c1] | LC-MS: m/z 324.05 (M + H)⁺ |
| 638 | II.29 | 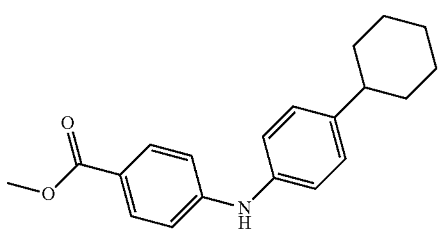 [SMILES: COC(=O)c1ccc(Nc2ccc(C3CCCCC3)cc2)cc1] | LC-MS: m/z 310.1 (M + H)⁺ |
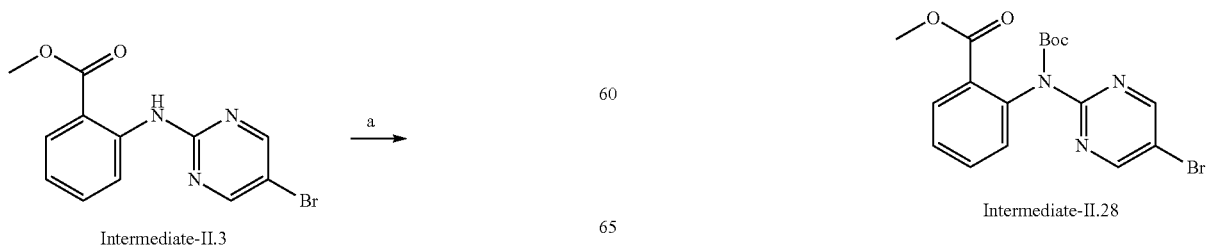
Intermediate-II.28

Step-a: Synthesis of methyl 2-((5-bromopyrimidin-2-yl)(tert-butoxycarbonyl)amino)benzoate (II.28)

To a solution of Intermediate-II.3 (1.3 g, 4.3 mmol, 1 eq.) in THF (30 mL), DMAP (0.1 g, 0.84 mmol, 0.2 eq.), pyridine (0.67 g, 8.7 mmol, 2 eq.), Boc anhydride (1.38 g, 6.3 mmol, 1.5 eq.) were added and heated at 60° C. overnight. Reaction mass was concentrated in vacuo and purified by combi-flash to afford title product as off-white solid (1.4 g, 82%). LC-MS: m/z 408.2 (M+H)$^+$ The below intermediates were prepared by a procedure similar to Intermediate-II.28 using appropriate reactants and reagents and in presence of suitable solvents and appropriate reaction conditions.

| CP | Intermediate No. | Reactant | Structure | Analytical data |
|---|---|---|---|---|
| 142 | II.29 | II.4 | 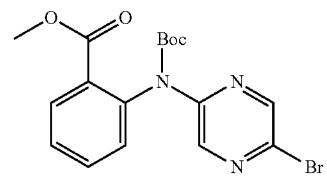 [SMILES: COC(=O)c1ccccc1N(C(=O)OC(C)(C)C)c1cnc(Br)cn1] | LC-MS: m/z 408.9 (M + H)$^+$ |
| 152 | II.30 | II.5 | 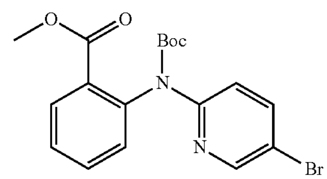 | LC-MS: m/z 409.9 (M + H)$^{2+}$ |
| 175 | II.31 | II.7 | 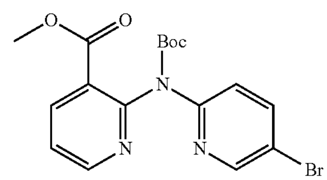 [SMILES: COC(=O)c1cccnc1N(C(=O)OC(C)(C)C)c1ccc(Br)cn1] | LC-MS: m/z 410.1 (M + H)$^{2+}$ |

The below intermediates were prepared by a procedure similar to Intermediate-II using appropriate reactants and reagents employing suitable Pd catalysts and ligands and in presence of suitable solvents and appropriate reaction conditions.

| CP | Intermediate No. | Reactant | Structure | Analytical data |
|---|---|---|---|---|
| 357 | II.32 | Int-II | 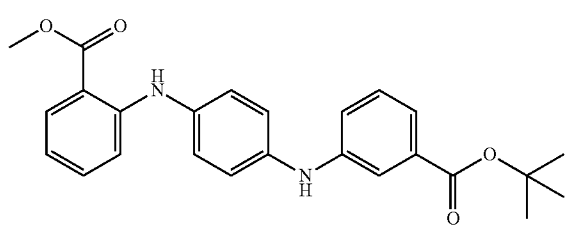 [SMILES: COC(=O)c1ccccc1Nc1ccc(Nc2cccc(C(=O)OC(C)(C)C)c2)cc1] | LC-MS: m/z 419.1 (M + H)$^+$ |
| 363 | II.33 | I.1 | 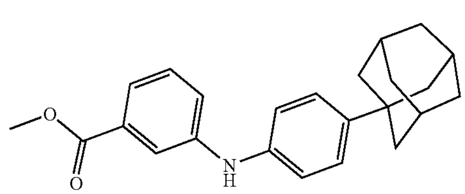 [SMILES: COC(=O)c1cccc(Nc2ccc(C34CC5CC(CC(C5)C3)C4)cc2)c1] | $^1$H NMR (400 MHz, DMSO-d6) δ 8.28 (s, 1H), 7.6 (s, 1H), 7.33-7.25 (m, 5H), 7.04 (d, J = 8.8 Hz, 2H), 3.82 (s, 3H), 2.05 (s, 3H), 1.84 (s, 6H), 1.73 (s, 6H). LC-MS: m/z 362.3 (M + H)$^+$ |

| CP | Intermediate No. | Reactant | Structure | Analytical data |
|---|---|---|---|---|
| 394 | II.34 | | (structure of methyl 2-((3-(tert-butoxycarbonyl)phenyl)amino)nicotinate) | LC-MS: m/z 329.2 (M + H)+ |
| 315, 316 | II.35 | I.1 | (structure of methyl 4-((4-(adamantan-1-yl)phenyl)amino)benzoate) | LC-MS: m/z 362.3 (M + H)+ |

Intermediates-IIIa & IIIb

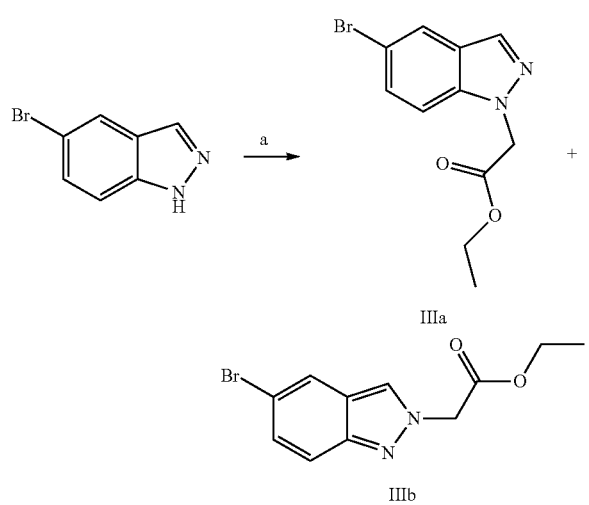

IIIa

IIIb

Step-a: Synthesis of ethyl 2-(5-bromo-1H-indazol-1-yl)acetate & ethyl 2-(5-bromo-2H-indazol-2-yl)acetate (IIIa & IIIb)

A solution of 5-bromo-1H-indazole (1 g, 5.1 mmol, 1.0 eq.) in acetonitrile (25 mL) was added with potassium carbonate (1.8 g, 12.8 mmol, 2.5 eq.) under stirring. Ethyl bromoacetate (0.7 mL, 6.1 mmol, 1.2 eq.) was added drop wise and reaction mass was heated at reflux overnight. Reaction mass was concentrated in vacuo, adsorbed over silica after water washings and purified by combi-flash to afford title products IIIa (400 mg, 28%, white solid) and IIIb (180 mg, 13%, yellow solid).

Intermediate-IIIa: $^1$H NMR (400 MHz, DMSO-d6) δ 8.10 (s, 1H), 8.05 (s, 1H), 7.68-7.65 (m, 1H), 7.53-7.51 (m, 1H), 5.40 (s, 2H), 4.18-4.12 (m, 2H), 1.19 (t, J=6.8 Hz, 3H); LC-MS: m/z 283.0 (M+H)+

Intermediate-IIIb: $^1$H NMR (400 MHz, DMSO-d6) δ 8.41 (s, 1H), 8.02 (s, 1H), 7.60-7.58 (m, 1H), 7.35-7.32 (m, 1H), 5.42 (s, 2H), 4.20-4.15 (m, 2H), 1.18 (t, J=6.4 Hz, 3H); LC-MS: m/z 283.0 (M+H)+

The below intermediates were prepared by a procedure similar to Intermediates-IIIa & IIIb using appropriate reactants and reagents and in presence of suitable solvents and appropriate reaction conditions.

| CP | Intermediate No. | Structure | Analytical data |
|---|---|---|---|
| 187 | III.1 | (structure) | $^1$H NMR (400 MHz, DMSO-d6) δ 7.49 (d, J = 7.6 Hz, 2H), 7.25 (d, J = 8.0 Hz, 2H), 3.81 (d, J = 13.6 Hz, 1H), 3.58 (s, 3H), 3.49 (d, J = 12.4 Hz, 1H), 3.27 (dd, $J_1$ = 5.2 Hz, $J_2$ = 8.8 Hz, 1H), 2.85-2.80 (m, 1H), 2.38-2.32 (m, 1H), 2.09-2.04 (m, 1H), 1.84-1.71 (m, 3H). |
| 192 | III.2 | (structure) | $^1$H NMR (400 MHz, DMSO-d6) δ 7.62 (s, 1H), 7.54 (d, J = 8.8 Hz, 2H), 7.15 (s, 1H), 7.11 (d, J = 8.4 Hz, 2H), 5.58 (s, 2H), 4.25-4.23 (m, 2H), 2.50 (t, J = 2.0 Hz, 3H). LC-MS: m/z 308.9 (M + H)+ |

| CP | Intermediate No. | Structure | Analytical data |
|---|---|---|---|
| 195 | III.3 | (methyl 2-((4-Boc-piperazin-1-yl)methyl)nicotinate) | Proceeded with crude/only TLC reference |
| 197 | III.4 | (ethyl 2-(5-bromo-1H-benzimidazol-1-yl)acetate) | $^1$H NMR (400 MHz, DMSO-d6) δ 8.24 (d, J = 9.2 Hz, 1H), 7.88 (dd, J$_1$ = 1.6 Hz, J$_2$ = 10 Hz, 1H), 7.27-7.55 (m, 1H), 7.42-7.34 (m, 1H), 5.26 (d, J = 2.8 Hz, 2H), 4.20-4.14 (m, 2H), 1.25-1.20 (m, 3H). LC-MS: m/z 282.9 (M + H)$^+$ |
| 201 | III.5 | (1-(4-bromobenzyl)-1H-1,2,4-triazole) | $^1$H NMR (400 MHz, DMSO-d6) δ 8.65 (s, 1H), 7.98 (s, 1H), 7.56 (d, J = 8.4 Hz, 2H), 7.23 (d, J = 8.4 Hz, 2H), 5.4 (s, 2H). LC-MS: m/z 238 (M + H)$^+$ |
| 202 | III.6 | (1-(2-chloro-4-adamantylbenzyl)-4-nitro-1H-pyrazole) | $^1$H NMR (400 MHz, DMSO-d6) δ 9.00 (s, 1H), 8.29 (s, 1H), 7.43-7.42 (m, 1H), 7.37-7.35 (m, 1H), 7.22-7.19 (m, 1H), 5.47 (s, 2H), 2.05 (s, 3H), 1.84 (s, 6H), 1.72 (s, 6H). LC-MS: m/z 372.1 (M + H)$^+$ |
| 210 | III.7 | (ethyl 2-(6-bromo-1H-indazol-1-yl)acetate) | $^1$H NMR (400 MHz, DMSO-d6) δ 8.14 (s, 1H), 8.03 (s, 1H), 7.74 (d, J = 8.4 Hz, 1H), 7.29 (dd, J$_1$ = 1.6 Hz, J$_2$ = 8.4 Hz, 1H), 5.38 (s, 2H), 4.14 (q, J = 14 Hz, 2H), 1.20 (t, J = 7.6 Hz, 3H). LC-MS: m/z 285.0 (M + H)$^{2+}$ |
| 213 | III.8 | (ethyl 1-(4-bromobenzyl)-1H-pyrazole-4-carboxylate) | $^1$H NMR (400 MHz, DMSO-d6) δ 8.47 (s, 1H), 7.87 (s, 1H), 7.56-7.54 (dd, J$_1$ = 0.8 Hz, J$_2$ = 6.4 Hz, 2H), 7.22 (d, J = 8.0 Hz, 2H), 5.35 (s, 2H), 4.23-4.18 (m, 2H), 1.26 (t, J = 7.6 Hz, 3H). LC-MS: m/z 309.0 (M + H)$^+$ |
| 214 | III.9 | (methyl 2-(4-bromobenzyl)nicotinate) | LC-MS: m/z 306.0 (M + H)$^+$ |
| 217 | III.10 | (ethyl 1-(4-bromobenzyl)-1H-pyrrole-2-carboxylate) | $^1$H NMR (400 MHz, DMSO-d6) δ 7.51-7.49 (dd, J$_1$ = 2.0 Hz, J$_2$ = 6.8 Hz, 2H), 7.29 (t, J = 2.0 Hz, 1H), 7.0 (d, J = 8.0 Hz, 2H), 6.91-6.9 (dd, J$_1$ = 2.0 Hz, J$_2$ = 4.0 Hz, 1H), 6.20-6.18 (dd, J$_1$ = 1.2 Hz, J$_2$ = 4.0 Hz, 1H), 5.51 (s, 2H), 4.16-4.11 (m, 2H), 1.12 (t, J = 6.8 Hz, 3H). LC-MS: m/z 308.0 (M + H)$^+$ |

| Intermediate CP No. | | Structure | Analytical data |
|---|---|---|---|
| 219 | III.11 | 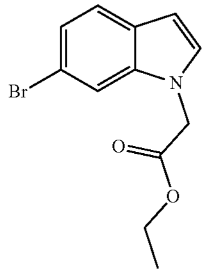 [SMILES: CCOC(=O)Cn1ccc2ccc(Br)cc21] | ¹H NMR (400 MHz, DMSO-d6) δ 7.70 (s, 1H), 7.51 (d, J = 2.0 Hz, 1H), 7.36 (s, 1H), 7.18-7.14 (m, 1H), 6.3 (s, 1H), 5.14 (s, 2H), 4.17-4.12 (m, 2H), 1.24-1.19 (m, 3H). LC-MS: m/z 282.1 (M + H)⁺ |
| 220 | III.12 | 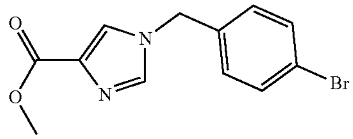 [SMILES: COC(=O)c1cn(Cc2ccc(Br)cc2)cn1] | ¹H NMR (400 MHz, DMSO-d6) δ 8.01 (d, J = 0.8 Hz, 1H), 7.92 (s, 1H), 7.58 (s, 1H), 7.52 (d, J = 6.0 Hz, 1H), 7.34-7.33 (m, 2H), 5.25 (s, 2H), 3.72 (s, 3H). LC-MS: m/z 295.0 (M + H)⁺ |
| 221 | III.13 | 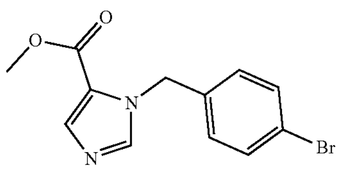 [SMILES: COC(=O)c1cncn1Cc1ccc(Br)cc1] | ¹H NMR (400 MHz, DMSO-d6) δ 8.19 (s, 1H), 7.71 (d, J = 1.2 Hz, 1H), 7.49-7.47 (dd, J₁ = 0.8 Hz, J₂ = 7.6 Hz, 1H), 7.37 (s, 1H), 7.3 (t, J = 8.0 Hz, 1H), 7.13 (d, J = 7.6 Hz, 1H), 5.52 (s, 2H), 3.73 (s, 3H). LC-MS: m/z 295.1 (M + H)⁺ |
| 227 | III.14 | 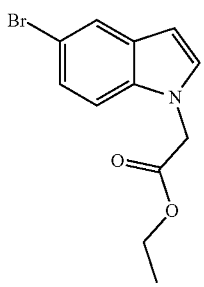 [SMILES: CCOC(=O)Cn1ccc2cc(Br)ccc21] | ¹H NMR (400 MHz, DMSO-d6) δ 7.74 (d, J = 1.2 Hz, 1H), 7.39-7.37 (m, 2H), 7.23 (dd, J₁ = 1.6 Hz, J₂ = 8.8 Hz, 1H), 6.45 (d, J = 3.2 Hz, 1H), 5.13 (s, 2H), 4.13 (q, J = 14.4 Hz, 2H), 1.2 (t, J = 7.2 Hz, 3H). LC-MS: m/z 282.0 (M + H)⁺ |
| 250 | III.15 | 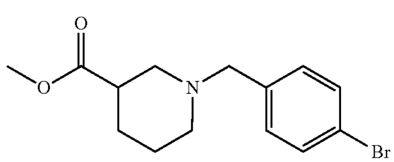 [SMILES: COC(=O)C1CCCN(Cc2ccc(Br)cc2)C1] | ¹H NMR (400 MHz, DMSO-d6) δ 7.51 (d, J = 8.3 Hz, 2H), 7.24 (d, J = 8.3 Hz, 2H), 3.57 (s, 3H), 3.43 (s, 2H), 2.75-2.67 (m, 1H), 2.60-2.51 (m, 1H), 2.33-2.32 (m, 1H), 2.17-2.12 (m, 1H), 2.07-2.05 (m, 1H), 1.79-1.77 (m, 1H), 1.67-1.63 (m, 1H), 1.49-1.39 (m, 2H). LC-MS: m/z 314.0 (M + H)²⁺ |

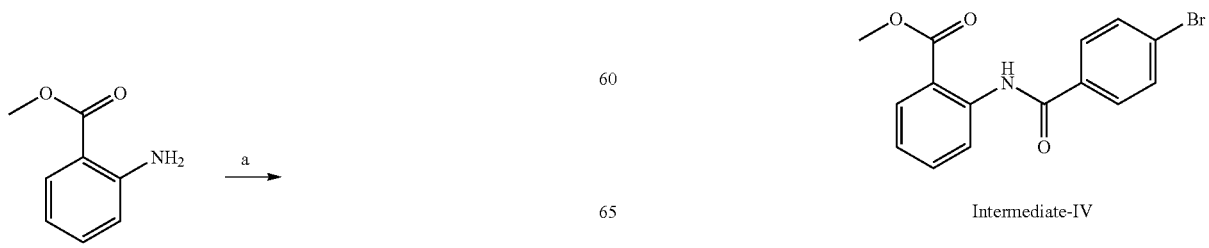

Intermediate-IV a →

Intermediate-IV

Step-a: Synthesis of methyl 2-(4-bromobenzamido)benzoate (Intermediate-IV)

A solution of methyl 2-aminobenzoate (5 g, 33.1 mmol, 1.0 eq.) in DCM (50 mL) was added with triethylamine (11 g, 108 mmol, 3 eq.) followed by 4-bromobenzoyl chloride (7.2 g, 33.1 mmol, 1.0 eq.) and stirred at RT overnight. Reaction mixture was extracted with ethyl acetate from water and concentrated in vacuo. The crude was washed with n-pentane and dried to afford title product (9 g, 85%).

$^1$H NMR (400 MHz, DMSO-d6) δ 11.52 (s, 1H), 8.47 (d, J=8.3 Hz, 1H), 8.04 (d, J=8.4 Hz, 1H), 7.89 (d, J=8.8 Hz, 2H), 7.83 (d, J=8.8 Hz, 2H), 7.67 (t, J=7.3 Hz, 1H), 7.24 (t, J=7.3 Hz, 1H), 3.87 (s, 3H).

The below intermediates were prepared by a procedure similar to Intermediate-IV using appropriate reactants and reagents and in presence of suitable solvents and appropriate reaction conditions.

| CP | Intermediate No. | Structure | Analytical data |
|---|---|---|---|
| 178 | IV.1 | 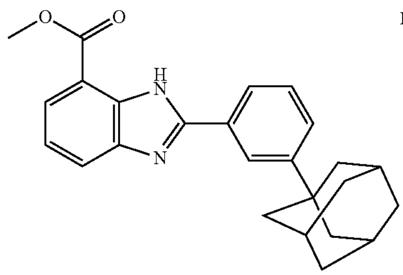 [SMILES: COC(=O)c1cccc2nc(-c3cccc(C45CC6CC(CC(C6)C4)C5)c3)[nH]c12] | LC-MS: m/z 387.4 (M + H)$^+$ |
| 239 | IV.2 | 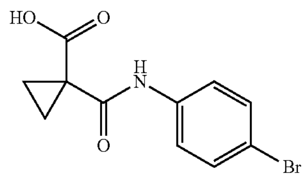 [SMILES: O=C(O)C1(C(=O)Nc2ccc(Br)cc2)CC1] | $^1$H NMR (400 MHz, DMSO-d6) δ6 13.10 (bs, 1H), 10.63 (s, 1H), 7.58 (d, J = 5.4 Hz, 2H), 7.47 (d, J = 6.8 Hz, 2H), 1.44 (s, 4H). LC-MS: m/z 284.0 (M + H)$^+$ |
| 291 | IV.3 | 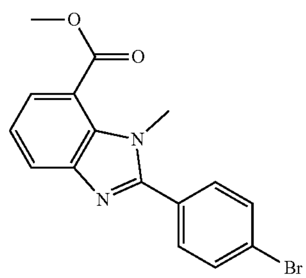 [SMILES: COC(=O)c1cccc2nc(-c3ccc(Br)cc3)n(C)c12] | LC-MS: m/z 345.0 (M + H)$^+$ |
| 317 | IV.4 | 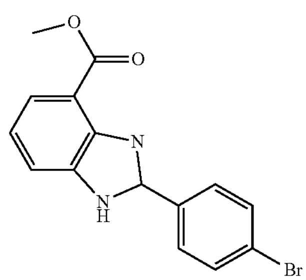 [SMILES: COC(=O)c1cccc2c1NC(c1ccc(Br)cc1)N2] | Proceeded with crude/only TLC reference |
| 328 | IV.5 | 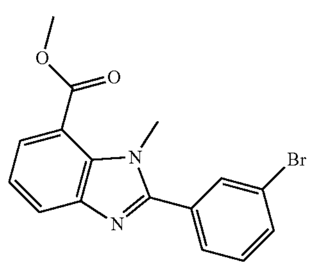 [SMILES: COC(=O)c1cccc2nc(-c3cccc(Br)c3)n(C)c12] | LC-MS: m/z 345.0 (M + H)$^{2+}$ |

Intermediate-V

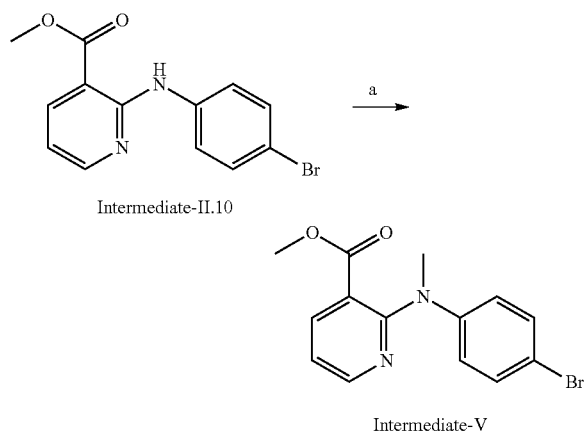

Step-a: Synthesis of methyl 2-((4-bromophenyl)(methyl)amino)nicotinate (Intermediate-V)

A solution of Intermediate-II.10 (0.4 g, 1.3 mmol, 1.0 eq.) in DMF (3 mL) was added with sodium hydride (50% o, 0.16 g, 3.9 mmol, 3 eq.) and stirred for 10 min. Iodomethane (0.25 mL, 3.9 mmol, 3 eq.) was added drop wise and stirred at RT overnight in a seal tube. Reaction mass was poured in to water, extracted with ethyl acetate and concentrated in vacuo. The crude was purified by combi-flash to afford title product as a colourless liquid (0.21 g, 500%).

$^1$H NM/R (400 MHz, DMSO-d6) δ 8.46 (dd, $J_1$=2.0 Hz, $J_2$=4.0 Hz, 1H), 7.85 (dd, $J_1$=2.0 Hz, $J_2$=7.6 Hz, 1H), 7.44-7.40 (m, 2H), 7.05 (dd, $J_1$=3.6 Hz, $J_2$=7.2 Hz, 1H), 6.94-6.90 (m, 2H), 3.44 (s, 3H), 3.29 (s, 3H), LC-MS: m/z 321.0 (M+H)$^+$

The below intermediates were prepared by a procedure similar to Intermediate-V using appropriate reactants and reagents and in presence of suitable solvents and appropriate reaction conditions.

| CP | Intermediate No. | Reactant | Structure | Analytical data |
|---|---|---|---|---|
| 241 | V.1 | II.9 | 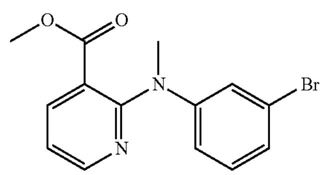 [SMILES: COC(=O)c1cccnc1N(C)c1cccc(Br)c1] | $^1$H NMR (400 MHz, DMSO-d6) δ 8.49-8.48 (m, 1H), 7.89-7.87 (m, 1H), 7.21-7.14 (m, 2H), 7.11-7.07 (m, 2H), 6.94-6.91 (m, 1H), 3.43 (s, 3H), 3.32 (s, 3H). LC-MS: m/z 321.0 (M + H)$^+$ |
| 239 | V.2 | IV.2 | 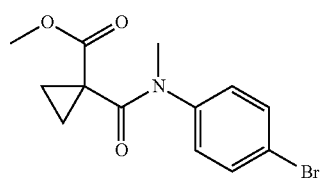 [SMILES: COC(=O)C1(C(=O)N(C)c2ccc(Br)cc2)CC1] | $^1$H NMR (400 MHz, DMSO-d6) δ 7.6 (d, J = 8.3 Hz, 2H), 7.27 (d, J = 6.8 Hz, 2H), 3.39 (s, 3H), 3.19 (s, 3H), 1.38 (m, 2H), 1.07 (s, 2H). |
| 252 | V.3 | II.4 | 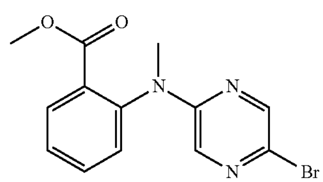 [SMILES: COC(=O)c1ccccc1N(C)c1cnc(Br)cn1] | $^1$H NMR (400 MHz, DMSO-d6) δ 8.19 (d, J = 1.6 Hz, 1H), 7.92 (dd, $J_1$ = 1.6 Hz, $J_2$ = 8.0 Hz, 1H), 7.72-7.63 (m, 1H), 7.57 (s, 1H), 7.52-7.47 (m, 2H), 3.62 (s, 3H), 3.30 (s, 3H). LC-MS: m/z 323.9 (M + H)$^{2+}$ |
| 255 | V.4 | II.20 | 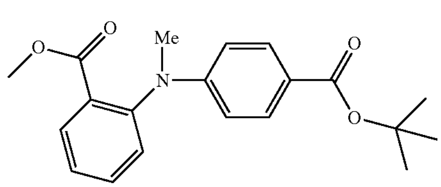 | $^1$H NMR (400 MHz, DMSO-d6) δ 7.90-7.80 (m, 1H), 7.80-7.70 (m, 1H), 7.65 (d, J = 9.6 Hz, 2H), 7.50-7.40 (m, 2H), 6.48 (d, J = 9.2 Hz, 2H), 3.56 (s, 3H), 3.25 (s, 3H), 1.50 (s, 9H). LC-MS: m/z 342.1 (M + H)$^+$ |
| 258 | V.5 | II.15 | 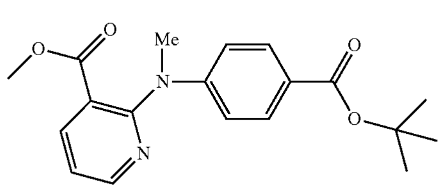 [SMILES: COC(=O)c1cccnc1N(C)c1ccc(C(=O)OC(C)(C)C)cc1] | $^1$H NMR (400 MHz, DMSO-d6) δ 8.57 (dd, $J_1$ = 2.0 Hz, $J_2$ = 4.9 Hz, 1H), 8.00 (dd, $J_1$ = 1.9 Hz, $J_2$ = 7.8 Hz, 1H), 7.73 (d, J = 9.3 Hz, 2H), 7.23 (m, 1H), 6.89 (d, J = 8.8 Hz, 2H), 3.45 (s, 3H), 3.32 (s, 3H), 1.52 (s, 9H). |

-continued

| CP | Intermediate No. | Reactant | Structure | Analytical data |
|---|---|---|---|---|
| 317 | V.6 | IV.4 | 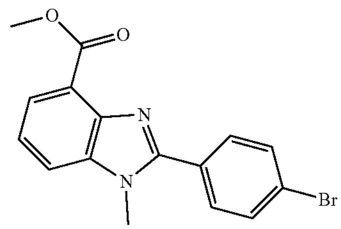 [SMILES: COC(=O)c1cccc2c1nc(-c1ccc(Br)cc1)n2C] | LC-MS: m/z 344.9 (M + H)$^{+2}$ |
| 353 | V.7 | II.25 | 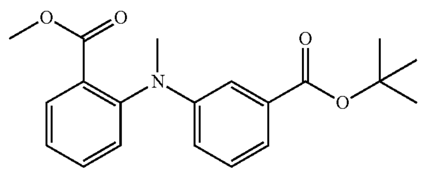 [SMILES: COC(=O)c1ccccc1N(C)c1cccc(C(=O)OC(C)(C)C)c1] | $^1$H NMR (400 MHz, DMSO-d6) δ 7.79 (d, J = 7.2 Hz, 1H), 7.68 (t, J = 8.0 Hz, 1H), 7.43-7.36 (m, 2H), 7.25-7.21 (m, 2H), 7.04 (s, 1H), 6.75 (d, J = 6.8 Hz, 1H), 3.54 (s, 3H), 3.22 (s, 3H), 1.49 (s, 9H). LC-MS: m/z 342.1 (M + H)$^+$ |
| 340 | V.8 | Int-IV | 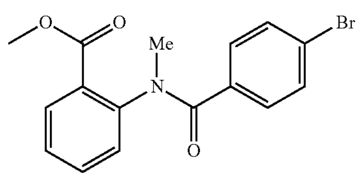 [SMILES: COC(=O)c1ccccc1N(C)C(=O)c1ccc(Br)cc1] | $^1$H NMR (400 MHz, DMSO-d6) δ 7.67 (d, J = 7.6 Hz, 1H), 7.60-7.58 (m, 1H), 7.52 (d, J = 8.0 Hz, 1H), 7.38-7.36 (m, 3H), 7.08 (d, J = 8.0 Hz, 2H), 3.78 (s, 3H), 3.29 (s, 3H). LC-MS: m/z 348.0 (M + H)$^+$ |
| 357 | V.9 | II.32 | 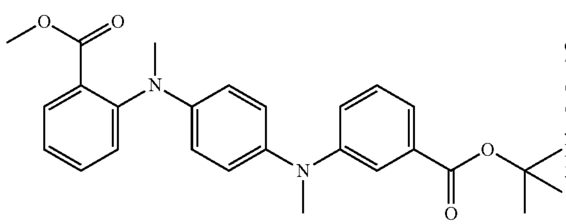 | $^1$H NMR (400 MHz, DMSO-d6) δ 7.69 (d, J = 8.0 Hz, 1H), 7.65-7.60 (m, 1H), 7.39-7.30 (m, 3H), 7.15-7.07 (m, 3H), 6.94 (d, J = 8.8 Hz, 2H), 6.76 (d, J = 8.0 Hz, 1H), 6.60 (d, J = 8.8 Hz, 2H), 3.56 (s, 3H), 3.22 (s, 3H), 3.18 (s, 3H), 2.03 (s, 9H), 1.64 (s, 6H). |
| 318 | V.10 | Int-II | 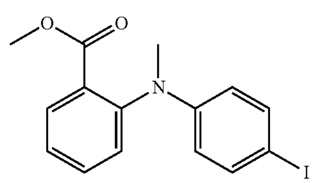 [SMILES: COC(=O)c1ccccc1N(C)c1ccc(I)cc1] | LC-MS: m/z 367.9 (M + H)$^+$ |

Intermediate-VI

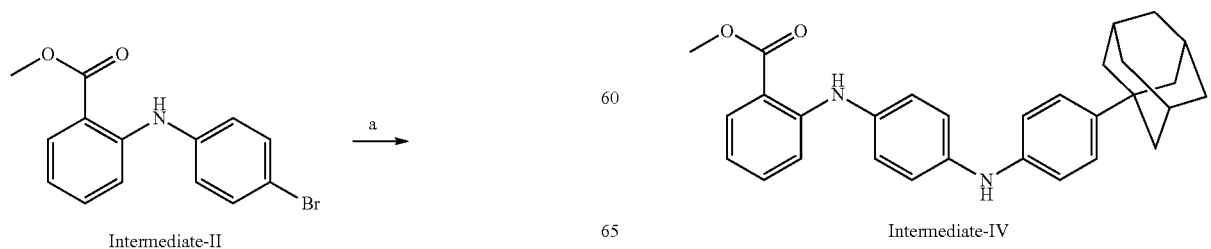

Intermediate-II → Intermediate-IV

Step-a: Synthesis of methyl 2-((4-((4-((3R,5R)-adamantan-1-yl)phenyl)amino) phenyl) amino) benzoate (Intermediate-VI)

A solution of Intermediate-II (0.5 g, 1.63 mmol, 1.0 eq.) and Intermediate-I.1 (0.37 g, 1.63 mmol, 1.0 eq.) in toluene (10 mL) was de-gassed with $N_2$ gas for 15 min. $Pd_2dba_3$ (0.12 g, 0.13 mmol, 0.08 eq.) and XPhos (0.16 g, 0.326 mmol, 0.2 eq.) were added and de-gassed for 5 min. Reaction mass was heated at 110° C. for 16 h. Reaction mass was filtered through celite, concentrated in vacuo and purified by combi-flash to afford the title product as pale yellow solid (0.26 g, 35%).

$^1$H NMR (400 MHz, DMSO-d6) δ 9.14 (s, 1H), 8.02 (s, 1H), 7.86 (dd, $J_1$=1.4 Hz, $J_2$=7.8 Hz, 1H), 7.35 (t, J=1.4 Hz, 1H), 7.21 (d, J=8.8 Hz, 2H), 7.12-6.96 (m, 7H), 6.69 (t, J=6.8 Hz, 1H), 3.85 (s, 3H), 2.04 (s, 3H), 1.83 (s, 6H), 1.72 (s, 6H); LC-MS: m/z 452.4 (M+H)$^+$

The below intermediates were prepared by a procedure similar to Intermediate-VI using appropriate reactants and reagents employing suitable Pd catalysts and ligands and in presence of suitable solvents and appropriate reaction conditions.

| CP | Intermediate No. | Reactant | Structure | Analytical data |
|---|---|---|---|---|
| 64 | VI.1 | Int-II & Int-I | 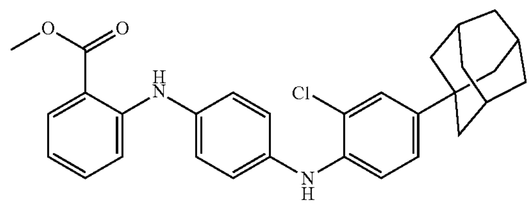 [SMILES: COC(=O)c1ccccc1Nc1ccc(Nc2ccc(C34CC5CC(CC(C5)C3)C4)cc2Cl)cc1] | $^1$H NMR (400 MHz, DMSO-d6) δ 9.17 (s, 1H), 7.86 (dd, $J_1$ = 2.0 Hz, $J_2$ = 9.8 Hz, 1H), 7.54 (s, 1H), 7.36-7.34 (m, 2H), 7.20 (s, 2H), 7.13 (d, J = 8.8 Hz, 2H), 6.06 (s, 1H), 7.03 (d, J = 4.9 Hz, 1H), 7.01 (s, 1H), 6.72 (t, J = 6.8 Hz, 1H), 3.85 (s, 3H), 2.05 (bs, 3H), 1.84 (bs, 6H), 1.31 (bs, 6H). LC-MS: m/z 487.2 (M + H)$^+$ |
| 93 | VI.2 | Int-II & I.33 | 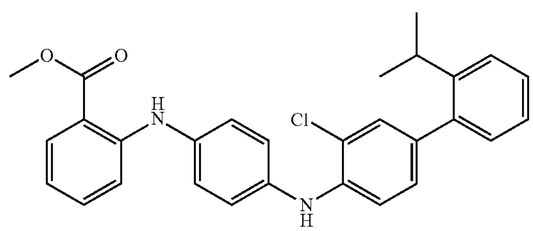 [SMILES: COC(=O)c1ccccc1Nc1ccc(Nc2ccc(-c3ccccc3C(C)C)cc2Cl)cc1] | $^1$H NMR (400 MHz, DMSO-d6) δ 9.22 (s, 1H), 7.89-7.87 (dd, $J_1$ = 2.0 Hz, $J_2$ = 8.4 Hz, 1H), 7.71 (s, 1H), 7.42-7.23 (m, 6H), 7.21-7.19 (m, 4H), 7.15-7.07 (m, 3H), 6.74 (t, J = 7.3 Hz, 1H), 3.86 (s, 3H), 3.06-3.02 (m, 1H), 1.14 (d, J = 12.8 Hz, 6H). LC-MS: m/z 471.1 (M + H)$^+$ |
| 113 | VI.3 | Int-II & I.5 | 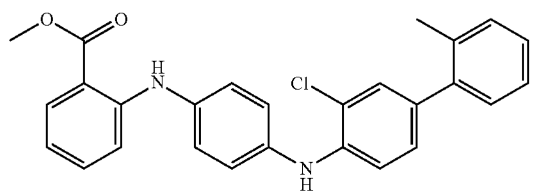 [SMILES: COC(=O)c1ccccc1Nc1ccc(Nc2ccc(-c3ccccc3C)cc2Cl)cc1] | $^1$H NMR (400 MHz, DMSO-d6) δ 9.22 (s, 1H), 7.89-7.87 (dd, $J_1$ = 1.5 Hz, $J_2$ = 7.9 Hz, 1H), 7.72 (s, 1H), 7.38-7.37 (m, 2H), 7.29-7.17 (m, 10H), 7.08 (d, J = 8.3 Hz, 1H), 6.75 (d, J = 8.3 Hz, 1H), 3.86 (s, 3H), 2.27 (s, 3H). LC-MS: m/z 442.4 (M + H)$^+$ |
| 115 | VI.4 | Int-II & I.6 | 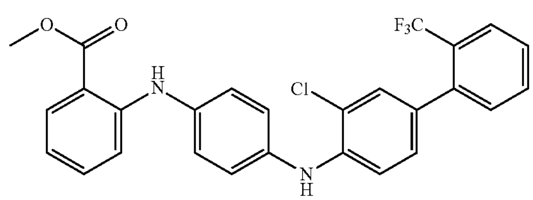 [SMILES: COC(=O)c1ccccc1Nc1ccc(Nc2ccc(-c3ccccc3C(F)(F)F)cc2Cl)cc1] | $^1$H NMR (400 MHz, DMSO-d6) δ 9.40 (s, 1H), 7.96 (d, J = 8.3 Hz, 1H), 7.73 (d, J = 7.9 Hz, 1H), 7.54 (d, J = 7.3 Hz, 1H), 7.48-7.45 (m, 1H), 7.34-7.32 (m, 1H), 7.31 (d, J = 8.8 Hz, 1H), 7.25 (d, J = 3.9 Hz, 1H), 7.24-7.18 (m, 6H), 7.10 (d, J = 9.3 Hz, 1H), 6.72-6.68 (m, 1H), 6.18 (s, 1H), 3.91 (s, 3H). LC-MS: m/z 497.1 (M + H)$^+$ |

| CP | Intermediate No. | Reactant | Structure | Analytical data |
|---|---|---|---|---|
| 116 | VI.5 | Int-II & I.7 | 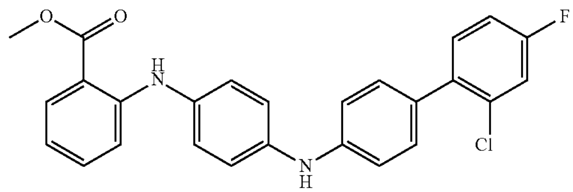 [SMILES: COC(=O)c1ccccc1Nc1ccc(Nc2ccc(-c3ccc(F)cc3Cl)cc2)cc1] | $^1$H NMR (400 MHz, DMSO-d6) δ 9.20 (s, 1H), 8.34 (s, 1H), 7.87 (d, J = 6.8 Hz, 1H), 7.51 (dd, J$_1$ = 2.4 Hz, J$_2$ = 8.8 Hz, 1H), 7.45 (t, J = 6.4 Hz, 1H), 7.36 (t, J = 7.3 Hz, 1H), 7.30-7.25 (m, 3H), 7.17 (s, 4H), 7.11 (d, J = 8.8 Hz, 2H), 7.04 (d, J = 8.4 Hz, 1H), 6.73 (t, J = 7.3 Hz, 1H), 3.85 (s, 3H). |
| 118 | VI.6 | Int-II & I.8 | 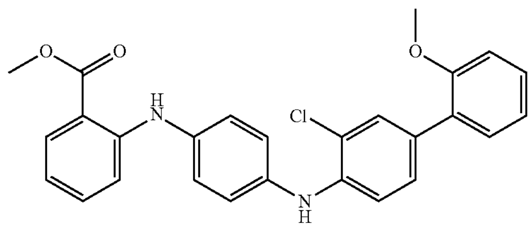 [SMILES: COC(=O)c1ccccc1Nc1ccc(Nc2ccc(-c3ccccc3OC)cc2Cl)cc1] | $^1$H NMR (400 MHz, DMSO-d6) δ 9.22 (s, 1H), 7.89-7.87 (dd, J$_1$ = 1.5 Hz, J$_2$ = 7.9 Hz, 1H), 7.71 (s, 1H), 7.53 (d, J = 1.9 Hz, 1H), 7.41-7.36 (m, 1H), 7.34-7.29 (dd, J$_1$ = 1.9 Hz, J$_2$ = 8.3 Hz, 3H), 6.24 (d, J = 8.3 Hz, 1H), 7.21-7.15 (m, 4H), 7.09 (t, J = 9.3 Hz, 2H), 7.01 (t, J = 7.4 Hz, 1H), 6.76-6.72 (dd, J$_1$ = = 1.0 Hz, J$_2$ = 8.3 Hz, 1H), 3.86 (s, 3H), 3.79 (s, 3H). LC-MS: m/z 458.3 (M + H)$^+$ |
| 121 | VI.7 | Int-II & I.9 | 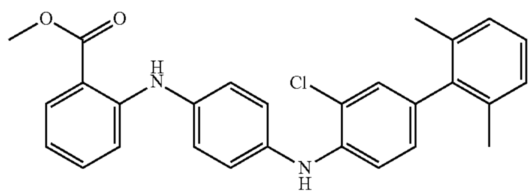 [SMILES: COC(=O)c1ccccc1Nc1ccc(Nc2ccc(-c3c(C)cccc3C)cc2Cl)cc1] | $^1$H NMR (400 MHz, DMSO-d6) δ 9.22 (s, 1H), 7.91-7.87 (m, 1H), 7.69 (s, 1H), 7.50 (d, J = 8.8 Hz, 1H), 7.38-7.36 (m, 1H), 7.30-7.06 (m, 8H), 6.99-6.96 (dd, J$_1$ = 2.0 Hz, J$_2$ = 8.3 Hz, 1H), 6.88-6.80 (m, 1H), 6.74 (t, J = 6.8 Hz, 1H), 3.86 (s, 3H), 2.03 (s, 6H). LC-MS: m/z 457.1 (M + H)$^+$ |
| 122 | VI.8 | Int-II & I.10 | 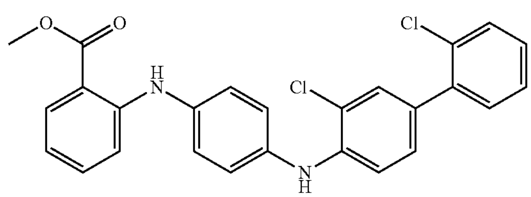 [SMILES: COC(=O)c1ccccc1Nc1ccc(Nc2ccc(-c3ccccc3Cl)cc2Cl)cc1] | $^1$H NMR (400 MHz, DMSO-d6) δ 9.24 (s, 1H), 7.88 (d, J = 7.9 Hz, 1H), 7.78 (s, 1H), 7.55 (d, J = 7.3 Hz, 1H), 7.49 (s, 1H), 7.43-7.37 (m, 4H), 7.26 (s, 2H), 7.21 (s, 4H), 7.1 (d, J = 8.3 Hz, 1H), 6.75 (t, J = 7.3 Hz, 1H), 3.86 (s, 3H). LC-MS: m/z 463.1 (M + H)$^+$ |
| 125 | VI.9 | Int-I | 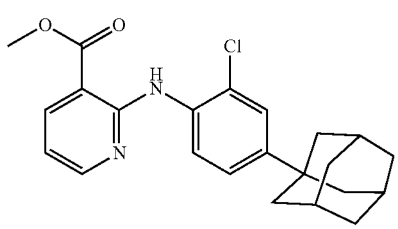 [SMILES: COC(=O)c1cccnc1Nc1ccc(C23CC4CC(CC(C4)C2)C3)cc1Cl] | LC-MS: m/z 396.3 (M + H)$^+$ |

-continued

| CP | Intermediate No. | Reactant | Structure | Analytical data |
|---|---|---|---|---|
| 126 | VI.10 | Int-II & I.11 | 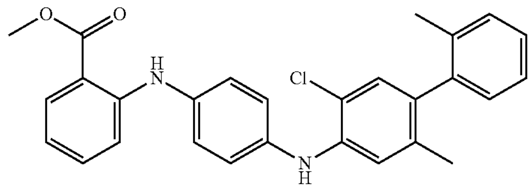 [SMILES: COC(=O)c1ccccc1Nc1ccc(Nc2cc(C)c(-c3ccccc3C)cc2Cl)cc1] | ¹H NMR (400 MHz, DMSO-d6) δ 9.21 (s, 1H), 7.87 (d, J = 1.5 Hz, 1H), 7.62 (s, 1H), 7.35 (t, J = 6.8 Hz, 1H), 7.29-7.06 (m, 11H), 6.73 (t, J = 7.3 Hz, 1H), 3.86 (s, 3H), 2.05 (s, 3H), 1.90 (s, 3H). LC-MS: m/z 457.1 (M + H)⁺ |
| 135 | VI.11 | Int-II | 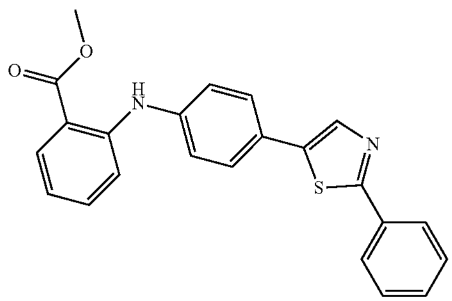 [SMILES: COC(=O)c1ccccc1Nc1ccc(-c2cnc(-c3ccccc3)s2)cc1] | ¹H NMR (400 MHz, DMSO-d6) δ 9.39 (s, 1H), 8.26 (s, 1H), 7.99-7.92 (m, 4H), 7.70 (d, J = 8.4 Hz, 2H), 7.55-7.46 (m, 4H), 7.38-7.33 (m, 2H), 6.89 (t, J = 8.0 Hz, 1H), 3.87 (s, 3H). LC-MS: m/z 387.0 (M + H)⁺ |
| 140 | VI.12 | Int-II & I.12 | 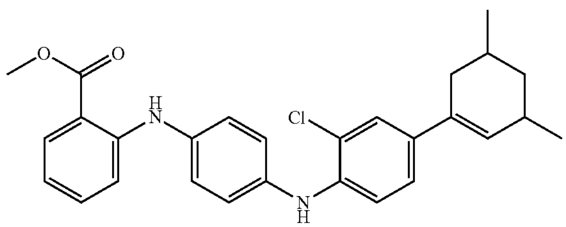 | ¹H NMR (400 MHz, DMSO-d6) δ 9.19 (s, 1H), 7.87 (d, J = 7.9 Hz, 1H), 7.65 (s, 1H), 7.43 (s, 1H), 7.36 (t, J = 6.8 Hz, 1H), 7.27 (d, J = 6.8 Hz, 1H), 7.19-7.03 (m, 6H), 6.74 (t, J = 7.3 Hz, 1H), 5.92 (s, 1H), 3.85 (s, 3H), 2.35 (m, 2H), 1.75 (m, 4H), 0.99 (m, 6H). LC-MS: m/z 460.3 (M + H)⁺ |
| 141 | VI.13 | II.28 & Int-I | 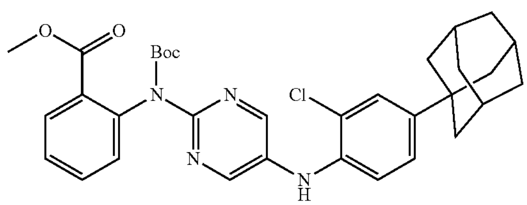 [SMILES: COC(=O)c1ccccc1N(C(=O)OC(C)(C)C)c1ncc(Nc2ccc(C34CC5CC(CC(C5)C3)C4)cc2Cl)cn1] | ¹H NMR (400 MHz, DMSO-d6) δ 8.36 (s, 2H), 8.02 (s, 1H), 7.87 (dd, J₁ = 1.2 Hz, J₂ = 4.8 Hz, 1H), 7.55-7.53 (m, 1H), 7.41-7.38 (m, 2H), 7.24-7.19 (m, 2H), 7.12-7.10 (m, 1H), 3.74 (s, 3H), 2.05 (s, 3H), 1.82 (s, 6H), 1.72 (s, 6H), 1.34 (s, 9H). |
| 142 | VI.14 | II.29 & Int-I | 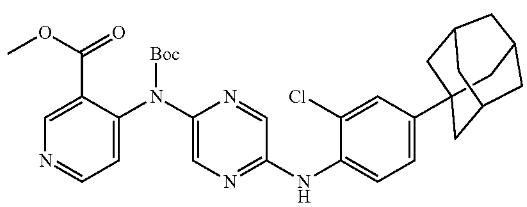 [SMILES: COC(=O)c1cnccc1N(C(=O)OC(C)(C)C)c1cnc(Nc2ccc(C34CC5CC(CC(C5)C3)C4)cc2Cl)cn1] | ¹H NMR (400 MHz, DMSO-d6) δ 8.81 (s, 1H), 8.28 (s, 1H), 8.05 (d, J = 1.2 Hz, 1H), 7.87-7.85 (m, 1H), 7.76 (d, J = 8.4 Hz, 1H), 7.58-7.54 (m, 1H), 7.41-7.38 (m, 2H), 7.32-7.28 (m, 2H), 3.77 (s, 3H), 2.05 (s, 3H), 1.85 (s, 6H), 1.73 (s, 6H). LC-MS: m/z 589.1 (M + H)⁺ |
| 144, 152 | VI.15 | II.30 & Int-I | 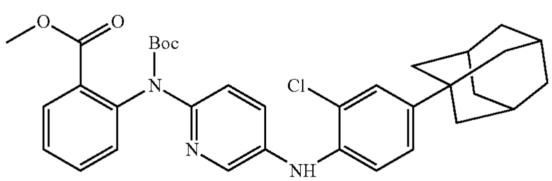 [SMILES: COC(=O)c1ccccc1N(C(=O)OC(C)(C)C)c1ccc(Nc2ccc(C34CC5CC(CC(C5)C3)C4)cc2Cl)cn1] | ¹H NMR (400 MHz, DMSO-d6) δ 7.96 (d, J = 3.2 Hz, 1H), 7.84 (dd, J₁ = 1.2 Hz, J₂ = 7.6 Hz, 1H), 7.79 (s, 1H), 7.56 (t, J = 2.0 Hz, 1H), 7.47-7.46 (m, 1H), 7.41-7.35 (m, 3H), 7.27 (dd, J₁ = 1.2 Hz, J₂ = 8.0 Hz, 1H), 7.21 (d, J = 2.8 Hz, 1H), 7.15 |

-continued

| CP | Intermediate No. | Reactant | Structure | Analytical data |
|---|---|---|---|---|
| | | | | (d, J = 8.0 Hz, 1H), 3.75 (s, 3H), 2.04 (s, 3H), 1.82 (s, 6H), 1.72 (s, 6H), 1.32 (s, 9H). LC-MS: m/z 588.1 (M + H)+ |
| 158 | VI.16 | II.6 & Int-I | 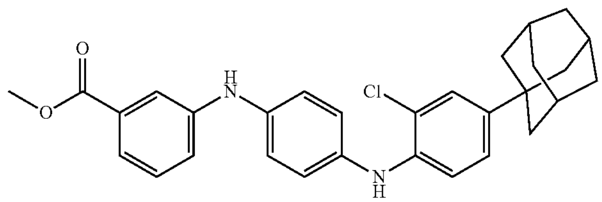 [SMILES: COC(=O)c1cccc(Nc2ccc(Nc3ccc(C45CC6CC(CC(C6)C4)C5)cc3Cl)cc2)c1] | ¹H NMR (400 MHz, DMSO-d6) δ 8.17 (s, 1H), 7.37-7.04 (m, 12H), 3.82 (bs, 3H), 2.04 (s, 3H), 1.85 (s, 6H), 1.72 (s, 6H). LC-MS: m/z 487.1 (M + H)+ |
| 170 | VI.17 | I.4 | 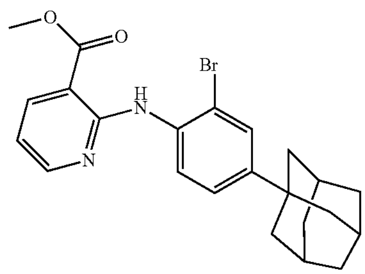 [SMILES: COC(=O)c1cccnc1Nc1ccc(C23CC4CC(CC(C4)C2)C3)cc1Br] | ¹H NMR (400 MHz, DMSO-d6) δ 10.25 (s, 1H), 8.41 (dd, J₁ = 2.0 Hz, J₂ = 4.4 Hz, 1H), 8.35 (d, J = 8.8 Hz, 1H), 8.30 (dd, J₁ = 2.0 Hz, J₂ = 8.0 Hz, 1H), 7.56 (d, J = 2.0 Hz, 1H), 7.37 (dd, J₁ = 1.6 Hz, J₂ = 8.8 Hz, 1H), 6.95 (dd, J₁ = 4.4 Hz, J₂ = 8.0 Hz, 1H), 3.92 (s, 3H), 2.06 (s, 3H), 1.86 (s, 6H), 1.74 (s, 6H). |
| 173 | VI.18 | Int-I | 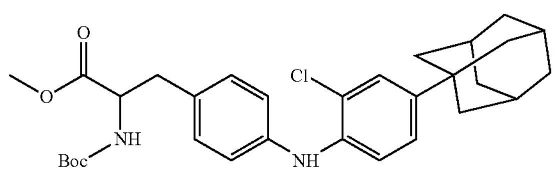 [SMILES: COC(=O)C(Cc1ccc(Nc2ccc(C34CC5CC(CC(C5)C3)C4)cc2Cl)cc1)NC(=O)OC(C)(C)C] | ¹H NMR (400 MHz, DMSO-d6) δ 7.43 (d, J = 10.4 Hz, 2H), 7.32 (d, J = 2.0 Hz, 1H), 7.18-7.17 (m, 2H), 7.08 (d, J = 8.4 Hz, 2H), 6.93 (d, J = 8.4 Hz, 2H), 4.1 (m, 1H), 3.61 (d, J = 2.4 Hz, 4H), 2.90 (m, 2H), 2.80 (m, 1H), 2.05 (s, 3H), 1.83 (s, 6H), 1.73 (s, 6H), 1.34-1.30 (m, 15H). |
| 175 | VI.19 | II.31 & Int-I | 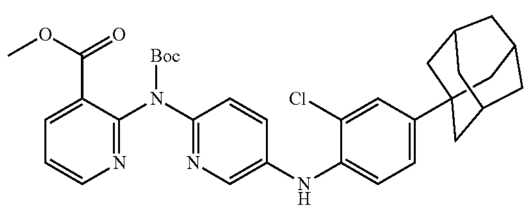 [SMILES: COC(=O)c1cccnc1N(C(=O)OC(C)(C)C)c1ccc(Nc2ccc(C34CC5CC(CC(C5)C3)C4)cc2Cl)cn1] | ¹H NMR (400 MHz, DMSO-d6) δ 8.55 (d, J = 2.8 Hz, 1H), 8.28 (d, J = 6.0 Hz, 1H), 7.92 (s, 1H), 7.77 (s, 1H), 7.46-7.42 (m, 3H), 7.36 (d, J = 1.6 Hz, 1H), 7.23 (dd, J₁ = 2.0 Hz, J₂ = 8.8 Hz, 1H), 7.15 (d, J = 8.4 Hz, 1H), 3.78 (s, 3H), 2.04 (s, 3H), 1.83 (s, 6H), 1.72 (s, 6H), 1.34 (s, 9H). LC-MS: m/z 589.1 (M + H)+ |
| 177 | VI.20 | I.15 | 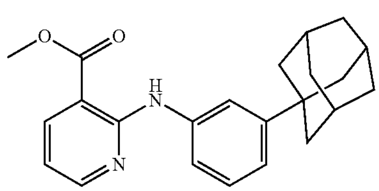 [SMILES: COC(=O)c1cccnc1Nc1cccc(C23CC4CC(CC(C4)C2)C3)c1] | ¹H NMR (400 MHz, DMSO-d6) δ 10.06 (s, 1H), 8.41 (dd, J₁ = 2.0 Hz, J₂ = 4.9 Hz, 1H), 8.26 (dd, J₁ = 1.9 Hz, J₂ = 7.8 Hz, 1H), 7.68 (d, J = 6.8 Hz, 1H), 7.50 (s, 1H), 7.26 (t, J = 7.8 Hz, 1H), 7.05 (d, J = 7.9 Hz, 1H), 6.88-6.85 (m, 1H), 3.90 (s, 3H), 2.06 (s, 3H), 1.88 (s, 6H), 1.74 (s, 6H). LC-MS: m/z 363.1 (M + H)+ |

-continued

| CP | Intermediate No. | Reactant | Structure | Analytical data |
|---|---|---|---|---|
| 185 | VI.21 | IIIa & Int-I | 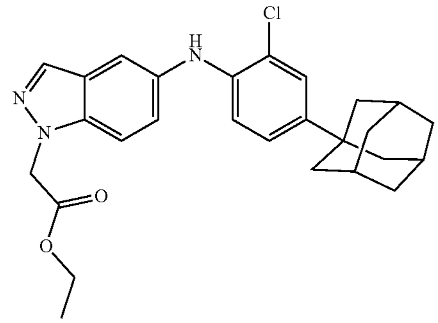 [SMILES: CCOC(=O)Cn1ncc2cc(Nc3ccc(C45CC6CC(CC(C6)C4)C5)cc3Cl)ccc21] | LC-MS: m/z 464.3 (M + H)⁺ |
| 187 | VI.22 | III.1 & Int-I | 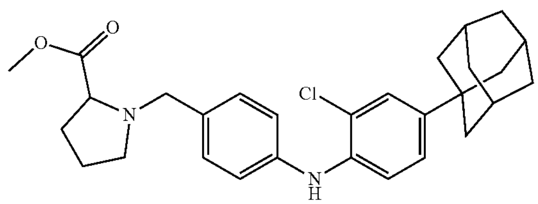 [SMILES: COC(=O)C1CCCN1Cc1ccc(Nc2ccc(C34CC5CC(CC(C5)C3)C4)cc2Cl)cc1] | ¹H NMR (400 MHz, DMSO-d6) δ 7.77 (s, 1H), 7.33 (s, 1H), 7.18 (s, 2H), 7.12 (d, J = 8.4 Hz, 2H), 6.95 (d, J = 8.8 Hz, 2H), 3.78-3.72 (m, 1H), 3.56 (s, 3H), 3.43-3.39 (m, 1H), 3.25-3.21 (m, 1H), 2.89-2.80 (m, 1H), 2.38-2.32 (m, 1H), 2.09-2.01 (m, 4H), 1.89-1.81 (m, 7H), 1.82-1.69 (m, 8H). |
| 192 | VI.23 | III.2 & Int-I | 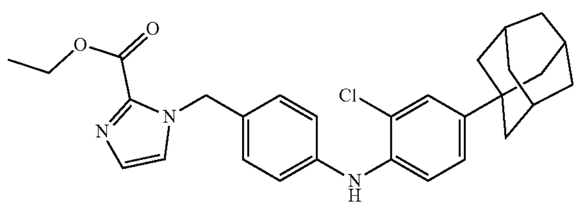 [SMILES: CCOC(=O)c1nccn1Cc1ccc(Nc2ccc(C34CC5CC(CC(C5)C3)C4)cc2Cl)cc1] | ¹H NMR (400 MHz, DMSO-d6) δ 7.61 (s, 1H), 7.57 (s, 1H), 7.34 (s, 1H), 7.19 (d, J = 0.8 Hz, 2H), 7.10-7.08 (m, 3H), 6.94 (d, J = 8.4 Hz, 2H), 5.49 (s, 2H), 4.31-4.25 (m, 2H), 2.04 (s, 3H), 1.83 (s, 6H), 1.72 (s, 6H), 1.28 (t, J = 6.8 Hz, 3H). |
| 197 | VI.24 | III.4 & Int-I | 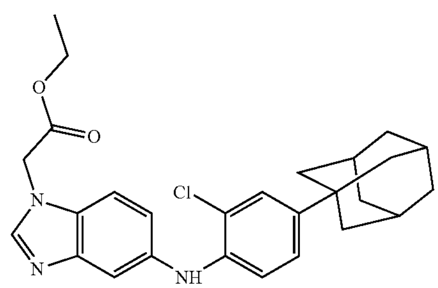 [SMILES: CCOC(=O)Cn1cnc2cc(Nc3ccc(C45CC6CC(CC(C6)C4)C5)cc3Cl)ccc21] | LC-MS: m/z 464.1 (M + H)⁺ |
| 199 | VI.25 | IIIb & Int-I | 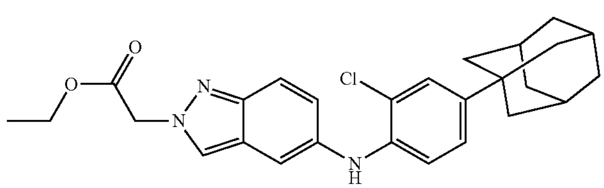 [SMILES: CCOC(=O)Cn1cc2cc(Nc3ccc(C45CC6CC(CC(C6)C4)C5)cc3Cl)ccc2n1] | LC-MS: m/z 464.1 (M + H)⁺ |
| 200 | VI.26 | II.9 & I.15 | 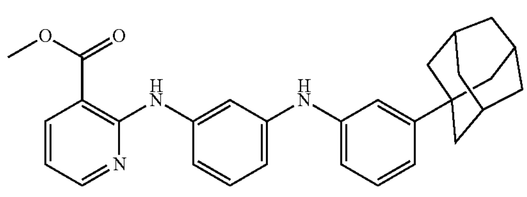 [SMILES: COC(=O)c1cccnc1Nc1cccc(Nc2cccc(C34CC5CC(CC(C5)C3)C4)c2)c1] | ¹H NMR (400 MHz, DMSO-d6) δ 10.09 (s, 1H), 8.38 (t, J = 1.4 Hz, 1H), 8.25 (d, J = 7.8 Hz, 1H), 8.12 (s, 1H), 7.66 (s, 1H), 7.19-7.11 (m, 3H), 7.02 (d, J = 7.8 Hz, 1H), 6.95 (d, J = 7.8 Hz, 1H), 6.89-6.83 (m, 2H), 6.70 (d, J = 7.8 Hz, 1H), |

-continued

| CP | Intermediate No. | Reactant | Structure | Analytical data |
|---|---|---|---|---|
| | | | | 3.89 (s, 3H), 2.04 (s, 3H), 1.75 (s, 6H), 1.72 (s, 6H). LC-MS: m/z 454.3 (M + H)+ |
| 210 | VI.27 | III.7 & Int-I | 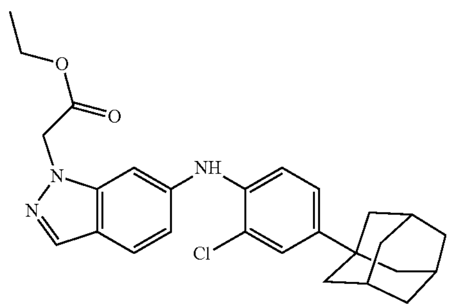 [SMILES: CCOC(=O)Cn1ncc2ccc(Nc3ccc(C45CC6CC(CC(C6)C4)C5)cc3Cl)cc21] | ¹H NMR (400 MHz, DMSO-d6) +67 7.91 (s, 1H), 7.77 (s, 1H), 7.58 (d, J = 8.4 Hz, 1H), 7.37 (d, J = 2.0 Hz, 1H), 7.32 (d, J = 8.8 Hz, 1H), 7.23-7.21 (m, 1H), 6.99 (s, 1H), 6.92 (d, J = 8.0 Hz, 1H), 5.19 (s, 2H), 4.12 (q, J = 14 Hz, 2H), 2.05 (s, 3H), 1.85 (s, 6H), 1.73 (s, 6H), 1.17 (t, J = 6.8 Hz, 3H). LC-MS: m/z 464.2 (M + H)+ |
| 213 | VI.28 | III.8 & Int-I | 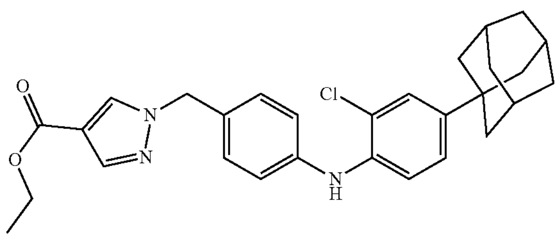 [SMILES: CCOC(=O)c1cnn(Cc2ccc(Nc3ccc(C45CC6CC(CC(C6)C4)C5)cc3Cl)cc2)c1] | ¹H NMR (400 MHz, DMSO-d6) δ 8.38 (s, 1H), 7.85 (s, 1H), 7.64 (s, 1H), 7.34 (s, 1H), 7.21 (s, 2H), 7.17 (d, J = 8.4 Hz, 2H), 6.94 (d, J = 8.4 Hz, 2H), 5.24 (s, 2H), 4.23-4.17 (q, J = 3.6 Hz, 2H), 2.04 (s, 3H), 1.83 (s, 6H), 1.72 (s, 6H), 1.25 (t, J = 7.2 Hz, 3H). |
| 214 | VI.29 | III.9 & Int-I | 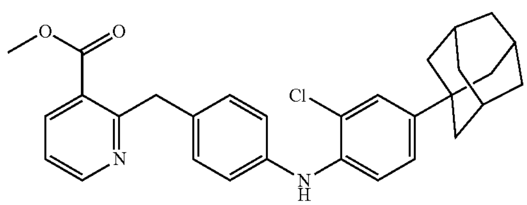 [SMILES: COC(=O)c1cccnc1Cc1ccc(Nc2ccc(C34CC5CC(CC(C5)C3)C4)cc2Cl)cc1] | ¹H NMR (400 MHz, DMSO-d6) δ 8.69-8.68 (m, 1H), 8.15-8.13 (m, 1H), 7.41-7.39 (m, 2H), 7.30 (d, J = 2.0 Hz, 1H), 7.15-7.14 (m, 2H), 7.12-7.03 (m, 3H), 6.94-6.89 (m, 1H), 4.34 (s, 2H), 3.83 (s, 3H), 2.03 (s, 3H), 1.81 (s, 6H), 1.71 (s, 6H). LC-MS: m/z 487.2 (M + H)+ |
| 217 | VI.30 | III.10 & Int-I | 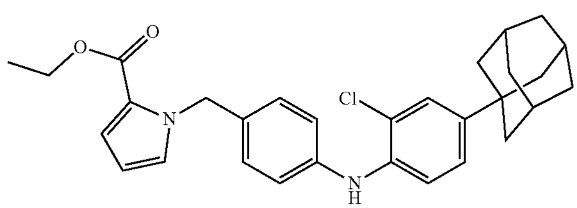 [SMILES: CCOC(=O)c1cccn1Cc1ccc(Nc2ccc(C34CC5CC(CC(C5)C3)C4)cc2Cl)cc1] | ¹H NMR (400 MHz, DMSO-d6) δ 7.54 (s, 1H), 7.32 (s, 1H), 7.24 (t, J = 2.0 Hz, 1H), 7.17 (s, 2H), 7.01 (d, J = 8.4 Hz, 2H), 6.93 (d, J = 8.0 Hz, 2H), 6.88-6.87 (m, 1H), 6.15-6.14 (m, 1H), 5.43 (s, 2H), 4.20-4.15 (q, J = 7.2 Hz, 2H), 2.04 (s, 3H), 1.82 (s, 6H), 1.72 (s, 6H), 1.23 (t, J = 6.8 Hz, 3H). LC-MS: m/z 489.2 (M + H)+ |
| 218 | VI.31 | Int-V & Int-I | 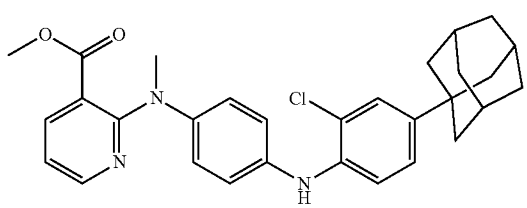 [SMILES: COC(=O)c1cccnc1N(C)c1ccc(Nc2ccc(C34CC5CC(CC(C5)C3)C4)cc2Cl)cc1] | ¹H NMR (400 MHz, DMSO-d6) δ 8.36-8.34 (dd, J₁ = 2.0 Hz, J₂ = 4.8 Hz, 1H), 7.71-7.67 (m, 1H), 7.5 (s, 1H), 7.32 (d, J = 1.6 Hz, 1H), 7.22-7.19 (dd, J₁ = 2.4 Hz, J₂ = 8.8 Hz, 1H), 7.12 (d, J = 8.4 Hz, 1H), 6.95-6.80 (m, 5H), 3.37 (s, 3H), 3.29 (s, 3H), 2.04 (s, 3H), 1.83 (s, 6H), 1.72 (s, 6H). LC-MS: m/z 502.2 (M +H)+ |

-continued

| CP | Intermediate No. | Reactant | Structure | Analytical data |
|---|---|---|---|---|
| 219 | VI.32 | III.11 & Int-I | 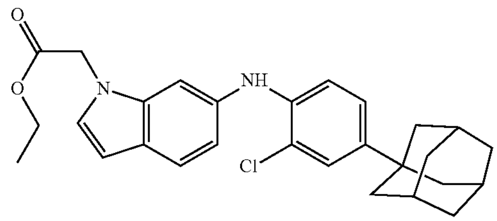 [SMILES: CCOC(=O)Cn1ccc2ccc(Nc3ccc(C45CC6CC(CC(C6)C4)C5)cc3Cl)cc21] | ¹H NMR (400 MHz, DMSO-d6) δ 7.44 (d, J = 8.0 Hz, 1H), 7.29 (s, 2H), 7.20 (d, J = 2.8 Hz, 1H), 7.09-7.06 (m, 3H), 6.87 (dd, J₁ = 1.6 Hz, J₂ = 8.4 Hz, 1H), 6.37 (d, J = 2.8 Hz, 1H), 5.11 (s, 2H), 4.16-4.12 (m, 2H), 2.03 (s, 3H), 1.81 (d, J = 2.8 Hz, 6H), 1.71 (s, 6H), 1.19 (t, J = 7.2 Hz, 3H). LC-MS: m/z 463.2 (M + H)⁺ |
| 220 | VI.33 | III.12 & Int-I | 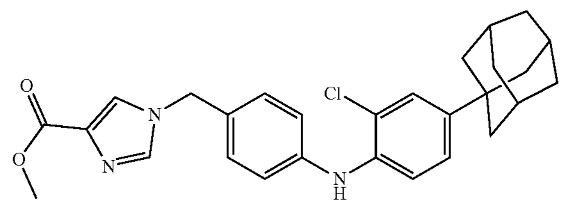 [SMILES: COC(=O)c1cn(Cc2ccc(Nc3ccc(C45CC6CC(CC(C6)C4)C5)cc3Cl)cc2)cn1] | ¹H NMR (400 MHz, DMSO-d6) δ 7.93 (d, J = 0.8 Hz, 1H), 7.85 (d, J = 0.8 Hz, 1H), 7.67 (s, 1H), 7.34 (s, 1H), 7.19 (t, J = 7.2 Hz, 3H), 6.89 (d, J = 8.4 Hz, 2H), 6.74 (d, J = 8.0 Hz, 1H), 5.17 (s, 2H), 3.72 (s, 3H), 2.05 (s, 3H), 1.83 (s, 6H), 1.73 (s, 6H). LC-MS: m/z 476.2 (M + H)⁺ |
| 221 | VI.34 | III.13 & Int-I | 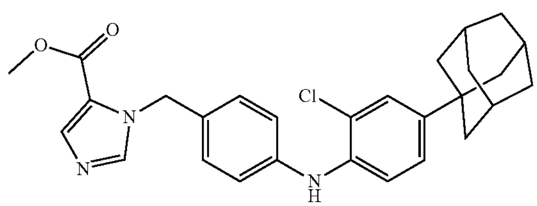 [SMILES: COC(=O)c1cncn1Cc1ccc(Nc2ccc(C34CC5CC(CC(C5)C3)C4)cc2Cl)cc1] | ¹H NMR (400 MHz, DMSO-d6) δ 8.10 (s, 1H), 7.69 (s, 1H), 7.64 (s, 1H), 7.34 (d, J = 2.0 Hz, 1H), 7.21-7.13 (m, 3H), 6.85 (d, J = 8.4 Hz, 1H), 6.77 (s, 1H), 6.61 (d, J = 8.0 Hz, 1H), 5.45 (s, 2H), 3.73 (s, 3H), 2.05 (s, 3H), 1.84 (s, 6H), 1.73 (s, 6H). LC-MS: m/z 476.3 (M + H)⁺ |
| 227 | VI.35 | III.14 & Int-I | 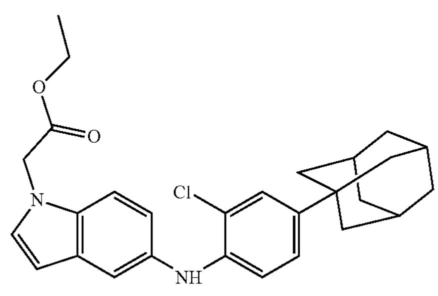 [SMILES: CCOC(=O)Cn1ccc2cc(Nc3ccc(C45CC6CC(CC(C6)C4)C5)cc3Cl)ccc21] | LC-MS: m/z 463.2 (M + H)⁺ |
| 233 | VI.36 | II.9 & Int-I | 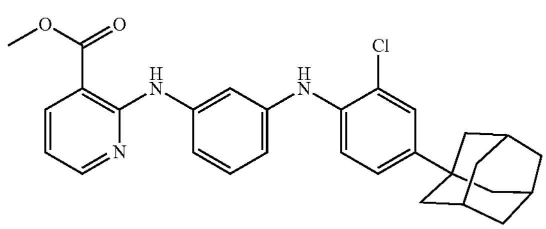 [SMILES: COC(=O)c1cccnc1Nc1cccc(Nc2ccc(C34CC5CC(CC(C5)C3)C4)cc2Cl)c1] | ¹H NMR (400 MHz, DMSO-d6) δ 10.03 (s, 1H), 8.38 (dd, J₁ = 2.0 Hz, J₂ = 4.9 Hz, 1H), 8.24 (dd, J₁ = 2.0 Hz, J₂ = 7.8 Hz, 1H), 7.56 (s, 1H), 7.48 (s, 1H), 7.32 (m, 2H), 7.23 (m, 1H), 7.14 (m, 2H), 6.88 (m, 1H), 6.68 (m, 1H), 3.90 (s, 3H), 2.08 (s, 3H), 1.85 (s, 6H), 1.72 (s, 6H). LC-MS: m/z 488.2 (M + H)⁺ |

-continued

| CP | Intermediate No. | Reactant | Structure | Analytical data |
|---|---|---|---|---|
| 239 | VI.37 | V.2 & Int-I | 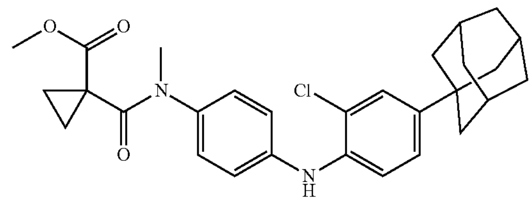 [SMILES: COC(=O)C1(C(=O)N(C)c2ccc(Nc3ccc(C45CC6CC(CC(C6)C4)C5)cc3Cl)cc2)CC1] | ¹H NMR (400 MHz, DMSO-d6) δ 7.74 (s, 1H), 7.36 (s, 1H), 7.23 (m, 2H), 7.1 (d, J = 8.8 Hz, 2H), 6.95 (d, J = 8.8 Hz, 2H), 3.41 (s, 3H), 3.15 (s, 3H), 2.05 (bs, 3H), 1.84 (bs, 6H), 1.72 (bs, 6H), 1.3 (m, 2H), 1.05 (m, 2H). LC-MS: m/z 493.2 (M + H)⁺ |
| 241 | VI.38 | V.1 & Int-I | 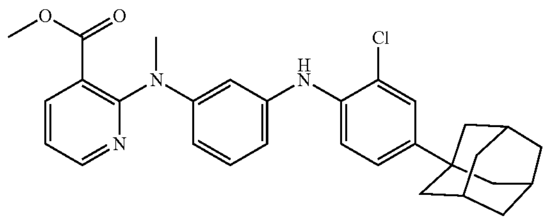 [SMILES: COC(=O)c1cccnc1N(C)c1cccc(Nc2ccc(C34CC5CC(CC(C5)C3)C4)cc2Cl)c1] | ¹H NMR (400 MHz, DMSO-d6) δ 8.39 (dd, J₁ = 2.0 Hz, J₂ = 4.8 Hz, 1H), 7.79 (dd, J₁ = 2.0 Hz, J₂ = 8.0 Hz, 1H), 7.54 (s, 1H), 7.32 (d, J = 2.0 Hz, 1H), 7.25 (d, J = 8.4 Hz, 1H), 7.18 (dd, J₁ = 2.0 Hz, J₂ = 8.4 Hz, 1H), 7.10 (t, J = 8.0 Hz, 1H), 6.95 (dd, J₁ = 3.2 Hz, J₂ = 7.6 Hz, 1H), 6.66 (dd, J₁ = 2.0 Hz, J₂ = 8.4 Hz, 1H), 6.60 (t, J = 2.0 Hz, 1H), 6.46 (dd, J₁ = 1.6 Hz, J₂ = 7.6 Hz, 1H), 3.39 (s, 3H), 3.31 (s, 3H), 2.04 (s, 3H), 1.82 (s, 6H), 1.72 (s, 6H). LC-MS: m/z 502.1 (M + H)⁺ |
| 243 | VI.39 | II.13 & Int-I | 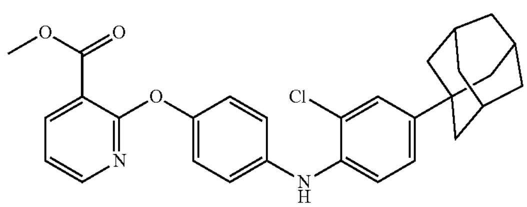 [SMILES: COC(=O)c1cccnc1Oc1ccc(Nc2ccc(C34CC5CC(CC(C5)C3)C4)cc2Cl)cc1] | ¹H NMR (400 MHz, DMSO-d6) δ 8.29 (dd, J₁ = 2.0 Hz, J₂ = 4.9 Hz, 1H), 8.25 (dd, J₁ = 2.0 Hz, J₂ = 7.3 Hz, 1H), 7.54 (s, 1H), 7.34 (s, 1H), 7.22 (m, 3H), 7.04 (d, J = 9.3 Hz, 2H), 6.99 (d, J = 9.2 Hz, 2H), 3.86 (s, 3H), 2.05 (s, 3H), 1.84 (s, 6H), 1.72 (s, 6H). LC-MS: m/z 489.0 (M + H)⁺ |
| 245 | VI.40 | Int-V & I.1 | 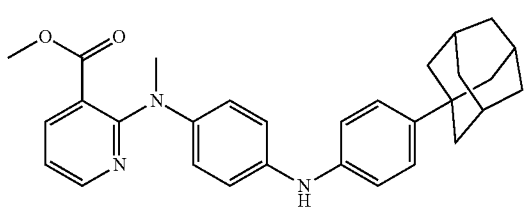 [SMILES: COC(=O)c1cccnc1N(C)c1ccc(Nc2ccc(C34CC5CC(CC(C5)C3)C4)cc2)cc1] | ¹H NMR (400 MHz, DMSO-d6) δ 8.33 (dd, J₁ = 2.0 Hz, J₂ = 4.8 Hz, 1H), 7.97 (s, 1H), 7.65 (dd, J₁ = 2.0 Hz, J₂ = 7.2 Hz, 1H), 7.2 (d J = 8.8 Hz, 2H), 6.97-6.94 (m, 4H), 6.89-6.82 (m, 3H), 3.35 (s, 3H), 3.27 (s, 3H), 2.04 (s, 3H), 1.82 (s, 6H), 1.72 (s, 6H). LC-MS: m/z 468.1 (M + H)⁺ |
| 247 | VI.41 | II.9 & I.1 | 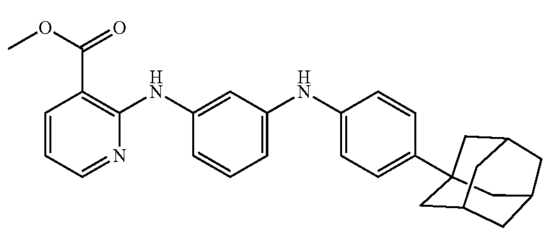 [SMILES: COC(=O)c1cccnc1Nc1cccc(Nc2ccc(C34CC5CC(CC(C5)C3)C4)cc2)c1] | ¹H NMR (400 MHz, DMSO-d6) δ 10.03 (s, 1H), 8.41 (dd, J₁ = 2.0 Hz, J₂ = 4.4 Hz, 1H), 8.25 (dd, J₁ = 1.9 Hz, J₂ = 7.8 Hz, 1H), 8.05 (s, 1H), 7.56 (t, J = 2.0 Hz, 1H), 7.24 (d, J = 8.4 Hz, 2H), 7.15 (t, J = 7.8 Hz, 1H), 7.13 (d, J = 7.8 Hz, 2H), 7.06 (d, J = 8.8 Hz, 1H), 6.88 (m, 1H), 6.71 (dd, J₁ = 1.5 Hz, J₂ = 7.8 Hz, |

-continued

| CP | Intermediate No. | Reactant | Structure | Analytical data |
|---|---|---|---|---|
| | | | | 1H), 3.89 (s, 3H), 2.04 (bs, 3H), 1.84 (s, 6H), 1.73 (s, 6H). |
| 250 | VI.42 | III.15 & Int-I | 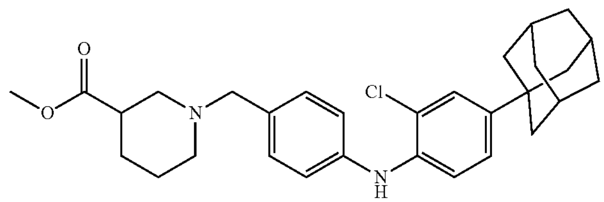 [SMILES: COC(=O)C1CCCN(Cc2ccc(Nc3ccc(C45CC6CC(CC(C6)C4)C5)cc3Cl)cc2)C1] | ¹H NMR (400 MHz, DMSO-d6) δ 7.48 (s, 1H), 7.33 (s, 1H), 7.19 (d, J = 1.0 Hz, 2H), 7.12 (d, J = 8.4 Hz, 2H), 6.97 (d, J = 8.0 Hz, 2H), 3.57 (s, 3H), 3.37 (s, 2H), 2.80-2.78 (m, 1H), 2.64-2.61 (m, 1H), 2.10-1.99 (m, 5H), 1.83-1.72 (m, 14H), 1.63-1.62 (m, 1H), 1.47-1.40 (m, 2H). LC-MS: m/z 493.1 (M + H)⁺ |
| 252 | VI.43 | V.3 & Int-I | 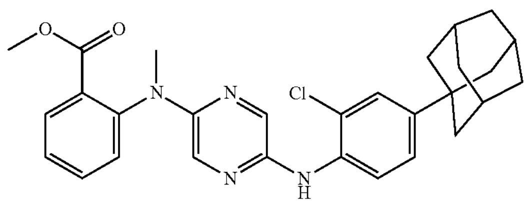 [SMILES: COC(=O)c1ccccc1N(C)c1cnc(Nc2ccc(C34CC5CC(CC(C5)C3)C4)cc2Cl)cn1] | ¹H NMR (400 MHz, DMSO-d6) δ 8.04 (s, 1H), 7.94 (d, J = 1.6 Hz, 1H), 7.77 (dd, J₁ = 1.2 Hz, J₂ = 7.6 Hz, 1H), 7.68-7.64 (m, 2H), 7.48 (d, J = 1.6 Hz, 1H), 7.43-7.35 (m, 2H), 7.30 (d, J = 2.4 Hz, 1H), 7.18 (dd, J₁ = 2.0 Hz, J₂ = 8.4 Hz, 1H), 3.55 (s, 3H), 3.31 (s, 3H), 2.04 (s, 3H), 1.82 (s, 6H). LC-MS: m/z 503.1 (M + H)⁺ |
| 276, 293 | VI.44 | Int-II | 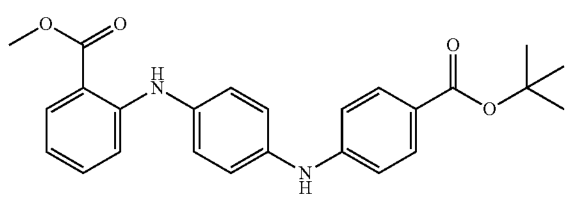 [SMILES: COC(=O)c1ccccc1Nc1ccc(Nc2ccc(C(=O)OC(C)(C)C)cc2)cc1] | ¹H NMR (400 MHz, DMSO-d6) δ 9.23 (s, 1H), 8.69 (s, 1H), 7.88 (dd, J₁ = 1.4 Hz, J₂ = 7.8 Hz, 1H), 7.73 (d, J = 8.8 Hz, 2H), 7.41-7.37 (m, 1H), 7.23-7.17 (m, 4H), 7.10 (d, J = 7.9 Hz, 1H), 7.02 (d, J = 8.8 Hz, 2H), 6.77-6.73 (m, 1H), 3.75 (s, 3H), 1.51 (s, 9H). |
| 277 | VI.45 | Int-II & I.16 | 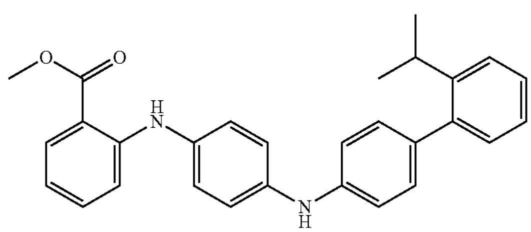 [SMILES: COC(=O)c1ccccc1Nc1ccc(Nc2ccc(-c3ccccc3C(C)C)cc2)cc1] | ¹H NMR (400 MHz, DMSO-d6) δ 9.18 (s, 1H), 8.24 (s, 1H), 7.87 (dd, J₁ = 1.2 Hz, J₂ = 7.6 Hz, 1H), 7.40-7.28 (m, 3H), 7.20-7.10 (m, 10H), 7.02 (d, J = 8.4 Hz, 1H), 6.71 (t, J = 7.6 Hz, 1H), 3.85 (s, 3H), 3.11-3.07 (m, 1H), 1.13 (d, J = 2.8 Hz, 6H). LC-MS: m/z 437.1 (M + H)⁺ |
| 287 | VI.46 | Int-II & I.17 | 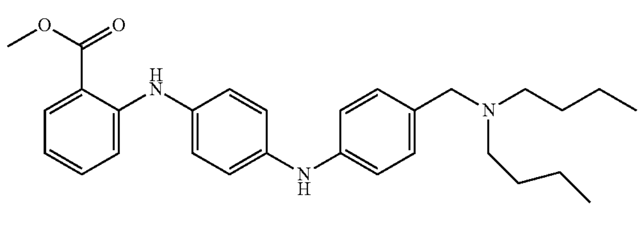 [SMILES: CCCCN(CCCC)Cc1ccc(Nc2ccc(Nc3ccccc3C(=O)OC)cc2)cc1] | ¹H NMR (400 MHz, DMSO-d6) δ 9.15 (s, 1H), 8.07 (s, 1H), 7.86 (dd, J₁ = 1.2 Hz, J₂ = 7.6 Hz, 1H), 7.37-7.33 (m, 1H), 7.15-7.06 (m, 3H), 7.04-6.98 (m, 2H), 6.72-6.68 (m, 1H), 3.85 (s, 3H), 3.40 (s, 3H), 2.36-2.32 (m, 5H), 1.43-1.30 (m, 5H), 1.29-1.21 (m, 5H), 0.84 (t, J = 7.2 Hz, 6H). LC-MS: m/z 460.1 (M + H)⁺ |

-continued

| CP | Intermediate No. | Reactant | Structure | Analytical data |
|---|---|---|---|---|
| 291 | VI.47 | IV.3 & I.1 | 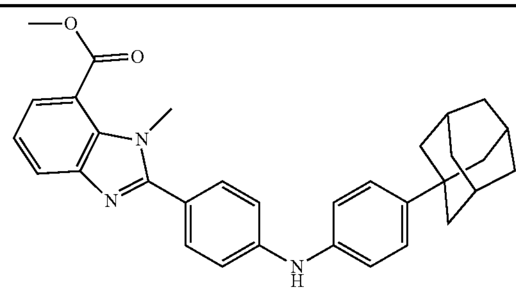 | ¹H NMR (400 MHz, DMSO-d6) δ 8.49 (s, 1H), 7.87 (d, J = 7.2 Hz, 1H), 7.7-7.65 (m, 3H), 7.32-7.28 (m, 3H), 7.17-7.13 (m, 4H), 3.94 (s, 3H), 3.8 (s, 3H), 2.06 (s, 3H), 1.83 (s, 6H), 1.74 (s, 6H). LC-MS: m/z 492.1 (M + H)⁺ |
| 292 | VI.48 | Int-II & I.19 | 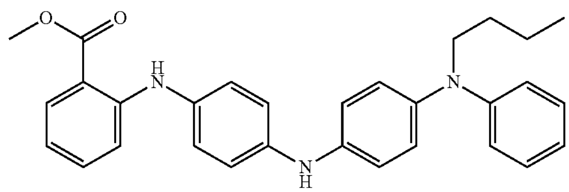 [SMILES: CCCCN(c1ccccc1)c1ccc(Nc2ccc(Nc3ccccc3C(=O)OC)cc2)cc1] | ¹H NMR (400 MHz, DMSO-d6) δ 9.16 (s, 1H), 8.11 (s, 1H), 7.86 (dd, J₁ = 1.5 Hz, J₂ = 7.8 Hz, 1H), 7.33 (t, J = 1.5 Hz, 1H), 7.15-7.07 (m, 8H), 7.02-6.98 (m, 3H), 6.72-6.65 (m, 4H), 3.85 (s, 3H), 3.57 (t, J = 7.3 Hz, 2H), 1.58-1.51 (m, 2H), 1.36-1.30 (m, 2H), 0.88 (t, J = 7.3 Hz, 3H). LC-MS: m/z 466.1 (M + H)⁺ |
| 295 | VI.49 | Int-II & I.2 | 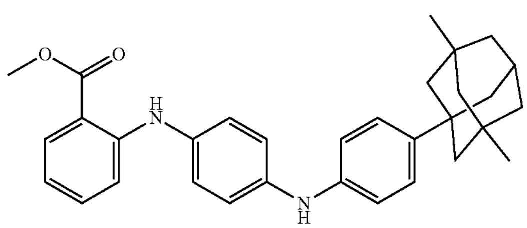 [SMILES: COC(=O)c1ccccc1Nc1ccc(Nc2ccc(C34CC5CC(C)(CC(C)(C5)C3)C4)cc2)cc1] | ¹H NMR (400 MHz, DMSO-d6) δ 9.14 (s, 1H), 8.02 (s, 1H), 7.86 (dd, J₁ = 1.6 Hz, J₂ = 8.0 Hz, 1H), 7.35 (t, J = 8.4 Hz, 1H), 7.21 (d, J = 8.8 Hz, 2H), 7.12-7.04 (m, 4H), 7.01-7.69 (m, 3H), 6.69 (t, J = 7.2 Hz, 1H), 3.85 (s, 3H), 2.13-2.12 (m, 1H), 1.66 (s, 2H), 1.50-1.32 (m, 8H), 1.17 (s, 2H), 0.85 (s, 6H). LC-MS: m/z 481.0 (M + H)⁺ |
| 309 | VI.50 | V.10 & I.21 | 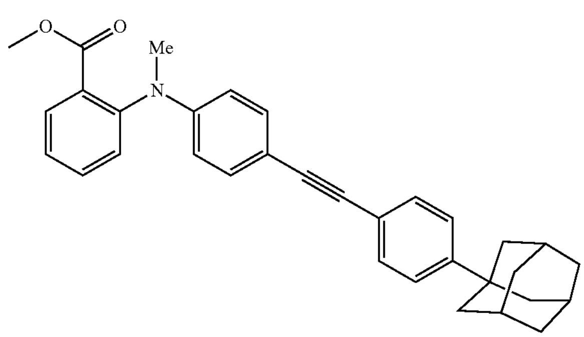 [SMILES: COC(=O)c1ccccc1N(C)c1ccc(C#Cc2ccc(C34CC5CC(CC(C5)C3)C4)cc2)cc1] | ¹H NMR (400 MHz, DMSO-d6) δ 7.8 (d, J = 7.6 Hz, 1H), 7.71-7.61 (m, 1H), 7.44-7.35 (m, 6H), 7.28 (d, J = 8.4 Hz, 2H), 6.50 (d, J = 8.4 Hz, 2H), 3.56 (s, 3H), 3.23 (s, 3H), 2.05 (s, 3H), 1.85 (s, 6H), 1.73 (s, 6H). LC-MS: m/z 476.1 (M + H)⁺ |
| 317 | VI.51 | V.6 & I.1 | 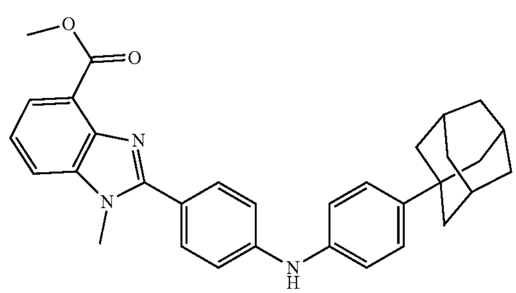 [SMILES: COC(=O)c1cccc2c1nc(-c1ccc(Nc3ccc(C45CC6CC(CC(C6)C4)C5)cc3)cc1)n2C] | ¹H NMR (400 MHz, DMSO-d6) δ 8.49 (s, 1H), 7.84 (d, J = 7.6 Hz, 1H), 7.78-7.71 (m, 3H), 7.35-7.29 (m, 3H), 7.19-7.13 (m, 4H), 3.91 (s, 3H), 3.89 (s, 3H), 2.06 (s, 3H), 1.86 (s, 6H), 1.74 (s, 6H). LC-MS: m/z 492.3 (M + H)⁺ |

| CP | Intermediate No. | Reactant | Structure | Analytical data |
|---|---|---|---|---|
| 318 | VI.52 | V.10 & I.22 | 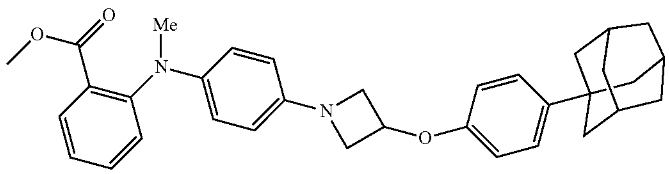 [SMILES: COC(=O)c1ccccc1N(C)c1ccc(N2CC(Oc3ccc(C45CC6CC(CC(C6)C4)C5)cc3)C2)cc1] | $^1$H NMR (400 MHz, DMSO-d6) δ 7.50-7.46 (m, 2H), 7.27 (d, J = 8.8 Hz, 2H), 7.19-7.17 (m, 1H), 7.08 (t, J = 7.6 Hz, 1H), 6.80 (d, J = 8.8 Hz, 2H), 6.64 (d, J = 8.8 Hz, 2H), 6.37 (d, J = 8.8 Hz, 2H), 5.09-5.06 (m, 1H), 4.23-4.20 (m, 2H), 3.64-3.61 (m, 2H), 3.45 (s, 3H), 3.15 (s, 3H), 2.04 (s, 3H), 1.83 (s, 6H), 1.72 (s, 6H). LC-MS: m/z 523.3 (M + H)$^+$ |
| 323 | VI.53 | Int-II & I.26 | 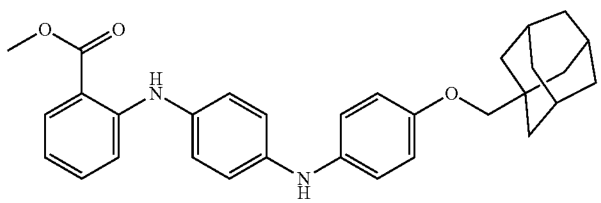 [SMILES: COC(=O)c1ccccc1Nc1ccc(Nc2ccc(OCC34CC5CC(CC(C5)C3)C4)cc2)cc1] | $^1$H NMR (400 MHz, DMSO-d6) δ 9.11 (s, 1H), 7.86-7.83 (m, 2H), 7.34 (t, J = 7.6 Hz, 1H), 7.07 (d, J = 8.4 Hz, 2H), 7.02 (d, J = 8.8 Hz, 2H), 6.96-6.92 (m, 3H), 6.85 (d, J = 8.8 Hz, 2H), 6.68 (t, J = 7.2 Hz, 1H), 3.85 (s, 3H), 3.48 (s, 2H), 1.99 (s, 3H), 1.74-1.63 (m, 13H). LC-MS: m/z 483.3 (M + H)$^+$ |
| 327 | VI.54 | II.23 & I.16 | 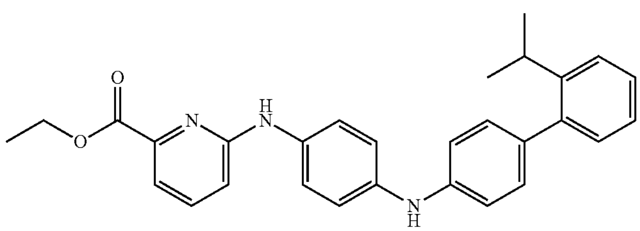 [SMILES: CCOC(=O)c1cccc(Nc2ccc(Nc3ccc(-c4ccccc4C(C)C)cc3)cc2)n1] | $^1$H NMR (400 MHz, DMSO-d6) δ 9.18 (s, 1H), 8.04 (s, 1H), 7.72-7.67 (m, 3H), 7.37 (t, J = 6.4 Hz, 2H), 7.29 (t, J = 6.4 Hz, 1H), 7.18 (t, J = 6.8 Hz, 1H), 7.11-6.97 (m, 8H), 4.34-4.29 (m, 2H), 3.13-3.08 (m, 1H), 1.34 (t, J = 7.2 Hz, 3H), 1.12 (d, J = 6.8 Hz, 6H). LC-MS: m/z 452.3 (M + H)$^+$ |
| 328 | VI.55 | IV.5 & I.1 | 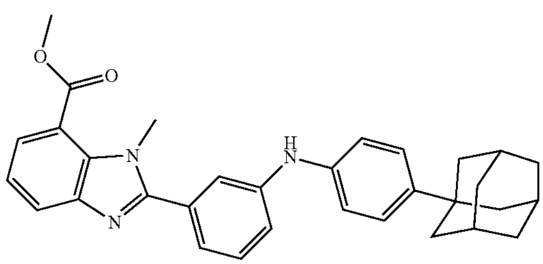 [SMILES: COC(=O)c1cccc2nc(-c3cccc(Nc4ccc(C56CC7CC(CC(C7)C5)C6)cc4)c3)n(C)c12] | $^1$H NMR (400 MHz, DMSO-d6) δ 6 8.44 (s, 1H), 7.93-7.91 (m, 1H), 7.72-7.67 (m, 1H), 7.45 (t, J = 2.0 Hz, 1H), 7.4 (t, J = 7.6 Hz, 1H), 7.33 (t, J = 8.0 Hz, 1H), 7.28-7.27 (m, 2H), 7.23-7.17 (m, 2H), 7.12-7.1 (m, 2H), 3.94 (s, 3H), 3.78 (s, 3H), 2.08 (s, 3H), 1.84 (s, 6H), 1.72 (s, 6H). LC-MS: m/z 492.3 (M + H)$^+$ |
| 337 | VI.56 | V.10 & I.27 | 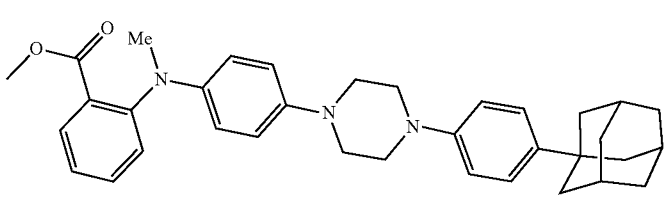 [SMILES: COC(=O)c1ccccc1N(C)c1ccc(N2CCN(c3ccc(C45CC6CC(CC(C6)C4)C5)cc3)CC2)cc1] | LC-MS: m/z 536.3 (M + H)$^+$ |

-continued

| CP | Intermediate No. | Reactant | Structure | Analytical data |
|---|---|---|---|---|
| 340 | VI.57 | V.8 & I.1 | 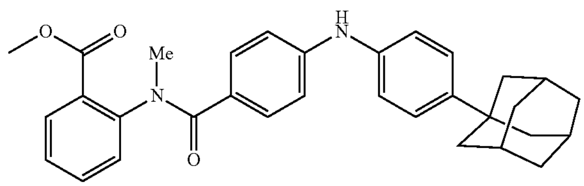 [SMILES: COC(=O)c1ccccc1N(C)C(=O)c1ccc(Nc2ccc(C34CC5CC(CC(C5)C3)C4)cc2)cc1] | ¹H NMR (400 MHz, DMSO-d6) δ 8.23 (bs, 1H), 7.70-7.59 (m, 2H), 7.47 (d, J = 7.2 Hz, 1H), 7.4-7.3 (m, 1H), 7.23 (d, J = 8.4 Hz, 2H), 6.99 (d, J = 8.0 Hz, 4H), 6.72 (bs, 2H), 3.73 (s, 3H), 3.28 (s, 3H), 2.04 (s, 3H), 1.83 (s, 6H), 1.72 (s, 6H). LC-MS: m/z 495.3 (M + H)⁺ |
| 349 | VI.58 | Int-IV & I.4 | 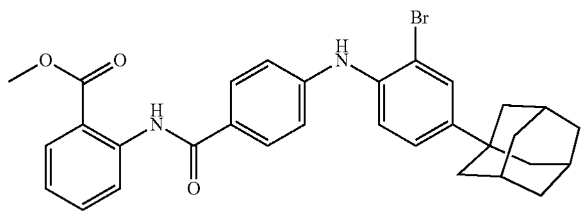 [SMILES: COC(=O)c1ccccc1NC(=O)c1ccc(Nc2ccc(C34CC5CC(CC(C5)C3)C4)cc2Br)cc1] | ¹H NMR (400 MHz, DMSO-d6) δ 11.52 (s, 1H), 8.64 (d, J = 8.3 Hz, 1H), 8.24 (s, 1H), 8.02 (d, J = 8.4 Hz, 1H), 7.80 (d, J = 8.8 Hz, 2H), 7.64-7.62 (m, 1H), 7.60 (s, 1H), 7.38-7.37 (m, 2H), 7.21-7.19 (m, 1H), 6.95 (d, J = 8.3 Hz, 2H), 3.91 (s, 3H), 2.07 (s, 3H), 1.88 (s, 6H), 1.74 (s, 6H). LC-MS: m/z 561.2 (M + H)²⁺ |
| 350 | VI.59 | Int-IV & Int-I | 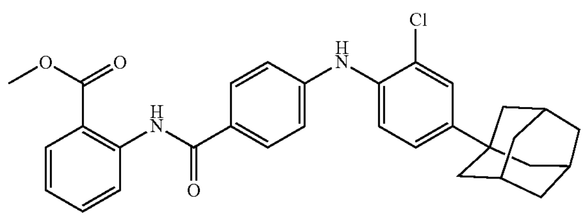 | ¹H NMR (400 MHz, DMSO-d6) δ 11.54 (s, 1H), 8.65-8.63 (dd, J₁ = 1.2 Hz, J₂ = 8.4 Hz, 1H), 8.35 (s, 1H), 8.01 (d, J = 1.6 Hz, 1H), 7.81 (d, J = 8.8 Hz, 2H), 7.69-7.64 (m, 1H), 7.45 (d, J = 2.0 Hz, 1H), 7.39 (d, J = 8.4 Hz, 1H), 7.34 (d, J = 2.0 Hz, 1H), 7.22-7.18 (dd, J₁ = 1.2 Hz, J₂ = 8.4 Hz, 1H), 6.99 (d, J = 8.8 Hz, 2H), 3.91 (s, 3H), 2.07 (s, 3H), 1.99 (s, 6H), 1.74 (s, 6H). LC-MS: m/z 515.1 (M + H)²⁺ |
| 361 | VI.60 | Int-IV & I.30 | 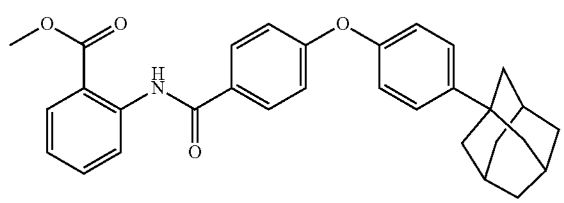 [SMILES: COC(=O)c1ccccc1NC(=O)c1ccc(Oc2ccc(C34CC5CC(CC(C5)C3)C4)cc2)cc1] | ¹H NMR (400 MHz, DMSO-d6) δ 11.55 (s, 1H), 8.56 (d, J = 8.3 Hz, 1H), 8.02 (d, J = 7.8 Hz, 1H), 7.97 (d, J = 8.8 Hz, 2H), 7.68 (t, J = 7.0 Hz, 1H), 7.44 (d, J = 8.8 Hz, 2H), 7.24 (t, J = 7.0 Hz, 1H), 7.13 (d, J = 8.3 Hz, 2H), 7.07 (d, J = 8.8 Hz, 2H), 3.89 (s, 3H), 2.07 (s, 3H), 1.89 (s, 6H), 1.75 (s, 6H). LC-MS: m/z 482.3 (M + H)¹⁺ |
| 385 | VI.61 | Int-II.10 & I.19 | 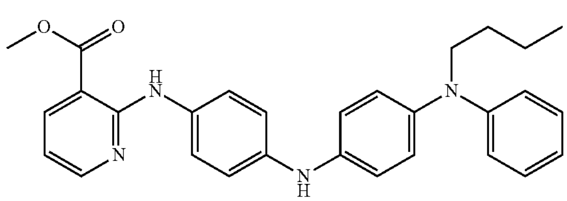 [SMILES: CCCCN(c1ccccc1)c1ccc(Nc2ccc(Nc3ncccc3C(=O)OC)cc2)cc1] | LC-MS: m/z 467.3 (M + H)⁺ |

-continued

| CP | Intermediate No. | Reactant | Structure | Analytical data |
|---|---|---|---|---|
| 386 | VI.62 | II.10 | 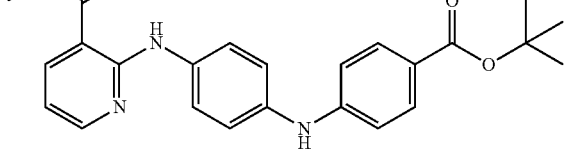 | ¹H NMR (400 MHz, DMSO-d6) δ 10.01 (s, 1H), 8.63 (s, 1H), 8.39 (dd, J₁ = 2.0 Hz, J₂ = 4.8 Hz, 1H), 8.24 (dd, J₁ = 2.0 Hz, J₂ = 27.6 Hz, 1H), 7.72 (d, J = 8.4 Hz, 2H), 7.65 (d, J = 8.8 Hz, 2H), 7.16 (d, J = 8.8 Hz, 2H), 6.98 (d, J = 8.8 Hz, 2H), 6.86 (dd, J₁ = 4.8 Hz, J₂ = 7.6 Hz, 1H), 3.91 (s, 3H), 1.52 (s, 9H). LC-MS: m/z 420.1 (M + H)⁺ |
| 388 | VI.63 | Int-II & I.28 | 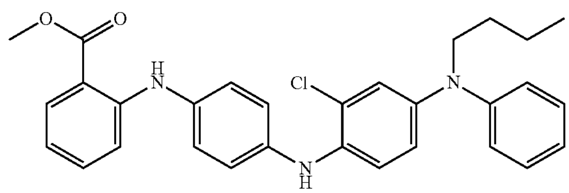 [SMILES: CCCCN(c1ccccc1)c1ccc(Nc2ccc(Nc3ccccc3C(=O)OC)cc2)c(Cl)c1] | ¹H NMR (400 MHz, DMSO-d6) δ 9.15 (s, 1H), 7.86 (dd, J₁ = 1.2 Hz, J₂ = 7.6 Hz, 1H), 7.55 (s, 1H), 7.37-7.26 (m, 1H), 7.25-7.19 (m, 3H), 7.11 (d, J = 8.4 Hz, 2H), 7.04 (d, J = 2.8 Hz, 1H), 7.0-6.96 (m, 3H), 6.91-6.85 (m, 4H), 6.70 (t, J = 6.8 Hz, 1H), 3.63 (t, J = 7.2 Hz, 3H), 1.56-1.5 (m, 2H), 1.36-1.3 (m, 2H), 0.88 (t, J = 7.2 Hz, 3H). LC-MS: m/z 500.2 (M + H)⁺ |
| 389 | VI.64 | II.10 & I.28 | 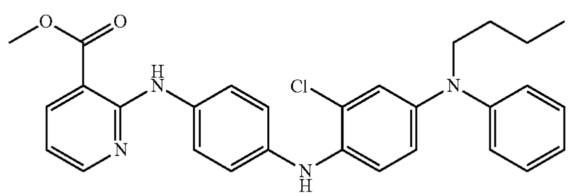 [SMILES: CCCCN(c1ccccc1)c1ccc(Nc2ccc(Nc3ncccc3C(=O)OC)cc2)c(Cl)c1] | ¹H NMR (400 MHz, DMSO-d6) δ 9.91 (s, 1H), 8.35 (dd, J₁ = 2.0 Hz, J₂ = 4.8 Hz, 1H), 8.22 (dd, J₁ = 2.0 Hz, J₂ = 7.6 Hz, 1H), 7.53 (d, J = 8.8 Hz, 2H), 7.44 (s, 1H), 7.24-7.20 (m, 2H), 7.16 (d, J = 8.8 Hz, 1H), 7.05 (d, J = 2.4 Hz, 1H), 6.99 (d, J = 8.8 Hz, 2H), 3.89 (s, 3H), 3.61 (t, J = 7.2 Hz, 2H), 1.56-1.52 (m, 2H), 1.36-1.30 (m, 2H), 0.88 (t, J = 7.2 Hz, 3H). LC-MS: m/z 501.2 (M + H)⁺ |
| 127 | VI. 65 | II.2 & Int-I | 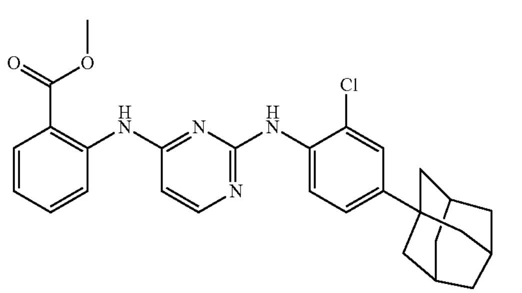 [SMILES: COC(=O)c1ccccc1Nc1ccnc(Nc2ccc(C34CC5CC(CC(C5)C3)C4)cc2Cl)n1] | ¹H NMR (400 MHz, DMSO-d6) δ 10.16 (s, 1H), 8.41 (s, 1H), 8.34 (d, J = 8.8 Hz, 1H), 8.05 (d, J = 5.6 Hz, 1H), 7.90 (d, J = 8.0 Hz, 1H), 7.70 (d, J = 8.8 Hz, 1H), 7.43-7.39 (m, 2H), 7.32-07.30 (m, 1H), 7.08 (t, J = 8.0 Hz, 1H), 6.32 (d, J = 6.0 Hz, 1H), 3.83 (s, 3H), 2.07 (s, 3H), 1.88 (s, 6H), 1.74 (s, 6H). |

195
Intermediate-VII

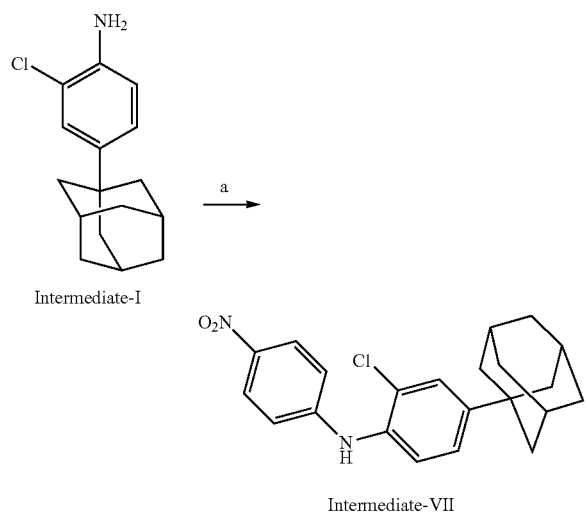

Intermediate-I

Intermediate-VII

196

Step-d: Synthesis of 4-((3R,5R)-adamantan-1-yl)-2-chloro-N-(4-nitrophenyl) aniline (Intermediate-VII)

A solution of Intermediate-I (8.5 g, 32.5 mmol, 1 eq.) and 4-bromonitrobenzene (6.57 g, 32.5 mmol, 1 eq.) in toluene (100 mL) was de-gassed by bubbling Nitrogen gas for 5 minutes. Cesium carbonate (16 g, 48.9 mmol, 1.5 eq.) was added followed by Palladium acetate (0.72 g, 3.25 mmol, 0.1 eq.) and XPhos (2.32 g, 4.88 mmol, 0.15 eq.) and de-gassed again for 5 min. Reaction mixture was heated at 110° C. under stirring for 16 h. Reaction mixture was cooled to RT, diluted with ethyl acetate and filtered through celite. The organic layer was adsorbed over silica and purified by flash column chromatography. Desired product was eluted in 5 to 10% ethyl acetate in hexanes. Concentrated in vacuo to afford dark yellow oil (7 g, 57%).

$^1$H NMR (400 MHz, DMSO-d6) δ 8.98 (s, 1H), 8.09-8.07 (m, 2H), 7.44 (s, 1H), 7.38 (s, 2H), 6.83-6.79 (m, 2H), 2.06 (s, 3H), 1.88 (s, 6H), 1.74 (s, 6H); LC-MS: m/z 383.2 (M+H)$^+$

The below intermediates were prepared by a procedure similar to Intermediate-VII using appropriate reactants and reagents employing suitable Pd catalysts and ligands and in presence of suitable solvents and appropriate reaction conditions.

| CP | Intermediate No. | Structure | Analytical data |
|---|---|---|---|
| 58, 59, 60, 61, 266 | VII.1 | (structure: O₂N-phenyl(CF₃)-NH-phenyl-adamantyl) | LC-MS: m/z 415.05 (M − H)⁻. |
| 62 | VII.2 | (structure: O₂N-phenyl(F)-NH-phenyl-adamantyl) | n/a |
| 66, 128, 129, 211 | VII.3 | (structure: O₂N-phenyl(CF₃)-NH-phenyl(Cl)-adamantyl) | LC-MS: m/z 449.1 (M − H)⁻ |
| 67, 275 | VII.4 | (structure: Br-pyridyl-NH-phenyl-adamantyl) | $^1$H NMR (400 MHz, DMSO-d6) δ 9.06 (s, 1H), 8.15 (d, J = 2.8 Hz, 1H), 7.66 (dd, J₁ = 2.8 Hz, J₂ = 8.8 Hz, 1H), 7.49 (d, J = 8.8 Hz, 2H), 7.23 (d, J = 8.8 Hz, 2H), 6.75 (d, J = 8.8 Hz, 1H), 2.03 (s, 3H), 1.82 (s, 6H), 1.71 (s, 6H). |
| 132, 133 | VII.5 | (structure: O₂N-phenyl-NH-phenyl(Cl)-(2-methylphenyl)) | $^1$H NMR (400 MHz, DMSO-d6) δ 9.00 (s, 1H), 8.10 (d, J = 9.2 Hz, 2H), 7.55-7.50 (m, 2H), 7.37-7.28 (m, 5H), 6.96 (d, J = 9.2 Hz, 2H), 2.28 (s, 3H). LC-MS: m/z 339.5 (M + H)⁺ |

-continued

| CP | Intermediate No. | Structure | Analytical data |
|---|---|---|---|
| 106, 145 | VII.6 | (ethyl 4-((2-chloro-4-(adamantan-1-yl)phenyl)amino)benzoate) | ¹H NMR (400 MHz, DMSO-d6) δ 8.34 (s, 1H), 7.76 (d, J = 8.8 Hz, 2H), 7.43 (s, 1H), 7.34-7.33 (m, 2H), 6.87 (d, J = 8.8 Hz, 2H), 4.24 (m, 2H), 2.04 (s, 3H), 1.86 (s, 6H), 1.73 (s, 6H), 1.28 (t, J = 6.8 Hz, 3H). LC-MS: m/z 410.1 (M + H)⁺ |
| 169 | VII.7 | (N-(2-chloro-4-(adamantan-1-yl)phenyl)-N-(5-nitropyridin-2-yl)acetamide) | LC-MS: m/z 426.2 (M + H)⁺ |
| 191 | VII.8 | (N-(3-(adamantan-1-yl)phenyl)-4-nitroaniline) | ¹H NMR (400 MHz, DMSO-d6) δ 9.25 (s, 1H), 8.09 (d, J = 9.3 Hz, 2H), 7.32 (t, J = 7.8 Hz, 1H), 7.17 (s, 1H), 7.12-7.07 (m, 2H), 7.03 (d, J = 9.3 Hz, 2H), 2.06 (s, 3H), 1.87 (s, 6H), 1.74 (s, 6H). LC-MS: m/z 349.1 (M + H)⁺ |
| 204, 261 | VII.9 | (N-(2-chloro-4-(adamantan-1-yl)phenyl)-3-nitroaniline) | LC-MS: m/z 383.0 (M + H)⁺ |
| 249 | VII.10 | (N-(2-chloro-4-(adamantan-1-yl)phenyl)-N-methyl-4-nitroaniline) | LC-MS: m/z 397.0 (M + H)⁺ |
| 271 | VII.11 | (N-(4-(adamantan-1-yl)phenyl)-4-nitro-2-(trifluoromethyl)aniline) | ¹H NMR (400 MHz, DMSO-d6) δ 8.60 (s, 1H), 8.32 (d, J = 2.8 Hz, 1H), 8.19 (dd, J₁ = 2.8 Hz, J₂ = 9.2 Hz, 1H), 7.44 (d, J = 8.0 Hz, 2H), 7.24 (d, J = 8.4 Hz, 2H), 6.98 (d, J = 9.2 Hz, 1H), 2.07 (s, 3H), 1.89 (s, 6H), 1.75 (s, 6H). LC-MS: m/z 415.05 (M − H)⁻ |
| 272 | VII.12 | (methyl 2-((4-nitrophenyl)amino)benzoate) | ¹H NMR (400 MHz, DMSO-d6) δ 9.86 (s, 1H), 8.18 (d, J = 9.3 Hz, 2H), 8.04 (dd, J₁ = 1.4 Hz, J₂ = 8.3 Hz, 1H), 7.53-7.45 (m, 2H), 7.23 (s, 2H), 6.96 (t, J = 6.9 Hz, 1H), 3.93 (s, 3H). |

-continued

| CP | Intermediate No. | Structure | Analytical data |
|---|---|---|---|
| 289, 311, 379 | VII.13 | 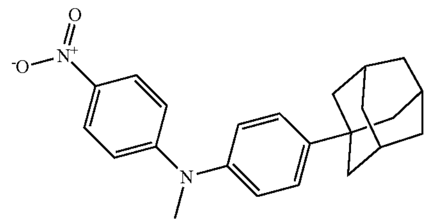 | ¹H NMR (400 MHz, DMSO-d6) δ 8.05 (dd, $J_1$ = 2.0 Hz, $J_2$ = 7.4 Hz, 2H), 7.48 (d, J = 8.4 Hz, 2H), 7.25 (d, J = 8.3 Hz, 2H), 6.74 (dd, $J_1$ = 2.0 Hz, $J_2$ = 7.4 Hz, 2H), 3.36 (s, 3H), 2.80 (s, 3H), 1.89 (s, 6H), 1.75 (s, 6H). LC-MS: m/z 363.1 (M + H)⁺ |
| 297, 300 | VII.14 | 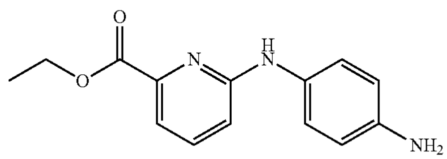 [SMILES: CCOC(=O)c1cccc(Nc2ccc(N)cc2)n1] | ¹H NMR (400 MHz, DMSO-d6) δ 8.75 (s, 1H), 7.58 (t, J = 7.6 Hz, 1H), 7.33-7.27 (m, 3H), 6.83 (d, J = 8.4 Hz, 1H), 6.54 (d, J = 8.8 Hz, 2H), 4.76 (s, 2H), 4.33-4.26 (m, 2H), 1.32 (t, J = 7.6 Hz, 3H). LC-MS: m/z 258.1 (M + H)⁺ |
| 298, 299 | VII.15 | 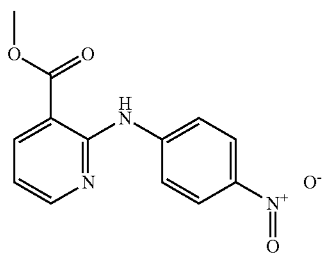 | ¹H NMR (400 MHz, DMSO-d6) δ 10.58 (s, 1H), 8.55 (dd, $J_1$ = 2.0 Hz, $J_2$ = 4.8 Hz, 1H), 8.35 (dd, $J_1$ = 2.0 Hz, $J_2$ = 7.6 Hz, 1H), 8.24-8.20 (m, 2H), 8.05-8.01 (m, 2H), 7.10 (dd, $J_1$ = 4.4 Hz, $J_2$ = 7.6 Hz, 1H), 3.93 (s, 3H). LC-MS: m/z 274.10 (M + H)⁺ |
| 319 | VII.16 | 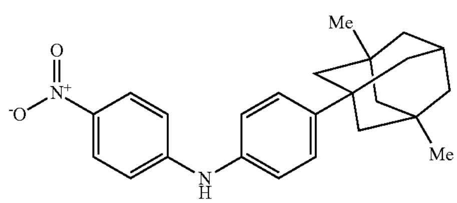 | ¹H NMR (400 MHz, DMSO-d6) δ 9.22 (s, 1H), 8.06 (dd, $J_1$ = 2.0 Hz, $J_2$ = 7.6 Hz, 2H), 7.36 (d, J = 8.4 Hz, 2H), 7.17 (d, J = 8.8 Hz, 2H), 7.00 (d, J = 9.2 Hz, 2H), 2.14 (m, 1H), 1.69 (s, 2H), 1.53-1.36 (m, 8H), 1.19 (s, 2H), 0.86 (s, 6H). LC-MS: m/z 377.1 (M + H)⁺ |
| 320 | VII.17 | 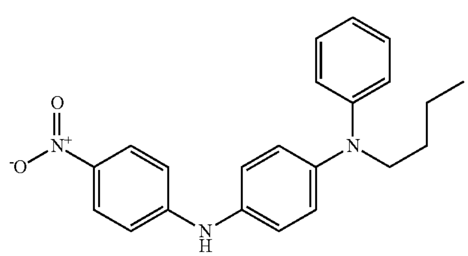 | ¹H NMR (400 MHz, DMSO-d6) δ 9.40 (s, 1H), 8.07 (d, J = 9.3 Hz, 2H), 7.24 (m, 2H), 7.18 (d, J = 8.8 Hz, 2H), 7.00 (m, 4H), 6.96-6.91 (m, 3H), 3.60 (m, 2H), 1.60 (m, 2H), 1.40-1.35 (m, 2H), 0.88 (t, J = 7.4 Hz, 3H). |
| 338 | VII.18 | 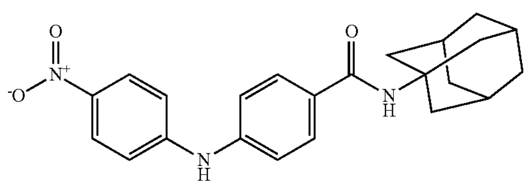 | ¹H NMR (400 MHz, DMSO-d6) δ 9.48 (s, 1H), 8.12 (d, J = 9.2 Hz, 2H), 7.80 (d, J = 8.8 Hz, 2H), 7.46 (s, 1H), 7.24 (d, J = 8.4 Hz, 2H), 7.15 (d, J = 8.8 Hz, 2H), 2.06 (s, 9H), 1.65 (s, 6H). LC-MS: m/z 392.1 (M + H)⁺ |
| 352 | VII.19 | 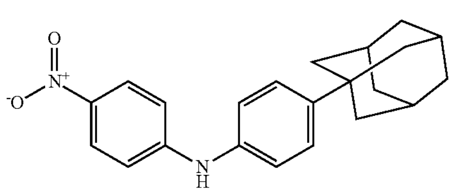 | LC-MS: m/z 349.1 (M + H)⁺ |

-continued

| CP | Intermediate No. | Structure | Analytical data |
|---|---|---|---|
| 378 | VII.20 | 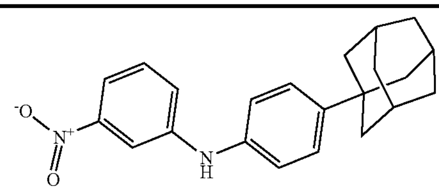 | LC-MS: m/z 349.2 (M + H)+ |
| 271 | VII.21 | 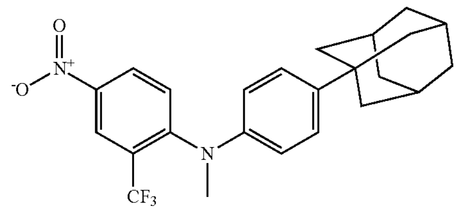 | LC-MS: m/z 431.15 (M + H)+ |
| 521, 541, 605, 606, 607, 608, 613, 648 | VII.22 | 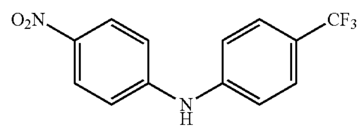 [SMILES: O=[N+]([O-])c1ccc(Nc2ccc(C(F)(F)F)cc2)cc1] | LC-MS: m/z 283.1 (M + H)+ |
| 522, 536, 558 | VII.23 | 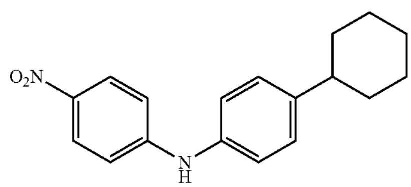 [SMILES: O=[N+]([O-])c1ccc(Nc2ccc(C3CCCCC3)cc2)cc1] | LC-MS: m/z 297.2 (M + H)+ |
| 528 | VII.24 | 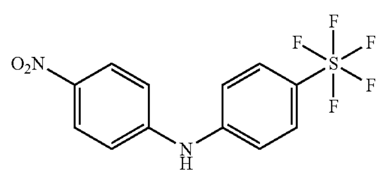 [SMILES: O=[N+]([O-])c1ccc(Nc2ccc(S(F)(F)(F)(F)F)cc2)cc1] | LC-MS: m/z 339.0 (M − H)− |
| 535 | VII.25 | 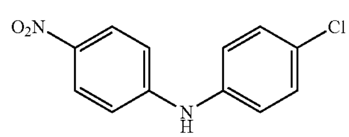 [SMILES: O=[N+]([O-])c1ccc(Nc2ccc(Cl)cc2)cc1] | 1H NMR (400 MHz, DMSO-d6): δ 9.36 (s, 1H), 8.10 (d, J = 9.2 Hz, 2H), 7.42 (d, J = 8.8 Hz, 2H), 7.26 (d, J = 8.8 Hz, 2H), 7.08 (d, J = 9.2 Hz, 2H). |
| 537 | VII.26 | 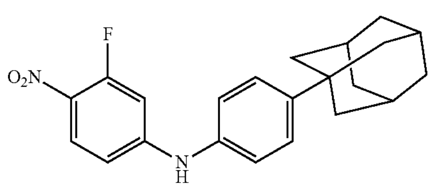 | LC-MS: m/z 367.2 (M + H)+ |
| 538 | VII.27 | 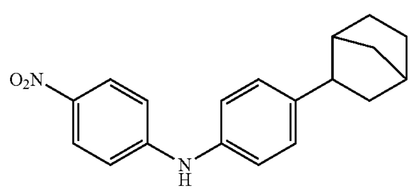 [SMILES: O=[N+]([O-])c1ccc(Nc2ccc(C3CC4CCC3C4)cc2)cc1] | 1H NMR (400 MHz, DMSO-d6) δ 9.22 (s, 1H), 8.06 (dd, J1 = 2 Hz & J2 = 7.6 Hz, 2H), 7.22 (d, J = 8.4 Hz, 2H), 7.15 (dd, J1 = 1.6 Hz & J2 = 6.4 Hz, 2H), 6.99 (dd, J1 = 2 Hz & J2 = 7.2 Hz, 2H), 271-2.69 (m, 1H), 2.33 (brs, 1H), 2.27 (brs, 1H), 1.73-1.70 (m, 1H), 1.55-1.46 (m, 4H), 1.35-1.29 (m, 2H), 1.16-1.14 (m, 1H). LC-MS: m/z 309.1 (M + H)+. |

-continued

| CP | Intermediate No. | Structure | Analytical data |
|---|---|---|---|
| 542 | VII.28 | O₂N-C₆H₄-NH-C₆H₃(Cl)(Cl) (2,4-dichloro) | LC-MS: m/z 283.0 (M + H)+ |
| 545 | VII.29 | O₂N-C₆H₄-NH-C₆H₄-OMe (2-methoxy) | LC-MS: m/z 245.1 (M + H)+ |
| 547 | VII.30 | O₂N-C₆H₄-NH-C₆H₄-morpholinyl | 1H NMR (400 MHz, DMSO-d6): δ 9.08 (s, 1H), 8.03 (d, J = 9.2 Hz, 2H), 7.12 (d, J = 8.8 Hz, 2H), 6.98 (d, J = 8.8 Hz, 2H), 6.87 (d, J = 9.2 Hz, 2H), 3.75-3.73 (m, 4H), 3.10-3.08 (m, 4H). LC-MS: m/z 300.1 (M + H)+. |
| 548 | VII.31 | O₂N-C₆H₄-NH-C₆H₄-OCF₃ | 1H NMR (400 MHz, DMSO-d6): δ 9.41 (s, 1H), 8.11 (d, J = 9.2 Hz, 2H), 7.38-7.32 (m, 4H), 7.10 (d, J = 9.2 Hz, 2H). LC-MS: m/z 297.1 (M − H)− |
| 549 | VII.32 | O₂N-C₆H₃(F)-NH-C₆H₄-cyclohexyl | LC-MS: m/z 315.2 (M + H)+ |
| 551 | VII.33 | O₂N-C₆H₃(Me)-NH-C₆H₄-adamantyl | LC-MS: m/z 363.1 (M + H)+ |
| 553 | VII.34 | O₂N-C₆H₄-NH-C₆H₄-OCH₂CF₃ | 1H NMR (400 MHz, DMSO-d6): δ 9.17 (s, 1H), 8.06 (d, J = 9.2 Hz, 2H), 7.21 (d, J = 8.8 Hz, 2H), 7.10 (d, J = 8.8 Hz, 2H), 6.92 (d, J = 8.8 Hz, 2H), 4.75 (q, J = 9.2 Hz, 2H). |
| 554, 567 | VII.35 | O₂N-C₆H₄-NH-C₆H₄-CHO | LC-MS: m/z 241.2 (M − H)− |
| 555, 556, 574, 583, 584, 552, 557, 582, 593 | VII.36 | O₂N-C₆H₄-NH-C₆H₄-Br | LC-MS: m/z 312.2 (M + H)+ |

-continued

| CP | Intermediate No. | Structure | Analytical data |
|---|---|---|---|
| 560, 579, 580, 614, 619, 620, 621, 625, 627, 628, 629 | VII.37 | $O_2N$-phenyl(methyl)-NH-phenyl-cyclohexyl<br>Also for CP compounds 630, 631, 632, 633, 634, 635, 636, 637, 640, 653, 656, 657, 678, 679 | LC-MS: m/z 311.1 (M + H)+ |
| 563 | VII.38 | $O_2N$-phenyl(methyl)-NH-phenyl-$CF_3$ | 1H NMR (400 MHz, DMSO-d6): δ 9.43 (s, 1H), 8.03 (d, J = 10 Hz, 1H), 7.64 (d, J = 8.8 Hz, 2H), 7.35 (d, J = 8.4 Hz, 2H), 7.08-7.06 (m, 2H), 2.53 (s, 3H). |
| 565 | VII.39 | $O_2N$-phenyl(methyl)-NH-phenyl-O-$CH_2CF_3$ | LC-MS: m/z 327.0 (M + H)+ |
| 568 | VII.40 | $O_2N$-phenyl(F)-NH-phenyl-O-$CH_2CF_3$ | LC-MS: m/z 328.95 (M − H)− |
| 571 | VII.41 | $O_2N$-phenyl(methyl)-NH-phenyl-$SF_5$ | LC-MS: m/z 355.1 (M + H)+ |
| 572 | VII.42 | $O_2N$-phenyl(F)-NH-phenyl-$CF_3$ | LC-MS: m/z 298.95 (M − H)−. |
| 573 | VII.43 | $O_2N$-phenyl(F)-NH-phenyl-$SF_5$ | LC-MS: m/z 357.0 (M − H)−. |
| 576 | VII.44 | $O_2N$-phenyl-NH-pyridyl-$CF_3$ | LC-MS: m/z 284.0 (M + H)+ |

| CP | Intermediate No. | Structure | Analytical data |
|---|---|---|---|
| 577 | VII.45 | 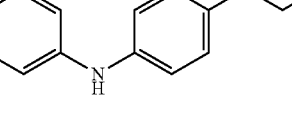 | LC-MS: m/z 323.3 (M + H)+ |
| 578 | VII.46 | 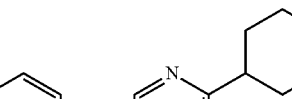 | LC-MS: m/z 298.2 (M + H)+ |
| 581 | VII.47 | 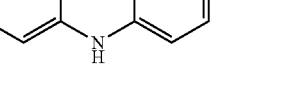 | LC-MS: m/z 296.0 (M + 2)+ |
| 585 | VII.48 | 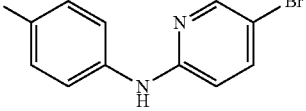 | LC-MS: m/z 327.1 (M + H)+ |
| 588 | VII.49 | 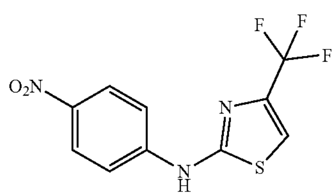 [SMILES: O=[N+]([O-])c1ccc(Nc2nc(C(F)(F)F)cs2)cc1] | LC-MS: m/z 289.95 (M + H) |
| 589 | VII.50 | 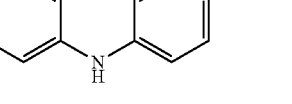 | LC-MS: m/z 315.1 (M − H)− |
| 590 | VII.51 | 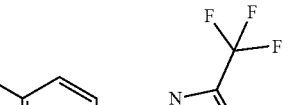 | LC-MS: m/z 311.1 (M − H)− |
| 592 | VII.52 | 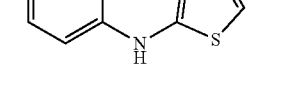 | LC-MS: m/z 316.9 (M + H)+ |

| CP | Intermediate No. | Structure | Analytical data |
|---|---|---|---|
| 594 | VII.53 | 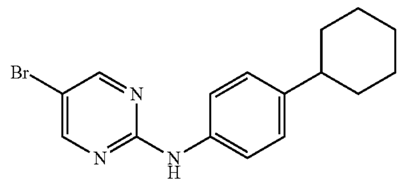 [SMILES: Brc1cnc(Nc2ccc(C3CCCCC3)cc2)nc1] | LC-MS: m/z 332.1 (M − H) − |
| 595 | VII.54 | 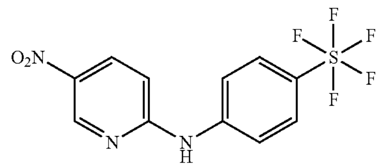 [SMILES: O=[N+]([O-])c1ccc(Nc2ccc(S(F)(F)(F)(F)F)cc2)nc1] | LC-MS: m/z 342.0 (M + H) + |
| 596 | VII.55 | 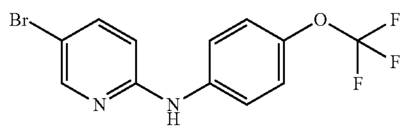 [SMILES: FC(F)(F)Oc1ccc(Nc2ccc(Br)cn2)cc1] | LC-MS: m/z 335.0 (M + H) + |
| 597 | VII.56 | 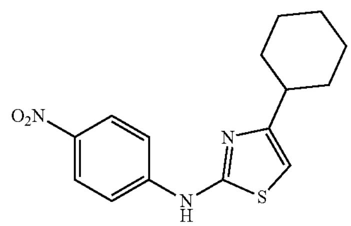 [SMILES: O=[N+]([O-])c1ccc(Nc2nc(C3CCCCC3)cs2)cc1] | LC-MS: m/z 304.2 (M + H)+ |
| 602 | VII.57 | 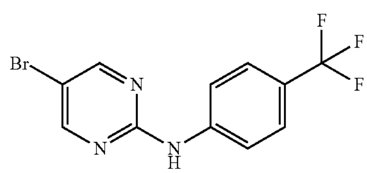 [SMILES: FC(F)(F)c1ccc(Nc2ncc(Br)cn2)cc1] | LC-MS: m/z 320.0 (M + H)+ |
| 609, 652, 673 | VII.58 | 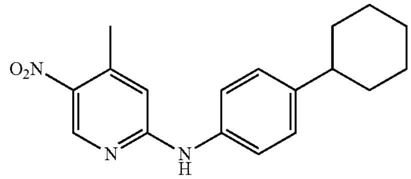 | LC-MS: m/z 312.2 (M + H)+ |
| 612 | VII.59 | 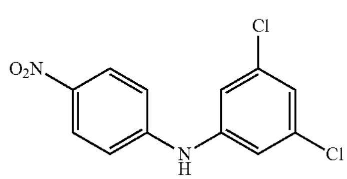 [SMILES: O=[N+]([O-])c1ccc(Nc2cc(Cl)cc(Cl)c2)cc1] | LC-MS: m/z 283.0 (M + H)+ |
| 617 | VII.60 | 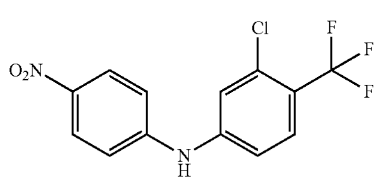 [SMILES: O=[N+]([O-])c1ccc(Nc2ccc(C(F)(F)F)c(Cl)c2)cc1] | LC-MS: m/z 315.0 (M − H)− |

-continued
| CP | Intermediate No. | Structure | Analytical data |
|---|---|---|---|
| 618 | VII.61 | 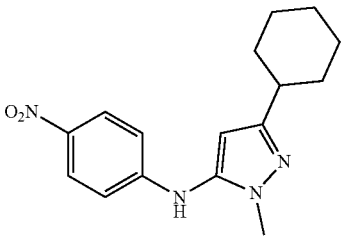 [SMILES: Cn1nc(C2CCCCC2)cc1Nc1ccc([N+](=O)[O-])cc1] | Proceeded with crude/TLC reference |
| 622 | VII.62 | 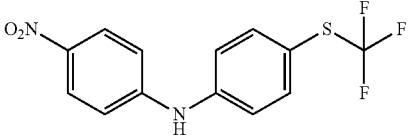 [SMILES: O=[N+]([O-])c1ccc(Nc2ccc(SC(F)(F)F)cc2)cc1] | LC-MS: m/z 315.0 (M + H)+ |
| 624 | VII.63 | 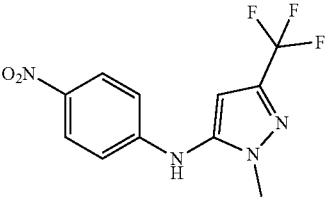 [SMILES: Cn1nc(C(F)(F)F)cc1Nc1ccc([N+](=O)[O-])cc1] | LC-MS: m/z 287.0 (M + H)+ |
| 626 | VII.64 | 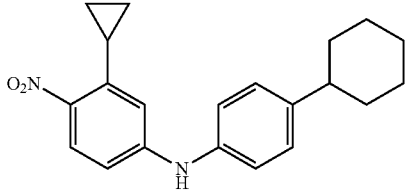 [SMILES: O=[N+]([O-])c1ccc(Nc2ccc(C3CCCCC3)cc2)cc1C1CC1] | LC-MS: m/z 337.2 (M + H)+ |
| 641, 661, 662 | VII.65 | 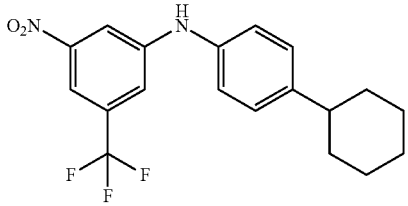 [SMILES: O=[N+]([O-])c1cc(Nc2ccc(C3CCCCC3)cc2)cc(C(F)(F)F)c1] | LC-MS: m/z 363.1 (M1H)− |
| 660, 675, 676 | VII.66 | 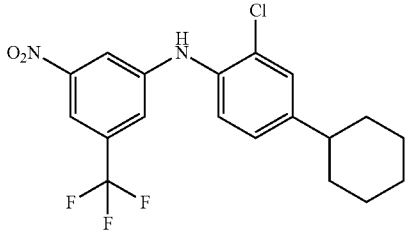 [SMILES: O=[N+]([O-])c1cc(Nc2ccc(C3CCCCC3)cc2Cl)cc(C(F)(F)F)c1] | LC-MS: m/z 397.1 (M − H)− |
| 598, 643, 654, 655 | VII.67 | 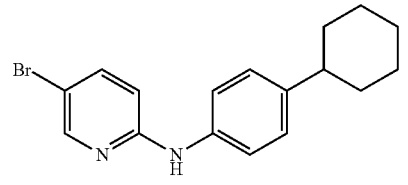 [SMILES: Brc1ccc(Nc2ccc(C3CCCCC3)cc2)nc1] | LC-MS: m/z 333.1 (M + H)+ |

-continued
| CP | Intermediate No. | Structure | Analytical data |
|---|---|---|---|
| 646 | VII.68 | 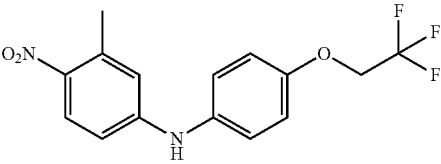 [SMILES: Cc1cc(Nc2ccc(OCC(F)(F)F)cc2)ccc1[N+](=O)[O-]] | LC-MS: m/z 327.1 (M + H)+ |
| 647 | VII.69 | 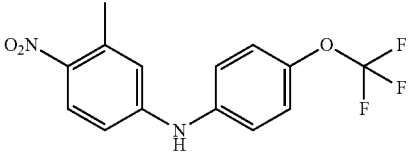 [SMILES: Cc1cc(Nc2ccc(OC(F)(F)F)cc2)ccc1[N+](=O)[O-]] | LC-MS: m/z 313.1 (M + H)+ |
| 659 | VII.70 | 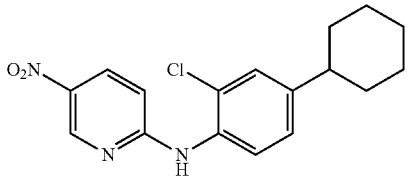 [SMILES: O=[N+]([O-])c1ccc(Nc2ccc(C3CCCCC3)cc2Cl)nc1] | LC-MS: m/z 332.1 (M + H)+ |
| 663 | VII.71 | 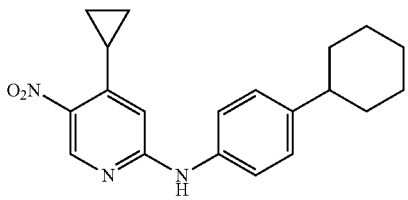 [SMILES: O=[N+]([O-])c1cnc(Nc2ccc(C3CCCCC3)cc2)cc1C1CC1] | LC-MS: m/z 338.2 (M + H)+ |
| 671, 680, 681 | VII.72 | 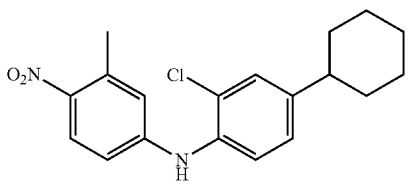 | LC-MS: m/z 345.1 (M + H)+ |
| 682, 677 | VII.73 | 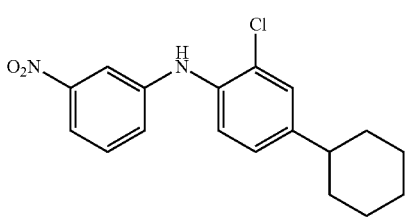 | LC-MS: m/z 331.1 (M + H)+ |

The below intermediates were prepared by a procedure similar to Intermediate-V using appropriate reactants and reagents employing suitable Pd catalysts and ligands and in presence of suitable solvents and appropriate reaction conditions.

| CP | Intermediate No. | Reactant | Structure | Analytical data |
|---|---|---|---|---|
| 249 | VII.74 | VII | 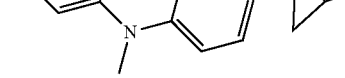 | LC-MS: m/z 397.0 (M + H)$^+$ |
| 289, 311, 379 | VII.75 | VII.17 | 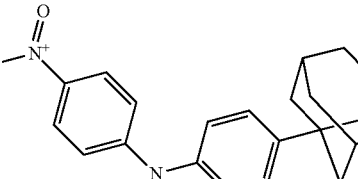<br>Also for CP compounds 453, 472, 473, 525, 526 | $^1$H NMR (400 MHz, DMSO-d6) δ 8.05 (dd, J$_1$ = 2.0 Hz, J$_2$ = 7.4 Hz, 2H), 7.48 (d, J = 8.4 Hz, 2H), 7.25 (d, J = 8.3 Hz, 2H), 6.74 (dd, J$_1$ = 2.0 Hz, J$_2$ = 7.4 Hz, 2H), 3.36 (s, 3H), 2.80 (s, 3H), 1.89 (s, 6H), 1.75 (s, 6H). LC-MS: m/z 363.1 (M + H)$^+$ |
| 271 | VII.76 | VII.10 | 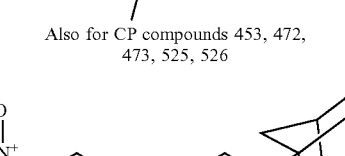 | LC-MS: m/z 431.15 (M + H)$^+$ |
| 521, 541, 605, 606, 607, 608, 613, 648 | VII.77 | VII.19 | 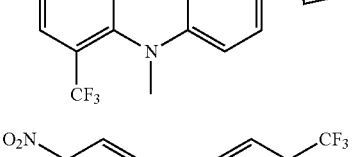 | LC-MS: m/z 297.1 (M + H)$^+$. |
| 522, 536, 558 | VII.78 | VII.20 | 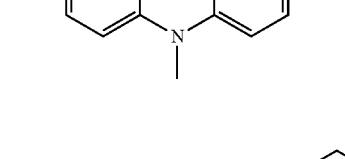 | LC-MS: m/z 311.1 (M + H)$^+$ |
| 528 | VII.79 | VII.21 | 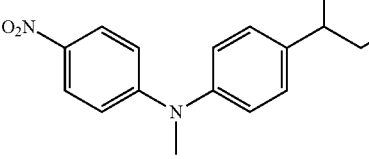 | LC-MS: m/z 355.1 (M + H)$^+$ |
| 535 | VII.80 | VII.22 | 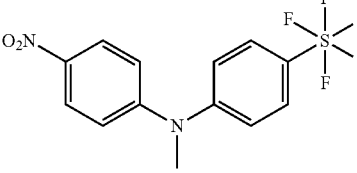 | $^1$H NMR (400 MHz, DMSO-d$_6$): δ 8.06 (d, J = 9.2 Hz, 2H), 7.55 (d, J = 8.8 Hz, 2H), 7.36 (d, J = 8.4 Hz, 2H), 6.81 (d, J = 9.2 Hz, 2H), 3.37 (s, 3H). |

-continued

| CP | Intermediate No. | Reactant | Structure | Analytical data |
|---|---|---|---|---|
| 537 | VII.81 | VII.23 | (structure) | LC-MS: m/z 381.2 (M + H)⁺ |
| 538 | VII.82 | VII.24 | (structure) | ¹H NMR (400 MHz, DMSO-d₆): δ 8.03 (dd, J₁ = 2.4 Hz & J₂ = 7.6 Hz, 2H), 7.33 (d, J = 8.4 Hz, 2H), 7.23-7.20 (m, 2H), 6.72 (dd, J₁ = 2 Hz & J₂ = 7.6 Hz, 2H), 3.35 (s, 3H), 2.79-2.75 (m, 1H), 2.34-2.31 (m, 2H), 1.76-1.73 (m, 1H), 1.56-1.50 (m, 4H), 1.36-1.16 (m, 3H). LC-MS: m/z 323.2 (M + H)⁺ |
| 542 | VII.83 | VII.25 | (structure) | LC-MS: m/z 297.1 (M + H)⁺ |
| 545 | VII.84 | VII.26 | (structure) | LC-MS: m/z 259.1 (M + H)⁺ |
| 547 | VII.85 | VII.27 | (structure) | ¹H NMR (400 MHz, DMSO-d₆): δ 8.02 (d, J = 9.6 Hz, 2H), 7.16 (d, J = 8.8 Hz, 2H, 7.04 (d, J = 8.8 Hz, 2H), 6.67 (d, J = 9.6 Hz, 2H), 3.76-3.74 (m, 4H), 3.32 (s, 3H), 3.16-3.13 (m, 4H). LC-MS: m/z 314.2 (M + H)⁺ |
| 548 | VII.86 | VII.28 | (structure) | ¹H NMR (400 MHz, DMSO-d₆): δ 8.07 (d, J = 9.2 Hz, 2H), 7.48-7.45 (m, 4H), 6.81 (d, J = 9.2 Hz, 2H), 3.39 (s, 3H). LC-MS: m/z 313.1 (M + H)⁺ |
| 549 | VII.87 | VII.29 | (structure) | LC-MS: m/z 329.2 (M + H)⁺. |

US 12,187,722 B2

-continued

| CP | Intermediate No. | Reactant | Structure | Analytical data |
|---|---|---|---|---|
| 551 | VII.88 | VII.30 | (structure) | LC-MS: m/z 377.3 (M + H)+. |
| 552 | VII.89 | VII.33 | (structure) | LC-MS: m/z 345.1 (M + H)+. |
| 553 | VII.90 | VII.31 | (structure) | LC-MS: m/z 327.1 (M + H)+. |
| 554, 567 | VII.91 | VII.32 | (structure) | LC-MS: m/z 257.2 (M + H)+. |
| 555 | VII.92 | VII.33 | (structure) | LC-MS: m/z 312.2 (M + H)+. |
| 556 | VII.93 | VII.33 | (structure) | LC-MS: m/z 241.2 (M − H)− |
| 557 | VII.94 | VII.33 | (structure) | LC-MS: m/z 312.2 (M + H)+ |

-continued
| CP | Intermediate No. | Reactant | Structure | Analytical data |
|---|---|---|---|---|
| 560, 579, 580, 614, 619, 620, 621, 625, 627 | VII.95 | VII.34 | 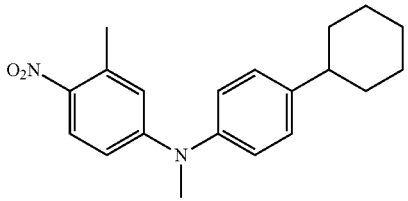 [SMILES: Cc1cc(N(C)c2ccc(C3CCCCC3)cc2)ccc1[N+](=O)[O-]]<br>Also for CP compounds 628, 629, 630, 631, 632, 633, 634, 635, 636, 637, 640, 653, 656, 657, 678, 679 | LC-MS: m/z 325.2 (M + H)$^+$ |
| 563 | VII.96 | VII.35 | 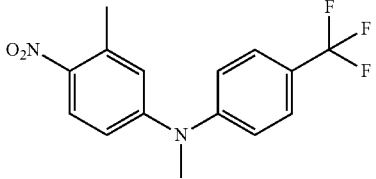 | LC-MS: m/z 311.05 (M + H)$^+$ |
| 565 | VII.97 | VII.36 | 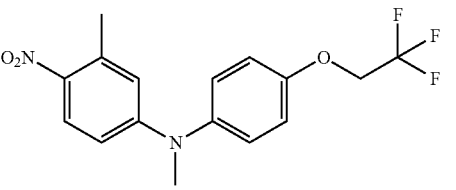 [SMILES: Cc1cc(N(C)c2ccc(OCC(F)(F)F)cc2)ccc1[N+](=O)[O-]] | LC-MS: m/z 341.0 (M + H)$^+$ |
| 568 | VII.98 | VII.37 | 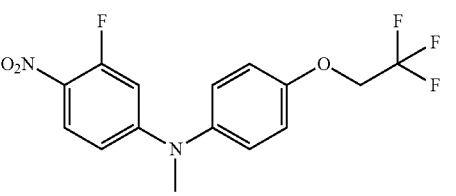 [SMILES: CN(c1ccc(OCC(F)(F)F)cc1)c1ccc([N+](=O)[O-])c(F)c1] | $^1$H NMR (400 MHz, DMSO-d$_6$): δ 7.98-7.94 (m, 1H), 7.31 (d, J = 8.8 Hz, 2H), 7.19 (d, J = 8.8 Hz, 2H), 6.57 (dd, J$_1$ = 2.0 Hz & J$_2$ = 14.8 Hz, 1H), 6.42 (dd, J$_1$ = 2.0 Hz & J$_2$ = 9.2 Hz, 1H), 4.82 (q, J = 8.8 Hz, 2H), 3.34 (s, 3H). |
| 571 | VII.99 | VII.38 | 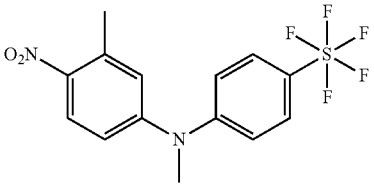 | LC-MS: m/z 369.1 (M + H)$^+$ |
| 572 | VII.100 | VII.39 | 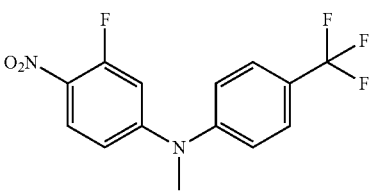 | LC-MS: m/z 315.1 (M + H)$^+$ |
| 573 | VII.101 | VII.40 | 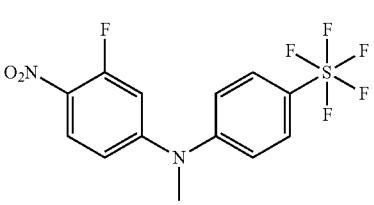 | LC-MS: m/z 357.0 (M − H)$^-$ |

-continued

| CP | Intermediate No. | Reactant | Structure | Analytical data |
|---|---|---|---|---|
| 574, 583, 584 | VII.102 | VII.33 | 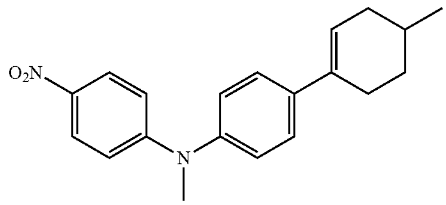 | LC-MS: m/z 284.0 (M + H)+ |
| 576 | VII.103 | VII.41 | 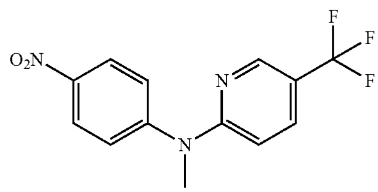 | LC-MS: m/z 298 (M + H)+ |
| 577 | VII.104 | VII.42 | 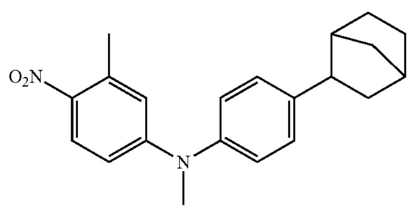 | LC-MS: m/z 337.2.0 (M + H)+ |
| 578 | VII.105 | VII.43 | 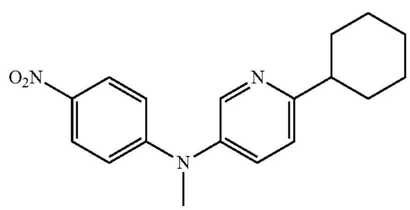 [SMILES: CN(c1ccc([N+](=O)[O-])cc1)c1ccc(C2CCCCC2)nc1] | LC-MS: m/z 312.2 (M + H)+ |
| 581 | VII.106 | VII.44 | 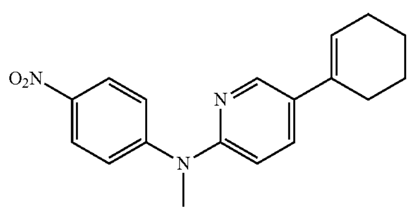 [SMILES: CN(c1ccc([N+](=O)[O-])cc1)c1ccc(C2=CCCCC2)cn1] | LC-MS: m/z 310.1 (M + H)+ |
| 582 | VII.107 | VII.33 | 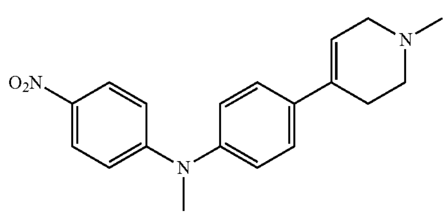 [SMILES: CN1CC=C(c2ccc(N(C)c3ccc([N+](=O)[O-])cc3)cc2)CC1] | LC-MS: m/z 324.2 (M + H)+ |
| 585 | VII.108 | VII.45 | 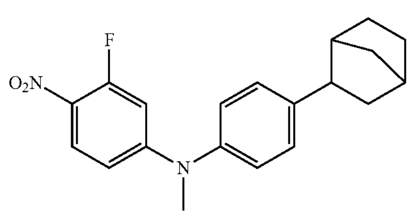 [SMILES: CN(c1ccc(C2CC3CCC2C3)cc1)c1ccc([N+](=O)[O-])c(F)c1] | LC-MS: 342.1 m/z (M + H)+ |

-continued

| CP | Intermediate No. | Reactant | Structure | Analytical data |
|---|---|---|---|---|
| 588 | VII.109 | VII.46 | 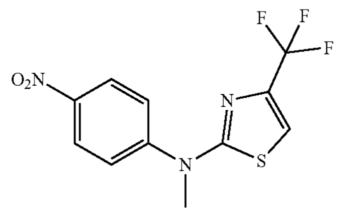 [SMILES: CN(c1ccc([N+](=O)[O-])cc1)c1nc(C(F)(F)F)cs1] | LC-MS: m/z 304.1 (M + H)$^+$ |
| 589 | VII.110 | VII.47 | 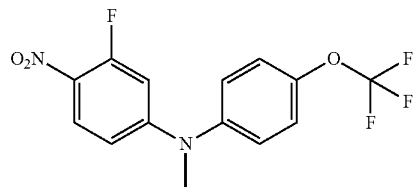 [SMILES: CN(c1ccc(OC(F)(F)F)cc1)c1ccc([N+](=O)[O-])c(F)c1] | LC-MS: m/z 331.1 (M − H)$^-$ |
| 590 | VII.111 | VII.48 | 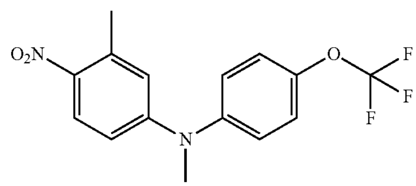 [SMILES: Cc1cc(N(C)c2ccc(OC(F)(F)F)cc2)ccc1[N+](=O)[O-]] | LC-MS: m/z 327.1 (M − H)$^-$ |
| 592 | VII.112 | VII.49 | 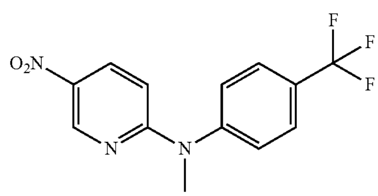 | LC-MS: m/z 331.0 (M − H)$^-$ |
| 593 | VII.113 | VII.33 | 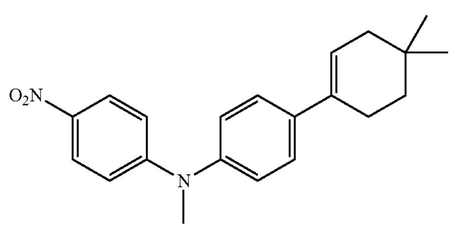 [SMILES: CN(c1ccc(C2=CCC(C)(C)CC2)cc1)c1ccc([N+](=O)[O-])cc1] | LC-MS: m/z 337.1 (M + H)$^+$ |
| 594 | VII.114 | VII.50 | 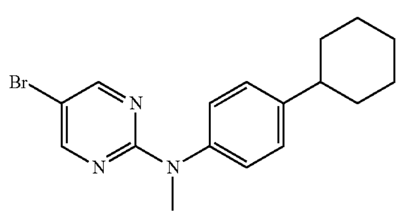 [SMILES: CN(c1ccc(C2CCCCC2)cc1)c1ncc(Br)cn1] | LC-MS: m/z 346.0 (M + H)$^+$ |
| 595 | VII.115 | VII.51 | 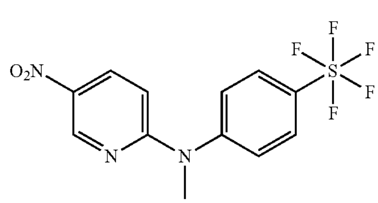 [SMILES: CN(c1ccc(S(F)(F)(F)(F)F)cc1)c1ccc([N+](=O)[O-])cn1] | LC-MS: m/z 356.1 (M − H)$^-$ |

-continued

| CP | Intermediate No. | Reactant | Structure | Analytical data |
|---|---|---|---|---|
| 597 | VII.116 | VII.53 | 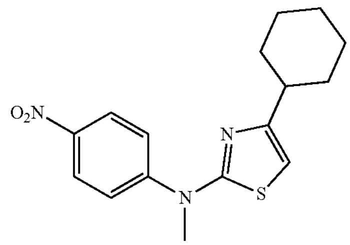 [SMILES: CN(c1ccc([N+](=O)[O-])cc1)c1nc(C2CCCCC2)cs1] | LC-MS: m/z 318.1 (M + H)+ |
| 602 | VII.117 | VII.54 | 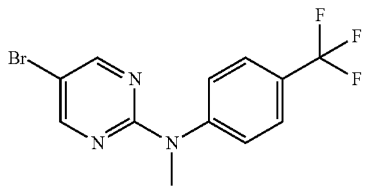 [SMILES: CN(c1ccc(C(F)(F)F)cc1)c1ncc(Br)cn1] | LC-MS: m/z 332.0 (M + H)+ |
| 603 | VII.118 | VII.52 | 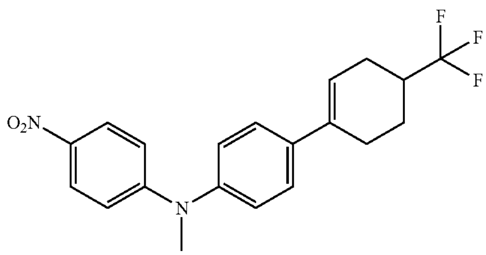 [SMILES: CN(c1ccc(C2=CCC(C(F)(F)F)CC2)cc1)c1ccc([N+](=O)[O-])cc1] | LC-MS: m/z 377.1 (M + H)+ |
| 609, 652, 673 | VII.119 | VII.55 | 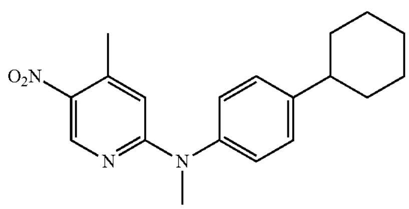 [SMILES: Cc1cc(N(C)c2ccc(C3CCCCC3)cc2)ncc1[N+](=O)[O-]] | LC-MS: m/z 326.2 (M + H)+ |
| 612 | VII.120 | VII.56 | 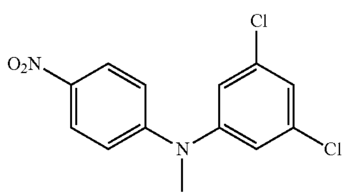 [SMILES: CN(c1ccc([N+](=O)[O-])cc1)c1cc(Cl)cc(Cl)c1] | LC-MS: m/z 297.0 (M + H)+ |
| 617 | VII.121 | VII.57 | 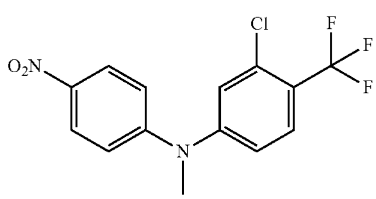 [SMILES: CN(c1ccc([N+](=O)[O-])cc1)c1ccc(C(F)(F)F)c(Cl)c1] | LC-MS: m/z 331.0 (M + H)+ |
| 618 | VII.122 | VII.58 | 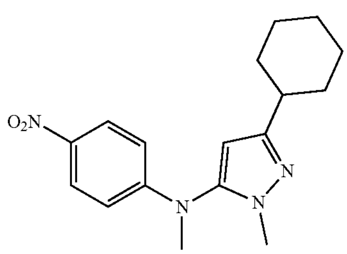 [SMILES: CN(c1ccc([N+](=O)[O-])cc1)c1cc(C2CCCCC2)nn1C] | LC-MS: m/z 315.2 (M + H)+ |

-continued

| CP | Intermediate No. | Reactant | Structure | Analytical data |
|---|---|---|---|---|
| 622 | VII.123 | VII.59 | O₂N–C₆H₄–N(CH₃)–C₆H₄–S–CF₃ | LC-MS: m/z 329.0 (M + H)⁺ |
| 624 | VII.124 | VII.60 | O₂N–C₆H₄–N(CH₃)–(1-methyl-3-(trifluoromethyl)pyrazol-5-yl) | LC-MS: m/z 301.0 (M + H)⁺ |
| 626 | VII.125 | VII.61 | 4-nitro-3-cyclopropyl-phenyl–N(CH₃)–C₆H₄–cyclohexyl | LC-MS: m/z 351.1 (M + H)⁺ |
| 598, 643, 654, 655 | VII.126 | VII.64 | 5-bromo-pyridin-2-yl–N(CH₃)–C₆H₄–cyclohexyl | LC-MS: m/z 345.1 (M + H)⁺ |
| 646 | VII.127 | VII.65 | 4-nitro-3-methyl-phenyl–N(CH₃)–C₆H₄–O–CH₂CF₃ | LC-MS: m/z 340.95 (M + H)⁺ |
| 647 | VII.128 | VII.66 | 4-nitro-3-methyl-phenyl–N(CH₃)–C₆H₄–O–CF₃ | LC-MS: m/z 326.95 (M + H)⁺ |
| 659 | VII.129 | VII.67 | 5-nitro-pyridin-2-yl–N(CH₃)–(2-chloro-4-cyclohexyl-phenyl) | LC-MS: m/z 346.1 (M + H)⁺ |

-continued

| CP | Intermediate No. | Reactant | Structure | Analytical data |
|---|---|---|---|---|
| 663 | VII.130 | VII.68 | 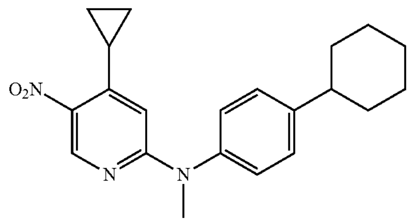 [SMILES: CN(c1ccc(C2CCCCC2)cc1)c1ccc([N+](=O)[O-])c(C2CC2)c1] | LC-MS: m/z 352.2 (M + H)$^+$ |
| 671, 681 | VII.131 | VII.69 | 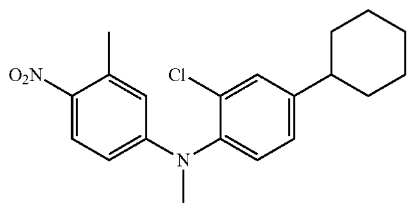 [SMILES: Cc1cc(N(C)c2ccc(C3CCCCC3)cc2Cl)ccc1[N+](=O)[O-]] | LC-MS: m/z 359.1 (M + H)$^+$ |

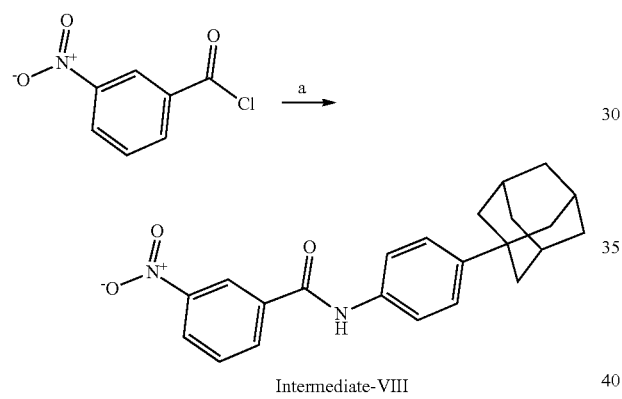

Intermediate-VII

Intermediate-VIII

Step-a: Synthesis of N-(4-((3R,5R)-adamantan-1-yl)phenyl)-3-nitrobenzamide (Intermediate-VIII)

The title compound (1.6 g, 960) was synthesized from intermediate-I.1 (1 g, 4.4 mmol, 1 eq.) and 3-nitrobenzoyl chloride (0.82 g, 4.4 mmol, 1 eq.) using a procedure similar to Intermediate-IV. LC-MS: m/z 377.2 (M+H)$^+$ The below intermediates were prepared by a procedure similar to Intermediate-VII using appropriate reactants and reagents and in presence of suitable solvents and appropriate reaction conditions.

| CP | Intermediate No. | Structure | Analytical data |
|---|---|---|---|
| 366, 367 | VIII.1 | 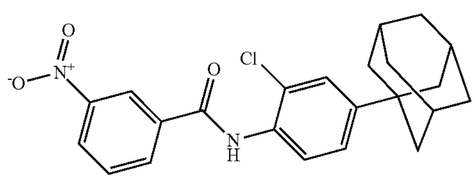 | $^1$H NMR (400 MHz, DMSO-d6) δ 10.43 (s, 1H), 8.80 (s, 1H), 8.47-8.40 (m, 2H), 7.85 (t, J = 7.6 Hz, 1H), 7.51-7.49 (m, 2H), 7.41-7.39 (m, 1H), 2.08 (s, 3H), 1.89 (s, 6H), 1.75 (s, 6H). LC-MS: m/z 411.1 (M + H)$^+$ |
| 373 | VIII.2 | 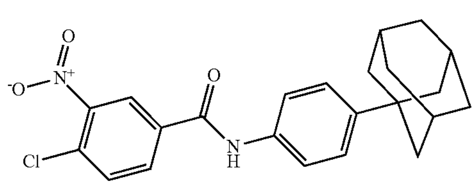 | LC-MS: m/z 411.05 (M + H)$^+$ |

-continued

| CP | Intermediate No. | Structure | Analytical data |
|---|---|---|---|
| 395 | VIII.3 | 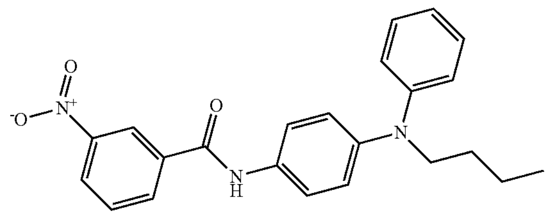 | ¹H NMR (400 MHz, DMSO-d6) δ 10.53 (s, 1H), 8.79 (t, J = 2.0 Hz, 1H), 8.45-8.39 (m, 2H), 7.84 (t, J = 8.0 Hz, 1H), 7.72-7.69 (m, 2H), 7.25-7.21 (m, 2H), 7.06-7.03 (m, 2H), 6.91-6.90 (m, 2H), 6.88-6.84 (m, 1H), 3.67 (t, J = 7.2 Hz, 2H), 1.59-1.53 (m, 2H), 1.36-1.29 (m, 2H), 0.88 (t, J = 7.2 Hz, 3H). LC-MS: m/z 390.2 (M + H)⁺ |
| 339 | VIII.4 | 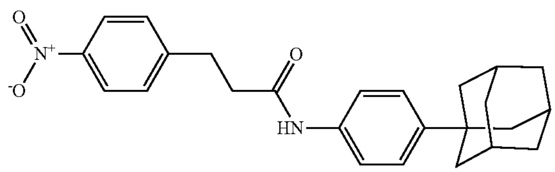 | LC-MS: m/z 405.1 (M + H)⁺ |
| 586 | VIII.5 | 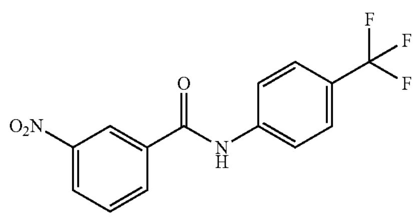 [SMILES: O=C(Nc1ccc(C(F)(F)F)cc1)c1cccc([N+](=O)[O-])c1] | LC-MS: m/z 309.1 (M − H)– |
| 642 | VIII.6 | 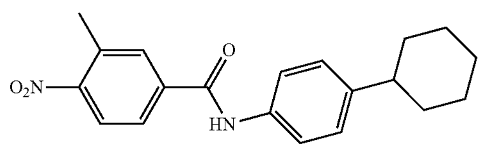 [SMILES: Cc1cc(C(=O)Nc2ccc(C3CCCCC3)cc2)ccc1[N+](=O)[O-]] | LC-MS: m/z 339.05 (M + H)+ |
| 649 | VIII.7 | 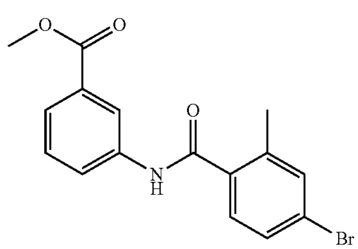 [SMILES: COC(=O)c1cccc(NC(=O)c2ccc(Br)cc2C)c1] | 1H NMR (400 MHz, DMSO-d6) δ 10.57 (s, 1H), 8.45 (s, 1H), 7.93 (d, J = 8.0 Hz, 1H), 7.71-7.68 (m, 1H), 7.58 (s, 1H), 7.54-7.44 (m, 3H), 3.86 (s, 3H), 2.38 (s, 3H). |
| 665, 666, 669, 672 | VIII.8 | 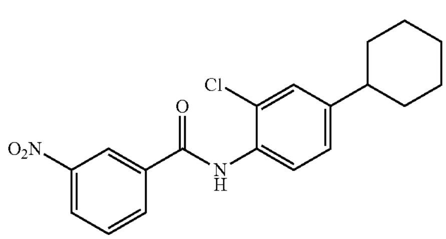 [SMILES: O=C(Nc1ccc(C2CCCCC2)cc1Cl)c1cccc([N+](=O)[O-])c1] | LC-MS: m/z 359.1 (M + H)⁺ |

Intermediate-IX

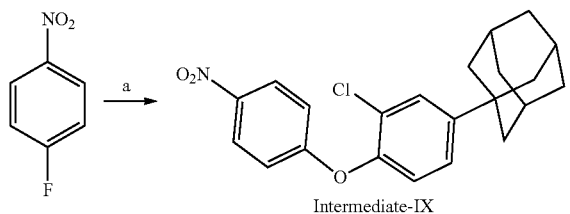 [SMILES: O=[N+]([O-])c1ccc(F)cc1 ; O=[N+]([O-])c1ccc(Oc2ccc(C34CC5CC(CC(C5)C3)C4)cc2Cl)cc1]

Step-a: Synthesis of (3R,5R)-1-(3-chloro-4-(4-nitro-phenoxy)phenyl)adamantane (Intermediate-IX)

A solution of 4-fluoronitrobenzene (0.6 mL, 5.7 mmol) and Intermediate-1.25 (1.5 g, 6.84 mmol, 1.2 eq.) in DMSO (10 mL) was added with potassium carbonate (1.57 g, 11.4 mmol, 2 eq.) and allowed to stir at RT overnight. Reaction mass was poured on to cold water and obtained solid was filtered and dried to afford title compound as off-white solid (2 g, 910%).

$^1$H NMR (400 MHz, DMSO-d6) δ 8.26 (d, J=9.3 Hz, 2H), 7.58 (s, 1H), 7.47 (d, J=2.0 Hz, 1H), 7.32 (d, J=8.8 Hz, 1H), 7.1 (d, J=8.3 Hz, 2H), 2.07 (bs, 2H), 1.89 (s, 6H), 1.7 (s, 6H). LC-MS: m/z 382.0 (M−H)$^-$

The below intermediates were prepared by a procedure similar to Intermediate-IX using appropriate reactants and reagents and in presence of suitable solvents and appropriate reaction conditions.

| CP | Intermediate No. | Reactant | Structure | Analytical data |
|---|---|---|---|---|
| 270, 314 | IX.1 | I.30 | 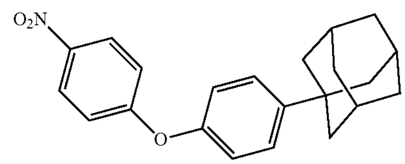 [SMILES: O=[N+]([O-])c1ccc(Oc2ccc(C34CC5CC(CC(C5)C3)C4)cc2)cc1] | $^1$H NMR (400 MHz, DMSO-d6) δ 8.24 (d, J = 8.8 Hz, 2H), 7.47 (d, J = 8.8 Hz, 2H), 7.11 (m, 4H), 2.07 (s, 3H), 1.88 (s, 6H), 1.71 (s, 6H). |
| 360 | IX.2 | I.32 | 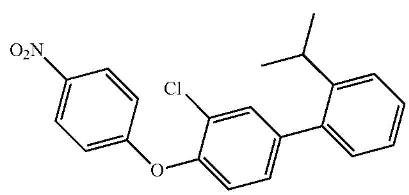 [SMILES: CC(C)c1ccccc1-c1ccc(Oc2ccc([N+](=O)[O-])cc2)c(Cl)c1] | $^1$H NMR (400 MHz, DMSO-d6) δ 8.31 (d, J = 8.8 Hz, 2H), 7.57 1H), 7.44-7.36 (m, 4H), 7.26 (t, J = 7.3 Hz, 1H), 7.19 (t, J = 8.8 Hz, 3H), 2.99-2.95 (m, 1H), 1.17 (d, J = 6.8 Hz, 6H). |
| 383, 384 529, 531, | IX.3 | I.31 | 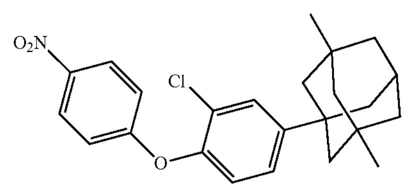 [SMILES: CC12CC3CC(C)(C1)CC(c1ccc(Oc4ccc([N+](=O)[O-])cc4)c(Cl)c1)(C3)C2] | $^1$H NMR (400 MHz, DMSO-d6) δ 8.27-8.23 (m, 2H), 7.58 (d, J = 2.0 Hz, 1H), 7.45 (dd, J$_1$ = 2.4 Hz, J$_2$ = 8.8 Hz, 1H), 7.31 (d, J = 8.4 Hz, 1H), 7.09-7.03 (m, 2H), 2.17-2.14 (m, 1H), 1.72 (s, 2H), 1.55-1.36 (m, 8H), 1.20 (s, 2H), 0.87 (s, 6H). |
| 534 | IX.4 | | 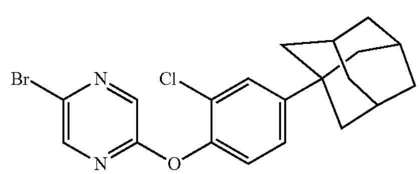 [SMILES: Clc1cc(C23CC4CC(CC(C4)C2)C3)ccc1Oc1cnc(Br)cn1] | LC-MS: m/z 419.0 (M + H)$^+$ |
| 540 | IX.5 | | 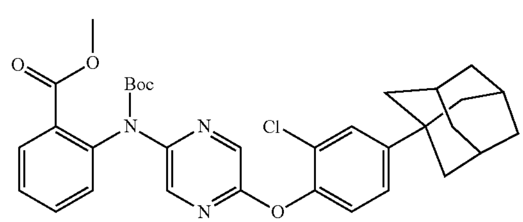 | LC-MS: m/z 576.2 (M + H)$^+$. |

-continued

| CP | Intermediate No. | Reactant | Structure | Analytical data |
|---|---|---|---|---|
| 543, 544 | IX-6 | | 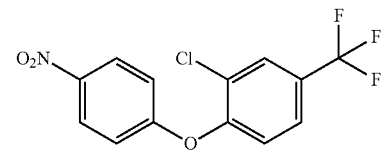 [SMILES: O=[N+]([O-])c1ccc(Oc2ccc(C(F)(F)F)cc2Cl)cc1] | $^1$H NMR (400 MHz, DMSO-d6) δ 8.35-8.27 (m, 2H), 8.15 (s, 1H), 7.84 (d, J = 8.4 Hz, 2H), 7.24 (d, J = 9.2 Hz, 2H). |
| 546, 550 | IX.7 | | 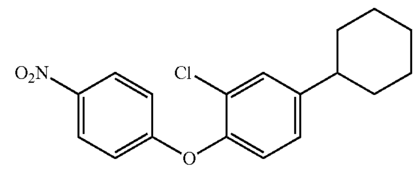 [SMILES: O=[N+]([O-])c1ccc(Oc2ccc(C3CCCCC3)cc2Cl)cc1] | Proceeded with crude/TLC reference |
| 561, 564 | IX.8 | | 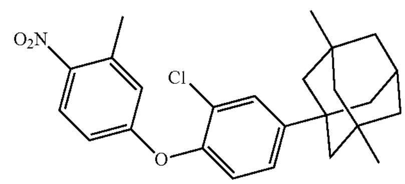 [SMILES: Cc1cc(Oc2ccc(C34CC5CC(C)(CC(C)(C5)C3)C4)cc2Cl)ccc1[N+](=O)[O-]] | $^1$H NMR (400 MHz, DMSO-d$_6$): δ 8.06 (d, J = 9.2 Hz, 1H), 7.56 (d, J = 1.6 Hz, 1H), 7.44-7.42 (m, 1H), 7.26 (d, J = 8.4 Hz, 1H), 7.04 (d, J = 2 Hz, 1H), 6.81-6.78 (m, 1H), 2.52 (s, 3H), 2.15 (s, 1H), 1.72-1.19 (m, 12H), 0.86-0.84 (m, 6H). |
| 566, 591 | IX.9 | | 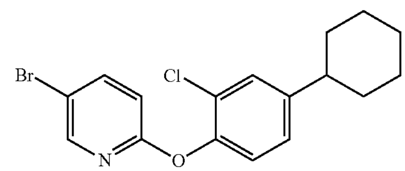 [SMILES: Clc1cc(C2CCCCC2)ccc1Oc1ccc(Br)cn1] | LC-MS: m/z 368.0 (M + 2H)$^+$ |
| 569, 570 | IX.10 | | 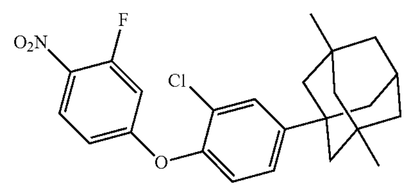 [SMILES: CC12CC3CC(C)(C1)CC(c1ccc(Oc4ccc([N+](=O)[O-])c(F)c4)c(Cl)c1)(C3)C2] | Proceeded with crude/TLC reference |
| 575 | IX.11 | | 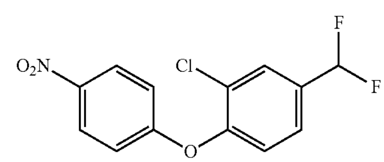 [SMILES: O=[N+]([O-])c1ccc(Oc2ccc(C(F)F)cc2Cl)cc1] | $^1$H NMR (400 MHz, DMSO-d$_6$): δ 8.29-8.26 (m, 2H), 7.93 (s, 1H), 7.69 (d, J = 8.4 Hz, 1H), 7.50 (d, J = 8.4 Hz, 1H), 7.24-6.96 (m, 3H). |
| 587 | IX.12 | | 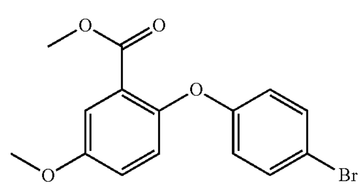 [SMILES: COC(=O)c1cc(OC)ccc1Oc1ccc(Br)cc1] | LC-MS: m/z 338.85 (M + H)$^+$ |
| 599 | IX.13 | | 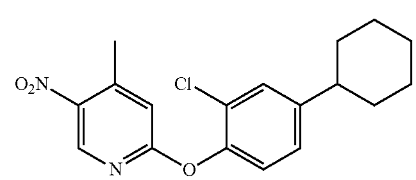 | LC-MS: m/z 361.3 (M + H)$^+$ |
| 600 | IX.14 | | 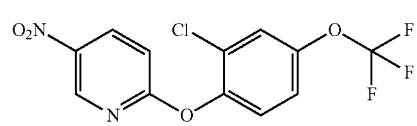 [SMILES: O=[N+]([O-])c1ccc(Oc2ccc(OC(F)(F)F)cc2Cl)nc1] | LC-MS: m/z 334.05 (M+)$^+$ |

-continued

| CP | Intermediate No. | Reactant | Structure | Analytical data |
|---|---|---|---|---|
| 601 | IX.15 | | 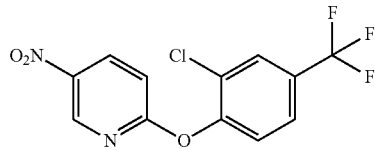 [SMILES: O=[N+]([O-])c1ccc(Oc2ccc(C(F)(F)F)cc2Cl)nc1] | LC-MS: m/z 319.0 (M + H)+ |
| 615 | IX.16 | | 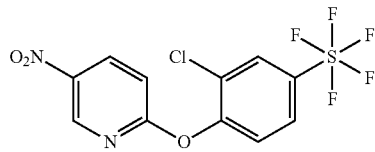 [SMILES: O=[N+]([O-])c1ccc(Oc2ccc(S(F)(F)(F)(F)F)cc2Cl)nc1] | LC-MS: m/z 377.0 (M + H)+ |
| 616 | IX.17 | | 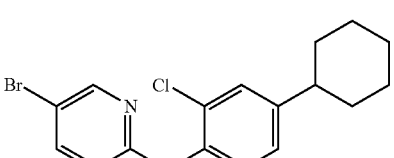 | LC-MS: m/z 388.0 (M + H)+ |

Intermediate-X

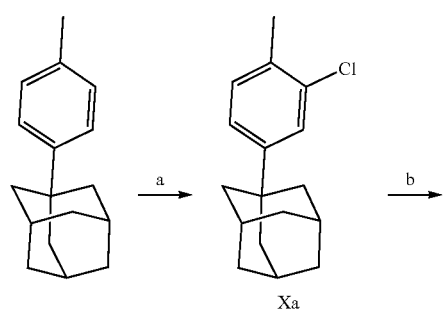

Xa

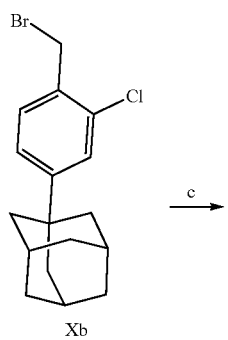

Xb

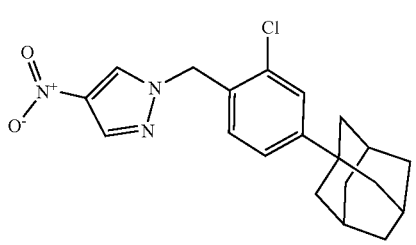

Intermediate-X

Step-a: Synthesis of (3r,5r,7r)-1-(3-chloro-4-methylphenyl)adamantane (Xa)

A solution of (3r,5r,7r)-1-(p-tolyl)adamantane (2 g, 8.8 mmol) in acetic acid was added with N-chlorosuccinimide in portions for a period of 30 minutes. Reaction mass was heated at 75° C. overnight. Reaction mass was poured on to cold water and obtained solid was filtered off and dried under vacuum. Title compound was obtained as white solid (2.2 g, 960%). $^1$H NM/R (400 MHz, DMSO-d6) δ 7.31 (d, J=1.9 Hz, 1H), 7.26-7.22 (m, 2H), 2.27 (s, 3H), 2.04 (s, 3H), 1.83 (s, 6H), 1.72 (s, 6H).

Step-b: Synthesis of (3r,5r,7r)-1-(4-(bromomethyl)-3-chlorophenyl)adamantane (Xb)

A solution of compound Xa (1 g, 3.8 mmol) in carbon tetrachloride (40 mL) was added with Bromine (0.61 g, 3.8 mmol) drop wise and Benzoyl peroxide (catalytic). Reaction mass was heated to reflux overnight. Concentrated in vacuo and crude was purified by column chromatography to afford title product as off-white solid (0.5 g, 380%). $^1$H NMR (400 MHz, DMSO-d6) δ 7.38 (d, J=8.0 Hz, 2H), 7.24 (m, 1H), 4.58 (s, 2H), 2.10 (s, 3H), 1.81 (s, 6H), 1.72 (s, 6H).

Step-c: Synthesis of 1-(4-((3R,5R)-adamantan-1-yl)-2-chlorobenzyl)-4-nitro-1H-pyrazole Intermediate-X)

This intermediate was prepared according to a similar procedure described for Intermediate-III by using Intermediate-Xb (0.3 g, 0.88 mmol, 1 eq.) and 4-nitropyrazole (0.12 g, 1.06 mmol, 1.2 eq.) to afford title product as an off-white solid (0.3 g, 91M). $^1$H NMR (400 MHz, DMSO-d6) δ 8.99 (s, 1H), 8.28 (s, 1H), 7.41 (d, J=2.0 Hz, 1H), 7.35 (dd, J$_1$=1.9 Hz, J$_2$=8.3 Hz, 1H), 7.21 (d, J=8.3 Hz, 1H), 5.47 (s, 2H), 2.04 (s, 3H), 1.83 (s, 6H), 1.72 (s, 6H).

The below intermediates were prepared by a procedure similar to Intermediate-X using appropriate reactants and reagents and in presence of suitable solvents and appropriate reaction conditions.

| CP | Intermediate No. | Reactant | Structure | Analytical data |
|---|---|---|---|---|
| 226 | XIII.1 | 3-nitro-1H-1,2,4-triazole | 1-[(2-chloro-4-adamantyl-benzyl)]-3-nitro-1,2,4-triazole | $^1$H NMR (400 MHz, DMSO-d6) δ 9.02 (s, 1H), 7.44 (s, 1H), 7.39 (s, 1H), 5.63 (s, 2H), 2.05 (s, 3H), 1.85 (d, J = 2.4 Hz, 6H), 1.72 (s, 6H). LC-MS: m/z 373.2 (M + H)$^+$ |
| 228 | XIII.2 | 6-nitroindoline | 1-[(2-chloro-4-adamantyl-benzyl)]-6-nitroindoline | $^1$H NMR (400 MHz, DMSO-d6) δ 7.47 (dd, J$_1$ = 2.0 Hz, J$_2$ = 8.0 Hz, 1H), 7.42 (d, J = 1.6 Hz, 1H), 7.34-7.33 (m, 2H), 7.25 (d, J = 8.0 Hz, 1H), 7.21 (d, J = 2.0 Hz, 1H), 4.45 (s, 2H), 3.49 (t, J = 8.8 Hz, 2H), 3.07 (t, J = 8.0 Hz, 2H), 2.05 (s, 3H), 1.85 (s, 6H), 1.73 (s, 6H). LC-MS: m/z 423.2 (M + H)$^+$ |
| 240 | XIII.3 | 4-nitro-1H-imidazole | 1-[(2-chloro-4-adamantyl-benzyl)]-4-nitroimidazole | $^1$H NMR (400 MHz, DMSO-d6) δ 8.39 (d, J = 1.2 Hz, 1H), 7.96 (d, J = 1.6 Hz, 1H), 7.44 (d, J = 2.0 Hz, 1H), 7.36-7.35 (m, 1H), 7.22 (d, J = 8.0 Hz, 1H), 5.39 (s, 2H), 2.05 (s, 3H), 1.84 (d, J = 2.8 Hz, 6H), 1.72 (s, 6H). LC-MS: m/z 372.2 (M + H)$^+$ |
| 194 | XIII.4 | II.8 | methyl 2-[4-(2-chloro-4-adamantyl-benzyl)piperazin-1-yl]nicotinate | LC-MS: m/z 480.1 (M + H)$^+$ |
| 195 | XIII.5 | III.3 | methyl 2-[[4-(2-chloro-4-adamantyl-benzyl)piperazin-1-yl]methyl]nicotinate | LC-MS: m/z 494.1 (M + H)$^+$ |

Intermediate-XI

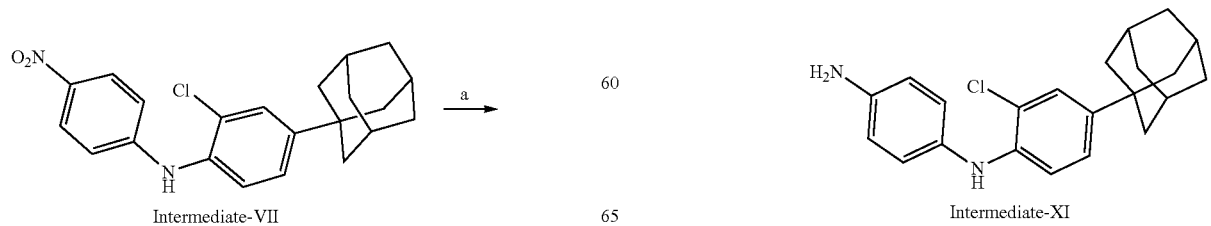

Intermediate-VII → Intermediate-XI

Step-a: Synthesis of N1-(4-((3R,5R)-adamantan-1-yl)-2-chlorophenyl)benzene-1,4-diamine (Intermediate-XI)

To a solution of Intermediate-VII (7 g, 18.3 mmol, 1 eq.) in THF:water (50 mL+50 mL), ammonium chloride (19.42 g, 36.6 mmol, 20 eq.) followed by Zinc dust (11.91 g, 183 mmol, 10 eq.) were added and stirred at RT for 16 h. Reaction mixture was diluted with ethyl acetate and filtered through celite. The filtrate was washed with water followed by brine. The organic layer was dried over anhydrous Sodium sulfate and concentrated in vacuo. The crude was washed with n-pentane and dried in vacuo to afford desired product as yellow gum (5.9 g, 91%). This was used in next step without further purification.

$^1$H NM/R (400 MHz, DMSO-d6) δ 7.20 (d, J=1.9 Hz, 1H) 7.04 (dd, $J_1$=2.0 Hz, $J_2$=8.3 Hz, 1H), 6.84 (d, J=8.8 Hz, 2H), 6.78 (s, 1H), 6.72 (d, J=8.8 Hz, 1H), 6.54 (d, J=8.8 Hz, 2H), 4.85 (s, 2H), 2.02 (s, 3H), 1.78 (s, 6H), 1.70 (s, 6H); LC-MS: m/z 353.1 (M+H)$^+$

The below intermediates were prepared by a procedure similar to Intermediate-XI using appropriate reactants and reagents and in presence of suitable solvents and appropriate reaction conditions.

| CP | Intermediate No. | Reactant | Structure | Analytical data |
|---|---|---|---|---|
| 128 | XI.1 | VII.3 | 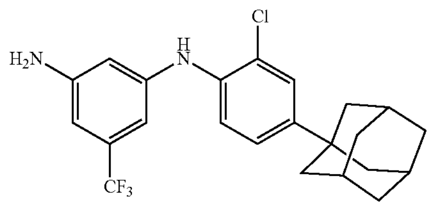 [SMILES: Nc1cc(Nc2ccc(C34CC5CC(CC(C5)C3)C4)cc2Cl)cc(C(F)(F)F)c1] | LC-MS: m/z 421.1 (M + H)$^+$ |
| 132, 133 | XI.2 | VII.5 | 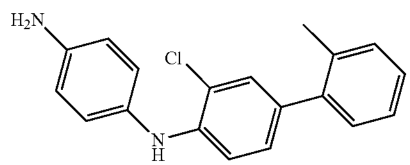 | $^1$H NMR (400 MHz, DMSO-d6) δ 7.25-7.19 (m, 4H), 7.16-7.14 (m, 1H), 7.06-7.02 (m, 2H), 6.91 (d, J = 8.4 Hz, 2H), 6.78 (d, J = 8.4 Hz, 1H), 6.58 (d, J = 8.4 Hz, 2H), 4.93 (s, 2H), 2.24 (s, 3H). LC-MS: m/z 309.0 (M + H)$^+$ |
| 169 | XI.3 | VII.7 | 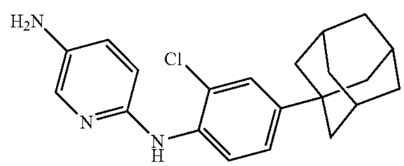 [SMILES: Nc1ccc(Nc2ccc(C34CC5CC(CC(C5)C3)C4)cc2Cl)nc1] | $^1$H NMR (400 MHz, DMSO-d6) δ 9.35-8.91 (bs, 1H), 7.80-7.78 (bs, 1H), 7.62-7.57 (m, 2H), 7.45 (d, J = 2.0 Hz, 1H), 7.35 (dd, $J_1$ = 2.4 Hz, $J_2$ = 8.8 Hz, 1H), 7.01 (d, J = 9.2 Hz, 1H), 2.07 (s, 3H), 1.87 (s, 6H), 1.74 (s, 6H). LC-MS: m/z 354.1 (M + H)$^+$ |
| 191 | XI.4 | VII.8 | 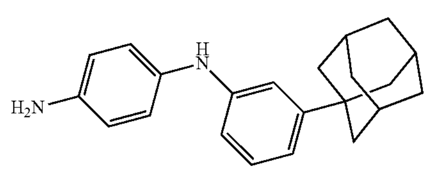 [SMILES: Nc1ccc(Nc2cccc(C34CC5CC(CC(C5)C3)C4)c2)cc1] | $^1$H NMR (400 MHz, DMSO-d6) δ 7.34 (s, 1H), 7.02-6.98 (m, 1H), 6.80-6.79 (m, 3H), 6.61-6.51 (m, 4H), 4.71 (s, 2H), 2.02 (s, 3H), 1.74 (s, 6H), 1.67 (s, 6H). LC-MS: m/z 319.1 (M + H)$^+$ |
| 203 | XI.5 | I.24 | 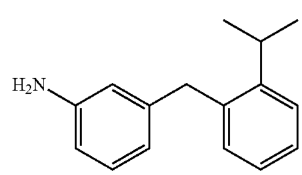 [SMILES: CC(C)c1ccccc1Cc1cccc(N)c1] | $^1$H NMR (400 MHz, DMSO-d6) δ 7.28 (d, J = 7.8 Hz, 1H), 7.21-7.17 (m, 1H), 7.10 (d, J = 3.9 Hz, 2H), 6.88 (t, J = 7.9 Hz, 1H), 6.35 (dd, $J_1$ = 1.5 Hz, $J_2$ = 8.3 Hz, 1H), 6.27 (m, 2H), 4.91 (s, 2H), 3.86 (s, 2H), 3.13 (m, 1H), 1.06 (d, J = 6.9 Hz, 6H). LC-MS: m/z 226.3 (M + H)$^+$ |
| 228 | XI.6 | X.2 | 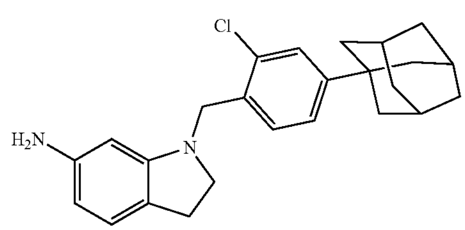 [SMILES: Nc1ccc2c(c1)N(Cc1ccc(C34CC5CC(CC(C5)C3)C4)cc1Cl)CC2] | $^1$H NMR (400 MHz, DMSO-d6) δ 7.38 (d, J = 1.6 Hz, 1H), 7.36-7.30 (m, 2H), 6.69 (d, J = 7.6 Hz, 1H), 5.84 (dd, $J_1$ = 2.0 Hz, $J_2$ = 8.0 Hz, 1H), 5.78 (d, J = 1.2 Hz, 1H), 4.68 (s, 2H), 4.18 (s, 2H), 3.26 (t, J = 8.0 Hz, 2H), 2.75 (t, J = 7.6 Hz, 2H), 2.05 (s, 3H), 1.85 (s, 6H), 1.73 (s, 6H). LC-MS: m/z 393.2 (M + H)$^+$ |

| CP | Intermediate No. | Reactant | Structure | Analytical data |
|---|---|---|---|---|
| 204, 237, 261 | XI.7 | VII.9 | | $^1$H NMR (400 MHz, DMSO-d6) δ 7.30 (s, 1H), 7.19 (s, 2H), 7.13 (s, 1H), 6.87-6.83 (m, 1H), 6.26 (s, 1H), 6.20 (d, J = 7.8 Hz, 1H), 6.10 (d, J = 7.8 Hz, 1H), 4.92 (s, 2H), 2.04 (s, 3H), 1.83 (s, 6H), 1.72 (s, 6H). LC-MS: m/z 353.1 (M + H)$^+$ |
| 232 | XI.8 | Int-X | 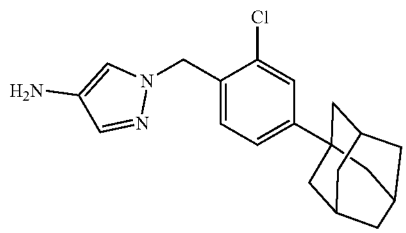 [SMILES: Nc1cnn(Cc2ccc(C34CC5CC(CC(C5)C3)C4)cc2Cl)c1] | LC-MS: m/z 342.2 (M + H)$^+$ |
| 226 | XI.9 | X.1 | 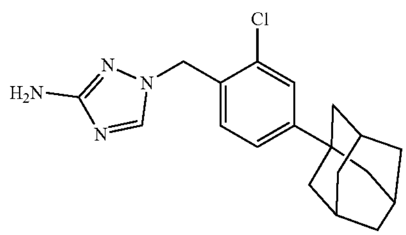 [SMILES: Nc1ncn(Cc2ccc(C34CC5CC(CC(C5)C3)C4)cc2Cl)n1] | $^1$H NMR (400 MHz, DMSO-d6) δ 8.08 (s, 1H), 7.37-7.30 (m, 2H), 7.20-7.10 (m, 1H), 5.25 (s, 2H), 5.17 (s, 2H), 2.04 (s, 3H), 1.83 (s, 6H), 1.72 (s, 6H). LC-MS: m/z 343.2 (M + H)$^+$ |
| 240 | XI.10 | X.3 | 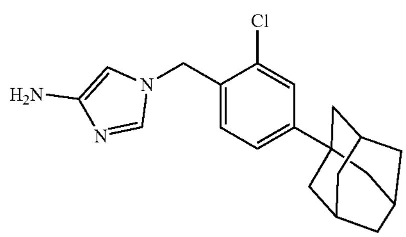 [SMILES: Nc1cn(Cc2ccc(C34CC5CC(CC(C5)C3)C4)cc2Cl)cn1] | $^1$H NMR (400 MHz, DMSO-d6) δ 7.59 (s, 1H), 7.40-7.38 (m, 1H), 7.34-7.32 (m, 1H), 7.15 (d, J = 8.0 Hz, 1H), 6.24 (d, J = 1.2 Hz, 1H), 5.18 (s, 2H), 4.61 (s, 2H), 2.10 (s, 3H), 1.82 (s, 6H), 1.73 (s, 6H). LC-MS: m/z 342.2 (M + H)$^+$ |
| 249 | XI.11 | VII.10 | 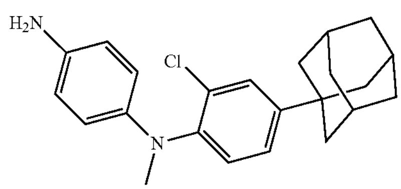 [SMILES: CN(c1ccc(N)cc1)c1ccc(C23CC4CC(CC(C4)C2)C3)cc1Cl] | LC-MS: m/z 367.1 (M + H)$^+$ |
| 270, 314 | XI.12 | IX.1 | 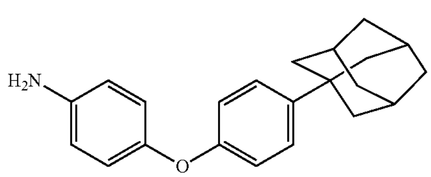 [SMILES: Nc1ccc(Oc2ccc(C34CC5CC(CC(C5)C3)C4)cc2)cc1] | $^1$H NMR (400 MHz, DMSO-d6) δ 7.26 (d, J = 8.8 Hz, 2H), 6.72 (m, 4H), 6.56 (d, J = 2.0 Hz, 2H), 4.93 (s, 2H), 2.03 (s, 3H), 1.82 (s, 6H), 1.68 (s, 6H). |
| 272 | XI.13 | VII.12 | 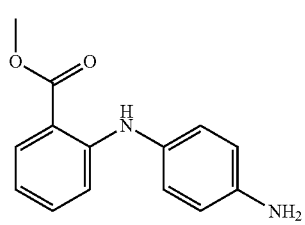 [SMILES: COC(=O)c1ccccc1Nc1ccc(N)cc1] | $^1$H NMR (400 MHz, DMSO-d6) δ 9.16 (s, 1H), 7.92 (dd, J$_1$ = 1.4 Hz, J$_2$ = 7.8 Hz, 1H), 7.25-7.21 (m, 1H), 7.04 (d, J = 8.3 Hz, 2H), 6.91 (d, J = 8.8 Hz, 1H), 6.70 (d, J = 2.0 Hz, 2H), 6.64-6.60 (m, 1H), 3.89 (s, 3H), 3.62 (s, 2H). |

-continued

| CP | Intermediate No. | Reactant | Structure | Analytical data |
|---|---|---|---|---|
| 284, 321 | XI.14 | Int-IX | 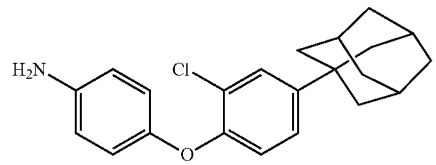 [SMILES: Nc1ccc(Oc2ccc(C34CC5CC(CC(C5)C3)C4)cc2Cl)cc1] | ¹H NMR (400 MHz, DMSO-d6) δ 7.40 (s, 1H), 7.23 (d, J = 8.8 Hz, 1H), 6.73 (d, J = 8.3 Hz, 3H), 6.58 (d, J = 8.8 Hz, 2H), 4.97 (s, 2H), 2.03 (bs, 3H), 1.82 (s, 6H), 1.71 (s, 6H). |
| 271, 273 | XI.15 | VII.21 | 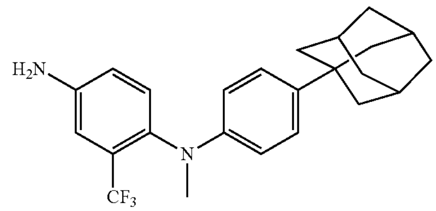 [SMILES: CN(c1ccc(C23CC4CC(CC(C4)C2)C3)cc1)c1ccc(N)cc1C(F)(F)F] | ¹H NMR (400 MHz, DMSO-d6) δ 7.08 (d, J = 8.8 Hz, 2H), 6.92 (d, J = 8.0 Hz, 2H), 6.83 (d, J = 2.4 Hz, 1H), 6.38 (d, J = 9.2 Hz, 2H), 5.59 (s, 2H), 3.00 (s, 2H), 2.02 (s, 3H), 1.78 (s, 6H), 1.70 (s, 6H). |
| 289 311 | XI.16 | VII.13 | 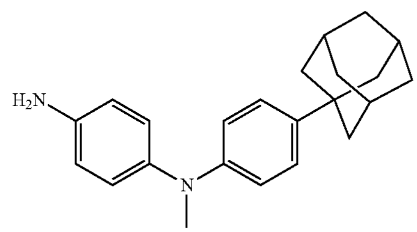 [SMILES: CN(c1ccc(N)cc1)c1ccc(C23CC4CC(CC(C4)C2)C3)cc1] | ¹H NMR (400 MHz, DMSO-d6) δ 7.09 (d, J = 8.8 Hz, 2H), 6.81 (m, 2H), 6.57-6.55 (m, 4H), 4.96 (s, 2H), 3.09 (s, 3H), 2.02 (s, 3H), 1.79 (s, 6H), 1.70 (s, 6H). LC-MS: m/z 333.1 (M + H)⁺ |
| 298, 299 | XI.17 | VII.15 | 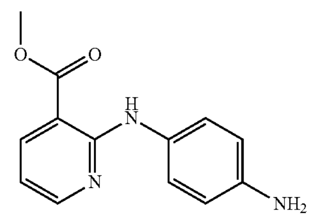 [SMILES: COC(=O)c1cccnc1Nc1ccc(N)cc1] | ¹H NMR (400 MHz, DMSO-d6) δ 9.67 (s, 1H), 8.29 (dd, J₁ = 1.6 Hz, J₂ = 4.4 Hz, 1H), 8.17 (dd, J₁ = 1.6 Hz, J₂ = 7.6 Hz, 1H), 7.26-7.22 (m, 2H), 6.73 (dd, J₁ = 4.8 Hz, J₂ = 8.0 Hz, 1H), 6.57-6.53 (m, 2H), 4.87 (s, 2H), 3.87 (s, 3H). LC-MS: m/z 244.15 (M + H)⁺ |
| 319 | XI.18 | VII.16 | 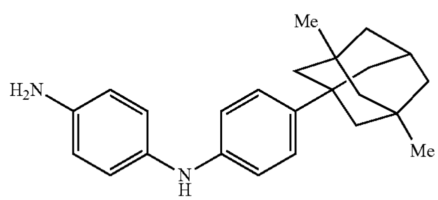 [SMILES: CC12CC3CC(C)(C1)CC(c1ccc(Nc4ccc(N)cc4)cc1)(C3)C2] | ¹H NMR (400 MHz, DMSO-d6) δ 7.28 (s, 1H), 7.06 (d, J = 8.8 Hz, 2H), 6.78 (d, J = 8.8 Hz, 2H), 6.72 (d, J = 8.8 Hz, 2H), 6.51 (d, J = 8.4 Hz, 2H), 4.68 (s, 2H), 2.10 (bs, 1H), 1.61 (s, 2H), 1.45-1.33 (m, 8H), 1.15 (s, 2H), 0.83 (s, 6H). LC-MS: m/z 347.3 (M + H)⁺ |
| 320 | XI.19 | VII.17 | 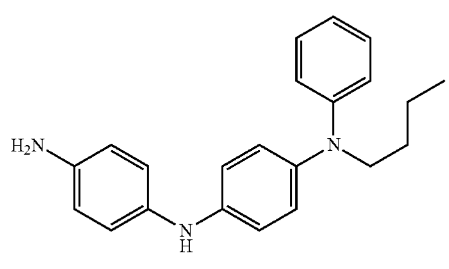 [SMILES: CCCCN(c1ccccc1)c1ccc(Nc2ccc(N)cc2)cc1] | ¹H NMR (400 MHz, DMSO-d6) δ 7.46 (s, 1H), 7.07 (t, J = 7.9 Hz, 2H), 6.90 (d, J = 8.8 Hz, 2H), 6.83 (m, 4H), 6.57 (m, 5H), 4.74 (s, 2H), 3.52 (t, J = 7.3 Hz, 2H), 1.52 (m, 2H), 1.32 (m, 2H), 0.87 (t, J = 6.9 Hz, 3H). |
| 338 | XI.20 | VII.18 | 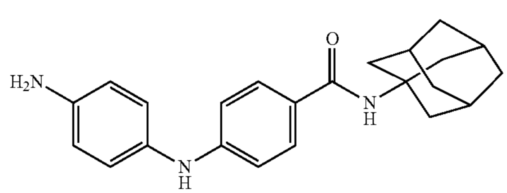 [SMILES: Nc1ccc(Nc2ccc(C(=O)NC34CC5CC(CC(C5)C3)C4)cc2)cc1] | ¹H NMR (400 MHz, DMSO-d6) δ 7.85 (s, 1H), 7.56 (d, J = 8.8 Hz, 2H), 7.08 (s, 1H), 6.84 (d, J = 8.4 Hz, 2H), 6.70 (d, J = 8.0 Hz, 2H), 6.55 (d, J = 8.4 Hz, 2H), 4.84 (s, 2H), 2.04 (s, 9H), 1.64 (s, 6H). LC-MS: m/z 362.3 (M + H)⁺ |

| CP | Intermediate No. | Reactant | Structure | Analytical data |
|---|---|---|---|---|
| 339 | XI.21 | VIII.4 | H₂N-C₆H₄-CH₂CH₂-C(=O)-NH-C₆H₄-adamantyl | ¹H NMR (400 MHz, DMSO-d6) δ 9.76 (s, 1H), 7.48 (d, J = 8.4 Hz, 2H), 7.25 (d, J = 8.8 Hz, 2H), 7.87 (d, J = 8.0 Hz, 2H), 7.46 (d, J = 8.0 Hz, 2H), 4.82 (s, 2H), 2.69 (t, J = 8.4 Hz, 2H), 2.49-2.46 (m, 2H), 2.04 (s, 3H), 1.82 (s, 6H), 1.72 (s, 6H). LC-MS: m/z 375.3 (M + H)⁺ |
| 345 | XI.22 | XI.16 | iPrNH-C₆H₄-N(Me)-C₆H₄-adamantyl | ¹H NMR (400 MHz, DMSO-d6) δ 7.09 (d, J = 8.8 Hz, 2H), 6.86 (d, J = 8.3 Hz, 2H), 6.56 (t, J = 9.3 Hz, 4H), 5.27 (d, J = 7.8 Hz, 1H), 3.50-3.49 (m, 1H), 3.10 (s, 3H), 2.02 (s, 3H), 1.79 (s, 6H), 1.71 (s, 6H), 1.13 (d, J = 6.3 Hz, 6H). |
| 358, 359, 376 | XI.23 | Int-VIII | H₂N-C₆H₄-C(=O)-NH-C₆H₄-adamantyl (meta-amino) | ¹H NMR (400 MHz, DMSO-d6) δ 10.06 (s, 1H), 7.66 (d, J = 8.8 Hz, 3H), 7.38-7.28 (m, 3H), 7.15-7.03 (m, 3H), 6.73 (d, J = 6.8 Hz, 1H), 5.28 (s, 2H), 2.05 (s, 3H), 1.85 (s, 6H), 1.73 (s, 6H). |
| 360 | XI.24 | IX.2 | H₂N-C₆H₄-O-C₆H₃(Cl)-C₆H₄-iPr | ¹H NMR (400 MHz, DMSO-d6) δ 7.41-7.38 (m, 3H), 7.21-7.12 (m, 3H), 6.84-6.78 (m, 3H), 6.63 (d, J = 8.0 Hz, 2H), 5.06 (s, 2H), 2.96-2.93 (m, 1H), 1.13 (d, J = 8.0 Hz, 6H). LC-MS: m/z 338.1 (M + H)⁺ |
| 383 | XI.25 | IX.3 | H₂N-C₆H₄-NH-C₆H₃(Cl)-dimethyladamantyl | ¹H NMR (400 MHz, DMSO-d6) δ 7.39 (d, J = 2.0 Hz, 1H), 7.21 (dd, J₁ = 2.4 Hz, J₂ = 8.8 Hz, 1H), 6.73-6.71 (m, 3H), 6.57 (d, J = 8.4 Hz, 2H), 4.97 (s, 2H), 2.13-2.11 (m, 1H), 1.65 (s, 2H), 1.49-1.31 (m, 8H), 1.16 (s, 2H), 0.84 (s, 6H). LC-MS: m/z 382.1 (M + H)⁺ |
| 366, 367 | XI.26 | VIII.1 | H₂N-C₆H₄-C(=O)-NH-C₆H₃(Cl)-adamantyl | ¹H NMR (400 MHz, DMSO-d6) δ 9.65 (s, 1H), 7.52 (d, J = 8.4 Hz, 1H), 7.43 (s, 1H), 7.35 (dd, J₁ = 1.2 Hz, J₂ = 8.0 Hz, 1H), 7.16-7.08 (m, 3H), 6.75 (d, J = 7.6 Hz, 1H), 5.31 (s, 2H), 2.07 (s, 3H), 1.88 (s, 6H), 1.74 (s, 6H). LC-MS: m/z 381.1 (M + H)⁺ |
| 373 | XI.27 | VIII.2 | H₂N-C₆H₃(Cl)-C(=O)-NH-C₆H₄-adamantyl | ¹H NMR (400 MHz, DMSO-d6) δ 10.05 (s, 1H), 7.65 (d, J = 7.6 Hz, 2H), 7.32-7.27 (m, 4H), 7.09 (d, J = 7.6 Hz, 1H), 5.57 (s, 2H), 2.05 (s, 3H), 1.85 (s, 6H), 1.73 (s, 6H). |

-continued

| CP | Intermediate No. | Reactant | Structure | Analytical data |
|---|---|---|---|---|
| 395 | XI.28 | VIII.3 | 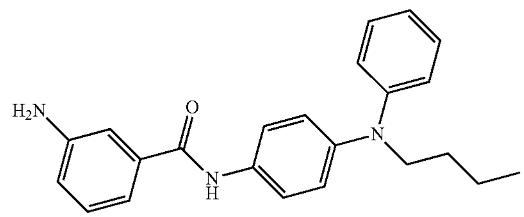 [SMILES: CCCCN(c1ccccc1)c1ccc(NC(=O)c2cccc(N)c2)cc1] | $^1$H NMR (400 MHz, DMSO-d6) δ 10.03 (s, 1H), 7.71-7.67 (m, 2H), 7.19-7.02 (m, 7H), 6.84-6.82 (m, 4H), 5.33 (s, 2H), 3.64 (t, J = 7.2 Hz, 2H), 1.60-1.54 (m, 2H), 1.34-13.2 (m, 2H), 0.88 (t, J = 7.6 Hz, 3H). LC-MS: m/z 360.2 (M + H)$^+$ |
| 378 | XI.29 | VII.20 | 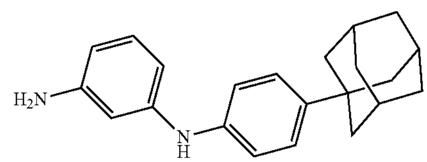 [SMILES: Nc1cccc(Nc2ccc(C34CC5CC(CC(C5)C3)C4)cc2)c1] | LC-MS: m/z 319.2 (M + H)$^+$ |
| 348 | XI.30 | VII.19 | 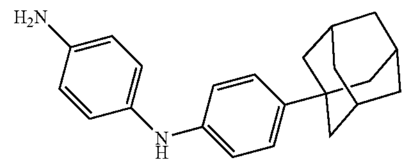 [SMILES: Nc1ccc(Nc2ccc(C34CC5CC(CC(C5)C3)C4)cc2)cc1] | LC-MS: m/z 319.5 (M + H)$^+$ |
| 266 | XI.31 | VII.1 | 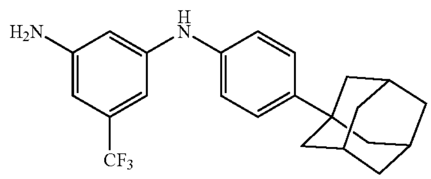 [SMILES: Nc1cc(Nc2ccc(C34CC5CC(CC(C5)C3)C4)cc2)cc(C(F)(F)F)c1] | LC-MS: m/z 387.15 (M + H)$^+$ |
| 521, 541, 605, 606, 607, 608, 613, 648 | XI.32 | VII.74 | 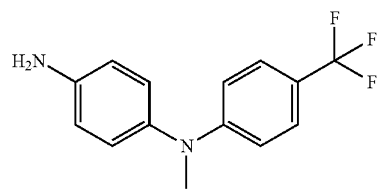 [SMILES: CN(c1ccc(N)cc1)c1ccc(C(F)(F)F)cc1] | LC-MS: m/z 267.1 (M + H)$^+$ |
| 522, 558 | XI.33 | VII.75 | 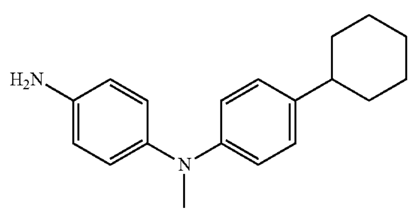 | LC-MS: m/z 281.2 (M + H)$^+$. |
| 528 | XI.34 | VII.76 | 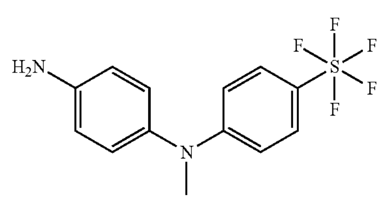 | LC-MS: m/z 325.1 (M + H)$^+$. |
| 535 | XI.35 | VII.77 | 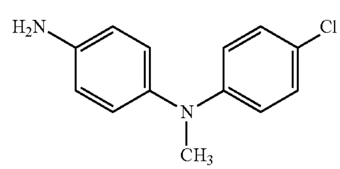 [SMILES: CN(c1ccc(N)cc1)c1ccc(Cl)cc1] | LC-MS: m/z 233.1 (M + H)$^+$. |

-continued

| CP | Intermediate No. | Reactant | Structure | Analytical data |
|---|---|---|---|---|
| 537 | XI.36 | VII.78 | 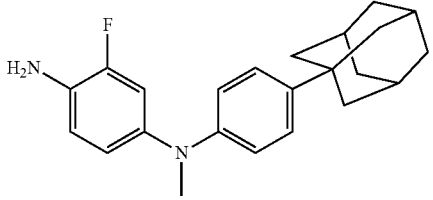 [SMILES: CN(c1ccc(C23CC4CC(CC(C4)C2)C3)cc1)c1ccc(N)c(F)c1] | LC-MS: m/z 350.2 (M + H)+. |
| 538 | XI.37 | VII.79 | 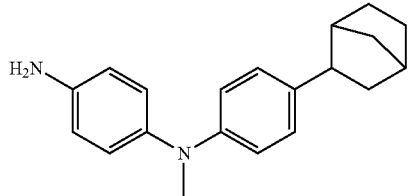 | $^1$H NMR (400 MHz, DMSO-$d_6$): δ 6.95 (d, J = 8.8 Hz, 2H), 6.8 (d, J = 8.4 Hz, 2H), 6.55 (dd, $J_1$ = 5.2 Hz & $J_2$ = 8.4 Hz, 4H), 4.98 (s, 2H), 3.08 (s, 3H), 2.57-2.55 (m, 1H), 2.28 (s, 1H), 2.15 (s, 1H), 1.63-1.41 (m, 4H), 1.35-1.07 (m, 4H). LC-MS: m/z 293.2 (M + H)+. |
| 542 | XI.38 | VII.80 | 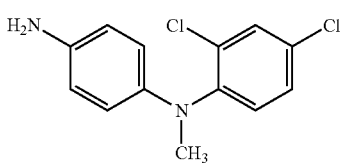 | LC-MS: m/z 267.1 (M + H)+. |
| 543, 544 | XI.39 | IX.6 | 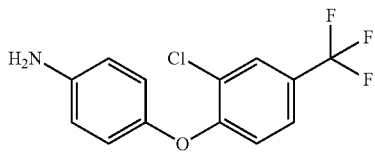 | LC-MS: m/z 288.0 (M + H)+. |
| 545 | XI.40 | VII.81 | 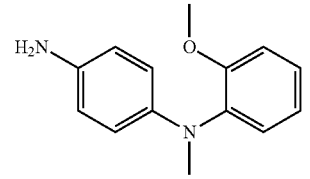 | LC-MS: m/z 229.1 (M + H)+. |
| 546 | XI.41 | IX.7 | 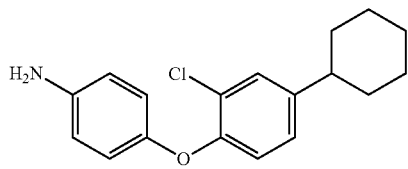 | LC-MS: m/z 302.1 (M + H)+. |
| 547 | XI.42 | VII.82 | 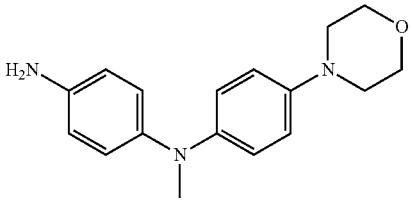 | $^1$H NMR (400 MHz, DMSO-$d_6$): δ 6.80-6.73 (m, 4H), 6.63 (d, J = 8.8 Hz, 2H), 6.53 (d, J = 8.4 Hz, 2H), 4.87 (s, 2H), 3.71-3.69 (m, 4H), 3.05 (s, 3H), 2.95-2.92 (m, 4H). LC-MS: m/z 284.2 (M + H)+. |
| 548 | XI.43 | VII.83 | 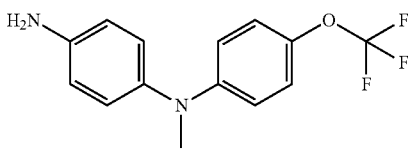 | $^1$H NMR (400 MHz, DMSO-$d_6$) δ 7.08 (d, J = 8.8 Hz, 2H), 6.86-6.83 (m, 2H), 6.61-6.58 (m, 4H), 5.08 (s, 2H), 3.13 (s, 3H). LC-MS: m/z 283.1 (M + H)+. |

-continued

| CP | Intermediate No. | Reactant | Structure | Analytical data |
|---|---|---|---|---|
| 549 | XI.44 | VII.84 | H₂N–(3-F-C₆H₃)–N(Me)–C₆H₄–cyclohexyl | LC-MS: m/z 299.2 (M + H)+. |
| 550 | XI.45 | IX.7 | H₂N–C₆H₄–O–(2-Cl-C₆H₃)–cyclohexyl | LC-MS: m/z 302.1 (M + H)+. |
| 551 | XI.46 | VII.85 | H₂N–(3-Me-C₆H₃)–N(Me)–C₆H₄–adamantyl | LC-MS: m/z 347.3 (M + H)+. |
| 552 | XI.47 | VII.86 | H₂N–C₆H₄–N(Me)–C₆H₄–(4,4-difluorocyclohexyl) | LC-MS: m/z 317.2 (M + H)+. |
| 553 | XI.48 | VII.87 | H₂N–C₆H₄–N(Me)–C₆H₄–O–CH₂CF₃ | LC-MS: m/z 297.1 (M + H)+. |
| 554 | XI.49 | VII.88 | H₂N–C₆H₄–N(Me)–C₆H₄–CHF₂ | LC-MS: m/z 249.1 (M + H)+. |
| 555 | XI.50 | VII.89 | H₂N–C₆H₄–N(Me)–C₆H₄–piperidinyl | LC-MS: m/z 282.5 (M + H)+. |

-continued

| CP | Intermediate No. | Reactant | Structure | Analytical data |
|---|---|---|---|---|
| 556 | XI.51 | VII.90 | 4-amino-N-methyl-N-(4-cyclobutylphenyl)aniline | LC-MS: m/z 253.2 (M + H)+ |
| 557 | XI.52 | VII.91 | 4-amino-N-methyl-N-[4-(4,4-difluorocyclohex-1-en-1-yl)phenyl]aniline | LC-MS: m/z 315.2 (M + H)+ |
| 560, 579, 580, 614, 619, 620, 621, 625, 627, 628, 629 | XI.53 | VII.92 | 4-amino-3-methyl-N-methyl-N-(4-cyclohexylphenyl)aniline<br>Also for CP compounds 630, 631, 632, 633, 634, 635, 636, 637, 640, 653, 656, 657, 678, 679 | LC-MS: m/z 295.2 (M + H)+ |
| 561, 564 | XI.54 | IX.8 | 4-amino-3-methyl-phenyl 2-chloro-4-(adamantyl)phenyl ether | LC-MS: m/z 396.1 (M + H)+. |
| 563 | XI.55 | VII.93 | 4-amino-3-methyl-N-methyl-N-[4-(trifluoromethyl)phenyl]aniline | 1H NMR (400 MHz, DMSO-d6): δ 7.38 (d, J = 8.8 Hz, 2H), 6.79-6.74 (m, 2H), 6.66-6.64 (m, 3H), 4.91 (s, 2H), 3.18 (s, 3H), 2.04 (s, 3H). |
| 565 | XI.56 | VII.94 | 4-amino-3-methyl-N-methyl-N-[4-(2,2,2-trifluoroethoxy)phenyl]aniline | LC-MS: m/z 311.2 (M + H)+. |
| 566 | XI.57 | IX.9 | methyl 2-aminobenzoate | procured |

-continued

| CP | Intermediate No. | Reactant | Structure | Analytical data |
|---|---|---|---|---|
| 568 | XI.58 | VII.95 | 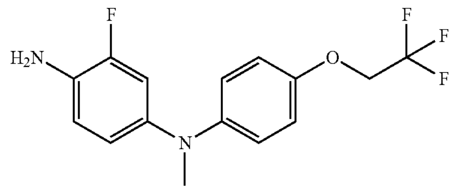 | LC-MS: m/z 314.05 (M + H)+. |
| 569, 570 | XI.59 | IX.10 | 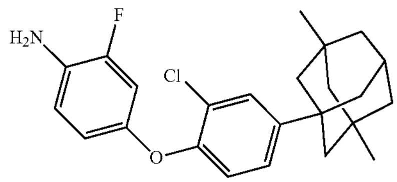 [SMILES: CC12CC3CC(C)(C1)CC(c1ccc(Oc4ccc(N)c(F)c4)c(Cl)c1)(C3)C2] | LC-MS: m/z 400.2 (M + H)+ |
| 571 | XI.60 | VII.96 | 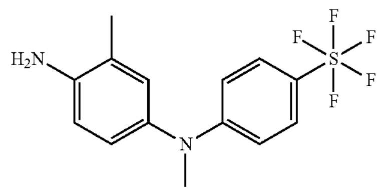 | LC-MS: m/z 339.1 (M + H)+ |
| 572 | XI.61 | VII.97 | 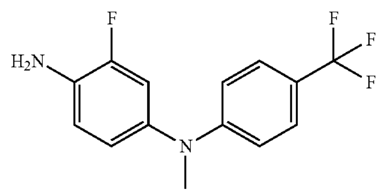 | LC-MS: m/z 285.1 (M + H)+ |
| 573 | XI.62 | VII.98 | 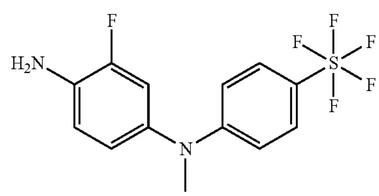 [SMILES: CN(c1ccc(S(F)(F)(F)(F)F)cc1)c1ccc(N)c(F)c1] | $^1$H NMR (400 MHz, DMSO-d$_6$): δ 7.60-7.57 (m, 2H), 6.97-6.93 (m, 1H), 6.82-6.79 (m, 1H), 6.64 (d, J = 9.2 Hz, 2H), 5.25 (s, 2H), 3.20 (s, 3H). |
| 574, 583, 584 | XI.63 | VII.99 | 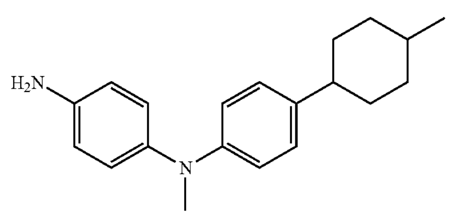 [SMILES: CC1CCC(c2ccc(N(C)c3ccc(N)cc3)cc2)CC1] | LC-MS: m/z 295.2 (M + H)+. |
| 575 | XI.64 | IX.11 | 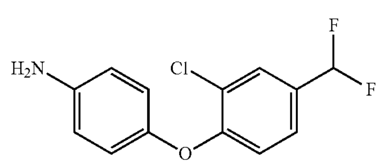 | LC-MS: m/z 270.1 (M + H)+. |
| 576 | XI.65 | VII.100 | 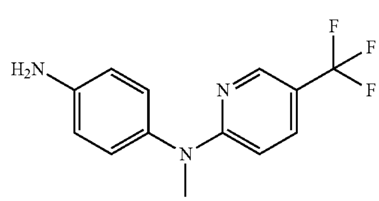 | LC-MS: m/z 268 (M + H)+ |

-continued

| CP | Intermediate No. | Reactant | Structure | Analytical data |
|---|---|---|---|---|
| 577 | XI.66 | VII.101 | 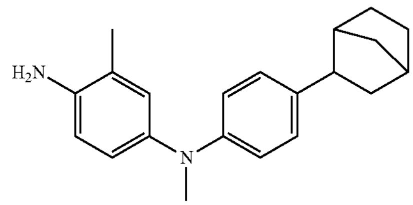 | LC-MS: m/z 307.2 (M + H)+ |
| 578 | XI.67 | VII.102 | 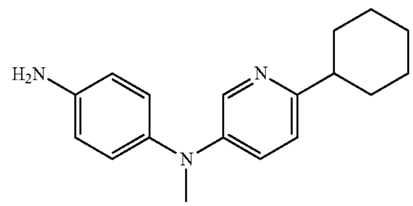 | LC-MS: m/z 282.0 (M + H)+ |
| 581 | XI.68 | VII.103 | 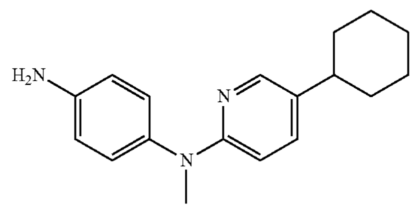 | LC-MS: m/z 282.4 (M + H)+ |
| 582 | XI.69 | VII.104 | 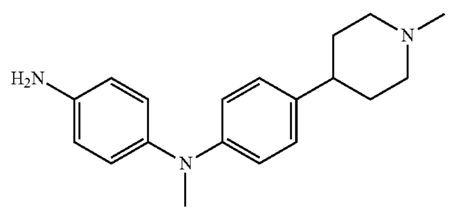 [SMILES: CN1CCC(c2ccc(N(C)c3ccc(N)cc3)cc2)CC1] | LC-MS: m/z 296.15 (M + H)+ |
| 585 | XI.70 | VII.105 | 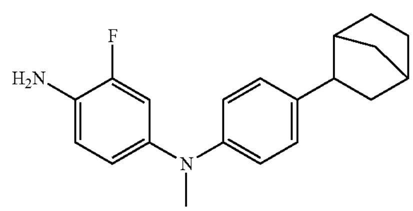 | LC-MS: m/z 311.1 (M + H)+ |
| 586 | XI.71 | VIII.5 | 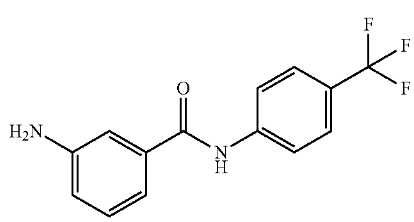 | LC-MS: m/z 279.0 (M − H)− |
| 588 | XI.72 | VII.106 | 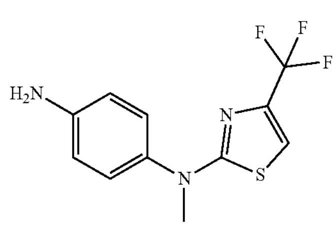 [SMILES: CN(c1ccc(N)cc1)c1nc(C(F)(F)F)cs1] | LC-MS: m/z 274.1 (M − H)− |

-continued
| CP | Intermediate No. | Reactant | Structure | Analytical data |
|---|---|---|---|---|
| 589 | XI.73 | VII.107 | 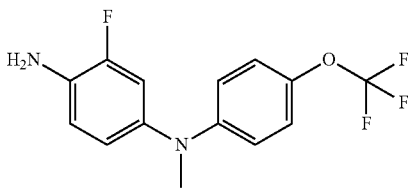 | LC-MS: m/z 301.1 (M + H)+ |
| 590 | XI.74 | VII.108 | 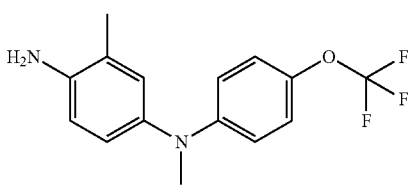 | LC-MS: m/z 297.2 (M − H)− |
| 592 | XI.75 | VII.109 | 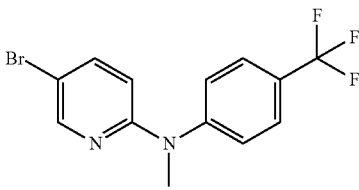 [SMILES: CN(c1ccc(C(F)(F)F)cc1)c1ccc(Br)cn1] | LC-MS: m/z 331.0 (M + H)+ |
| 593 | XI.76 | VII.110 | 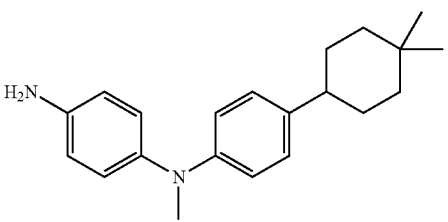 | LC-MS: m/z 309.3 (M + H)+ |
| 595 | XI.77 | VII.112 | 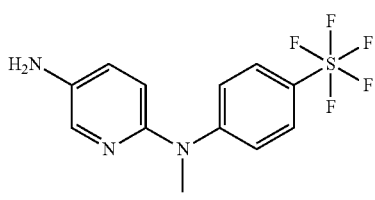 | LC-MS: m/z 326.0 (M + H)+ |
| 596 | XI.78 | VII.52 | 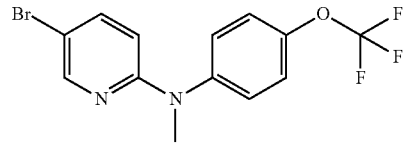 [SMILES: CN(c1ccc(OC(F)(F)F)cc1)c1ccc(Br)cn1] | LC-MS: m/z 349.0 (M + H)+ |
| 597 | XI.79 | VII.113 | 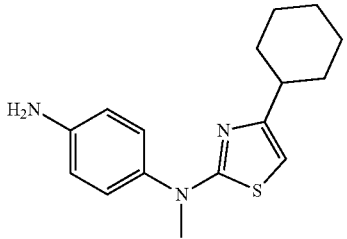 | LC-MS: m/z 288.1 (M + H)+ |

-continued

| CP | Intermediate No. | Reactant | Structure | Analytical data |
|---|---|---|---|---|
| 643, 654, 655 | XI.80 | VII.123 | H₂N-pyridine-N(CH₃)-phenyl-cyclohexyl | LC-MS: m/z 282.1 (M + H)⁺ |
| 599 | XI.81 | IX.13 | H₂N-(4-methyl)pyridine-O-(2-chloro)phenyl-cyclohexyl | LC-MS: m/z 317.2 (M + H)⁺ |
| 600 | XI.82 | IX.14 | H₂N-pyridine-O-(2-chloro)phenyl-OCF₃ | LC-MS: m/z 305.0 (M + H)⁺ |
| 601 | XI.83 | IX.15 | H₂N-pyridine-O-(2-chloro)phenyl-CF₃ | LC-MS: m/z 289.0 (M + H)⁺ |
| 603 | XI.84 | VII.115 | H₂N-phenyl-N(CH₃)-phenyl-cyclohexyl-CF₃ | LC-MS: m/z 349.2 (M + H)⁺ |
| 609, 652, 673, | XI.85 | VII.116 | H₂N-(4-methyl)pyridine-N(CH₃)-phenyl-cyclohexyl | LC-MS: m/z 296.2 (M + H)⁺ |
| 612 | XI.86 | VII.117 | H₂N-phenyl-N(CH₃)-(3,5-dichloro)phenyl | LC-MS: m/z 267.1 (M + H)⁺ |
| 615 | XI.87 | IX.16 | H₂N-pyridine-O-(2-chloro)phenyl-SF₅ | LC-MS: m/z 335.05 (M + H)⁺ |

-continued
| CP | Intermediate No. | Reactant | Structure | Analytical data |
|---|---|---|---|---|
| 617 | XI.88 | VII.118 | 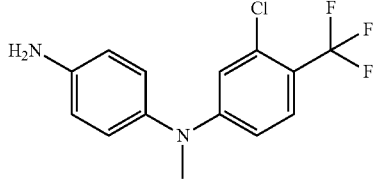 | LC-MS: m/z 301.0 (M + H)$^+$ |
| 618 | XI.89 | VII.119 | 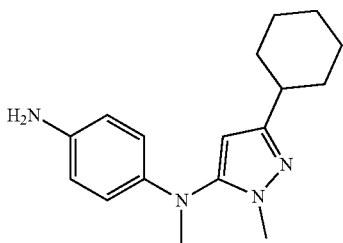 | LC-MS: m/z 285.2 (M + H)$^+$ |
| 622 | XI.90 | VII.120 | 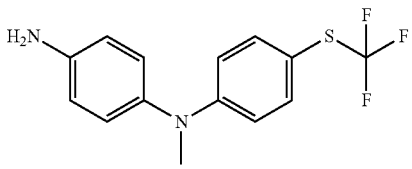 | LC-MS: m/z 299.0 (M + H)$^+$ |
| 624 | XI.91 | VII.121 | 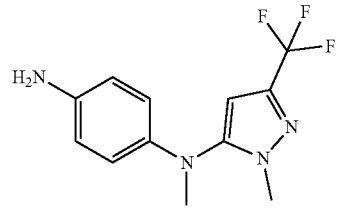 [SMILES: CN(c1ccc(N)cc1)c1cc(C(F)(F)F)nn1C] | LC-MS: m/z 271.1 (M + H)$^+$ |
| 626 | XI.92 | VII.122 | 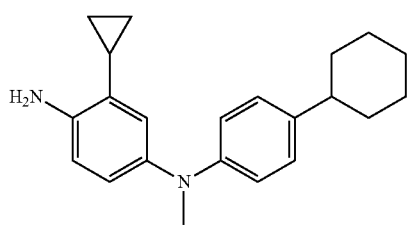 | LC-MS: m/z 321.30 (M + H)$^+$ |
| 641 | XI.93 | VII.62 | 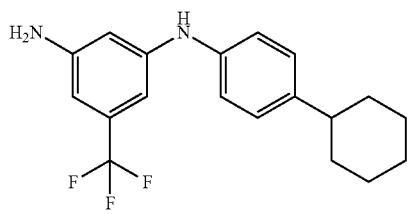 | LC-MS: m/z 335.05 (M + H)$^+$ |
| 642 | XI.94 | VIII.6 | 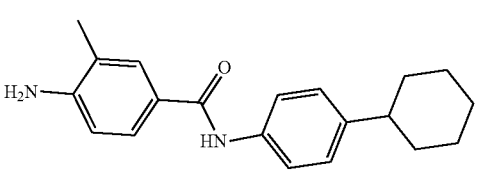 [SMILES: Cc1cc(C(=O)Nc2ccc(C3CCCCC3)cc2)ccc1N] | LC-MS: m/z 309.1 (M + H)$^+$ |

| CP | Intermediate No. | Reactant | Structure | Analytical data |
|---|---|---|---|---|
| 646 | XI.95 | VII.124 | 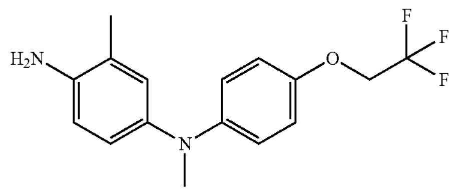 | LC-MS: m/z 311.2 (M + H)$^+$ |
| 647 | XI.96 | VII.125 | 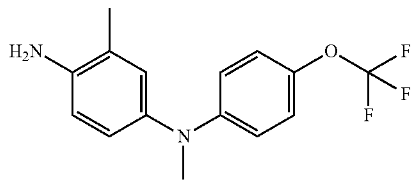 | LC-MS: m/z 297.1 (M + H)$^+$ |
| 659 | XI.97 | VII.126 | 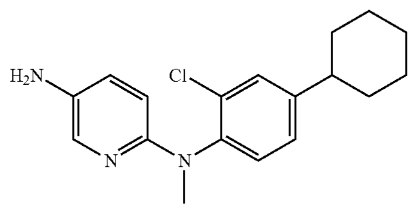 | LC-MS: m/z 316.2 (M + H)$^+$ |
| 660, 675, 676 | XI.98 | VII.63 | 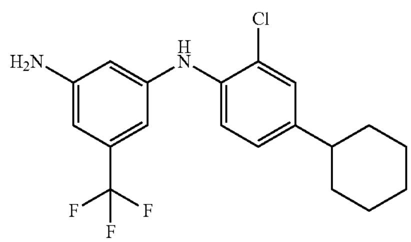 | LC-MS: m/z 369.00 (M + H)$^+$ |
| 661, 662 | XI.99 | VII.62 | 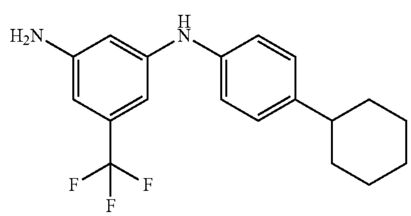 | LC-MS: m/z 335.05 (M + H)$^+$ |
| 663 | XI.100 | VII.127 | 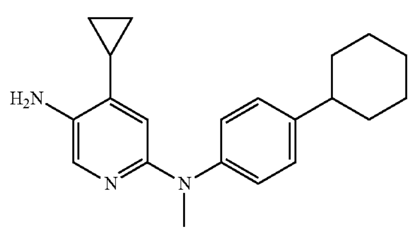 | LC-MS: m/z 322.2 (M + H)$^+$ |
| 665, 666, 669, 672 | XI.101 | VIII.8 | 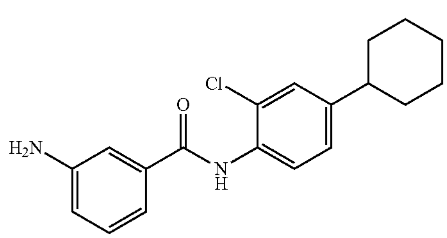 | LC-MS: m/z 329.1 (M + H)$^+$ |

-continued

| CP | Intermediate No. | Reactant | Structure | Analytical data |
|---|---|---|---|---|
| 671, 681 | XI.102 | VII.128 | 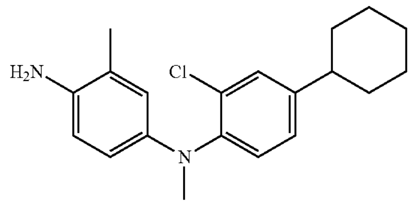 | LC-MS: m/z 329.2 (M + H)+ |
| 680 | XI.103 | VII.69 | 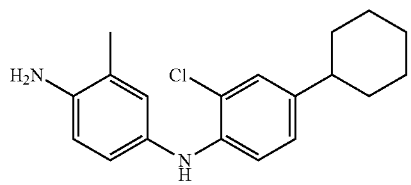 | LC-MS: m/z 315.1 (M + H)+ |
| 682, 677 | XI.104 | VII.70 | 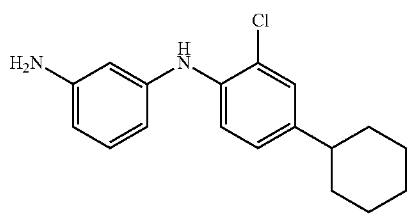 [SMILES: Nc1cccc(Nc2ccc(C3CCCCC3)cc2Cl)c1] | LC-MS: m/z 301.2 (M + H)+ |

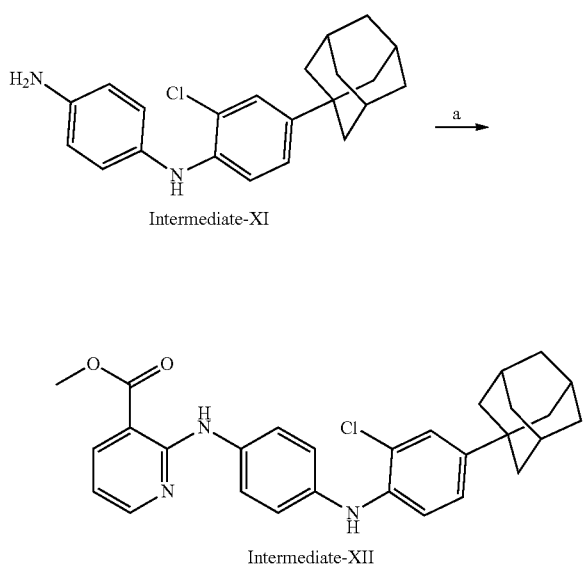

Intermediate-XI

Intermediate-XII

Step-a: Synthesis of methyl 2-((4-((4-((3r,5r,7r)-adamantan-1-yl)-2-chlorophenyl) amino)phenyl) amino) nicotinate (Intermediate-XII)

A solution of Intermediate-XI (8 g, 22.72 mmol, 1 eq.) and methyl 2-chloronicotinate (4.27 g, 25 mmol, 1.1 eq.) in toluene (100 mL) was de-gassed by bubbling Nitrogen gas for 5 minutes. Cesium carbonate (11.1 g, 34.1 mmol, 1.5 eq.) was added followed by Palladium acetate (0.5 g, 2.27 mmol, 0.1 eq.) and rac. BINAP (2.12 g, 3.41 mmol, 0.15 eq.) and de-gassed again for 5 min. Reaction mixture was heated at 110° C. under stirring for 16 h. Reaction mixture was cooled to RT, diluted with ethyl acetate and filtered through celite. The organic layer was adsorbed over silica and purified by flash column chromatography. Desired product was eluted in 10% ethyl acetate in hexanes. Concentrated in vacuo to afford yellow solid (5.4 g, 49%).

$^1$H NMR (400 MHz, DMSO-d6) δ 9.93 (s, 1H), 8.37 (dd, $J_1$=2.0 Hz, $J_2$=4.4 Hz, 1H), 8.22 (dd, $J_1$=2.0 Hz, $J_2$=7.6 Hz, 1H), 7.55 (d, J=8.8 Hz, 2H), 7.41 (s, 1H), 7.31 (d, J=1.6 Hz, 1H), 7.19-7.12 (m, 2H), 7.04 (d, J=8.8 Hz, 2H), 6.84-6.81 (m, 1H), 3.89 (s, 3H), 2.04 (s, 3H), 1.83 (s, 6H), 1.72 (s, 6H); LC-MS: m/z 488.1 (M+H)+

The below intermediates were prepared by a procedure similar to Intermediate-XII using appropriate reactants and reagents employing suitable Pd catalysts and ligands and in presence of suitable solvents and appropriate reaction conditions.

| CP | Intermediate No. | Reactant | Structure | Analytical data |
|---|---|---|---|---|
| 57 | XII.1 | VII.1 | 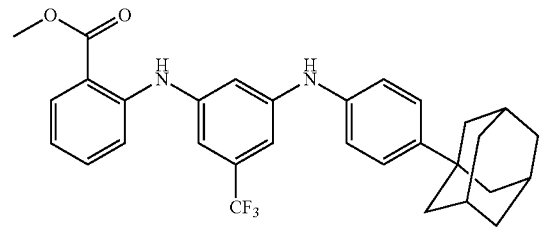 [SMILES: COC(=O)c1ccccc1Nc1cc(Nc2ccc(C34CC5CC(CC(C5)C3)C4)cc2)cc(C(F)(F)F)c1] | ¹H NMR (500 MHz, CDCl₃) δ 9.45 (s, 1H), 8.01 (s, 1H), 7.45-7.23. (d, 2H), 7.23-7.01 (m, 6H), 6.98-7.01 (d, 2H), 6.94 (s, 1H), 3.93 (s, 3H), 5.99 (s, 1H) 2.21-1.98 (m, 15H) LC-MS: m/z 521.2 (M + H)⁺ |
| 59 | XII.2 | XI.31 | 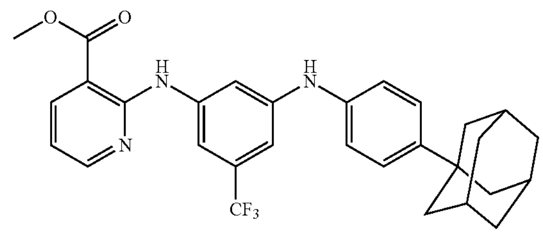 [SMILES: COC(=O)c1cccnc1Nc1cc(Nc2ccc(C34CC5CC(CC(C5)C3)C4)cc2)cc(C(F)(F)F)c1] | ¹H NMR (500 MHz, DMSO-d6) δ 9.45 (s, 1H), 8.01 (s, 1H), 7.49-7.33. (d, 2H), 7.23-7.01 (m, 5H), 6.91-7.04 (d, 2H), 6.94 (s, 1H), 3.93 (s, 3H), 5.99 (s, 1H) 2.21-1.98 (m, 15H) LC-MS: m/z 522.2 (M + H)⁺ |
| 60 | XII.3 | XI.31 | 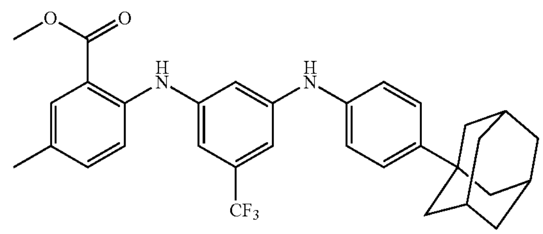 [SMILES: COC(=O)c1cc(C)ccc1Nc1cc(Nc2ccc(C34CC5CC(CC(C5)C3)C4)cc2)cc(C(F)(F)F)c1] | LC-MS: m/z 535.6 (M + H)⁺ |
| 61 | XII.4 | XI.31 | 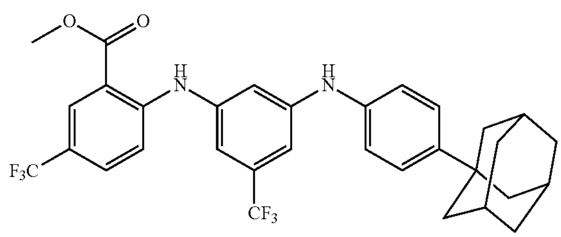 [SMILES: COC(=O)c1cc(C(F)(F)F)ccc1Nc1cc(Nc2ccc(C34CC5CC(CC(C5)C3)C4)cc2)cc(C(F)(F)F)c1] | LC-MS: m/z 589.2 (M + H)⁺ |
| 62 | XII.5 | | 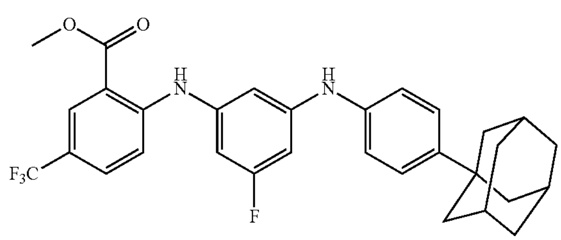 [SMILES: COC(=O)c1cc(C(F)(F)F)ccc1Nc1cc(F)cc(Nc2ccc(C34CC5CC(CC(C5)C3)C4)cc2)c1] | LC-MS: m/z 539.5 (M + H)⁺ |
| 65 | XII.6 | | 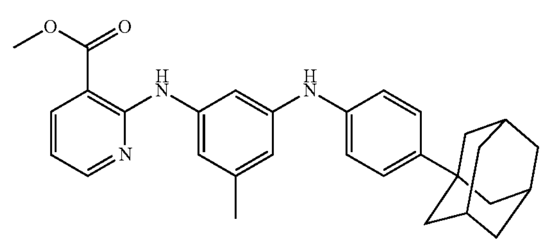 [SMILES: COC(=O)c1cccnc1Nc1cc(C)cc(Nc2ccc(C34CC5CC(CC(C5)C3)C4)cc2)c1] | LC-MS: m/z 468.3 (M + H)⁺ |

-continued

| CP | Intermediate No. | Reactant | Structure | Analytical data |
|---|---|---|---|---|
| 66 | XII.7 | XI.1 | 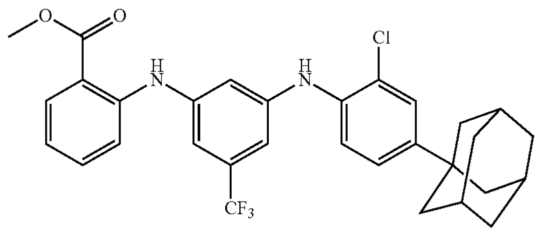 [SMILES: COC(=O)c1ccccc1Nc1cc(Nc2ccc(C34CC5CC(CC(C5)C3)C4)cc2Cl)cc(C(F)(F)F)c1] | LC-MS: m/z 556 (M + H)⁺ |
| 67 | XII.8 | XI.3 | 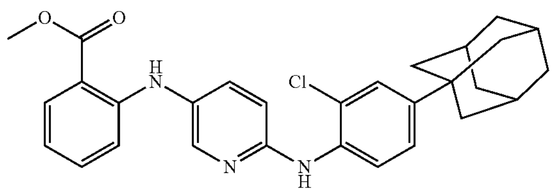 [SMILES: COC(=O)c1ccccc1Nc1ccc(Nc2ccc(C34CC5CC(CC(C5)C3)C4)cc2Cl)nc1] | LC-MS: m/z 489 (M + H)⁺ |
| 146 | XII.9 | I.13 | 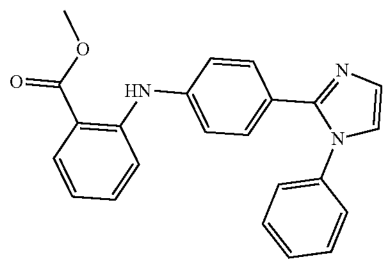 [SMILES: COC(=O)c1ccccc1Nc1ccc(-c2nccn2-c2ccccc2)cc1] | $^1$H NMR (400 MHz, DMSO-d6) δ 9.29 (s, 1H), 7.89 (dd, J$_1$ = 1.6 Hz, J$_2$ = 8.0 Hz, 1H), 7.49-742 (m, 5H), 7.33-7.25 (m, 5H), 7.15-7.13 (m, 3H), 6.94-6.86 (m, 1H), 3.83 (s, 3H). LC-MS: m/z 370.1 (M + H)⁺ |
| 156 | XII.10 | Int-XI | 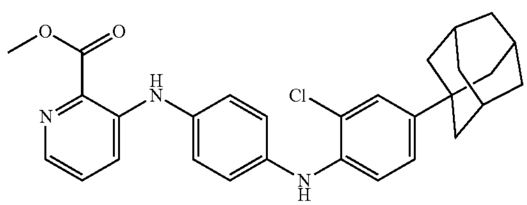 [SMILES: COC(=O)c1ncccc1Nc1ccc(Nc2ccc(C34CC5CC(CC(C5)C3)C4)cc2Cl)cc1] | $^1$H NMR (400 MHz, DMSO-d6) δ 9.05 (s, 1H), 7.93 (dd, J$_1$ = 1.2 Hz, J$_2$ = 3.6 Hz, 1H), 7.59 (s, 1H), 7.42-7.34 (m, 3H), 7.21 (s, 2H), 7.13 (d, J = 8.8 Hz, 1H), 7.05 (d, J = 8.8 Hz, 2H), 3.87 (s, 3H), 2.04 (s, 3H), 1.83 (s, 6H), 1.72 (s, 6H). LC-MS: m/z 488.1 (M + H)⁺ |
| 157 | XII.11 | Int-XI | 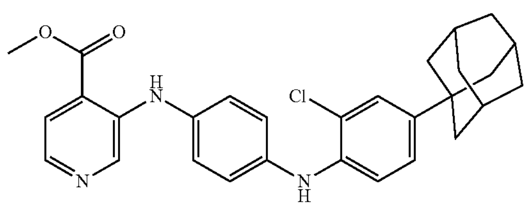 [SMILES: COC(=O)c1ccncc1Nc1ccc(Nc2ccc(C34CC5CC(CC(C5)C3)C4)cc2Cl)cc1] | $^1$H NMR (400 MHz, DMSO-d6) δ 8.77 (s, 1H), 8.38 (s, 1H), 7.95 (d, J = 5.6 Hz, 1H), 7.63 (d, J = 4.8 Hz, 1H), 7.60 (s, 1H), 7.34 (s, 1H), 7.22 (s, 2H), 7.18 (d, J = 8.8 Hz, 2H), 7.05 (d, J = 8.8 Hz, 2H), 3.89 (s, 3H), 2.05 (s, 3H), 1.83 (s, 6H), 1.72 (s, 6H). LC-MS: m/z 488.1 (M + H)⁺ |
| 159 | XII.12 | Int-XI | 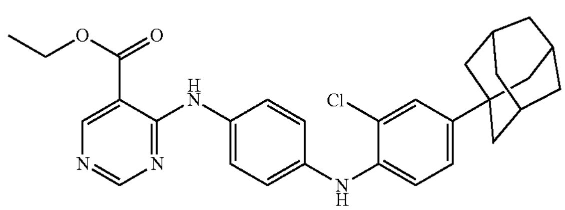 [SMILES: CCOC(=O)c1cncnc1Nc1ccc(Nc2ccc(C34CC5CC(CC(C5)C3)C4)cc2Cl)cc1] | $^1$H NMR (400 MHz, DMSO-d6) δ 9.96 (s, 1H), 8.88 (s, 1H), 8.69 (s, 1H), 7.58 (s, 1H), 7.50 (d, J = 8.8 Hz, 2H), 7.34 (s, 1H), 7.21 (s, 2H), 7.04 (d, J = 8.8 Hz, 2H), 4.38 (q, 2H), 2.05 (s, 3H), 1.83 (s, 6H), 1.72 (s, 6H), 1.36 (t, J = 7.2 Hz, 3H). LC-MS: m/z 503.2 (M + H)⁺ |

-continued

| CP | Intermediate No. | Reactant | Structure | Analytical data |
|---|---|---|---|---|
| 160 | XII.13 | Int-XI | 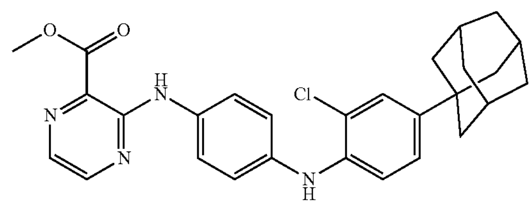 [SMILES: COC(=O)c1nccnc1Nc1ccc(Nc2ccc(C34CC5CC(CC(C5)C3)C4)cc2Cl)cc1] | LC-MS: m/z 489.1 (M + H)+ |
| 163 | XII.14 | Int-XI | 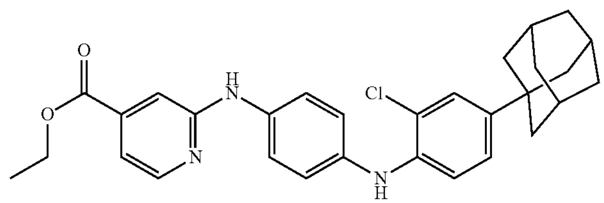 [SMILES: CCOC(=O)c1ccnc(Nc2ccc(Nc3ccc(C45CC6CC(CC(C6)C4)C5)cc3Cl)cc2)c1] | LC-MS: m/z 502.1 (M + H)+ |
| 168 | XII.15 | Int-XI | 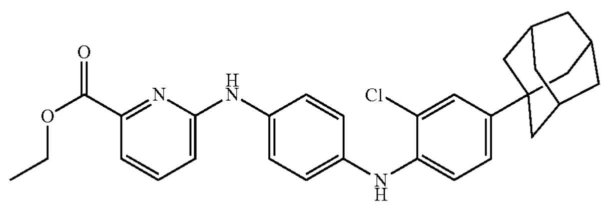 [SMILES: CCOC(=O)c1cccc(Nc2ccc(Nc3ccc(C45CC6CC(CC(C6)C4)C5)cc3Cl)cc2)n1] | 1H NMR (400 MHz, DMSO-d6) δ 9.17 (s, 1H), 7.70 (d, J = 8.8 Hz, 2H), 7.66 (d, J = 8.0 Hz, 1H), 7.37 (d, J = 7.2 Hz, 1H), 7.29 (d, J = 2.0 Hz, 1H), 7.26 (s, 1H), 7.14 (dd, J$_1$ = 2.0 Hz, J$_2$ = 8.8 Hz, 1H), 7.04 (t, J = 8.8 Hz, 3H), 6.98 (d, J = 8.4 Hz, 1H), 4.31 (q, 2H), 2.04 (s, 3H), 1.82 (s, 6H), 1.72 (s, 6H), 1.33 (t, J = 6.8 Hz, 3H). LC-MS: m/z 502.2 (M + H)+ |
| 169 | XII.16 | XI.3 | 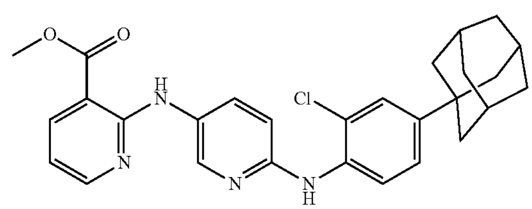 [SMILES: COC(=O)c1cccnc1Nc1ccc(Nc2ccc(C34CC5CC(CC(C5)C3)C4)cc2Cl)nc1] | 1H NMR (400 MHz, DMSO-d6) δ 9.73 (s, 1H), 8.35-8.32 (m, 2H), 8.22 (dd, J$_1$ = 1.6 Hz, J$_2$ = 7.6 Hz, 1H), 8.17 (s, 1H), 7.91 (d, J = 8.8 Hz, 1H), 7.85 (dd, J$_1$ = 2.8 Hz, J$_2$ = 9.2 Hz, 1H), 7.34 (d, J = 2.4 Hz, 1H), 7.27 (dd, J$_1$ = 2.4 Hz, J$_2$ = 8.8 Hz, 1H), 6.98 (d, J = 8.8 Hz, 1H), 6.84 (dd, J$_1$ = 4.4 Hz, J$_2$ = 8.0 Hz, 1H), 3.90 (s, 3H), 2.06 (s, 3H), 1.86 (s, 6H), 1.74 (s, 6H). LC-MS: m/z 489.1 (M + H)+ |
| 191 | XII.17 | XI.4 | 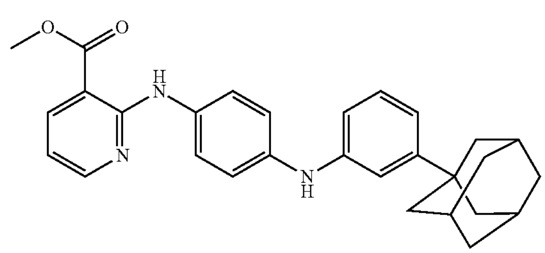 [SMILES: COC(=O)c1cccnc1Nc1ccc(Nc2cccc(C34CC5CC(CC(C5)C3)C4)c2)cc1] | 1H NMR (400 MHz, DMSO-d6) δ 9.90 (s, 1H), 8.60 (m, 1H), 8.40 (m, 1H), 7.97 (s, 1H), 7.54 (d, J = 8.8 Hz, 2H), 7.13 (m, 1H), 7.03 (m, 3H), 6.81 (m, 3H), 3.92 (s, 3H), 2.05 (s, 3H), 1.84 (s, 6H), 1.73 (s, 6H). LC-MS: m/z 454.1 (M + H)+ |

-continued

| CP | Intermediate No. | Reactant | Structure | Analytical data |
|---|---|---|---|---|
| 202 236 | XII.18 | XI.8 | 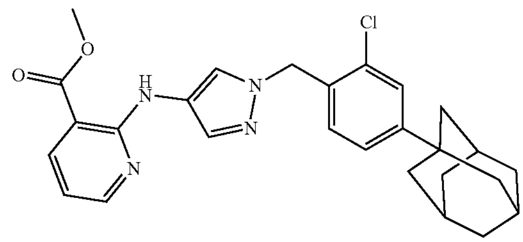 [SMILES: COC(=O)c1cccnc1Nc1cnn(Cc2ccc(C34CC5CC(CC(C5)C3)C4)cc2Cl)c1] | ¹H NMR (400 MHz, DMSO-d6) δ 9.78 (s, 1H), 8.40 (dd, J₁ = 2.0 Hz, J₂ = 5.2 Hz, 1H), 8.21 (s, 1H), 8.19-8.18 (m, 1H), 7.72 (s, 1H), 7.31 (d, J = 1.6 Hz, 1H), 7.29 (d, J = 2.0 Hz, 1H), 6.95 (d, J = 8.4 Hz, 1H), 6.80 (dd, J₁ = 4.4 Hz, J₂ = 7.2 Hz, 1H), 5.37 (s, 2H), 3.88 (s, 3H), 2.04 (s, 3H), 1.83 (s, 6H), 1.72 (s, 6H). LC-MS: m/z 477.2 (M + H)⁺ |
| 203 | XII.19 | XI.5 | 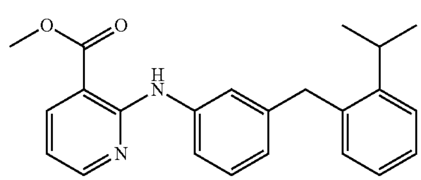 [SMILES: COC(=O)c1cccnc1Nc1cccc(Cc2ccccc2C(C)C)c1] | ¹H NMR (400 MHz, DMSO-d6) δ 10.04 (s, 1H), 8.36 (dd, J₁ = 2.0 Hz, J₂ = 4.9 Hz, 1H), 8.24 (dd, J₁ = 2.0 Hz, J₂ = 7.8 Hz, 1H), 7.62 (d, J = 1.0 Hz, 1H), 7.36 (s, 1H), 7.30 (d, J = 7.3 Hz, 1H), 7.24-7.11 (m, 4H), 6.88-6.85 (m, 1H), 6.78 (d, J = 7.8 Hz, 1H), 4.06 (s, 2H), 3.88 (s, 3H), 3.17 (m, 1H), 1.15 (d, J = 6.8 Hz, 6H). LC-MS: m/z 361.2 (M + H)⁺ |
| 204 | XII.20 | XI.7 | 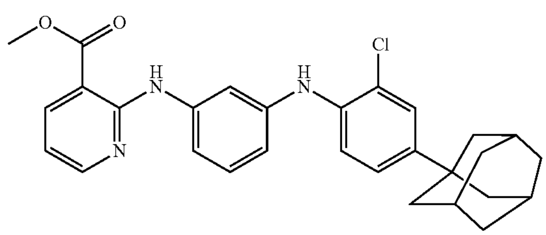 [SMILES: COC(=O)c1cccnc1Nc1cccc(Nc2ccc(C34CC5CC(CC(C5)C3)C4)cc2Cl)c1] | ¹H NMR (400 MHz, DMSO-d6) δ 10.04 (s, 1H), 8.39 (dd, J₁ = 2.0 Hz, J₂ = 4.8 Hz, 1H), 8.25 (dd, J₁ = 1.6 Hz, J₂ = 7.6 Hz, 1H), 7.57 (s, 1H), 7.48 (s, 1H), 7.36-7.31 (m, 2H), 7.24 (dd, J₁ = 2.0 Hz, J₂ = 8.4 Hz, 1H), 7.15 (d, J = 6.0 Hz, 2H), 6.88 (dd, J₁ = 4.8 Hz, J₂ = 7.6 Hz, 1H), 6.70-6.68 (m, 1H), 3.89 (s, 3H), 2.05 (s, 3H), 1.85 (s, 6H), 1.73 (s, 6H). LC-MS: m/z 488.3 (M + H)⁺ |
| 205 | XII.21 | Int-XI | 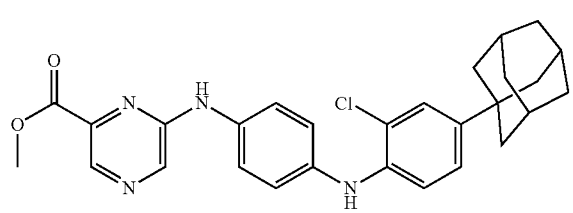 [SMILES: COC(=O)c1cncc(Nc2ccc(Nc3ccc(C45CC6CC(CC(C6)C4)C5)cc3Cl)cc2)n1] | ¹H NMR (400 MHz, DMSO-d6) δ 9.68 (s, 1H), 8.43 (s, 1H), 8.35 (s, 1H), 7.68 (d, J = 8.8 Hz, 2H), 7.38 (s, 1H), 7.31 (d, J = 2.0 Hz, 1H), 7.16 (d, J = 2.0 Hz, 1H), 7.12 (d, J = 8.8 Hz, 1H), 7.06 (d, J = 8.8 Hz, 2H), 3.89 (s, 3H), 2.05 (s, 3H), 1.83 (s, 6H), 1.72 (s, 6H). LC-MS: m/z 489.3 (M + H)⁺ |

-continued

| CP | Intermediate No. | Reactant | Structure | Analytical data |
|---|---|---|---|---|
| 206 | XII.22 | Int-XI | 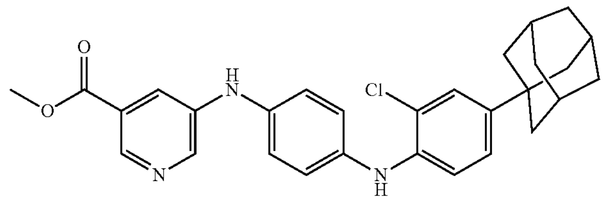 | ¹H NMR (400 MHz, DMSO-d6) δ 8.43 (dd, J₁ = 2.9 Hz, J₂ = 4.4 Hz, 2H), 8.38 (s, 1H), 7.71 (t, J = 2.9 Hz, 1H), 7.20-7.17 (m, 2H), 7.06-7.04 (m, 4H), 3.85 (s, 3H), 2.04 (s, 3H), 1.82 (s, 6H), 1.72 (s, 6H). |
| 207 | XII.23 | Int-XI | 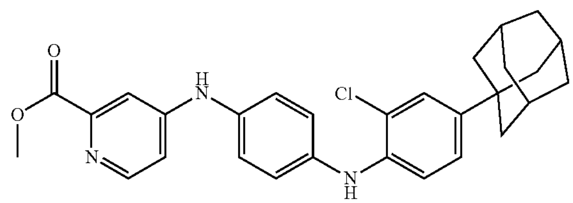 [SMILES: COC(=O)c1cc(Nc2ccc(Nc3ccc(C45CC6CC(CC(C6)C4)C5)cc3Cl)cc2)ccn1] | ¹H NMR (400 MHz, DMSO-d6) δ 8.82 (s, 1H), 8.21 (d, J = 5.4 Hz, 1H), 7.54 (s, 1H), 7.45 (d, J = 2.4 Hz, 1H), 7.34 (s, 1H), 7.20 (s, 2H), 7.11-7.04 (m, 4H), 6.93-6.91 (m, 1H), 3.82 (s, 3H), 2.04 (s, 3H), 1.83 (s, 6H), 1.72 (s, 6H). |
| 211, 268 | XII.24 | XI.1 | 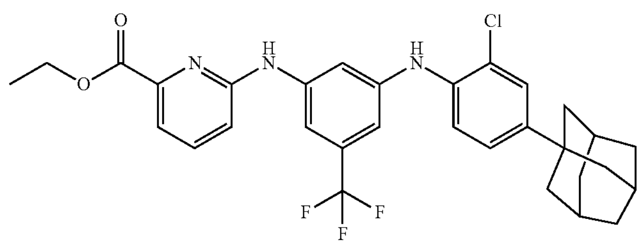 [SMILES: CCOC(=O)c1cccc(Nc2cc(Nc3ccc(C45CC6CC(CC(C6)C4)C5)cc3Cl)cc(C(F)(F)F)c2)n1] | LC-MS: m/z 570.2 (M + H)⁺ |
| 226 | XII.25 | XI.9 | 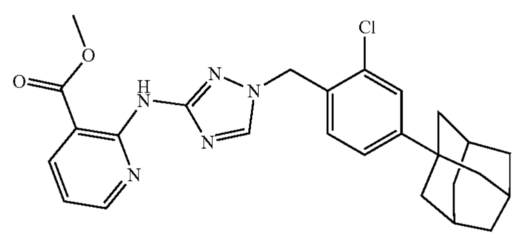 [SMILES: COC(=O)c1cccnc1Nc1ncn(Cc2ccc(C34CC5CC(CC(C5)C3)C4)cc2Cl)n1] | LC-MS: m/z 478.2 (M + H)⁺ |
| 228 | XII.26 | XI.6 | 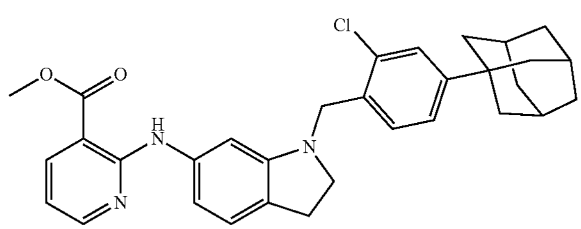 [SMILES: COC(=O)c1cccnc1Nc1ccc2c(c1)N(Cc1ccc(C34CC5CC(CC(C5)C3)C4)cc1Cl)CC2] | ¹H NMR (400 MHz, DMSO-d6) δ 9.96 (s, 1H), 8.33 (dd, J₁ = 2.0 Hz, J₂ = 5.2 Hz, 1H), 8.21 (dd, J₁ = 2.0 Hz, J₂ = 8.0 Hz, 1H), 7.42-7.40 (m, 2H), 7.33 (dd, J₁ = 1.6 Hz, J₂ = 8.0 Hz, 1H), 7.00-6.92 (m, 3H), 6.82 (dd, J₁ = 4.8 Hz, J₂ = 7.6 Hz, 1H), 4.31 (s, 2H), 3.88 (s, 3H), 3.37 (t, J = 8.0 Hz, 2H), 2.89 (t, J = 8.2 Hz, 2H), 2.05 (s, 3H), 1.85 (d, J = 2.4 Hz, 6H), 1.73 (s, 6H). LC-MS: m/z 528.2 (M + H)⁺ |

-continued

| CP | Intermediate No. | Reactant | Structure | Analytical data |
|---|---|---|---|---|
| 240 | XII.27 | XI.10 | 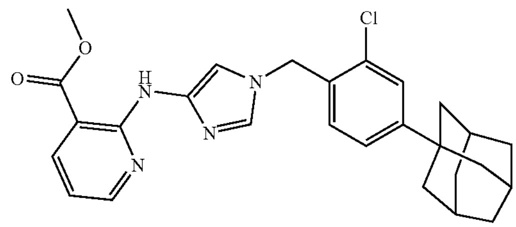 [SMILES: COC(=O)c1cccnc1Nc1cn(Cc2ccc(C34CC5CC(CC(C5)C3)C4)cc2Cl)cn1] | LC-MS: m/z 477.2 (M + H)+ |
| 249 | XII.28 | XI.11 | 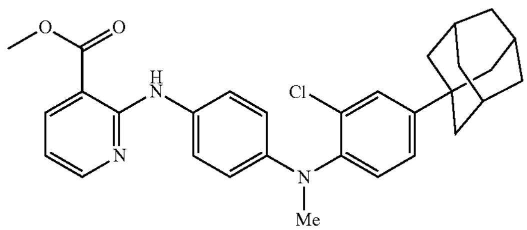 [SMILES: COC(=O)c1cccnc1Nc1ccc(N(C)c2ccc(C34CC5CC(CC(C5)C3)C4)cc2Cl)cc1] | 1H NMR (400 MHz, DMSO-d6) δ 9.79 (s, 1H), 8.31 (dd, J1 = 2.0 Hz, J2 = 4.8 Hz, 1H), 8.19 (dd, J1 = 2.0 Hz, J2 = 8.0 Hz, 1H), 7.48 (d, J = 2.0 Hz, 1H), 7.43-7.39 (m, 3H), 7.29 (d, J = 8.0 Hz, 1H), 6.77 (dd, J1 = 4.4 Hz, J2 = 8.4 Hz, 1H), 6.52 (d, J = 8.8 Hz, 2H), 3.88 (s, 3H), 3.18 (s, 3H), 2.07 (s, 3H), 1.89 (s, 6H), 1.74 (s, 6H). LC-MS: m/z 502.1 (M + H)+ |
| 261 | XII.29 | XI.7 | 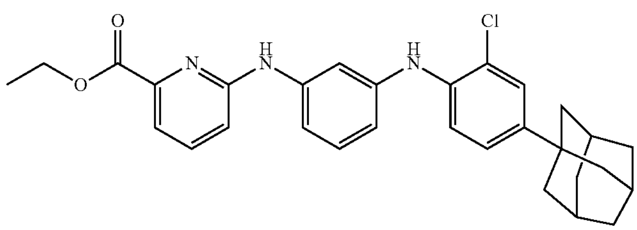 [SMILES: CCOC(=O)c1cccc(Nc2cccc(Nc3ccc(C45CC6CC(CC(C6)C4)C5)cc3Cl)c2)n1] | 1H NMR (400 MHz, DMSO-d6) δ 9.21 (s, 1H), 7.69 (t, J = 8.0 Hz, 1H), 7.43-7.38 (m, 4H), 7.32 (dd, J1 = 2.0 Hz, J2 = 10.8 Hz, 2H), 7.20 (dd, J1 = 2.0 Hz, J2 = 8.4 Hz, 1H), 7.13 (t, J = 8.0 J = 8.0 Hz, 1H), 6.63 (t, J = 8.4 Hz, 1H), 4.28-4.23 (q, 2H), 2.05 (s, 3H), 1.83 (s, 6H), 1.72 (s, 6H), 1.26 (t, J = 7.2 Hz, 3H). LC-MS: m/z 500.1 (M − H)− |
| 262 | XII.30 | Int-XI | 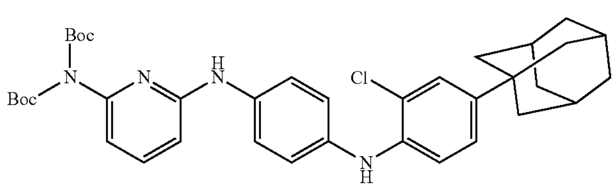 [SMILES: CC(C)(C)OC(=O)N(C(=O)OC(C)(C)C)c1cccc(Nc2ccc(Nc3ccc(C45CC6CC(CC(C6)C4)C5)cc3Cl)cc2)n1] | 1H NMR (400 MHz, DMSO-d6) δ 8.99 (s, 1H), 7.56 (t, J = 8.0 Hz, 1H), 7.47 (d, J = 8.8 Hz, 2H), 7.28-7.23 (m, 2H), 7.13 (dd, J1 = 2.0 Hz, J2 = 8.8 Hz, 1H), 7.11-6.93 (m, 4H), 6.66 (d, J = 8.4 Hz, 1H), 6.58 (d, J = 7.2 Hz, 1H), 2.04 (s, 3H), 1.81 (s, 6H), 1.71 (s, 6H), 1.42 (s, 18H). LC-MS: m/z 645.1 (M + H)+ |

-continued

| CP | Intermediate No. | Reactant | Structure | Analytical data |
|---|---|---|---|---|
| 263 | XII.31 | XI.1 | 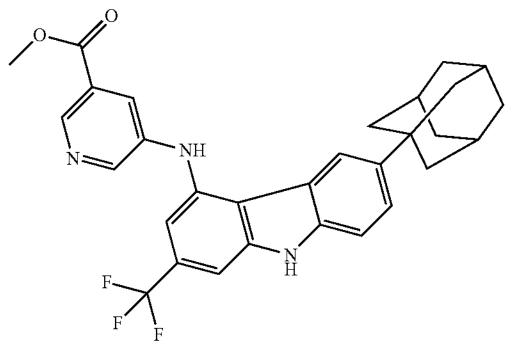 [SMILES: COC(=O)c1cncc(Nc2cc(C(F)(F)F)cc3[nH]c4ccc(C56CC7CC(CC(C7)C5)C6)cc4c23)c1] | ¹H NMR (400 MHz, DMSO-d6) δ 11.68 (s, 1H), 9.11 (s, 1H), 8.53 (d, J = 1.6 Hz, 1H), 8.29 (d, J = 2.4 Hz, 1H), 7.61 (s, 1H), 7.55 (s, 1H), 7.51-7.46 (m, 2H), 7.36 (s, 1H), 7.23 (s, 1H), 3.78 (s, 3H), 1.97 (s, 3H), 1.72-1.61 (m, 13H). LC-MS: m/z 520.2 (M + H)⁺ |
| 267 | XII.32 | XI.1 | 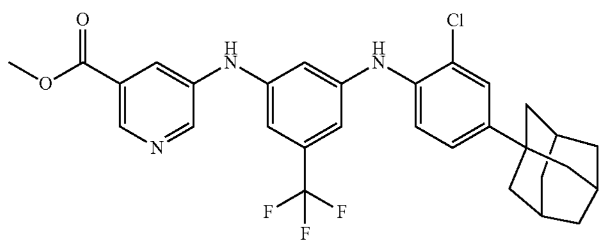 [SMILES: COC(=O)c1cncc(Nc2cc(Nc3ccc(C45CC6CC(CC(C6)C4)C5)cc3Cl)cc(C(F)(F)F)c2)c1] | ¹H NMR (400 MHz, DMSO-d6) δ 8.84 (s, 1H), 8.56 (dd, J₁ = 1.6 Hz, J₂ = 6.4 Hz, 2H), 8.12 (s, 1H), 7.91 (d, J = 2.4 Hz, 1H), 7.41 (d, J = 2.0 Hz, 1H), 7.36-7.28 (m, 2H), 6.84 (s, 1H), 6.74 (d, J = 15.6 Hz, 2H), 3.89 (s, 3H), 2.05 (s, 3H), 1.84 (s, 6H), 1.73 (s, 6H). LC-MS: m/z 556.0 (M + H)⁺ |
| 271 | XII.33 | XI.15 | 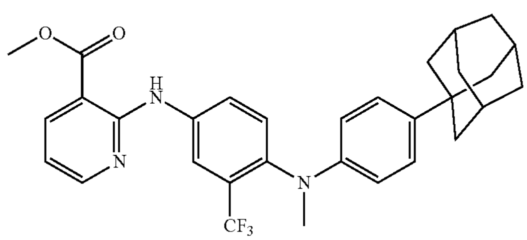 | ¹H NMR (400 MHz, DMSO-d6) δ 10.25 (s, 1H), 8.47 (dd, J₁ = 2.0 Hz, J₂ = 4.8 Hz, 1H), 8.33-8.30 (m, 2H), 7.96 (dd, J₁ = 2.4 Hz, J₂ = 8.4 Hz, 1H), 7.30 (d, J = 8.4 Hz, 1H), 7.13 (d, J = 8.8 Hz, 2H), 6.98 (dd, J₁ = 4.4 Hz, J₂ = 7.6 Hz, 1H), 6.45 (d, J = 8.8 Hz, 2H), 3.93 (s, 3H), 3.09 (s, 3H), 2.02 (s, 3H), 1.80 (s, 6H), 1.71 (s, 6H). LC-MS: m/z 536.1 (M + H)⁺ |
| 273 | XII.34 | XI.15 | 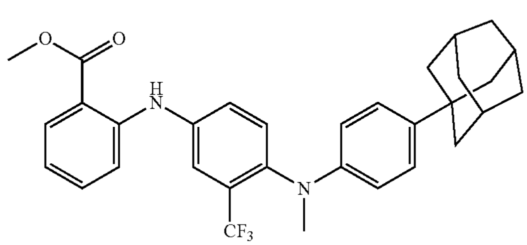 [SMILES: COC(=O)c1ccccc1Nc1ccc(N(C)c2ccc(C34CC5CC(CC(C5)C3)C4)cc2)c(C(F)(F)F)c1] | ¹H NMR (400 MHz, DMSO-d6) δ 9.31 (s, 1H), 7.92 (dd, J₁ = 1.2 Hz, J₂ = 7.6 Hz, 1H), 7.77-7.74 (m, 1H), 7.61 (d, J = 2.4 Hz, 1H), 7.56 (dd, J₁ = 2.4 Hz, J₂ = 8.8 Hz, 1H), 7.52-7.46 (m, 2H), 7.36 (d, J = 8.4 Hz, 1H), 7.26 (d, J = 8.0 Hz, 1H), 7.13 (d, J = 8.8 Hz, 1H), 6.94 (t, J = 7.6 Hz, 1H), 6.47 (d, J = 9.2 Hz, 1H), 3.86 (s, 3H), 3.31 (s, 3H), 2.02 (s, 3H), 1.80 (s, 6H), 1.71 (s, 6H). LC-MS: m/z 535.1 (M + H)⁺ |

-continued

| CP | Intermediate No. | Reactant | Structure | Analytical data |
|---|---|---|---|---|
| 275 | XII.35 | XI.3 | 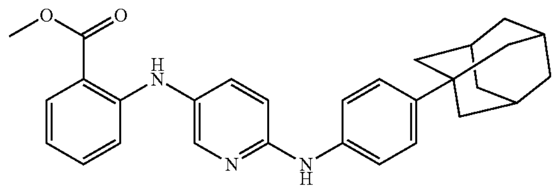 [SMILES: COC(=O)c1ccccc1Nc1ccc(Nc2ccc(C34CC5CC(CC(C5)C3)C4)cc2)nc1] | ¹H NMR (400 MHz, CDCl3) δ 9.19 (s, 1H), 8.11 (d, J = 2.4 Hz, 1H), 7.95 (dd, J₁ = 1.6 Hz, J₂ = 8.4 Hz, 1H), 7.41 (dd, J₁ = 2.8 Hz, J₂ = 8.8 Hz, 1H), 7.34 (d, J = 8.8 Hz, 2H), 7.30-7.26 (m, 3H), 6.92-6.86 (m, 2H), 6.69 (t, J = 8.0 Hz, 1H), 6.63 (s, 1H), 3.91 (s, 3H), 2.10 (s, 3H), 1.91 (s, 6H), 1.81-1.73 (m, 6H). LC-MS: m/z 454.1 (M + H)⁺ |
| 284 | XII.36 | XI.14 | 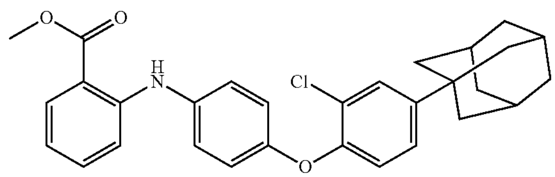 [SMILES: COC(=O)c1ccccc1Nc1ccc(Oc2ccc(C34CC5CC(CC(C5)C3)C4)cc2Cl)cc1] | ¹H NMR (400 MHz, DMSO-d6) δ 9.23 (s, 1H), 7.89 (d, J = 1.9 Hz, 1H), 7.76 (m, 1H), 7.49 (m, 2H), 7.26 (d, J = 8.8 Hz, 2H), 7.10 (m, 2H), 6.97 (d, J = 8.8 Hz, 2H), 6.77 (m, 1H), 3.86 (s, 3H), 2.05 (s, 3H), 1.81 (s, 6H), 1.70 (s, 6H). |
| 289 | XII.37 | XI.16 | 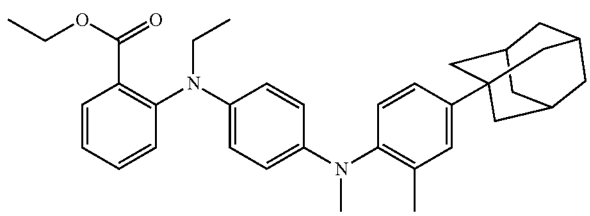 | ¹H NMR (400 MHz, DMSO-d6) δ 7.67-7.59 (m, 2H), 7.34-7.27 (m, 2H), 7.12 (d, J = 8.8 Hz, 2H), 6.88 (d, J = 8.8 Hz, 2H), 6.65 (d, J = 8.4 Hz, 2H), 6.55 (d, J = 8.8 Hz, 2H), 4.01-3.95 (m, 2H), 3.71-3.66 (m, 2H), 3.12 (s, 3H), 2.03 (s, 3H), 1.84 (s, 6H), 1.68 (s, 6H), 1.16 (t, J = 6.8 Hz, 3H), 1.07 (t, J = 7.6 Hz, 3H). LC-MS: m/z 509.1 (M + H)⁺ |
| 290 | XII.38 | XI.16 | 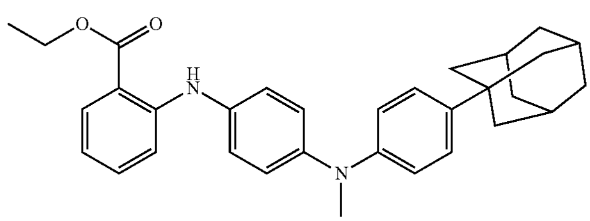 [SMILES: CCOC(=O)c1ccccc1Nc1ccc(N(C)c2ccc(C34CC5CC(CC(C5)C3)C4)cc2)cc1] | ¹H NMR (400 MHz, DMSO-d6) δ 9.23 (s, 1H), 7.88 (d, J = 8.4 Hz, 1H), 7.75-7.73 (m, 1H), 7.52-7.46 (m, 1H), 7.42-7.36 (m, 1H), 7.26 (d, J = 8.8 Hz, 2H), 7.15 (d, J = 8.8 Hz, 2H), 7.06 (d, J = 8.4 Hz, 1H), 6.99-6.95 (m, 2H), 6.75-6.71 (m, 1H), 4.33-4.31 (m, 2H), 3.23 (s, 3H), 2.05 (s, 3H), 1.85 (s, 6H), 1.73 (s, 6H), 1.34 (t, J = 6.9 Hz, 3H). LC-MS: m/z 481.0 (M + H)⁺ |

-continued

| CP | Intermediate No. | Reactant | Structure | Analytical data |
|---|---|---|---|---|
| 311 | XII.39 | XI.16 | 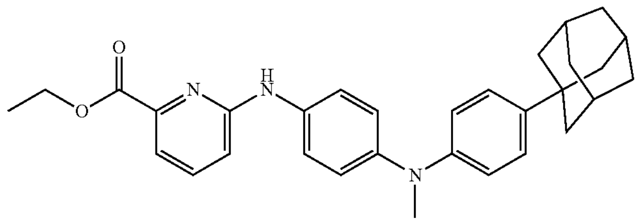 [SMILES: CCOC(=O)c1cccc(Nc2ccc(N(C)c3ccc(C45CC6CC(CC(C6)C4)C5)cc3)cc2)n1] | LC-MS: m/z 482.1 (M + H)⁺ |
| 314 | XII.40 | XI.12 | 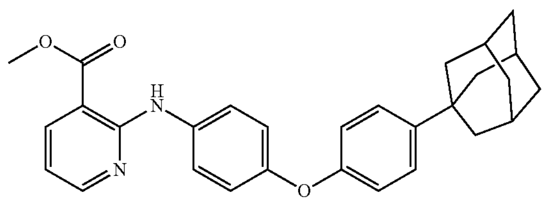 [SMILES: COC(=O)c1cccnc1Nc1ccc(Oc2ccc(C34CC5CC(CC(C5)C3)C4)cc2)cc1] | ¹H NMR (400 MHz, DMSO-d6) δ 10.02 (s, 1H), 8.39 (dd, J₁ = 1.9 Hz, J₂ = 4.9 Hz, 1H), 6.25 (dd, J₁ = 1.9 Hz, J₂ = 7.8 Hz, 1H), 7.70 (d, J = 8.8 Hz, 2H), 7.34 (d, J = 8.9 Hz, 2H), 6.99 (d, J = 8.8 Hz, 2H), 6.89-6.88 (m, 3H), 3.90 (s, 3H), 2.05 (s, 3H), 1.84 (s, 6H), 1.73 (s, 6H). |
| 319 | XII.41 | XI.18 | 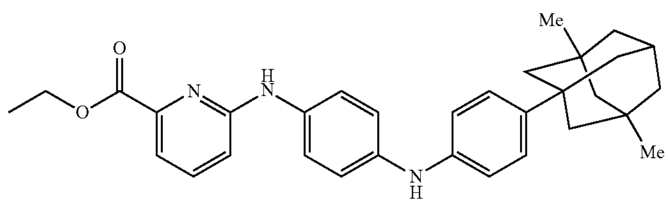 [SMILES: CCOC(=O)c1cccc(Nc2ccc(Nc3ccc(C45CC6CC(C)(CC(C)(C6)C4)C5)cc3)cc2)n1] | ¹H NMR (400 MHz, DMSO-d6) δ 9.07 (s, 1H), 7.78 (s, 1H), 7.66-7.62 (m, 3H), 7.34 (d, J = 7.6 Hz, 1H), 7.16 (d, J = 8.8 Hz, 2H), 7.01-6.92 (m, 5H), 4.33-4.28 (m, 2H), 2.12 (s, 1H), 1.65 (s, 2H), 1.49-1.31 (m, 11H), 1.17 (s, 2H), 0.85 (s, 6H). LC-MS: m/z 496.3 (M + H)⁺ |
| 320 | XII.42 | XI.19 | 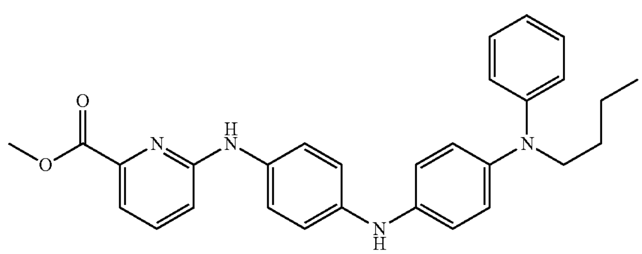 [SMILES: CCCCN(c1ccccc1)c1ccc(Nc2ccc(Nc3cccc(C(=O)OC)n3)cc2)cc1] | ¹H NMR (400 MHz, DMSO-d6) δ 9.12 (s, 1H), 7.91 (s, 1H), 7.65 (m, 3H), 7.36 (d, J = 6.9 Hz, 1H), 7.11 (t, J = 7.8 Hz, 2H), 7.02 (m, 7H), 6.65 (m, 3H), 4.32 (m, 2H), 3.56 (t, J = 7.3 Hz, 2H), 1.50 (m, 2H), 1.30 (m, 5H), 0.88 (t, J = 7.3 Hz, 3H). |
| 321 | XII.43 | XI.14 | 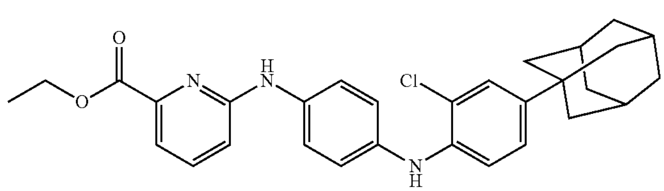 [SMILES: CCOC(=O)c1cccc(Nc2ccc(Nc3ccc(C45CC6CC(CC(C6)C4)C5)cc3Cl)cc2)n1] | ¹H NMR (400 MHz, DMSO-d6) δ 9.34 (s, 1H), 7.85 (d, J = 8.8 Hz, 2H), 7.70 (t, J = 7.4 Hz, 1H), 7.47 (d, J = 2.4 Hz, 1H), 7.42 (d, J = 7.4 Hz, 1H), 7.30 (dd, J₁ = 2.5 Hz, J₂ = 8.8 Hz, 1H), 7.03 (d, J = 8.8 Hz, 1H), 6.92 (m, 3H), 4.32 (m, 2H), 2.05 (s, 3H), 1.85 (s, 6H), 1.72 (s, 6H), 1.33 (t, J = 6.8 Hz, 3H). |

-continued

| CP | Intermediate No. | Reactant | Structure | Analytical data |
|---|---|---|---|---|
| 322 | XII.44 | XI.16 | 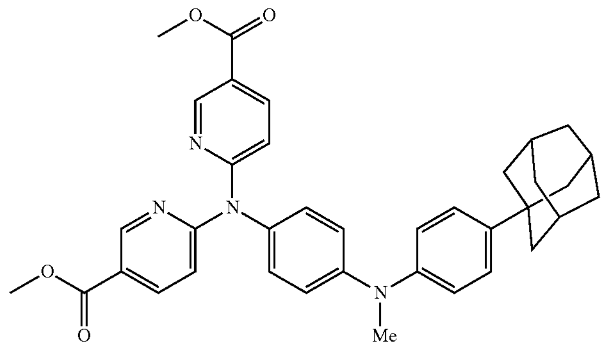 [SMILES: COC(=O)c1ccc(N(c2ccc(N(C)c3ccc(C45CC6CC(CC(C6)C4)C5)cc3)cc2)c2ccc(C(=O)OC)cn2)nc1] | ¹H NMR (400 MHz, DMSO-d6) δ 8.75 (d, J = 2.4 Hz, 1H), 8.15 (dd, J₁ = 2.4 Hz, J₂ = 8.8 Hz, 2H), 7.36 (d, J = 8.8 Hz, 2H), 7.15-7.12 (m, 4H), 7.05 (d, J = 9.2 Hz, 2H), 6.91 (t, J = 6.0 Hz, 3H), 3.85 (s, 6H), 3.28 (s, 3H), 2.06 (s, 3H), 1.87 (s, 6H), 1.74 (s, 6H). LC-MS: m/z 603.3 (M + H)⁺ |
| 338 | XII.45 | XI.20 | 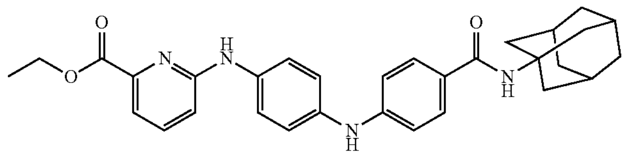 [SMILES: CCOC(=O)c1cccc(Nc2ccc(Nc3ccc(C(=O)NC45CC6CC(CC(C6)C4)C5)cc3)cc2)n1] | ¹H NMR (400 MHz, DMSO-d6) δ 9.21 (s, 1H), 8.27 (s, 1H), 7.75 (d, J = 8.8 Hz, 2H), 7.70-7.63 (m, 3H), 7.38 (t, J = 7.6 Hz, 1H), 7.18 (s, 1H), 7.08 (d, J = 8.4 Hz, 2H), 6.99 (d, J = 8.0 Hz, 1H), 6.91 (d, J = 8.4 Hz, 2H), 4.34-4.29 (m, 2H), 2.05 (s, 9H), 1.65 (s, 6H), 1.34 (t, J = 7.2 Hz, 3H). LC-MS: m/z 511.3 (M + H)⁺ |
| 339 | XII.46 | XI.21 | 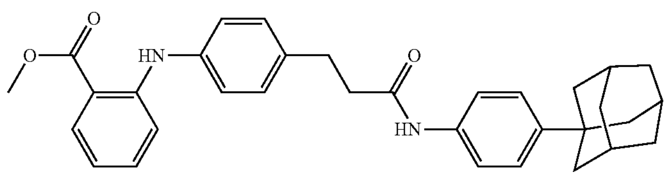 [SMILES: COC(=O)c1ccccc1Nc1ccc(CCC(=O)Nc2ccc(C34CC5CC(CC(C5)C3)C4)cc2)cc1] | ¹H NMR (400 MHz, DMSO-d6) δ 9.80 (s, 1H), 9.25 (s, 1H), 7.88 (d, J = 7.2 Hz, 1H), 7.49 (d, J = 8.8 Hz, 2H), 7.37 (t, J = 8.8 Hz, 1H), ¹H NMR (400 MHz, DMSO-d6) δ 7.27-7.23 (m, 4H), 7.17-7.12 (m, 3H), 6.76 (t, J = 7.6 Hz, 1H), 3.84 (s, 3H), 3.30 (t, J = 7.2 Hz, 2H), 2.60 (t, J = 7.6 Hz, 2H), 2.04 (s, 3H), 1.82 (s, 6H), 1.72 (s, 6H). LC-MS: m/z 509.3 (M + H)⁺ |
| 345 | XII.47 | XI.22 | 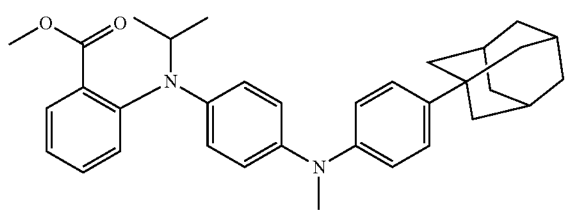 [SMILES: COC(=O)c1ccccc1N(c1ccc(N(C)c2ccc(C34CC5CC(CC(C5)C3)C4)cc2)cc1)C(C)C] | LC-MS: m/z 509.4 (M + H)⁺ |
| 352 | XII.48 | XI.30 | 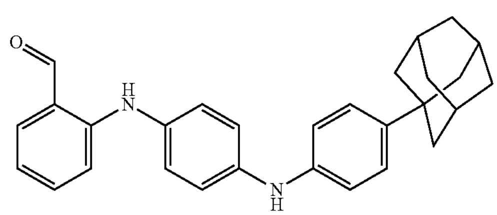 [SMILES: O=Cc1ccccc1Nc1ccc(Nc2ccc(C34CC5CC(CC(C5)C3)C4)cc2)cc1] | ¹H NMR (400 MHz, DMSO-d6) δ 8.82 (s, 1H), 8.26 (s, 1H), 8.12 (d, J = 6.8 Hz, 1H), 7.73 (d, J = 7.6 Hz, 1H), 7.60-7.41 (m, 2H), 7.29-7.21 (m, 4H), 7.08 (t, J = 8.8 Hz, 5H), 2.08 (s, 3H), 1.84 (s, 6H), 1.73 (s, 6H). LC-MS: m/z 423.3 (M + H)⁺ |

-continued

| CP | Intermediate No. | Reactant | Structure | Analytical data |
|---|---|---|---|---|
| 358 | XII.49 | XI.28 | 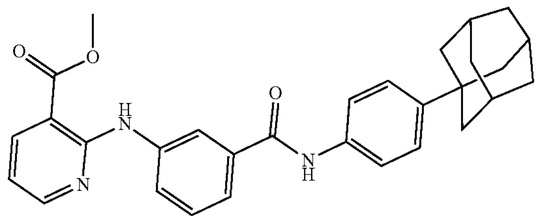 [SMILES: COC(=O)c1cccnc1Nc1cccc(C(=O)Nc2ccc(C34CC5CC(CC(C5)C3)C4)cc2)c1] | $^1$H NMR (400 MHz, DMSO-d6) δ 10.24 (s, 1H), 10.19 (s, 1H), 8.45 (dd, $J_1$ = 2.0 Hz, $J_2$ = 4.8 Hz, 1H), 8.29 (dd, $J_1$ = 2.0 Hz, $J_2$ = 7.6 Hz, 1H), 8.17 (s, 1H), 8.03 (dd, $J_1$ = 1.2 Hz, $J_2$ = 8.0 Hz, 1H), 7.70 (d, J = 8.8 Hz, 2H), 7.60 (d, J = 8.0 Hz, 1H), 7.48 (t, J = 8.0 Hz, 1H), 7.33 (d, J = 8.8 Hz, 2H), 6.94 (dd, $J_1$ = 4.8 Hz, $J_2$ = 8.0 Hz, 1H), 3.92 (s, 3H), 2.06 (s, 3H), 1.86 (d, J = 2.4 Hz, 6H), 1.74 (s, 6H). LC-MS: m/z 482.3 (M + H)$^+$ |
| 359 | XII.50 | XI.28 | 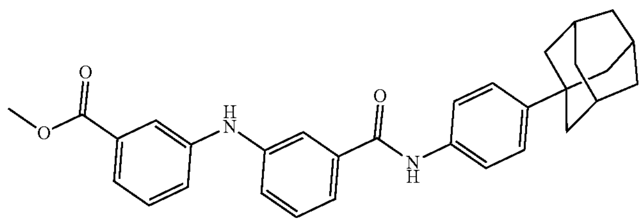 [SMILES: COC(=O)c1cccc(Nc2cccc(C(=O)Nc3ccc(C45CC6CC(CC(C6)C4)C5)cc3)c2)c1] | $^1$H NMR (400 MHz, DMSO-d6) δ 10.14 (s, 1H), 8.65 (s, 1H), 7.69-7.67 (m, 3H), 7.61 (s, 1H), 7.45-7.38 (m, 5H), 7.33-7.31 (m, 3H), 3.83 (s, 3H), 2.05 (s, 3H), 1.85 (d, J = 2.8 Hz, 6H), 1.73 (s, 6H). LC-MS: m/z 481.2 (M + H)$^+$ |
| 360 | XII.51 | XI.24 | 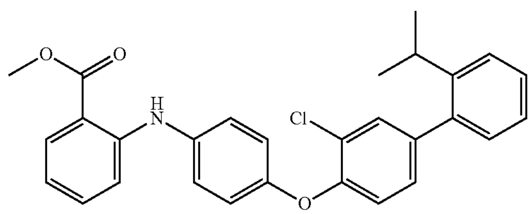 | $^1$H NMR (400 MHz, DMSO-d6) δ 9.26 (s, 1H), 7.90 (d, J = 7.9 Hz, 1H), 7.45 (m, 4H), 7.37-7.07 (m, 9H), 6.79 (t, J = 7.8 Hz, 1H), 3.86 (s, 3H), 2.97 (m, 1H), 1.20 (d, J = 6.9 Hz, 6H). |
| 362 | XII.52 | XI.16 | 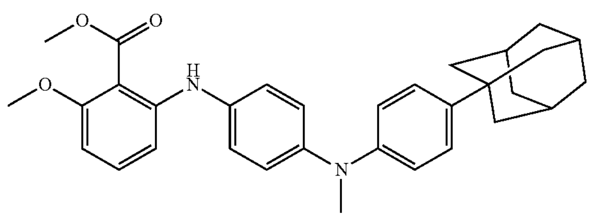 [SMILES: COC(=O)c1c(Nc2ccc(N(C)c3ccc(C45CC6CC(CC(C6)C4)C5)cc3)cc2)cccc1OC] | $^1$H NMR (400 MHz, DMSO-d6) δ 7.57 (s, 1H), 7.24-7.19 (m, 3H), 7.01 (d, J = 8.8 Hz, 2H), 6.94 (d, J = 8.8 Hz, 2H), 6.83 (d, J = 8.3 Hz, 2H), 6.68 (d, J = 8.3 Hz, 1H), 6.53 (d, J = 8.3 Hz, 1H), 3.75 (s, 6H), 3.19 (s, 3H), 2.04 (s, 3H), 1.82 (s, 6H), 1.72 (s, 6H). |
| 366 | XII.53 | XI.26 | 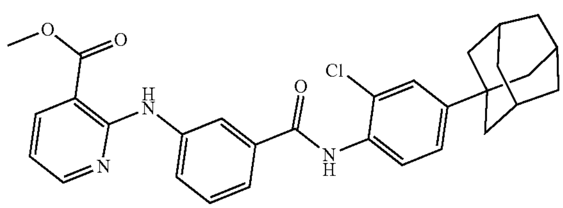 [SMILES: COC(=O)c1cccnc1Nc1cccc(C(=O)Nc2ccc(C34CC5CC(CC(C5)C3)C4)cc2Cl)c1] | $^1$H NMR (400 MHz, DMSO-d6) δ 10.24 (s, 1H), 9.96 (s, 1H), 8.45 (dd, $J_1$ = 2.0 Hz, $J_2$ = 4.8 Hz, 1H), 8.30 (dd, $J_1$ = 2.0 Hz, $J_2$ = 7.6 Hz, 1H), 8.23 (s, H), 8.07-8.04 (m, 1H), 7.64 (d, J = 8.0 Hz, 1H), 7.55-7.46 (m, 3H), 7.38 (dd, $J_1$ = 2.4 Hz, $J_2$ = 8.0 Hz, 1H), 6.95 (dd, $J_1$ = 4.8 Hz, $J_2$ = 7.6 Hz, 1H), 3.92 (s, 3H), 2.08 (s, 3H), 1.89 (s, 6H), 1.75 (s, |

-continued

| CP | Intermediate No. | Reactant | Structure | Analytical data |
|---|---|---|---|---|
| 367 | XII.54 | XI.26 | 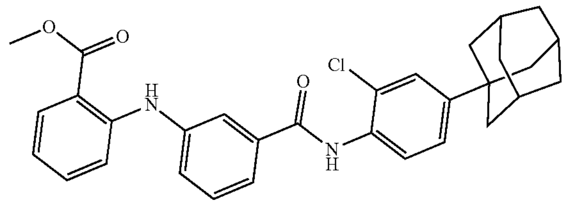 [SMILES: COC(=O)c1ccccc1Nc1cccc(C(=O)Nc2ccc(C34CC5CC(CC(C5)C3)C4)cc2Cl)c1] | ¹H NMR (400 MHz, DMSO-d6) δ 10.00 (s, 1H), 9.42 (s, 1H), 7.93 (dd, J₁ = 1.6 Hz, J₂ = 8.0 Hz, 1H), 7.83 (s, 1H), 7.70-7.60 (m, 1H), 7.51-7.34 (m, 5H), 7.40-7.30 (m, 2H), 6.90-6.86 (m, 1H), 3.87 (s, 3H), 2.07 (s, 3H), 1.88 (d, J = 2.4 Hz, 6H), 1.74 (s, 6H). LC-MS: m/z 515.3 (M + H)⁺ |
| 373 | XII.55 | XI.27 | 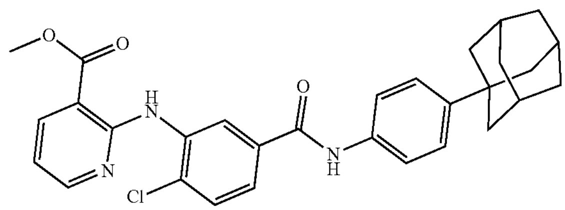 [SMILES: COC(=O)c1cccnc1Nc1cc(C(=O)Nc2ccc(C34CC5CC(CC(C5)C3)C4)cc2)ccc1Cl] | ¹H NMR (400 MHz, DMSO-d6) δ 10.63 (s, 1H), 10.23 (s, 1H), 9.15 (d, J = 1.6 Hz, 1H), 8.50 (dd, J₁ = 2.0 Hz, J₂ = 4.8 Hz, 1H), 8.35 (dd, J₁ = 2.0 Hz, J₂ = 7.6 Hz, 1H), 7.70-7.67 (m, 3H), 7.63-7.61 (m, 1H), 7.33 (d, J = 8.8 Hz, 2H), 7.02 (dd, J₁ = 4.4 Hz, J₂ = 7.6 Hz, 1H), 3.94 (s, 3H), 2.06 (s, 3H), 1.87 (s, 6H), 1.74 (s, 6H). LC-MS: m/z 516.2 (M + H)⁺ |
| 375 352 | XII.56 | XII.48 | 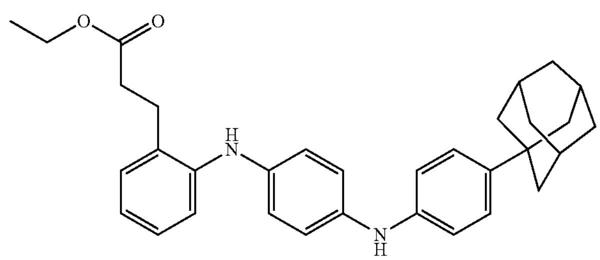 [SMILES: CCOC(=O)CCc1ccccc1Nc1ccc(Nc2ccc(C34CC5CC(CC(C5)C3)C4)cc2)cc1] | ¹H NMR (400 MHz, DMSO-d6) δ 7.71 (s, 1H), 7.16-6.77 (m, 13H), 4.07-4.00 (m, 2H), 2.87 (t, J = 7.6 Hz, 2H), 2.59 (d, J = 8.0 Hz, 2H), 2.04 (s, 3H), 1.81 (s, 6H), 1.69 (s, 6H), 1.15 (t, J = 4.0 Hz, 3H), LC-MS: m/z 495.3 (M + H)⁺ |
| 376 | XII.57 | XI.28 | 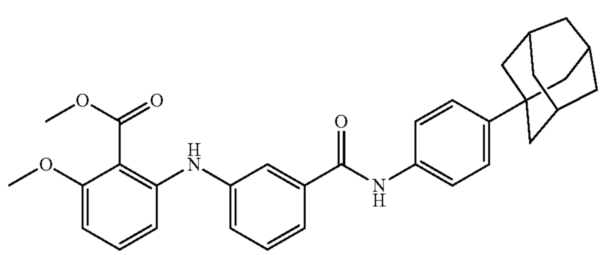 [SMILES: COC(=O)c1c(Nc2cccc(C(=O)Nc3ccc(C45CC6CC(CC(C6)C4)C5)cc3)c2)cccc1OC] | ¹H NMR (400 MHz, DMSO-d6) δ 10.09 (s, 1H), 7.87 (s, 1H), 7.67 (d, J = 8.8 Hz, 2H), 7.54 (s, 1H), 7.38 (d, J = 18.4 Hz, 1H), 7.34-7.28 (m, 4H), 7.20-7.10 (m, 1H), 7.85 (d, J = 8.0 Hz, 1H), 6.70 (d, J = 8.4 Hz, 1H), 3.78 (s, 3H), 3.72 (s, 3H), 2.06 (s, 3H), 1.86 (d, J = 2.4 Hz, 6H), 1.74 (s, 6H). LC-MS: m/z 511.2 (M + H)⁺ |

| CP | Intermediate No. | Reactant | Structure | Analytical data |
|---|---|---|---|---|
| 377 | XII.58 | XI.30 | 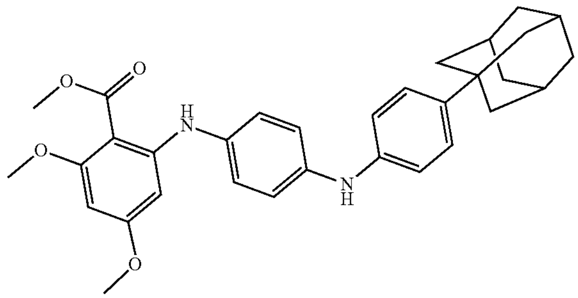 [SMILES: COC(=O)c1c(Nc2ccc(Nc3ccc(C45CC6CC(CC(C6)C4)C5)cc3)cc2)cc(OC)cc1OC] | ¹H NMR (400 MHz, DMSO-d6) δ 8.23 (s, 1H), 7.93 (s, 1H), 7.20 (d, J = 8.8 Hz, 2H), 7.03-6.97 (m, 6H), 6.06 (d, J = 2.0 Hz, 1H), 6.00 (d, J = 2.0 Hz, 1H), 3.74 (s, 3H), 3.73 (s, 3H), 3.67 (s, 3H), 2.04 (s, 3H), 1.82 (s, 6H), 1.72 (s, 6H). LC-MS: m/z 513.3 (M + H)⁺ |
| 379 | XII.59 | XI.16 | 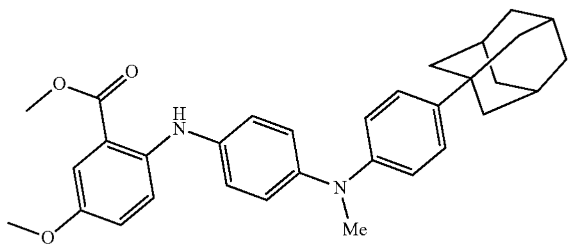 [SMILES: COC(=O)c1cc(OC)ccc1Nc1ccc(N(C)c2ccc(C34CC5CC(CC(C5)C3)C4)cc2)cc1] | ¹H NMR (400 MHz, DMSO-d6) δ 8.82 (s, 1H), 7.36 (d, J = 2.4 Hz, 1H), 7.24 (d, J = 8.8 Hz, 2H), 7.10 (dd, J₁ = 2.0 Hz, J₂ = 5.2 Hz, 4H), 6.97 (d, J = 8.4 Hz, 2H), 6.90 (d, J = 8.8 Hz, 2H), 3.85 (s, 3H), 3.72 (s, 3H), 3.21 (s, 3H), 2.04 (s, 3H), 1.83 (s, 6H), 1.76 (s, 6H). LC-MS: m/z 497.3 (M + H)⁺ |
| 380 | XII.60 | XI.30 | 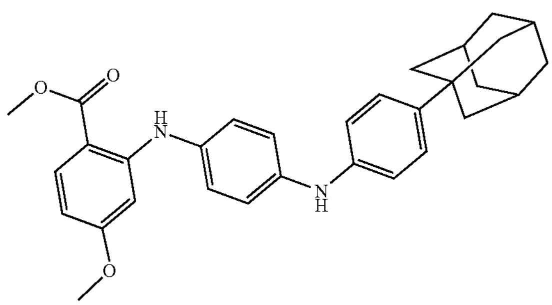 [SMILES: COC(=O)c1ccc(OC)cc1Nc1ccc(Nc2ccc(C34CC5CC(CC(C5)C3)C4)cc2)cc1] | ¹H NMR (400 MHz, DMSO-d6) δ 9.29 (s, 1H), 8.03 (s, 1H), 7.82 (d, J = 8.8 Hz, 1H), 7.22 (d, J = 6.0 Hz, 2H), 7.13 (d, J = 8.8 Hz, 2H), 7.07 (d, J = 8.8 Hz, 2H), 7.02 (d, J = 8.0 Hz, 2H), 6.41 (d, J = 2.4 Hz, 1H), 6.32 (dd, J₁ = 2.4 Hz, J₂ = 9.2 Hz, 1H), 3.81 (s, 3H), 3.69 (s, 3H), 2.05 (s, 3H), 1.83 (d, J = 2.8 Hz, 6H), 1.73 (s, 6H). LC-MS: m/z 483.3 (M + H)⁺ |
| 382 | XII.61 | XI.14 | 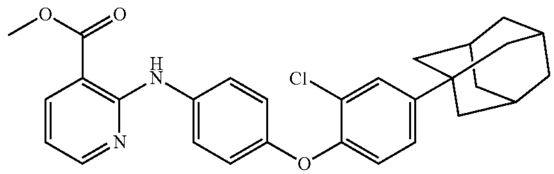 [SMILES: COC(=O)c1cccnc1Nc1ccc(Oc2ccc(C34CC5CC(CC(C5)C3)C4)cc2Cl)cc1] | ¹H NMR (400 MHz, DMSO-d6) δ 10.01 (s, 1H), 8.38 (dd, J₁ = 2.0 Hz, J₂ = 4.9 Hz, 1H), 8.25 (dd, J₁ = 1.9 Hz, J₂ = 7.8 Hz, 1H), 7.69 (dd, J₁ = 2.0 Hz, J₂ = 6.8 Hz, 2H), 7.49 (d, J = 2.5 Hz, 1H), 7.32 (dd, J₁ = 2.4 Hz, J₂ = 8.8 Hz, 1H), 6.98 (d, J = 8.3 Hz, 1H), 6.95 (dd, J₁ = 1.9 Hz, J₂ = 6.8 Hz, 2H), 6.87 (dd, J₁ = 4.4 Hz, J₂ = 7.3 Hz, 1H), 3.90 (s, 3H), 2.06 (s, 3H), 1.86 (s, 6H), 1.73 (s, 6H). LC-MS: m/z 489.1 (M + H)⁺ |

| CP | Intermediate No. | Reactant | Structure | Analytical data |
|---|---|---|---|---|
| 383 | XII.62 | XI.25 | 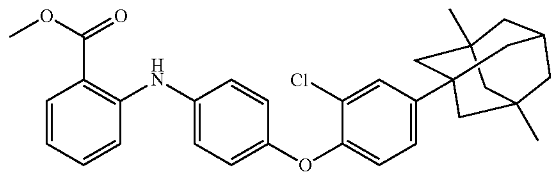 [SMILES: COC(=O)c1ccccc1Nc1ccc(Oc2ccc(C34CC5CC(C)(CC(C)(C5)C3)C4)cc2Cl)cc1] | $^1$H NMR (400 MHz, DMSO-d6) δ 9.24 (s, 1H), 7.88 (dd, $J_1$ = 1.6 Hz, $J_2$ = 8.0 Hz, 1H), 7.50 (d, J = 2.4 Hz, 1H), 7.39-7.32 (m, 2H), 7.26 (d, J = 8.8 Hz, 2H), 7.10-7.03 (m, 2H), 6.95 (d, J = 8.8 Hz, 2H), 6.77 (t, J = 8.0 Hz, 1H), 3.85 (s, 3H), 2.16-2.12 (m, 1H), 1.69 (s, 2H), 1.53-1.35 (m, 8H), 1.18 (s, 2H), 0.86 (s, 6H). |
| 384 | XII.63 | XI.25 | 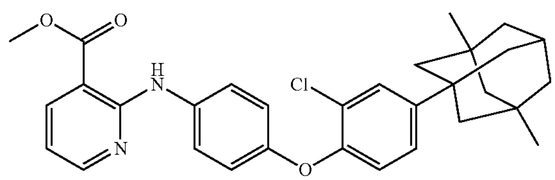 [SMILES: COC(=O)c1cccnc1Nc1ccc(Oc2ccc(C34CC5CC(C)(CC(C)(C5)C3)C4)cc2Cl)cc1] | $^1$H NMR (400 MHz, DMSO-d6) δ 10.02 (s, 1H), 8.38 (dd, $J_1$ = 2.0 Hz, $J_2$ = 4.8 Hz, 1H), 8.25 (dd, $J_1$ = 2.0 Hz, $J_2$ = 7.6 Hz, 1H), 7.70-7.67 (m, 2H), 7.48 (d, J = 2.4 Hz, 1H), 7.33-7.30 (m, 1H), 6.98-6.93 (m, 3H), 6.89-6.86 (m, 1H), 3.90 (s, 3H), 2.14-2.13 (m, 1H), 1.69-1.68 (m, 2H), 1.52-1.35 (m, 8H), 1.18 (s, 2H), 0.86 (s, 6H). |
| 395 | XII.64 | XI.28 | 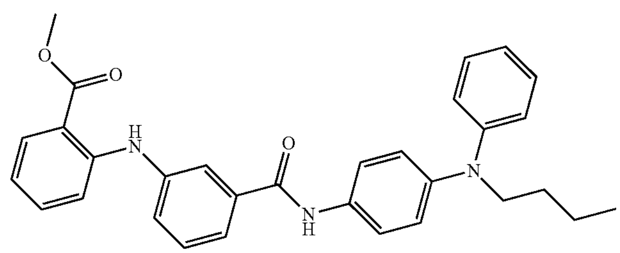 [SMILES: CCCCN(c1ccccc1)c1ccc(NC(=O)c2cccc(Nc3ccccc3C(=O)OC)c2)cc1] | $^1$H NMR (400 MHz, DMSO-d6) δ 10.17 (s, 1H), 9.41 (s, 1H), 7.92 (dd, $J_1$ = 1.2 Hz, $J_2$ = 7.6 Hz, 1H), 7.8 (s, 1H), 7.69 (d, J = 9.2 Hz, 2H), 7.64 (d, J = 7.6 Hz, 1H), 7.52-7.44 (m, 3H), 7.31 (d, J = 8.4 Hz, 1H), 7.22-7.18 (m, 2H), 7.03 (d, J = 8.8 Hz, 2H), 6.89-6.79 (m, 4H), 3.87 (s, 3H), 3.65 (t, J = 7.6 Hz, 2H), 1.58-1.51 (m, 2H), 1.38-1.30 (m, 2H), 0.88 (t, J = 7.6 Hz, 3H). LC-MS: m/z 494.3 (M + H)$^+$ |
| 398 | XII.65 | XI.28 | 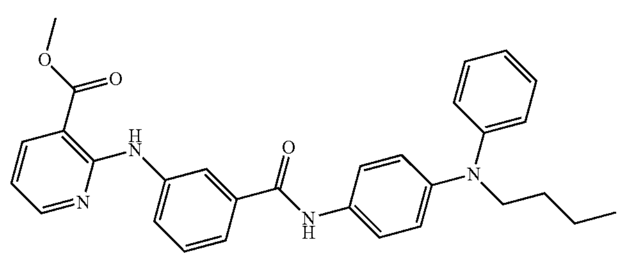 [SMILES: CCCCN(c1ccccc1)c1ccc(NC(=O)c2cccc(Nc3ncccc3C(=O)OC)c2)cc1] | $^1$H NMR (400 MHz, DMSO-d6) δ 10.21-10.17 (m, 2H), 8.44 (d, J = 2.8 Hz, 1H), 8.27 (dd, $J_1$ = 1.6 Hz, $J_2$ = 8.0 Hz, 1H), 8.15 (s, 1H), 8.01 (d, J = 8.4 Hz, 1H), 7.69 (d, J = 8.8 Hz, 2H), 7.59 (d, J = 8.0 Hz, 1H), 7.46 (t, J = 8.0 Hz, 1H), 7.19 (t, J = 8.4 Hz, 2H), 7.02 (d, J = 8.8 Hz, 2H), 6.92 (dd, $J_1$ = 4.8 Hz, $J_2$ = 8.0 Hz, 1H), 6.85-6.77 (m, 3H), 3.91 (s, 3H), 3.64 (t, J = 7.2 Hz, 2H), 1.55-1.52 (m, 2H), 1.35-1.29 (m, |

-continued

| CP | Intermediate No. | Reactant | Structure | Analytical data |
|---|---|---|---|---|
| | | | | 2H), 0.87 (t, J = 4.8 Hz, 3H). LC-MS: m/z 495.3 (M + H)+ |
| 420 | XII.66 | XI.16 | 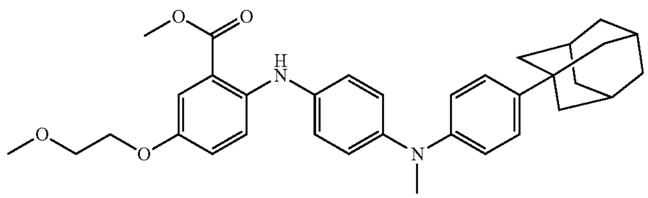 [SMILES: COCCOc1ccc(Nc2ccc(N(C)c3ccc(C45CC6CC(CC(C6)C4)C5)cc3)cc2)c(C(=O)OC)c1] | 1H NMR (400 MHz, DMSO-d6) δ 8.83 (s, 1H), 7.37 (s, 1H), 7.24 (d, J = 8.8 Hz, 2H), 7.12-7.10 (m, 4H), 6.95 (d, J = 8.8 Hz, 2H), 6.90 (d, J = 8.4 Hz, 2H), 4.04 (t, J = 4.4 Hz, 2H), 3.85 (s, 3H), 3.63 (t, J = 4.8 Hz, 2H), 3.30 (s, 3H), 3.21 (s, 3H), 2.04 (s, 3H), 1.83 (d, J = 2.4 Hz, 6H), 1.72 (s, 6H). LC-MS: m/z 541.2 (M + H)+ |
| 270 | XII.67 | XI.12 | 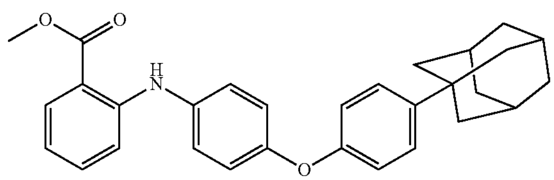 [SMILES: COC(=O)c1ccccc1Nc1ccc(Oc2ccc(C34CC5CC(CC(C5)C3)C4)cc2)cc1] | LC-MS: m/z 454.1 (M + H)+ |
| 266 | XII.68 | XI.31 | 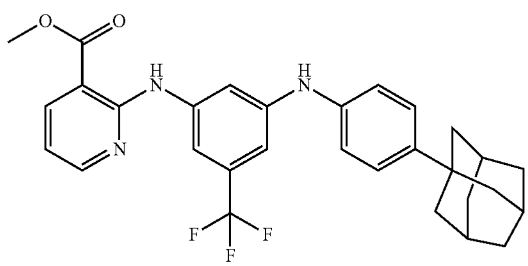 [SMILES: COC(=O)c1cccnc1Nc1cc(Nc2ccc(C34CC5CC(CC(C5)C3)C4)cc2)cc(C(F)(F)F)c1] | LC-MS: m/z 522.1 (M + H)+ |
| 231 | XII.69 | Int-XI | 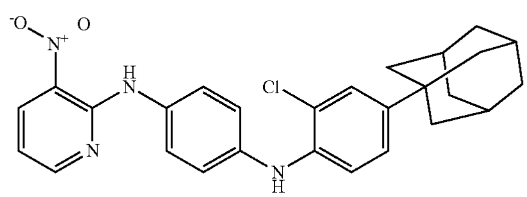 | 1H NMR (400 MHz, DMSO-d6) δ 9.90 (s, 1H), 8.52-8.47 (m, 2H), 7.55 (s, 1H), 7.47 (d, J = 8.8 Hz, 2H), 7.34 (s, 1H), 7.20 (s, 2H), 7.03 (d, J = 8.8 Hz, 2H), 6.94-6.91 (m, 1H), 2.05 (s, 3H), 1.84 (s, 6H), 1.72 (s, 6H). LC-MS: m/z 475.2 (M + H)+ |
| 453 | XII.70 | XI.16 | 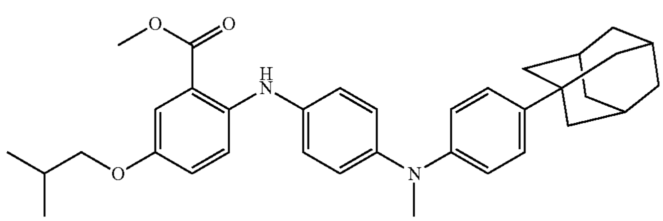 [SMILES: COC(=O)c1cc(OCC(C)C)ccc1Nc1ccc(N(C)c2ccc(C34CC5CC(CC(C5)C3)C4)cc2)cc1] | 1H NMR (400 MHz, DMSO-d6): δ 8.79 (s, 1H), 7.54-7.52 (m, 1H), 7.44-7.42 (m, 1H), 7.28-6.98 (m, 9H), 3.85 (s, 3H), 3.80 (d, J = 2.4 Hz, 2H), 3.37 (s, 3H), 2.04 (s, 3H), 2.00-1.96 (m, 1H), 1.83 (s, 6H), 1.72 (s, 6H), 0.97 (d, J = 6.4 Hz, 6H). |

-continued

| CP | Intermediate No. | Reactant | Structure | Analytical data |
|---|---|---|---|---|
| 521 | XII.71 | XI.32 | 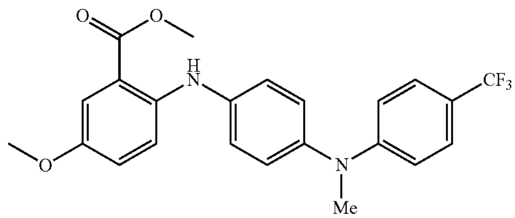 [SMILES: COC(=O)c1cc(OC)ccc1Nc1ccc(N(C)c2ccc(C(F)(F)F)cc2)cc1] | LC-MS: m/z 431.2 (M + H)+ |
| 522 | XII.72 | XI.33 | 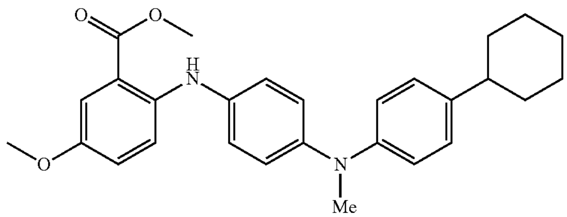 [SMILES: COC(=O)c1cc(OC)ccc1Nc1ccc(N(C)c2ccc(C3CCCCC3)cc2)cc1] | LC-MS: m/z 445.2 |
| 525 | XII.73 | VII.78 | 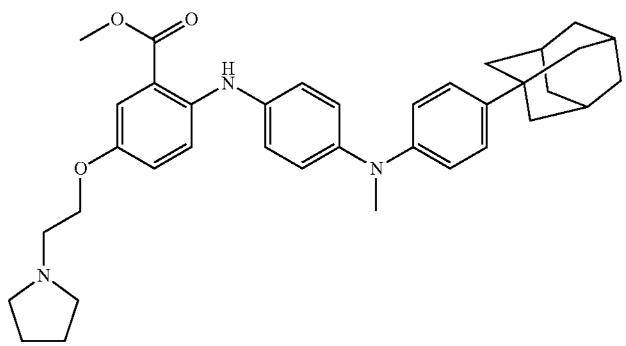 [SMILES: COC(=O)c1cc(OCCN2CCCC2)ccc1Nc1ccc(N(C)c2ccc(C34CC5CC(CC(C5)C3)C4)cc2)cc1] | LC-MS: m/z 580.4 (M + H)+ |
| 526 | XII.74 | XI.16 | 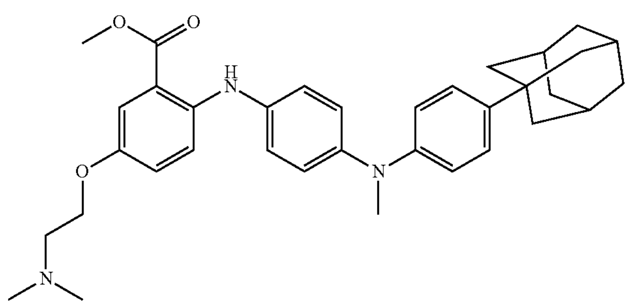 [SMILES: COC(=O)c1cc(OCCN(C)C)ccc1Nc1ccc(N(C)c2ccc(C34CC5CC(CC(C5)C3)C4)cc2)cc1] | LC-MS: m/z 554.4 (M + H)+ |
| 528 | XII.75 | XI.34 | 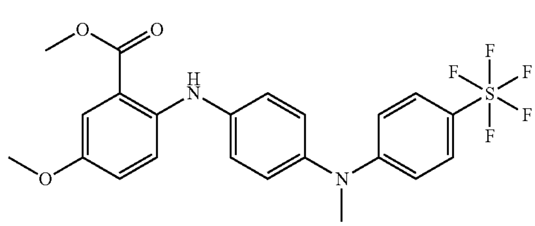 [SMILES: COC(=O)c1cc(OC)ccc1Nc1ccc(N(C)c2ccc(S(F)(F)(F)(F)F)cc2)cc1] | LC-MS: m/z 489.1 (M + H)+ |
| 535 | XII.76 | XI.35 | 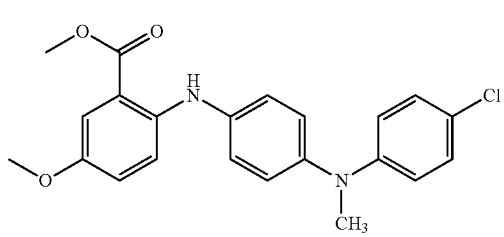 [SMILES: COC(=O)c1cc(OC)ccc1Nc1ccc(N(C)c2ccc(Cl)cc2)cc1] | LC-MS: m/z 396.1 (M + H)+ |

-continued

| CP | Intermediate No. | Reactant | Structure | Analytical data |
|---|---|---|---|---|
| 536 | XII.77 | VII.81 | 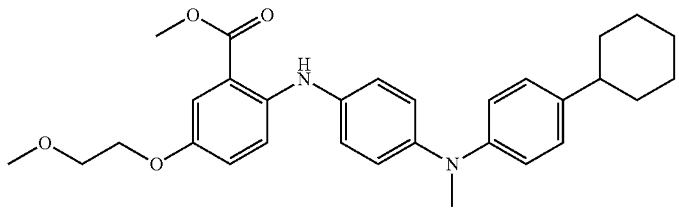 [SMILES: COCCOc1ccc(Nc2ccc(N(C)c3ccc(C4CCCCC4)cc3)cc2)c(C(=O)OC)c1] | LC-MS: m/z 488.3 (M + H)+ |
| 537 | XII.78 | XI.36 | 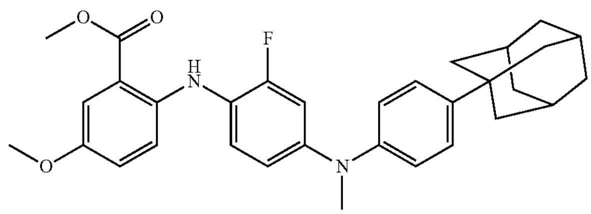 [SMILES: COC(=O)c1cc(OC)ccc1Nc1ccc(N(C)c2ccc(C34CC5CC(CC(C5)C3)C4)cc2)cc1F] | LC-MS: m/z 514.3 (M + H)+ |
| 538 | XII.79 | XI.37 | 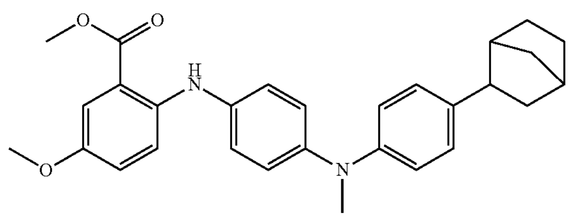 [SMILES: COC(=O)c1cc(OC)ccc1Nc1ccc(N(C)c2ccc(C3CC4CCC3C4)cc2)cc1] | LC-MS: m/z 456.3 (M + H)+ |
| 541 | XII.80 | VII.80 | 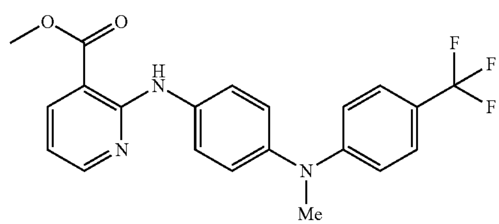 [SMILES: COC(=O)c1cccnc1Nc1ccc(N(C)c2ccc(C(F)(F)F)cc2)cc1] | LC-MS: m/z 402.1 (M + H)+. |
| 542 | XII.81 | XI.38 | 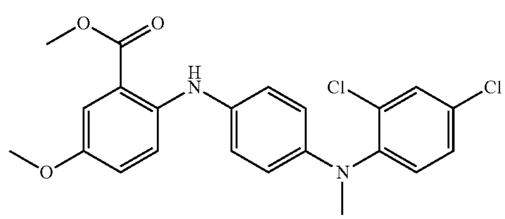 [SMILES: COC(=O)c1cc(OC)ccc1Nc1ccc(N(C)c2ccc(Cl)cc2Cl)cc1] | LC-MS: m/z 431.31 (M + H)+ |
| 543 | XII.82 | XI.39 | 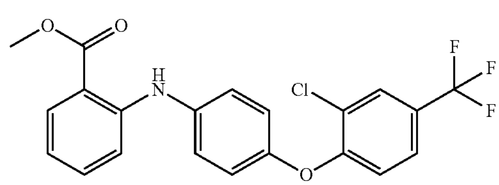 [SMILES: COC(=O)c1ccccc1Nc1ccc(Oc2ccc(C(F)(F)F)cc2Cl)cc1] | LC-MS: m/z 422.1 (M + H)+ |
| 544 | XII.83 | XI.39 | 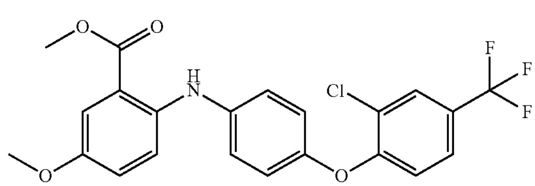 [SMILES: COC(=O)c1cc(OC)ccc1Nc1ccc(Oc2ccc(C(F)(F)F)cc2Cl)cc1] | LC-MS: m/z 452.1 (M + H)+ |

-continued
| CP | Intermediate No. | Reactant | Structure | Analytical data |
|---|---|---|---|---|
| 545 | XII.84 | XI.40 | 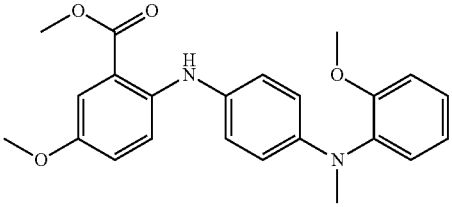 [SMILES: COC(=O)c1cc(OC)ccc1Nc1ccc(N(C)c2ccccc2OC)cc1] | LC-MS: m/z 392.2 (M + H)+ |
| 546 | XII.85 | XI.41 | 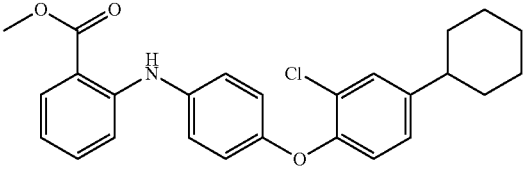 [SMILES: COC(=O)c1ccccc1Nc1ccc(Oc2ccc(C3CCCCC3)cc2Cl)cc1] | LC-MS: m/z 436.2 |
| 547 | XII.86 | XI.42 | 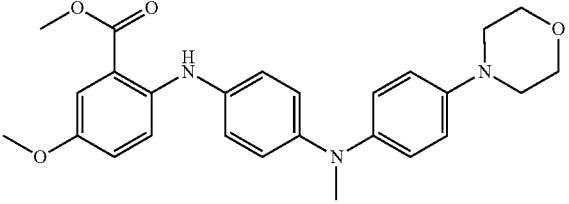 [SMILES: COC(=O)c1cc(OC)ccc1Nc1ccc(N(C)c2ccc(N3CCOCC3)cc2)cc1] | LC-MS: m/z 448.2 (M + H)+. |
| 548 | XII.87 | XI.43 | 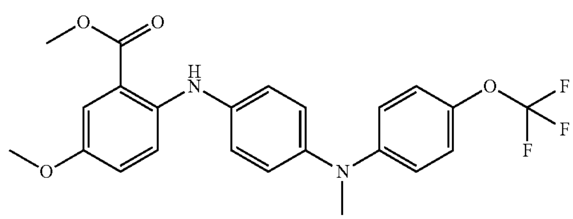 [SMILES: COC(=O)c1cc(OC)ccc1Nc1ccc(N(C)c2ccc(OC(F)(F)F)cc2)cc1] | LC-MS: m/z 447.1 (M + H)+. |
| 549 | XII.88 | XI.44 | 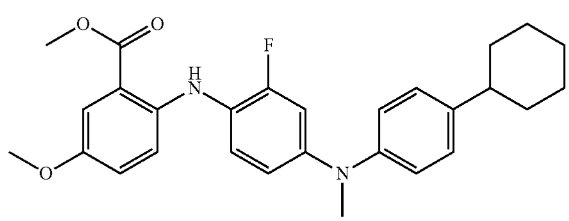 [SMILES: COC(=O)c1cc(OC)ccc1Nc1ccc(N(C)c2ccc(C3CCCCC3)cc2)cc1F] | LC-MS: m/z 463.2 (M + H)+. |
| 550 | XII.89 | XI.45 | 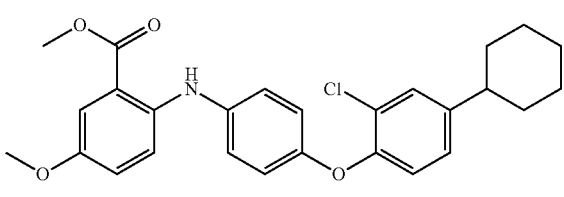 [SMILES: COC(=O)c1cc(OC)ccc1Nc1ccc(Oc2ccc(C3CCCCC3)cc2Cl)cc1] | LC-MS: m/z 466.2 (M + H)+ |
| 551 | XII.90 | XI.46 | 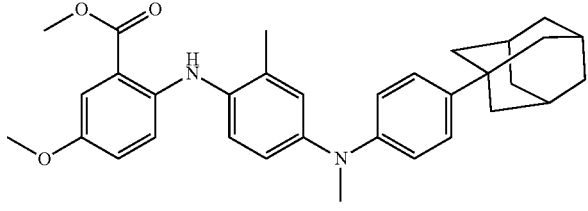 [SMILES: COC(=O)c1cc(OC)ccc1Nc1ccc(N(C)c2ccc(C34CC5CC(CC(C5)C3)C4)cc2)cc1C] | LC-MS: m/z 511.4 (M + H)+ |

-continued
| CP | Intermediate No. | Reactant | Structure | Analytical data |
|---|---|---|---|---|
| 552 | XII.91 | XI.47 | 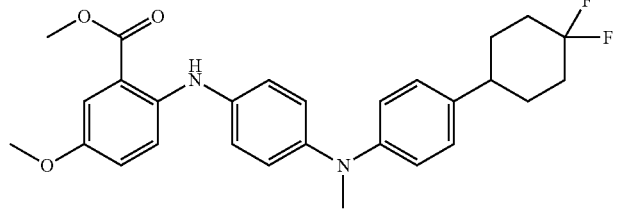 | LC-MS: m/z 481.2 (M + H)+ |
| 553 | XII.92 | XI.48 | 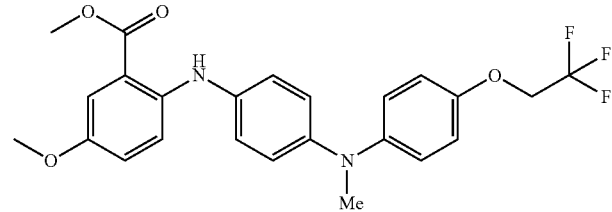 [SMILES: COC(=O)c1cc(OC)ccc1Nc1ccc(N(C)c2ccc(OCC(F)(F)F)cc2)cc1] | LC-MS: m/z 461.1 (M + H)+. |
| 554 | XII.93 | XI.49 | 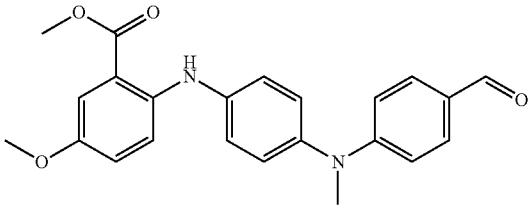 [SMILES: COC(=O)c1cc(OC)ccc1Nc1ccc(N(C)c2ccc(C=O)cc2)cc1] | LC-MS: m/z 391.3 (M + H)+ |
| 555 | XII.94 | XI.50 | 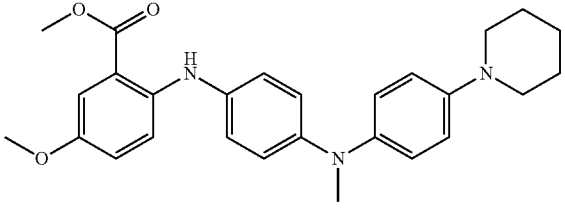 [SMILES: COC(=O)c1cc(OC)ccc1Nc1ccc(N(C)c2ccc(N3CCCCC3)cc2)cc1] | LC-MS: m/z 446.3 (M + H)+. |
| 556 | XII.95 | XI.51 | 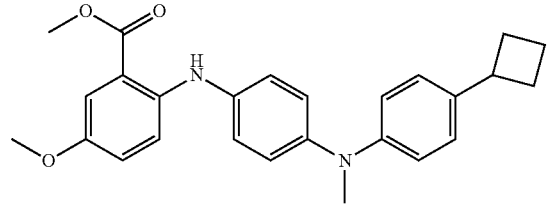 [SMILES: COC(=O)c1cc(OC)ccc1Nc1ccc(N(C)c2ccc(C3CCC3)cc2)cc1] | LC-MS: m/z 417.2 (M + H)+ |
| 557 | XII.96 | XI.52 | 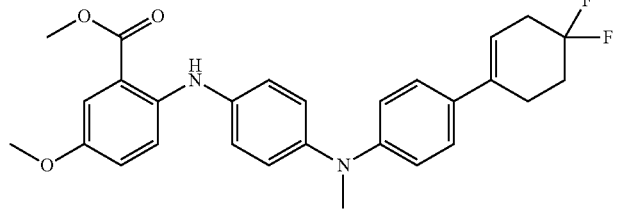 | LC-MS: m/z 479.2 (M + H)+ |
| 558 | XII.97 | XI.33 | 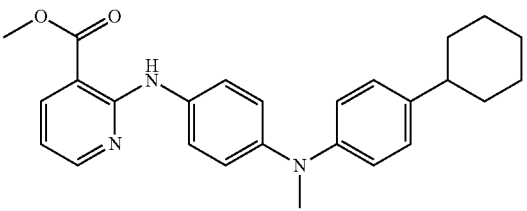 [SMILES: COC(=O)c1cccnc1Nc1ccc(N(C)c2ccc(C3CCCCC3)cc2)cc1] | LC-MS: m/z 416.2 (M + H)+ |

-continued

| CP | Intermediate No. | Reactant | Structure | Analytical data |
|---|---|---|---|---|
| 559 | XII.98 | XI.31 | 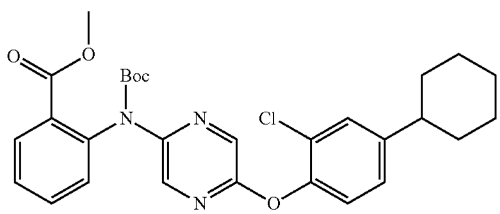 [SMILES: COC(=O)c1ccccc1N(C(=O)OC(C)(C)C)c1cnc(Oc2ccc(C3CCCCC3)cc2Cl)cn1] | LC-MS: m/z 538.2 (M + H)+ |
| 560 | XII.99 | XI.53 | 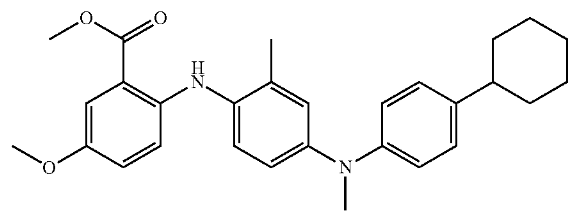 [SMILES: COC(=O)c1cc(OC)ccc1Nc1ccc(N(C)c2ccc(C3CCCCC3)cc2)cc1C] | LC-MS: m/z 459.3 (M + H)+ |
| 561 | XII.100 | XI.54 | 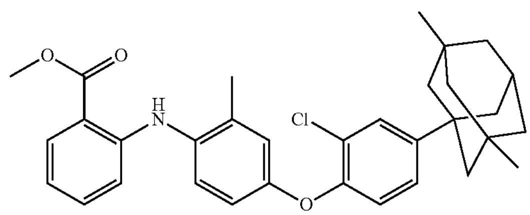 [SMILES: COC(=O)c1ccccc1Nc1ccc(Oc2ccc(C34CC5CC(C)(CC(C)(C5)C3)C4)cc2Cl)cc1C] | Proceeded with crude/TLC reference |
| 563 | XII.101 | XI.55 | 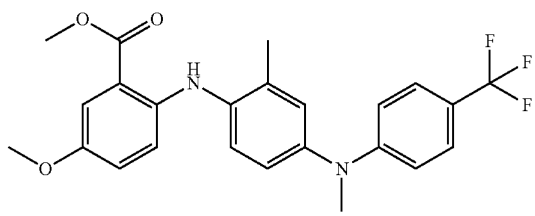 [SMILES: COC(=O)c1cc(OC)ccc1Nc1ccc(N(C)c2ccc(C(F)(F)F)cc2)cc1C] | LC-MS: m/z 444.1 (M + H)+ |
| 564 | XII.102 | XI.54 | 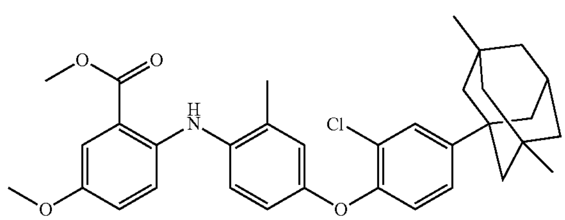 | LC-MS: m/z 515.15 (M + H)+. |
| 565 | XII.103 | XI.56 | 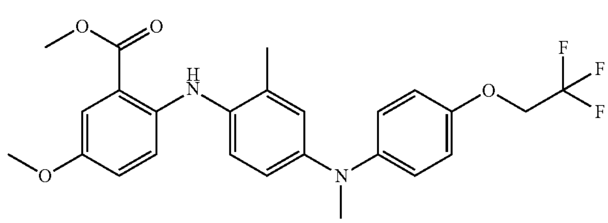 [SMILES: COC(=O)c1cc(OC)ccc1Nc1ccc(N(C)c2ccc(OCC(F)(F)F)cc2)cc1C] | LC-MS: m/z 475.1 (M + H)+. |
| 566 | XII.104 | XI.57 | 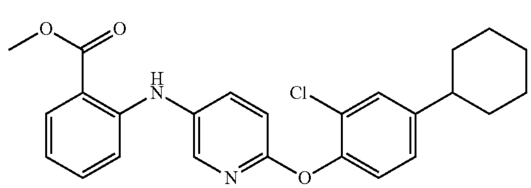 [SMILES: COC(=O)c1ccccc1Nc1ccc(Oc2ccc(C3CCCCC3)cc2Cl)nc1] | LC-MS: m/z 437.2 (M + H)+ |

-continued

| CP | Intermediate No. | Reactant | Structure | Analytical data |
|---|---|---|---|---|
| 567 | XII.105 | VII.88 | 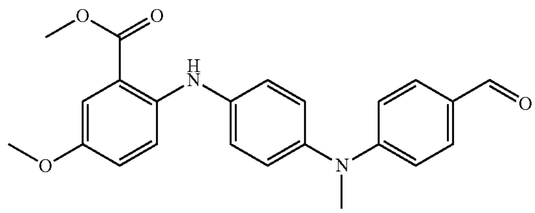 [SMILES: COC(=O)c1cc(OC)ccc1Nc1ccc(N(C)c2ccc(C=O)cc2)cc1] | LC-MS: m/z 391.3 (M + H)+ |
| 568 | XII.106 | XI.58 | 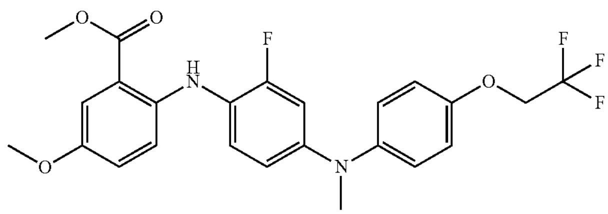 [SMILES: COC(=O)c1cc(OC)ccc1Nc1ccc(N(C)c2ccc(OCC(F)(F)F)cc2)cc1F] | LC-MS: m/z 479.2 (M + H)+ |
| 570 | XII.107 | XI.59 | 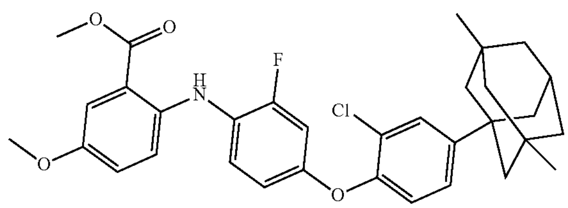 | LC-MS: m/z 449.3 (M + H)+ |
| 571 | XII.108 | XI.60 | 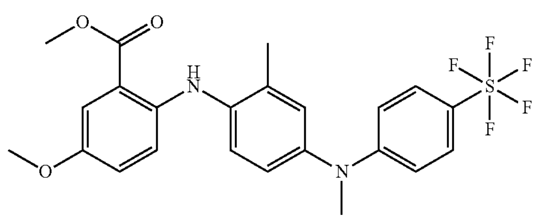 [SMILES: COC(=O)c1cc(OC)ccc1Nc1ccc(N(C)c2ccc(S(F)(F)(F)(F)F)cc2)cc1C] | LC-MS: m/z 503.2 (M + H)+ |
| 572 | XII.109 | XI.61 | 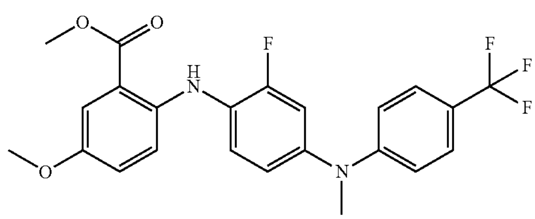 [SMILES: COC(=O)c1cc(OC)ccc1Nc1ccc(N(C)c2ccc(C(F)(F)F)cc2)cc1F] | LC-MS: m/z 449.3 (M + H)+ |
| 573 | XII.110 | XI.62 | 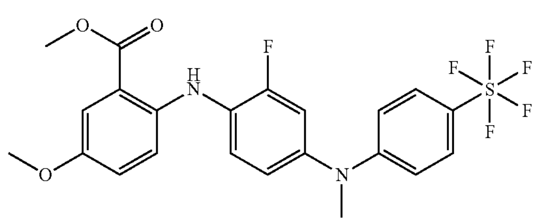 | LC-MS: m/z 507.1 (M + H)+ |
| 574 | XII.111 | XI.63 | 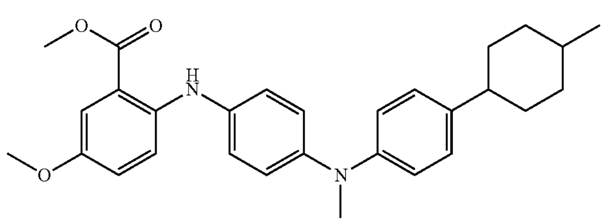 | LC-MS: m/z 459.3 (M + H)+ |

-continued

| CP | Intermediate No. | Reactant | Structure | Analytical data |
|---|---|---|---|---|
| 575 | XII.112 | XI.64 | 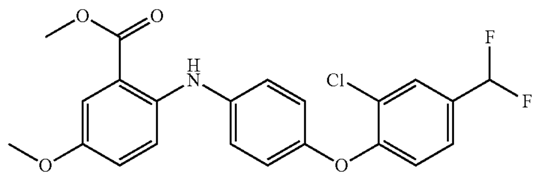 [SMILES: COC(=O)c1cc(OC)ccc1Nc1ccc(Oc2ccc(C(F)F)cc2Cl)cc1] | LC-MS: m/z 434.1 (M + H)+ |
| 576 | XII.113 | XI.65 | 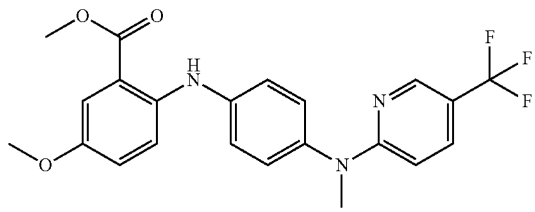 [SMILES: COC(=O)c1cc(OC)ccc1Nc1ccc(N(C)c2ccc(C(F)(F)F)cn2)cc1] | LC-MS: m/z 431.55 (M + H)+ |
| 577 | XII.114 | XI.66 | 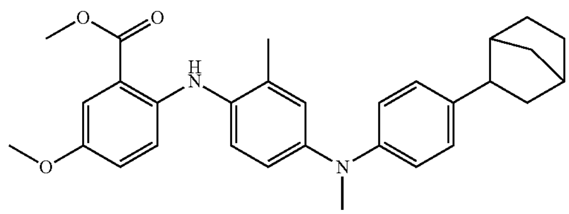 [SMILES: COC(=O)c1cc(OC)ccc1Nc1ccc(N(C)c2ccc(C3CC4CCC3C4)cc2)cc1C] | LC-MS: m/z 469.25 (M − H)+ |
| 578 | XII.115 | XI.67 | 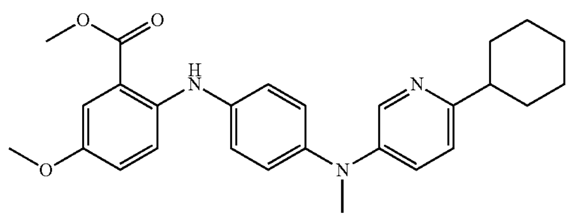 [SMILES: COC(=O)c1cc(OC)ccc1Nc1ccc(N(C)c2ccc(C3CCCCC3)nc2)cc1] | LC-MS: m/z 446.05 (M + H)+ |
| 579 | XII.116 | XI.53 | 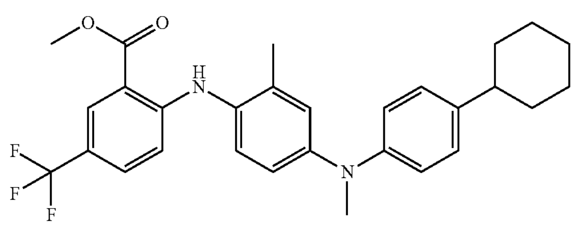 [SMILES: COC(=O)c1cc(C(F)(F)F)ccc1Nc1ccc(N(C)c2ccc(C3CCCCC3)cc2)cc1C] | LC-MS: m/z 496.05 (M + H)+ |
| 580 | XII.117 | XI.53 | 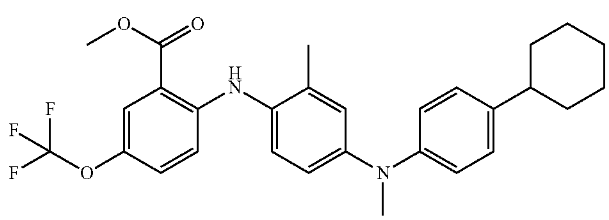 [SMILES: COC(=O)c1cc(OC(F)(F)F)ccc1Nc1ccc(N(C)c2ccc(C3CCCCC3)cc2)cc1C] | LC-MS: m/z 512.10 (M + H)+. |
| 581 | XII.118 | XI.68 | 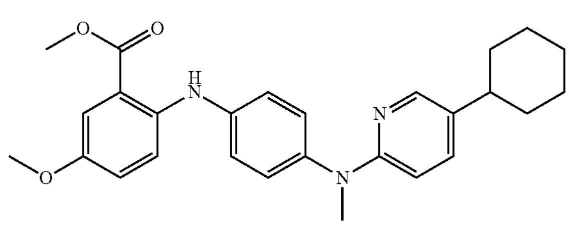 [SMILES: COC(=O)c1cc(OC)ccc1Nc1ccc(N(C)c2ccc(C3CCCCC3)cn2)cc1] | LC-MS: m/z 446.65 (M + H)+ |

| CP | Intermediate No. | Reactant | Structure | Analytical data |
|---|---|---|---|---|
| 582 | XII.119 | XI.69 | 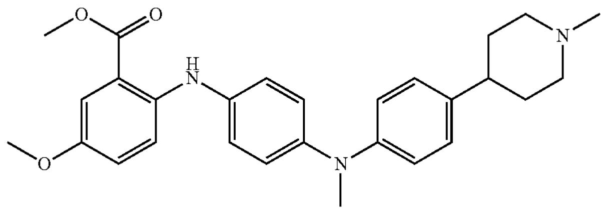 | 1H NMR (400 MHz, DMSO-d6) δ 8.83 (s, 1H), 7.35 (d, J = 2.8 Hz, 1H), 7.15-7.10 (m, 6H), 7.00-6.98 (m, 2H), 6.90-6.87 (m, 2H 3.85 (s, 3H), 3.72 (s, 3H), 3.24-3.21 (m, 5H), 2.67-2.58 (m, 6H), 1.85-1.74 (m, 4H) LC-MS: m/z 459.25 (M + H)+ |
| 585 | XII.120 | XI.70 | 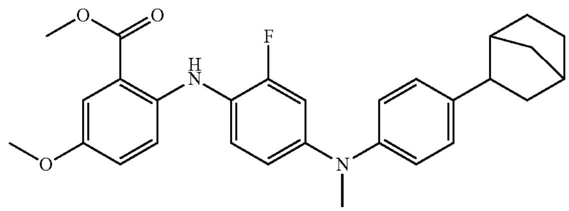 [SMILES: COC(=O)c1cc(OC)ccc1Nc1ccc(N(C)c2ccc(C3CC4CCC3C4)cc2)cc1F] | LC-MS: m/z 475.3 (M + H)+ |
| 586 | XII.121 | XI.71 | 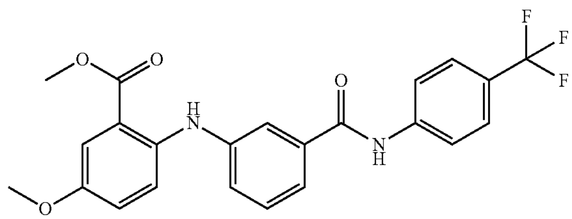 [SMILES: COC(=O)c1cc(OC)ccc1Nc1cccc(C(=O)Nc2ccc(C(F)(F)F)cc2)c1] | LC-MS: m/z 445.0 (M + H)+ |
| 587 | XII.122 | IX.12 | 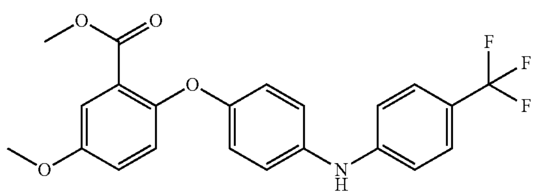 [SMILES: COC(=O)c1cc(OC)ccc1Oc1ccc(Nc2ccc(C(F)(F)F)cc2)cc1] | LC-MS: m/z 418.2 (M + H)+ |
| 588 | XII.123 | XI.72 | 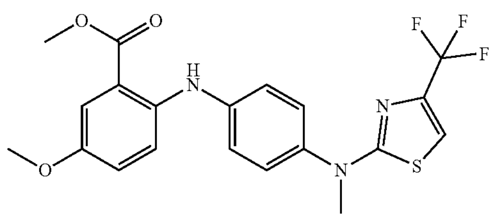 [SMILES: COC(=O)c1cc(OC)ccc1Nc1ccc(N(C)c2nc(C(F)(F)F)cs2)cc1] | LC-MS: m/z 438.1 (M + H)+ |
| 589 | XII.124 | XI.73 | 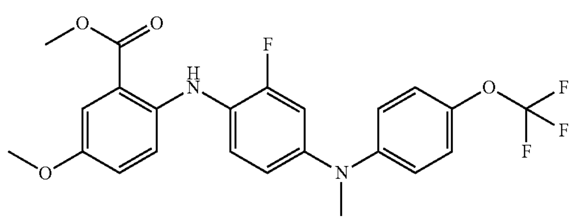 [SMILES: COC(=O)c1cc(OC)ccc1Nc1ccc(N(C)c2ccc(OC(F)(F)F)cc2)cc1F] | LC-MS: m/z 465.2 (M + H)+ |
| 590 | XII.125 | XI.74 | 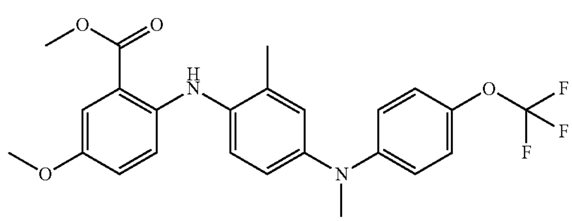 [SMILES: COC(=O)c1cc(OC)ccc1Nc1ccc(N(C)c2ccc(OC(F)(F)F)cc2)cc1C] | LC-MS: m/z 461.2 (M + H)+ |

| CP | Intermediate No. | Reactant | Structure | Analytical data |
|---|---|---|---|---|
| 591 | XII.126 | IX.9 | 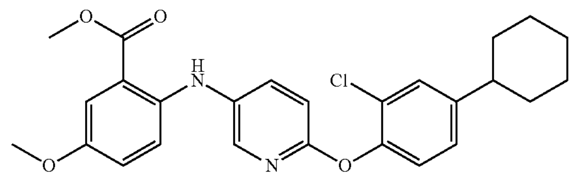 [SMILES: COC(=O)c1cc(OC)ccc1Nc1ccc(Oc2ccc(C3CCCCC3)cc2Cl)nc1] | LC-MS: m/z 467.05 (M + H)+ |
| 592 | XII.127 | XI.75 | 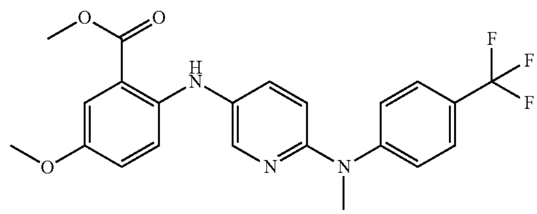 [SMILES: COC(=O)c1cc(OC)ccc1Nc1ccc(N(C)c2ccc(C(F)(F)F)cc2)nc1] | LC-MS: m/z 432.2 (M + H)+ |
| 593 | XII.128 | XI.76 | 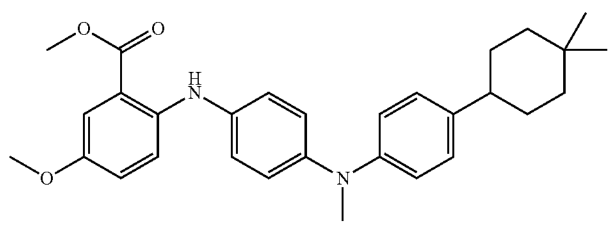 | LC-MS: m/z 472.1 (M + H)+ |
| 594 | XII.129 | VII.111 | 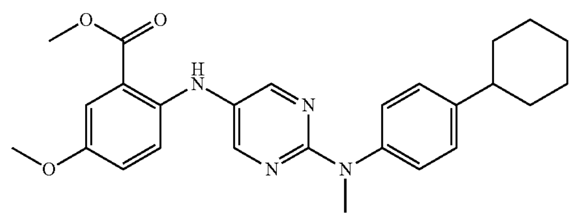 [SMILES: COC(=O)c1cc(OC)ccc1Nc1cnc(N(C)c2ccc(C3CCCCC3)cc2)nc1] | LC-MS: m/z 447.1 (M + H)+ |
| 595 | XII.130 | XI.77 | 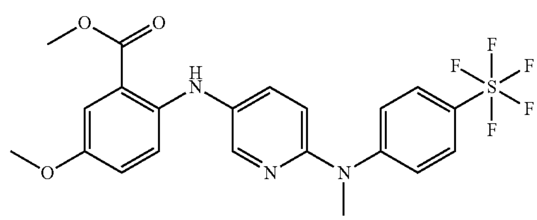 [SMILES: COC(=O)c1cc(OC)ccc1Nc1ccc(N(C)c2ccc(S(F)(F)(F)(F)F)cc2)nc1] | LC-MS: m/z 490.1 (M + H)+ |
| 596 | XII.131 | XI.78 | 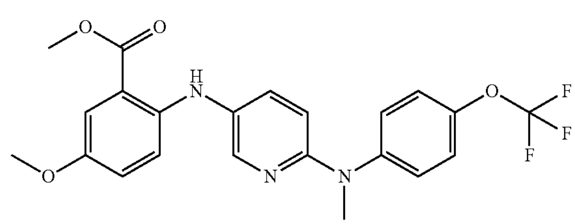 [SMILES: COC(=O)c1cc(OC)ccc1Nc1ccc(N(C)c2ccc(OC(F)(F)F)cc2)nc1] | LC-MS: m/z 448.2 (M + H)+ |
| 597 | XII.132 | XI.79 | 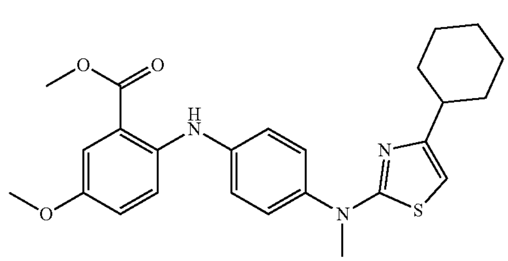 [SMILES: COC(=O)c1cc(OC)ccc1Nc1ccc(N(C)c2nc(C3CCCCC3)cs2)cc1] | LC-MS: m/z 452.2 (M + H)+ |

-continued
| CP | Intermediate No. | Reactant | Structure | Analytical data |
|---|---|---|---|---|
| 598 | XII.133 | VII.123 | 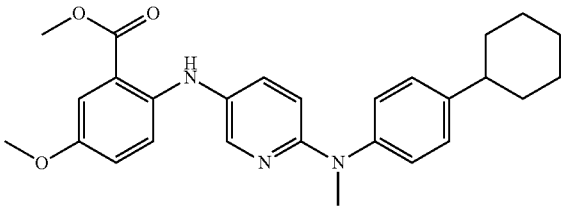 [SMILES: COC(=O)c1cc(OC)ccc1Nc1ccc(N(C)c2ccc(C3CCCCC3)cc2)nc1] | LC-MS: m/z 446.05 (M + H)+ |
| 599 | XII.134 | XI.81 | 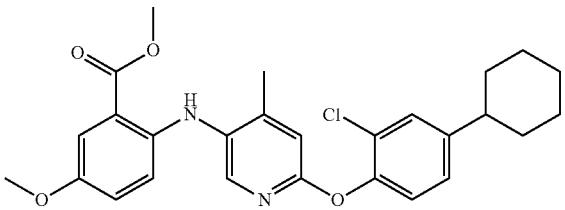 [SMILES: COC(=O)c1cc(OC)ccc1Nc1cnc(Oc2ccc(C3CCCCC3)cc2Cl)cc1C] | LC-MS: m/z 481.2 (M + H)+ |
| 600 | XII.135 | XI.82 | 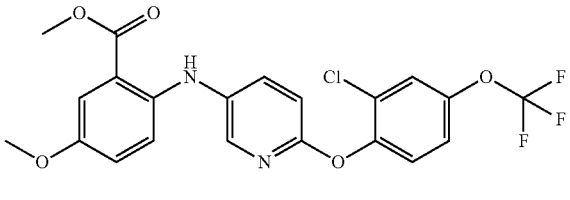 [SMILES: COC(=O)c1cc(OC)ccc1Nc1ccc(Oc2ccc(OC(F)(F)F)cc2Cl)nc1] | LC-MS: m/z 469.05 (M + H)+ |
| 601 | XII.136 | XI.83 | 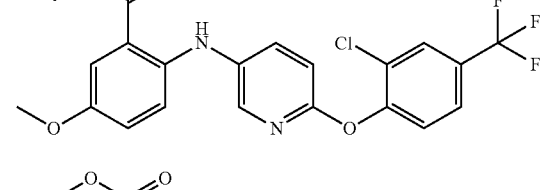 | LC-MS: m/z 453.9 (M + H)+ |
| 602 | XII.137 | VII.114 | 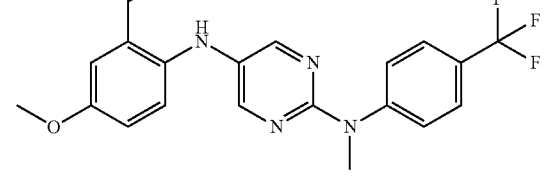 | LC-MS: m/z 433.10 (M + H)+ |
| 603 | XII.138 | XI.84 | 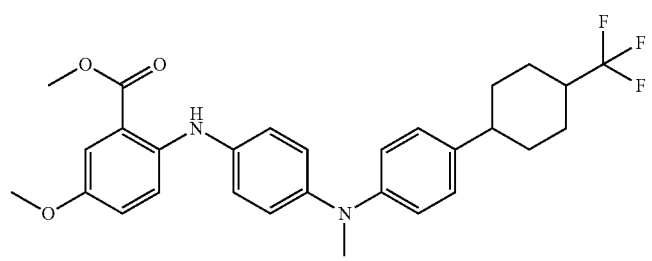 [SMILES: COC(=O)c1cc(OC)ccc1Nc1ccc(N(C)c2ccc(C3CCC(C(F)(F)F)CC3)cc2)cc1] | LC-MS: m/z 513.2 (M + H)+ |
| 609 | XII.139 | XI.85 | 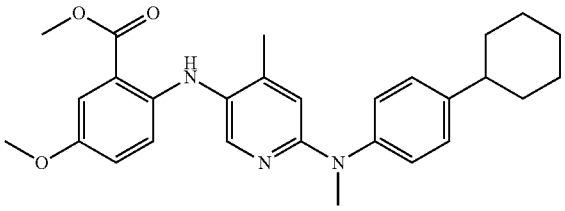 [SMILES: COC(=O)c1cc(OC)ccc1Nc1cnc(N(C)c2ccc(C3CCCCC3)cc2)cc1C] | LC-MS: m/z 460.3 (M + H)+ |

-continued

| CP | Intermediate No. | Reactant | Structure | Analytical data |
|---|---|---|---|---|
| 612 | XII.140 | XI.86 | 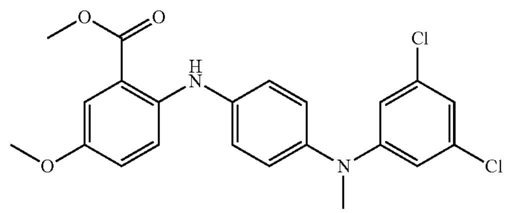 [SMILES: COC(=O)c1cc(OC)ccc1Nc1ccc(N(C)c2cc(Cl)cc(Cl)c2)cc1] | LC-MS: m/z 431.1 (M + H)+ |
| 613 | XII.141 | XI.32 | 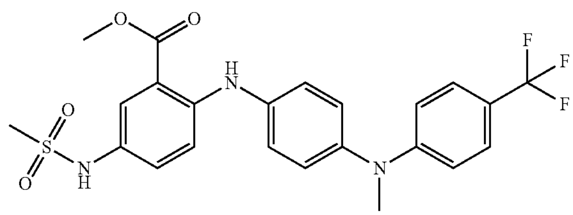 [SMILES: COC(=O)c1cc(NS(C)(=O)=O)ccc1Nc1ccc(N(C)c2ccc(C(F)(F)F)cc2)cc1] | LC-MS: m/z 494.2 (M + H)+ |
| 614 | XII.142 | XI.53 | 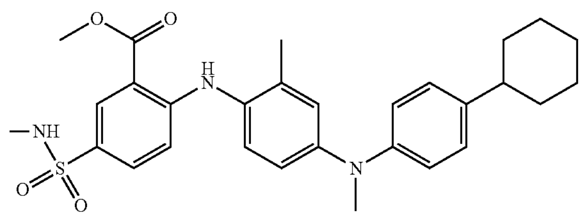 [SMILES: CNS(=O)(=O)c1ccc(Nc2ccc(N(C)c3ccc(C4CCCCC4)cc3)cc2C)c(C(=O)OC)c1] | LC-MS: m/z 522.2 (M + H)+ |
| 615 | XII.143 | XI.87 | 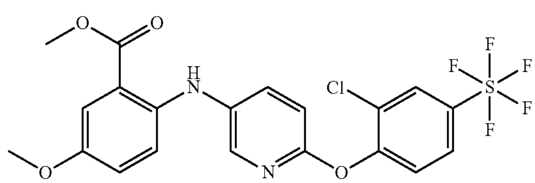 [SMILES: COC(=O)c1cc(OC)ccc1Nc1ccc(Oc2ccc(S(F)(F)(F)(F)F)cc2Cl)nc1] | LC-MS: m/z 511.0 (M + H)+ |
| 616 | XII.144 | IX.18 | 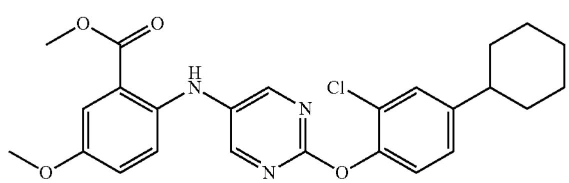 [SMILES: COC(=O)c1cc(OC)ccc1Nc1cnc(Oc2ccc(C3CCCCC3)cc2Cl)nc1] | LC-MS: m/z 468.1 (M + H)+ |
| 617 | XII.145 | XI.88 | 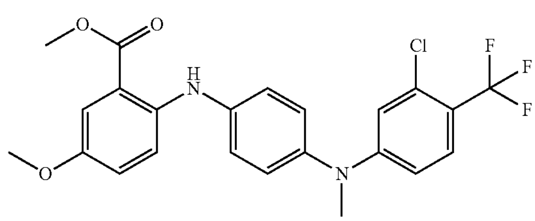 [SMILES: COC(=O)c1cc(OC)ccc1Nc1ccc(N(C)c2ccc(C(F)(F)F)c(Cl)c2)cc1] | LC-MS: m/z 465.1 (M + H)+ |
| 618 | XII.146 | XI.89 | 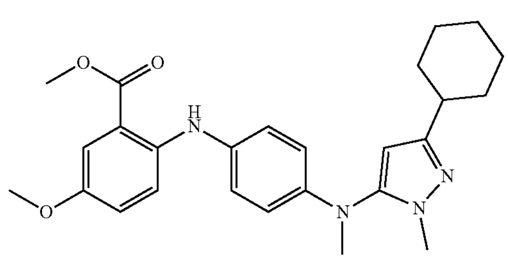 [SMILES: COC(=O)c1cc(OC)ccc1Nc1ccc(N(C)c2cc(C3CCCCC3)nn2C)cc1] | LC-MS: m/z 449.2 (M + H)+ |

-continued

| CP | Intermediate No. | Reactant | Structure | Analytical data |
|---|---|---|---|---|
| 619 | XII.147 | XI.53 | 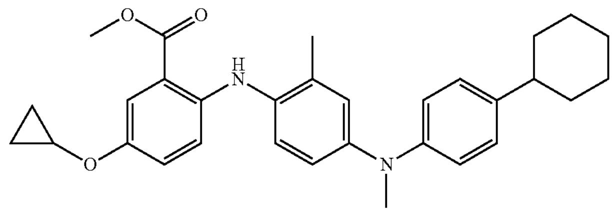 [SMILES: COC(=O)c1cc(OC2CC2)ccc1Nc1ccc(N(C)c2ccc(C3CCCCC3)cc2)cc1C] | LC-MS: m/z 485.2 (M + H)+ |
| 620 | XII.148 | XI.53 | 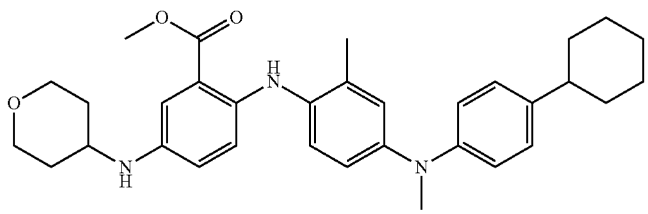 [SMILES: COC(=O)c1cc(NC2CCOCC2)ccc1Nc1ccc(N(C)c2ccc(C3CCCCC3)cc2)cc1C] | LC-MS: m/z 528.2 (M + H)+ |
| 621 | XII.149 | XI.53 | 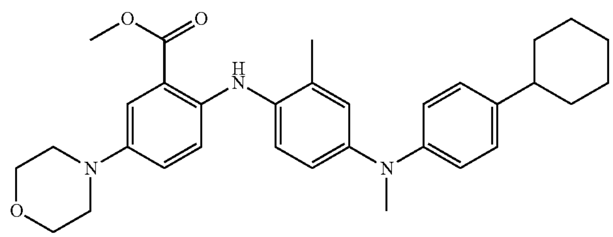 | LC-MS: m/z 528.4 (M + H)+ |
| 622 | XII.150 | XI.90 | 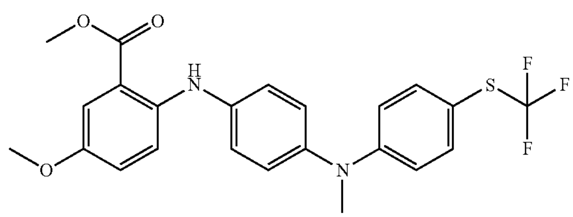 [SMILES: COC(=O)c1cc(OC)ccc1Nc1ccc(N(C)c2ccc(SC(F)(F)F)cc2)cc1] | LC-MS: m/z 463.0 (M + H)+ |
| 624 | XII.151 | XI.91 | 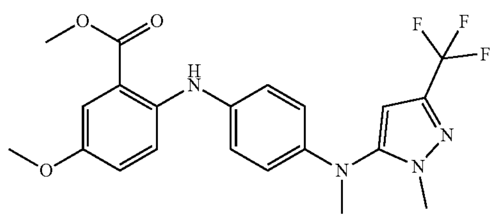 [SMILES: COC(=O)c1cc(OC)ccc1Nc1ccc(N(C)c2cc(C(F)(F)F)nn2C)cc1] | LC-MS: m/z 435.1 (M + H)+ |
| 625 | XII.152 | XI.53 | 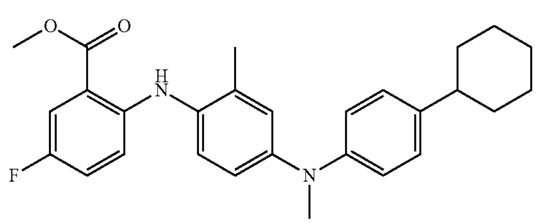 [SMILES: COC(=O)c1cc(F)ccc1Nc1ccc(N(C)c2ccc(C3CCCCC3)cc2)cc1C] | LC-MS: m/z 447.2 (M + H)+ |
| 626 | XII.153 | XI.92 | 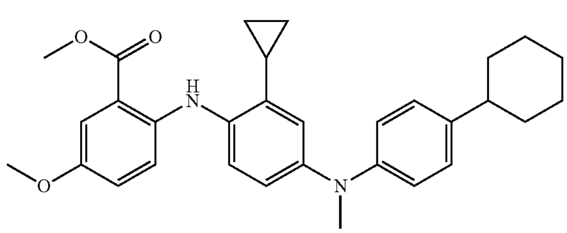 [SMILES: COC(=O)c1cc(OC)ccc1Nc1ccc(N(C)c2ccc(C3CCCCC3)cc2)cc1C1CC1] | LC-MS: m/z 484.2 (M + H)+ |

| CP | Intermediate No. | Reactant | Structure | Analytical data |
|---|---|---|---|---|
| 627 | XII.154 | XI.53 | 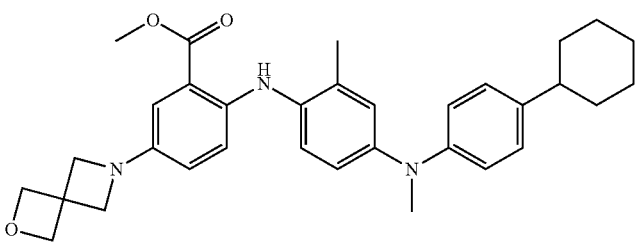 [SMILES: COC(=O)c1cc(N2CC3(COC3)C2)ccc1Nc1ccc(N(C)c2ccc(C3CCCCC3)cc2)cc1C] | LC-MS: m/z 526.3 (M + H)+ |
| 628 | XII.155 | XI.53 | 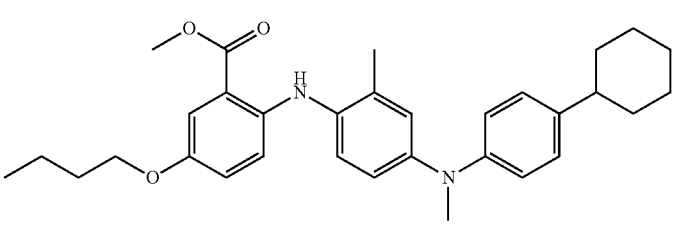 [SMILES: CCCCOc1ccc(Nc2ccc(N(C)c3ccc(C4CCCCC4)cc3)cc2C)c(C(=O)OC)c1] | $^1$H NMR (400 MHz, DMSO-d6) δ 8.90-8.69 (s, 1H), 7.82-7.79 (m, 1H), 7.57-7.42 (m, 2H), 7.39-7.35 (m, 2H), 7.14-7.10 (m, 2H), 6.93 (s, 1H), 6.83-6.78 (m, 1H), 6.74 (d, J = 9.2 Hz, 1H), 3.92-3.89 (m, 2H), 3.87 (s, 3H), 3.22 (s, 3H), 2.47-2.30 (m, 1H), 2.13 (s, 3H), 1.80-1.65 (m, 6H), 1.48-1.18 (m, 8H), 0.96-0.94 (m, 3H). |
| 630 | XII.156 | XI.53 | 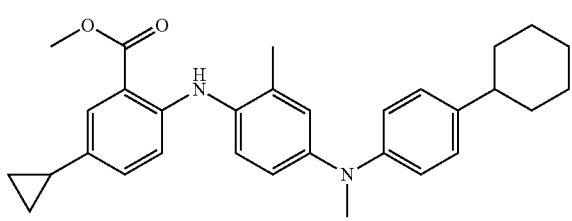 [SMILES: COC(=O)c1cc(C2CC2)ccc1Nc1ccc(N(C)c2ccc(C3CCCCC3)cc2)cc1C] | 1H NMR (400 MHz, DMSO-d6) δ 8.86 (s, 1H), 7.61 (d, J = 2.4 Hz, 1H), 7.15-7.07 (m, 4H), 6.95-6.90 (m, 3H), 6.79 (dd, J1 = 2.8 Hz, J2 = 8.8 Hz, 1H), 6.64 (d, J = 8.0 Hz, 1H), 3.86 (s, 3H), 3.23 (s, 3H), 2.46-2.42 (m, 1H), 2.11 (s, 3H), 1.87-1.68 (m, 6H), 1.39-1.30 (m, 5H), 0.87-0.83 (m, 2H), 0.56-0.52 (m, 2H). |
| 631 | XII.157 | XI.53 | 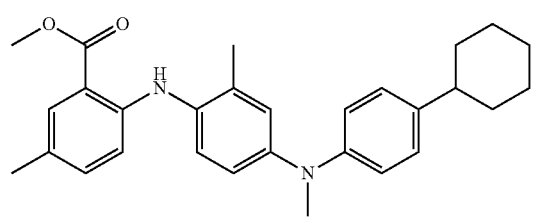 [SMILES: COC(=O)c1cc(C)ccc1Nc1ccc(N(C)c2ccc(C3CCCCC3)cc2)cc1C] | 1H NMR (400 MHz, DMSO-d6) δ 8.88 (s, 1H), 7.68 (s, 1H), 7.20-7.12 (m, 4H), 6.95-6.92 (m, 3H), 6.80-6.78 (m, 1H), 6.65-6.64 (d, J = 8.4 Hz, 1H), 3.84 (s, 3H), 3.22 (s, 3H), 2.24 (s, 1H), 2.20 (s, 3H), 2.10 (s, 3H), 1.80-1.77 (m, 6H), 1.39-1.33 (m, 4H). |
| 632 | XII.158 | XI.53 | 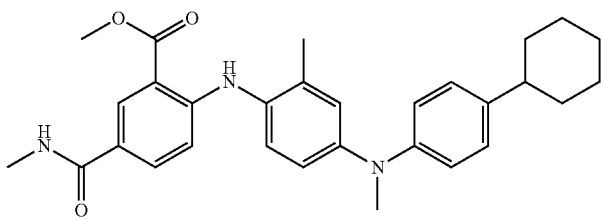 | LC-MS: m/z 486.3 (M + H)+ |

-continued

| CP | Intermediate No. | Reactant | Structure | Analytical data |
|---|---|---|---|---|
| 633 | XII.159 | XI.53 | 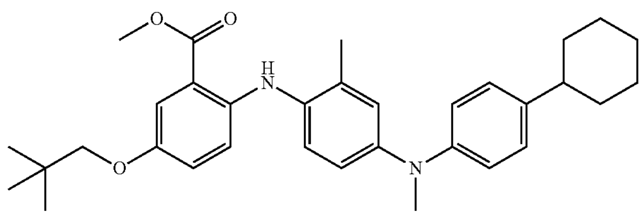 [SMILES: COC(=O)c1cc(OCC(C)(C)C)ccc1Nc1ccc(N(C)c2ccc(C3CCCCC3)cc2)cc1C] | 1H NMR (400 MHz, DMSO-d6) δ 8.70 (s, 1H), 7.36 (d, J = 3.2 Hz, 2H), 7.13-7.10 (m, 3H), 6.93-6.91 (m, 3H), 6.75-6.73 (m, 2H), 4.05-4.00 (m, 1H), 3.86 (s, 3H), 3.56 (s, 2H), 3.22 (s, 3H), 2.12 (s, 3H), 1.79-1.68 (m, 2H), 1.30-1.16 (m, 8H), 0.99 (s, 9H). |
| 634 | XII.160 | XI.53 | 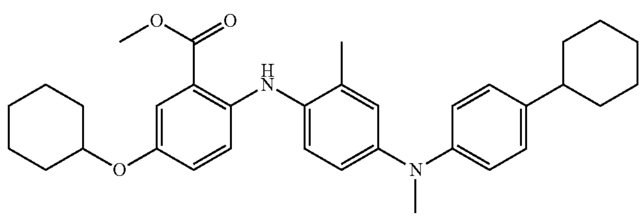 [SMILES: COC(=O)c1cc(OC2CCCCC2)ccc1Nc1ccc(N(C)c2ccc(C3CCCCC3)cc2)cc1C] | 1H NMR (400 MHz, DMSO-d6) δ 8.67 (s, 1H), 7.35 (d, J = 2.8 Hz, 1H), 7.10 (dd, J1 = 2.4 Hz, J2 = 8.4 Hz, 3H), 7.05 (dd, J1 = 3.2 Hz, J2 = 9.2 Hz, 1H), 6.91-6.89 (m, 3H), 6.77 (dd, J1 = 2.4 Hz, J2 = 8.4 Hz, 1H), 6.71 (d, J = 9.2 Hz, 1H), 4.14-4.10 (m, 1H), 3.83 (s, 3H), 3.20 (s, 3H), 2.45-2.35 (m, 1H), 2.10 (s, 3H), 1.86-1.67 (m, 7H), 1.50-1.20 (m, 13H). |
| 635 | XII.161 | XI.53 | 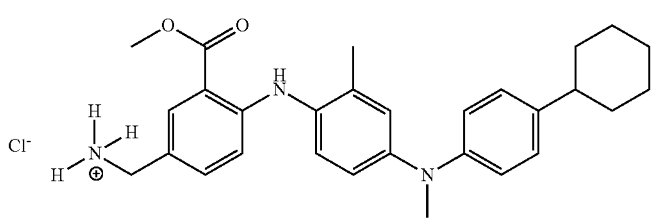 | LC-MS: m/z 444.2 (M − 95)+ COCF3 fragment |
| 636 | XII.162 | XI.53 | 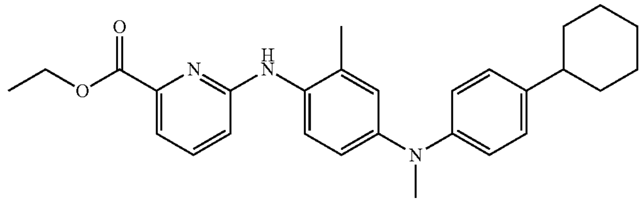 [SMILES: CCOC(=O)c1cccc(Nc2ccc(N(C)c3ccc(C4CCCCC4)cc3)cc2C)n1] | LC-MS: m/z 444.20 (M + H)+. |
| 637 | XII.163 | XI.53 | 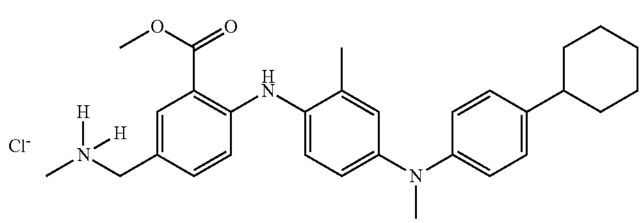 | LC-MS: m/z 568.3 (M + H)+ |

-continued

| CP | Intermediate No. | Reactant | Structure | Analytical data |
|---|---|---|---|---|
| 640 | XII.164 | XI.53 | 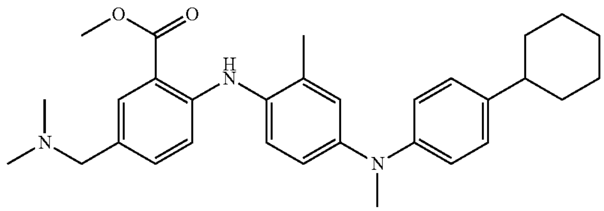 | LC-MS: m/z 456.3 (M − H)+ |
| 641 | XII.165 | XI.93 | 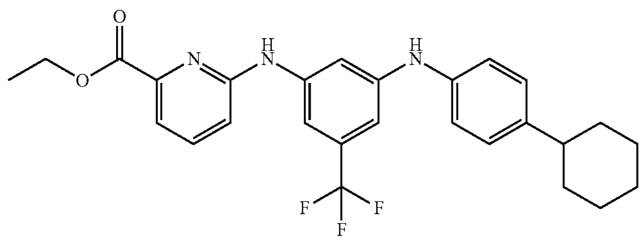 [SMILES: CCOC(=O)c1cccc(Nc2cc(Nc3ccc(C4CCCCC4)cc3)cc(C(F)(F)F)c2)n1] | LC-MS: m/z 484.1 (M + H)+ |
| 642 | XII.166 | XI.94 | 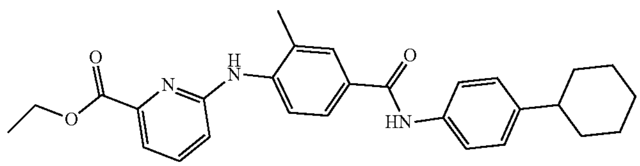 [SMILES: CCOC(=O)c1cccc(Nc2ccc(C(=O)Nc3ccc(C4CCCCC4)cc3)cc2C)n1] | LC-MS: m/z 458.2 (M + H)+ |
| 643 | XII.167 | XI.81 | 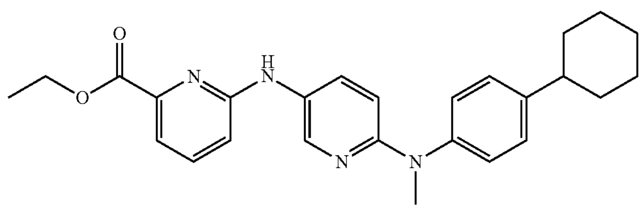 [SMILES: CCOC(=O)c1cccc(Nc2ccc(N(C)c3ccc(C4CCCCC4)cc3)nc2)n1] | LC-MS: m/z 431.25 (M + H)+ |
| 646 | XII.168 | XI.95 | 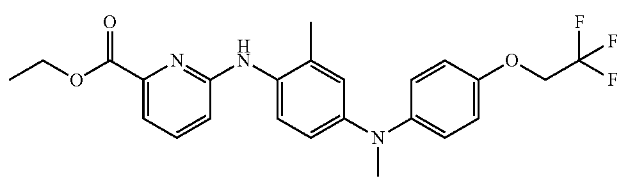 [SMILES: CCOC(=O)c1cccc(Nc2ccc(N(C)c3ccc(OCC(F)(F)F)cc3)cc2C)n1] | LC-MS: m/z 460.2 (M + H)+ |
| 647 | XII.169 | XI.96 | 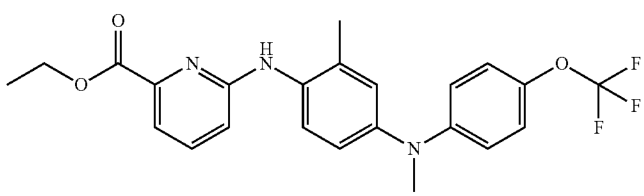 [SMILES: CCOC(=O)c1cccc(Nc2ccc(N(C)c3ccc(OC(F)(F)F)cc3)cc2C)n1] | LC-MS: m/z 446.1 (M + H)+ |
| 648 | XII.170 | XI.32 | 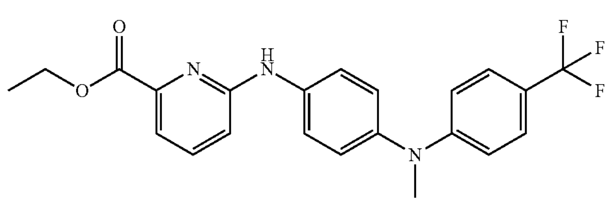 [SMILES: CCOC(=O)c1cccc(Nc2ccc(N(C)c3ccc(C(F)(F)F)cc3)cc2)n1] | LC-MS: m/z 416.05 (M + H)+ |

-continued

| CP | Intermediate No. | Reactant | Structure | Analytical data |
|---|---|---|---|---|
| 649 | XII.171 | VIII.7 | 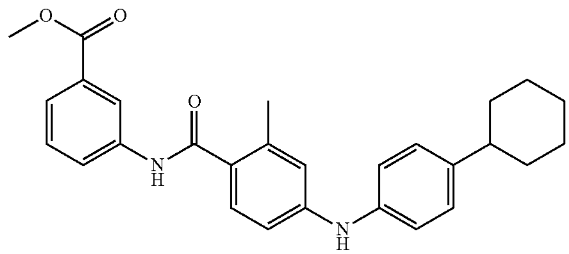 [SMILES: COC(=O)c1cccc(NC(=O)c2ccc(Nc3ccc(C4CCCCC4)cc3)cc2C)c1] | LC-MS: m/z 443.3 (M + H)+ |
| 650 | XII.172 | VII | 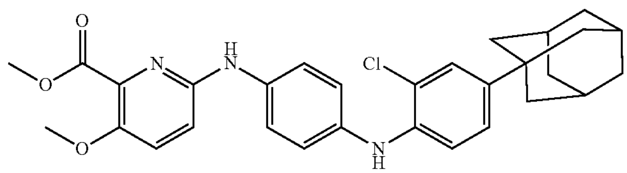 [SMILES: COC(=O)c1nc(Nc2ccc(Nc3ccc(C45CC6CC(CC(C6)C4)C5)cc3Cl)cc2)ccc1OC] | LC-MS: m/z 519.2 (M + H)+ |
| 652 | XII.173 | XI.85 | 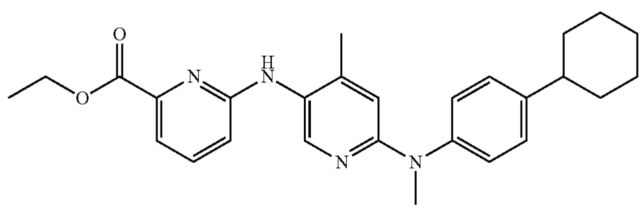 [SMILES: CCOC(=O)c1cccc(Nc2cnc(N(C)c3ccc(C4CCCCC4)cc3)cc2C)n1] | LC-MS: m/z 445.3 (M + H)+ |
| 654 | XII.174 | XI.80 | 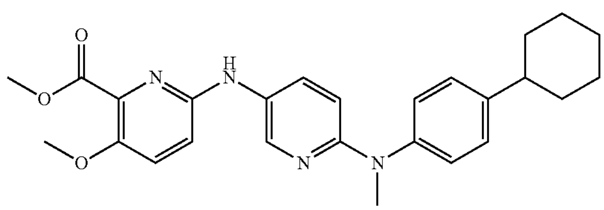 [SMILES: COC(=O)c1nc(Nc2ccc(N(C)c3ccc(C4CCCCC4)cc3)nc2)ccc1OC] | LC-MS: m/z 447.0 (M + H)+ |
| 655 | XII.175 | XI.80 | 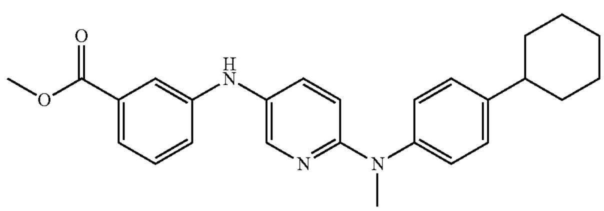 [SMILES: COC(=O)c1cccc(Nc2ccc(N(C)c3ccc(C4CCCCC4)cc3)nc2)c1] | LC-MS: m/z 416.2 (M + H)+ |
| 656 | XII.176 | XI.53 | 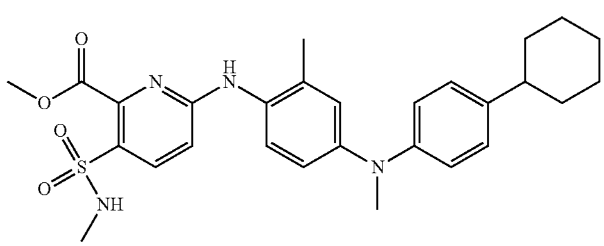 [SMILES: CNS(=O)(=O)c1ccc(Nc2ccc(N(C)c3ccc(C4CCCCC4)cc3)cc2C)nc1C(=O)OC] | LC-MS: m/z 522.2 (M + H)+ |
| 659 | XII.177 | XI.97 | 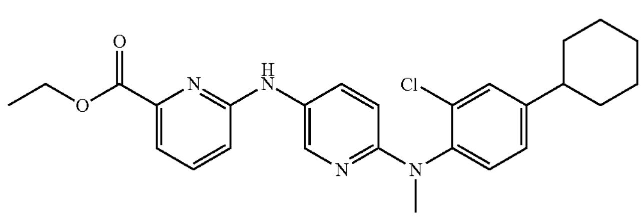 [SMILES: CCOC(=O)c1cccc(Nc2ccc(N(C)c3ccc(C4CCCCC4)cc3Cl)nc2)n1] | LC-MS: m/z 465.2 (M + H)+ |

-continued
| CP | Intermediate No. | Reactant | Structure | Analytical data |
|---|---|---|---|---|
| 660 | XII.178 | XI.98 | 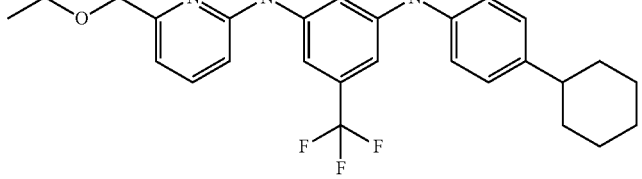 | LC-MS: m/z 518.1 (M + H)+ |
| 661 | XII.179 | XI.99 | 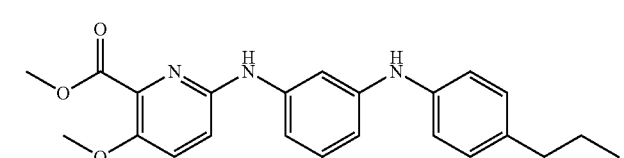 | LC-MS: m/z 499.2 (M − H)+ |
| 662 | XII.180 | XI.99 | 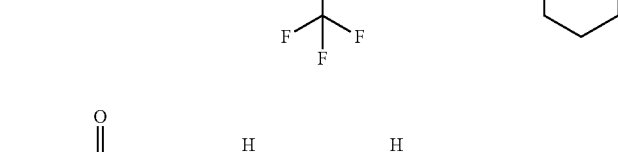 | LC-MS: m/z 469.2 (M + H)+ |
| 663 | XII.181 | XI.100 | 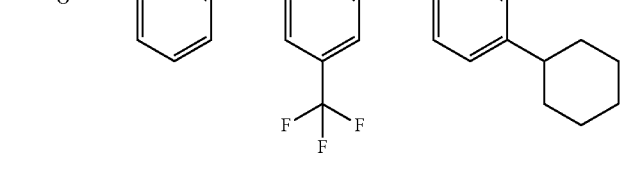 | LC-MS: m/z 471.2 (M + H)+ |
| 665 | XII.182 | XI.101 | 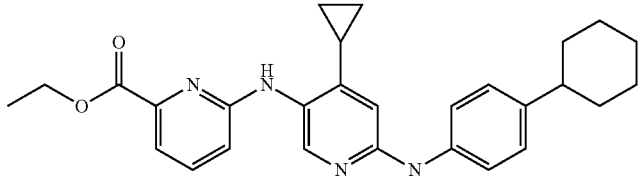 | LC-MS: m/z 464.2 (M + H)+ |
| 666 | XII.183 | XI.101 | 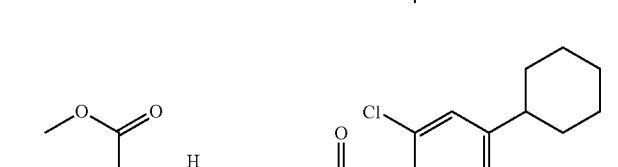 | LC-MS: m/z 463.2 (M + H)+ |

-continued

| CP | Intermediate No. | Reactant | Structure | Analytical data |
|---|---|---|---|---|
| 669 | XII.184 | XI.101 | 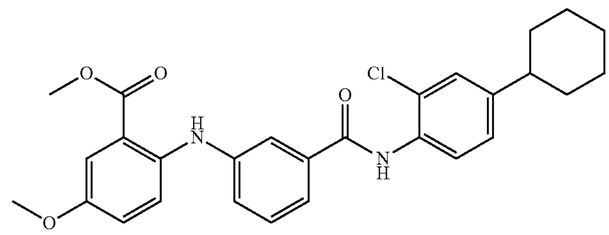 [SMILES: COC(=O)c1cc(OC)ccc1Nc1cccc(C(=O)Nc2ccc(C3CCCCC3)cc2Cl)c1] | LC-MS: m/z 493.2 (M + H)+ |
| 671 | XII.185 | XI.102 | 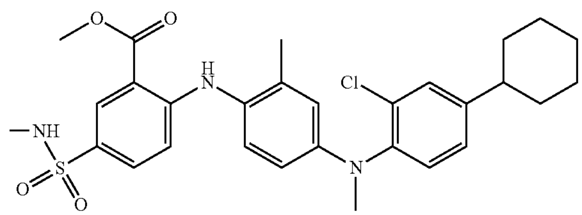 [SMILES: CNS(=O)(=O)c1ccc(Nc2ccc(N(C)c3ccc(C4CCCCC4)cc3Cl)cc2C)c(C(=O)OC)c1] | LC-MS: m/z 556.2 (M + H)+ |
| 672 | XII.186 | XI.101 | 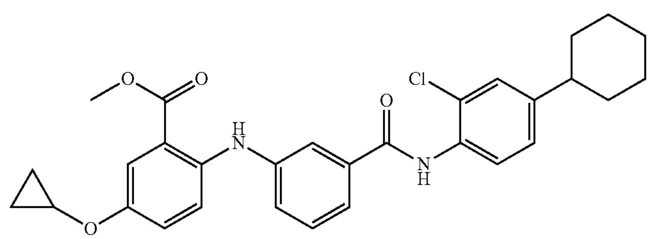 [SMILES: COC(=O)c1cc(OC2CC2)ccc1Nc1cccc(C(=O)Nc2ccc(C3CCCCC3)cc2Cl)c1] | LC-MS: m/z 519.2 (M + H)+ |
| 673 | XII.187 | XI.85 | 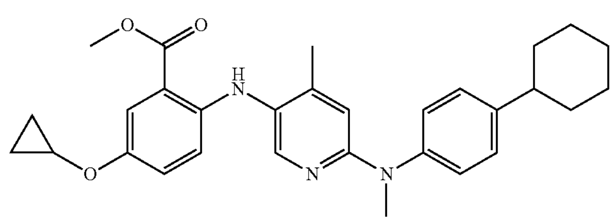 [SMILES: COC(=O)c1cc(OC2CC2)ccc1Nc1cnc(N(C)c2ccc(C3CCCCC3)cc2)cc1C] | LC-MS: m/z 486.25 (M + H)+ |
| 675 | XII.188 | XI.98 | 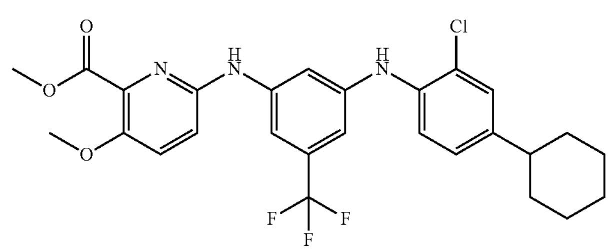 [SMILES: COC(=O)c1nc(Nc2cc(Nc3ccc(C4CCCCC4)cc3Cl)cc(C(F)(F)F)c2)ccc1OC] | LC-MS: m/z 534.2 (M + H)+ |
| 676 | XII.189 | XI.98 | 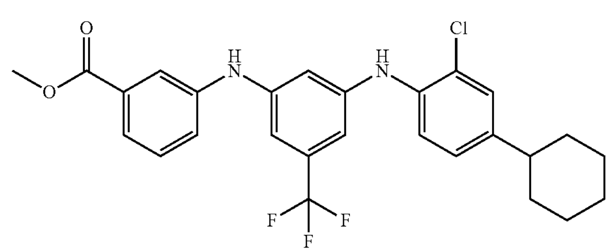 [SMILES: COC(=O)c1cccc(Nc2cc(Nc3ccc(C4CCCCC4)cc3Cl)cc(C(F)(F)F)c2)c1] | LC-MS: m/z 503.2 (M + H)+ |

-continued
| CP | Intermediate No. | Reactant | Structure | Analytical data |
|---|---|---|---|---|
| 677 | XII.190 | XI.104 | 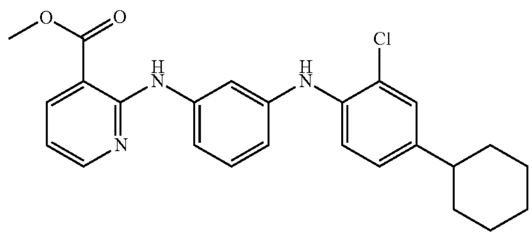 [SMILES: COC(=O)c1cccnc1Nc1cccc(Nc2ccc(C3CCCCC3)cc2Cl)c1] | LC-MS: m/z 436.1 (M + H)+ |
| 678 | XII.191 | XI.53 | 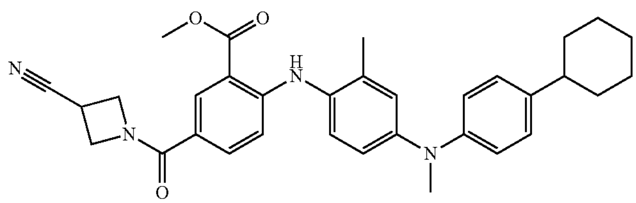 [SMILES: COC(=O)c1cc(C(=O)N2CC(C#N)C2)ccc1Nc1ccc(N(C)c2ccc(C3CCCCC3)cc2)cc1C] | LC-MS: m/z 537.3 (M + H)+ |
| 680 | XII.192 | XI.103 | 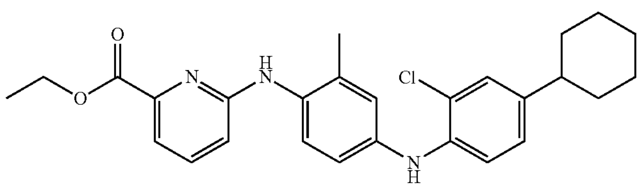 [SMILES: CCOC(=O)c1cccc(Nc2ccc(Nc3ccc(C4CCCCC4)cc3Cl)cc2C)n1] | LC-MS: m/z 464.1 (M + H)+ |
| 681 | XII.193 | XI.102 | 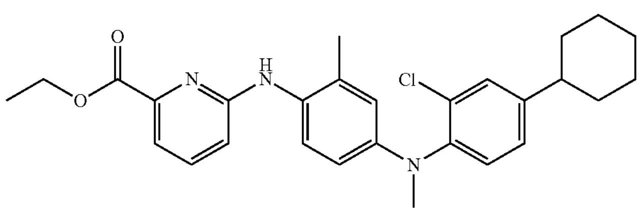 [SMILES: CCOC(=O)c1cccc(Nc2ccc(N(C)c3ccc(C4CCCCC4)cc3Cl)cc2C)n1] | LC-MS: m/z 478.2 (M + H)+ |
| 682 | XII.194 | XI.104 | 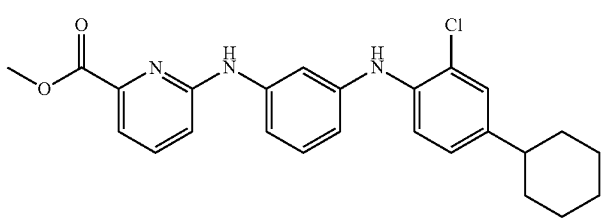 | LC-MS: m/z 450.2 (M + H)+ |
Intermediate-XIII
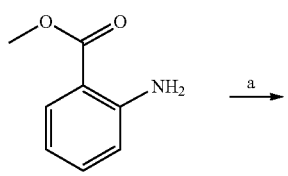
a →
-continued
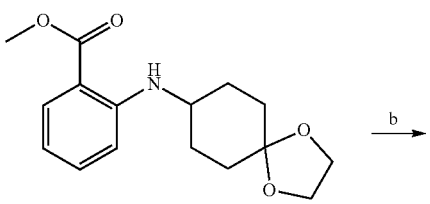
XIIIa
b →

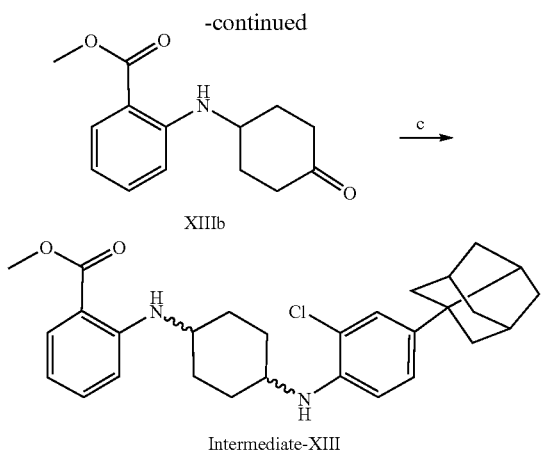

Step-a: Synthesis of methyl 2-((1,4-dioxaspiro[4.5]decan-8-yl)amino)benzoate (XIIIa)

A solution of methyl anthranilate (3 g, 20 mmol, 1 eq.) and 1,4-Cyclohexanedione monoethylene acetal (4.6 g, 30 mmol, 1.5 eq.) in dichloroethane (50 mL) was added with acetic acid (20 mL) and stirred at RT for 2 h. Reaction mass was cooled to 0° C. and added with sodium triacetoxyborohydride (6.3 g, 30 mmol, 1.5 eq.) and allowed to stir at RT for 36 h. Reaction mass was added with saturated bicarbonate solution and extracted with dichloromethane, purified by combi-flash to afford title product (1.01 g, 17%).

$^1$H NMR (400 MHz, DMSO-d6) δ 7.77 (d, J=7.6 Hz, 1H), 7.71 (d, J=7.6 Hz, 1H), 7.39-7.35 (m, 1H), 6.83 (d, J=8.8 Hz, 1H), 6.57-6.53 (m, 1H), 3.87 (s, 4H), 3.78 (s, 3H), 3.60-3.58 (m, 1H), 1.95-1.90 (m, 2H), 1.70-1.61 (m, 4H), 1.60-1.48 (m, 2H); LC-MS: m/z 292.0 (M+H)$^+$

Step-b: Synthesis of methyl 2-((4-oxocyclohexyl)amino)benzoate (XIIIb)

A solution of compound XIIIa (1.01 g, 3.4 mmol, 1 eq.) in acetone (30 mL) was added with 2N HCl (10 mL) and allowed to stir at RT overnight. Reaction mass was extracted with ethyl acetate from water and concentrated in vacuo. The crude was used further without purification.

$^1$H NMR (400 MHz, DMSO-d6) δ 7.81 (dd, J$_1$=0.8 Hz, J$_2$=7.6 Hz, 1H), 7.75 (d, J=7.6 Hz, 1H), 6.94 (d, J=8.8 Hz, 1H), 6.59 (t, J=7.6 Hz, 1H), 3.97-3.95 (m, 1H), 3.79 (s, 3H), 2.57-2.53 (m, 2H), 2.29-2.19 (m, 4H), 1.77-1.72 (m, 2H); LC-MS: m/z 248.2 (M+H)$^+$

Step-c: Synthesis of methyl 2-((4-((4-((3r,5r,7r)-adamantan-1-yl)-2-chlorophenyl) amino)cyclohexyl) amino) benzoate (Intermediate-XIII)

A solution of compound XIIIb (0.5 g, 2.02 mmol, 1 eq.) and Intermediate-I (0.53 g, 2.02 mmol, 1 eq.) in acetic acid (10 mL) was added with sodium triacetoxyborohydride (1.28 g, 6.06 mmol, 3 eq.) and heated at 8° C. for 16 h. Reaction mass was extracted with ethyl acetate from sat. bicarbonate and brine and concentrated in vacuo. Crude was purified by combi-flash to afford title compound as pale pink liquid (0.67 g, 67%). LC-MS: m/z 493.3 (M+H)$^+$ The below intermediates were prepared by a procedure similar to Intermediate-XIII using appropriate reactants and reagents and in presence of suitable solvents and appropriate reaction conditions.

| CP | Intermediate No. | Reactant | Structure | Analytical data |
|---|---|---|---|---|
| 102, 103 | XIII.1 | Int-XI | 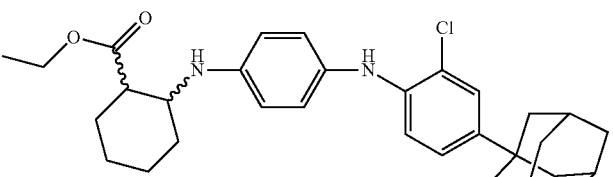 | $^1$H NMR (400 MHz, DMSO-d6) δ 7.27 (s, 1H), 7.02 (dd, J$_1$ = 2.4 Hz, J$_2$ = 8.8 Hz, 1H), 6.98 (d, J = 8.8 Hz, 2H), 6.85 (d, J = 8.8 Hz, 1H), 6.61 (d, J = 8.8 Hz, 2H), 5.74 (s, 1H), 4.15-4.03 (m, 2H), 3.52 (m, 1H), 3.39 (s, 1H), 2.31-2.18 (m, 3H), 2.07 (s, 3H), 1.98-1.92 (m, 1H), 1.84 (s, 6H), 1.81-1.61 (m, 9H), 1.18 (t, J = 7.2 Hz, 3H), 1.12-1.05 (m, 1H). LC-MS: m/z 507.2 (M + H)$^+$ |
| 128, 129 | XIII.2 | XI.1 | 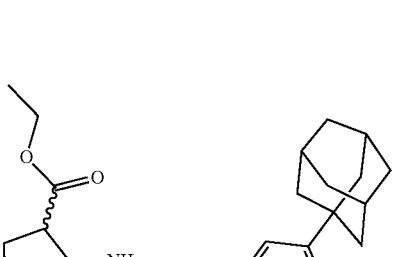 | LC-MS: m/z 561.2 (M + H)$^+$ |

-continued
| CP | Intermediate No. | Reactant | Structure | Analytical data |
|---|---|---|---|---|
| 130 | XIII.3 | Int-I.1 | 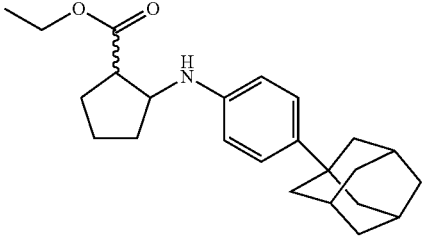 [SMILES: CCOC(=O)C1CCCC1Nc1ccc(C23CC4CC(CC(C4)C2)C3)cc1] | LC-MS: m/z 368.2 (M + H)$^+$ |
| 131 | XIII.4 | Int-I.1 | 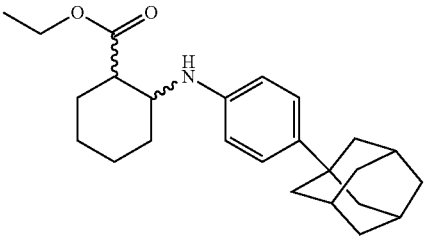 [SMILES: CCOC(=O)C1CCCCC1Nc1ccc(C23CC4CC(CC(C4)C2)C3)cc1] | $^1$H NMR (400 MHz, DMSO-d6) δ 7.02 (d, J = 8.4 Hz, 2H), 6.59 (d, J = 8.8 Hz, 2H), 5.01 (d, J = 9.6 Hz, 1H), 3.98-3.88 (m, 3H), 2.75-2.68 (m, 1H), 2.08 (s, 3H), 2.00-1.82 (m, 1H), 1.77 (m, 8H), 1.73-1.46 (m, 4H), 1.36-1.23 (m, 2H), 1.07 (t, J = 7.6 Hz, 3H). LC-MS: m/z 382.2 (M + H)$^+$ |
| 136 | XIII.5 | Int-XI | 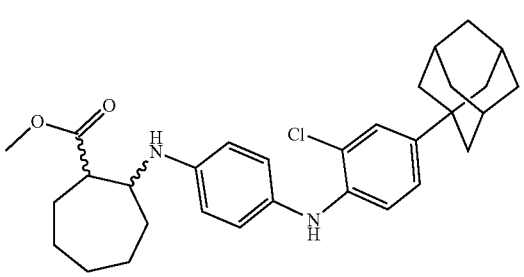 [SMILES: COC(=O)C1CCCCCC1Nc1ccc(Nc2ccc(C34CC5CC(CC(C5)C3)C4)cc2Cl)cc1] | LC-MS: m/z 507.3 (M + H)$^+$ |
| 162 | XIII.6 | Int-XI | 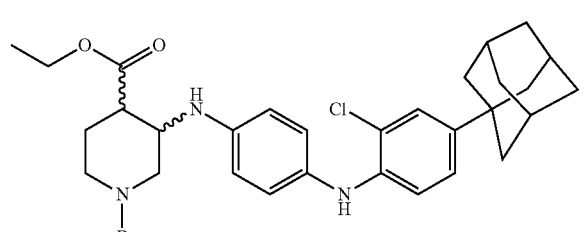 | LC-MS: m/z 608.2 (M + H)$^+$ |
| 172 | XIII.7 | Int-XI | 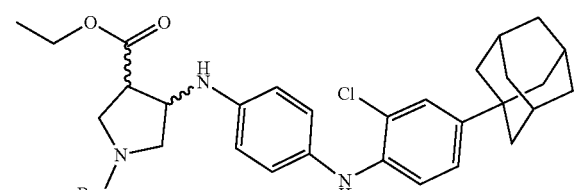 | LC-MS: m/z 594.2 (M + H)$^+$ |
| 244 | XIII.8 | Int-I | 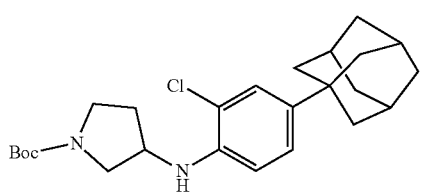 [SMILES: CC(C)(C)OC(=O)N1CCC(Nc2ccc(C34CC5CC(CC(C5)C3)C4)cc2Cl)C1] | LC-MS: m/z 375.1 (M − 55)$^+$ Boc fragment |

-continued
| CP | Intermediate No. | Reactant | Structure | Analytical data |
|---|---|---|---|---|
| 248 | XIII.9 | Int-I | | ¹H NMR (400 MHz, DMSO-d6) δ 7.19 (d, J = 1.9 Hz, 1H), 7.13 (d, J = 8.8 Hz, 1H), 6.76 (d, J = 8.8 Hz, 1H), 4.65-4.63 (m, 1H), 3.61-3.60 (m, 2H), 3.37-3.36 (m, 1H), 3.15-3.08 (m, 2H), 2.02 (bs, 3H), 1.89-1.88 (m, 1H), 1.73 (s, 6H), 1.70 (s, 6H), 1.63-1.62 (m, 2H), 1.26 (s, 9H). |
| 244 | XIII.10 | XIII.8 | 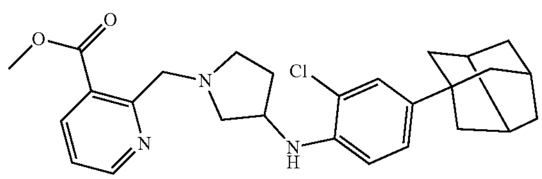 | ¹H NMR (400 MHz, DMSO-d6) δ 8.60 (s, 1H), 8.00 (s, 1H), 7.40 (s, 1H), 7.18 (d, J = 2.0 Hz, 1H), 7.11 (dd, J₁ = 2.0 Hz, J₂ = 8.8 Hz, 1H), 6.63 (d, J = 8.8 Hz, 1H), 4.60 (s, 1H), 3.97-3.89 (bs, 1H), 3.84 (s, 3H), 2.02 (s, 3H), 1.77 (s, 6H), 1.67 (s, 6H). LC-MS: m/z 480.1 (M + H)⁺ |
| 248 | XIII.11 | XIII.9 | | LC-MS: m/z 494.1 (M + H)⁺ |
| 567 | XIII.12 | XII.105 | 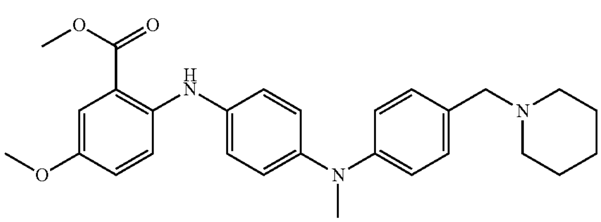 [SMILES: COC(=O)c1cc(OC)ccc1Nc1ccc(N(C)c2ccc(CN3CCCCC3)cc2)cc1] | LC-MS: m/z 460.3 (M + H)+. |
Intermediate-XIV
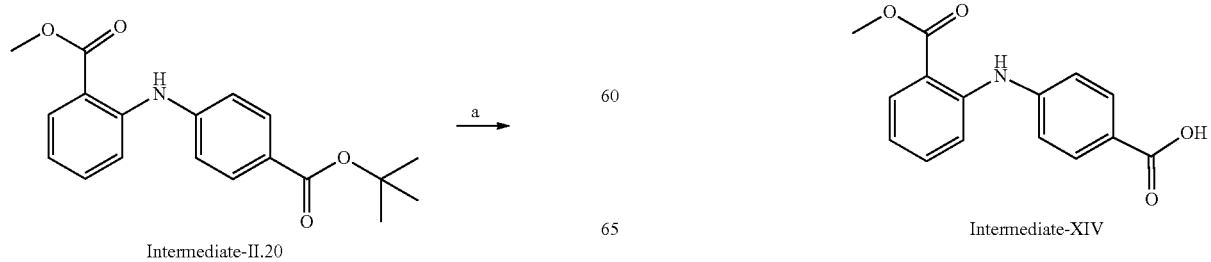

Step-a: Synthesis of 4-((2-(methoxycarbonyl)phenyl)amino)benzoic acid (Intermediate-XIV)

A solution of Intermediate-II.20 (3 g, 9.1 mmol, 1 eq.) in DCM (30 mL) was cooled in ice for 10 minutes. TFA (3 mL) was added drop wise and allowed to stir at RT for 16 h. Reaction mass was concentrated in vacuo. The crude was triturated with n-pentane and dried in vacuo to afford title product as pale green solid (2.0 g, 800).

$^1$H NMR (400 MHz, DMSO-d6) δ 12.58 (s, 1H), 9.40 (s, 1H), 7.93 (dd, $J_1$=0.6 Hz, $J_2$=8.0 Hz, 1H), 7.87 (dd, $J_1$=2.0 Hz, $J_2$=6.8 Hz, 2H), 7.52-7.46 (m, 2H), 7.26 (d, J=8.8 Hz, 2H), 7.01-6.97 (m, 1H), 3.84 (s, 3H); LC-MS: m/z 272.1 (M+H)$^+$

Alternate or General Procedure for Synthesizing the Corresponding Carboxylic Acid Compounds which are Having Methyl & Ethyl Esters To a solution of ester (1 mmol) in THF:MeH:H$_2$O (4+4+2 mL), LiOH.H$_2$O (5 mmol) was added and stirred at RT for 16 h. Reaction mass was concentrated in vacuo, diluted with water and acidified with 2 N HCl to pH 5. The precipitate obtained was filtered and dried under vacuum. This solid was washed with 10% ether in hexane mixture and dried to afford desired acid.

The below intermediates were prepared by a procedure similar to Intermediate-XIV using appropriate reactants and reagents and in presence of suitable solvents and appropriate reaction conditions.

| CP | Intermediate No. | Reactant | Structure | Analytical data |
|---|---|---|---|---|
| 106, 107, 145, 215 | XIV.1 | VII.6 | 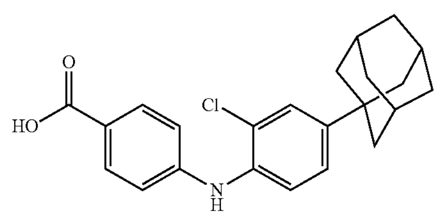 [SMILES: O=C(O)c1ccc(Nc2ccc(C34CC5CC(CC(C5)C3)C4)cc2Cl)cc1] | $^1$H NMR (400 MHz, DMSO-d6) δ 12.26 (s, 1H), 8.27 (s, 1H), 7.75 (d, J = 8.8 Hz, 1H), 7.43 (s, 1H), 7.35-7.3 (m, 2H), 6.86 (d, J = 8.9 Hz, 2H), 2.06 (s, 3H), 1.86 (s, 6H), 1.73 (s, 6H). LC-MS: m/z 382.1 (M + H)$^+$ |
| 254, 301 | XIV.2 | II.15 | 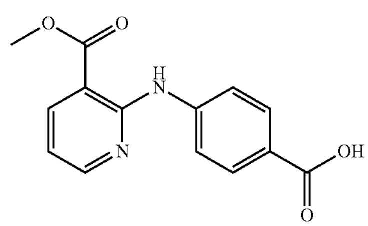 [SMILES: COC(=O)c1cccnc1Nc1ccc(C(=O)O)cc1] | $^1$H NMR (400 MHz, DMSO-d6) δ 12.59 (s, 1H), 10.38 (s, 1H), 8.49 (dd, $J_1$ = 1.9 Hz, $J_2$ = 4.4 Hz, 1H), 8.31 (dd, $J_1$ = 2.0 Hz, $J_2$ = 5.8 Hz, 1H), 7.89 (m, 4H), 7.0 (m, 1H), 3.92 (s, 3H). |
| 255 | XIV.3 | V.4 | 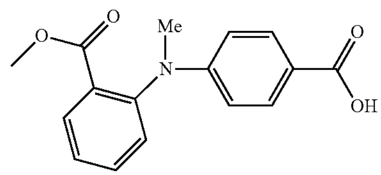 | $^1$H NMR (400 MHz, DMSO-d6) δ 7.9-7.8 (m, 1H), 7.80-7.70 (m, 1H), 7.64 (d, J = 9.6 Hz, 2H), 7.52-7.40 (m, 2H), 6.47 (d, J = 9.2 Hz, 2H), 3.55 (s, 3H), 3.24 (s, 3H), 1.49 (s, 9H). LC-MS: m/z 286.1 (M + H)$^+$ |
| 258 | XIV.4 | V.5 | 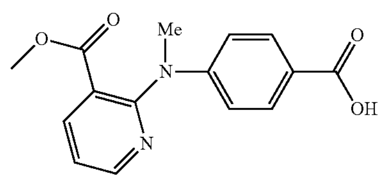 [SMILES: COC(=O)c1cccnc1N(C)c1ccc(C(=O)O)cc1] | $^1$H NMR (400 MHz, DMSO-d6) δ 8.57 (dd, $J_1$ = 2.0 Hz, $J_2$ = 4.9 Hz, 1H), 8.01 (dd, $J_1$ = 1.4 Hz, $J_2$ = 7.3 Hz, 1H), 7.78 (d, J = 8.8 Hz, 2H), 7.23-7.20 (m, 3H). |
| 259, 346 | XIV.5 | II.16 | 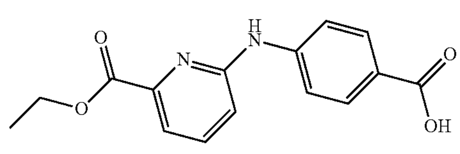 [SMILES: CCOC(=O)c1cccc(Nc2ccc(C(=O)O)cc2)n1] | $^1$H NMR (400 MHz, DMSO-d6) δ 12.5 (s, 1H), 9.75 (s, 1H), 7.97 (d, J = 8.8 Hz, 2H), 7.85 (d, J = 8.8 Hz, 2H), 7.79 (m, 1H), 7.53 (d, J = 6.8 Hz, 1H), 7.14 (d, J = 8.3 Hz, 1H), 4.35 (m, 2H), 1.38 (t, J = 2.0 Hz, 3H). |
| 265 | XIV.6 | II.18 | 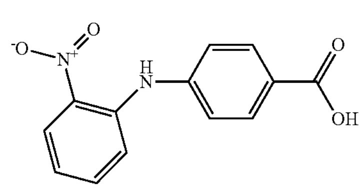 | $^1$H NMR (400 MHz, DMSO-d6) δ 12.64 (s, 1H), 9.29 (s, 1H), 8.11 (dd, $J_1$ = 1.6 Hz, $J_2$ = 8.4 Hz, 1H), 7.89 (d, J = 8.8 Hz, 2H), 7.63-7.58 (m, 1H), 7.50-7.46 (m, 1H), 7.30 (d, J = 8.8 Hz, 2H), 7.12-7.06 (m, 1H). LC-MS: m/z 257.1 (M − H)$^-$. |

| CP | Intermediate No. | Reactant | Structure | Analytical data |
|---|---|---|---|---|
| 293, 294, 276 | XIV.7 | VI.44 | 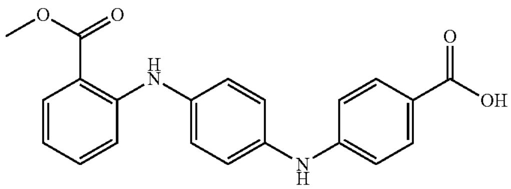 [SMILES: COC(=O)c1ccccc1Nc1ccc(Nc2ccc(C(=O)O)cc2)cc1] | $^1$H NMR (400 MHz, DMSO-d6) δ 9.23 (s, 1H), 8.68 (s, 1H), 7.89 (d, J = 6.9 Hz, 1H), 7.78 (d, J = 8.8 Hz, 2H), 7.41-7.40 (m, 1H), 7.23-7.20 (m, 4H), 7.11 (d, J = 8.3 Hz, 1H), 7.03 (d, J = 8.8 Hz, 2H), 6.76 (t, J = 7.6 Hz, 1H), 3.86 (s, 3H). |
| 302 | XIV.8 | II.21 | 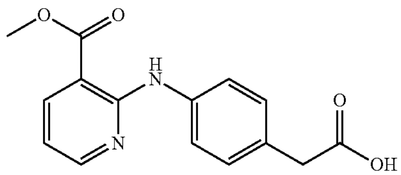 [SMILES: COC(=O)c1cccnc1Nc1ccc(CC(=O)O)cc1] | $^1$H NMR (400 MHz, DMSO-d6) δ 12.2 (s, 1H), 10.05 (s, 1H), 8.41-8.40 (m, 1H), 8.26 (d, J = 7.8 Hz, 2H), 7.64 (d, J = 8.3 Hz, 2H), 7.22 (d, J = 1.9 Hz, 2H), 6.92-6.89 (m, 1H), 3.90 (s, 3H), 3.52 (s, 3H). |
| 303 | XIV.9 | II.22 | 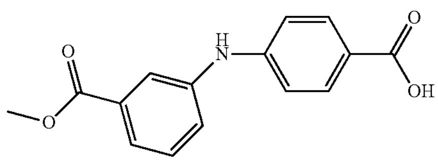 [SMILES: COC(=O)c1cccc(Nc2ccc(C(=O)O)cc2)c1] | $^1$H NMR (400 MHz, DMSO-d6) δ 12.4 (s, 1H), 8.92 (s, 1H), 7.82 (d, J = 8.8 Hz, 2H), 7.74 (s, 1H), 7.54-7.52 (m, 2H), 7.45-7.44 (m, 2H), 7.09 (d, J = 8.8 Hz, 2H), 3.84 (s, 3H). LC-MS: m/z 272.0 (M + H)$^+$ |
| 315, 316 | XIV.10 | II.35 | 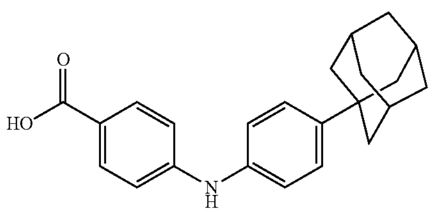 [SMILES: O=C(O)c1ccc(Nc2ccc(C34CC5CC(CC(C5)C3)C4)cc2)cc1] | LC-MS: m/z 348.1 (M + H)$^+$ |
| 330 | XIV.11 | II.24 | 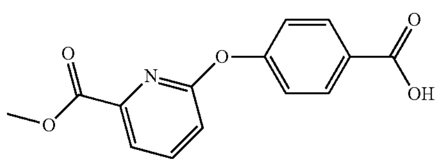 [SMILES: COC(=O)c1cccc(Oc2ccc(C(=O)O)cc2)n1] | $^1$H NMR (400 MHz, DMSO-d6) δ 12.95 (s, 1H), 8.10 (t, J = 7.8 Hz, 1H), 7.99 (d, J = 8.3 Hz, 2H), 7.88 (d, J = 7.4 Hz, 1H), 7.38 (d, J = 8.3 Hz, 1H), 7.26 (d, J = 8.3 Hz, 2H), 3.82 (s, 3H). LC-MS: m/z 274.0 (M + H)$^+$ |
| 333, 341, 395, 408 | XIV.12 | II.25 | 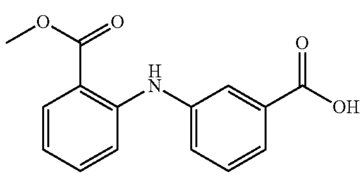 [SMILES: COC(=O)c1ccccc1Nc1cccc(C(=O)O)c1] | $^1$H NMR (400 MHz, DMSO-d6) δ 13.01 (s, 1H), 9.32 (s, 1H), 7.92-7.90 (m, 1H), 7.77-7.76 (m, 1H), 7.62-7.60 (m, 1H), 7.48-7.44 (m, 3H), 7.28-7.24 (m, 1H), 6.90-6.86 (m, 1H), 3.89 (s, 3H). LC-MS: m/z 272.1 (M + H)$^+$ |
| 334 | XIV.13 | II.26 | 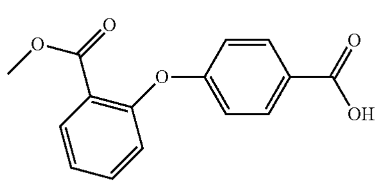 [SMILES: COC(=O)c1ccccc1Oc1ccc(C(=O)O)cc1] | $^1$H NMR (400 MHz, DMSO-d6) δ 12.79 (s, 1H), 7.93-7.90 (m, 3H), 7.71-7.67 (m, 1H), 7.40 (t, J = 7.6 Hz, 1H), 7.23 (d, J = 8.0 Hz, 1H), 6.93 (d, J = 8.8 Hz, 2H), 3.67 (s, 3H). LC-MS: m/z 273.1 (M + H)$^+$ |
| 353 | XIV.14 | V.7 | 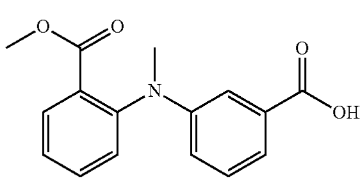 [SMILES: COC(=O)c1ccccc1N(C)c1cccc(C(=O)O)c1] | $^1$H NMR (400 MHz, DMSO-d6) δ 12.80 (s, 1H), 7.78 (d, J = 7.2 Hz, 1H), 7.67 (t, J = 7.6 Hz, 1H), 7.42-7.37 (m, 2H), 7.27-7.21 (m, 2H), 7.07 (s, 1H), 6.77 (d, J = 7.2 Hz, 1H), 3.50 (s, 3H), 3.22 (s, 3H). LC-MS: m/z 284.1 (M + H)$^+$ |

-continued

| CP | Intermediate No. | Reactant | Structure | Analytical data |
|---|---|---|---|---|
| 357 | XIV.15 | V.9 | 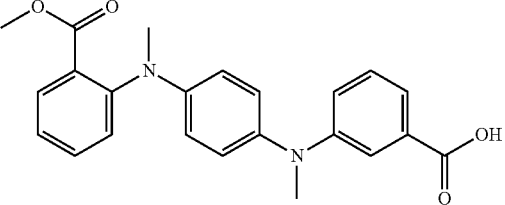 [SMILES: COC(=O)c1ccccc1N(C)c1ccc(N(C)c2cccc(C(=O)O)c2)cc1] | LC-MS: m/z 391.2 (M + H)+ |
| 394 | XIV.16 | II.34 | 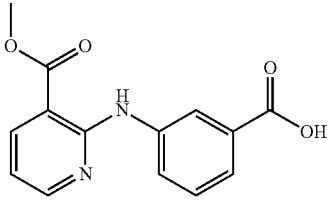 [SMILES: COC(=O)c1cccnc1Nc1cccc(C(=O)O)c1] | $^1$H NMR (400 MHz, DMSO-d6) δ 12.97 (s, 1H), 8.45 (dd, $J_1$ = 2.0 Hz, $J_2$ = 4.8 Hz, 1H), 8.34 (t, J = 2.0 Hz, 1H), 8.28 (dd, $J_1$ = 2.0 Hz, $J_2$ = 8.0 Hz, 1H), 7.92-7.90 (m, 1H), 7.62-7.59 (m, 1H), 7.45 (t, J = 8.0 Hz, 1H), 6.94 (dd, $J_1$ = 4.8 Hz, $J_2$ = 7.6 Hz, 1H), 3.91 (s, 3H). LC-MS: m/z 273.1 (M + H)+ |
| 363 | XIV.17 | II.33 | 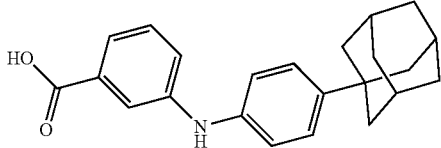 [SMILES: O=C(O)c1cccc(Nc2ccc(C34CC5CC(CC(C5)C3)C4)cc2)c1] | $^1$H NMR (400 MHz, DMSO-d6) δ 12.81 (s, 1H), 8.25 (s, 1H), 7.60 (s, 1H), 7.33-7.21 (m, 5H), 7.04 (d, J = 8.4 Hz, 2H), 2.04 (s, 3H), 1.84 (s, 6H), 1.72 (s, 6H). LC-MS: m/z 348.1 (M + H)+ |
| 386, 387 | XIV.18 | VI.62 | 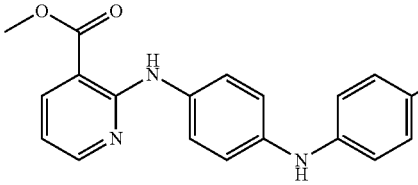 | $^1$H NMR (400 MHz, DMSO-d6) δ 10.02 (s, 1H), 8.64 (s, 1H), 8.39-8.38 (m, 1H), 8.26-8.24 (m, 1H), 7.76 (d, J = 6.8 Hz, 2H), 7.66-7.63 (m, 2H), 7.18-7.15 (m, 2H), 6.99-6.97 (m, 2H), 6.86 (dd, $J_1$ = 4.8 Hz, $J_2$ = 8.0 Hz, 1H), 3.90 (s, 3H). LC-MS: m/z 364.2 (M + H)+ |
| 638 | XIV.19 | II.29 | 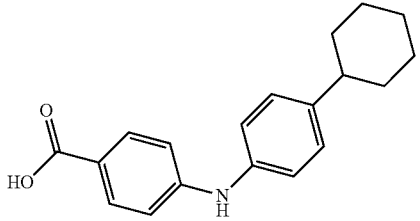 [SMILES: O=C(O)c1ccc(Nc2ccc(C3CCCCC3)cc2)cc1] | LC-MS: m/z 296.2 (M + H)+ |
| 651 | XIV.20 | II.28 | 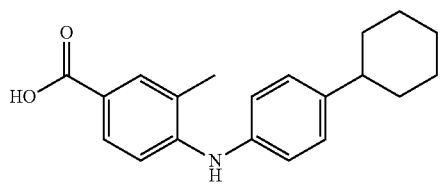 [SMILES: Cc1cc(C(=O)O)ccc1Nc1ccc(C2CCCCC2)cc1] | LC-MS: m/z 310.05 (M + H)+ |

Intermediate-XV

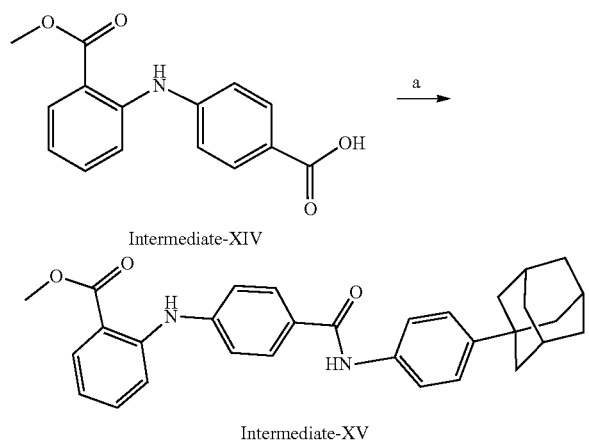

Step-a: Synthesis of methyl 2-(4-(4-((3R,5S)-adamantan-1-yl)phenyl)carbamoyl) phenyl) amino) benzoate (Intermediate-XV)

A solution of compound-XIV (0.2 g, 0.74 mmol, 1 eq.) and Intermediate-I.1 (0.185 g, 0.81 mmol, 1.1 eq.) was cooled in ice. HATU (0.34 g, 0.89 mmol, 1.2 eq.) followed by DIPEA (0.39 mL, 2.22 mmol, 3 eq.) were added and allowed to stir at RT for 16 h. Reaction mass was added to ice water slowly under stirring. The obtained precipitate was filtered, washed with cold water twice followed by n-pentane twice and dried in vacuo to afford title compound as cream coloured solid (0.35 g, 98%).

$^1$H NM/R (400 MHz, DMSO-d6) δ 10.01 (s, 1H), 9.43 (s, 1H), 7.96-7.91 (m, 3H), 7.69 (d, J=8.4 Hz, 2H), 7.54-7.49 (m, 1H), 7.45 (d, J=8.0 Hz, 1H), 7.34-7.31 (m, 4H), 6.95 (t, J=6.8 Hz, 1H), 3.86 (s, 3H), 2.06 (s, 3H), 1.87 (s, 6H), 1.74 (s, 6H); LC-MS: m/z 481.1 (M+H)$^+$

The below intermediates were prepared by a procedure similar to Intermediate-XV using appropriate reactants and reagents and in presence of suitable solvents and appropriate reaction conditions.

| CP | Intermediate No. | Reactant | Structure | Analytical data |
|---|---|---|---|---|
| 71 | XV.1 | Int-XIV & I.4 | 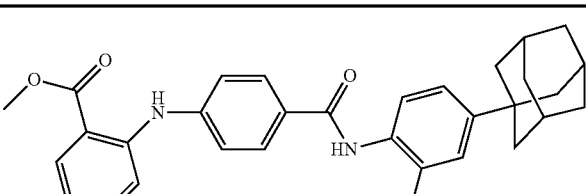 | LC-MS: m/z 560.1 (M + H)$^+$ |
| 106 | XV.2 | XIV.1 | 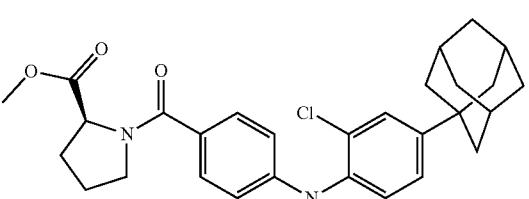 | $^1$H NMR (400 MHz, DMSO-d6) δ 8.03 (s, 1H), 7.47-7.4 (m, 3H), 7.33-7.27 (m, 2H), 6.9 (d, J = 8.3 Hz, 2H), 4.46-4.44 (m, 1H), 3.64-3.61 (m, 5H), 2.32 (m, 1H), 2.05 (s, 3H), 1.85 (s, 9H), 1.73 (s, 6H). LC-MS: m/z 493.2 (M + H)$^+$ |
| 107 | XV.3 | XIV.1 | 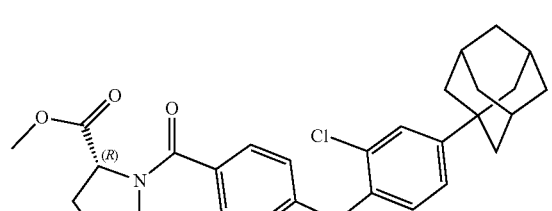 | $^1$H NMR (400 MHz, DMSO-d6) δ 8.03 (s, 1H), 7.47-7.4 (m, 3H), 7.33-7.27 (m, 2H), 6.9 (d, J = 8.3 Hz, 2H), 4.46-4.44 (m, 1H), 3.64-3.61 (m, 5H), 2.32 (m, 1H), 2.05 (s, 3H), 1.85 (s, 9H), 1.73 (s, 6H). LC-MS: m/z 493.2 (M + H)$^+$ |
| 109 | XV.4 | Int-XI | 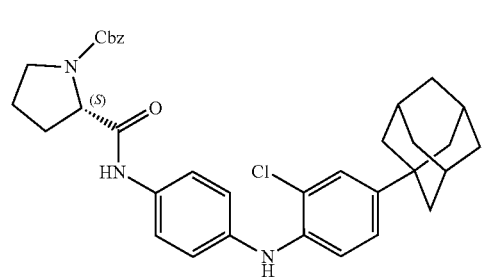 | LC-MS: m/z 584.2 (M + H)$^+$ |

-continued

| CP | Intermediate No. | Reactant | Structure | Analytical data |
|---|---|---|---|---|
| 145 | XV.5 | XIV.1 | 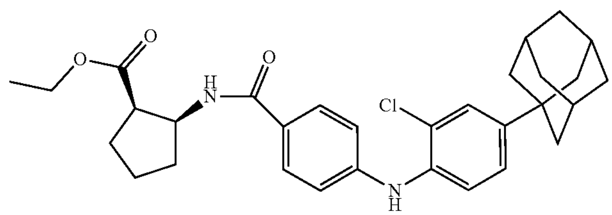 [SMILES: CCOC(=O)[C@@H]1CCC[C@@H]1NC(=O)c1ccc(Nc2ccc(C34CC5CC(CC(C5)C3)C4)cc2Cl)cc1] | ¹H NMR (400 MHz, DMSO-d6) δ 7.99 (s, 1H), 7.85 (d, J = 7.8 Hz, 1H), 7.65 (d, J = 8.8 Hz, 2H), 7.39 (s, 1H), 7.29-7.28 (m, 2H), 6.90 (d, J = 8.8 Hz, 2H), 4.60-4.58 (m, 1H), 3.91-3.87 (m, 2H), 3.02-2.98 (m, 1H), 2.05 (s, 3H), 1.97-1.76 (m, 10H), 1.72 (s, 6H), 1.40-1.30 (m, 2H), 0.88 (t, J = 7.2 Hz, 3H). LC-MS: m/z 521.1 (M + H)⁺ |
| 161 | XV.6 | I.16 | 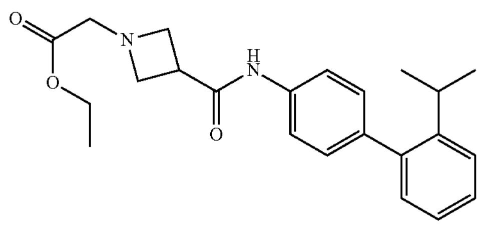 [SMILES: CCOC(=O)CN1CC(C(=O)Nc2ccc(-c3ccccc3C(C)C)cc2)C1] | LC-MS: m/z 381 (M + H)⁺ |
| 186 | XV.7 | Int-XI | 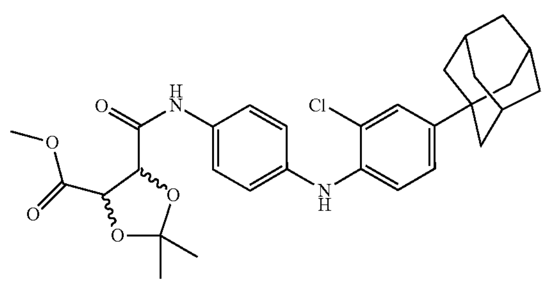 [SMILES: COC(=O)C1OC(C)(C)OC1C(=O)Nc1ccc(Nc2ccc(C34CC5CC(CC(C5)C3)C4)cc2Cl)cc1] | LC-MS: m/z 539.1 (M + H)⁺ |
| 212 | XV.8 | XI.1 | 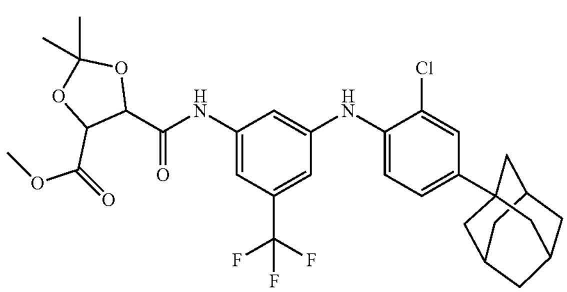 [SMILES: COC(=O)C1OC(C)(C)OC1C(=O)Nc1cc(Nc2ccc(C34CC5CC(CC(C5)C3)C4)cc2Cl)cc(C(F)(F)F)c1] | ¹H NMR (400 MHz, DMSO-d6) δ 10.36 (s, 1H), 8.15 (s, 1H), 7.55 (s, 1H), 7.43 (d, J = 1.2 Hz, 2H), 7.31 (d, J = 0.8 Hz, 2H), 6.94 (s, 1H), 4.88 (d, J = 5.2 Hz, 1H), 4.76 (d, J = 5.2 Hz, 1H), 3.71 (s, 3H), 2.06 (s, 3H), 1.86 (s, 6H), 1.73 (s, 6H), 1.42 (d, J = 3.2 Hz, 6H), LC-MS: m/z 607.2 (M + H)⁺ |
| 215 | XV.9 | XIV.1 | 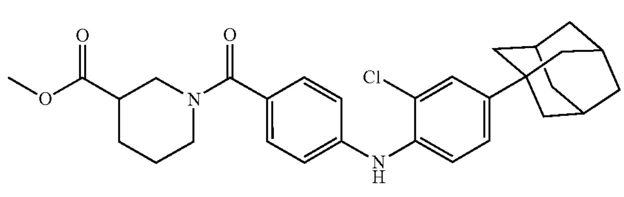 [SMILES: COC(=O)C1CCCN(C(=O)c2ccc(Nc3ccc(C45CC6CC(CC(C6)C4)C5)cc3Cl)cc2)C1] | LC-MS: m/z 507.3 (M + H)⁺ |
| 230 | XV.10 | Int-XI | 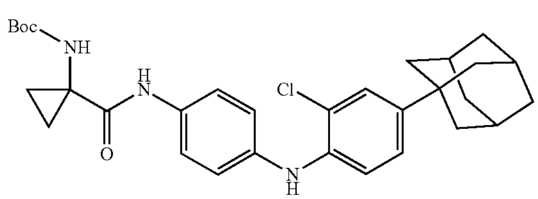 [SMILES: CC(C)(C)OC(=O)NC1(C(=O)Nc2ccc(Nc3ccc(C45CC6CC(CC(C6)C4)C5)cc3Cl)cc2)CC1] | LC-MS: m/z 536.3 (M + H)⁺ |

-continued

| CP | Intermediate No. | Reactant | Structure | Analytical data |
|---|---|---|---|---|
| 254 | XV.11 | XIV.2 | 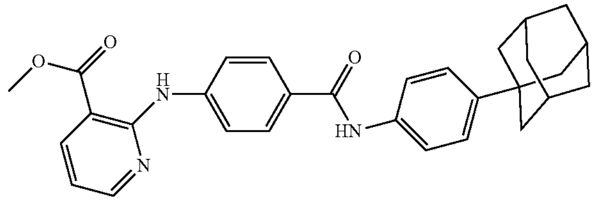 [SMILES: COC(=O)c1cccnc1Nc1ccc(C(=O)Nc2ccc(C34CC5CC(CC(C5)C3)C4)cc2)cc1] | ¹H NMR (400 MHz, DMSO-d6) δ δ 10.35 (s, 1H), 10.02 (s, 1H), 8.51 (dd, J₁ = 2.0 Hz, J2 = 4.5 Hz, 1H), 8.31 (dd, J1 = 2.0 Hz, J₂ = 7.8 Hz, 1H), 7.96 (d, J = 8.8 Hz, 2H), 7.89 (d, J = 8.8 Hz, 2H), 7.69 (d, J = 8.3 Hz, 2H), 7.32 (d, J = 8.8 Hz, 2H), 6.99 (m, 1H), 3.92 (s, 3H), 2.06 (s, 3H), 1.82 (s, 6H), 1.74 (s, 6H). |
| 255 | XV.12 | XIV.3 | 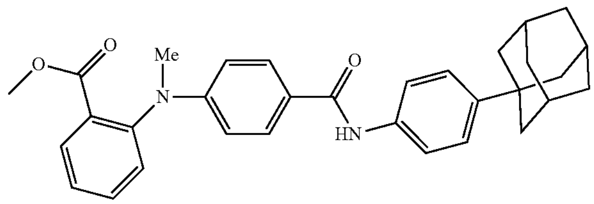 [SMILES: COC(=O)c1ccccc1N(C)c1ccc(C(=O)Nc2ccc(C34CC5CC(CC(C5)C3)C4)cc2)cc1] | ¹H NMR (400 MHz, DMSO-d6) δ 9.79 (s, 1H), 7.84 (dd, J1 = 1.2 Hz, J2 = 7.6 Hz, 1H), 7.77 (d, J = 8.8 Hz, 2H), 7.73-7.69 (m, 1H), 7.65 (d, J = 8.8 Hz, 2H), 7.48-7.40 (m, 2H), 7.28 (d, J = 8.8 Hz, 2H), 6.53 (d, J = 8.8 Hz, 2H), 3.57 (s, 3H), 3.27 (s, 3H), 2.05 (s, 3H), 1.85 (s, 6H), 1.73 (s, 6H), LC-MS: m/z 495.1 (M + H)⁺ |
| 258 | XV.13 | XIV.4 | 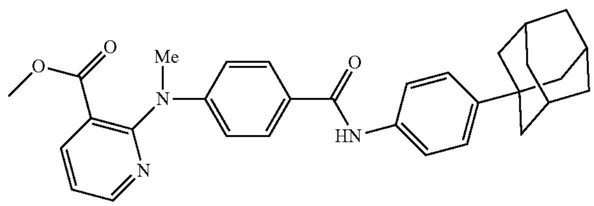 | ¹H NMR (400 MHz, DMSO-d6) δ δ 9.98 (s, 1H), 8.5 (m, 1H), 7.97 (d, J = 7.3 Hz, 1H), 7.87 (d, J = 8.3 Hz, 2H), 7.68 (d, J = 8.3 Hz, 2H), 7.3 (d, J = 8.8 Hz, 2H), 7.18-7 (m, 1H), 6.98 (d, J = 8.8 Hz, 2H), 3.48 (s, 3H), 3.32 (s, 3H), 2.05 (s, 3H), 1.83 (s, 6H), 1.73 (s, 6H). |
| 259 | XV.14 | XIV.5 | 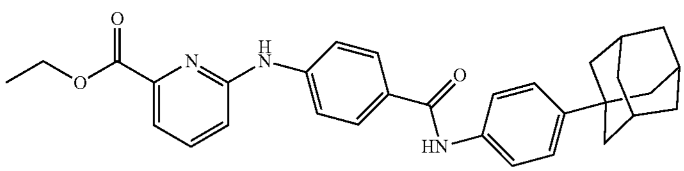 [SMILES: CCOC(=O)c1cccc(Nc2ccc(C(=O)Nc3ccc(C45CC6CC(CC(C6)C4)C5)cc3)cc2)n1] | ¹H NMR (400 MHz, DMSO-d6) δ δ 9.99 (s, 1H), 9.7 (s, 1H), 8.01 (d, J = 9.3 Hz, 2H), 7.93 (d, J = 8.8 Hz, 2H), 7.81 (m, 1H), 7.69 (d, J = 8.8 Hz, 2H), 7.52 (d, J = 6.8 Hz, 1H), 7.31 (d, J = 8.8 Hz, 2H), 7.13 (d, J = 8.3 Hz, 1H), 4.35 (m, 2H), 2.06 (s, 3H), 1.87 (s, 6H), 1.74 (s, 6H), 1.38 (t, J = 7.4 Hz, 3H). |
| 272 | XV.15 | XI.13 | 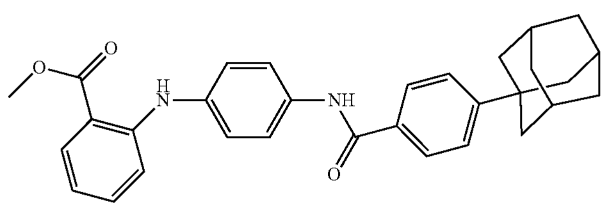 [SMILES: COC(=O)c1ccccc1Nc1ccc(NC(=O)c2ccc(C34CC5CC(CC(C5)C3)C4)cc2)cc1] | ¹H NMR (400 MHz, DMSO-d6) δ δ 10.17 (s, 1H), 9.28 (s, 1H), 7.91-7.88 (m, 3H), 7.78 (d, J = 8.8 Hz, 2H), 7.51 (d, J = 8.4 Hz, 2H), 7.42-7.38 (m, 1H), 7.24 (d, J = 8.8 Hz, 2H), 7.14 (d, J = 8.0 Hz, 1H), 6.66-6.65 (m, 1H), 3.86 (s, 3H), 2.08 (s, 3H), 1.90 (s, 6H), 1.76 (s, 6H). LC-MS: m/z 479.0 (M − H)⁻. |
| 274 | XV.16 | Int-XIV | 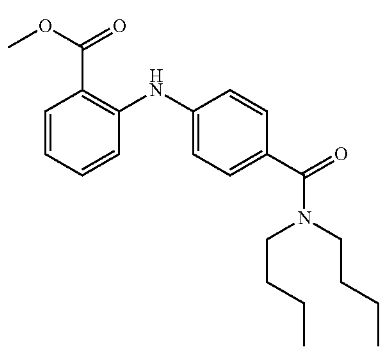 [SMILES: CCCCN(CCCC)C(=O)c1ccc(Nc2ccccc2C(=O)OC)cc1] | ¹H NMR (400 MHz, DMSO-d6) δ 9.34 (s, 1H), 7.92 (dd, J₁ = 1.5 Hz, J₂ = 7.8 Hz, 1H), 7.46 (t, J = 1.5 Hz, 1H), 7.30-7.20 (m, 5H), 6.90-6.86 (m, 1H), 3.89 (s, 3H), 3.40-3.30 (m, 4H), 1.52-1.49 (m, 4H), 1.12-1.08 (m, 4H), 0.84-0.78 (m, 6H). |

-continued

| CP | Intermediate No. | Reactant | Structure | Analytical data |
|---|---|---|---|---|
| 285 | XV.17 | Int-XIV | 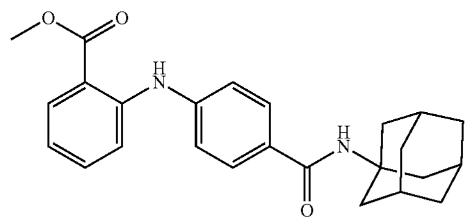 [SMILES: COC(=O)c1ccccc1Nc1ccc(C(=O)NC23CC4CC(CC(C4)C2)C3)cc1] | ¹H NMR (400 MHz, DMSO-d6) δ δ 9.38 (s, 1H), 7.92 (d, J = 6.8 Hz, 1H), 7.78 (d, J = 8.0 Hz, 2H), 7.50-7.43 (m, 2H), 7.37 (d, J = 8.0 Hz, 1H), 7.27-7.23 (m, 2H), 6.91 (t, J = 7.6 Hz, 1H), 3.85 (s, 3H), 2.07 (s, 9H), 1.66 (s, 6H), 1.66 (s, 6H). LC-MS: m/z 405.1 (M + H)⁺ |
| 288 | XV.18 | Int-XIV | 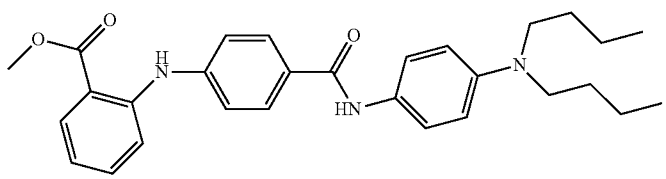 [SMILES: CCCCN(CCCC)c1ccc(NC(=O)c2ccc(Nc3ccccc3C(=O)OC)cc2)cc1] | ¹H NMR (400 MHz, DMSO-d6) δ 9.78 (s, 1H), 9.42 (s, 1H), 7.92 (d, J = 6.8 Hz, 3H), 7.52-7.50 (m, 3H), 7.44 (d, J = 7.3 Hz, 1H), 7.31 (d, J = 8.8 Hz, 2H), 6.94 (t, J = 6.8 Hz, 1H), 6.63 (d, J = 9.3 Hz, 2H), 3.86 (s, 3H), 3.23 (t, J = 7.2 Hz, 4H), 1.50-1.45 (m, 4H), 1.34-1.30 (m, 4H), 0.89 (t, J = 7.2 Hz, 6H). |
| 293, 276 | XV.19 | XIV.7 | 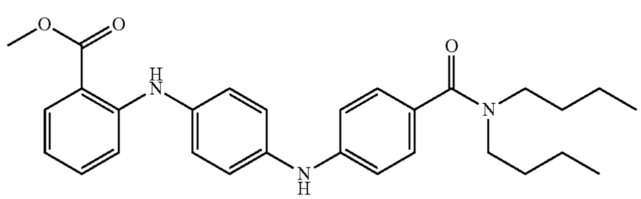 [SMILES: CCCCN(CCCC)C(=O)c1ccc(Nc2ccc(Nc3ccccc3C(=O)OC)cc2)cc1] | ¹H NMR (400 MHz, DMSO-d6) δ 9.20 (s, 1H), 8.38 (s, 1H), 7.88 (dd, J₁ = 1.4 Hz, J₂ = 7.8 Hz, 1H), 7.37-7.36 (m, 1H), 7.19-7.16 (m, 6H), 7.05-7.04 (m, 3H), 6.75-6.71 (m, 1H), 3.85 (s, 3H), 3.32-3.30 (m, 4H), 1.52-1.49 (m, 4H), 1.23-1.22 (m, 4H), 0.85-0.84 (m, 6H). |
| 294 | XV.20 | XIV.7 | 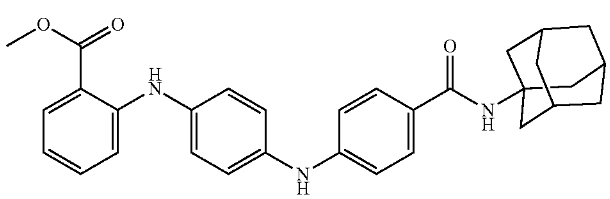 [SMILES: COC(=O)c1ccccc1Nc1ccc(Nc2ccc(C(=O)NC34CC5CC(CC(C5)C3)C4)cc2)cc1] | ¹H NMR (400 MHz, DMSO-d6) δ 9.21 (s, 1H), 8.47 (s, 1H), 7.89-7.87 (dd, J1 = 1.6 Hz, J2 = 7.6 Hz, 1H), 7.68 (d, J = 8.8 Hz, 2H), 7.36 (t, J = 8.4 Hz, 1H), 7.24 (s, 1H), 7.21-7.14 (m, 4H), 7.06 (d, J = 8.0 Hz, 1H), 7.0 (d, J = 8.8 Hz, 2H), 6.74 (t, J = 7.6 Hz, 1H), 3.86 (s, 3H), 2.06 (s, 9H), 1.65 (s, 6H). LC-MS: m/z 496.0 (M + H)⁺ |
| 297 | XV.21 | VII.14 | 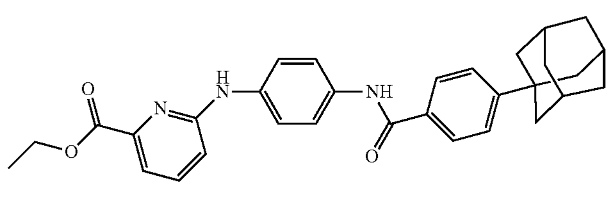 [SMILES: CCOC(=O)c1cccc(Nc2ccc(NC(=O)c3ccc(C45CC6CC(CC(C6)C4)C5)cc3)cc2)n1] | ¹H NMR (400 MHz, DMSO-d6) δ 10.09 (s, 1H), 9.29 (s, 1H), 7.90 (d, J = 8.3 Hz, 2H), 7.83 (d, J = 6.3 Hz, 2H), 7.72-7.7 (m, 3H), 7.51 (d, J = 8.3 Hz, 2H), 7.40 (d, J = 7.3 Hz, 1H), 7.03 (d, J = 8.3 Hz, 1H), 4.35-4.34 (m, 2H), 2.08 (s, 3H), 1.93 (s, 6H), 1.76 (s, 6H), 1.37 (t, J = 7.4 Hz, 3H). |
| 301 | XV.22 | XIV.2 | 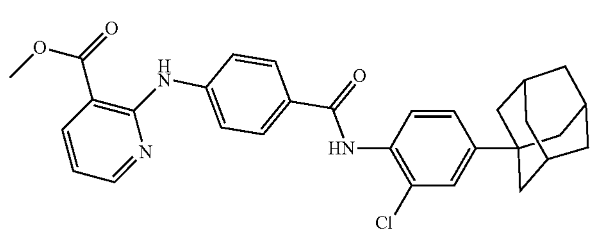 [SMILES: COC(=O)c1cccnc1Nc1ccc(C(=O)Nc2ccc(C34CC5CC(CC(C5)C3)C4)cc2Cl)cc1] | LC-MS: m/z 516.0 (M + H)⁺ |

-continued

| CP | Intermediate No. | Reactant | Structure | Analytical data |
|---|---|---|---|---|
| 302 | XV.23 | XIV.8 | 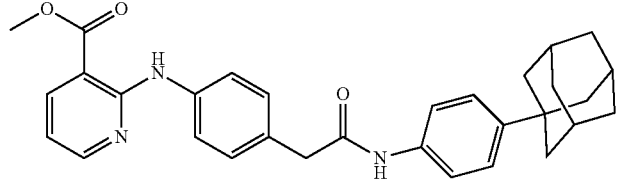 [SMILES: COC(=O)c1cccnc1Nc1ccc(CC(=O)Nc2ccc(C34CC5CC(CC(C5)C3)C4)cc2)cc1] | $^1$H NMR (400 MHz, DMSO-d6) δ 10.05 (s, 1H), 10.03 (s, 1H), 8.41-8.40 (m, 1H), 8.26-8.25 (m, 1H), 7.65 (d, J = 8.3 Hz, 2H), 7.52 (d, J = 8.8 Hz, 2H), 7.27-7.26 (m, 4H), 6.88-6.87 (m, 1H), 3.89 (s, 3H), 3.57 (s, 2H), 2.04 (s, 3H), 1.82 (s, 6H), 1.72 (s, 6H). |
| 303 | XV.24 | XIV.9 | 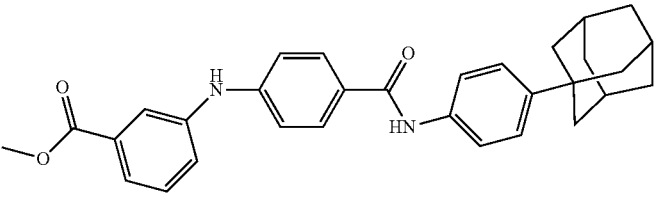 [SMILES: COC(=O)c1cccc(Nc2ccc(C(=O)Nc3ccc(C45CC6CC(CC(C6)C4)C5)cc3)cc2)c1] | $^1$H NMR (400 MHz, DMSO-d6) δ 9.92 (s, 1H), 8.85 (s, 1H), 7.89 (d, J = 8.0 Hz, 2H), 7.75 (s, 1H), 7.68 (d, J = 8.8 Hz, 2H), 7.51-7.43 (m, 3H), 7.30 (d, J = 8.8 Hz, 2H), 7.15 (d, J = 8.8 Hz, 2H), 3.85 (s, 3H), 2.06 (s, 3H), 1.86 (s, 6H), 1.74 (s, 6H). LC-MS: m/z 481.3 (M + H)$^+$ |
| 313 | XV.25 | Int-XIV | 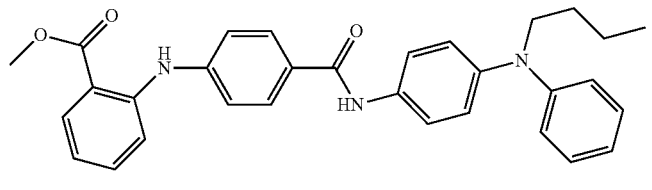 [SMILES: CCCCN(c1ccccc1)c1ccc(NC(=O)c2ccc(Nc3ccccc3C(=O)OC)cc2)cc1] | $^1$H NMR (400 MHz, DMSO-d6) δ 10.04 (s, 1H), 9.43 (s, 1H), 7.96-7.94 (m, 3H), 7.72 (d, J = 8.8 Hz, 2H), 7.51 (m, 1H), 7.46 (d, J = 7.3 Hz, 1H), 7.34 (d, J = 8.3 Hz, 2H), 7.20 (t, J = 7.4 Hz, 2H), 7.05 (d, J = 8.8 Hz, 2H), 7.93 (t, J = 6.9 Hz, 1H), 6.82 (m, 3H), 3.86 (s, 3H), 3.65 (t, J = 7.3 Hz, 2H), 1.56-1.55 (m, 2H), 1.37-1.36 (m, 2H), 0.88 (t, J = 3.9 Hz, 3H). |
| 315 | XV.26 | XIV.10 | 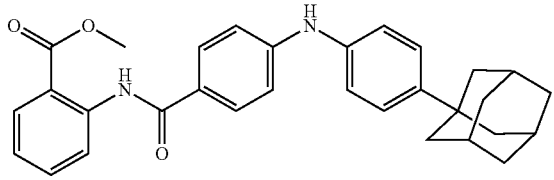 [SMILES: COC(=O)c1ccccc1NC(=O)c1ccc(Nc2ccc(C34CC5CC(CC(C5)C3)C4)cc2)cc1] | $^1$H NMR (400 MHz, DMSO-d6) δ 11.53 (s, 1H), 8.66 (d, J = 7.4 Hz, 2H), 8.03 (d, J = 6.8 Hz, 1H), 7.82 (d, J = 8.8 Hz, 2H), 7.66-7.65 (m, 1H), 7.32 (d, J = 8.8 Hz, 2H), 7.21-7.10 (m, 5H), 3.91 (s, 3H), 2.06 (s, 3H), 1.89 (s, 6H), 1.71 (s, 6H). |
| 316 | XV.27 | XIV.10 | 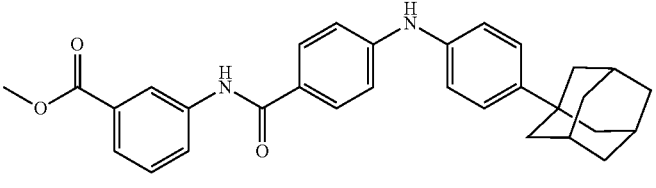 [SMILES: COC(=O)c1cccc(NC(=O)c2ccc(Nc3ccc(C45CC6CC(CC(C6)C4)C5)cc3)cc2)c1] | $^1$H NMR (400 MHz, DMSO-d6) δ 10.13 (s, 1H), 8.56 (s, 1H), 8.45 (s, 1H), 8.07 (d, J = 7.8 Hz, 1H), 7.88 (d, J = 8.3 Hz, 2H), 7.66 (d, J = 13 Hz, 1H), 7.47 (t, J = 7.9 Hz, 1H), 7.31 (d, J = 8.3 Hz, 2H), 7.14 (d, J = 8.8 Hz, 2H), 7.08 (d, J = 8.3 Hz, 2H), 3.87 (s, 3H), 2.06 (s, 3H), 1.82 (s, 6H), 1.74 (s, 6H). |
| 324 | XV.28 | XIV.5 | 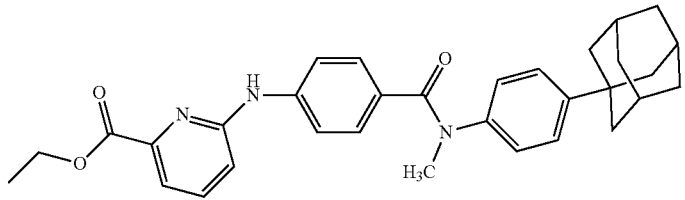 [SMILES: CCOC(=O)c1cccc(Nc2ccc(C(=O)N(C)c3ccc(C45CC6CC(CC(C6)C4)C5)cc3)cc2)n1] | $^1$H NMR (400 MHz, DMSO-d6) δ 9.47 (s, 1H), 7.75-7.67 (m, 2H), 7.45 (d, J = 7.6 Hz, 1H), 7.26 (d, J = 8.4 Hz, 2H), 7.18 (d, J = 8.4 Hz, 2H), 7.09-7.02 (m, 3H), 6.47 (d, J = 8.8 Hz, 1H), 4.30 (q, J = 6.8 Hz, 2H), 3.33 (s, 3H), 2.01 (s, 3H), 1.8-0 (s, 6H), 1.70 (s, 6H), 1.32 (t, J = 6.8 Hz, 3H). LC-MS: m/z 510.3 (M + H)$^+$ |

-continued

| CP | Intermediate No. | Reactant | Structure | Analytical data |
|---|---|---|---|---|
| 329 | XV.29 | Int-XIV | 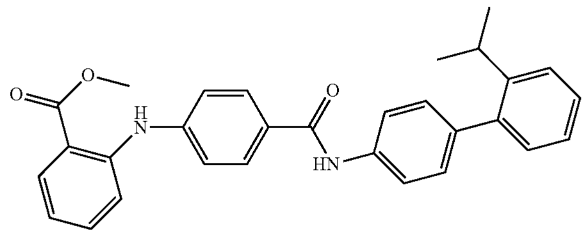 [SMILES: COC(=O)c1ccccc1Nc1ccc(C(=O)Nc2ccc(-c3ccccc3C(C)C)cc2)cc1] | $^1$H NMR (400 MHz, DMSO-d6) δ 10.17 (s, 1H), 9.45 (s, 1H), 7.99-7.93 (m, 3H), 7.83 (d, J = 8.4 Hz, 2H), 7.52-7.40 (m, 3H), 7.36-7.34 (m, 3H), 7.26-7.21 (m, 3H), 7.13 (d, J = 6.8 Hz, 1H), 7.00-6.90 (m, 1H), 3.87 (s, 3H), 3.10-3.00 (m, 1H), 1.13 (d, J = 6.8 Hz, 6H). LC-MS: m/z 465.1 (M + H)$^+$ |
| 330 | XV.30 | XIV.11 | 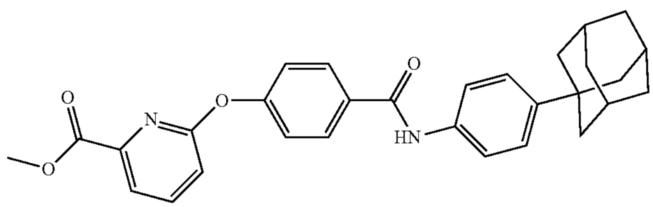 [SMILES: COC(=O)c1cccc(Oc2ccc(C(=O)Nc3ccc(C45CC6CC(CC(C6)C4)C5)cc3)cc2)n1] | $^1$H NMR (400 MHz, DMSO-d6) δ 10.20 (s, 1H), 8.12-8.08 (m, 1H), 8.02 (dd, $J_1$ = 2.0 Hz, $J_2$ = 6.8 Hz, 2H), 7.88 (dd, $J_1$ = 4.0 Hz, $J_2$ = 8.0 Hz, 1H), 7.70 (d, J = 8.0 Hz, 2H), 7.40-7.37 (m, 1H), 7.33 (dd, $J_1$ = 0.8 Hz, $J_2$ = 2.0 Hz, 4H), 3.82 (s, 3H), 2.06 (s, 3H), 1.87 (s, 6H), 1.74 (s, 6H). LC-MS: m/z 483.1 (M + H)$^+$ |
| 333 | XV.31 | XIV.13 | 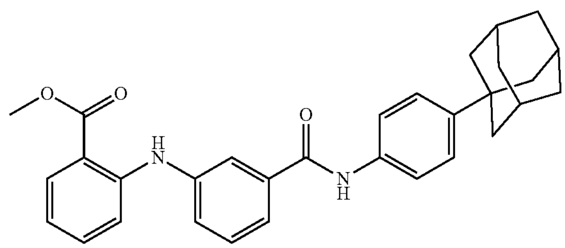 [SMILES: COC(=O)c1ccccc1Nc1cccc(C(=O)Nc2ccc(C34CC5CC(CC(C5)C3)C4)cc2)c1] | $^1$H NMR (400 MHz, DMSO-d6) δ 10.15 (s, 1H), 9.40 (s, 1H), 7.92 (d, J = 8.0 Hz, 1H), 7.79 (s, 1H), 7.69-7.62 (m, 3H), 7.50-7.46 (m, 3H), 7.33-7.29 (m, 3H), 6.90-6.80 (m, 1H), 3.87 (s, 3H), 2.06 (s, 3H), 1.86 (s, 6H), 1.74 (s, 6H). LC-MS: m/z 481.2 (M + H)$^+$ |
| 334 | XV.32 | XIV.14 | 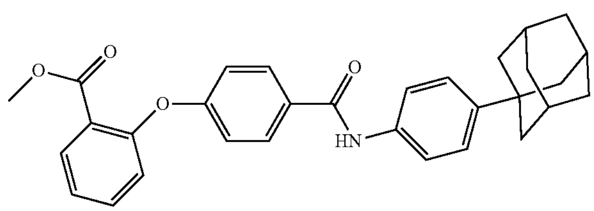 [SMILES: COC(=O)c1ccccc1Oc1ccc(C(=O)Nc2ccc(C34CC5CC(CC(C5)C3)C4)cc2)cc1] | $^1$H NMR (400 MHz, DMSO-d6) δ 10.08 (s, 1H), 7.96 (d, J = 8.3 Hz, 2H), 7.91 (d, J = 6.8 Hz, 1H), 7.68-7.66 (m, 3H), 7.40-7.37 (m, 1H), 7.32 (d, J = 8.8 Hz, 2H), 7.20 (d, J = 7.8 Hz, 1H), 6.98 (d, J = 8.3 Hz, 2H), 3.70 (s, 3H), 2.06 (s, 3H), 1.86 (s, 6H), 1.74 (s, 6H). LC-MS: m/z 482.3 (M + H)$^+$ |
| 335 | XV.33 | Int-XIV | 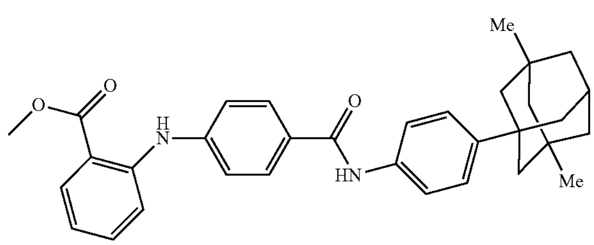 [SMILES: COC(=O)c1ccccc1Nc1ccc(C(=O)Nc2ccc(C34CC5CC(C)(CC(C)(C5)C3)C4)cc2)cc1] | $^1$H NMR (400 MHz, DMSO-d6) δ 10.0 (s, 1H), 9.43 (s, 1H), 7.96-7.92 (m, 3H), 7.68 (d, J = 8.8 Hz, 2H), 7.51-7.49 (m, 1H), 7.44 (d, J = 8.4 Hz, 1H), 7.33-7.29 (m, 4H), 6.95 (t, J = 7.6 Hz, 1H), 3.86 (s, 3H), 2.14 (m, 1H), 1.69 (s, 2H), 1.53-1.33 (m, 8H), 1.19 (s, 2H), 0.86 (s, 6H). LC-MS: m/z 509.3 (M + H)$^+$ |
| 336 | XV.34 | XIV.10 | 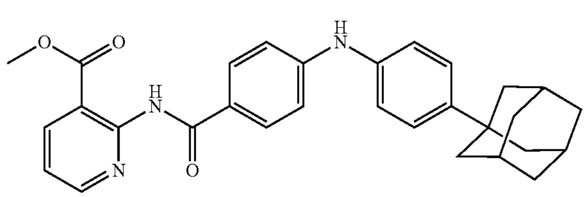 [SMILES: COC(=O)c1cccnc1NC(=O)c1ccc(Nc2ccc(C34CC5CC(CC(C5)C3)C4)cc2)cc1] | LC-MS: m/z 482.2 (M + H)$^+$ |

-continued

| CP | Intermediate No. | Reactant | Structure | Analytical data |
|---|---|---|---|---|
| 341 | XV.35 | XIV.13 | 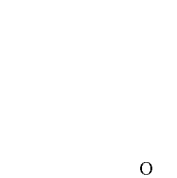 | ¹H NMR (400 MHz, DMSO-d6) δ 10.14 (s, 1H), 9.40 (s, 1H), 7.92 (d, J = 8.0 Hz, 1H), 7.80 (s, 1H), 7.68 (d, J = 8.0 Hz, 2H), 7.64 (d, J = 7.2 Hz, 1H), 7.51-7.44 (m, 3H), 7.32-7.30 (m, 3H), 6.87 (t, J = 8.0 Hz, 1H), 3.87 (s, 3H), 2.14 (s, 1H), 1.68 (s, 2H), 1.53-1.33 (m, 8H), 1.19 (s, 2H), 0.86 (s, 6H). LC-MS: m/z 509.3 (M + H)⁺ |
| 343 | XV.36 | XIV.13 | 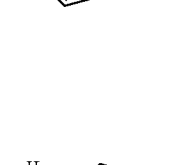 | ¹H NMR (400 MHz, DMSO-d6) δ 10.32 (s, 1H), 9.42 (s, 1H), 7.93 (d, J = 8.0 Hz, 1H), 7.84-7.82 (m, 3H), 7.66 (d, J = 6.8 Hz, 1H), 7.54-7.12 (m, 10H), 6.88 (t, J = 7.20 Hz, 1H), 3.87 (s, 3H), 2.04-2.01 (m, 1H), 1.12 (d, J = 6.8 Hz, 6H). LC-MS: m/z 465.1 (M + H)⁺ |
| 344 | XV.37 | Int-I.1 | 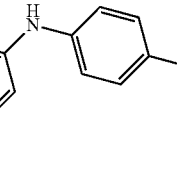 | ¹H NMR (400 MHz, DMSO-d6) δ 11.64 (s, 1H), 10.36 (s, 1H), 8.53 (dd, J₁ = 0.8 Hz, J₂ = 8.4 Hz, 1H), 8.14-8.08 (m, 4H), 8.03 (dd, J₁ = 1.6 Hz, J₂ = 8.0 Hz, 1H), 7.73-7.71 (m, 3H), 7.36-7.34 (m, 2H), 7.30-7.25 (m, 1H), 3.90 (s, 3H), 2.07 (s, 3H), 1.87 (d, J = 2.4 Hz, 6H), 1.74 (s, 6H). LC-MS: m/z 509.3 (M + H)⁺ |
| 346 | XV.38 | XIV.5 | 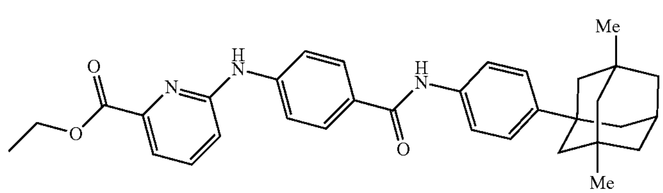 [SMILES: CCOC(=O)c1cccc(Nc2ccc(C(=O)Nc3ccc(C45CC6CC(C)(CC(C)(C6)C4)C5)cc3)cc2)n1] | ¹H NMR (400 MHz, DMSO-d6) δ 9.94 (s, 1H), 9.70 (s, 1H), 8.00 (d, J = 8.8 Hz, 2H), 7.93 (d, J = 8.8 Hz, 2H), 7.79 (t, J = 7.6 Hz, 1H), 7.69 (d, J = 8.8 Hz, 2H), 7.51 (d, J = 7.6 Hz, 1H), 7.30 (d, J = 8.8 Hz, 2H), 7.13 (d, J = 8.0 Hz, 1H), 4.38-4.33 (m, 2H), 2.14 (m, 1H), 1.69 (s, 2H), 1.53-1.33 (m, 11H), 1.19 (s, 2H), 0.86 (s, 6H). LC-MS: m/z 524.3 (M + H)⁺ |
| 353 | XV.39 | XIV.15 | 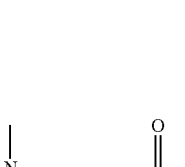 | LC-MS: m/z 495.1 (M + H)⁺ |

| CP | Intermediate No. | Reactant | Structure | Analytical data |
|---|---|---|---|---|
| 363 | XV.40 | XIV.18 | (structure) | ¹H NMR (400 MHz, DMSO-d6) δ 11.61 (s, 1H), 8.61 (d, J = 8.4 Hz, 1H), 8.38 (s, 1H), 8.02 (d, J = 7.2 Hz, 1H), 7.70-7.63 (m, 2H), 7.42-7.22 (m, 6H), 7.11 (d, J = 8.8 Hz, 2H), 3.90 (s, 3H), 2.05 (s, 3H), 1.85 (s, 6H), 1.73 (s, 6H). LC-MS: m/z 481.2 (M + H)⁺ |
| 364 | XV.41 | XIV.18 | (structure) | ¹H NMR (400 MHz, DMSO-d6) 10.39 (s, 1H), 8.46 (t, J = 2.0 Hz, 1H), 8.29 (s, 1H), 8.04 (dd, J₁ = 0.8 Hz, J₂ = 8.0 Hz, 1H), 7.69-7.67 (m, 1H), 7.59 (s, 1H), 7.49 (t, J = 8.0 Hz, 1H), 7.36-7.20 (m, 5H), 7.08 (d, J = 8.8 Hz, 2H), 3.87 (s, 3H), 2.05 (s, 3H), 1.84 (s, 6H), 1.72 (s, 6H). LC-MS: m/z 481.2 (M + H)⁺ |
| 368 | XV.42 | | (structure) | LC-MS: m/z 523.3 (M + H)⁺ |
| 369 | XV.43 | | (structure) | LC-MS: m/z 509.2 (M + H)⁺ |
| 386 | XV.44 | XIV.19 | (structure) | ¹H NMR (400 MHz, DMSO-d6) δ 9.97 (s, 1H), 8.38 (dd, J₁ = 2.0 Hz, J₂ = 4.8 Hz, 1H), 8.33 (s, 1H), 8.24 (dd, J₁ = 2.0 Hz, J₂ = 8.0 Hz, 1H), 7.60 (d, J = 8.8 Hz, 2H), 7.19 (d, J = 8.8 Hz, 2H), 7.13 (d, J = 3.2 Hz, 2H), 6.99 (d, J = 8.8 Hz, 2H), 6.84 (dd, J₁ = 2.8 Hz, J₂ = 8.0 Hz, 1H), 3.90 (s, 3H), 3.29 (s, 6H), 1.54-1.47 (m, 4H), 1.23-1.20 (m, 4H), 0.85 (s, 6H). LC-MS: m/z 475.3 (M + H)⁺ |

-continued

| CP | Intermediate No. | Reactant | Structure | Analytical data |
|---|---|---|---|---|
| 387 | XV.45 | XIV.19 | 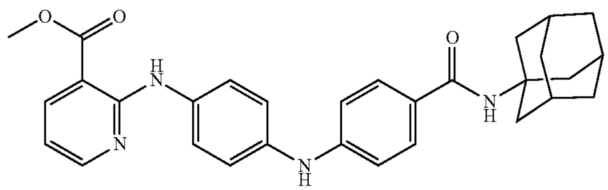 [SMILES: COC(=O)c1cccnc1Nc1ccc(Nc2ccc(C(=O)NC34CC5CC(CC(C5)C3)C4)cc2)cc1] | $^1$H NMR (400 MHz, DMSO-d6) δ 9.97 (s, 1H), 8.39-8.38 (m, 2H), 8.24 (dd, J$_1$ = 2.0 Hz, J$_2$ = 8.0 Hz, 1H), 7.64 (dd, J$_1$ = 8.4 Hz, J$_2$ = 19.2 Hz, 4H), 7.21 (s, 1H), 7.12 (d, J = 8.8 Hz, 2H), 6.96 (d, J = 8.8 Hz, 2H), 6.84 (dd, J$_1$ = 4.8 Hz, J$_2$ = 8.0 Hz, 1H), 3.90 (s, 3H), 1.99 (s, 10H), 1.65 (s, 6H). LC-MS: m/z 497.3 (M + H)$^+$ |
| 394 | XV.46 | XIV.17 & I.3 | 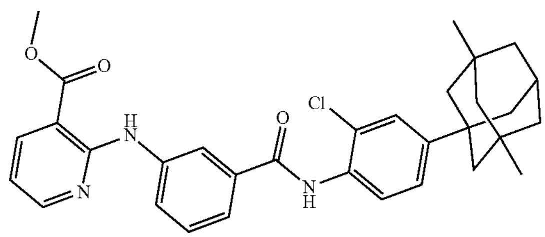 [SMILES: COC(=O)c1cccnc1Nc1cccc(C(=O)Nc2ccc(C34CC5CC(C)(CC(C)(C5)C3)C4)cc2Cl)c1] | LC-MS: m/z 544.3 (M + H)$^+$ |
| 407 | XV.47 | Int-XIV & I.29 | 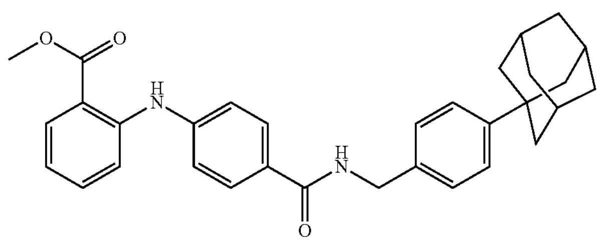 [SMILES: COC(=O)c1ccccc1Nc1ccc(C(=O)NCc2ccc(C34CC5CC(CC(C5)C3)C4)cc2)cc1] | $^1$H NMR (400 MHz, DMSO-d6) δ 9.41 (s, 1H), 8.89 (t, J = 6.0 Hz, 1H), 7.93-7.91 (m, 1H), 7.87 (d, J = 8.8 Hz, 2H), 7.51-7.48 (m, 1H), 7.43-7.40 (m, 1H), 7.33-7.22 (m, 6H), 6.95-6.91 (m, 1H), 4.43 (d, J = 6.0 Hz, 2H), 3.84 (s, 3H), 2.05 (s, 3H), 1.84 (s, 6H), 1.73 (s, 6H), LC-MS: m/z 495.3 (M + H)$^+$ |
| 408 | XV.48 | XIV.13 & I.29 | 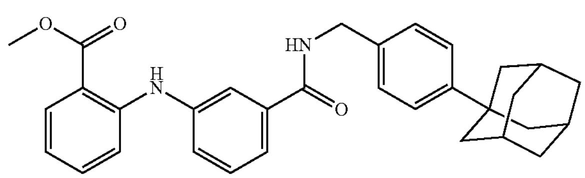 [SMILES: COC(=O)c1ccccc1Nc1cccc(C(=O)NCc2ccc(C34CC5CC(CC(C5)C3)C4)cc2)c1] | $^1$H NMR (400 MHz, DMSO-d6) δ 9.39 (s, 1H), 9.02 (t, J = 6.0 Hz, 1H), 7.95-7.90 (m, 1H), 7.76 (s, 1H), 7.60-7.55 (m, 1H), 7.45-7.42 (m, 3H), 7.32-7.23 (m, 5H), 6.87-6.83 (m, 1H), 4.42 (d, J = 6.0 Hz, 2H), 3.86 (s, 3H), 2.04 (s, 3H), 1.84 (s, 6H), 1.76 (s, 6H), LC-MS: m/z 495.3 (M + H)$^+$ |
| 638 | XV.49 | XIV.20 | 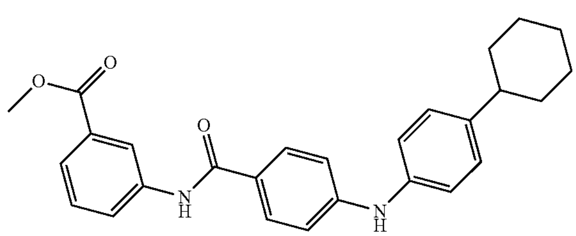 [SMILES: COC(=O)c1cccc(NC(=O)c2ccc(Nc3ccc(C4CCCCC4)cc3)cc2)c1] | LC-MS: m/z 429.2 (M + H)+ |
| 651 | XV.50 | XIV.21 | 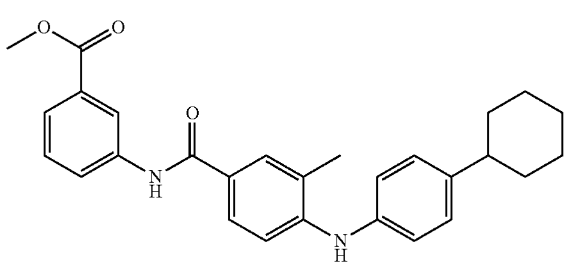 [SMILES: COC(=O)c1cccc(NC(=O)c2ccc(Nc3ccc(C4CCCCC4)cc3)c(C)c2)c1] | LC-MS: m/z 443.2 (M + H)+ |

| CP | Intermediate No. | Reactant | Structure | Analytical data |
|---|---|---|---|---|
| 664 | XV.51 | XIV.13 | 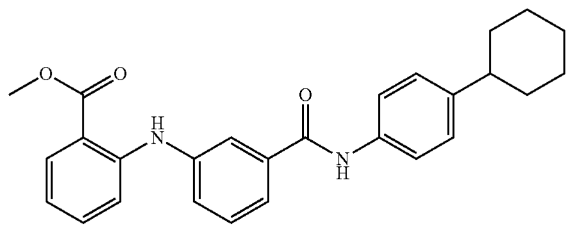 [SMILES: COC(=O)c1ccccc1Nc1cccc(C(=O)Nc2ccc(C3CCCCC3)cc2)c1] | LC-MS: m/z 429.1 (M + H)+ |

Intermediate-XVI

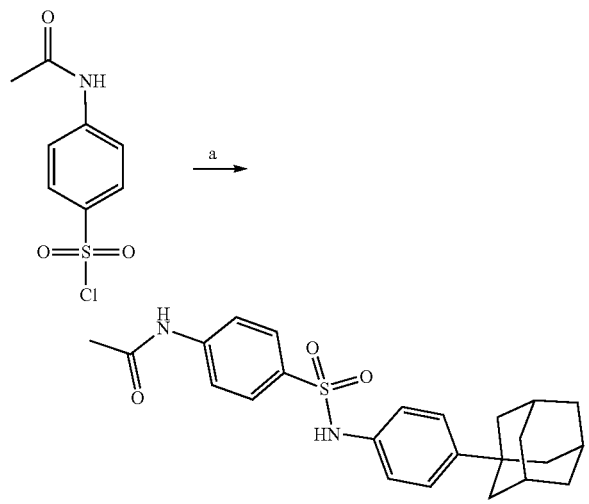

Intermediate-XVI

Step-a: Synthesis of N-(4-(N-(4-((3r,5r,7r)-adamantan-1-yl) phenyl)sulfamoyl)phenyl) acetamide (Intermediate-XVI)

A solution of Intermediate-I.1 (0.5 g, 2.2 mmol) in dichloromethane (10 mL) was cooled to ° C. and added with triethylamine (0.66 g, 6.6 mmol, 3 eq.) followed by 4-acetamidobenzenesulfonyl chloride (0.51 g, 2.2 mmol) and stirred at RT for 3 h. Reaction mass was concentrated in vacuo and added with cold water. The obtained solid was filtered and dried under vacuum to afford title product (0.88 g, 94%). LC-MS: m/z 425.1 (M+H)$^+$ The below intermediates were prepared by a procedure similar to Intermediate-XVI using appropriate reactants and reagents and in presence of suitable solvents and appropriate reaction conditions.

| CP | Intermediate No. | Reactant | Structure | Analytical data |
|---|---|---|---|---|
| 372 | XVI.1 | Int-I.1 | 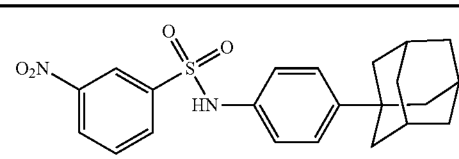 | LC-MS: m/z 411.1 (M − H)$^-$ |
| 393, 392 | XVI.2 | Int-I | 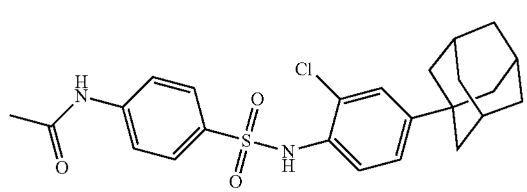 [SMILES: CC(=O)Nc1ccc(S(=O)(=O)Nc2ccc(C34CC5CC(CC(C5)C3)C4)cc2Cl)cc1] | $^1$H NMR (400 MHz, DMSO-d6) δ 9.73 (s, 1H), 8.80 (dd, J = 1.6 Hz, J$_2$ = 6.4 Hz, 1H), 8.31-8.30 (m, 1H), 7.71 (d, J = 8.8 Hz, 2H), 7.63 (d, J = 9.2 Hz, 2H), 7.29 (d, J = 2.8 Hz, 1H), 7.26-7.24 (m, 1H), 7.13 (d, J = 8.8 Hz, 1H), 2.08 (s, 3H), 2.04 (s, 3H), 1.78 (s, 6H), 1.66 (s, 6H). LC-MS: m/z 459.1 (M + H)$^+$ |

-continued

| CP | Intermediate No. | Reactant | Structure | Analytical data |
|---|---|---|---|---|
| 396 & 397 | XVI.3 | Int-I | 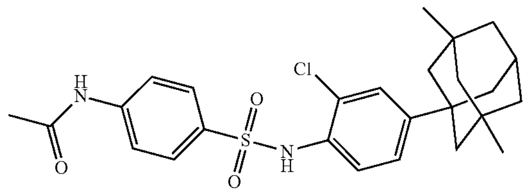 [SMILES: CC(=O)Nc1ccc(S(=O)(=O)Nc2ccc(C34CC5CC(C)(CC(C)(C5)C3)C4)cc2Cl)cc1] | $^1$H NMR (400 MHz, DMSO-d6) δ 10.32 (s, 1H), 9.76 (s, 1H), 7.71 (d, J = 8.8 Hz, 2H), 7.62 (d, J = 8.8 Hz, 2H), 7.29 (d, J = 2.0 Hz, 1H), 7.24 (dd, J$_1$ = 2.0 Hz, J$_2$ = 8.4 Hz, 1H), 7.13 (d, J = 8.4 Hz, 1H), 2.11-2.09 (m, 1H), 2.07 (s, 3H), 1.62 (s, 2H), 1.45-1.29 (m, 8H), 1.15 (s, 1H), 0.83 (s, 6H). LC-MS: m/z 485.1 (M + H)$^+$ |
| 342 | XVI.4 | | 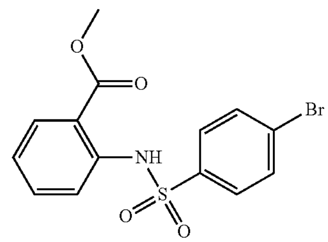 [SMILES: COC(=O)c1ccccc1NS(=O)(=O)c1ccc(Br)cc1] | $^1$H NMR (400 MHz, DMSO-d6) δ 10.4 (s, 1H), 7.84 (d, J = 8.3 Hz, 1H), 7.78 (d, J = 8.3 Hz, 2H), 7.7 (d, J = 8.3 Hz, 2H), 7.56 (t, J = 7.6 Hz, 1H), 7.43 (d, J = 8.0 Hz, 1H), 7.22 (t, J = 7.6 Hz, 1H), 3.8 (s, 3H). LC-MS: m/z 371.95 (M + H)$^{+2}$. |

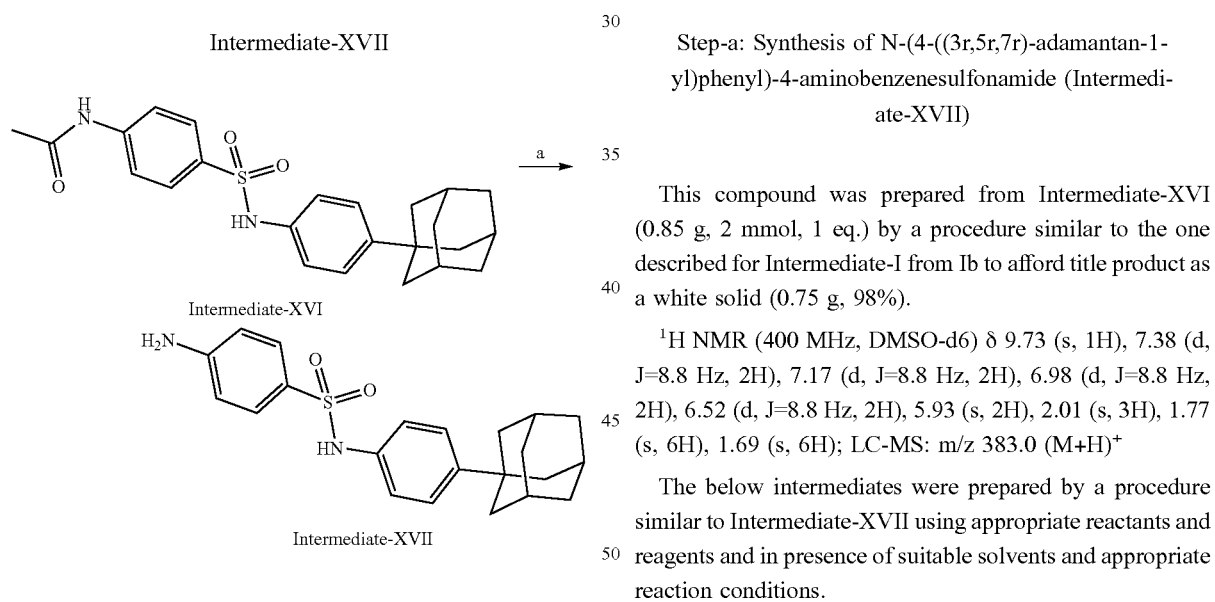

Intermediate-XVII

Step-a: Synthesis of N-(4-((3r,5r,7r)-adamantan-1-yl)phenyl)-4-aminobenzenesulfonamide (Intermediate-XVII)

This compound was prepared from Intermediate-XVI (0.85 g, 2 mmol, 1 eq.) by a procedure similar to the one described for Intermediate-I from Ib to afford title product as a white solid (0.75 g, 98%).

$^1$H NMR (400 MHz, DMSO-d6) δ 9.73 (s, 1H), 7.38 (d, J=8.8 Hz, 2H), 7.17 (d, J=8.8 Hz, 2H), 6.98 (d, J=8.8 Hz, 2H), 6.52 (d, J=8.8 Hz, 2H), 5.93 (s, 2H), 2.01 (s, 3H), 1.77 (s, 6H), 1.69 (s, 6H); LC-MS: m/z 383.0 (M+H)$^+$

The below intermediates were prepared by a procedure similar to Intermediate-XVII using appropriate reactants and reagents and in presence of suitable solvents and appropriate reaction conditions.

| CP | Intermediate No. | Reactant | Structure | Analytical data |
|---|---|---|---|---|
| 372 | XVII.1 | XVI.1 | 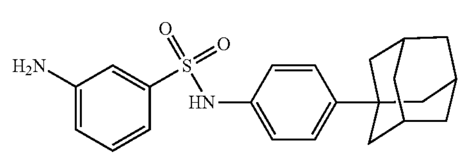 [SMILES: Nc1cccc(S(=O)(=O)Nc2ccc(C34CC5CC(CC(C5)C3)C4)cc2)c1] | LC-MS: m/z 383.1 (M + H)$^+$ |

| CP | Intermediate No. | Reactant | Structure | Analytical data |
|---|---|---|---|---|
| 392, 393 | XVII.2 | XVI.2 | 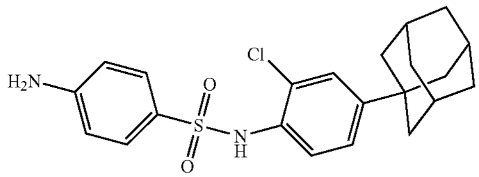 [SMILES: Nc1ccc(S(=O)(=O)Nc2ccc(C34CC5CC(CC(C5)C3)C4)cc2Cl)cc1] | ¹H NMR (400 MHz, DMSO-d6) δ 9.31 (s, 1H), 7.38-7.32 (m, 2H), 7.28 (d, J = 2.0 Hz, 1H), 7.24-7.22 (m, 1H), 7.15 (d, J = 8.8 Hz, 1H), 6.55-6.52 (m, 2H), 5.98 (s, 2H), 2.02 (s, 3H), 1.79 (s, 6H), 1.69 (s, 6H). LC-MS: m/z 417.1 (M + H)⁺ |
| 396, 397 | XVII.3 | XVI.3 | 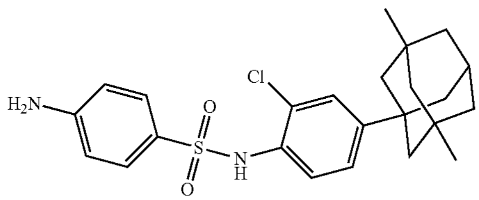 [SMILES: CC12CC3CC(C)(C1)CC(c1ccc(NS(=O)(=O)c4ccc(N)cc4)c(Cl)c1)(C3)C2] | ¹H NMR (400 MHz, DMSO-d6) δ 9.26 (s, 1H), 7.33 (d, J = 8.4 Hz, 2H), 7.27 (s, 1H), 7.22 (d, J = 8.8 Hz, 1H), 7.15 (d, J = 8.4 Hz, 1H), 6.53 (d, J = 8.4 Hz, 2H), 5.96 (s, 2H), 2.1 (m, 1H), 1.61 (s, 2H), 1.45-1.29 (m, 8H), 1.15 (s, 2H), 0.83 (s, 6H). LC-MS: m/z 445.1 (M + H)⁺ |

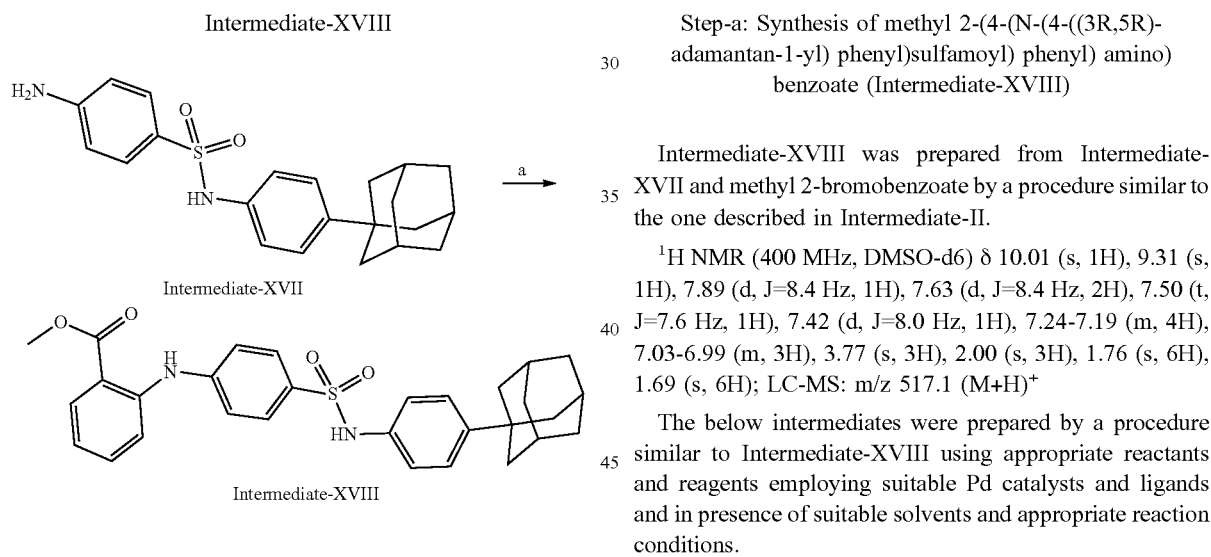

Intermediate-XVIII

Step-a: Synthesis of methyl 2-(4-(N-(4-((3R,5R)-adamantan-1-yl) phenyl)sulfamoyl) phenyl) amino) benzoate (Intermediate-XVIII)

Intermediate-XVIII was prepared from Intermediate-XVII and methyl 2-bromobenzoate by a procedure similar to the one described in Intermediate-II.

¹H NMR (400 MHz, DMSO-d6) δ 10.01 (s, 1H), 9.31 (s, 1H), 7.89 (d, J=8.4 Hz, 1H), 7.63 (d, J=8.4 Hz, 2H), 7.50 (t, J=7.6 Hz, 1H), 7.42 (d, J=8.0 Hz, 1H), 7.24-7.19 (m, 4H), 7.03-6.99 (m, 3H), 3.77 (s, 3H), 2.00 (s, 3H), 1.76 (s, 6H), 1.69 (s, 6H); LC-MS: m/z 517.1 (M+H)⁺

The below intermediates were prepared by a procedure similar to Intermediate-XVIII using appropriate reactants and reagents employing suitable Pd catalysts and ligands and in presence of suitable solvents and appropriate reaction conditions.

| CP | Intermediate No. | Reactant | Structure | Analytical data |
|---|---|---|---|---|
| 306 | XVIII.1 | Int-XVII | 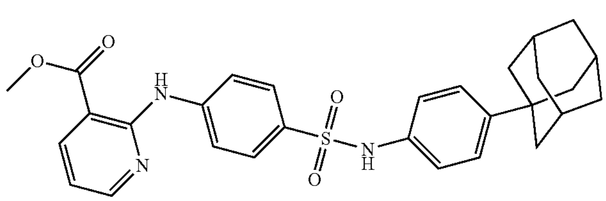 [SMILES: COC(=O)c1cccnc1Nc1ccc(S(=O)(=O)Nc2ccc(C34CC5CC(CC(C5)C3)C4)cc2)cc1] | ¹H NMR (400 MHz, DMSO-d6) δ 10.33 (s, 1H), 10.05 (s, 1H), 8.48-8.47 (m, 1H), 8.31-8.29 (m, 1H), 7.89 (d, J = 8.8 Hz, 2H), 7.69 (d, J = 8.8 Hz, 2H), 7.20 (d, J = 8.8 Hz, 2H), 7.03-6.99 (m, 3H), 3.90 (s, 3H), 1.99 (s, 3H), 1.76 (s, 6H), 1.68 (s, 6H). LC-MS: m/z 518.0 (M + H)⁺ |

-continued

| CP | Intermediate No. | Reactant | Structure | Analytical data |
|---|---|---|---|---|
| 312 | XVIII.2 | Int-XVII | 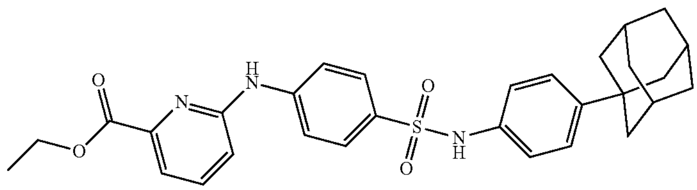 [SMILES: CCOC(=O)c1cccc(Nc2ccc(S(=O)(=O)Nc3ccc(C45CC6CC(CC(C6)C4)C5)cc3)cc2)n1] | ¹H NMR (400 MHz, DMSO-d6) δ 9.96 (s, 1H), 9.81 (s, 1H), 7.99 (d, J = 8.8 Hz, 2H), 7.79 (t, J = 8.0 Hz, 1H), 7.63 (d, J = 8.8 Hz, 2H), 7.53 (d, J = 7.2 Hz, 1H), 7.19 (d, J = 8.8 Hz, 2H), 7.11 (d, J = 8.4 Hz, 1H), 7.02 (d, J = 8.4 Hz, 2H), 4.36-4.30 (m, 2H), 1.98 (s, 3H), 1.76 (s, 6H), 1.68 (s, 6H), 1.35 (t, J = 6.8 Hz, 3H). LC-MS: m/z 532.2 (M + H)⁺ |
| 342 | XVIII.3 | XVI.4 | 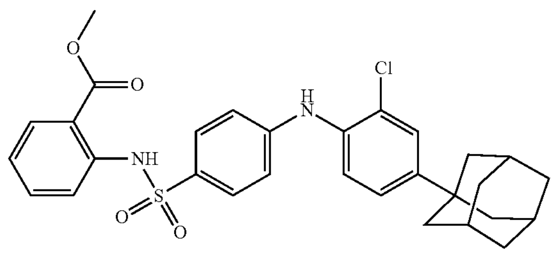 [SMILES: COC(=O)c1ccccc1NS(=O)(=O)c1ccc(Nc2ccc(C34CC5CC(CC(C5)C3)C4)cc2Cl)cc1] | ¹H NMR (400 MHz, DMSO-d6) δ 10.33 (s, 1H), 8.49 (s, 1H), 7.89-8-7.86 (m, 1H), 7.58-7.56 (m, 3H), 7.51-7.49 (m, 1H), 7.43 (s, 1H), 7.34-7.27 (m, 2H), 7.16-7.12 (m, 1H), 6.81 (d, J = 8.8 Hz, 2H), 3.84 (s, 3H), 2.05 (s, 3H), 1.85 (s, 6H), 1.73 (s, 6H). LC-MS: m/z 551.1 (M + H)⁺ |
| 372 | XVIII.4 | XVII.1 | 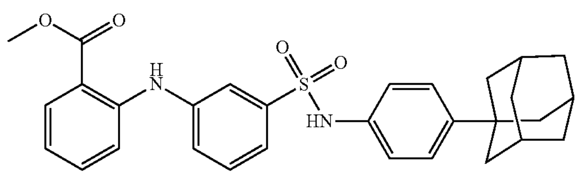 [SMILES: COC(=O)c1ccccc1Nc1cccc(S(=O)(=O)Nc2ccc(C34CC5CC(CC(C5)C3)C4)cc2)c1] | LC-MS: m/z 517.2 (M + H)⁺ |
| 392 | XVIII.5 | XVII.2 | 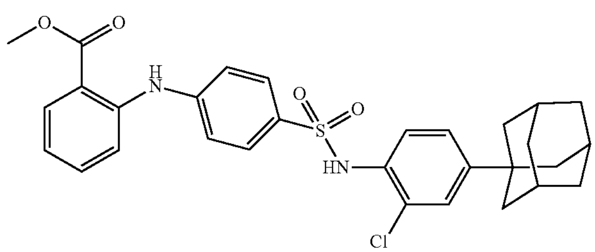 [SMILES: COC(=O)c1ccccc1Nc1ccc(S(=O)(=O)Nc2ccc(C34CC5CC(CC(C5)C3)C4)cc2Cl)cc1] | ¹H NMR (400 MHz, DMSO-d6) δ 9.72 (s, 1H), 9.37 (s, 1H), 7.92 (dd, J₁ = 1.6 Hz, J₂ = 8.0 Hz, 1H), 7.61 (d, J = 9.2 Hz, 2H), 7.55-7.51 (m, 1H), 7.45 (d, J = 7.6 Hz, 1H), 7.32 (d, J = 2.4 Hz, 1H), 7.27-7.25 (m, 3H), 7.17 (d, J = 8.4 Hz, 1H), 7.04-7.00 (m, 1H), 3.81 (s, 3H), 2.02 (s, 3H), 1.80 (d, J = 2.8 Hz, 6H), 1.70 (s, 6H). |
| 393 | XVIII.6 | XVII.2 | 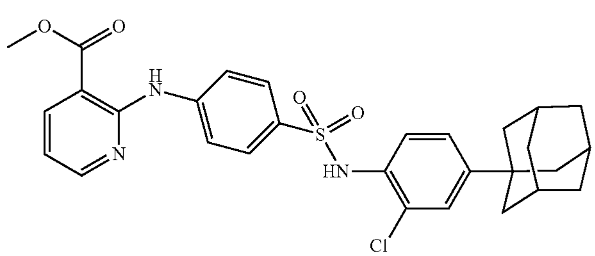 [SMILES: COC(=O)c1cccnc1Nc1ccc(S(=O)(=O)Nc2ccc(C34CC5CC(CC(C5)C3)C4)cc2Cl)cc1] | ¹H NMR (400 MHz, DMSO-d6) δ 10.38 (s, 1H), 9.72 (s, 1H), 8.49 (dd, J₁ = 2.0 Hz, J₂ = 4.8 Hz, 1H), 8.31 (dd, J₁ = 2.0 Hz, J₂ = 7.6 Hz, 1H), 7.92 (d, J = 8.8 Hz, 2H), 7.67 (d, J = 8.8 Hz, 2H), 7.30 (d, J = 2.0 Hz, 1H), 7.25-7.24 (m, 1H), 7.17 (d, J = 8.4 Hz, 1H), 7.02 (dd, J₁ = 4.8 Hz, J₂ = 7.6 Hz, 1H), 3.91 (s, 3H), 2.01 (s, 3H), 1.79 (s, 6H), 1.69 (s, 6H). LC-MS: m/z 552.2 (M + H)⁺ |

| CP | Intermediate No. | Reactant | Structure | Analytical data |
|---|---|---|---|---|
| 396 | XVIII.7 | XVII.3 | (structure) | LC-MS: m/z 577.2 (M + H)⁻ |
| 397 | XVIII.8 | XVII.3 | (structure) | $^1$H NMR (400 MHz, DMSO-d6) δ 10.40 (s, 1H), 9.75 (s, 1H), 8.49 (dd, $J_1$ = 2.0 Hz, $J_2$ = 4.8 Hz, 1H), 8.32 (dd, $J_1$ = 1.6 Hz, $J_2$ = 7.6 Hz, 1H), 7.93 (d, J = 8.4 Hz, 2H), 7.65 (d, J = 8.8 Hz, 2H), 7.29-7.24 (m, 2H), 7.16 (d, J = 8.4 Hz, 1H), 7.02 (dd, $J_1$ = 4.8 Hz, $J_2$ = 7.6 Hz, 1H), 3.91 (s, 3H), 2.10-2.09 (m, 1H), 1.62 (s, 2H), 1.45-1.29 (m, 8H), 1.14 (s, 2H), 0.82 (s, 6H). LC-MS: m/z 580.2 (M + H)⁺ |

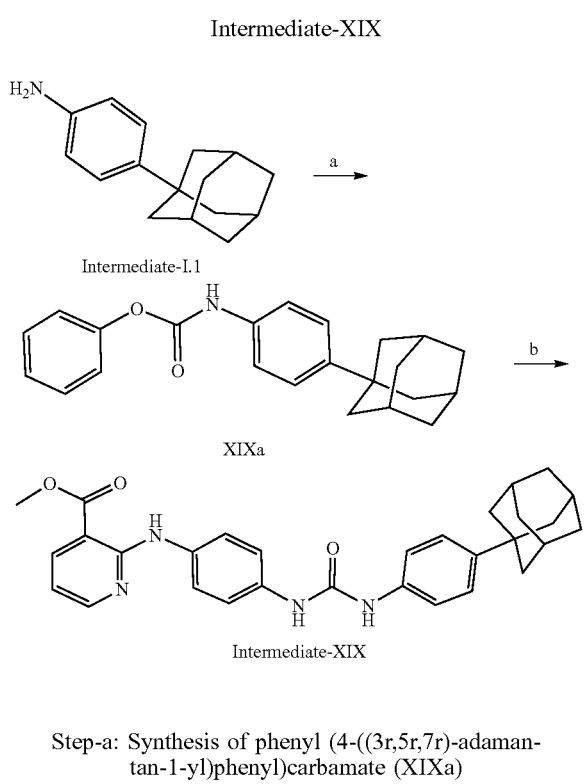

Intermediate-XIX

Step-a: Synthesis of phenyl (4-((3r,5r,7r)-adamantan-1-yl)phenyl)carbamate (XIXa)

A solution of Intermediate-I.1 (0.5 g, 2.2 mmol, 1 eq.) and phenyl chloroformate (0.42 g, 2.64 mmol, 1.2 eq.) in DCM was added with triethylamine (0.44 g, 4.4 mmol, 2 eq.) and stirred at RT for 2 h. Reaction mixture was washed with water, concentrated in vacuo and purified by combi-flash to afford title compound as white solid (0.48 g, 630%).

$^1$H NMR (400 MHz, DMSO-d6) δ10.10 (s, 1H), 7.44-7.39 (m, 4H), 7.31-7.19 (m, 5H), 2.05 (s, 3H), 1.84 (s, 6H), 1.73 (s, 6H); LC-MS: m/z 348.1 (M+H)⁺

Step-b: Synthesis of methyl 2-(4-(3-(4-((3R,5R)-adamantan-1-yl) phenyl)ureido)phenyl) amino) nicotinate (Intermediate-XIX)

Intermediate-XIXa (0.285 g, 0.82 mmol, 1 eq.) and methyl 2-((4-aminophenyl)amino) nicotinate (0.2 g, 0.82 mmol, 1 eq.) were taken in THF (20 mL) and added with triethylamine (0.8 mL) and refluxed overnight. Reaction mass was concentrated in vacuo, the obtained crude was washed with n-hexane twice and dried under vacuum. The crude was taken further without purification.

$^1$H NMR (400 MHz, DMSO-d6) δ 9.96 (s, 1H), 8.52 (d, J=14.0 Hz, 2H), 8.38-8.37 (m, 1H), 7.76 (d, J=8.4 Hz, 2H), 7.41-7.35 (m, 4H), 7.25 (d, J=8.4 Hz, 2H), 6.84 (dd, $J_1$=4.4 Hz, $J_2$=8.0 Hz, 1H), 3.87 (s, 3H), 2.05 (s, 3H), 1.84 (s, 6H), 1.73 (s, 6H); LC-MS: m/z 497.2 (M+H)⁺

The below intermediates were prepared by a procedure similar to Intermediate-XIX using appropriate reactants and reagents and in presence of suitable solvents and appropriate reaction conditions.

| CP | Intermediate No. | Reactant | Structure | Analytical data |
|---|---|---|---|---|
| 300 | XIX.1 | VII.14 & Int-I.1 | 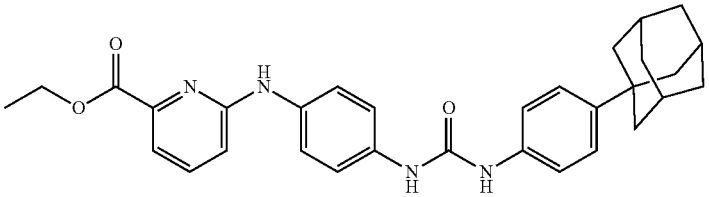 [SMILES: CCOC(=O)c1cccc(Nc2ccc(NC(=O)Nc3ccc(C45CC6CC(CC(C6)C4)C5)cc3)cc2)n1] | ¹H NMR (400 MHz, DMSO-d6) δ 9.18 (s, 1H), 8.45 (d, J = 13.2 Hz, 2H), 7.73-7.66 (m, 3H), 7.39-7.34 (m, 5H), 7.25 (d, J = 8.4 Hz, 2H), 6.99 (d, J = 8.4 Hz, 1H), 4.35-4.30 (m, 2H), 2.05 (s, 3H), 1.84 (s, 6H), 1.73 (s, 6H), 1.35 (t, J = 7.2 Hz, 3H). LC-MS: m/z 511.1 (M + H)⁺ |
| 307 | XIX.2 | XI.13 & Int-I.1 | 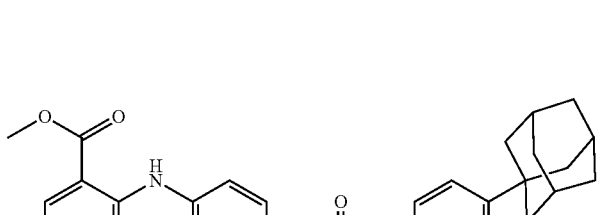 | ¹H NMR (400 MHz, DMSO-d6) δ 9.21 (s, 1H), 8.61 (s, 1H), 8.52 (s, 1H), 7.88 (d, J = 7.8 Hz, 1H), 7.47 (d, J = 8.3 Hz, 2H), 7.38-7.36 (m, 3H), 7.26 (d, J = 8.8 Hz, 2H), 7.18 (d, J = 8.3 Hz, 2H), 7.05 (d, J = 8.3 Hz, 1H), 6.75-6.73 (m, 1H), 3.85 (s, 3H), 2.05 (s, 3H), 1.84 (s, 6H), 1.73 (s, 6H). LC-MS: m/z 496.1 (M + H)⁺ |
| 299 | XIX.3 | XI.17 & Int-I.1 | 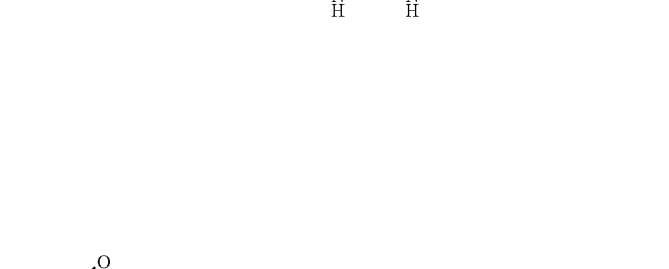 | LC-MS: m/z 511.1 (M + H)⁺ |

Intermediate-XIX.4

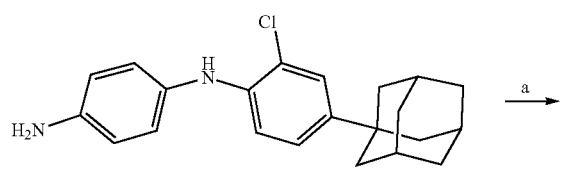

Intermediate-XI

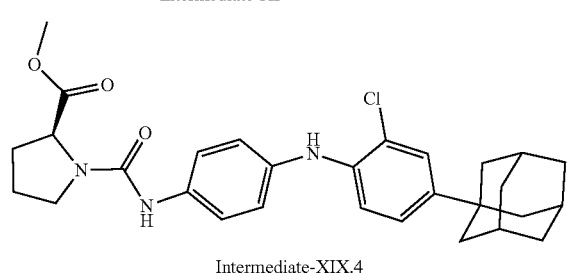

Intermediate-XIX.4

Step-a: Synthesis of methyl ((4-((4-((3R,5S)-adamantan-1-yl)-2-chlorophenyl) amino)phenyl) carbamoyl) prolinate (XIX.4)

A solution of Intermediate-XI (0.1 g, 0.283 mmol, 1 eq.) in DCM (10 mL) at 0° C. was added with triphosgene (0.084 g, 0.283 mmol, 1 eq.) drop wise and stirred at 0° C. for 1 h. This solution was added to a solution of methyl prolinate (0.056 g, 0.32 mmol, 1.2 eq.) in DCM (10 mL) and stirred at 0° C. for 1 h. Quenched with sat. bicarbonate solution and extracted with DCM, purified by column chromatography to afford title product as pale brown solid (0.13 g, 90%).

¹H NMR (400 MHz, DMSO-d6) δ 8.18 (s, 1H), 7.34 (d, J=8.8 Hz, 2H), 7.28 (d, J=2.0 Hz, 1H), 7.26 (s, 1H), 7.14 (dd, $J_1$=2.0 Hz, $J_2$=8.0 Hz, 1H), 7.04 (d, J=8.8 Hz, 1H), 6.96 (d, J=9.6 Hz, 2H), 4.37-4.34 (m, 1H), 3.62 (s, 3H), 3.56-3.46 (m, 2H), 2.21-2.14 (m, 1H), 2.03 (s, 3H), 1.98-1.84 (m, 3H), 1.81 (d, J=2.4 Hz, 6H), 1.71 (s, 6H); LC-MS: m/z 508.4 (M+H)⁺

The below intermediates were prepared by a procedure similar to Intermediate-XIX.4 using appropriate reactants and reagents and in presence of suitable solvents and appropriate reaction conditions.

| CP | Intermediate No. | Reactant | Structure | Analytical data |
|---|---|---|---|---|
| 114 | XIX.5 | Int-XI | (structure) | $^1$H NMR (400 MHz, DMSO-d6) δ 8.18 (s, 1H), 7.34 (d, J = 8.8 Hz, 2H), 7.28 (d, J = 2.0 Hz, 1H), 7.26 (s, 1H), 7.14 (dd, J$_1$ = 2.0 Hz, J$_2$ = 8.0 Hz, 1H), 7.04 (d, J = 8.8 Hz, 1H), 6.96 (d, J = 9.6 Hz, 2H), 4.37-4.34 (m, 1H), 3.62 (s, 3H), 3.56-3.46 (m, 2H), 2.21-2.14 (m, 1H), 2.03 (s, 3H), 1.98-1.84 (m, 3H), 1.81 (d, J = 2.4 Hz, 6H), 1.71 (s, 6H). LC-MS: m/z 508.2 (M + H)$^+$ |
| 134 | XIX.6 | XI.2 | (structure) | $^1$H NMR (400 MHz, DMSO-d6) δ 8.24 (s, 1H), 7.47 (s, 1H), 7.41 (d, J = 6.8 Hz, 2H), 7.33 (d, J = 1.6 Hz, 1H), 7.28-7.17 (m, 4H), 7.13-7.06 (m, 4H), 4.38-4.35 (m, 1H), 3.76 (s, 3H), 3.63-3.48 (m, 2H), 2.27 (s, 3H), 2.25-2.17 (m, 1H), 1.96-1.84 (m, 3H). LC-MS: m/z 464.1 (M + H)$^+$ |

Intermediate-XX

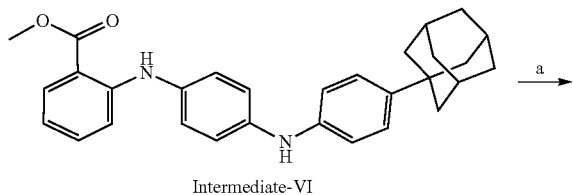

Intermediate-VI

→ a →

Intermediate-XX

Step-a: Synthesis of methyl 2-((4-((4-((3R,5R)-adamantan-1-yl)phenyl)(methyl) amino) phenyl)(methyl) amino) benzoate (Intermediate-XX)

A solution of intermediate-VI (4 g, 8.85 mmol, 1 eq.) in DMF (80 mL) was cooled to 0° C. and added with sodium hydride (1.06 g, 44.2 mmol, 5 eq.) portion wise and stirred for 15 minutes. Methyl iodide (6.3 g, 44.2 mmol, 5 eq.) was added drop wise and the reaction mass was heated at 80° C. for 16 h in a seal tube. Reaction mass was cooled to RT and poured in to cold water. The precipitated solid was filtered and dried. This crude was absorbed over silica and purified by combi-flash to afford title product as pale-yellow solid (3 g, 70.70%).

$^1$H NMR (400 MHz, DMSO-d6) δ 7.65 (dd, J$_1$=2.0 Hz, J$_2$=8.0 Hz, 1H), 7.60 (t, J=7.6 Hz, 1H), 7.33 (d, J=7.6 Hz, 1H), 7.26 (t, J=7.2 Hz, 1H), 7.13 (d, J=8.8 Hz, 2H), 6.90 (d, J=8.8 Hz, 2H), 6.67 (d, J=8.8 Hz, 2H), 6.59 (d, J=8.8 Hz, 2H), 3.55 (s, 3H), 3.20 (s, 3H), 3.13 (s, 3H), 2.02 (s, 3H), 1.80 (s, 6H), 1.71 (s, 6H); LC-MS: m/z 480.25 (M+H)$^+$

The below intermediates were prepared by a procedure similar to Intermediate-XX using appropriate reactants and reagents and in presence of suitable solvents and appropriate reaction conditions.

| CP | Intermediate No. | Reactant | Structure | Analytical data |
|---|---|---|---|---|
| 198 | XX.1 | Int-XII | 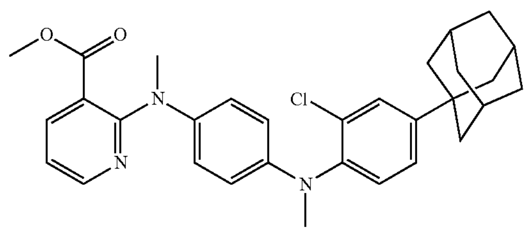 [SMILES: COC(=O)c1cccnc1N(C)c1ccc(N(C)c2ccc(C34CC5CC(CC(C5)C3)C4)cc2Cl)cc1] | ¹H NMR (400 MHz, DMSO-d6) δ 8.31 (dd, J₁ = 2.0 Hz, J₂ = 4.8 Hz, 1H), 7.62 (dd, J₁ = 2.0 Hz, J₂ = 7.2 Hz, 1H), 7.49 (d, J = 2.4 Hz, 1H), 7.41 (dd, J₁ = 2.4 Hz, J₂ = 8.4 Hz, 1H), 7.26 (d, J = 8.4 Hz, 1H), 6.85-6.80 (m, 3H), 6.42 (d, J = 9.2 Hz, 2H), 3.31 (s, 3H), 3.25 (s, 3H), 3.15 (s, 3H), 2.07 (s, 3H), 1.89 (s, 6H), 1.74 (s, 6H). |
| 233 | XX.2 | VI.36 | 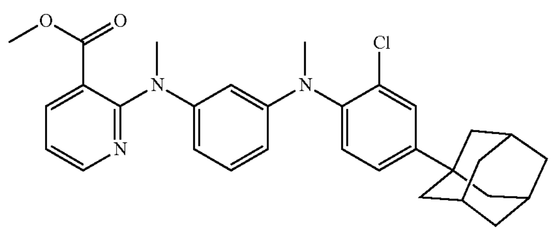 | LC-MS: m/z 480.25 (M + H)⁺ |
| 236 | XX.3 | XII.18 | 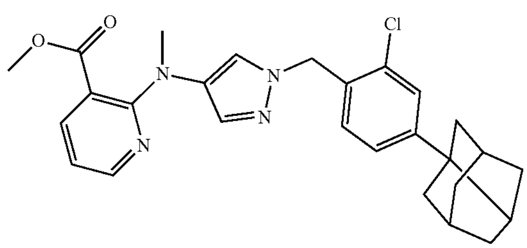 | ¹H NMR (400 MHz, DMSO-d6) δ 8.31 (dd, J₁ = 2.0 Hz, J₂ = 4.9 Hz, 1H), 7.71 (s, 1H), 7.70 (d, J = 1.4 Hz, 1H), 7.39 (d, J = 1.9 Hz, 1H), 7.32 (d, J = 2.0 Hz, 2H), 7.04 (d, J = 8.3 Hz, 1H), 6.88-6.85 (m, 1H), 5.28 (s, 2H), 3.39 (s, 3H), 3.26 (s, 3H), 2.04 (s, 3H), 1.83 (s, 6H), 1.72 (s, 6H). LC-MS: m/z 491.3 (M + H)⁺ |
| 246 | XX.4 | VI.40 | 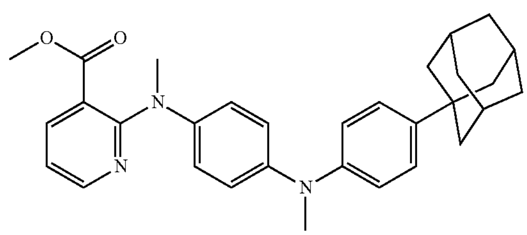 [SMILES: COC(=O)c1cccnc1N(C)c1ccc(N(C)c2ccc(C34CC5CC(CC(C5)C3)C4)cc2)cc1] | ¹H NMR (400 MHz, DMSO-d6) δ 8.35 (d, J = 3.2 Hz, 1H), 7.69 (d, J = 5.6 Hz, 1H), 7.25 (d, J = 8.4 Hz, 2H), 6.92-6.86 (m, 7H), 3.37 (s, 3H), 3.31 (s, 3H), 3.19 (s, 3H), 2.04 (s, 3H), 1.84 (s, 6H), 1.72 (s, 6H). LC-MS: m/z 482.1 (M + H)⁺ |
| 247 | XX.5 | VI.41 | 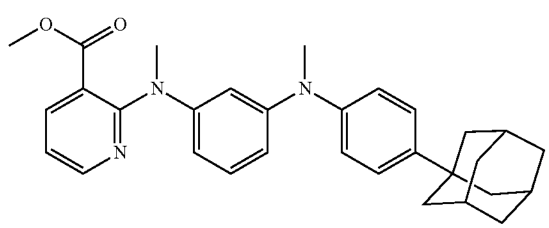 [SMILES: COC(=O)c1cccnc1N(C)c1cccc(N(C)c2ccc(C34CC5CC(CC(C5)C3)C4)cc2)c1] | ¹H NMR (400 MHz, DMSO-d6) δ 8.37 (dd, J₁ = 1.9 Hz, J₂ = 4.8 Hz, 1H), 7.78 (dd, J₁ = 2.0 Hz, J₂ = 7.4 Hz, 1H), 7.25 (d, J = 8.3 Hz, 2H), 7.12 (t, J = 7.8 Hz, 1H), 7.00 (d, J = 8.8 Hz, 2H), 6.94-6.90 (m, 1H), 6.56 (dd, J₁ = 2.0 Hz, J₂ = 8.3 Hz, 1H), 6.51 (dd, J₁ = 1.5 Hz, J₂ = 7.9 Hz, 1H), 6.40 (t, J = 1.9 Hz, 1H), 3.38 (s, 3H), 3.30 (s, 3H), 3.17 (s, 3H), 2.04 (s, 3H), 1.82 (s, 6H), 1.72 (s, 6H). LC-MS: m/z 482.1 (M + H)⁺ |
| 260 | XX.6 | Int-XV | 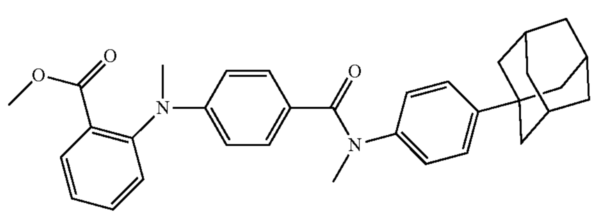 | LC-MS: m/z 495.2 (M + H)⁺ (Obtained acid directly) |

-continued

| CP | Intermediate No. | Reactant | Structure | Analytical data |
|---|---|---|---|---|
| 266 | XX.7 | XII.68 | 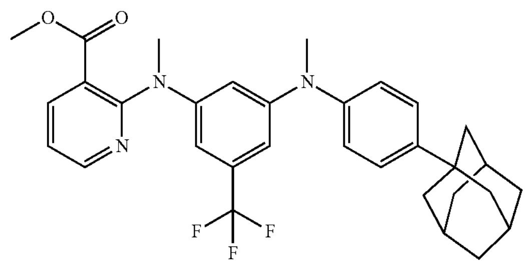 | LC-MS: m/z 536.1 (M + H)+ (obtained acid directly) |
| 270 | XX.8 | XII.67 | 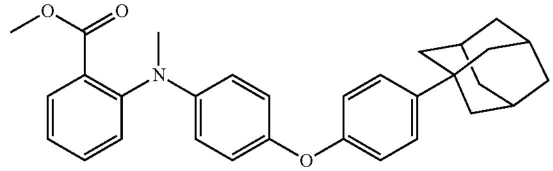 [SMILES: COC(=O)c1ccccc1N(C)c1ccc(Oc2ccc(C34CC5CC(CC(C5)C3)C4)cc2)cc1] | LC-MS: m/z 468.1 (M + H)+ |
| 271 | XX.9 | XII.33 | 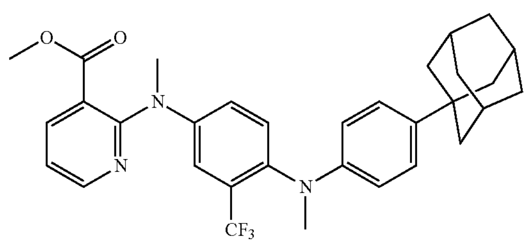 [SMILES: COC(=O)c1cccnc1N(C)c1ccc(N(C)c2ccc(C34CC5CC(CC(C5)C3)C4)cc2)c(C(F)(F)F)c1] | 1H NMR (400 MHz, DMSO-d6) δ 8.52 (dd, J1 = 1.2 Hz, J2 = 4.8 Hz, 1H), 7.93 (dd, J1 = 1.6 Hz, J2 = 7.6 Hz, 1H), 7.30 (d, J = 9.2 Hz, 2H), 7.22 (d, J = 8.4 Hz, 1H), 7.14-7.11 (m, 3H), 6.44 (d, J = 8.8 Hz, 2H), 3.50 (s, 3H), 3.42 (s, 3H), 3.05 (s, 3H), 2.02 (s, 3H), 1.74 (s, 6H), 1.67 (s, 6H). LC-MS: m/z 550.1 (M + H)+ |
| 273 | XX.10 | XII.34 | 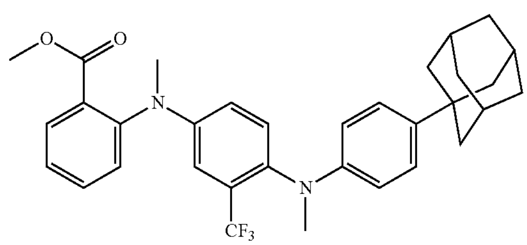 [SMILES: COC(=O)c1ccccc1N(C)c1ccc(N(C)c2ccc(C34CC5CC(CC(C5)C3)C4)cc2)c(C(F)(F)F)c1] | 1H NMR (400 MHz, DMSO-d6) δ 7.82-7.78 (m, 1H), 7.42-7.38 (m, 1H), 7.46-7.44 (m, 2H), 7.11-7.05 (m, 3H), 6.81-6.78 (m, 2H), 6.38 (d, J = 8.8 Hz, 2H), 3.60 (s, 3H), 3.27 (s, 3H), 3.02 (s, 3H), 2.02 (s, 3H), 1.79 (s, 6H), 1.70 (s, 6H). LC-MS: m/z 549.1 (M + H)+ |
| 275 | XX.11 | XII.35 | 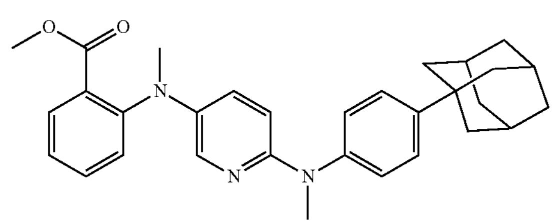 [SMILES: COC(=O)c1ccccc1N(C)c1ccc(N(C)c2ccc(C34CC5CC(CC(C5)C3)C4)cc2)nc1] | 1H NMR (400 MHz, DMSO-d6) δ 7.69 (d, J = 2.8 Hz, 1H), 7.56-7.52 (m, 2H), 7.32 (d, J = 8.4 Hz, 2H), 7.26 (d, J = 8.0 Hz, 1H), 7.15 (t, J = 6.8 Hz, 1H), 7.10 (d, J = 8.8 Hz, 2H), 6.93 (dd, J1 = 2.8 Hz, J2 = 9.2 Hz, 1H), 6.53 (d, J = 9.2 Hz, 1H), 3.53 (s, 3H), 3.29 (s, 3H), 3.18 (s, 3H), 2.05 (s, 3H), 1.86 (s, 6H), 1.73 (s, 6H). LC-MS: m/z 482.25 (M + H)+ |
| 276 | XX.12 | XV.19 | 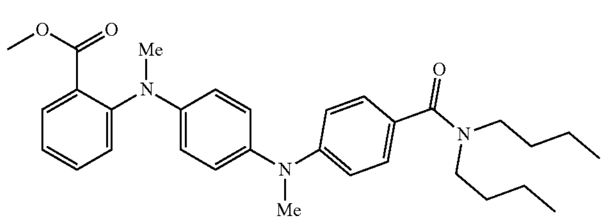 [SMILES: CCCCN(CCCC)C(=O)c1ccc(N(C)c2ccc(N(C)c3ccccc3C(=O)OC)cc2)cc1] | 1H NMR (400 MHz, DMSO-d6) δ 7.71 (d, J = 6.4 Hz, 1H), 7.63 (t, J = 7.3 Hz, 1H), 7.36 (m, 2H), 7.16 (m, 1H), 7.13 (d, J = 8.8 Hz, 2H), 6.99 (d, J = 8.8 Hz, 2H), 6.62 (m, 4H), 3.57 (s, 3H), 3.28 (m, 4H), 3.25 (s, 3H), 3.18 (s, 3H), 1.50 (m, 4H), 1.23 (m, 4H), 0.86 (m, 6H). |

-continued

| CP | Intermediate No. | Reactant | Structure | Analytical data |
|---|---|---|---|---|
| 277 | XX.13 | VI.45 | 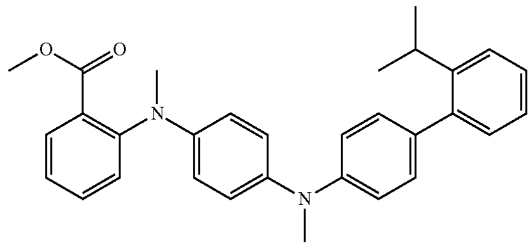 | LC-MS: m/z 451.1 (M + H)+ (obtained acid directly) |
| 286 | XX.14 | XII.36 | 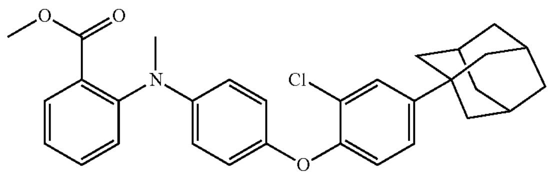 [SMILES: COC(=O)c1ccccc1N(C)c1ccc(Oc2ccc(C34CC5CC(CC(C5)C3)C4)cc2Cl)cc1] | ¹H NMR (400 MHz, DMSO-d6) δ 7.69 (dd, J₁ = 1.6 Hz, J₂ = 8.0 Hz, 1H), 7.64-7.60 (m, 1H), 7.43 (d, J = 2.8 Hz, 1H), 7.36-7.25 (m, 3H), 6.84-6.78 (m, 3H), 6.60 (d, J = 8.8 Hz, 2H), 3.54 (s, 3H), 3.21 (s, 3H), 2.04 (s, 3H), 1.83 (s, 6H), 1.72 (s, 6H). LC-MS: m/z 502.1 (M + H)+ |
| 296 | XX.15 | VI.49 | 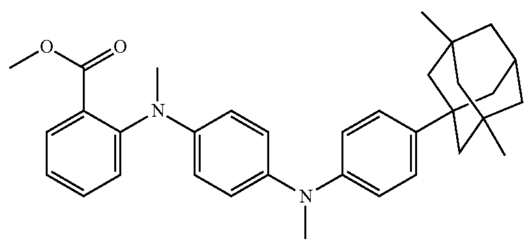 [SMILES: COC(=O)c1ccccc1N(C)c1ccc(N(C)c2ccc(C34CC5CC(C)(CC(C)(C5)C3)C4)cc2)cc1] | ¹H NMR (400 MHz, DMSO-d6) δ 7.68-7.55 (m, 2H), 7.38-7.05 (m, 4H), 6.95-6.83 (m, 2H), 6.75-6.55 (m, 4H), 3.54 (s, 3H), 3.20 (s, 3H), 3.13 (s, 3H), 2.10 (m, 1H), 1.62 (s, 2H), 1.46-1.33 (m, 8H), 1.16 (s, 2H), 0.83 (s, 6H). LC-MS: m/z 509.2 (M + H)+ |
| 305 | XX.16 | VI.45 | 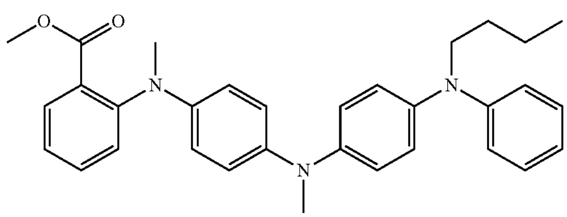 [SMILES: CCCCN(c1ccccc1)c1ccc(N(C)c2ccc(N(C)c3ccccc3C(=O)OC)cc2)cc1] | ¹H NMR (400 MHz, DMSO-d6) δ 7.67 (d, J = 7.8 Hz, 1H), 7.63-7.59 (m, 1H), 7.35 (d, J = 8.4 Hz, 1H), 7.30-7.26 (m, 1H), 7.10 (t, J = 8.0 Hz, 2H), 6.94 (t, J = 8.4 Hz, 4H), 6.73 (d, J = 8.8 Hz, 2H), 6.65-6.60 (m, 5H), 3.56-3.53 (m, 5H), 3.21 (s, 3H), 3.17 (s, 3H), 1.53-1.48 (m, 2H), 1.33-1.28 (m, 2H), 0.87 (t, J = 6.9 Hz, 3H). LC-MS: m/z 494.1 (M + H)+ |
| 310 | XX.17 | Int-XV | 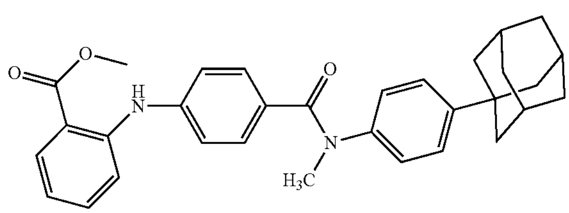 [SMILES: COC(=O)c1ccccc1Nc1ccc(C(=O)N(C)c2ccc(C34CC5CC(CC(C5)C3)C4)cc2)cc1] | ¹H NMR (400 MHz, DMSO-d6) δ 9.24 (s, 1H), 7.88 (d, J = 8.0 Hz, 1H), 7.40-7.38 (m, 1H), 7.28-7.19 (m, 5H), 7.09 (d, J = 8.4 Hz, 2H), 7.02 (d, J = 8.4 Hz, 2H), 6.88 (t, J = 7.2 Hz, 1H), 3.90 (s, 3H), 3.34 (s, 3H), 2.02 (s, 3H), 1.81 (s, 6H), 1.70 (s, 6H). LC-MS: m/z 495.1 (M + H)+ |
| 314 | XX.18 | XII.40 | 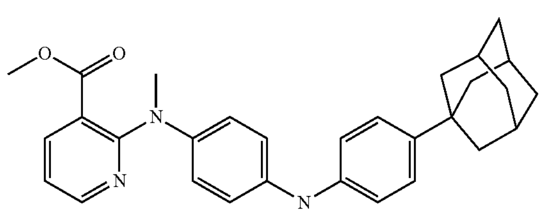 [SMILES: COC(=O)c1cccnc1N(C)c1ccc(Nc2ccc(C34CC5CC(CC(C5)C3)C4)cc2)cc1] | ¹H NMR (400 MHz, DMSO-d6) δ 8.39 (dd, J₁ = 1.4 Hz, J₂ = 4.4 Hz, 1H), 7.44 (dd, J₁ = 2.0 Hz, J₂ = 7.9 Hz, 1H), 7.35 (d, J = 8.8 Hz, 2H), 7.03 (d, J = 9.3 Hz, 2H), 6.9-6.89 (m, 5H), 3.41 (s, 3H), 3.31 (s, 3H), 2.09 (s, 3H), 1.85 (s, 6H), 1.73 (s, 6H). LC-MS: m/z 469.3 (M + H)+ |

-continued

| CP | Intermediate No. | Reactant | Structure | Analytical data |
|---|---|---|---|---|
| 325 | XX.19 | XVIII.1 | 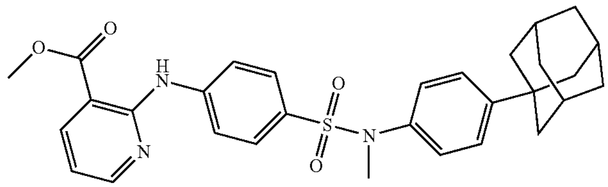 | LC-MS: m/z 532.2 (M + H)+ |
| 326 | XX.20 | VI.53 | 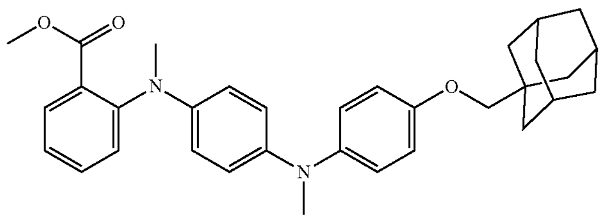 [SMILES: COC(=O)c1ccccc1N(C)c1ccc(N(C)c2ccc(OCC34CC5CC(CC(C5)C3)C4)cc2)cc1] | LC-MS: m/z 511.4 (M + H)+ |
| 355 | XX.21 | XX.19 | 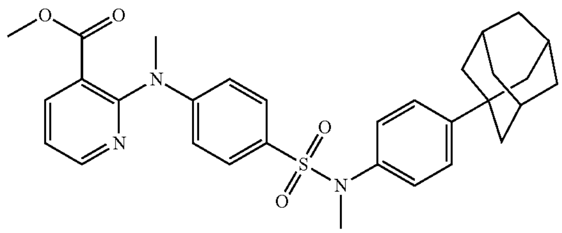 [SMILES: COC(=O)c1cccnc1N(C)c1ccc(S(=O)(=O)N(C)c2ccc(C34CC5CC(CC(C5)C3)C4)cc2)cc1] | LC-MS: m/z 546.1 (M + H)+ |
| 357 | XX.22 | XIV.16 | 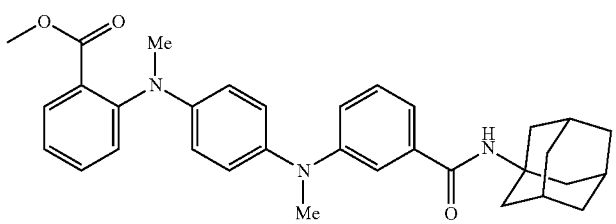 [SMILES: COC(=O)c1ccccc1N(C)c1ccc(N(C)c2cccc(C(=O)NC34CC5CC(CC(C5)C3)C4)c2)cc1] | $^1$H NMR (400 MHz, DMSO-d6) δ 7.69 (d, J = 8.0 Hz, 1H), 7.65-7.60 (m, 1H), 7.39-7.30 (m, 3H), 7.15-7.07 (m, 3H), 6.94 (d, J = 8.8 Hz, 2H), 6.76 (d, J = 8.0 Hz, 1H), 6.60 (d, J = 8.8 Hz, 2H), 3.56 (s, 3H), 3.22 (s, 3H), 3.18 (s, 3H), 2.03 (s, 9H), 1.64 (s, 6H). LC-MS: m/z 524.3 (M + H)+ |
| 360 | XX.23 | XII.51 | 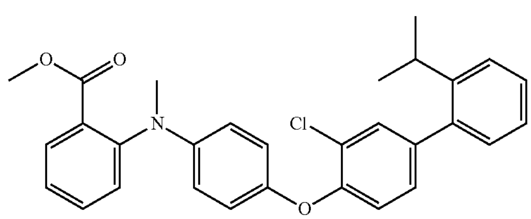 [SMILES: COC(=O)c1ccccc1N(C)c1ccc(Oc2ccc(-c3ccccc3C(C)C)cc2Cl)cc1] | $^1$H NMR (400 MHz, DMSO-d6) δ 7.71 (d, J = 7.8 Hz, 1H), 7.61 (d, J = 7.4 Hz, 1H), 7.43 (d, J = 7.8 Hz, 2H), 7.35-7.30 (m, 3H), 7.21-7.16 (m, 3H), 6.94 (d, J = 8.8 Hz, 2H), 6.86 (d, J = 8.4 Hz, 1H), 6.64 (d, J = 8.8 Hz, 2H), 3.56 (s, 3H), 3.22 (s, 3H), 2.94 (m, 1H), 1.13 (d, J = 6.4 Hz, 6H), LC-MS: m/z 486.2 (M + H)+ |
| 362 | XX.24 | XII.52 | 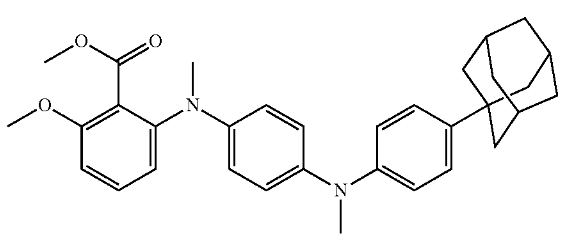 [SMILES: COC(=O)c1c(OC)cccc1N(C)c1ccc(N(C)c2ccc(C34CC5CC(CC(C5)C3)C4)cc2)cc1] | $^1$H NMR (400 MHz, DMSO-d6) δ 7.45 (t, J = 8.0 Hz, 1H), 7.13 (t, J = 8.4 Hz, 2H), 6.97 (d, J = 8.4 Hz, 1H), 6.91 (d, J = 8.8 Hz, 2H), 6.81 (d, J = 8.0 Hz, 1H), 6.71-6.57 (m, 4H), 3.79 (s, 3H), 3.57 (s, 3H), 3.14 (s, 3H), 3.09 (s, 3H), 2.03 (s, 3H), 1.80 (s, 6H), 1.71 (s, 6H). LC-MS: m/z 511.2 (M + H)+ |

-continued

| CP | Intermediate No. | Reactant | Structure | Analytical data |
|---|---|---|---|---|
| 587 | XX.25 | XII.122 | 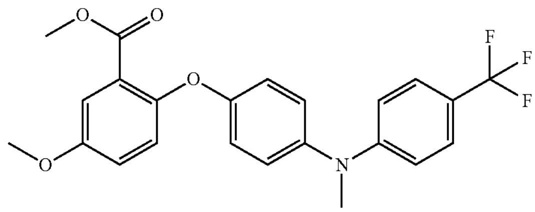 | LC-MS: m/z 418.2 (M + H)+ |

The below compounds were prepared by a procedure similar to Intermediate-VI using appropriate reactants and reagents employing suitable Pd catalysts and ligands and in presence of suitable solvents and appropriate reaction conditions.

| No | Compound No | Reactant | Structure | Analytical data |
|---|---|---|---|---|
| 51 | 1 | | 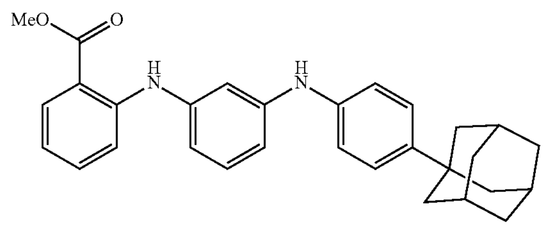 [SMILES: COC(=O)c1ccccc1Nc1cccc(Nc2ccc(C34CC5CC(CC(C5)C3)C4)cc2)c1] | $^1$H NMR (500 MHz, CDCl$_3$) δ 9.45 (s, 1H), 8.01 (s, 1H), 7.5-7.7.30 (m, 2H), 7.2-7.1 (m, 2H), 6.98 (s, 1H), 6.8 (s, 1H), 6.78-6.26 (m, 4H), 5.99 (s, 1H), 3.90 (s, 3H), 2.23-1.97 (m, 15H) LC-MS: m/z 453.3 (M + H)$^+$ |
| 54 | 2 | | 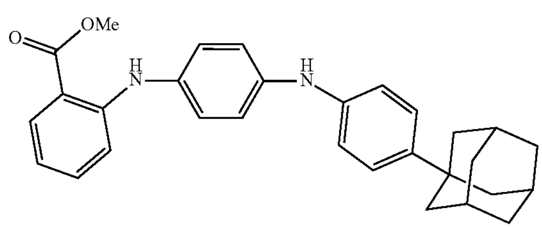 | LC-MS: m/z 453.1 (M + H)$^+$ |
| 57 | 3 | | 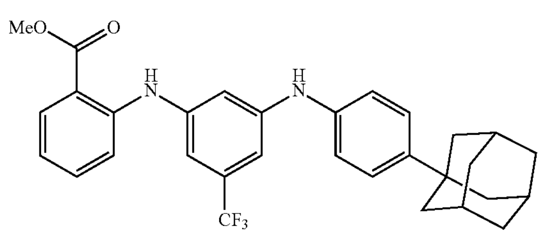 | $^1$H NMR (500 MHz, CDCl$_3$) δ 9.45 (s, 1H), 8.01 (s, 1H), 7.45-7.23. (d, 2H), 7.23-7.01 (m, 6H), 6.98-7.01 (d, 2H), 6.94 (s, 1H), 3.93 (s, 3H), 5.99 (s, 1H), 2.21-1.98 (m, 15H) LC-MS: m/z 521.6 (M + H)$^+$ |

-continued

| No | Compound No | Reactant | Structure | Analytical data |
|---|---|---|---|---|
| 68 | 4 | | (methyl 2-((4-((4-(adamantan-1-yl)phenyl)carbamoyl)phenyl)amino)benzoate) | LC-MS: m/z 481.1 (M + H)⁺ |
| 70 | 5 | | (methyl 2-((4-((2-bromo-4-(adamantan-1-yl)phenyl)carbamoyl)phenyl)amino)benzoate) | LC-MS: m/z 561.2 (M + H)²⁺ |
| 79 | 6 | | (methyl 2-((4-((2-chloro-4-(adamantan-1-yl)phenyl)carbamoyl)phenyl)amino)benzoate) | LC-MS: m/z 515.3 (M + H)⁺ |
| 85 | 7 | Int-XI | 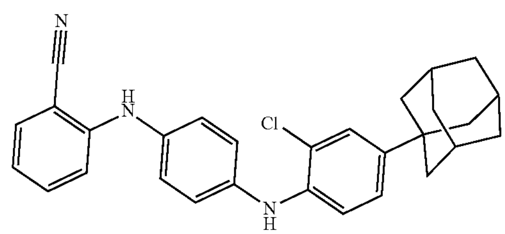 [SMILES: N#Cc1ccccc1Nc1ccc(Nc2ccc(C34CC5CC(CC(C5)C3)C4)cc2Cl)cc1] | ¹H NMR (400 MHz, DMSO-d6) δ 8.17 (s, 1H), 7.58 (dd, J₁ = 1.6 Hz, J₂ = 8.0 Hz, 1H), 7.44-7.40 (m, 2H), 7.32 (d, J = 2.0 Hz, 1H), 7.20-7.12 (m, 2H), 7.09-7.01 (m, 5H), 6.84 (t, J = 7.2 Hz, 1H), 2.04 (s, 3H), 1.83 (s, 6H), 1.72 (s, 6H). LC-MS: m/z 454.1 (M + H)⁺ |
| 104 | 8 | Int-XI | 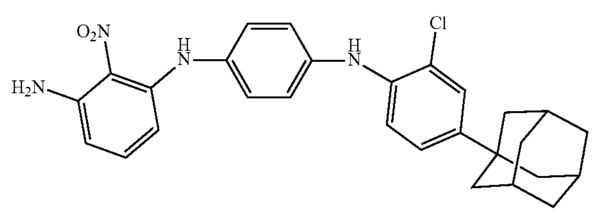 [SMILES: Nc1cccc(Nc2ccc(Nc3ccc(C45CC6CC(CC(C6)C4)C5)cc3Cl)cc2)c1[N+](=O)[O-]] | ¹H NMR (400 MHz, DMSO-d6) δ 9.23 (s, 1H), 7.57 (s, 1H), 7.34 (s, 1H), 7.2 (d, J = 4.8 Hz, 4H), 7.12 (d, J = 8.8 Hz, 2H), 7.03-6.99 (m, 3H), 6.2 (d, J = 8.4 Hz, 1H), 6.05 (d, J = 8.4 Hz, 1H), 2.04 (s, 3H), 1.83 (s, 6H), 1.72 (s, 6H). LC-MS: m/z 489.2 (M + H)⁺ |
| 201 | 9 | III.5 & Int-1 | 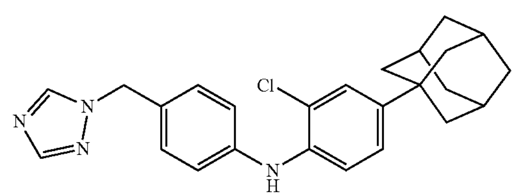 [SMILES: Clc1cc(C23CC4CC(CC(C4)C2)C3)ccc1Nc1ccc(Cn2cncn2)cc1] | ¹H NMR (400 MHz, DMSO-d6) δ 8.59 (s, 1H), 7.95 (s, 1H), 7.64 (s, 1H), 7.34 (s, 1H), 7.21 (s, 2H), 7.16 (d J = 8.4 Hz, 2H), 6.94 (d, J = 8.4 Hz, 2H), 5.28 (s, 2H), 2.04 (s, 3H), 1.83 (s, 6H), 1.72 (s, 6H). LC-MS: m/z 350.2 (M + H)⁺; Triazole fragment |
| 225 | 10 | Int-XI | 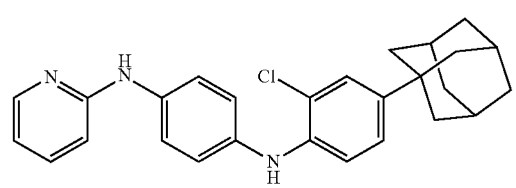 [SMILES: Clc1cc(C23CC4CC(CC(C4)C2)C3)ccc1Nc1ccc(Nc2ccccn2)cc1] | ¹H NMR (500 MHz, CDCl₃) δ 8.18-8.17 (m, 1H), 7.49-7.45 (m, 1H), 7.32 (d, J = 1.6 Hz, 1H), 7.28-7.25 (m, 2H), 7.16-7.09 (m, 4H), 6.76 (d, J = 8.0 Hz, 1H), 6.72-6.69 (m, 1H), 6.40 (s, 1H), 5.93 (s, 1H), 2.09 (s, 3H), 1.87 (s, 6H), 1.80-1.71 (m, 6H). LC-MS: m/z 430.3 (M + H)⁺ |

-continued

| No | Compound No | Reactant | Structure | Analytical data |
|---|---|---|---|---|
| 264 | 11 | Compound 10 | 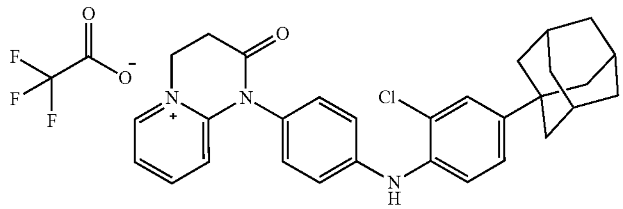 [SMILES: O=C([O-])C(F)(F)F ; O=C1CC[n+]2ccccc2N1c1ccc(Nc2ccc(C34CC5CC(CC(C5)C3)C4)cc2Cl)cc1] | ¹H NMR (400 MHz, DMSO-d6) δ 8.71 (d, J = 6.0 Hz, 1H), 8.26 (t, J = 7.2 Hz, 1H), 8.05 (s, 1H), 7.63 (t, J = 6.4 Hz, 1H), 7.42 (d, J = 2.0 Hz, 1H), 7.37 (d, J = 8.4 Hz, 1H), 7.31-7.29 (m, 1H), 7.19 (d, J = 8.8 Hz, 2H), 7.09 (d, J = 8.8 Hz, 2H), 6.92 (d, J = 8.8 Hz, 1H), 4.96 (t, J = 6.8 Hz, 2H), 3.22 (t, J = 7.2 Hz, 2H), 2.06 (s, 3H), 1.86 (s, 6H), 1.73 (s, 6H). LC-MS: m/z 484.1 (M)⁺ ion |
| 238 | 12 | XII.28 | 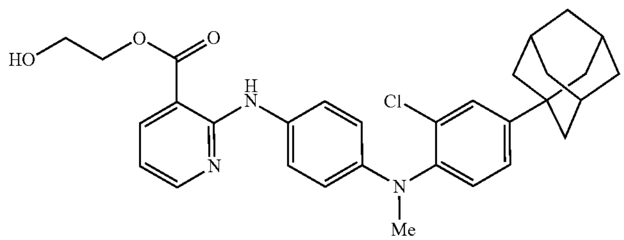 [SMILES: CN(c1ccc(Nc2ncccc2C(=O)OCCO)cc1)c1ccc(C23CC4CC(CC(C4)C2)C3)cc1Cl] | ¹H NMR (400 MHz, DMSO-d6) δ 9.77 (s, 1H), 8.32-8.27 (m, 2H), 7.48-7.39 (m, 4H), 7.29 (d, J = 8.3 Hz, 1H), 6.83-6.76 (m, 1H), 6.52 (d, J = 9.3 Hz, 2H), 4.99-4.95 (m, 1H), 4.31 (t, J = 4.9 Hz, 2H), 3.74-3.71 (m, 2H), 3.18 (s, 3H), 2.07 (s, 3H), 1.89 (s, 6H), 1.74 (s, 6H). LC-MS: m/z 532.2 (M + H)⁺ |
| 347 | 13 | II.27 & 1.1 | 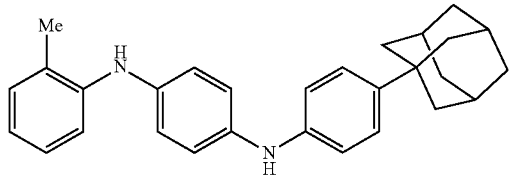 [SMILES: Cc1ccccc1Nc1ccc(Nc2ccc(C34CC5CC(CC(C5)C3)C4)cc2)cc1] | ¹H NMR (400 MHz, DMSO-d6) δ 7.69 (s, 1H), 7.15 (d, J = 8.8 Hz, 2H), 7.10 (d, J = 7.2 Hz, 1H), 7.02-6.96 (m, 5H), 6.90 (d, J = 8.8 Hz, 4H), 6.73 (t, J = 7.6 Hz, 1H), 2.19 (s, 3H), 2.03 (s, 3H), 1.82 (s, 6H), 1.72 (s, 6H). LC-MS: m/z 409.3 (M + H)⁺ |
| 352 | 14 | XII.48 | 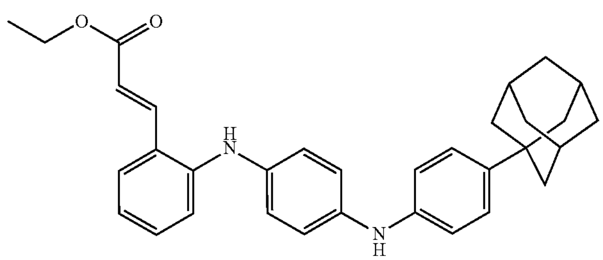 [SMILES: CCOC(=O)/C=C/c1ccccc1Nc1ccc(Nc2ccc(C34CC5CC(CC(C5)C3)C4)cc2)cc1] | ¹H NMR (400 MHz, DMSO-d6) δ 7.95 (d, J = 16.0 Hz, 1H), 7.86 (s, 1H), 7.79 (s, 1H), 7.68 (dd, J₁ = 1.2 Hz, J₂ = 8.0 Hz, 1H), 7.267-7.22 (m, 1H), 7.17 (d, J = 8.4 Hz, 2H), 7.09 (d, J = 7.6 Hz, 1H), 6.98 (d, J = 9.2 Hz, 2H), 6.94-6.85 (m, 5H), 6.49 (d, J = 16.0 Hz, 1H), 4.18 (q, J = 14.0 Hz, 2H), 2.04 (s, 3H), 1.82 (d, J = 2.34 Hz, 6H), 1.72 (s, 6H), 1.25 (t, J = 9.2 Hz, 3H). LC-MS: m/z 493.2 (M + H)⁺ |
| 375 | 15 | XII.56 | 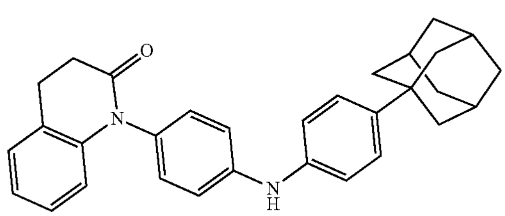 [SMILES: O=C1CCc2ccccc2N1c1ccc(Nc2ccc(C34CC5CC(CC(C5)C3)C4)cc2)cc1] | ¹H NMR (400 MHz, DMSO-d6) δ 8.24 (s, 1H), 7.31-7.24 (m, 3H), 7.12-6.94 (m, 8H), 6.33 (d, J = 8.0 Hz, 1H), 3.0 (t, J = 6.8 Hz, 2H), 2.68 (t, J = 5.6 Hz, 2H), 2.05 (s, 3H), 1.85 (d, J = 2.8 Hz, 6H), 1.70 (s, 6H). LC-MS: m/z 449.3 (M + H)⁺ |
| 354 | 16 | XV.14 | 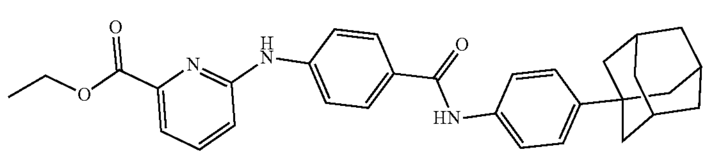 [SMILES: CCOC(=O)c1cccc(Nc2ccc(C(=O)Nc3ccc(C45CC6CC(CC(C6)C4)C5)cc3)cc2)n1] | ¹H NMR (400 MHz, DMSO-d6) δ 9.95 (s, 1H), 9.70 (s, 1H), 8.01 (d, J = 8.8 Hz, 2H), 7.92 (d, J = 8.8 Hz, 2H), 7.81-7.75 (m, 1H), 7.69 (d, J = 8.4 Hz, 2H), 7.51 (d, J = 7.6 Hz, 1H), 7.31 (d, J = 8.8 Hz, 2H), 7.13 (d, J = 8.0 Hz, 1H), 4.36-4.35 (m, 2H), 2.06 (s, 3H), 1.86 (s, 6H), 1.74 (s, 6H), 1.38 (t, J = 7.2 Hz, 3H). LC-MS: m/z 496.2 (M + H)⁺ |

| No | Compound No | Reactant | Structure | Analytical data |
|---|---|---|---|---|
| 381 | 17 | Int-XII | 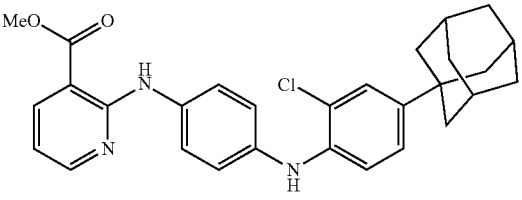 [SMILES: COC(=O)c1cccnc1Nc1ccc(Nc2ccc(C34CC5CC(CC(C5)C3)C4)cc2Cl)cc1] | $^1$H NMR (400 MHz, DMSO-d6) δ 9.93 (s, 1H), 8.37 (dd, $J_1$ = 2.0 Hz, $J_2$ = 4.4 Hz, 1H), 8.22 (dd, $J_1$ = 2.0 Hz, $J_2$ = 7.6 Hz, 1H), 7.55 (d, J = 8.8 Hz, 2H), 7.41 (s, 1H), 7.31 (d, J = 1.6 Hz, 1H), 7.19-7.12 (m, 2H), 7.04 (d, J = 8.8 Hz, 2H), 6.84-6.81 (m, 1H), 3.89 (s, 3H), 2.04 (s, 3H), 1.83 (s, 6H), 1.72 (s, 6H). LC-MS: m/z 488.1 (M + H)$^+$ |
| 351 | 18 | Int-XI | 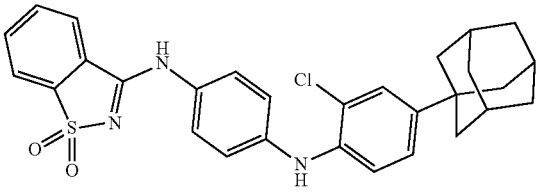 [SMILES: O=S1(=O)N=C(Nc2ccc(Nc3ccc(C45CC6CC(CC(C6)C4)C5)cc3Cl)cc2)c2ccccc21] | $^1$H NMR (400 MHz, DMSO-d6) δ 10.76 (s, 1H), 8.45 (d, J = 7.2 Hz, 1H), 8.04 (d, J = 6.8 Hz, 1H), 7.90-7.86 (m, 2H), 7.76 (s, 1H), 7.69 (d, J = 8.8 Hz, 2H), 7.37 (s, 1H), 7.28-7.25 (m, 2H), 7.08 (d, J = 8.4 Hz, 2H), 2.05 (s, 3H), 1.85 (s, 6H), 1.73 (s, 6H). LC-MS: m/z 518.05 (M + H)$^+$ |
| 406 | 19 | I.1 | 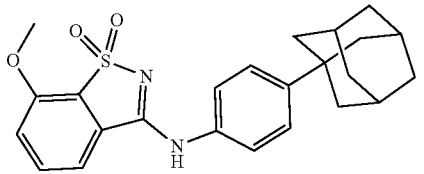 [SMILES: COc1cccc2c1S(=O)(=O)N=C2Nc1ccc(C23CC4CC(CC(C4)C2)C3)cc1] | $^1$H NMR (400 MHz, DMSO-d6) δ 10.71 (s, H), 8.01 (d, J = 7.6 Hz, 1H), 7.87 (t, J = 8.0 Hz, 1H), 7.77 (d, J = 8.8 Hz, 2H), 7.51-7.45 (m, 3H), 4.00 (s, 3H), 2.07 (s, 3H), 1.88 (s, 6H), 1.74 (s, 6H). LC-MS: m/z 423.2 (M + H)$^+$ |
| 472 | 20 | XI.16 | 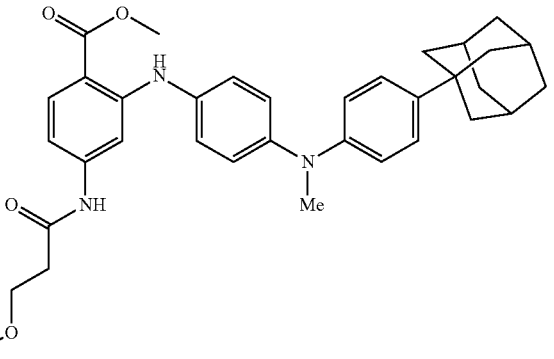 | 1H-NMR (400 MHz, CDCl3): δ 9.43 (s, 1H), 8.10 (s, 1H), 7.89 (d, J = 8.8 Hz, 1H), 7.33 (d, J = 2 Hz, 1H), 7.27 (d, J = 2 Hz, 2H), 7.16 (d, J = 8.4 Hz, 2H), 7.01-6.98 (m, 4H), 6.82 (dd, J1 = 1.6 Hz & J2 = 8.4 Hz, 1H), 3.87 (s, 3H), 3.69 (t, J = 5.2 Hz, 2H), 3.41 (s, 3H), 3.30 (s, 3H), 2.58 (t, J = 5.6 Hz, 2H), 2.08 (s, 3H), 1.90 (s, 6H), 1.72 (s, 6H). LC-MS: m/z 568.3 (M + H)+. |
| 529 | 21 | XI.25 | 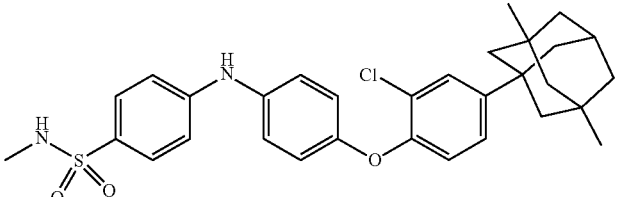 | 1H NMR (400 MHz, DMSO-d6): δ 8.68 (s, 1H), 7.55 (d, J = 8.8 Hz, 2H), 7.48 (d, J = 2.4 Hz, 1H), 7.32 (dd, J1 = 1.6 & J2 = 8 Hz, 2H), 7.09 (d, J = 5.2 Hz, 1H), 7.05-6.99 (m, 3H), 6.93 (d, J = 8.8 Hz, 2H), 2.36 (d, J = 5.2 Hz, 3H), 2.14 (s, 1H), 1.69 (s, 2H), 1.52-1.35 (m, 8H), 1.18 (s, 2H), 0.86 (s, 6H). LC-MS: m/z 424.2 (M + H)+ |
| 531 | 22 | XI.25 | 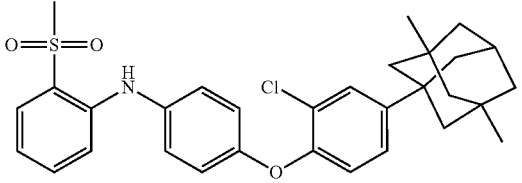 [SMILES: CC12CC3CC(C)(C1)CC(c1ccc(Oc4ccc(Nc5ccccc5S(C)(=O)=O)cc4)c(Cl)c1)(C3)C2] | 1H NMR (400 MHz, DMSO-d6): δ 7.75 (d, J = 4.4 Hz, 2H), 7.51-7.47 (m, 2H), 7.34 (dd, J1 = 2 Hz, & J2 = 8.4 Hz, 1H), 7.24 (d, J = 8.4 Hz, 2H), 7.14 (d, J = 8 Hz, 1H), 7.05-6.94 (m, 4H), 3.24 (s, 3H), 2.14 (s, 1H), 1.69 (s, 2H), 1.53-1.33 (m, 8H), 1.18 (s, 2H), 0.86 (s, 6H). LC-MS: m/z 536.2 (M + H)+ |

-continued

| Com-pound No | No | Reactant | Structure | Analytical data |
|---|---|---|---|---|
| 534 | 23 | IX.4 | 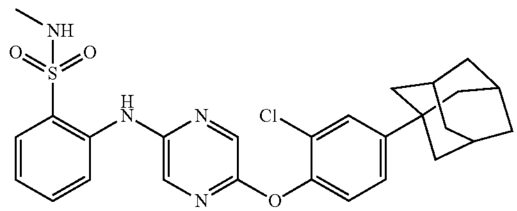 [SMILES: CNS(=O)(=O)c1ccccc1Nc1cnc(Oc2ccc(C34CC5CC(CC(C5)C3)C4)cc2Cl)cn1] | 1H NMR (400 MHz, DMSO-d6): δ 8.50 (s, 1H), 8.22 (s, 1H), 8.07 (d, J = 8.4 Hz, 1H), 8.02 (s, 1H), 7.77-7.73 (m, 2H), 7.56 (d, J = 8 Hz, 1H), 7.49 (d, J = 1.2 Hz, 1H), 7.37 (dd, J1 = 2 Hz & J2 = 8.4 Hz, 1H), 7.21 (d, J = 8 Hz, 1H), 7.13 (t, J = 7.6 Hz, 1H), 2.41 (d, J = 4.8 Hz, 3H), 2.06 (s, 3H), 1.88 (s, 6H), 1.74 (s, 6H), LC-MS: m/z 525.2 (M + H)+. |
| 608 | 24 | XI.32 | 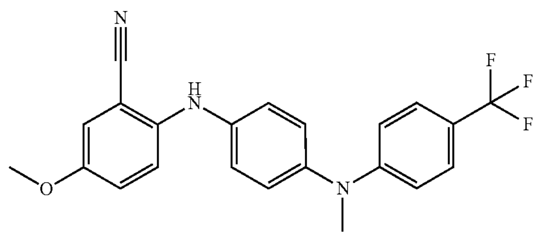 [SMILES: COc1ccc(Nc2ccc(N(C)c3ccc(C(F)(F)F)cc3)cc2)c(C#N)c1] | 1H NMR (400 MHz, DMSO-d6) δ 8.27 (s, 1H), 7.44 (d, J = 8.8 Hz, 2H), 7.33-7.31 (m, 2H), 7.21 (dd, J1 = 3.2 Hz, J2 = 9.2 Hz, 1H), 7.10 (dd, J1 = 2.0 Hz, J2 = 6.4 Hz, 2H), 6.99 (dd, J1 = 2.4 Hz, J2 = 6.8 Hz, 2H), 6.76 (d, J = 8.8 Hz, 2H), 3.78 (s, 3H), 3.25 (s, 3H). LC-MS: m/z 398.1 (M + H)+. |
| 629 | 25 | XI.53 | 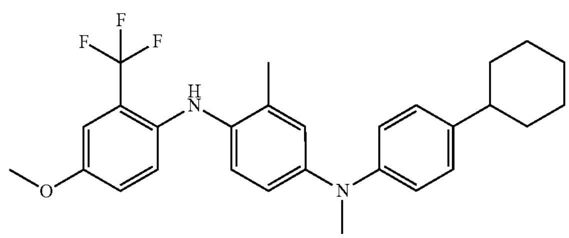 [SMILES: COc1ccc(Nc2ccc(N(C)c3ccc(C4CCCCC4)cc3)cc2C)c(C(F)(F)F)c1] | 1H NMR (400 MHz, DMSO-d6) δ 7.11-7.07 (m, 4H), 6.87 (s, 1H), 6.83 (d, J = 8.8 Hz, 2H), 6.77 (d, J = 2.4 Hz, 2H), 6.71 (d, J = 8.4 Hz, 1H), 6.53 (s, 1H), 3.75 (s, 3H), 3.18 (s, 3H), 2.05 (s, 3H), 2.49-2.48 (m, 1H), 1.77-1.76 (m, 5H), 1.37-1.32 (m, 5H). LC-MS: m/z 469.3 (M + H)+. |
| 657 | 26 | XI.53 | 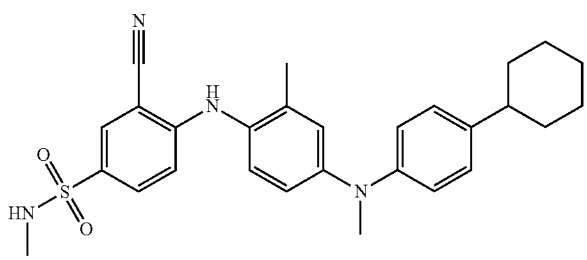 [SMILES: CNS(=O)(=O)c1ccc(Nc2ccc(N(C)c3ccc(C4CCCCC4)cc3)cc2C)c(C#N)c1] | 1H NMR (400 MHz, DMSO-d6) δ 8.55 (s, 1H), 7.84 (d, J = 2.0 Hz, 1H), 7.64 (dd, J1 = 2.0 Hz, J2 = 9.6 Hz, 1H), 7.25 (d, J = 4.8 Hz, 1H), 7.18 (d, J = 8.4 Hz, 2H), 7.03 (d, J = 8.0 Hz, 3H), 6.86 (d, J = 2.0 Hz, 1H), 6.74 (dd, J1 = 2.4 Hz, J2 = 8.4 Hz, 1H), 6.49 (d, J = 8.8 Hz, 1H), 3.24 (s, 3H), 2.46-2.43 (m, 1H), 2.38 (d, J = 4.8 Hz, 3H), 2.06 (s, 3H), 1.80-1.68 (m, 5H), 1.40-1.29 (m, 5H). LC-MS: m/z 489.2 (M + H)+. |
| 688 | 27 | VII | 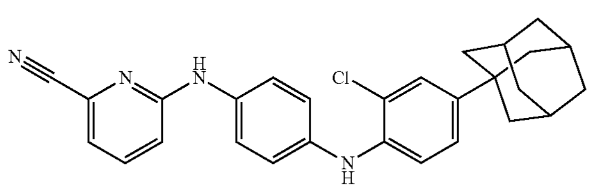 [SMILES: N#Cc1cccc(Nc2ccc(Nc3ccc(C45CC6CC(CC(C6)C4)C5)cc3Cl)cc2)n1] | 1H NMR (400 MHz, DMSO-d6) δ 9.35 (s, 1H), 7.70-7.66 (m, 1H), 7.50-7.48 (m, 2H), 7.38 (s, 1H), 7.31-7.26 (m, 2H), 7.18-7.15 (m, 1H), 7.21-7.10 (m, 1H), 7.06-7.02 (m, 3H), 2.04 (s, 3H), 1.82 (s, 6H), 1.72 (s, 6H). LC-MS: m/z 455.20 (M + H)+ |

-continued

| No | Compound No | Reactant | Structure | Analytical data |
|---|---|---|---|---|
| 694 | 28 | VII | 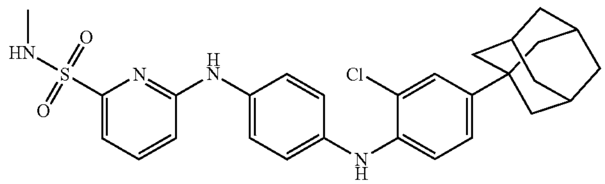 [SMILES: CNS(=O)(=O)c1cccc(Nc2ccc(Nc3ccc(C45CC6CC(CC(C6)C4)C5)cc3Cl)cc2)n1] | 1H NMR (400 MHz, DMSO-d6) δ 9.32 (s, 1H), 7.72 (t, J = 7.6 Hz, 1H), 7.62 (d, J = 8.4 Hz, 2H), 7.43-7.42 (m, 1H), 7.32-7.30 (m, 2H), 7.17 (d, J = 7.2 Hz, 2H), 7.09 (d, J = 8.4 Hz, 1H), 7.03 (d, J = 8.8 Hz, 2H), 6.94 (d, J = 8.0 Hz, 1H), 2.60 (d, J = 4.4 Hz, 3H), 2.04 (s, 3H), 1.83 (s, 6H), 1.72 (s, 6H). LC-MS: m/z m/z 523.2 (M + H)+ |

The below compounds were prepared by a procedure similar to Intermediate-XIII using appropriate reactants and reagents and in presence of suitable solvents and appropriate reaction conditions.

| CP | Compound No | Reactant | Structure | Analytical data |
|---|---|---|---|---|
| 86 | 29 | Int-XI | 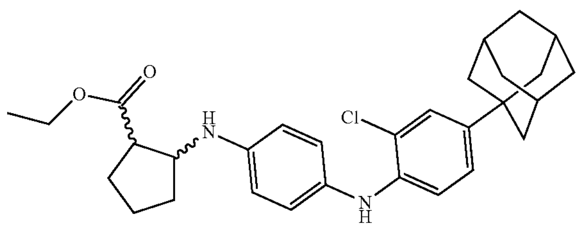 [SMILES: CCOC(=O)C1CCCC1Nc1ccc(Nc2ccc(C34CC5CC(CC(C5)C3)C4)cc2Cl)cc1] | $^1$H NMR (400 MHz, DMSO-d6) δ 7.20 (d, J = 2.0 Hz, 1H), 7.03 (dd, J$_1$ = 1.6 Hz, J$_2$ = 8.0 Hz, 1H), 6.87 (d, J = 8.8 Hz, 2H), 6.82 (s, 1H), 6.71 (d, J = 8.8 Hz, 1H), 6.60 (d, J = 8.8 Hz, 2H), 5.28 (d, J = 8.4 Hz, 1H), 4.03-4.00 (m, 1H), 3.89-3.81 (m, 2H), 3.11-3.06 (m, 1H), 2.02-1.90 (m, 5H), 1.88-1.78 (m, 8H), 1.73-1.61 (m, 7H), 1.56-1.49 (m, 1H), 0.96 (t, J = 7.2 Hz, 3H). LC-MS: m/z (M + H)+ |
| 87 | 30 | Int-XI | 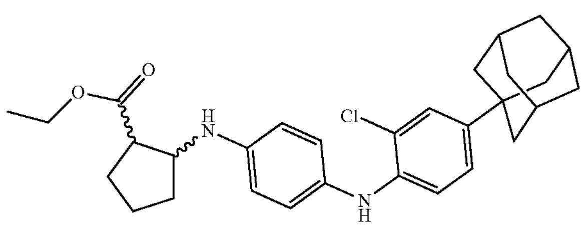 [SMILES: CCOC(=O)C1CCCC1Nc1ccc(Nc2ccc(C34CC5CC(CC(C5)C3)C4)cc2Cl)cc1] | $^1$H NMR (400 MHz, DMSO-d6) δ (d, J = 2.0 Hz, 1H), 7.03 (dd, J$_1$ = 1.6 Hz, J$_2$ = 8.0 Hz, 1H), 6.89 (d, J = 8.8 Hz, 2H), 6.83 (s, 1H), 6.71 (d, J = 8.8 Hz, 1H), 6.53 (d, J = 8.8 Hz, 2H), 5.55-5.50 (m, 1H), 4.05-4.03 (m, 2H), 3.97-3.91 (m, 1H), 2.69-2.61 (m, 1H), 2.02-1.95 (m, 5H), 1.79 (s, 6H), 1.78-1.68 (m, 9H), 1.54-1.45 (m, 1H), 1.15 (t, J = 7.2 Hz, 3H). LC-MS: m/z 493.2 (M + H)$^+$ |
| 516 | 31 | Compound 257 | 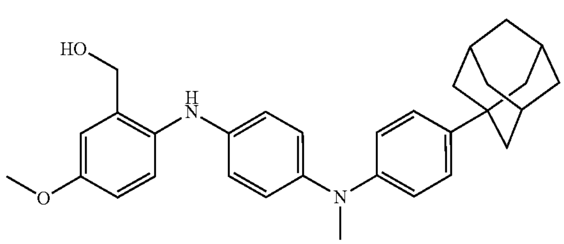 [SMILES: COc1ccc(Nc2ccc(N(C)c3ccc(C45CC6CC(CC(C6)C4)C5)cc3)cc2)c(CO)c1] | 1H-NMR (400 MHz, DMSO-d6): 7.14-7.02 (m, 5H), 6.91 (d, J = 8.8 Hz, 2H), 6.79-6.76 (m, 1H), 6.71-6.50 (m, 4H), 5.21-5.17 (m, 1H), 4.46 (d, J = 7 Hz, 2H), 3.74 (s, 3H), 3.13 (s, 3H), 2.03 (s, 3H), 1.81-1.79 (m, 6H), 1.72-1.70 (m, 6H). LC-MS: m/z 469.3 (M + H)+. |

The below compound was prepared by a procedure similar to Intermediate-XI using appropriate reactants and reagents and in presence of suitable solvents and appropriate reaction conditions.

| CP | Compound No | Reactant | Structure | Analytical data |
|---|---|---|---|---|
| 231 | 32 | XII.69 | 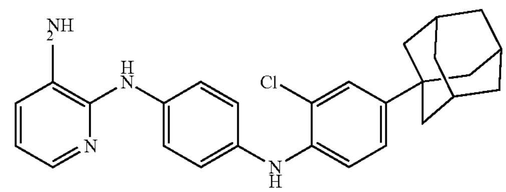 [SMILES: Nc1cccnc1Nc1ccc(Nc2ccc(C34CC5CC(CC(C5)C3)C4)cc2Cl)cc1] | $^1$H NMR (400 MHz, DMSO-d6) δ 7.60 (s, 1H), 7.55 (d, J = 8.8 Hz, 2H), 7.46 (dd, $J_1$ = 1.2 Hz, $J_2$ = 4.8 Hz, 1H), 7.27 (d, J = 2.0 Hz, 1H), 7.15-7.11 (m, 2H), 7.02-7.00 (m, 3H), 6.87-6.85 (m, 1H), 6.58-6.56 (m, 1H), 5.00 (s, 2H), 2.03 (s, 3H), 1.81 (s, 6H), 1.71 (s, 6H). LC-MS: m/z 445.2 (M + H)$^+$ |

The below compound was prepared by a procedure similar to Intermediate-XIX using appropriate reactants and reagents and in presence of suitable solvents and appropriate reaction conditions.

| CP | Compound No | Reactant | Structure | Analytical data |
|---|---|---|---|---|
| 82 | 33 | I.1 | 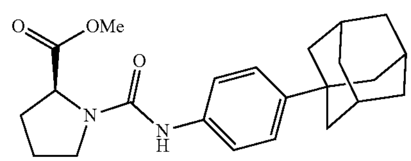 [SMILES: COC(=O)[C@@H]1CCCN1C(=O)Nc1ccc(C23CC4CC(CC(C4)C2)C3)cc1] | $^1$H NMR (400 MHz, DMSO-d6) δ 8.20 (s, 1H), 7.38 (d, J = 8.8 Hz, 2H), 7.20 (d, J = 8.8 Hz, 2H), 4.37-4.34 (m, 1H), 3.60 (s, 3H), 3.56-3.45 (m, 2H), 2.20-2.16 (m, 1H), 2.03 (s, 3H), 1.96-1.92 (m, 3H), 1.83 (d, J = 2.0 Hz, 6H), 1.72 (s, 6H). LC-MS: m/z 383.1 (M + H)$^+$ |

Synthesis of 2-((4-((4-((3R,5R)-adamantan-1-yl)phenyl)amino) phenyl)amino)benzoic acid (Compound-24 (CP-55))

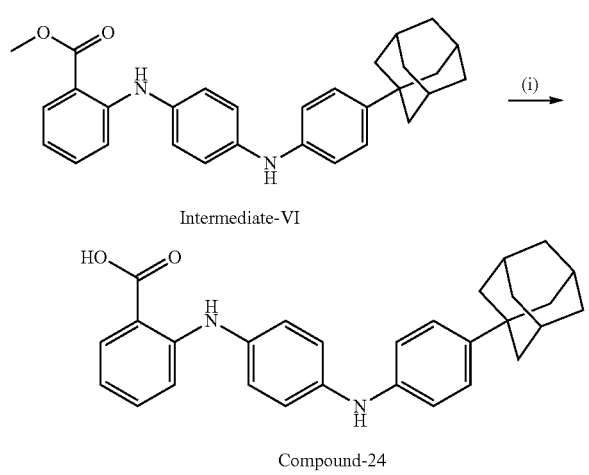

Intermediate-VI

Compound-24

To a solution of Intermediate-VI (8.5 g, 16.5 mmol, 1 eq.) in THF:MeOH:H$_2$O (40+40+20 mL) LiOH×H$_2$O (3.3 g, 82.4 mmol, 5 eq.) was added and stirred at RT for 16 h. Reaction mass was concentrated in vacuo, diluted with water and acidified with 2 N HCl to pH 5. The precipitate obtained was filtered and dried under vacuum. This solid was washed with 10% ether in hexane mixture and dried to afford title product as off-white solid (5.5 g, 670).

$^1$H NM/R (400 MHz, DMSO-d6) δ 12.99 (s, 1H), 9.42 (s, 1H), 8.00 (s, 1H), 7.85 (d, J=6.8 Hz, 1H), 7.32 (t, 1H), 7.21 (d, J=8.8 Hz, 2H), 7.11-6.96 (m, 7H), 6.67 (t, J=3.4 Hz, 1H), 2.08 (s, 3H), 1.83 (s, 6H), 1.72 (s, 6H); LC-MS: m/z 438.4 (M+H)$^+$

The below compounds were prepared by a procedure similar to the one described in compound-24 by using appropriate reagents in the presence of suitable solvents at appropriate reaction conditions. The physiochemical characteristics of the compounds are also summarized.

| CP | Compound No | Reactant | Structure | Analytical data |
|---|---|---|---|---|
| 52 | 25 | | 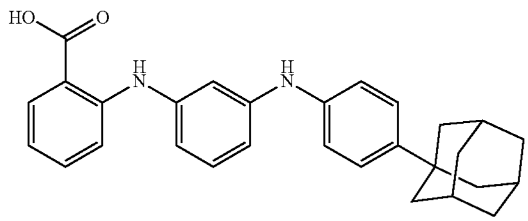 [SMILES: O=C(O)c1ccccc1Nc1cccc(Nc2ccc(C34CC5CC(CC(C5)C3)C4)cc2)c1] | LC-MS: m/z 439.1 (M + H)+ |
| 58 | 26 | | 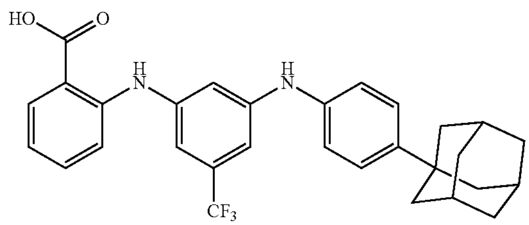 [SMILES: O=C(O)c1ccccc1Nc1cc(Nc2ccc(C34CC5CC(CC(C5)C3)C4)cc2)cc(C(F)(F)F)c1] | LC-MS: m/z 507.2 (M + H)+ |
| 59 | 27 | | 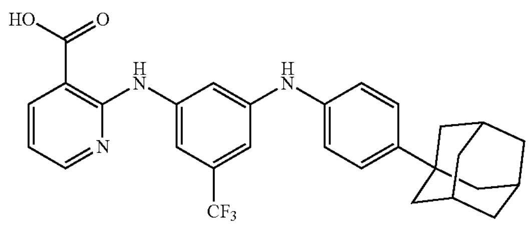 [SMILES: O=C(O)c1cccnc1Nc1cc(Nc2ccc(C34CC5CC(CC(C5)C3)C4)cc2)cc(C(F)(F)F)c1] | LC-MS: m/z 506.2 (M − H)− |
| 60 | 28 | | 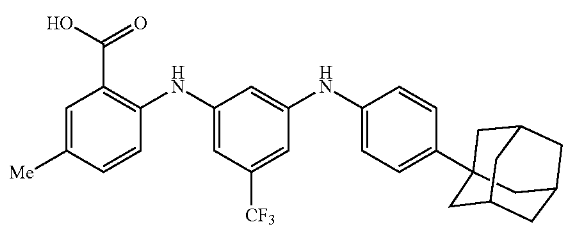 [SMILES: Cc1ccc(Nc2cc(Nc3ccc(C45CC6CC(CC(C6)C4)C5)cc3)cc(C(F)(F)F)c2)c(C(=O)O)c1] | LC-MS: m/z 521.2 (M + H)+ |
| 61 | 29 | | 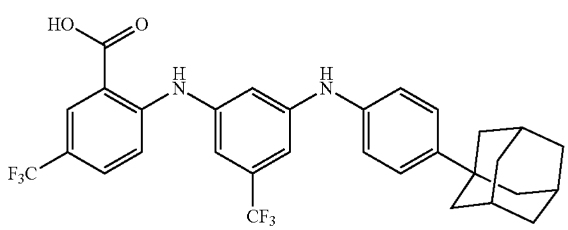 [SMILES: O=C(O)c1cc(C(F)(F)F)ccc1Nc1cc(Nc2ccc(C34CC5CC(CC(C5)C3)C4)cc2)cc(C(F)(F)F)c1] | LC-MS: m/z 575.2 (M + H)+ |
| 62 | 30 | | 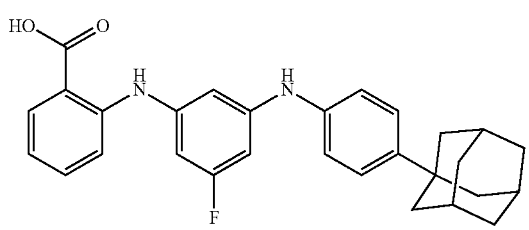 | LC-MS: m/z 457.2 (M + H)+ |

| CP | Compound No | Reactant | Structure | Analytical data |
|---|---|---|---|---|
| 64 | 31 | VI.1 | 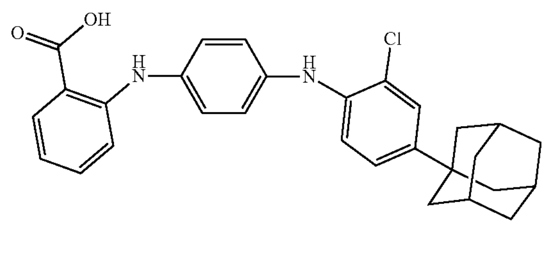 [SMILES: O=C(O)c1ccccc1Nc1ccc(Nc2ccc(C34CC5CC(CC(C5)C3)C4)cc2Cl)cc1] | ¹H NMR (400 MHz, DMSO-d6) δ 12.99 (bs, 1H), 9.48 (s, 1H), 7.86 (d, J = 7.3 Hz, 1H), 7.52 (s, 1H), 7.33 (t, J = 7.4 Hz, 2H), 7.20 (s, 2H), 7.13 (d, J = 8.8 Hz, 2H), 7.05 (d, J = 8.8 Hz, 2H), 7.01 (s, 1H), 6.68 (t, J = 7.4 Hz, 1H), 2.04 (s, 3H), 1.83 (s, 6H), 1.72 (s, 6H). LC-MS: m/z 472.1 (M + H)⁺ |
| 65 | 32 | | 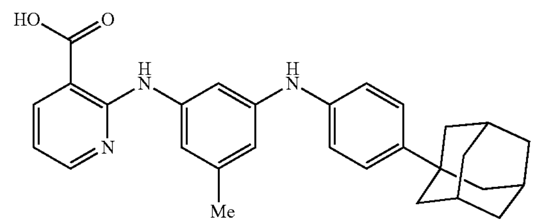 [SMILES: Cc1cc(Nc2ccc(C34CC5CC(CC(C5)C3)C4)cc2)cc(Nc2ncccc2C(=O)O)c1] | LC-MS: m/z 454.1 (M + H)⁺ |
| 66 | 33 | | 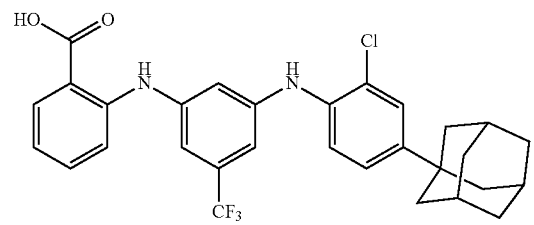 [SMILES: O=C(O)c1ccccc1Nc1cc(Nc2ccc(C34CC5CC(CC(C5)C3)C4)cc2Cl)cc(C(F)(F)F)c1] | LC-MS: m/z 539.1 (M − H)⁻ |
| 67 | 34 | | 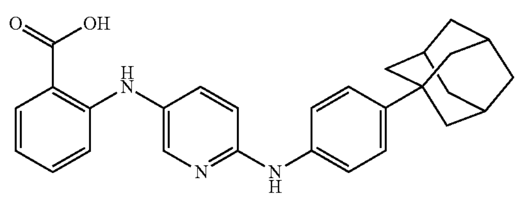 [SMILES: O=C(O)c1ccccc1Nc1ccc(Nc2ccc(C34CC5CC(CC(C5)C3)C4)cc2)nc1] | MLC-MS: m/z 440.2 (M + H)⁺ |
| 69 | 35 | Int-XV | 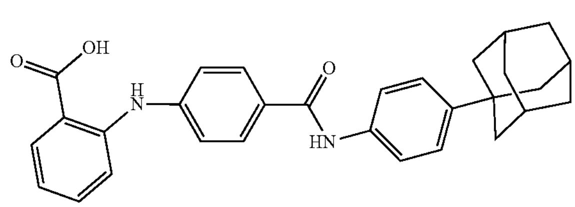 [SMILES: O=C(Nc1ccc(C23CC4CC(CC(C4)C2)C3)cc1)c1ccc(Nc2ccccc2C(=O)O)cc1] | ¹H NMR (400 MHz, DMSO-d6) δ 13.2 (s, 1H), 10.02 (s, 1H), 9.81 (s, 1H), 7.97-7.94 (m, 3H), 7.69 (d, J = 8.8 Hz, 2H), 7.51-7.43 (m, 2H), 7.35-7.31 (m, 4H), 6.93-6.89 (m, 1H), 2.06 (s, 3H), 1.87 (s, 6H), 1.74 (s, 6H). LC-MS: m/z 467.1 (M + H)⁺ |
| 71 | 36 | | 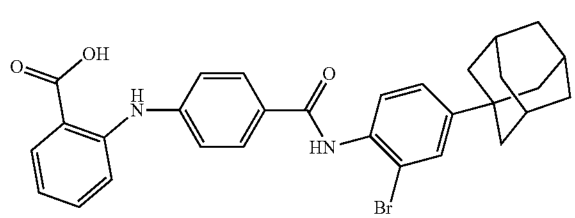 [SMILES: O=C(Nc1ccc(C23CC4CC(CC(C4)C2)C3)cc1Br)c1ccc(Nc2ccccc2C(=O)O)cc1] | LC-MS: m/z 545.1 (M)⁺ |

-continued

| CP | Compound No | Reactant | Structure | Analytical data |
|---|---|---|---|---|
| 80 | 37 | | 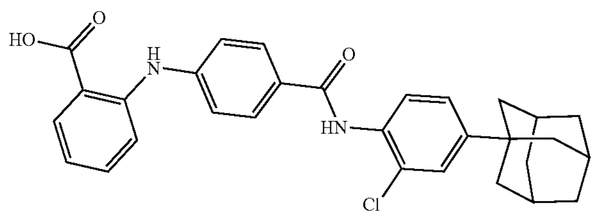 [SMILES: O=C(Nc1ccc(C23CC4CC(CC(C4)C2)C3)cc1Cl)c1ccc(Nc2ccccc2C(=O)O)cc1] | LC-MS: m/z 501.1 (M − H)+ |
| 83 | 38 | Compound 23 | 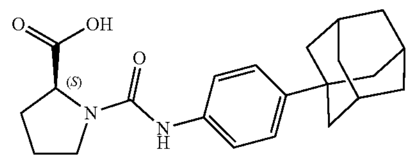 | 1H NMR (400 MHz, DMSO-d6) δ 12.36 (s, 1H), 8.16 (s, 1H), 7.38 (d, J = 8.8 Hz, 2H), 7.19 (d, J = 8.8 Hz, 2H), 4.31-4.28 (m, 1H), 3.54-3.50 (m, 1H), 3.46-3.40 (m, 1H), 2.16-2.14 (m, 1H), 2.03 (s, 3H), 1.95-1.85 (m, 3H), 1.82 (s, 6H), 1.72 (s, 6H). LC-MS: m/z 369.1 (M + H)+ |
| 88 | 39 | Compound 20 | 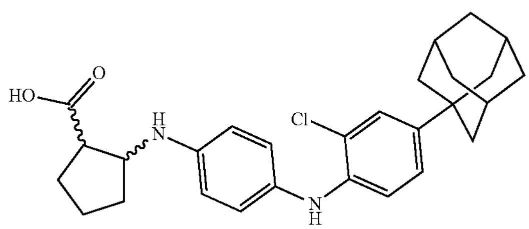 [SMILES: O=C(O)C1CCCC1Nc1ccc(Nc2ccc(C34CC5CC(CC(C5)C3)C4)cc2Cl)cc1] | 1H NMR (400 MHz, DMSO-d6) δ 7.21 (d, J = 2.4 Hz, 1H), 7.03 (d, J = 1.6 Hz, 1H), 6.87 (d, J = 8.4 Hz, 2H), 6.83 (s, 1H), 6.75 (d, J = 8.8 Hz, 1H), 6.61 (d, J = 8.8 Hz, 2H), 3.96-3.90 (m, 1H), 2.99-2.93 (m, 1H), 2.02-1.79 (m, 6H), 1.78-1.69 (m, 7H), 1.70-1.62 (m, 7H), 1.59-1.51 (m, 1H). LC-MS: m/z 465.2 (M + H)+ |
| 89 | 40 | Compound 21 | 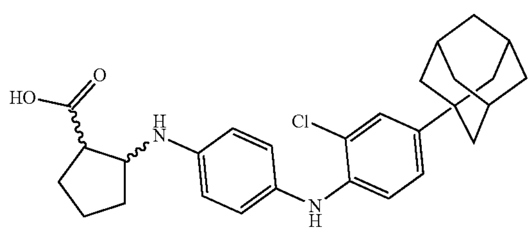 | 1H NMR (400 MHz, DMSO-d6) δ 7.21 (d, J = 2.4 Hz, 1H), 7.06 (dd, J1 = 2.0 Hz, J2 = 8.8 Hz, 1H), 6.89 (d, J = 8.8 Hz, 2H), 6.76 (d, J = 8.0 Hz, 1H), 6.56 (d, J = 8.8 Hz, 2H), 3.93-3.91 (m, 1H), 2.61-2.59 (m, 1H), 2.02-1.97 (m, 5H), 1.78 (s, 6H), 1.75-1.66 (m, 9H), 1.52-1.44 (m, 1H). LC-MS: m/z 465.1 (M + H)+ |
| 93 | 41 | VI.2 | 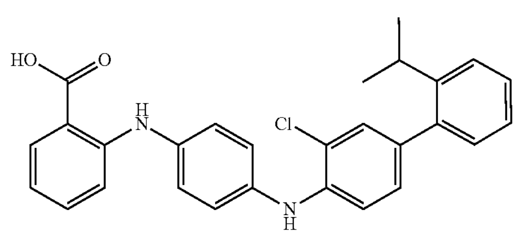 [SMILES: CC(C)c1ccccc1-c1ccc(Nc2ccc(Nc3ccccc3C(=O)O)cc2)c(Cl)c1] | 1H NMR (400 MHz, DMSO-d6) δ 13.00 (bs, 1H), 9.52 (s, 1H), 7.88 (dd, J1 = 1.5 Hz, J2 = 8.3 Hz, 1H), 7.69 (s, 1H), 7.42-7.30 (m, 4H), 7.25 (dd, J1 = 8.3 Hz, J2 = 12.7 Hz, 1H), 7.21-7.07 (m, 8H), 6.71 (t, J = 7.3 Hz, 1H), 3.06-3.02 (m, 1H), 1.14 (d, J = 6.8 Hz, 6H). LC-MS: m/z 457.1 (M + H)+ |

-continued

| CP | Compound No | Reactant | Structure | Analytical data |
|---|---|---|---|---|
| 98 | 42 | Isomer-1 of compound 41 | 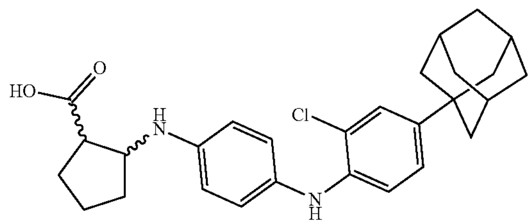 [SMILES: O=C(O)C1CCCC1Nc1ccc(Nc2ccc(C34CC5CC(CC(C5)C3)C4)cc2Cl)cc1] | ¹H NMR (400 MHz, DMSO-d6) δ 7.21 (d, J = 4.0 Hz, 1H), 7.04 (dd, J₁ = 2.0 Hz, J₂ = 8.4 Hz, 1H), 6.87 (d, J = 8.8 Hz, 2H), 6.82 (s, 1H), 6.74 (d, J = 8.8 Hz, 1H), 6.60 (d, J = 8.8 Hz, 2H), 3.93-3.89 (m, 1H), 2.95-2.92 (m, 1H), 2.02 (s, 3H), 1.99-1.93 (m, 1H), 1.88-1.78 (m, 8H), 1.74-1.63 (m, 7H), 1.57-1.50 (m, 1H), 1.35-1.33 (m, 1H). LC-MS: m/z 465.2 (M + H)⁺ |
| 99 | 43 | Isomer-2 of compound 41 | 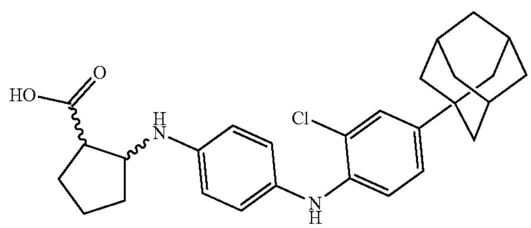 | ¹H NMR (400 MHz, DMSO-d6) δ 7.20 (d, J = 2.0 Hz, 1H), 7.04 (d, J = 8.8 Hz, 1H), 6.87 (d, J = 8.8 Hz, 2H), 6.82 (s, 1H), 6.75 (d, J = 8.8 Hz, 1H), 6.60 (d, J = 8.8 Hz, 2H), 3.93-3.89 (m, 1H), 2.95-2.92 (m, 1H), 2.02 (s, 3H), 1.99-1.92 (m, 1H), 1.88-1.78 (m, 8H), 1.74-1.63 (m, 7H), 1.57-1.50 (m, 1H), 1.35-1.33 (m, 1H). LC-MS: m/z 465.2 (M + H)⁺ |
| 100 | 44 | Isomer-1 of compound 42 | 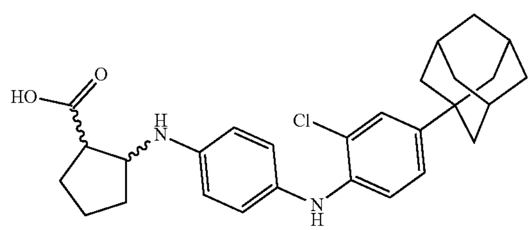 | ¹H NMR (400 MHz, DMSO-d6) δ 12.15 (bs, 1H), 7.21 (d, J = 2.4 Hz, 1H), 7.04 (dd, J₁ = 2.4 Hz, J₂ = 8.8 Hz, 1H), 6.89 (d, J = 8.8 Hz, 2H), 6.83 (s, 1H), 6.74 (d, J = 8.8 Hz, 1H), 6.55 (d, J = 8.8 Hz, 2H), 5.50 (bs, 1H), 3.92 (m, 1H), 2.67-2.57 (m, 1H), 2.02 (s, 3H), 1.99-1.93 (m, 2H), 1.79 (s, 6H), 1.75-1.68 (m, 9H), 1.50-1.44 (m, 1H). LC-MS: m/z 46.52 (M + H)⁺ |
| 101 | 45 | Isomer-2 of compound 42 | 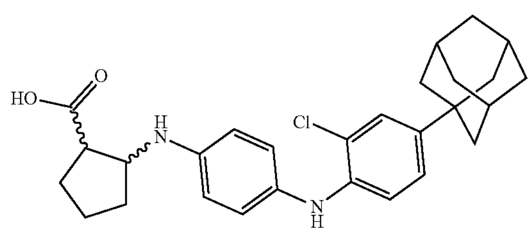 | ¹H NMR (400 MHz, DMSO-d6) δ 12.18 (bs, 1H), 7.21 (d, J = 2.0 Hz, 1H), 7.04 (dd, J₁ = 1.6 Hz, J₂ = 8.8 Hz, 1H), 6.89 (d, J = 8.8 Hz, 2H), 6.83 (s, 1H), 6.74 (d, J = 8.8 Hz, 1H), 6.55 (d, J = 8.8 Hz, 2H), 5.50 (bs, 1H), 3.93-3.91 (m, 1H), 2.67-2.57 (m, 1H), 2.02-1.94 (m, 5H), 1.78 (s, 6H), 1.77-1.68 (m, 8H), 1.49-1.46 (m, 1H). LC-MS: m/z 465.2 (M + H)⁺ |

-continued

| CP | Compound No | Reactant | Structure | Analytical data |
|---|---|---|---|---|
| 102 | 46 | XIII.1 | 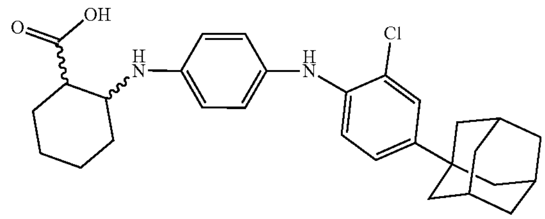 [SMILES: O=C(O)C1CCCCC1Nc1ccc(Nc2ccc(C34CC5CC(CC(C5)C3)C4)cc2Cl)cc1] | ¹H NMR (400 MHz, DMSO-d6) δ 7.21 (d, J = 2.0 Hz, 1H), 7.04 (dd, J₁ = 2.4 Hz, J₂ = 8.8 Hz, 1H), 6.89 (s, 1H), 6.87 (s, 2H), 6.77 (d, J = 8.0 Hz, 1H), 6.66 (d, J = 8.8 Hz, 2H), 3.87 (s, 1H), 2.62 (m, 1H), 2.02 (s, 3H), 1.91-1.78 (m, 8H), 1.70 (s, 6H), 1.68-1.42 (m, 4H), 1.41-1.25 (m, 2H). LC-MS: m/z 479.2 (M + H)⁺ |
| 103 | 47 | XIII.1 | 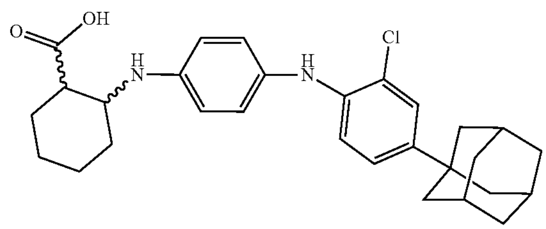 [SMILES: O=C(O)C1CCCCC1Nc1ccc(Nc2ccc(C34CC5CC(CC(C5)C3)C4)cc2Cl)cc1] | ¹H NMR (400 MHz, DMSO-d6) δ 12.00 (bs, 1H), 7.20 (d, J = 2.0 Hz, 1H), 7.03 (d, J = 6.8 Hz, 1H), 6.87 (d, J = 8.8 Hz, 2H), 6.82 (s, 1H), 6.75 (d, J = 8.8 Hz, 1H), 6.57 (d, J = 8.0 Hz, 2H), 5.20 (bs, 1H), 3.40-3.36 (m, 1H), 2.22-2.01 (m, 1H), 2.02 (s, 3H), 1.82-1.78 (m, 2H), 1.78 (s, 6H), 1.70-1.65 (m, 9H), 1.51-1.42 (m, 1H), 1.38-1.29 (m, 1H), 1.09-1.02 (m, 1H), LC-MS: m/z 479.2 (M + H)⁺ |
| 106 | 48 | XV.2 | 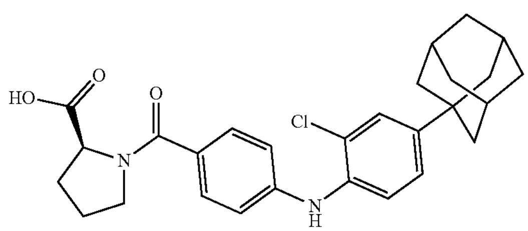 [SMILES: O=C(O)[C@@H]1CCCN1C(=O)c1ccc(Nc2ccc(C34CC5CC(CC(C5)C3)C4)cc2Cl)cc1] | ¹H NMR (400 MHz, DMSO-d6) δ 12.4 (bs, 1H), 8.01 (bs, 1H), 7.44-7.40 (m, 3H), 7.33-7.27 (m, 2H), 6.91 (d, J = 8.3 Hz, 2H), 4.37 (m, 1H), 3.58 (bs, 2H), 2.25-2.22 (m, 1H), 2.05 (s, 3H), 1.85 (s, 9H), 1.73 (s, 6H). LC-MS: m/z 479.2 (M + H)⁺ |
| 107 | 49 | XV.3 | 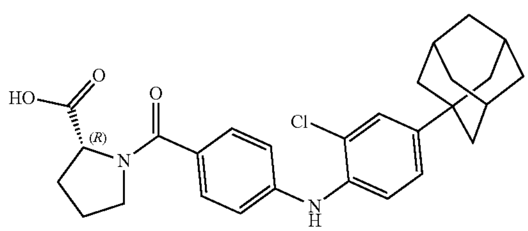 | ¹H NMR (400 MHz, DMSO-d6) δ 12.4 (bs, 1H), 7.99 (bs, 1H), 7.42-7.38 (m, 3H), 7.31-7.25 (m, 2H), 6.89 (d, J = 8.3 Hz, 2H), 4.35 (m, 1H), 3.56 (m, 2H), 2.23-2.20 (m, 1H), 2.03 (s, 3H), 1.83 (s, 9H), 1.71 (s, 6H). LC-MS: m/z 479.2 (M + H)⁺ |
| 108 | 50 | XIX.4 | 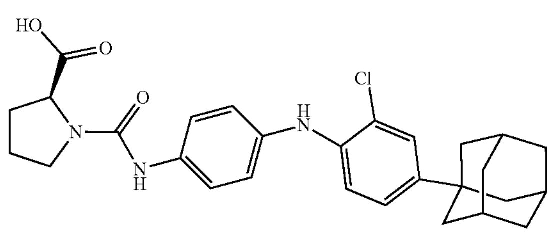 [SMILES: O=C(O)[C@@H]1CCCN1C(=O)Nc1ccc(Nc2ccc(C34CC5CC(CC(C5)C3)C4)cc2Cl)cc1] | ¹H NMR (400 MHz, DMSO-d6) δ 12.36 (s, 1H), 8.13 (s, 1H), 7.35 (d, J = 8.8 Hz, 2H), 7.28 (d, J = 2.4 Hz, 1H), 7.25 (s, 1H), 7.14 (dd, J₁ = 2.0 Hz, J₂ = 8.0 Hz, 1H), 7.04 (d, J = 8.8 Hz, 1H), 6.96 (d, J = 8.8 Hz, 2H), 4.31-4.29 (m, 1H), 3.56-3.42 (m, 2H), 2.18-2.12 (m, 1H), 2.03 (s, 3H), 1.95-1.84 (m, 3H), 1.81 (s, 6H), 1.71 (s, 6H). LC-MS: m/z 494.2 (M + H)⁺ |

-continued

| CP | Compound No | Reactant | Structure | Analytical data |
|---|---|---|---|---|
| 113 | 51 | VI.3 | 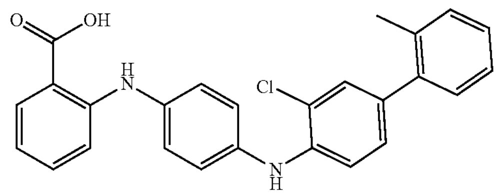 [SMILES: Cc1ccccc1-c1ccc(Nc2ccc(Nc3ccccc3C(=O)O)cc2)c(Cl)c1] | $^1$H NMR (400 MHz, DMSO-d6) δ 12.96 (s, 1H), 9.52 (s, 1H), 7.88 (dd, J$_1$ = 1.5 Hz, J$_2$ = 7.8 Hz, 1H), 7.7 (s, 1H), 7.38-7.34 (m, 2H), 7.30-7.16 (m, 10H), 7.08 (d, J = 8.3 Hz, 1H), 6.71 (t, J = 7.3 Hz, 1H), 2.27 (s, 3H). LC-MS: m/z 429.1 (M + H)$^+$ |
| 114 | 52 | XIX.5 | 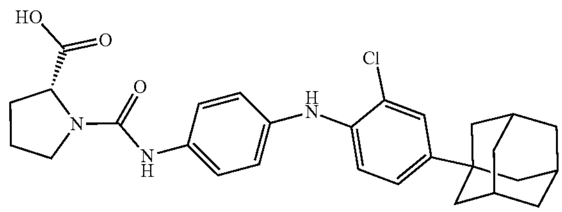 [SMILES: O=C(O)[C@H]1CCCN1C(=O)Nc1ccc(Nc2ccc(C34CC5CC(CC(C5)C3)C4)cc2Cl)cc1] | $^1$H NMR (400 MHz, DMSO-d6) δ 12.36 (s, 1H), 8.13 (s, 1H), 7.35 (d, J = 8.8 Hz, 2H), 7.28 (d, J = 2.4 Hz, 1H), 7.25 (s, 1H), 7.14 (dd, J$_1$ = 2.0 Hz, J$_2$ = 8.0 Hz, 1H), 7.04 (d, J = 8.8 Hz, 1H), 6.96 (d, J = 8.8 Hz, 2H), 4.31-4.29 (m, 1H), 3.56-3.42 (m, 2H), 2.18-2.12 (m, 1H), 2.03 (s, 3H), 1.95-1.84 (m, 3H), 1.81 (s, 6H), 1.71 (s, 6H). LC-MS: m/z 492.4 (M + H)$^-$ |
| 115 | 53 | VI.4 | 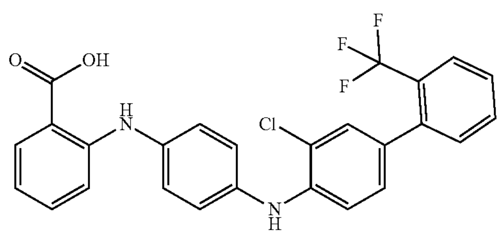 [SMILES: O=C(O)c1ccccc1Nc1ccc(Nc2ccc(-c3ccccc3C(F)(F)F)cc2Cl)cc1] | $^1$H NMR (400 MHz, DMSO-d6) δ 13.00 (s, 1H), 9.52 (s, 1H), 7.88 (d, J = 7.9 Hz, 1H), 7.82 (d, J = 7.8 Hz, 1H), 7.75-7.69 (m, 2H), 7.60 (t, J = 7.8 Hz, 1H), 7.44 (d, J = 7.2 Hz, 1H), 7.38-7.25 (m, 2H), 7.23-7.18 (m, 5H), 7.14-7.09 (m, 2H), 6.72 (t, J = 8.0 Hz, 1H). LC-MS: m/z 483.1 (M + H)$^+$ |
| 116 | 54 | VI.5 | 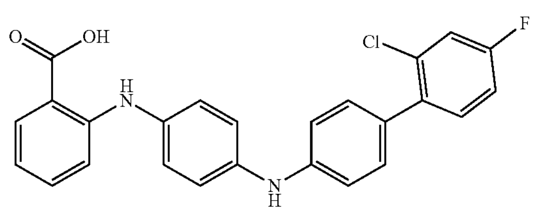 [SMILES: O=C(O)c1ccccc1Nc1ccc(Nc2ccc(-c3ccc(F)cc3Cl)cc2)cc1] | $^1$H NMR (400 MHz, DMSO-d6) δ 13.00 (bs, 1H), 9.49 (s, 1H), 8.32 (s, 1H), 8.87 (dd, J$_1$ = 7.8 Hz, J$_2$ = 7.8 Hz, 1H), 7.88 (d, J = 1.4 Hz, 1H), 7.51 (dd, J$_1$ = 2.4 Hz, J$_2$ = 8.8 Hz, 1H), 7.43 (dd, J$_1$ = 6.4 Hz, J2 = 8.8 Hz, 4H), 7.19-7.14 (m, 4H), 7.10 (d, J = 8.3 Hz, 2H), 7.04 (d, J = 8.3 Hz, 1H), 6.70 (t, J = 7.9 Hz, 1H). LC-MS: m/z 433.1 (M + H)$^+$ |
| 117 | 55 | VI.5 | 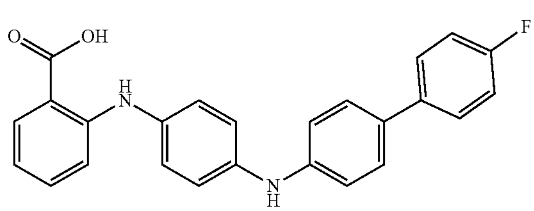 [SMILES: O=C(O)c1ccccc1Nc1ccc(Nc2ccc(-c3ccc(F)cc3)cc2)cc1] | $^1$H NMR (400 MHz, DMSO-d6) δ 12.93 (s, 1H), 9.47 (s, 1H), 8.28 (s, 1H), 7.87 (d, J = 9.3 Hz, 1H), 7.64 (dd, J$_1$ = 5.4 Hz, J$_2$ = 8.3 Hz, 2H), 7.52 (d, J = 8.3 Hz, 2H), 7.33 (t, J = 7.4 Hz, 1H), 7.24 (t, J = 8.8 Hz, 2H), 7.14 (m, 6H), 7.03 (d, J = 8.3 Hz, 1H), 6.70 (t, J = 7.3 Hz, 1H). LC-MS: m/z (M + H)$^+$ |

-continued

| CP | Compound No | Reactant | Structure | Analytical data |
|---|---|---|---|---|
| 118 | 56 | VI.6 | (structure) | ¹H NMR (400 MHz, DMSO-d6) δ 12.96 (s, 1H), 9.51 (s, 1H), 7.88 (d, J1 = 1.5 Hz, J2 = 8.3 Hz, 1H), 7.69 (s, 1H), 7.53 (d, J = 2.0 Hz, 1H), 7.38-7.29 (m, 4H), 7.24-7.15 (m, 5H), 7.09 (t, J = 8.4 Hz, 2H), 7.01 (t, J = 7.4 Hz, 1H), 6.71 (t, J = 7.8 Hz, 1H), 3.79 (s, 3H). LC-MS: m/z 445.1 (M + H)⁺ |
| 121 | 57 | VI.7 | (structure) | ¹H NMR (400 MHz, DMSO-d6) δ 12.95 (s, 1H), 9.53 (s, 1H), 7.89 (d, J = 1.0 Hz, 1H), 7.66 (s, 1H), 7.37-7.23 (m, 2H), 7.21-7.14 (m, 5H), 7.13-7.06 (m, 4H), 6.97 (dd, J₁ = 1.4 Hz, J₂ = 8.3 Hz, 1H), 6.71 (t, J = 7.3 Hz, 1H), 2.03 (s, 6H). LC-MS: m/z 442.4 (M + H)⁺ |
| 122 | 58 | VI.8 | (structure) | ¹H NMR (400 MHz, DMSO-d6) δ 12.98 (s, 1H), 9.54 (s, 1H), 7.88 (dd, J₁ = 0.9 Hz, J₂ = 7.8 Hz, 1H), 7.77 (s, 1H), 7.55 (dd, J₁ = 6.8 Hz, J₂ = 8.3 Hz, 1H), 7.48 (d, J = 1.5 Hz, 1H), 7.44-7.35 (m, 4H), 7.28-7.25 (m, 2H), 7.23-7.19 (m, 4H), 7.10 (d, J = 8.3 Hz, 1H), 6.72 (t, J = 7.3 Hz, 1H). LC-MS: m/z 449 (M + H)⁺ |
| 124 | 59 | Int-XII | (structure) | ¹H NMR (400 MHz, DMSO-d6) δ 12.18 (bs, 1H), 8.16-8.13 (m, 2H), 7.62 (d, J = 8.8 Hz, 2H), 7.27 (d, J = 2.0 Hz, 1H), ¹H NMR (400 MHz, DMSO-d6) δ 7.22 (s, 1H), 7.13 (dd, J₁ = 2.4 Hz, J₂ = 8.4 Hz, 1H), 7.04-7.02 (m, 3H), 6.66 (dd, J₁ = 4.8 Hz, J₂ = 7.2 Hz, 1H), 2.03 (s, 3H), 1.82 (s, 6H), 1.71 (s, 6H). LC-MS: m/z 474 (M + H)⁺ |
| 125 | 60 | VI.9 | (structure) | ¹H NMR (400 MHz, DMSO-d6) δ 13.61 (s, 1H), 10.6 (s, 1H), 8.5 (d, J = 8.8 Hz, 1H), 8.4 (dd, J₁ = 2.0 Hz, J₂ = 4.8 Hz, 1H), 8.28 (dd, J₁ = 2.0 Hz, J₂ = 8.0 Hz, 1H), 7.4 (d, J = 2.0 Hz, 1H), 7.32 (dd, J₁ = 2.0 Hz, J₂ = 8.8 Hz, 1H), 6.92 (dd, J₁ = 4.4 Hz J₂ = 7.2 Hz, 1H), 2.06 (s, 3H), 1.86 (d, J = 2.8 Hz, 6H), 1.7 (s, 6H). LC-MS: m/z 383.0 (M + H)⁺ |

-continued

| CP | Compound No | Reactant | Structure | Analytical data |
|---|---|---|---|---|
| 126 | 611 | VI.10 | 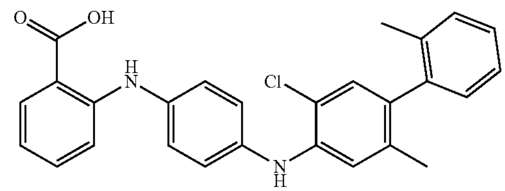 [SMILES: Cc1ccccc1-c1cc(Cl)c(Nc2ccc(Nc3ccccc3C(=O)O)cc2)cc1C] | $^1$H NMR (400 MHz, DMSO-d6) δ 13.00 (bs, 1H), 9.52 (bs, 1H), 7.87 (dd, $J_1$ = 1.5 Hz, $J_2$ = 7.8 Hz, 1H), 7.59 (s, 1H), 7.35-7.05 (m, 12H), 6.71 (t, J = 6.9 Hz, 1H), 2.05 (s, 3H), 1.90 (s, 3H). LC-MS: m/z 443.1(M + H)$^+$ |
| 127 | 62 | VI.65 | 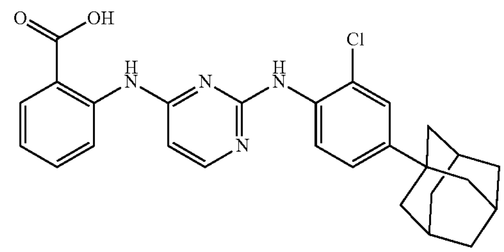 [SMILES: O=C(O)c1ccccc1Nc1ccnc(Nc2ccc(C34CC5CC(CC(C5)C3)C4)cc2Cl)n1] | $^1$H NMR (400 MHz, DMSO-d6) δ 13.45 (s, 1H), 10.79 (s, 1H), 8.55 (s, 1H), 8.49 (d, J = 8.4 Hz, 1H), 8.04 (d, J = 6.0 Hz, 1H), 7.94 (d, J = 7.2 Hz, 1H), 7.66 (d, J = 8.4 Hz, 1H), 7.41 (d, J = 2.0 Hz, 1H), 7.37-7.32 (m, 2H), 7.02 (t, J = 7.2 Hz, 1H), 6.29 (d, J = 5.2 Hz, 1H), 2.08 (s, 3H), 1.89 (s, 6H), 1.75 (s, 6H). LC-MS: m/z 475.1 (M + H)$^+$ |
| 128 | 63 | XIII.2 | 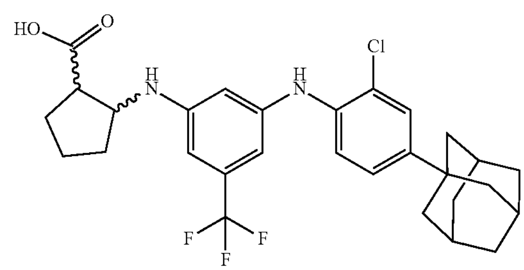 [SMILES: O=C(O)C1CCCC1Nc1cc(Nc2ccc(C34CC5CC(CC(C5)C3)C4)cc2Cl)cc(C(F)(F)F)c1] | $^1$H NMR (400 MHz, DMSO-d6) δ 11.9 (bs, 1H), 7.64 (s, 1H), 7.36 (s, 1H), 7.26-7.23 (m, 2H), 6.47 (bs, 1H), 6.40 (d, J = 9.3 Hz, 2H), 6.10 (bs, 1H), 3.91 (m, 1H), 2.94 (m, 1H), 2.05 (bs, 3H), 1.94 (m, 2H), 1.84 (s, 6H), 1.80-1.63 (m, 8H), 1.55-1.50 (m, 2H). LC-MS: m/z 533.2 (M + H)$^+$ |
| 129 | 64 | XIII.2 | 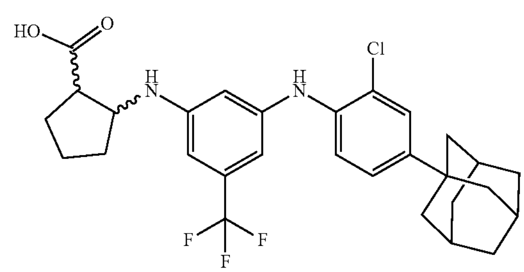 [SMILES: O=C(O)C1CCCC1Nc1cc(Nc2ccc(C34CC5CC(CC(C5)C3)C4)cc2Cl)cc(C(F)(F)F)c1] | $^1$H NMR (400 MHz, DMSO-d6) δ 12.18 (s, 1H), 7.69 (s, 1H), 7.37 (s, 1H), 7.26 (s, 2H), 7.41-7.38 (m, 2H), 6.30 (s, 1H), 6.08 (d, J = 6.8 Hz, 1H), 3.92-3.89 (m, 1H), 2.05 (s, 3H), 2.02-1.91 (m, 2H), 1.85 (s, 6H), 1.73 (s, 6H), 1.70-1.60 (m, 2H), 1.52-1.38 (m, 3H). LC-MS: m/z 533.2 (M + H)$^+$ |
| 130 | 65 | XIII.3 | 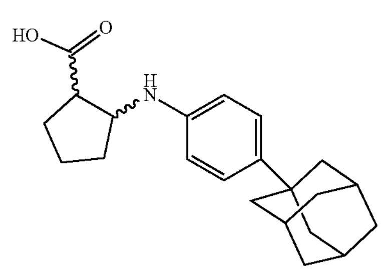 [SMILES: O=C(O)C1CCCC1Nc1ccc(C23CC4CC(CC(C4)C2)C3)cc1] | $^1$H NMR (400 MHz, DMSO-d6) δ 7.0 (d, J = 8.0 Hz, 2H), 6.53 (d, J = 8.4 Hz, 2H), 3.93-3.88 (m, 1H), 2.94-2.64 (m, 1H), 1.99 (bs, 5H), 1.95-1.77 (m, 2H), 1.75 (bs, 7H), 1.72-1.54 (bs, 7H). LC-MS: m/z 340.1 (M + H)$^+$ |

-continued

| CP | Compound No | Reactant | Structure | Analytical data |
|---|---|---|---|---|
| 131 | 66 | XIII.4 | 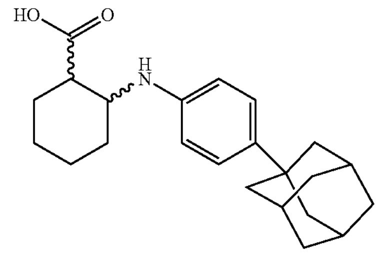 [SMILES: O=C(O)C1CCCCC1Nc1ccc(C23CC4CC(CC(C4)C2)C3)cc1] | ¹H NMR (400 MHz, DMSO-d6) δ 7.02 (d, J = 8.8 Hz, 2H), 6.55 (d, J = 8.4 Hz, 2H), 3.74 (bs, 1H), 2.08 (bs, 3H), 2.01-1.88 (m, 1H), 1.77-1.73 (bs, 6H), 1.70 (bs, 8H), 1.53-1.47 (m, 4H), 1.37-1.27 (m, 2H). LC-MS: m/z 354.1 (M + H)⁺ |
| 134 | 67 | XIX.6 | 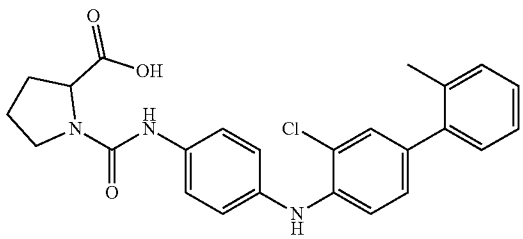 [SMILES: Cc1ccccc1-c1ccc(Nc2ccc(NC(=O)N3CCCC3C(=O)O)cc2)c(Cl)c1] | ¹H NMR (400 MHz, DMSO-d6) δ 12.37 (bs, 1H), 8.21 (bs, 1H), 7.46-7.41 (m, 3H), 7.39 (s, 1H), 7.33-7.17 (m, 4H), 7.13-7.06 (m, 4H), 4.3 (d, J = 6.4 Hz, 1H), 3.55-3.47 (m, 2H), 2.25 (s, 3H), 2.19-2.13 (m, 1H), 1.96-1.88 (m, 3H). LC-MS: m/z 450.1 (M + H)⁺ |
| 135 | 68 | VI.11 | 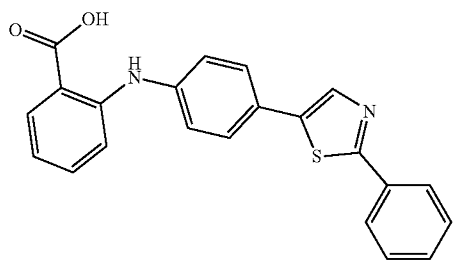 [SMILES: O=C(O)c1ccccc1Nc1ccc(-c2cnc(-c3ccccc3)s2)cc1] | ¹H NMR (400 MHz, DMSO-d6) δ 12.30-10.99 (bs, 1H), 8.20 (s, 1H), 8.00-7.91 (m, 4H), 7.63 (d, J = 8.8 Hz, 2H), 7.55-7.48 (m, 4H), 7.33-7.23 (m, 3H), 6.75 (t, J = 7.6 Hz, 1H). LC-MS: m/z 373.3 (M + H)⁺ |
| 136 | 69 | XIII.5 | 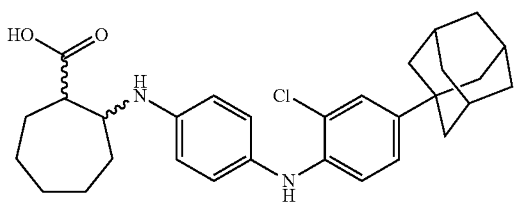 [SMILES: O=C(O)C1CCCCCC1Nc1ccc(Nc2ccc(C34CC5CC(CC(C5)C3)C4)cc2Cl)cc1] | ¹H NMR (400 MHz, DMSO-d6) δ 7.21 (d, J = 2.0 Hz, 1H), 7.05 (dd, J₁ = 2.0 Hz, J₂ = 10.8 Hz, 1H), 6.88 (d, J = 8.4 Hz, 2H), 6.83 (s, 1H), 6.76 (d, J = 8.8 Hz, 1H), 6.58 (d, J = 8.4 Hz, 2H), 3.8 (s, 1H), 2.03 (s, 3H), 1.90-1.83 (m, 1H), 1.80-1.65 (m, 17H), 1.64-1.56 (m, 3H), 1.52-1.41 (m, 3H). LC-MS: m/z 507.3 (M + H)⁺ |
| 138 | 70 | Int-XIII | 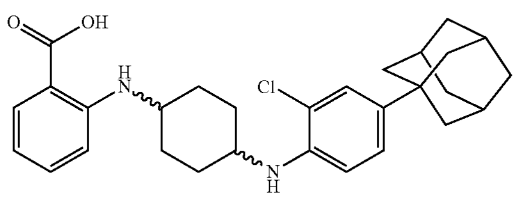 [SMILES: O=C(O)c1ccccc1NC1CCC(Nc2ccc(C34CC5CC(CC(C5)C3)C4)cc2Cl)CC1] | ¹H NMR (400 MHz, DMSO-d6) δ 12.53 (bs, 1H), 8.81 (s, 1H), 7.79 (d, J = 8.0 Hz, 1H), 7.36-7.32 (m, 1H), 7.18 (d, J = 2.0 Hz, 1H), 7.12 (d, J = 8.8 Hz, 1H), 6.79-6.74 (m, 2H), 6.52 (d, J = 7.2 Hz, 1H), 4.51 (d, J = 7.2 Hz, 1H), 3.7 (s, 1H), 3.48 (s, 1H), 2.02 (s, 3H), 1.78-1.7 (m, 18H), 1.58-1.55 (m, 2H). LC-MS: m/z 479.3 (M + H)⁺ |
| 139 | 71 | Int-XIII | 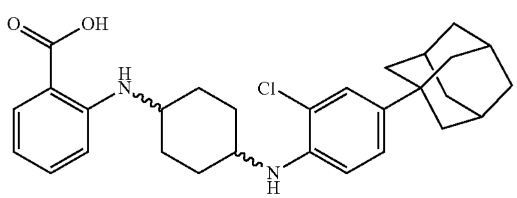 [SMILES: O=C(O)c1ccccc1NC1CCC(Nc2ccc(C34CC5CC(CC(C5)C3)C4)cc2Cl)CC1] | ¹H NMR (400 MHz, DMSO-d6) δ 12.53 (s, 1H), 7.78-7.76 (m, 2H), 7.34 (t, J = 8.0 Hz, 1H), 7.17 (d, J = 2.0 Hz, 1H), 7.11 (dd, J₁ = 1.2 Hz, J₂ = 8.0 Hz, 1H), 6.78-6.73 (m, 2H), 6.54-6.50 (m, 1H), 4.5 (d, J = 8.4 Hz, 1H), 3.4- |

-continued

| CP | Compound No | Reactant | Structure | Analytical data |
|---|---|---|---|---|
| | | | | 3.35 (m, 2H), 2.08-1.98 (m, 7H), 1.78 (s, 6H), 1.7 (s, 6H), 1.47-1.23 (m, 4H). LC-MS: m/z 479.4 (M + H)+ |
| 140 | 72 | VI.12 | 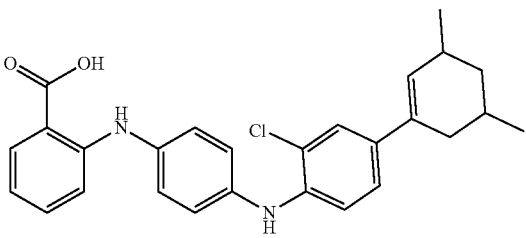 [SMILES: CC1C=C(c2ccc(Nc3ccc(Nc4ccccc4C(=O)O)cc3)c(Cl)c2)CC(C)C1] | $^1$H NMR (400 MHz, DMSO-d6) δ 13.00 (bs, 1H), 9.49 (bs, 1H), 7.86 (dd, $J_1$ = 1.5 Hz, $J_2$ = 7.9 Hz, 1H), 7.42 (s, 1H), 7.37 (s, 1H), 7.34 (m, 1H), 7.28-7.25 (m, 1H), 7.18-7.04 (m, 6H), 6.70 (t, J = 7.4 Hz, 1H), 5.91 (s, 1H), 2.38-2.32 (m, 2H), 1.91-1.89 (m, 2H), 1.77-1.74 (m, 2H), 1.05 (m, 6H). LC-MS: m/z 446.3 (M + H)+ |
| 141 | 73 | VI.13 | 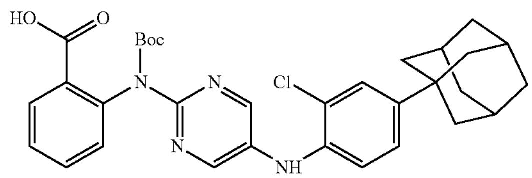 [SMILES: CC(C)(C)OC(=O)N(c1ncc(Nc2ccc(C34CC5CC(CC(C5)C3)C4)cc2Cl)cn1)c1ccccc1C(=O)O] | $^1$H NMR (400 MHz, DMSO-d6) δ 13.00-12.8 (bs, 1H), 8.34 (s, 2H), 7.90-7.82 (m, 2H), 7.32 (d, J = 10.0 Hz, 2H), 7.26-7.13 (m, 3H), 6.96 (bs, 1H), 1.98 (s, 3H), 1.83 (d, J = 2.4 Hz, 6H), 1.72 (s, 6H), 1.33 (s, 9H). LC-MS: m/z 575.1 (M + H)+ |
| 142 | 74 | VI.14 | 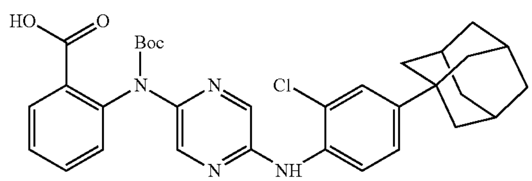 [SMILES: CC(C)(C)OC(=O)N(c1cnc(Nc2ccc(C34CC5CC(CC(C5)C3)C4)cc2Cl)cn1)c1ccccc1C(=O)O] | $^1$H NMR (400 MHz, DMSO-d6) δ 12.91 (bs, 1H), 8.77 (s, 1H), 8.30 (s, 1H), 8.05 (s, 1H), 7.89-7.86 (m, 1H), 7.77 (d, J = 8.4 Hz, 1H), 7.55-7.51 (m, 1H), 7.38-7.37 (m, 2H), 7.27 (t, J = 2.0 Hz, 2H), 2.05 (s, 3H), 1.85 (s, 6H), 1.73 (s, 6H), 1.33 (s, 9H). LC-MS: m/z 575.1 (M + H)+ |
| 143 | 75 | Int-XI | 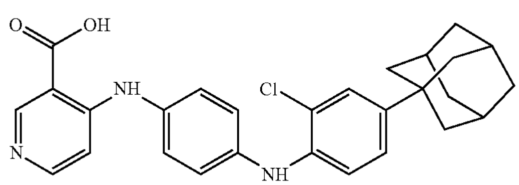 [SMILES: O=C(O)c1cnccc1Nc1ccc(Nc2ccc(C34CC5CC(CC(C5)C3)C4)cc2Cl)cc1] | $^1$H NMR (400 MHz, DMSO-d6) δ 13.40-13.00 (bs, 1H), 8.66 (s, 1H), 8.09 (d, J = 2.0 Hz, 1H), 7.76 (s, 1H), 7.37 (d, J = 1.2 Hz, 1H), 7.28-7.22 (m, 2H), 7.17 (d, J = 7.6 Hz, 2H), 7.06 (d, J = 8.0 Hz, 2H), 6.89 (d, J = 6.8 Hz, 1H), 2.05 (s, 3H), 1.89-1.84 9bs, 6H), 1.73 (s, 6H). LC-MS: m/z 474.1 (M + H)+ |
| 144 | 76 | VI.15 | 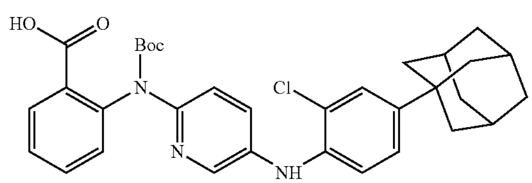 [SMILES: CC(C)(C)OC(=O)N(c1ccc(Nc2ccc(C34CC5CC(CC(C5)C3)C4)cc2Cl)cn1)c1ccccc1C(=O)O] | $^1$H NMR (400 MHz, DMSO-d6) δ 12.86 (bs, 1H), 7.97 (d, J = 2.8 Hz, 1H), 7.86 (dd, $J_1$ = 1.6 Hz, $J_2$ = 8.0 Hz, 1H), 7.77 (s, 1H), 7.54-7.48 (m, 2H), 7.41-7.33 (m, 3H), 7.21 (d, J = 8.4 Hz, 2H), 7.14 (d, J = 8.4 Hz, 1H), 2.04 (s, 3H), 1.83 (s, 6H), 1.72 (s, 6H), 1.32 (s, 9H). LC-MS: m/z 574.1 (M + H)+ |

-continued

| CP | Compound No | Reactant | Structure | Analytical data |
|---|---|---|---|---|
| 145 | 77 | XV.5 | 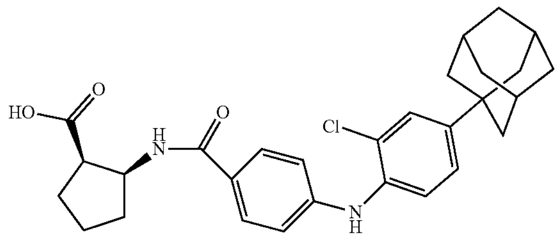 [SMILES: O=C(N[C@H]1CCC[C@H]1C(=O)O)c1ccc(Nc2ccc(C34CC5CC(CC(C5)C3)C4)cc2Cl)cc1] | ¹H NMR (400 MHz, DMSO-d6) δ 11.93 (bs, 1H), 7.99 (s, 1H), 7.83 (bs, 1H), 7.66 (d, J = 8.8 Hz, 2H), 7.40 (s, 1H), 7.29-7.26 (m, 2H), 6.90 (d, J = 8.8 Hz, 2H), 4.54-4.50 (m, 1H), 2.92-2.90 (m, 1H), 2.08 (bs, 3H), 2.05 (m, 2H), 1.85 (s, 6H), 1.83-1.80 (m, 2H), 1.73 (s, 6H), 1.52-1.49 (m, 2H). LC-MS: m/z (M + H)⁺ |
| 146 | 78 | XII.9 | 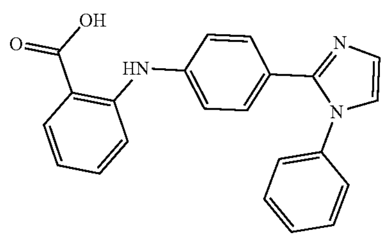 [SMILES: O=C(O)c1ccccc1Nc1ccc(-c2nccn2-c2ccccc2)cc1] | ¹H NMR (400 MHz, DMSO-d6) δ 13.2 (s, 1H), 9.7 (s, 1H), 7.9 (dd, J₁ = 1.6 Hz, J₂ = 8.0 Hz, 1H), 7.52-7.39 (m, 5H), 7.34-7.24 (m, 5H), 7.16-7.13 (m, 3H), 6.82 (t, J = 8.0 Hz, 1H). LC-MS: m/z 356.0 (M + H)⁺ |
| 148 | 79 | | 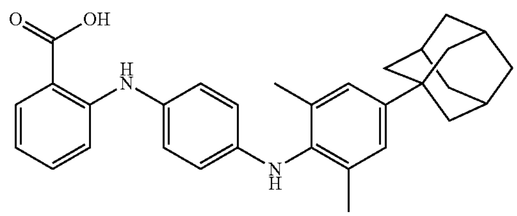 [SMILES: Cc1cc(C23CC4CC(CC(C4)C2)C3)cc(C)c1Nc1ccc(Nc2ccccc2C(=O)O)cc1] | LC-MS: m/z 467.3 (M + H)⁺ |
| 149 | 80 | | 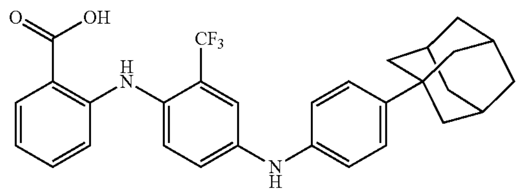 [SMILES: O=C(O)c1ccccc1Nc1ccc(Nc2ccc(C34CC5CC(CC(C5)C3)C4)cc2)cc1C(F)(F)F] | LC-MS: m/z 507.2 (M + H)⁺ |
| 151 | 81 | | 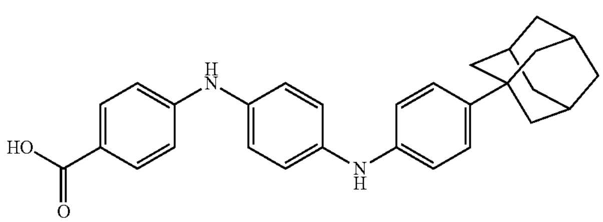 [SMILES: O=C(O)c1ccc(Nc2ccc(Nc3ccc(C45CC6CC(CC(C6)C4)C5)cc3)cc2)cc1] | LC-MS: m/z 438.2 (M)⁺ |
| 156 | 82 | XII.10 | 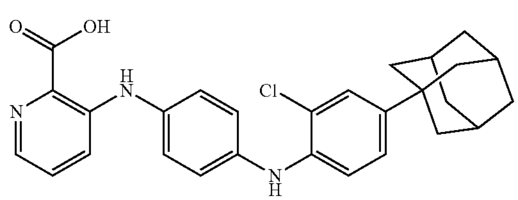 [SMILES: O=C(O)c1ncccc1Nc1ccc(Nc2ccc(C34CC5CC(CC(C5)C3)C4)cc2Cl)cc1] | ¹H NMR (400 MHz, DMSO-d6) δ 11.2 (s, 1H), 7.74 (s, 1H), 7.50 (d, J = 8.4 Hz, 1H), 7.4 (s, 1H), 7.31 (d, J = 2.0 Hz, 1H), 7.19-7.03 (m, 7H), 2.05 (s, 3H), 1.83 (s, 6H), 1.72 (s, 6H). LC-MS: m/z 474.1 (M + H)⁺ |

-continued

| CP | Compound No | Reactant | Structure | Analytical data |
|---|---|---|---|---|
| 157 | 83 | XII.11 | 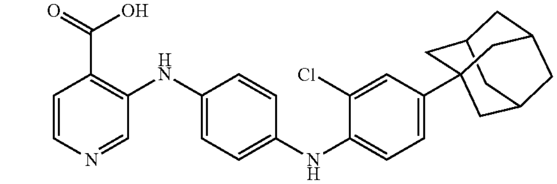 [SMILES: O=C(O)c1ccncc1Nc1ccc(Nc2ccc(C34CC5CC(CC(C5)C3)C4)cc2Cl)cc1] | ¹H NMR (400 MHz, DMSO-d6) δ 13.80-13.2 (bs, 1H), 9.50-9.0 (bs, 1H), 8.39 (s, 1H), 7.92 (d, J = 5.2 Hz, 1H), 7.64 (d, J = 4.8 Hz, 1H), 7.55 (s, 1H), 7.34 (s, 1H), 7.21 (s, 2H), 7.14 (d, J = 9.2 Hz, 2H), 7.05 (d, J = 8.8 Hz, 2H), 2.05 (s, 3H), 1.83 (s, 6H), 1.72 (s, 6H). LC-MS: m/z 474.1 (M + H)⁺ |
| 158 | 84 | VI.16 | 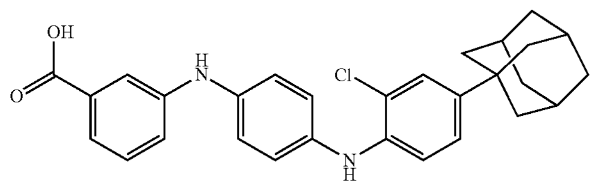 [SMILES: O=C(O)c1cccc(Nc2ccc(Nc3ccc(C45CC6CC(CC(C6)C4)C5)cc3Cl)cc2)c1] | ¹H NMR (400 MHz, DMSO-d6) δ 12.80 (bs, 1H), 8.13 (s, 1H), 7.53 (s, 1H), 7.28 (s, 4H), 7.15-7.14 (m, 2H), 7.08-7.04 (m, 5H), 2.04 (s, 3H), 1.82 (s, 6H), 1.72 (s, 6H). LC-MS: m/z 472.1 (M + H)⁺ |
| 159 | 85 | XII.12 | 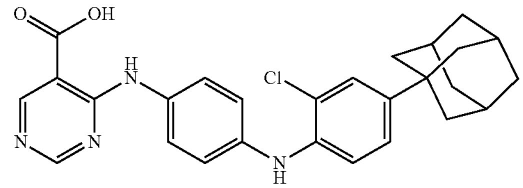 [SMILES: O=C(O)c1cncnc1Nc1ccc(Nc2ccc(C34CC5CC(CC(C5)C3)C4)cc2Cl)cc1] | ¹H NMR (400 MHz, DMSO-d6) δ 13.82 (bs, 1H), 10.41 (bs, 1H), 8.83 (bs, 1H), 8.68 (s, 1H), 7.55 (s, 1H), 7.52 (d, J = 8.8 Hz, 2H), 7.33 (d, J = 0.8 Hz, 1H), 7.22-7.17 (m, 2H), 7.04 (d, J = 8.8 Hz, 2H), 2.04 (s, 3H), 1.83 (s, 6H), 1.72 (s, 6H). LC-MS: m/z 475.2 (M + H)⁺ |
| 160 | 86 | XII.13 | 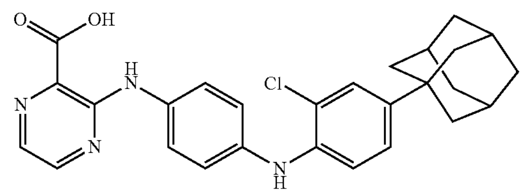 [SMILES: O=C(O)c1nccnc1Nc1ccc(Nc2ccc(C34CC5CC(CC(C5)C3)C4)cc2Cl)cc1] | ¹H NMR (400 MHz, DMSO-d6) δ 10.17 (s, 1H), 8.37 (d, J = 2.4 Hz, 1H), 8.04 (d, J = 2.0 Hz, 1H), 7.51 (d, J = 8.4 Hz, 2H), 7.47 (s, 1H), 7.32 (d, J = 1.6 Hz, 1H), 7.18-7.14 (m, 2H), 7.04 (d, J = 8.8 Hz, 2H), 2.04 (s, 3H), 1.83 (s, 6H), 1.72 (s, 6H). LC-MS: m/z 475.2 (M + H)⁺ |
| 161 | 87 | XV.6 | 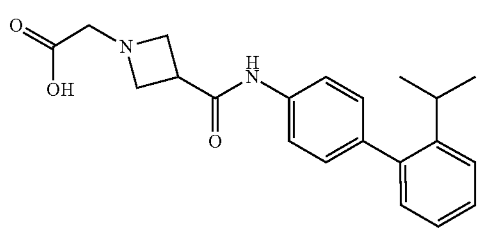 [SMILES: CC(C)c1ccccc1-c1ccc(NC(=O)C2CN(CC(=O)O)C2)cc1] | ¹H NMR (400 MHz, DMSO-d6) δ 10.11 (s, 1H), 7.66 (d, J = 8.4 Hz, 2H), 7.41-7.39 (m, 1H), 7.35-7.31 (m, 1H), 7.23-7.18 (m, 3H), 7.11-7.09 (m, 1H), 3.93 (t, J = 8.8 Hz, 2H), 3.79 (t, J = 7.2 Hz, 2H), 3.62-3.54 (m, 2H), 3.52-3.49 (m, 2H), 3.02-2.95 (m, 1H), 1.10 (d, J = 6.8 Hz, 6H). LC-MS: m/z 353.1 (M + H)⁺ |
| 162 | 88 | XIII.6 | 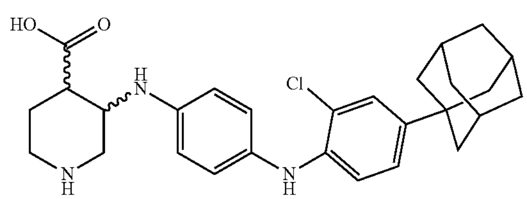 [SMILES: O=C(O)C1CCNCC1Nc1ccc(Nc2ccc(C34CC5CC(CC(C5)C3)C4)cc2Cl)cc1] | ¹H NMR (400 MHz, DMSO-d6) δ 7.21-7.20 (m, 1H), 7.05-7.02 (m, 1H), 6.89-6.85 (m, 3H), 6.82-6.74 (m, 2H), 6.65-6.58 (m, 5H), 3.79 (bs, 1H), 3.14-3.11 (m, 1H), 2.92-2.81 (m, 3H), 2.60-2.56 (m, 1H), 2.34-2.32 (m, 1H), 2.02 (s, 3H), 1.78 (s, 7H), 1.70 (s, 8H). LC-MS: m/z 480.2 (M + H)⁺ |

| CP | Compound No | Reactant | Structure | Analytical data |
|---|---|---|---|---|
| 163 | 89 | XII.14 | 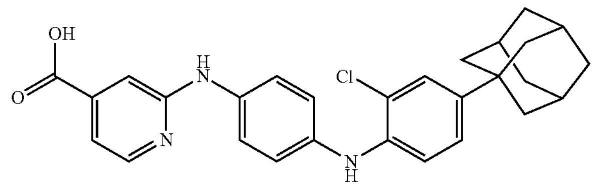 [SMILES: O=C(O)c1ccnc(Nc2ccc(Nc3ccc(C45CC6CC(CC(C6)C4)C5)cc3Cl)cc2)c1] | ¹H NMR (400 MHz, DMSO-d6) δ 13.80 (bs, 1H), 9.12 (s, 1H), 8.23 (d, J = 4.8 Hz, 1H), 7.55 (d, J = 8.4 Hz, 2H), 7.28-7.27 (m, 3H), 7.13 (d, J = 1.2 Hz, 1H), 7.06-7.03 (m, 4H), 2.04 (s, 3H), 1.82 (s, 6H), 1.71 (s, 6H). LC-MS: m/z 474.3 (M + H)⁺ |
| 168 | 90 | XII.15 | 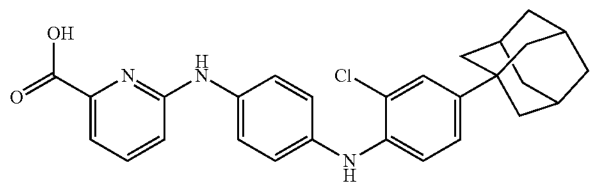 [SMILES: O=C(O)c1cccc(Nc2ccc(Nc3ccc(C45CC6CC(CC(C6)C4)C5)cc3Cl)cc2)n1] | ¹H NMR (400 MHz, DMSO-d6) δ 12.80 (bs, 1H), 9.12 (s, 1H), 7.70-7.64 (m, 3H), 7.36 (d, J = 7.2 Hz, 1H), 7.29 (d, J = 1.6 Hz, 1H), 7.25 (s, 1H), 7.15 (dd, J₁ = 1.2 Hz, J₂ = 8.0 Hz, 1H), 7.07-7.02 (m, 3H), 6.96 (d, J = 8.4 Hz, 1H), 2.04 (s, 3H), 1.82 (s, 6H), 1.72 (s, 6H). LC-MS: m/z 474.3 (M + H)⁺ |
| 169 | 91 | XII.16 | 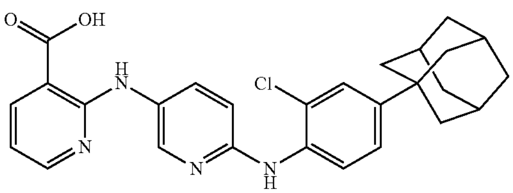 [SMILES: O=C(O)c1cccnc1Nc1ccc(Nc2ccc(C34CC5CC(CC(C5)C3)C4)cc2Cl)nc1] | ¹H NMR (400 MHz, DMSO-d6) δ 13.95 (bs, 1H), 13.2 (bs, 1H), 8.35 (d, J = 2.4 Hz, 1H), 8.30 (dd, J₁ = 2.0 Hz, J₂ = 5.2 Hz, 1H), 8.20 (dd, J₁ = 1.6 Hz, J₂ = 8.0 Hz, 1H), 8.12 (s, 1H), 7.92 (d, J = 8.8 Hz, 1H), 7.87 (dd, J₁ = 2.8 Hz, J₂ = 8.8 Hz, 1H), 7.34 (d, J = 2.4 Hz, 1H), 7.26 (dd, J₁ = 2.0 Hz, J₂ = 8.8 Hz, 1H), 6.98 (d, J = 8.8 Hz, 1H), 6.80 (dd, J₁ = 4.8 Hz, J₂ = 8.0 Hz, 1H), 2.06 (s, 3H), 1.86 (s, 6H), 1.74 (s, 6H). LC-MS: m/z 475.2 (M + H)⁺ |
| 170 | 92 | VI.17 | 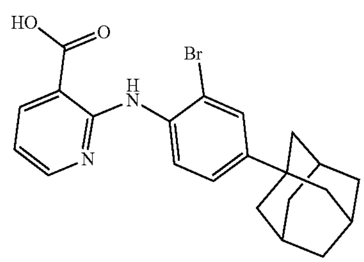 [SMILES: O=C(O)c1cccnc1Nc1ccc(C23CC4CC(CC(C4)C2)C3)cc1Br] | ¹H NMR (400 MHz, DMSO-d6) δ 13.59 (bs, 1H), 10.58 (bs, 1H), 8.38-8.37 (m, 1H), 8.36 (s, 1H), 8.27 (dd, J₁ = 1.6 Hz, J₂ = 7.6 Hz, 1H), 7.55 (d, J = 2.4 Hz, 1H), 7.35 (dd, J₁ = 2.4 Hz, J₂ = 8.8 Hz, 1H), 6.91 (dd, J₁ = 4.8 Hz, J₂ = 7.6 Hz, 1H), 2.06 (s, 3H), 1.86 (s, 6H), 1.73 (s, 6H). LC-MS: m/z 428.9 (M + H)⁺ |
| 172 | 93 | XIII.7 | 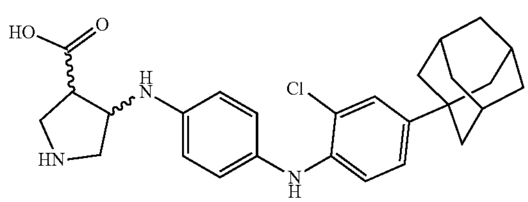 [SMILES: O=C(O)C1CNCC1Nc1ccc(Nc2ccc(C34CC5CC(CC(C5)C3)C4)cc2Cl)cc1] | ¹H NMR (400 MHz, DMSO-d6) δ 7.21 (d, J = 1.2 Hz, 1H), 7.04 (d, J = 6.8 Hz, 1H), 6.93-6.88 (m, 3H), 6.77 (d, J = 8.4 Hz, 1H), 6.61 (d, J = 8.4 Hz, 2H), 5.70 (bs, 1H), 4.09 (bs, 1H), 3.30-3.27 (m, 3H), 3.21-3.17 (m, 1H), 2.87-2.84 (m, 1H), 2.67 (m, 1H), 2.02 (s, 3H), 1.78 (s, 6H), 1.70 (s, 6H). LC-MS: m/z 466.3 (M + H)⁺ |

-continued

| CP | Compound No | Reactant | Structure | Analytical data |
|---|---|---|---|---|
| 173 | 94 | VI.18 | (structure) | ¹H NMR (400 MHz, DMSO-d6) δ 12.6 (bs, 1H), 7.42 (s, 1H), 7.32 (s, 1H), 7.16 (s, 2H), 7.09 (d, J = 7.6 Hz, 2H), 7.08-7.00 (m, 1H), 6.93 (d, J = 8.4 Hz, 2H), 4.1 (m, 1H), 2.90 (m, 1H), 2.80 (m, 1H), 2.05 (s, 3H), 1.83 (s, 6H), 1.72 (s, 6H), 1.33 (s, 9H). LC-MS: m/z 523.2 (M − H)⁺ |
| 174 | 95 | VI.18 & Compound 82 | (structure) | ¹H NMR (400 MHz, DMSO-d6) δ 7.49 (s, 1H), 7.33 (s, 1H), 7.19 (s, 1H), 7.11 (d, J = 8.4 Hz, 2H), 6.95 (d, J = 8.0 Hz, 2H), 3.65 (m, 1H), 3.12-3.10 (m, 1H), 2.90-2.80 (m, 1H), 2.04 (s, 3H), 1.83 (s, 6H), 1.72 (s, 6H). LC-MS: m/z 425.3 (M + H)⁺ |
| 177 | 96 | VI.20 | (structure) | ¹H NMR (400 MHz, DMSO-d6) δ 13.50 (bs, 1H), 10.41 (bs, 1H), 8.37 (dd, J₁ = 1.9 Hz, J₂ = 4.9 Hz, 1H), 8.24 (dd, J₁ = 2.0 Hz, J₂ = 7.8 Hz, 1H), 7.66 (d, J = 7.8 Hz, 1H), 7.50 (s, 1H), 7.25 (t, J = 7.8 Hz, 1H), 7.03 (d, J = 7.8 Hz, 1H), 6.85-6.82 (m, 1H), 2.06 (s, 3H), 1.88 (s, 6H), 1.74 (s, 6H). LC-MS: m/z 349.2 (M + H)⁺ |
| 178 | 97 | IV.1 | (structure) | ¹H NMR (400 MHz, DMSO-d6) δ 12.5 (bs, 1H), 8.24 (s, 1H), 8.07 (d, J = 6.8 Hz, 1H), 8.01 (s, 0.3H), 7.84 (m, 0.6H), 7.78-7.73 (m, 2H), 7.51-7.46 (m, 2H), 7.25-7.19 (m, 1.5H), 2.09 (s, 3H), 1.98 (s, 6H), 1.77 (s, 6H), 1.49 (s, 2H). LC-MS: m/z 373.1 (M + H)⁺ |
| 182 294 | 98 | XV.20 | (structure) | ¹H NMR (400 MHz, DMSO-d6) δ 12.95 (s, 1H), 9.5 (s, 1H), 8.45 (s, 1H), 7.88 (dd, J₁ = 1.6 Hz, J₂ = 8.0 Hz, 1H), 7.67 (d, J = 8.8 Hz, 2H), 7.35 (t, J = 1.6 Hz, 1H), 7.23 (s, 1H), 7.20-7.14 (m, 4H), 7.07 (d, J = 8.4 Hz, 1H), 6.99 (d, J = 8.8 Hz, 2H), 6.73-6.69 (m, 1H), 2.06 (s, 9H), 1.65 (s, 6H). LC-MS: m/z 482.1 (M + H)⁺ |
| 183 | 99 | | (structure) | LC-MS: m/z 453.3 (M + H)⁺ |

-continued

| CP | Compound No | Reactant | Structure | Analytical data |
|---|---|---|---|---|
| 184 | 100 | Int-XX | 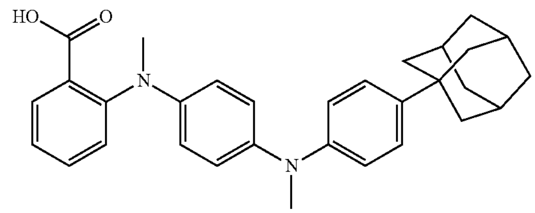 [SMILES: CN(c1ccc(N(C)c2ccccc2C(=O)O)cc1)c1ccc(C23CC4CC(CC(C4)C2)C3)cc1] | ¹H NMR (400 MHz, DMSO-d6) δ 12.80 (bs, 1H), 7.75 (dd, J₁ = 0.8 Hz, J₂ = 7.2 Hz, 1H), 7.58 (t, J = 8.0 Hz, 1H), 7.31 (t, J = 7.6 Hz, 2H), 7.12 (d, J = 8.8 Hz, 2H), 6.90 (d, J = 9.2 Hz, 2H), 6.67 (d, J = 8.8 Hz, 2H), 6.56 (d, J = 8.8 Hz, 2H), 3.18 (s, 3H), 3.13 (s, 3H), 2.02 (s, 3H), 1.80 (s, 6H), 1.71 (s, 6H). LC-MS: m/z 467.3 (M + H)⁺ |
| 185 | 101 | VI.21 | 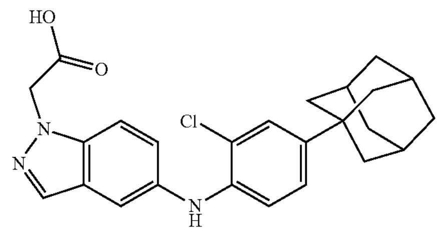 [SMILES: O=C(O)Cn1ncc2cc(Nc3ccc(C45CC6CC(CC(C6)C4)C5)cc3Cl)ccc21] | ¹H NMR (400 MHz, DMSO-d6) δ 7.81 (s, 1H), 7.38 (d, J = 8.8 Hz, 1H), 7.32-7.28 (m, 3H), 7.15-7.12 (m, 2H), 6.97 (d, J = 8.8 Hz, 1H), 4.72 (s, 2H), 2.02 (s, 3H), 1.81 (s, 6H), 1.71 (s, 6H). LC-MS: m/z 436.0 (M + H)⁺ |
| 186 | 102 | XV.7 | 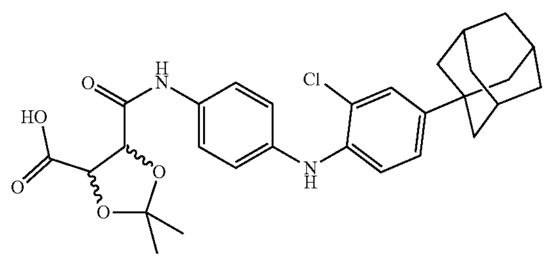 [SMILES: CC1(C)OC(C(=O)O)C(C(=O)Nc2ccc(Nc3ccc(C45CC6CC(CC(C6)C4)C5)cc3Cl)cc2)O1] | ¹H NMR (400 MHz, DMSO-d6) δ 11.59-11.3 (bs, 1H), 7.46 (d, J = 8.8 Hz, 2H), 7.39 (s, 1H), 7.30 (d, J = 2.4 Hz, 1H), 7.16 (dd, J₁ = 2.0 Hz, J₂ = 8.4 Hz, 1H), 7.10 (d, J = 8.0 Hz, 1H), 7.00 (d, J = 8.8 Hz, 2H), 4.47 (d, J = 8.0 Hz, 1H), 4.33 (d, J = 7.2 Hz, 1H), 2.04 (s, 3H), 1.82 (s, 6H), 1.72 (s, 6H), 1.38 (s, 3H), 1.35 (s, 3H), 1.25-1.22 (m, 1H). LC-MS: m/z 525.1 (M + H)+ |
| 187 | 103 | VI.22 | 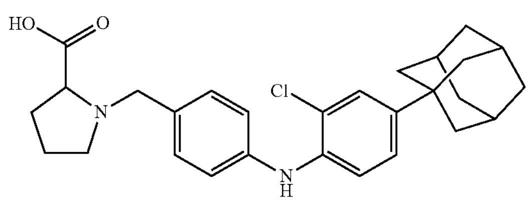 [SMILES: O=C(O)C1CCCN1Cc1ccc(Nc2ccc(C34CC5CC(CC(C5)C3)C4)cc2Cl)cc1] | ¹H NMR (400 MHz, DMSO-d6) δ 7.66 (s, 1H), 7.36 (s, 1H), 7.26-7.23 (m, 4H), 6.96 (d, J = 8.4 Hz, 2H), 4.03 (d, J = 13.2 Hz, 1H), 3.83 (d, J = 12.8 Hz, 1H), 3.21-3.18 (m, 2H), 2.78-2.71 (m, 1H), 2.33-2.32 (m, 1H), 2.15-2.02 (m, 4H), 1.95-1.79 (m, 4H), 1.74-1.63 (m, 8H). LC-MS: m/z 465.3 (M + H)⁺ |
| 191 | 104 | XII.17 | 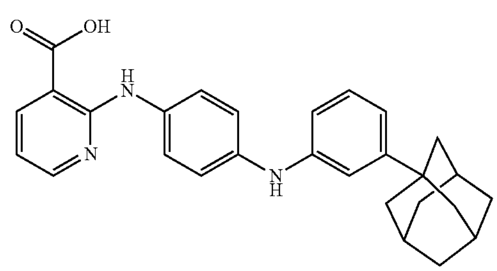 [SMILES: O=C(O)c1cccnc1Nc1ccc(Nc2cccc(C34CC5CC(CC(C5)C3)C4)c2)cc1] | ¹H NMR (400 MHz, DMSO-d6) δ 13.40 (bs, 1H), 10.20 (s, 1H), 8.34 (dd, J₁ = 1.9 Hz, J₂ = 4.9 Hz, 1H), 8.22 (dd, J₁ = 1.9 Hz, J₂ = 7.8 Hz, 1H), 7.95 9bs, 1H0, 7.55 (d, J = 8.8 Hz, 2H), 7.13 (t, J = 7.8 Hz, 1H), 7.05-7.00 (m, 3H), 6.85 (d, J = 7.8 Hz, 1H), 6.83-6.77 (m, 2H), 2.05 (s, 3H), 1.76 (s, 6H), 1.69 (s, 6H). LC-MS: m/z 440.1 (M + H)⁺ |

-continued

| CP | Compound No | Reactant | Structure | Analytical data |
|---|---|---|---|---|
| 192 | 105 | VI.23 | 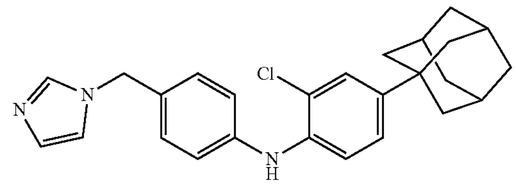 [SMILES: Clc1cc(C23CC4CC(CC(C4)C2)C3)ccc1Nc1ccc(Cn2ccnc2)cc1] | ¹H NMR (400 MHz, DMSO-d6) δ 7.72 (s, 1H), 7.61 (s, 1H), 7.34 (s, 1H), 7.20 (s, 2H), 7.16-7.13 (m, 3H), 6.95 (d, J = 8.4 Hz, 2H), 6.89 (s, 1H), 5.07 (s, 2H), 2.05 (s, 3H), 1.83 (s, 6H), 1.72 (s, 6H). LC-MS: m/z 350.2 (M + H)⁺ |
| 194 | 106 | X.4 | 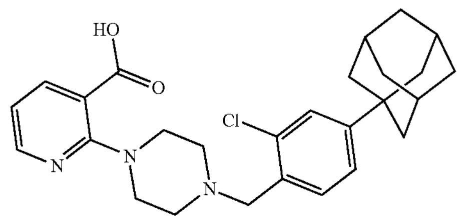 [SMILES: O=C(O)c1cccnc1N1CCN(Cc2ccc(C34CC5CC(CC(C5)C3)C4)cc2Cl)CC1] | ¹H NMR (400 MHz, DMSO-d6) δ 13.0 (s, 1H), 8.26-8.25 (m, 1H), 7.92 (d, J = 7.2 Hz, 1H), 7.44 (d, J = 7.6 Hz, 1H), 7.34-7.31 (m, 2H), 6.84 (dd, J₁ = 4.4 Hz, J₂ = 7.2 Hz, 1H), 3.57 (s, 2H), 3.33 (m, 8H), 2.05 (s, 2H), 1.85 (s, 6H), 1.73 (s, 6H). LC-MS: m/z 466.1 (M + H)⁺ |
| 195 | 107 | X.5 | 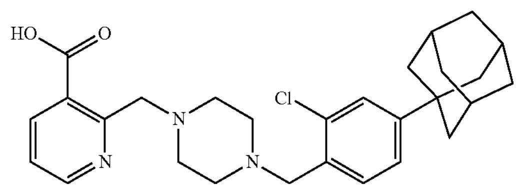 [SMILES: O=C(O)c1cccnc1CN1CCN(Cc2ccc(C34CC5CC(CC(C5)C3)C4)cc2Cl)CC1] | ¹H NMR (400 MHz, DMSO-d6) δ 8.56 (dd, J₁ = 1.6 Hz, J₂ = 4.8 Hz, 1H), 8.18 (d, J = 7.6 Hz, 1H), 7.46 (dd, J₁ = 4.8 Hz, J₂ = 7.6 Hz, 1H), 7.42-7.40 (m, 1H), 7.38-7.30 (m, 2H), 4.18 (s, 2H), 3.56 (s, 2H), 2.8 (s, 4H), 2.55-2.54 (m, 4H), 2.04 (s, 3H), 1.84 (s, 6H), 1.72 (s, 6H). LC-MS: m/z 480.1 (M + H)⁺ |
| 197 | 108 | VI.24 | 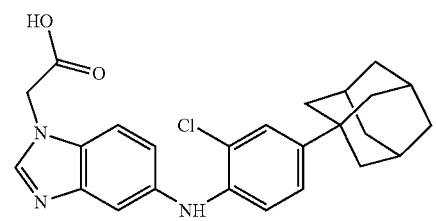 [SMILES: O=C(O)Cn1cnc2cc(Nc3ccc(C45CC6CC(CC(C6)C4)C5)cc3Cl)ccc21] | ¹H NMR (400 MHz, DMSO-d6) δ 13.2 (bs, 1.5H), 8.10 (s, 0.4H), 8.03 (s, 1H), 7.52 (d, J = 7.6 Hz, 1H), 7.45-7.40 (m, 2H), 7.31 (m, 2H), 7.17 (s, 1H), 7.14 (s, 2.5 H), 7.04-6.98 (m, 2H), 5.05 (s, 1H), 4.99 (s, 2H), 2.04 (s, 5H), 1.90 (s, 9H), 1.72 (s, 9H). LC-MS: m/z 436.2 (M + H)⁺ |
| 198 | 109 | XX.1 | 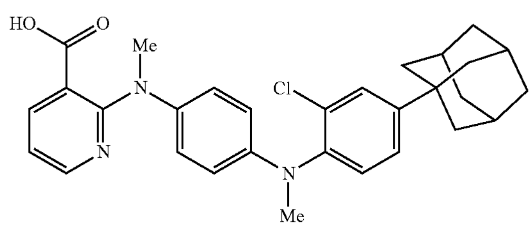 [SMILES: CN(c1ccc(N(C)c2ncccc2C(=O)O)cc1)c1ccc(C23CC4CC(CC(C4)C2)C3)cc1Cl] | ¹H NMR (400 MHz, DMSO-d6) δ 12.35 (s, 1H), 8.28 (d, J = 3.2 Hz, 1H), 7.70 (d, J = 5.6 Hz, 1H), 7.47 (d, J = 1.6 Hz, 1H), 7.38 (d, J = 8.4 Hz, 1H), 7.24 (d, J = 8.4 Hz, 1H), 6.84-6.81 (m, 3H), 6.43 (d, J = 8.8 Hz, 2H), 3.3 (s, 3H), 3.13 (s, 3H), 2.06 (s, 3H), 1.88 (s, 6H), 1.74 (s, 6H). LC-MS: m/z 502.2 (M + H)⁺ |
| 199 | 110 | VI.25 | 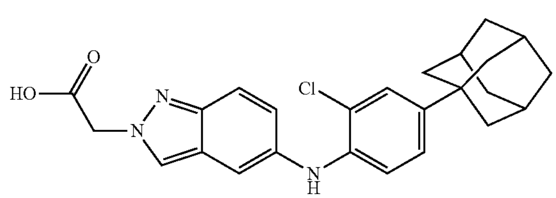 [SMILES: O=C(O)Cn1cc2cc(Nc3ccc(C45CC6CC(CC(C6)C4)C5)cc3Cl)ccc2n1] | ¹H NMR (400 MHz, DMSO-d6) δ 13.2 (bs, 1H), 8.15 (s, 1H), 7.52 (d, J = 9.2 Hz, 1H), 7.37-7.31 (m, 2H), 7.19-7.08 (m, 4H), 5.21 (s, 2H), 2.05 (s, 3H), 1.83 (s, 6H), 1.72 (s, 1H). LC-MS: m/z 436.3 (M + H)⁺ |

-continued

| CP | Compound No | Reactant | Structure | Analytical data |
|---|---|---|---|---|
| 200 | 111 | VI.26 | 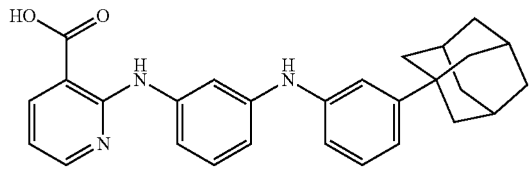 [SMILES: O=C(O)c1cccnc1Nc1cccc(Nc2cccc(C34CC5CC(CC(C5)C3)C4)c2)c1] | ¹H NMR (400 MHz, DMSO-d6) δ 13.50 (bs, 1H), 10.40 (s, 1H), 8.36 (dd, J₁ = 2.0 Hz, J₂ = 4.9 Hz, 1H), 8.23 (dd, J₁ = 1.9 Hz, J₂ = 7.3 Hz, 1H), 8.11 (s, 1H), 7.66 (s, 1H), 7.19-7.11 (m, 3H), 7.02 (d, J = 8.3 Hz, 1H), 6.95 (d, J = 7.8 Hz, 1H), 6.86-6.83 (m, 2H), 6.70 (d, J = 7.8 Hz, 1H), 1.98 (s, 3H), 1.85 (s, 6H), 1.68 (s, 6H). LC-MS: m/z 440.3 (M + H)⁺ |
| 202 | 112 | XII.18 | 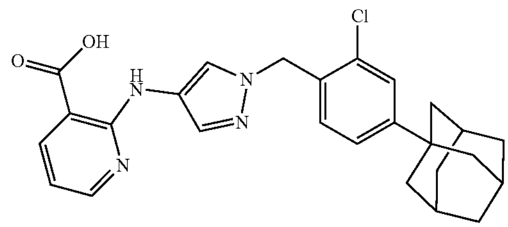 [SMILES: O=C(O)c1cccnc1Nc1cnn(Cc2ccc(C34CC5CC(CC(C5)C3)C4)cc2Cl)c1] | ¹H NMR (400 MHz, DMSO-d6) δ 13.4 (bs, 1H), 10.2 (bs, 1H), 8.33 (d, J = 2.8 Hz, 1H), 8.22 (s, 1H), 8.16 (dd, J₁ = 1.2 Hz, J₂ = 7.2 Hz, 1H), 7.67 (s, 1H), 7.39 (d, J = 2.0 Hz, 1H), 7.31=7.29 (m, 1H), 6.94 (d, J = 8.4 Hz, 1H), 6.74 (dd, J₁ = 5.2 Hz, J₂ = 7.6 Hz, 1H), 5.36 (bs, 2H), 2.04 (s, 3H), 1.83 (s, 6H), 1.72 (s, 6H). LC-MS: m/z 463.2 (M + H)⁺ |
| 203 | 113 | XII.19 | 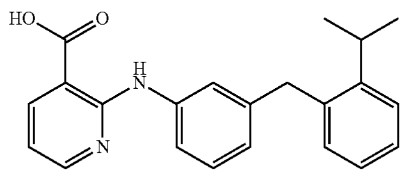 [SMILES: CC(C)c1ccccc1Cc1cccc(Nc2ncccc2C(=O)O)c1] | ¹H NMR (400 MHz, DMSO-d6) δ 13.54 (s, 1H), 10.40 (s, 1H), 8.32 (dd, J₁ = 1.9 Hz, J₂ = 4.8 Hz, 1H), 8.23 (dd, J₁ = 2.0 Hz, J₂ = 7.8 Hz, 1H), 7.61 (d, J = 8.3 Hz, 1H), 7.39 (s, 1H), 7.30 (d, J = 8.3 Hz, 1H), 7.23-7.10 (m, 4H), 6.84 (m, 1H), 6.75 (d, J = 8.0 Hz, 1H), 4.02 (s, 2H), 3.16 (m, 1H), 1.10 (d, J = 6.8 Hz, 6H). LC-MS: m/z 347.2 (M + H)⁺ |
| 204 | 114 | XII.20 | 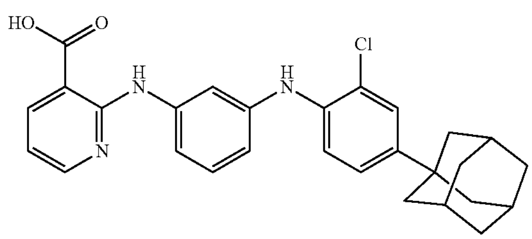 [SMILES: O=C(O)c1cccnc1Nc1cccc(Nc2ccc(C34CC5CC(CC(C5)C3)C4)cc2Cl)c1] | ¹H NMR (400 MHz, DMSO-d6) δ 8.13 (d, J = 7.6 Hz, 2H), 7.48 (s, 1H), 7.42 (s, 1H), 7.33 (d, J = 2.0 Hz, 1H), 7.29 (d, J = 8.4 Hz, 1H), 7.26-7.21 (m, 3H), 7.09 (t, J = 7.6 Hz, 1H), 6.67 (s, 1H), 6.55 (d, J = 7.6 Hz, 1H), 2.05 (s, 3H), 1.85 (s, 6H), 1.73 (s, 6H). LC-MS: m/z 474.2 (M + H)⁺ |
| 205 | 115 | XII.21 | 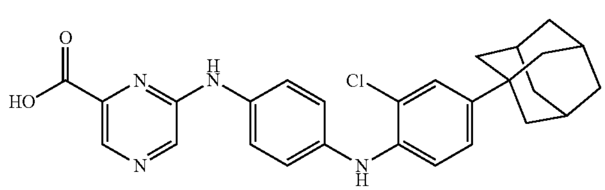 [SMILES: O=C(O)c1cncc(Nc2ccc(Nc3ccc(C45CC6CC(CC(C6)C4)C5)cc3Cl)cc2)n1] | ¹H NMR (400 MHz, DMSO-d6) δ 13.3 (bs, 1H), 9.63 (s, 1H), 8.41 (s, 1H), 8.33 (s, 1H), 7.70 (d, J = 8.8 Hz, 2H), 7.36 (s, 1H), 7.30 (d, J = 2.4 Hz, 1H), 7.18-7.16 (m, 1H), 7.11 (d, J = 8.4 Hz, 1H), 7.05 (d, J = 9.2 Hz, 2H), 2.05 (s, 3H), 1.83 (s, 6H), 1.72 (s, 6H). LC-MS: m/z 475.2 (M + H)⁺ |

-continued

| CP | Compound No | Reactant | Structure | Analytical data |
|---|---|---|---|---|
| 206 | 116 | XII.22 | 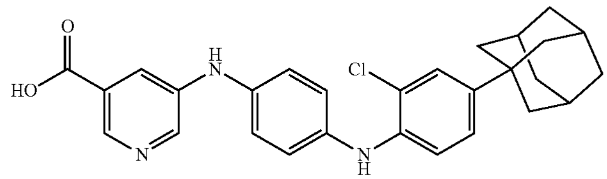 [SMILES: O=C(O)c1cncc(Nc2ccc(Nc3ccc(C45CC6CC(CC(C6)C4)C5)cc3Cl)cc2)c1] | ¹H NMR (400 MHz, DMSO-d6) δ 13.20 (bs, 1H), 8.40 (t, J = 1.9 Hz, 2H), 8.33 (s, 1H), 7.71 (m, 1H), 7.39 (s, 1H), 7.31 (s, 1H), 7.17-7.06 (m, 6H), 2.04 (s, 3H), 1.82 (s, 6H), 1.72 (s, 6H). LC-MS: m/z 474.2 (M + H)⁺ |
| 207 | 117 | XII.23 | 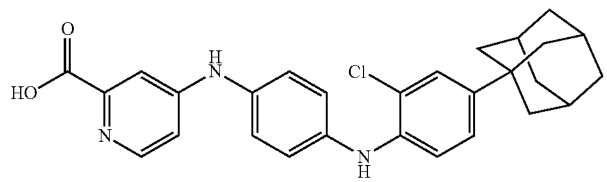 [SMILES: O=C(O)c1cc(Nc2ccc(Nc3ccc(C45CC6CC(CC(C6)C4)C5)cc3Cl)cc2)ccn1] | ¹H NMR (400 MHz, DMSO-d6) δ 9.96 (s, 1H), 7.99 (d, J = 6.8 Hz, 1H), 7.77 (s, 1H), 7.37 (s, 1H), 7.32 (s, 1H), 7.29-7.23 (m, 2H), 7.15 (d, J = 8.8 Hz, 2H), 7.06 (d, J = 8.8 Hz, 2H), 6.9 (dd, J₁ = 2.5 Hz, J₂ = 6.9 Hz, 1H), 2.05 (bs, 3H), 1.84 (s, 6H), 1.73 (s, 6H). LC-MS: m/z 474.2 (M + H)⁺ |
| 210 | 118 | VI.27 | 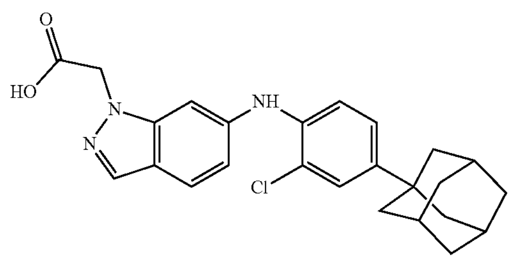 [SMILES: O=C(O)Cn1ncc2ccc(Nc3ccc(C45CC6CC(CC(C6)C4)C5)cc3Cl)cc21] | ¹H NMR (400 MHz, DMSO-d6) δ 12.88 (bs, 1H), 7.88 (s, 1H), 7.75 (s, 1H), 7.57 (d, J = 8.8 Hz, 1H), 7.37 (d, J = 1.6 Hz, 1H), 7.31 (d, J = 8.0 Hz, 1H), 7.21 (dd, J₁ = 2.0 Hz, J₂ = 8.8 Hz, 1H), 7.02 (s, 1H), 6.91 (dd, J₁ = 1.6 Hz, J₂ = 8.8 Hz, 1H), 5.05 (s, 2H), 2.05 (s, 3H), 1.85 (s, 6H), 1.73 (s, 6H). LC-MS m/z 436.2 (M + H)⁺ |
| 211 | 119 | XII.24 | 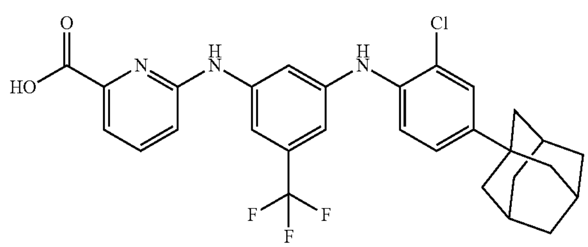 [SMILES: O=C(O)c1cccc(Nc2cc(Nc3ccc(C45CC6CC(CC(C6)C4)C5)cc3Cl)cc(C(F)(F)F)c2)n1] | ¹H NMR (400 MHz, DMSO-d6) δ 12.8 (bs, 1H), 9.5 (bs, 1H), 8.2 (bs, 1H), 7.9 9bs, 1H), 7.7 (bs, 1H), 7.46 (bs, 1H), 7.40 (bs, 2H), 7.30 (bs, 1H), 7.20 (bs, 1H), 7.00 (bs, 1H), 6.82 (bs, 1H), 2.05 (s, 3H), 1.90 (s, 6H), 1.73 (s, 6H). LC-MS: m/z 542.2 (M + H)⁺ |
| 212 | 120 | XV.8 | 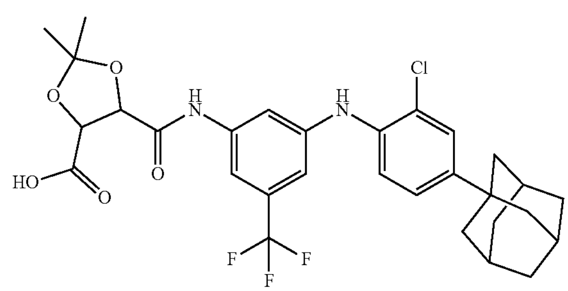 [SMILES: CC1(C)OC(C(=O)O)C(C(=O)Nc2cc(Nc3ccc(C45CC6CC(CC(C6)C4)C5)cc3Cl)cc(C(F)(F)F)c2)O1] | ¹H NMR (400 MHz, DMSO-d6) δ 13.2 (bs, 1H), 10.16 (bs, 1H), 8.15 (s, 1H), 7.53 (s, 1H), 7.42 (d, J = 6.0 Hz, 2H), 7.32 (s, 2H), 6.92 (s, 1H), 4.71 (d, J = 6.0 Hz, 1H), 4.67 (d, J = 6.0 Hz, 1H), 2.06 (s, 3H), 1.86 (s, 6H), 1.73 (s, 6H), 1.4 (s, 6H). LC-MS: m/z 593.2 (M + H)⁺ |
| 213 | 121 | VI.28 | 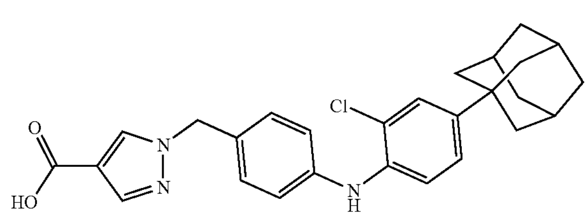 [SMILES: O=C(O)c1cnn(Cc2ccc(Nc3ccc(C45CC6CC(CC(C6)C4)C5)cc3Cl)cc2)c1] | ¹H NMR (400 MHz, DMSO-d6) δ 12.25 (bs, 1H), 8.29 (s, 1H), 7.79 (s, 1H), 7.63 (s, 1H), 7.40 (s, 1H), 7.22 (s, 2H), 7.19-7.15 (m, 2H), 6.97-6.92 (m, 2H), 5.23 (s, 2H), 2.05 (s, 3H), 1.83 (s, 6H), 1.72 (s, 6H). LC-MS: m/z 350.2 (M + H)⁺ |

-continued

| CP | Compound No | Reactant | Structure | Analytical data |
|---|---|---|---|---|
| 214 | 122 | VI.29 | 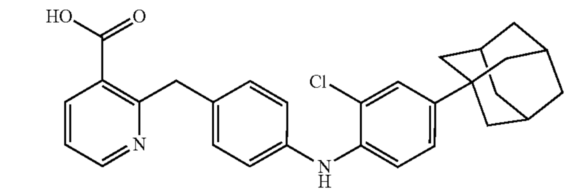 [SMILES: O=C(O)c1cccnc1Cc1ccc(Nc2ccc(C34CC5CC(CC(C5)C3)C4)cc2Cl)cc1] | ¹H NMR (400 MHz, DMSO-d6) δ 13.45 (bs, 1H), 8.59 (d, J = 3.6 Hz, 1H), 8.09 (d, J = 6.8 Hz, 1H), 7.36-7.30 (m, 3H), 7.16-7.11 (m, 2H), 7.07 (d, J = 8.4 Hz, 2H), 6.90 (d, J = 7.6 Hz, 2H), 4.39 (s, 2H), 2.03 (s, 3H), 1.81 (s, 6H), 1.71 (s, 6H). LC-MS: m/z 473.2 (M + H)⁺ |
| 215 | 123 | XV.9 | 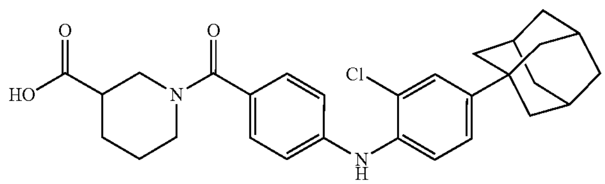 [SMILES: O=C(O)C1CCCN(C(=O)c2ccc(Nc3ccc(C45CC6CC(CC(C6)C4)C5)cc3Cl)cc2)C1] | ¹H NMR (400 MHz, DMSO-d6) δ 12.39 (s, 1H), 7.94 (s, 1H), 7.39 (d, J = 2.0 Hz, 1H), 7.33-7.24 (m, 4H), 6.92 (d, J = 8.8 Hz, 2H), 4.20-3.99 (m, 1H), 3.98-3.62 (m, 1H), 3.10-2.92 (m, 2H), 2.45-2.37 (m, 1H), 2.06 (s, 3H), 2.01-1.97 (m, 1H), 1.85 (s, 6H), 1.73 (s, 6H), 1.69-1.55 (m, 2H), 1.44-1.39 (m, 1H). LC-MS: m/z 493.2 (M + H)⁺ |
| 217 | 124 | VI.30 | 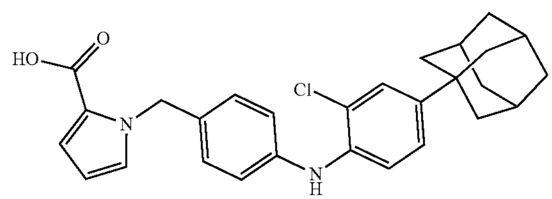 [SMILES: O=C(O)c1cccn1Cc1ccc(Nc2ccc(C34CC5CC(CC(C5)C3)C4)cc2Cl)cc1] | ¹H NMR (400 MHz, DMSO-d6) δ 12.15 (bs, 1H), 7.52 (s, 1H), 7.32 (s, 1H), 7.18 (s, 3H), 7.02 (d, J = 8.8 Hz, 2H), 6.93 (d, J = 8.4 Hz, 2H), 6.84-6.82 (m, 1H), 6.12-6.10 (m, 1H), 5.44 (s, 2H), 2.04 (s, 3H), 1.82 (s, 6H), 1.72 (s, 6H). LC-MS: m/z 461.2 (M + H)⁺ |
| 218 | 125 | VI.31 | 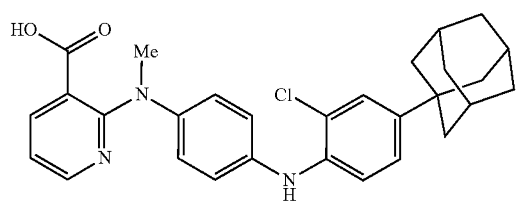 [SMILES: CN(c1ccc(Nc2ccc(C34CC5CC(CC(C5)C3)C4)cc2Cl)cc1)c1ncccc1C(=O)O] | ¹H NMR (400 MHz, DMSO-d6) δ 12.41 (s, 1H), 8.33 (dd, J₁ = 2.0 Hz, J₂ = 4.8 Hz, 1H), 7.75 (dd, J₁ = 2.0 Hz, J₂ = 7.2 Hz, 1H), 7.42 (s, 1H), 7.31 (s, 1H), 7.17 (s, 2H), 6.94 (d, J = 8.8 Hz, 2H), 6.89-6.86 (m, 3H), 3.32 (s, 3H), 2.04 (s, 3H), 1.82 (s, 6H), 1.72 (s, 6H). LC-MS: m/z 488.1 (M + H)⁺ |
| 219 | 126 | VI.32 | 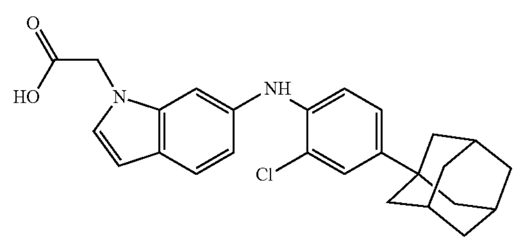 [SMILES: O=C(O)Cn1ccc2ccc(Nc3ccc(C45CC6CC(CC(C6)C4)C5)cc3Cl)cc21] | ¹H NMR (400 MHz, DMSO-d6) δ 12.89 (s, 1H), 7.43 (d, J = 8.4 Hz, 1H), 7.28 (s, 2H), 7.20 (d, J = 3.2 Hz, 1H), 7.09 (S, 3H), 6.86 (dd, J₁ = 1.6 Hz, J₂ = 8.4 Hz, 1H), 6.36 (d, J = 2.8 Hz, 1H), 4.9 (s, 2H), 2.04 (s, 3H), 1.81 (s, 6H), 1.71 (s, 6H). LC-MS: m/z 435.2 (M + H)⁺ |
| 220 | 127 | VI.33 | 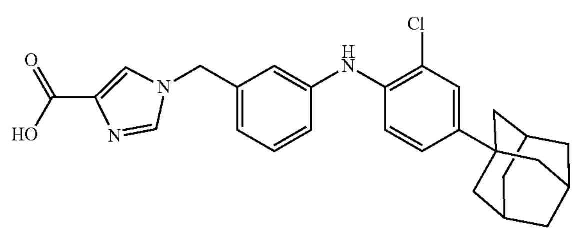 [SMILES: O=C(O)c1cn(Cc2cccc(Nc3ccc(C45CC6CC(CC(C6)C4)C5)cc3Cl)c2)cn1] | ¹H NMR (400 MHz, DMSO-d6) δ 12.00 (bs, 1H), 7.82 (d, J = 6.4 Hz, 2H), 7.67 (s, 1H), 7.34 (s, 1H), 7.21-7.17 (m, 3H), 6.89 (d, J = 5.6 Hz, 2H), 6.74 (d, J = 7.6 Hz, 1H), 5.16 (s, 2H), 2.05 (s, 3H), 1.84 (s, 6H), 1.73 (s, 6H). LC-MS: m/z 462.3 (M + H)⁺ |

-continued

| CP | Compound No | Reactant | Structure | Analytical data |
|---|---|---|---|---|
| 221 | 128 | VI.34 | 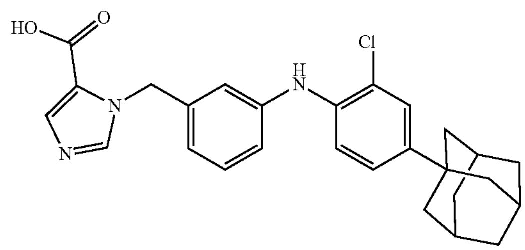 [SMILES: O=C(O)c1cncn1Cc1cccc(Nc2ccc(C34CC5CC(CC(C5)C3)C4)cc2Cl)c1] | ¹H NMR (400 MHz, DMSO-d6) δ 12.75 (bs, 1H), 8.03 (s, 1H), 7.62 (d, J = 2.8 Hz, 2H), 7.33 (d, J = 1.2 Hz, 1H), 7.19-7.15 (m, 3H), 6.88-6.86 (m, 1H), 6.78 (s, 1H), 6.61-6.56 (m, 1H), 5.46 (s, 2H), 2.05 (s, 3H), 1.84 (s, 6H), 1.73 (s, 6H). LC-MS: m/z 462.2 (M + H)⁺ |
| 226 | 129 | XII.25 | 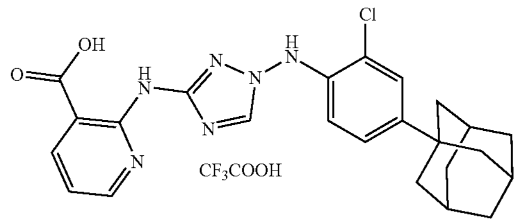 [SMILES: O=C(O)c1cccnc1Nc1ncn(Nc2ccc(C34CC5CC(CC(C5)C3)C4)cc2Cl)n1 ; "CF3COOH"] | ¹H NMR (400 MHz, DMSO-d6) δ 12.5 (bs, 1H), 8.38 (s, 1H), 8.18 (d, J = 7.6 Hz, 1H), 8.11 (d, J = 3.6 Hz, 1H), 7.41 (d, J = 2.0 Hz, 1H), 7.34 (dd, J₁ = 1.6 Hz, J₂ = 7.6 Hz, 1H), 7.10 (d, J = 8.0 Hz, 1H), 6.74 (dd, J₁ = 4.8 Hz, J₂ = 7.2 Hz, 1H), 5.38 (s, 2H), 2.04 (s, 3H), 1.84 (d, J = 2.4 Hz, 6H), 1.69 (s, 6H). LC-MS: m/z 464.2 (M + H)⁺ |
| 227 | 130 | VI.35 | 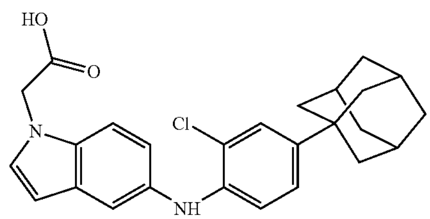 [SMILES: O=C(O)Cn1ccc2cc(Nc3ccc(C45CC6CC(CC(C6)C4)C5)cc3Cl)ccc21] | ¹H NMR (400 MHz, DMSO-d6) δ 12.9 (s, 1H), 7.32-7.26 (m, 3H), 7.09-7.07 (m, 2H), 6.95 (dd, J₁ = 2.0 Hz, J₂ = 8.4 Hz, 1H), 6.93 (d, J = 7.2 Hz, 1H), 6.35 (d, J = 2.4 Hz, 1H), 4.97 (s, 2H), 2.03 (s, 3H), 1.80 (s, 6H), 1.71 (s, 6H). LC-MS: m/z 435.2 (M + H)⁺ |
| 228 | 131 | XII.26 | 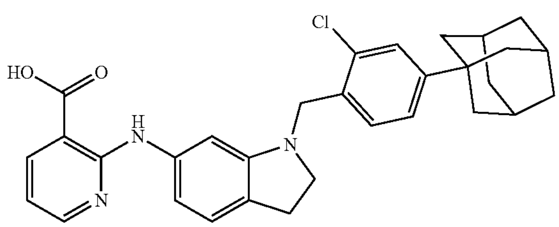 [SMILES: O=C(O)c1cccnc1Nc1ccc2c(c1)N(Cc1ccc(C34CC5CC(CC(C5)C3)C4)cc1Cl)CC2] | ¹H NMR (400 MHz, DMSO-d6) δ 13.4 (bs, 1H), 10.2 (s, 1H), 8.40-8.30 (m, 2H), 7.40-7.39 (m, 2H), 7.38-7.30 (m, 1H), 699-6.90 (m, 2H), 6.90-6.80 (m, 1H), 6.80-6.70 (m, 1H), 4.30 (s, 2H), 3.36 (m, 2H), 2.9 (m, 2H), 2.05 (s, 3H), 1.85 (d, J = 2.4 Hz, 6H), 1.73 (s, 6H). LC-MS: m/z 514.2 (M + H) |
| 233 | 132 | XX.2 | 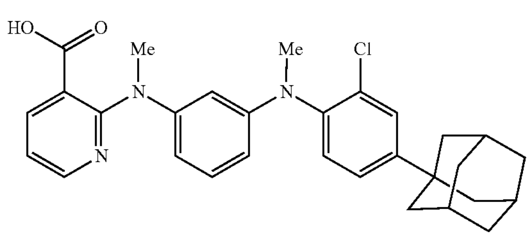 [SMILES: CN(c1cccc(N(C)c2ncccc2C(=O)O)c1)c1ccc(C23CC4CC(CC(C4)C2)C3)cc1Cl] | ¹H NMR (400 MHz, DMSO-d6) δ 12.53 (bs, 1H), 8.35 (dd, J₁ = 1.9 Hz, J₂ = 4.4 Hz, 1H), 7.83 (dd, J₁ = 2.0 Hz, J₂ = 7.8 Hz, 1H), 7.43 (d, J = 2.4 Hz, 1H), 7.34 (dd, J₁ = 1.9 Hz, J₂ = 8.8 Hz, 1H), 7.23 (d, J = 8.4 Hz, 1H), 7.0-6.92 (m, 2H), 6.3 (dd, J₁ = 1.9 Hz, J₂ = 8.3 Hz, 1H), 6.1 (dd, J₁ = 1.9 Hz, J₂ = 8.3 Hz, 1H), 6.04 (d, J = 2.5 Hz, 1H), 3.34 (s, 3H), 3.07 (s, 3H), 2.06 (s, 3H), 1.86 (s, 6H), 1.74 (s, 6H). LC-MS: m/z 502.3 (M + H)⁺ |

-continued

| CP | Compound No | Reactant | Structure | Analytical data |
|---|---|---|---|---|
| 236 | 133 | XX.3 | 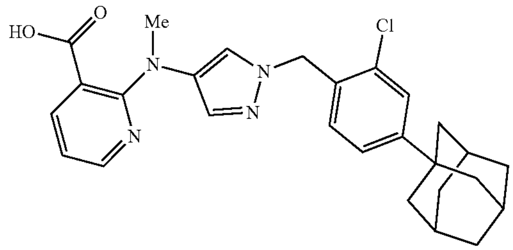 [SMILES: CN(c1cnn(Cc2ccc(C34CC5CC(CC(C5)C3)C4)cc2Cl)c1)c1ncccc1C(=O)O] | $^1$H NMR (400 MHz, DMSO-d6) δ 12.60 (bs, 1H), 8.30 (dd, J$_1$ = 2.0 Hz, J$_2$ = 4.9 Hz, 1H), 7.82 (dd, J$_1$ = 1.5 Hz, J$_2$ = 7.4 Hz, 1H), 7.71 (s, 1H), 7.38 (d, J = 2.9 Hz, 2H), 7.32 (dd, J$_1$ = 1.9 Hz, J$_2$ = 8.3 Hz, 1H), 6.88 (m, 2H), 5.27 (s, 2H), 3.25 (s, 2H), 2.08 (s, 3H), 1.83 (s, 6H), 1.72 (s, 6H). LC-MS: m/z 477.2 (M + H)$^+$ |
| 240 | 134 | XII.27 | 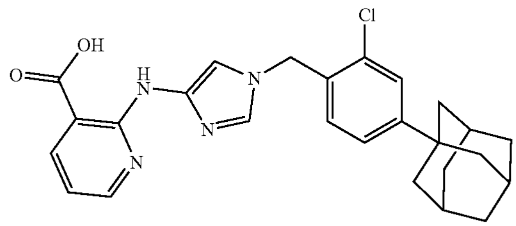 [SMILES: O=C(O)c1cccnc1Nc1cn(Cc2ccc(C34CC5CC(CC(C5)C3)C4)cc2Cl)cn1] | $^1$H NMR (400 MHz, DMSO-d6) δ 13.82-13.2 (bs, 1H), 10.44 (s, 1H), 8.37 (dd, J$_1$ = 1.6 Hz, J$_2$ = 4.4 Hz, 1H), 8.19 (dd, J$_1$ = 1.6 Hz, J$_2$ = 7.6 Hz, 1H), 7.60 (d, J = 1.6 Hz, 1H), 7.42 (dd, J$_1$ = 1.6 Hz, J$_2$ = 8.0 Hz, 2H), 7.34 (dd, J$_1$ = 2.0 Hz, J$_2$ = 8.4 Hz, 1H), 7.11 (d, J = 8.4 Hz, 1H), 6.78 (dd, J$_1$ = 4.8 Hz, J$_2$ = 8.0 Hz, 1H), 5.26 (s, 2H), 2.04 (s, 3H), 1.82 (d, J = 6.8 Hz, 6H), 1.71 (s, 6H). LC-MS: m/z 463.2 (M + H)$^+$ |
| 241 | 135 | VI.38 | 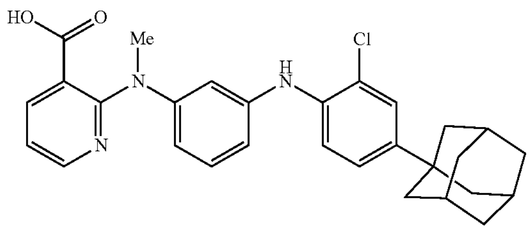 | $^1$H NMR (400 MHz, DMSO-d6) δ 12.61 (s, 1H), 8.39 (dd, J$_1$ = 2.0 Hz, J$_2$ = 4.8 Hz, 1H), 7.89 (dd, J$_1$ = 2.0 Hz, J$_2$ = 7.6 Hz, 1H), 7.46 (s, 1H), 7.29 (dd, J$_1$ = 2.0 Hz, J$_2$ = 8.4 Hz, 2H), 7.16 (dd, J$_1$ = 2.0 Hz, J$_2$ = 8.4 Hz, 1H), 7.07-6.98 (m, 2H), 6.61 (t, J = 8.4 Hz, 2H), 6.41 (t, J = 1.6 Hz, 1H), 3.36 (s, 3H), 2.04 (s, 3H), 1.82 (s, 6H), 1.72 (s, 6H). LC-MS: m/z 488.1 (M + H)$^+$ |
| 243 | 136 | VI.39 | 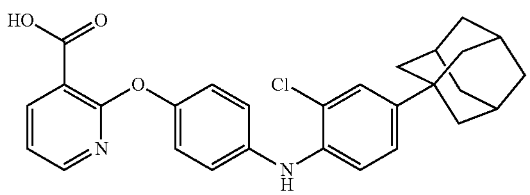 [SMILES: O=C(O)c1cccnc1Oc1ccc(Nc2ccc(C34CC5CC(CC(C5)C3)C4)cc2Cl)cc1] | $^1$H NMR (400 MHz, DMSO-d6) δ 13.2 (bs, 1H), 8.23 (s, 1H), 8.13 (d, J = 6.9 Hz, 1H), 7.52 (s, 1H), 7.33 (s, 1H), 7.19 (m, 3H), 7.04 (d, J = 8.8 Hz, 2H), 6.98 (d, J = 8.8 Hz, 2H), 2.04 (s, 3H), 1.83 (s, 6H), 1.72 (s, 6H). LC-MS: m/z 475.1 |
| 244 | 137 | XIII.10 | 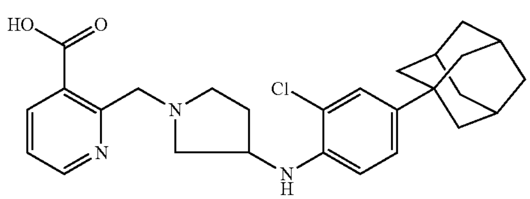 [SMILES: O=C(O)c1cccnc1CN1CCC(Nc2ccc(C34CC5CC(CC(C5)C3)C4)cc2Cl)C1] | $^1$H NMR (400 MHz, DMSO-d6) δ 8.59 (dd, J$_1$ = 1.6 Hz, J$_2$ = 4.4 Hz, 1H), 8.22 (dd, J$_1$ = 2.0 Hz, J$_2$ = 8.0 Hz, 1H), 7.49 (dd, J$_1$ = 4.8 Hz, J$_2$ = 8.0 Hz, 1H), 7.20 (d, J = 2.0 Hz, 1H), 7.12 (dd, J$_1$ = 2.4 Hz, J$_2$ = 8.8 Hz, 1H), 6.69 (d, J = 8.8 Hz, 1H), 5.26 (d, J = 7.2 Hz, 1H), 4.45 (s, 2H), 4.24-4.20 (m, 1H), 3.36-3.20 (m 2H), 3.10-3.02 (m, 2H), 2.36-2.32 (m, 1H), 2.02 (s, 3H), 1.78 (s, 6H), 1.67 (s, 6H). LC-MS: m/z 466.20 |

| CP | Compound No | Reactant | Structure | Analytical data |
|---|---|---|---|---|
| 245 | 138 | VI.40 | 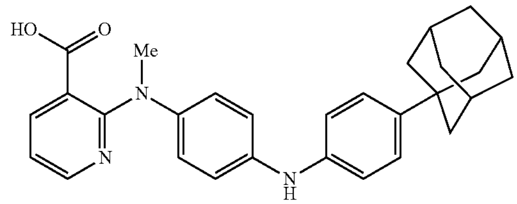 [SMILES: CN(c1ccc(Nc2ccc(C34CC5CC(CC(C5)C3)C4)cc2)cc1)c1ncccc1C(=O)O] | ¹H NMR (400 MHz, DMSO-d6) δ 12.8-12.0 (bs, 1H), 8.2 (s, 1H), 7.87 (s, 1H), 7.67 (d, J = 5.6 Hz, 1H), 7.17 (d, J = 8.8 Hz, 2H), 6.95-6.89 (m, 4H), 6.85-6.82 (m, 3H), 3.3 (s, 3H), 2.03 (s, 3H), 1.82 (s, 6H), 1.71 (s, 6H). LC-MS: m/z 454.1 (M + H)⁺ |
| 246 | 139 | XX.4 | 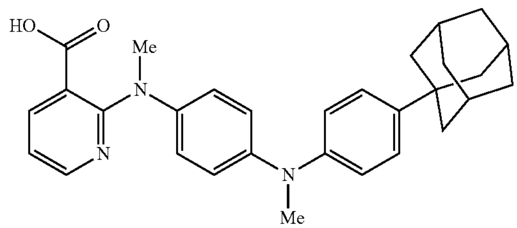 | ¹H NMR (400 MHz, DMSO-d6) δ 12.49 (s, 1H), 8.34 (s, 1H), 7.77-7.76 (m, 1H), 7.24-7.22 (m, 2H), 6.93-6.87 (m, 7H), 3.19 (s, 3H), 2.04 (s, 3H), 1.83 (s, 6H), 1.72 (s, 6H). LC-MS: m/z 468.1 (M + H)⁺ |
| 247 | 140 | XX.5 | 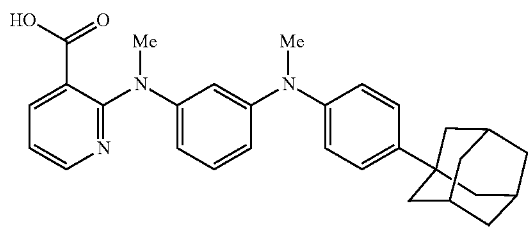 [SMILES: CN(c1ccc(C23CC4CC(CC(C4)C2)C3)cc1)c1cccc(N(C)c2ncccc2C(=O)O)c1] | ¹H NMR (400 MHz, DMSO-d6) δ 12.57 (s, 1H), 8.36 (dd, J₁ = 2.0 Hz, J₂ = 4.9 Hz, 1H), 7.86 (dd, J₁ = 1.4 Hz, J₂ = 7.3 Hz, 1H), 7.23 (d, J = 8.3 Hz, 2H), 7.09 (d, J = 8.4 Hz, 1H), 6.95 (m, 3H), 6.5 (m, 2H), 6.39 (t, J = 2.4 Hz, 1H), 3.35 (s, 3H), 3.16 (s, 3H), 2.04 (bs, 3H), 1.82 (s, 6H), 1.69 (s, 6H). LC-MS: m/z 468.1 (M + H)⁺ |
| 248 | 141 | XIII.11 | 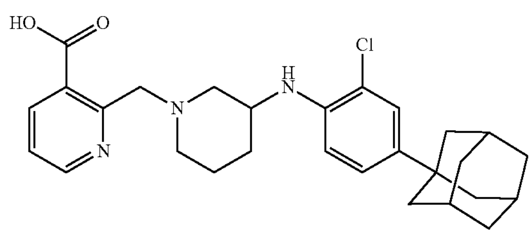 [SMILES: O=C(O)c1cccnc1CN1CCCC(Nc2ccc(C34CC5CC(CC(C5)C3)C4)cc2Cl)C1] | ¹H NMR (400 MHz, DMSO-d6) δ 10.80-12.80 (bs, 1H), 8.54 (d, J = 3.4 Hz, 1H), 8.14 (d, J = 6.8 Hz, 1H), 7.42 (m, 1H), 7.16 (d, J = 2.4 Hz, 1H), 7.09 (dd, J1 = 1.9 Hz, J2 = 8.3 Hz, 1H), 6.67 (d, J = 8.8 Hz, 1H), 4.87 (d, J = 8.0 Hz, 1H), 4.16 (m, 2H), 3.57 (bs, 1H), 2.98 (d, J = 9.2 Hz, 1H), 2.7 (m, 1H), 2.57 (m, 3H), 2.08 (s, 3H), 1.82-1.77 (m, 9H), 1.73 (m, 7H), 1.58-1.49 (m, 3H). LC-MS: m/z 480.1 (M + H)⁺ |
| 249 | 142 | XII.28 | 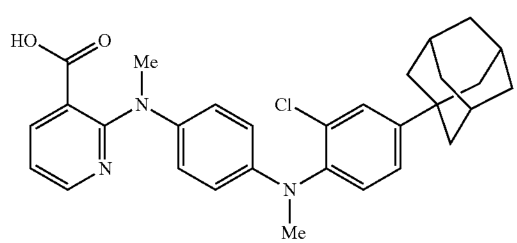 [SMILES: CN(c1ccc(N(C)c2ncccc2C(=O)O)cc1)c1ccc(C23CC4CC(CC(C4)C2)C3)cc1Cl] | ¹H NMR (400 MHz, DMSO-d6) δ 13.4 (bs, 1H), 10.6 (bs, 1H), 8.22-8.21 (m, 1H), 8.16 (dd, J₁ = 1.6 Hz, J₂ = 7.2 Hz, 1H), 7.47-7.38 (m, 4H), 7.27 (d, J = 8.4 Hz, 1H), 6.72 (dd, J₁ = 4.4 Hz, J₂ = 7.6 Hz, 1H), 6.52 (d, J = 8.8 Hz, 2H), 3.17 (s, 3H), 2.07 (s, 3H), 1.89 (s, 6H), 1.74 (s, 6H). LC-MS: m/z 487.2 (M + H)⁺ |

-continued

| CP | Compound No | Reactant | Structure | Analytical data |
|---|---|---|---|---|
| 250 | 143 | VI.42 | 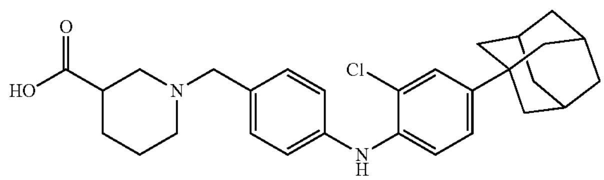 | $^1$H NMR (400 MHz, DMSO-d6) δ 12.80 (s, 1H), 9.80 (s, 1H), 7.88 (s, 1H), 7.39 (d, J = 1.4 Hz, 1H), 7.33-7.27 (m, 4H), 6.98 (d, J = 8.3 Hz, 2H), 4.20-4.17 (bs, 2H), 3.49-3.42 (m, 1H), 2.85-2.70 (m, 3H), 2.06 (s, 3H), 1.91-1.85 (m, 7H), 1.84-1.72 (m, 8H), 1.57-1.40 (m, 1H). LC-MS: m/z 479.1 (M + H)$^{+2}$ |
| 252 | 144 | VI.43 | 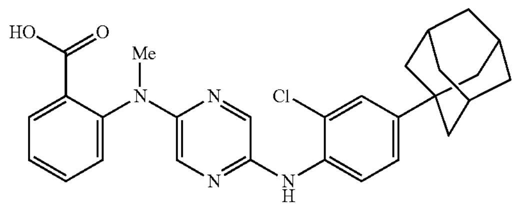 | $^1$H NMR (400 MHz, DMSO-d6) δ 12.72 (s, 1H), 7.99 (s, 1H), 7.96 (d, J = 1.6 Hz, 1H), 7.80 (dd, J$_1$ = 1.6 Hz, J$_2$ = 7.6 Hz, 1H), 7.68-7.61 (m, 2H), 7.42-7.35 (m, 3H), 7.29 (d, J = 2.0 Hz, 1H), 7.17 (dd, J$_1$ = 2.4 Hz, J$_2$ = 8.8 Hz, 1H), 3.30 (s, 3H), 2.08 (s, 3H), 1.82 (s, 6H), 1.71 (s, 6H). LC-MS: m/z 487.1 (M − H)$^+$ |
| 254 | 145 | XV.11 | 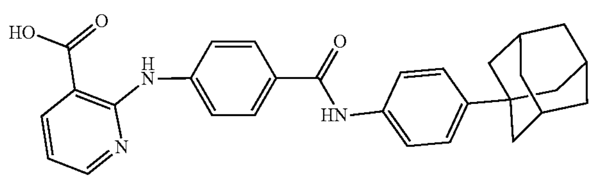 | $^1$H NMR (400 MHz, DMSO-d6) δ 13.72 (bs, 1H), 10.74 (bs, 1H), 10.02 (s, 1H), 8.46 (dd, J$_1$ = 1.9 Hz, J$_2$ = 5.0 Hz, 1H), 8.30 (dd, J$_1$ = 2.0 Hz, J$_2$ = 7.8 Hz, 1H), 7.95 (d, J = 8.8 Hz, 2H), 7.88 (d, J = 8.8 Hz, 2H), 7.69 (d, J = 8.8 Hz, 2H), 7.32 (d, J = 8.8 Hz, 2H), 6.96 (m, 1H), 2.06 (s, 3H), 1.87 (s, 6H), 1.74 (s, 6H). LC-MS: m/z 468.1 (M + H)$^+$ |
| 255 | 146 | XV.12 | 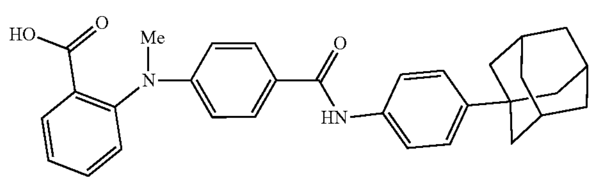 | $^1$H NMR (400 MHz, DMSO-d6) δ 13.00-12.8 (bs, 1H), 9.77 (s, 1H), 7.85 (d, J = 6.4 Hz, 1H), 7.77 (d, J = 8.8 Hz, 2H), 7.66-7.64 (m, 3H), 7.50-7.42 (m, 1H), 7.36 (d, J = 8.0 Hz, 1H), 7.28 (d, J = 8.8 Hz, 2H), 6.52 (d, J = 8.8 Hz, 2H), 3.26 (s, 3H), 2.05 (s, 3H), 1.85 (s, 6H), 1.73 (s, 6H). LC-MS: m/z 481.1 (M + H)$^+$ |
| 258 | 147 | XV.13 | 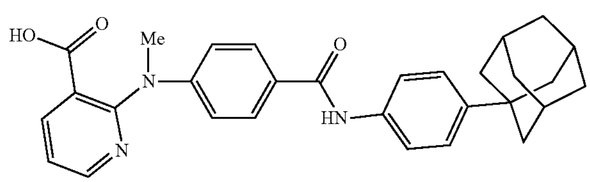 | $^1$H NMR (400 MHz, DMSO-d6) δ 9.87 (s, 1H), 8.43 (bs, 1H), 7.95 (d, J = 6.9 Hz, 1H), 7.80 (d, J = 8.8 Hz, 2H), 7.67 (d, J = 8.8 Hz, 2H), 7.29 (d, J = 8.3 Hz, 2H), 7.19 (m, 1H), 6.82 (d, J = 8.3 Hz, 2H), 3.38 (s, 3H), 2.05 (s, 3H), 1.86 (s, 6H), 1.73 (s, 6H). LC-MS: m/z 482.25 (M + H)$^+$ |

-continued

| CP | Compound No | Reactant | Structure | Analytical data |
|---|---|---|---|---|
| 259 | 148 | XV.14 | 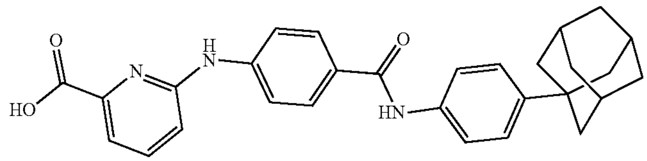 [SMILES: O=C(Nc1ccc(C23CC4CC(CC(C4)C2)C3)cc1)c1ccc(Nc2cccc(C(=O)O)n2)cc1] | ¹H NMR (400 MHz, DMSO-d6) δ 13.00 (bs, 1H), 9.93 (s, 1H), 9.71 (s, 1H), 8.03 (d, J = 8.8 Hz, 2H), 7.94 (d, J = 8.8 Hz, 2H), 7.79 (m, 1H), 7.70 (d, J = 8.8 Hz, 2H), 7.51 (d, J = 7.3 Hz, 1H), 7.31 (d, J = 8.8 Hz, 2H), 7.12 (d, J = 8.3 Hz, 1H), 2.06 (s, 3H), 1.83 (s, 6H), 1.74 (s, 6H). LC-MS: m/z 468.20 (M + H)⁺ |
| 260 | 149 | XX.6 | 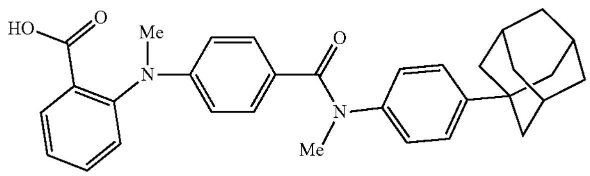 | ¹H NMR (400 MHz, DMSO-d6) δ 12.00-11.8 (bs, 1H), 7.65 (d, J = 8.0 Hz, 2H), 7.5 (d, J = 8.4 Hz, 1H), 7.4-7.35 (m, 1H), 7.32-7.2 (m, 1H), 7.25-7.15 (m, 3H), 6.86 (d, J = 8.4 Hz, 2H), 6.42 (bs, 2H), 3.16 (s, 3H), 3.07 (s, 3H), 2.02 (s, 3H), 1.78 (s, 6H), 1.72 (s, 6H). LC-MS: m/z 495.2 (M + H)⁺ |
| 261 | 150 | XII.29 | 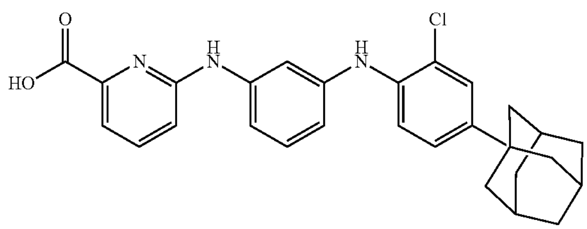 | ¹H NMR (400 MHz, DMSO-d6) δ 10.4 (bs, 1H), 7.62 (t, J = 8.0 Hz, 1H), 7.54 (s, 1H), 7.34-7.31 (m, 3H), 7.24 (dd, J₁ = 1.2 Hz, J₂ = 8.4 Hz, 1H), 7.17-7.09 (m, 2H), 7.04 (s, 1H), 6.97 (d, J = 7.2 Hz, 1H), 6.63 (d, J = 8.4 Hz, 1H), 2.05 (s, 3H), 1.84 (s, 6H), 1.73 (s, 6H). LC-MS: m/z 474.1 (M + H)⁺ |
| 263 | 151 | XII.31 | 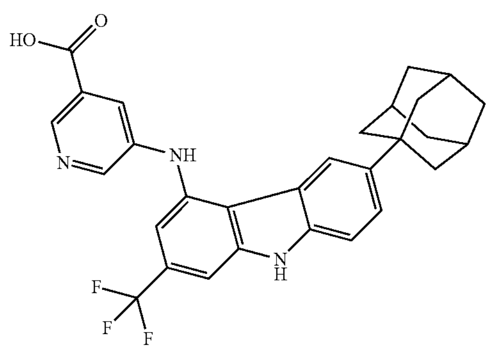 [SMILES: O=C(O)c1cncc(Nc2cc(C(F)(F)F)cc3[nH]c4ccc(C56CC7CC(CC(C7)C5)C6)cc4c23)c1] | ¹H NMR (400 MHz, DMSO-d6) δ 13.2 (bs, 1H), 11.67 (s, 1H), 9.07 (s, 1H), 8.52 (d, J = 2.0 Hz, 1H), 8.28 (d, J = 2.4 Hz, 1H), 7.60 (s, 1H), 7.51-7.45 (m, 3H), 7.34 (s, 1H), 7.22 (s, 1H), 1.91 (s, 2H), 1.72-1.64 (m, 13H). LC-MS: m/z 506.0 (M + H)⁺ |
| 266 | 152 | XX.7 | 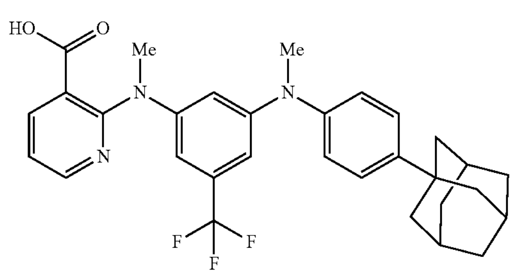 [SMILES: CN(c1ccc(C23CC4CC(CC(C4)C2)C3)cc1)c1cc(N(C)c2ncccc2C(=O)O)cc(C(F)(F)F)c1] | ¹H NMR (400 MHz, DMSO-d6) δ 12.8 (bs, 1H), 8.43 (dd, J₁ = 2.0 Hz, J₂ = 4.4 Hz, 1H), 7.96 (dd, J₁ = 2.0 Hz, J₂ = 7.6 Hz, 1H), 7.30 (d, J = 8.8 Hz, 2H), 7.08-7.04 (m, 3H), 6.59-6.58 (m, 2H), 6.37 (s, 1H), 3.37 (s, 3H), 3.2 (s, 3H), 2.06 (s, 3H), 1.83 (d, J = 2.4 Hz, 6H), 1.73 (s, 6H). LC-MS: m/z 536.1 (M + H)⁺ |

-continued

| CP | Compound No | Reactant | Structure | Analytical data |
|---|---|---|---|---|
| 267 | 153 | XII.32 | 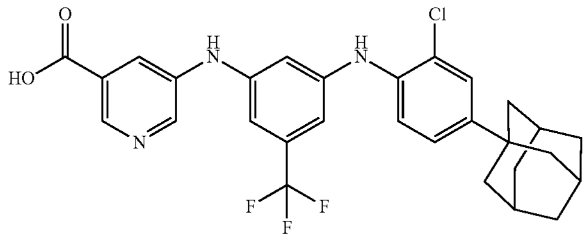 [SMILES: O=C(O)c1cncc(Nc2cc(Nc3ccc(C45CC6CC(CC(C6)C4)C5)cc3Cl)cc(C(F)(F)F)c2)c1] | $^1$H NMR (400 MHz, DMSO-d6) δ 13.4 (bs, 1H), 8.83 (s, 1H), 8.54 (dd, $J_1$ = 0.8 Hz, $J_2$ = 12.0 Hz, 2H), 8.14 (s, 1H), 7.91 (s, 1H), 7.41 (d, J = 2.0 Hz, 1H), 7.35-7.28 (m, 2H), 6.84 (s, 1H), 6.73 (d, J = 13.6 Hz, 2H), 2.05 (s, 3H), 1.84 (s, 6H), 1.72 (s, 6H). LC-MS: m/z 542.2 (M + H)$^+$ |
| 268 | 154 | XII.24 | 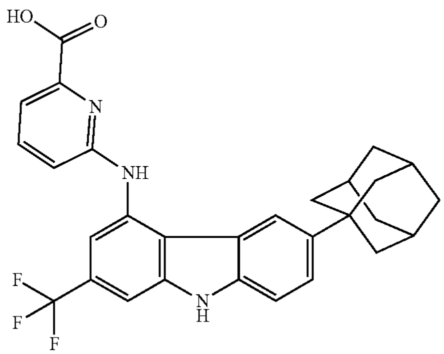 [SMILES: O=C(O)c1cccc(Nc2cc(C(F)(F)F)cc3[nH]c4ccc(C56CC7CC(CC(C7)C5)C6)cc4c23)n1] | $^1$H NMR (400 MHz, DMSO-d6) δ 12.80 (bs, 1H), 11.58 (s, 1H), 9.5 (s, 1H), 7.6 (t, J = 7.2 Hz, 2H), 7.49-7.43 (m, 5H), 6.63 (d, J = 8.4 Hz, 1H), 1.99 (s, 3H), 1.72-1.60 (m, 12H). LC-MS: m/z 506.2 (M + H)$^+$ |
| 270 | 155 | XX.8 | 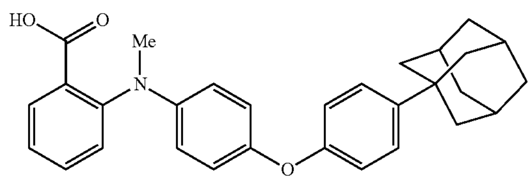 | $^1$H NMR (400 MHz, DMSO-d6) δ 12.8 (bs, 1H), 7.80 (m, 1H), 7.60 (m, 1H), 7.29 (m, 4H), 6.83 (t, J = 9.3 Hz, 4H), 6.57 (d, J = 8.8 Hz, 2H), 3.19 (s, 3H), 2.04 (s, 3H), 1.82 (s, 6H), 1.71 (s, 6H). LC-MS: m/z (M + H)$^+$ LC-MS: m/z 454.1 (M + H)$^+$ |
| 271 | 156 | XX.9 | 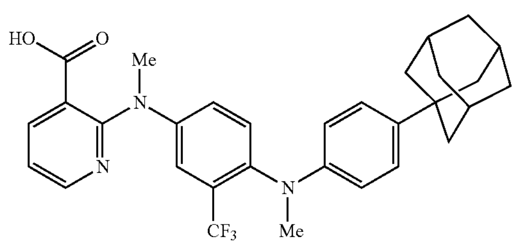 | $^1$H NMR (400 MHz, DMSO-d6) δ 12.91 (s, 1H), 8.52 (dd, $J_1$ = 1.6 Hz, $J_2$ = 4.4 Hz, 1H), 8.03 (dd, $J_1$ = 1.6 Hz, $J_2$ = 7.2 Hz, 1H), 7.21-7.16 (m, 4H), 7.12 (d, J = 8.8 Hz, 2H), 6.44 (d, J = 8.8 Hz, 2H), 3.44 (s, 3H), 3.06 (s, 3H), 2.02 (s, 3H), 1.79 (s, 6H), 1.67 (s, 6H). LC-MS: m/z 536.1 (M + H)$^+$ |
| 272 | 157 | XV.15 | 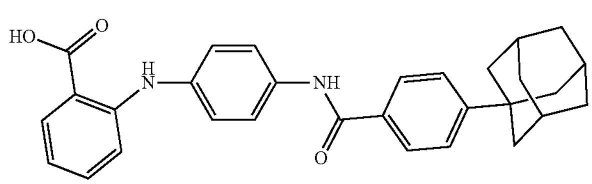 | $^1$H NMR (400 MHz, DMSO-d6) δ 13.00 (bs, 1H), 10.16 (s, 1H), 9.6 (bs, 1H), 7.89 (m, 3H), 7.77 (d, J = 9.3 Hz, 2H), 7.51 (d, J = 8.4 Hz, 2H), 7.38 (m, 1H), 7.23 (d, J = 8.8 Hz, 2H), 7.14 (d, J = 8.8 Hz, 1H), 6.74 (m, 1H), 2.08 (s, 3H), 1.90 (s, 6H), 1.76 (s, 6H). LC-MS: m/z 467.1 (M + H)$^+$ |

-continued

| CP | Compound No | Reactant | Structure | Analytical data |
|---|---|---|---|---|
| 273 | 158 | XX.10 | 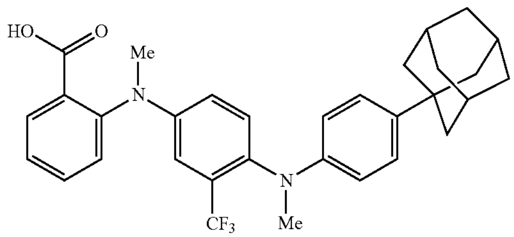 | $^1$H NMR (400 MHz, DMSO-d6) δ 12.9 (bs, 1H), 7.85 (dd, J$_1$ = 1.2 Hz, J$_2$ = 8.8 Hz, 1H), 7.70-7.66 (m, 1H), 7.46-7.39 (m, 2H), 7.10-7.04 (m, 3H), 6.78-6.73 (m, 2H), 6.39 (d, J = 8.8 Hz, 2H), 3.31 (s, 3H), 3.02 (s, 3H), 2.02 (s, 3H), 1.74 (s, 6H), 1.67 (s, 6H). LC-MS: m/z 535.1 (M + H)$^+$ |
| 274 | 159 | XV.16 | 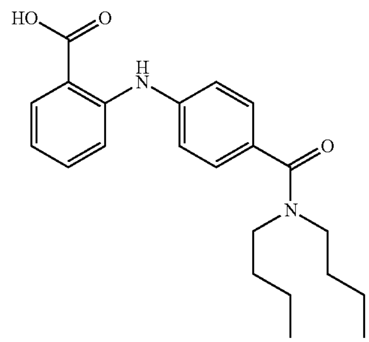 [SMILES: CCCCN(CCCC)C(=O)c1ccc(Nc2ccccc2C(=O)O)cc1] | $^1$H NMR (400 MHz, DMSO-d6) δ 13.15 (s, 1H), 9.71 (s, 1H), 7.94-7.91 (m, 1H), 7.46-7.42 (m, 1H), 7.34-7.25 (m, 5H), 6.85 (t, J = 7.2 Hz, 1H), 1.56-1.48 (m, 5H), 1.33-1.12 (m, 6H), 0.92-0.74 (m, 7H). LC-MS: m/z 369.1 (M + H)$^+$ |
| 275 | 160 | XX.11 | 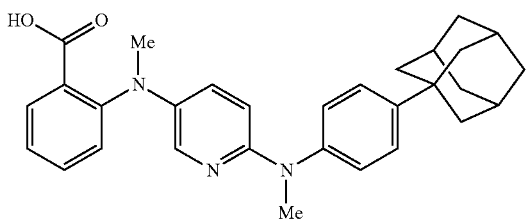 | $^1$H NMR (400 MHz, DMSO-d6) δ 12.72 (s, 1H), 7.68-7.65 (m, 2H), 7.53 (t, J = 8.4 Hz, 1H), 7.30 (d, J = 8.8 Hz, 2H), 7.26-7.19 (m, 2H), 7.09 (d, J = 8.8 Hz, 2H), 6.88 (dd, J$_1$ = 3.2 Hz, J$_2$ = 8.8 Hz, 1H), 6.55 (d, J = 9.6 Hz, 1H), 3.29 (s, 3H), 3.18 (s, 3H), 2.05 (s, 3H), 1.85 (s, 6H), 1.73 (s, 6H). LC-MS: m/z 468.1 (M + H)$^+$ |
| 276 | 161 | XX.12 | 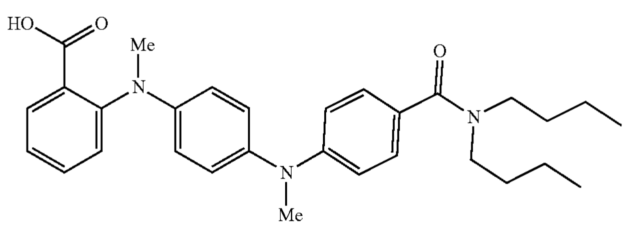 [SMILES: CCCCN(CCCC)C(=O)c1ccc(N(C)c2ccc(N(C)c3ccccc3C(=O)O)cc2)cc1] | $^1$H NMR (400 MHz, DMSO-d6) δ 12.79 (s, 1H), 7.79 (dd, J$_1$ = 1.5 Hz, J$_2$ = 7.3 Hz, 1H), 7.62 (t, J = 1.5 Hz, 1H), 7.35 (m, 2H), 7.14 (d, J = 8.8 Hz, 2H), 6.98 (d, J = 8.8 Hz, 2H), 6.63 (d, J = 8.8 Hz, 2H), 6.57 (d, J = 9.3 Hz, 2H), 3.26 (m, 1H), 3.20 (s, 3H), 3.18 (s, 3H), 1.48 (m, 4H), 1.23 (m, 4H), 0.83 (m, 6H). LC-MS: m/z 488.7 (M + H)$^+$ |
| 277 | 162 | XX.13 | 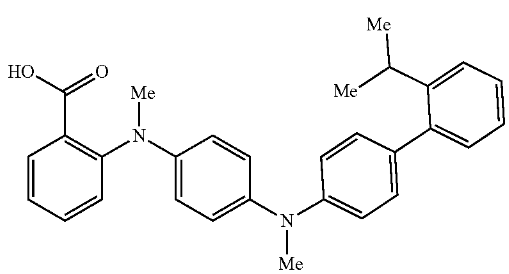 [SMILES: CC(C)c1ccccc1-c1ccc(N(C)c2ccc(N(C)c3ccccc3C(=O)O)cc2)cc1] | $^1$H NMR (400 MHz, DMSO-d6) δ 12.79 (s, 1H), 7.78 (d, J = 7.6 Hz, 1H), 7.60-7.59 (m, 1H), 7.37-7.25 (m, 4H), 7.17-7.14 (m, 1H), 7.08-7.00 (m, 5H), 6.72 (d, J = 8.8 Hz, 2H), 6.59 (d, J = 8.8 Hz, 2H), 3.2 (s, 6H), 3.08-3.04 (m, 1H), 1.1 (d, J = 6.8 Hz, 6H). LC-MS: m/z 451.1 (M + H)$^+$ |

-continued

| CP | Compound No | Reactant | Structure | Analytical data |
|---|---|---|---|---|
| 278 | 163 | | 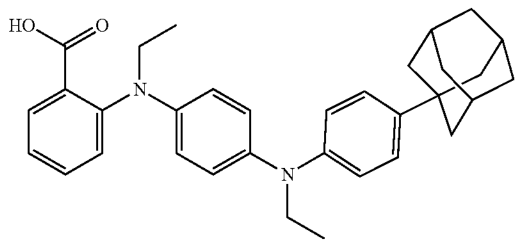 | LC-MS: m/z 495.2 (M + H)+ |
| 279 | 164 | | 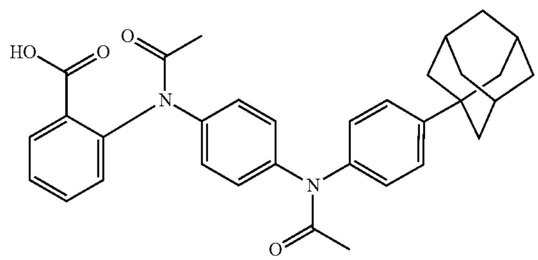 | LC-MS: m/z 523.6 (M + H)+ |
| 282 | 165 | | 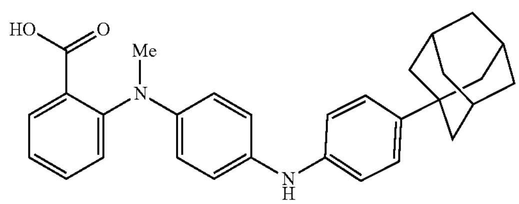 | LC-MS: m/z 453.1 (M + H)+ |
| 284 | 166 | XII.36 | 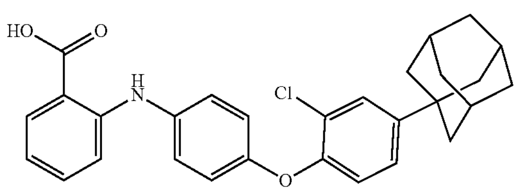 | $^{1}$H NMR (400 MHz, DMSO-d6) δ 11.90 (bs, 1H), 7.88 (d, J = 7.4 Hz, 1H), 7.46 (s, 1H), 7.30 (d, J = 2.4 Hz, 1H), 7.11 (m, 4H), 6.91 (m, 4H), 6.63 (m, 1H), 2.05 (s, 3H), 1.85 (s, 6H), 1.72 (s, 6H). LC-MS: 474.0 (M + H)+ |
| 285 | 167 | XV.17 | 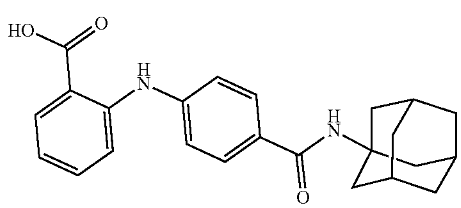 | $^{1}$H NMR (400 MHz, DMSO-d6) δ 13.2 (bs, 1H), 9.90 (bs, 1H), 7.93 (d, J = 8.0 Hz, 1H), 7.77 (d, J = 8.8 Hz, 2H), 7.45-7.43 (m, 2H), 7.36 (d, J = 7.6 Hz, 1H), 7.30 (d, J = 8.8 Hz, 2H), 6.86 (t, J = 7.2 Hz, 1H), 2.07 (s, 9H), 1.66 (s, 6H). LC-MS: m/z 391.0 (M + H)+ |
| 286 | 168 | XX.14 | 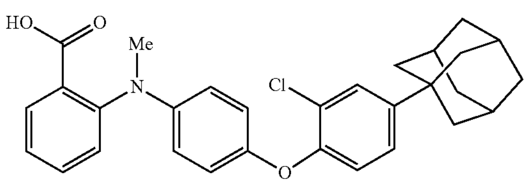 | $^{1}$H NMR (400 MHz, DMSO-d6) δ 12.7 (bs, 1H), 7.75 (dd, J$_1$ = 1.6 Hz, J$_2$ = 8.0 Hz, 1H), 7.61-7.57 (m, 1H), 7.43 (d, J = 2.0 Hz, 1H), 7.43-7.23 (m, 3H), 6.81 (t, J = 9.2 Hz, 3H), 6.57 (d, J = 8.8 Hz, 2H), 3.19 (s, 3H), 2.04 (s, 3H), 1.83 (s, 6H), 1.72 (s, 6H). LC-MS: m/z 488.0 (M + H)+ |

-continued

| CP | Compound No | Reactant | Structure | Analytical data |
|---|---|---|---|---|
| 287 | 169 | VI.46 | (structure) | $^1$H NMR (400 MHz, DMSO-d6) δ 13.60-12.00 (bs, 1H), 9.50 (s, 1H), 8.34 (s, 1H), 7.87 (dd, $J_1$ = 1.2 Hz, $J_2$ = 8.0 Hz, 1H), 7.36-7.03 (m, 10H), 6.70 (t, J = 7.2 Hz, 1H), 4.06-4.02 (m, 2H), 2.88-2.83 (m, 3H), 1.68-1.55 (m, 4H), 1.33-1.10 (m, 5H), 0.89 (t, J = 7.2 Hz, 6H). LC-MS: m/z 444.1 (M + H)$^+$ |
| 288 | 170 | XV.18 | (structure) | $^1$H NMR (400 MHz, DMSO-d6) δ 13.2 (bs, 1H), 11.9 (bs, 1H), 10.38 (bs, 1H), 9.8 (s, 1H), 7.96 (m, 4H), 7.7 (bs, 1H), 7.47 (m, 2H), 7.36 (m, 2H), 6.92 (m, 1H), 6.6 (bs, 1H), 3.44 (m, 4H), 1.53 (m, 4H), 1.27 (m, 4H), 0.84 (m, 6H). LC-MS: m/z 460.1 (M + H)$^+$ |
| 289 | 71 | XII.37 | (structure) | $^1$H NMR (400 MHz, DMSO-d6) δ 12.85 (bs, 1H), 7.77 (dd, $J_1$ = 1.2 Hz, $J_2$ = 8.0 Hz, 1H), 7.61-7.57 (m, 1H), 7.35-7.32 (m, 1H), 7.28 (d, J = 8.0 Hz, 1H), 7.13 (d, J = 8.4 Hz, 2H), 6.88 (d, J = 9.6 Hz, 2H), 6.67 (d, J = 8.8 Hz, 2H), 6.55 (d, J = 6.8 Hz, 2H), 3.66-3.61 (m, 2H), 3.13 (s, 3H), 2.03 (s, 3H), 1.79 (s, 6H), 1.71 (s, 6H), 1.13 (t, J = 7.6 Hz, 3H). LC-MS: m/z 481.1 (M + H)$^+$ |
| 290 | 172 | XII.38 | (structure) | $^1$H NMR (400 MHz, DMSO-d6) δ 12.8 (bs, 1H), 9.48 (s, 1H), 7.87 (dd, $J_1$ = 1.2 Hz, $J_2$ = 7.6 Hz, 1H), 7.35 (t, J = 6.8 Hz, 1H), 7.26 (d, J = 8.8 Hz, 2H), 7.15 (d, J = 8.8 Hz, 2H), 7.05 (d, J = 8.8 Hz, 1H), 6.99-6.94 (m, 4H), 6.70 (t, J = 7.2 Hz, 1H), 3.23 (s, 3H), 2.05 (s, 3H), 1.84 (s, 6H), 1.78 (s, 6H). LC-MS: m/z 453.1 (M + H)$^+$ |
| 291 | 173 | VI.47 | (structure) | $^1$H NMR (400 MHz, DMSO-d6) δ 13.2 (s, 1H), 8.48 (s, 1H), 7.83 (d, J = 7.2 Hz, 1H), 7.70-7.65 (m, 3H), 7.31-7.25 (m, 3H), 7.16-7.13 (m, 4H), 3.84 (s, 3H), 2.06 (s, 3H), 1.86 (s, 6H), 1.74 (s, 6H). LC-MS: m/z 478.1 (M + H)$^+$ |

-continued

| CP | Compound No | Reactant | Structure | Analytical data |
|---|---|---|---|---|
| 292 | 174 | VI.48 | 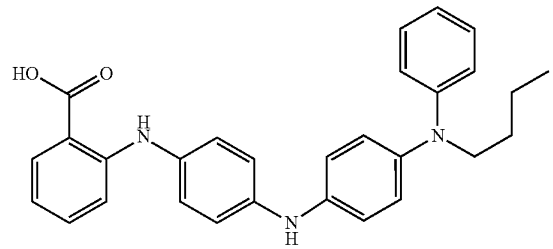 [SMILES: CCCCN(c1ccccc1)c1ccc(Nc2ccc(Nc3ccccc3C(=O)O)cc2)cc1] | $^1$H NMR (400 MHz, DMSO-d6) δ 12.91 (s, 1H), 9.40 (s, 1H), 8.09 (s, 1H), 7.87 (d, J = 1.4 Hz, 1H), 7.33 (t, J = 6.8 Hz, 1H), 7.15-7.08 (m, 8H), 7.01-6.98 (m, 3H), 6.70-6.65 (m, 4H), 3.58 (t, J = 7.8 Hz, 2H), 1.58-1.51 (m, 2H), 1.38-1.28 (m, 2H), 0.88 (t, J = 7.3 Hz, 3H), LC-MS: m/z 452.1 (M + H)$^+$ |
| 293 | 175 | XV.19 | 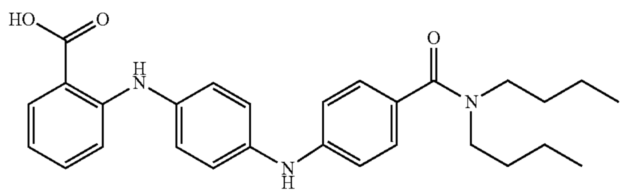 [SMILES: CCCCN(CCCC)C(=O)c1ccc(Nc2ccc(Nc3ccccc3C(=O)O)cc2)cc1] | $^1$H NMR (400 MHz, DMSO-d6) δ 12.99 (bs, 1H), 9.50 (bs, 1H), 8.36 (s, 1H), 7.88 (dd, J$_1$ = 1.4 Hz, J$_2$ = 7.8 Hz, 1H), 7.36 (t, 1H), 7.21-7.13 (m, 6H), 7.06-7.01 (m, 3H), 6.70 (t, J = 7.8 Hz, 1H), 3.30 (m, 4H), 1.52-1.49 (m, 4H), 1.23 (m, 4H), 0.86-0.84 (m, 6H). LC-MS: m/z 460.1 (M + H)$^+$ |
| 294 | 176 | XV.20 | 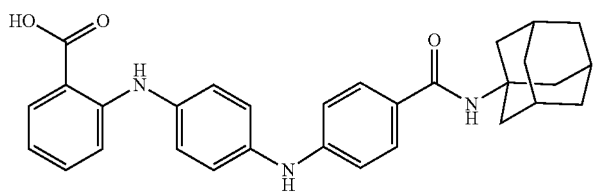 [SMILES: O=C(NC12CC3CC(CC(C3)C1)C2)c1ccc(Nc2ccc(Nc3ccccc3C(=O)O)cc2)cc1] | $^1$H NMR (400 MHz, DMSO-d6) δ 12.95 (s, 1H), 9.5 (s, 1H), 8.45 (s, 1H), 7.88 (dd, J$_1$ = 1.6 Hz, J$_2$ = 8.0 Hz, 1H), 7.67 (d, J = 8.8 Hz, 2H), 7.35 (t, J = 1.6 Hz, 1H), 7.23 (s, 1H), 7.20-7.14 (m, 4H), 7.07 (d, J = 8.4 Hz, 1H), 6.99 (d, J = 8.8 Hz, 2H), 6.73-6.69 (m, 1H), 2.06 (s, 9H), 1.65 (s, 6H). LC-MS: m/z 482.1 (M + H)$^+$ |
| 295 | 177 | VI.49 | 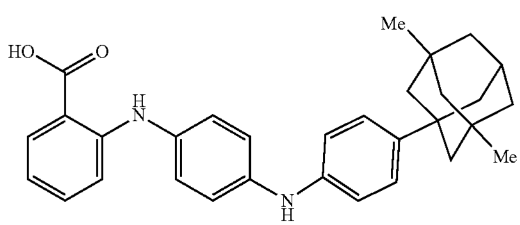 [SMILES: CC12CC3CC(C)(C1)CC(c1ccc(Nc4ccc(Nc5ccccc5C(=O)O)cc4)cc1)(C3)C2] | $^1$H NMR (400 MHz, DMSO-d6) δ 12.83 (bs, 1H), 9.42 (s, 1H), 7.99 (s, 1H), 7.85 (dd, J$_1$ = 1.6 Hz, J$_2$ = 7.6 Hz, 1H), 7.32 (t, J = 8.8 Hz, 1H), 7.20 (d, J = 8.8 Hz, 2H), 7.11-7.04 (m, 4H), 7.01-6.96 (m, 3H), 6.67 (t, J = 7.6 Hz, 1H), 2.13-2.12 (m, 1H), 1.66 (s, 2H), 1.50-1.32 (m, 8H), 1.17 (s, 2H), 0.85 (s, 6H). LC-MS: m/z 467.1 (M + H)$^+$ |
| 296 | 178 | XX.15 | 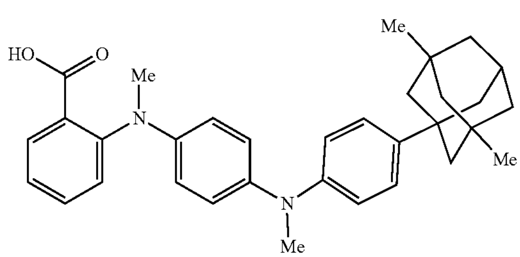 [SMILES: CN(c1ccc(N(C)c2ccccc2C(=O)O)cc1)c1ccc(C23CC4CC(C)(CC(C)(C4)C2)C3)cc1] | $^1$H NMR (400 MHz, DMSO-d6) δ 12.79 (s, 1H), 7.75 (d, J = 8.0 Hz, 1H), 7.58 (t, J = 6.8 Hz, 1H), 7.33-7.29 (m, 2H), 7.11 (d, J = 8.8 Hz, 2H), 6.89 (d, J = 8.8 Hz, 2H), 7.67 (d, J = 8.8 Hz, 2H), 7.01 (d, J = 8.8 Hz, 2H), 3.18 (s, 3H), 3.12 (s, 3H), 2.10 (m, 1H), 1.62 (s, 2H), 1.46-1.30 (m, 8H), 1.16 (s, 2H), 0.83 (s, 6H). LC-MS: m/z 495.1 (M + H)$^+$ |

-continued

| CP | Compound No | Reactant | Structure | Analytical data |
|---|---|---|---|---|
| 297 | 179 | XV.21 | 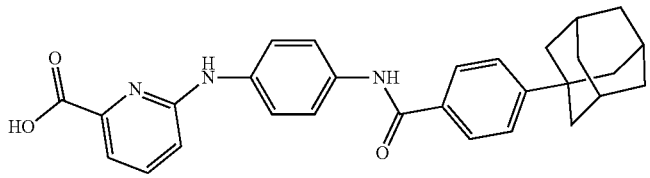 [SMILES: O=C(Nc1ccc(Nc2cccc(C(=O)O)n2)cc1)c1ccc(C23CC4CC(CC(C4)C2)C3)cc1] | ¹H NMR (400 MHz, DMSO-d6) δ 12.84 (bs, 1H), 10.04 (s, 1H), 9.23 (s, 1H), 7.89 (d, J = 8.3 Hz, 2H), 7.78 (d, J = 8.3 Hz, 2H), 7.67 (m, 3H), 7.51 (d, J = 8.3 Hz, 2H), 7.40 (d, J = 6.8 Hz, 1H), 7.01 (d, J = 8.3 Hz, 1H), 2.08 (s, 3H), 1.91 (s, 6H), 1.76 (s, 6H). LC-MS: m/z 468.0 (M + H)⁺ |
| 298 | 180 | XI.17 | 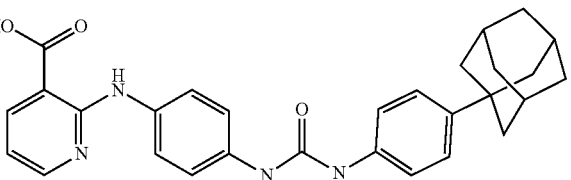 | ¹H NMR (400 MHz, DMSO-d6) δ 13.4 (bs, 1H), 10.27 (s, 1H), 8.51 (d, J = 13.6 Hz, 2H), 8.34 (s, 1H), 8.21 (d, J = 6.8 Hz, 1H), 7.58 (d, J = 7.2 Hz, 2H), 7.40-7.35 (m, 4H), 7.25 (d, J = 7.2 Hz, 2H), 6.81 (bs, 1H), 2.04 (s, 3H), 1.84 (s, 6H), 1.73 (s, 6H). LC-MS: m/z 483.1 (M + H)⁺ |
| 299 | 181 | XIX.3 | 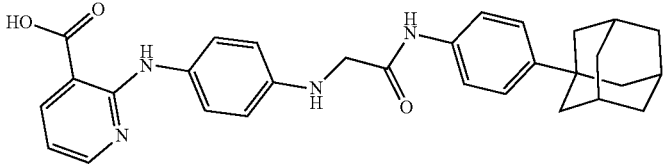 [SMILES: O=C(CNc1ccc(Nc2ncccc2C(=O)O)cc1)Nc1ccc(C23CC4CC(CC(C4)C2)C3)cc1] | ¹H NMR (400 MHz, DMSO-d6) δ 13.80-12.80 (bs, 1H), 10.05 (bs, 1H), 9.86 (s, 1H), 8.25 (d, J = 2.8 Hz, 1H), 8.15 (d, J = 7.2 Hz, 1H), 7.53 (d, J = 8.4 Hz, 2H), 7.34 (d, J = 8.8 Hz, 2H), 7.27 (d, J = 8.0 Hz, 2H), 6.71 (dd, J₁ = 4.8 Hz, J₂ = 8.0 Hz, 1H), 6.58 (d, J = 8.8 Hz, 2H), 5.85 (bs, 1H), 3.82 (bs, 2H), 2.04 (s, 3H), 1.82 (s, 6H), 1.72 (s, 6H). LC-MS: m/z 497.1 (M + H)⁺ |
| 300 | 182 | XIX.1 | 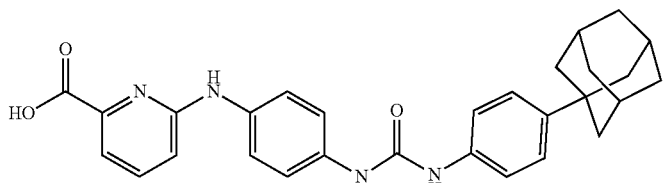 | ¹H NMR (400 MHz, DMSO-d6) δ 13.00 (bs, 1H), 9.13 (s, 1H), 8.50 (s, 1H), 8.43 (s, 1H), 7.68 (m, 3H), 7.37 (m, 5H), 7.25 (d, J = 8.3 Hz, 2H), 6.98 (d, J = 8.3 Hz, 1H), 2.05 (s, 3H), 1.76 (s, 6H), 1.73 (s, 6H). LC-MS: m/z 483.1 (M + H)⁺ |
| 301 | 183 | XV.22 | 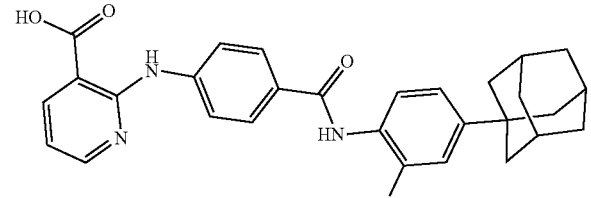 | ¹H NMR (400 MHz, DMSO-d6) δ 9.76 (bs, 1H), 8.32 (bs, 1H), 8.25 (m, 1H), 7.95 (d, J = 8.8 Hz, 2H), 7.89 (d, J = 8.8 Hz, 2H), 7.54 (d, J = 8.3 Hz, 1H), 7.45 (s, 1H), 7.37 (m, 1H), 6.86 (m, 1H), 2.07 (s, 3H), 1.88 (s, 6H), 1.74 (s, 6H). LC-MS: m/z 502.0 (M + H)⁺ |

-continued

| CP | Compound No | Reactant | Structure | Analytical data |
|---|---|---|---|---|
| 302 | 184 | XV.23 | 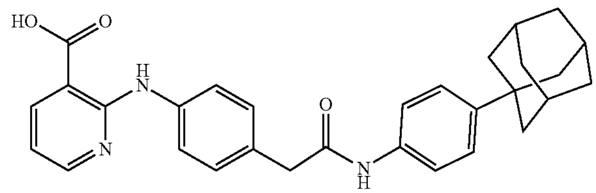 | ¹H NMR (400 MHz, DMSO-d6) δ 14.00-13.00 (bs, 1H), 10.36 (s, 1H), 10.02 (s, 1H), 8.36 (m, 1H), 8.24 (d, J = 7.8 Hz, 1H), 7.65 (d, J = 8.3 Hz, 2H), 7.52 (d, J = 8.8 Hz, 2H), 7.28-7.25 (m, 4H), 6.86-6.83 (m, 1H), 3.56 (s, 2H), 2.03 (s, 3H), 1.82 (s, 6H), 1.71 (s, 6H). LC-MS: m/z 482.1 (M + H)⁺ |
| 303 | 185 | XV.24 | 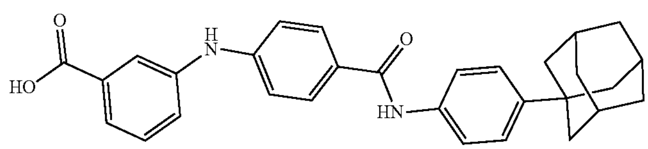 | ¹H NMR (400 MHz, DMSO-d6) δ 12.93 (bs, 1H), 9.91 (s, 1H), 8.81 (s, 1H), 7.88 (d, J = 8.8 Hz, 2H), 7.75 (s, 1H), 7.68 (d, J = 8.8 Hz, 2H), 7.48-7.39 (m, 3H), 7.30 (d, J = 8.8 Hz, 2H), 7.14 (d, J = 8.0 Hz, 2H), 2.05 (s, 3H), 1.86 (s, 6H), 1.73 (s, 6H). LC-MS: m/z 467.1 (M + H)⁺ |
| 304 | 186 | Int-VI | 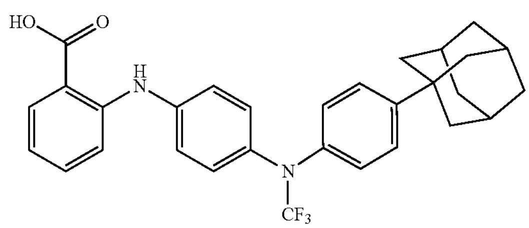 | ¹H NMR (400 MHz, DMSO-d6) δ 13.20 (bs, 1H), 9.66 (s, 1H), 7.90 (d, J = 8.4 Hz, 1H), 7.40-7.38 (m, 3H), 7.26-7.24 (m, 5H), 7.20 (d, J = 8.4 Hz, 2H), 6.82 (t, J = 7.2 Hz, 1H), 2.04 (s, 3H), 1.84 (s, 6H), 1.72 (s, 6H). LC-MS: m/z 507.1 (M + H)⁺ |
| 305 | 187 | XX.16 | 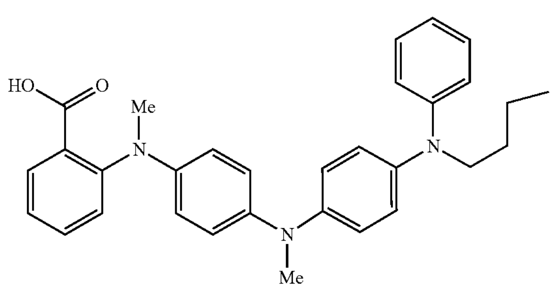 [SMILES: CCCCN(c1ccccc1)c1ccc(N(C)c2ccc(N(C)c3ccccc3C(=O)O)cc2)cc1] | ¹H NMR (400 MHz, DMSO-d6) δ 12.80 (s, 1H), 7.75 (m, 1H), 7.59 (t, 1H), 7.32-7.30 (m, 2H), 7.12-7.08 (m, 2H), 6.93 (t, J = 8.3 Hz, 4H), 6.74 (d, J = 8.3 Hz, 2H), 6.64 (d, J = 7.3 Hz, 2H), 6.58 (d, J = 7.8 Hz, 3H), 3.56-3.54 (m, 2H), 3.19 (s, 3H), 3.16 (s, 3H), 1.51-1.49 (m, 2H), 1.33-1.28 (m, 2H), 0.87 (t, J = 7.3 Hz, 3H), LC-MS: m/z 480.1 (M + H)⁺ |

| CP | Compound No | Reactant | Structure | Analytical data |
|---|---|---|---|---|
| 306 | 188 | XVIII.1 | 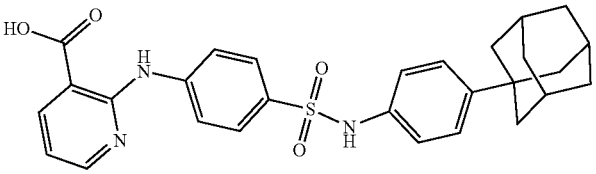 | ¹H NMR (400 MHz, DMSO-d6) δ 13.79 (bs, 1H), 10.77 (s, 1H), 10.03 (s, 1H), 8.44-8.43 (m, 1H), 8.28 (dd, J₁ = 1.6 Hz, J₂ = 8.0 Hz, 1H), 7.89 (d, J = 8.4 Hz, 2H), 7.69 (d, J = 8.8 Hz, 2H), 7.19 (d, J = 8.8 Hz, 2H), 7.03-6.96 (m, 3H), 1.99 (s, 3H), 1.76 (s, 6H), 1.68 (s, 6H). LC-MS: m/z 504.0 (M + H)⁺ |
| 307 | 189 | XIX.2 | 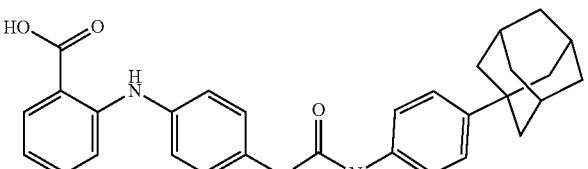 | ¹H NMR (400 MHz, DMSO-d6) δ 12.95 (bs, 1H), 9.50 (bs, 1H), 8.60 (s, 1H), 8.52 (s, 1H), 7.88 (d, J = 7.9 Hz, 1H), 7.46 (d, J = 8.3 Hz, 2H), 7.36 (m, 3H), 7.26 (d, J = 8.3 Hz, 2H), 7.17 (d, J = 8.8 Hz, 2H), 7.05 (d, J = 8.3 Hz, 1H), 6.70 (t, J = 7.4 Hz, 1H), 2.05 (s, 3H), 1.84 (s, 6H), 1.73 (s, 6H). LC-MS: m/z 482.0 (M + H)⁺ |
| 308 | 190 | Int-XVIII | 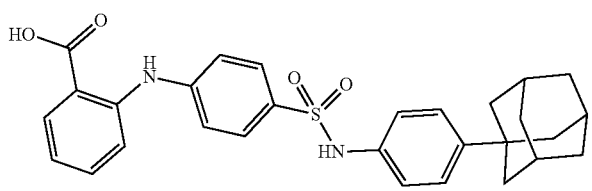 | ¹H NMR (400 MHz, DMSO-d6) δ 13.25 (bs, 1H), 10.02 (s, 1H), 9.75 (s, 1H), 7.92 (d, J = 8.0 Hz, 1H), 7.65 (d, J = 8.4 Hz, 2H), 7.49-7.41 (m, 2H), 7.28 (d, J = 8.4 Hz, 2H), 7.20 (d, J = 8.4 Hz, 2H), 7.02 (d, J = 8.4 Hz, 2H), 6.96 (t, J = 7.2 Hz, 1H), 2.00 (s, 3H), 1.77 (s, 6H), 1.69 (s, 6H). LC-MS: m/z 503.0 (M + H)⁺ |

-continued

| CP | Compound No | Reactant | Structure | Analytical data |
|---|---|---|---|---|
| 309 | 191 | VI.50 | 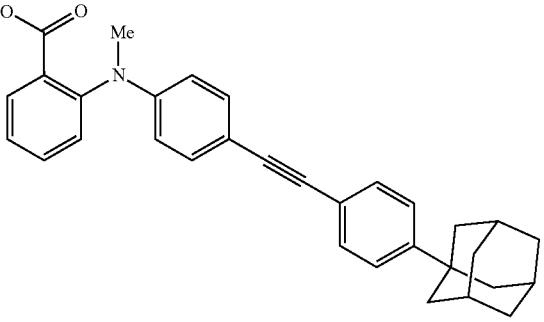 | $^1$H NMR (400 MHz, DMSO-d6) δ 12.8 (s, 1H), 7.81 (d, J = 7.2 Hz, 1H), 7.66-7.62 (m, 1H), 7.41-7.32 (m, 6H), 7.27 (d, J = 8.8 Hz, 2H), 6.48 (d, J = 8.0 Hz, 2H), 3.22 (s, 3H), 2.05 (s, 3H), 1.85 (s, 6H), 1.73 (s, 6H). LC-MS: m/z 462.1 (M + H)$^+$ |
| 310 | 192 | XX.17 | 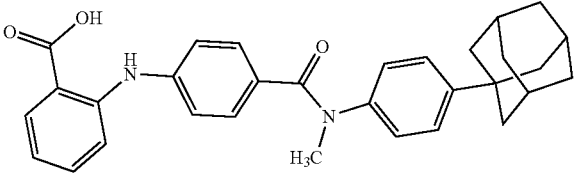 | $^1$H NMR (400 MHz, DMSO-d6) δ 13.2 (bs, 1H), 9.8 (bs, 1H), 7.9 (m, 1H), 7.40-7.30 (m, 1H), 7.27 (d, J = 8.4 Hz, 2H), 7.21-7.19 (m, 3H), 7.08 (d, J = 8.4 Hz, 2H), 7.02 (d, J = 8.4 Hz, 2H), 6.90-6.80 (m, 1H), 3.34 (s, 3H), 2.02 (s, 3H), 1.81 (s, 6H), 1.70 (s, 6H). LC-MS: m/z 481.0 (M + H)$^+$ |
| 311 | 193 | XII.39 | 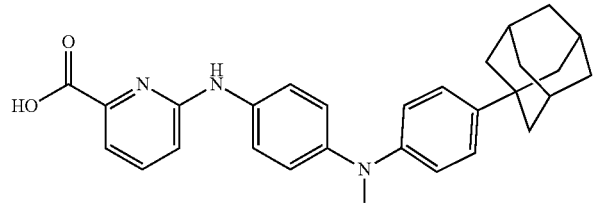 | $^1$H NMR (400 MHz, DMSO-d6) δ 10.40-10.00 (bs, 1H), 7.57 (t, J = 8.0 Hz, 1H), 7.50-7.40 (m, 2H), 7.28 (d, J = 7.2 Hz, 1H), 7.20 (d, J = 8.8 Hz, 2H), 7.02 (d, J = 8.0 Hz, 2H), 6.95 (d, J = 8.4 Hz, 1H), 6.84 (d, J = 8.8 Hz, 2H), 3.22 (s, 3H), 2.04 (s, 3H), 1.83 (s, 6H), 1.72 (s, 6H). LC-MS: m/z m/z 454.0 (M + H)$^+$ |
| 312 | 194 | XVIII.2 | 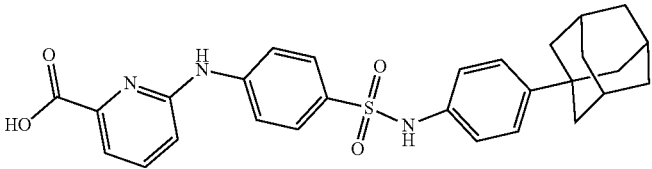 | $^1$H NMR (400 MHz, DMSO-d6) δ 13.10 (bs, 1H), 9.97 (s, 1H), 9.76 (s, 1H), 7.97 (d, J = 8.8 Hz, 2H), 7.77 (t, J = 7.6 Hz, 1H), 7.64 (d, J = 8.8 Hz, 2H), 7.51 (d, J = 7.2 Hz, 1H), 7.19 (d, J = 8.8 Hz, 2H), 7.08 (d, J = 8.0 Hz, 1H), 7.02 (d, J = 8.4 Hz, 2H), 1.99 (s, 3H), 1.76 (s, 6H), 1.68 (s, 6H). LC-MS: m/z 504.2 (M + H)$^+$ |

-continued

| CP | Compound No | Reactant | Structure | Analytical data |
|---|---|---|---|---|
| 313 | 195 | XV.25 | 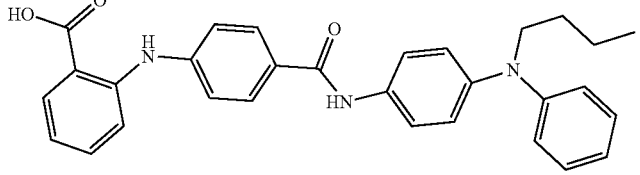 | $^1$H NMR (400 MHz, DMSO-d6) δ 9.96 (s, 1H), 7.90 (t, J = 8.8 Hz, 3H), 7.70 (d, J = 8.8 Hz, 2H), 7.35 (m, 1H), 7.23-7.21 (m, 1H), 7.19-7.15 (m, 4H), 7.02 (d, J = 8.8 Hz, 2H), 6.82-6.76 (m, 4H), 3.63 (t, J = 7.4 Hz, 2H), 1.53-1.51 (m, 2H), 1.35-1.31 (m, 2H), 0.86 (t, J = 7.3 Hz, 3H), LC-MS: m/z 480.2 (M + H)$^+$ |
| 314 | 196 | XX.18 | 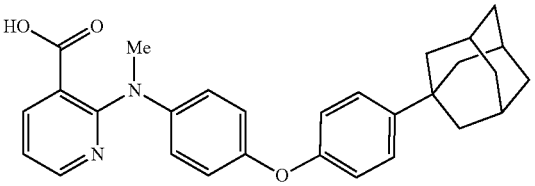 [SMILES: CN(c1ccc(Oc2ccc(C34CC5CC(CC(C5)C3)C4)cc2)cc1)c1ncccc1C(=O)O] | $^1$H NMR (400 MHz, DMSO-d6) δ 12.60 (bs, 1H), 8.37 (dd, J$_1$ = 2.0 Hz, J$_2$ = 4.9 Hz, 1H), 7.81 (dd, J$_1$ = 1.9 Hz, J$_2$ = 7.8 Hz, 1H), 7.35 (d, J = 3.4 Hz, 2H), 6.99-6.87 (m, 7H), 3.40 (s, 3H), 2.08 (s, 3H), 1.76 (s, 6H), 1.69 (s, 6H). LC-MS: m/z 455.3 (M + H)$^+$ |
| 315 | 197 | XV.26 | 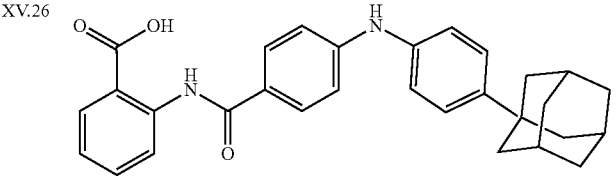 | $^1$H NMR (400 MHz, DMSO-d6) δ 13.6 (bs, 1H), 12.1 (s, 1H), 8.74 (d, J = 8.3 Hz, 1H), 8.64 (s, 1H), 8.05 (d, J = 7.8 Hz, 1H), 7.81 (d, J = 8.4 Hz, 2H), 7.63 (d, J = 7.3 Hz, 1H), 7.32 (d, J = 8.3 Hz, 2H), 7.17-7.05 (m, 5H), 2.06 (bs, 3H), 1.86 (s, 6H), 1.74 (s, 6H). LC-MS: m/z 467.3 (M + H)$^+$ |
| 316 | 198 | XV.27 | 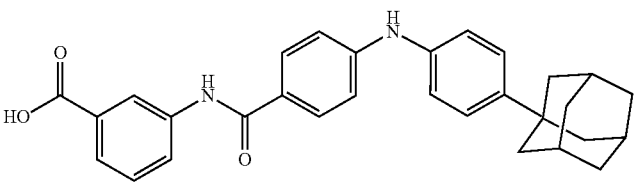 | $^1$H NMR (400 MHz, DMSO-d6) δ 12.90 (bs, 1H), 10.10 (s, 1H), 8.55 (s, 1H), 8.40 (s, 1H), 8.04 (d, J = 7.8 Hz, 1H), 7.88 (d, J = 8.3 Hz, 2H), 7.64 (d, J = 7.9 Hz, 1H), 7.44 (t, J = 7.9 Hz, 1H), 7.31 (d, J = 8.3 Hz, 2H), 7.07 (d, J = 8.3 Hz, 2H), 7.02 (d, J = 5.4 Hz, 2H), 2.06 (s, 3H), 1.86 (s, 6H), 1.73 (s, 6H). LC-MS: m/z 467.3 (M + H)$^+$ |
| 317 | 199 | VI.51 | 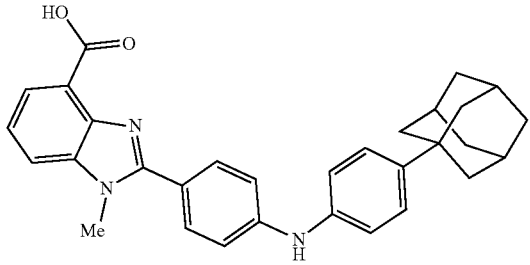 | $^1$H NMR (400 MHz, DMSO-d6) δ 13.80-12.40 (s, 1H), 8.65 (s, 1H), 7.99 (d, J = 7.2 Hz, 1H), 7.89 (d, J = 7.2 Hz, 1H), 7.78 (d, J = 8.8 Hz, 2H), 7.48 (t, J = 7.6 Hz, 1H), 7.32 (d, J = 8.4 Hz, 2H), 7.20-7.15 (m, 4H), 3.99 (s, 3H), 2.06 (s, 3H), 1.87 (s, 6H), 1.74 (s, 6H). LC-MS: m/z 478.2 (M + H)$^+$ |

| CP | Compound No | Reactant | Structure | Analytical data |
|---|---|---|---|---|
| 318 | 200 | VI.52 | 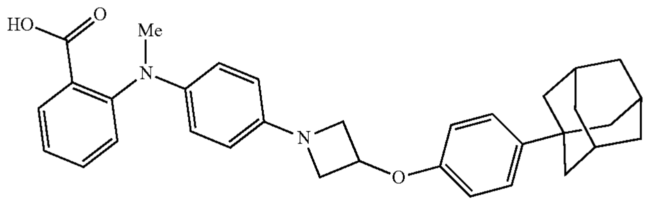 | ¹H NMR (400 MHz, DMSO-d6) δ 12.95 (s, 1H), 7.67 (d, J = 6.4 Hz, 1H), 7.50-7.46 (m, 1H), 7.27 (d, J = 8.8 Hz, 2H), 7.20-7.17 (m, 2H), 6.80 (d, J = 8.8 Hz, 2H), 6.63 (d, J = 8.8 Hz, 2H), 6.37 (d, J = 8.4 Hz, 2H), 5.03-5.01 (m, 1H), 4.23-4.19 (m, 2H), 3.64-3.61 (m, 2H), 3.14 (s, 3H), 2.04 (s, 3H), 1.83 (s, 6H), 1.72 (s, 6H). LC-MS: m/z 509.3 (M + H)⁺ |
| 319 | 201 | XII.41 | 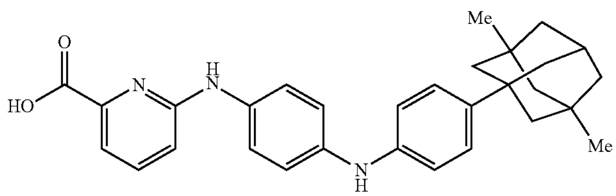 [SMILES: CC12CC3CC(C)(C1)CC(c1ccc(Nc4ccc(Nc5cccc(C(=O)O)n5)cc4)cc1)(C3)C2] | ¹H NMR (400 MHz, DMSO-d6) δ 13.00 (bs, 1H), 9.04 (s, 1H), 7.78 (m, 1H), 7.62 (d, J = 7.2 Hz, 3H), 7.34 (d, J = 6.4 Hz, 1H), 7.16 (d, J = 8.0 Hz, 2H), 7.00-6.92 (m, 5H), 2.12 (m, 1H), 1.65 (s, 2H), 1.49-1.32 (m, 8H), 1.17 (s, 2H), 0.85 (s, 6H). LC-MS: m/z 468.3 (M + H)⁺ |
| 320 | 202 | XII.42 | 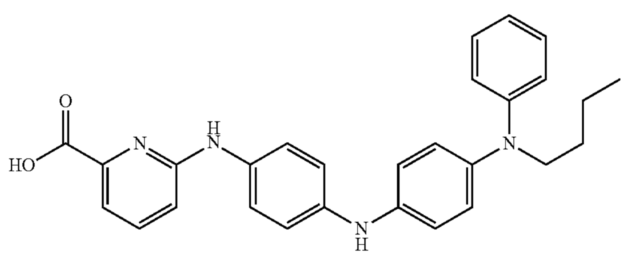 [SMILES: CCCCN(c1ccccc1)c1ccc(Nc2ccc(Nc3cccc(C(=O)O)n3)cc2)cc1] | ¹H NMR (400 MHz, DMSO-d6) δ 12.99 (bs, 1H), 9.07 (s, 1H), 7.90 (s, 1H), 7.64 (m, 3H), 7.36 (d, J = 6.8 Hz, 2H), 7.11 (t, J = 7.9 Hz, 2H), 7.00 (m, 6H), 6.66 (m, 3H), 3.56 (m, 2H), 1.54 (m, 2H), 1.34 (m, 2H), 0.88 (t, J = 7.3 Hz, 3H). LC-MS: m/z 453.3 (M + H)⁺ |
| 321 | 203 | XII.43 | 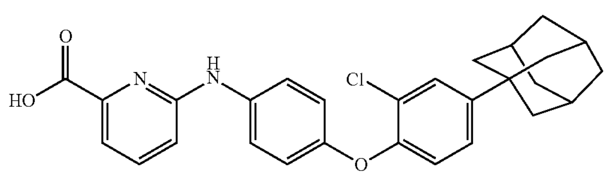 [SMILES: O=C(O)c1cccc(Nc2ccc(Oc3ccc(C45CC6CC(CC(C6)C4)C5)cc3Cl)cc2)n1] | ¹H NMR (400 MHz, DMSO-d6) δ 10.4 (bs, 1H), 7.59 (m, 1H), 7.47 (m, 3H), 7.32 (d, J = 2.4 Hz, 2H), 6.96 (m, 4H), 2.05 (bs, 3H), 1.86 (s, 6H), 1.76 (s, 6H). LC-MS: m/z 475.2 (M + H)⁺ |
| 322 | 204 | XII.44 | 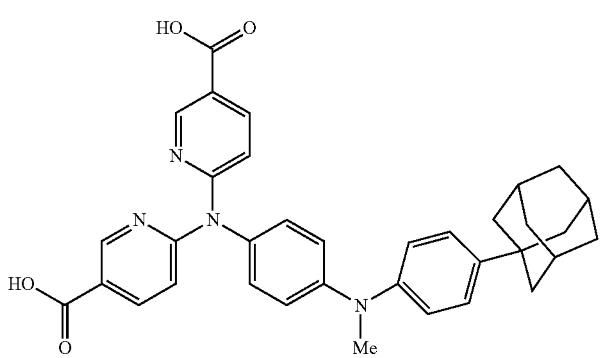 [SMILES: CN(c1ccc(N(c2ccc(C(=O)O)cn2)c2ccc(C(=O)O)cn2)cc1)c1ccc(C23CC4CC(CC(C4)C2)C3)cc1] | ¹H NMR (400 MHz, DMSO-d6) δ 13.50-12.50 (bs, 2H), 8.72 (d, J = 2.0 Hz, 2H), 8.11 (dd, J₁ = 2.0 Hz, J₂ = 8.4 Hz, 2H), 7.35 (d, J = 8.0 Hz, 2H), 7.14-7.03 (m, 6H), 6.90 (d, J = 9.2 Hz, 2H), 3.27 (s, 3H), 2.05 (s, 3H), 1.86 (s, 6H), 1.73 (s, 6H). LC-MS: m/z 493.4 |

-continued

| CP | Compound No | Reactant | Structure | Analytical data |
|---|---|---|---|---|
| 323 | 205 | VI.53 | 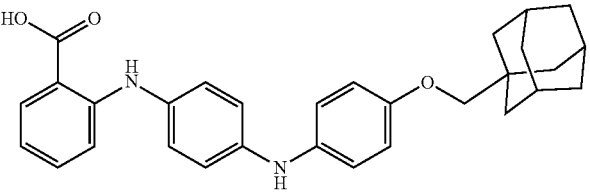 [SMILES: O=C(O)c1ccccc1Nc1ccc(Nc2ccc(OCC34CC5CC(CC(C5)C3)C4)cc2)cc1] | $^1$H NMR (400 MHz, DMSO-d6) δ 13.00-12.80 (bs, 1H), 9.50-9.40 (bs, 1H), 7.84 (d, J = 7.6 Hz, 1H), 7.8 (s, 1H), 7.3 (t, J = 8.0 Hz, 1H), 7.07-6.83 (m, 9H), 6.65 (t, J = 7.2 Hz, 1H), 3.47 (s, 2H), 1.98 (s, 3H), 1.73-1.62 (m, 12H). LC-MS: m/z 469.2 (M + H)$^+$ |
| 324 | 206 | XV.28 | 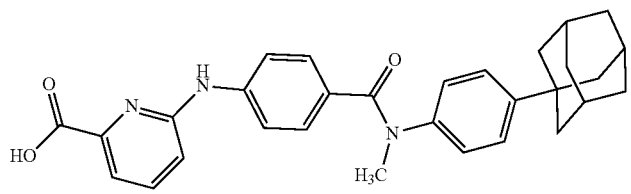 [SMILES: CN(C(=O)c1ccc(Nc2cccc(C(=O)O)n2)cc1)c1ccc(C23CC4CC(CC(C4)C2)C3)cc1] | $^1$H NMR (400 MHz, DMSO-d6) δ 12.92 (s, 1H), 9.41 (s, 1H), 7.73-J = 7.6 Hz, 1H), 7.26 (d, J = 8.4 Hz, 2H), 7.17 (d, J = 8.8 Hz, 2H), 7.08 (d, J = 8.8 Hz, 2H), 7.0 (d, J = 8.4 Hz, 1H), 3.33 (s, 3H), 2.01 (s, 3H), 1.79 (s, 6H), 1.69 (s, 6H). LC-MS: m/z 482.3 (M + H)$^+$ |
| 325 | 207 | XX.19 | 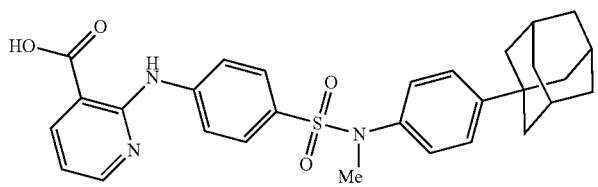 [SMILES: CN(c1ccc(C23CC4CC(CC(C4)C2)C3)cc1)S(=O)(=O)c1ccc(Nc2ncccc2C(=O)O)cc1] | $^1$H NMR (400 MHz, DMSO-d6) δ 13.85 (bs, 1H), 11.20 (bs, 1H), 8.46 (dd, $J_1$ = 2.0 Hz, $J_2$ = 4.8 Hz, 1H), 8.31 (dd, $J_1$ = 1.6 Hz, $J_2$ = 7.6 Hz, 1H), 7.94 (d, J = 8.8 Hz, 2H), 7.44 (dd, J = 8.8 Hz, 2H), 7.32 (d, J = 8.4 Hz, 2H), 7.05-6.98 (m, 3H), 3.09 (s, 3H), 2.04 (s, 3H), 1.84 (s, 6H), 1.72 (s, 6H). LC-MS: m/z 518.3 (M + H)$^+$ |
| 326 | 208 | XX.20 | 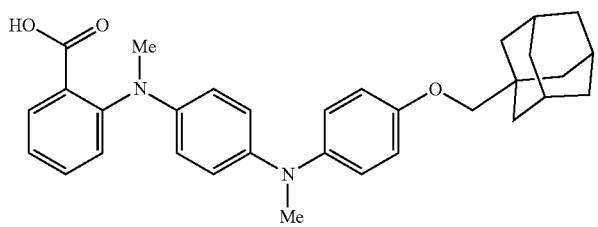 [SMILES: CN(c1ccc(OCC23CC4CC(CC(C4)C2)C3)cc1)c1ccc(N(C)c2ccccc2C(=O)O)cc1] | $^1$H NMR (400 MHz, DMSO-d6) δ 12.89 (bs, 1H), 7.71 (d, J = 7.6 Hz, 1H), 7.55-7.51 (m, 1H), 7.26 (t, J = 7.6 Hz, 2H), 6.81-6.76 (m, 6H), 6.55 (d, J = 9.2 Hz, 2H), 3.50 (s, 2H), 3.16 (s, 3H), 3.05 (s, 3H), 1.97 (s, 3H), 1.69-1.60 (m, 12H). LC-MS: m/z 497.3 (M + H)$^+$ |
| 327 | 209 | VI.54 | 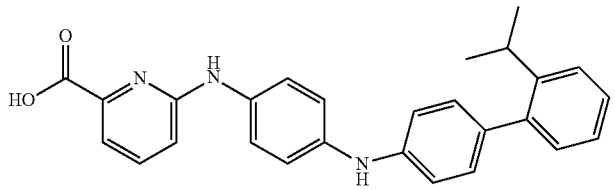 [SMILES: CC(C)c1ccccc1-c1ccc(Nc2ccc(Nc3cccc(C(=O)O)n3)cc2)cc1] | $^1$H NMR (400 MHz, DMSO-d6) δ 7.62-7.60 (m, 3H), 7.39-7.28 (m, 4H), 7.19 (t, J = 7.2 Hz, 1H), 7.12-7.04 (m, 7H), 6.91 (d, J = 8.0 Hz, 2H), 3.11-3.08 (m, 1H), 1.12 (d, J = 6.8 Hz, 6H). LC-MS: m/z 424.2 (M + H)$^+$ |
| 328 | 210 | VI.55 | 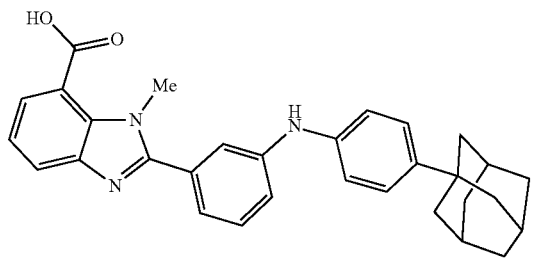 [SMILES: Cn1c(-c2cccc(Nc3ccc(C45CC6CC(CC(C6)C4)C5)cc3)c2)nc2cccc(C(=O)O)c21] | $^1$H NMR (400 MHz, DMSO-d6) δ 14.00-13.20 (bs, 1H), 8.50 (s, 1H), 8.02 (d, J = 8.4 Hz, 1H), 7.92 (d, J = 7.2 Hz, 1H), 7.59 (t, J = 8.0 Hz, 1H), 7.51-7.47 (m, 2H), 7.31-7.27 (m, 4H), 7.16 (d, J = 8.4 Hz, 2H), 3.96 (s, 3H), 2.04 (s, 3H), 1.84 (s, 6H), 1.72 (s, 6H). LC-MS: m/z 478.2 (M + H)$^+$ |

-continued

| CP | Compound No | Reactant | Structure | Analytical data |
|---|---|---|---|---|
| 329 | 211 | XV.29 | 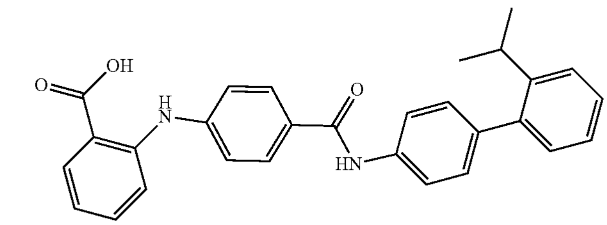 [SMILES: CC(C)c1ccccc1-c1ccc(NC(=O)c2ccc(Nc3ccccc3C(=O)O)cc2)cc1] | ¹H NMR (400 MHz, DMSO-d6) δ 10.80-10.20 (bs, 1H), 10.16 (s, 1H), 7.98-7.94 (m, 3H), 7.84 (d, J = 8.4 Hz, 2H), 7.44-7.35 (m, 3H), 7.33-7.24 (m, 3H), 7.21-7.20 (m, 3H), 7.13 (d, J = 7.2 Hz, 1H), 6.90-6.86 (m, 1H), 3.07-3.01 (m, 1H), 1.13 (d, J = 7.2 Hz, 6H). LC-MS: m/z 451.2 (M + H)⁺ |
| 330 | 212 | XV.30 | 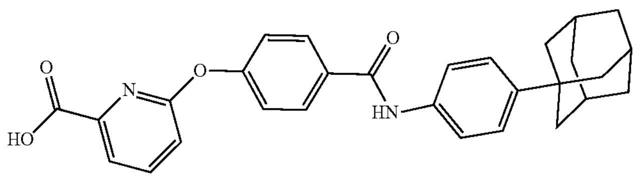 [SMILES: O=C(Nc1ccc(C23CC4CC(CC(C4)C2)C3)cc1)c1ccc(Oc2cccc(C(=O)O)n2)cc1] | ¹H NMR (400 MHz, DMSO-d6) δ 13.21 (s, 1H), 10.19 (s, 1H), 8.07 (t, J = 7.8 Hz, 1H), 8.02 (d, J = 8.3 Hz, 2H), 7.85 (d, J = 7.4 Hz, 1H), 7.70 (d, J = 8.3 Hz, 2H), 7.33 (m, 5H), 2.06 (s, 3H), 1.87 (s, 6H), 1.74 (s, 6H). LC-MS: m/z 469.2 (M + H)⁺ |
| 331 | 213 | | 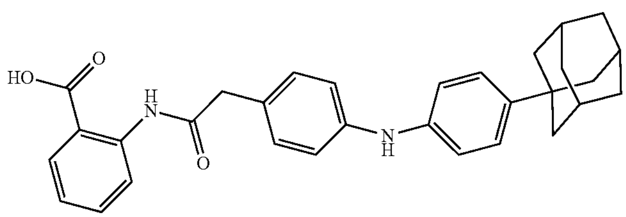 [SMILES: O=C(Cc1ccc(Nc2ccc(C34CC5CC(CC(C5)C3)C4)cc2)cc1)Nc1ccccc1C(=O)O] | LC-MS: m/z 481.2 (M + H)⁺ |
| 333 | 214 | XV.31 | 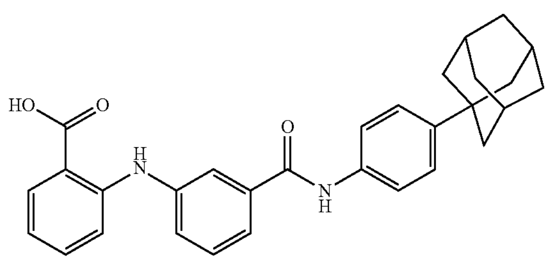 [SMILES: O=C(Nc1ccc(C23CC4CC(CC(C4)C2)C3)cc1)c1cccc(Nc2ccccc2C(=O)O)c1] | ¹H NMR (400 MHz, DMSO-d6) δ 13.17-13.16 (bs, 1H), 10.17 (s, 1H), 9.77 (s, 1H), 6.93 (dd, J₁ = 1.6 Hz, J₂ = 8.0 Hz, 1H), 7.79 (s, 1H), 7.69 (d, J = 8.8 Hz, 2H), 7.63-7.62 (m, 1H), 7.49-7.42 (m, 3H), 7.33-7.29 (m, 3H), 6.85-6.81 (m, 1H), 2.06 (s, 3H), 1.83 (s, 6H), 1.70 (s, 6H). LC-MS: m/z 467.3 (M + H)⁺ |
| 334 | 215 | XV.32 | 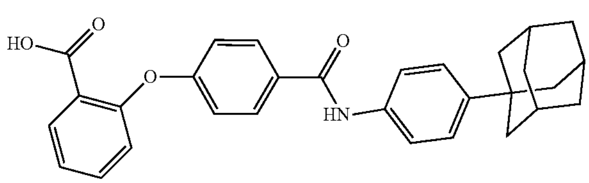 [SMILES: O=C(Nc1ccc(C23CC4CC(CC(C4)C2)C3)cc1)c1ccc(Oc2ccccc2C(=O)O)cc1] | ¹H NMR (400 MHz, DMSO-d6) δ 12.95 (s, 1H), 10.06 (s, 1H), 7.94 (d, J = 8.3 Hz, 2H), 7.90 (d, J = 7.3 Hz, 1H), 7.68-7.63 (m, 3H), 7.37 (t, J = 6.8 Hz, 1H), 7.32 (d, J = 8.8 Hz, 2H), 7.16 (d, J = 8.3 Hz, 1H), 6.96 (d, J = 8.3 Hz, 2H), 2.06 (s, 3H), 1.86 (s, 6H), 1.74 (s, 6H). LC-MS: m/z 468.1 (M + H)⁺ |

-continued

| CP | Compound No | Reactant | Structure | Analytical data |
|---|---|---|---|---|
| 335 | 216 | XV.33 | (structure) | ¹H NMR (400 MHz, DMSO-d6) δ 12.65 (bs, 1H), 9.91 (s, 1H), 7.93-7.87 (m, 3H), 7.68 (d, J = 8.8 Hz, 2H), 7.34 (d, J = 8.0 Hz, 1H), 7.29 (d, J = 8.8 Hz, 2H), 7.22-7.16 (m, 3H), 6.74 (t, J = 7.6 Hz, 1H), 2.14-2.13 (m, 1H), 1.69 (s, 2H), 1.53-1.33 (m, 8H), 0.86 (s, 6H). LC-MS: m/z 495.3 (M + H)⁺ |
| 336 | 217 | | (structure) | LC-MS: m/z 468.2 (M + H)⁺ |
| 337 | 218 | VI.56 | (structure) | ¹H NMR (400 MHz, DMSO-d6) δ 12.8 (bs, 1H), 7.70 (d, J = 7.6 Hz, 1H), 7.53 (t, J = 8.0 Hz, 1H), 7.26-7.19 (m, 4H), 6.92 (d, J = 8.8 Hz, 2H), 6.85 (d, J = 8.8 Hz, 2H), 6.59 (d, J = 7.2 Hz, 2H), 3.20-3.19 (m, 4H), 3.16 (s, 3H), 3.12-3.11 (m, 4H), 2.04 (s, 3H), 1.82 (s, 6H), 1.72 (s, 6H). LC-MS: m/z 522.3 (M + H)⁺ |
| 338 | 219 | XII.45 | (structure) | ¹H NMR (400 MHz, DMSO-d6) δ 13.00 (bs, 1H), 9.16 (s, 1H), 8.26 (s, 1H), 7.73 (d, J = 8.4 Hz, 2H), 7.68-7.63 (m, 3H), 7.37 (d, J = 6.8 Hz, 1H), 7.18 (s, 1H), 7.08 (d, J = 8.8 Hz, 2H), 6.98 (d, J = 8.4 Hz, 1H), 6.91 (d, J = 8.4 Hz, 2H), 2.05 (s, 9H), 1.65 (s, 6H). LC-MS: m/483.1z (M + H)⁺ |
| 339 | 220 | XII.46 | (structure) | ¹H NMR (400 MHz, DMSO-d6) δ 12.0 (s, 1H), 9.81 (s, 1H), 7.86 (d, J = 7.6 Hz, 1H), 7.49 (d, J = 8.4 Hz, 2H), 7.25 (d, J = 8.8 Hz, 2H), 7.13-7.01 (m, 6H), 6.58 (t, J = 6.8 Hz, 1H), 2.83 (t, J = 7.6 Hz, 2H), 2.56 (t, J = 8.0 Hz, 2H), 2.04 (s, 3H), 1.83 (s, 6H), 1.72 (s, 6H). LC-MS: m/z 495.3 (M + H)⁺ |
| 340 | 221 | VI.57 | (structure) | ¹H NMR (400 MHz, DMSO-d6) δ 13.0 (bs, 1H), 8.20 (bs, 1H), 7.70-7.60 (m, 1H), 7.60-7.50 (m, 1H), 7.35-7.31 (m, 2H), 7.23 (d, J = 8.4 Hz, 2H), 7.10-6.97 (m, 4H), 6.71 (bs, 2H), 3.26 (s, 3H), 2.04 (s, 3H), 1.82 (s, 6H), 1.72 (s, 6H). LC-MS: m/z 481.2 (M + H)⁺ |

-continued

| CP | Compound No | Reactant | Structure | Analytical data |
|----|----|----|----|----|
| 341 | 222 | XV.35 | 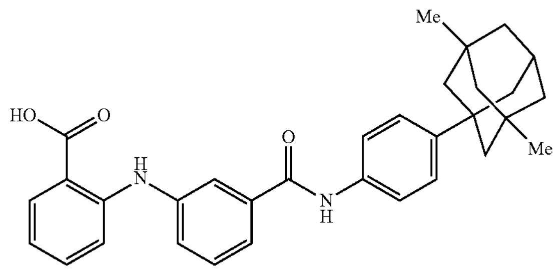 [SMILES: CC12CC3CC(C)(C1)CC(c1ccc(NC(=O)c4cccc(Nc5ccccc5C(=O)O)c4)cc1)(C3)C2] | $^1$H NMR (400 MHz, DMSO-d6) δ 13.10 (bs, 1H), 10.14 (s, 1H), 9.88 (bs, 1H), 7.93 (d, J = 7.6 Hz, 1H), 7.79 (s, 1H), 7.68 (d, J = 8.8 Hz, 2H), 7.61 (d, J = 7.6 Hz, 1H), 7.50-7.40 (m, 3H), 7.32-7.29 (m, 3H), 6.82 (t, J = 7.6 Hz, 1H), 2.14-2.10 (m, 1H), 1.68 (s, 2H), 1.53-1.43 (m, 8H), 1.18 (s, 2H), 0.86 (s, 6H). LC-MS: m/z 495.3 (M + H)$^+$ |
| 342 | 223 | XVIII.3 | 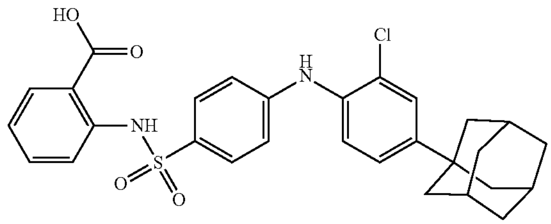 [SMILES: O=C(O)c1ccccc1NS(=O)(=O)c1ccc(Nc2ccc(C34CC5CC(CC(C5)C3)C4)cc2Cl)cc1] | $^1$H NMR (400 MHz, DMSO-d6) δ 13.8 (bs, 1H), 11.0 (bs, 1H), 8.84 (s, 1H), 7.90 (d, J = 7.2 Hz, 1H), 7.59 (d, J = 8.8 Hz, 2H), 7.55-7.48 (m, 2H), 7.43 (s, 1H), 7.33-7.28 (m, 2H), 7.09 (t, J = 8.0 Hz, 1H), 6.82 (d, J = 8.8 Hz, 2H), 2.05 (s, 3H), 1.85 (s, 6H), 1.73 (s, 6H). LC-MS: m/z 535 (M + H)$^-$ |
| 343 | 224 | XV.36 | 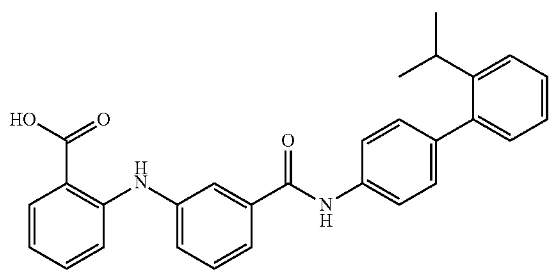 [SMILES: CC(C)c1ccccc1-c1ccc(NC(=O)c2cccc(Nc3ccccc3C(=O)O)c2)cc1] | $^1$H NMR (400 MHz, DMSO-d6) δ 10.32 (s, 1H), 7.94 (d, J = 7.6 Hz, 1H), 7.84-7.80 (m, 3H), 7.62 (d, J = 7.6 Hz, 1H), 7.52-7.46 (m, 4H), 7.43-7.31 (m, 2H), 7.27-7.19 (m, 3H), 7.13 (d, J = 8.0 Hz, 1H), 6.82 (t, J = 7.6 Hz, 1H), 3.05-3.01 (m, 1H), 1.13 (d, J = 6.8 Hz, 6H). LC-MS: m/z 451.2 (M + H)$^+$ |
| 344 | 225 | XV.37 | 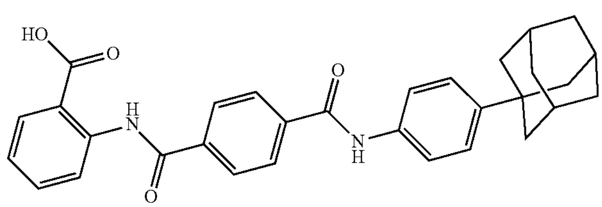 [SMILES: O=C(Nc1ccc(C23CC4CC(CC(C4)C2)C3)cc1)c1ccc(C(=O)Nc2ccccc2C(=O)O)cc1] | $^1$H NMR (400 MHz, DMSO-d6) δ 14.00-13.8 (bs, 1H), 12.30 (s, 1H), 10.35 (s, 1H), 8.71 (d, J = 8.0 Hz, 1H), 8.14-8.07 (m, 5H), 7.27-7.67 (m, 3H), 7.35 (d, J = 8.0 Hz, 2H), 7.24 (t, J = 8.0 Hz, 1H), 2.06 (s, 3H), 1.87 (s, 6H), 1.74 (s, 6H). LC-MS: m/z 495.1 (M + H)$^+$ |
| 345 | 226 | XII.47 | 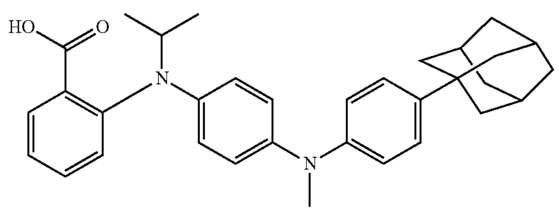 [SMILES: CC(C)N(c1ccc(N(C)c2ccc(C34CC5CC(CC(C5)C3)C4)cc2)cc1)c1ccccc1C(=O)O] | $^1$H NMR (400 MHz, DMSO-d6) δ 13.42 (s, 1H), 7.81 (d, J = 6.9 Hz, 1H), 7.61 (t, J = 7.3 Hz, 1H), 7.41 (t, J = 7.8 Hz, 1H), 7.28 (d, J = 7.9 Hz, 1H), 7.14 (d, J = 8.8 Hz, 2H), 6.86 (d, J = 8.8 Hz, 2H), 6.70 (d, J = 8.3 Hz, 2H), 6.59 (d, J = 8.8 Hz, 2H), 4.25-4.19 (m, 1H), 3.13 (s, 3H), 2.03 (s, 3H), 1.80 (s, 6H), 1.71 (s, 6H), 1.00 (d, J = 6.3 Hz, 6H). LC-MS: m/z 495.3 (M + H)$^+$ |

| CP | Compound No | Reactant | Structure | Analytical data |
|---|---|---|---|---|
| 346 | 227 | XV.38 | 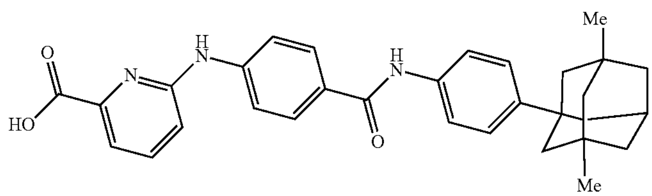 [SMILES: CC12CC3CC(C)(C1)CC(c1ccc(NC(=O)c4ccc(Nc5cccc(C(=O)O)n5)cc4)cc1)(C3)C2] | ¹H NMR (400 MHz, DMSO-d6) δ 13.10 (bs, 1H), 9.94 (s, 1H), 9.69 (s, 1H), 8.01 (d, J = 8.8 Hz, 2H), 7.94 (d, J = 8.8 Hz, 2H), 7.78 (t, J = 7.6 Hz, 1H), 7.70 (d, J = 8.8 Hz, 2H), 7.51 (d, J = 7.2 Hz, 1H), 7.30 (d, J = 8.4 Hz, 2H), 7.10 (d, J = 8.0 Hz, 1H), 2.15-2.13 (m, 1H), 1.69 (s, 2H), 1.53-1.33 (m, 8H), 1.19 (s, 2H), 0.86 (s, 6H). LC-MS: m/z 496.2 (M + H)⁺ |
| 349 | 228 | VI.58 | 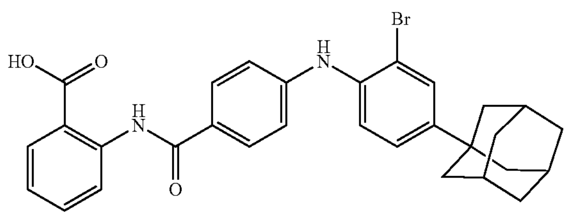 [SMILES: O=C(Nc1ccccc1C(=O)O)c1ccc(Nc2ccc(C34CC5CC(CC(C5)C3)C4)cc2Br)cc1] | ¹H NMR (400 MHz, DMSO-d6) δ 15.33 (s, 1H), 8.63 (d, J = 8.3 Hz, 1H), 8.04 (s, 1H), 7.99 (d, J = 7.3 Hz, 1H), 7.87 (d, J = 8.3 Hz, 2H), 7.58 (s, 1H), 7.36 (s, 2H), 7.27 (t, J = 7.3 Hz, 1H), 6.96-6.90 (m, 4H), 2.06 (s, 3H), 1.87 (s, 6H), 1.74 (s, 6H). LC-MS: m/z 545.1 (M + H)⁻ |
| 350 | 229 | VI.59 | 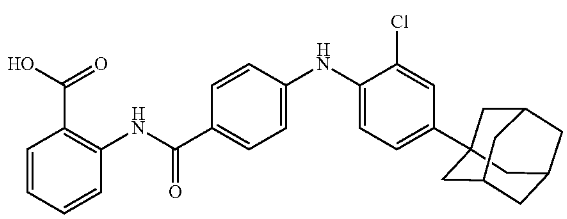 [SMILES: O=C(Nc1ccccc1C(=O)O)c1ccc(Nc2ccc(C34CC5CC(CC(C5)C3)C4)cc2Cl)cc1] | ¹H NMR (400 MHz, DMSO-d6) δ 13.6 (bs, 1H), 12.02 (s, 1H), 8.73 (d, J = 8.3 Hz, 1H), 8.30 (s, 1H), 8.04 (d, J = 6.8 Hz, 1H), 7.79 (d, J = 8.4 Hz, 2H), 7.64 (d, J = 7.3 Hz, 1H), 7.44 (D, J = 1.5 Hz, 1H), 7.39-7.32 (m, 2H), 7.16 (t, J = 7.8 Hz, 1H), 6.99 (d, J = 8.3 Hz, 2H), 2.07 (s, 3H), 1.87 (s, 6H), 1.74 (s, 6H). LC-MS: m/z 501.1 (M + H)⁺ |
| 353 | 230 | XV.39 | 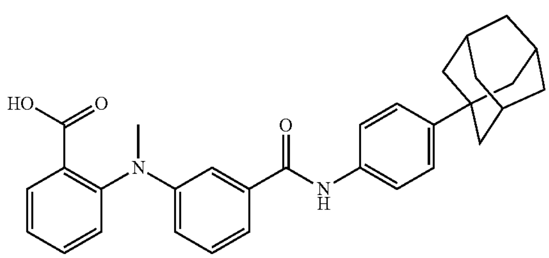 [SMILES: CN(c1cccc(C(=O)Nc2ccc(C34CC5CC(CC(C5)C3)C4)cc2)c1)c1ccccc1C(=O)O] | ¹H NMR (400 MHz, DMSO-d6) δ 12.8 (bs, 1H), 10.02 (s, 1H), 7.80 (d, J = 7.6 Hz, 1H), 7.66-7.61 (m, 3H), 7.41-7.29 (m, 4H), 7.32-7.21 (m, 2H), 7.09 (s, 1H), 6.62 (d, J = 7.2 Hz, 1H), 3.25 (s, 3H), 2.05 (s, 3H), 1.85 (s, 6H), 1.73 (s, 6H). LC-MS: m/z 481.2 (M + H)⁺ |
| 355 | 231 | XX.21 | 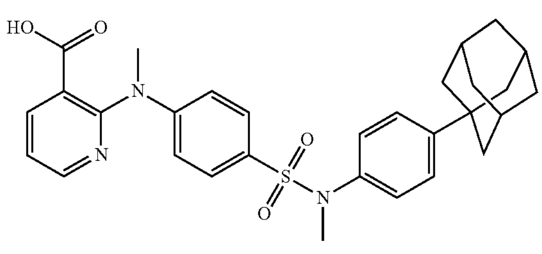 [SMILES: CN(c1ccc(S(=O)(=O)N(C)c2ccc(C34CC5CC(CC(C5)C3)C4)cc2)cc1)c1ncccc1C(=O)O] | ¹H NMR (400 MHz, DMSO-d6) δ 13.01 (bs, 1H), 8.57 (d, J = 3.2 Hz, 1H), 8.13-8.11 (m, 1H), 7.34-7.26 (m, 5H), 7.03 (d, J = 8.4 Hz, 2H), 6.80 (d, J = 8.8 Hz, 2H), 3.38 (s, 3H), 3.03 (s, 3H), 2.04 (s, 3H), 1.84 (s, 6H), 1.72 (s, 6H). LC-MS: m/z 532.2 (M + H)⁺ |

| CP | Compound No | Reactant | Structure | Analytical data |
|---|---|---|---|---|
| 356 | 232 | | (structure) | LC-MS: m/z 493.4 (M − H)+ |
| 357 | 233 | XX.22 | (structure) | $^1$H NMR (400 MHz, DMSO-d6) δ 7.42-7.38 (m, 2H), 7.17-7.15 (m, 1H), 7.11 (t, J = 7.6 Hz, 2H), 7.03-7.01 (m, 3H), 6.87 (d, J = 8.8 Hz, 2H), 6.71-6.69 (m, 1H), 6.51 (d, J = 9.2 Hz, 2H), 3.16 (s, 3H), 3.15 (s, 3H), 2.04 (s, 9H), 1.64 (s, 6H). LC-MS: m/z 510.3 (M + H)+ |
| 358 | 234 | XII.49 | (structure) | $^1$H NMR (400 MHz, DMSO-d6) δ 13.68 (s, 1H), 10.58 (s, 1H), 10.19 (s, 1H), 8.43 (dd, J$_1$ = 2.0 Hz, J$_2$ = 4.8 Hz, 1H), 8.28 (dd, J$_1$ = 1.7 Hz, J$_2$ = 7.6 Hz, 1H), 8.14 (s, 1H), 8.06 (d, J = 8.0 Hz, 1H), 7.7 (d, J = 8.4 Hz, 2H), 7.59 (d, J = 7.6 Hz, 1H), 7.47 (t, J = 7.6 Hz, 1H), 7.33 (d, J = 4.8 Hz, 2H), 6.92 (dd, J$_1$ = 4.8 Hz, J$_2$ = 7.6 Hz, 1H), 2.06 (s, 3H), 1.86 (s, 6H), 1.74 (s, 6H). LC-MS: m/z 468.1 (M + H)+ |
| 359 | 235 | XII.50 | (structure) | $^1$H NMR (400 MHz, DMSO-d6) δ 12.85 (s, 1H), 10.12 (s, 1H), 8.57 (s, 1H), 7.68-7.61 (m, 4H), 7.45-7.27 (m, 8H), 2.05 (s, 3H), 1.86 (s, 6H), 1.73 (s, 6H). LC-MS: m/z 465.1 (M − H)− |
| 360 | 236 | XX.23 | (structure) | $^1$H NMR (400 MHz, DMSO-d6) δ 12.99 (bs, 1H), 7.78 (d, J = 7.9 Hz, 1H), 7.60 (d, J = 7.8 Hz, 1H), 7.43 (d, J = 8.8 Hz, 2H), 7.37-7.31 (m, 3H), 7.23-7.12 (m, 3H), 6.94 (d, J = 8.8 Hz, 2H), 6.87 (d, J = 8.3 Hz, 1H), 6.61 (d, J = 8.8 Hz, 2H), 3.17 (s, 3H), 2.97-2.91 (m, 1H), 1.09 (d, J = 7.3 Hz, 6H), LC-MS: m/z 472.2 (M + H)+ |
| 361 | 237 | VI.60 | (structure) | $^1$H NMR (400 MHz, DMSO-d6) δ 13.75 (s, 1H), 12.15 (s, 1H), 8.69 (d, J = 8.3 Hz, 1H), 8.05 (d, J = 8.3 Hz, 1H), 7.96 (d, J = 8.8 Hz, 2H), 7.65 (t, J = 7.3 Hz, 1H), 7.43 (d, J = 8.8 Hz, 2H), 7.20 (t, J = 7.8 Hz, 1H), 7.12 (d, J = 8.8 Hz, 2H), 7.07 (d, J = 8.3 Hz, 2H), 2.07 (s, 3H), |

| CP | Compound No | Reactant | Structure | Analytical data |
|---|---|---|---|---|
| | | | | 1.88 (s, 6H), 1.74 (s, 6H). LC-MS: m/z 468.1 (M + H)⁺ |
| 362 | 238 | XX.24 | 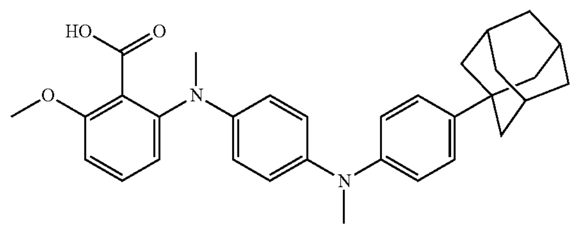 [SMILES: COc1cccc(N(C)c2ccc(N(C)c3ccc(C45CC6CC(CC(C6)C4)C5)cc3)cc2)c1C(=O)O] | ¹H NMR (400 MHz, DMSO-d6) δ 12.76 (s, 1H), 7.41 (t, J = 8.3 Hz, 1H), 7.12 (d, J = 8.8 Hz, 2H), 7.00 (d, J = 8.3 Hz, 1H), 6.91 (d, J = 8.4 Hz, 2H), 6.76 (d, J = 7.8 Hz, 1H), 6.66 (d, J = 8.3 Hz, 2H), 6.60 (d, J = 8.8 Hz, 2H), 3.82 (s, 3H), 3.13 (s, 3H), 3.09 (s, 3H), 2.02 (s, 3H), 1.80 (s, 6H), 1.71 (s, 6H). LC-MS: m/z 497.3 (M + H)⁺ |
| 363 | 239 | XV.40 | 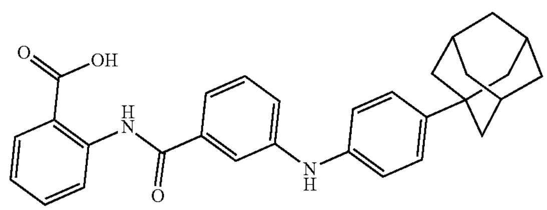 [SMILES: O=C(Nc1ccccc1C(=O)O)c1cccc(Nc2ccc(C34CC5CC(CC(C5)C3)C4)cc2)c1] | ¹H NMR (400 MHz, DMSO-d6) δ 8.66 (d, J = 8.4 Hz, 1H), 8.29 (s, 1H), 8.02 (dd, J₁ = 1.2 Hz, J₂ = 7.6 Hz, 2H), 7.65 (s, 1H), 7.44-7.32 (m, 3H), 7.26 (d, J = 8.4 Hz, 2H), 7.20 (d, J = 7.6 Hz, 1H), 7.10-7.04 (m, 2H), 2.05 (s, 3H), 1.85 (s, 6H), 1.73 (s, 6H). LC-MS: m/z 467.3 (M + H)⁺ |
| 364 | 240 | XV.41 | 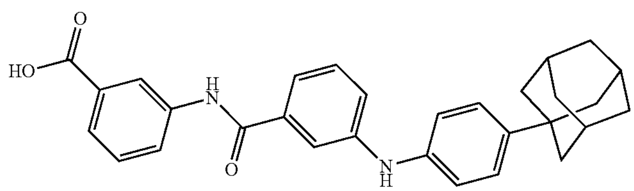 [SMILES: O=C(O)c1cccc(NC(=O)c2cccc(Nc3ccc(C45CC6CC(CC(C6)C4)C5)cc3)c2)c1] | ¹H NMR (400 MHz, DMSO-d6) δ 10.4 (s, 1H), 8.4 (s, 1H), 8.26 (s, 1H), 8.00 (d, J = 9.2 Hz, 1H), 7.66 (d, J = 7.6 Hz, 1H), 7.59 (s, 1H), 7.45 (t, J = 7.6 Hz, 1H), 7.35-7.32 (m, 2H), 7.26 (d, J = 8.8 Hz, 2H), 7.21-7.19 (m, 1H), 7.08 (d, J = 8.8 Hz, 2H), 2.05 (s, 3H), 1.84 (s, 6H), 1.73 (s, 6H). LC-MS: m/z 467.3 (M + H)⁺ |
| 366 | 241 | XII.53 | 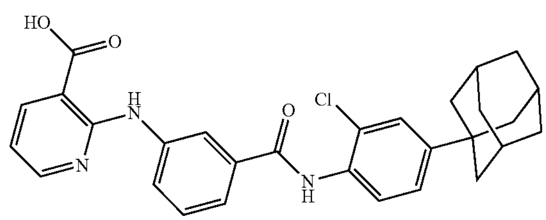 [SMILES: O=C(Nc1ccc(C23CC4CC(CC(C4)C2)C3)cc1Cl)c1cccc(Nc2ncccc2C(=O)O)c1] | ¹H NMR (400 MHz, DMSO-d6) δ 13.69 (bs, 1H), 10.61 (s, 1H), 9.99 (s, 1H), 8.42 (dd, J₁ = 1.0 Hz, J₂ = 4.8 Hz, 1H), 8.28 (dd, J₁ = 1.0 Hz, J₂ = 7.6 Hz, 1H), 8.20 (s, 1H), 8.09 (d, J = 8.0 Hz, 1H), 7.67 (m, 1H), 7.54-7.46 (m, 3H), 7.39-7.38 (m, 1H), 6.92 (dd, J₁ = 4.8 Hz, J₂ = 7.6 Hz, 1H), 2.07 (s, 3H), 1.88 (d, J = 2.4 Hz, 6H), 1.71 (s, 6H). LC-MS: 502.2 (M + H)⁺ |
| 367 | 242 | XII.54 | 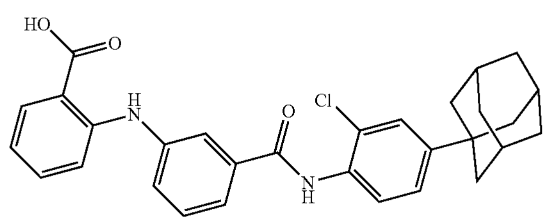 [SMILES: O=C(Nc1ccc(C23CC4CC(CC(C4)C2)C3)cc1Cl)c1cccc(Nc2ccccc2C(=O)O)c1] | ¹H NMR (400 MHz, DMSO-d6) δ 10.0 (s, 1H), 9.81-9.79 (bs, 1H), 7.93 (dd, J₁ = 1.2 Hz, J₂ = 7.6 Hz, 1H), 7.82 (s, 1H), 7.65-7.63 (m, 1H), 7.51-7.43 (m, 5H), 7.38-7.36 (m, 1H), 7.32 (d, J = 8.0 Hz, 1H), 6.86-6.82 (m, 1H), 2.07 (s, 3H), 1.86 (d, J = 2.4 Hz, 6H), 1.74 (s, 6H). LC-MS: m/z 501.1 (M + H)⁺ |

-continued

| CP | Compound No | Reactant | Structure | Analytical data |
|---|---|---|---|---|
| 369 | 243 | | (structure: 2-carboxyphenyl-NH-C(O)-CH2-phenyl-N(Me)-phenyl-adamantyl) | LC-MS: m/z 493.4 (M − H)+ |
| 370 | 244 | Compound 14 | (structure: indole-N-phenyl-NH-phenyl-adamantyl) | $^1$H NMR (400 MHz, DMSO-d6) δ 8.24 (s, 1H), 7.63 (d, J = 8.0 Hz, 1H), 7.45 (d, J = 8.8 Hz, 1H), 7.53 (d, J = 3.2 Hz, 1H), 7.39 (d, J = 8.8 Hz, 2H), 7.26 (d, J = 8.8 Hz, 2H), 7.19-7.14 (m, 3H), 7.11-7.07 (m, 3H), 6.63 (d, J = 2.4 Hz, 1H), 2.06 (s, 3H), 1.85 (d, J = 2.4 Hz, 6H), 1.73 (s, 6H). LC-MS: m/z 491.3 (M + H)+ |
| 371 | 245 | Compound 14 | (structure: HOOC-CH=CH-phenyl-NH-phenyl-NH-phenyl-adamantyl) | $^1$H NMR (400 MHz, DMSO-d6) δ 7.70-7.58 (m, 4H), 7.21-7.14 (m, 3H), 7.07 (d, J = 8.0 Hz, 1H), 6.96 (d, J = 8.8 Hz, 2H), 6.89-6.84 (m, 5H), 6.35 (d, J = 15.6 Hz, 1H), 2.04 (s, 3H), 1.86 (s, 6H), 1.72 (s, 6H). LC-MS: m/z 465.3 (M + H)+ |
| 372 | 246 | XVIII.4 | (structure: 2-carboxyphenyl-NH-phenyl-SO2-NH-phenyl-adamantyl) | $^1$H NMR (400 MHz, DMSO-d6) δ 13.21 (bs, 1H), 10.11 (s, 1H), 9.71 (bs, 1H), 7.92 (dd, J$_1$ = 1.6 Hz, J$_2$ = 8.0 Hz, 1H), 7.53 (s, 1H), 7.49-7.35 (m, 4H), 7.23 (d, J = 8.4 Hz, 2H), 7.07-7.01 (m, 3H), 6.90 (t, J = 7.6 Hz, 1H), 2.00 (s, 3H), 1.76 (s, 6H), 1.68 (s, 6H). LC-MS: m/z 503.2 (M + H)+ |
| 373 | 247 | XII.55 | (structure: 3-carboxy-2-(NH-)pyridine, with chloro-phenyl-C(O)-NH-phenyl-adamantyl) | $^1$H NMR (400 MHz, DMSO-d6) δ 11.89 (s, 1H), 10.22 (s, 1H), 9.22 (s, 1H), 8.36-8.28 (m, 2H), 7.7-7.51 (m, 4H), 7.33 (d, J = 8.0 Hz, 2H), 6.93 (s, 1H), 2.06 (s, 3H), 1.86 (s, 6H), 1.73 (s, 6H). LC-MS: m/z 502.2 (M + H)+ |

-continued

| CP | Compound No | Reactant | Structure | Analytical data |
|---|---|---|---|---|
| 376 | 248 | XII.57 | 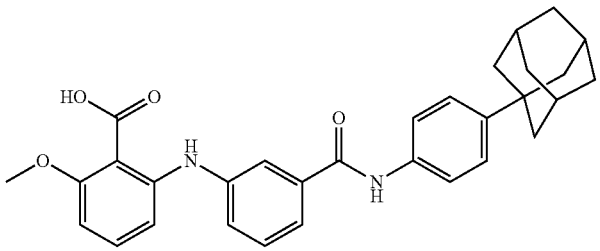 [SMILES: COc1cccc(Nc2cccc(C(=O)Nc3ccc(C45CC6CC(CC(C6)C4)C5)cc3)c2)c1C(=O)O] | ¹H NMR (400 MHz, DMSO-d6) δ 13.00-12.8 (bs, 1H), 10.07 (s, 1H), 8.03 (bs, 1H), 7.66 (d, J = 8.4 Hz, 2H), 7.56 (s, 1H), 7.41 (d, J = 8.0 Hz, 1H), 7.36-7.26 (m, 4H), 7.21 (dd, J₁ = 0.8 Hz, J₂ = 7.6 Hz, 1H), 6.86 (d, J = 8.0 Hz, 1H), 6.68 (d, J = 8.4 Hz, 1H), 3.79 (s, 3H), 2.06 (s, 3H), 1.85 (d, J = 2.4 Hz, 6H), 1.73 (s, 6H). LC-MS: m/z 497.3 (M + H)⁺ |
| 377 | 249 | XII.58 | 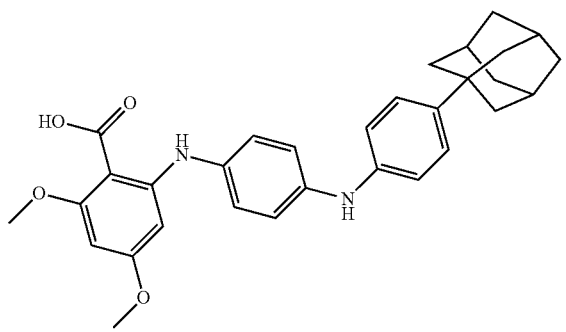 [SMILES: COc1cc(Nc2ccc(Nc3ccc(C45CC6CC(CC(C6)C4)C5)cc3)cc2)c(C(=O)O)c(OC)c1] | ¹H NMR (400 MHz, DMSO-d6) δ 12.16 (s, 1H), 9.12 (s, 1H), 7.99 (s, 1H), 7.21 (d, J = 8.4 Hz, 2H), 7.08-6.98 (m, 6H), 6.07 (d, J = 2.4 Hz, 1H), 6.0 (d, J = 2.4 Hz, 1H), 3.81 (s, 3H), 3.67 (s, 3H), 2.04 (s, 3H), 1.83 (s, 6H), 1.72 (s, 6H). LC-MS: m/z 499.2 (M + H)⁺ |
| 379 | 250 | XII.59 | 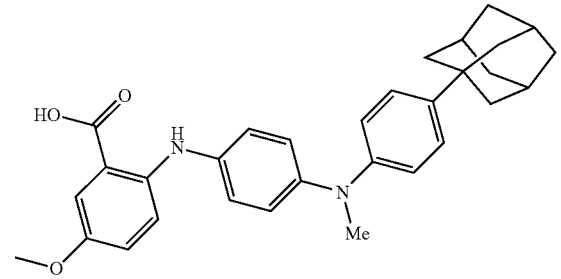 [SMILES: COc1ccc(Nc2ccc(N(C)c3ccc(C45CC6CC(CC(C6)C4)C5)cc3)cc2)c(C(=O)O)c1] | ¹H NMR (400 MHz, DMSO-d6) δ 13.2 (bs, 1H), 9.2 (bs, 1H), 7.39 (d, J = 2.9 Hz, 1H), 7.22 (d, J = 8.8 Hz, 2H), 7.11 (d, J = 6.3 Hz, 1H), 7.09 (d, J = 5.8 Hz, 2H), 7.03 (dd, J₁ = 2.4 Hz, J₂ = 8.8 Hz, 1H), 6.97 (d, J = 8.8 Hz, 2H), 6.88 (d, J = 8.8 Hz, 2H), 3.71 (s, 3H), 3.21 (s, 3H), 2.04 (s, 3H), 1.83 (s, 6H), 1.72 (s, 6H). LC-MS: m/z 483.3 (M + H)⁺ |
| 380 | 251 | XII.60 | 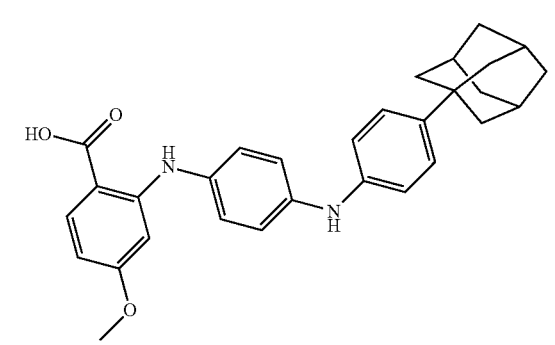 [SMILES: COc1ccc(C(=O)O)c(Nc2ccc(Nc3ccc(C45CC6CC(CC(C6)C4)C5)cc3)cc2)c1] | ¹H NMR (400 MHz, DMSO-d6) δ 9.57 (s, 1H), 8.04 (s, 1H), 7.80 (d, J = 8.8 Hz, 1H), 7.22 (d, J = 8.4 Hz, 2H), 7.12 (d, J = 8.8 Hz, 2H), 7.06 (d, J = 8.8 Hz, 2H), 7.01 (d, J = 8.8 Hz, 2H), 6.41 (d, J = 2.0 Hz, 1H), 6.28 (dd, J₁ = 2.4 Hz, J₂ = 8.8 Hz, 2H), 3.69 (s, 3H), 2.06 (s, 3H), 1.83 (d, J = 2.0 Hz, 2H), 1.69 (s, 6H). LC-MS: m/z 469.3 (M + H)⁺ |
| 381 | 252 | XII.61 | 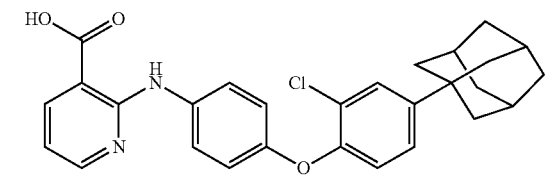 [SMILES: O=C(O)c1cccnc1Nc1ccc(Oc2ccc(C34CC5CC(CC(C5)C3)C4)cc2Cl)cc1] | ¹H NMR (400 MHz, DMSO-d6) δ 13.62 (bs, 1H), 10.36 (s, 1H), 8.36 (dd, J₁ = 2.0 Hz, J₂ = 4.8 Hz, 1H), 8.24 (dd, J₁ = 2.0 Hz, J₂ = 8.0 Hz, 1H), 7.71-7.67 (m, 2H), 7.49 (d, J = 2.0 Hz, 1H), 7.35 (dd, J₁ = 2.4 Hz, J₂ = 8.8 Hz, JH), 6.98-6.93 (m, 3H), 6.85 (dd, J₁ = 4.8 Hz, H₂ = 7.6 Hz, 1H), 2.06 (s, |

| CP | Compound No | Reactant | Structure | Analytical data |
|---|---|---|---|---|
| | | | | 3H), 1.86 (s, 6H), 1.76 (s, 6H). LC-MS: m/z 475.2 (M + H)+ |
| 383 | 253 | XII.62 | 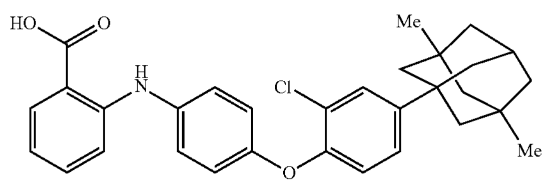 [SMILES: CC12CC3CC(C)(C1)CC(c1ccc(Oc4ccc(Nc5ccccc5C(=O)O)cc4)c(Cl)c1)(C3)C2] | $^1$H NMR (400 MHz, DMSO-d6) δ 13.15 (bs, 1H), 9.65 (bs, 1H), 7.88 (dd, $J_1$ = 1.6 Hz, $J_2$ = 8.0 Hz, 1H), 7.49 (d, J = 2.4 Hz, 1H), 7.37-7.33 (m, 2H), 7.32 (d, J = 2.0 Hz, 2H), 7.09 (d, J = 8.4 Hz, 1H), 7.03 (d, J = 8.8 Hz, 1H), 6.94 (d, J = 8.8 Hz, 2H), 6.74 (t, J = 7.6 Hz, 1H), 2.14 (m, 1H), 1.69 (s, 2H), 1.53-1.32 (m, 8H), 1.18 (s, 2H), 0.86 (s, 6H). LC-MS: m/z 502.2 (M + H)+ |
| 384 | 254 | XII.63 | 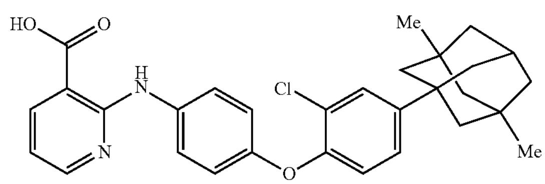 [SMILES: CC12CC3CC(C)(C1)CC(c1ccc(Oc4ccc(Nc5ncccc5C(=O)O)cc4)c(Cl)c1)(C3)C2] | $^1$H NMR (400 MHz, DMSO-d6) δ 11.20 (bs, 1H), 8.27-8.26 (m, 1H), 8.20 (dd, $J_1$ = 2.4 Hz, $J_2$ = 7.6 Hz, 1H), 7.72-7.68 (m, 2H), 7.47 (d, J = 2.4 Hz, 1H), 7.30 (dd, $J_1$ = 2.4 Hz, $J_2$ = 8.8 Hz, 1H), 6.94-6.92 (m, 3H), 6.80-6.77 (m, 1H), 2.14-2.13 (m, 1H), 1.68 (s, 2H), 1.52-1.23 (m, 8H), 1.18 (s, 2H), 0.85 (s, 6H). LC-MS: m/z 503.3 (M + H)+ |
| 385 | 255 | VI.61 | 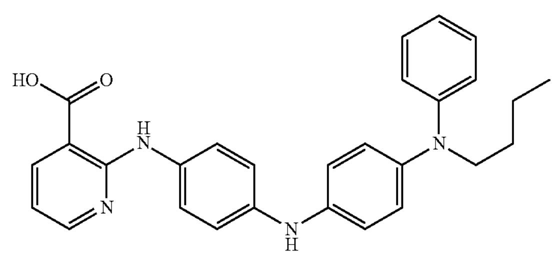 [SMILES: CCCCN(c1ccccc1)c1ccc(Nc2ccc(Nc3ncccc3C(=O)O)cc2)cc1] | $^1$H NMR (400 MHz, DMSO-d6) δ 13.49 (s, 1H), 10.29 (s, 1H), 8.33 (s, 1H), 8.21 (d, J = 6.4 Hz, 1H), 8.08-8.05 (bs, 1H), 7.60-7.52 (bs, 2H), 7.22-6.46 (m, 12H), 3.60-3.58 (bs, 2H), 1.60-1.54 (bs, 2H), 1.33 (bs, 2H), 0.85 (t, J = 6.8 Hz, 3H). LC-MS: m/z 453.3 (M + H)+ |
| 386 | 256 | XV.44 | 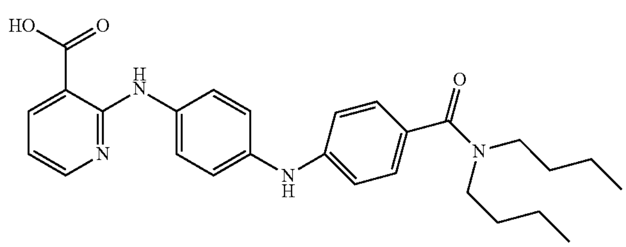 [SMILES: CCCCN(CCCC)C(=O)c1ccc(Nc2ccc(Nc3ncccc3C(=O)O)cc2)cc1] | $^1$H NMR (400 MHz, DMSO-d6) δ 13.5 (bs, 1H), 10.42 (bs, 1H), 8.31-8.26 (m, 2H), 8.18 (d, J = 7.6 Hz, 1H), 7.57 (d, J = 8.4 Hz, 2H), 7.16-7.06 (m, 4H), 6.94 (d, J = 8.4 Hz, 2H), 6.77 (dd, $J_1$ = 4.8 Hz, $J_2$ = 7.6 Hz, 1H), 3.27 (m, 6H), 1.84-1.45 (m, 4H), 1.30-1.1 (m, 4H), 0.90-0.70 (m, 6H). LC-MS: m/z 461.3 (M + H)+ |
| 387 | 257 | XV.45 | 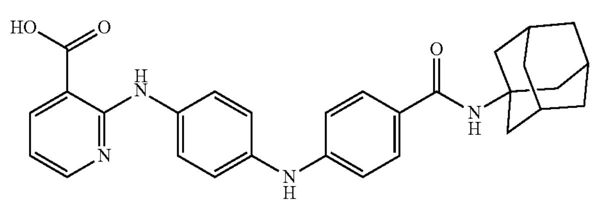 [SMILES: O=C(NC12CC3CC(CC(C3)C1)C2)c1ccc(Nc2ccc(Nc3ncccc3C(=O)O)cc2)cc1] | $^1$H NMR (400 MHz, DMSO-d6) δ 10.34 (s, 1H), 8.50-8.40 (bs, 1H), 8.34-8.25 (m, 2H), 7.66 (d, J = 8.4 Hz, 2H), 7.60 (d, J = 8.4 Hz, 2H), 7.25 (s, 1H), 7.13 (d, J = 8.8 Hz, 2H), 6.97 (d, J = 8.8 Hz, 2H), 6.84 (dd, $J_1$ = 4.8 Hz, $J_2$ = 7.6 Hz, 1H), 2.06 (s, 9H), 1.65 (s, 6H). LC-MS: m/z 483.1 (M + H)+ |

| CP | Compound No | Reactant | Structure | Analytical data |
|---|---|---|---|---|
| 388 | 258 | VI.63 | 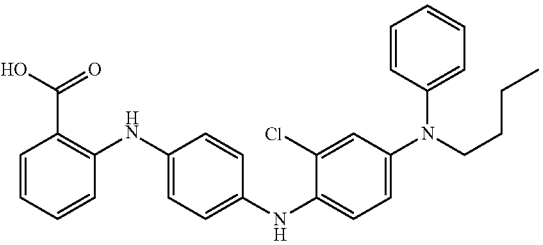 [SMILES: CCCCN(c1ccccc1)c1ccc(Nc2ccc(Nc3ccccc3C(=O)O)cc2)c(Cl)c1] | $^1$H NMR (400 MHz, DMSO-d6) δ 12.9 (s, 1H), 9.46 (s, 1H), 7.85 (dd, J$_1$ = 1.6 Hz, J$_2$ = 8.4 Hz, 1H), 7.52 (s, 1H), 7.34-7.30 (m, 1H), 7.26-7.18 (m, 3H), 7.11 (d, J = 8.8 Hz, 2H), 7.04 (d, J = 2.4 Hz, 1H), 7.00-6.97 (m, 3H), 6.91-6.84 (m, 4H), 6.67 (t, J = 8.0 Hz, 1H), 3.62 (t, J = 7.2 Hz, 2H), 1.58-1.50 (m, 2H), 1.38-1.29 (m, 2H), 0.88 (t, J = 7.6 Hz, 3H). LC-MS: m/z 486.2 (M + H)$^+$ |
| 389 | 259 | VI.64 | 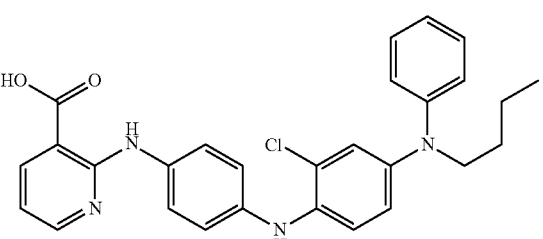 | $^1$H NMR (400 MHz, DMSO-d6) δ 13.24 (s, 1H), 10.2 (s, 1H), 8.32 (s, 1H), 8.22 (d, J = 7.6 Hz, 1H), 7.53 (bs, 2H), 7.22-6.84 (m, 12H), 3.51 (bs, 2H), 1.54 (s, 2H), 1.34-1.23 (m, 2H), 0.88 (t, J = 6.8 Hz, 3H). LC-MS: m/z 487.2 (M + H)$^+$ |
| 392 | 260 | XVIII.5 | 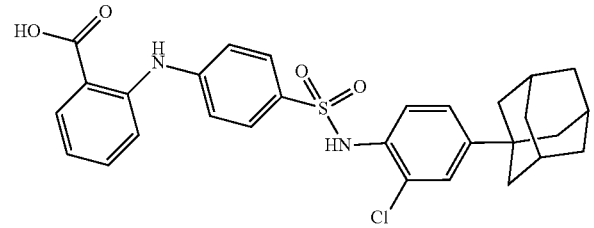 [SMILES: O=C(O)c1ccccc1Nc1ccc(S(=O)(=O)Nc2ccc(C34CC5CC(CC(C5)C3)C4)cc2Cl)cc1] | $^1$H NMR (400 MHz, DMSO-d6) δ 13.40-13.20 (bs, 1H), 9.79 (s, 1H), 9.70 (s, 1H), 7.95 (dd, J$_1$ = 1.2 Hz, J$_2$ = 8.0 Hz, 1H), 7.62 (d, J = 8.8 Hz, 2H), 7.52-7.43 (m, 2H), 7.32-7.25 (m, 4H), 7.25-7.20 (m, 1H), 6.99-6.95 (m, 1H), 2.02 (s, 3H), 1.79 (d, J = 2.4 Hz, 6H), 1.67 (s, 6H). LC-MS: m/z 537.2 (M + H)$^+$ |
| 393 | 261 | XVIII.6 | 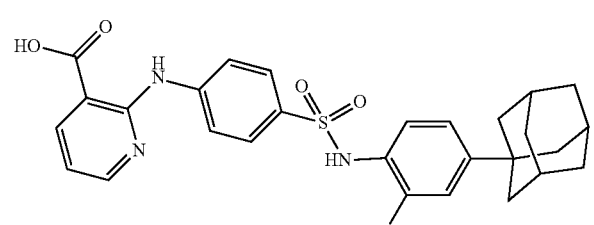 | $^1$H NMR (400 MHz, DMSO-d6) δ 13.8 (bs, 1H), 10.85 (s, 1H), 9.71 (s, 1H), 8.46 (dd, J$_1$ = 2.0 Hz, J$_2$ = 4.8 Hz, 1H), 8.31 (dd, J$_1$ = 1.6 Hz, J$_2$ = 7.6 Hz, 1H), 7.92 (d, J = 8.8 Hz, 2H), 7.66 (d, J = 8.8 Hz, 2H), 7.30 (d, J = 2.0 Hz, 1H), 7.26 (dd, J$_1$ = 2.0 Hz, J$_2$ = 8.4 Hz, 1H), 7.17 (d, J = 8.0 Hz, 1H), 6.99 (dd, J$_1$ = 5.2 Hz, J$_2$ = 8.0 Hz, 1H), 2.02 (s, 3H), 1.79 (s, 6H), 1.66 (s, 6H). LC-MS: m/z 538.0 (M + H)$^+$ |
| 394 | 262 | XV.46 | 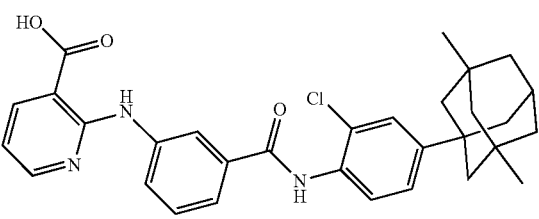 [SMILES: CC12CC3CC(C)(C1)CC(c1ccc(NC(=O)c4cccc(Nc5ncccc5C(=O)O)c4)c(Cl)c1)(C3)C2] | $^1$H NMR (400 MHz, DMSO-d6) δ 13.70 (bs, 1H), 10.80 (bs, 1H), 9.94 (s, 1H), 8.40 (dd, J$_1$ = 2.0 Hz, J$_2$ = 4.8 Hz, 1H), 8.27 (dd, J$_1$ = 2.0 Hz, J$_2$ = 7.6 Hz, 1H), 8.20 (s, 1H), 8.07 (d, J = 7.6 Hz, 1H), 7.60 (d, J = 8.0 Hz, 1H), 7.53 (d, J = 8.4 Hz, 1H), 7.49-7.46 (m, 2H), 7.37 (dd, J$_1$ = 2.0, J$_2$ = 8.4 Hz, 1H), 6.90 (dd, J$_1$ = 4.4 Hz, J$_2$ = 7.2 Hz, 1H), 2.16-2.15 (m, 1H), 1.71 (s, |

| CP | Compound No | Reactant | Structure | Analytical data |
|---|---|---|---|---|
| | | | | 2H), 1.56-1.34 (m, 8H), 1.20 (s, 2H), 0.87 (s, 6H). LC-MS: m/z 503.2 (M + H)⁺ |
| 395 | 263 | XII.64 | 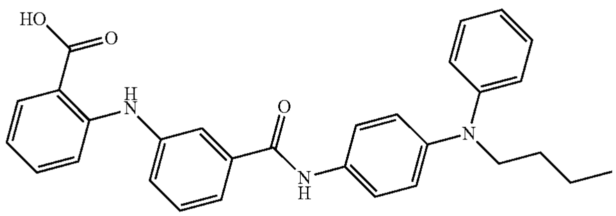 [SMILES: CCCCN(c1ccccc1)c1ccc(NC(=O)c2cccc(Nc3ccccc3C(=O)O)c2)cc1] | ¹H NMR (400 MHz, DMSO-d6) δ 11.40-11.0 (bs, 1H), 10.17 (s, 1H), 7.92 (d, J = 7.2 Hz, 1H), 7.73-7.69 (m, 3H), 7.51 (d, J = 7.2 Hz, 1H), 7.45-7.38 (m, 2H), 7.29 (d, J = 2.4 Hz, 2H), 7.22-7.18 (m, 2H), 7.03 (d, J = 8.8 Hz, 2H), 6.86-6.74 (m, 4H), 3.65 (t, J = 7.2 Hz, 2H), 1.56-1.53 (m, 2H), 1.36-1.3 (m, 2H), 0.88 (t, J = 7.6 Hz, 3H). LC-MS: m/z 480.3 (M + H)⁺ |
| 396 | 264 | XVIII.7 | 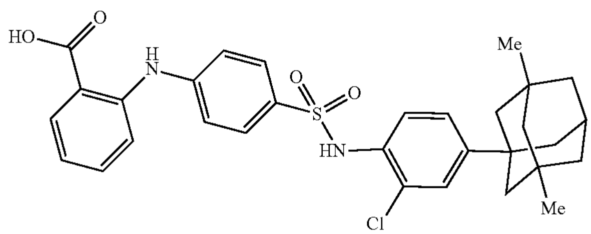 [SMILES: CC12CC3CC(C)(C1)CC(c1ccc(NS(=O)(=O)c4ccc(Nc5ccccc5C(=O)O)cc4)c(Cl)c1)(C3)C2] | ¹H NMR (400 MHz, DMSO-d6) δ 13.31 (s, 1H), 9.80 (s, 1H), 9.73 (s, 1H), 7.94 (dd, J₁ = 1.6 Hz, J₂ = 8.0 Hz, 1H), 7.60 (d, J = 8.8 Hz, 2H), 7.52-7.43 (m, 2H), 7.32-7.24 (m, 4H), 7.16 (d, J = 8.4 Hz, 1H), 6.97 (t, J = 7.6 Hz, 1H), 2.11-2.09 (m, 1H), 1.62 (s, 2H), 1.42-1.32 (m, 8H), 1.15 (s, 2H), 0.83 (s, 6H). LC-MS: m/z 565.2 (M + H)⁺ |
| 397 | 265 | XVIII.8 | 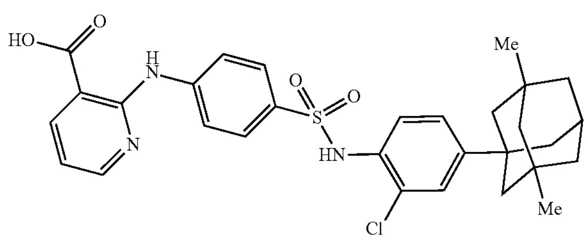 [SMILES: CC12CC3CC(C)(C1)CC(c1ccc(NS(=O)(=O)c4ccc(Nc5ncccc5C(=O)O)cc4)c(Cl)c1)(C3)C2] | ¹H NMR (400 MHz, DMSO-d6) δ 13.80 (bs, 1H), 10.80 (s, 1H), 9.69 (s, 1H), 8.46 (dd, J₁ = 1.6 Hz, J₂ = 4.4 Hz, 1H), 8.30 (dd, J₁ = 1.6 Hz, J₂ = 7.6 Hz, 1H), 7.92 (d, J = 9.2 Hz, 2H), 7.65 (d, J = 8.8 Hz, 2H), 7.29 (d, J = 2.0 Hz, 1H), 7.25 (dd, J₁ = 2.0 Hz, J2 = 8.4 Hz, 1H), 7.16 (d, J = 8.4 Hz, 1H), 6.99 (dd, J₁ = 4.8 Hz, J₂ = 7.6 Hz, 1H), 2.11-2.09 (m, 1H), 1.62 (s, 2H), 1.46-1.29 (m, 8H), 1.15 (s, 2H), 0.82 (s, 6H). LC-MS: m/z 566.2 (M + H)⁺ |
| 398 | 266 | XII.65 | 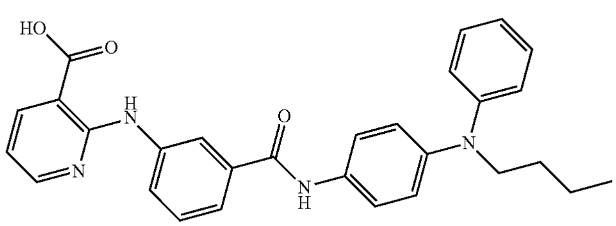 [SMILES: CCCCN(c1ccccc1)c1ccc(NC(=O)c2cccc(Nc3ncccc3C(=O)O)c2)cc1] | ¹H NMR (400 MHz, DMSO-d6) δ 13.7 (s, 1H), 10.61 (s, 1H), 10.22 (s, 1H), 8.43 (dd, J₁ = 2.0 Hz, J₂ = 4.8 Hz, 1H), 8.28 (dd, J₁ = 2.0 Hz, J₂ = 7.6 Hz, 1H), 8.14 (s, 1H), 8.05 (s, 1H), 7.71 (d, J = 8.8 Hz, 2H), 7.52 (s, 1H), 7.47 (s, 1H), 7.23-7.21 (m, 2H), 7.04 (d, J = 8.8 Hz, 2H), 6.92-6.80 (m, 4H), 3.66 (t, J = 7.2 Hz, 2H), 1.57-1.53 (m, 2H), 1.36-1.31 (m, 2H), 0.88 (t, J = 7.6 Hz, 3H). LC-MS: m/z 481.2 (M + H)⁺ |

| CP | Compound No | Reactant | Structure | Analytical data |
|---|---|---|---|---|
| 407 | 267 | XV.47 | 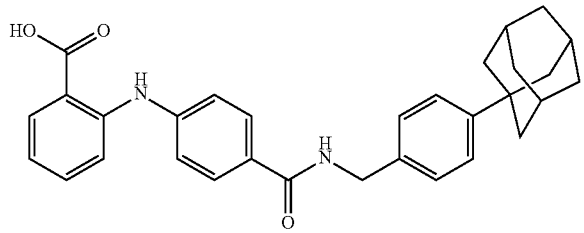 [SMILES: O=C(NCc1ccc(C23CC4CC(CC(C4)C2)C3)cc1)c1ccc(Nc2ccccc2C(=O)O)cc1] | ¹H NMR (400 MHz, DMSO-d6) δ 13.19 (s, 1H), 9.78 (s, 1H), 8.85 (t, J = 5.8 Hz, 1H), 7.93 (dd, J₁ = 1.5 Hz, J₂ = 8.3 Hz, 1H), 7.87 (d, J = 8.3 Hz, 2H), 7.49-7.40 (m, 2H), 7.32-7.23 (m, 6H), 6.89 (t, J = 6.9 Hz, 1H), 4.43 (d, J = 5.9 Hz, 2H), 2.05 (s, 3H), 1.85 (s, 6H), 1.73 (s, 6H). LC-MS: m/z 481.3 (M + H)⁺ |
| 408 | 268 | XV.48 | 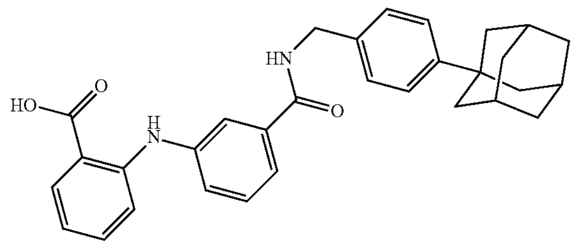 [SMILES: O=C(NCc1ccc(C23CC4CC(CC(C4)C2)C3)cc1)c1cccc(Nc2ccccc2C(=O)O)c1] | ¹H NMR (400 MHz, DMSO-d6) δ 12.00 (bs, 1H), 8.96 (t, J = 5.9 Hz, 1H), 7.91 (d, J = 7.8 Hz, 1H), 7.64 (s, 1H), 7.38-7.16 (m, 10H), 6.68 (t, J = 7.4 Hz, 1H), 4.41 (d, J = 5.9 Hz, 2H), 2.04 (s, 3H), 1.84 (s, 6H), 1.72 (s, 6H). LC-MS: m/z 481.3 (M + H)⁺ |
| 420 | 269 | XII.66 | 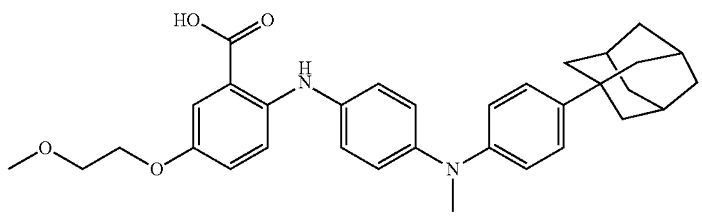 | ¹H NMR (400 MHz, DMSO-d6) δ 13.2-13.0 (bs, 1H) 9.3-9.0 (bs, 1H), 7.38 (d, J = 2.8 Hz, 1H), 7.24-7.22 (m, 2H), 7.11-7.05 (m, 4H), 6.98-6.96 (m, 2H), 6.89 (d, J = 9.2 Hz, 2H), 4.04-4.02 (m, 2H), 3.64-3.62 (m, 2H), 3.21 (s, 2H), 2.04 (s, 3H), 1.83 (s, 6H), 1.72 (s, 6H). LC-MS: m/z 572.3 (M + H)⁺ |
| 453 | 35 | XII.70 | 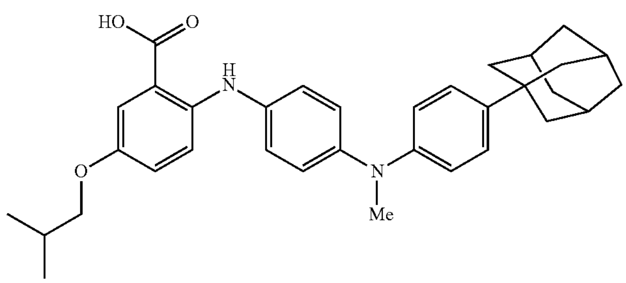 [SMILES: CC(C)COc1ccc(Nc2ccc(N(C)c3ccc(C45CC6CC(CC(C6)C4)C5)cc3)cc2)c(C(=O)O)c1] | 1H NMR (400 MHz, DMSO-d6): δ 13.10 (s, 1H), 9.12 (s, 1H), 7.37 (d, J = 2.0 Hz, 1H), 7.23 (d, J = 8.4 Hz, 2H), 7.10 (d, J = 9.2 Hz, 2H), 7.05 (dd, J1 = 2.8 Hz, J2 = 9.2 Hz, 2H), 6.97 (d, J = 8.8 Hz, 2H), 6.89 (d, J = 8.8 Hz, 2H), 3.68 (d, J = 6.4 Hz, 2H), 3.21 (s, 3H), 2.04 (s, 3H), 2.01-1.98 (m, 1H), 1.83 (d, J = 2.6 Hz, 6H), 1.72 (s, 6H), 0.97 (d, J = 6.8 Hz, 6H). LC-MS: m/z 525.3 (M + H)+ |
| 473 | 36 | Compound 20 | 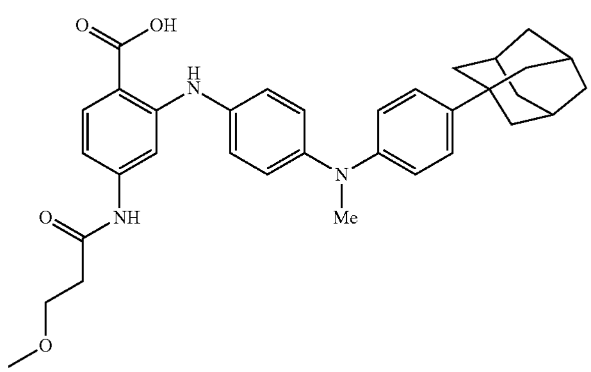 [SMILES: COCCC(=O)Nc1ccc(C(=O)O)c(Nc2ccc(N(C)c3ccc(C45CC6CC(CC(C6)C4)C5)cc3)cc2)c1] | 1H-NMR (400 MHz, DMSO-d6): 12.67 (s, 1H), 10.01 (s, 1H), 9.57 (s, 1H), 7.78 (d, J = 8.8 Hz, 1H), 7.43 (s, 1H), 7.27 (d, J = 8.4 Hz, 2H), 7.15 (d, J = 8.4 Hz, 2H), 7.01-6.95 (m, 5H), 3.57 (t, J = 5.6 Hz, 2H), 3.24 (s, 3H), 3.21 (s, 3H), 2.04 (s, 3H), 1.85 (s, 6H), 1.73 (s, 6H). LC-MS: m/z 554.3 (M + H)+ |

-continued

| CP | Compound No | Reactant | Structure | Analytical data |
|---|---|---|---|---|
| 521 | 37 | XII.71 | 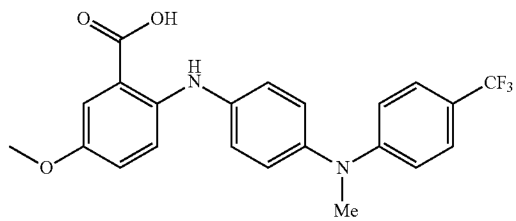 [SMILES: COc1ccc(Nc2ccc(N(C)c3ccc(C(F)(F)F)cc3)cc2)c(C(=O)O)c1] | 1H NMR (400 MHz, DMSO-d6): δ 13.20 (bs, 1H), 9.22 (bs, 1H), 7.46 (d, J = 8.8 Hz, 2H), 7.41 (d, J = 2.8 Hz, 1H), 7.29 (d, J = 9.2 Hz, 1H), 7.23-7.09 (m, 5H), 6.81 (d, J = 8.8 Hz, 2H), 3.74 (s, 3H), 3.27 (s, 3H). LC-MS: m/z 417.2 (M + H)+. |
| 522 | 38 | XII.72 | 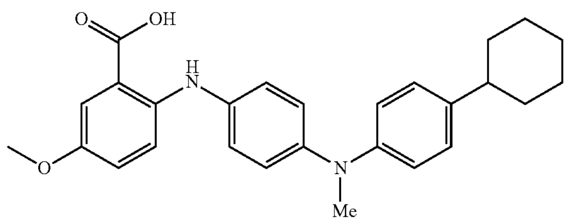 [SMILES: COc1ccc(Nc2ccc(N(C)c3ccc(C4CCCCC4)cc3)cc2)c(C(=O)O)c1] | 1H NMR (400 MHz, DMSO-d6): δ 13.09 (bs, 1H), 9.08 (s, 1H), 7.35 (d, J = 2.8 Hz, 1H), 7.10-7.02 (m, 6H), 6.94 (d, J = 8.8 Hz, 2H), 6.85 (d, J = 8.8 Hz, 2H), 3.69 (s, 3H), 3.18 (s, 3H), 2.42-2.39 (m, 1H), 1.76-1.65 (m, 5H), 1.38-1.20 (m, 5H). LC-MS: m/z 431.2 (M + H)+. |
| 525 | 39 | XII.73 | 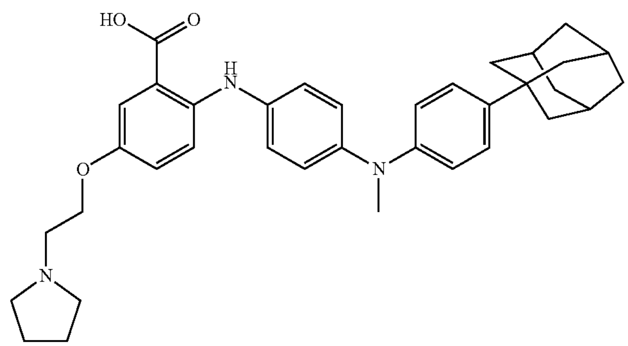 [SMILES: CN(c1ccc(Nc2ccc(OCCN3CCCC3)cc2C(=O)O)cc1)c1ccc(C23CC4CC(CC(C4)C2)C3)cc1] | 1H NMR (400 MHz, CDCl3) δ 7.71 (s, 1H), 7.26-7.12 (m, 5H), 6.99 (d, J = 8 Hz, 2H), 6.88-6.83 (m, 3H), 4.41 (s, 2H), 3.49-3.22 (m, 10H), 2.10-2.07 (m, 7H), 1.89 (s, 5H), 1.79-1.75 (s, 6H). LC-MS: m/z 566.3 (M + H)+. |
| 526 | 40 | XII.74 | 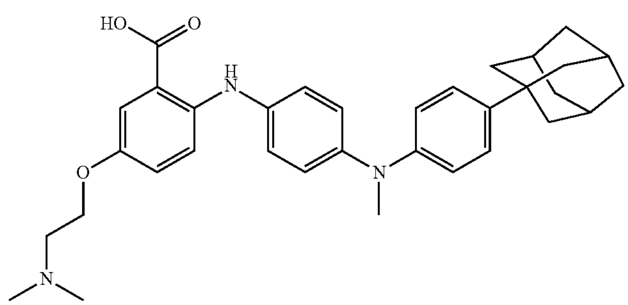 [SMILES: CN(C)CCOc1ccc(Nc2ccc(N(C)c3ccc(C45CC6CC(CC(C6)C4)C5)cc3)cc2)c(C(=O)O)c1] | 1H NMR (400 MHz, DMSO-d6): δ 7.46 (d, J = 2 Hz, 1H), 7.22 (d, J = 8.4 Hz, 2H), 7.12-7.04 (m, 4H), 6.97 (d, J = 8 Hz, 2H), 6.88 (d, J = 8.4 Hz, 2H), 4.13 (t, J = 5.2 Hz, 2H), 3.2 (s, 3H), 3.06 (s, 2H), 2.55 (s, 6H), 2.04 (s, 3H), 1.83 (s, 6H), 1.72 (s, 6H). LC-MS: m/z 540.3 (M + H)+. |
| 527 | 41 | XII.75 | 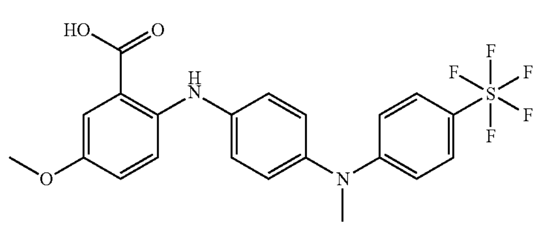 [SMILES: COc1ccc(Nc2ccc(N(C)c3ccc(S(F)(F)(F)(F)F)cc3)cc2)c(C(=O)O)c1] | 1H NMR (400 MHz, DMSO-d6): δ 13.18 (s, 1H), 9.25 (s, 1H), 7.61 (dd, J1 = 2.4 & J2 = 7.6 Hz, 2H), 7.41 (d, J = 3.2 Hz, 1H), 7.30 (d, J = 9.2 Hz, 1H), 7.23-7.16 (m, 4H), 7.09 (dd, J1 = 3.2 Hz, & J2 = 9.2 Hz, 1H), 6.73 (d, J = 9.2 Hz, 2H), 3.74 (s, 3H), 3.27 (s, 3H). LC-MS: m/z 475.1 (M + H)+. |

-continued

| CP | Compound No | Reactant | Structure | Analytical data |
|---|---|---|---|---|
| 535 | 42 | XII.76 | 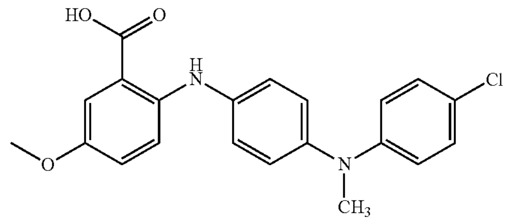 [SMILES: COc1ccc(Nc2ccc(N(C)c3ccc(Cl)cc3)cc2)c(C(=O)O)c1] | 1H NMR (400 MHz, DMSO-d6): δ 13.15 (s, 1H), 9.10 (s, 1H), 7.39 (d, J = 3.2 Hz, 1H), 7.23-7.16 (m, 5H), 7.11-7.07 (m, 3H), 6.81 (dd, J1 = 2.4 Hz, & J2 = 6.8 Hz, 2H), 3.73 (s, 3H), 3.21 (s, 3H). LC-MS: m/z 382.84 (M + H)+ |
| 536 | 43 | XII.77 | 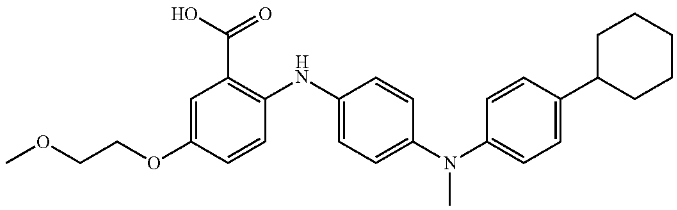 [SMILES: COCCOc1ccc(Nc2ccc(N(C)c3ccc(C4CCCCC4)cc3)cc2)c(C(=O)O)c1] | 1H NMR (400 MHz, DMSO-d6): δ 7.39 (d, J = 2.8 Hz, 1H), 7.08 (d, J = 8.4 Hz, 5H), 7.03-7.02 (m, 1H), 6.95 (d, J = 8.8 Hz, 2H), 6.85 (d, J = 8.0 Hz, 2H), 4.02 (t, J = 4.0 Hz, 2H), 3.62 (t, J = 4.8 Hz, 2H), 3.30 (s, 3H), 3.19 (s, 3H), 2.46-2.42 (m, 1H), 1.77-1.65 (m, 5H), 1.37-1.23 (m, 5H). LC-MS: m/z 474.3 (M + H)+. |
| 537 | 44 | XII.78 | 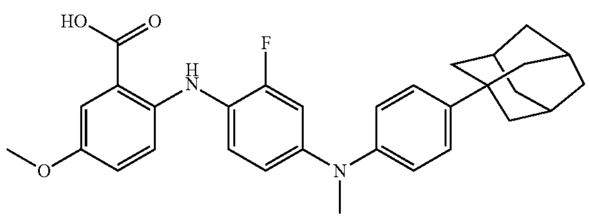 [SMILES: COc1ccc(Nc2ccc(N(C)c3ccc(C45CC6CC(CC(C6)C4)C5)cc3)cc2F)c(C(=O)O)c1] | 1H NMR (400 MHz, DMSO-d6): δ 13.18 (bs, 1H), 8.95 (s, 1H), 7.37-7.32 (m, 3H), 7.22 (t, J = 9.2 Hz, 1H), 7.08-7.03 (m, 3H), 6.83-6.75 (m, 2H), 6.66 (d, J = 8.4 Hz, 1H), 3.70 (s, 3H), 3.23 (s, 3H), 2.05 (s, 3H), 1.86 (s, 6H), 1.73 (s, 6H). LC-MS: m/z 501.3 (M + H)+. |
| 538 | 45 | XII.79 | 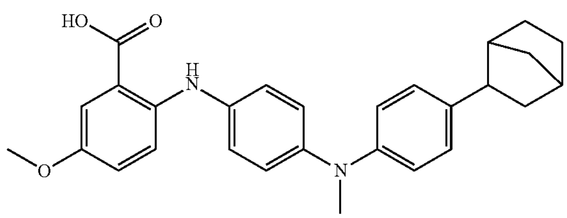 [SMILES: COc1ccc(Nc2ccc(N(C)c3ccc(C4CC5CCC4C5)cc3)cc2)c(C(=O)O)c1] | 1H NMR (400 MHz, DMSO-d6): δ 11.6-11.2 (bs, 1H), 7.47 (s, 1H), 7.09 (d, J = 8.8 Hz, 1H), 7.04-7.01 (m, 4H), 6.94 (d, J = 8.8 Hz, 2H), 6.81-6.78 (m, 1H), 6.74 (d, J = 8.4 Hz, 2H), 3.68 (s, 3H), 3.16 (s, 3H), 2.61-2.59 (m, 1H), 2.29 (s, 1H), 2.19 (s, 1H), 1.66-1.65 (m, 1H), 1.58-1.51 (m, 3H), 1.44 (d, J = 10 Hz, 1H), 1.31-1.21 (m, 2H), 1.11-1.09 (m, 1H). LC-MS: m/z 443.2 (M + H)+. |
| 541 | 46 | XII.80 | 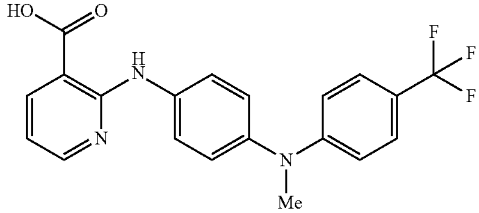 [SMILES: CN(c1ccc(Nc2ncccc2C(=O)O)cc1)c1ccc(C(F)(F)F)cc1] | 1H NMR (400 MHz, DMSO-d6): δ 10.48 (s, 1H), 8.39 (dd, J1 = 2.0 Hz & J2 = 4.8 Hz, 1H), 8.27 (dd, J1 = 2 Hz, & J2 = 8.0 Hz, 1H), 7.78 (d, J = 8.8 Hz, 2H), 7.46 (d, J = 8.8 Hz, 2H), 7.21 (d, J = 8.8 Hz, 2H), 6.90-6.87 (m, 1H), 6.82 (d, J = 8.8 Hz, 2H), 3.29 (s, 3H). LC-MS: m/z 388.1 (M + H)+. |

-continued

| CP | Compound No | Reactant | Structure | Analytical data |
|---|---|---|---|---|
| 542 | 47 | XII.81 | 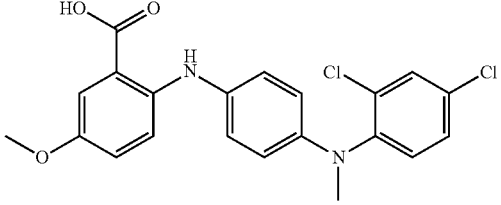 [SMILES: COc1ccc(Nc2ccc(N(C)c3ccc(Cl)cc3Cl)cc2)c(C(=O)O)c1] | 1H NMR (400 MHz, DMSO-d6): δ 13.10-12.90 (bs, 1H), 9.02 (s, 1H), 7.23 (d, J = 2.0 Hz, 1H), 7.49 (dd, J1 = 2.0 Hz & J2 = 8.0 Hz, 1H), 7.40 (d, J = 8.8 Hz, 1H), 7.35 (d, J = 2.4 Hz, 2H), 7.05-6.94 (m, 4H), 6.60 (d, J = 8.8 Hz, 2H), 3.70 (s, 3H), 3.19 (s, 3H). LC-MS: m/z 419.1 (M + H)+. |
| 543 | 48 | XII.82 | 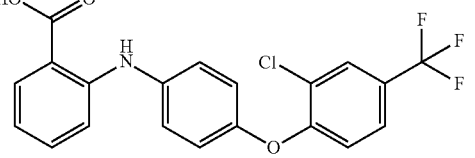 | 1H NMR (400 MHz, DMSO-d6): δ 13.1 (bs, 1H), 9.63 (s, 1H), 8.03 (d, J = 2 Hz, 1H), 7.92-7.90 (m, 1H), 7.69 (dd, J1 = 1.6 Hz, & J2 = 8.8 Hz, 1H), 7.40-7.33 (m, 3H), 7.21-7.10 (m, 4H), 6.81-6.77 (m, 1H). LC-MS: m/z 408 (M + H)+. |
| 544 | 49 | XII.83 | 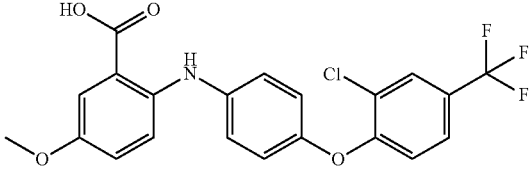 [SMILES: COc1ccc(Nc2ccc(Oc3ccc(C(F)(F)F)cc3Cl)cc2)c(C(=O)O)c1] | 1H NMR (400 MHz, DMSO-d6): δ 13.22 (bs, 1H), 9.17 (s, 1H), 8.01 (d, J = 2 Hz, 1H), 7.67 (dd, J1 = 1.6 Hz, & J2 = 8.8 Hz, 1H), 7.40 (d, J = 3.2 Hz, 1H), 7.26-7.23 (m, 3H), 7.12-7.07 (m, 4H), 3.73 (s, 3H). LC-MS: m/z 438.0 (M + H)+. |
| 545 | 50 | XII.84 | 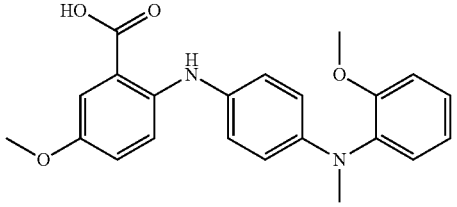 [SMILES: COc1ccc(Nc2ccc(N(C)c3ccccc3OC)cc2)c(C(=O)O)c1] | 1H NMR (400 MHz, DMSO-d6): δ 12.96 (bs, 1H), 8.97 (bs, 1H), 7.33 (d, J = 2.8 Hz, 1H), 7.27 (t, J = 7.8 Hz, 1H), 7.18 (d, J = 8.0 Hz, 1H), 7.12 (d, J = 8.0 Hz, 1H), 7.01-6.96 (m, 4H), 6.89 (d, J = 8.8 Hz, 1H), 6.33 (d, J = 8.8 Hz, 2H), 3.73 (s, 3H), 3.69 (s, 3H), 3.17 (s, 3H). LC-MS: m/z 379.2 (M + H)+. |
| 546 | 51 | XII.85 | 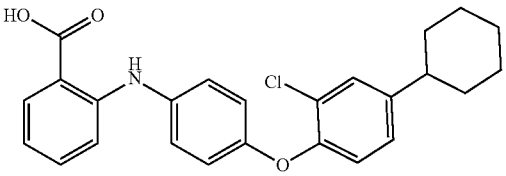 [SMILES: O=C(O)c1ccccc1Nc1ccc(Oc2ccc(C3CCCCC3)cc2Cl)cc1] | 1H NMR (400 MHz, DMSO-d6): δ 13.03 (s, 1H), 9.54 (s, 1H), 7.88 (d, J = 8 Hz, 1H), 7.42-7.34 (m, 2H), 7.26-7.20 (m, 3H), 7.09 (d, J = 8.4 Hz, 1H), 7.02 (d, J = 8.4 Hz, 1H), 6.95 (d, J = 8 Hz, 2H), 6.74 (t, J = 7.2 Hz, 1H), 1.80-1.67 (m, 5H), 1.44-1.11 (m, 6H). LC-MS: m/z 422.1 (M + H)+. |
| 547 | 52 | XII.86 | 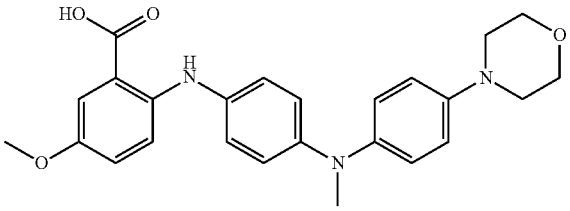 [SMILES: COc1ccc(Nc2ccc(N(C)c3ccc(N4CCOCC4)cc3)cc2)c(C(=O)O)c1] | 1H NMR (400 MHz, DMSO-d6): δ 13.0 (s, 1H), 9.1 (s, 1H), 7.35 (d, J = 2.8 Hz, 1H), 7.04-6.91 (m, 8H), 6.79 (d, J = 8.8 Hz, 2H), 3.74-3.70 (m, 7H), 3.17 (s, 3H), 3.06-3.04 (m, 4H). LC-MS: m/z 434.2 (M + H)+. |

| CP | Compound No | Reactant | Structure | Analytical data |
|---|---|---|---|---|
| 548 | 53 | XII.87 | (structure) | 1H NMR (400 MHz, DMSO-d6): δ 13.2 (s, 1H), 9.2 (s, 1H), 7.39 (d, J = 3.2 Hz, 1H), 7.24-7.09 (m, 8H), 6.84 (d, J = 8.8 Hz, 2H), 3.73 (s, 3H), 3.23 (s, 3H). LC-MS: m/z 433.1 (M + H)+. |
| 549 | 54 | XII.88 | (structure) | 1H NMR (400 MHz, DMSO-d6): δ 13.15 (bs, 1H), 8.94 (s, 1H), 7.37 (d, J = 2.8 Hz, 1H), 7.24-7.19 (m, 3H), 7.06-7.03 (m, 3H), 6.82-6.74 (m, 2H), 6.64 (dd, J1 = 2 Hz, & J2 = 8.8 Hz, 1H), 3.70 (s, 3H), 3.23 (s, 3H), 2.46-2.42 (m, 1H), 1.80-1.68 (m, 5H), 1.40-1.21 (m, 5H). LC-MS: m/z 449.2 (M + H)+. |
| 550 | 55 | XII.89 | (structure) | 1H NMR (400 MHz, DMSO-d6): δ 13.1 (bs, 1H), 9.1 (bs, 1H), 7.39 (dd, J1 = 2.8 & J2 = 9.2 Hz, 2H), 7.20-7.13 (m, 4H), 7.08-7.05 (m, 1H), 6.98-6.90 (m, 3H), 3.72 (s, 3H), 1.79-1.67 (m, 5H), 1.40-1.33 (m, 5H), one proton merged in DMSO. LC-MS: m/z 452.1 (M + H)+. |
| 551 | 56 | XII.90 | (structure) | 1H NMR (400 MHz, DMSO-d6): δ 13.07 (bs, 1H), 8.95 (s, 1H), 7.27 (d, J = 3.2 Hz, 1H), 7.23 (dd, J1 = 6.8 Hz & J2 = 8.8 Hz, 2H), 7.13 (d, J = 8.4 Hz, 1H), 7.03 (dd, J1 = 3.2 Hz & J2 = 9.2 Hz, 1H), 6.94-6.89 (m, 3H), 6.82-6.76 (m, 2H), 3.70 (s, 3H), 3.21 (s, 3H), 3.21 (s, 3H), 1.98 (s, 3H), 1.84 (s, 6H), 1.69 (s, 6H). LC-MS: m/z 497.3 (M + H)+. |
| 552 | 57 | XII.91 | (structure) | 1H NMR (400 MHz, DMSO-d6): δ 13.1 (s, 1H), 9.11 (s, 1H), 7.38 (d, J = 2.8 Hz, 1H), 7.14-7.05 (m, 6H), 6.98 (d, J = 8.8 Hz, 2H), 6.86 (d, J = 8 Hz, 2H), 3.71 (s, 3H), 3.20 (s, 3H), 2.67-2.59 (m, 1H), 2.08-1.83 (m, 6H), 1.66-1.56 (m, 2H). LC-MS: m/z 467.2 (M + H)+. |
| 553 | 58 | XII.92 | (structure) | 1H NMR (400 MHz, DMSO-d6): δ 13.06 (bs, 1H), 9.07 (bs, 1H), 7.37 (s, 1H), 7.08-7.0 (m, 8H), 6.87 (d, J = 7.6 Hz, 2H), 4.70 (q, J = 8.8 Hz, 2H), 3.71 (s, 3H), 3.19 (s, 3H). LC-MS: m/z 447 (M + H)+. |

| CP | Compound No | Reactant | Structure | Analytical data |
|---|---|---|---|---|
| 554 | 59 | XII.93 | (structure) | 1H NMR (400 MHz, DMSO-d6): δ 13.0 (bs, 1H), 9.1 (bs, 1H), 7.37 (d, J = 2.8 Hz, 1H), 7.11-7.06 (m, 6H), 6.95-6.85 (m, 4H), 3.71 (s, 3H), 3.19 (s, 3H), 2.23 (s, 3H). LC-MS: m/z 363.1 (M + H)+. |
| 555 | 60 | XII.94 | (structure) | 1H NMR (400 MHz, DMSO-d6): δ 13.2 (s, 1H), 11.73 (s, 1H), 9.1 (s, 1H), 7.59 (brm, 2H), 7.40-7.12 (brm, 7H), 6.84 (brm, 2H), 3.73 (s, 3H), 3.41-3.25 (brm, 7H), 2.01-1.77 (brm, 5H), 1.53 (brm, 1H). LC-MS: m/z 432.4 (M + H)+. |
| 556 | 61 | XII.95 | (structure) | 1H NMR (400 MHz, DMSO-d6): δ 13.1 (bs, 1H), 9.12 (bs, 1H), 7.37 (d, J = 3.2 Hz, 1H), 7.13-7.04 (m, 6H), 6.96 (d, J = 8.8 Hz, 2H), 6.89 (d, J = 8.4 Hz, 2H), 3.71 (s, 3H), 3.45-3.41 (m, 1H), 3.20 (s, 3H), 2.25-2.22 (m, 2H), 2.07-1.91 (m, 3H), 1.82-1.77 (m, 1H). LC-MS: m/z 403.2 (M + H)+. |
| 557 | 62 | XII.96 | (structure) | 1H NMR (400 MHz, DMSO-d6): δ 13.15 (bs, 1H), 9.18 (bs, 1H), 7.39 (d, J = 2.8 Hz, 1H), 7.30 (d, J = 8.8 Hz, 2H), 7.20-7.14 (m, 3H), 7.10-7.05 (m, 3H), 6.82 (d, J = 8.8 Hz, 2H), 5.87 (bs, 1H), 3.72 (s, 3H), 3.23 (s, 3H), 2.73-2.61 (m, 4H), 2.18-2.11 (m, 2H). LC-MS: m/z 465.2 (M + H)+. |
| 558 | 63 | XII.97 | (structure) | 1H NMR (400 MHz, DMSO-d6): δ 10.24 (bs, 1H), 8.32 (d, J = 2.8 Hz, 1H), 8.21 (d, J = 7.6 Hz, 1H), 7.59 (d, J = 8.8 Hz, 2H), 7.08 (d, J = 8.8 Hz, 2H), 6.98 (d, J = 8.8 Hz, 2H), 6.85-6.78 (m, 3H), 3.21 (s, 3H), 2.40-2.32 (m, 1H), 1.78-1.67 (m, 5H), 1.37-1.23 (m, 5H). LC-MS: m/z 402.3 (M + H)+. |
| 560 | 64 | XII.99 | (structure) | 1H NMR (400 MHz, DMSO-d6): δ 13.04 (s, 1H), 8.94 (s, 1H), 7.37 (d, J = 2.4 Hz, 1H), 7.13-7.10 (m, 3H), 7.04-7.01 (m, 1H), 6.92-6.88 (m, 3H), 6.81-6.75 (m, 2H), 3.70 (s, 3H), 3.21 (s, 3H), 2.42-2.40 (m, 1H), 2.12 (s, 3H), 1.78-1.67 (m, 5H), 1.40-1.23 (m, 4H), 1.22 (s, 1H). LC-MS: m/z 445.3 (M + H)+. |

-continued

| Compound No | Reactant | Structure | Analytical data |
|---|---|---|---|
| 561 65 | XII.100 | | 1H NMR (400 MHz, DMSO-d6): δ 13.0 (s, 1H), 9.39 (s, 1H), 7.87 (dd, J1 = 2 Hz & J2 = 8.0 Hz, 1H), 7.49 (d, J = 2.4 Hz, 1H), 7.36-7.26 (m, 3H), 7.05 (d, J = 8.4 Hz, 1H), 6.97 (d, J = 2.4 Hz, 1H), 6.79-6.68 (m, 3H), 2.16 (s, 3H), 1.69-1.18 (m, 13H), 0.85 (s, 6H). LC-MS: m/z 515.15 (M + H)+. |
| 563 66 | XII.101 | | 1H NMR (400 MHz, DMSO-d6): δ 13.21 (s, 1H), 9.13 (s, 1H), 7.46 (d, J = 8.8 Hz, 2H), 7.41 (d, J = 2.8 Hz, 1H), 7.32 (d, J = 8.4 Hz, 1H), 7.16 (d, J = 2.4 Hz, 1H), 7.11-7.04 (m, 3H), 6.83 (d, J = 8.8 Hz, 2H), 3.73 (s, 3H), 3.28 (s, 3H), 2.21 (s, 3H). LC-MS: m/z 431.1 (M + H)+. |
| 564 67 | XII.102 | | 1H NMR (400 MHz, DMSO-d6) δ 13.1 (s, 1H), 9.0 (s, 1H), 7.48 (d, J = 2.4 Hz, 1H), 7.33 (dd, J1 = 2.0 Hz, J2 = 2.4 Hz, 3H), 7.05-6.94 (m, 3H), 6.81-6.73 (m, 2H), 3.71 (s, 3H), 2.14 (s, 3H), 1.69 (s, 2H), 1.52-1.18 (m, 11H), 0.86-0.84 (m, 6H). LC-MS: m/z 547.2 (M + 2)+ |
| 565 68 | XII.103 | | 1H NMR (400 MHz, DMSO-d6) δ 13.05 (bs, 1H), 8.91 (s, 1H), 7.36 (d, J = 2.8 Hz, 1H), 7.08 (d, J = 8.4 Hz, 1H), 7.05-6.95 (m, 5H), 6.81 (s, 1H), 6.71-6.68 (m, 2H), 4.74-4.67 (m, 2H), 3.69 (s, 3H), 3.20 (s, 3H), 2.09 (s, 3H). LC-MS: m/z 461.2 (M + H)+. |
| 566 69 | XII.104 | | 1H NMR (400 MHz, DMSO-d6) δ 13.06 (s, 1H), 9.45 (s, 1H), 8.03 (d, J = 2.4 Hz, 1H), 7.89-7.87 (m, 1H), 7.80 (dd, J1 = 2.4 Hz, J2 = 8.8 Hz, 1H), 7.40-7.34 (m, 2H), 7.26-7.20 (m, 2H), 7.10 (d, J = 8.4 Hz, 1H), 6.94 (d, J = 8.4 Hz, 1H), 6.76 (t, J = 7.2 Hz, 1H), 2.58-2.52 (m, 1H), 1.80-1.68 (m, 5H), 1.46-1.23 (m, 5H). LC-MS: m/z 423.1 (M + H)+. |

-continued

| CP | Compound No | Reactant | Structure | Analytical data |
|---|---|---|---|---|
| 567 | 70 | XIII.12 | 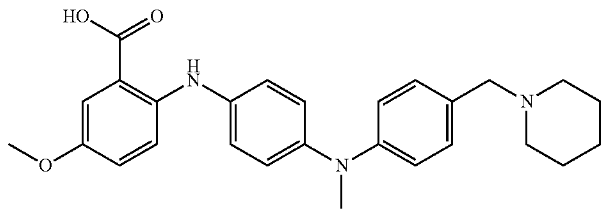 | 1H NMR (400 MHz, CDCl3): δ 7.55 (d, J = 3.2 Hz, 1H), 7.33 (d, J = 8.4 Hz, 2H), 7.24 (s, 1H), 7.16-7.14 (m, 2H), 7.08-7.06 (m, 2H), 7.03-7.0 (m, 1H), 6.76 (d, J = 8.4 Hz, 2H), 4.07 (s, 2H), 3.80 (s, 3H), 3.5 (s, 2H), 3.25 (s, 3H), 2.56 (s, 3H), 2.73 (s, 2H), 1.82 (s, 4H). LC-MS: m/z 446.2 (M + H)+ |
| 568 | 71 | XII.106 | 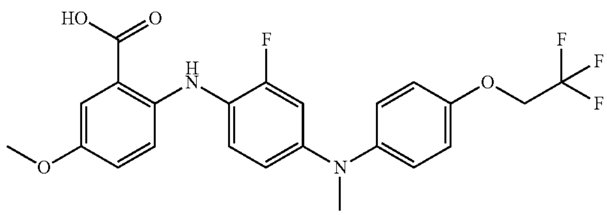 | 1H NMR (400 MHz, DMSO-d6): δ 13.15 (s, 1H), 8.9 (s, 1H), 7.36 (d, J = 2.8 Hz, 1H), 7.22-7.02 (m, 6H), 6.76 (d, J = 8.8 Hz, 1H), 6.67 (dd, J1 = 2.4 Hz & J2 = 13.6 Hz, 1H), 6.54 (dd, J1 = 2.4 Hz & J2 = 8.8 Hz, 1H), 4.75 (q, J = 8.8 Hz, 2H), 3.70 (s, 3H), 3.21 (s, 3H). LC-MS: m/z 465.1 (M + H)+. |
| 569 | 72 | XII.107 | 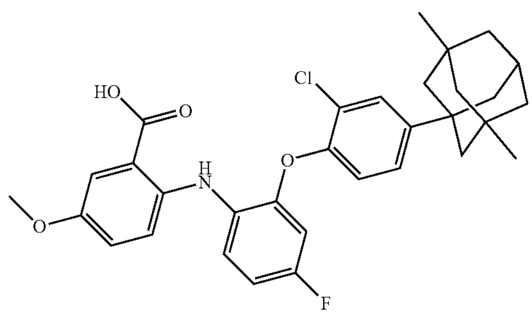 [SMILES: COc1ccc(Nc2ccc(F)cc2Oc2ccc(C34CC5CC(C)(CC(C)(C5)C3)C4)cc2Cl)c(C(=O)O)c1] | 1H NMR (400 MHz, DMSO-d6): δ 13.13 (s, 1H), 9.22 (s, 1H), 7.49-7.45 (m, 2H), 7.35 (d, J = 2.8 Hz, 1H), 7.27 (dd, J1 = 1.6 & J2 = 8, 1H), 7.15 (d, J = 8.8 Hz, 1H), 7.08 (dd, J1 = 2.8 Hz & J2 = 9.2, 1H), 7.01-6.96 (m, 2H), 6.68 (dd, J1 = 3.2 Hz & J2 = 10, 1H), 3.71 (s, 3H), 2.13 (s, 1H), 1.66 (s, 2H), 1.5-1.3 (m, 8H), 1.17 (s, 2H), 0.88 (s, 6H). LC-MS: m/z 550.2 (M + H)+. |
| 570 | 73 | XII.107 | 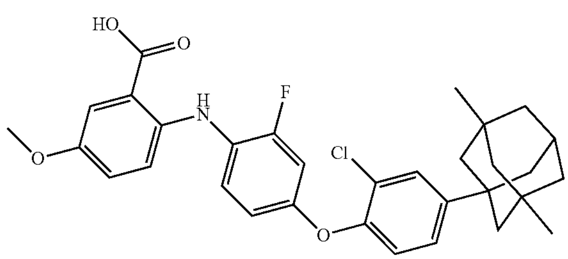 [SMILES: COc1ccc(Nc2ccc(Oc3ccc(C45CC6CC(C)(CC(C)(C6)C4)C5)cc3Cl)cc2F)c(C(=O)O)c1] | 1H NMR (400 MHz, DMSO-d6): δ 13.26 (s, 1H), 9.11 (s, 1H), 7.50 (d, J = 2 Hz, 1H), 7.42-7.34 (m, 3H), 7.11-7.06 (m, 2H), 7.01-6.94 (m, 2H), 6.72 (d, J = 8.8 Hz, 1H), 3.72 (s, 3H), 2.14 (s, 1H), 1.69 (s, 2H), 1.53-1.33 (m, 8H), 1.23-1.18 (m, 2H), 0.86 (s, 6H). LC-MS: m/z 550.2 (M + H)+ |
| 571 | 74 | XII.108 | 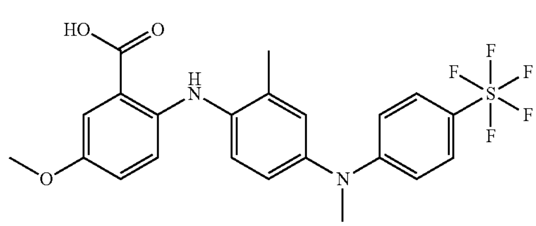 [SMILES: COc1ccc(Nc2ccc(N(C)c3ccc(S(F)(F)(F)(F)F)cc3)cc2C)c(C(=O)O)c1] | 1H NMR (400 MHz, DMSO-d6): δ 13.4 (bs, 1H), 9.14 (s, 1H), 7.62 (d, J = 9.2 Hz, 2H), 7.42 (d, J = 2.4 Hz, 1H), 7.33 (d, J = 8.4 Hz, 1H), 7.18 (d, J = 2 Hz, 1H), 7.12-7.06 (m, 3H), 6.76 (d, J = 8.8 Hz, 2H), 3.74 (s, 3H), 3.29 (s, 3H), 2.22 (s, 3H). LC-MS: m/z 489.1 (M + H)+. |

| CP | Compound No | Reactant | Structure | Analytical data |
|---|---|---|---|---|
| 572 | 75 | XII.109 | 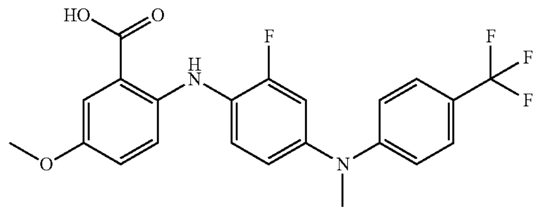 | 1H NMR (400 MHz, DMSO-d6): δ 13.35 (s, 1H), 9.25 (s, 1H), 7.51 (d, J = 8.8 Hz, 2H), 7.46-7.41 (m, 2H), 7.23-7.11 (m, 3H), 7.03-7.01 (m, 1H), 6.93 (d, J = 8.8 Hz, 2H), 3.74 (s, 3H), 3.30 (s, 3H). LC-MS: m/z 435.1 (M + H)+. |
| 573 | 76 | XII.110 | 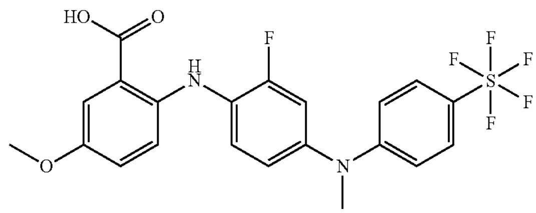 | 1H NMR (400 MHz, DMSO-d6): δ 13.4 (bs, 1H), 9.27 (s, 1H), 7.65 (d, J = 9.2 Hz, 2H), 7.48-7.43 (m, 2H), 7.28-7.11 (m, 3H), 7.05 (d, J = 8.4 Hz, 1H), 6.85 (d, J = 9.2 Hz, 2H), 3.75 (s, 3H), 3.30 (s, 3H). LC-MS: m/z 493.1 (M + H)+. |
| 574 | 77 | XII.111 | 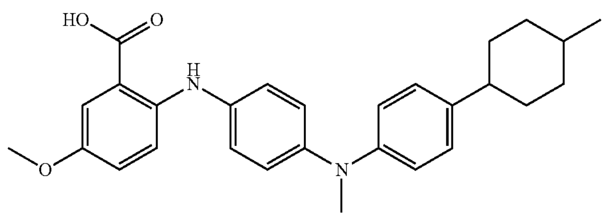 | 1H NMR (400 MHz, DMSO-d6): δ 13.30-12.80 (bs, 1H), 9.11 (s, 1H), 7.37 (d, J = 2.8 Hz, 1H), 7.15-7.07 (m, 6H), 6.98-6.95 (m, 2H), 6.90-6.87 (m, 2H), 3.71 (S, 3H), 3.21 (s, 3H), 1.91-1.88 (m, 1H), 1.80-1.30 (m, 9H), 1.0 (d, J = 6.8 Hz, 3H). LC-MS: m/z 445.3 (M + H)+. |
| 575 | 78 | XII.112 | 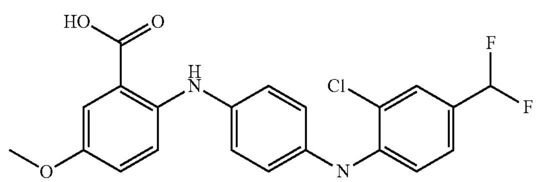 [SMILES: COc1ccc(Nc2ccc(Nc3ccc(C(F)F)cc3Cl)cc2)c(C(=O)O)c1] | 1H NMR (400 MHz, DMSO-d6): δ 13.2 (s, 1H), 9.2 (s, 1H), 7.8 (s, 1H), 7.53 (d, J = 8.8 Hz, 1H), 7.40 (d, J = 2.8 Hz, 1H), 7.24-7.20 (m, 3H), 7.16-6.88 (m, 5H), 3.73 (s, 3H). LC-MS: m/z 420.2 (M + H)+. |
| 576 | 79 | XII.113 | 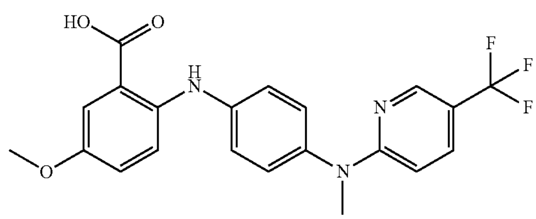 | 1H NMR (400 MHz, DMSO-d6) δ 13.24 (s, 1H), 9.20 (s, 1H), 8.46 (s, 1H), 7.67 (dd, J1 = 2.0 Hz, J2 = 8.8 Hz, 1H), 7.42 (d, J = 2.8 Hz, 1H), 7.34 (d, J = 8.8 Hz, 1H), 7.24 (m, 4H), 7.12 (dd, J1 = 3.6 Hz, J2 = 9.2 Hz, 1H), 6.49 (d, J = 8.8 Hz, 1H), 3.74 (s, 3H), 3.41 (s, 3H). LC-MS: m/z 471.66 (M + H)+ |
| 577 | 80 | XII.114 | 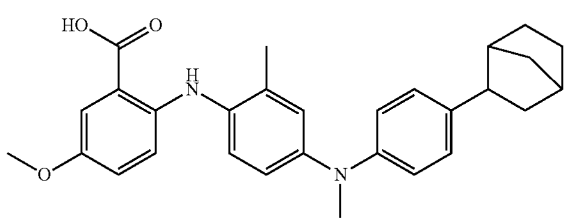 [SMILES: COc1ccc(Nc2ccc(N(C)c3ccc(C4CC5CCC4C5)cc3)cc2C)c(C(=O)O)c1] | 1H NMR (400 MHz, DMSO-d6) δ 13.1 (s, 1H), 8.90 (s, 1H), 7.37 (d, J = 3.6 Hz, 1H), 7.11 (d, J = 8.4 Hz, 3H), 7.02 (dd, J1 = 3.2 Hz, J2 = 9.2 Hz, 1H), 6.92-6.88 (m, 3H), 6.81-6.75 (m, 2H), 3.70 (s, 3H), 3.21 (s, 3H), 2.67-2.65 (m, 1H), 2.32-2.31 (m, 1H), 2.22 (s, 1H), 2.11 (s, 3H), 1.71-1.40 (m, 4H), 1.40-1.11 (m, 4H). LC-MS: m/z 456.15 (M + H)+ |

-continued

| CP | Compound No | Reactant | Structure | Analytical data |
|---|---|---|---|---|
| 578 | 81 | XII.115 | 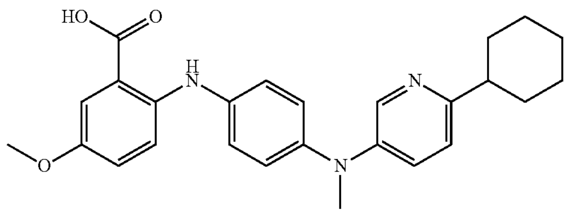 [SMILES: COc1ccc(Nc2ccc(N(C)c3ccc(C4CCCCC4)nc3)cc2)c(C(=O)O)c1] | 1H NMR (400 MHz, DMSO-d6) δ 13.30 (s, 1H), 9.18 (s, 1H), 7.98 (d, J = 2.4 Hz, 1H), 7.56 (d, J = 10 Hz, 2H), 7.41 (d, J = 2.8 Hz, 1H), 7.30-7.17 (m, 5H), 7.13-7.10 (m, 1H), 3.74 (s, 3H), 3.30 (s, 3H), 1.25-1.21 (m, 7H), 1.10 (s, 4H). LC-MS: m/z 432.3 (M + H)+ |
| 579 | 82 | XII.116 | 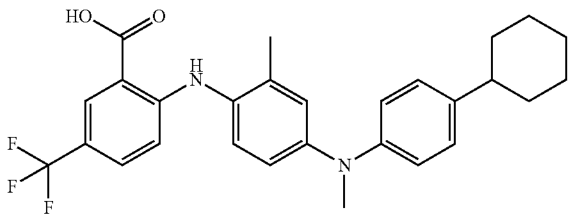 [SMILES: Cc1cc(N(C)c2ccc(C3CCCCC3)cc2)ccc1Nc1ccc(C(F)(F)F)cc1C(=O)O] | 1H NMR (400 MHz, DMSO-d6) δ 13.45 (s, 1H), 9.61 (s, 1H), 8.09 (s, 1H), 7.60-7.57 (m, 1H), 7.17 (d, J = 8.4 Hz, 2H), 7.12 (d, J = 8.8 Hz, 1H), 7.01 (d, J = 8.8 Hz, 2H), 6.91 (d, J = 2.4 Hz, 1H), 6.77 (dd, J1 = 2.8 Hz, J2 = 8.8 Hz, 1H), 6.68 (d, J = 9.2 Hz, 1H), 3.24 (s, 3H), 2.46-2.42 (m, 1H), 2.09 (s, 3H), 1.80-1.68 (m, 5H), 1.43-1.23 (m, 5H). LC-MS: m/z 481.10 (M + H)+. |
| 580 | 83 | XII.117 | 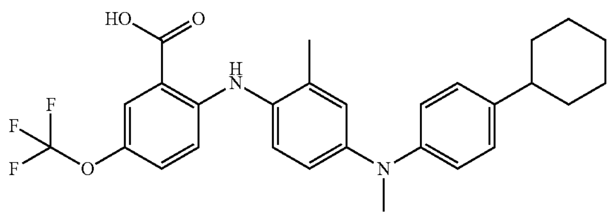 [SMILES: Cc1cc(N(C)c2ccc(C3CCCCC3)cc2)ccc1Nc1ccc(OC(F)(F)F)cc1C(=O)O] | 1H NMR (400 MHz, DMSO-d6) δ 13.38 (bs, 1H), 9.29 (s, 1H), 7.72 (s, 1H), 7.33 (dd, J1 = 2.4 Hz, J2 = 9.6 Hz, 1H), 7.14 (t, J = 8.4 Hz, 3H), 6.98 (d, J = 8.4 Hz, 2H), 6.91 (d, J = 1.6 Hz, 1H), 6.78 (dd, J1 = 1.6 Hz, J2 = 8.0 Hz, 1H), 6.67 (d, J = 9.2 Hz, 1H), 3.23 (s, 3H), 2.46-2.42 (m, 1H), 2.10 (s, 3H), 1.79-1.68 (m, 5H), 1.39-1.20 (m, 5H). LC-MS: m/z 498.15 (M + H)+ |
| 581 | 84 | XII.118 | 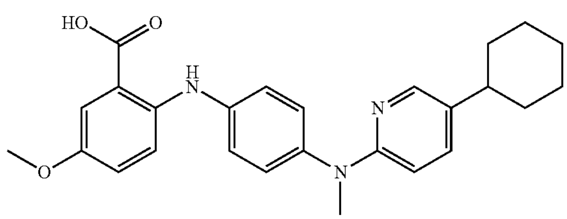 [SMILES: COc1ccc(Nc2ccc(N(C)c3ccc(C4CCCCC4)cn3)cc2)c(C(=O)O)c1] | 1H NMR (400 MHz, DMSO-d6) δ 13.28 (s, 1H), 9.20 (s, 1H), 7.85 (s, 1H), 7.67 (s, 1H), 7.42 (d, J = 3.2 Hz, 1H), 7.35-7.23 (m, 5H), 7.14-7.11 (m, 1H), 6.70 (d, J = 6.70 Hz, 1H), 3.78 (s, 3H), 3.40 (s, 3H), 1.78-1.72 (m, 6H), 1.38-1.32 (m, 5H). LC-MS: m/z 432.60 (M + H)+ |
| 582 | 85 | XII.119 | 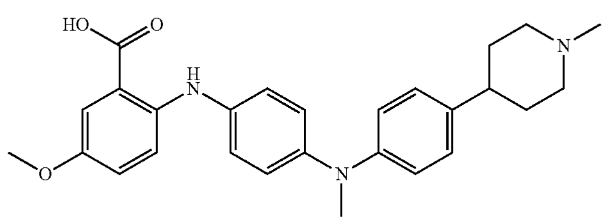 | 1H NMR (400 MHz, DMSO-d6) δ 9.2 (s, 1H), 7.38 (d, J = 3.2 Hz, 1H), 7.15-7.07 (m, 6H), 6.99 (d, J = 8.8 Hz, 2H), 6.88 (d, J = 8.8 Hz, 2H 3.72 (s, 3H), 3.48 (brm, 2H), 3.21 (s, 3H), 3.08-2.99 (brm, 2H), 2.77 (s, 3H), 2.68 (brm, 1H), 2.0-1.8 (brm, 4H). LC-MS? m/z 445.24 (M + H)+. |

-continued

| CP | Compound No | Reactant | Structure | Analytical data |
|---|---|---|---|---|
| 583 | 86 | Compound 319 | 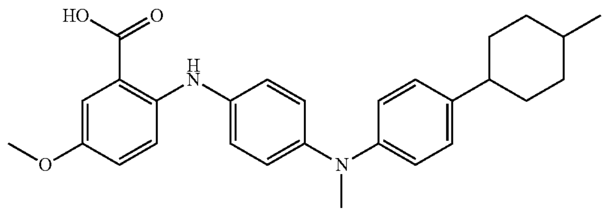 | 1H NMR (400 MHz, DMSO-d6) δ 13.12 (s, 1H), 9.10 (d, J = 5.2 Hz, 1H), 7.37 (d, J = 3.2 Hz, 1H), 7.15-7.07 (m, 6H), 6.98-6.95 (m, 2H), 6.88 (d, J = 8.8 Hz, 2H), 3.71 (s, 3H), 3.21 (s, 3H), 2.46-2.44 (m, 1H), 1.91-1.88 (m, 1H), 1.72-1.45 (m, 8H), 1.00 (d, J = 7.2 Hz, 3H). LC-MS: m/z 445.2 (M + H)+ |
| 584 | 87 | Compound 319 | 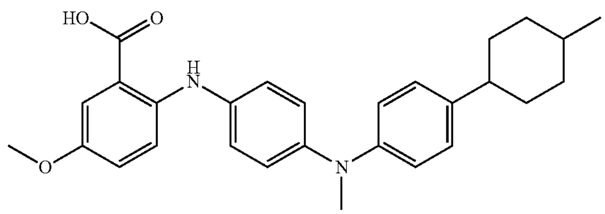 | 1H NMR (400 MHz, DMSO-d6) δ 13.20-12.90 (bs, 1H), 9.21-8.95 (bs, 1H), 7.37 (d, J = 2.8 Hz, 1H), 7.11-7.04 (m, 6H), 6.96 (d, J = 8.8 Hz, 2H), 6.87 (d, J = 8.8 Hz, 2H), 3.71 (s, 3H), 3.20 (s, 3H), 2.40-2.32 (m, 1H), 1.80-1.74 (m, 4H), 1.42-1.35 (m, 3H), 1.10-0.95 (m, 2H), 0.90 (d, J = 6.4 Hz, 3H). LC-MS: m/z 445.3 (M + H)+ |
| 585 | 88 | XII.120 | 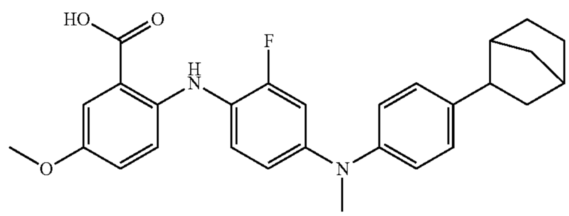 | 1H NMR (400 MHz, DMSO-d6) δ 13.15 (s, 1H), 8.95 (s, 1H), 7.37 (d, J = 3.6 Hz, 1H), 7.24-7.18 (m, 3H), 7.06-7.03 (m, 3H), 6.82-6.74 (m, 2H), 6.64 (dd, J1 = 2.0 Hz, J2 = 8.4 Hz, 1H), 3.70 (s, 3H), 3.21 (s, 3H), 2.70-2.67 (m, 1H), 2.33-2.26 (m, 2H), 1.72-1.69 (m, 1H), 1.62-1.42 (m, 4H), 1.40-1.11 (m, 4H). LC-MS: m/z 461.2 (M + H)+ |
| 586 | 89 | XII.121 | 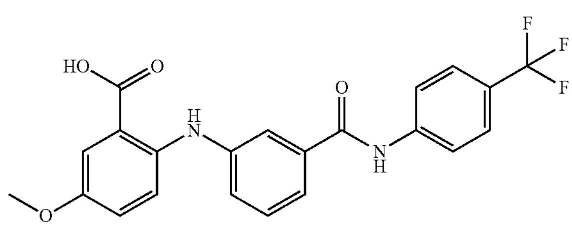 [SMILES: COc1ccc(Nc2cccc(C(=O)Nc3ccc(C(F)(F)F)cc3)c2)c(C(=O)O)c1] | 1H NMR (400 MHz, DMSO-d6) δ 13.3 (s, 1H), 10.55 (s, 1H), 9.50-9.2 (brs, 1H), 8.0 (d, J = 8.4 Hz, 2H), 7.71 (dd, J1 = 8.8 Hz, J2 = 12.8 Hz, 3H), 7.52-7.51 (m, 1H), 7.47-7.33 (m, 4H), 7.14-7.12 (m, 1H), 3.75 (s, 3H). LC-MS: m/z 431.1 (M + H)+ |
| 587 | 90 | XX.25 | 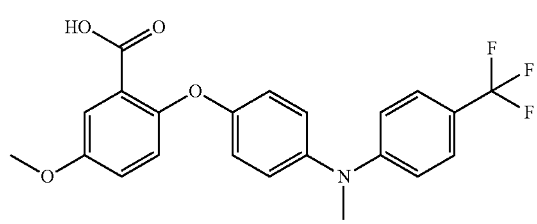 [SMILES: COc1ccc(Oc2ccc(N(C)c3ccc(C(F)(F)F)cc3)cc2)c(C(=O)O)c1] | 1H NMR (400 MHz, DMSO-d6) δ 12.5 (s, 1H), 7.45 (d, J = 8.8 Hz, 2H), 7.31 (d, J = 2.8 Hz, 1H), 7.19-7.06 (m, 4H), 6.88 (d, J = 8.8 Hz, 2H), 6.77 (d, J = 8.8 Hz, 2H) 3.79 (s, 3H), 3.25 (s, 3H). LC-MS: m/z 418.2 (M + H)+ |
| 588 | 91 | XII.123 | 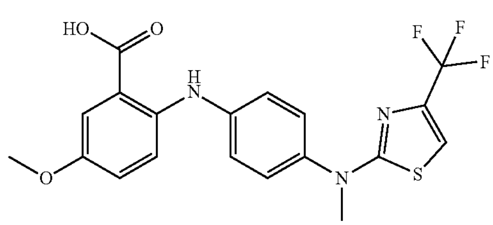 [SMILES: COc1ccc(Nc2ccc(N(C)c3nc(C(F)(F)F)cs3)cc2)c(C(=O)O)c1] | 1H NMR (400 MHz, DMSO-d6) δ 13.50-12.90 (brs, 1H), 9.60-9.10 (brs, 1H), 7.42-7.32 (m, 5H), 7.23 (d, J = 8.8 Hz, 2H)), 7.12 (dd, J1 = 2.8 Hz, J2 = 8.8 Hz, 1H), 3.75 (s, 3H), 3.42 (s, 3H). LC-MS: m/z 424.0 (M + H)+ |

| CP | Compound No | Reactant | Structure | Analytical data |
|---|---|---|---|---|
| 589 | 92 | XII.124 | 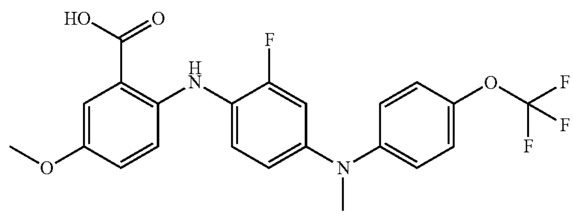 | 1H NMR (400 MHz, DMSO-d6) δ 13.2 (s, 1H), 9.09 (brs, 1H), 7.4 (d, J = 3.2 Hz, 1H), 7.32 (m, 1H), 7.25 (d, J = 8.8 Hz, 2H), 7.12-7.00 (m, 5H), 6.86-6.82 (m, 1H), 3.70 (s, 3H), 3.26 (s, 3H). LC-MS: m/z 451.2 (M + H)+ |
| 590 | 93 | XII.125 | 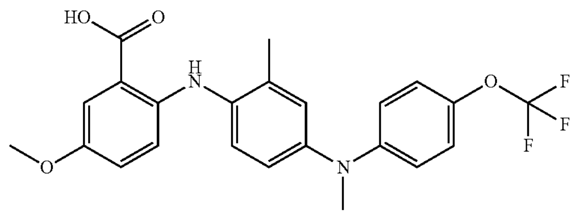 | 1H NMR (400 MHz, DMSO-d6) δ 13.18 (s, 1H), 9.05 (s, 1H), 7.39 (d, J = 3.2 Hz, 1H), 7.25-7.19 (m, 3H), 7.08-7.05 (m, 2H), 6.98-6.86 (m, 4H), 3.72 (s, 3H), 3.24 (s, 3H), 2.17 (s, 3H). LC-MS: m/z 447.2 (M + H)+ |
| 591 | 94 | XII.126 | 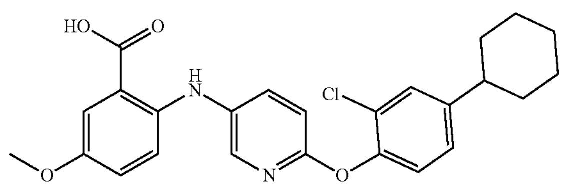 [SMILES: COc1ccc(Nc2ccc(Oc3ccc(C4CCCCC4)cc3Cl)nc2)c(C(=O)O)c1] | 1H NMR (400 MHz, DMSO-d6) δ 13.20 (bs, 1H), 9.08 (bs, 1H), 7.97 (d, J = 2.8 Hz, 1H), 7.73 (dd, J1 = 3.2 Hz, J2 = 9.2 Hz, 1H), 7.39-7.38 (m, 2H), 7.24-7.17 (m, 2H), 7.07-6.99 (m, 3H), 3.71 (s, 3H), 2.57-2.52 (m, 1H), 1.8-1.68 (m, 5H) 1.43-1.31 (m, 5H). LC-MS: m/z 453.2 (M + H)+ |
| 592 | 95 | XII.127 | 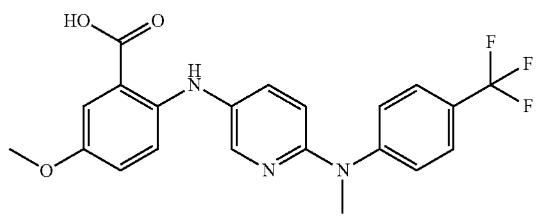 | 1H NMR (400 MHz, DMSO-d6) δ 13.55-12.95 (brs, 1H), 9.05 (s, 1H), 8.18 (d, J = 2.4 Hz, 1H), 7.64 (d, J = 8.4 Hz, 2H), 7.54 (dd, J1 = 2.4 Hz, J2 = 8.8 Hz, 1H), 7.39 (d, J = 2.8 Hz, 1H), 7.34 (d, J = 8.4 Hz, 2H), 7.09-7.02 (m, 3H), 3.72 (s, 3H), 3.44 (s, 3H). LC-MS: m/z 481.2 (M + H)+ |
| 593 | 96 | XII.128 | 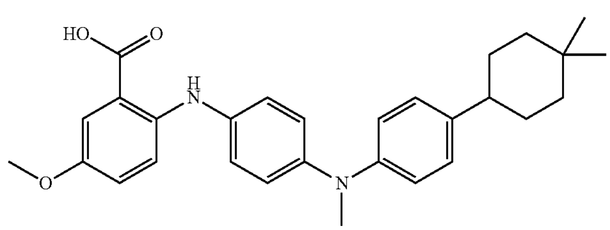 | 1H NMR (400 MHz, DMSO-d6) δ 13.11 (s, 1H), 9.20 (s, 1H), 7.37 (d, J = 2.8 Hz, 1H), 7.14-7.03 (m, 6H), 6.98-6.86 (m, 4H), 3.71 (s, 3H), 3.20 (s, 3H), 2.33-2.32 (m, 1H), 1.58-1.42 (m, 6H), 1.33-1.29 (m, 2H), 0.95-0.93 (m, 6H). LC-MS: m/z 459.3 (M + H)+ |
| 594 | 97 | XII.129 | 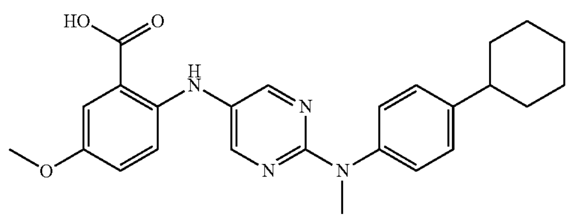 [SMILES: COc1ccc(Nc2cnc(N(C)c3ccc(C4CCCCC4)cc3)nc2)c(C(=O)O)c1] | 1H NMR (400 MHz, DMSO-d6) δ 13.2-13.0 (brs, 1H), 9.0-8.7 (bs, 1H), 8.29 (s, 2H), 7.37 (d, J = 2.8 Hz, 1H), 7.23 (dd, J1 = 8.8 Hz, J2 = 11.6 Hz, 4H), 6.99 (dd, J1 = 3.2 Hz, J2 = 9.6 Hz, 1H), 6.73 (d, J = 8.8 Hz, 1H), 3.69 (s, 3H), 3.44 (s, 3H), 1.81-1.69 (m, 6H), 1.43-1.35 (m, 5H) LC-MS: m/z 433.2 (M + H)+ |

| CP | Compound No | Reactant | Structure | Analytical data |
|---|---|---|---|---|
| 595 | 98 | XII.130 | 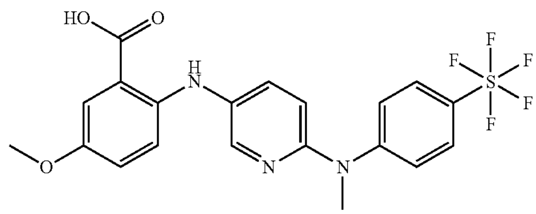 [SMILES: COc1ccc(Nc2ccc(N(C)c3ccc(S(F)(F)(F)(F)F)cc3)nc2)c(C(=O)O)c1] | 1H NMR (400 MHz, DMSO-d6) δ 13.15 (s, 1H), 9.05 (bs, 1H), 8.18 (d, J = 2.8 Hz, 1H), 7.79 (d, J = 9.2 Hz, 2H), 7.63 (dd, J1 = 2.8 Hz, J2 = 8.8 Hz, 1H), 7.40 (t, J = 1.6 Hz, 1H), 7.29 (d, J = 8.8 Hz, 2H), 7.12 (d, J = 9.2 Hz, 1H), 7.09 (d, J = 1.6 Hz, 2H). 3.37 (s, 3H), 3.44 (s, 3H), LC-MS: m/z 476.1 (M + H)+. |
| 596 | 99 | XII.131 | 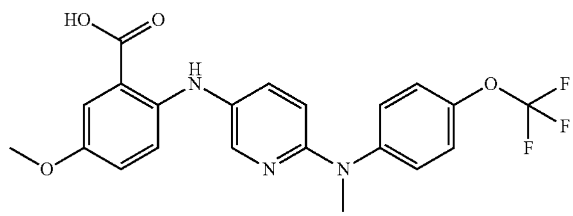 [SMILES: COc1ccc(Nc2ccc(N(C)c3ccc(OC(F)(F)F)cc3)nc2)c(C(=O)O)c1] | 1H NMR (400 MHz, DMSO-d6) δ 13.2 (s, 1H), 9.0 (s, 1H), 8.09 (d, J = 2.4 Hz, 1H), 7.44 (dd, J1 = 2.8 Hz, J2 = 8.8 Hz, 1H), 7.39-7.37 (m, 5H), 7.02 (dd, J1 = 3.2 Hz, J2 = 9.2 Hz, 1H), 6.88 (d, J = 8.8 Hz, 1H), 6.74 (d, J = 9.6 Hz, 1H), 3.70 (s, 3H), 3.39 (s, 3H). LC-MS: m/z 434.1 (M + H)+ |
| 597 | 100 | XII.132 | 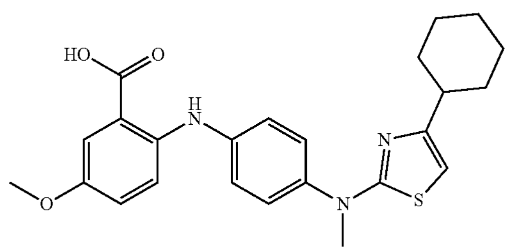 [SMILES: COc1ccc(Nc2ccc(N(C)c3nc(C4CCCCC4)cs3)cc2)c(C(=O)O)c1] | 1H NMR (400 MHz, DMSO-d6) δ 9.2 (s, 1H), 7.42-7.38 (m, 3H), 7.33 (d, J = 9.2 Hz, 1H) 7.22 (d, J = 8.8 Hz, 2H), 7.15-7.12 (m, 1H), 6.39 (s, 1H), 3.84 (s, 3H), 3.48 (s, 3H), 1.98-1.95 (m, 2H), 1.96-1.66 (m, 3H), 1.35-1.16 (m, 6H). LC-MS: m/z 438.2 (M + H)+ |
| 598 | 101 | XII.133 | 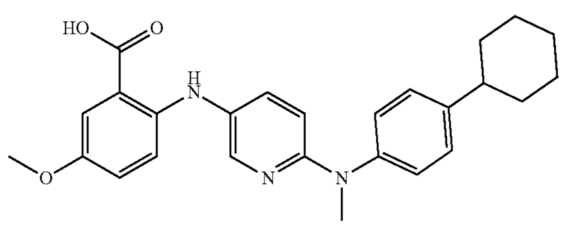 [SMILES: COc1ccc(Nc2ccc(N(C)c3ccc(C4CCCCC4)cc3)nc2)c(C(=O)O)c1] | 1H NMR (400 MHz, DMSO-d6) δ 13.60-12.80 (brs, 1H), 8.91 (s, 1H), 7.97 (s, 1H), 7.60 (s, 1H), 7.38-7.27 (m, 5H), 7.05 (dd, J1 = 2.8 Hz, J2 = 9.2 Hz, 1H), 6.87 (d, J = 9.2 Hz, 1H), 6.69 (d, J = 8.8 Hz, 1H), 3.71 (s, 3H), 3.42 (s, 3H), 1.75-1.65 (m, 5H), 1.50-1.10 (m, 6H) LC-MS: m/z 432.2 (M + H)+ |
| 599 | 102 | XII.134 | 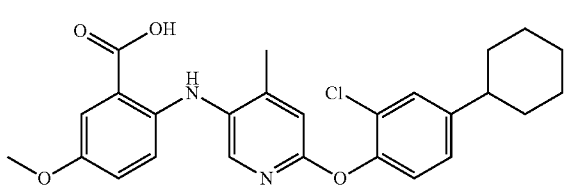 [SMILES: COc1ccc(Nc2cnc(Oc3ccc(C4CCCCC4)cc3Cl)cc2C)c(C(=O)O)c1] | 1H NMR (400 MHz, DMSO-d6) δ 13.15 (bs, 1H), 8.92 (s, 1H), 7.94 (s, 1H), 7.39-7.37 (m, 2H), 7.24-7.17 (m, 2H), 7.08 (s, 1H), 7.01 (dd, J1 = 3.2 Hz, J2 = 9.2 Hz, 1H), 6.57 (d, J = 9.2 Hz, 1H), 3.69 (s, 3H), 2.57-2.53 (m, 1H), 2.19 (s, 3H), 1.81-1.68 (m, 5H), 1.43-1.33 (m, 5H). LC-MS: m/z 467.1 (M + H)+ |

-continued

| CP | Compound No | Reactant | Structure | Analytical data |
|---|---|---|---|---|
| 600 | 103 | XII.135 | 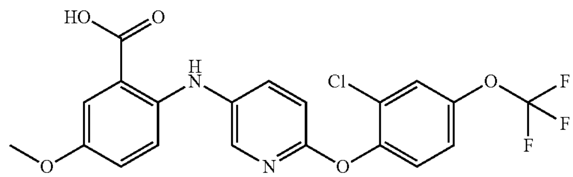 [SMILES: COc1ccc(Nc2ccc(Oc3ccc(OC(F)(F)F)cc3Cl)nc2)c(C(=O)O)c1] | 1H NMR (400 MHz, DMSO-d6) δ 13.10 (s, 1H), 9.06 (s, 1H), 8.00 (d, J = 2.0 Hz, 1H), 7.77-7.74 (m, 2H), 7.43 (s, 2H), 7.39 (s, 1H), 7.14 (d, J = 8.0 Hz, 1H), 7.04 (d, J = 9.2 Hz, 2H), 3.72 (s, 3H). LC-MS: m/z 455.0 (M + H)+. |
| 601 | 104 | XII.136 | 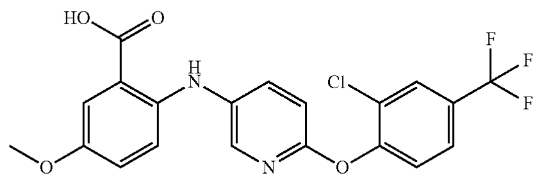 [SMILES: COc1ccc(Nc2ccc(Oc3ccc(C(F)(F)F)cc3Cl)nc2)c(C(=O)O)c1] | 1H NMR (400 MHz, DMSO-d6) δ 13.3 (s, 1H), 9.1 (s, 1H), 8.04-8.01 (m, 2H), 7.80-7.75 (m, 2H), 7.47 (d, J = 8.8 Hz, 1H), 7.40 (s, 1H), 7.10-7.05 (m, 2H), 3.72 (s, 3H). LC-MS: m/z 439.5.1 (M + H)+ |
| 602 | 105 | XII.137 | 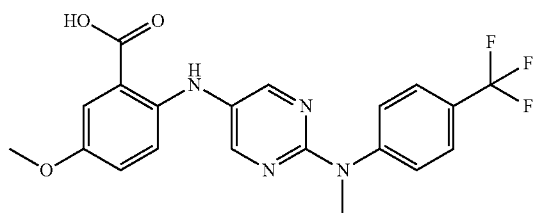 | 1H NMR (400 MHz, DMSO-d6) δ 13.16 (s, 1H), 8.90 (s, 1H), 8.39 (s, 2H), 7.71 (d, J = 8.4 Hz, 2H), 7.62 (d, J = 8.8 Hz, 2H), 7.38 (d, J = 3.2 Hz, 1H), 7.06-7.02 (m, 1H), 6.87-6.83 (m, 1H), 3.71 (s, 3H), 3.55 (s, 3H). LC-MS: m/z 410.10 (M + H)+ |
| 603 | 106 | XII.138 | 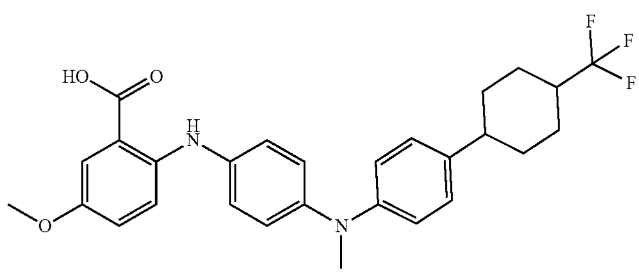 [SMILES: COc1ccc(Nc2ccc(N(C)c3ccc(C4CCC(C(F)(F)F)CC4)cc3)cc2)c(C(=O)O)c1] | 1H NMR (400 MHz, DMSO-d6) δ 7.39 (d, J = 2.8 Hz, 2H), 7.13-7.09 (m, 6H), 6.98 (d, J = 8.8 Hz, 2H), 6.86 (d, J = 8.4 Hz, 2H), 3.71 (s, 3H), 3.20 (s, 3H), 2.60-2.40 (m, 1H), 1.76-1.70 (m, 10H). LC-MS: m/z 498.25 (M + H)+ |
| 609 | 107 | XII.139 | 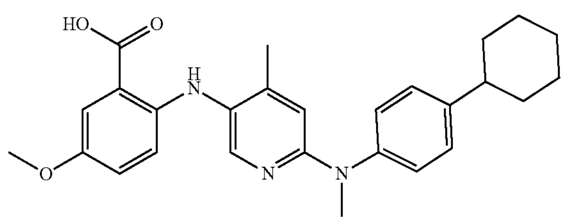 [SMILES: COc1ccc(Nc2cnc(N(C)c3ccc(C4CCCCC4)cc3)cc2C)c(C(=O)O)c1] | 1H NMR (400 MHz, DMSO-d6) δ 13.00 (s, 1H), 8.74 (s, 1H), 7.97 (s, 1H), 7.35 (d, J = 3.2 Hz, 1H), 7.27 (d, J = 8.0 Hz, 2H), 7.21 (d, J = 8.4 Hz, 2H), 6.99 (dd, J1 = 2.8 Hz, J2 = 8.8 Hz, 1H), 6.49 (s, 1H), 6.44 (d, J = 9.6 Hz, 1H), 3.69 (s, 3H), 3.36 (s, 3H), 1.96 (s, 3H), 1.81-1.69 (m, 5H), 1.43-1.23 (m, 6H). LC-MS: m/z 446.3 (M + H)+. |
| 612 | 108 | XII.140 | 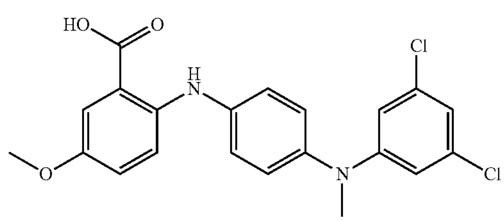 [SMILES: COc1ccc(Nc2ccc(N(C)c3cc(Cl)cc(Cl)c3)cc2)c(C(=O)O)c1] | 1H NMR (400 MHz, DMSO-d6) δ 13.22 (s, 1H), 9.20 (s, 1H), 7.40 (d, J = 2.8 Hz, 1H), 7.31 (d, J = 9.2 Hz, 1H), 7.23-7.01 (m, 5H), 6.80 (s, 1H), 6.61 (d, J = 1.2 Hz, 2H), 3.74 (s, 3H), 3.22 (s, 3H). LC-MS: m/z 417.1 (M + H)+. |

| CP | Compound No | Reactant | Structure | Analytical data |
|---|---|---|---|---|
| 613 | 109 | XII.141 | 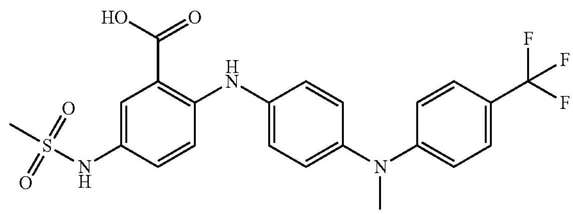 [SMILES: CN(c1ccc(Nc2ccc(NS(C)(=O)=O)cc2C(=O)O)cc1)c1ccc(C(F)(F)F)cc1] | 1H NMR (400 MHz, DMSO-d6) δ 13.26 (s, 1H), 9.51 (s, 1H), 9.39 (s, 1H), 7.79 (d, J = 2.0 Hz, 1H), 7.47 (d, J = 8.8 Hz, 2H), 7.33-7.21 (m, 6H), 6.85 (d, J = 8.8 Hz, 2H), 3.30 (s, 3H), 2.91 (s, 3H). LC-MS: m/z 480.1 (M + H)+. |
| 614 | 110 | XII.142 | 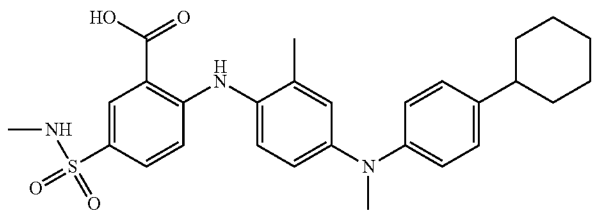 [SMILES: CNS(=O)(=O)c1ccc(Nc2ccc(N(C)c3ccc(C4CCCCC4)cc3)cc2C)c(C(=O)O)c1] | 1H NMR (400 MHz, DMSO-d6) δ 13.42 (s, 1H), 9.70 (s, 1H), 8.25 (d, J = 2.0 Hz, 1H), 7.62 (dd, J1 = 2.0 Hz, J2 = 8.8 Hz, 1H), 7.22-7.12 (m, 4H), 7.02 (d, J = 8.0 Hz, 2H), 6.90 (d, J = 2.4 Hz, 1H), 6.77 (dd, J1 = 2.4 Hz, J2 = 8.4 Hz, 1H), 6.69 (d, J = 8.8 Hz, 1H), 3.25 (s, 3H), 2.37 (d, J = 5.2 Hz, 3H), 2.10 (s, 3H), 1.80-1.68 (m, 5H), 1.40-1.23 (m, 6H). LC-MS: 508.2 (M + H)+. |
| 615 | 111 | XII.143 | 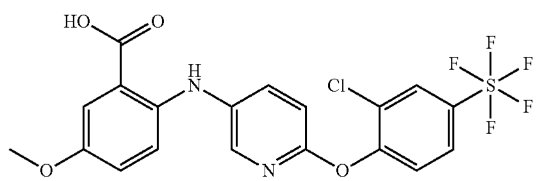 [SMILES: COc1ccc(Nc2ccc(Oc3ccc(S(F)(F)(F)(F)F)cc3Cl)nc2)c(C(=O)O)c1] | 1H NMR (400 MHz, DMSO-d6) δ 13.24 (s, 1H), 9.08 (s, 1H), 8.24 (d, J = 2.8 Hz, 1H), 8.03 (d, J = 2.8 Hz, 1H), 7.96-7.93 (m, 1H), 7.80-7.77 (m, 1H), 7.48 (d, J = 9.2 Hz, 1H), 7.40 (d, J = 2.0 Hz, 1H), 7.20 (d, J = 8.4 Hz, 1H), 7.09-7.08 (m, 2H), 3.73 (s, 3H). LC-MS: m/z 497.0 (M + H)+. |
| 616 | 112 | XII.144 | 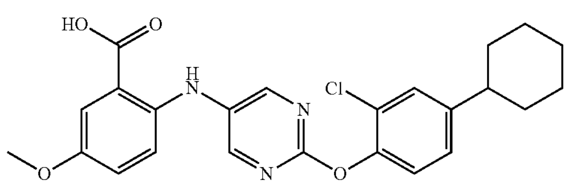 [SMILES: COc1ccc(Nc2cnc(Oc3ccc(C4CCCCC4)cc3Cl)nc2)c(C(=O)O)c1] | 1H NMR (400 MHz, DMSO-d6) δ 11.94-11.83 (bs, 1H), 8.41 (s, 2H), 7.50 (d, J = 2.4 Hz, 1H), 7.39 (s, 1H), 7.24 (s, 2H), 7.03 (d, J = 8.8 Hz, 1H), 6.79-6.76 (m, 1H), 3.77 (s, 3H), 3.60-3.50 (m, 1H), 1.91-1.68 (m, 5H), 1.51-1.22 (m, 5H), LC-MS: m/z 454.1 (M + H)+. |
| 617 | 113 | XII.145 | 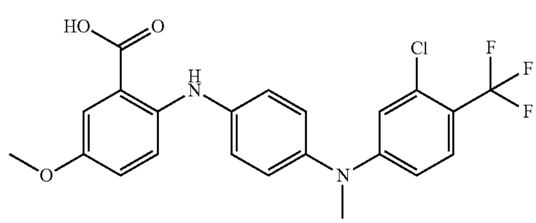 [SMILES: COc1ccc(Nc2ccc(N(C)c3ccc(C(F)(F)F)c(Cl)c3)cc2)c(C(=O)O)c1] | 1H NMR (400 MHz, DMSO-d6) δ 13.70-12.80 (bs, 1H), 9.80-8.90 (bs, 1H), 7.54-7.51 (m, 1H), 7.42 (d, J = 3.2 Hz, 1H), 7.32 (d, J = 9.2 Hz, 1H), 7.25-7.09 (m, 5H), 6.81 (d, J = 2.4 Hz, 1H), 6.68-6.65 (m, 1H), 3.74 (s, 3H), 3.28 (s, 3H). LC-MS: m/z 451.2 (M + H)+ |

| CP | Compound No | Reactant | Structure | Analytical data |
|---|---|---|---|---|
| 618 | 114 | XII.146 | 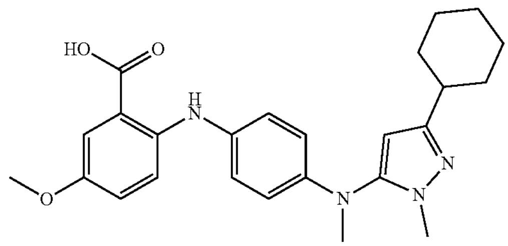 [SMILES: COc1ccc(Nc2ccc(N(C)c3cc(C4CCCCC4)nn3C)cc2)c(C(=O)O)c1] | 1H NMR (400 MHz, DMSO-d6) δ 13.40-12.80 (bs, 1H), 9.30-8.80 (bs, 1H), 7.34 (d, J = 2.8 Hz, 1H), 7.08-6.95 (m, 4H), 6.60-6.58 (m, 2H), 5.89 (s, 1H), 3.69 (s, 3H), 3.43 (s, 3H), 3.16 (s, 3H), 1.91-1.89 (m, 2H), 1.75-1.72 (m, 3H), 1.37-1.23 (m, 6H). LC-MS: m/z 435.2 (M + H)+ |
| 619 | 115 | XII.147 | 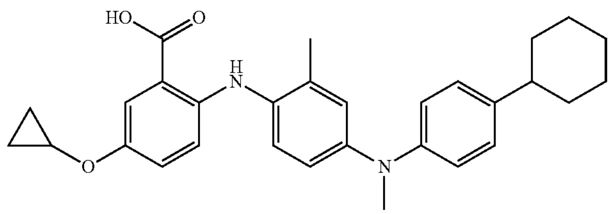 [SMILES: Cc1cc(N(C)c2ccc(C3CCCCC3)cc2)ccc1Nc1ccc(OC2CC2)cc1C(=O)O] | 1H NMR (400 MHz, DMSO-d6) δ 13.05 (bs, 1H), 8.96 (s, 1H), 7.54 (d, J = 2.8 Hz, 1H), 7.12-7.08 (m, 3H), 7.05 (dd, J1 = 2.8 Hz, J2 = 8.8 Hz, 1H), 6.90-6.87 (m, 3H), 6.79-6.72 (m, 2H), 3.78-3.72 (m, 1H), 3.19 (s, 3H), 2.46-2.40 (m, 1H), 2.10 (s, 3H), 1.76-1.66 (m, 5H), 1.39-1.28 (m, 5H), 0.72-0.70 (m, 2H), 0.69-0.66 (m, 2H). LC-MS: m/z 471.2 (M + H)+. |
| 620 | 116 | XII.148 | 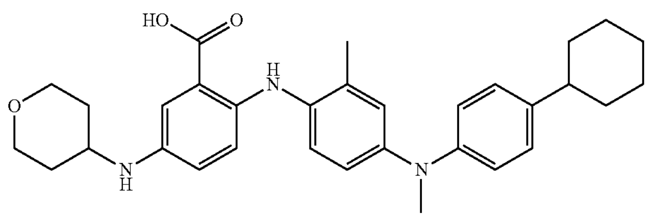 [SMILES: Cc1cc(N(C)c2ccc(C3CCCCC3)cc2)ccc1Nc1ccc(NC2CCOCC2)cc1C(=O)O] | 1H NMR (400 MHz, DMSO-d6) δ 8.67 (s, 1H), 7.14-7.04 (m, 4H), 6.92-6.88 (m, 2H), 6.84-6.75 (m, 5H), 3.84 (d, J = 10.4 Hz, 2H), 3.40-3.34 (m, 3H), 3.17 (s, 3H), 2.43-2.38 (m, 1H), 2.12 (s, 3H), 1.89-1.65 (m, 6H), 1.35-1.17 (m, 8H). LC-MS: m/z 514.3 (M + H)+. |
| 621 | 117 | XII.149 | 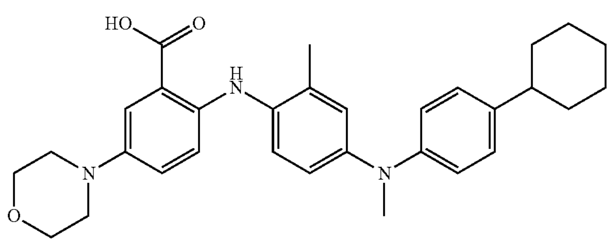 [SMILES: Cc1cc(N(C)c2ccc(C3CCCCC3)cc2)ccc1Nc1ccc(N2CCOCC2)cc1C(=O)O] | 1H NMR (400 MHz, DMSO-d6) δ 13.00-12.90 (bs, 1H), 8.96 (s, 1H), 7.38 (d, J = 2.8 Hz, 1H), 7.14-7.10 (m, 4H), 6.93-6.88 (m, 3H), 6.81-6.77 (m, 2H), 3.76-3.71 (m, 4H), 3.21 (s, 3H), 2.96-2.94 (m, 4H), 2.46-2.39 (m, 1H), 2.12 (s, 3H), 1.78-1.76 (m, 4H), 1.38-1.30 (m, 6H). LC-MS: m/z 499.2 (M + H)+. |
| 622 | 118 | XII.150 | 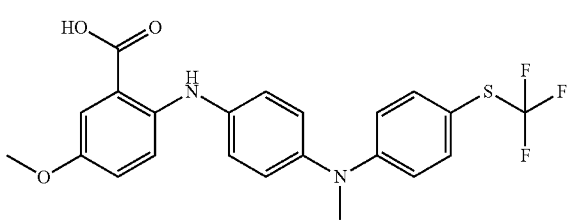 [SMILES: COc1ccc(Nc2ccc(N(C)c3ccc(SC(F)(F)F)cc3)cc2)c(C(=O)O)c1] | 1H NMR (400 MHz, DMSO-d6) δ 13.20 (s, 1H), 9.20 (s, 1H), 7.46-7.41 (m, 3H), 7.30 (d, J = 7.2 Hz, 1H), 7.23-7.10 (m, 5H), 6.77 (d, J = 8.8 Hz, 2H), 3.74 (s, 3H), 3.27 (s, 3H), LC-MS: m/z 449.1 (M + H)+ |

| CP | Compound No | Reactant | Structure | Analytical data |
|---|---|---|---|---|
| 623 | 119 | XII.153 | 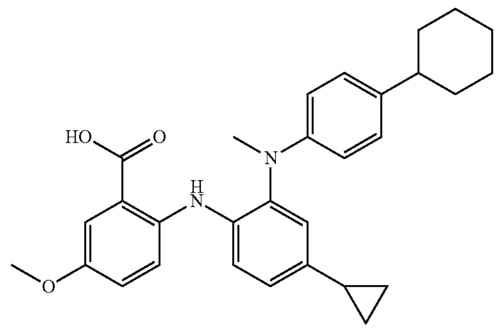 [SMILES: COc1ccc(Nc2ccc(C3CC3)cc2N(C)c2ccc(C3CCCCC3)cc2)c(C(=O)O)c1] | 1H NMR (400 MHz, DMSO-d6) δ 13.00 (s, 1H), 9.30 (s, 1H), 7.33-7.26 (m, 3H), 7.05 (dd, J1 = 2.8 Hz, J2 = 9.2 Hz, 1H), 6.94-6.87 (m, 4H), 6.48 (d, J = 8.8 Hz, 2H), 3.69 (s, 3H), 3.08 (s, 3H), 2.32-2.20 (m, 1H), 1.86-1.60 (m, 5H), 1.40-1.10 (m, 6H), 0.90-0.82 (m, 2H), 0.60-0.56 (m, 2H). LC-MS: m/z 471.2 (M + H)+. |
| 624 | 120 | XII.151 | 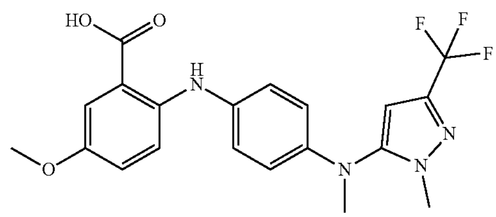 [SMILES: COc1ccc(Nc2ccc(N(C)c3cc(C(F)(F)F)nn3C)cc2)c(C(=O)O)c1] | 1H NMR (400 MHz, DMSO-d6) δ 13.2-12.8 (bs, 1H), 9.40-8.80 (bs, 1H), 7.36 (d, J = 1.6 Hz, 1H), 7.11 (d, J = 8.8 Hz, 2H), 7.03 (s, 2H), 6.68 (d, J = 8.8 Hz, 2H), 6.63 (s, 1H), 3.70 (s, 3H), 3.59 (s, 3H), 3.22 (s, 3H). LC-MS: m/z 421.2 (M + H)+ |
| 625 | 121 | XII.152 | 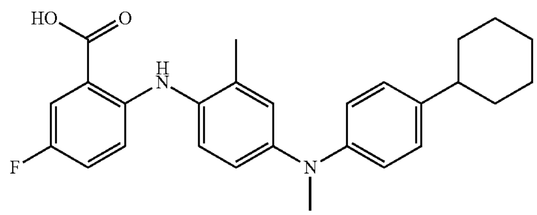 [SMILES: Cc1cc(N(C)c2ccc(C3CCCCC3)cc2)ccc1Nc1ccc(F)cc1C(=O)O] | 1H NMR (400 MHz, DMSO-d6) δ 13.26 (bs, 1H), 9.10 (s, 1H), 7.56 (dd, J1 = 3.2 Hz, J2 = 9.6 Hz, 1H), 7.23-7.22 (m, 1H), 7.14-7.11 (m, 3H), 6.96-6.91 (m, 3H), 6.79 (dd, J1 = 2.8 Hz, J2 = 8.8 Hz, 1H), 6.69-6.65 (m, 1H), 3.32 (s, 3H), 2.49-2.43 (m, 1H), 2.10 (s, 3H), 1.79-1.67 (m, 5H), 1.38-1.22 (m, 5H). LC-MS: m/z 433.2 (M + H)+. |
| 626 | 122 | XII.153 | 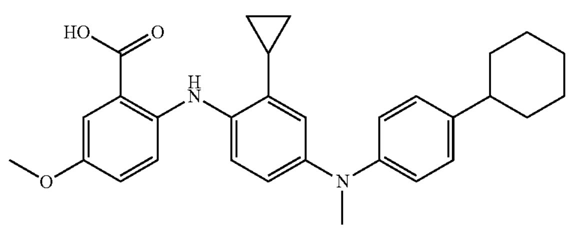 [SMILES: COc1ccc(Nc2ccc(N(C)c3ccc(C4CCCCC4)cc3)cc2C2CC2)c(C(=O)O)c1] | 1H NMR (400 MHz, DMSO-d6) δ 13.20 (bs, 1H), 9.30 (s, 1H), 7.38-7.36 (m, 1H), 7.16 (d, J = 8.4 Hz, 1H), 7.09-7.02 (m, 3H), 6.95 (d, J = 9.2 Hz, 1H), 6.84 (d, J = 8.4 Hz, 2H), 6.78 (dd, J1 = 2.8 Hz, J2 = 8.4 Hz, 1H), 6.65 (d, J = 2.8 Hz, 1H), 3.71 (s, 3H), 3.19 (s, 3H), 2.49-2.43 (m, 1H), 1.83-1.67 (m, 6H), 1.37-1.21 (m, 5H), 0.86 (dd, J1 = 1.6 Hz, J2 = 8.0 Hz, 2H), 0.57-0.53 (m, 2H). LC-MS: m/z 470.2 (M+)+. |
| 627 | 123 | XII.154 | 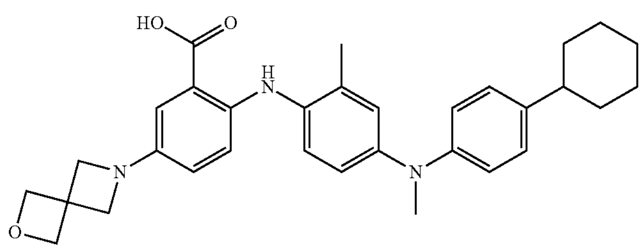 [SMILES: Cc1cc(N(C)c2ccc(C3CCCCC3)cc2)ccc1Nc1ccc(N2CC3(COC3)C2)cc1C(=O)O] | 1H NMR (400 MHz, DMSO-d6) δ 8.79 (bs, 1H), 7.10-7.08 (m, 3H), 6.92-6.79 (m, 6H), 6.64-6.62 (m, 1H), 4.69 (s, 4H), 3.88 (s, 4H), 3.19 (s, 3H), 2.46-2.40 (m, 1H), 2.11 (s, 3H), 1.78-1.67 (m, 5H), 1.37-1.29 (m, 5H). LC-MS: m/z 511.25 (M + H)+. |

-continued

| CP | Compound No | Reactant | Structure | Analytical data |
|---|---|---|---|---|
| 628 | 124 | XII.155 | 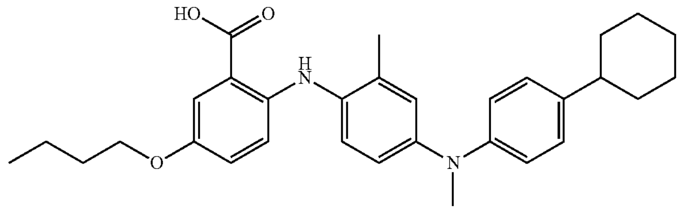 [SMILES: CCCCOc1ccc(Nc2ccc(N(C)c3ccc(C4CCCCC4)cc3)cc2C)c(C(=O)O)c1] | 1H NMR (400 MHz, DMSO-d6) δ 13.10-13.00 (bs, 1H), 8.90-9.10 (bs, 1H), 7.36 (d, J = 3.2 Hz, 1H), 7.14-7.10 (m, 3H), 7.02 (dd, J1 = 2.8 Hz, J2 = 9.2 Hz, 1H), 6.93-6.88 (m, 3H), 6.81-6.74 (m, 2H), 3.89 (t, J = 6.4 Hz, 2H), 3.21 (s, 3H), 2.45-2.30 (m, 1H), 2.12 (s, 3H), 1.78-1.64 (m, 6H), 1.43-1.33 (m, 8H), 0.94 (t, J = 4.4 Hz, 3H). LC-MS: m/z 486.2 (M + H)+. |
| 630 | 125 | XII.156 | 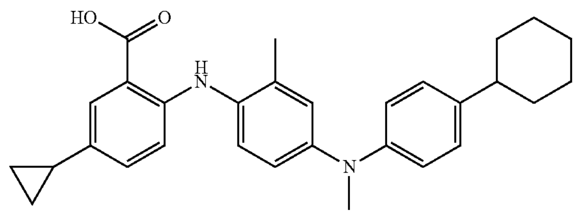 [SMILES: Cc1cc(N(C)c2ccc(C3CCCCC3)cc2)ccc1Nc1ccc(C2CC2)cc1C(=O)O] | 1H NMR (400 MHz, DMSO-d6) δ 12.83 (bs, 1H), 9.12 (s, 1H), 7.59 (d, J = 2.0 Hz, 1H), 7.12 (d, J = 8.8 Hz, 3H), 7.05 (dd, J1 = 2.0, J2 = 8.4 Hz, 1H), 6.93-6.91 (m, 3H), 6.79 (dd, J1 = 2.4 Hz, J2 = 8.4 Hz, 1H), 6.65 (d, J = 8.0 Hz, 1H), 3.21 (s, 3H), 2.46-2.42 (m, 1H), 2.10 (s, 3H), 1.92-1.67 (m, 6H), 1.41-1.33 (m, 5H), 0.86-0.82 (m, 2H), 0.54-0.51 (m, 2H). LC-MS: m/z 455.3 (M + H)+. |
| 631 | 126 | XII.157 | 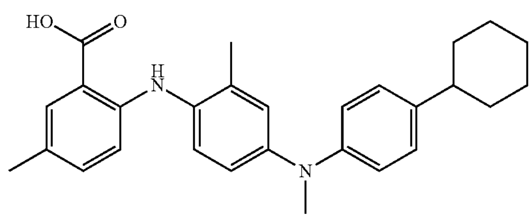 [SMILES: Cc1ccc(Nc2ccc(N(C)c3ccc(C4CCCCC4)cc3)cc2C)c(C(=O)O)c1] | 1H NMR (400 MHz, DMSO-d6) δ 12.8 (bs, 1H), 9.14 (s, 1H), 7.67 (d, J = 1.6 Hz, 1H), 7.16-7.11 (m, 4H), 6.93-6.91 (m, 3H), 6.81-6.78 (m, 1H), 6.67-6.64 (m, 1H), 3.22 (s, 3H), 2.43 (s, 1H), 2.20 (s, 3H), 2.11 (s, 3H), 1.80-1.68 (m, 5H), 1.38-1.23 (m, 5H). LC-MS: m/z 429.3 (M + H)+. |
| 632 | 127 | XII.158 | 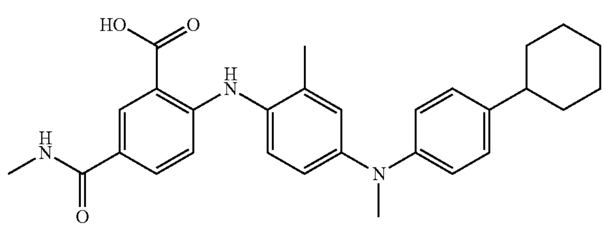 [SMILES: CNC(=O)c1ccc(Nc2ccc(N(C)c3ccc(C4CCCCC4)cc3)cc2C)c(C(=O)O)c1] | 1H NMR (400 MHz, DMSO-d6) δ 13.2 (bs, 1H), 9.60 (s, 1H), 8.42 (d, J = 2.4 Hz, 1H), 8.24 (d, J = 4.8 Hz, 1H), 7.76 (dd, J1 = 2.0, J2 = 8.8 Hz, 1H), 7.17-7.12 (m, 3H), 6.99 (d, J = 8.4 Hz, 2H), 6.91 (d, J = 2.4 Hz, 1H), 6.78 (dd, J1 = 2.8 Hz, J2 = 8.8 Hz, 1H), 6.62 (d, J = 9.2 Hz, 1H), 3.24 (s, 3H), 2.73 (d, J = 4.8 Hz, 3H), 2.46-2.44 (m, 1H), 2.10 (s, 3H), 1.79-1.68 (m, 5H), 1.39-1.16 (m, 5H). LC-MS: m/z 472.4 (M + H)+. |
| 633 | 128 | XII.159 | 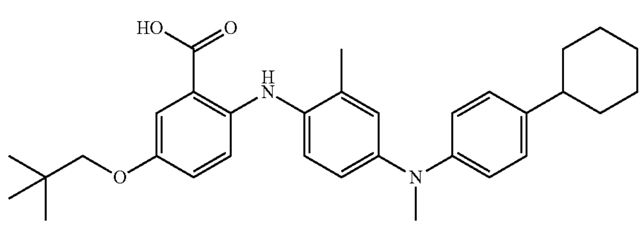 [SMILES: Cc1cc(N(C)c2ccc(C3CCCCC3)cc2)ccc1Nc1ccc(OCC(C)(C)C)cc1C(=O)O] | 1H NMR (400 MHz, DMSO-d6) δ 13.10-13.00 (bs, 1H), 8.96 (s, 1H), 7.36 (d, J = 3.2 Hz, 1H), 7.12 (dd, J1 = 4.4 Hz, J2 = 8.4 Hz, 3H), 7.04 (dd, J1 = 4.0 Hz, J2 = 9.2 Hz, 1H), 6.93-6.89 (m, 3H), 6.81-6.74 (m, 2H), 3.48 (s, 2H), 3.21 (s, 3H), |

| CP | Compound No | Reactant | Structure | Analytical data |
|---|---|---|---|---|
| | | | | 2.33-2.32 (m, 1H), 2.12 (s, 3H), 1.79-1.68 (m, 6H), 1.41-1.17 (m, 4H), 0.99 (s, 9H). LC-MS: m/z 501.4 (M+)+ |
| 634 | 129 | XII.160 | 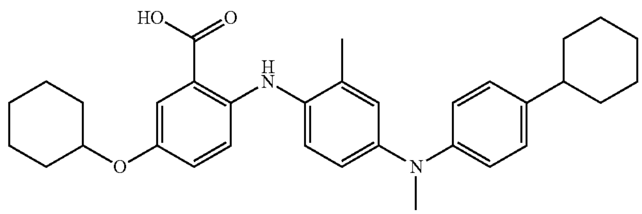 [SMILES: Cc1cc(N(C)c2ccc(C3CCCCC3)cc2)ccc1Nc1ccc(OC2CCCCC2)cc1C(=O)O] | 1H NMR (400 MHz, DMSO-d6) δ 13.10-12.90 (bs, 1H), 8.95 (s, 1H), 7.38 (d, J = 3.2 Hz, 1H), 7.12 (t, J = 8.0 Hz, 3H), 7.03 (dd, J1 = 2.8 Hz, J2 = 8.8 Hz, 1H), 6.92-6.89 (m, 3H), 6.80 (dd, J1 = 2.4 Hz, J2 = 8.0 Hz, 1H), 6.74 (d, J = 8.8 Hz, 1H), 4.15-4.09 (m, 1H), 3.21 (s, 3H), 2.45-2.38 (m, 1H), 2.12 (s, 3H), 1.89-1.86 (m, 2H), 1.79-1.68 (m, 4H), 1.55-1.24 (m, 14H). LC-MS: m/z 512.3 (M+)+. |
| 635 | 130 | XII.161 | 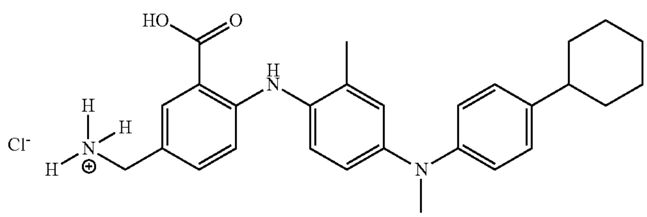 [SMILES: [Cl-] ; Cc1cc(N(C)c2ccc(C3CCCCC3)cc2)ccc1Nc1ccc(C[NH3+])cc1C(=O)O] | 1H NMR (400 MHz, DMSO-d6) δ 13.1 (s, 1H), 9.35 (s, 1H), 8.15 (s, 3H), 7.99 (d, J = 2.0 Hz, 1H), 7.41 (dd, J1 = 2.0 Hz, J2 = 8.8 Hz, 1H), 7.16-7.09 (m, 3H), 6.97 (d, J = 8.8 Hz, 2H), 6.92 (d, J = 2.4 Hz, 1H), 6.79 (dd, J1 = 2.8 Hz, J2 = 8.8 Hz, 1H), 6.65 (d, J = 8.4 Hz, 1H), 3.92-3.87 (m, 2H), 3.23 (s, 3H), 2.40 (s, 1H), 2.10 (s, 3H), 1.79-1.68 (m, 5H), 1.39-1.22 (m, 5H). LC-MS: m/z 427.2 (M + H)+. |
| 636 | 131 | XII.162 | 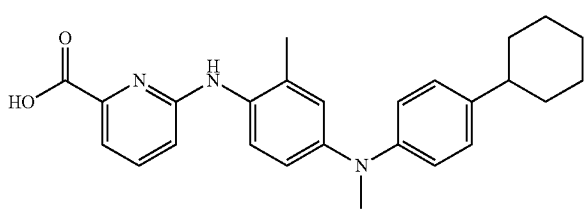 [SMILES: Cc1cc(N(C)c2ccc(C3CCCCC3)cc2)ccc1Nc1cccc(C(=O)O)n1] | 1H NMR (400 MHz, DMSO-d6) δ 8.33 (s, 1H), 7.61-7.59 (m, 1H), 7.38 (d, J = 8.4 Hz, 1H), 7.30 (d, J = 7.6 Hz, 1H), 7.11 (d, J = 8.8 Hz, 2H), 6.91-6.88 (m, 3H), 6.80-6.78 (m, 1H), 6.72 (d, J = 8.0 Hz, 1H), 3.21 (s, 3H), 2.49-2.45 (m, 1H), 2.15 (s, 3H), 1.79-1.67 (m, 5H), 1.38-1.33 (m, 5H). LC-MS: m/z 416.3 (M + H)+. |
| 637 | 132 | XII.163 | 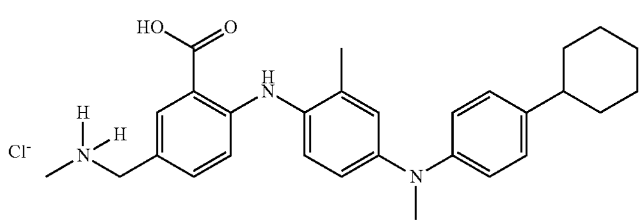 | 1H NMR (400 MHz, DMSO-d6) δ 9.62-9.50 (bs, 1H), 8.90-8.70 (bs, 1H), 8.02 (d, J = 1.2 Hz, 1H), 7.40 (d, J = 8.0 Hz, 1H), 7.16-7.10 (m, 3H), 6.98-6.91 (m, 3H), 6.79 (dd, J1 = 2.8 Hz, J2 = 8.8 Hz, 1H), 6.67 (d, J = 8.8 Hz, 1H), 3.98 (s, 2H), 3.23 (s, 3H), 2.54 (s, 1H), 2.50 (s, 3H), 2.10 (s, 3H), 1.79-1.68 (m, 5H), 1.39-1.23 (m, 5H). LC-MS: m/z 456.3 (M − H)+. |

-continued

| CP | Compound No | Reactant | Structure | Analytical data |
|---|---|---|---|---|
| 638 | 133 | XV.49 | 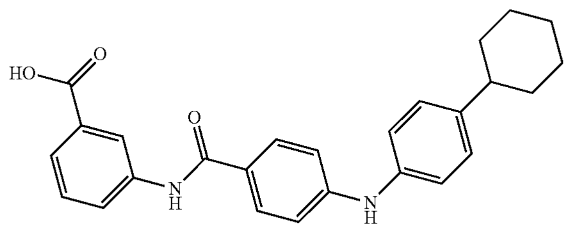 [SMILES: O=C(O)c1cccc(NC(=O)c2ccc(Nc3ccc(C4CCCCC4)cc3)cc2)c1] | 1H NMR (400 MHz, DMSO-d6) δ 13.00-12.90 (bs, 1H), 10.12 (s, 1H), 8.57 (s, 1H), 8.40 (t, J = 2.0 Hz, 1H), 8.03 (d, J = 8.4 Hz, 1H), 7.87 (d, J = 8.8 Hz, 2H), 7.63 (d, J = 8.8 Hz, 1H), 7.46 (d, J = 8.0 Hz, 1H), 7.17 (d, J = 8.4 Hz, 2H), 7.11-7.05 (m, 4H), 2.46-2.42 (m, 1H), 1.81-1.78 (m, 5H), 1.42-1.32 (m, 5H). LC-MS: m/z 415.2 (M + H)+. |
| 640 | 134 | XII.164 | 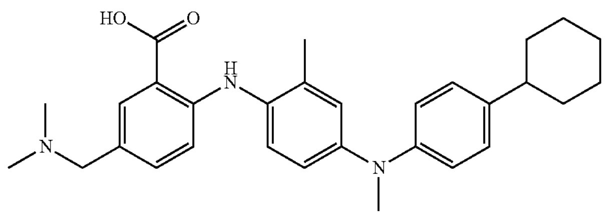 [SMILES: Cc1cc(N(C)c2ccc(C3CCCCC3)cc2)ccc1Nc1ccc(CN(C)C)cc1C(=O)O] | 1H NMR (400 MHz, DMSO-d6) δ 8.09 (s, 1H), 7.18 (d, J = 8.4 Hz, 2H), 7.10 (d, J = 8.4 Hz, 2H), 6.92 (d, J = 2.4 Hz, 1H), 6.87 (d, J = 8.4 Hz, 2H), 6.82-6.77 (m, 2H), 3.72 (s, 2H), 3.20 (s, 3H), 2.43 (s, 3H), 2.50 (s, 3H), 2.14 (s, 3H), 1.78-1.67 (m, 5H), 1.40-1.32 (m, 5H). LC-MS: m/z 470.3 (M + H)+. |
| 641 | 135 | XII.165 | 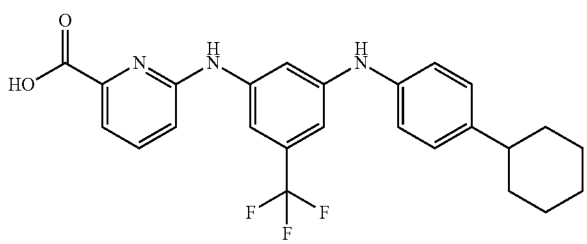 [SMILES: O=C(O)c1cccc(Nc2cc(Nc3ccc(C4CCCCC4)cc3)cc(C(F)(F)F)c2)n1] | 1H NMR (400 MHz, DMSO-d6) δ 8.38 (s, 1H), 7.68-7.64 (m, 1H), 7.37-7.31 (m, 3H), 7.17-7.03 (M, 6H), 6.78 (s, 1H), 2.46 (s, 1H), 1.79-1.68 (m, 5H), 1.39-1.16 (m, 5H). LC-MS: m/z 456.1 (M + H)+. |
| 642 | 136 | XII.166 | 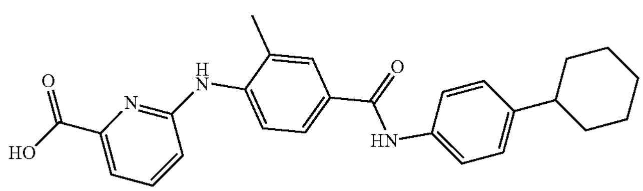 [SMILES: Cc1cc(C(=O)Nc2ccc(C3CCCCC3)cc2)ccc1Nc1cccc(C(=O)O)n1] | 1H NMR (400 MHz, DMSO-d6) δ 10.00 (s, 1H), 8.57 (s, 1H), 8.20 (d, J = 8.4 Hz, 1H), 7.82-7.66 (m, 5H), 7.47 (d, J = 7.6 Hz, 1H), 7.21-7.17 (m, 3H), 2.36 (s, 3H), 1.79-1.69 (m, 5H), 1.44-1.21 (m, 6H). LC-MS: m/z 430.2 (M + H)+. |
| 643 | 137 | XII.167 | 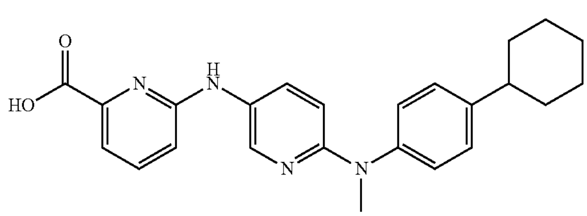 [SMILES: CN(c1ccc(C2CCCCC2)cc1)c1ccc(Nc2cccc(C(=O)O)n2)cn1] | 1H NMR (400 MHz, DMSO-d6) δ 12.80 (s, 1H), 9.06 (s, 1H), 8.67 (d, J = 2.0 Hz, 1H), 7.84 (dd, J1 = 2.8 Hz, J2 = 8.8 Hz, 1H), 7.64 (t, J = 8.0 Hz, 1H), 7.35 (d, J = 6.8 Hz, 1H), 7.23 (d, J = 8.4 Hz, 2H), 7.15 (d, J = 8.4 Hz, 2H), 6.91 (d, J = 8.4 Hz, 1H), 6.58 (d, J = 8.8 Hz, 1H), 3.34 (s, 3H), 1.90-1.69 (m, 5H), 1.42-1.22 (m, 6H). LC-MS: m/z 403.2 (M + H)+. |

-continued

| CP | Compound No | Reactant | Structure | Analytical data |
|---|---|---|---|---|
| 646 | 138 | XII.168 | 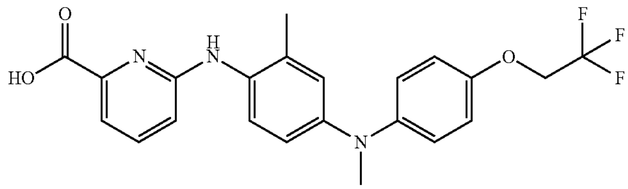 [SMILES: Cc1cc(N(C)c2ccc(OCC(F)(F)F)cc2)ccc1Nc1cccc(C(=O)O)n1] | 1H NMR (400 MHz, DMSO-d6) δ 13.20-12.40 (bs, 1H), 8.32 (s, 1H), 7.60 (t, J = 8.0 Hz, 1H), 7.33-7.28 (m, 2H), 7.05-7.00 (m, 4H), 6.78 (d, J = 2.4 Hz, 1H), 6.71-6.67 (m, 2H), 4.75-4.68 (m, 2H), 3.20 (s, 3H), 2.13 (s, 3H). LC-MS: m/z 432.2 (M + H)+. |
| 647 | 139 | XII.169 | 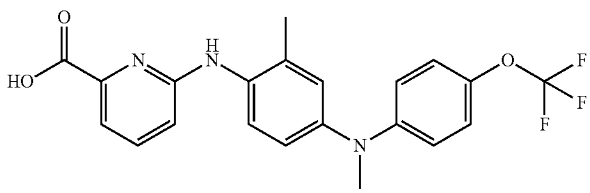 [SMILES: Cc1cc(N(C)c2ccc(OC(F)(F)F)cc2)ccc1Nc1cccc(C(=O)O)n1] | 1H NMR (400 MHz, DMSO-d6) δ 8.42 (s, 1H), 7.66-7.60 (m, 2H), 7.35 (d, J = 6.4 Hz, 1H), 7.19 (d, J = 8.0 Hz, 2H), 7.05 (d, J = 2.4 Hz, 1H), 6.97-6.85 (m, 4H), 3.25 (s, 3H), 2.21 (s, 3H). LC-MS: m/z 418.05 (M + H)+ |
| 648 | 140 | XII.170 | 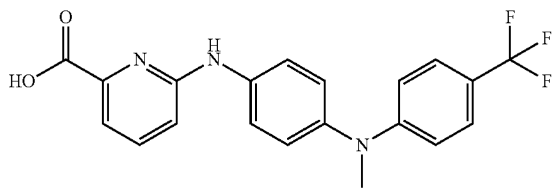 [SMILES: CN(c1ccc(Nc2cccc(C(=O)O)n2)cc1)c1ccc(C(F)(F)F)cc1] | 1H NMR (400 MHz, DMSO-d6) δ 9.43 (s, 1H), 7.91 (d, J = 9.2 Hz, 2H), 7.74-7.70 (m, 1H), 7.46-7.43 (m, 3H), 7.17 (d, J = 8.8 Hz, 2H), 7.05 (d, J = 8.0 Hz, 1H), 6.78 (d, J = 8.8 Hz, 2H), 3.28 (s, 3H). LC-MS: m/z 388.05 (M + H)+. |
| 649 | 141 | XII.171 | 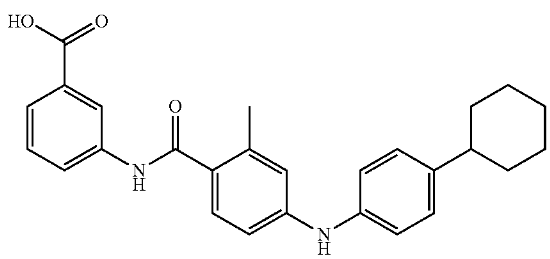 [SMILES: Cc1cc(Nc2ccc(C3CCCCC3)cc2)ccc1C(=O)Nc1cccc(C(=O)O)c1] | 1H NMR (400 MHz, DMSO-d6) δ 12.80 (bs, 1H), 10.21 (s, 1H), 8.40 (s, 1H), 8.32 (s, 1H), 7.92 (d, J = 8.4 Hz, 1H), 7.63 (d, J = 7.6 Hz, 1H), 7.45-7.39 (m, 2H), 7.14 (d, J = 8.4 Hz, 2H), 7.05 (d, J = 8.4 Hz, 2H), 6.88 (d, J = 7.2 Hz, 2H), 2.36 (s, 3H), 1.79-1.68 (m, 5H), 1.39-1.23 (m, 6H). LC-MS: m/z 429.2 (M + H)+. |
| 650 | 142 | XII.172 | 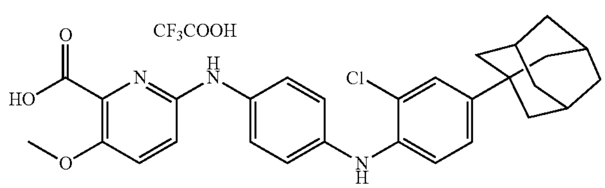 [SMILES: COc1ccc(Nc2ccc(Nc3ccc(C45CC6CC(CC(C6)C4)C5)cc3Cl)cc2)nc1C(=O)O ; "CF3COOH"] | 1H NMR (400 MHz, DMSO-d6) δ 12.90 (s, 1H), 8.80 (s, 1H), 7.53-7.50 (m, 4H), 7.27 (d, J = 2.0 Hz, 1H), 7.18 (s, 1H), 7.13-7.11 (m, 1H), 7.01 (d, J = 8.4 Hz, 2H), 6.92 (d, J = 8.8 Hz, 1H), 3.75 (s, 3H), 2.03 (s, 3H), 1.81-1.71 (m, 12H). LC-MS: m/z 506.3 (M + 2H)+. |
| 651 | 143 | XV.50 | 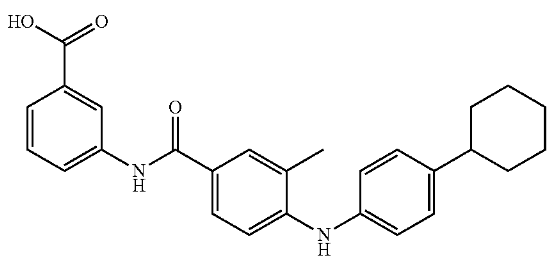 [SMILES: Cc1cc(C(=O)Nc2cccc(C(=O)O)c2)ccc1Nc1ccc(C2CCCCC2)cc1] | 1H NMR (400 MHz, DMSO-d6) δ 13.0 (s, 1H), 10.1 (s, 1H), 8.39 (s, 1H), 8.04 (d, J = 8.0 Hz, 1H), 7.82 (d, J = 1.6 Hz, 1H), 7.72-7.69 (m, 1H), 6.63 (d, J = 7.6 Hz, 1H), 7.55 (s, 1H), 7.46-7.44 (m, 1H), 7.16-7.11 (m, 3H), 7.07 (d, J = 8.8 Hz, 2H), 2.52-2.46 (m, 1H), 2.29 (S, 3H), 1.80-1.68 (m, 5H), 1.40-1.17 (m, 5H), LC-MS: m/z 427.2 (M + H)+. |

| CP | Compound No | Reactant | Structure | Analytical data |
|---|---|---|---|---|
| 652 | 144 | XII.173 | 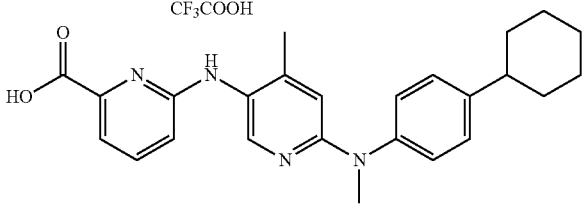 [SMILES: Cc1cc(N(C)c2ccc(C3CCCCC3)cc2)ncc1Nc1cccc(C(=O)O)n1 ; "CF3COOH"] | 1H NMR (400 MHz, DMSO-d6) δ 8.62 (s, 1H), 8.49 (s, 1H), 7.73-7.69 (m, 1H), 7.42 (d, J = 7.6 Hz, 1H), 7.36 (d, J = 8.4 Hz, 2H), 7.30 (d, J = 8.4 Hz, 2H), 7.22-7.09 (m, 1H) 6.76 (s, 1H), 3.42 (s, 3H), 2.25 (s, 3H), 1.85-1.70 (m, 5H), 1.45-1.23 (m, 6H). LC-MS: m/z 417.2 (M + H)+. |
| 654 | 145 | XII.174 | 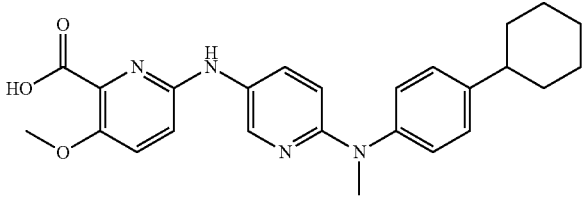 [SMILES: COc1ccc(Nc2ccc(N(C)c3ccc(C4CCCCC4)cc3)nc2)nc1C(=O)O] | 1H NMR (400 MHz, DMSO-d6) δ 12.90 (s, 1H), 8.76 (s, 1H), 8.52 (d, J = 2.4 Hz, 1H), 7.71-7.68 (m, 1H), 7.51 (d, J = 9.2 Hz, 1H), 7.23-7.12 (m, 4H), 6.87 (d, J = 9.2 Hz, 1H), 6.58 (d, J = 8.8 Hz, 1H), 3.74 (s, 3H), 3.29 (s, 3H), 2.49-2.47 (m, 1H), 1.81-1.79 (m, 5H), 1.39-1.37 (m, 5H). LC-MS: m/z 431.3 (M − H)+. |
| 655 | 146 | XII.175 | 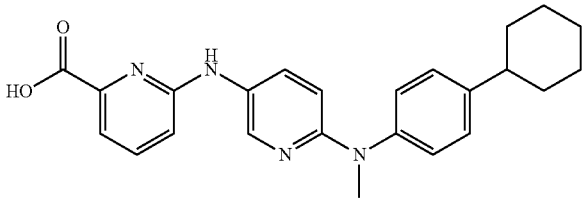 [SMILES: CN(c1ccc(C2CCCCC2)cc1)c1ccc(Nc2cccc(C(=O)O)n2)cn1] | 1H NMR (400 MHz, DMSO-d6) δ 7.70 (d, J = 2.4 Hz, 1H), 7.48-7.47 (m, 2H), 7.37 (dd, J1 = 6.8 Hz, J2 = 7.6 Hz, 1H), 7.27-7.13 (m, 5H), 7.05-7.03 (m, 1H), 6.70 (d, J = 9.2 Hz, 1H), 3.38 (s, 3H), 2.48-2.47 (m, 1H), 1.79-1.66 (m, 5H), 1.42-1.10 (m, 6H). LC-MS: m/z 402.5 (M + H)+. |
| 656 | 147 | XII.176 | 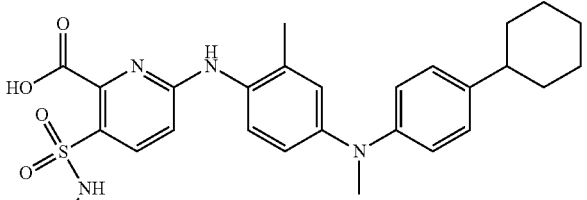 | 1H NMR (400 MHz, DMSO-d6) δ 8.02-7.60 (m, 2H), 7.14 (d, J = 8.4 Hz, 4H), 6.97 (d, J = 8.4 Hz, 2H), 6.80 (d, J = 2.4 Hz, 1H), 6.76-6.74 (m, 1H), 6.40-6.30 (m, 1H), 3.22 (d, J = 8.8 Hz, 3H), 2.40 (s, 3H), 2.14 (s, 3H), 1.89-1.72 (m, 5H), 1.42-1.31 (m, 6H). LC-MS: m/z 509.2 (M + H)+. |
| 659 | 148 | XII.177 | 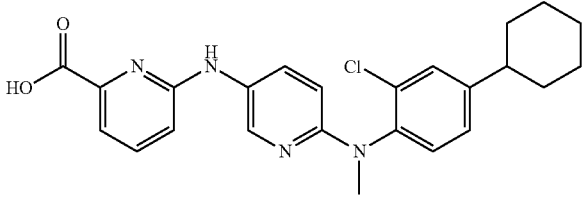 [SMILES: CN(c1ccc(Nc2cccc(C(=O)O)n2)cn1)c1ccc(C2CCCCC2)cc1Cl] | 1H NMR (400 MHz, DMSO-d6) δ 8.37 (bs, 1H), 7.65 (bs, 1H), 7.55 (t, J = 8.0 Hz, 1H), 7.43 (d, J = 1.6 Hz, 1H), 7.35 (d, J = 8.0 Hz, 2H), 7.30-7.25 (m, 2H), 6.75 (d, J = 7.6 Hz, 1H), 6.19 (d, J = 8.8 Hz, 1H), 3.29 (s, 3H), 2.45-2.41 (m, 1H), 1.84-1.69 (m, 5H), 1.45-1.32 (m, 5H). LC-MS: m/z 437.2 (M + H)+. |

-continued

| CP | Compound No | Reactant | Structure | Analytical data |
|---|---|---|---|---|
| 660 | 149 | XII.178 | 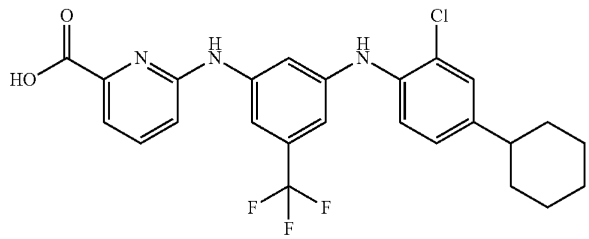 [SMILES: O=C(O)c1cccc(Nc2cc(Nc3ccc(C4CCCCC4)cc3Cl)cc(C(F)(F)F)c2)n1] | 1H NMR (400 MHz, DMSO-d6) δ 10.75 (bs, 1H), 8.03 (s, 1H), 7.66 (t, J = 8.0 Hz, 1H), 7.38-7.32 (m, 3H), 7.23-7.17 (m, 3H), 7.09 (d, J = 7.6 Hz, 1H), 6.72 (s, 1H), 2.45-2.41 (m, 1H), 1.79-1.67 (m, 5H), 1.43-1.30 (m, 5H). LC-MS: m/z 490.1 (M + H)+. |
| 661 | 150 | XII.179 | 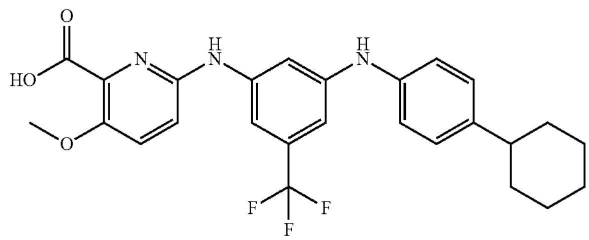 [SMILES: COc1ccc(Nc2cc(Nc3ccc(C4CCCCC4)cc3)cc(C(F)(F)F)c2)nc1C(=O)O] | 1H NMR (400 MHz, DMSO-d6) δ 8.96 (s, 1H), 8.25 (s, 1H), 7.49 (s, 1H), 7.37-7.34 (m, 2H), 7.16 (d, J = 8.0 Hz, 2H), 7.06 (d, J = 8.0 Hz, 2H), 6.75 (d, J = 8.4 Hz, 1H), 6.65 (s, 1H), 3.69 (s, 3H), 2.46-2.39 (m, 1H), 1.79-1.68 (m, 5H), 1.39-1.23 (m, 5H). LC-MS: m/z 486.2 (M + H)+. |
| 662 | 151 | XII.180 | 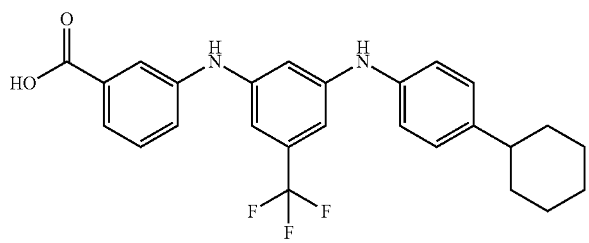 [SMILES: O=C(O)c1cccc(Nc2cc(Nc3ccc(C4CCCCC4)cc3)cc(C(F)(F)F)c2)c1] | 1H NMR (400 MHz, DMSO-d6) δ 12.90 (s, 1H), 8.60 (s, 1H), 8.36 (s, 1H), 7.69 (d, J = 2.0 Hz, 1H), 7.44-7.36 (m, 3H), 7.13 (d, J = 8.4 Hz, 2H), 7.04 (d, J = 8.4 Hz, 2H), 6.98 (s, 1H), 6.66 (d, J = 14.0 Hz, 2H), 1.77-1.75 (m, 6H), 1.38-1.22 (m, 5H). LC-MS: m/z 469.1 (M + H)+. |
| 663 | 152 | XII.181 | 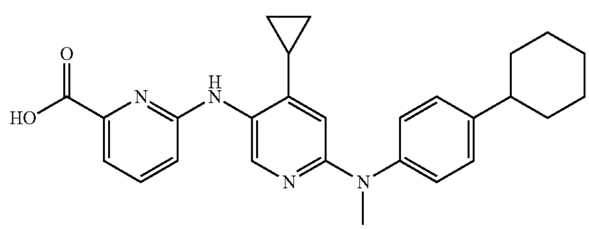 [SMILES: CN(c1ccc(C2CCCCC2)cc1)c1cc(C2CC2)c(Nc2cccc(C(=O)O)n2)cn1] | 1H NMR (400 MHz, DMSO-d6) δ 8.08 (s, 1H), 7.62 (t, J = 9.6 Hz, 1H), 7.32-7.24 (m, 3H), 7.17 (d, J = 8.0 Hz, 2H), 6.62 (d, J = 7.2 Hz, 1H), 6.06 (s, 1H), 3.34 (s, 3H), 1.81-1.69 (m, 7H), 1.42-1.23 (m, 5H), 0.84-0.82 (bs, 2H), 0.44-0.43 (m, 2H). LC-MS: m/z 443.2 (M + H)+. |
| 664 | 153 | XV.51 | 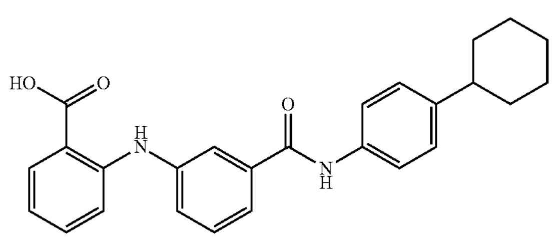 [SMILES: O=C(Nc1ccc(C2CCCCC2)cc1)c1cccc(Nc2ccccc2C(=O)O)c1] | 1H NMR (400 MHz, DMSO-d6) δ 13.20 (s, 1H), 10.14 (s, 1H), 9.90 (s, 1H), 7.93 (d, J = 6.8 Hz, 1H), 7.78 (s, 1H), 7.66-7.60 (m, 3H), 7.50-7.40 (m, 3H), 7.30 (d, J = 4.0 Hz, 1H), 7.18 (d, J = 8.4 Hz, 2H), 6.83 (t, J = 7.2 Hz, 1H), 1.78-1.68 (m, 5H), 1.44-1.23 (m, 6H). LC-MS: m/z 415.2 (M + H)+. |
| 665 | 154 | XII.182 | 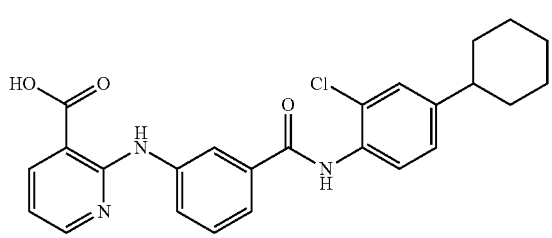 | 1H NMR (400 MHz, DMSO-d6) δ 13.72 (bs, 1H), 10.60 (s, 1H), 9.95 (s, 1H), 8.42 (d, J = 2.8 Hz, 1H), 8.29-8.27 (m, 1H), 8.20 (s, 1H), 8.07 ((d, J = 8.4 Hz, 1H), 7.62 (d, J = 7.2 Hz, 1H), 7.50-7.46 (m, 2H), 7.38 (s, 1H), 7.24 (d, J = 8.4 Hz, 1H), 6.93-6.90 (m, 1H), |

| CP | Compound No | Reactant | Structure | Analytical data |
|---|---|---|---|---|
| | | | | 2.49-2.47 (m, 1H), 1.81-1.69 (m, 5H), 1.43-1.23 (m, 5H). LC-MS: m/z 450.1 (M + H)+. |
| 666 | 155 | XII.183 | 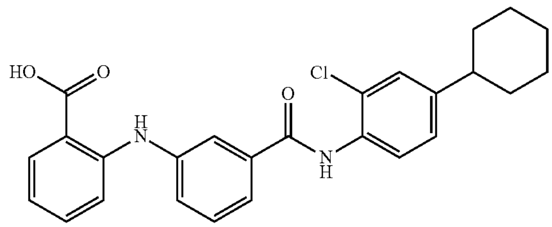 [SMILES: O=C(Nc1ccc(C2CCCCC2)cc1Cl)c1cccc(Nc2ccccc2C(=O)O)c1] | 1H NMR (400 MHz, DMSO-d6) δ 13.19 (s, 1H), 9.97 (s, 1H), 9.75 (s, 1H), 7.93 (dd, J1 = 0.8 Hz, J2 = 7.6 Hz, 1H), 7.81 (s, 1H), 7.640 (d, J = 6.0 Hz, 1H), 7.52-7.38 (m, 5H), 7.31 (d, J = 8.4 Hz, 1H), 7.24-7.22 (m, 1H), 6.86-6.82 (m, 1H), 2.49-2.43 (m, 1H), 1.81-1.68 (m, 5H) 1.46-1.22 (m, 5H). LC-MS: m/z 449.05 (M + H)+. |
| 669 | 156 | XII.184 | 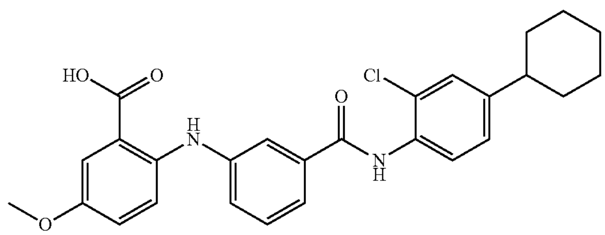 | 1H NMR (400 MHz, DMSO-d6) δ 13.25 (bs, 1H), 9.91 (s, 1H), 9.29 (bs, 1H), 7.70 (s, 1H), 7.53 (d, J = 8 Hz, 1H), 7.47-7.32 (m, 6H), 7.23 (d, J = 8 Hz, 1H), 7.12 (dd, J1 = 2.8 Hz, J2 = 8.8 Hz, 1H), 3.74 (s, 3H), 2.45-2.41 (m, 1H), 1.81-1.68 (m, 5H), 1.46-1.31 (m, 5H). LC-MS: m/z 479.2 (M + H)+. |
| 671 | 157 | XII.185 | 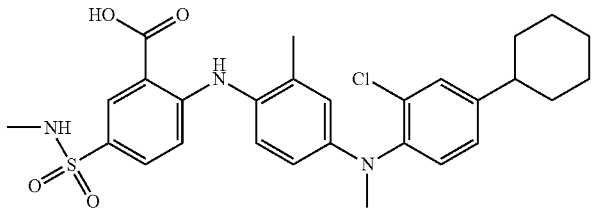 | 1H NMR (400 MHz, DMSO-d6) δ 13.40 (s, 1H), 9.61 (s, 1H), 8.23 (d, J = 2.0 Hz, 1H), 7.60 (dd, J1 = 2.4 Hz, J2 = 9.2 Hz, 1H), 7.44 (s, 1H), 7.30 (s, 2H), 7.21 (d, J = 6.5 Hz, 1H), 7.04 (d, J = 8.8 Hz, 1H), 6.60-6.50 (m, 2H), 6.33 (dd, J1 = 2.8 Hz, J2 = 8.2 Hz, 1H), 3.19 (s, 3H), 2.36 (d, J = 4.8 Hz, 3H), 2.07 (s, 3H), 1.84-1.68 (m, 5H), 1.44-1.16 (m, 6H). LC-MS: m/z 542.2 (M + H)+. |
| 672 | 158 | XII.186 | 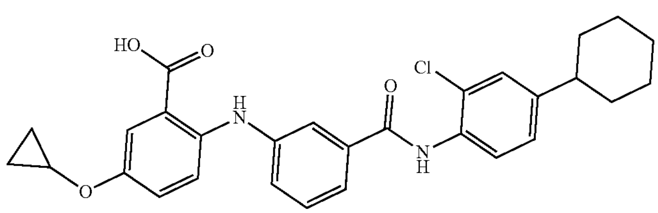 [SMILES: O=C(Nc1ccc(C2CCCCC2)cc1Cl)c1cccc(Nc2ccc(OC3CC3)cc2C(=O)O)c1] | 1H NMR (400 MHz, DMSO-d6) δ 9.88 (s, 1H), 7.63 (dd, J1 = 2.8 Hz, J2 = 6.8 Hz, 2H), 7.47 (d, J = 8 Hz, 1H), 7.41-7.33 (m, 3H), 7.29-7.21 (m, 3H), 6.97 (d, J = 7.6 Hz, 1H), 3.80-3.75 (m, 1H), 2.45-2.41 (m, 1H), 1.81-1.68 (m, 5H), 1.46-1.32 (m, 5H), 0.74-0.73 (m, 2H), 0.64-0.60 (m, 2H). LC-MS: m/z 505.2 (M + H)+. |
| 673 | 159 | XII.187 | 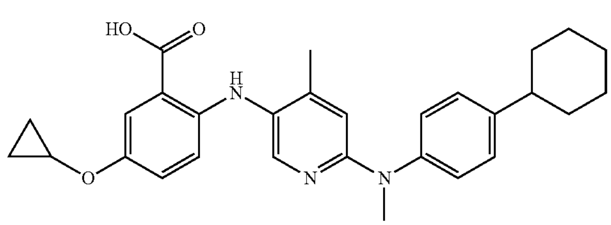 [SMILES: Cc1cc(N(C)c2ccc(C3CCCCC3)cc2)ncc1Nc1ccc(OC2CC2)cc1C(=O)O] | 1H NMR (400 MHz, DMSO-d6) δ 8.75-9.00 (bs, 1H), 7.97 (s, 1H), 7.55 (d, J = 2.4 Hz, 1H), 7.26 (d, J = 8.4 Hz, 2H), 7.20 (d, J = 8.4 Hz, 2H), 7.00 (dd, J1 = 2.4 Hz, J2 = 9.2 Hz, 1H), 6.49 (s, 1H), 6.43 (d, J = 9.2 Hz, 1H), 3.78-3.71 (m, 1H), |

-continued

| CP | Compound No | Reactant | Structure | Analytical data |
|---|---|---|---|---|
| | | | | 3.35 (s, 3H), 2.45-2.41 (m, 1H), 1.97 (s, 3H), 1.85-1.69 (m, 5H), 1.46-1.32 (m, 5H), 0.75-0.70 (m, 2H), 0.65-0.58 (m, 2H). LC-MS: m/z 472.25 (M + H)+. |
| 675 | 160 | XII.188 | 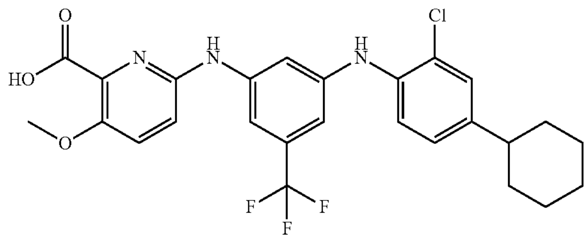 [SMILES: COc1ccc(Nc2cc(Nc3ccc(C4CCCCC4)cc3Cl)cc(C(F)(F)F)c2)nc1C(=O)O] | 1H NMR (400 MHz, DMSO-d6) δ 8.74 (s, 1H), 7.80 (s, 1H), 7.53 (s, 1H), 7.33-7.09 (m, 5H), 6.05 (s, 1H), 6.57 (d, J = 8.4 Hz, 1H), 3.63 (s, 3H), 2.49-2.47 (m, 1H), 1.80-1.67 (m, 5H), 1.40-1.33 (m, 5H). LC-MS: m/z 518.1 (M + H)+. |
| 676 | 161 | XII.189 | 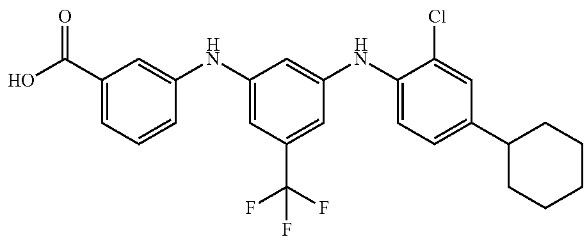 [SMILES: O=C(O)c1cccc(Nc2cc(Nc3ccc(C4CCCCC4)cc3Cl)cc(C(F)(F)F)c2)c1] | 1H NMR (400 MHz, DMSO-d6) δ 12.92 (s, 1H), 8.58 (s, 1H), 8.02 (s, 1H), 7.65 (s, 1H), 7.45-7.29 (m, 5H), 7.17-7.15 (m, 1H), 6.80 (s, 1H), 6.67 (s, 2H), 2.60-2.40 (m, 1H), 1.79-1.67 (m, 5H), 1.36-1.22 (m, 5H). LC-MS: m/z 489.2 (M + H)+. |
| 677 | 162 | XII.190 | 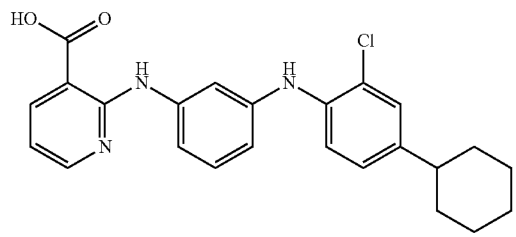 [SMILES: O=C(O)c1cccnc1Nc1cccc(Nc2ccc(C3CCCCC3)cc2Cl)c1] | 1H NMR (400 MHz, DMSO-d6) δ 13.60 (s, 1H), 10.48 (s, 1H), 8.34-8.33 (m, 1H), 8.22 (dd, J1 = 2.0 Hz, J2 = 8.0 Hz, 1H), 7.54 (s, 1H), 7.47 (s, 1H), 7.29-7.20 (m, 2H), 7.15-7.09 (m, 3H), 6.83 (dd, J1 = 4.8 Hz, J2 = 7.6 Hz, 1H), 6.65-6.63 (m, 1H), 2.49-2.45 (m, 1H), 1.77-1.67 (m, 5H), 1.42-1.18 (m, 5H). LC-MS: m/z 422.1 (M + H)+. |
| 678 | 163 | XII.191 | 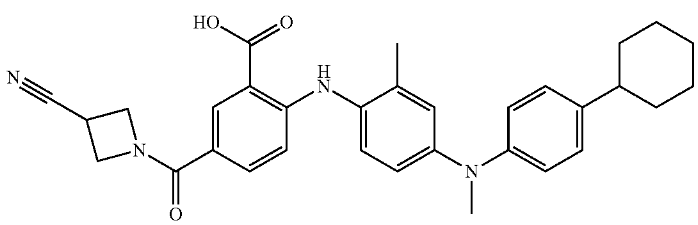 [SMILES: Cc1cc(N(C)c2ccc(C3CCCCC3)cc2)ccc1Nc1ccc(C(=O)N2CC(C#N)C2)cc1C(=O)O] | 1H NMR (400 MHz, DMSO-d6) δ 13.2 (s, 1H), 9.70 (s, 1H), 8.18 (d, J = 2.4 Hz, 1H), 7.57 (dd, J1 = 2.4 Hz, J2 = 8.8 Hz, 1H), 7.17-7.12 (m, 3H), 6.99 (d, J = 8.8 Hz, 2H), 6.91 (d, J = 2.4 Hz, 1H), 6.78 (dd, J1 = 2.8 Hz, J2 = 8.4 Hz, 1H), 6.60 (d, J = 8.8 Hz, 1H), 4.40 (bs, 4H), 3.90-3.80 (m, 1H), 3.24 (s, 3H), 2.45-2.42 (m, 1H), 2.10 (s, 3H), 1.79-1.77 (m, 5H), 1.39-1.34 (m, 5H). LC-MS: m/z 523.3 (M + H)+ |
| 679 | 164 | XII.191 | 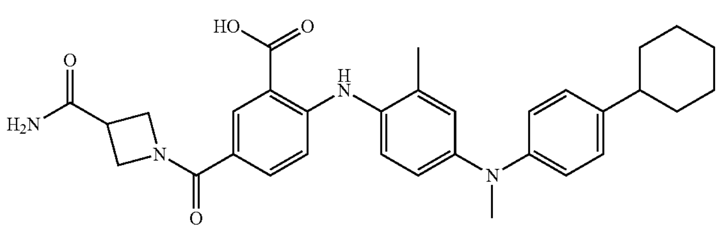 [SMILES: Cc1cc(N(C)c2ccc(C3CCCCC3)cc2)ccc1Nc1ccc(C(=O)N2CC(C(N)=O)C2)cc1C(=O)O] | 1H NMR (400 MHz, DMSO-d6) δ 13.19 (s, 1H), 9.61 (s, 1H), 8.19 (s, 1H), 7.58 (dd, J1 = 1.6 Hz, J2 = 8.8 Hz, 1H), 7.47 (s, 1H), 7.17-7.12 (m, 3H), 7.03-6.98 (m, 3H), 6.91 (s, 1H), 6.78 (dd, J1 = 2.2 Hz, J2 = 8.8 Hz, 1H), 6.62 (d, J = 8.8 Hz, 1H), 4.39-3.98 (m, 4H), 3.23 (s, |

-continued

| CP | Compound No | Reactant | Structure | Analytical data |
|---|---|---|---|---|
| | | | | 3H), 2.49-2.43 (m, 1H), 2.10 (s, 3H), 1.79-1.68 (m, 6H), 1.42-1.30 (m, 5H). LC-MS: m/z 541.3 (M + H)+ |
| 680 | 165 | XII.192 | 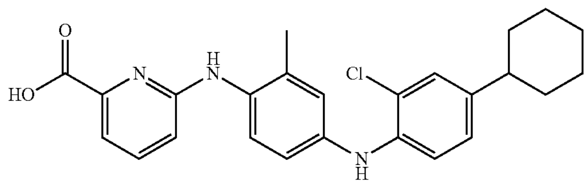 [SMILES: Cc1cc(Nc2ccc(C3CCCCC3)cc2Cl)ccc1Nc1cccc(C(=O)O)n1] | 1H NMR (400 MHz, DMSO-d6) δ 8.86 (s, 1H), 7.62-7.56 (m, 2H), 7.33-7.22 (m, 3H), 7.11-7.02 (m, 2H), 6.96 (d, J = 2.0 Hz, 1H), 6.88-6.83 (m, 1H), 6.41 (d, J = 8.4 Hz, 1H), 2.47-2.42 (m, 1H), 2.09 (s, 3H), 1.81-1.66 (m, 5H), 1.42-1.22 (m, 5H). LC-MS: m/z 436.2 (M + H)+ |
| 681 | 166 | XII.193 | 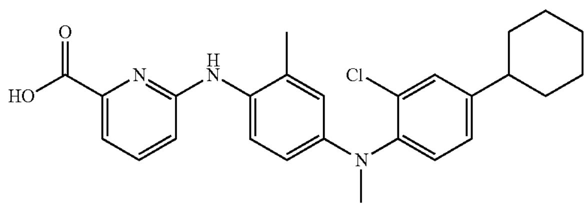 [SMILES: Cc1cc(N(C)c2ccc(C3CCCCC3)cc2Cl)ccc1Nc1cccc(C(=O)O)n1] | 1H NMR (400 MHz, DMSO-d6) δ 8.25 (s, 1H), 7.56-7.54 (m, 1H), 7.41 (s, 1H), 7.28-7.23 (m, 3H), 7.15-7.12 (m, 1H), 6.57-6.47 (m, 2H), 6.30 (d, J = 5.6 Hz, 1H), 3.17 (s, 3H), 2.04 (s, 3H), 1.86-1.66 (m, 5H), 1.44-1.15 (m, 6H). LC-MS: m/z 450.2 (M + H)+ |
| 682 | 167 | XII.194 | 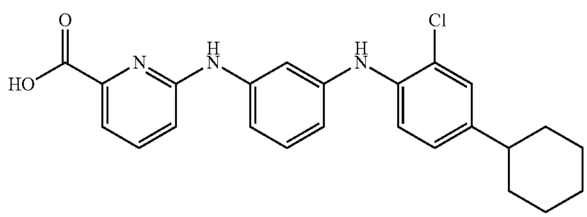 [SMILES: O=C(O)c1cccc(Nc2cccc(Nc3ccc(C4CCCCC4)cc3Cl)c2)n1] | 1H NMR (400 MHz, DMSO-d6) δ 10.4 (s, 1H), 7.62-7.55 (m, 2H), 7.32-7.26 (m, 4H), 7.16-6.95 (m, 5H), 6.61 (d, J = 7.6 Hz, 1H), 2.44-2.32 (m, 1H), 1.84-1.67 (m, 5H), 1.38-1.19 (m, 5H). LC-MS: m/z 422.0 (M + H)+ |

The below compounds were prepared by a procedure similar to Intermediate-XV using appropriate reactants and reagents and in presence of suitable solvents and appropriate reaction conditions.

| CP | Compound No | Reactant | Structure | Analytical data |
|---|---|---|---|---|
| 72 | 277 | Compound 24 | 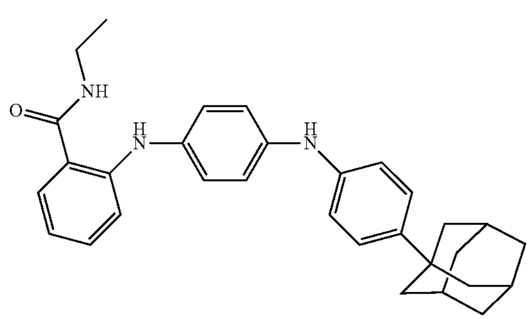 [SMILES: CCNC(=O)c1ccccc1Nc1ccc(Nc2ccc(C34CC5CC(CC(C5)C3)C4)cc2)cc1] | LC-MS: m/z 466.1 (M + H)+ |

-continued

| CP | Compound No | Reactant | Structure | Analytical data |
|---|---|---|---|---|
| 94 | 278 | Int-XI | 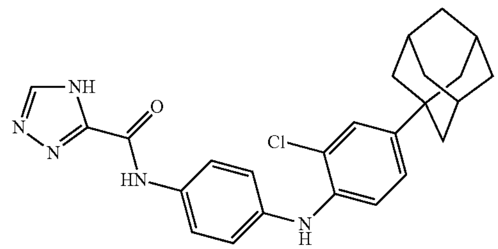 [SMILES: O=C(Nc1ccc(Nc2ccc(C34CC5CC(CC(C5)C3)C4)cc2Cl)cc1)c1nnc[nH]1] | ¹H NMR (400 MHz, DMSO-d6) δ 14.55 (bs, 1H), 10.20 (bs, 1H), 8.72 (bs, 1H), 7.68 (d, J = 8.8 Hz, 2H), 7.49 (s, 1H), 7.32 (d, J = 2.0 Hz, 1H), 7.20-7.15 (m, 2H), 7.02 (d, J = 8.8 Hz, 2H), 2.04 (s, 3H), 1.83 (s, 6H), 1.72 (s, 6H). LC-MS: m/z 448.1 (M + H)⁺ |
| 111 | 279 | Compound 31 | 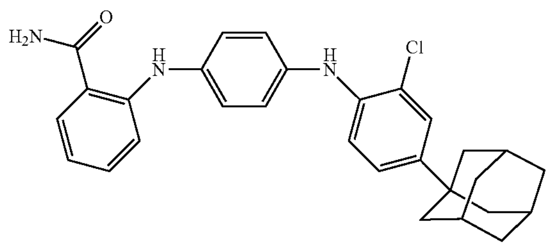 [SMILES: NC(=O)c1ccccc1Nc1ccc(Nc2ccc(C34CC5CC(CC(C5)C3)C4)cc2Cl)cc1] | ¹H NMR (400 MHz, DMSO-d6) δ 9.91 (s, 1H), 7.99 (s, 1H), 7.68 (dd, J₁ = 1.6 Hz, J₂ = 8.0 Hz, 1H), 7.42 (s, 1H), 7.37 (s, 1H), 7.31 (d, J = 2.0 Hz, 1H), 7.29-7.24 (m, 1H), 7.19-7.12 (m, 2H), 7.08-7.02 (m, 5H), 6.68 (t, J = 7.2 Hz, 1H), 2.04 (s, 3H), 1.83 (s, 6H), 1.72 (s, 6H). LC-MS: m/z 472.2 (M + H)⁺ |
| 112 | 280 | Compound 279 | 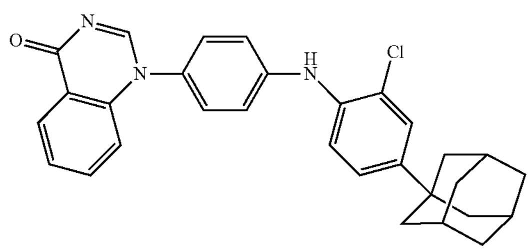 [SMILES: O=c1ncn(-c2ccc(Nc3ccc(C45CC6CC(CC(C6)C4)C5)cc3Cl)cc2)c2ccccc12] | ¹H NMR (400 MHz, DMSO-d6) δ 8.45 (s, 1H), 8.14-8.12 (m, 2H), 7.74-7.70 (m, 1H), 7.51 (t, J = 8.4 Hz, 1H), 7.43-7.38 (m, 4H), 7.33-7.29 (m, 1H), 7.01 (d, J = 8.8 Hz, 2H), 6.98 (d, J = 8.4 Hz, 1H), 2.06 (s, 3H), 1.87 (s, 6H), 1.73 (s, 6H). LC-MS: m/z 482.1 (M + H)⁺ |
| 120 | 281 | Compound 31 | 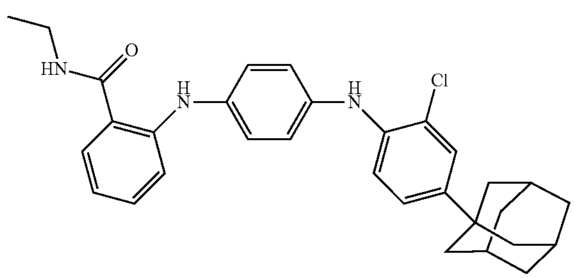 [SMILES: CCNC(=O)c1ccccc1Nc1ccc(Nc2ccc(C34CC5CC(CC(C5)C3)C4)cc2Cl)cc1] | ¹H NMR (400 MHz, DMSO-d6) δ 9.61 (s, 1H), 8.48 (m, 1H), 7.61 (dd, J₁ = 1.6 Hz, J₂ = 8.0 Hz, 1H), 7.40 (s, 1H), 7.31 (d, J = 2.4 Hz, 1H), 7.26 (t, J = 8.4 Hz, 1H), 7.19-7.01 (m, 7H), 6.74-6.70 (m, 1H), 3.29-3.24 (m, 2H), 2.04 (s, 3H), 1.82 (s, 6H), 1.72 (s, 6H), 1.12 (t, J = 7.2 Hz, 3H). LC-MS: m/z 500.2 (M + H)⁺ |
| 123 | 282 | Compound 31 | 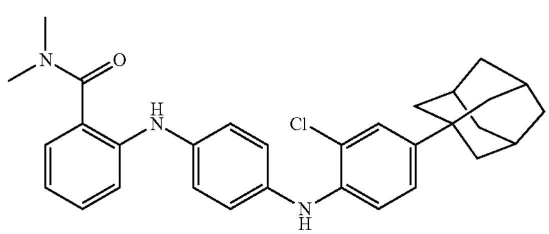 [SMILES: CN(C)C(=O)c1ccccc1Nc1ccc(Nc2ccc(C34CC5CC(CC(C5)C3)C4)cc2Cl)cc1] | ¹H NMR (400 MHz, DMSO-d6) δ 7.41 (s, 1H), 7.29 (d, J = 2.0 Hz, 1H), 7.27 (s, 1H), 7.24-7.21 (m, 1H), 7.18-7.13 (m, 2H), 7.10-7.03 (m, 2H), 6.99 (s, 4H), 6.83 (t, J = 7.2 Hz, 1H), 2.91 (s, 6H), 2.04 (s, 3H), 1.82 (s, 6H), 1.71 (s, 6H). LC-MS: m/z 500.4 (M + H)⁺ |
| 164 | 283 | Compound 31 | 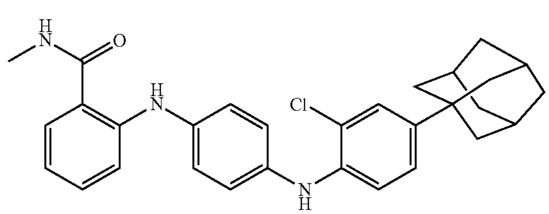 [SMILES: CNC(=O)c1ccccc1Nc1ccc(Nc2ccc(C34CC5CC(CC(C5)C3)C4)cc2Cl)cc1] | ¹H NMR (400 MHz, DMSO-d6) δ 9.62 (s, 1H), 8.45 (s, 1H), 7.59 (dd, J₁ = 1.6 Hz, J₂ = 8.0 Hz, 1H), 7.40 (s, 1H), 7.31 (d, J = 2.0 Hz, 1H), 7.26 (t, J = 6.8 Hz, 1H), 7.20-7.02 (m, 7H), 6.72 (t, J = 7.6 Hz, 1H), 2.77 (d, J = 5.2 Hz, 3H), 2.04 (s, 3H), 1.83 (s, 6H), 1.72 (s, 6H). LC-MS: m/z 485.2 (M + H)⁺ |

-continued

| CP | Compound No | Reactant | Structure | Analytical data |
|---|---|---|---|---|
| 208 | 284 | Compound 92 | 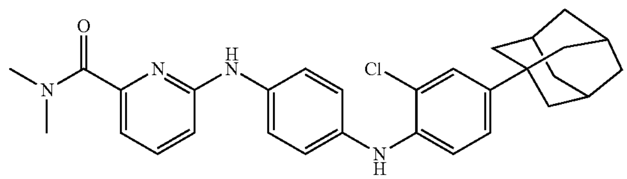 [SMILES: CN(C)C(=O)c1cccc(Nc2ccc(Nc3ccc(C45CC6CC(CC(C6)C4)C5)cc3Cl)cc2)n1] | ¹H NMR (400 MHz, DMSO-d6) δ 9.0 (s, 1H), 7.6 (d, J = 7.3 Hz, 1H), 7.5 (d, J = 8.9 Hz, 2H), 7.29 (d, J = 2.9 Hz, 1H), 7.26 (s, 1H), 7.15 (m, 1H), 7.07-7.01 (m, 3H), 6.79 (t, J = 8.3 Hz, 2H), 2.98 (s, 6H), 2.04 (s, 3H), 1.82 (s, 6H), 1.72 (s, 6H). LC-MS: m/z 501.3 (M + H)⁺ |
| 209 | 285 | Compound 60 | 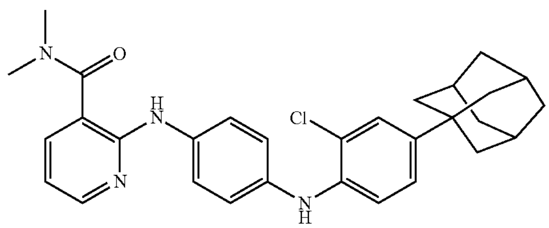 | ¹H NMR (400 MHz, DMSO-d6) δ 8.23 (s, 1H), 8.15 (dd, J₁ = 2.0 Hz, J₂ = 7.6 Hz, 1H), 7.55 (dd, J₁ = 2.0 Hz, J₂ = 7.6 Hz, 1H), 7.45 (d, J = 8.8 Hz, 2H), 7.29 (s, 2H), 7.16 (dd, J₁ = 2.8 Hz, J₂ = 8.8 Hz, 1H), 7.07 (d, J = 8.4 Hz, 1H), 7.01 (d, J = 8.8 Hz, 2H), 6.78 (dd, J₁ = 4.8 Hz, J₂ = 7.2 Hz, 1H), 2.97 (s, 6H), 2.04 (s, 3H), 1.82 (s, 6H), 1.72 (s, 6H). LC-MS: m/z 501.3 (M + H)⁺ |
| 605 | 168 | Compound 279 | 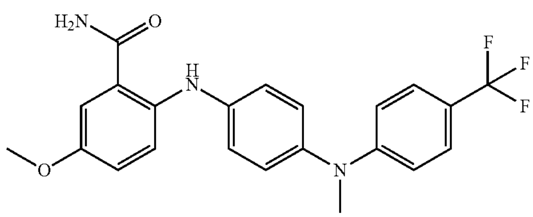 [SMILES: COc1ccc(Nc2ccc(N(C)c3ccc(C(F)(F)F)cc3)cc2)c(C(N)=O)c1] | 1H NMR (400 MHz, DMSO-d6) δ 9.35 (s, 1H), 8.08 (s, 1H), 7.51 (bs, 1H), 7.44 (d, J = 8.4 Hz, 2H), 7.30-7.27 (m, 2H), 7.12-7.00 (m, 5H), 6.77 (d, J = 8.8 Hz, 2H), 3.76 (s, 3H), 3.25 (s, 3H). LC-MS: m/z 416.10 (M + H)+. |
| 606 | 169 | Compound 279 | 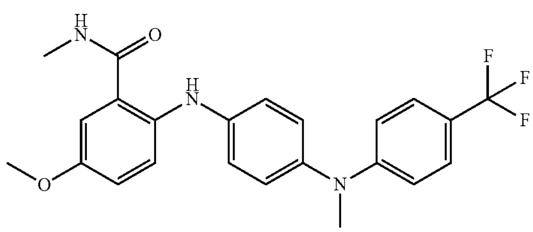 [SMILES: CNC(=O)c1cc(OC)ccc1Nc1ccc(N(C)c2ccc(C(F)(F)F)cc2)cc1] | 1H NMR (400 MHz, DMSO-d6) δ 9.06 (s, 1H), 8.49-8.52 (m, 1H), 7.42 (d, J = 8.8 Hz, 2H), 7.28 (d, J = 8.8 Hz, 1H), 7.17 (d, J = 2.4 Hz, 1H), 7.09-7.03 (m, 4H), 7.01-6.96 (m, 1H), 6.74 (d, J = 8.8 Hz, 2H), 3.75 (s, 3H), 3.23 (s, 3H), 2.74 (d, J = 4.8 Hz, 3H). LC-MS: m/z 430.2 (M + H)+. |
| 607 | 170 | Compound 279 | 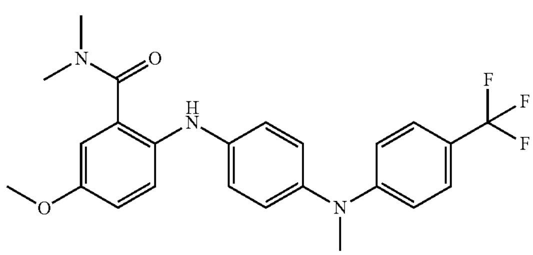 [SMILES: COc1ccc(Nc2ccc(N(C)c3ccc(C(F)(F)F)cc3)cc2)c(C(=O)N(C)C)c1] | 1H NMR (400 MHz, DMSO-d6) δ 7.42 (d, J = 8.8 Hz, 3H), 7.22 (d, J = 8.8 Hz, 1H), 7.00 (d, J = 8.4 Hz, 2H), 6.97-6.94 (m, 1H), 6.89 (d, J = 8.8 Hz, 2H), 6.81 (d, J = 3.2 Hz, 1H), 6.72 (d, J = 8.8 Hz, 2H), 3.75 (s, 3H), 3.22 (s, 3H), 2.90 (s, 3H), 2.81 (s, 3H). LC-MS: m/z 444.2 (M + H)+. |
| 653 | 171 | XI.53 | 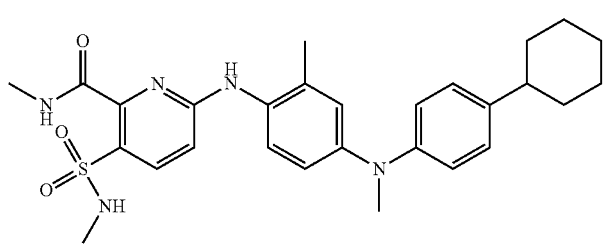 [SMILES: CNC(=O)c1nc(Nc2ccc(N(C)c3ccc(C4CCCCC4)cc3)cc2C)ccc1S(=O)(=O)NC] | 1H NMR (400 MHz, DMSO-d6) δ 9.00 (s, 1H), 8.43 (d, J = 4.8 Hz, 1H), 7.83 (d, J = 8.8 Hz, 1H), 7.22-7.14 (m, 3H), 6.97 (d, J = 8.4 Hz, 2H), 6.87 (d, J = 2.0 Hz, 1H), 6.77-6.75 (m, 2H), 6.56-6.51 (m, 1H), 3.23 (s, 3H), 2.73 (d, J = 4.8 Hz, 3H), 2.45 (d, J = 5.2 Hz, 3H), 2.14 (s, 3H), 1.79-1.68 (m, 5H), 1.44-1.34 (m, 6H). LC-MS: m/z 522.2 (M + H)+ |

The below compounds were prepared by a procedure similar to Intermediate-XIV using appropriate reactants and reagents and in presence of suitable solvents and appropriate reaction conditions.

| CP | Compound No | Reactant | Structure | Analytical data |
|---|---|---|---|---|
| 109 | 286 | XV.4 | 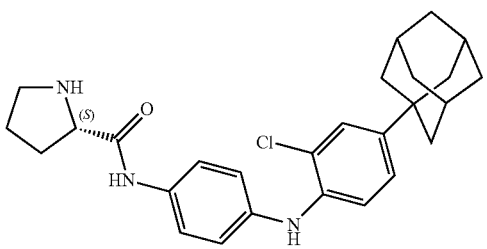 | $^1$H NMR (400 MHz, DMSO-d6) δ 9.86 (s, 1H), 7.50 (d, J = 8.8 Hz, 2H), 7.41 (s, 1H), 7.31 (s, 1H), 7.18 (m, 1H), 7.11 (s, 1H), 6.98 (d, J = 4.0 Hz, 2H), 3.74 (m, 1H), 2.95 (t, J = 6.9 Hz, 2H), 2.08 (m, 4H), 1.90 (m, 7H), 1.68 (m, 7H), 1.56-1.48 (m, 1H). LC-MS: m/z 450.2 (M + H)$^+$ |
| 230 | 287 | XV.10 | 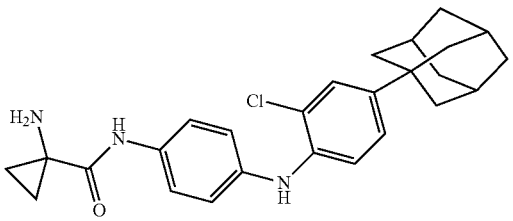 [SMILES: NC1(C(=O)Nc2ccc(Nc3ccc(C45CC6CC(CC(C6)C4)C5)cc3Cl)cc2)CC1] | $^1$H NMR (400 MHz, DMSO-d6) δ 9.88 (s, 1H), 7.51 (d, J = 8.8 Hz, 2H), 7.38 (s, 1H), 7.30 (d, J = 2.0 Hz, 1H), 7.16-7.14 (m, 1H), 7.1 (d, J = 8.8 Hz, 1H), 6.99 (d, J = 8.8 Hz, 2H), 2.04 (s, 3H), 1.82 (s, 6H), 1.72 (s, 6H), 1.17-1.15 (m, 2H), 0.87-0.84 (m, 2H). LC-MS: m/z 436.2 (M + H)$^+$ |
| 152 | 288 | Compound 77 | 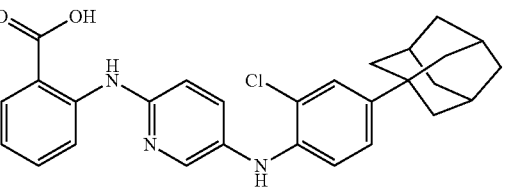 | $^1$H NMR (400 MHz, DMSO-d6) δ 13.21 (bs, 1H), 10.60 (bs, 1H), 8.48 (d, J = 8.0 Hz, 1H), 8.08 (d, J = 2.8 Hz, 1H), 7.94 (dd, J$_1$ = 1.6 Hz, J$_2$ = 8.0 Hz, 1H), 7.51-7.44 (m, 3H), 7.31 (d, J = 2.0 Hz, 1H), 7.16 (dd, J$_1$ = 1.6 Hz, J$_2$ = 8.0 Hz, 1H), 6.98 (t, J = 8.4 Hz, 2H), 6.87 (t, J = 8.4 Hz, 1H), 2.04 (s, 3H), 1.82 (s, 6H), 1.72 (s, 6H). LC-MS: m/z 474.3 (M + H)$^+$ |
| 155 | 289 | Compound 288 | 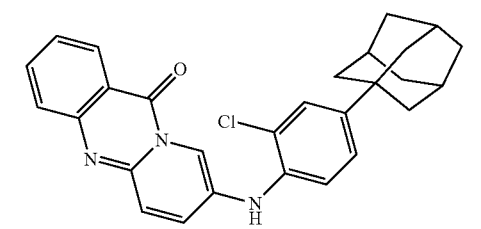 [SMILES: O=c1c2ccccc2nc2ccc(Nc3ccc(C45CC6CC(CC(C6)C4)C5)cc3Cl)cn12] | $^1$H NMR (400 MHz, DMSO-d6) δ 8.36 (d, J = 2.4 Hz, 1H), 8.26 (dd, J$_1$ = 1.2 Hz, J$_2$ = 8.0 Hz, 1H), 8.07 (s, 1H), 7.88-7.84 (m, 1H), 7.75-7.70 (m, 2H), 7.56 (d, J = 10 Hz, 1H), 7.51-7.47 (m, 1H), 7.43 (d, J = 2.0 Hz, 1H), 7.32-7.26 (m, 2H), 2.06 (s, 3H), 1.87 (s, 6H), 1.74 (s, 6H). LC-MS: m/z 456.3 (M + H)$^+$ |

-continued

| CP | Compound No | Reactant | Structure | Analytical data |
|---|---|---|---|---|
| 153 | 290 | Compound 75 | 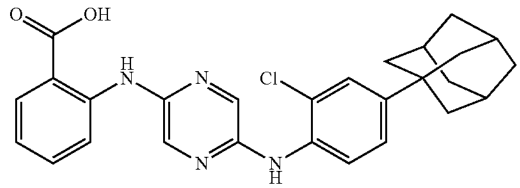 [SMILES: O=C(O)c1ccccc1Nc1cnc(Nc2ccc(C34CC5CC(CC(C5)C3)C4)cc2Cl)cn1] | $^1$H NMR (400 MHz, DMSO-d6) δ 13.21 (bs, 1H), 10.46 (bs, 1H), 8.45 (s, 1H), 8.14 (d, J = 8.0 Hz, 1H), 8.11 (d, J = 8.8 Hz, 1H), 8.04 (s, 1H), 7.94 (dd, $J_1$ = 1.6 Hz, $J_2$ = 8.0 Hz, 1H), 7.78 (d, J = 8.4 Hz, 1H), 7.47 (t, J = 8.4 Hz, 1H), 7.35 (d, J = 2.4 Hz, 1H), 7.26 (dd, $J_1$ = 2.4 Hz, $J_2$ = 8.8 Hz, 1H), 6.87 (t, J = 7.2 Hz, 1H), 2.05 (s, 3H), 1.85 (s, 6H), 1.73 (s, 6H). LC-MS: m/z 475.5 (M + H)$^+$ |
| 154 | 291 | Compound 74 | 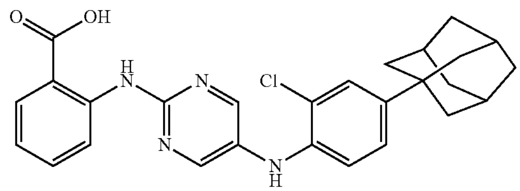 [SMILES: O=C(O)c1ccccc1Nc1ncc(Nc2ccc(C34CC5CC(CC(C5)C3)C4)cc2Cl)cn1] | $^1$H NMR (400 MHz, DMSO-d6) δ 13.43 (bs, 1H), 11.21 (bs, 1H), 8.82 (d, J = 7.6 Hz, 1H), 8.44 (s, 2H), 8.0 (dd, $J_1$ = 2.0 Hz, $J_2$ = 8.4 Hz, 1H), 7.60-7.54 (m, 2H), 7.32 (d, J = 2.0 Hz, 1H), 7.16 (dd, $J_1$ = 2.4 Hz, $J_2$ = 8.8 Hz, 1H), 7.02-6.95 (m, 2H), 2.04 (s, 3H), 1.82-1.81 (bs, 6H), 1.72 (s, 6H). LC-MS: m/z 475.2 (M + H)$^+$ |
| 175 | 292 | VI.19 | 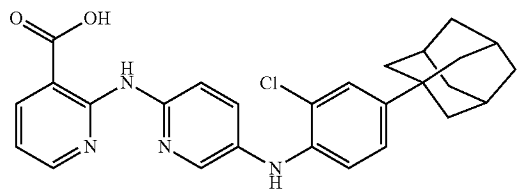 [SMILES: O=C(O)c1cccnc1Nc1ccc(Nc2ccc(C34CC5CC(CC(C5)C3)C4)cc2Cl)cn1] | $^1$H NMR (400 MHz, DMSO-d6) δ 13.65 (bs, 1H), 10.95 (bs, 1H), 8.42 (s, 2H), 8.29 (dd, $J_1$ = 2.0 Hz, $J_2$ = 8.0 Hz, 1H), 8.10 (d, J = 3.2 Hz, 1H), 7.54 (m, 2H), 7.32 (d, J = 2.0 Hz, 1H), 7.16 (dd, $J_1$ = 2.0 Hz, $J_2$ = 8.4 Hz, 1H), 7.02 (d, J = 8.4 Hz, 1H), 6.92 (dd, $J_1$ = 5.2 Hz, $J_2$ = 8.0 Hz, 1H), 2.08 (s, 3H), 1.82 (s, 6H), 1.72 (s, 6H). LC-MS: m/z 475.2 (M + H)$^+$ |
| 540 | 172 | IX.5 | 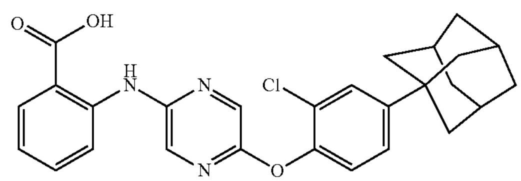 [SMILES: O=C(O)c1ccccc1Nc1cnc(Oc2ccc(C34CC5CC(CC(C5)C3)C4)cc2Cl)cn1] | 1H NMR (400 MHz, DMSO-d6): δ 13.38 (s, 1H), 10.75 (s, 1H), 8.36 (d, J = 8.4 Hz, 1H), 8.26 (d, J = 1.6 Hz, 1H), 8.05 (d, J = 1.2 Hz, 1H), 7.97 (dd, $J_1$ = 1.6 Hz & $J_2$ = 8.0 Hz, 1H), 7.55-7.51 (m, 1H), 7.49 (d, J = 2.4 Hz, 1H), 7.38-7.35 (m, 1H), 7.22 (d, J = 8.8 Hz, 1H), 6.97 (t, J = 8 Hz, 1H), 2.06 (s, 3H), 1.88 (s, 6H), 1.74 (s, 6H), LC-MS: m/z 476.2 (M + H)+ |
| 559 | 173 | XII.98 | 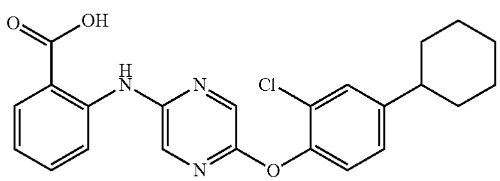 [SMILES: O=C(O)c1ccccc1Nc1cnc(Oc2ccc(C3CCCCC3)cc2Cl)cn1] | 1H NMR (400 MHz, DMSO-d6): δ 13.38 (bs, 1H), 11.05 (bs, 1H), 8.36 (d, J = 8.8 Hz, 1H), 8.24 (s, 1H), 8.02 (s, 1H), 7.97 (d, J = 6.8 Hz, 1H), 7.50 (t, J = 7.6 Hz, 1H), 7.41 (d, J = 1.6 Hz, 1H), 7.24-7.17 (m, 2H), 6.95 (t, J = 7.2 Hz, 1H), 2.58-2.52 (m, 1H), 1.81-1.68 (m, 5H), 1.42-1.31 (m, 5H). LC-MS: m/z 424.2 (M + H)+. |

Synthesis of 2-((4-(4-((3r,5r,7r)-adamantan-1-yl)-2-chlorophenyl)amino)phenyl)carbamoyl) benzoic acid (Compound-293) (CP-119)

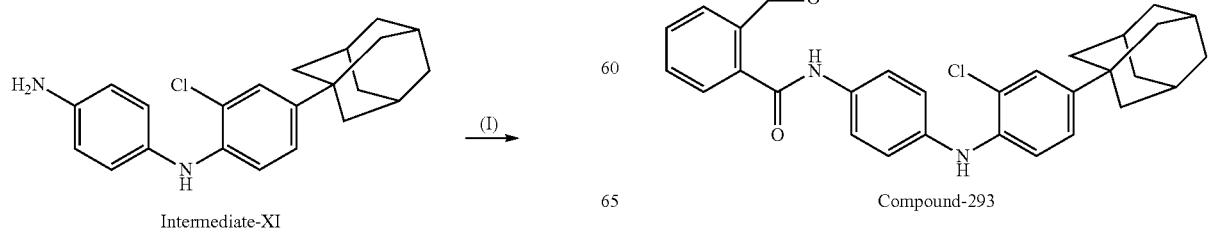

Compound-293

Step (i): A solution of Intermediate-XI (0.05 g, 0.16 mmol, 1 eq.) and phthalic anhydride (0.024 g, 0.16 mmol, 1 eq.) in DCM was stirred at RT for 2 h. The precipitate obtained was filtered and dried in vacuo to afford title product as pale-yellow solid (0.01 g, 12.50%).

$^1$H NMR (400 MHz, DMSO-d6) δ12.98 (s, 1H), 10.17 (s, 1H), 7.86 (d, J=7.8 Hz, 1H), 7.63 (d, J=7.3 Hz, 1H), 7.57-7.52 (m, 4H), 7.41 (s, 1H), 7.31 (d, J=1.6 Hz, 1H), 7.17-7.12 (m, 2H), 7.04 (d, J=8.8 Hz, 2H), 2.05 (s, 3H), 1.83 (s, 6H), 1.72 (s, 6H). LC-MS: m/z 501.1 (M+H)$^{+2}$

The below compounds were prepared by a procedure similar to Compound 293 using appropriate reactants and reagents and in presence of suitable solvents and appropriate reaction conditions.

| CP | Compound No | Reactant | Structure | Analytical data |
|---|---|---|---|---|
| 90 | 294 | Int-I.1 | 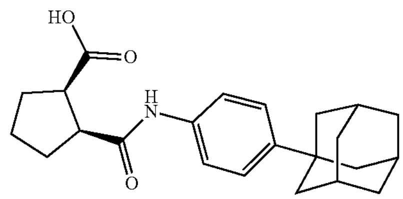 [SMILES: O=C(Nc1ccc(C23CC4CC(CC(C4)C2)C3)cc1)[C@H]1CCC[C@H]1C(=O)O] | $^1$H NMR (400 MHz, DMSO-d6) δ 11.80 (bs, 1H), 9.75 (s, 1H), 7.47 (d, J = 8.8 Hz, 2H), 7.23 (d, J = 8.8 Hz, 2H), 3.12-3.08 (m, 1H), 2.93-2.91 (m, 1H), 2.00-1.92 (m, 4H), 1.91-1.75 (m, 16H), 1.72-1.54 (m, 1H). LC-MS: m/z 368.1 (M + H)$^+$ |
| 96 | 295 | Int-XI | 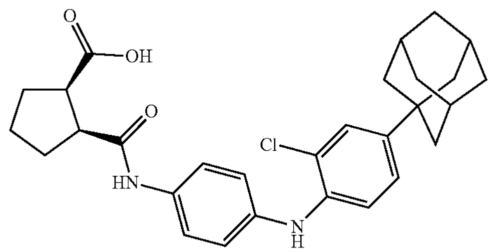 [SMILES: O=C(Nc1ccc(Nc2ccc(C34CC5CC(CC(C5)C3)C4)cc2Cl)cc1)[C@H]1CCC[C@H]1C(=O)O] | $^1$H NMR (400 MHz, DMSO-d6) δ 11.9 (bs, 1H), 9.71 (bs, 1H), 7.43 (d, J = 8.8 Hz, 2H), 7.33 (s, 1H), 7.30 (d, J = 2.5 Hz, 1H), 7.16-7.14 (m, 1H), 7.08 (m, 1H), 6.97 (d, J = 8.8 Hz, 2H), 3.12-3.08 (m, 1H), 2.94-2.90 (m, 1H), 2.04 (s, 4H), 1.99-1.82 (m, 10H), 1.71 (m, 7H). LC-MS: m/z 493.3 (M + H)$^+$ |
| 105 | 296 | Int-I.1 | 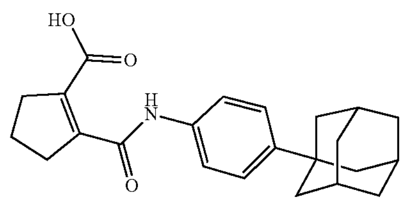 [SMILES: O=C(O)C1=C(C(=O)Nc2ccc(C34CC5CC(CC(C5)C3)C4)cc2)CCC1] | $^1$H NMR (400 MHz, DMSO-d6) δ 7.52 (d, J = 8.8 Hz, 2H), 7.27 (d, J = 8.4 Hz, 2H), 2.72 (t, J = 7.2 Hz, 2H), 2.67-2.63 (m, 2H), 2.05 (s, 3H), 1.79 (d, J = 7.6 Hz, 8H), 1.69 (s, 6H). LC-MS: m/z 366.1 (M + H)$^+$ |
| 110 | 297 | Int-XI | 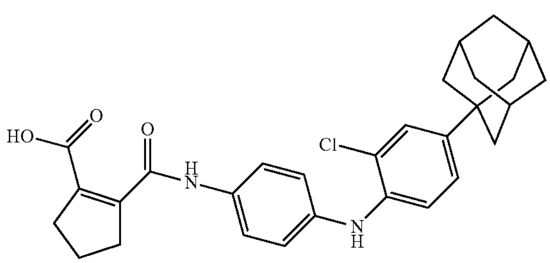 [SMILES: O=C(O)C1=C(C(=O)Nc2ccc(Nc3ccc(C45CC6CC(CC(C6)C4)C5)cc3Cl)cc2)CCC1] | $^1$H NMR (400 MHz, DMSO-d6) δ 12.9 (bs, 1H), 10.06 (s, 1H), 7.47 (d, J = 8.8 Hz, 2H), 7.42 (s, 1H), 7.30 (d, J = 2.0 Hz, 1H), 7.17-7.10 (m, 2H), 6.98 (d, J = 8.8 Hz, 2H), 2.76 (t, J = 7.6 Hz, 2H), 2.74-2.62 (m, 2H), 2.03 (s, 3H), 1.90-1.86 (m, 2H), 1.81-1.80 (bs, 6H), 1.71 (s, 6H). LC-MS: m/z 491.1 (M + H)$^+$ |
| 132 | 298 | XI.2 | 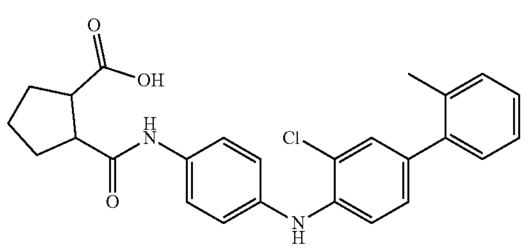 | $^1$H NMR (400 MHz, DMSO-d6) δ 11.83 (s, 1H), 9.74 (s, 1H), 7.54 (s, 1H), 7.5 (d, J = 8.8 Hz, 2H), 7.34 (s, 1H), 7.28-7.15 (m, 4H), 7.13 (s, 2H), 7.09 (d, J = 8.8 Hz, 2H), 3.13-3.09 (m, 1H), 2.96-2.90 (m, 1H), 2.25 (s, 3H), 2.04-1.77 (m, 4H). LC-MS: m/z 449.1 (M + H)$^+$ |
| 133 | 299 | XI.2 | 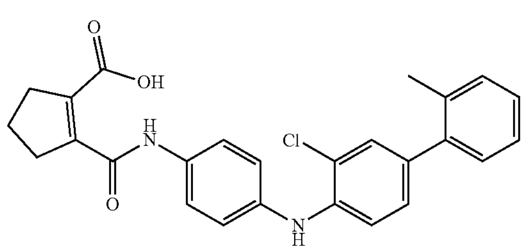 [SMILES: Cc1ccccc1-c1ccc(Nc2ccc(NC(=O)C3=C(C(=O)O)CCC3)cc2)c(Cl)c1] | $^1$H NMR (400 MHz, DMSO-d6) δ 12.85 (bs, 1H), 10.15 (s, 1H), 7.62 (s, 1H), 7.55 (d, J = 8.8 Hz, 2H), 7.35 (d, J = 2.0 Hz, 1H), 7.29-7.11 (m, 8H), 2.80-2.76 (m, 2H), 2.65-2.63 (m, 2H), 2.26 (s, 3H), 1.94-1.88 (m, 2H). LC-MS: m/z 447.1 (M + H)$^+$ |

-continued

| CP | Compound No | Reactant | Structure | Analytical data |
|---|---|---|---|---|
| 176 | 300 | Int-XI | 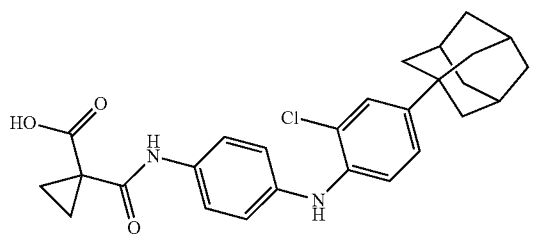 [SMILES: O=C(O)C1(C(=O)Nc2ccc(Nc3ccc(C45CC6CC(CC(C6)C4)C5)cc3Cl)cc2)CC1] | ¹H NMR (400 MHz, DMSO-d6) δ 13.05 (bs, 1H), 10.42 (bs, 1H), 7.46 (d, J = 8.8 Hz, 2H), 7.42 (s, 1H), 7.31 (d, J = 2.0 Hz, 1H), 7.16 (m, 1H), 7.12 (m, 1H), 6.98 (d, J = 8.8 Hz, 2H), 2.04 (s, 3H), 1.82 (s, 6H), 1.72 (s, 6H), 1.41 (s, 4H). LC-MS: m/z 465.3 (M + H)⁺ |
| 216 | 301 | XI.1 | 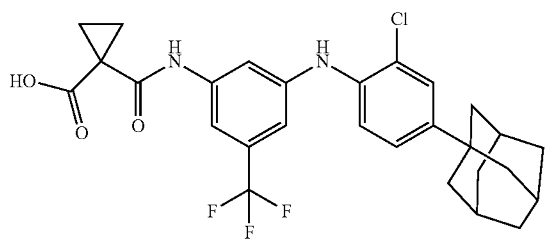 [SMILES: O=C(O)C1(C(=O)Nc2cc(Nc3ccc(C45CC6CC(CC(C6)C4)C5)cc3Cl)cc(C(F)(F)F)c2)CC1] | ¹H NMR (400 MHz, DMSO-d6) δ 14.8 (bs, 1H), 8.04 (s, 1H), 7.46 (s, 1H), 7.41 (s, 1H), 7.30 (s, 2H), 7.19 (s, 1H), 6.82 (s, 1H), 2.06 (s, 3H), 1.86 (d, J = 2.4 Hz, 6H), 1.63 (s, 6H), 1.19 (d, J = 5.6 Hz, 2H), 1.10 (d, J = 5.6 Hz, 2H). LC-MS: m/z 533.2 (M + H)⁺ |
| 229 | 302 | Compound 300 | 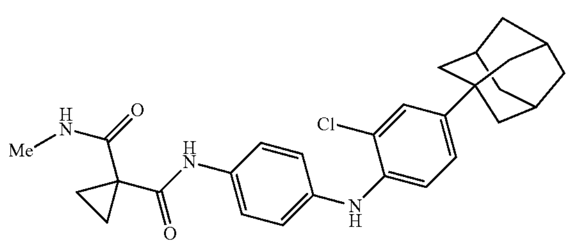 [SMILES: CNC(=O)C1(C(=O)Nc2ccc(Nc3ccc(C45CC6CC(CC(C6)C4)C5)cc3Cl)cc2)CC1] | ¹H NMR (400 MHz, DMSO-d6) δ 10.56 (s, 1H), 7.82 (d, J = 4.4 Hz, 1H), 7.47-7.42 (m, 3H), 7.31 (d, J = 2.0 Hz, 1H), 7.19-7.16 (m, 1H), 7.11 (d, J = 8.4 Hz, 1H), 6.98 (d, J = 8.8 Hz, 2H), 2.62 (d, J = 4.4 Hz, 3H), 2.04 (s, 3H), 1.83 (s, 6H), 1.72 (s, 6H), 1.36-1.29 (m, 4H). LC-MS: m/z 478.3 (M + H)⁺ |
| 237 | 303 | XI.7 | 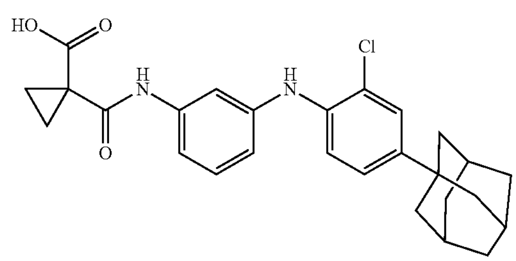 [SMILES: O=C(O)C1(C(=O)Nc2cccc(Nc3ccc(C45CC6CC(CC(C6)C4)C5)cc3Cl)c2)CC1] | ¹H NMR (400 MHz, DMSO-d6) δ 7.53 (s, 1H), 7.34 (d, J = 2.0 Hz, 1H), 7.30 (s, 1H), 7.25-7.22 (m, 2H), 7.11 (t, J = 7.6 Hz, 1H), 7.03 (d, J = 8.0 Hz, 1H), 6.50 (d, J = 8.0 Hz, 1H), 2.05 (s, 3H), 1.84 (s, 6H), 1.73 (s, 6H), 1.34-1.24 (m, 4H). LC-MS: m/z 465.2 (M + H)⁺ |
| 239 | 304 | VI.37 | 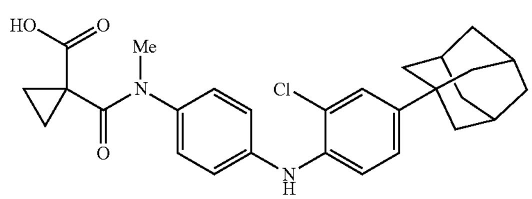 [SMILES: CN(C(=O)C1(C(=O)O)CC1)c1ccc(Nc2ccc(C34CC5CC(CC(C5)C3)C4)cc2Cl)cc1] | ¹H NMR (400 MHz, DMSO-d6) δ 12.4 (bs, 1H), 7.7 (s, 1H), 7.36 (s, 1H), 7.23 (s, 2H), 7.14 (d, J = 7.8 Hz, 2H), 6.95 (d, J = 8.3 Hz, 2H), 3.13 (s, 3H), 2.08 (s, 3H), 1.83 (s, 6H), 1.72 (s, 6H), 1.17 (m, 2H), 0.85 (m, 2H). LC-MS: m/z 479.2 (M + H)⁺ |
| 348 | 305 | XI.30 | 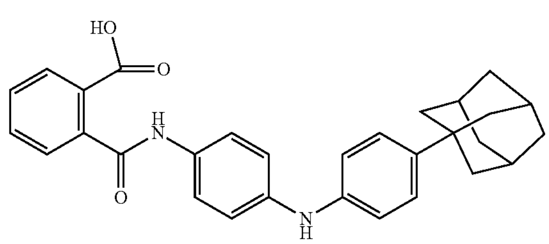 [SMILES: O=C(O)c1ccccc1C(=O)Nc1ccc(Nc2ccc(C34CC5CC(CC(C5)C3)C4)cc2)cc1] | ¹H NMR (400 MHz, DMSO-d6) δ 12.85 (bs, 1H), 10.11 (bs, 1H), 7.91 (s, 1H), 7.85 (d, J = 8.0 Hz, 1H), 7.64 (t, J = 7.6 Hz, 1H), 7.57-7.52 (m, 4H), 7.19 (d, J = 8.8 Hz, 2H), 7.02-6.96 (m, 4H), 2.04 (s, 3H), 1.83 (s, 6H), 1.73 (s, 6H). LC-MS: m/z 465.2 (M − H)⁺ |

| CP | Compound No | Reactant | Structure | Analytical data |
|---|---|---|---|---|
| 378 | 306 | XI.29 | [structure] | $^1$H NMR (400 MHz, DMSO-d6) δ 12.97 (s, 1H), 10.19 (s, 1H), 8.06 (s, 1H), 7.85 (d, J = 7.6 Hz, 1H), 7.63 (t, J = 7.2 Hz, 1H), 7.57-7.50 (m, 3H), 7.21 (d, J = 8.4 Hz, 2H), 7.13-7.10 (m, 2H), 7.04 (d, J = 8.4 Hz, 2H), 6.71 (d, J = 7.2 Hz, 1H), 2.04 (s, 3H), 1.83 (s, 6H), 1.72 (s, 6H). LC-MS: m/z 467.3 (M + H)$^+$ |

Experimental procedure and physiochemical characteristics of the compound CP-453

Intermediate

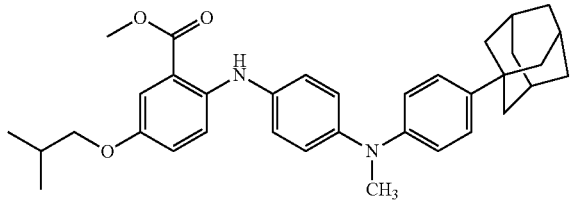 [SMILES: COC(=O)c1cc(OCC(C)C)ccc1Nc1ccc(N(C)c2ccc(C34CC5CC(CC(C5)C3)C4)cc2)cc1]

The above intermediate was prepared by a procedure similar to Intermediate-XII by using Intermediate-XI.16 (0.145 g, 0.43 mmol, 1 eq.) and methyl 2-bromo-5-isobutoxybenzoate (0.125 g, 0.43 mmol, 1 eq.) to afford title product as brown solid (0.05 g, 22%). $^1$H NMR (400 MHz, DMSO-d$_6$): δ 8.79 (s, 1H), 7.54-7.52 (m, 1H), 7.44-7.42 (m, 1H), 7.28-6.98 (m, 9H), 3.85 (s, 3H), 3.80 (d, J=2.4 Hz, 2H), 3.37 (s, 3H), 2.04 (s, 3H), 2.00-1.96 (m, 1H), 1.83 (s, 6H), 1.72 (s, 6H), 0.97 (d, J=6.4 Hz, 6H).

Final Compound

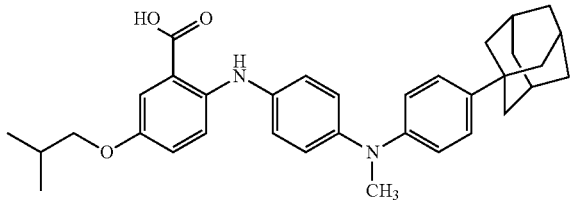

The above compound was prepared by a procedure similar to the one described in compound-24 by using appropriate reagents in the presence of suitable solvents at appropriate reaction conditions. The physiochemical characteristics of the compound also summarized.

$^1$H NMR (400 MHz, DMSO-d$_6$): δ 13.10 (s, 1H), 9.12 (s, 1H), 7.37 (d, J=2.0 Hz, 1H), 7.23 (d, J=8.4 Hz, 2H), 7.10 (d, J=9.2 Hz, 2H), 7.05 (dd, J$_1$=2.8 Hz, J$_2$=9.2 Hz, 2H), 6.97 (d, J=8.8 Hz, 2H), 6.89 (d, J=8.8 Hz, 2H), 3.68 (d, J=6.4 Hz, 2H), 3.21 (s, 3H), 2.04 (s, 3H), 2.01-1.98 (m, 1H), 1.83 (d, J=2.6 Hz, 6H), 1.72 (s, 6H), 0.97 (d, J=6.8 Hz, 6H). LC-MS: 525.3 (M+H)$^+$

Biological Assays
In Vitro Palmitoylation

Recombinant GST-TEAD2 or His$_6$TEAD2 (500 ng) protein was pre-incubated with the compounds at indicated concentrations for 15 min. and then incubated with 1 μM of alkyne palmitoyl-5 CoA (Cayman Chemical) for 30 min or 50 mM MES, pH 6.4, followed by Click reaction with biotin-azide as previously described (Zheng, B. et al., J. Am. Chem. Soc., 2013, 135, 7082-7085). Click reaction was performed with 100 μM biotin-azide, 1 mM tris(2-carboxyethyl) phosphine hydrochloride (TCEP), 100 μM tris[(1-benzyl-1H-1,2,3-triazol-4-yl) methyl] amine (TBTA) and 1 mM CuSO$_4$ for 1 h at RT.

The reactions were terminated by the addition of 12 μL of 6×SDS-sample loading buffer (50 mM Tris-HCl, pH 6.8, 6% SDS, 48% Glycerol, 0.03% Bromophenol Blue, 30 mM EDTA, 9% MeSH). Samples were analysed by SDS-PAGE and Western blot was performed by probing with streptavidin HRP and histidine HRP antibodies independently. Bands intensity obtained from streptavidin blot were quantified using BIORAD, Gel doc system and the percentage of inhibition of Tead2 auto palmitoylation is determined by comparing to the DMSO control treated samples.

These compounds were tested for activity in inhibiting TEAD2 palmitoylation in the assay described above. The data for the compounds is provided in below table as a percentage of inhibition of TEAD2 palmitoylation by the compound at a concentration of 10 PM.

Cell Proliferation

HuH7 cells (or other cells) are cultured in DMEM supplemented with 10% FBS. The cells are seeded in 96-wells with 5000 cells/well density. After cell attached to the wells, compounds in DMSO solution were added (1% DMSO concentration) to the cells with serial dilutions for the indicated final concentration. The cells were further incubated for 3 days. The cell viability is then determined using CellTiter Glo, MTT or crystal violet staining. The inhibition curve is plotted by using GraphPad.

qRT-PCR

YAP target gene expression was analyzed with a LightCycler 480 (Roche). Total RNA was isolated from cells using TRIzol (Life Technologies) and then used to produce cDNA with the Transcriptor First Strand cDNA Synthesis Kit (Roche). The resulting cDNA was then used in reactions with the LightCycler 480 SYBR Green I Master mix (Roche) with probes detecting CTGF or CYR61, and GAPDH.

CMP Assay

7-Diethylamino-3-(4'-Maleimidylphenyl)-4-Methylcoumarin (CPM), which reacts with thiol of CoA liberated in the enzymatic reaction, and gives fluorescent signal (excitation ~350-380, emission-460-480). The assay detects the product (free CoA) which is produced from palmitoyl-CoA as a method to detect the enzymatic activity. Test compounds that inhibit TEAD activity are therefore able to block the CMP fluorescent signal.

TEAD2/4 protein (10 µL of a 50 ng/µL solution) and a solution the test compound (0.5 µL, variable concentration) were pre-incubated for 30 min at r.t. A mixture prepared from MES pH 6.4 buffer (6.5 µL of a 50 mM solution), EDTA (1 µL of a 20 mM solution), palmitoyl-CoA (1 µL of a 20 µM solution), and 7-diethylamino-3-(4'-maleimidylphenyl)-4-methylcoumarin (1 µL of a 10 µM solution) was added and the resulting mixture was mixed well using a pipette. The solution was then incubated at r.t. for 30-120 min. in the dark, and fluorescence was detected at 350 nm every 30 min. until the fluorescence signal is saturated. An $IC_{50}$ for the ability of the compound to inhibit fluorescence is calculated from the results.

Figure 3:
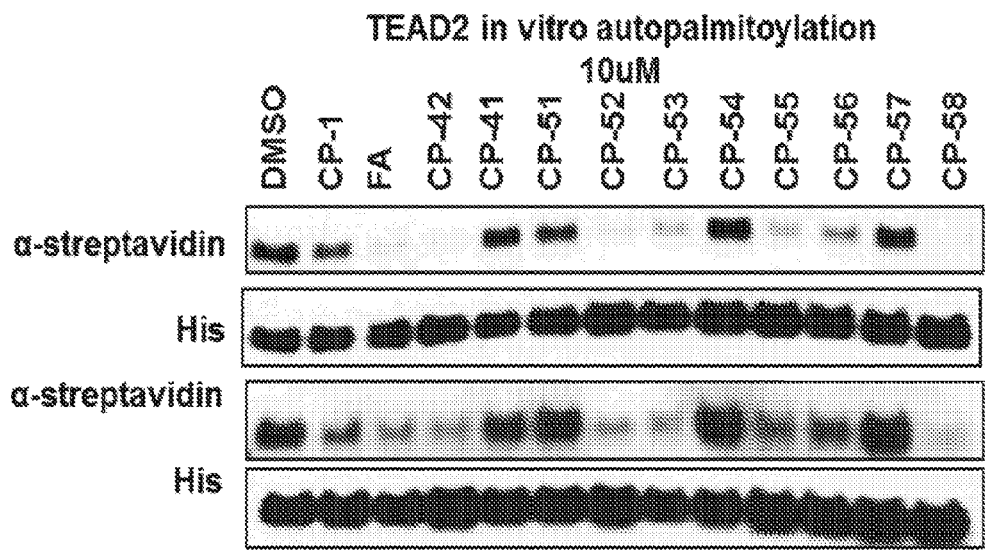
FIG. 3 is a picture showing the result of streptavidin and histidine blots showing the results of assays of the inhibition of TEAD2 in vitro autopalmitoylation by the compounds CP-1, flufenamic acid, CP-41, CP-42, CP-51, CP-52, CP-53, CP-54, CP-55, CP-56, CP-57, and CP-58.
Figure 4:
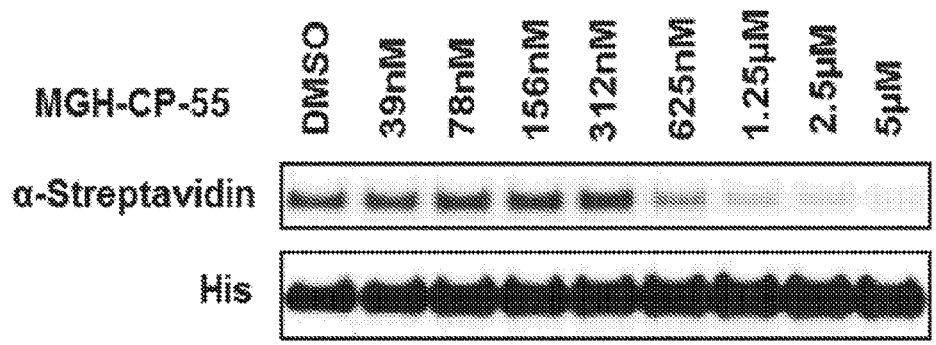
FIG. 4 is a picture showing the result of streptavidin and histidine blots showing the results of assays of the inhibition of TEAD2 in vitro autopalmitoylation by the compound CP-55 at various concentrations.
Figure 5:
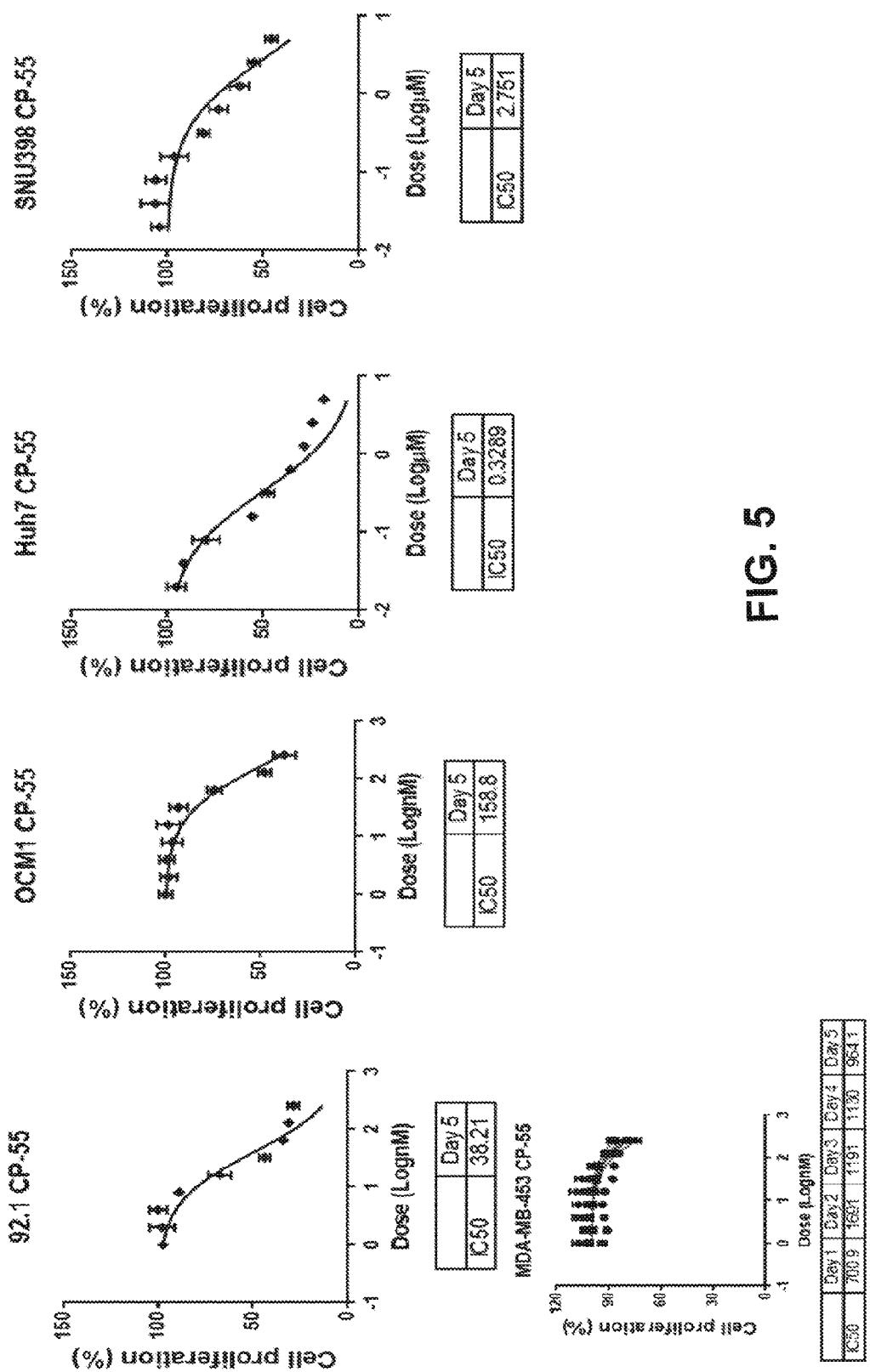
FIG. 5 is a collection of plots showing inhibition of cell proliferation in the 92.1 uveal melanoma cell line, cellosaurus OCM1 cell line, human hepatoma huh7 cell line, SNU398 human liver hepatocellular carcinoma cell line, and the MDA-MB-453 human mammary gland metastatic carcinoma cell line by the compound CP-55 at various concentrations.
Figure 6:
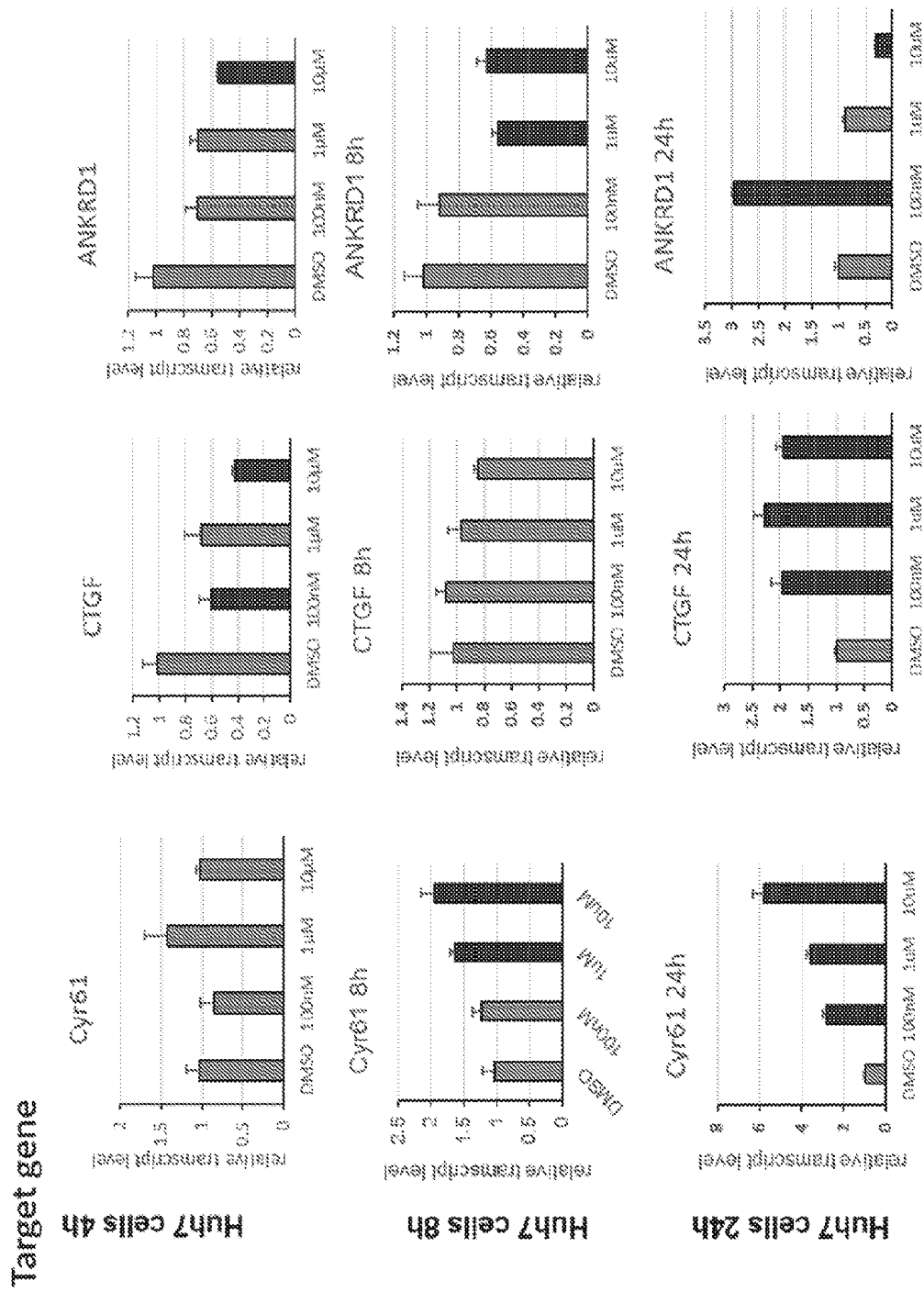
FIG. 6 is collection of plots showing inhibition of gene expression for the CYR61, CTGF and ANKRD1 genes in the huh7 human hepatoma cell line by the compound CP-55 at various time points and concentrations.
Figure 7:
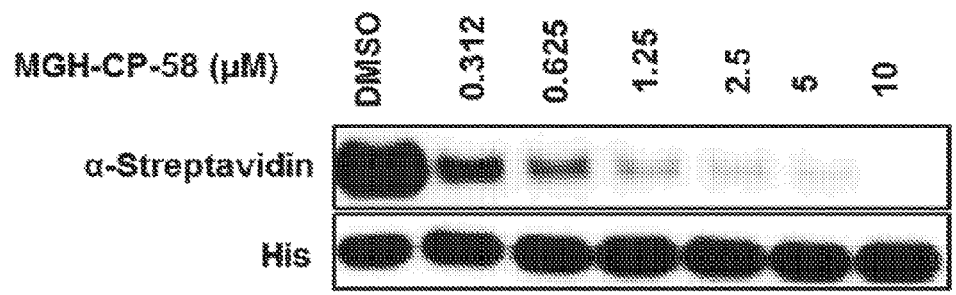
FIG. 7 is a picture showing the result of streptavidin and histidine blots showing the results of assays of the inhibition of TEAD2 in vitro autopalmitoylation by the compound CP-58 at various concentrations.
Figure 8:
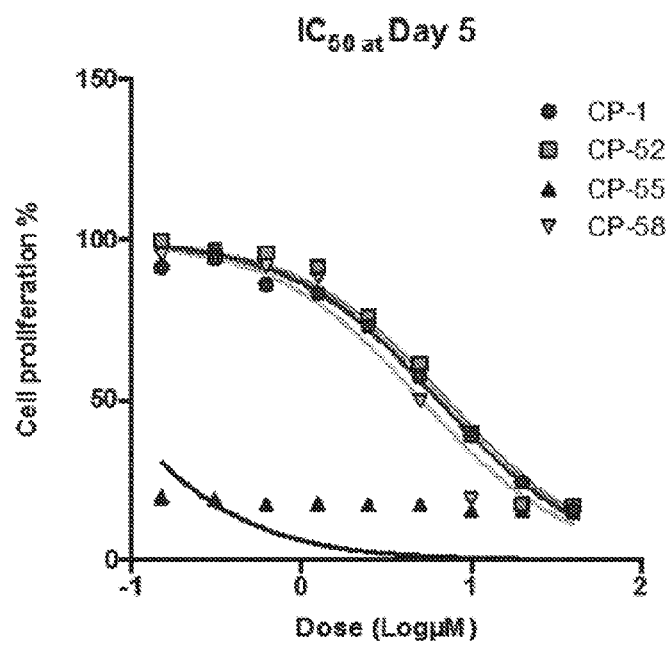
FIG. 8 is a plot showing inhibition of cell proliferation in the 92.1 uveal melanoma cell line by the compounds CP-1, CP-52, CP-55 and CP-58 at various concentrations.
Figure 11:
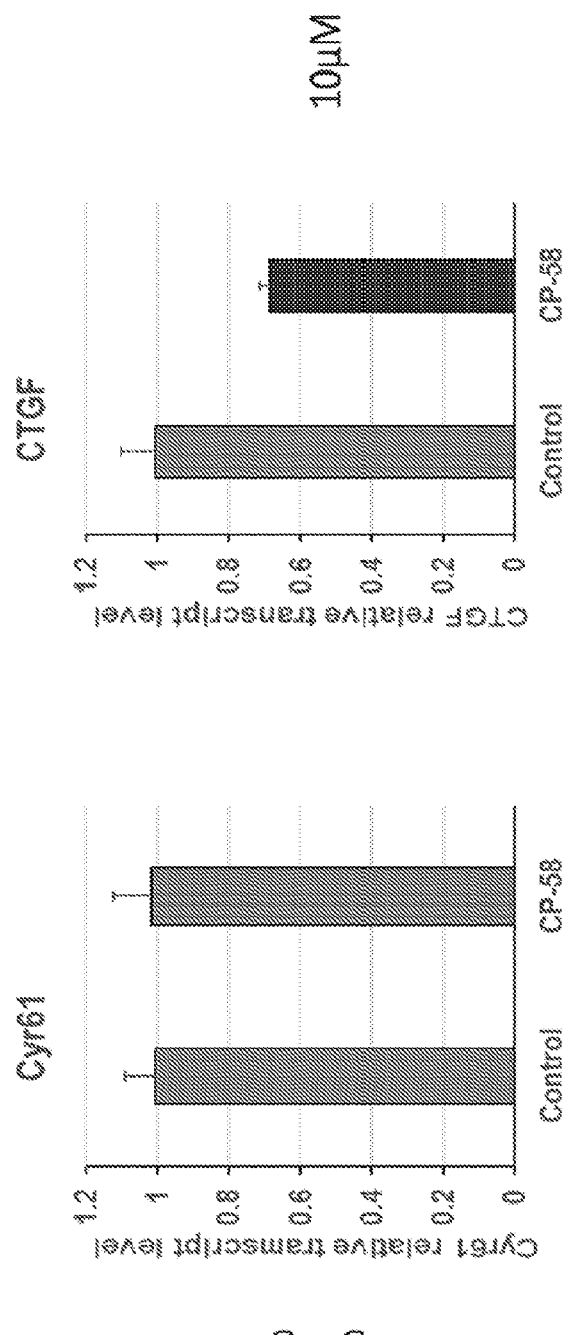
FIG. 11 is a pair of plots showing inhibition of gene expression for the genes CYR61 and CTGF and ANKRD1 genes in the huh7 human hepatoma cell line by the compound CP-58 after 24 h compared to control.
Figure 12:
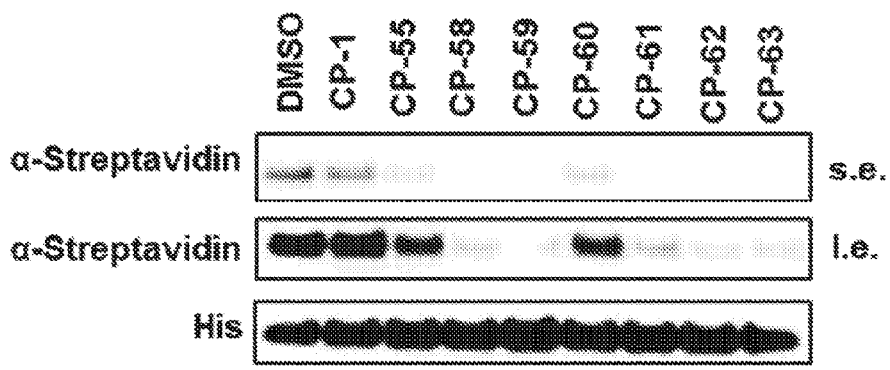
FIG. 12 is a picture showing the result of streptavidin and histidine blots showing the results of assays of the inhibition of TEAD2 in vitro autopalmitoylation by the compounds CP-1, CP-55, CP-58, CP-59, CP-60, CP-61 and CP-62.
Figure 13:
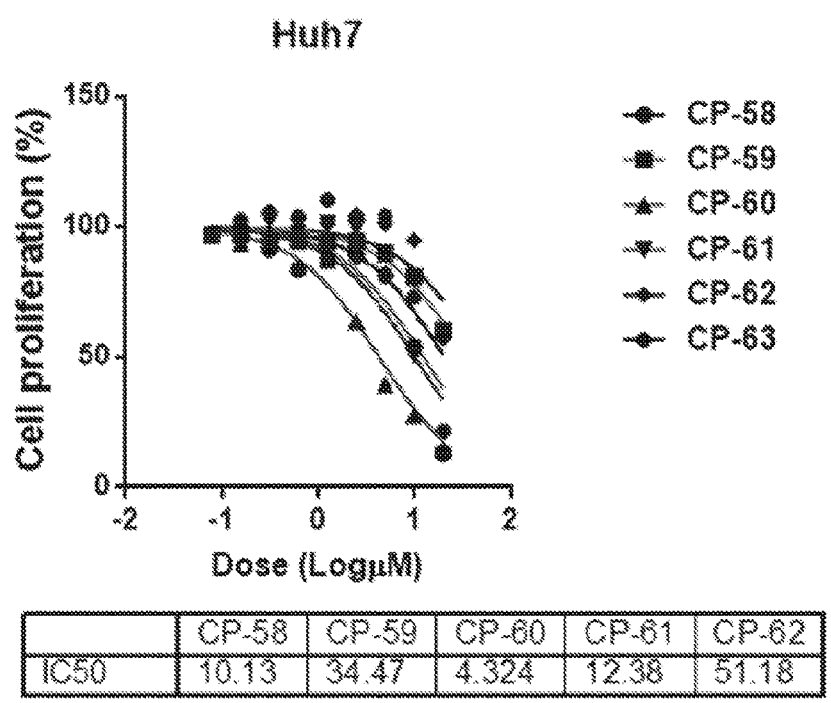
FIG. 13 is a plot inhibition of cell proliferation in the huh7 human hepatoma cell line by the compounds CP-58, CP-59, CP-60, CP-61 and CP-62 at various concentrations.

Results of the biological assays are shown in FIGS. 3-12 and Table 1 and Table 2.

Compounds Active as TEAD Palmitoylation Inhibitors

The Example compounds were tested for activity in inhibiting TEAD2 palmitoylation in the assay and CMP assay described above. The data for the compounds provided in Table 1 as a percentage of inhibition of TEAD2 palmitoylation by the compound at a concentration of 10 µM or the IC50 in the CMP assay.

TABLE 1

Activity of Compounds as TEAD Palmitoylation Inhibitors

| Compound structure | % of inhibition of TEAD2 palmitoylation at 10 µM | CMP $IC_{50}$ (µM) |
|---|---|---|
| (CP-41) | 50 | |
| (CP-51) | 1025 | |
| (CP-53) | 70 | 5.09 |

TABLE 1-continued

Activity of Compounds as TEAD Palmitoylation Inhibitors

| Compound structure | % of inhibition of TEAD2 palmitoylation at 10 µM | CMP IC$_{50}$ (µM) |
|---|---|---|
| (CP-56) | 5 | |
| (CP-76) | 5 | |
| (CP-78) | 80 | |
| (CP-91) | 20 | |
| (CP-92) | 20 | |

TABLE 1-continued
Activity of Compounds as TEAD Palmitoylation Inhibitors
| Compound structure | % of inhibition of TEAD2 palmitoylation at 10 µM | CMP IC$_{50}$ (µM) |
|---|---|---|
| (CP-95) | 20 | |
| (CP-97) | 8 | |
| (CP-150) | 80 | |
| (CP-181) | 100 | |
| (CP-193) | 100 | |
TABLE 2
Activity of Compounds as TEAD2 Palmitoylation Inhibitors
| CP | Cmpd. No | Structure | % of inhibition of TEAD2 palmitoylation at 10 µM or IC$_{50}$ µM |
|---|---|---|---|
| 51 | 1 | 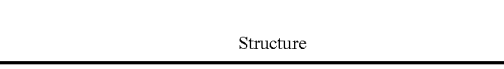 | 10 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 54 | 2 | 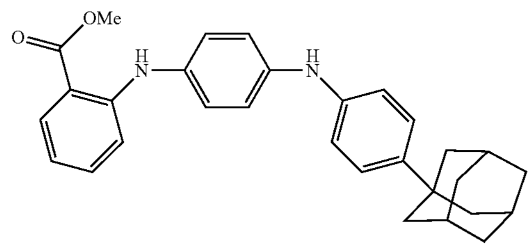 [SMILES: COC(=O)c1ccccc1Nc1ccc(Nc2ccc(C34CC5CC(CC(C5)C3)C4)cc2)cc1] | 0 |
| 57 | 3 | 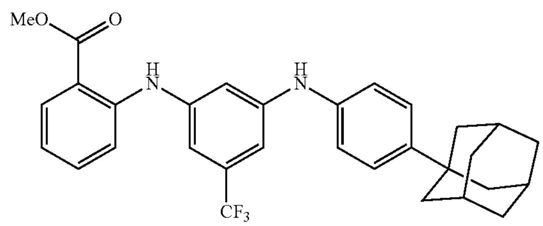 [SMILES: COC(=O)c1ccccc1Nc1cc(Nc2ccc(C34CC5CC(CC(C5)C3)C4)cc2)cc(C(F)(F)F)c1] | 0 |
| 68 | 4 | 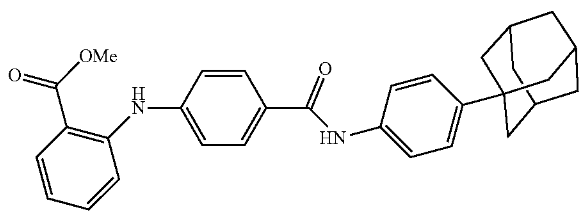 [SMILES: COC(=O)c1ccccc1Nc1ccc(C(=O)Nc2ccc(C34CC5CC(CC(C5)C3)C4)cc2)cc1] | 0 |
| 70 | 5 | 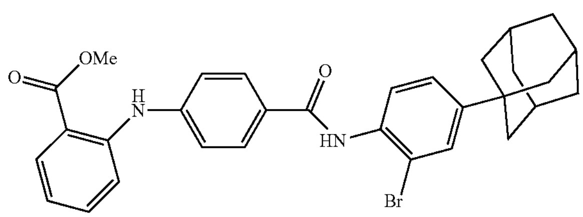 [SMILES: COC(=O)c1ccccc1Nc1ccc(C(=O)Nc2ccc(C34CC5CC(CC(C5)C3)C4)cc2Br)cc1] | 0 |
| 79 | 6 | 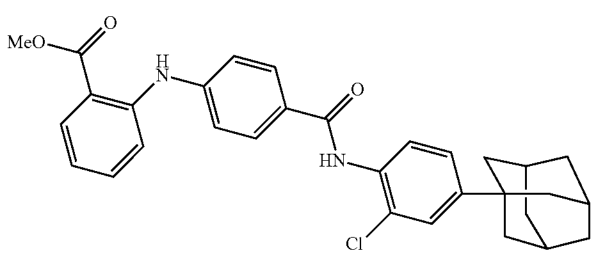 [SMILES: COC(=O)c1ccccc1Nc1ccc(C(=O)Nc2ccc(C34CC5CC(CC(C5)C3)C4)cc2Cl)cc1] | 0 |
| 85 | 7 | 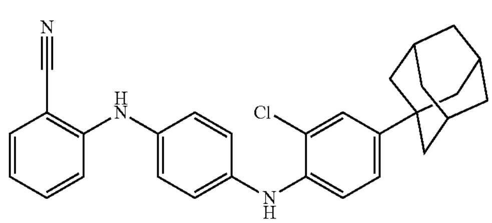 [SMILES: N#Cc1ccccc1Nc1ccc(Nc2ccc(C34CC5CC(CC(C5)C3)C4)cc2Cl)cc1] | 30 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 104 | 8 | 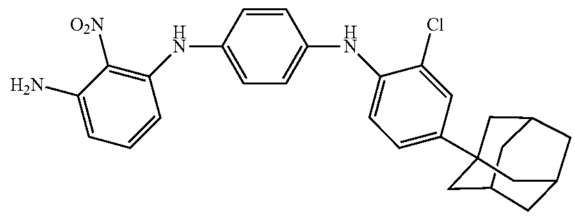 [SMILES: Nc1cccc(Nc2ccc(Nc3ccc(C45CC6CC(CC(C6)C4)C5)cc3Cl)cc2)c1[N+](=O)[O-]] | NA |
| 201 | 9 | 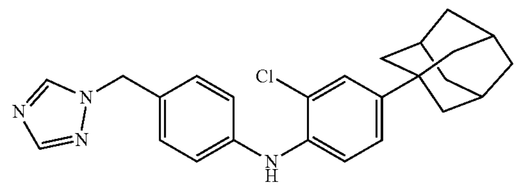 [SMILES: Clc1cc(C23CC4CC(CC(C4)C2)C3)ccc1Nc1ccc(Cn2cncn2)cc1] | 76 |
| 225 | 10 | 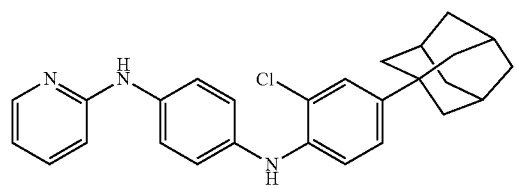 [SMILES: Clc1cc(C23CC4CC(CC(C4)C2)C3)ccc1Nc1ccc(Nc2ccccn2)cc1] | 0 |
| 264 | 11 | 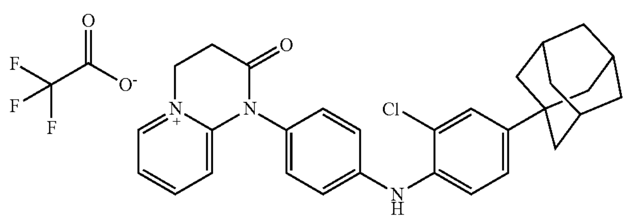 | 0 |
| 238 | 12 | 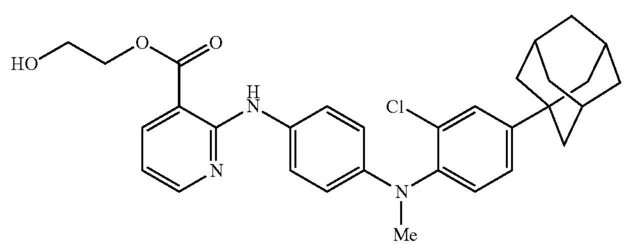 [SMILES: CN(c1ccc(Nc2ncccc2C(=O)OCCO)cc1)c1ccc(C23CC4CC(CC(C4)C2)C3)cc1Cl] | 85 |
| 347 | 13 | 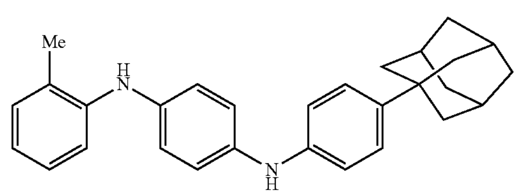 [SMILES: Cc1ccccc1Nc1ccc(Nc2ccc(C34CC5CC(CC(C5)C3)C4)cc2)cc1] | 26 |
| 352 | 14 | 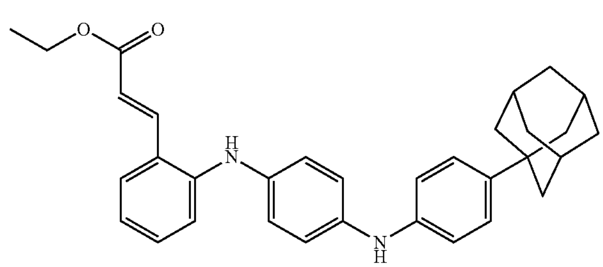 [SMILES: CCOC(=O)/C=C/c1ccccc1Nc1ccc(Nc2ccc(C34CC5CC(CC(C5)C3)C4)cc2)cc1] | 0 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 375 | 15 | 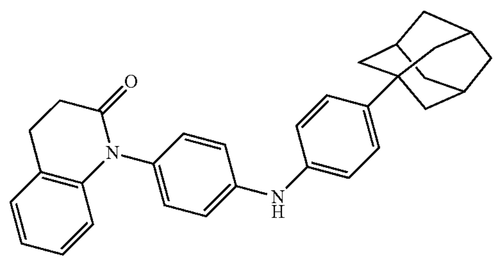 [SMILES: O=C1CCc2ccccc2N1c1ccc(Nc2ccc(C34CC5CC(CC(C5)C3)C4)cc2)cc1] | 12 |
| 354 | 16 | 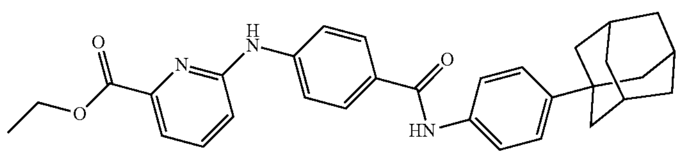 [SMILES: CCOC(=O)c1cccc(Nc2ccc(C(=O)Nc3ccc(C45CC6CC(CC(C6)C4)C5)cc3)cc2)n1] | 0 |
| 381 | 17 | 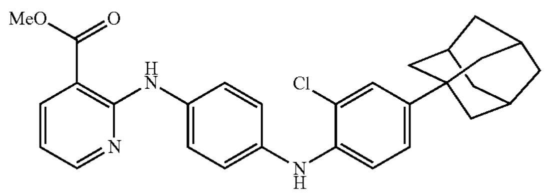 [SMILES: COC(=O)c1cccnc1Nc1ccc(Nc2ccc(C34CC5CC(CC(C5)C3)C4)cc2Cl)cc1] | 7 |
| 351 | 18 | 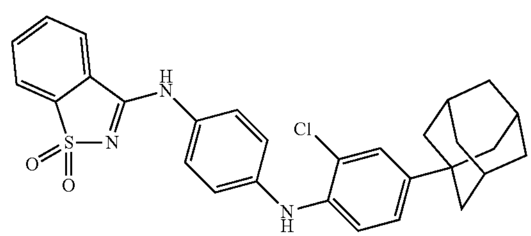 [SMILES: O=S1(=O)N=C(Nc2ccc(Nc3ccc(C45CC6CC(CC(C6)C4)C5)cc3Cl)cc2)c2ccccc21] | 35 |
| 406 | 19 | 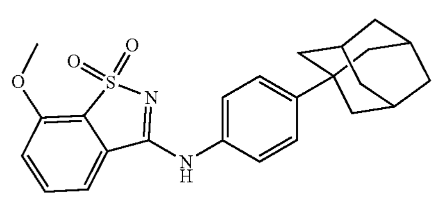 [SMILES: COc1cccc2c1S(=O)(=O)N=C2Nc1ccc(C23CC4CC(CC(C4)C2)C3)cc1] | 35 |
| 86 | 20 | 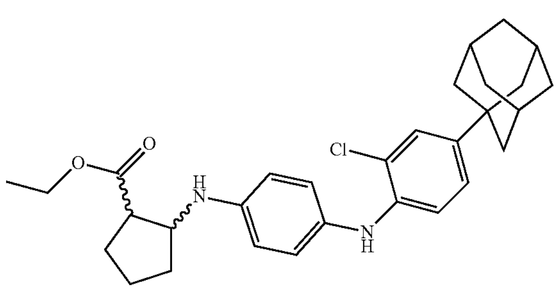 [SMILES: CCOC(=O)C1CCCC1Nc1ccc(Nc2ccc(C34CC5CC(CC(C5)C3)C4)cc2Cl)cc1] | NA |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 87 | 21 | 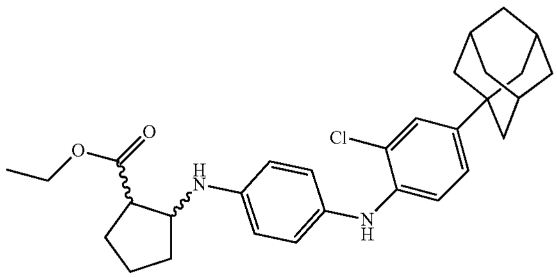 [SMILES: CCOC(=O)C1CCCC1Nc1ccc(Nc2ccc(C34CC5CC(CC(C5)C3)C4)cc2Cl)cc1] | NA |
| 231 | 22 | 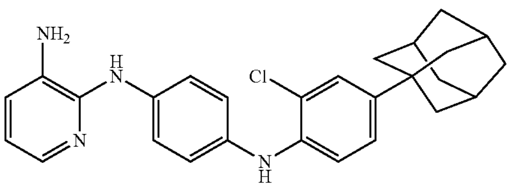 [SMILES: Nc1cccnc1Nc1ccc(Nc2ccc(C34CC5CC(CC(C5)C3)C4)cc2Cl)cc1] | 74 |
| 82 | 23 | 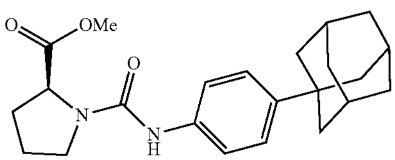 [SMILES: COC(=O)[C@@H]1CCCN1C(=O)Nc1ccc(C23CC4CC(CC(C4)C2)C3)cc1] | NA |
| 55 | 24 | 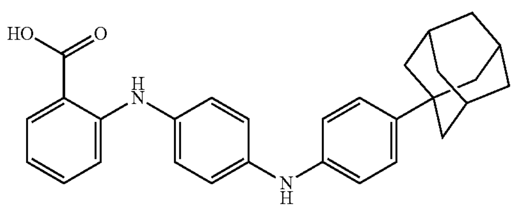 [SMILES: O=C(O)c1ccccc1Nc1ccc(Nc2ccc(C34CC5CC(CC(C5)C3)C4)cc2)cc1] | 56 |
| 52 | 25 | 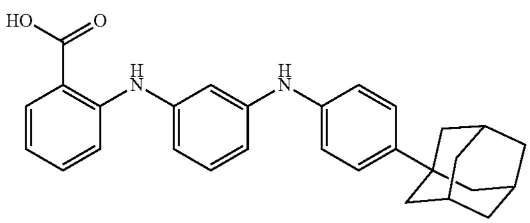 [SMILES: O=C(O)c1ccccc1Nc1cccc(Nc2ccc(C34CC5CC(CC(C5)C3)C4)cc2)c1] | 90 |
| 58 | 26 | 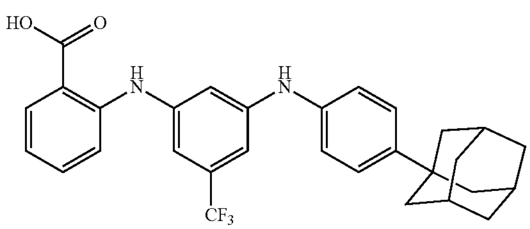 [SMILES: O=C(O)c1ccccc1Nc1cc(Nc2ccc(C34CC5CC(CC(C5)C3)C4)cc2)cc(C(F)(F)F)c1] | 90 |
| 59 | 27 | 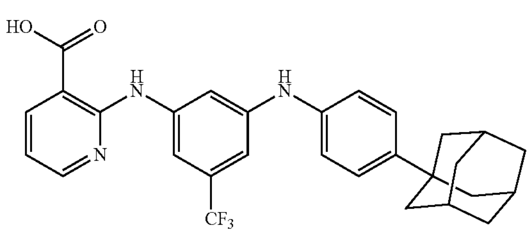 [SMILES: O=C(O)c1cccnc1Nc1cc(Nc2ccc(C34CC5CC(CC(C5)C3)C4)cc2)cc(C(F)(F)F)c1] | 90 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 60 | 28 | (2-COOH, 4-Me phenyl)-NH-(3-CF$_3$-5-aminophenyl)-NH-(4-adamantylphenyl) | 10 |
| 61 | 29 | (2-COOH, 4-CF$_3$ phenyl)-NH-(3-CF$_3$-5-aminophenyl)-NH-(4-adamantylphenyl) | 90 |
| 62 | 30 | (2-COOH phenyl)-NH-(3-F-5-aminophenyl)-NH-(4-adamantylphenyl) | 91 |
| 64 | 31 | (2-COOH phenyl)-NH-(1,4-phenylene)-NH-(2-Cl-4-adamantylphenyl) | 99, 84, 82, 0.377 μM |
| 65 | 32 | (3-COOH pyridin-2-yl)-NH-(3-Me-5-aminophenyl)-NH-(2-Cl-4-adamantylphenyl) | 60 |
| 66 | 33 | (2-COOH phenyl)-NH-(3-CF$_3$-5-aminophenyl)-NH-(2-Cl-4-adamantylphenyl) | 50 |

TABLE 2-continued
Activity of Compounds as TEAD2 Palmitoylation Inhibitors
| CP | Cmpd. No | Structure | % of inhibition of TEAD2 palmitoylation at 10 μM or IC$_{50}$ μM |
|---|---|---|---|
| 67 | 34 | 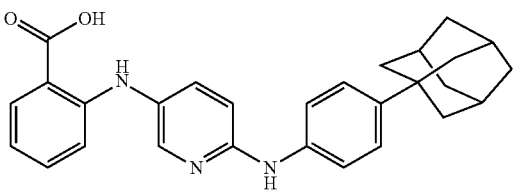 [SMILES: O=C(O)c1ccccc1Nc1ccc(Nc2ccc(C34CC5CC(CC(C5)C3)C4)cc2)nc1] | 14 |
| 69 | 35 | 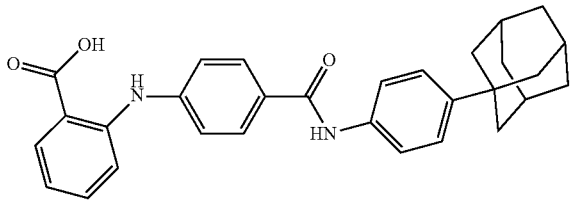 [SMILES: O=C(Nc1ccc(C23CC4CC(CC(C4)C2)C3)cc1)c1ccc(Nc2ccccc2C(=O)O)cc1] | 63, 86 |
| 71 | 36 | 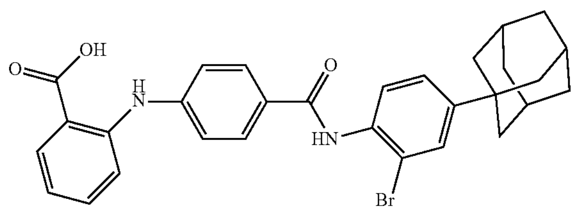 [SMILES: O=C(Nc1ccc(C23CC4CC(CC(C4)C2)C3)cc1Br)c1ccc(Nc2ccccc2C(=O)O)cc1] | 100 |
| 80 | 37 | 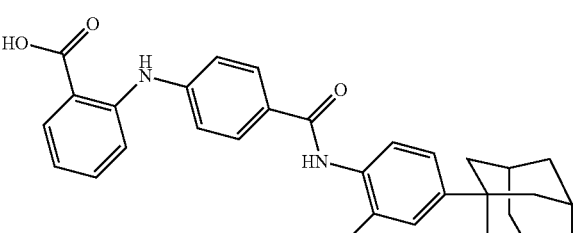 | 30 |
| 83 | 38 | 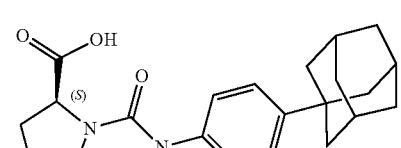 | 7 |
| 88 | 39 | 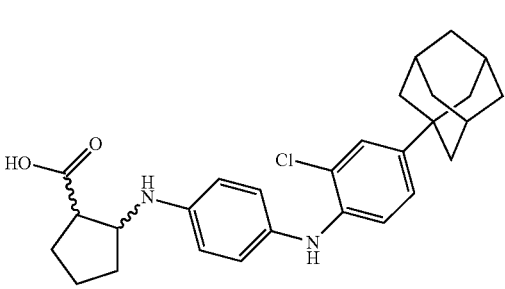 [SMILES: O=C(O)C1CCCC1Nc1ccc(Nc2ccc(C34CC5CC(CC(C5)C3)C4)cc2Cl)cc1] | 59 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 89 | 40 | 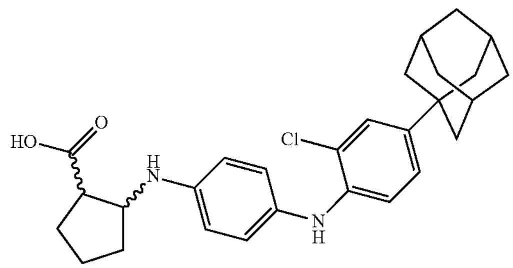 [SMILES: O=C(O)C1CCCC1Nc1ccc(Nc2ccc(C34CC5CC(CC(C5)C3)C4)cc2Cl)cc1] | 43 |
| 93 | 41 | 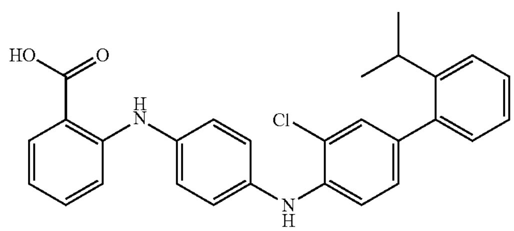 [SMILES: CC(C)c1ccccc1-c1ccc(Nc2ccc(Nc3ccccc3C(=O)O)cc2)c(Cl)c1] | 52 |
| 98 | 42 | 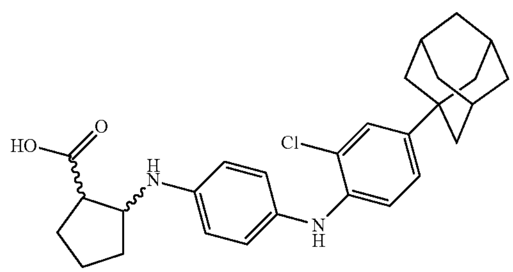 [SMILES: O=C(O)C1CCCC1Nc1ccc(Nc2ccc(C34CC5CC(CC(C5)C3)C4)cc2Cl)cc1] | NA |
| 99 | 43 | 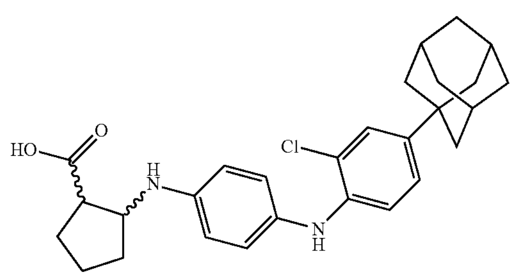 [SMILES: O=C(O)C1CCCC1Nc1ccc(Nc2ccc(C34CC5CC(CC(C5)C3)C4)cc2Cl)cc1] | NA |
| 100 | 44 | 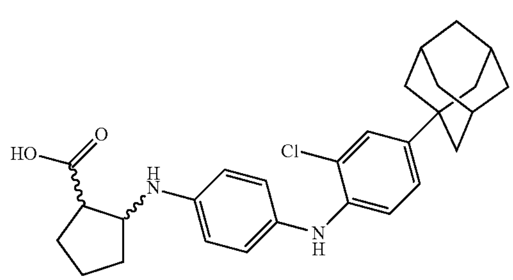 [SMILES: O=C(O)C1CCCC1Nc1ccc(Nc2ccc(C34CC5CC(CC(C5)C3)C4)cc2Cl)cc1] | NA |

TABLE 2-continued
Activity of Compounds as TEAD2 Palmitoylation Inhibitors
| CP | Cmpd. No | Structure | % of inhibition of TEAD2 palmitoylation at 10 μM or IC$_{50}$ μM |
|---|---|---|---|
| 101 | 45 | 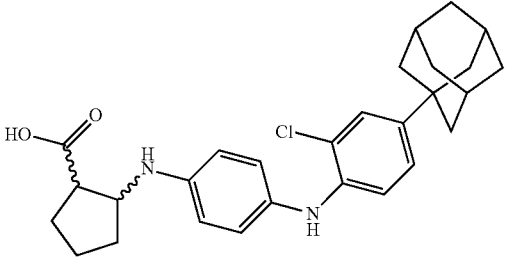 [SMILES: O=C(O)C1CCCC1Nc1ccc(Nc2ccc(C34CC5CC(CC(C5)C3)C4)cc2Cl)cc1] | NA |
| 102 | 46 | 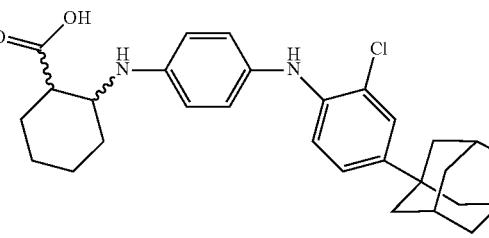 | 76 |
| 103 | 47 | 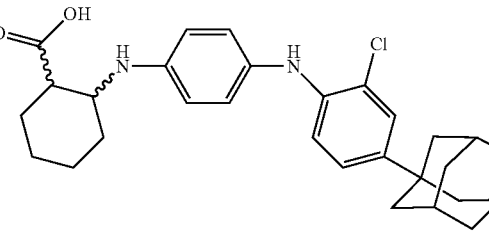 | 83 |
| 106 | 48 | 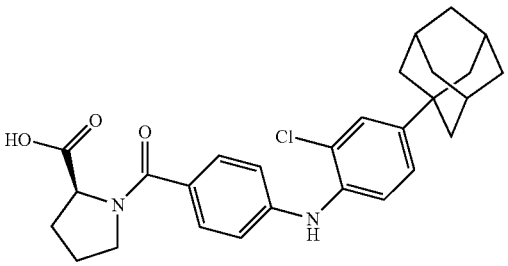 [SMILES: O=C(O)[C@@H]1CCCN1C(=O)c1ccc(Nc2ccc(C34CC5CC(CC(C5)C3)C4)cc2Cl)cc1] | 87 |
| 107 | 49 | 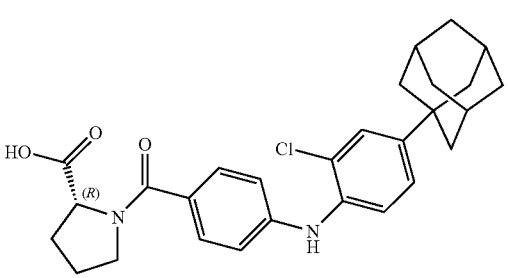 | NA |
| 108 | 50 | 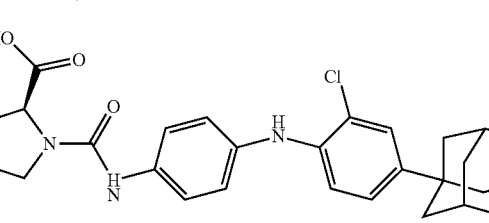 | 0 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 113 | 51 | 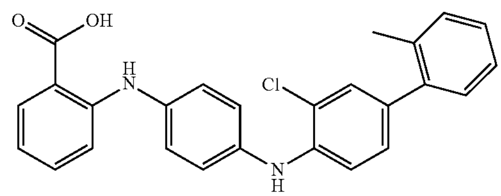 [SMILES: Cc1ccccc1-c1ccc(Nc2ccc(Nc3ccccc3C(=O)O)cc2)c(Cl)c1] | 79 |
| 114 | 52 | 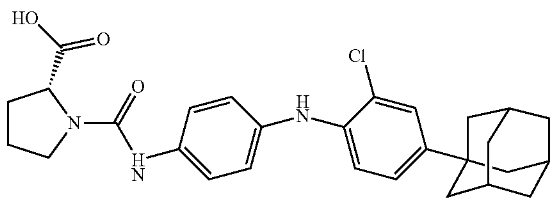 [SMILES: O=C(O)[C@H]1CCCN1C(=O)Nc1ccc(Nc2ccc(C34CC5CC(CC(C5)C3)C4)cc2Cl)cc1] | 79 |
| 115 | 53 | 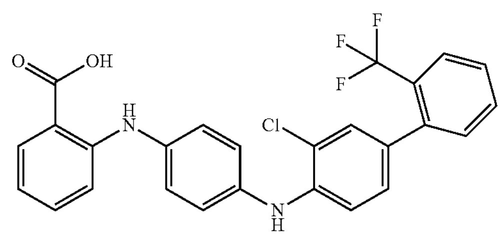 [SMILES: O=C(O)c1ccccc1Nc1ccc(Nc2ccc(-c3ccccc3C(F)(F)F)cc2Cl)cc1] | 5 |
| 116 | 54 | 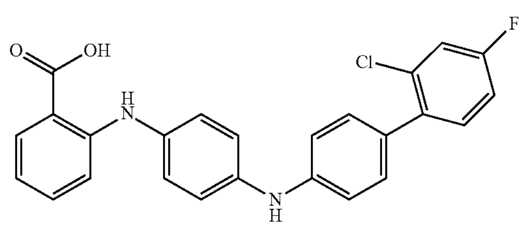 [SMILES: O=C(O)c1ccccc1Nc1ccc(Nc2ccc(-c3ccc(F)cc3Cl)cc2)cc1] | NA |
| 117 | 55 | 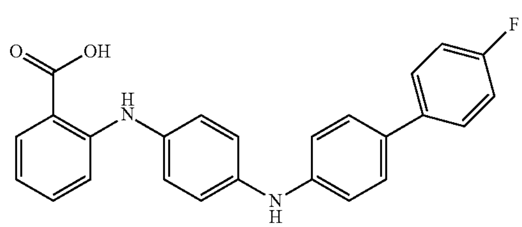 [SMILES: O=C(O)c1ccccc1Nc1ccc(Nc2ccc(-c3ccc(F)cc3)cc2)cc1] | NA |
| 118 | 56 | 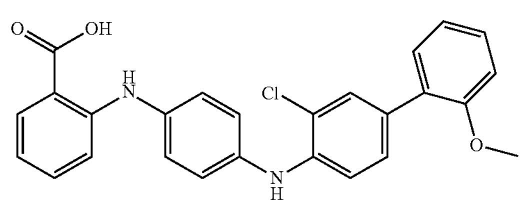 [SMILES: COc1ccccc1-c1ccc(Nc2ccc(Nc3ccccc3C(=O)O)cc2)c(Cl)c1] | 0 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 121 | 57 | 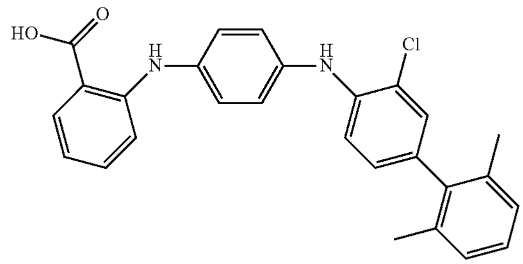 [SMILES: Cc1cccc(C)c1-c1ccc(Nc2ccc(Nc3ccccc3C(=O)O)cc2)c(Cl)c1] | NA |
| 122 | 58 | 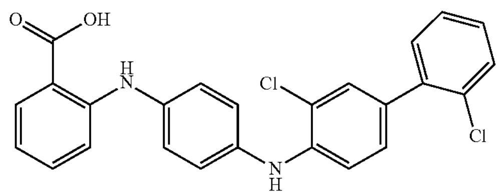 [SMILES: O=C(O)c1ccccc1Nc1ccc(Nc2ccc(-c3ccccc3Cl)cc2Cl)cc1] | 60 |
| 124 | 59 | 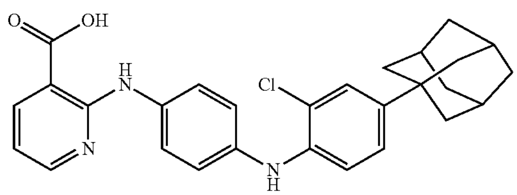 [SMILES: O=C(O)c1cccnc1Nc1ccc(Nc2ccc(C34CC5CC(CC(C5)C3)C4)cc2Cl)cc1] | 99 |
| 125 | 60 | 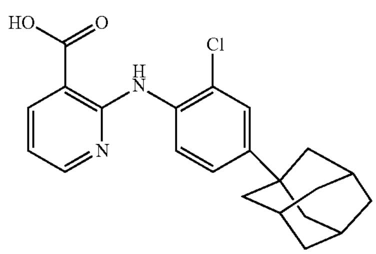 [SMILES: O=C(O)c1cccnc1Nc1ccc(C23CC4CC(CC(C4)C2)C3)cc1Cl] | 100 |
| 126 | 61 | 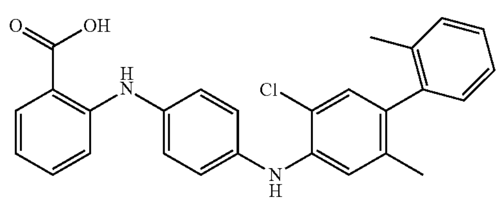 [SMILES: Cc1ccccc1-c1cc(Cl)c(Nc2ccc(Nc3ccccc3C(=O)O)cc2)cc1C] | 70 |
| 127 | 62 | 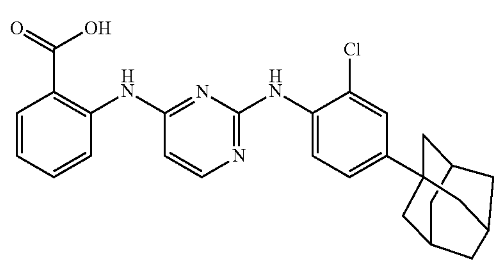 [SMILES: O=C(O)c1ccccc1Nc1ccnc(Nc2ccc(C34CC5CC(CC(C5)C3)C4)cc2Cl)n1] | 65 |

TABLE 2-continued
Activity of Compounds as TEAD2 Palmitoylation Inhibitors
| CP | Cmpd. No | Structure | % of inhibition of TEAD2 palmitoylation at 10 μM or IC$_{50}$ μM |
|---|---|---|---|
| 128 | 63 | 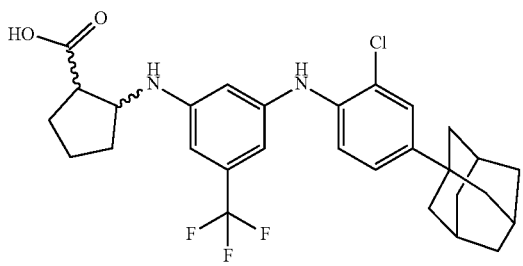 [SMILES: O=C(O)C1CCCC1Nc1cc(Nc2ccc(C34CC5CC(CC(C5)C3)C4)cc2Cl)cc(C(F)(F)F)c1] | NA |
| 129 | 64 | 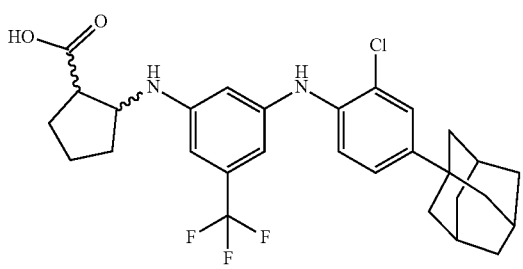 [SMILES: O=C(O)C1CCCC1Nc1cc(Nc2ccc(C34CC5CC(CC(C5)C3)C4)cc2Cl)cc(C(F)(F)F)c1] | 0 |
| 130 | 65 | 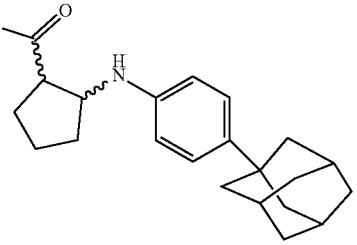 | 74 |
| 131 | 66 | 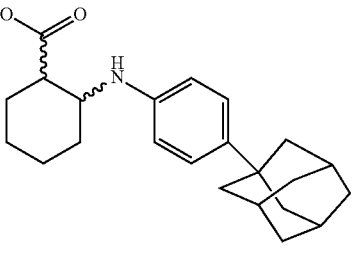 | 25 |
| 134 | 67 | 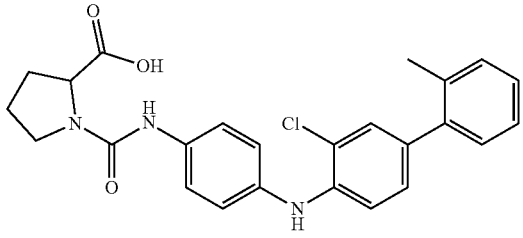 [SMILES: Cc1ccccc1-c1ccc(Nc2ccc(NC(=O)N3CCCC3C(=O)O)cc2)c(Cl)c1] | NO |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 135 | 68 | 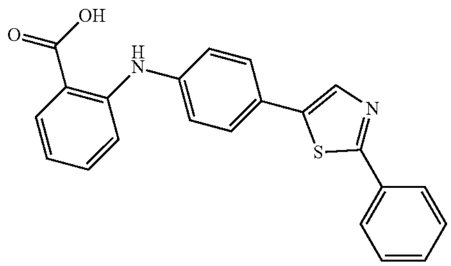 [SMILES: O=C(O)c1ccccc1Nc1ccc(-c2cnc(-c3ccccc3)s2)cc1] | YES |
| 136 | 69 | 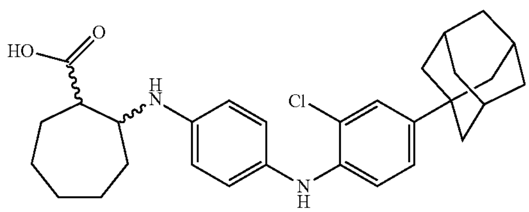 [SMILES: O=C(O)C1CCCCCC1Nc1ccc(Nc2ccc(C34CC5CC(CC(C5)C3)C4)cc2Cl)cc1] | NO |
| 138 | 70 | 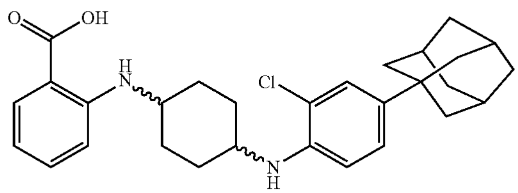 [SMILES: O=C(O)c1ccccc1NC1CCC(Nc2ccc(C34CC5CC(CC(C5)C3)C4)cc2Cl)CC1] | NO |
| 139 | 71 | 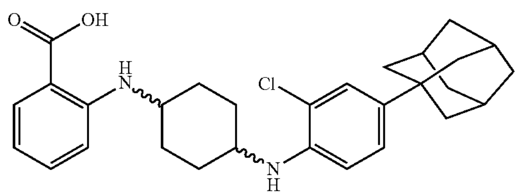 [SMILES: O=C(O)c1ccccc1NC1CCC(Nc2ccc(C34CC5CC(CC(C5)C3)C4)cc2Cl)CC1] | YES |
| 140 | 72 | 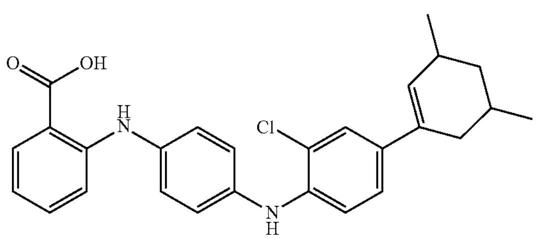 [SMILES: CC1C=C(c2ccc(Nc3ccc(Nc4ccccc4C(=O)O)cc3)c(Cl)c2)CC(C)C1] | NO |
| 141 | 73 | 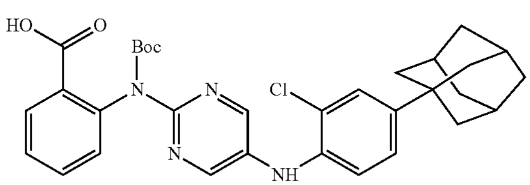 [SMILES: CC(C)(C)OC(=O)N(c1ncc(Nc2ccc(C34CC5CC(CC(C5)C3)C4)cc2Cl)cn1)c1ccccc1C(=O)O] | NO |
| 142 | 74 | 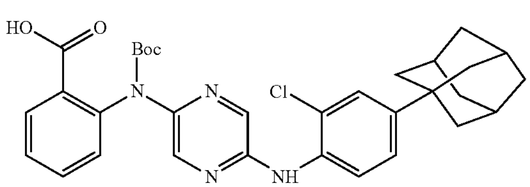 [SMILES: CC(C)(C)OC(=O)N(c1cnc(Nc2ccc(C34CC5CC(CC(C5)C3)C4)cc2Cl)cn1)c1ccccc1C(=O)O] | 31 |

TABLE 2-continued

Activity of Compounds as TEAD2 Palmitoylation Inhibitors

| CP | Cmpd. No | Structure | % of inhibition of TEAD2 palmitoylation at 10 µM or IC$_{50}$ µM |
|---|---|---|---|
| 143 | 75 | 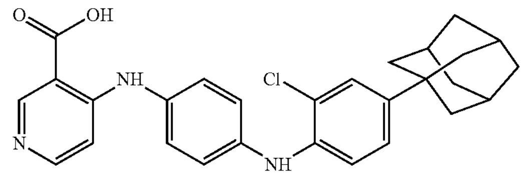 [SMILES: O=C(O)c1cnccc1Nc1ccc(Nc2ccc(C34CC5CC(CC(C5)C3)C4)cc2Cl)cc1] | 63 |
| 144 | 76 | 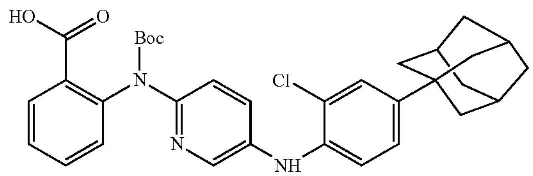 [SMILES: CC(C)(C)OC(=O)N(c1ccc(Nc2ccc(C34CC5CC(CC(C5)C3)C4)cc2Cl)cn1)c1ccccc1C(=O)O] | 34 |
| 145 | 77 | 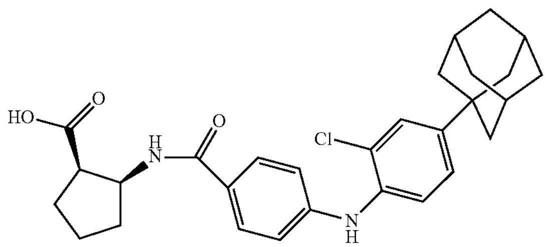 [SMILES: O=C(N[C@H]1CCC[C@H]1C(=O)O)c1ccc(Nc2ccc(C34CC5CC(CC(C5)C3)C4)cc2Cl)cc1] | 52 |
| 146 | 78 | 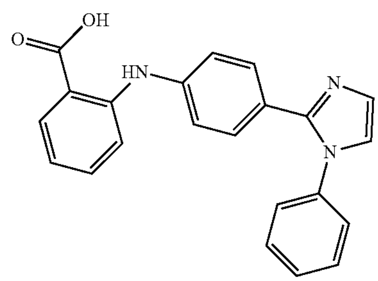 [SMILES: O=C(O)c1ccccc1Nc1ccc(-c2nccn2-c2ccccc2)cc1] | NO |
| 148 | 79 | 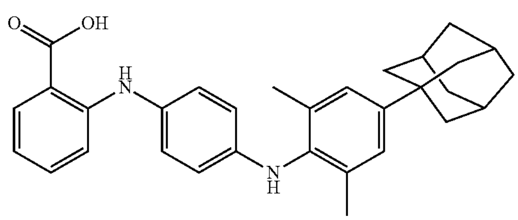 [SMILES: Cc1cc(C23CC4CC(CC(C4)C2)C3)cc(C)c1Nc1ccc(Nc2ccccc2C(=O)O)cc1] | 45 |
| 149 | 80 | 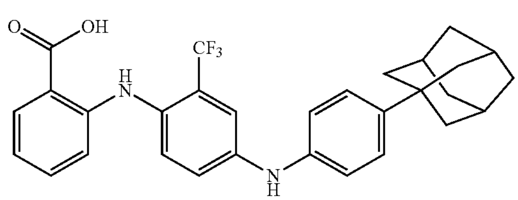 [SMILES: O=C(O)c1ccccc1Nc1ccc(Nc2ccc(C34CC5CC(CC(C5)C3)C4)cc2)cc1C(F)(F)F] | 40 |
| 151 | 81 | 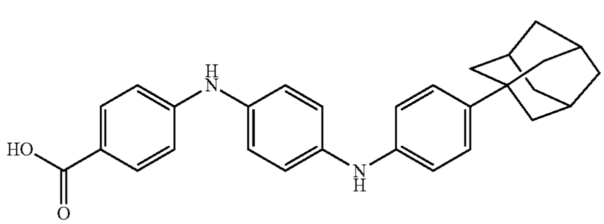 [SMILES: O=C(O)c1ccc(Nc2ccc(Nc3ccc(C45CC6CC(CC(C6)C4)C5)cc3)cc2)cc1] | 78 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 156 | 82 | 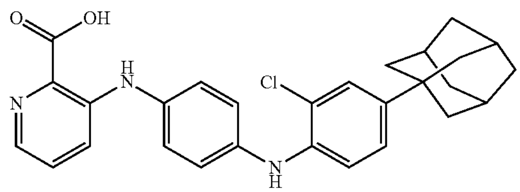 [SMILES: O=C(O)c1ncccc1Nc1ccc(Nc2ccc(C34CC5CC(CC(C5)C3)C4)cc2Cl)cc1] | 67 |
| 157 | 83 | 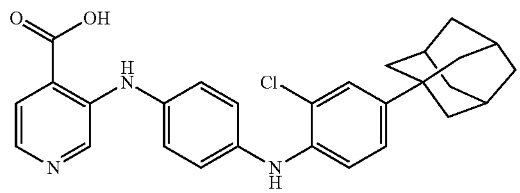 [SMILES: O=C(O)c1ccncc1Nc1ccc(Nc2ccc(C34CC5CC(CC(C5)C3)C4)cc2Cl)cc1] | 65 |
| 158 | 84 | 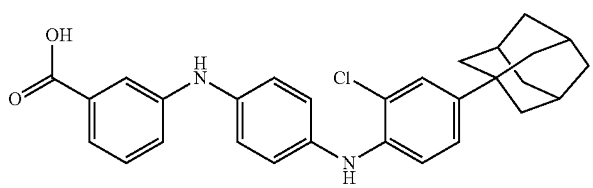 [SMILES: O=C(O)c1cccc(Nc2ccc(Nc3ccc(C45CC6CC(CC(C6)C4)C5)cc3Cl)cc2)c1] | 98 |
| 159 | 85 | 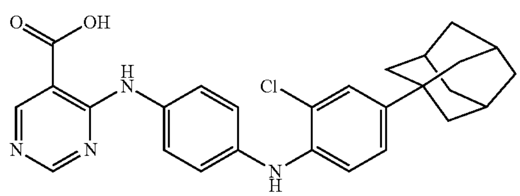 [SMILES: O=C(O)c1cncnc1Nc1ccc(Nc2ccc(C34CC5CC(CC(C5)C3)C4)cc2Cl)cc1] | 20 |
| 160 | 86 | 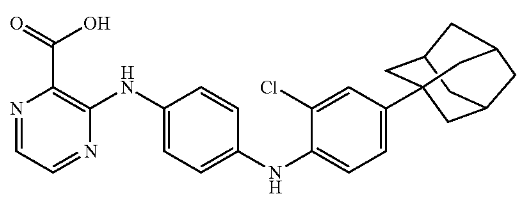 [SMILES: O=C(O)c1nccnc1Nc1ccc(Nc2ccc(C34CC5CC(CC(C5)C3)C4)cc2Cl)cc1] | 54 |
| 161 | 87 | 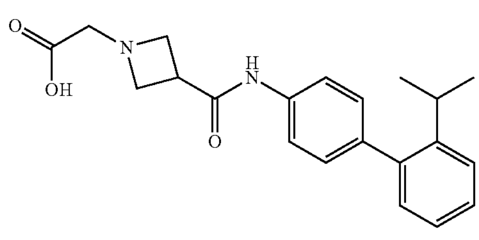 [SMILES: CC(C)c1ccccc1-c1ccc(NC(=O)C2CN(CC(=O)O)C2)cc1] | 4 |
| 162 | 88 | 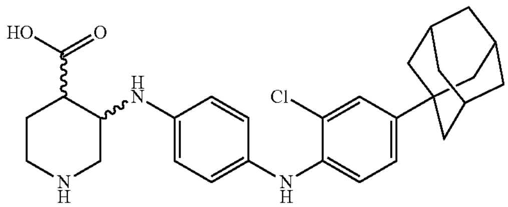 [SMILES: O=C(O)C1CCNCC1Nc1ccc(Nc2ccc(C34CC5CC(CC(C5)C3)C4)cc2Cl)cc1] | 12 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 163 | 89 | 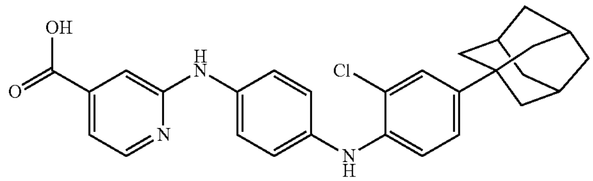 [SMILES: O=C(O)c1ccnc(Nc2ccc(Nc3ccc(C45CC6CC(CC(C6)C4)C5)cc3Cl)cc2)c1] | 90 |
| 168 | 90 | 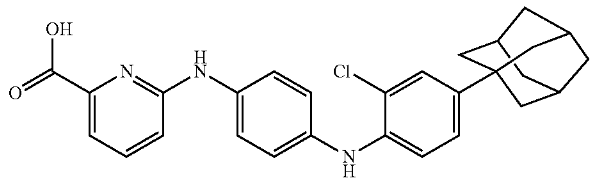 [SMILES: O=C(O)c1cccc(Nc2ccc(Nc3ccc(C45CC6CC(CC(C6)C4)C5)cc3Cl)cc2)n1] | 98, 0.446 μM |
| 169 | 91 | 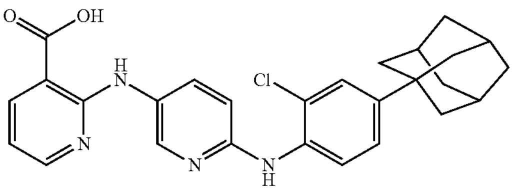 [SMILES: O=C(O)c1cccnc1Nc1ccc(Nc2ccc(C34CC5CC(CC(C5)C3)C4)cc2Cl)nc1] | 97 |
| 170 | 92 | 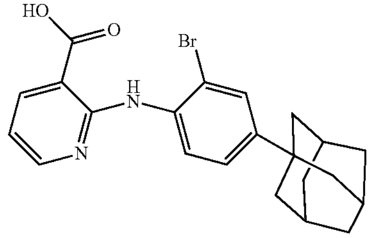 [SMILES: O=C(O)c1cccnc1Nc1ccc(C23CC4CC(CC(C4)C2)C3)cc1Br] | 90 |
| 172 | 93 | 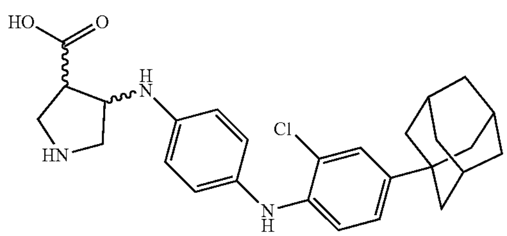 [SMILES: O=C(O)C1CNCC1Nc1ccc(Nc2ccc(C34CC5CC(CC(C5)C3)C4)cc2Cl)cc1] | 72 |
| 173 | 94 | 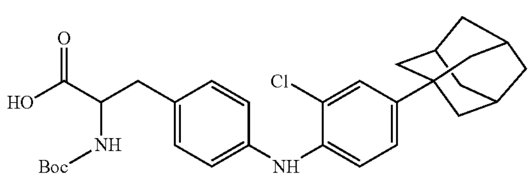 [SMILES: CC(C)(C)OC(=O)NC(Cc1ccc(Nc2ccc(C34CC5CC(CC(C5)C3)C4)cc2Cl)cc1)C(=O)O] | 91 |
| 174 | 95 | 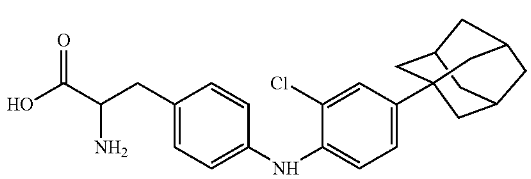 | 97 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 177 | 96 | 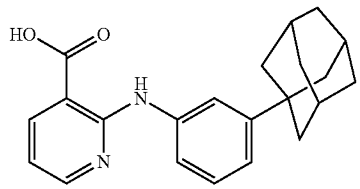 [SMILES: O=C(O)c1cccnc1Nc1cccc(C23CC4CC(CC(C4)C2)C3)c1] | 96 |
| 178 | 97 | 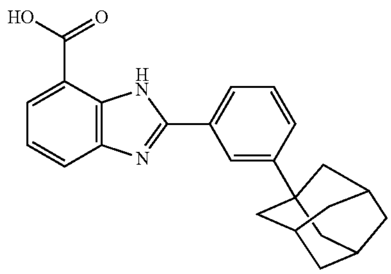 [SMILES: O=C(O)c1cccc2nc(-c3cccc(C45CC6CC(CC(C6)C4)C5)c3)[nH]c12] | 60 |
| 182 294 | 98 | | 89 |
| 183 | 99 | 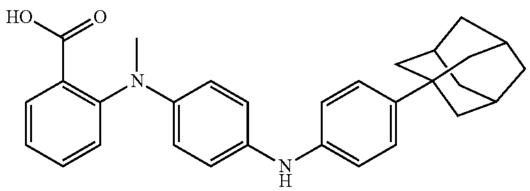 [SMILES: CN(c1ccc(Nc2ccc(C34CC5CC(CC(C5)C3)C4)cc2)cc1)c1ccccc1C(=O)O] | 85 |
| 184 | 100 | 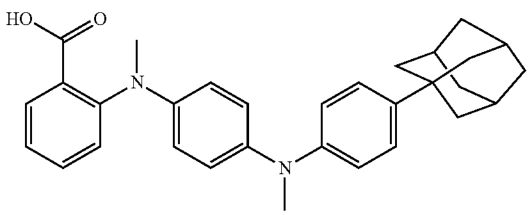 [SMILES: CN(c1ccc(N(C)c2ccccc2C(=O)O)cc1)c1ccc(C23CC4CC(CC(C4)C2)C3)cc1] | 100, 0.207 μM |
| 185 | 101 | 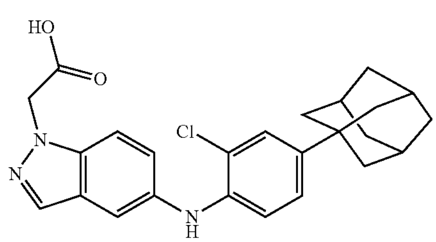 [SMILES: O=C(O)Cn1ncc2cc(Nc3ccc(C45CC6CC(CC(C6)C4)C5)cc3Cl)ccc21] | 62 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 186 | 102 | 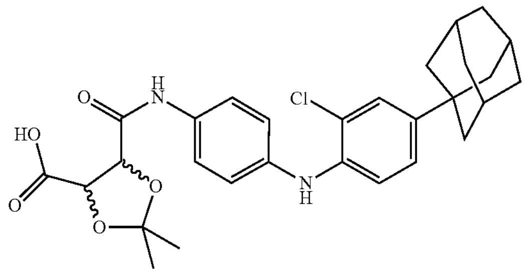 [SMILES: CC1(C)OC(C(=O)O)C(C(=O)Nc2ccc(Nc3ccc(C45CC6CC(CC(C6)C4)C5)cc3Cl)cc2)O1] | 77 |
| 187 | 103 | 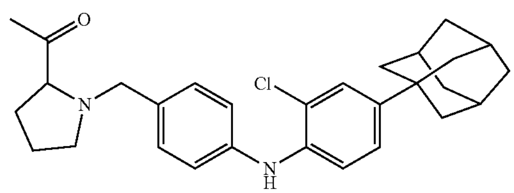 [SMILES: CC(=O)C1CCCN1Cc1ccc(Nc2ccc(C34CC5CC(CC(C5)C3)C4)cc2Cl)cc1] | 53 |
| 191 | 104 | 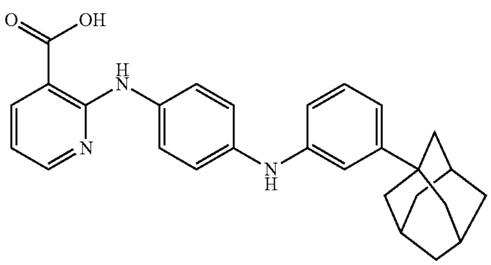 [SMILES: O=C(O)c1cccnc1Nc1ccc(Nc2cccc(C34CC5CC(CC(C5)C3)C4)c2)cc1] | 80 |
| 192 | 105 | 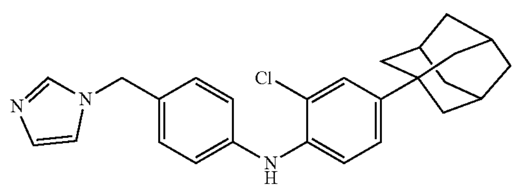 [SMILES: Clc1cc(C23CC4CC(CC(C4)C2)C3)ccc1Nc1ccc(Cn2ccnc2)cc1] | 96 |
| 194 | 106 | 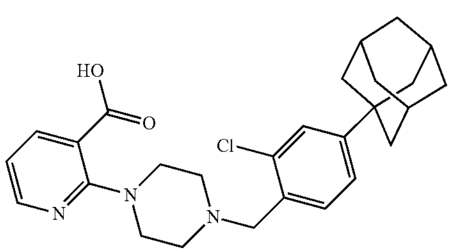 [SMILES: O=C(O)c1cccnc1N1CCN(Cc2ccc(C34CC5CC(CC(C5)C3)C4)cc2Cl)CC1] | 0 |
| 195 | 107 | 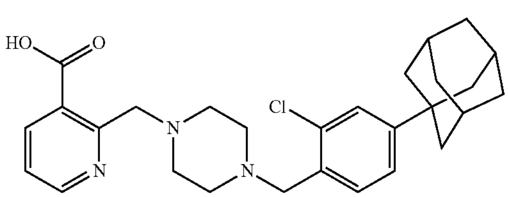 [SMILES: O=C(O)c1cccnc1CN1CCN(Cc2ccc(C34CC5CC(CC(C5)C3)C4)cc2Cl)CC1] | 14 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 197 | 108 | 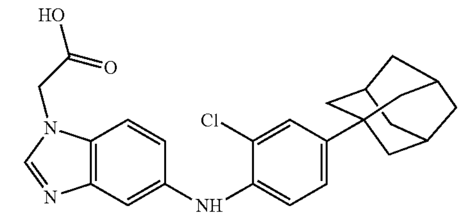 [SMILES: O=C(O)Cn1cnc2cc(Nc3ccc(C45CC6CC(CC(C6)C4)C5)cc3Cl)ccc21] | 86 |
| 198 | 109 | 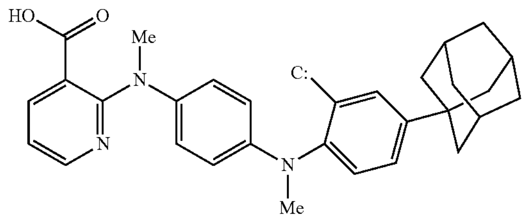 | 100, 0.346 μM |
| 199 | 110 | 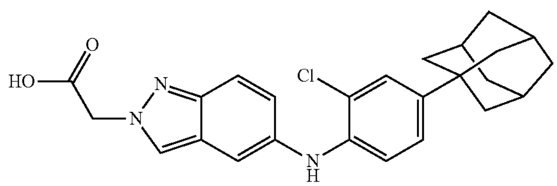 [SMILES: O=C(O)Cn1cc2cc(Nc3ccc(C45CC6CC(CC(C6)C4)C5)cc3Cl)ccc2n1] | 85 |
| 200 | 111 | 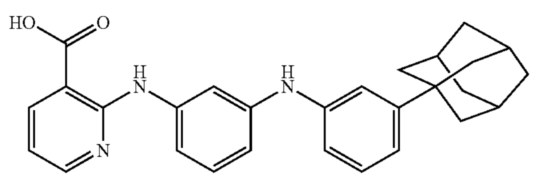 [SMILES: O=C(O)c1cccnc1Nc1cccc(Nc2cccc(C34CC5CC(CC(C5)C3)C4)c2)c1] | 80 |
| 202 | 112 | 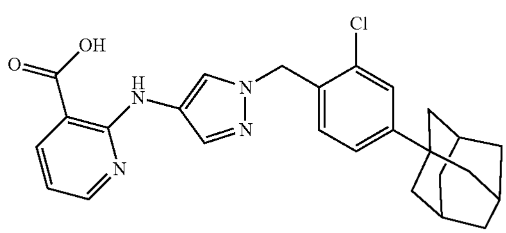 [SMILES: O=C(O)c1cccnc1Nc1cnn(Cc2ccc(C34CC5CC(CC(C5)C3)C4)cc2Cl)c1] | 100, 0.268 μM |
| 203 | 113 | 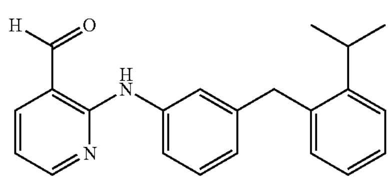 [SMILES: CC(C)c1ccccc1Cc1cccc(Nc2ncccc2C=O)c1] | 100 |
| 204 | 114 | 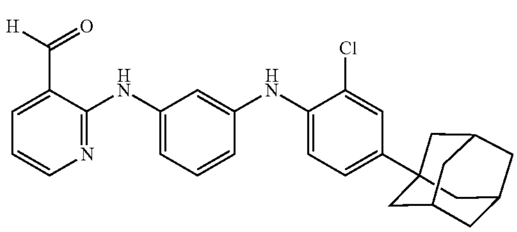 [SMILES: O=Cc1cccnc1Nc1cccc(Nc2ccc(C34CC5CC(CC(C5)C3)C4)cc2Cl)c1] | 98 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 205 | 115 | 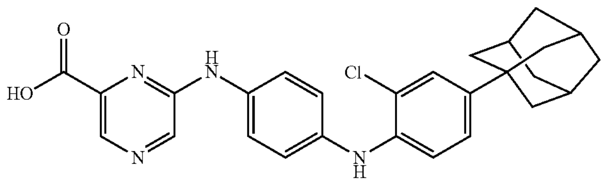 [SMILES: O=C(O)c1cncc(Nc2ccc(Nc3ccc(C45CC6CC(CC(C6)C4)C5)cc3Cl)cc2)n1] | 67 |
| 206 | 116 | 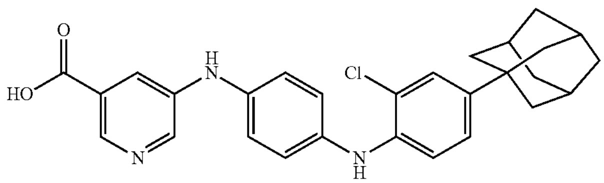 [SMILES: O=C(O)c1cncc(Nc2ccc(Nc3ccc(C45CC6CC(CC(C6)C4)C5)cc3Cl)cc2)c1] | 91 |
| 207 | 117 | 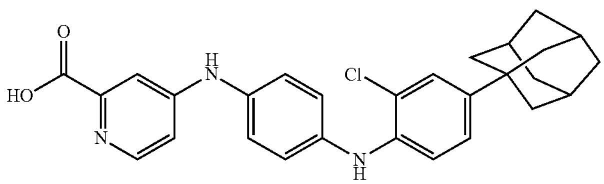 [SMILES: O=C(O)c1cc(Nc2ccc(Nc3ccc(C45CC6CC(CC(C6)C4)C5)cc3Cl)cc2)ccn1] | 9 |
| 210 | 118 | 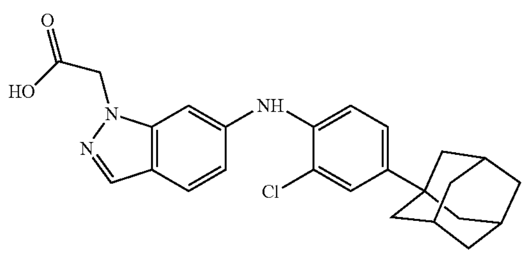 [SMILES: O=C(O)Cn1ncc2ccc(Nc3ccc(C45CC6CC(CC(C6)C4)C5)cc3Cl)cc21] | 78 |
| 211 | 119 | 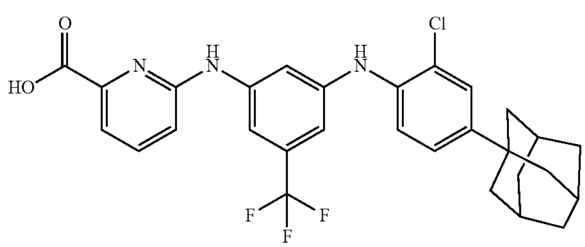 [SMILES: O=C(O)c1cccc(Nc2cc(Nc3ccc(C45CC6CC(CC(C6)C4)C5)cc3Cl)cc(C(F)(F)F)c2)n1] | 100, 0.106 μM |
| 212 | 120 | 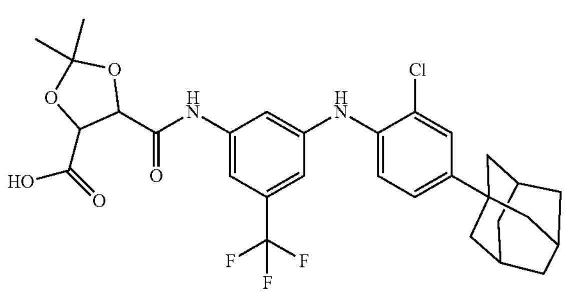 [SMILES: CC1(C)OC(C(=O)O)C(C(=O)Nc2cc(Nc3ccc(C45CC6CC(CC(C6)C4)C5)cc3Cl)cc(C(F)(F)F)c2)O1] | 79 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 213 | 121 | 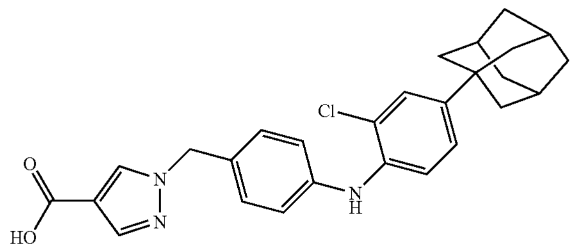 [SMILES: O=C(O)c1cnn(Cc2ccc(Nc3ccc(C45CC6CC(CC(C6)C4)C5)cc3Cl)cc2)c1] | 80 |
| 214 | 122 | 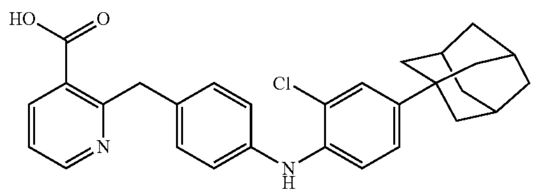 [SMILES: O=C(O)c1cccnc1Cc1ccc(Nc2ccc(C34CC5CC(CC(C5)C3)C4)cc2Cl)cc1] | 95 |
| 215 | 123 | 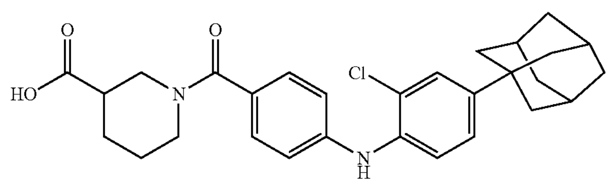 [SMILES: O=C(O)C1CCCN(C(=O)c2ccc(Nc3ccc(C45CC6CC(CC(C6)C4)C5)cc3Cl)cc2)C1] | 88 |
| 217 | 124 | 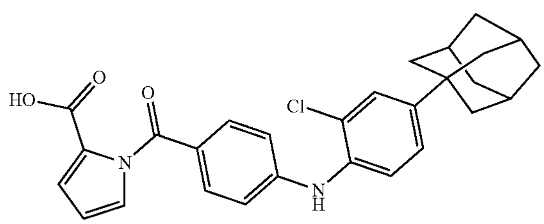 [SMILES: O=C(O)c1cccn1C(=O)c1ccc(Nc2ccc(C34CC5CC(CC(C5)C3)C4)cc2Cl)cc1] | 86 |
| 218 | 125 | 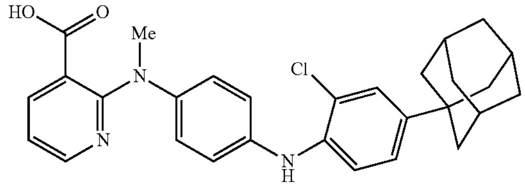 [SMILES: CN(c1ccc(Nc2ccc(C34CC5CC(CC(C5)C3)C4)cc2Cl)cc1)c1ncccc1C(=O)O] | 96, 0.771 μM |
| 219 | 126 | 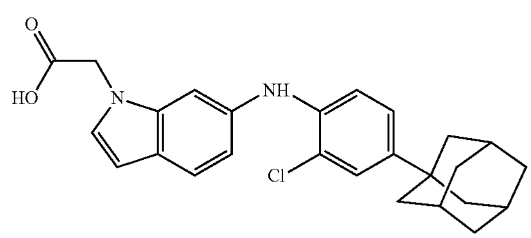 [SMILES: O=C(O)Cn1ccc2ccc(Nc3ccc(C45CC6CC(CC(C6)C4)C5)cc3Cl)cc21] | 86 |
| 220 | 127 | 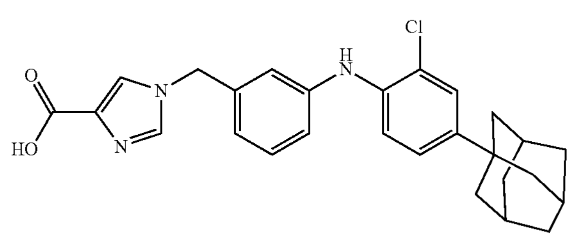 [SMILES: O=C(O)c1cn(Cc2cccc(Nc3ccc(C45CC6CC(CC(C6)C4)C5)cc3Cl)c2)cn1] | 27 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 221 | 128 | 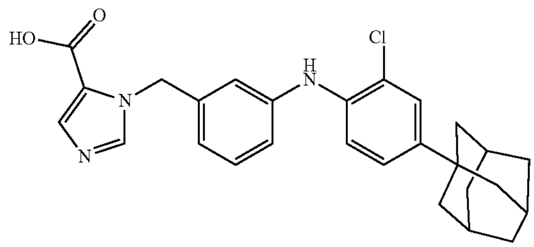 [SMILES: O=C(O)c1cncn1Cc1cccc(Nc2ccc(C34CC5CC(CC(C5)C3)C4)cc2Cl)c1] | 92 |
| 226 | 129 | 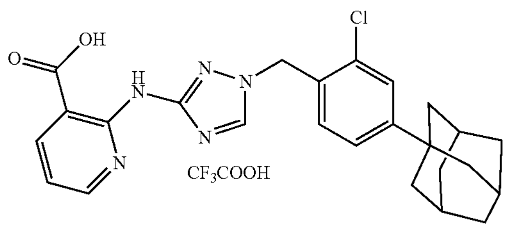 [SMILES: O=C(O)c1cccnc1Nc1ncn(Cc2ccc(C34CC5CC(CC(C5)C3)C4)cc2Cl)n1 ; "CF3COOH"] | 41 |
| 227 | 130 | 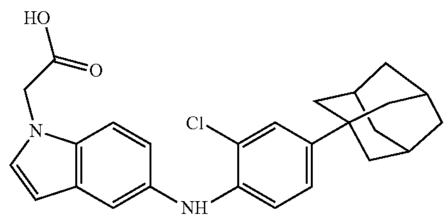 [SMILES: O=C(O)Cn1ccc2cc(Nc3ccc(C45CC6CC(CC(C6)C4)C5)cc3Cl)ccc21] | 100 |
| 228 | 131 | 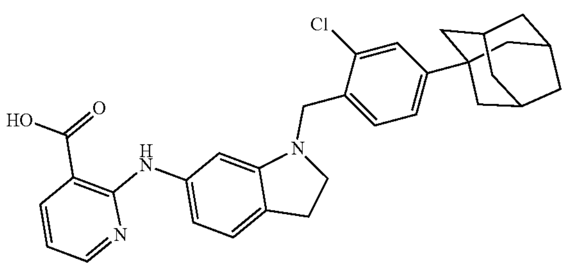 [SMILES: O=C(O)c1cccnc1Nc1ccc2c(c1)N(Cc1ccc(C34CC5CC(CC(C5)C3)C4)cc1Cl)CC2] | 37 |
| 233 | 132 | 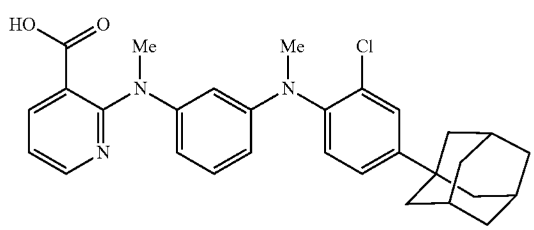 [SMILES: CN(c1cccc(N(C)c2ncccc2C(=O)O)c1)c1ccc(C23CC4CC(CC(C4)C2)C3)cc1Cl] | 100 |
| 236 | 133 | 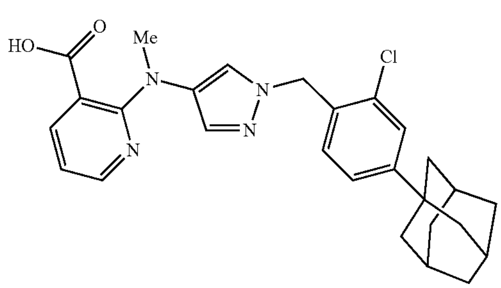 [SMILES: CN(c1cnn(Cc2ccc(C34CC5CC(CC(C5)C3)C4)cc2Cl)c1)c1ncccc1C(=O)O] | 93 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 240 | 134 | 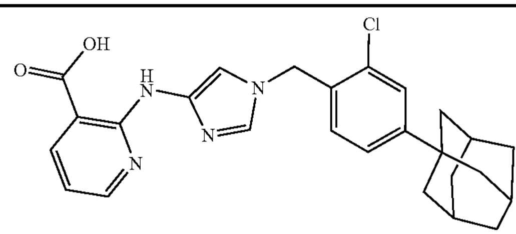 | 0 |
| 241 | 135 | 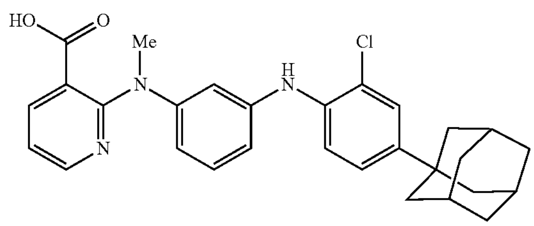 [SMILES: CN(c1cccc(Nc2ccc(C34CC5CC(CC(C5)C3)C4)cc2Cl)c1)c1ncccc1C(=O)O] | 100 |
| 243 | 136 | 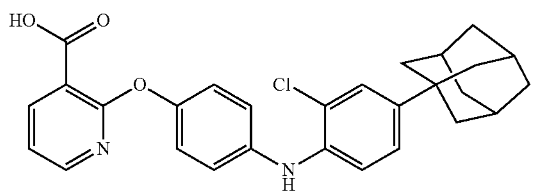 | 99 |
| 244 | 137 | 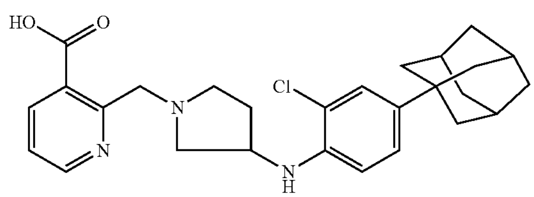 [SMILES: O=C(O)c1cccnc1CN1CCC(Nc2ccc(C34CC5CC(CC(C5)C3)C4)cc2Cl)C1] | 99 |
| 245 | 138 | 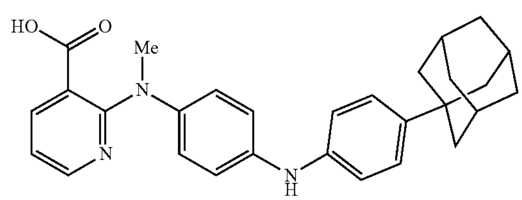 [SMILES: CN(c1ccc(Nc2ccc(C34CC5CC(CC(C5)C3)C4)cc2)cc1)c1ncccc1C(=O)O] | 24 |
| 246 | 139 | 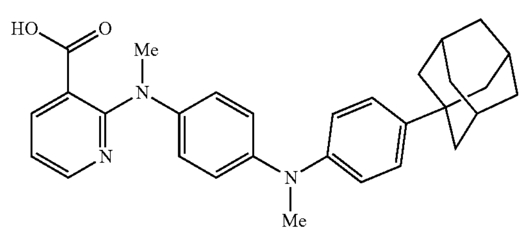 [SMILES: CN(c1ccc(N(C)c2ncccc2C(=O)O)cc1)c1ccc(C23CC4CC(CC(C4)C2)C3)cc1] | 95, 0.312 μM |
| 247 | 140 | 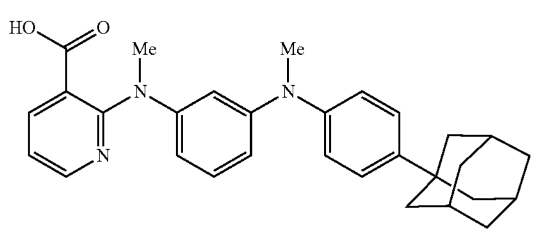 [SMILES: CN(c1ccc(C23CC4CC(CC(C4)C2)C3)cc1)c1cccc(N(C)c2ncccc2C(=O)O)c1] | 99 |

TABLE 2-continued

Activity of Compounds as TEAD2 Palmitoylation Inhibitors

| CP | Cmpd. No | Structure | % of inhibition of TEAD2 palmitoylation at 10 µM or IC$_{50}$ µM |
|---|---|---|---|
| 248 | 141 | 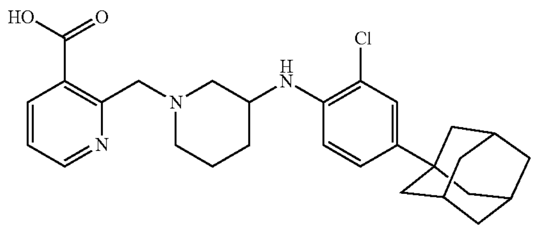 [SMILES: O=C(O)c1cccnc1CN1CCCC(Nc2ccc(C34CC5CC(CC(C5)C3)C4)cc2Cl)C1] | 95 |
| 249 | 142 | 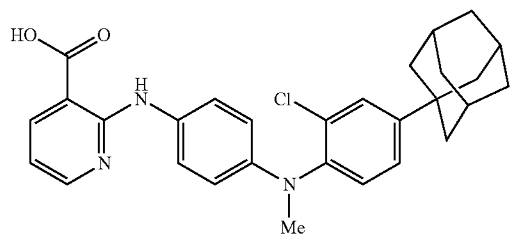 [SMILES: CN(c1ccc(Nc2ncccc2C(=O)O)cc1)c1ccc(C23CC4CC(CC(C4)C2)C3)cc1Cl] | 65 |
| 250 | 143 | 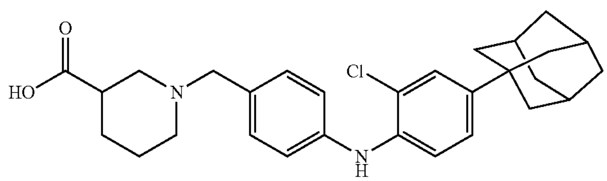 [SMILES: O=C(O)C1CCCN(Cc2ccc(Nc3ccc(C45CC6CC(CC(C6)C4)C5)cc3Cl)cc2)C1] | 22 |
| 252 | 144 | 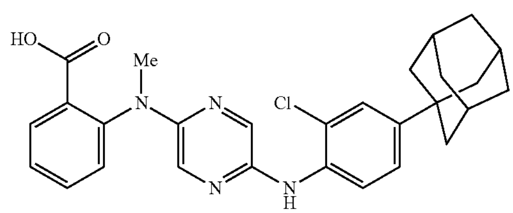 [SMILES: CN(c1cnc(Nc2ccc(C34CC5CC(CC(C5)C3)C4)cc2Cl)cn1)c1ccccc1C(=O)O] | 100 |
| 254 | 145 | 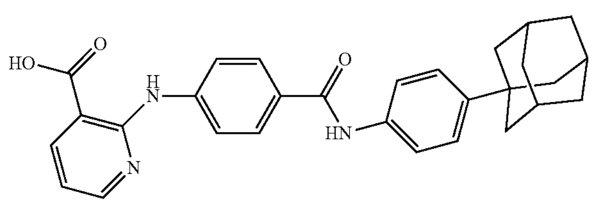 [SMILES: O=C(Nc1ccc(C23CC4CC(CC(C4)C2)C3)cc1)c1ccc(Nc2ncccc2C(=O)O)cc1] | 61, 84 |
| 255 | 146 | 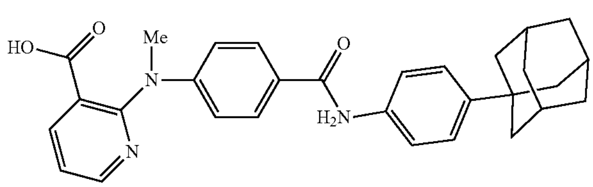 [SMILES: CN(c1ccc(C(=O)Nc2ccc(C34CC5CC(CC(C5)C3)C4)cc2)cc1)c1ncccc1C(=O)O] | 64 |
| 258 | 147 | 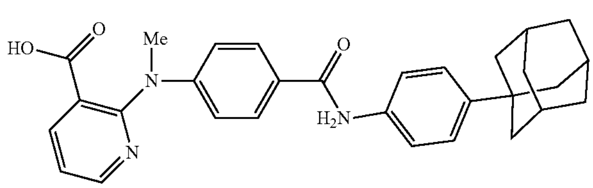 [SMILES: CN(c1ccc(C(=O)Nc2ccc(C34CC5CC(CC(C5)C3)C4)cc2)cc1)c1ncccc1C(=O)O] | 70 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 259 | 148 | 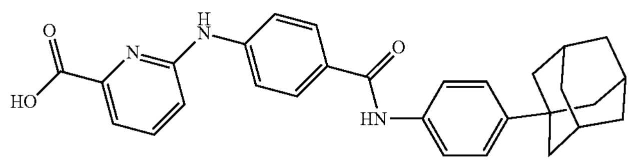 [SMILES: O=C(Nc1ccc(C23CC4CC(CC(C4)C2)C3)cc1)c1ccc(Nc2cccc(C(=O)O)n2)cc1] | 56, 69 |
| 260 | 149 | 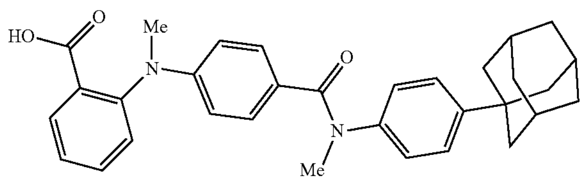 [SMILES: CN(C(=O)c1ccc(N(C)c2ccccc2C(=O)O)cc1)c1ccc(C23CC4CC(CC(C4)C2)C3)cc1] | 40 |
| 261 | 150 | 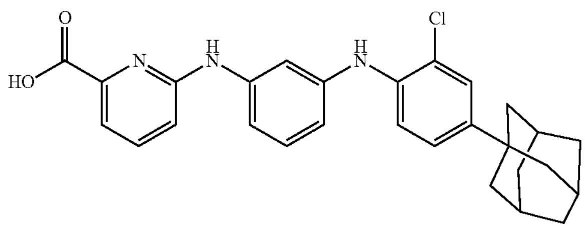 [SMILES: O=C(O)c1cccc(Nc2cccc(Nc3ccc(C45CC6CC(CC(C6)C4)C5)cc3Cl)c2)n1] | 100 |
| 263 | 151 | 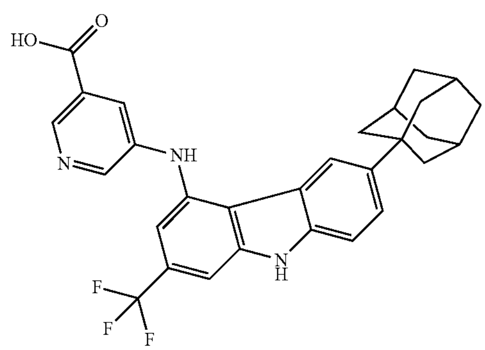 [SMILES: O=C(O)c1cncc(Nc2cc(C(F)(F)F)cc3[nH]c4ccc(C56CC7CC(CC(C7)C5)C6)cc4c23)c1] | 101 |
| 266 | 152 | 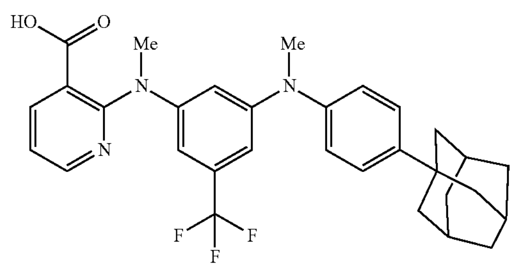 [SMILES: CN(c1ccc(C23CC4CC(CC(C4)C2)C3)cc1)c1cc(N(C)c2ncccc2C(=O)O)cc(C(F)(F)F)c1] | 102 |
| 267 | 153 | 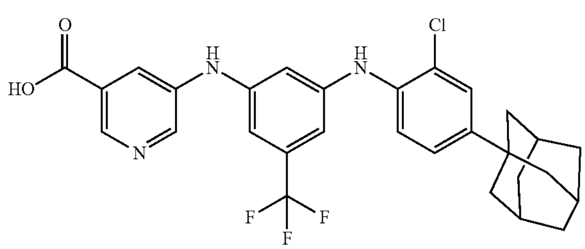 [SMILES: O=C(O)c1cncc(Nc2cc(Nc3ccc(C45CC6CC(CC(C6)C4)C5)cc3Cl)cc(C(F)(F)F)c2)c1] | 100 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 268 | 154 | 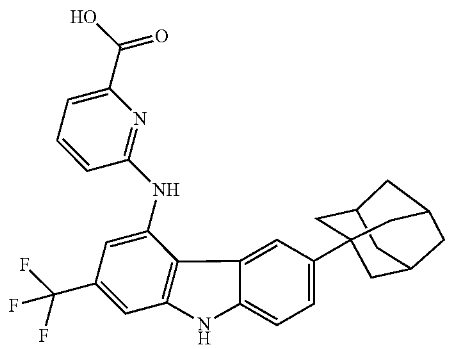 [SMILES: O=C(O)c1cccc(Nc2cc(C(F)(F)F)cc3[nH]c4ccc(C56CC7CC(CC(C7)C5)C6)cc4c23)n1] | 58, 43 |
| 270 | 155 | 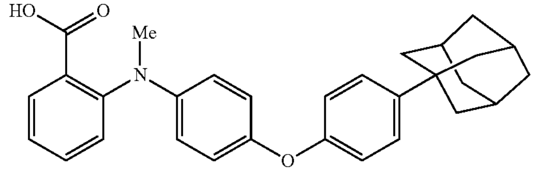 [SMILES: CN(c1ccc(Oc2ccc(C34CC5CC(CC(C5)C3)C4)cc2)cc1)c1ccccc1C(=O)O] | 99 |
| 271 | 156 | 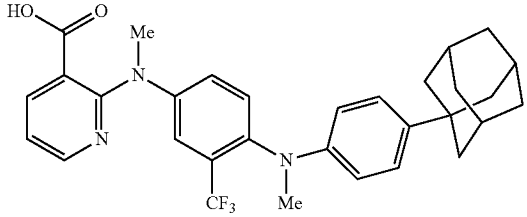 [SMILES: CN(c1ccc(C23CC4CC(CC(C4)C2)C3)cc1)c1ccc(N(C)c2ncccc2C(=O)O)cc1C(F)(F)F] | 92 |
| 272 | 157 | 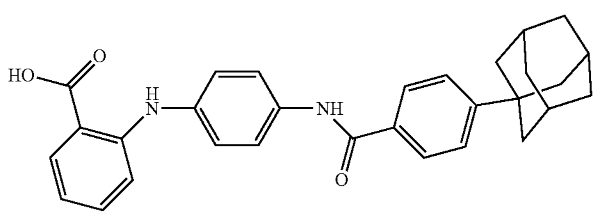 [SMILES: O=C(Nc1ccc(Nc2ccccc2C(=O)O)cc1)c1ccc(C23CC4CC(CC(C4)C2)C3)cc1] | 80 |
| 273 | 158 | 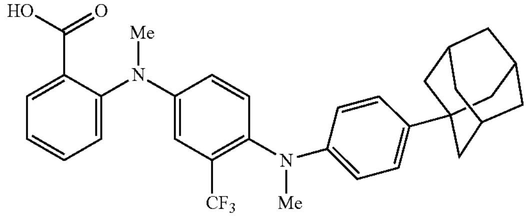 [SMILES: CN(c1ccc(N(C)c2ccc(C34CC5CC(CC(C5)C3)C4)cc2)c(C(F)(F)F)c1)c1ccccc1C(=O)O] | 100 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 274 | 159 | 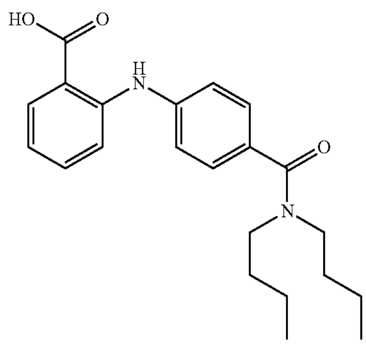 [SMILES: CCCCN(CCCC)C(=O)c1ccc(Nc2ccccc2C(=O)O)cc1] | 41 |
| 275 | 160 | 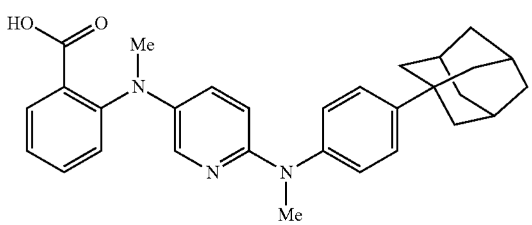 [SMILES: CN(c1ccc(C23CC4CC(CC(C4)C2)C3)cc1)c1ccc(N(C)c2ccccc2C(=O)O)cn1] | 84 |
| 276 | 161 | 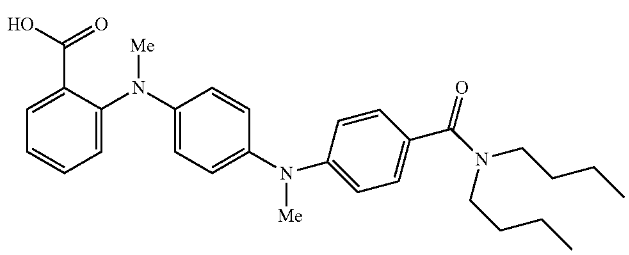 [SMILES: CCCCN(CCCC)C(=O)c1ccc(N(C)c2ccc(N(C)c3ccccc3C(=O)O)cc2)cc1] | 17, 43 |
| 277 | 162 | 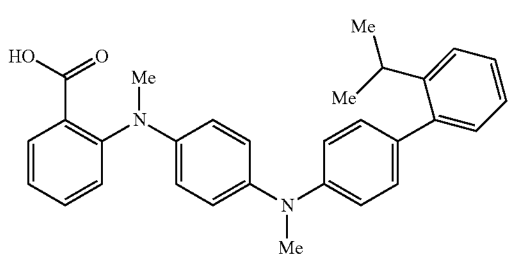 [SMILES: CC(C)c1ccccc1-c1ccc(N(C)c2ccc(N(C)c3ccccc3C(=O)O)cc2)cc1] | 25, 88 |
| 278 | 163 | 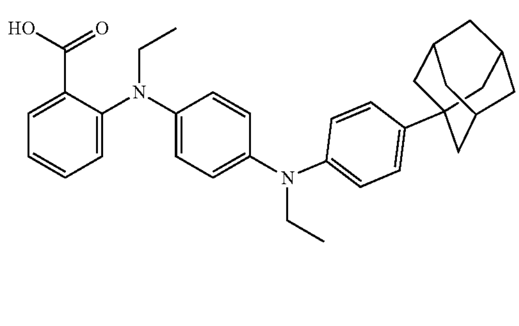 [SMILES: CCN(c1ccc(N(CC)c2ccccc2C(=O)O)cc1)c1ccc(C23CC4CC(CC(C4)C2)C3)cc1] | 85 |

TABLE 2-continued
Activity of Compounds as TEAD2 Palmitoylation Inhibitors
| CP | Cmpd. No | Structure | % of inhibition of TEAD2 palmitoylation at 10 µM or IC$_{50}$ µM |
|---|---|---|---|
| 279 | 164 | 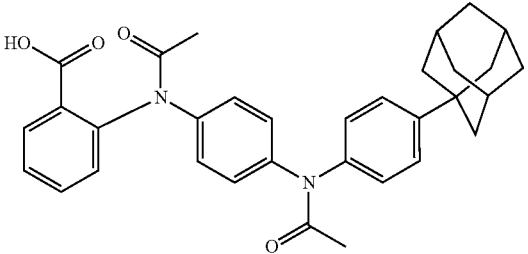 [SMILES: CC(=O)N(c1ccc(N(C(C)=O)c2ccccc2C(=O)O)cc1)c1ccc(C23CC4CC(CC(C4)C2)C3)cc1] | 20 |
| 282 | 165 | 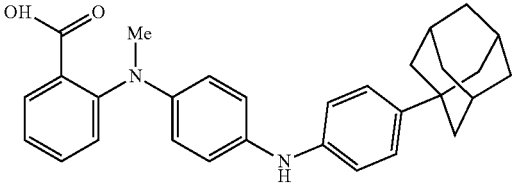 [SMILES: CN(c1ccc(Nc2ccc(C34CC5CC(CC(C5)C3)C4)cc2)cc1)c1ccccc1C(=O)O] | 85 |
| 284 | 166 | 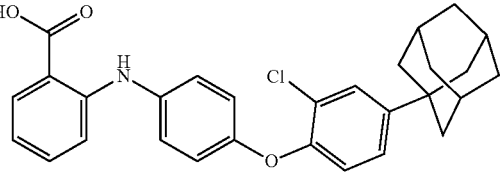 | 98 |
| 285 | 167 | 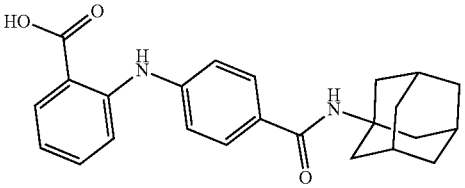 [SMILES: O=C(NC12CC3CC(CC(C3)C1)C2)c1ccc(Nc2ccccc2C(=O)O)cc1] | 43 |
| 286 | 168 | 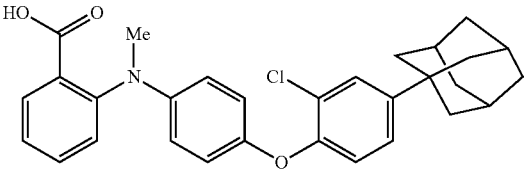 [SMILES: CN(c1ccc(Oc2ccc(C34CC5CC(CC(C5)C3)C4)cc2Cl)cc1)c1ccccc1C(=O)O] | 97, 0.173 µM |
| 287 | 169 | 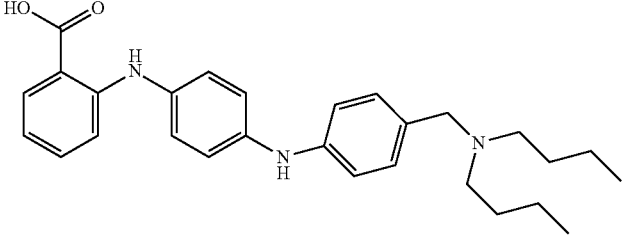 [SMILES: CCCCN(CCCC)Cc1ccc(Nc2ccc(Nc3ccccc3C(=O)O)cc2)cc1] | 42 |
| 288 | 170 | 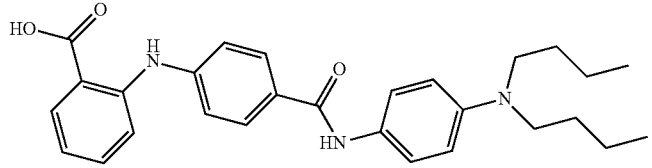 [SMILES: CCCCN(CCCC)c1ccc(NC(=O)c2ccc(Nc3ccccc3C(=O)O)cc2)cc1] | 62 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 289 | 171 | 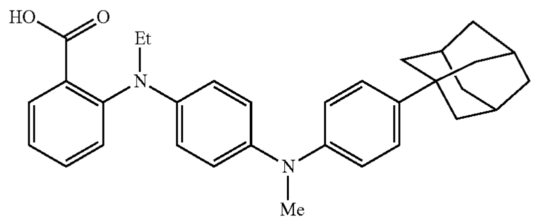 [SMILES: CCN(c1ccc(N(C)c2ccc(C34CC5CC(CC(C5)C3)C4)cc2)cc1)c1ccccc1C(=O)O] | 75 |
| 290 | 172 | 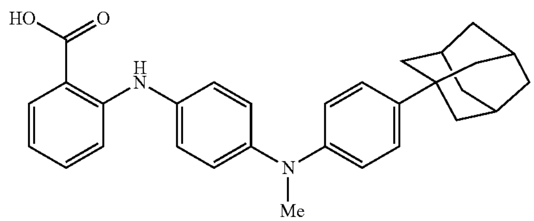 [SMILES: CN(c1ccc(Nc2ccccc2C(=O)O)cc1)c1ccc(C23CC4CC(CC(C4)C2)C3)cc1] | 100 |
| 291 | 173 | 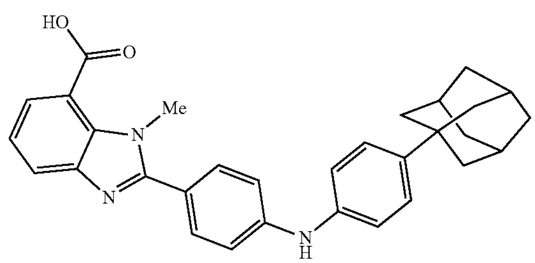 [SMILES: Cn1c(-c2ccc(Nc3ccc(C45CC6CC(CC(C6)C4)C5)cc3)cc2)nc2cccc(C(=O)O)c21] | 51 |
| 292 | 174 | 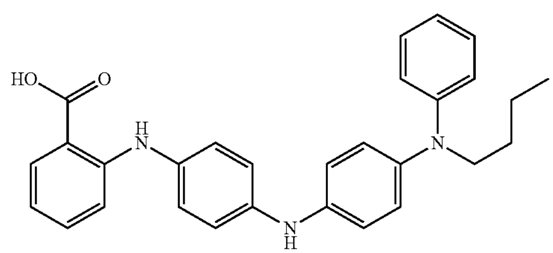 [SMILES: CCCCN(c1ccccc1)c1ccc(Nc2ccc(Nc3ccccc3C(=O)O)cc2)cc1] | 85 |
| 293 | 175 | 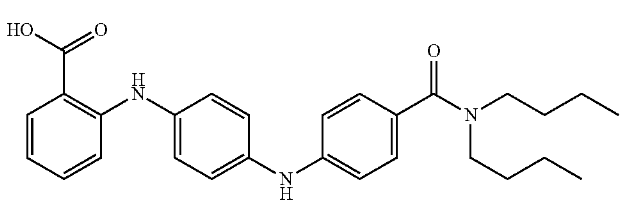 [SMILES: CCCCN(CCCC)C(=O)c1ccc(Nc2ccc(Nc3ccccc3C(=O)O)cc2)cc1] | 70 |
| 294 | 176 | 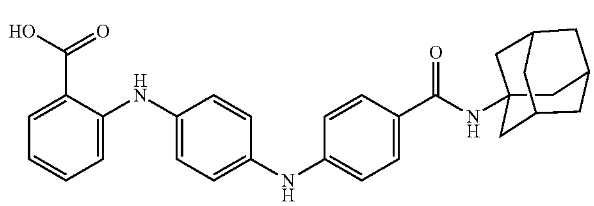 [SMILES: O=C(NC12CC3CC(CC(C3)C1)C2)c1ccc(Nc2ccc(Nc3ccccc3C(=O)O)cc2)cc1] | 89 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 295 | 177 | 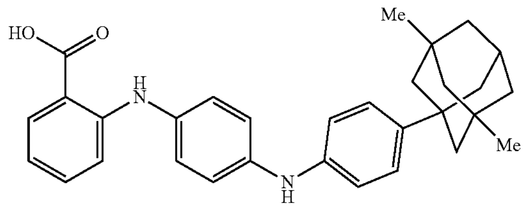 [SMILES: CC12CC3CC(C)(C1)CC(c1ccc(Nc4ccc(Nc5ccccc5C(=O)O)cc4)cc1)(C3)C2] | 56 |
| 296 | 178 | 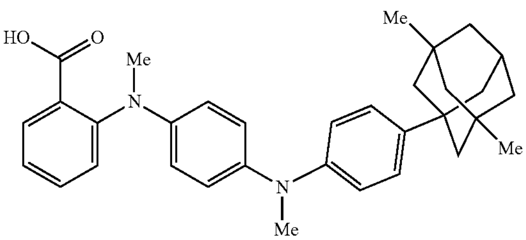 [SMILES: CN(c1ccc(N(C)c2ccccc2C(=O)O)cc1)c1ccc(C23CC4CC(C)(CC(C)(C4)C2)C3)cc1] | 100, 0.227 μM |
| 297 | 179 | 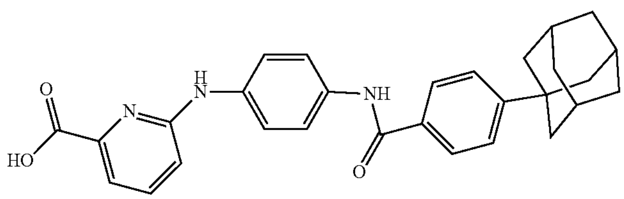 [SMILES: O=C(Nc1ccc(Nc2cccc(C(=O)O)n2)cc1)c1ccc(C23CC4CC(CC(C4)C2)C3)cc1] | 92, 35 |
| 298 | 180 | 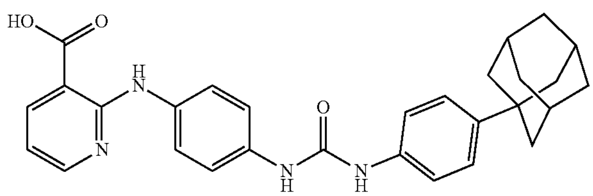 [SMILES: O=C(Nc1ccc(Nc2ncccc2C(=O)O)cc1)Nc1ccc(C23CC4CC(CC(C4)C2)C3)cc1] | 81 |
| 299 | 181 | 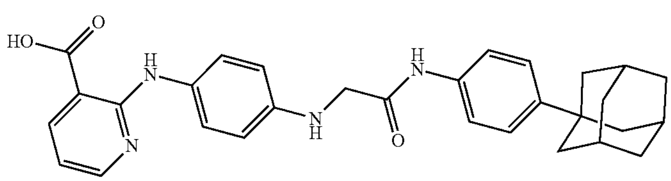 [SMILES: O=C(CNc1ccc(Nc2ncccc2C(=O)O)cc1)Nc1ccc(C23CC4CC(CC(C4)C2)C3)cc1] | 49, 41 |
| 300 | 182 | 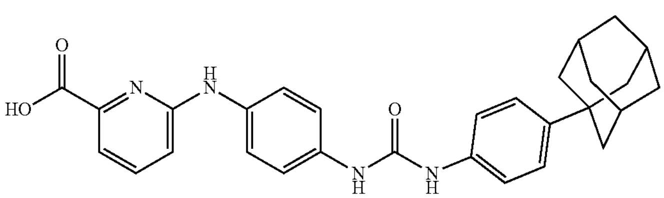 [SMILES: O=C(Nc1ccc(Nc2cccc(C(=O)O)n2)cc1)Nc1ccc(C23CC4CC(CC(C4)C2)C3)cc1] | 54 |
| 301 | 183 | 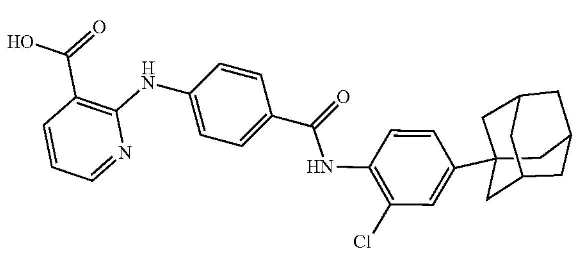 [SMILES: O=C(Nc1ccc(C23CC4CC(CC(C4)C2)C3)cc1Cl)c1ccc(Nc2ncccc2C(=O)O)cc1] | 100, 96 |

TABLE 2-continued
Activity of Compounds as TEAD2 Palmitoylation Inhibitors
| CP | Cmpd. No | Structure | % of inhibition of TEAD2 palmitoylation at 10 μM or IC$_{50}$ μM |
|---|---|---|---|
| 302 | 184 | 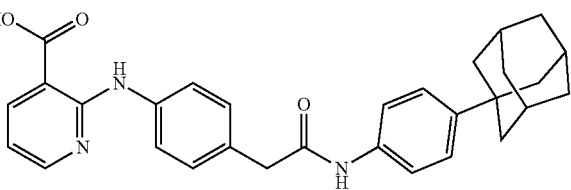 | 71 |
| 303 | 185 | 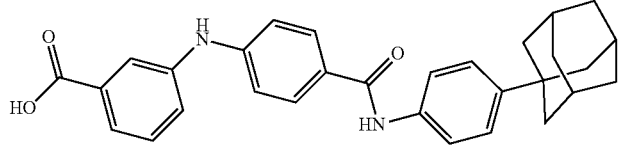 [SMILES: O=C(O)c1cccc(Nc2ccc(C(=O)Nc3ccc(C45CC6CC(CC(C6)C4)C5)cc3)cc2)c1] | 66, 91 |
| 304 | 186 | 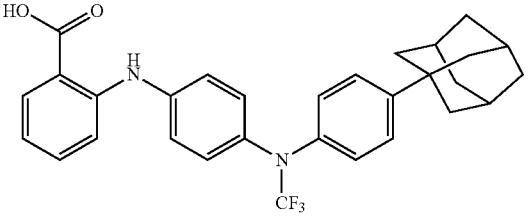 [SMILES: O=C(O)c1ccccc1Nc1ccc(N(c2ccc(C34CC5CC(CC(C5)C3)C4)cc2)C(F)(F)F)cc1] | 76 |
| 305 | 187 | 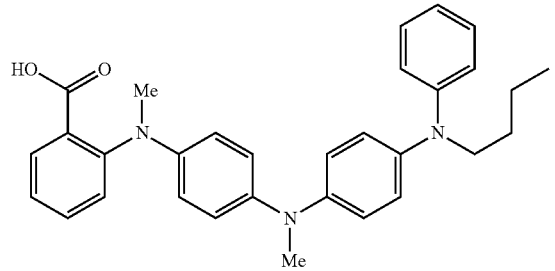 [SMILES: CCCCN(c1ccccc1)c1ccc(N(C)c2ccc(N(C)c3ccccc3C(=O)O)cc2)cc1] | 57 |
| 306 | 188 | 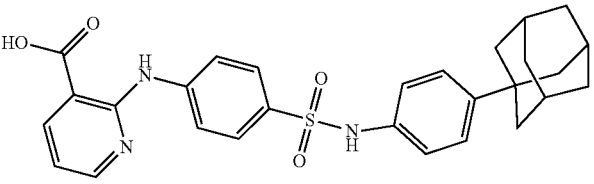 [SMILES: O=C(O)c1cccnc1Nc1ccc(S(=O)(=O)Nc2ccc(C34CC5CC(CC(C5)C3)C4)cc2)cc1] | 101 |
| 307 | 189 | 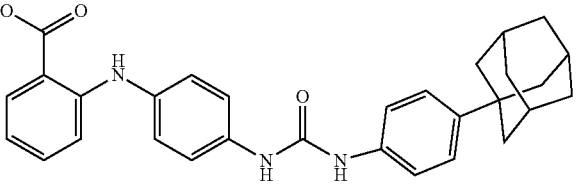 | 34 |
| 308 | 190 | 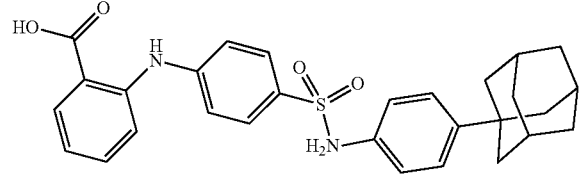 [SMILES: O=C(O)c1ccccc1Nc1ccc(S(=O)(=O)Nc2ccc(C34CC5CC(CC(C5)C3)C4)cc2)cc1] | 85 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 309 | 191 | 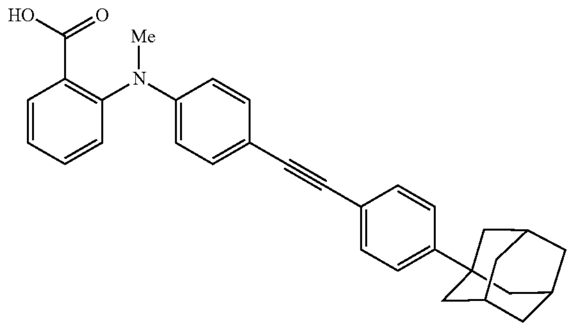 [SMILES: CN(c1ccc(C#Cc2ccc(C34CC5CC(CC(C5)C3)C4)cc2)cc1)c1ccccc1C(=O)O] | 85 |
| 310 | 192 | 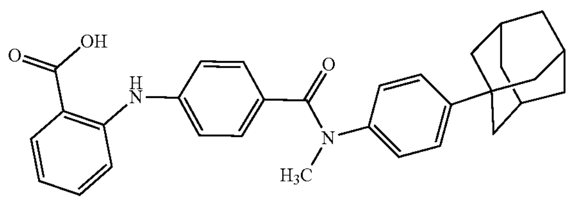 [SMILES: CN(C(=O)c1ccc(Nc2ccccc2C(=O)O)cc1)c1ccc(C23CC4CC(CC(C4)C2)C3)cc1] | 99 |
| 311 | 193 | 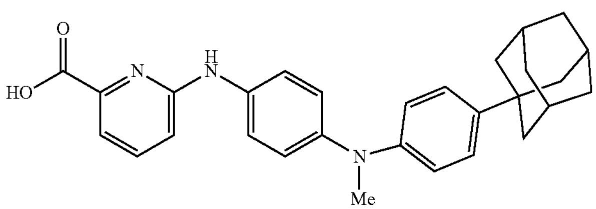 [SMILES: CN(c1ccc(Nc2cccc(C(=O)O)n2)cc1)c1ccc(C23CC4CC(CC(C4)C2)C3)cc1] | 86 |
| 312 | 194 | 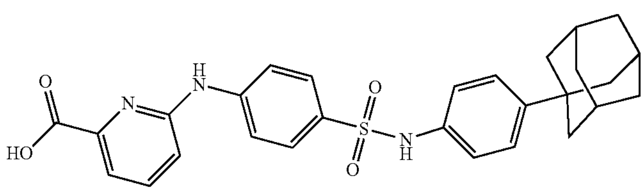 [SMILES: O=C(O)c1cccc(Nc2ccc(S(=O)(=O)Nc3ccc(C45CC6CC(CC(C6)C4)C5)cc3)cc2)n1] | 20 |
| 313 | 195 | 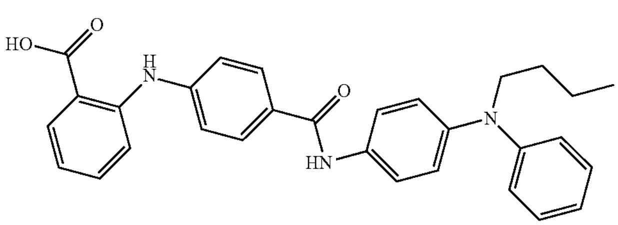 [SMILES: CCCCN(c1ccccc1)c1ccc(NC(=O)c2ccc(Nc3ccccc3C(=O)O)cc2)cc1] | 0 |
| 314 | 196 | 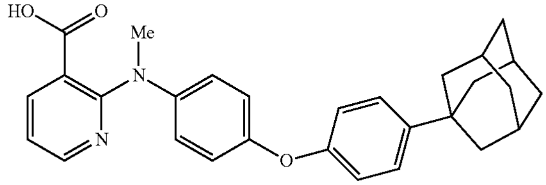 [SMILES: CN(c1ccc(Oc2ccc(C34CC5CC(CC(C5)C3)C4)cc2)cc1)c1ncccc1C(=O)O] | 100 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 315 | 197 | 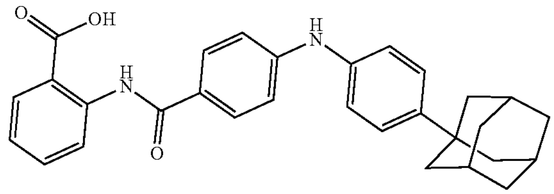 [SMILES: O=C(Nc1ccccc1C(=O)O)c1ccc(Nc2ccc(C34CC5CC(CC(C5)C3)C4)cc2)cc1] | 100 |
| 316 | 198 | 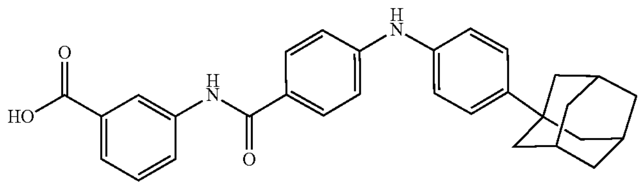 [SMILES: O=C(O)c1cccc(NC(=O)c2ccc(Nc3ccc(C45CC6CC(CC(C6)C4)C5)cc3)cc2)c1] | 99 |
| 317 | 199 | 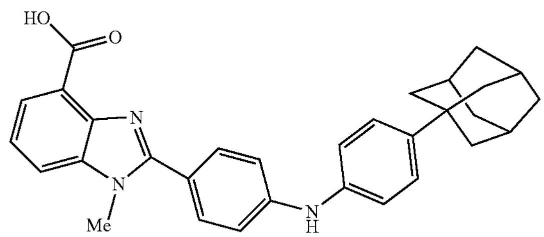 [SMILES: Cn1c(-c2ccc(Nc3ccc(C45CC6CC(CC(C6)C4)C5)cc3)cc2)nc2c(C(=O)O)cccc21] | 6 |
| 318 | 200 | 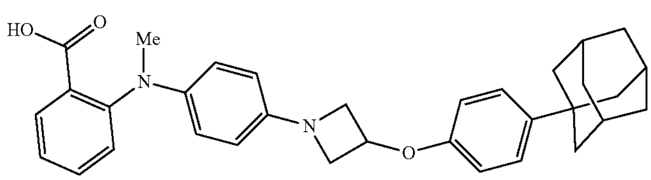 [SMILES: CN(c1ccc(N2CC(Oc3ccc(C45CC6CC(CC(C6)C4)C5)cc3)C2)cc1)c1ccccc1C(=O)O] | 32 |
| 319 | 201 | 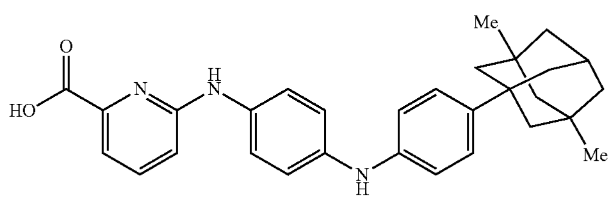 [SMILES: CC12CC3CC(C)(C1)CC(c1ccc(Nc4ccc(Nc5cccc(C(=O)O)n5)cc4)cc1)(C3)C2] | 43 |
| 320 | 202 | 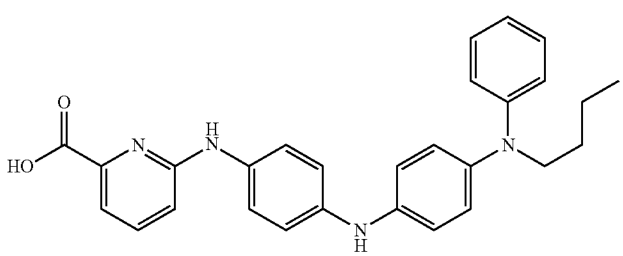 [SMILES: CCCCN(c1ccccc1)c1ccc(Nc2ccc(Nc3cccc(C(=O)O)n3)cc2)cc1] | 49 |
| 321 | 203 | 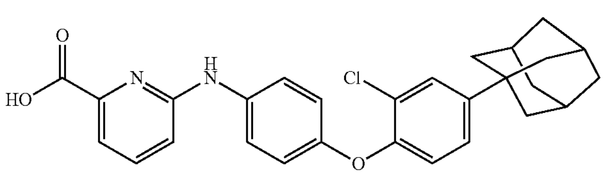 [SMILES: O=C(O)c1cccc(Nc2ccc(Oc3ccc(C45CC6CC(CC(C6)C4)C5)cc3Cl)cc2)n1] | 95 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 322 | 204 | 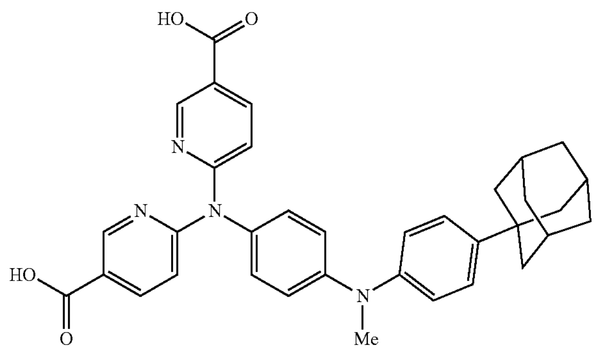 [SMILES: CN(c1ccc(N(c2ccc(C(=O)O)cn2)c2ccc(C(=O)O)cn2)cc1)c1ccc(C23CC4CC(CC(C4)C2)C3)cc1] | 99 |
| 323 | 205 | 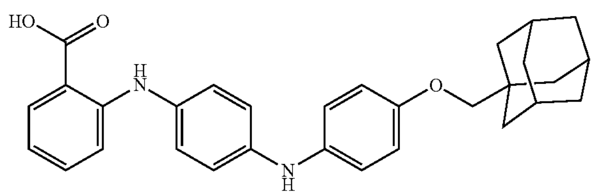 [SMILES: O=C(O)c1ccccc1Nc1ccc(Nc2ccc(OCC34CC5CC(CC(C5)C3)C4)cc2)cc1] | 74 |
| 324 | 206 | 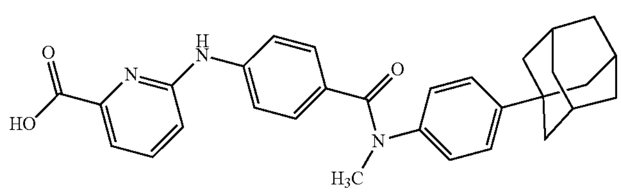 [SMILES: CN(C(=O)c1ccc(Nc2cccc(C(=O)O)n2)cc1)c1ccc(C23CC4CC(CC(C4)C2)C3)cc1] | 52 |
| 325 | 207 | 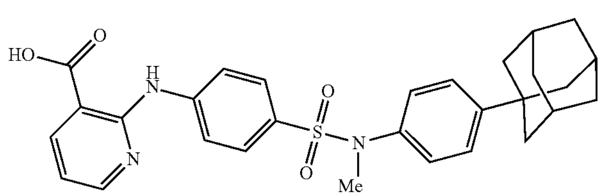 [SMILES: CN(c1ccc(C23CC4CC(CC(C4)C2)C3)cc1)S(=O)(=O)c1ccc(Nc2ncccc2C(=O)O)cc1] | 99 |
| 326 | 208 | 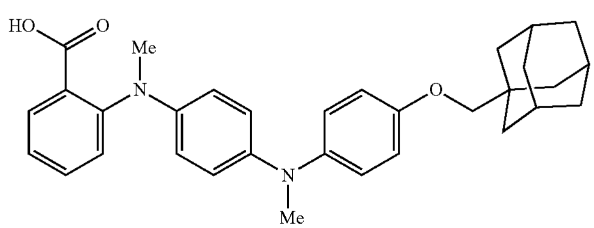 [SMILES: CN(c1ccc(OCC23CC4CC(CC(C4)C2)C3)cc1)c1ccc(N(C)c2ccccc2C(=O)O)cc1] | 100 |
| 327 | 209 | 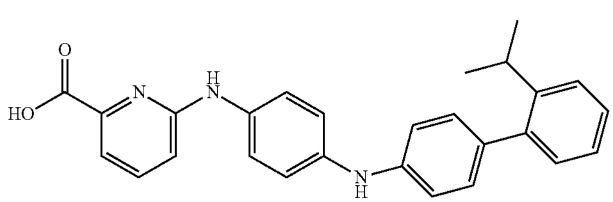 [SMILES: CC(C)c1ccccc1-c1ccc(Nc2ccc(Nc3cccc(C(=O)O)n3)cc2)cc1] | 54 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 328 | 210 | 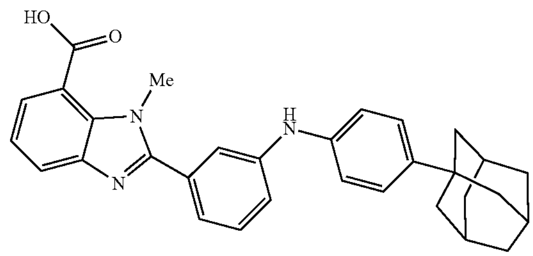 [SMILES: Cn1c(-c2cccc(Nc3ccc(C45CC6CC(CC(C6)C4)C5)cc3)c2)nc2cccc(C(=O)O)c21] | 100 |
| 329 | 211 | 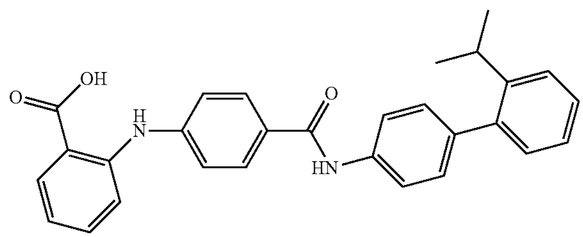 [SMILES: CC(C)c1ccccc1-c1ccc(NC(=O)c2ccc(Nc3ccccc3C(=O)O)cc2)cc1] | 67 |
| 330 | 212 | 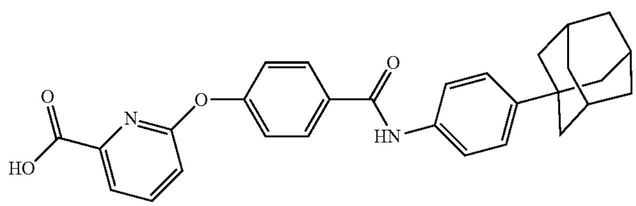 [SMILES: O=C(Nc1ccc(C23CC4CC(CC(C4)C2)C3)cc1)c1ccc(Oc2cccc(C(=O)O)n2)cc1] | 77 |
| 331 | 213 | 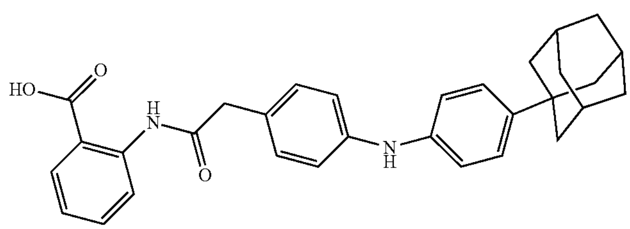 [SMILES: O=C(Cc1ccc(Nc2ccc(C34CC5CC(CC(C5)C3)C4)cc2)cc1)Nc1ccccc1C(=O)O] | 90 |
| 333 | 214 | 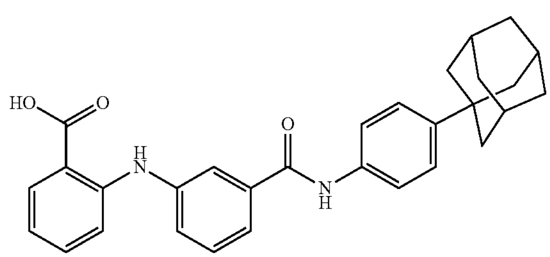 [SMILES: O=C(Nc1ccc(C23CC4CC(CC(C4)C2)C3)cc1)c1cccc(Nc2ccccc2C(=O)O)c1] | 88, 73 |
| 334 | 215 | 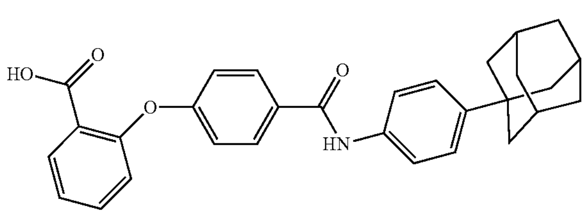 [SMILES: O=C(Nc1ccc(C23CC4CC(CC(C4)C2)C3)cc1)c1ccc(Oc2ccccc2C(=O)O)cc1] | 87 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 335 | 216 | 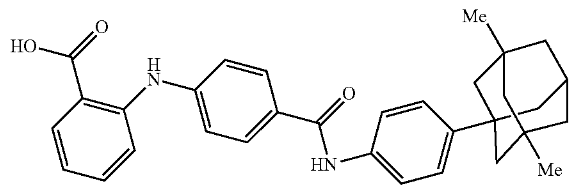 [SMILES: CC12CC3CC(C)(C1)CC(c1ccc(NC(=O)c4ccc(Nc5ccccc5C(=O)O)cc4)cc1)(C3)C2] | 89 |
| 336 | 217 | 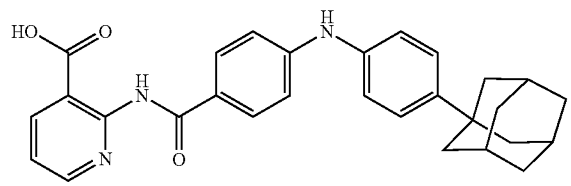 [SMILES: O=C(Nc1ncccc1C(=O)O)c1ccc(Nc2ccc(C34CC5CC(CC(C5)C3)C4)cc2)cc1] | 55 |
| 337 | 218 | 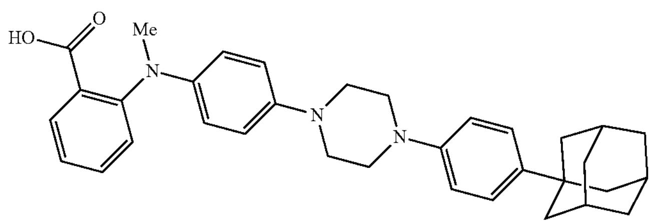 [SMILES: CN(c1ccc(N2CCN(c3ccc(C45CC6CC(CC(C6)C4)C5)cc3)CC2)cc1)c1ccccc1C(=O)O] | 0 |
| 338 | 219 | 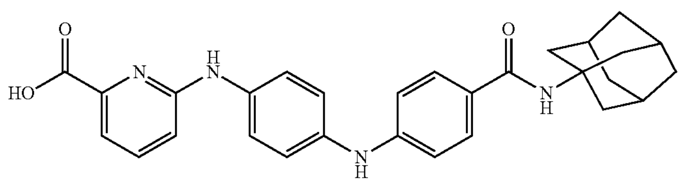 [SMILES: O=C(NC12CC3CC(CC(C3)C1)C2)c1ccc(Nc2ccc(Nc3cccc(C(=O)O)n3)cc2)cc1] | 0 |
| 339 | 220 | 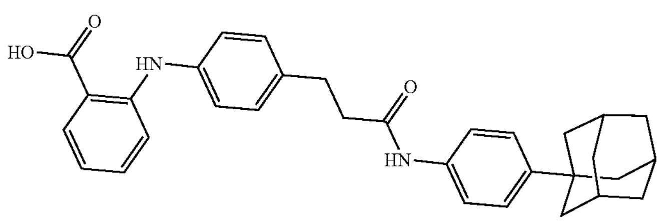 [SMILES: O=C(CCc1ccc(Nc2ccccc2C(=O)O)cc1)Nc1ccc(C23CC4CC(CC(C4)C2)C3)cc1] | 10 |
| 340 | 221 | 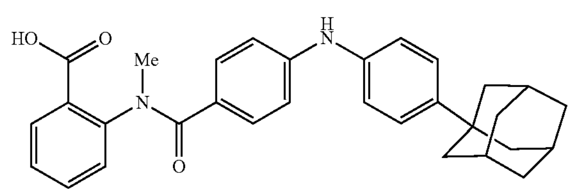 [SMILES: CN(C(=O)c1ccc(Nc2ccc(C34CC5CC(CC(C5)C3)C4)cc2)cc1)c1ccccc1C(=O)O] | 61 |
| 341 | 222 | 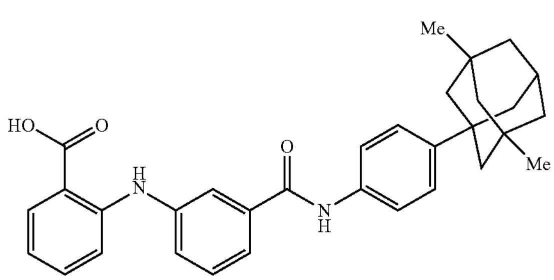 [SMILES: CC12CC3CC(C)(C1)CC(c1ccc(NC(=O)c4cccc(Nc5ccccc5C(=O)O)c4)cc1)(C3)C2] | 45 |

TABLE 2-continued
Activity of Compounds as TEAD2 Palmitoylation Inhibitors
| CP | Cmpd. No | Structure | % of inhibition of TEAD2 palmitoylation at 10 μM or IC$_{50}$ μM |
|---|---|---|---|
| 342 | 223 | 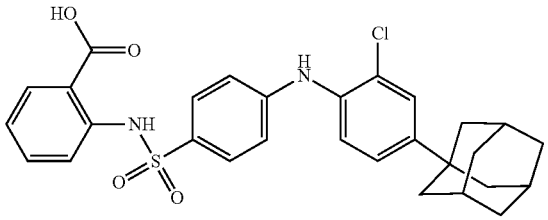 [SMILES: O=C(O)c1ccccc1NS(=O)(=O)c1ccc(Nc2ccc(C34CC5CC(CC(C5)C3)C4)cc2Cl)cc1] | 100 |
| 343 | 224 | 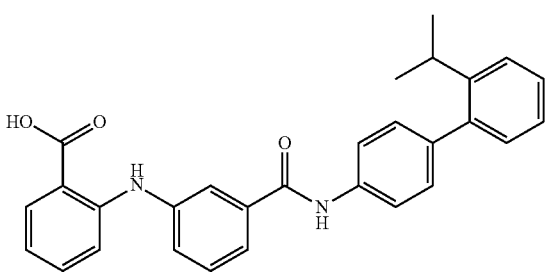 | 81 |
| 344 | 225 | 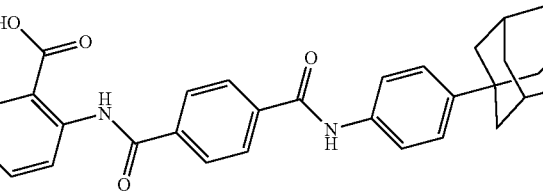 | 84 |
| 345 | 226 | 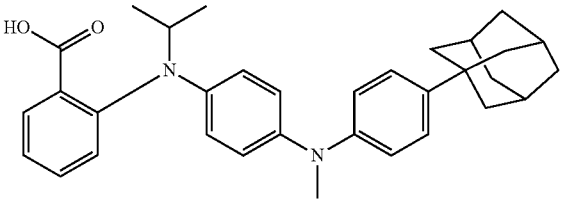 [SMILES: CC(C)N(c1ccc(N(C)c2ccc(C34CC5CC(CC(C5)C3)C4)cc2)cc1)c1ccccc1C(=O)O] | 17 |
| 346 | 227 | 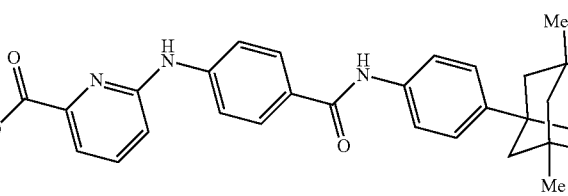 | 58 |
| 349 | 228 | 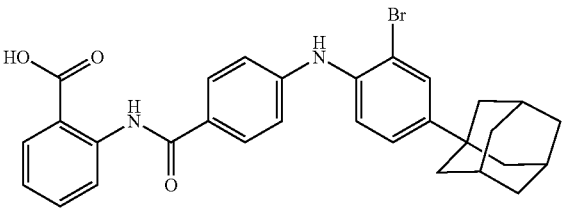 | 89 |

TABLE 2-continued
Activity of Compounds as TEAD2 Palmitoylation Inhibitors
| CP | Cmpd. No | Structure | % of inhibition of TEAD2 palmitoylation at 10 μM or IC$_{50}$ μM |
|---|---|---|---|
| 350 | 229 | 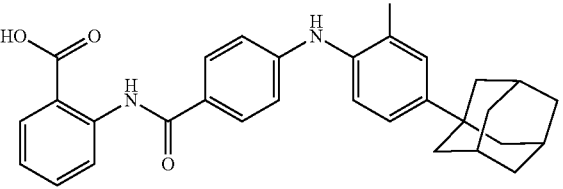 | 91 |
| 353 | 230 | 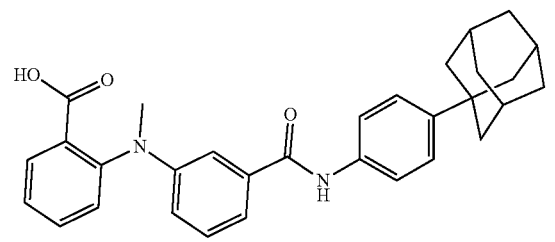 [SMILES: CN(c1cccc(C(=O)Nc2ccc(C34CC5CC(CC(C5)C3)C4)cc2)c1)c1ccccc1C(=O)O] | 0 |
| 355 | 231 | 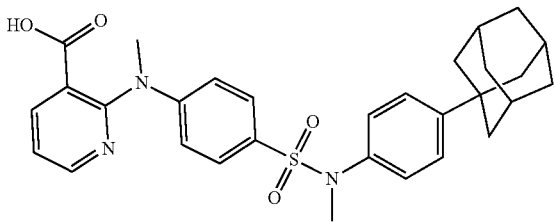 [SMILES: CN(c1ccc(S(=O)(=O)N(C)c2ccc(C34CC5CC(CC(C5)C3)C4)cc2)cc1)c1ncccc1C(=O)O] | 0 |
| 356 | 232 | 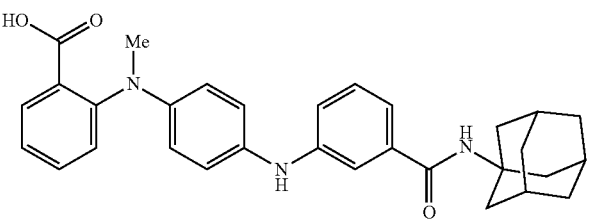 | 33 |
| 357 | 233 | 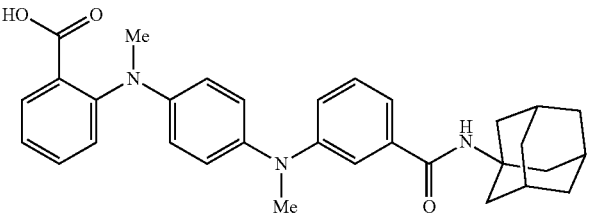 [SMILES: CN(c1ccc(N(C)c2ccccc2C(=O)O)cc1)c1cccc(C(=O)NC23CC4CC(CC(C4)C2)C3)c1] | 9 |
| 358 | 234 | 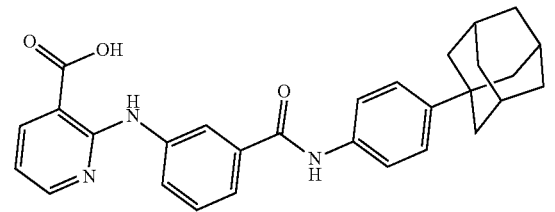 [SMILES: O=C(Nc1ccc(C23CC4CC(CC(C4)C2)C3)cc1)c1cccc(Nc2ncccc2C(=O)O)c1] | 64 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 359 | 235 | 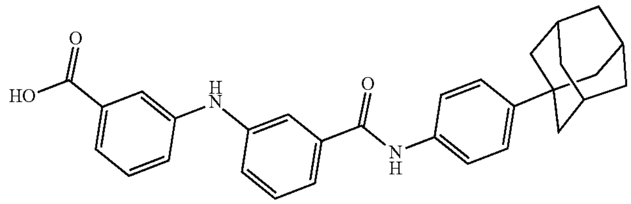 [SMILES: O=C(O)c1cccc(Nc2cccc(C(=O)Nc3ccc(C45CC6CC(CC(C6)C4)C5)cc3)c2)c1] | 84 |
| 360 | 236 | 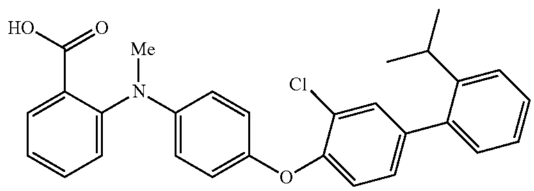 [SMILES: CC(C)c1ccccc1-c1ccc(Oc2ccc(N(C)c3ccccc3C(=O)O)cc2)c(Cl)c1] | 62 |
| 361 | 237 | 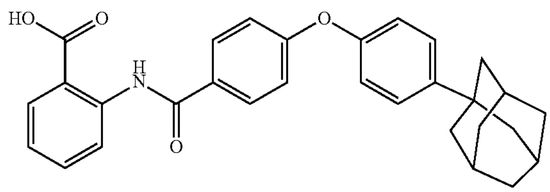 [SMILES: O=C(Nc1ccccc1C(=O)O)c1ccc(Oc2ccc(C34CC5CC(CC(C5)C3)C4)cc2)cc1] | 93 |
| 362 | 238 | 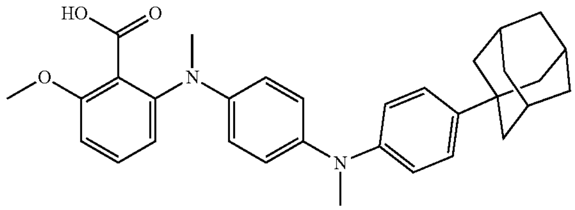 [SMILES: COc1cccc(N(C)c2ccc(N(C)c3ccc(C45CC6CC(CC(C6)C4)C5)cc3)cc2)c1C(=O)O] | 100 |
| 363 | 239 | 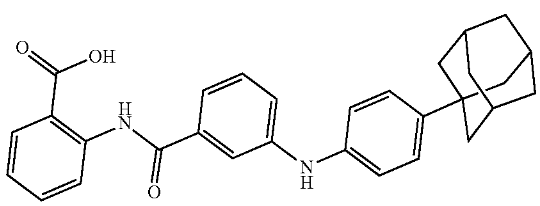 [SMILES: O=C(Nc1ccccc1C(=O)O)c1cccc(Nc2ccc(C34CC5CC(CC(C5)C3)C4)cc2)c1] | 98, 100 |
| 364 | 240 | 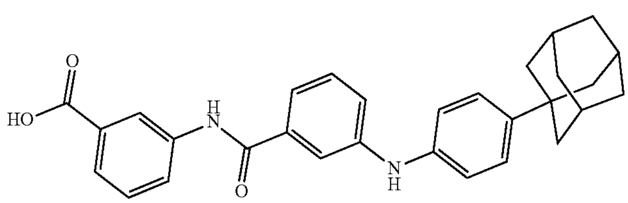 [SMILES: O=C(O)c1cccc(NC(=O)c2cccc(Nc3ccc(C45CC6CC(CC(C6)C4)C5)cc3)c2)c1] | 62 |
| 366 | 241 | 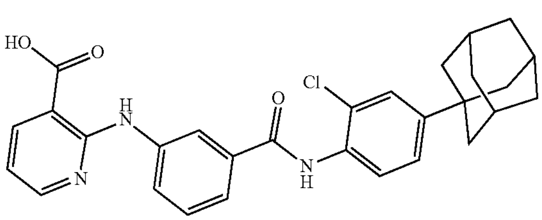 [SMILES: O=C(Nc1ccc(C23CC4CC(CC(C4)C2)C3)cc1Cl)c1cccc(Nc2ncccc2C(=O)O)c1] | 100 |

TABLE 2-continued
Activity of Compounds as TEAD2 Palmitoylation Inhibitors
| CP | Cmpd. No | Structure | % of inhibition of TEAD2 palmitoylation at 10 μM or IC$_{50}$ μM |
|---|---|---|---|
| 367 | 242 | 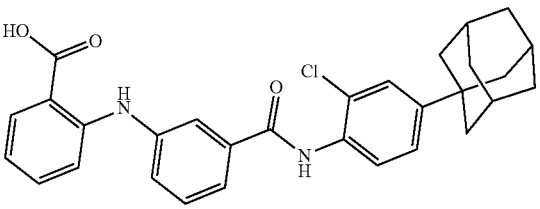 [SMILES: O=C(Nc1ccc(C23CC4CC(CC(C4)C2)C3)cc1Cl)c1cccc(Nc2ccccc2C(=O)O)c1] | 35, 58 |
| 369 | 243 | 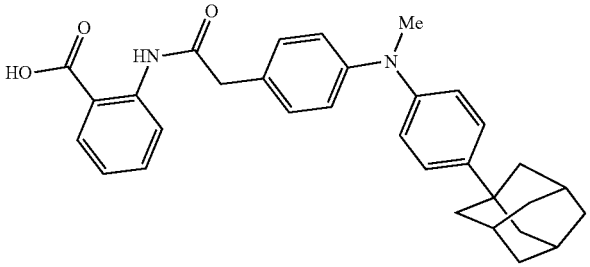 [SMILES: CN(c1ccc(CC(=O)Nc2ccccc2C(=O)O)cc1)c1ccc(C23CC4CC(CC(C4)C2)C3)cc1] | 67 |
| 370 | 244 | 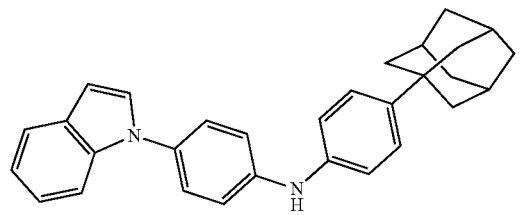 [SMILES: c1ccc2c(c1)ccn2-c1ccc(Nc2ccc(C34CC5CC(CC(C5)C3)C4)cc2)cc1] | 8 |
| 371 | 245 | 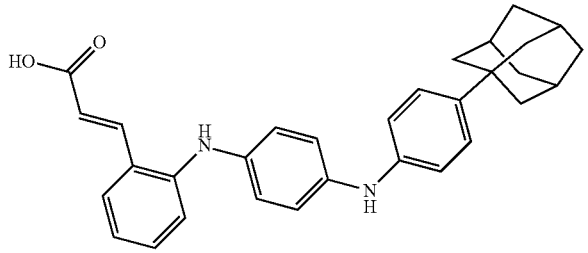 [SMILES: O=C(O)/C=C/c1ccccc1Nc1ccc(Nc2ccc(C34CC5CC(CC(C5)C3)C4)cc2)cc1] | 87 |
| 372 | 246 | 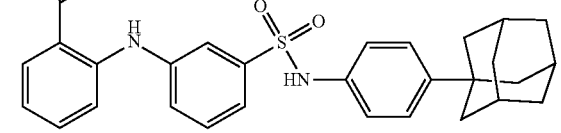 | 99 |
| 373 | 247 | 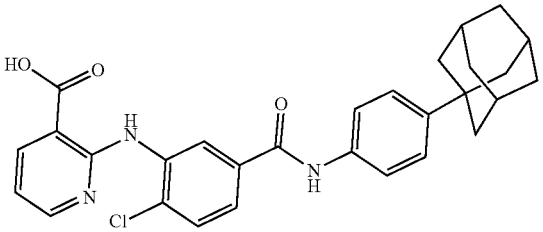 [SMILES: O=C(Nc1ccc(C23CC4CC(CC(C4)C2)C3)cc1)c1ccc(Cl)c(Nc2ncccc2C(=O)O)c1] | 95 |

TABLE 2-continued
Activity of Compounds as TEAD2 Palmitoylation Inhibitors
| CP | Cmpd. No | Structure | % of inhibition of TEAD2 palmitoylation at 10 μM or IC$_{50}$ μM |
|---|---|---|---|
| 376 | 248 | 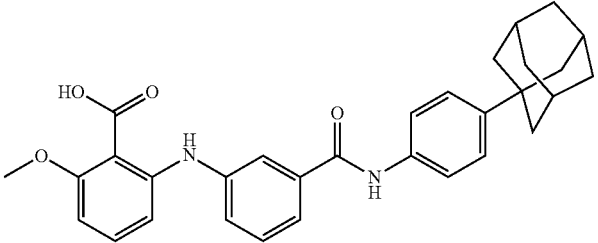 [SMILES: COc1cccc(Nc2cccc(C(=O)Nc3ccc(C45CC6CC(CC(C6)C4)C5)cc3)c2)c1C(=O)O] | 32 |
| 377 | 249 | 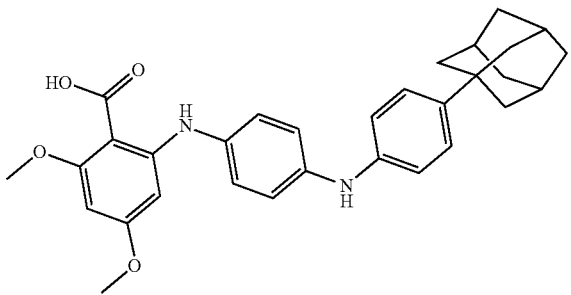 [SMILES: COc1cc(Nc2ccc(Nc3ccc(C45CC6CC(CC(C6)C4)C5)cc3)cc2)c(C(=O)O)c(OC)c1] | 1 |
| 379 | 250 | 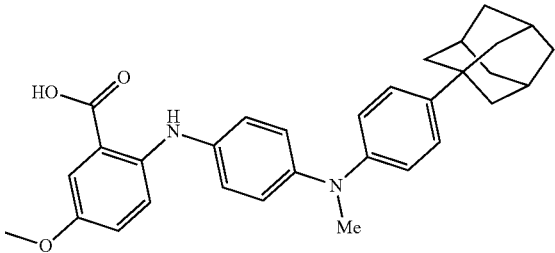 [SMILES: COc1ccc(Nc2ccc(N(C)c3ccc(C45CC6CC(CC(C6)C4)C5)cc3)cc2)c(C(=O)O)c1] | 89, 0.274 μM |
| 380 | 251 | 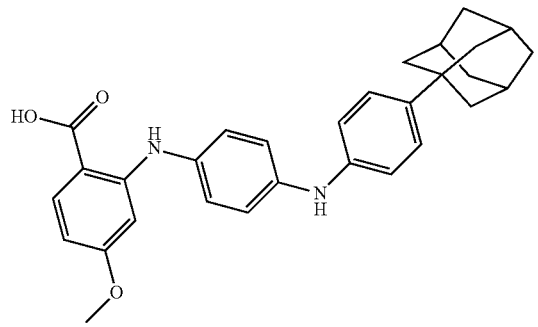 [SMILES: COc1ccc(C(=O)O)c(Nc2ccc(Nc3ccc(C45CC6CC(CC(C6)C4)C5)cc3)cc2)c1] | 27 |
| 382 | 252 | 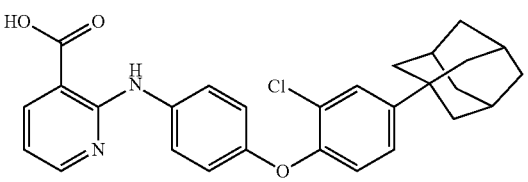 [SMILES: O=C(O)c1cccnc1Nc1ccc(Oc2ccc(C34CC5CC(CC(C5)C3)C4)cc2Cl)cc1] | 100, 0.053 μM |
| 383 | 253 | 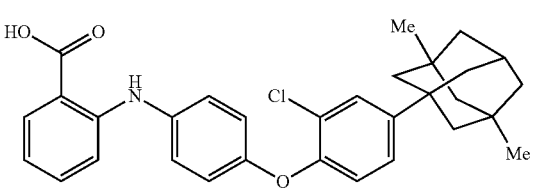 | 100, 0.099 μM |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 384 | 254 | 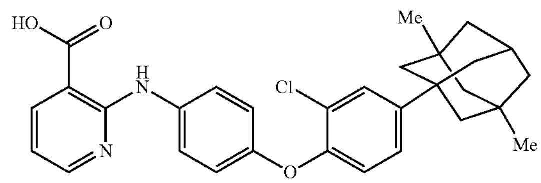 [SMILES: CC12CC3CC(C)(C1)CC(c1ccc(Oc4ccc(Nc5ncccc5C(=O)O)cc4)c(Cl)c1)(C3)C2] | 100, 0.297 μM |
| 385 | 255 | 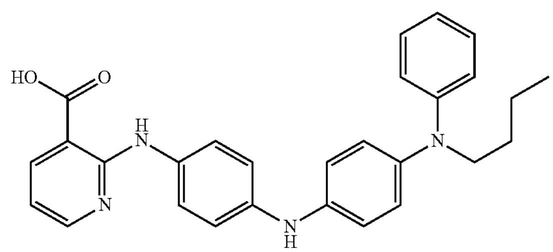 [SMILES: CCCCN(c1ccccc1)c1ccc(Nc2ccc(Nc3ncccc3C(=O)O)cc2)cc1] | 50 |
| 386 | 256 | 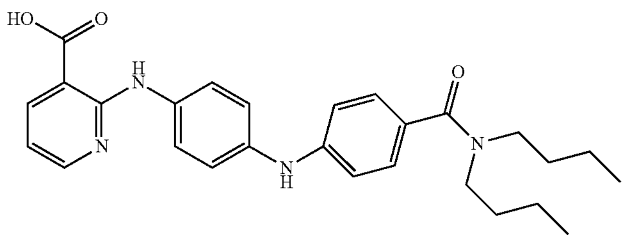 [SMILES: CCCCN(CCCC)C(=O)c1ccc(Nc2ccc(Nc3ncccc3C(=O)O)cc2)cc1] | 46 |
| 387 | 257 | 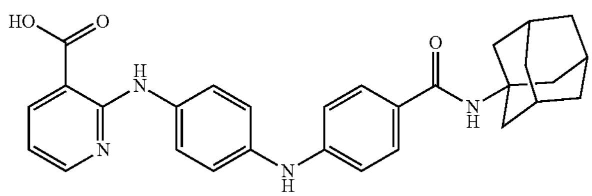 [SMILES: O=C(NC12CC3CC(CC(C3)C1)C2)c1ccc(Nc2ccc(Nc3ncccc3C(=O)O)cc2)cc1] | 55 |
| 388 | 258 | 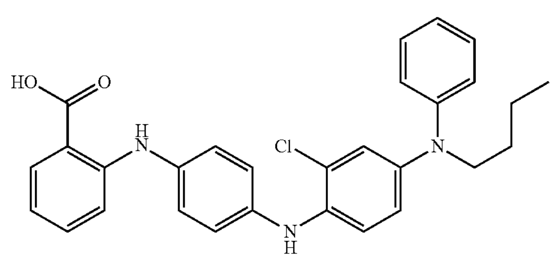 [SMILES: CCCCN(c1ccccc1)c1ccc(Nc2ccc(Nc3ccccc3C(=O)O)cc2)c(Cl)c1] | 0 |
| 389 | 259 | 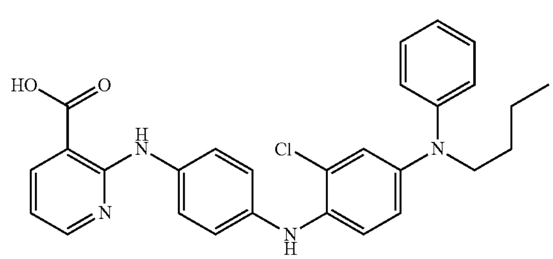 [SMILES: CCCCN(c1ccccc1)c1ccc(Nc2ccc(Nc3ncccc3C(=O)O)cc2)c(Cl)c1] | 83 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 392 | 260 | 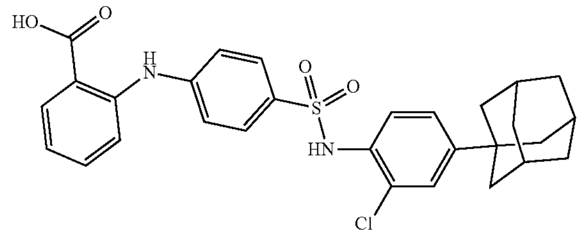 [SMILES: O=C(O)c1ccccc1Nc1ccc(S(=O)(=O)Nc2ccc(C34CC5CC(CC(C5)C3)C4)cc2Cl)cc1] | 71 |
| 393 | 261 | 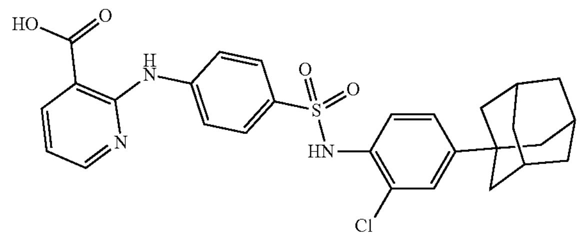 [SMILES: O=C(O)c1cccnc1Nc1ccc(S(=O)(=O)Nc2ccc(C34CC5CC(CC(C5)C3)C4)cc2Cl)cc1] | 98 |
| 394 | 262 | 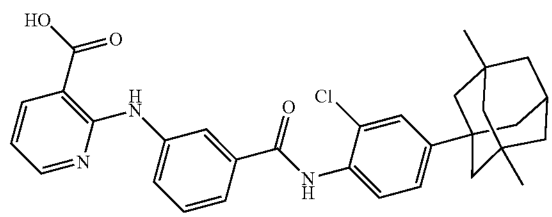 [SMILES: CC12CC3CC(C)(C1)CC(c1ccc(NC(=O)c4cccc(Nc5ncccc5C(=O)O)c4)c(Cl)c1)(C3)C2] | 85 |
| 395 | 263 | 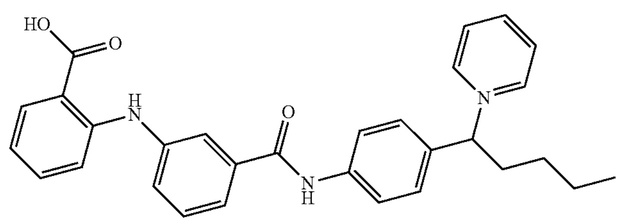 | 59 |
| 396 | 264 | 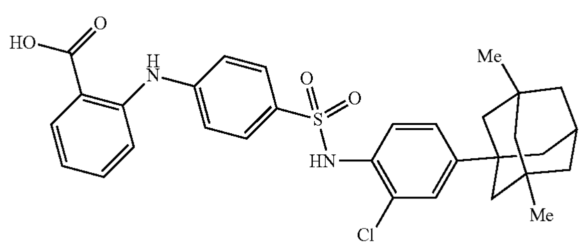 [SMILES: CC12CC3CC(C)(C1)CC(c1ccc(NS(=O)(=O)c4ccc(Nc5ccccc5C(=O)O)cc4)c(Cl)c1)(C3)C2] | 0 |
| 397 | 265 | 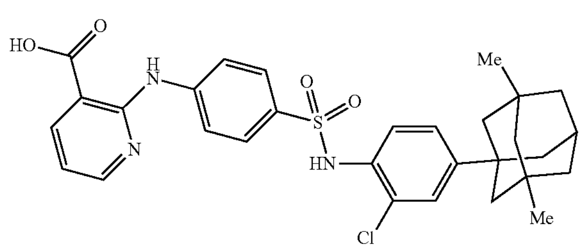 [SMILES: CC12CC3CC(C)(C1)CC(c1ccc(NS(=O)(=O)c4ccc(Nc5ncccc5C(=O)O)cc4)c(Cl)c1)(C3)C2] | 78 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 398 | 266 | 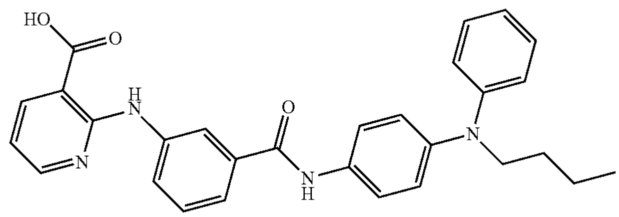 [SMILES: CCCCN(c1ccccc1)c1ccc(NC(=O)c2cccc(Nc3ncccc3C(=O)O)c2)cc1] | 81 |
| 407 | 267 | 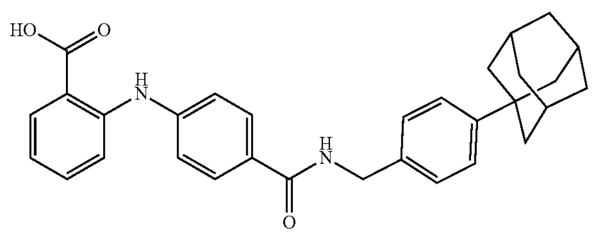 [SMILES: O=C(NCc1ccc(C23CC4CC(CC(C4)C2)C3)cc1)c1ccc(Nc2ccccc2C(=O)O)cc1] | 36 |
| 408 | 268 | 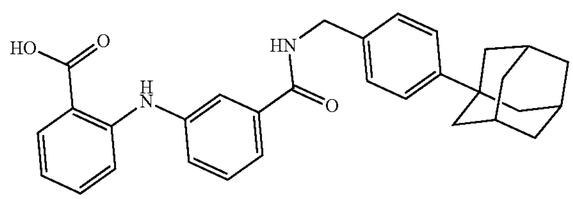 [SMILES: O=C(NCc1ccc(C23CC4CC(CC(C4)C2)C3)cc1)c1cccc(Nc2ccccc2C(=O)O)c1] | 10 |
| 420 | 269 | 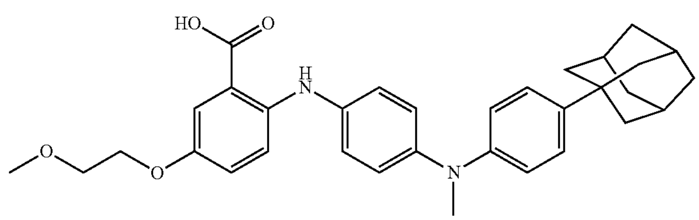 [SMILES: COCCOc1ccc(Nc2ccc(N(C)c3ccc(C45CC6CC(CC(C6)C4)C5)cc3)cc2)c(C(=O)O)c1] | 100 |
| 72 | 270 | 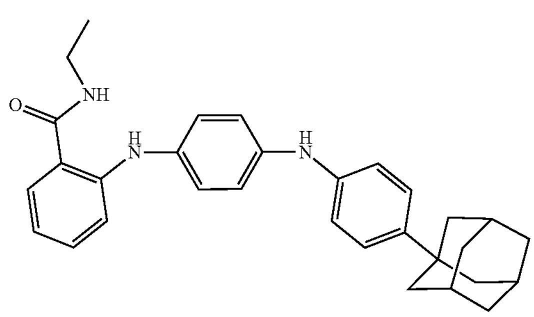 [SMILES: CCNC(=O)c1ccccc1Nc1ccc(Nc2ccc(C34CC5CC(CC(C5)C3)C4)cc2)cc1] | 23 |
| 94 | 271 | 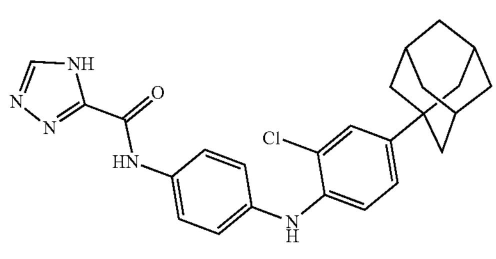 [SMILES: O=C(Nc1ccc(Nc2ccc(C34CC5CC(CC(C5)C3)C4)cc2Cl)cc1)c1nnc[nH]1] | NA |

TABLE 2-continued

Activity of Compounds as TEAD2 Palmitoylation Inhibitors

| CP | Cmpd. No | Structure | % of inhibition of TEAD2 palmitoylation at 10 µM or IC$_{50}$ µM |
|---|---|---|---|
| 111 | 272 | 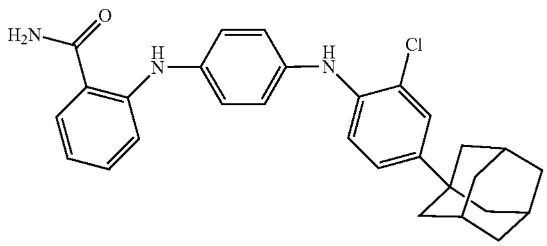 [SMILES: NC(=O)c1ccccc1Nc1ccc(Nc2ccc(C34CC5CC(CC(C5)C3)C4)cc2Cl)cc1] | 77 |
| 112 | 273 | 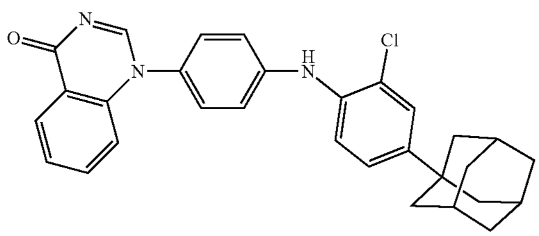 [SMILES: O=c1ncn(-c2ccc(Nc3ccc(C45CC6CC(CC(C6)C4)C5)cc3Cl)cc2)c2ccccc12] | 50 |
| 120 | 274 | 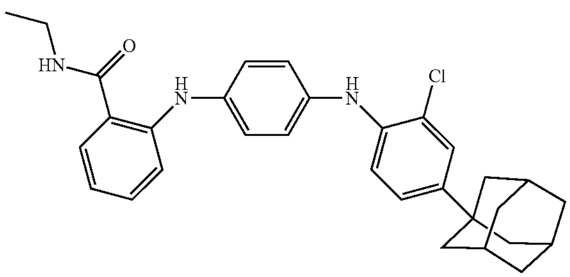 [SMILES: CCNC(=O)c1ccccc1Nc1ccc(Nc2ccc(C34CC5CC(CC(C5)C3)C4)cc2Cl)cc1] | 50 |
| 123 | 275 | 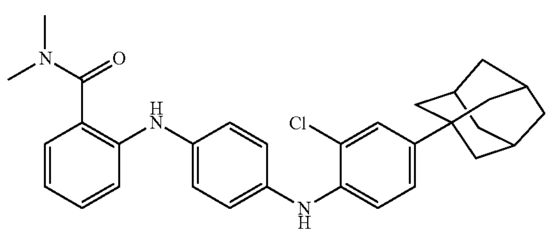 [SMILES: CN(C)C(=O)c1ccccc1Nc1ccc(Nc2ccc(C34CC5CC(CC(C5)C3)C4)cc2Cl)cc1] | 76 |
| 164 | 276 | 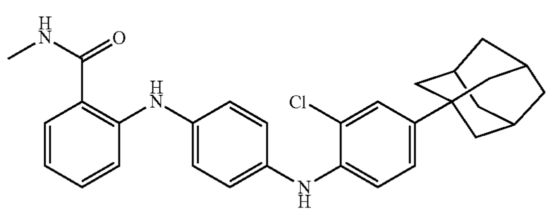 [SMILES: CNC(=O)c1ccccc1Nc1ccc(Nc2ccc(C34CC5CC(CC(C5)C3)C4)cc2Cl)cc1] | 52 |
| 208 | 277 | 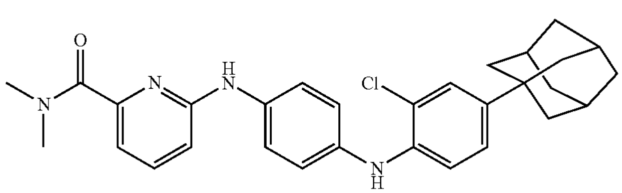 [SMILES: CN(C)C(=O)c1cccc(Nc2ccc(Nc3ccc(C45CC6CC(CC(C6)C4)C5)cc3Cl)cc2)n1] | 0 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 209 | 278 | 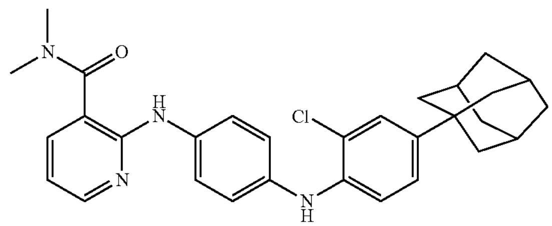 [SMILES: CN(C)C(=O)c1cccnc1Nc1ccc(Nc2ccc(C34CC5CC(CC(C5)C3)C4)cc2Cl)cc1] | 28 |
| 605 | 429 | 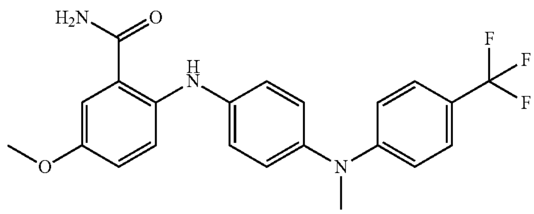 [SMILES: COc1ccc(Nc2ccc(N(C)c3ccc(C(F)(F)F)cc3)cc2)c(C(N)=O)c1] | 47 |
| 606 | 430 | 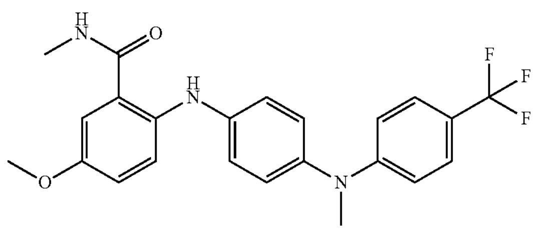 [SMILES: CNC(=O)c1cc(OC)ccc1Nc1ccc(N(C)c2ccc(C(F)(F)F)cc2)cc1] | 63 |
| 607 | 431 | 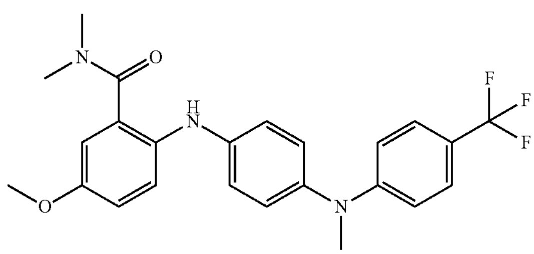 [SMILES: COc1ccc(Nc2ccc(N(C)c3ccc(C(F)(F)F)cc3)cc2)c(C(=O)N(C)C)c1] | 37 |
| 653 | 432 | 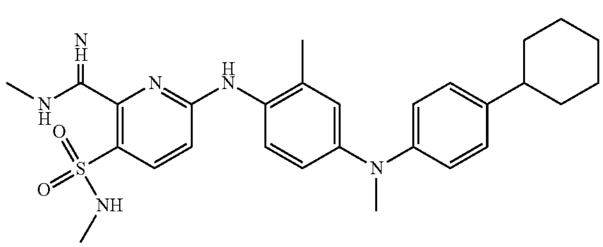 | 24 |
| 109 | 279 | 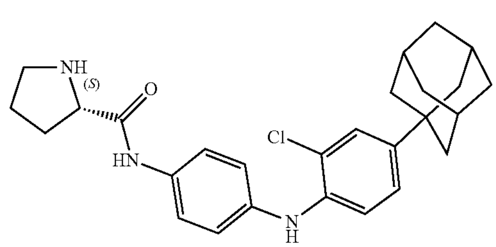 | NA |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 230 | 280 | 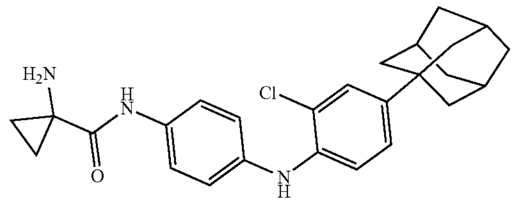 [SMILES: NC1(C(=O)Nc2ccc(Nc3ccc(C45CC6CC(CC(C6)C4)C5)cc3Cl)cc2)CC1] | 0 |
| 152 | 281 | 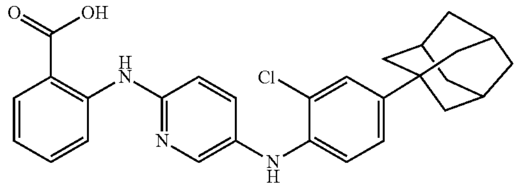 | 98 |
| 155 | 282 | 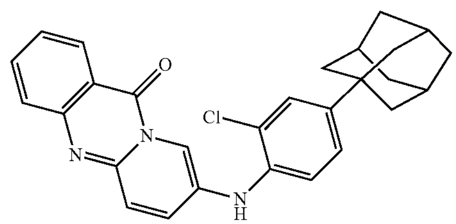 [SMILES: O=c1c2ccccc2nc2ccc(Nc3ccc(C45CC6CC(CC(C6)C4)C5)cc3Cl)cn12] | 14 |
| 153 | 283 | 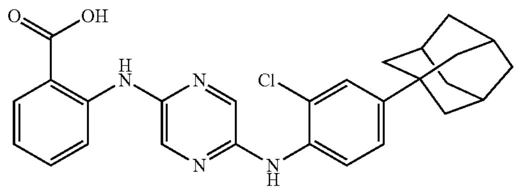 [SMILES: O=C(O)c1ccccc1Nc1cnc(Nc2ccc(C34CC5CC(CC(C5)C3)C4)cc2Cl)cn1] | 89, 0.064 μM |
| 154 | 284 | 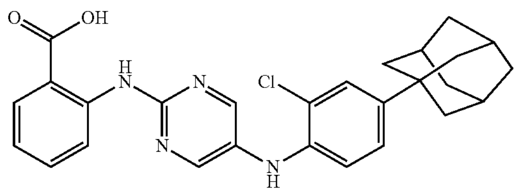 [SMILES: O=C(O)c1ccccc1Nc1ncc(Nc2ccc(C34CC5CC(CC(C5)C3)C4)cc2Cl)cn1] | 97 |
| 175 | 285 | 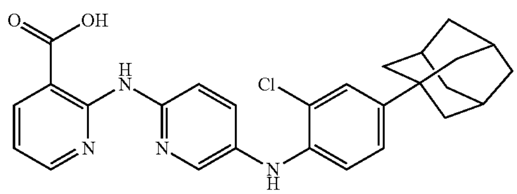 | 9 |
| 540 | 440 | 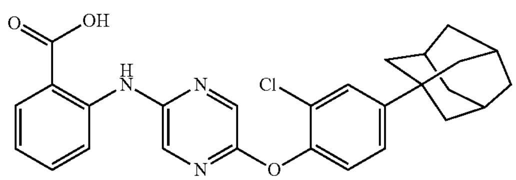 [SMILES: O=C(O)c1ccccc1Nc1cnc(Oc2ccc(C34CC5CC(CC(C5)C3)C4)cc2Cl)cn1] | 75 |

TABLE 2-continued
Activity of Compounds as TEAD2 Palmitoylation Inhibitors
| CP | Cmpd. No | Structure | % of inhibition of TEAD2 palmitoylation at 10 μM or IC$_{50}$ μM |
|---|---|---|---|
| 559 | 441 | 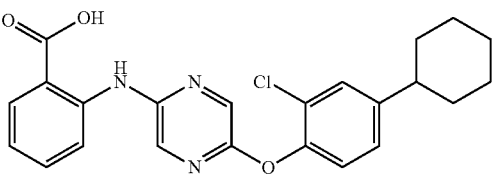 | 79 |
| 119 | 286 | 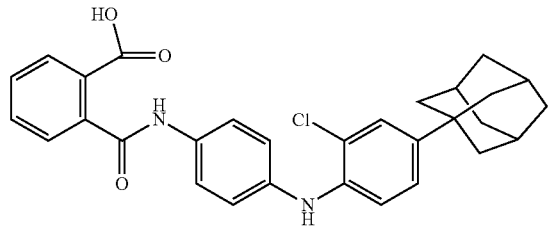 [SMILES: O=C(O)c1ccccc1C(=O)Nc1ccc(Nc2ccc(C34CC5CC(CC(C5)C3)C4)cc2Cl)cc1] | 98 |
| 90 | 287 | 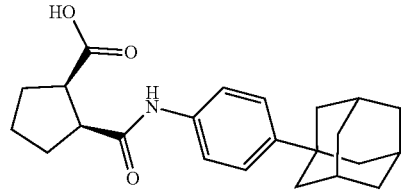 [SMILES: O=C(Nc1ccc(C23CC4CC(CC(C4)C2)C3)cc1)[C@H]1CCC[C@H]1C(=O)O] | 17 |
| 96 | 288 | 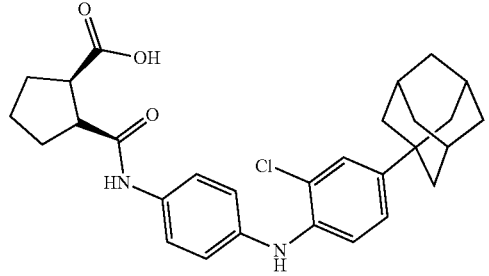 | NA |
| 105 | 289 | 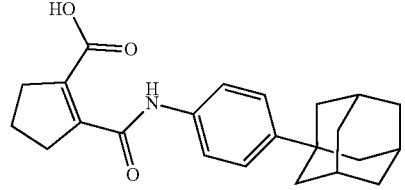 [SMILES: O=C(O)C1=C(C(=O)Nc2ccc(C34CC5CC(CC(C5)C3)C4)cc2)CCC1] | NA |
| 110 | 290 | 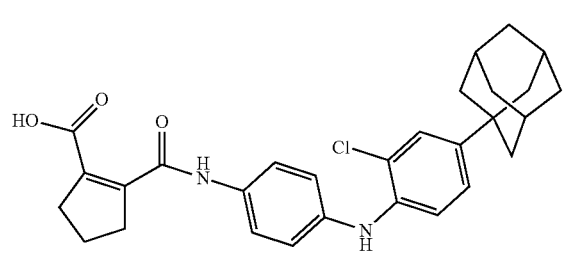 [SMILES: O=C(O)C1=C(C(=O)Nc2ccc(Nc3ccc(C45CC6CC(CC(C6)C4)C5)cc3Cl)cc2)CCC1] | 99 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 132 | 291 | 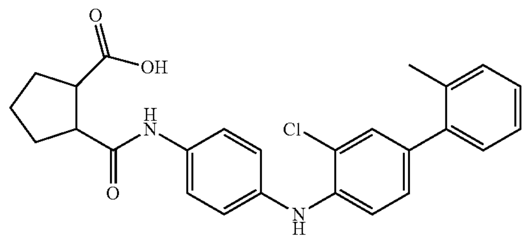 [SMILES: Cc1ccccc1-c1ccc(Nc2ccc(NC(=O)C3CCCC3C(=O)O)cc2)c(Cl)c1] | 14 |
| 133 | 292 | 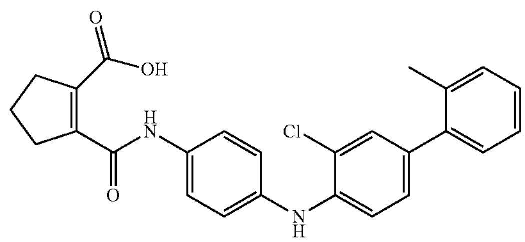 | 67 |
| 176 | 293 | 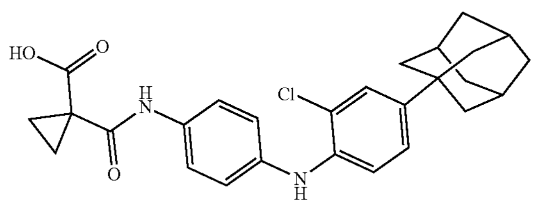 [SMILES: O=C(O)C1(C(=O)Nc2ccc(Nc3ccc(C45CC6CC(CC(C6)C4)C5)cc3Cl)cc2)CC1] | 86 |
| 216 | 294 | 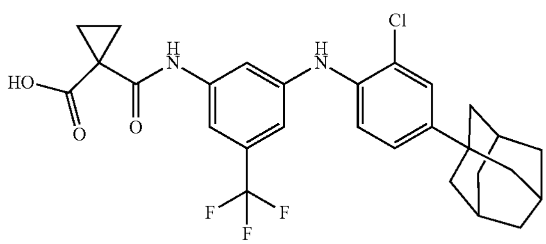 [SMILES: O=C(O)C1(C(=O)Nc2cc(Nc3ccc(C45CC6CC(CC(C6)C4)C5)cc3Cl)cc(C(F)(F)F)c2)CC1] | 96 |
| 229 | 295 | 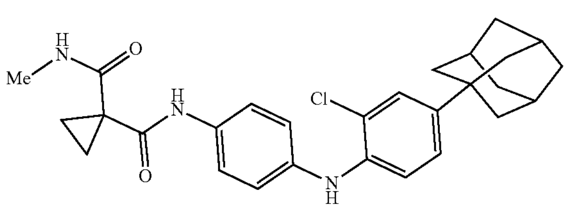 [SMILES: CNC(=O)C1(C(=O)Nc2ccc(Nc3ccc(C45CC6CC(CC(C6)C4)C5)cc3Cl)cc2)CC1] | 53 |
| 237 | 296 | 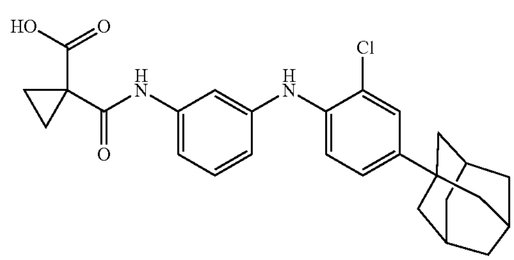 [SMILES: O=C(O)C1(C(=O)Nc2cccc(Nc3ccc(C45CC6CC(CC(C6)C4)C5)cc3Cl)c2)CC1] | 88 |

TABLE 2-continued

Activity of Compounds as TEAD2 Palmitoylation Inhibitors

| CP | Cmpd. No | Structure | % of inhibition of TEAD2 palmitoylation at 10 μM or IC$_{50}$ μM |
|---|---|---|---|
| 239 | 297 | 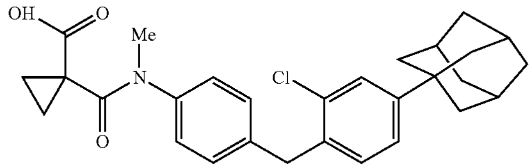 [SMILES: CN(C(=O)C1(C(=O)O)CC1)c1ccc(Cc2ccc(C34CC5CC(CC(C5)C3)C4)cc2Cl)cc1] | 69 |
| 348 | 298 | 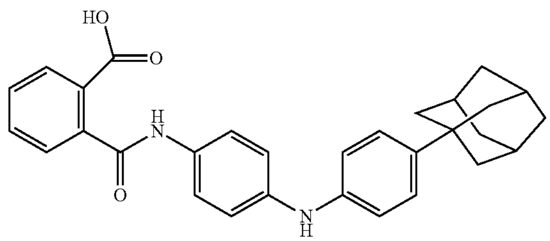 [SMILES: O=C(O)c1ccccc1C(=O)Nc1ccc(Nc2ccc(C34CC5CC(CC(C5)C3)C4)cc2)cc1] | 100 |
| 378 | 299 | 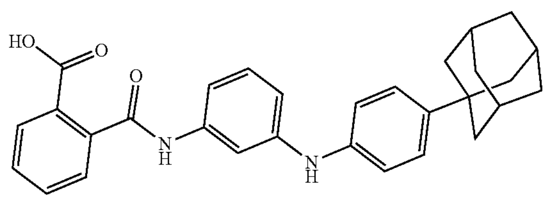 [SMILES: O=C(O)c1ccccc1C(=O)Nc1cccc(Nc2ccc(C34CC5CC(CC(C5)C3)C4)cc2)c1] | 97 |
| 453 | | 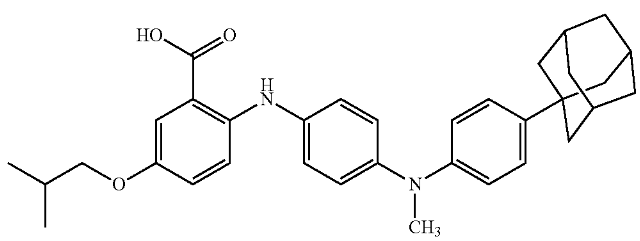 [SMILES: CC(C)COc1ccc(Nc2ccc(N(C)c3ccc(C45CC6CC(CC(C6)C4)C5)cc3)cc2)c(C(=O)O)c1] | 0 |

TABLE 3

Activity of Compounds as TEAD2 Palmitoylation Inhibitors

| CP | Structure | % of inhibition of TEAD2 palmitoylation at 10 μM | TEAD2 palmitoylation IC50 |
|---|---|---|---|
| CP-472 | 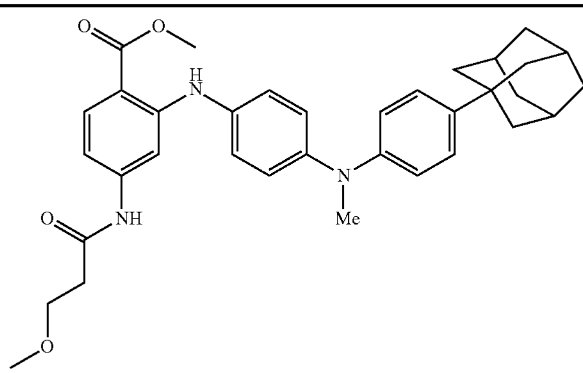 | 1 | |

TABLE 3-continued
Activity of Compounds as TEAD2 Palmitoylation Inhibitors
| CP | Structure | % of inhibition of TEAD2 palmitoylation at 10 μM | TEAD2 palmitoylation IC50 |
|---|---|---|---|
| CP-473 | 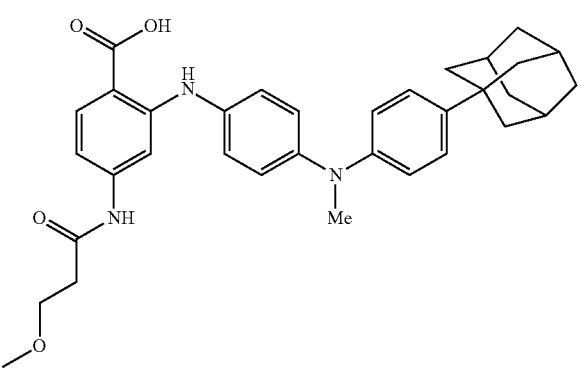 [SMILES: COCCC(=O)Nc1ccc(C(=O)O)c(Nc2ccc(N(C)c3ccc(C45CC6CC(CC(C6)C4)C5)cc3)cc2)c1] | 50 | |
| CP-516 | 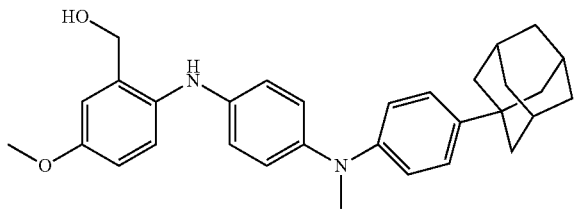 [SMILES: COc1ccc(Nc2ccc(N(C)c3ccc(C45CC6CC(CC(C6)C4)C5)cc3)cc2)c(CO)c1] | 20 | |
| CP-521 | 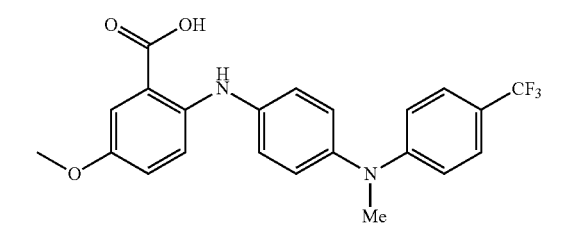 [SMILES: COc1ccc(Nc2ccc(N(C)c3ccc(C(F)(F)F)cc3)cc2)c(C(=O)O)c1] | 93 | 1.45 |
| CP-522 | 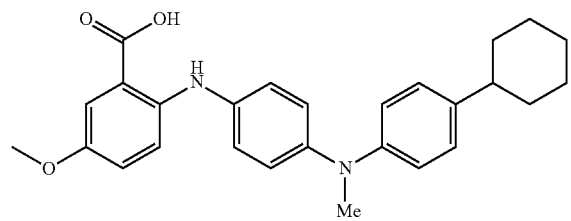 [SMILES: COc1ccc(Nc2ccc(N(C)c3ccc(C4CCCCC4)cc3)cc2)c(C(=O)O)c1] | 96 | 1.53 |
| CP-525 | 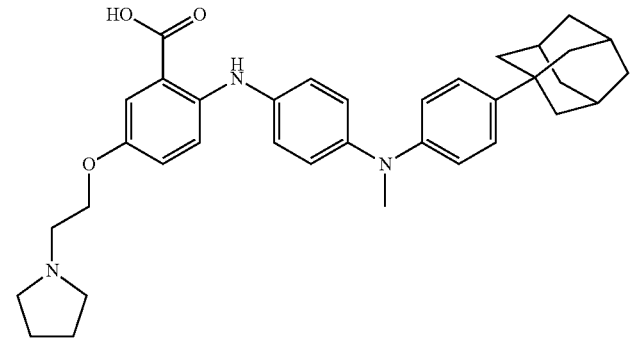 [SMILES: CN(c1ccc(Nc2ccc(OCCN3CCCC3)cc2C(=O)O)cc1)c1ccc(C23CC4CC(CC(C4)C2)C3)cc1] | PPT | |

TABLE 3-continued

Activity of Compounds as TEAD2 Palmitoylation Inhibitors

| CP | Structure | % of inhibition of TEAD2 palmitoylation at 10 μM | TEAD2 palmitoylation IC50 |
|---|---|---|---|
| CP-526 | 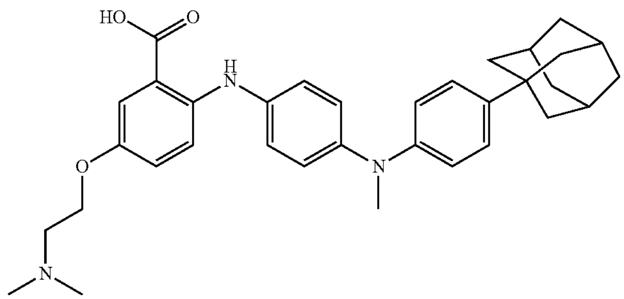 [SMILES: CN(C)CCOc1ccc(Nc2ccc(N(C)c3ccc(C45CC6CC(CC(C6)C4)C5)cc3)cc2)c(C(=O)O)c1] | 23 | |
| CP-528 | 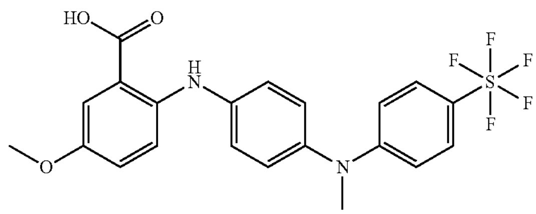 [SMILES: COc1ccc(Nc2ccc(N(C)c3ccc(S(F)(F)(F)(F)F)cc3)cc2)c(C(=O)O)c1] | 76 | 0.38 |
| CP-529 | 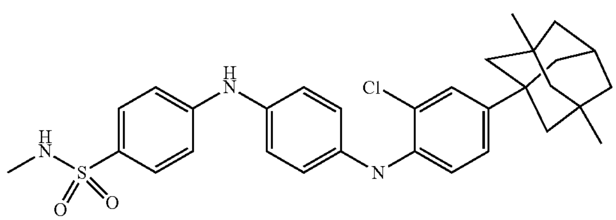 [SMILES: CNS(=O)(=O)c1ccc(Nc2ccc(Nc3ccc(C45CC6CC(C)(CC(C)(C6)C4)C5)cc3Cl)cc2)cc1] | 29 | |
| CP-531 | 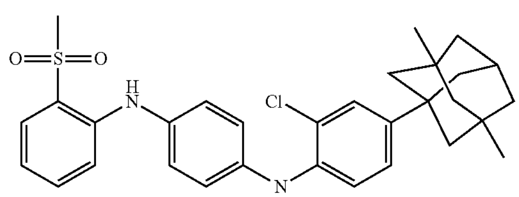 [SMILES: CC12CC3CC(C)(C1)CC(c1ccc(Nc4ccc(Nc5ccccc5S(C)(=O)=O)cc4)c(Cl)c1)(C3)C2] | 20 | |
| CP-534 | 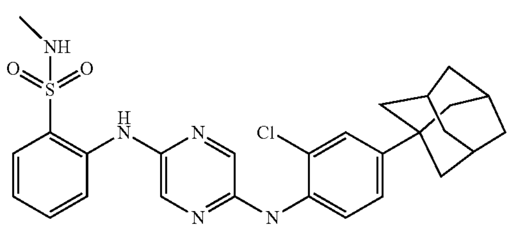 [SMILES: CNS(=O)(=O)c1ccccc1Nc1cnc(Nc2ccc(C34CC5CC(CC(C5)C3)C4)cc2Cl)cn1] | 31 | |
| CP-535 | 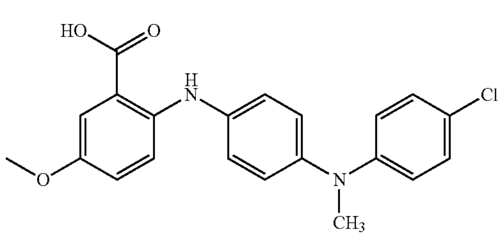 [SMILES: COc1ccc(Nc2ccc(N(C)c3ccc(Cl)cc3)cc2)c(C(=O)O)c1] | 54 | |

TABLE 3-continued
Activity of Compounds as TEAD2 Palmitoylation Inhibitors
| CP | Structure | % of inhibition of TEAD2 palmitoylation at 10 μM | TEAD2 palmitoylation IC50 |
|---|---|---|---|
| CP-536 | 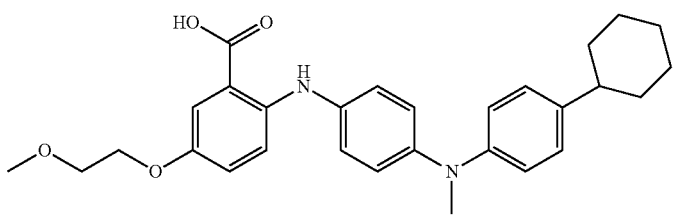 [SMILES: COCCOc1ccc(Nc2ccc(N(C)c3ccc(C4CCCCC4)cc3)cc2)c(C(=O)O)c1] | 84 | |
| CP-537 | 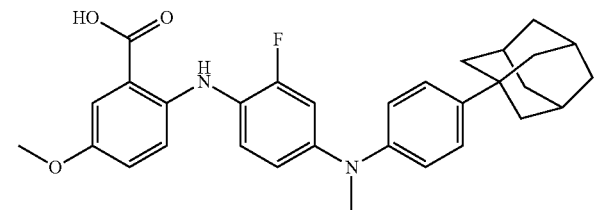 [SMILES: COc1ccc(Nc2ccc(N(C)c3ccc(C45CC6CC(CC(C6)C4)C5)cc3)cc2F)c(C(=O)O)c1] | 73 | |
| CP-538 | 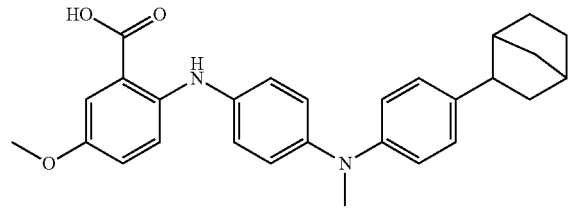 [SMILES: COc1ccc(Nc2ccc(N(C)c3ccc(C4CC5CCC4C5)cc3)cc2)c(C(=O)O)c1] | 85 | 0.68 |
| CP-540 | 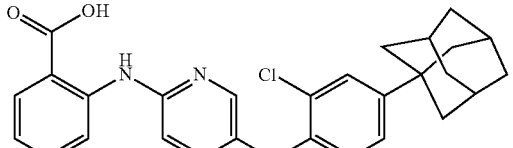 | 75 | |
| CP-541 | 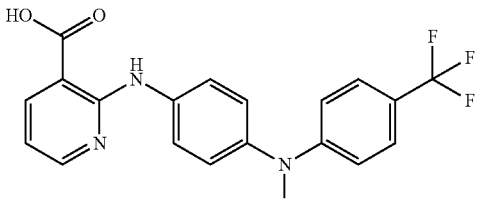 | 80 | |
| CP-542 | 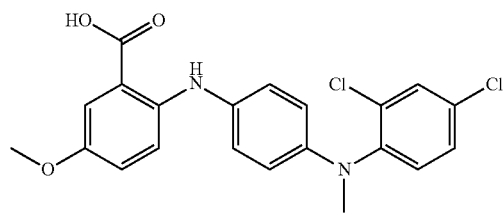 [SMILES: COc1ccc(Nc2ccc(N(C)c3ccc(Cl)cc3Cl)cc2)c(C(=O)O)c1] | 49 | |
| CP-543 | 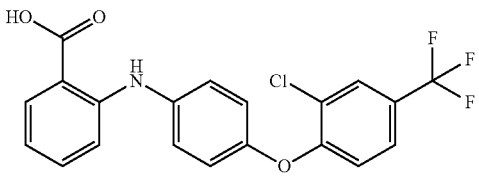 [SMILES: O=C(O)c1ccccc1Nc1ccc(Oc2ccc(C(F)(F)F)cc2Cl)cc1] | 98 | |

TABLE 3-continued

Activity of Compounds as TEAD2 Palmitoylation Inhibitors

| CP | Structure | % of inhibition of TEAD2 palmitoylation at 10 μM | TEAD2 palmitoylation IC50 |
|---|---|---|---|
| CP-544 | 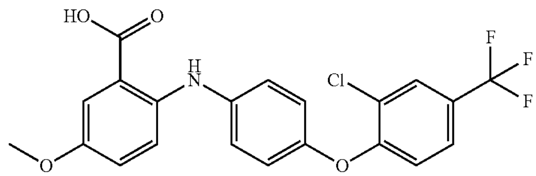 | 98 | |
| CP-545 | 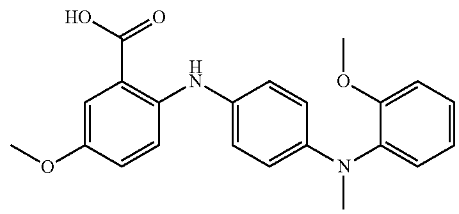 [SMILES: COc1ccc(Nc2ccc(N(C)c3ccccc3OC)cc2)c(C(=O)O)c1] | 6 | |
| CP-546 | 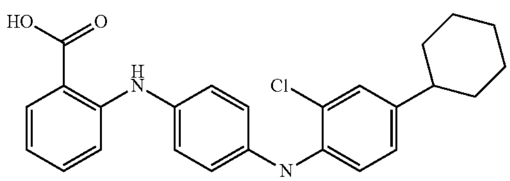 | 97 | |
| CP-547 | 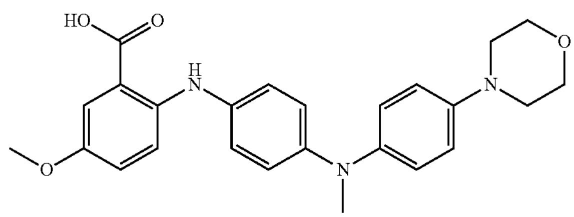 [SMILES: COc1ccc(Nc2ccc(N(C)c3ccc(N4CCOCC4)cc3)cc2)c(C(=O)O)c1] | 18 | |
| CP-548 | 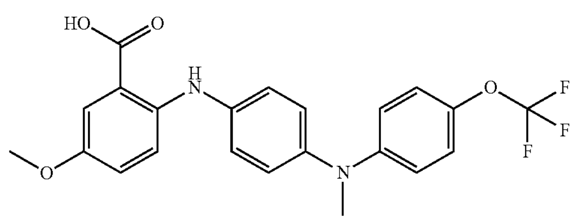 [SMILES: COc1ccc(Nc2ccc(N(C)c3ccc(OC(F)(F)F)cc3)cc2)c(C(=O)O)c1] | 86 | 0.45 |
| CP-549 | 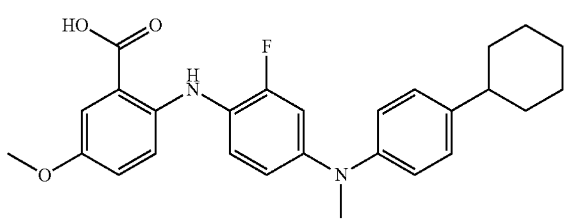 [SMILES: COc1ccc(Nc2ccc(N(C)c3ccc(C4CCCCC4)cc3)cc2F)c(C(=O)O)c1] | 85 | 2.4 |
| CP-550 | 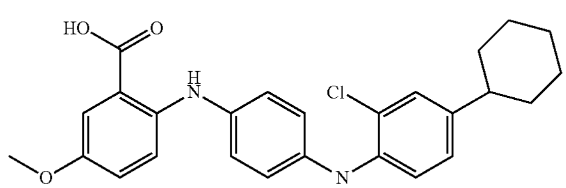 [SMILES: COc1ccc(Nc2ccc(Nc3ccc(C4CCCCC4)cc3Cl)cc2)c(C(=O)O)c1] | 96 | 0.79 |

TABLE 3-continued

Activity of Compounds as TEAD2 Palmitoylation Inhibitors

| CP | Structure | % of inhibition of TEAD2 palmitoylation at 10 μM | TEAD2 palmitoylation IC50 |
|---|---|---|---|
| CP-551 | 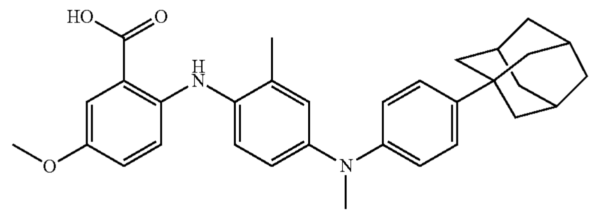 [SMILES: COc1ccc(Nc2ccc(N(C)c3ccc(C45CC6CC(CC(C6)C4)C5)cc3)cc2C)c(C(=O)O)c1] | 91 | 0.002 |
| CP-552 | 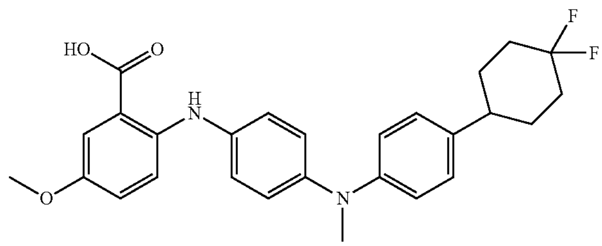 [SMILES: COc1ccc(Nc2ccc(N(C)c3ccc(C4CCC(F)(F)CC4)cc3)cc2)c(C(=O)O)c1] | 74 | |
| CP-553 | 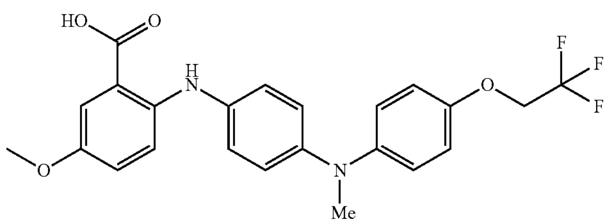 [SMILES: COc1ccc(Nc2ccc(N(C)c3ccc(OCC(F)(F)F)cc3)cc2)c(C(=O)O)c1] | 100 | 0.59 |
| CP-554 | 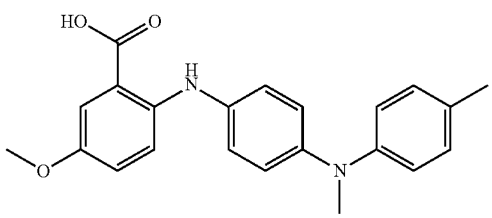 | 96 | 0.01 |
| CP-555 | 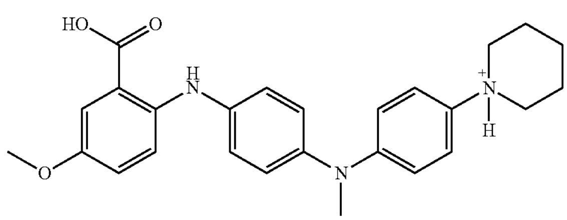 | 100 | 0.01 |
| CP-556 | 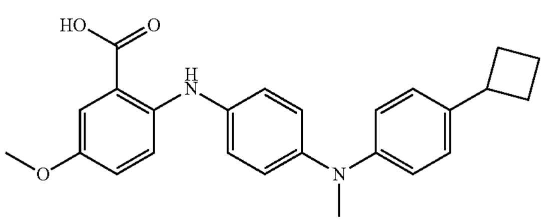 [SMILES: COc1ccc(Nc2ccc(N(C)c3ccc(C4CCC4)cc3)cc2)c(C(=O)O)c1] | 61 | |

TABLE 3-continued

Activity of Compounds as TEAD2 Palmitoylation Inhibitors

| CP | Structure | % of inhibition of TEAD2 palmitoylation at 10 μM | TEAD2 palmitoylation IC50 |
|---|---|---|---|
| CP-557 | 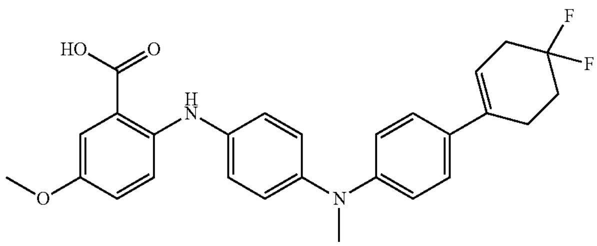 [SMILES: COc1ccc(Nc2ccc(N(C)c3ccc(C4=CCC(F)(F)CC4)cc3)cc2)c(C(=O)O)c1] | 34 | |
| CP-558 | 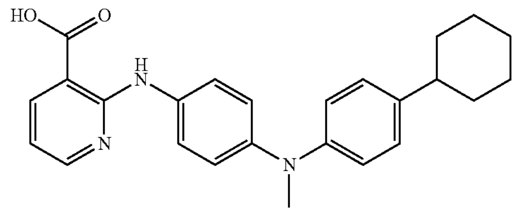 [SMILES: CN(c1ccc(Nc2ncccc2C(=O)O)cc1)c1ccc(C2CCCCC2)cc1] | 66 | |
| CP-559 | 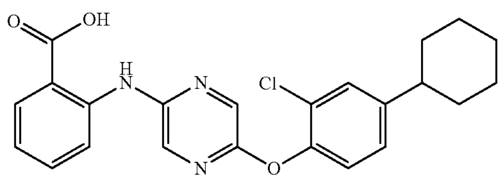 [SMILES: O=C(O)c1ccccc1Nc1cnc(Oc2ccc(C3CCCCC3)cc2Cl)cn1] | 79 | |
| CP-560 | 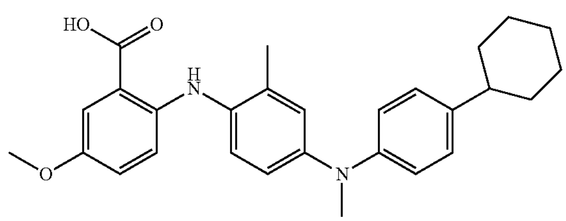 [SMILES: COc1ccc(Nc2ccc(N(C)c3ccc(C4CCCCC4)cc3)cc2C)c(C(=O)O)c1] | 90 | 0.011 |
| CP-561 | 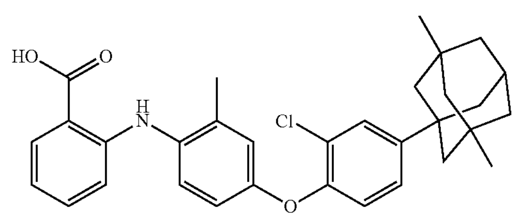 [SMILES: Cc1cc(Oc2ccc(C34CC5CC(C)(CC(C)(C5)C3)C4)cc2Cl)ccc1Nc1ccccc1C(=O)O] | 90 | |
| CP-563 | 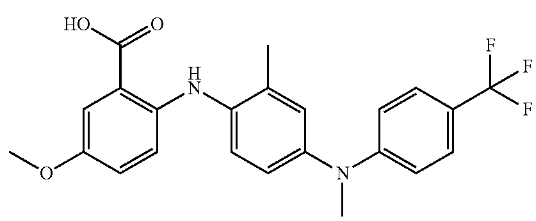 [SMILES: COc1ccc(Nc2ccc(N(C)c3ccc(C(F)(F)F)cc3)cc2C)c(C(=O)O)c1] | 80 | |
| CP-564 | 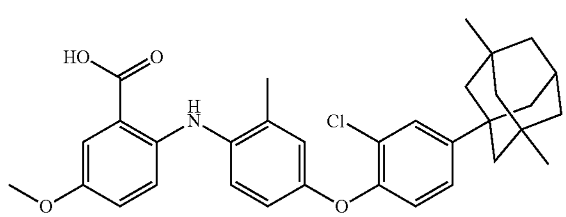 [SMILES: COc1ccc(Nc2ccc(Oc3ccc(C45CC6CC(C)(CC(C)(C6)C4)C5)cc3Cl)cc2C)c(C(=O)O)c1] | 89 | |

TABLE 3-continued

Activity of Compounds as TEAD2 Palmitoylation Inhibitors

| CP | Structure | % of inhibition of TEAD2 palmitoylation at 10 μM | TEAD2 palmitoylation IC50 |
|---|---|---|---|
| CP-565 | 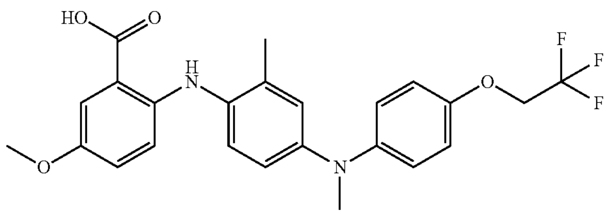 [SMILES: COc1ccc(Nc2ccc(N(C)c3ccc(OCC(F)(F)F)cc3)cc2C)c(C(=O)O)c1] | 100 | 0.51 |
| CP-566 | 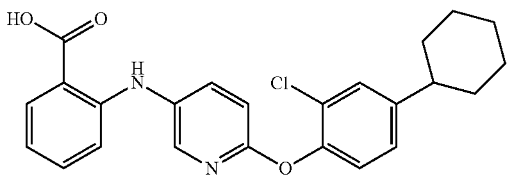 [SMILES: O=C(O)c1ccccc1Nc1ccc(Oc2ccc(C3CCCCC3)cc2Cl)nc1] | 99 | 0.38 |
| CP-567 | 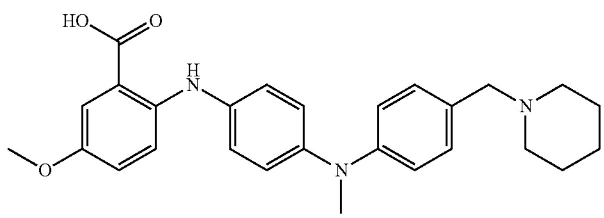 [SMILES: COc1ccc(Nc2ccc(N(C)c3ccc(CN4CCCCC4)cc3)cc2)c(C(=O)O)c1] | 6 | |
| CP-568 | 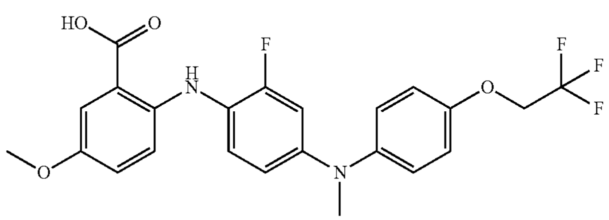 | 46 | |
| CP-569 | 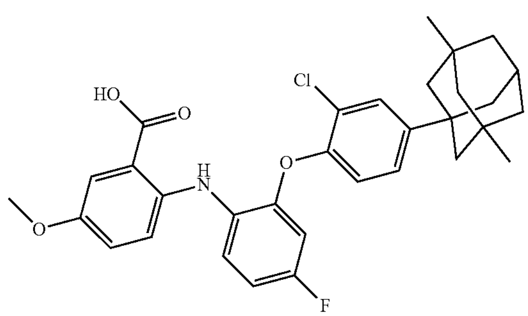 [SMILES: COc1ccc(Nc2ccc(F)cc2Oc2ccc(C34CC5CC(C)(CC(C)(C5)C3)C4)cc2Cl)c(C(=O)O)c1] | 59 | |
| CP-570 | 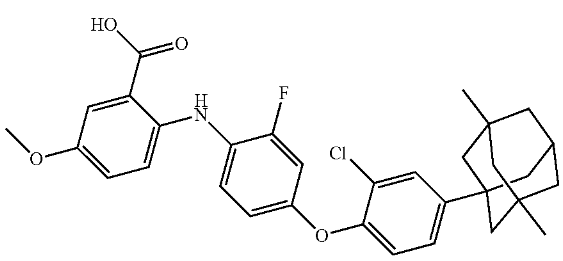 [SMILES: COc1ccc(Nc2ccc(Oc3ccc(C45CC6CC(C)(CC(C)(C6)C4)C5)cc3Cl)cc2F)c(C(=O)O)c1] | 73 | 0.65 |

TABLE 3-continued

Activity of Compounds as TEAD2 Palmitoylation Inhibitors

| CP | Structure | % of inhibition of TEAD2 palmitoylation at 10 μM | TEAD2 palmitoylation IC50 |
|---|---|---|---|
| CP-571 | 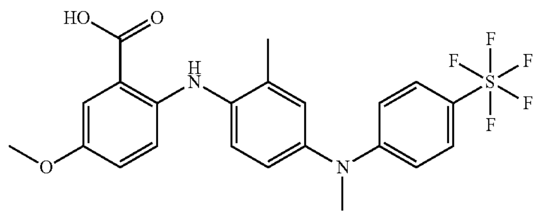 [SMILES: COc1ccc(Nc2ccc(N(C)c3ccc(S(F)(F)(F)(F)F)cc3)cc2C)c(C(=O)O)c1] | 94 | 0.36 |
| CP-572 | 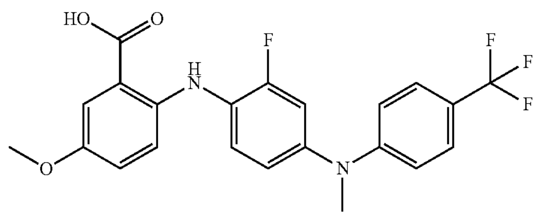 | 72 | |
| CP-573 | 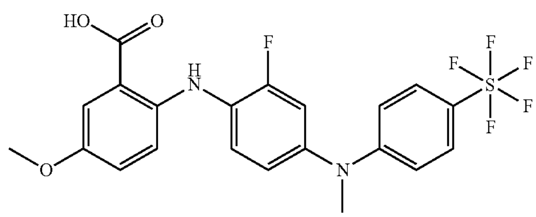 | 74 | |
| CP-574 | 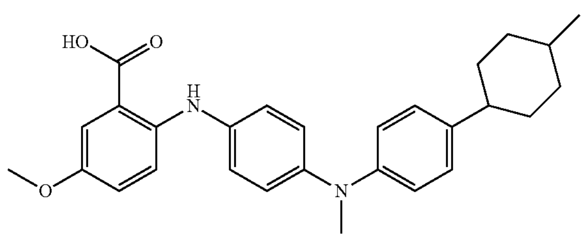 | 91 | |
| CP-575 | 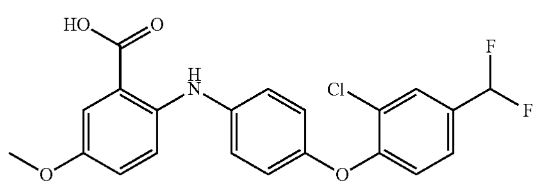 | 47 | |
| CP-576 | 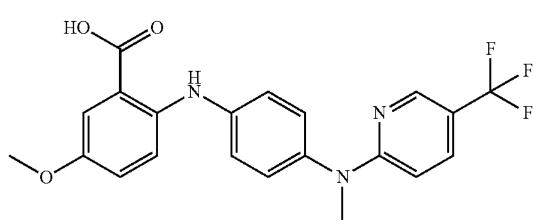 [SMILES: COc1ccc(Nc2ccc(N(C)c3ccc(C(F)(F)F)cn3)cc2)c(C(=O)O)c1] | 42 | |
| CP-577 | 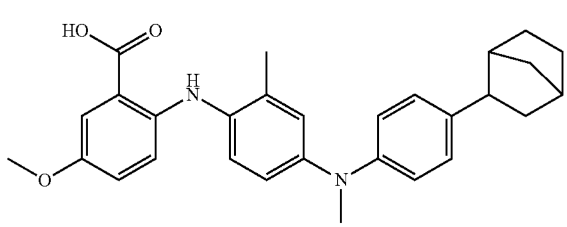 [SMILES: COc1ccc(Nc2ccc(N(C)c3ccc(C4CC5CCC4C5)cc3)cc2C)c(C(=O)O)c1] | 79 | |

TABLE 3-continued

Activity of Compounds as TEAD2 Palmitoylation Inhibitors

| CP | Structure | % of inhibition of TEAD2 palmitoylation at 10 μM | TEAD2 palmitoylation IC50 |
|---|---|---|---|
| CP-578 | 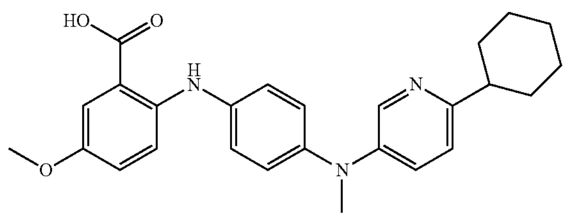 [SMILES: COc1ccc(Nc2ccc(N(C)c3ccc(C4CCCCC4)nc3)cc2)c(C(=O)O)c1] | 31 | |
| CP-579 | 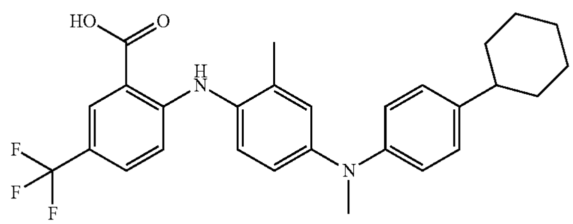 [SMILES: Cc1cc(N(C)c2ccc(C3CCCCC3)cc2)ccc1Nc1ccc(C(F)(F)F)cc1C(=O)O] | 61 | |
| CP-580 | 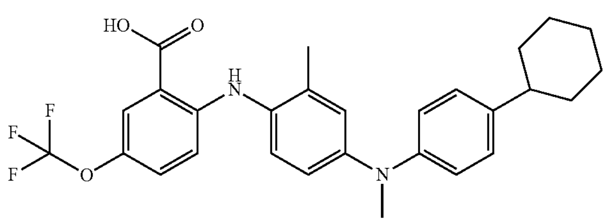 [SMILES: Cc1cc(N(C)c2ccc(C3CCCCC3)cc2)ccc1Nc1ccc(OC(F)(F)F)cc1C(=O)O] | 58 | |
| CP-581 | 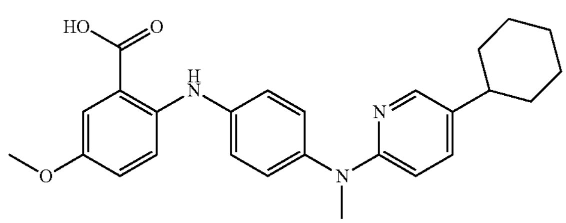 [SMILES: COc1ccc(Nc2ccc(N(C)c3ccc(C4CCCCC4)cn3)cc2)c(C(=O)O)c1] | 40 | |
| CP-582 | 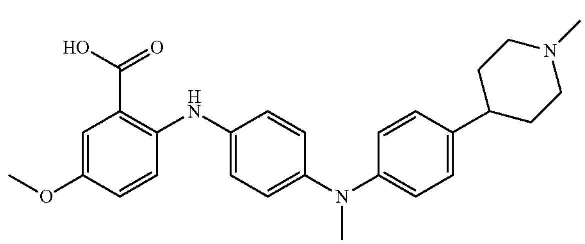 | 0 | |
| CP-583 | 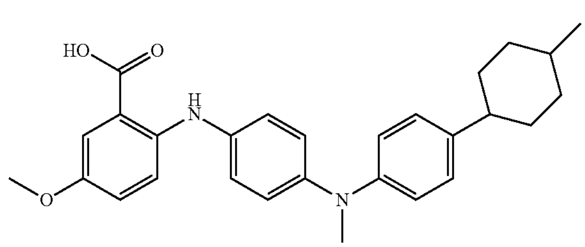 | 96 | 0.23 |

TABLE 3-continued

Activity of Compounds as TEAD2 Palmitoylation Inhibitors

| CP | Structure | % of inhibition of TEAD2 palmitoylation at 10 μM | TEAD2 palmitoylation IC50 |
|---|---|---|---|
| CP-584 | 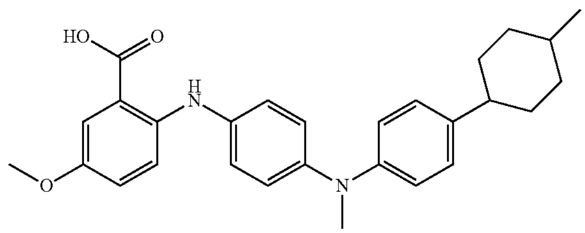 | 85 | 0.21 |
| CP-585 | 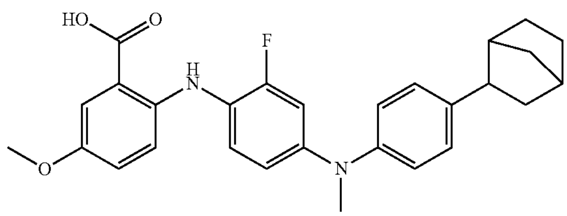 | 86 | 0.32 |
| CP-586 | 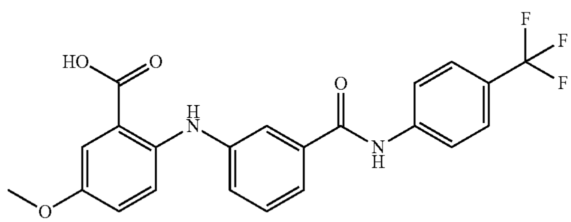 [SMILES: COc1ccc(Nc2cccc(C(=O)Nc3ccc(C(F)(F)F)cc3)c2)c(C(=O)O)c1] | 40 | |
| CP-587 | 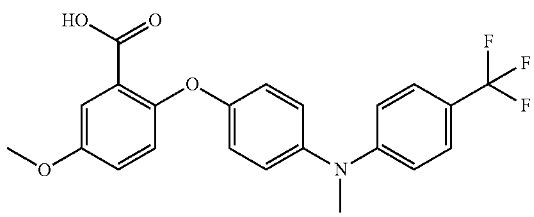 [SMILES: COc1ccc(Oc2ccc(N(C)c3ccc(C(F)(F)F)cc3)cc2)c(C(=O)O)c1] | 36 | |
| CP-588 | 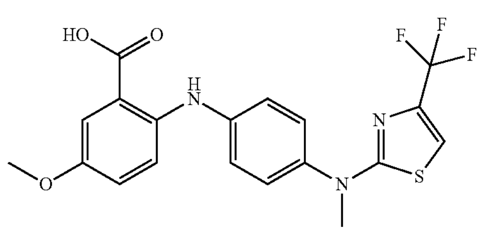 [SMILES: COc1ccc(Nc2ccc(N(C)c3nc(C(F)(F)F)cs3)cc2)c(C(=O)O)c1] | 36 | |
| CP-589 | 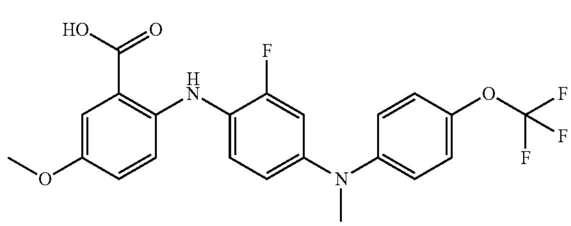 [SMILES: COc1ccc(Nc2ccc(N(C)c3ccc(OC(F)(F)F)cc3)cc2F)c(C(=O)O)c1] | 97 | 1.57 |

TABLE 3-continued

Activity of Compounds as TEAD2 Palmitoylation Inhibitors

| CP | Structure | % of inhibition of TEAD2 palmitoylation at 10 μM | TEAD2 palmitoylation IC50 |
|---|---|---|---|
| CP-590 | 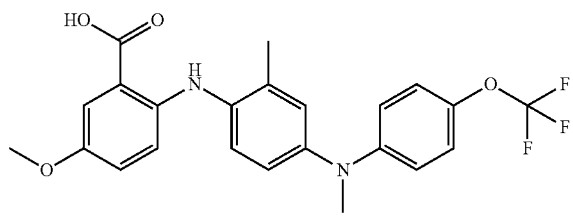 [SMILES: COc1ccc(Nc2ccc(N(C)c3ccc(OC(F)(F)F)cc3)cc2C)c(C(=O)O)c1] | 96 | 0.22 |
| CP-591 | 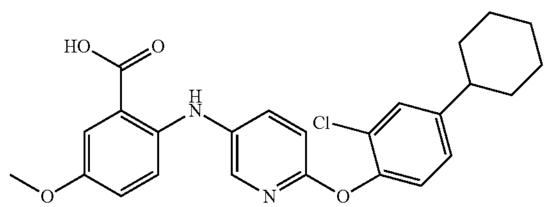 [SMILES: COc1ccc(Nc2ccc(Oc3ccc(C4CCCCC4)cc3Cl)nc2)c(C(=O)O)c1] | 88 | |
| CP-592 | 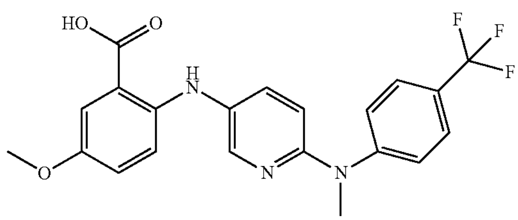 [SMILES: COc1ccc(Nc2ccc(N(C)c3ccc(C(F)(F)F)cc3)nc2)c(C(=O)O)c1] | 40 | |
| CP-593 | 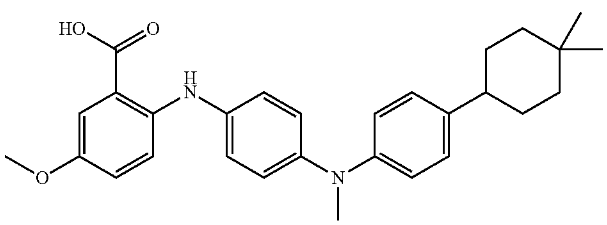 | 78 | 0.03 |
| CP-594 | 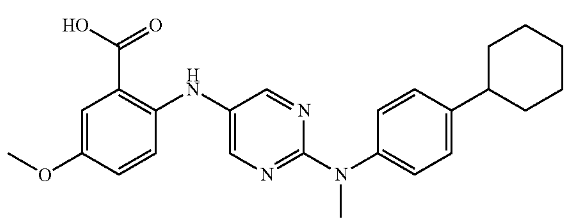 [SMILES: COc1ccc(Nc2cnc(N(C)c3ccc(C4CCCCC4)cc3)nc2)c(C(=O)O)c1] | 46 | |
| CP-595 | 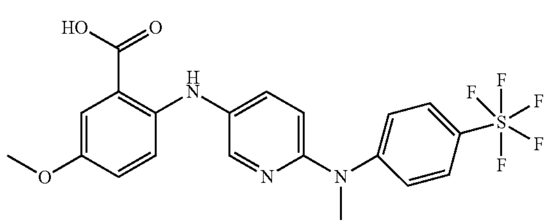 [SMILES: COc1ccc(Nc2ccc(N(C)c3ccc(S(F)(F)(F)(F)F)cc3)nc2)c(C(=O)O)c1] | 51 | |

TABLE 3-continued

Activity of Compounds as TEAD2 Palmitoylation Inhibitors

| CP | Structure | % of inhibition of TEAD2 palmitoylation at 10 μM | TEAD2 palmitoylation IC50 |
|---|---|---|---|
| CP-596 | 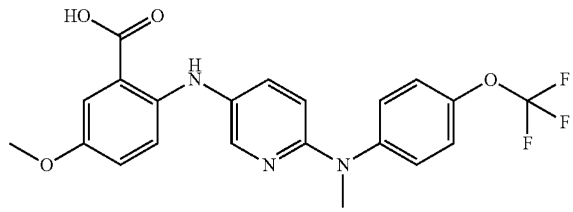 [SMILES: COc1ccc(Nc2ccc(N(C)c3ccc(OC(F)(F)F)cc3)nc2)c(C(=O)O)c1] | 48 | |
| CP-597 | 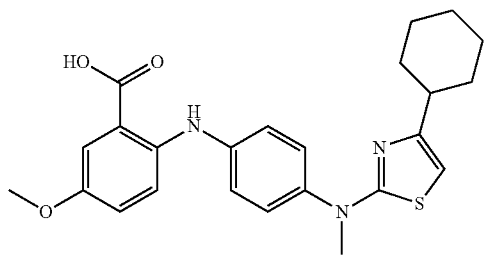 [SMILES: COc1ccc(Nc2ccc(N(C)c3nc(C4CCCCC4)cs3)cc2)c(C(=O)O)c1] | 63 | |
| CP-598 | 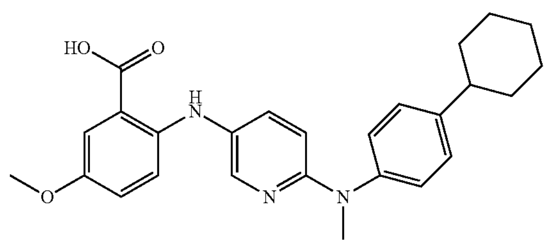 [SMILES: COc1ccc(Nc2ccc(N(C)c3ccc(C4CCCCC4)cc3)nc2)c(C(=O)O)c1] | 74 | 0.05 |
| CP-599 | 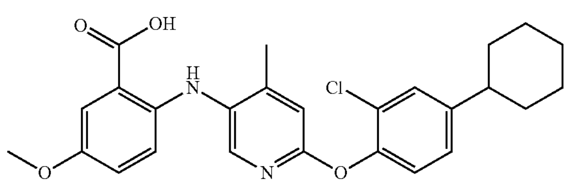 [SMILES: COc1ccc(Nc2cnc(Oc3ccc(C4CCCCC4)cc3Cl)cc2C)c(C(=O)O)c1] | 57 | |
| CP-600 | 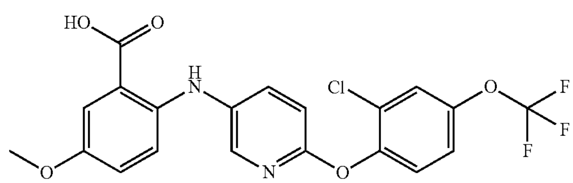 [SMILES: COc1ccc(Nc2ccc(Oc3ccc(OC(F)(F)F)cc3Cl)nc2)c(C(=O)O)c1] | 37 | |
| CP-601 | 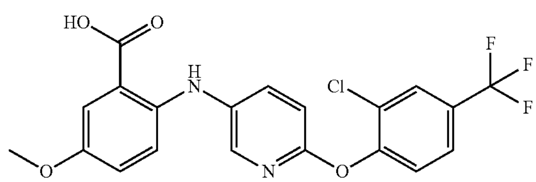 [SMILES: COc1ccc(Nc2ccc(Oc3ccc(C(F)(F)F)cc3Cl)nc2)c(C(=O)O)c1] | 46 | |
| CP-602 | 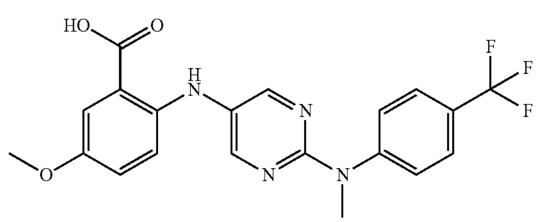 [SMILES: COc1ccc(Nc2cnc(N(C)c3ccc(C(F)(F)F)cc3)nc2)c(C(=O)O)c1] | 5 | |

TABLE 3-continued

Activity of Compounds as TEAD2 Palmitoylation Inhibitors

| CP | Structure | % of inhibition of TEAD2 palmitoylation at 10 μM | TEAD2 palmitoylation IC50 |
|---|---|---|---|
| CP-603 | 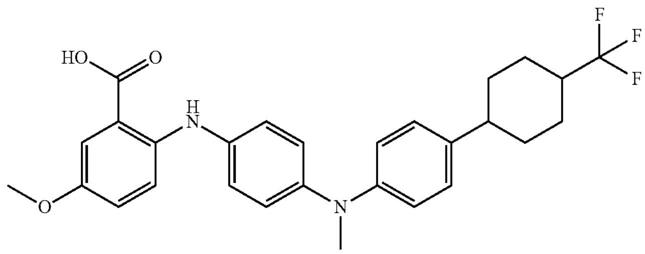 [SMILES: COc1ccc(Nc2ccc(N(C)c3ccc(C4CCC(C(F)(F)F)CC4)cc3)cc2)c(C(=O)O)c1] | 83 | |
| CP-605 | 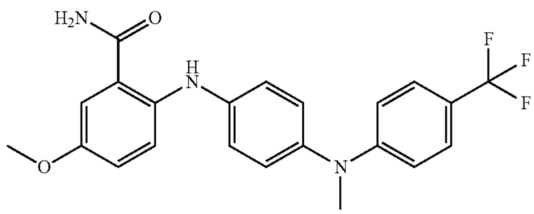 [SMILES: COc1ccc(Nc2ccc(N(C)c3ccc(C(F)(F)F)cc3)cc2)c(C(N)=O)c1] | 47 | |
| CP-606 | 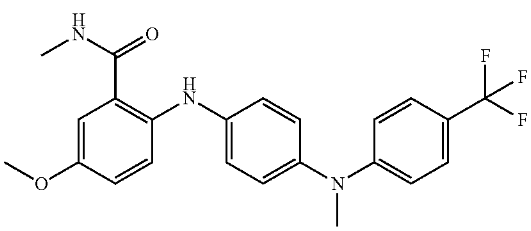 [SMILES: CNC(=O)c1cc(OC)ccc1Nc1ccc(N(C)c2ccc(C(F)(F)F)cc2)cc1] | 63 | |
| CP-607 | 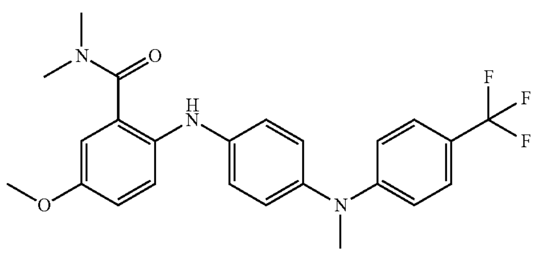 [SMILES: COc1ccc(Nc2ccc(N(C)c3ccc(C(F)(F)F)cc3)cc2)c(C(=O)N(C)C)c1] | 37 | |
| CP-608 | 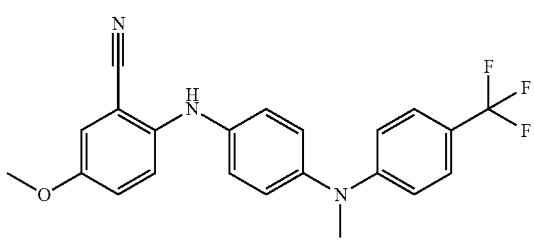 [SMILES: COc1ccc(Nc2ccc(N(C)c3ccc(C(F)(F)F)cc3)cc2)c(C#N)c1] | 43 | |
| CP-609 | 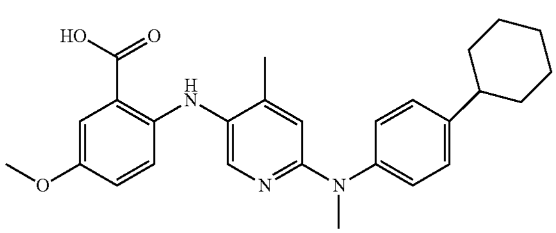 [SMILES: COc1ccc(Nc2cnc(N(C)c3ccc(C4CCCCC4)cc3)cc2C)c(C(=O)O)c1] | 54 | |

TABLE 3-continued

Activity of Compounds as TEAD2 Palmitoylation Inhibitors

| CP | Structure | % of inhibition of TEAD2 palmitoylation at 10 μM | TEAD2 palmitoylation IC50 |
|---|---|---|---|
| CP-612 | 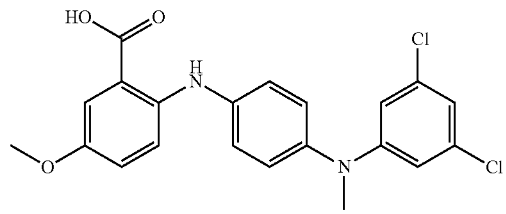 [SMILES: COc1ccc(Nc2ccc(N(C)c3cc(Cl)cc(Cl)c3)cc2)c(C(=O)O)c1] | 86 | |
| CP-613 | 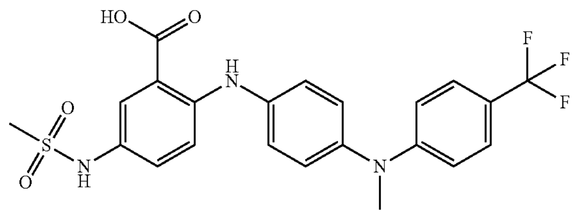 [SMILES: CN(c1ccc(Nc2ccc(NS(C)(=O)=O)cc2C(=O)O)cc1)c1ccc(C(F)(F)F)cc1] | 83 | |
| CP-614 | 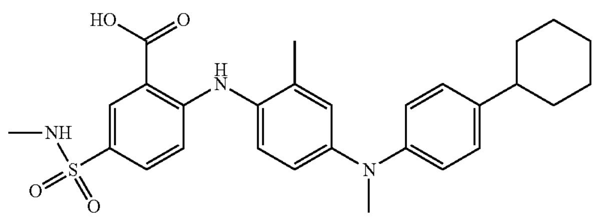 [SMILES: CNS(=O)(=O)c1ccc(Nc2ccc(N(C)c3ccc(C4CCCCC4)cc3)cc2C)c(C(=O)O)c1] | 83 | |
| CP-615 | 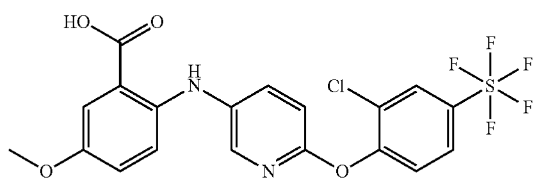 [SMILES: COc1ccc(Nc2ccc(Oc3ccc(S(F)(F)(F)(F)F)cc3Cl)nc2)c(C(=O)O)c1] | 82 | |
| CP-616 | 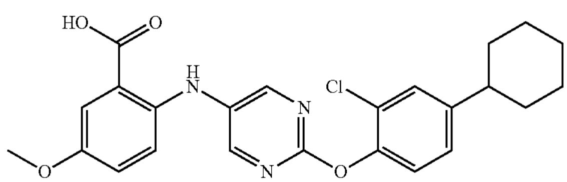 [SMILES: COc1ccc(Nc2cnc(Oc3ccc(C4CCCCC4)cc3Cl)nc2)c(C(=O)O)c1] | 73 | |
| CP-617 | 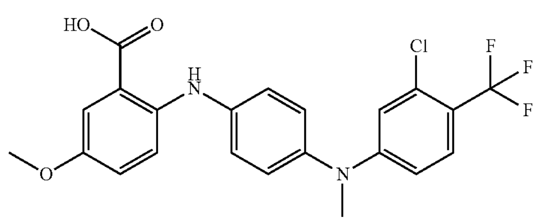 [SMILES: COc1ccc(Nc2ccc(N(C)c3ccc(C(F)(F)F)c(Cl)c3)cc2)c(C(=O)O)c1] | 76 | |
| CP-618 | 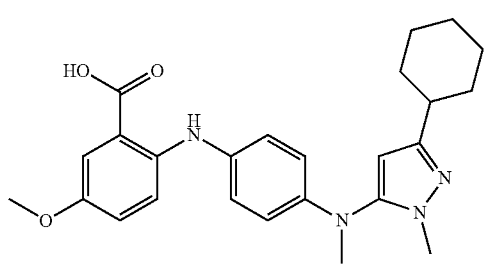 [SMILES: COc1ccc(Nc2ccc(N(C)c3cc(C4CCCCC4)nn3C)cc2)c(C(=O)O)c1] | 31 | |

TABLE 3-continued

Activity of Compounds as TEAD2 Palmitoylation Inhibitors

| CP | Structure | % of inhibition of TEAD2 palmitoylation at 10 μM | TEAD2 palmitoylation IC50 |
|---|---|---|---|
| CP-619 | 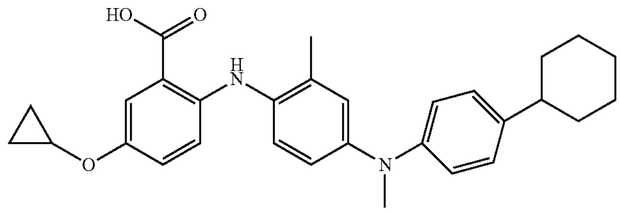 [SMILES: Cc1cc(N(C)c2ccc(C3CCCCC3)cc2)ccc1Nc1ccc(OC2CC2)cc1C(=O)O] | 96 | 0.75 |
| CP-620 | 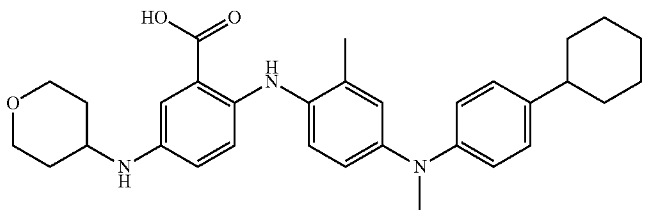 [SMILES: Cc1cc(N(C)c2ccc(C3CCCCC3)cc2)ccc1Nc1ccc(NC2CCOCC2)cc1C(=O)O] | 0 | |
| CP-621 | 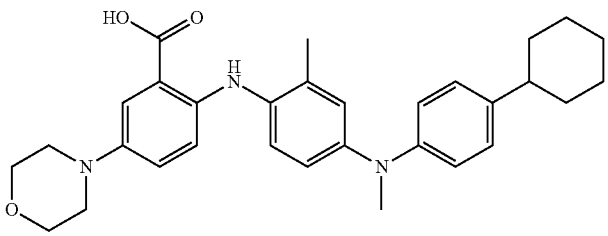 [SMILES: Cc1cc(N(C)c2ccc(C3CCCCC3)cc2)ccc1Nc1ccc(N2CCOCC2)cc1C(=O)O] | 47 | |
| CP-622 | 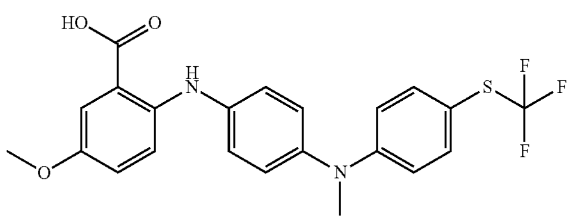 [SMILES: COc1ccc(Nc2ccc(N(C)c3ccc(SC(F)(F)F)cc3)cc2)c(C(=O)O)c1] | 94 | |
| CP-623 | 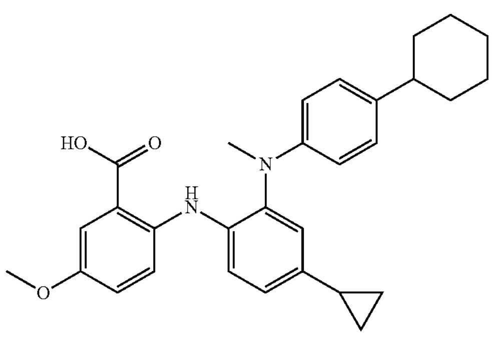 [SMILES: COc1ccc(Nc2ccc(C3CC3)cc2N(C)c2ccc(C3CCCCC3)cc2)c(C(=O)O)c1] | 73 | |
| CP-624 | 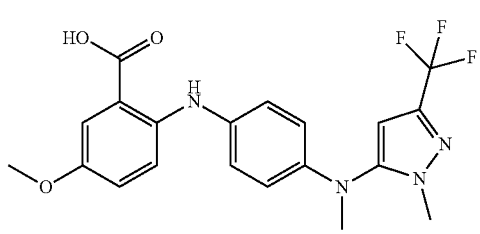 [SMILES: COc1ccc(Nc2ccc(N(C)c3cc(C(F)(F)F)nn3C)cc2)c(C(=O)O)c1] | 15 | |

TABLE 3-continued

Activity of Compounds as TEAD2 Palmitoylation Inhibitors

| CP | Structure | % of inhibition of TEAD2 palmitoylation at 10 μM | TEAD2 palmitoylation IC50 |
|---|---|---|---|
| CP-625 | 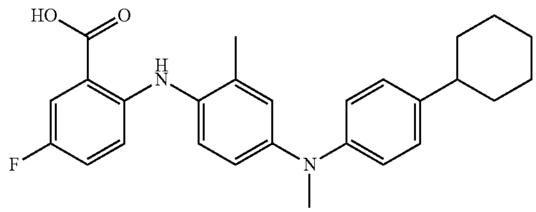 [SMILES: Cc1cc(N(C)c2ccc(C3CCCCC3)cc2)ccc1Nc1ccc(F)cc1C(=O)O] | 87 | |
| CP-626 | 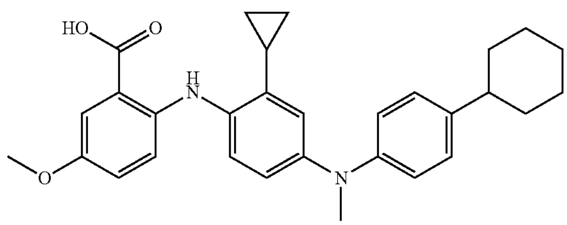 [SMILES: COc1ccc(Nc2ccc(N(C)c3ccc(C4CCCCC4)cc3)cc2C2CC2)c(C(=O)O)c1] | 87 | 0.382 |
| CP-627 | 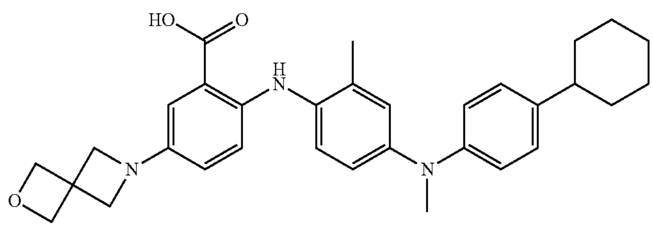 [SMILES: Cc1cc(N(C)c2ccc(C3CCCCC3)cc2)ccc1Nc1ccc(N2CC3(COC3)C2)cc1C(=O)O] | 51 | |
| CP-628 | 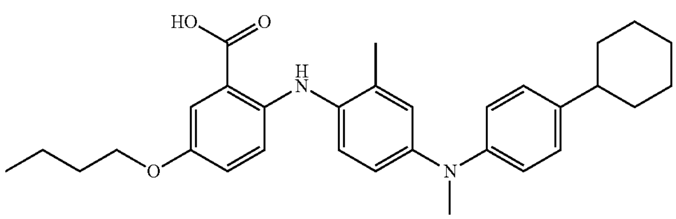 [SMILES: CCCCOc1ccc(Nc2ccc(N(C)c3ccc(C4CCCCC4)cc3)cc2C)c(C(=O)O)c1] | 40 | |
| CP-629 | 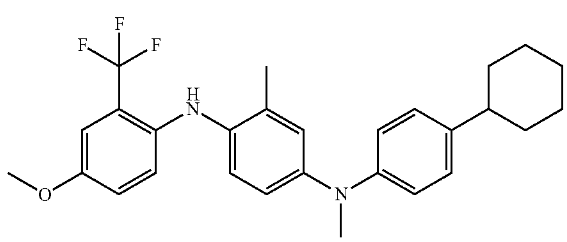 [SMILES: COc1ccc(Nc2ccc(N(C)c3ccc(C4CCCCC4)cc3)cc2C)c(C(F)(F)F)c1] | 24 | |
| CP-630 | 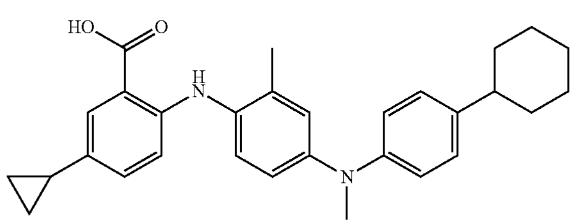 [SMILES: Cc1cc(N(C)c2ccc(C3CCCCC3)cc2)ccc1Nc1ccc(C2CC2)cc1C(=O)O] | 39 | |

TABLE 3-continued
Activity of Compounds as TEAD2 Palmitoylation Inhibitors
| CP | Structure | % of inhibition of TEAD2 palmitoylation at 10 μM | TEAD2 palmitoylation IC50 |
| --- | --- | --- | --- |
| CP-631 | 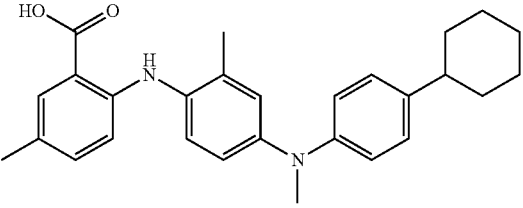 [SMILES: Cc1ccc(Nc2ccc(N(C)c3ccc(C4CCCCC4)cc3)cc2C)c(C(=O)O)c1] | 81 | |
| CP-632 | 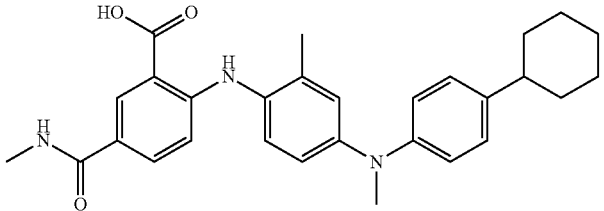 [SMILES: CNC(=O)c1ccc(Nc2ccc(N(C)c3ccc(C4CCCCC4)cc3)cc2C)c(C(=O)O)c1] | 73 | |
| CP-633 | 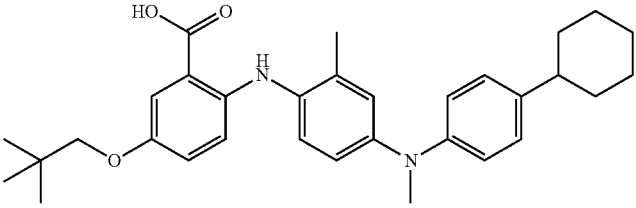 [SMILES: Cc1cc(N(C)c2ccc(C3CCCCC3)cc2)ccc1Nc1ccc(OCC(C)(C)C)cc1C(=O)O] | 25 | |
| CP-634 | 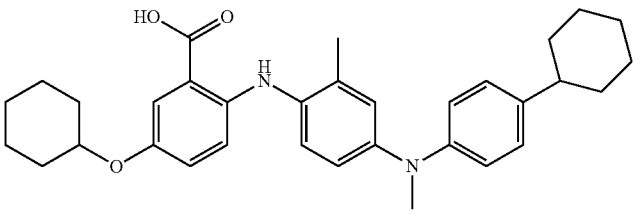 [SMILES: Cc1cc(N(C)c2ccc(C3CCCCC3)cc2)ccc1Nc1ccc(OC2CCCCC2)cc1C(=O)O] | 32 | |
| CP-635 | 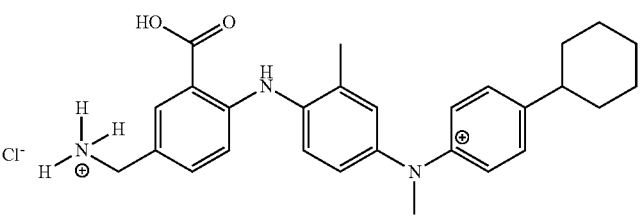 | 27 | |
| CP-636 | 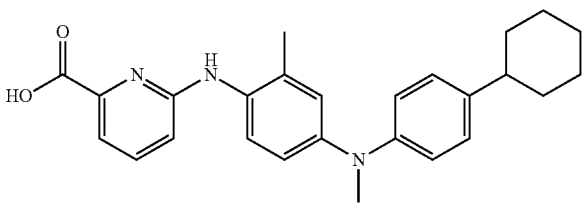 [SMILES: Cc1cc(N(C)c2ccc(C3CCCCC3)cc2)ccc1Nc1cccc(C(=O)O)n1] | 68 | |

TABLE 3-continued

Activity of Compounds as TEAD2 Palmitoylation Inhibitors

| CP | Structure | % of inhibition of TEAD2 palmitoylation at 10 μM | TEAD2 palmitoylation IC50 |
|---|---|---|---|
| CP-637 | 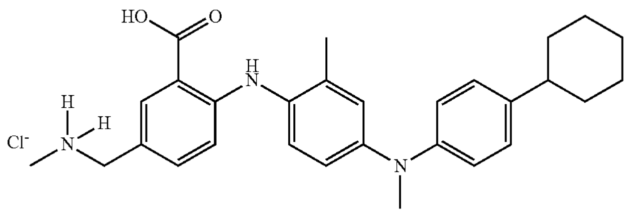 | 5 | |
| CP-638 | 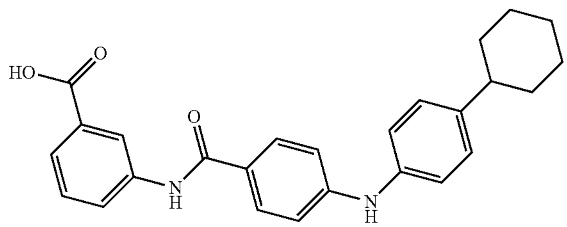 [SMILES: O=C(O)c1cccc(NC(=O)c2ccc(Nc3ccc(C4CCCCC4)cc3)cc2)c1] | 67 | |
| CP-640 | 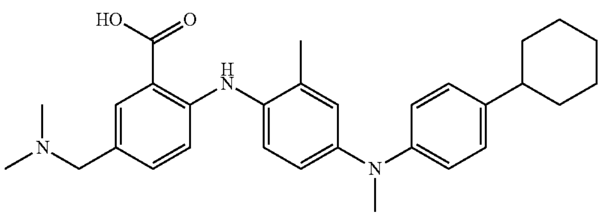 [SMILES: Cc1cc(N(C)c2ccc(C3CCCCC3)cc2)ccc1Nc1ccc(CN(C)C)cc1C(=O)O] | 20 | |
| CP-641 | 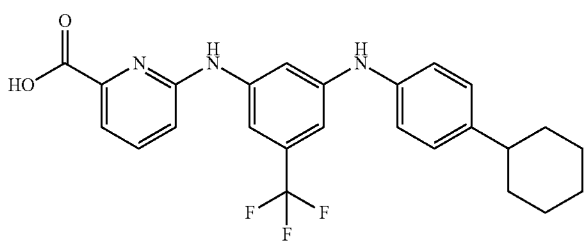 | 69 | |
| CP-642 | 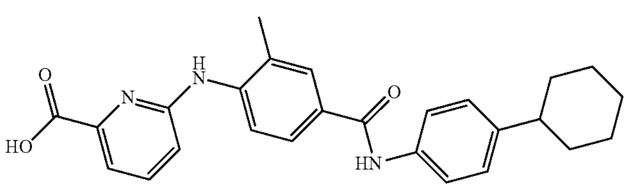 [SMILES: Cc1cc(C(=O)Nc2ccc(C3CCCCC3)cc2)ccc1Nc1cccc(C(=O)O)n1] | 55 | |
| CP-643 | 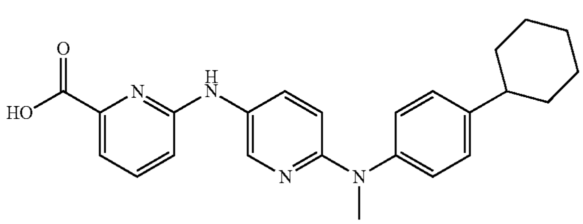 [SMILES: CN(c1ccc(C2CCCCC2)cc1)c1ccc(Nc2cccc(C(=O)O)n2)cn1] | 89 | |
| CP-646 | 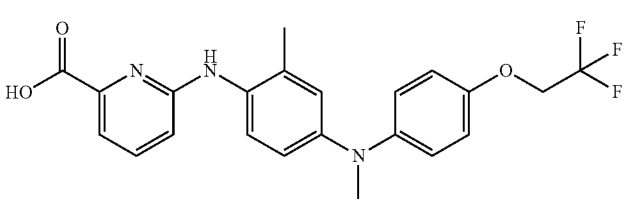 [SMILES: Cc1cc(N(C)c2ccc(OCC(F)(F)F)cc2)ccc1Nc1cccc(C(=O)O)n1] | 39 | |

TABLE 3-continued

Activity of Compounds as TEAD2 Palmitoylation Inhibitors

| CP | Structure | % of inhibition of TEAD2 palmitoylation at 10 μM | TEAD2 palmitoylation IC50 |
| --- | --- | --- | --- |
| CP-647 | 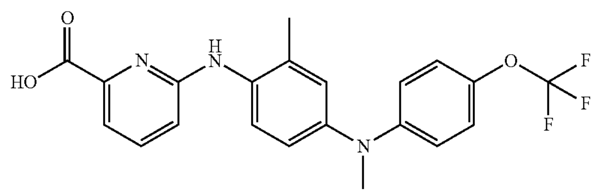 [SMILES: Cc1cc(N(C)c2ccc(OC(F)(F)F)cc2)ccc1Nc1cccc(C(=O)O)n1] | 87 | |
| CP-648 | 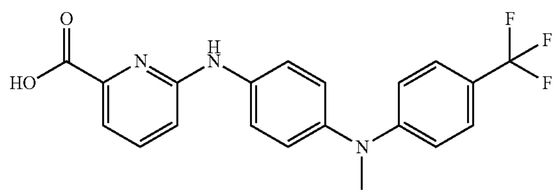 [SMILES: CN(c1ccc(Nc2cccc(C(=O)O)n2)cc1)c1ccc(C(F)(F)F)cc1] | 89 | |
| CP-649 | 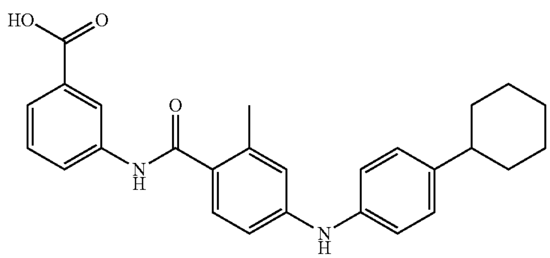 [SMILES: Cc1cc(Nc2ccc(C3CCCCC3)cc2)ccc1C(=O)Nc1cccc(C(=O)O)c1] | 99 | |
| CP-650 | 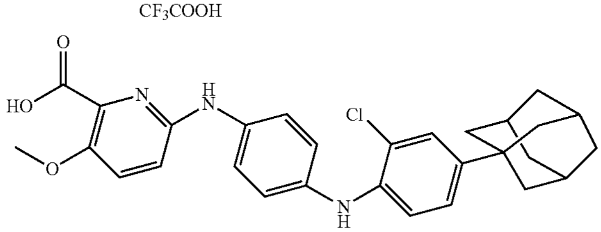 [SMILES: COc1ccc(Nc2ccc(Nc3ccc(C45CC6CC(CC(C6)C4)C5)cc3Cl)cc2)nc1C(=O)O ; "CF3COOH"] | 93 | |
| CP-651 | 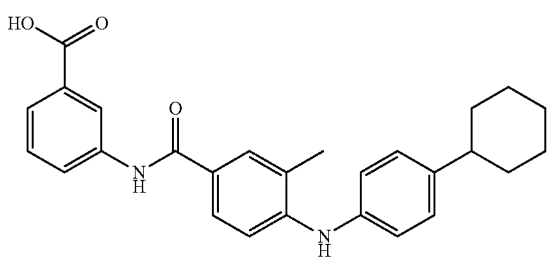 [SMILES: Cc1cc(C(=O)Nc2cccc(C(=O)O)c2)ccc1Nc1ccc(C2CCCCC2)cc1] | 85 | |
| CP-652 | 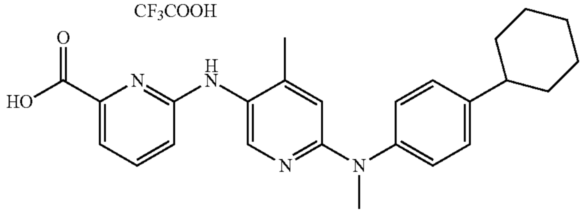 [SMILES: Cc1cc(N(C)c2ccc(C3CCCCC3)cc2)ncc1Nc1cccc(C(=O)O)n1 ; "CF3COOH"] | 37 | |

TABLE 3-continued

Activity of Compounds as TEAD2 Palmitoylation Inhibitors

| CP | Structure | % of inhibition of TEAD2 palmitoylation at 10 μM | TEAD2 palmitoylation IC50 |
|---|---|---|---|
| CP-653 | 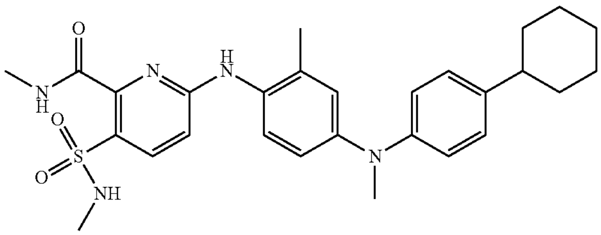 [SMILES: CNC(=O)c1nc(Nc2ccc(N(C)c3ccc(C4CCCCC4)cc3)cc2C)ccc1S(=O)(=O)NC] | 24 | |
| CP-654 | 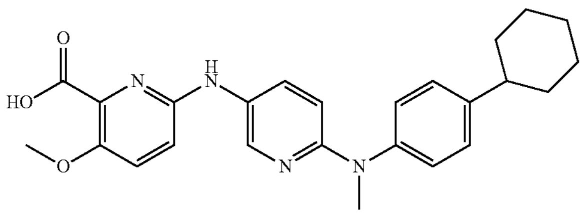 [SMILES: COc1ccc(Nc2ccc(N(C)c3ccc(C4CCCCC4)cc3)nc2)nc1C(=O)O] | 36 | |
| CP-655 | 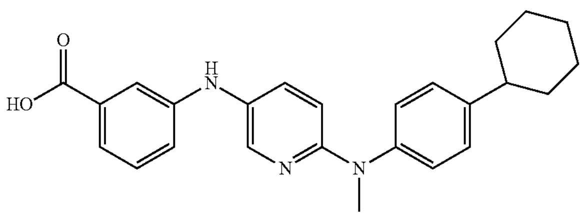 [SMILES: CN(c1ccc(C2CCCCC2)cc1)c1ccc(Nc2cccc(C(=O)O)c2)cn1] | 97 | |
| CP-656 | 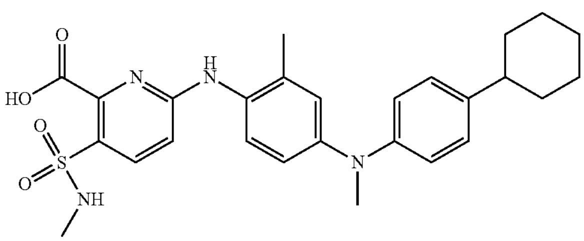 [SMILES: CNS(=O)(=O)c1ccc(Nc2ccc(N(C)c3ccc(C4CCCCC4)cc3)cc2C)nc1C(=O)O] | 90 | |
| CP-657 | 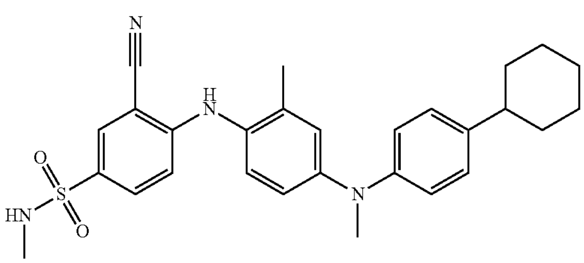 [SMILES: CNS(=O)(=O)c1ccc(Nc2ccc(N(C)c3ccc(C4CCCCC4)cc3)cc2C)c(C#N)c1] | 18 | |
| CP-659 | 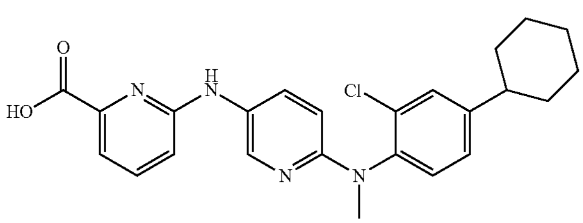 [SMILES: CN(c1ccc(Nc2cccc(C(=O)O)n2)cn1)c1ccc(C2CCCCC2)cc1Cl] | 46 | |

TABLE 3-continued

Activity of Compounds as TEAD2 Palmitoylation Inhibitors

| CP | Structure | % of inhibition of TEAD2 palmitoylation at 10 μM | TEAD2 palmitoylation IC50 |
| --- | --- | --- | --- |
| CP-660 | 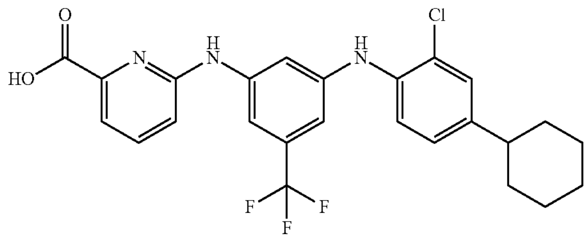 | 66 | |
| CP-661 | 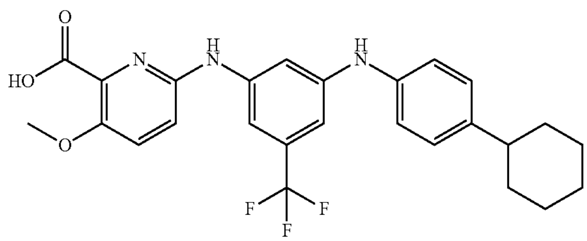 [SMILES: COc1ccc(Nc2cc(Nc3ccc(C4CCCCC4)cc3)cc(C(F)(F)F)c2)nc1C(=O)O] | 77 | |
| CP-662 | 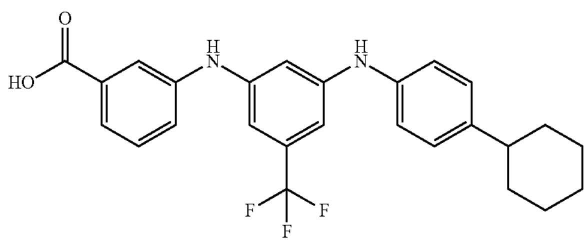 [SMILES: O=C(O)c1cccc(Nc2cc(Nc3ccc(C4CCCCC4)cc3)cc(C(F)(F)F)c2)c1] | 88 | |
| CP-663 | 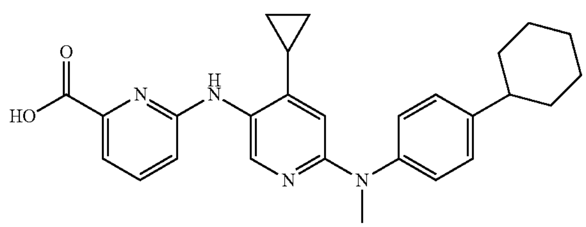 [SMILES: CN(c1ccc(C2CCCCC2)cc1)c1cc(C2CC2)c(Nc2cccc(C(=O)O)n2)cn1] | 45 | |
| CP-664 | 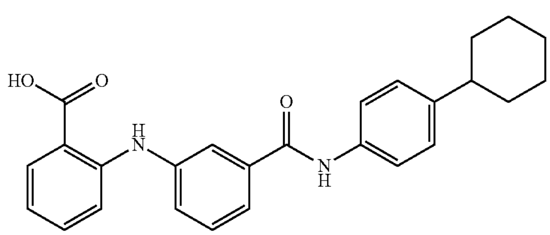 [SMILES: O=C(Nc1ccc(C2CCCCC2)cc1)c1cccc(Nc2ccccc2C(=O)O)c1] | 50 | |
| CP-665 | 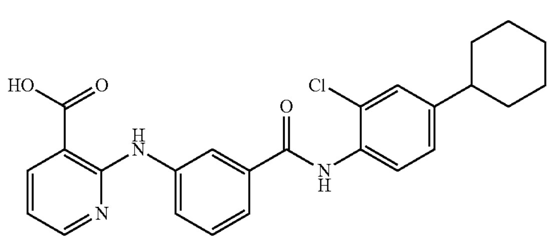 [SMILES: O=C(Nc1ccc(C2CCCCC2)cc1Cl)c1cccc(Nc2ncccc2C(=O)O)c1] | 96 | |

…
TABLE 3-continued
Activity of Compounds as TEAD2 Palmitoylation Inhibitors
| CP | Structure | % of inhibition of TEAD2 palmitoylation at 10 μM | TEAD2 palmitoylation IC50 |
|---|---|---|---|
| CP-666 | 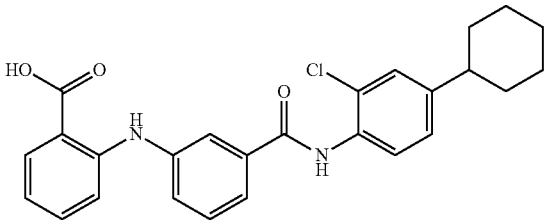 [SMILES: O=C(Nc1ccc(C2CCCCC2)cc1Cl)c1cccc(Nc2ccccc2C(=O)O)c1] | 79 | |
| CP-669 | 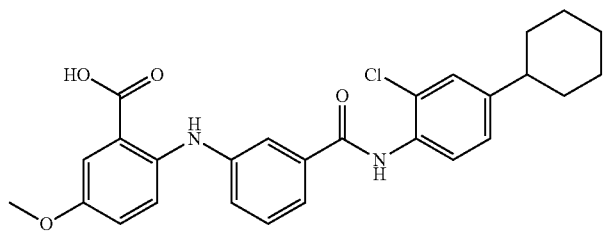 [SMILES: COc1ccc(Nc2cccc(C(=O)Nc3ccc(C4CCCCC4)cc3Cl)c2)c(C(=O)O)c1] | 75 | |
| CP-671 | 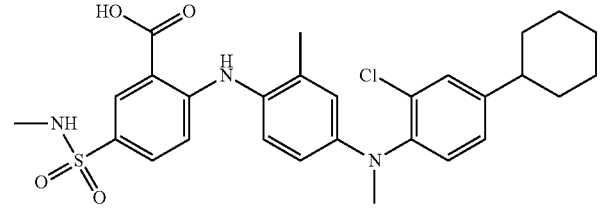 [SMILES: CNS(=O)(=O)c1ccc(Nc2ccc(N(C)c3ccc(C4CCCCC4)cc3Cl)cc2C)c(C(=O)O)c1] | 97 | |
| CP-672 | 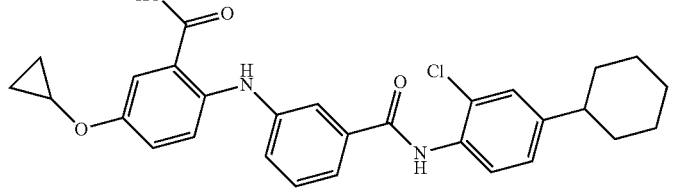 | 55 | |
| CP-673 | 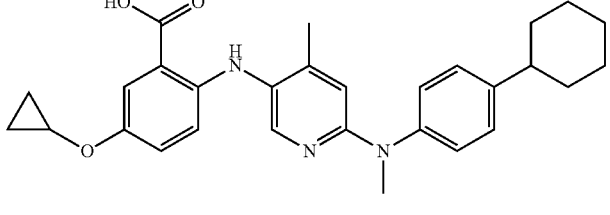 | 15 | |
| CP-675 | 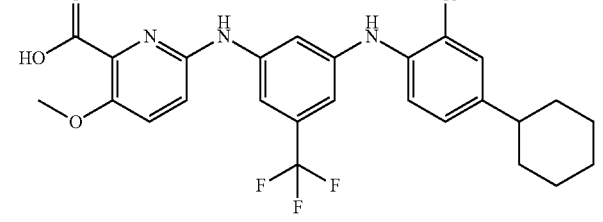 | 83 | |

TABLE 3-continued

Activity of Compounds as TEAD2 Palmitoylation Inhibitors

| CP | Structure | % of inhibition of TEAD2 palmitoylation at 10 μM | TEAD2 palmitoylation IC50 |
| --- | --- | --- | --- |
| CP-676 | 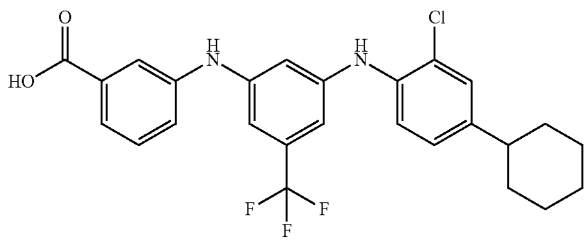 | 97 | |
| CP-677 | 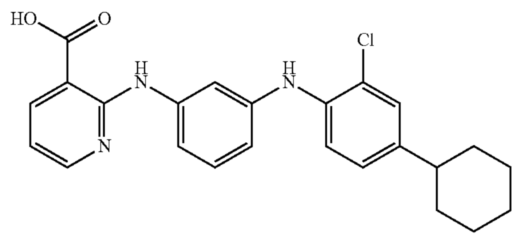 [SMILES: O=C(O)c1cccnc1Nc1cccc(Nc2ccc(C3CCCCC3)cc2Cl)c1] | 96 | |
| CP-678 | 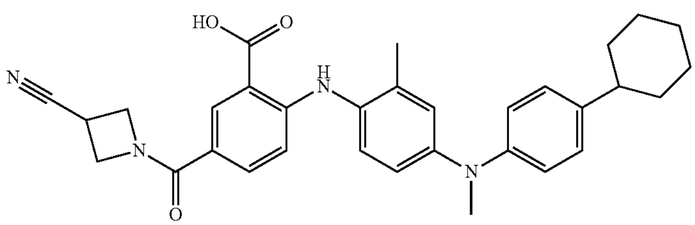 [SMILES: Cc1cc(N(C)c2ccc(C3CCCCC3)cc2)ccc1Nc1ccc(C(=O)N2CC(C#N)C2)cc1C(=O)O] | 59 | |
| CP-679 | 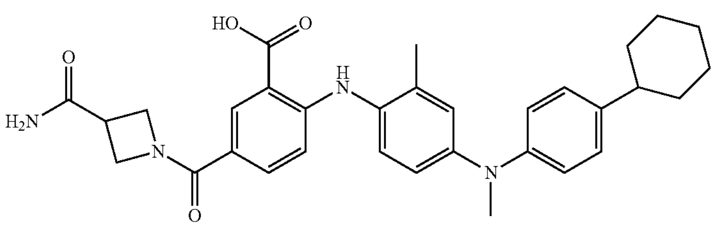 [SMILES: Cc1cc(N(C)c2ccc(C3CCCCC3)cc2)ccc1Nc1ccc(C(=O)N2CC(C(N)=O)C2)cc1C(=O)O] | 81 | |
| CP-680 | 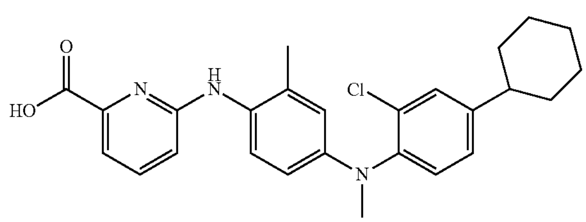 [SMILES: Cc1cc(N(C)c2ccc(C3CCCCC3)cc2Cl)ccc1Nc1cccc(C(=O)O)n1] | 52 | |
| CP-681 | 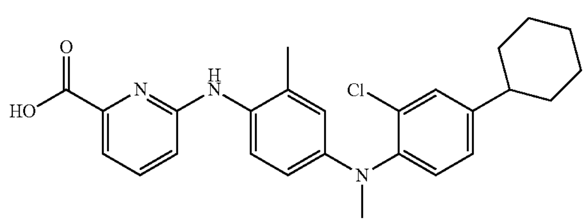 [SMILES: Cc1cc(N(C)c2ccc(C3CCCCC3)cc2Cl)ccc1Nc1cccc(C(=O)O)n1] | 8 | |

TABLE 3-continued

Activity of Compounds as TEAD2 Palmitoylation Inhibitors

| CP | Structure | % of inhibition of TEAD2 palmitoylation at 10 μM | TEAD2 palmitoylation IC50 |
|---|---|---|---|
| CP-682 | 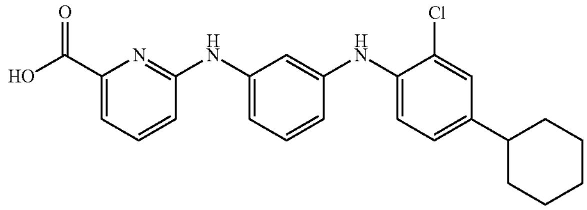 [SMILES: O=C(O)c1cccc(Nc2cccc(Nc3ccc(C4CCCCC4)cc3Cl)c2)n1] | 51 | |
| CP-688 | 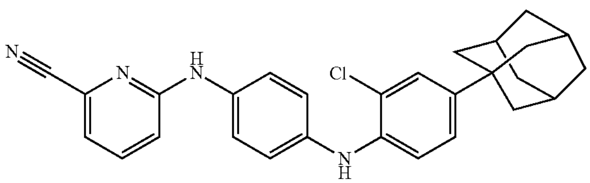 [SMILES: N#Cc1cccc(Nc2ccc(Nc3ccc(C45CC6CC(CC(C6)C4)C5)cc3Cl)cc2)n1] | 17 | |
| CP-694 | 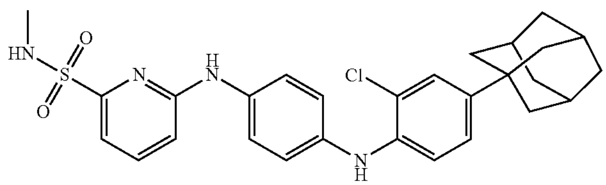 [SMILES: CNS(=O)(=O)c1cccc(Nc2ccc(Nc3ccc(C45CC6CC(CC(C6)C4)C5)cc3Cl)cc2)n1] | 79 | |
| CP-644 | 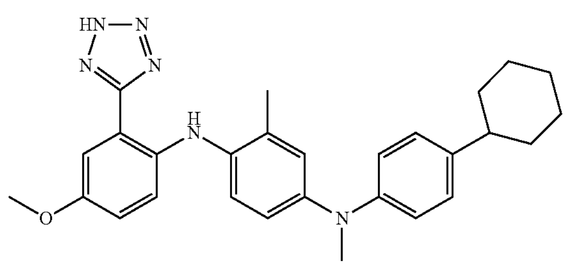 [SMILES: COc1ccc(Nc2ccc(N(C)c3ccc(C4CCCCC4)cc3)cc2C)c(-c2nn[nH]n2)c1] | | |

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:
1. A compound of Formula:

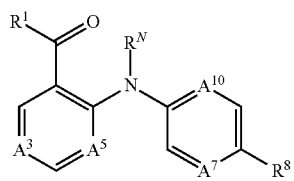

or a pharmaceutically acceptable salt thereof, wherein:
$R^N$ is H or $C_{1-6}$ alkyl;
$R^1$ is OH or $OC_{1-6}$ alkyl;
$A^3$ is $CR^3$ or N;
$A^5$ is CH or N;
$A^7$ is CH or N;
$A^{10}$ is CH or N;
$R^3$ is H, unsubstituted $C_{1-6}$ alkyl, $C_{2-6}$ alkenyl, $C_{2-6}$ alkynyl, halogen, $C_{1-6}$ haloalkyl, CN, $OR^{a1}$, $SR^{a1}$, $NR^{c1}R^{d1}$, $C(O)OR^{a1}$, $C(O)NR^{c1}R^{d1}$ or $C_{1-6}$ alkyl that is substituted by 1, 2, or 3 substituents each independently selected from halogen, $C_{1-6}$ haloalkyl, CN, $OR^{a1}$, $SR^{a1}$, and $NR^{c1}R^{d1}$, $R^8$ is $Cy^{8A}$, $OCy^{8A}$, $O(C_{1-3}$ alkylenyl)$Cy^{8A}$, $NHCy^{8A}$, $NH(C_{1-3}$ alkylenyl)$Cy^{8A}$, $N(C_{1-6}$ alkyl)$Cy^{8A}$, or $N(C_{1-6}$ alkyl)$(C_{1-3}$ alkylenyl)$Cy^{8A}$;

$Cy^{8A}$ is a group of one of the following formulae:

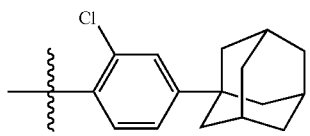

-continued

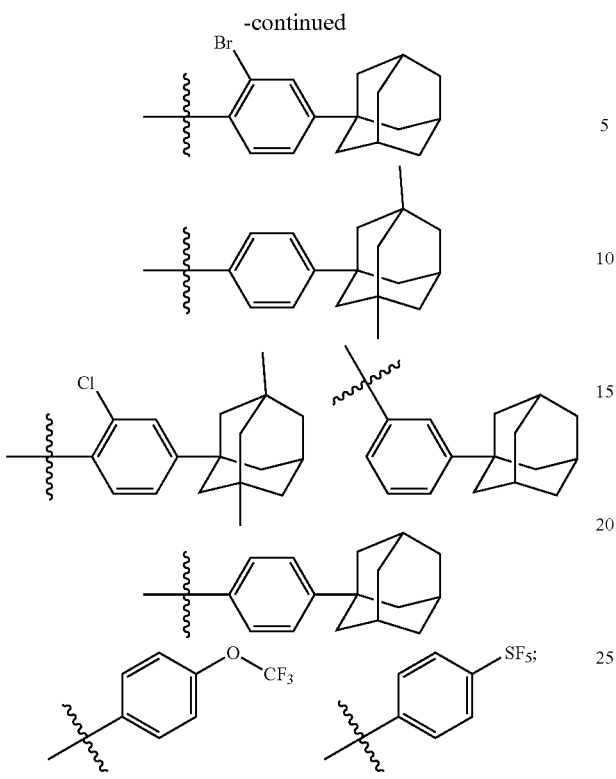

and

Rᵃ¹, Rᵇ¹, Rᶜ¹ and Rᵈ¹ are each independently selected from H, $C_{1-6}$ alkyl, HO—$C_{1-6}$ alkylene, $C_{1-6}$ alkoxy-$C_{1-6}$ alkylene, $C_{6-10}$ aryl, $C_{2-6}$ alkenyl and $C_{2-6}$ alkynyl.

2. The compound or pharmaceutically acceptable salt thereof of claim 1, wherein $A^3$ is $CR^3$.

3. The compound or pharmaceutically acceptable salt thereof of claim 2, wherein $R^3$ is H, $C_{1-6}$ alkyl or $C_{1-6}$ haloalkyl.

4. The compound or pharmaceutically acceptable salt thereof of claim 2, wherein $R^3$ is H.

5. The compound or pharmaceutically acceptable salt thereof of claim 1, wherein $A^3$ is N.

6. The compound or pharmaceutically acceptable salt thereof claim 1, wherein $A^5$ is CH.

7. The compound or pharmaceutically acceptable salt thereof of claim 1, wherein $A^5$ is N.

8. The compound or pharmaceutically acceptable salt thereof of claim 1, wherein $R^1$ is OH.

9. The compound or pharmaceutically acceptable salt thereof of claim 1, wherein $R^N$ is H.

10. The compound or pharmaceutically acceptable salt thereof of claim 1, wherein $A^7$ is CH.

11. The compound or pharmaceutically acceptable salt thereof of claim 1, wherein $A^7$ is N.

12. The compound or pharmaceutically acceptable salt thereof of claim 1, wherein $R^8$ is $NHCy^{8A}$.

13. The compound or pharmaceutically acceptable salt thereof of claim 1, wherein $Cy^{8A}$ is a group of one of the following formulae:

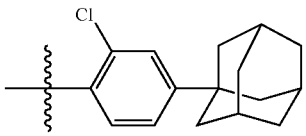

-continued

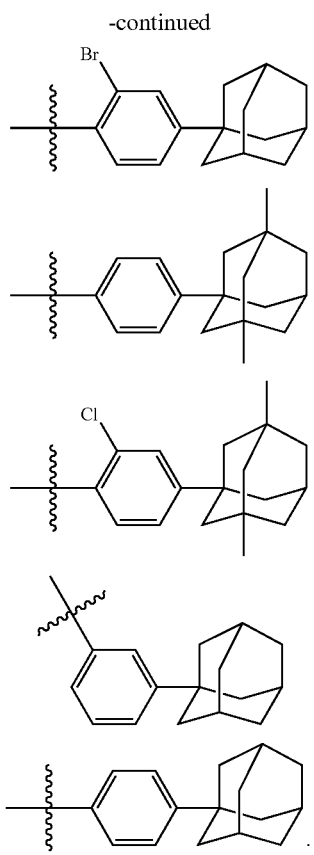

14. The compound or pharmaceutically acceptable salt thereof of claim 1, wherein $A^{10}$ is CH.

15. The compound or pharmaceutically acceptable salt thereof of claim 1, wherein $A^{10}$ is N.

16. The compound or pharmaceutically acceptable salt thereof of claim 1, wherein $R^1$ is OH.

17. The compound or pharmaceutically acceptable salt thereof of claim 1, wherein $R^1$ is $OC_{1-6}$ alkyl.

18. The compound of claim 1 wherein the compound is selected from the group consisting of:

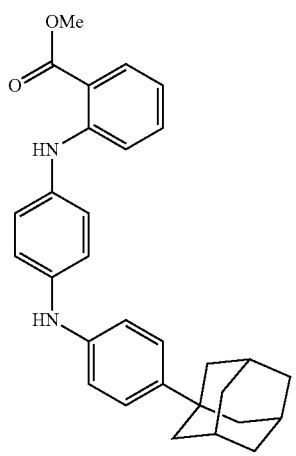

-continued
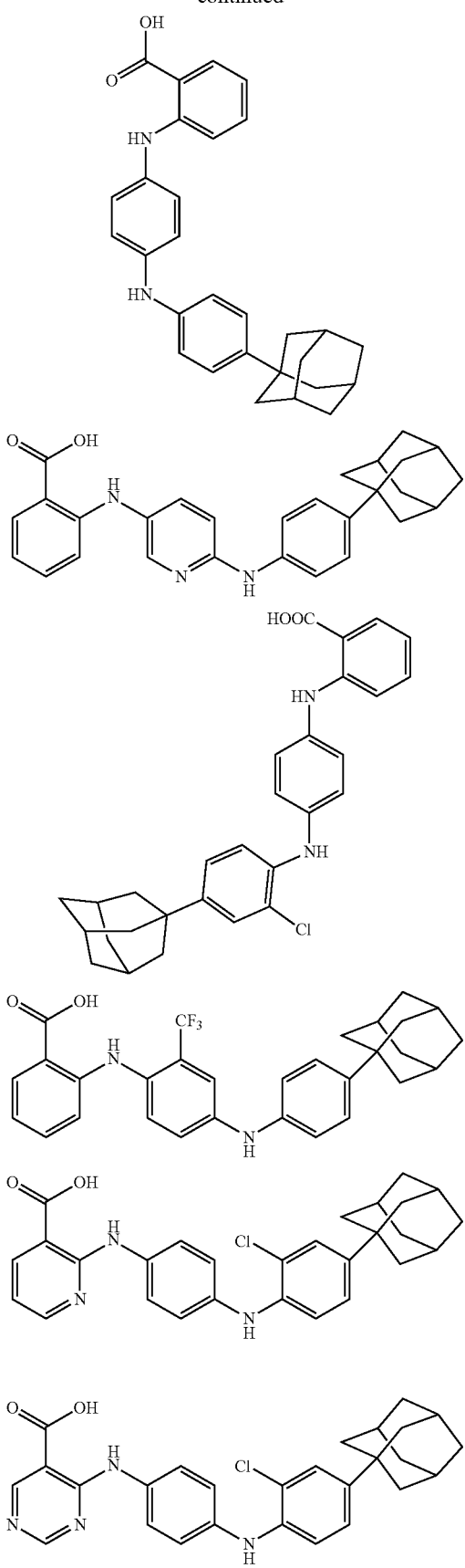
-continued
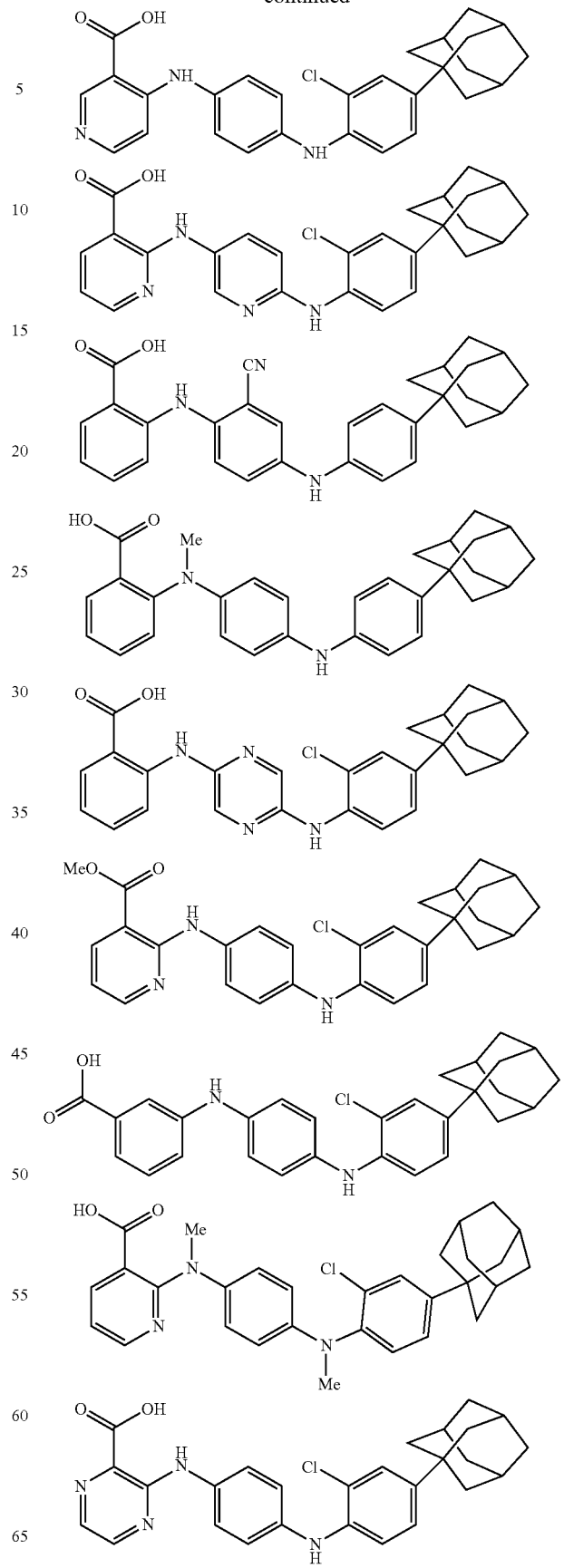

723
-continued
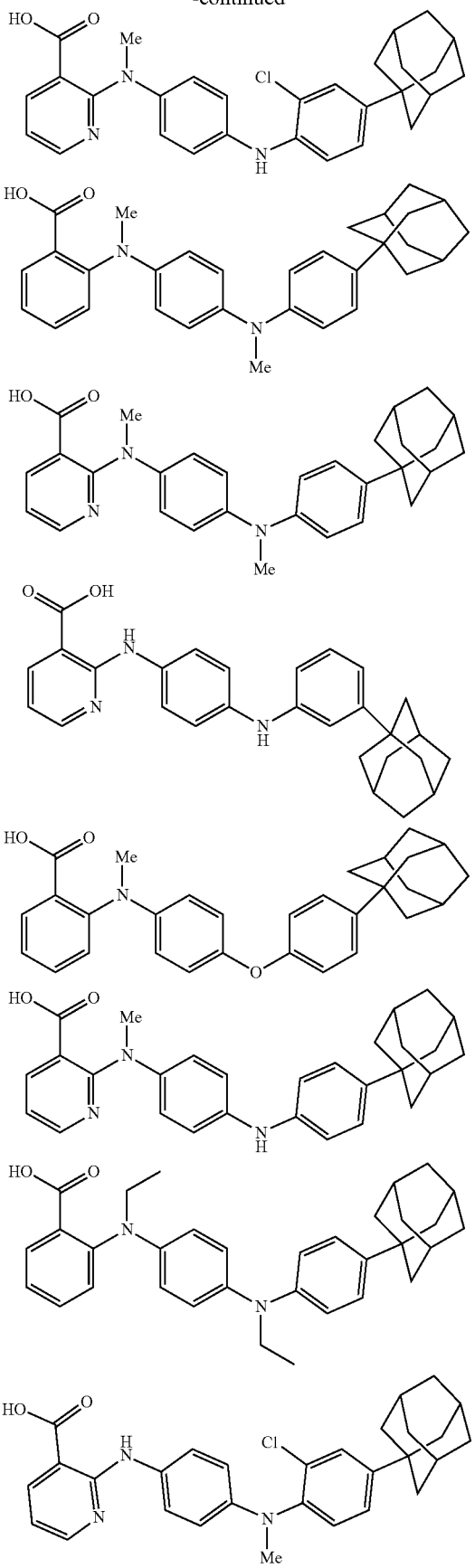
724
-continued
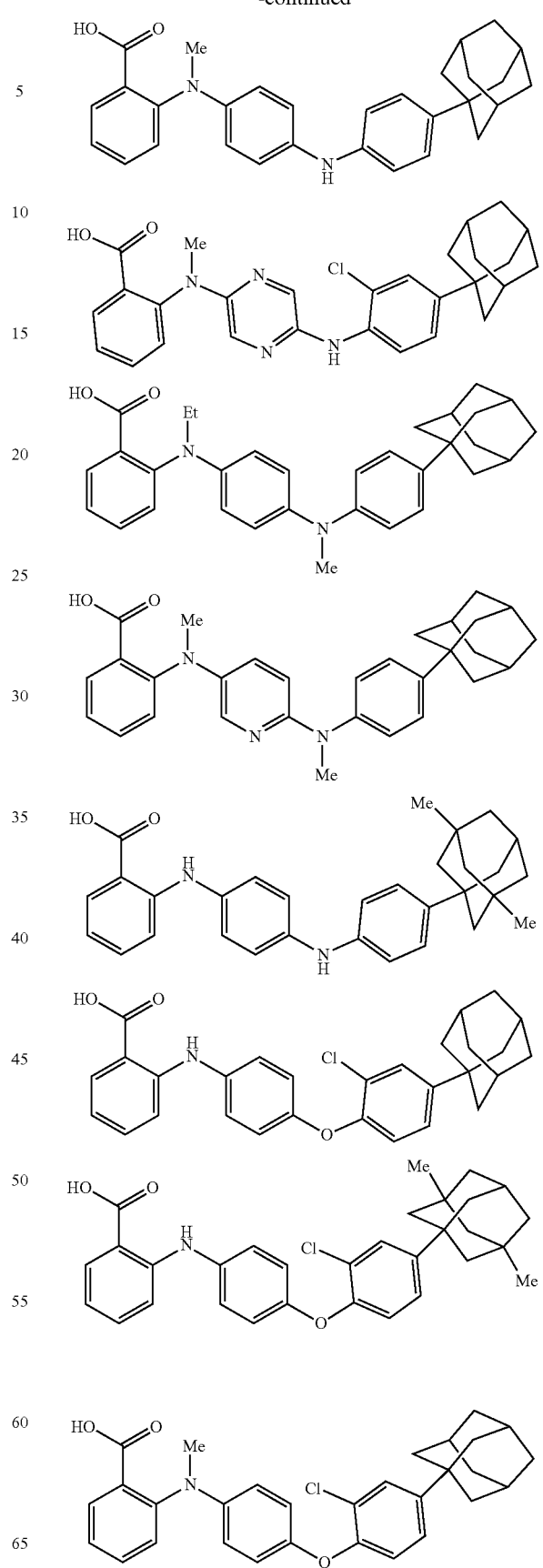

725
-continued
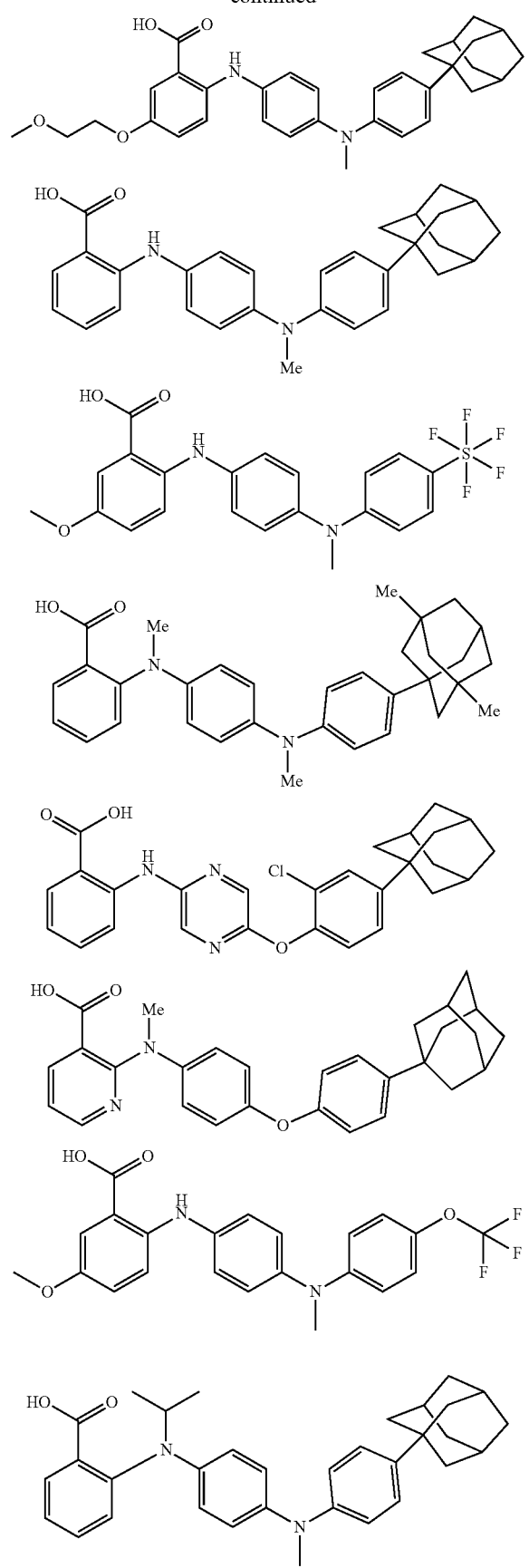
726
-continued
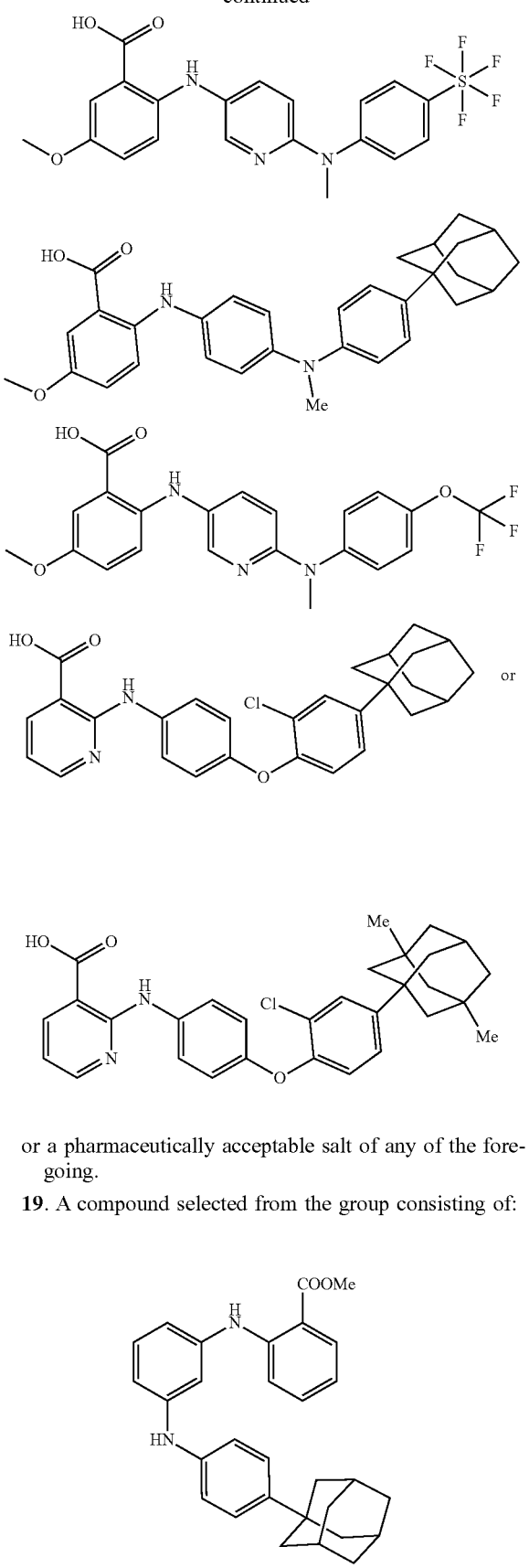
or a pharmaceutically acceptable salt of any of the foregoing.
19. A compound selected from the group consisting of:

727
-continued
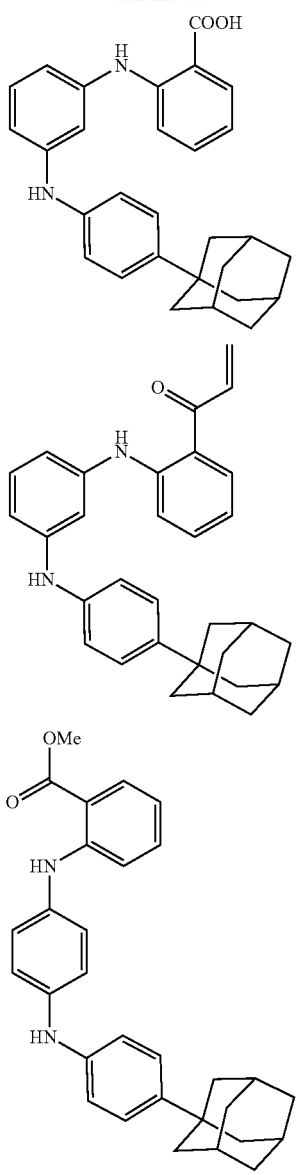
728
-continued
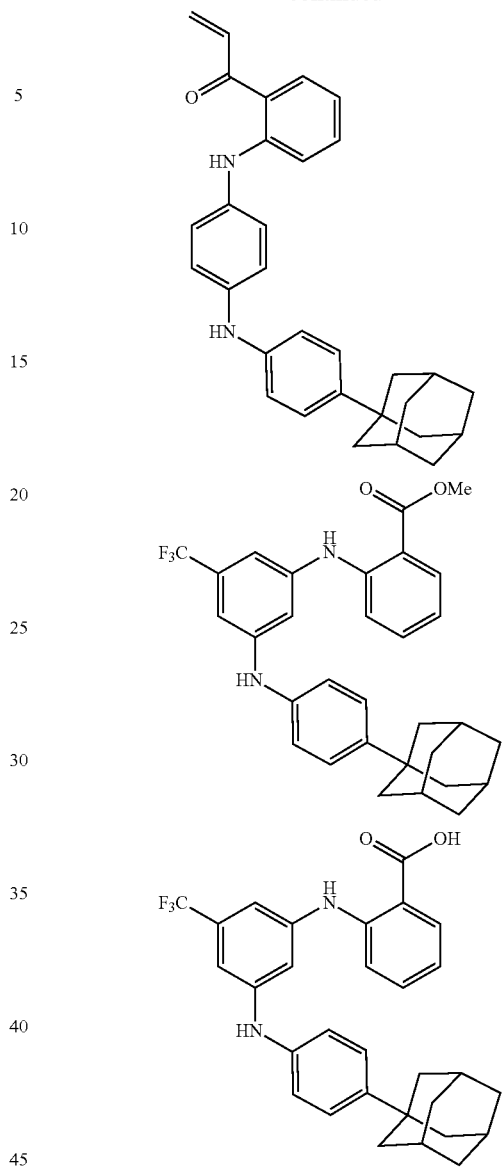
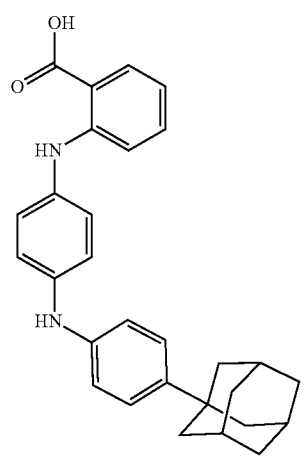

729
-continued
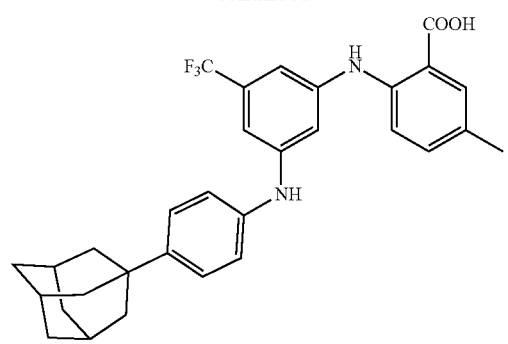
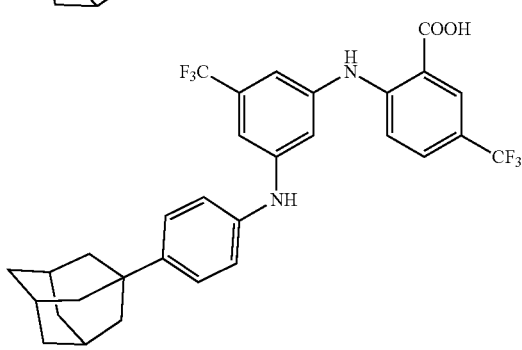
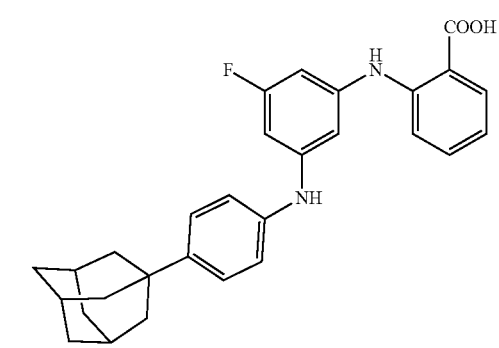
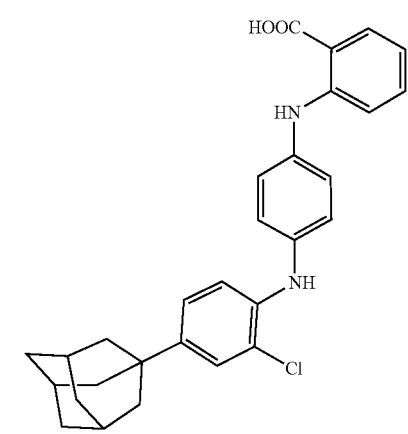
730
-continued
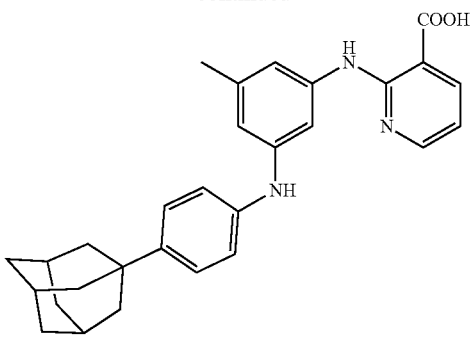
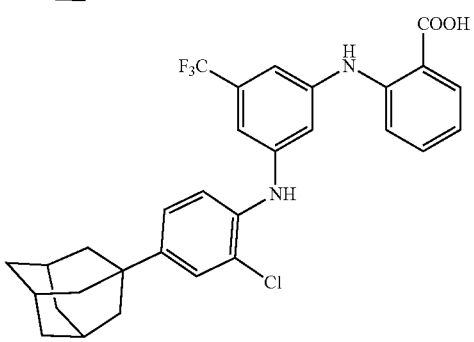
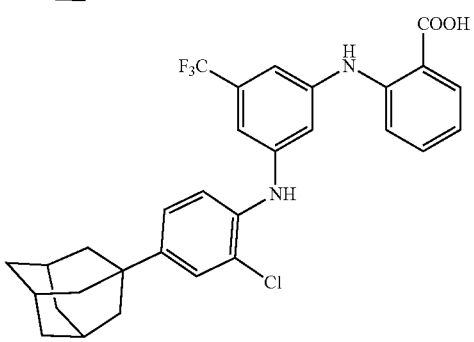
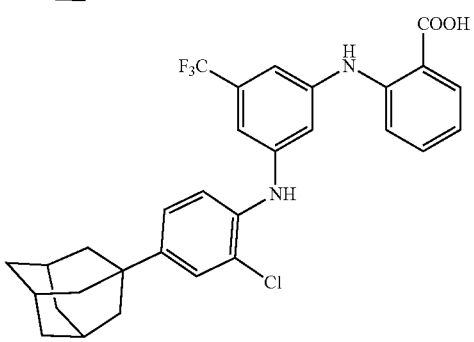
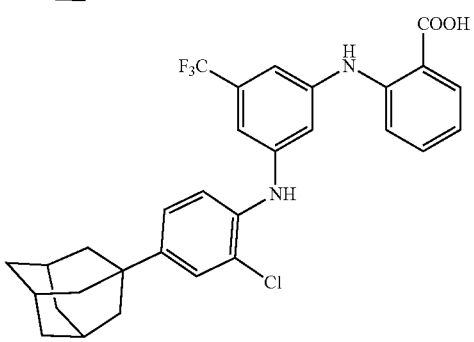
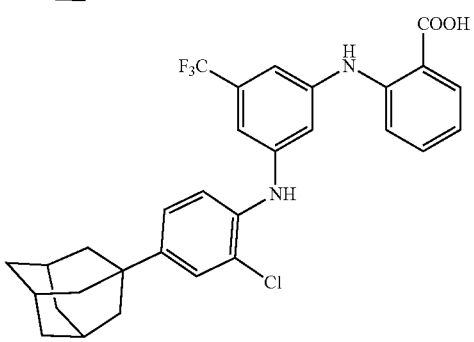
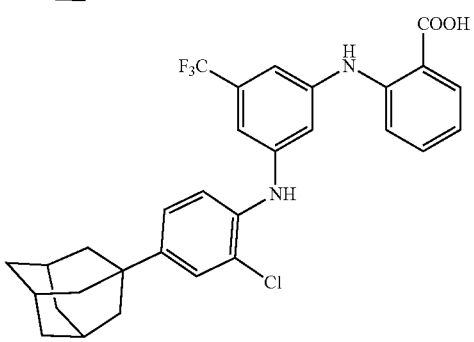
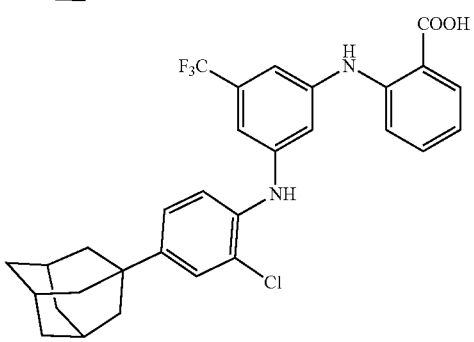

731
-continued
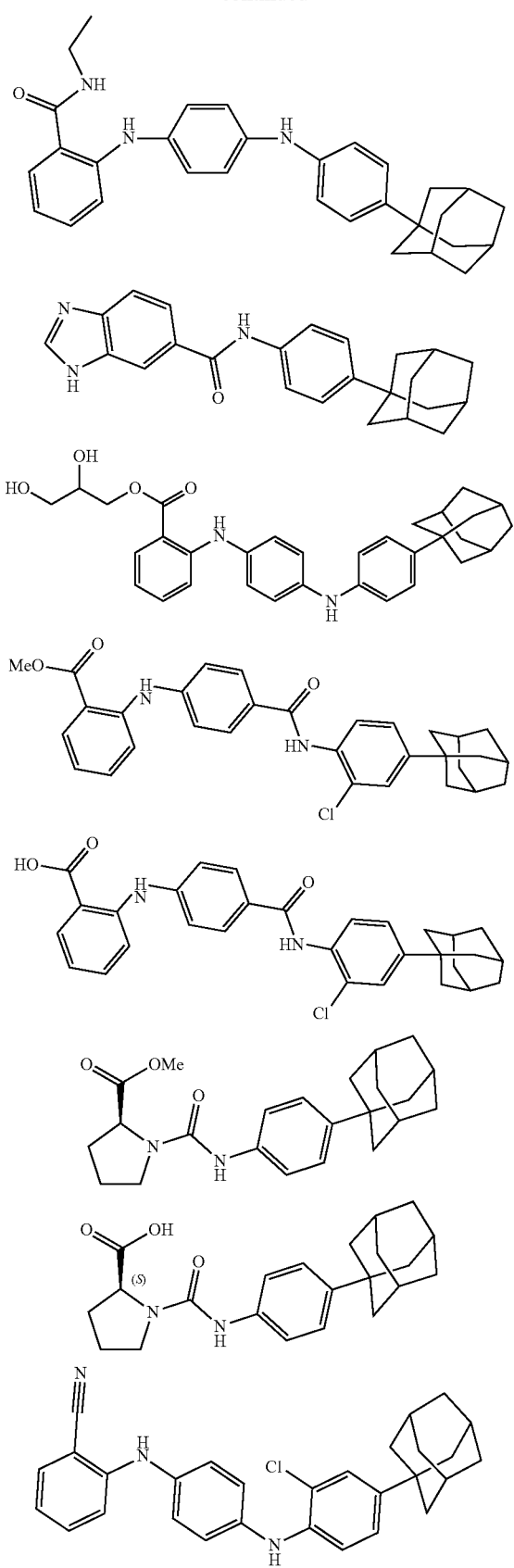
732
-continued
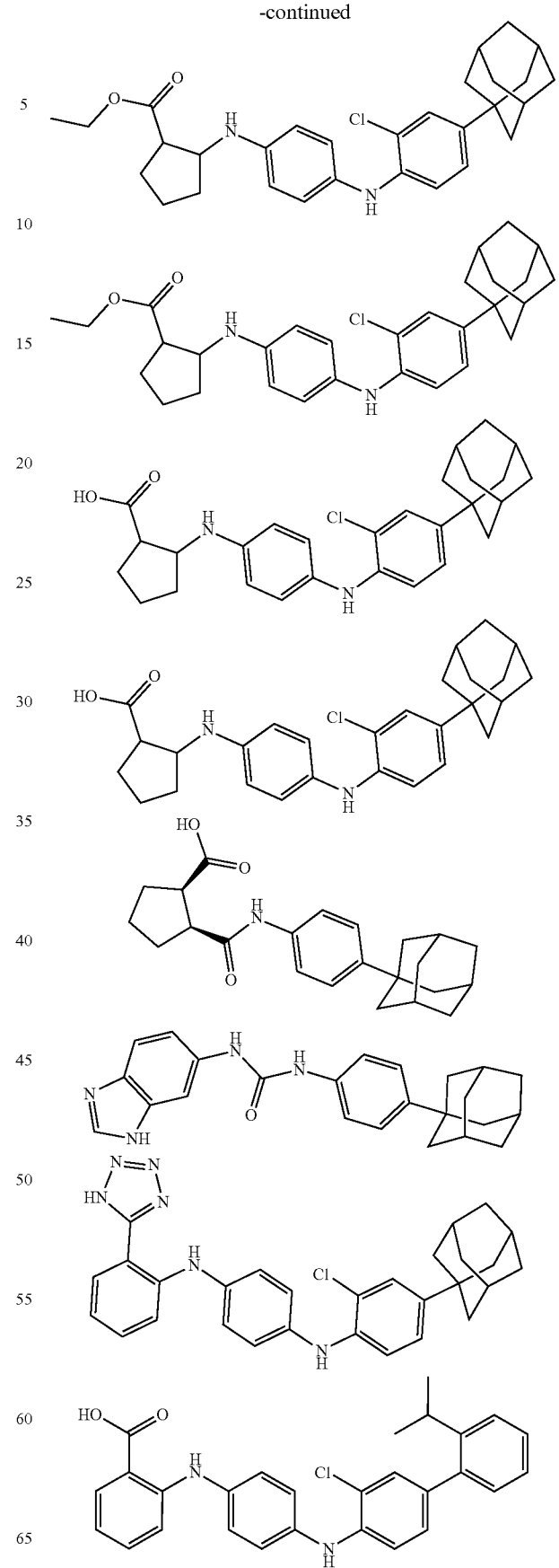

733
-continued
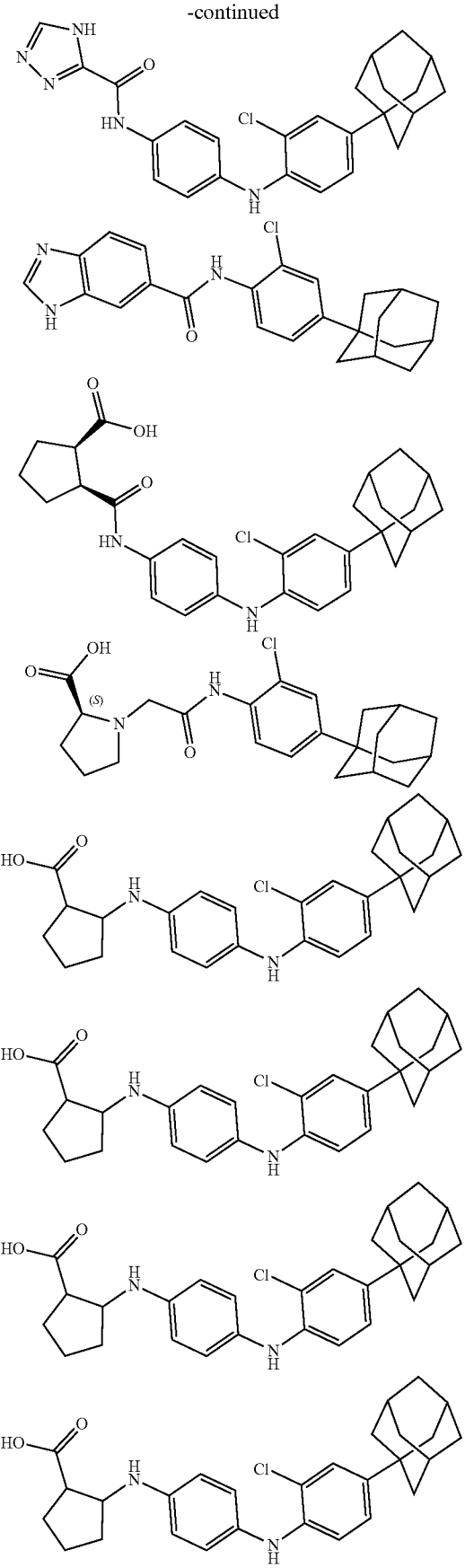
734
-continued
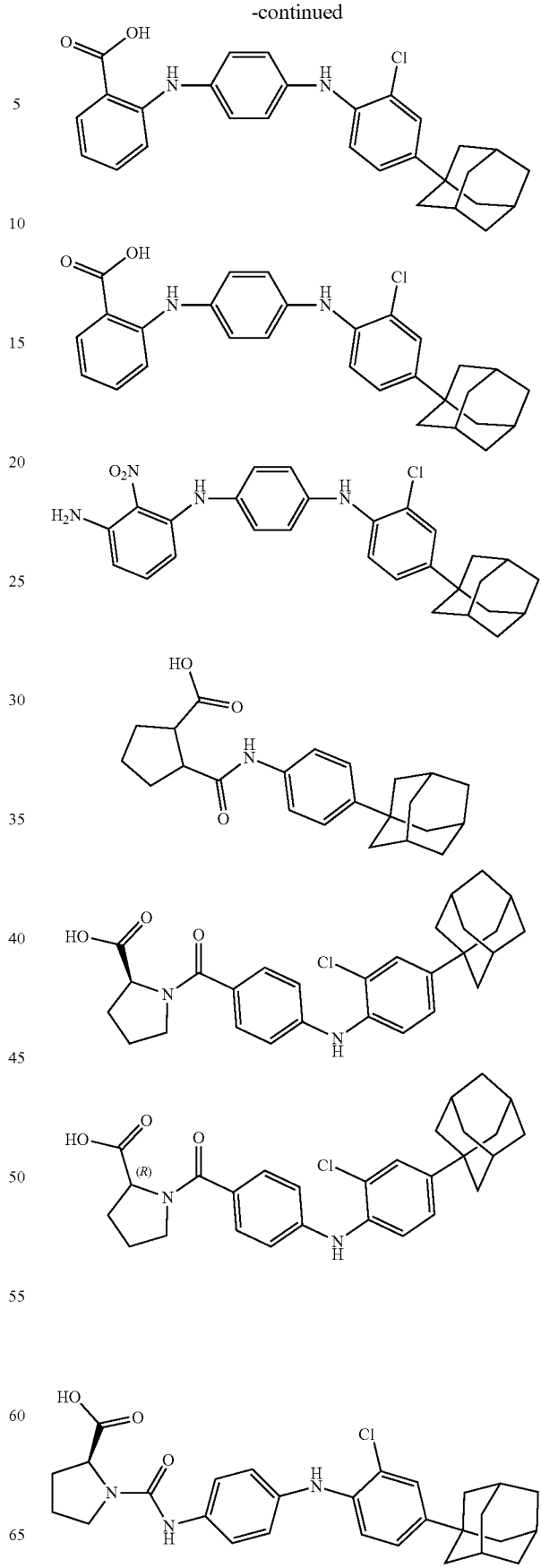

735
-continued
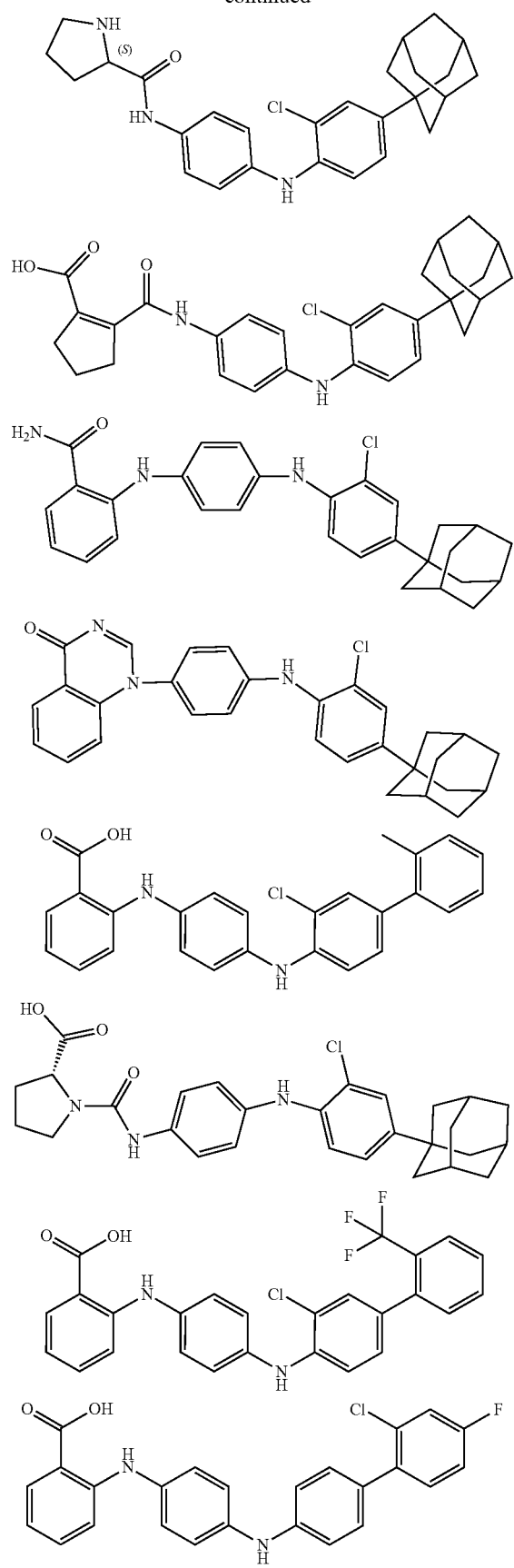
736
-continued
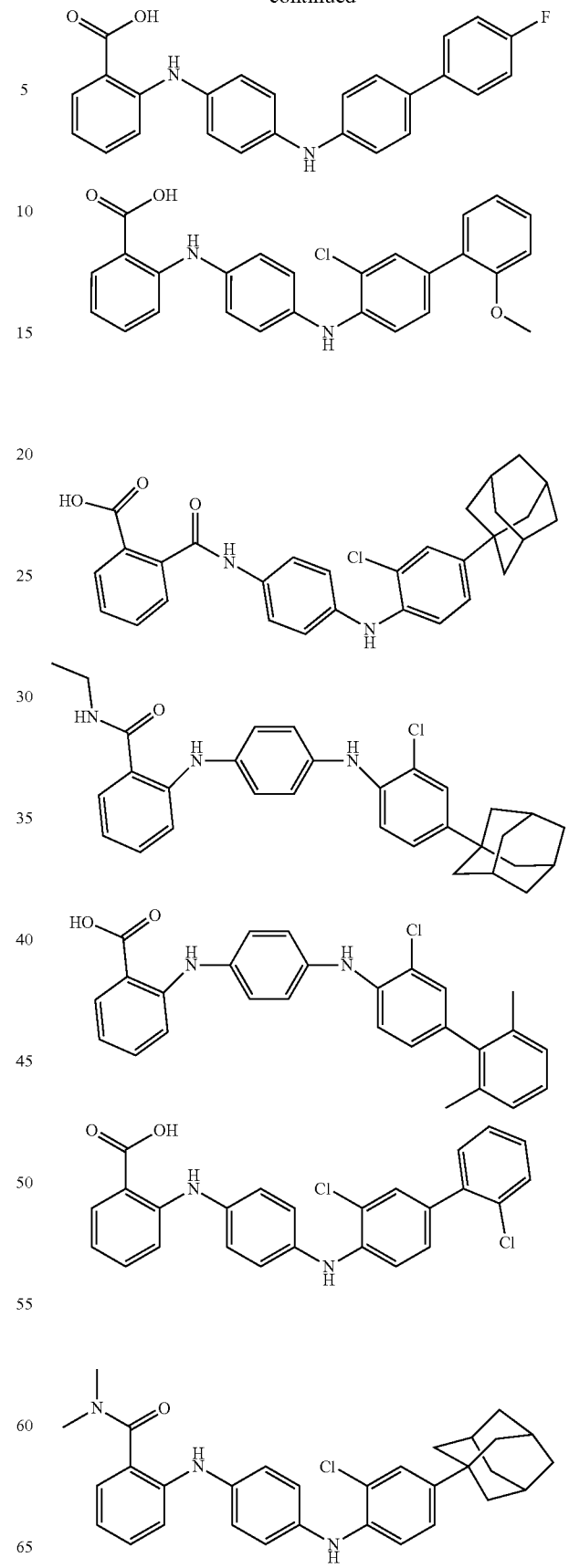

737
-continued
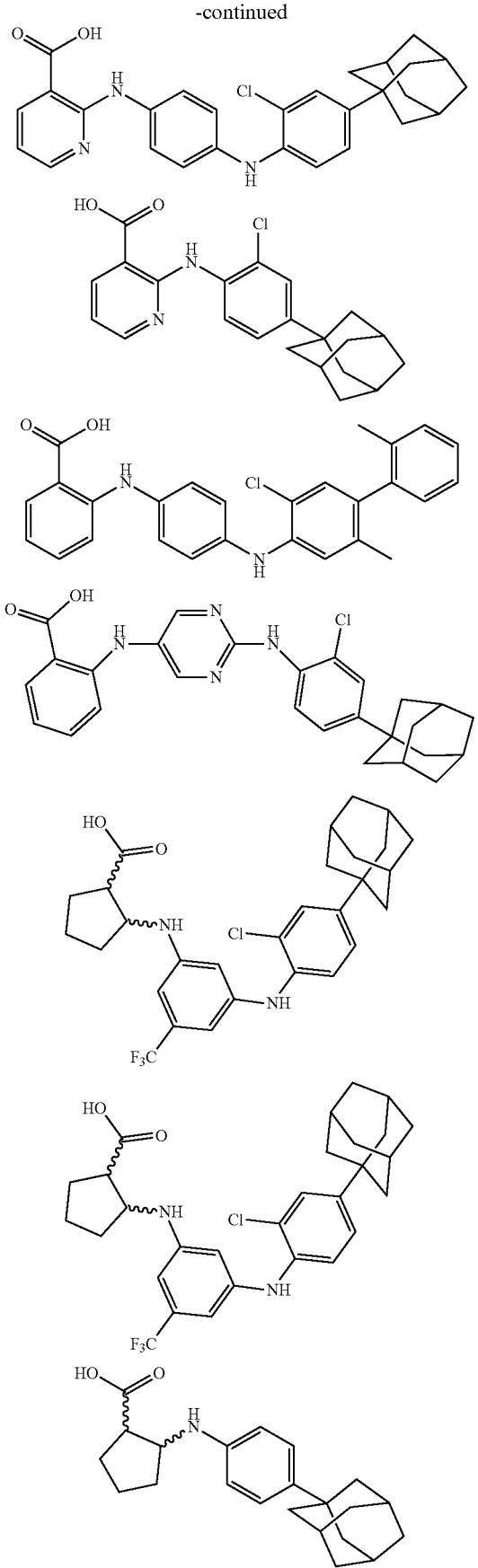
738
-continued
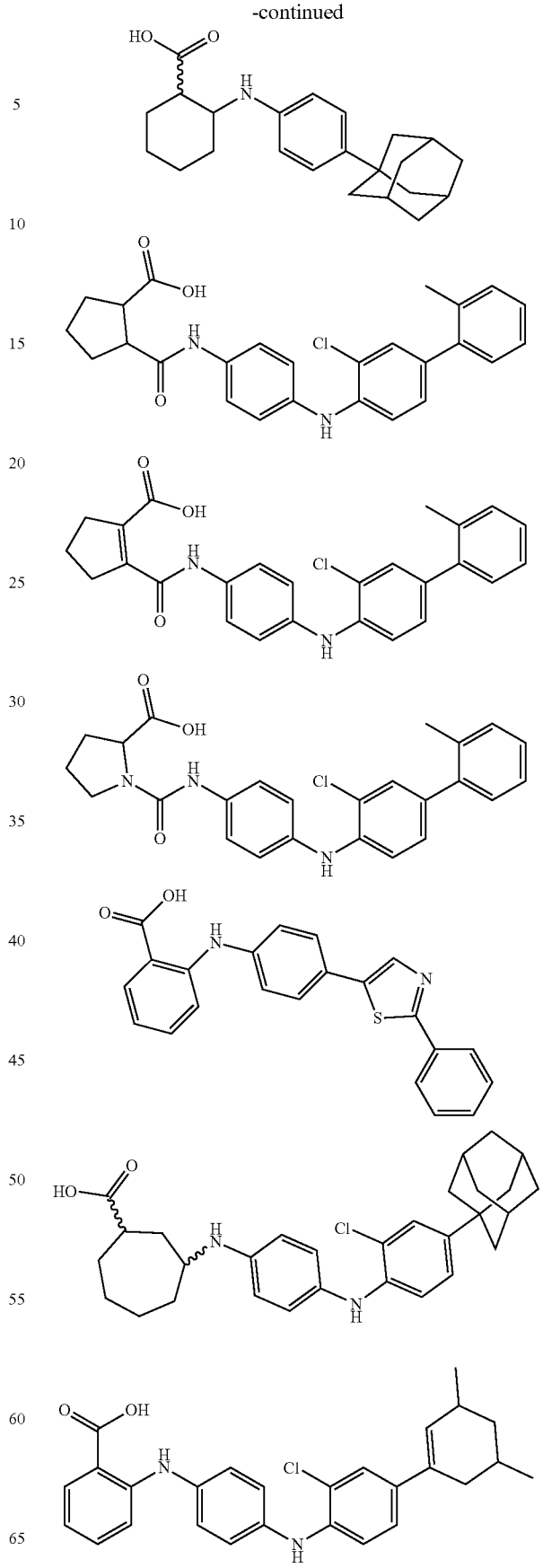

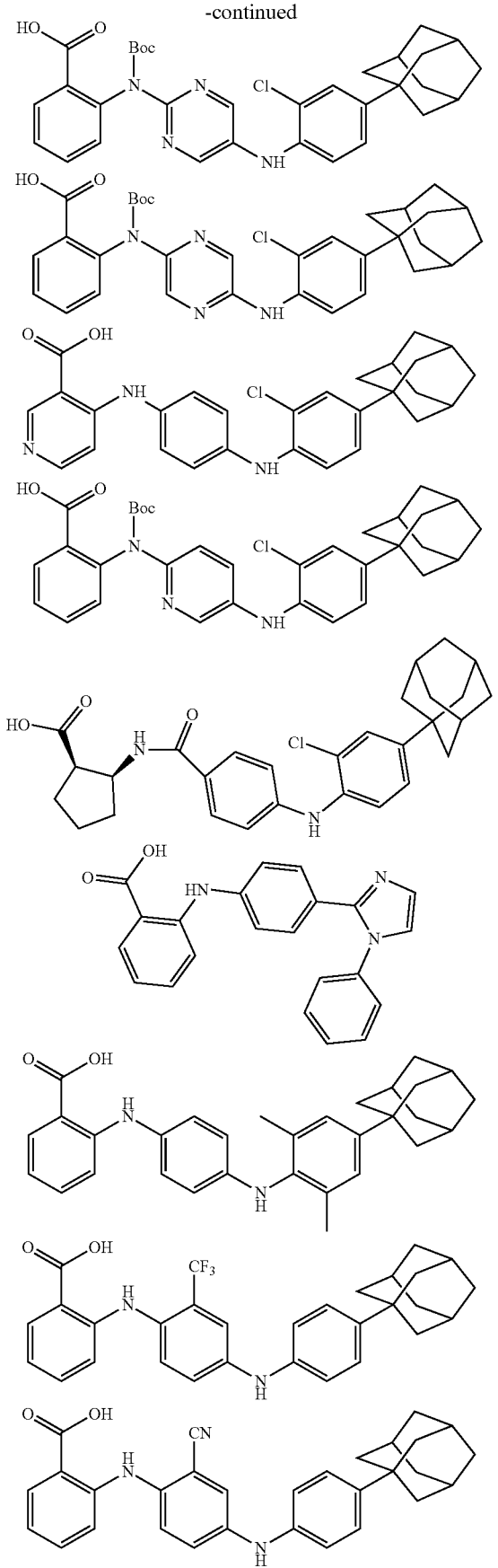
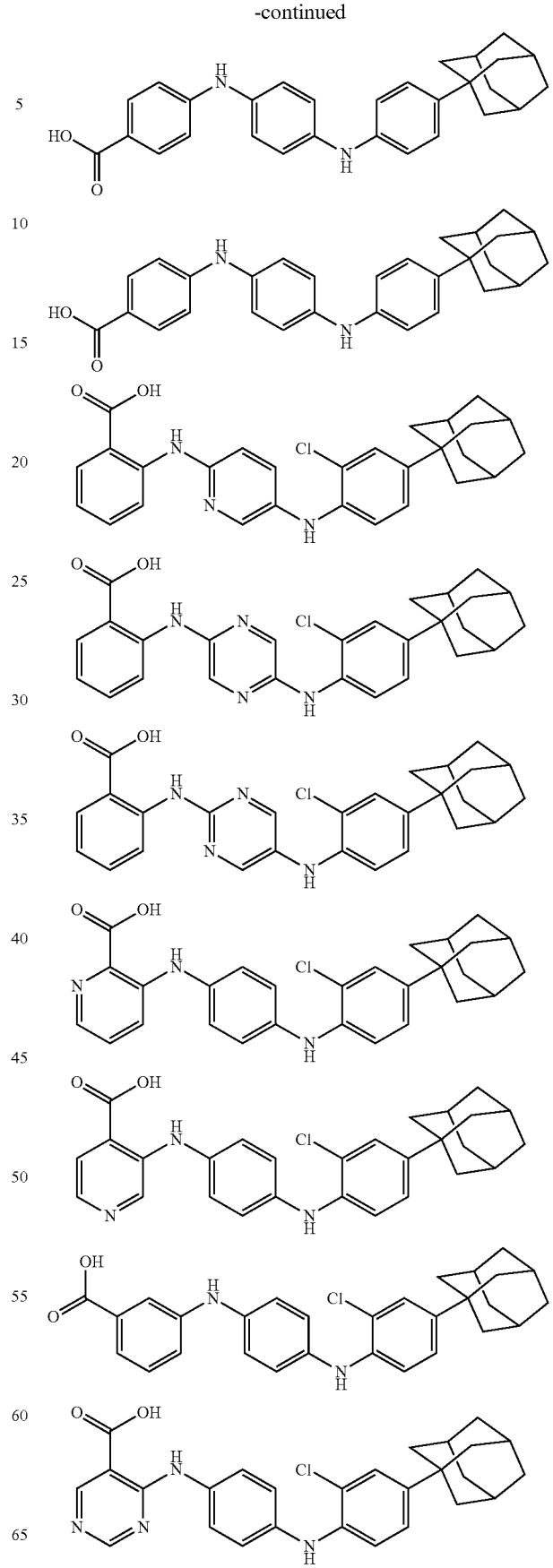

741
-continued
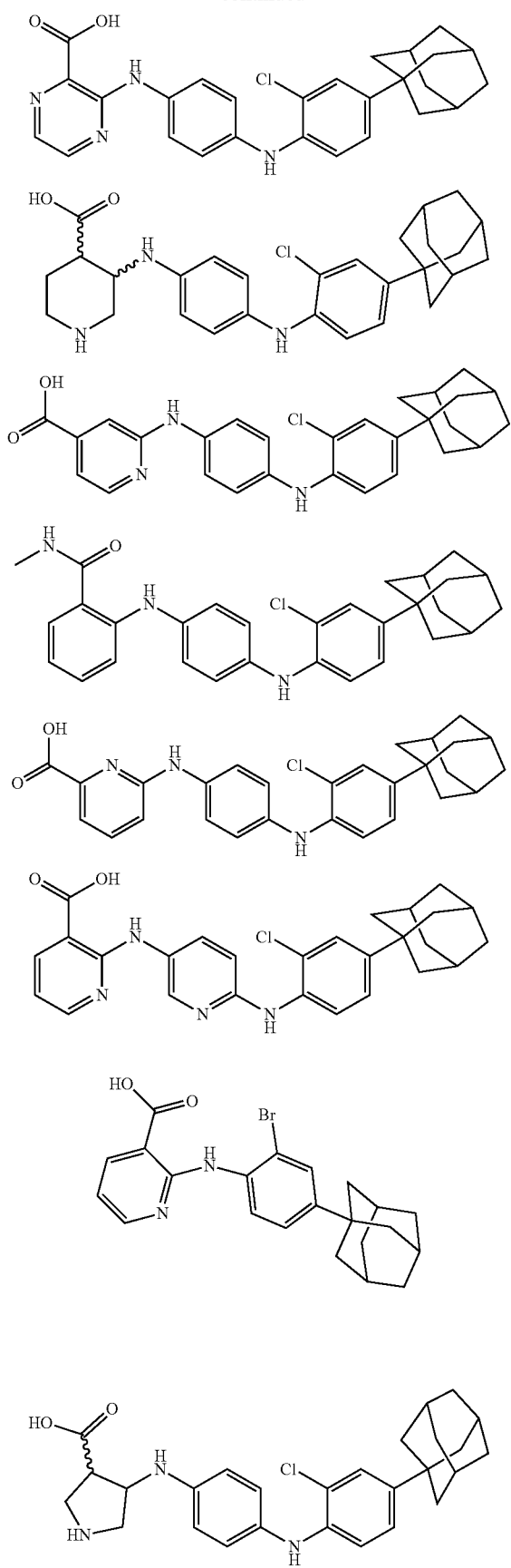
742
-continued
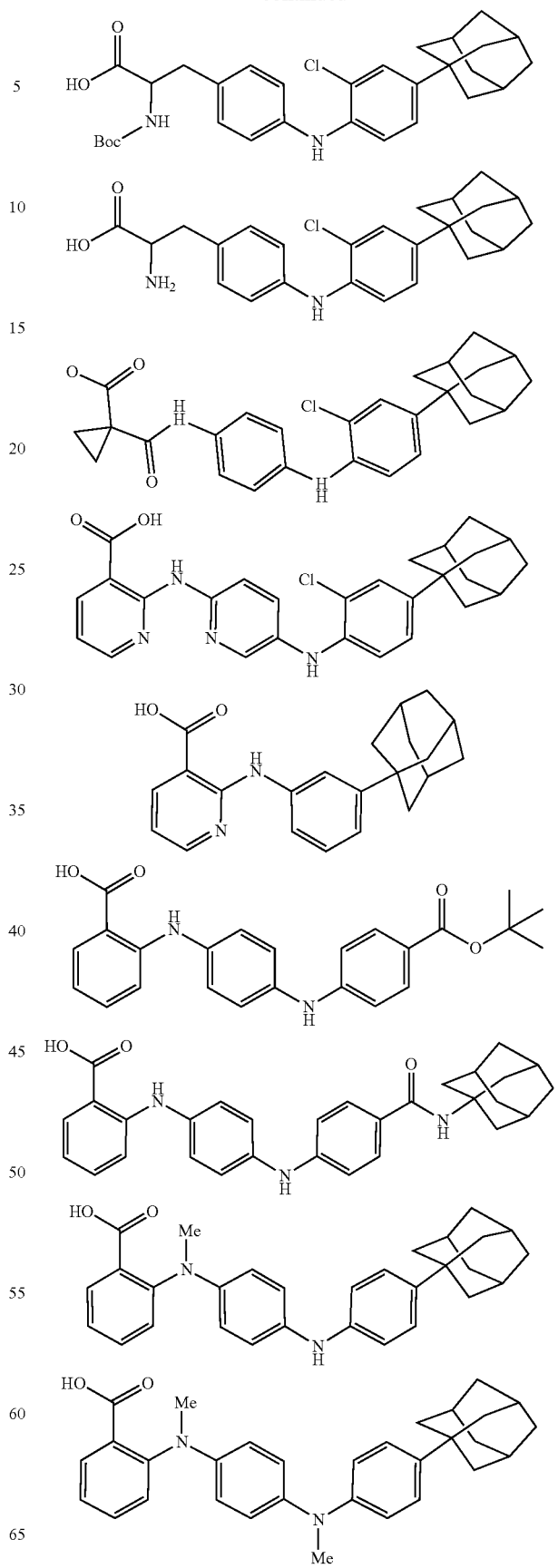

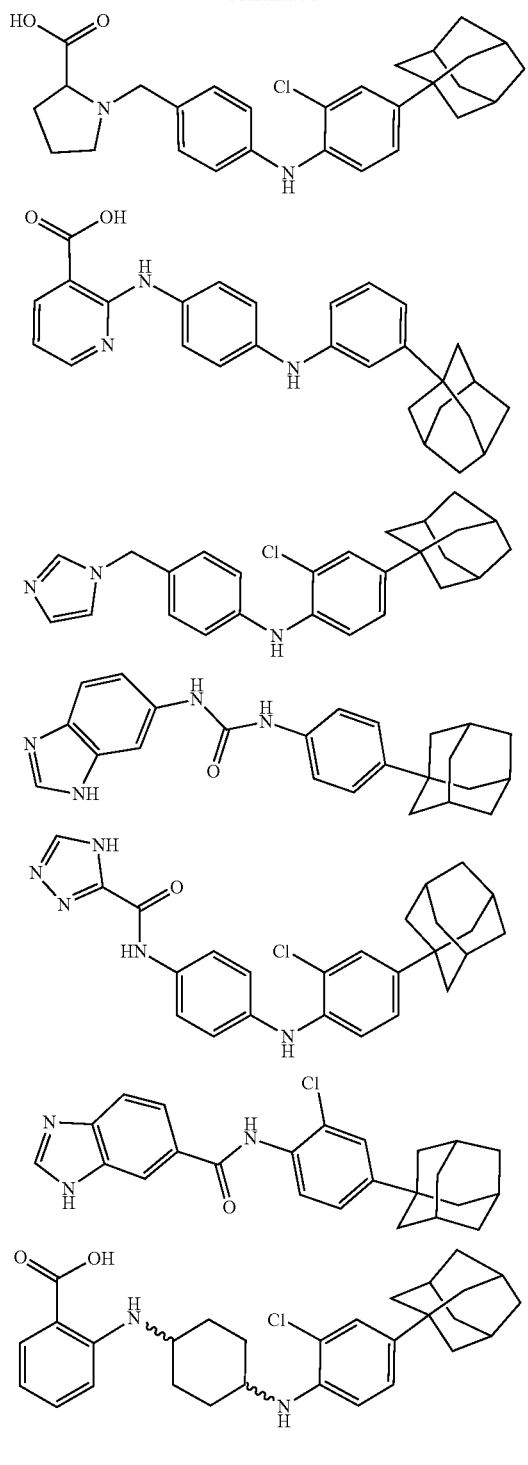
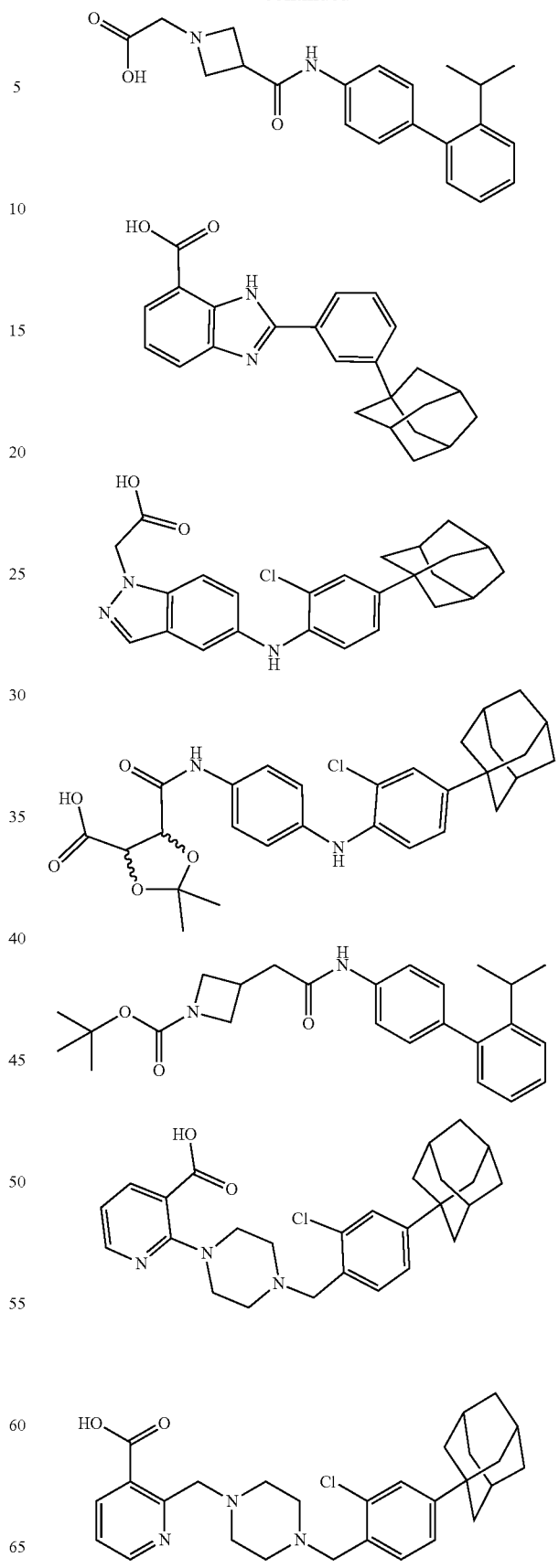

-continued
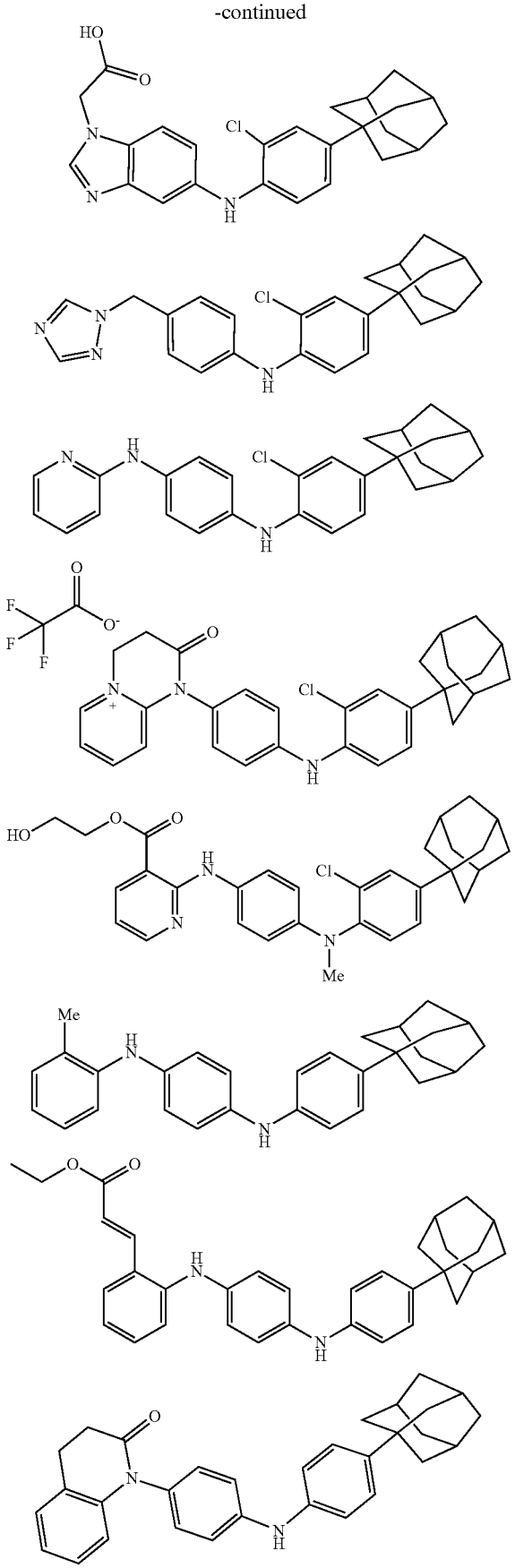
-continued
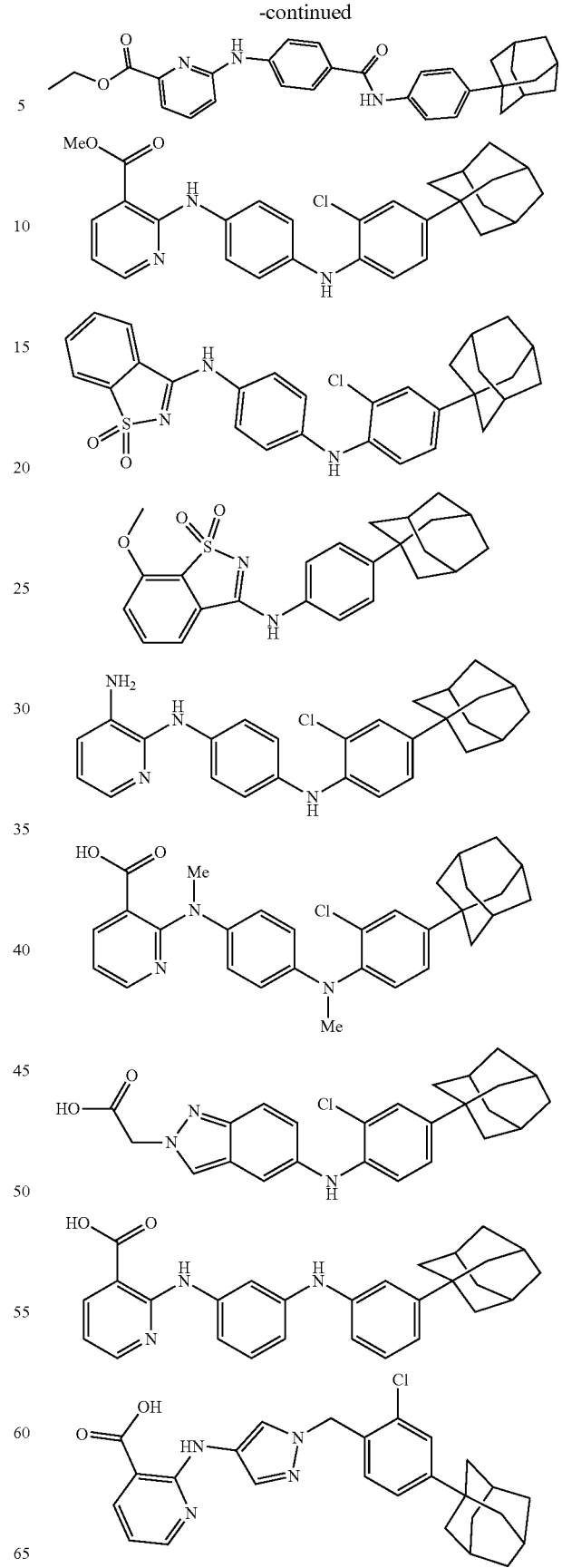

747
-continued
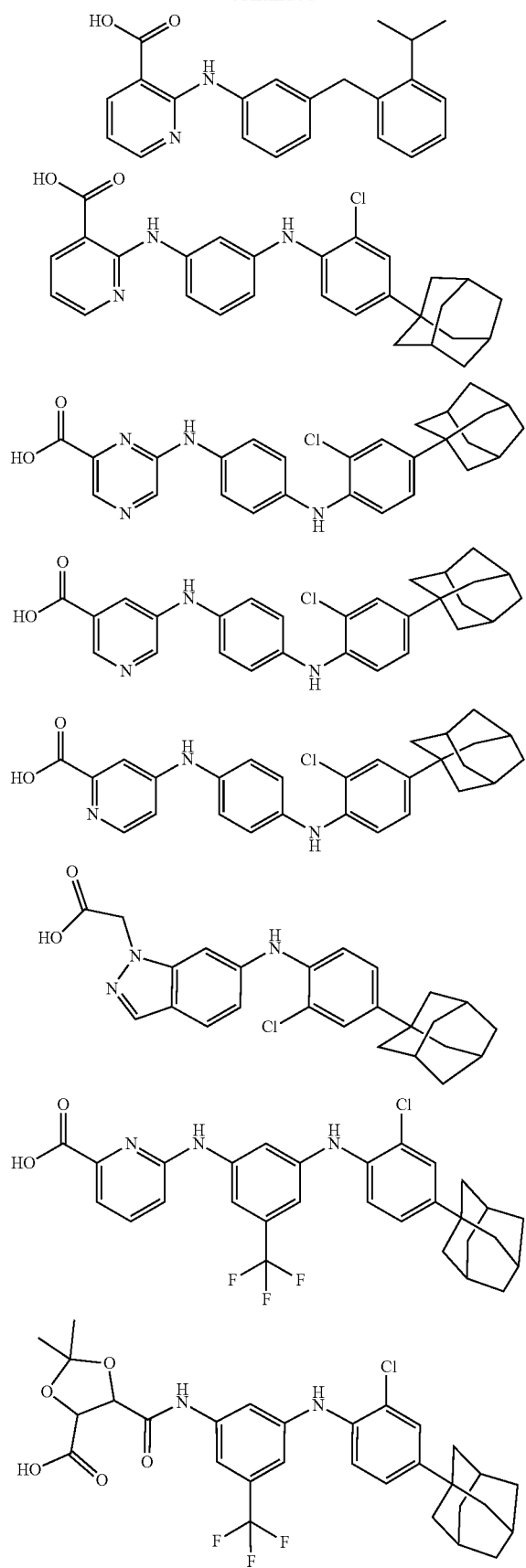
748
-continued
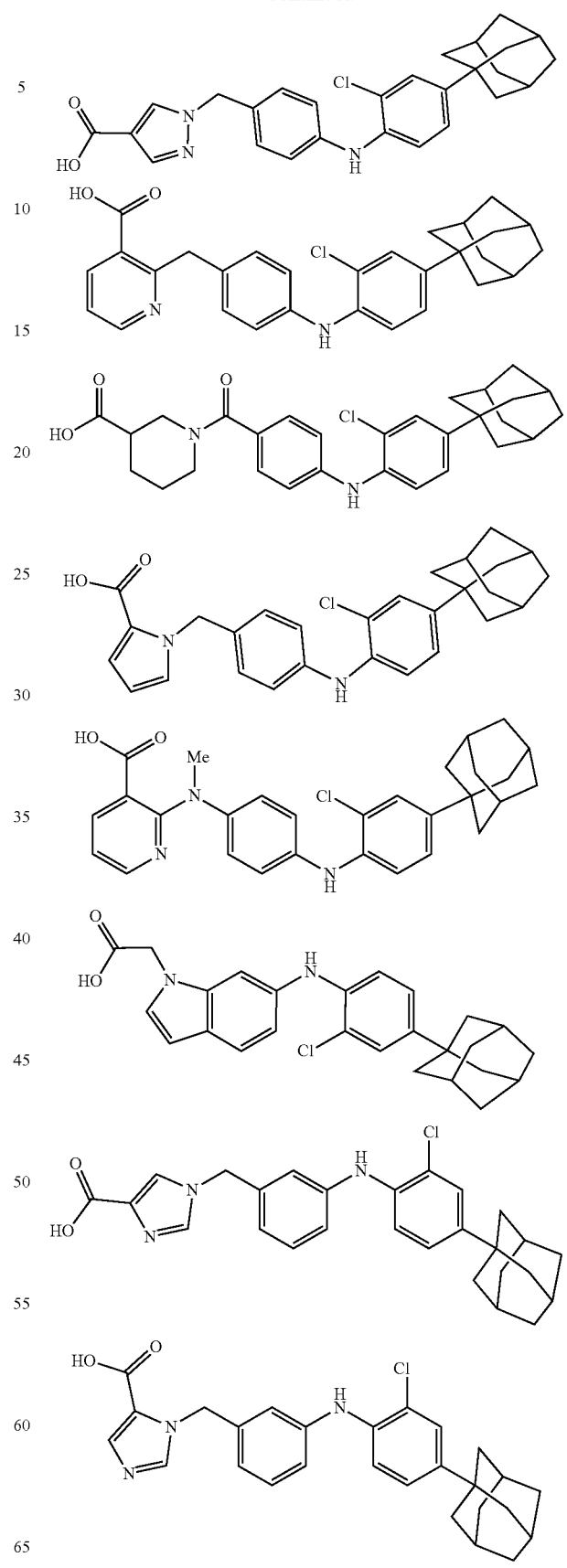

749
-continued
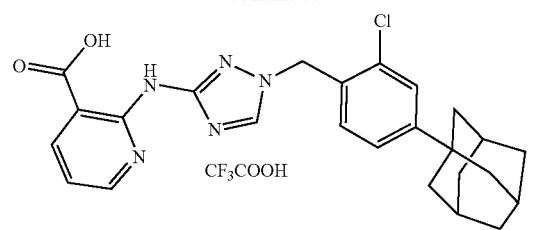
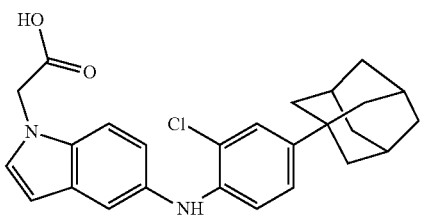
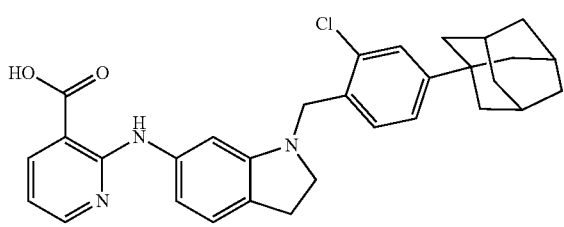
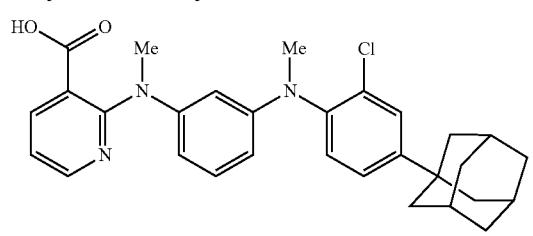
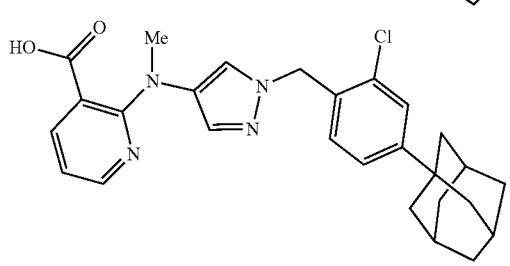
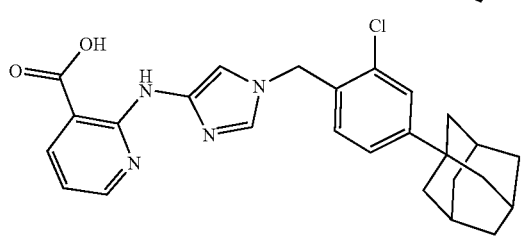
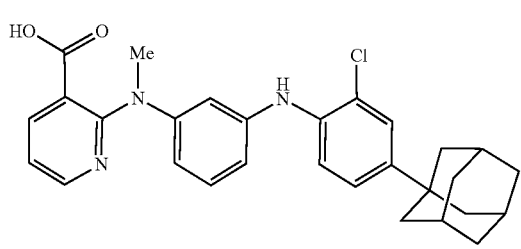
750
-continued
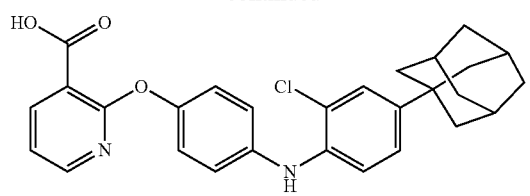
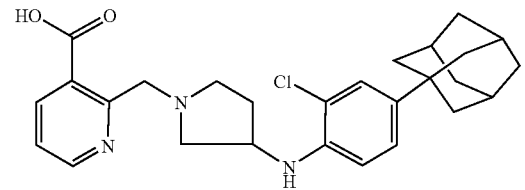
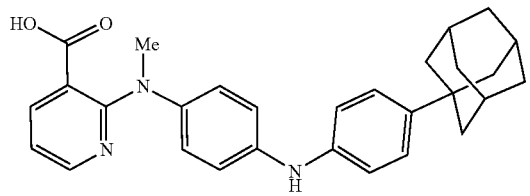
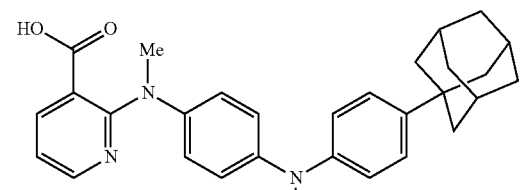
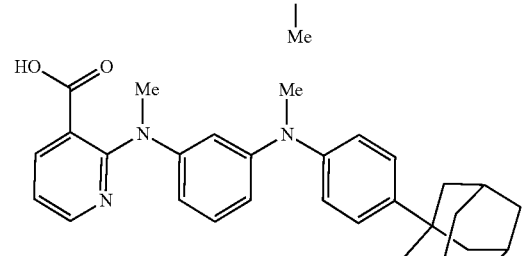
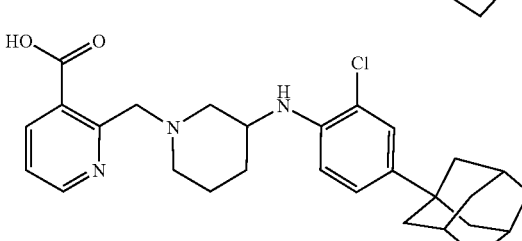
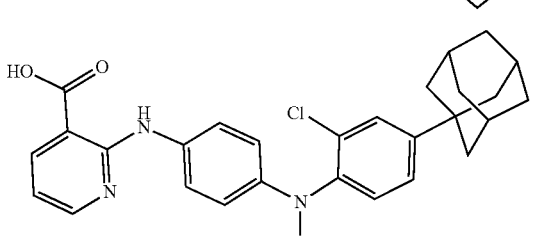
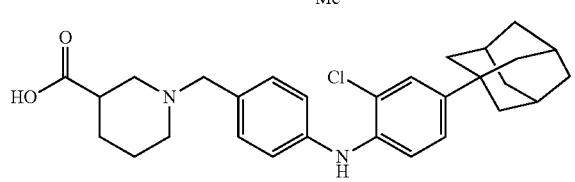

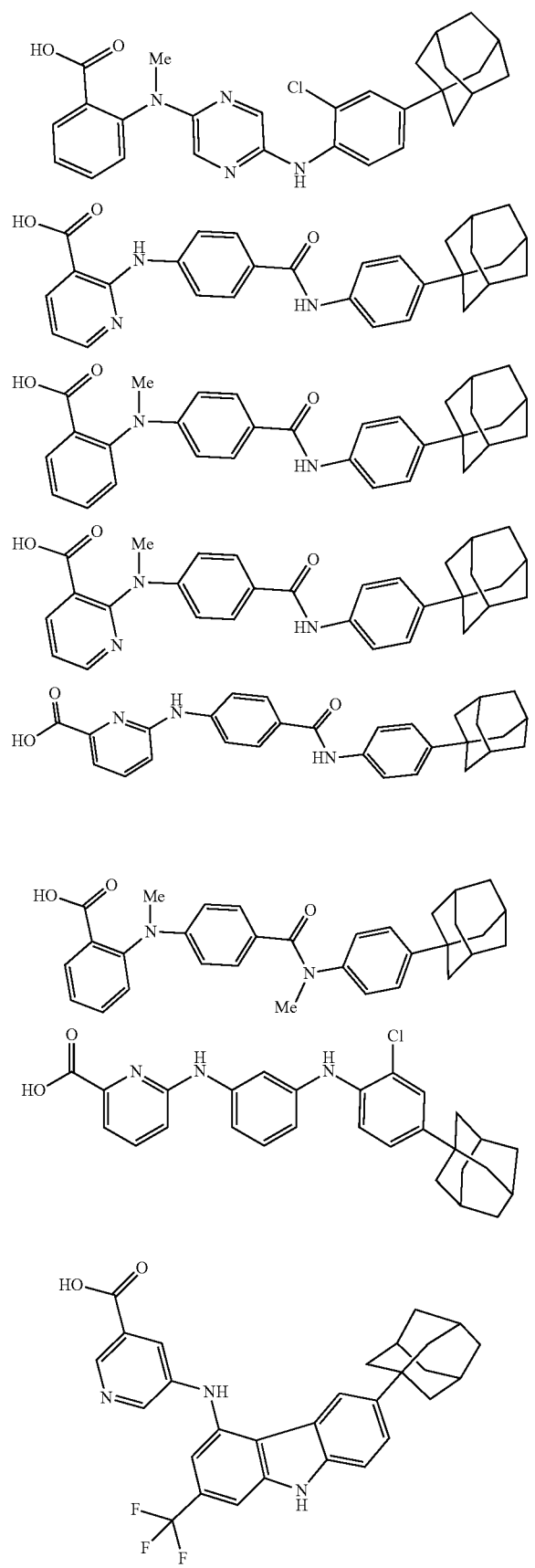
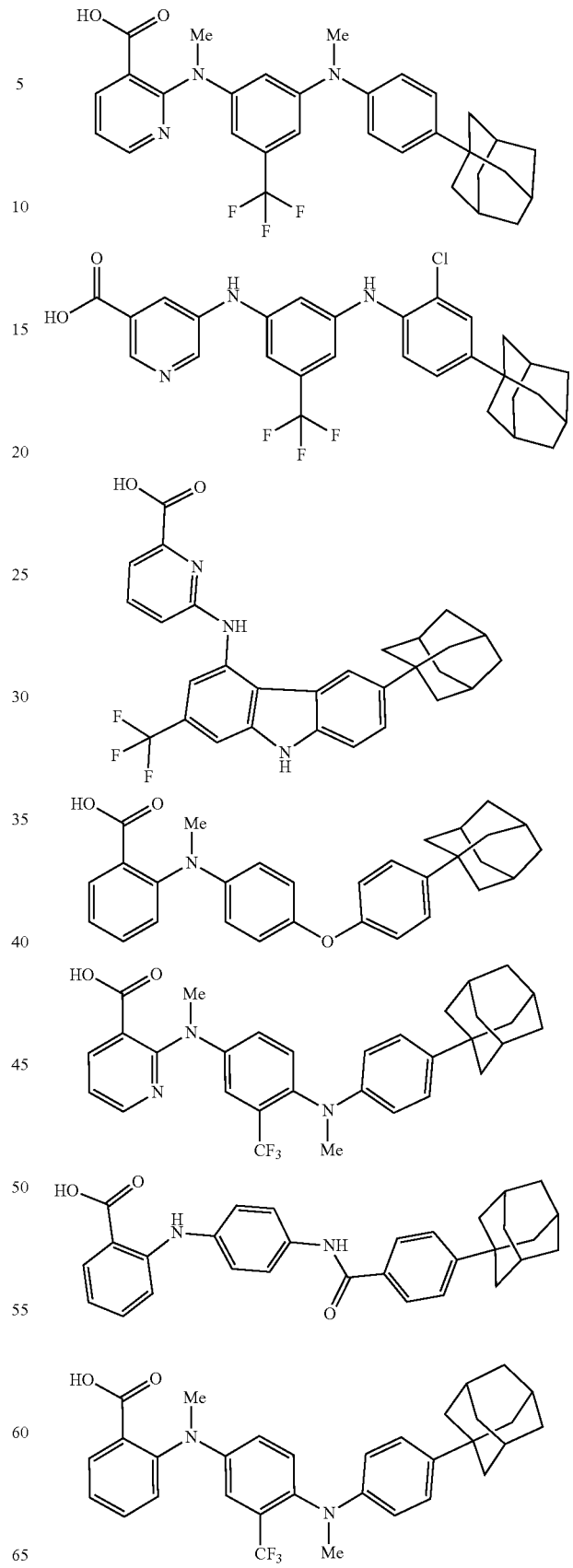

753
-continued
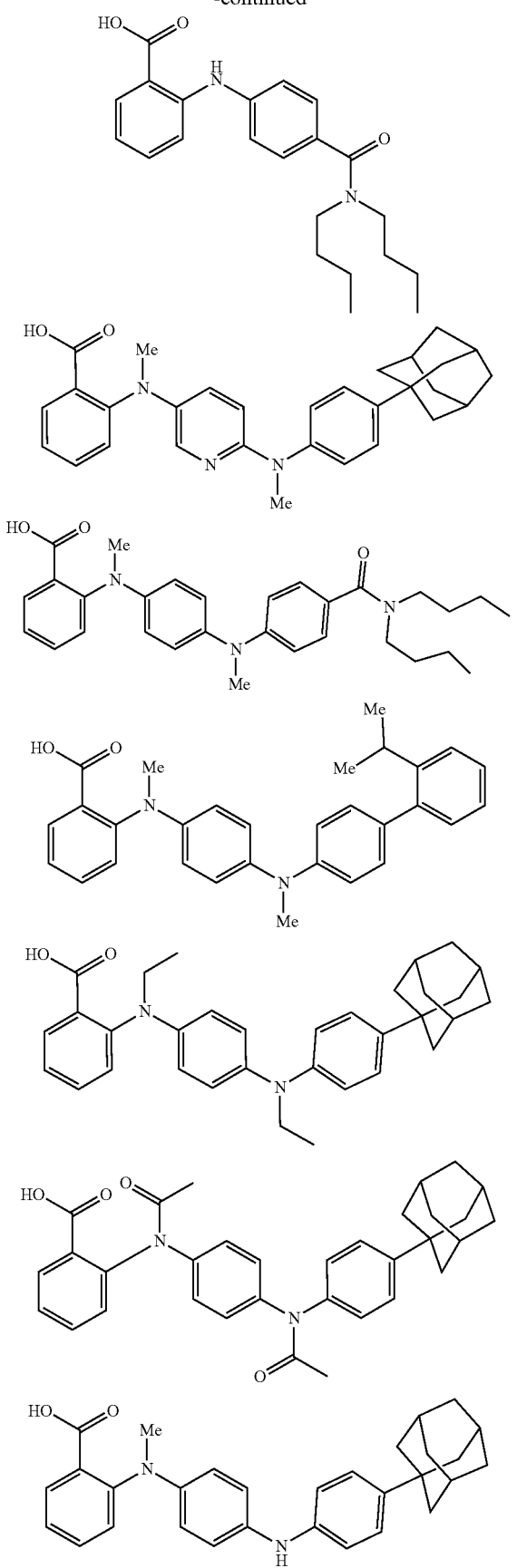
754
-continued
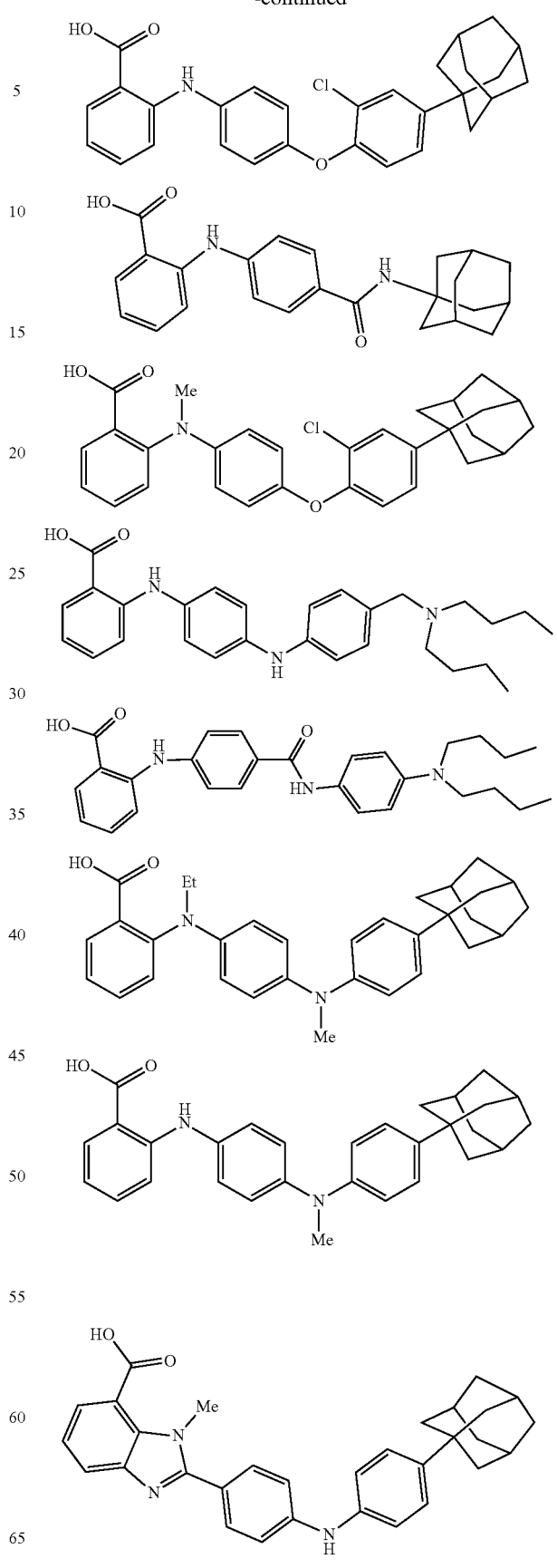

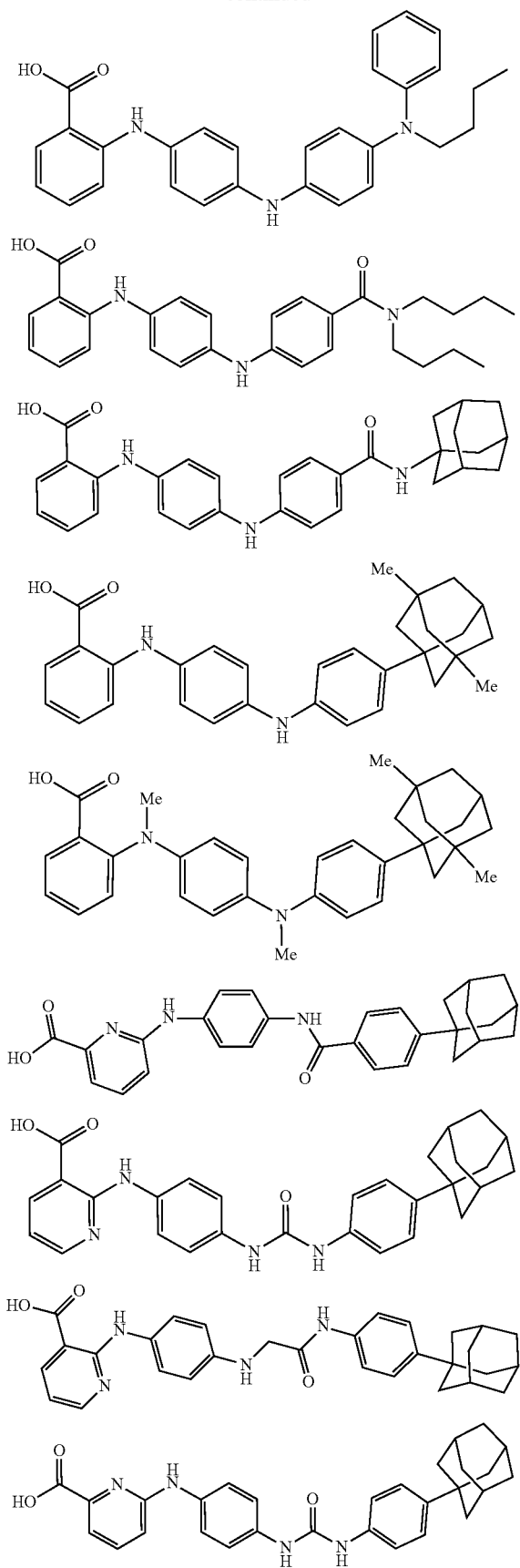
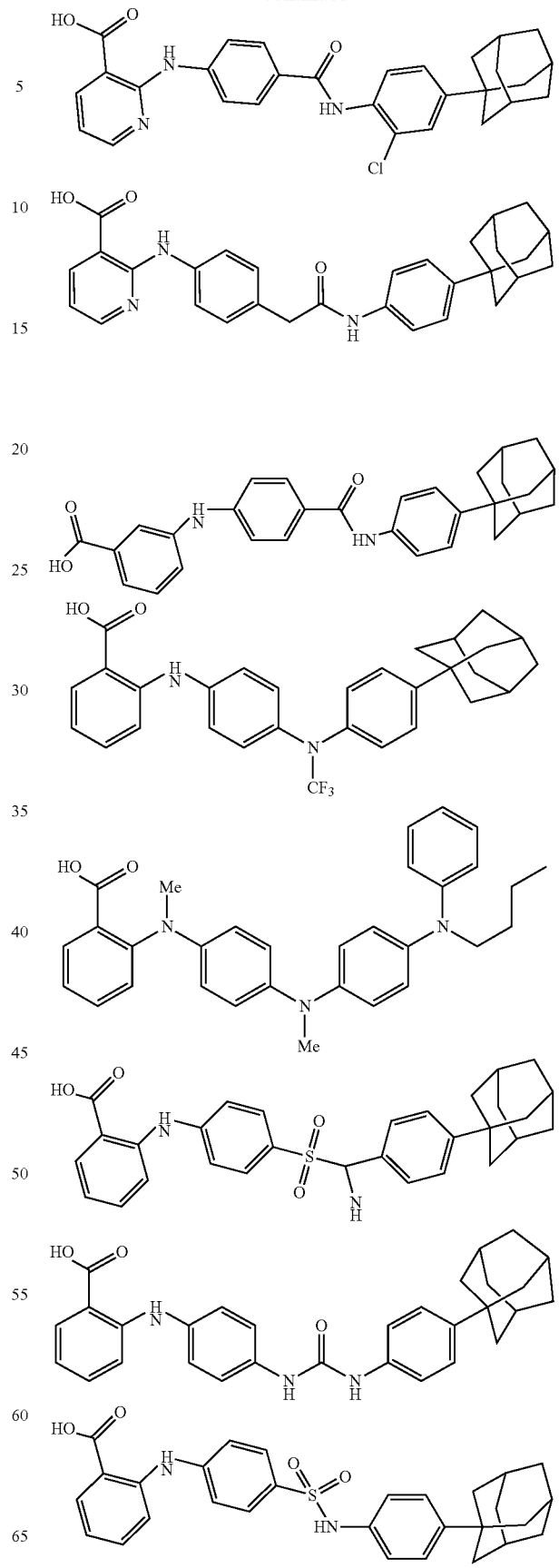

757
-continued
758
-continued
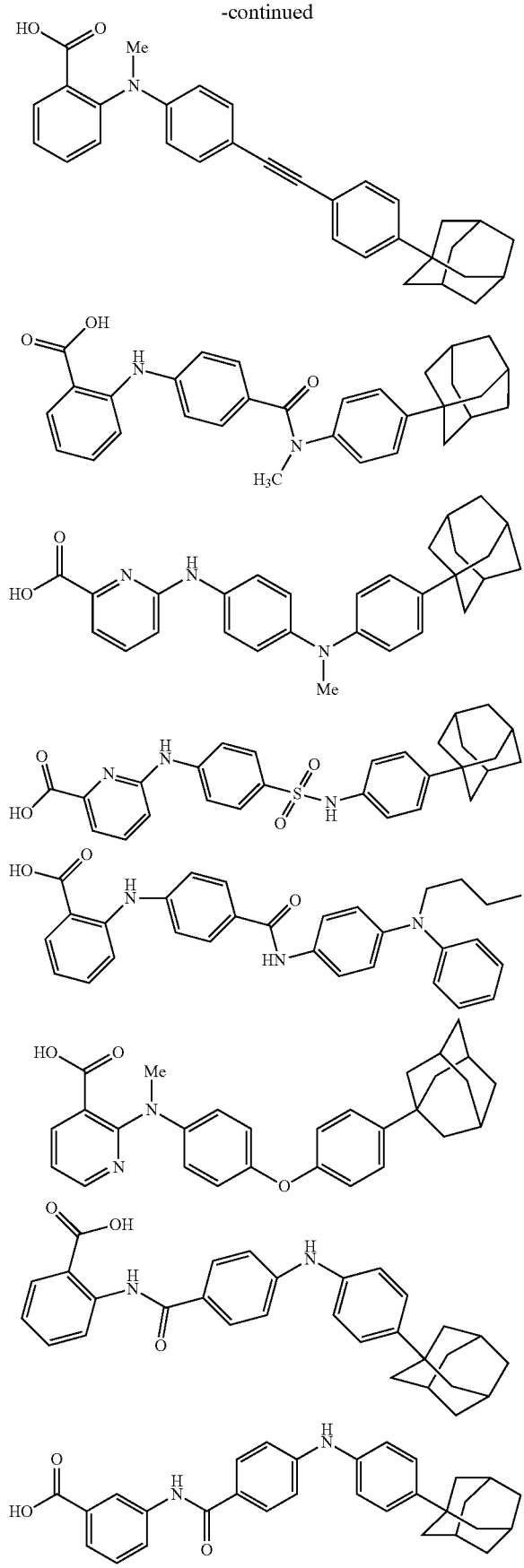
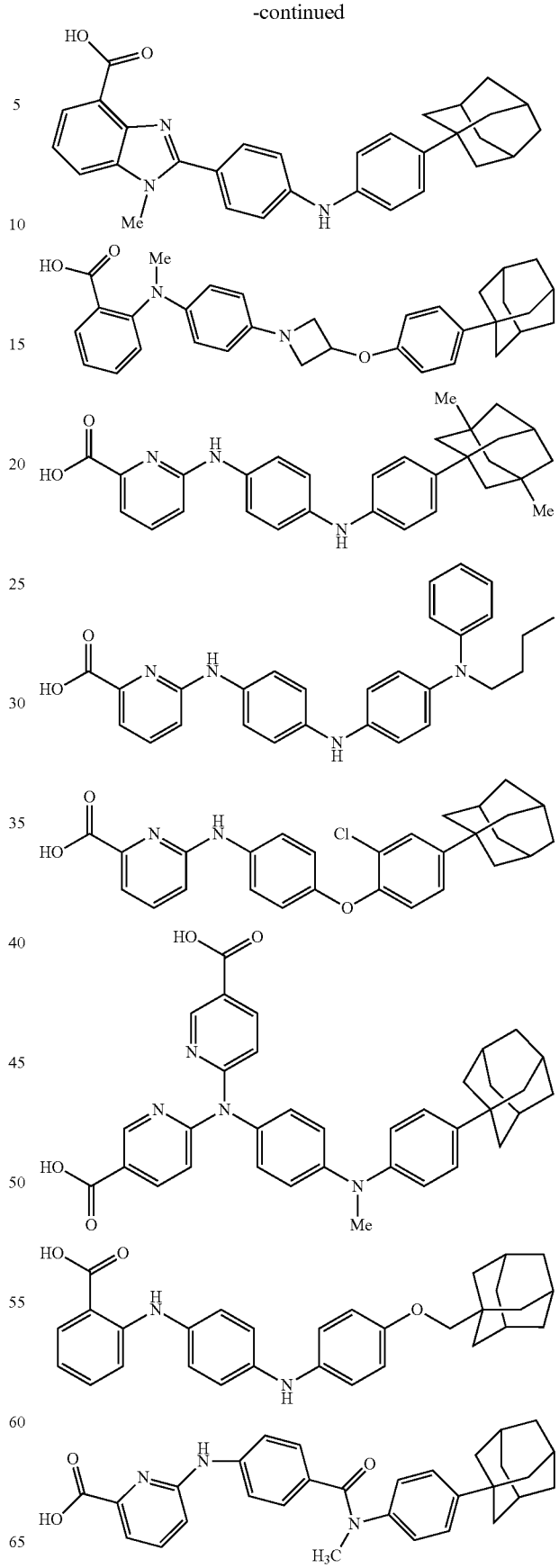

759
-continued
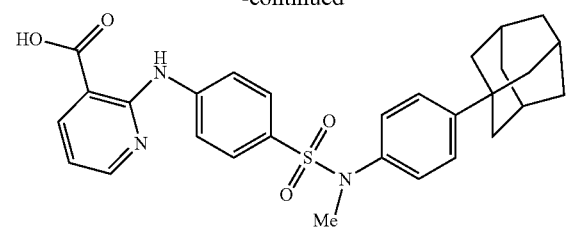
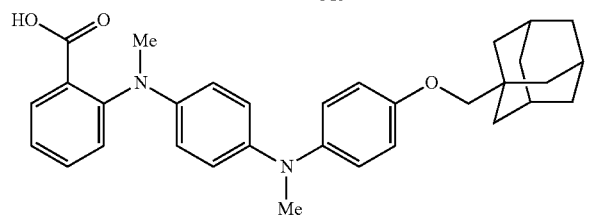
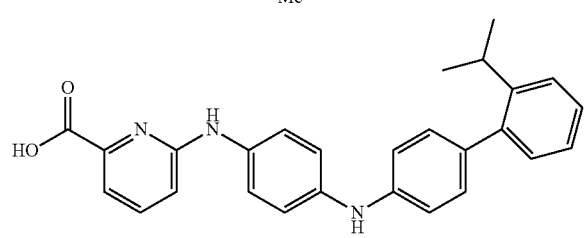
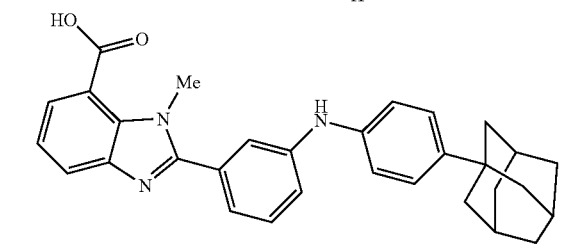
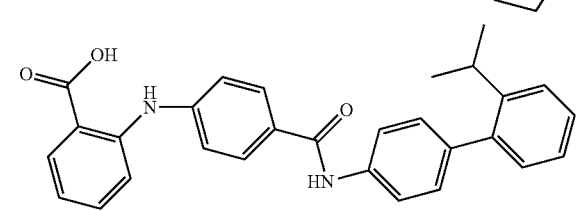
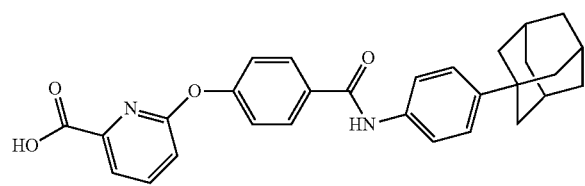
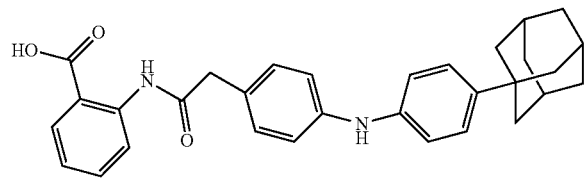
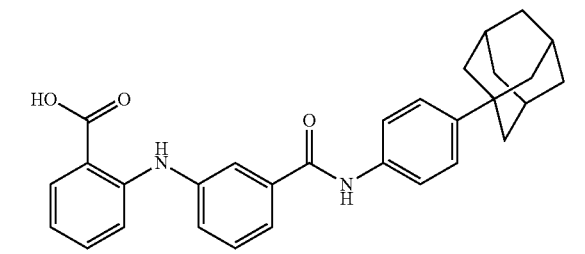
760
-continued
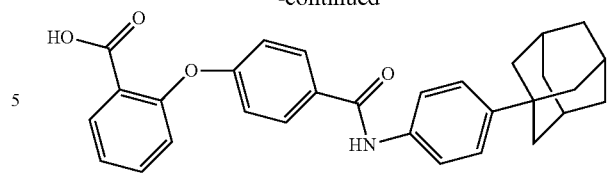
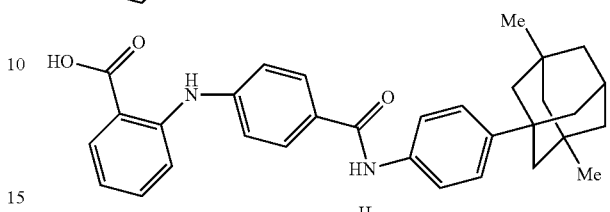
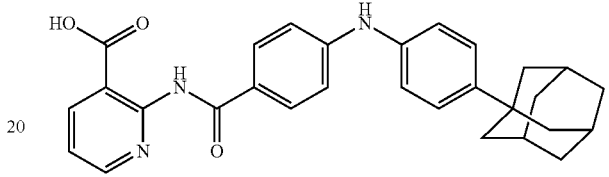
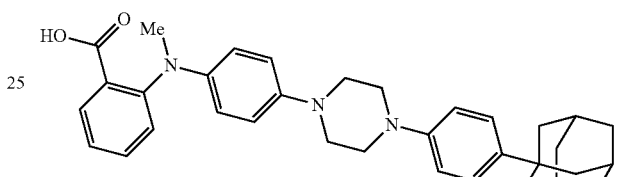
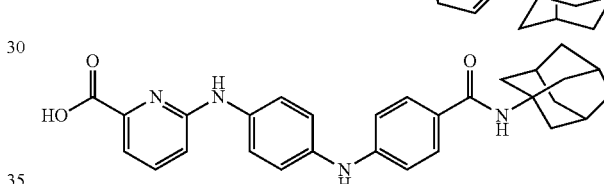
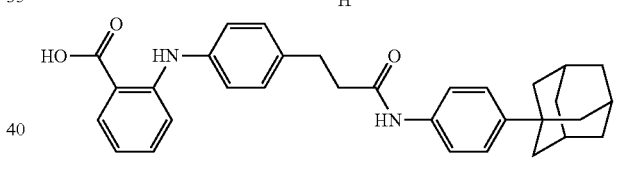
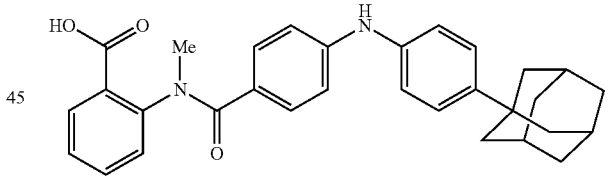
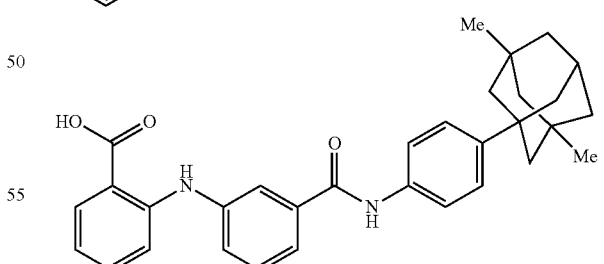
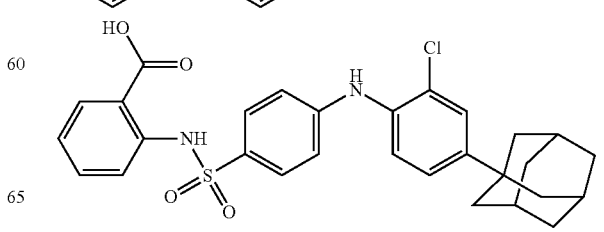

761
-continued
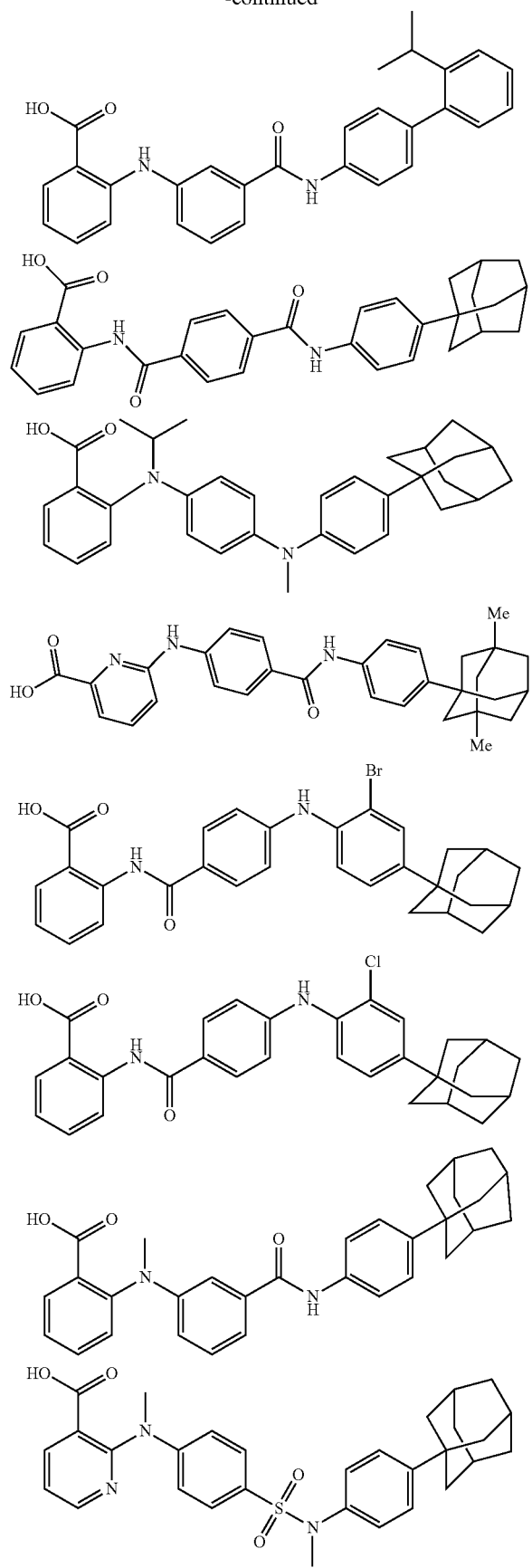
762
-continued
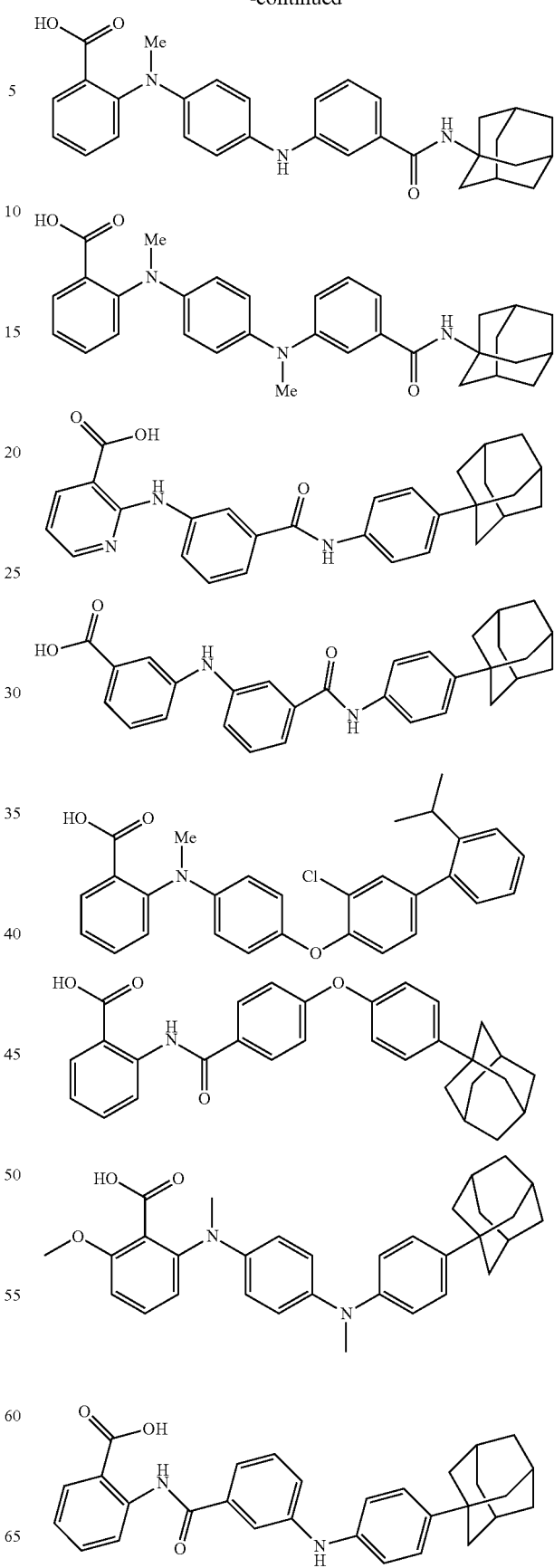

763
-continued
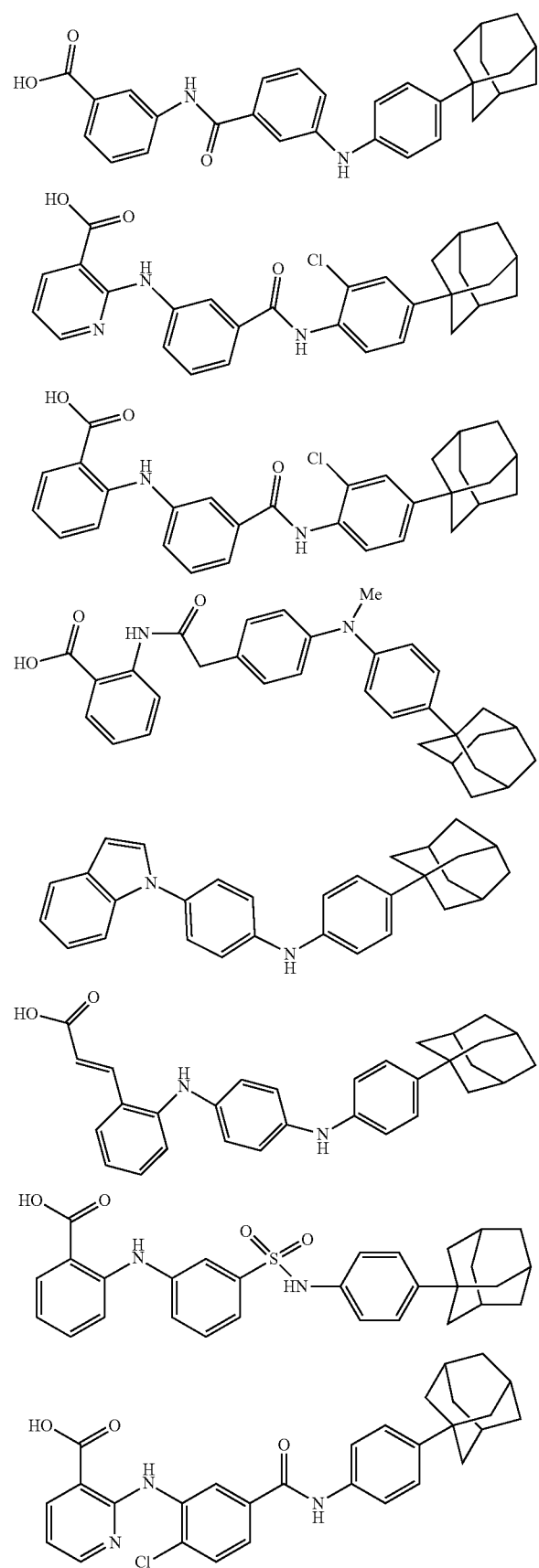
764
-continued
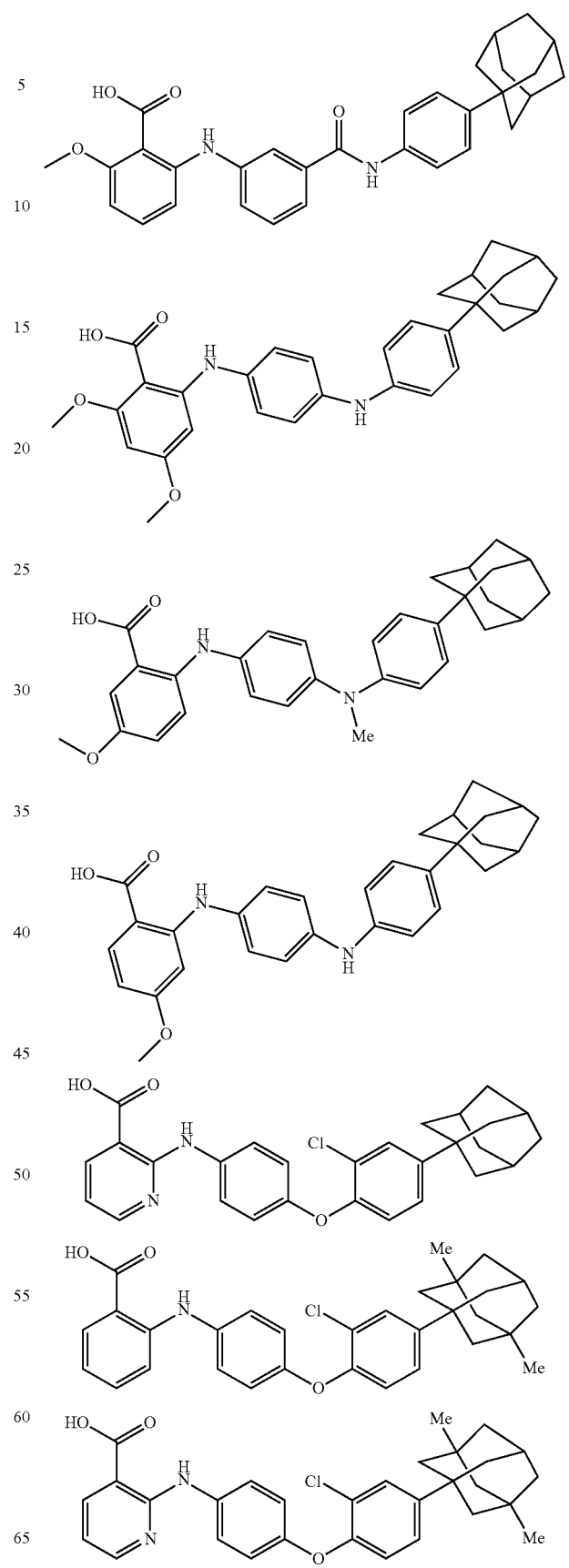

765
-continued
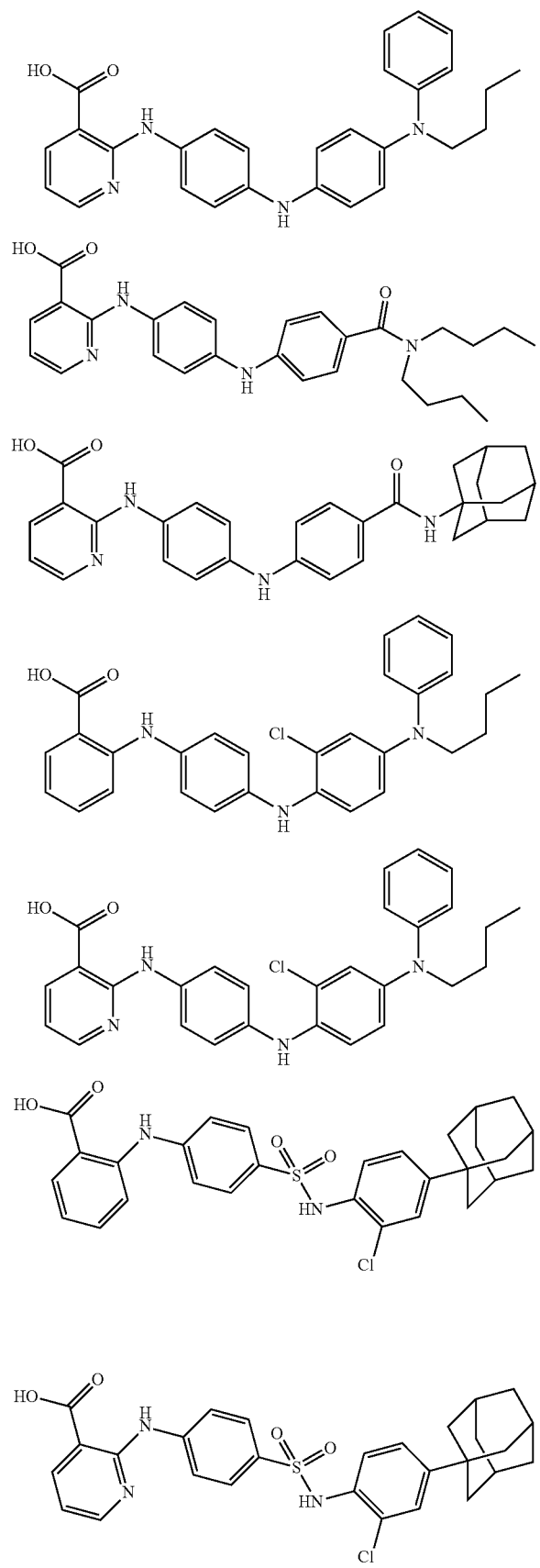
766
-continued
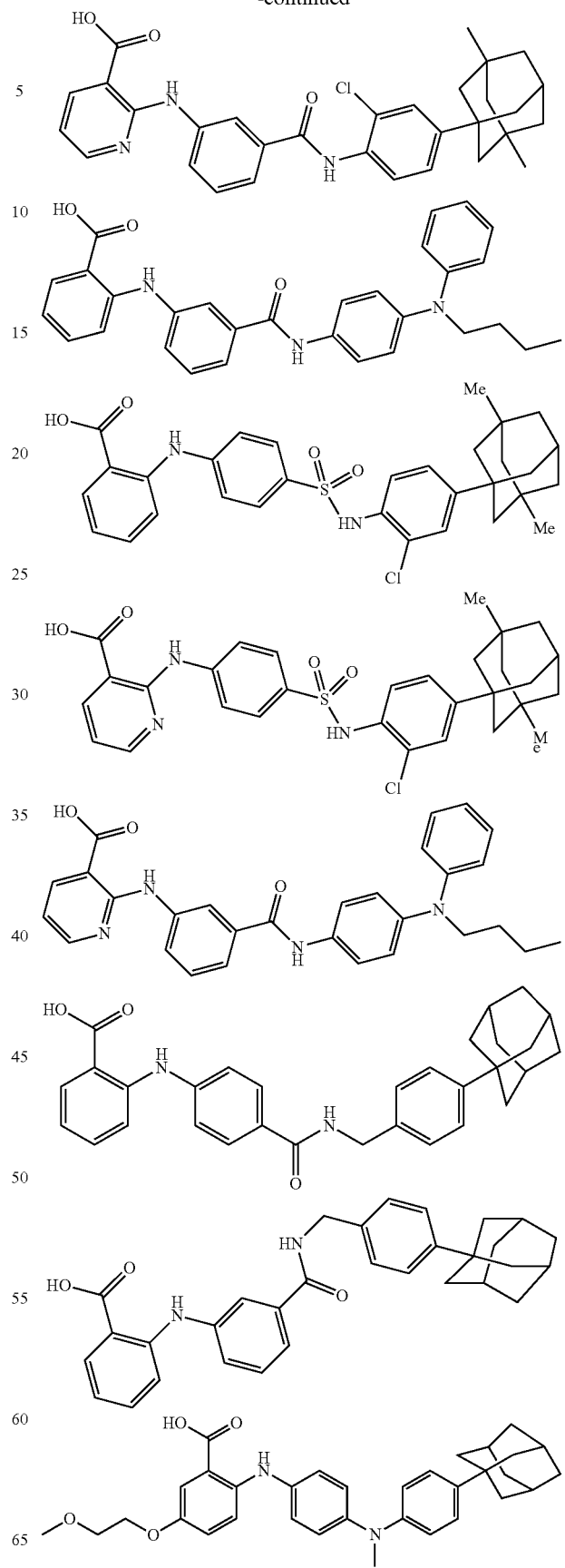

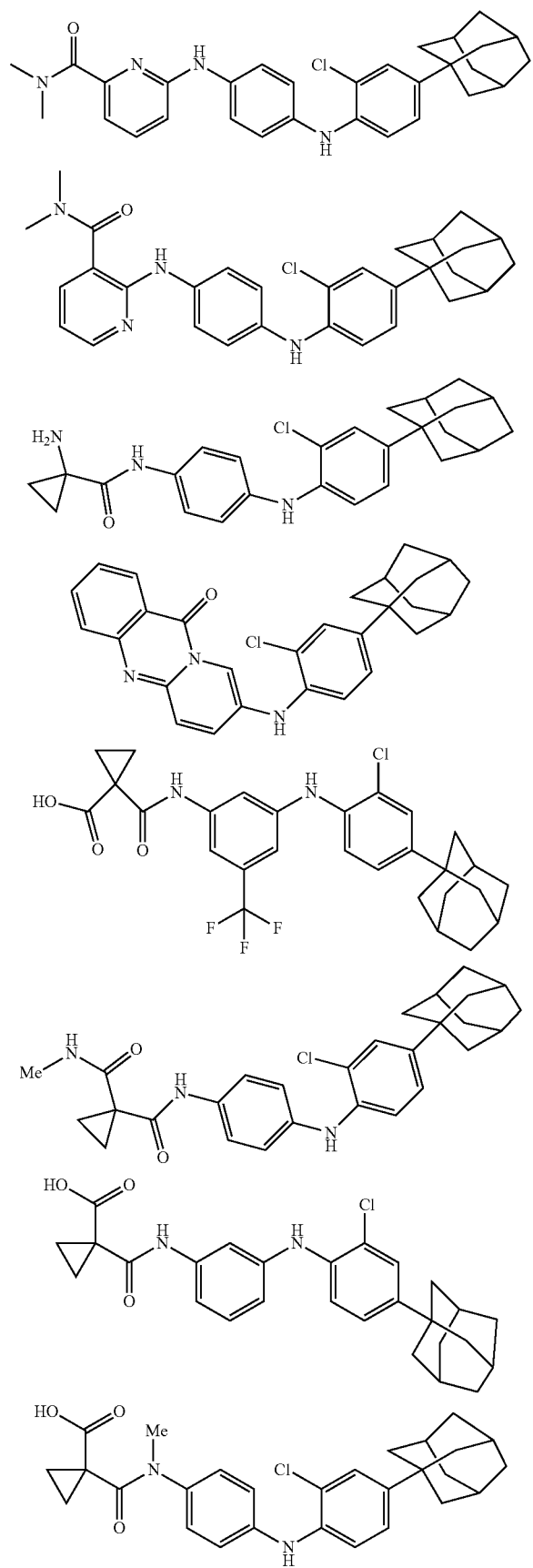
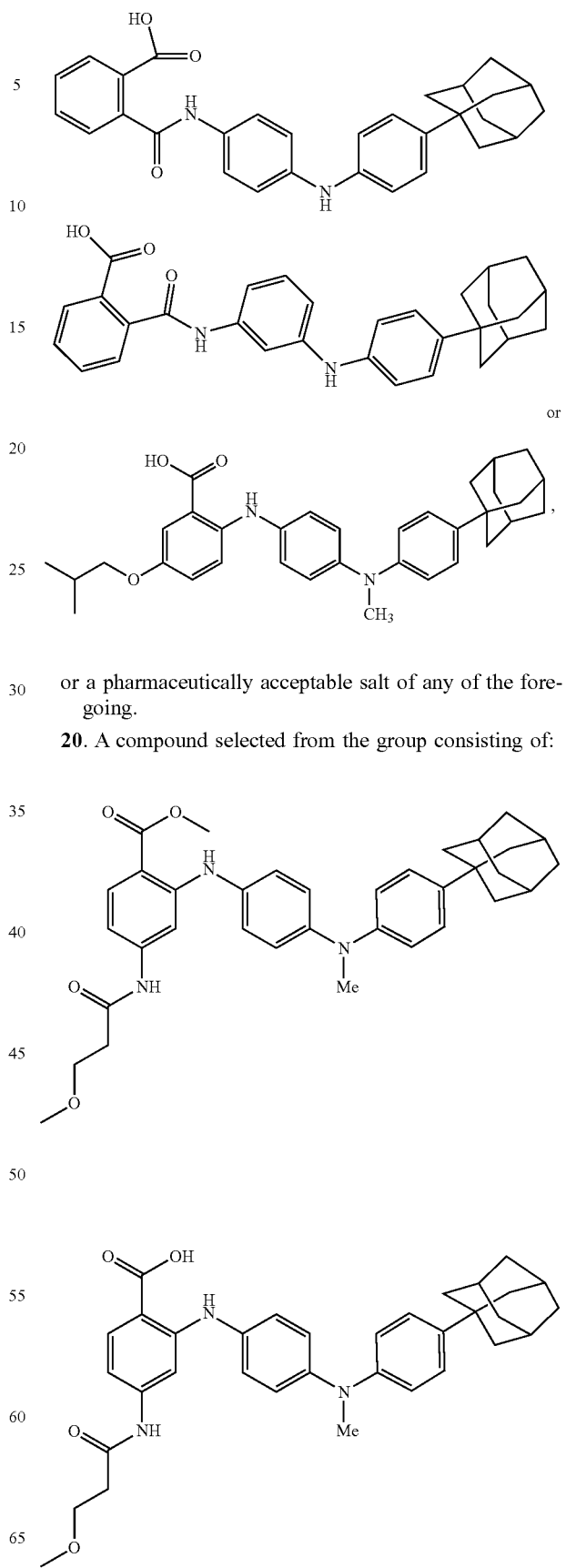
or a pharmaceutically acceptable salt of any of the foregoing.
20. A compound selected from the group consisting of:

769
-continued
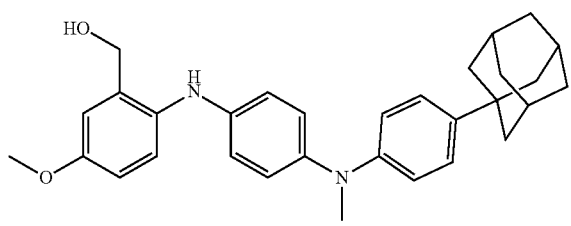
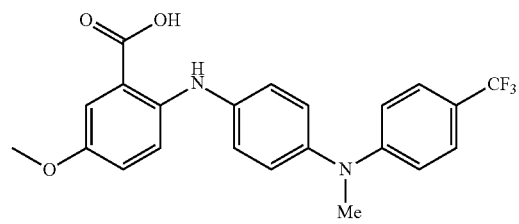
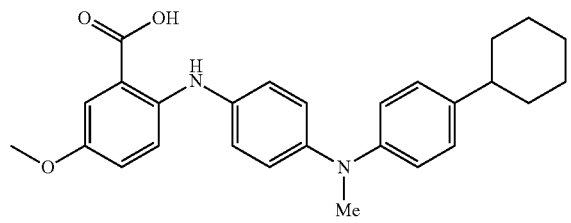
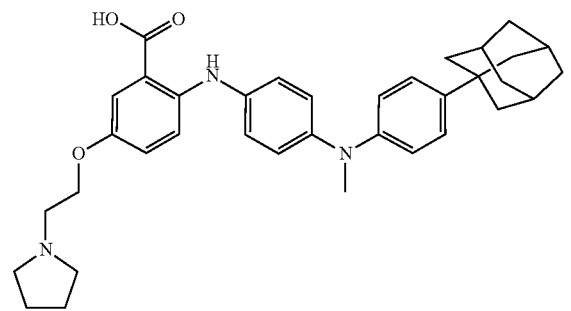
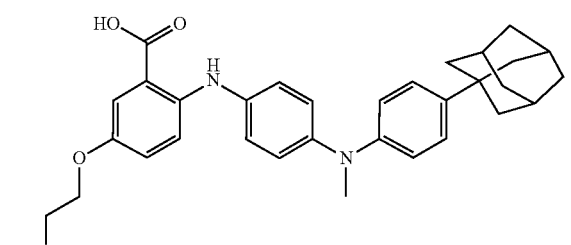
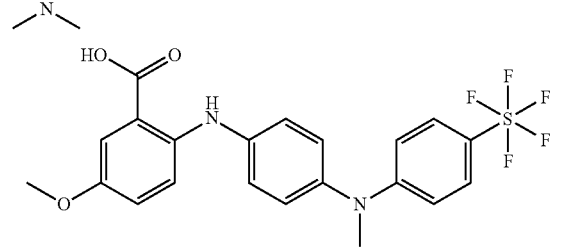
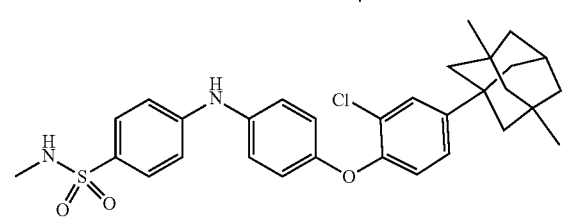
770
-continued
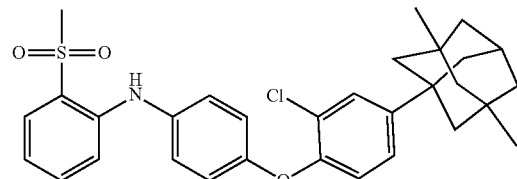
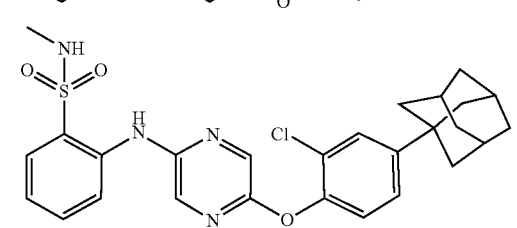
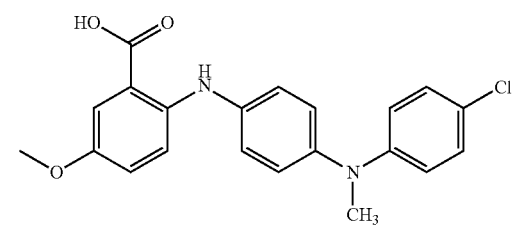
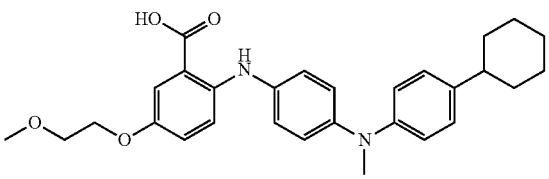
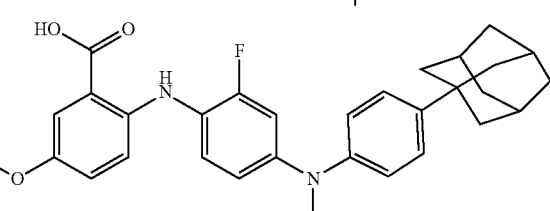
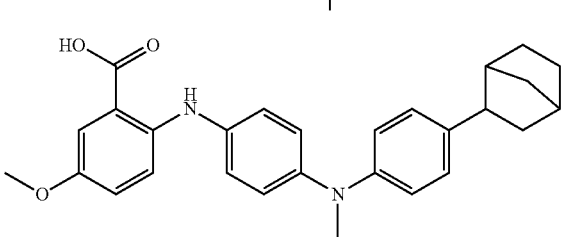
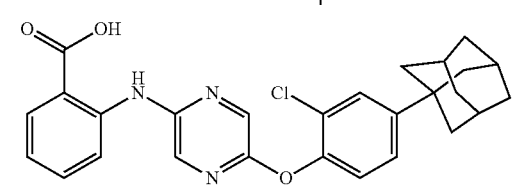
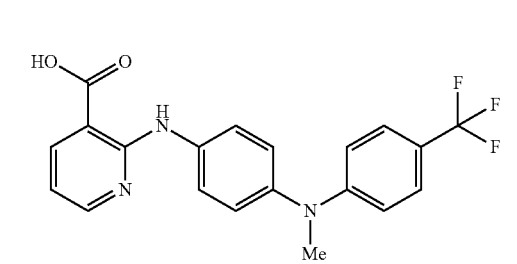

771
-continued
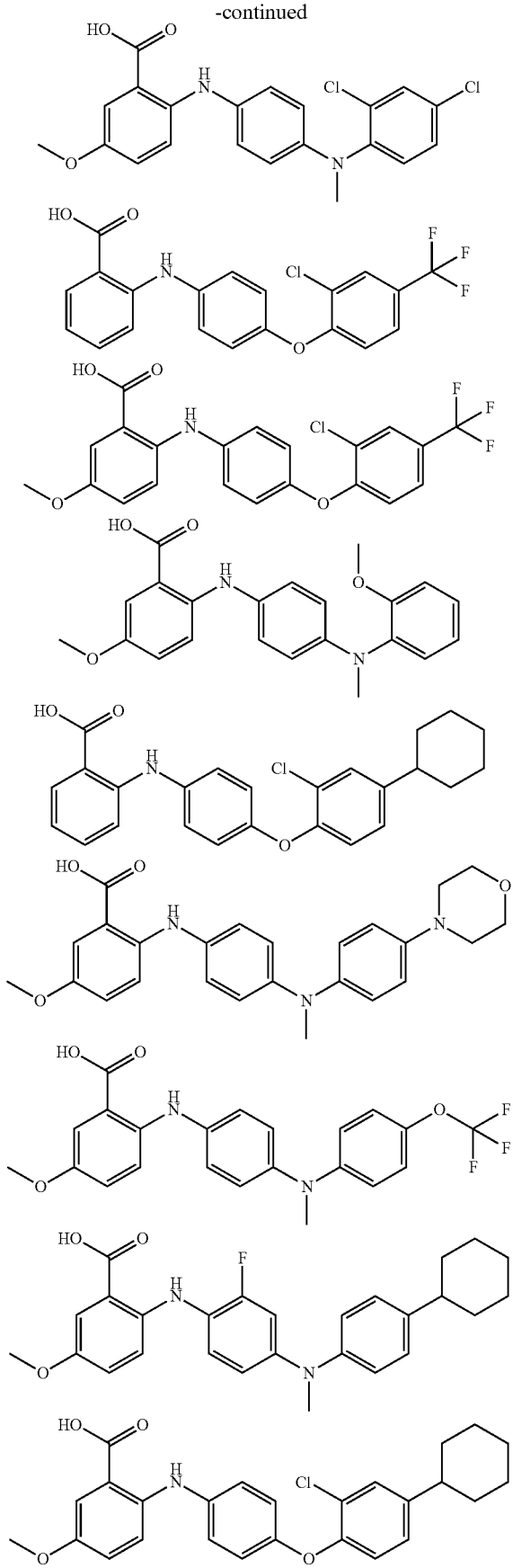
772
-continued
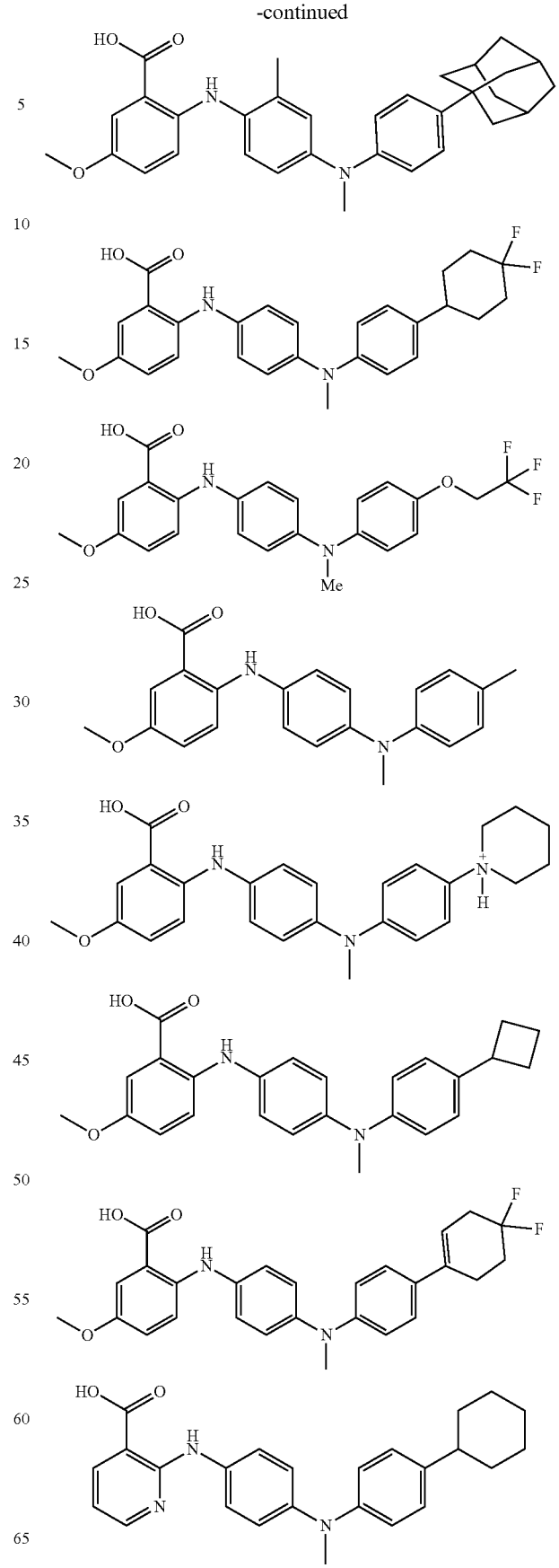

-continued
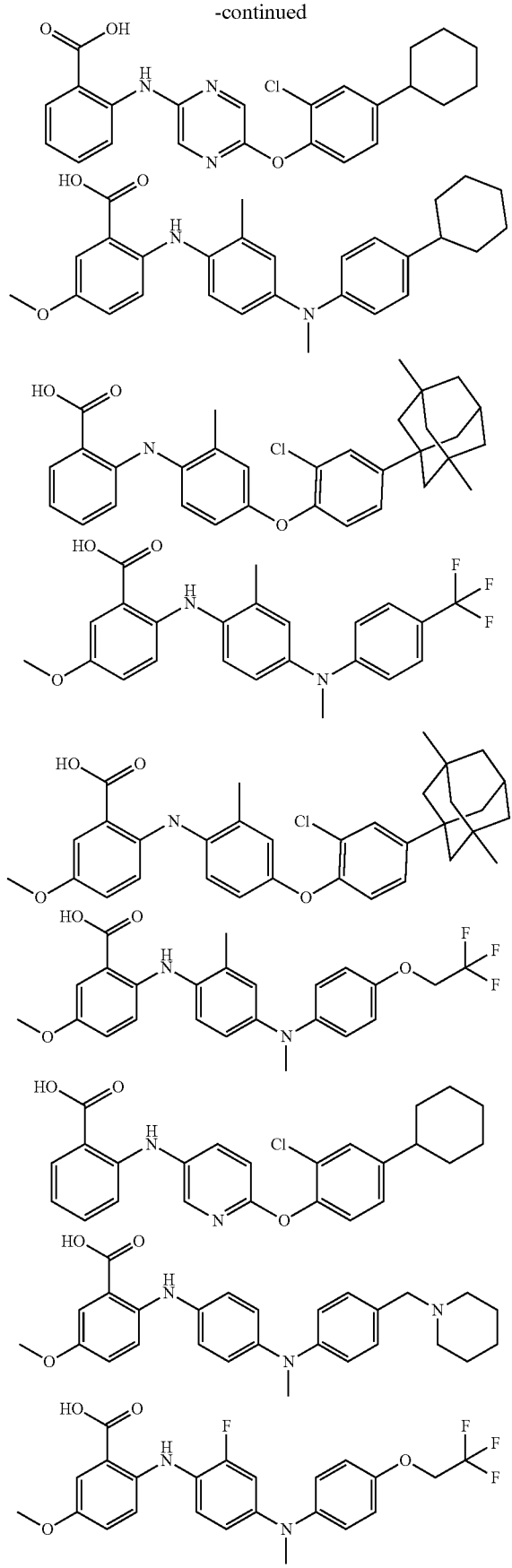
-continued
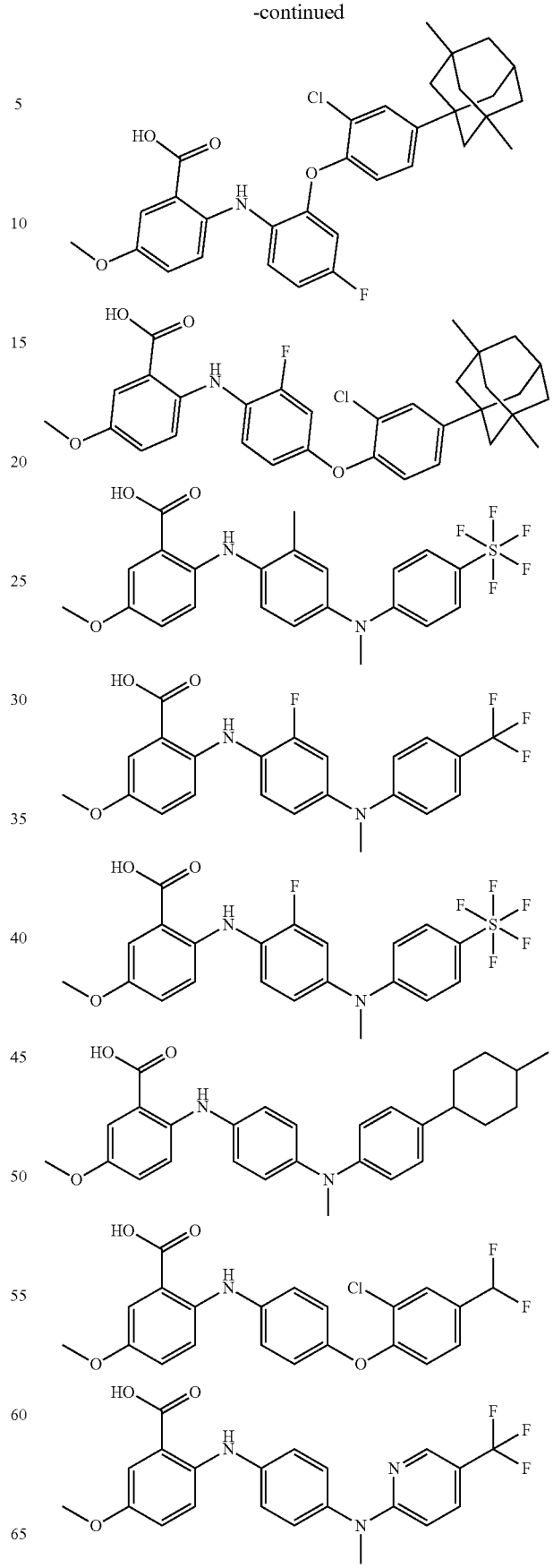

-continued
775
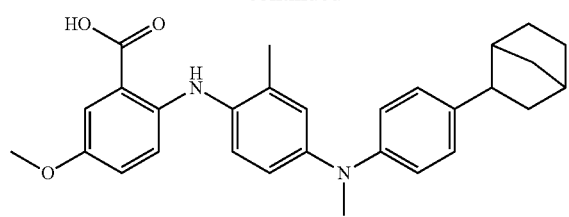
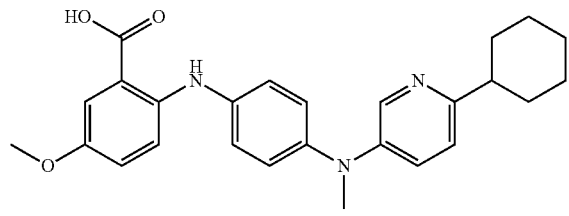
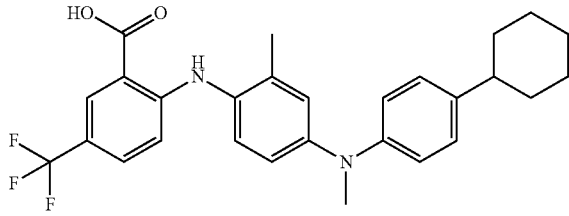
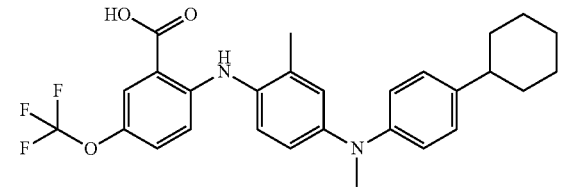
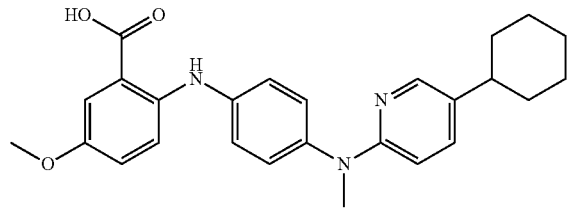
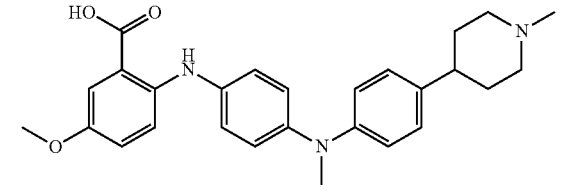
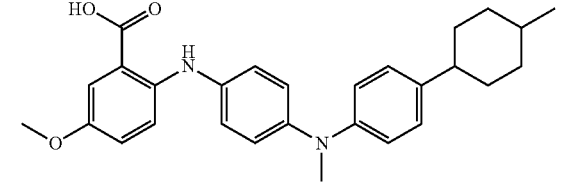
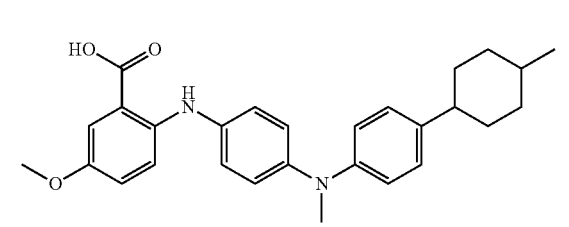
776
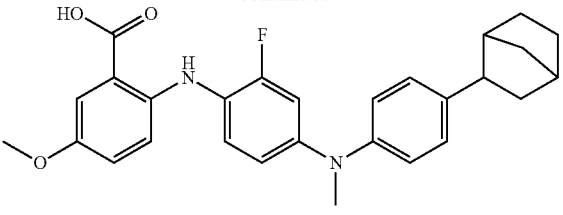
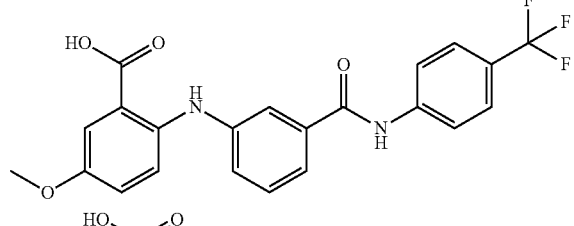
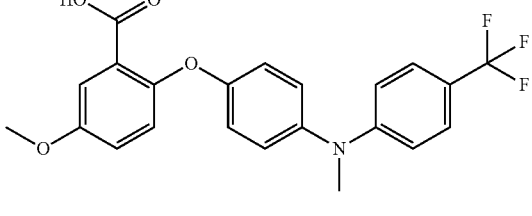
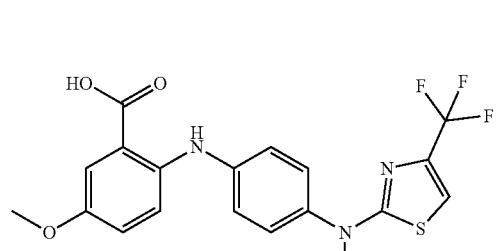
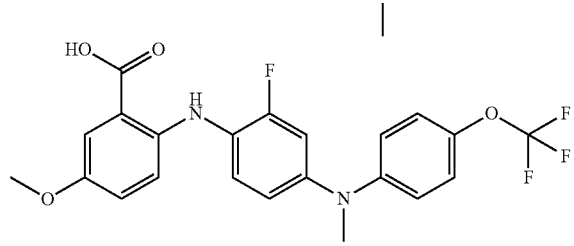
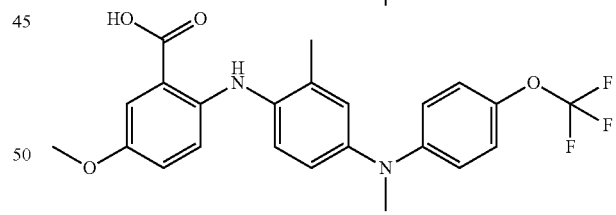
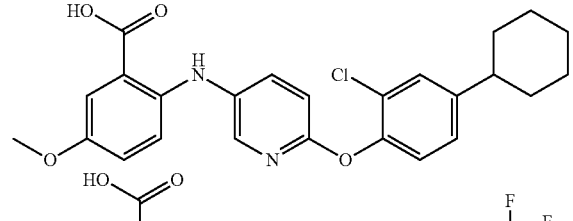
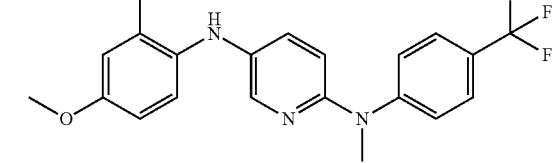

777
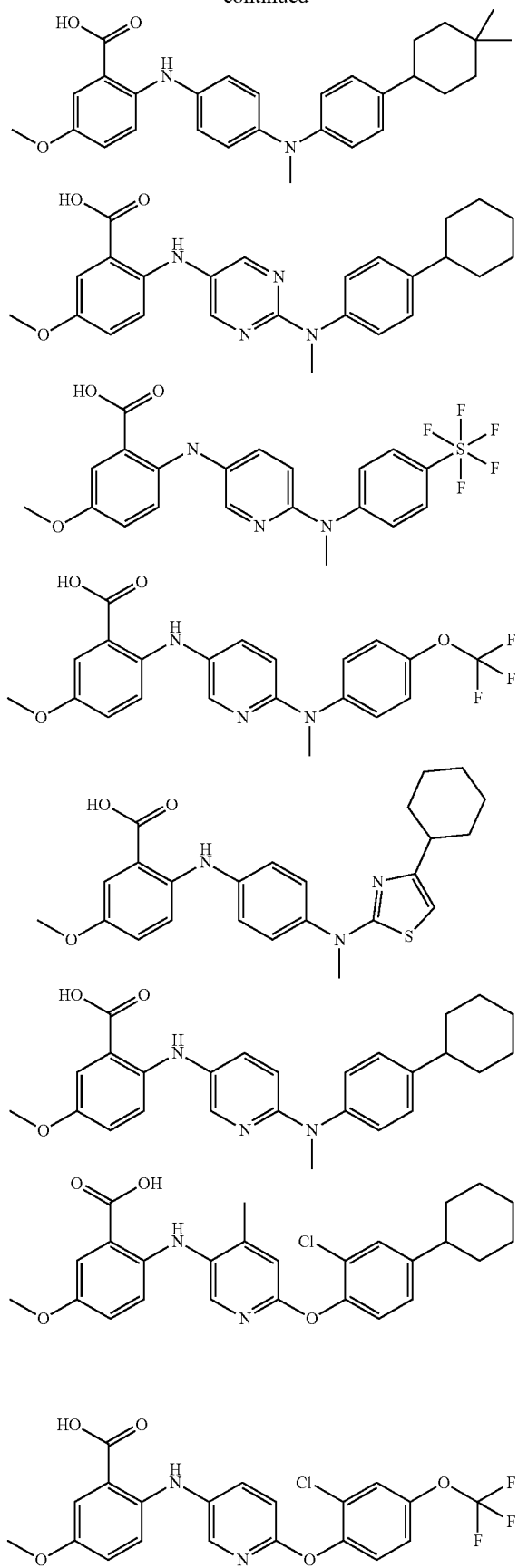
778
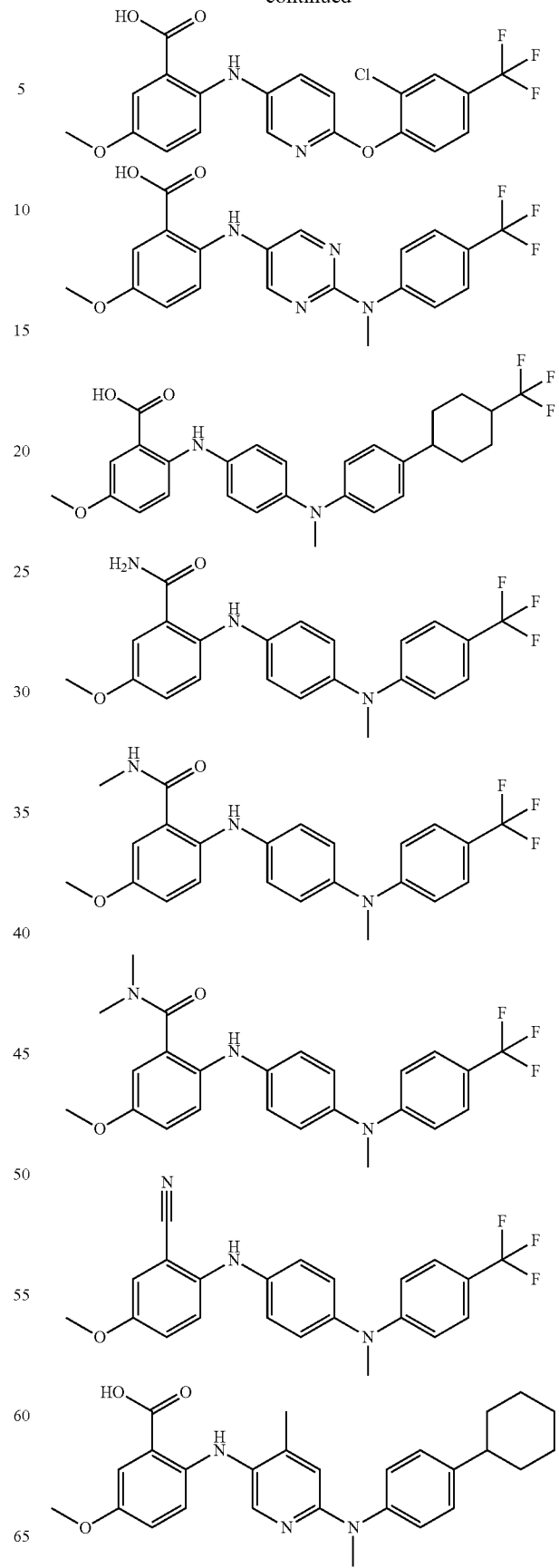

-continued
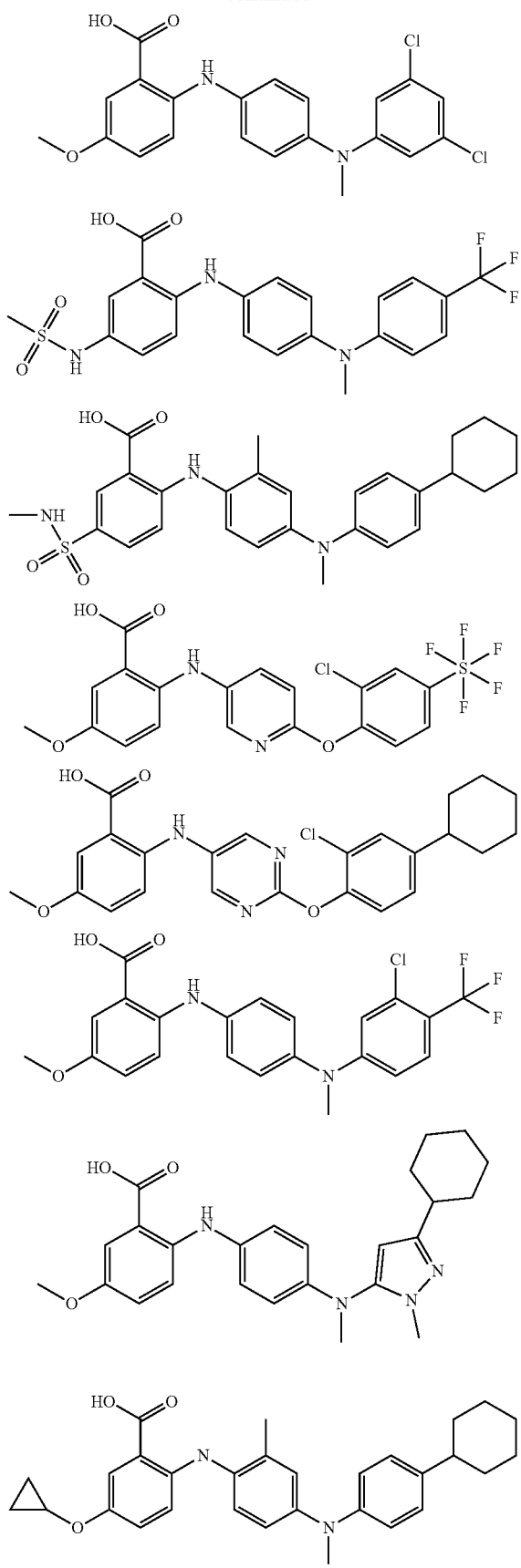
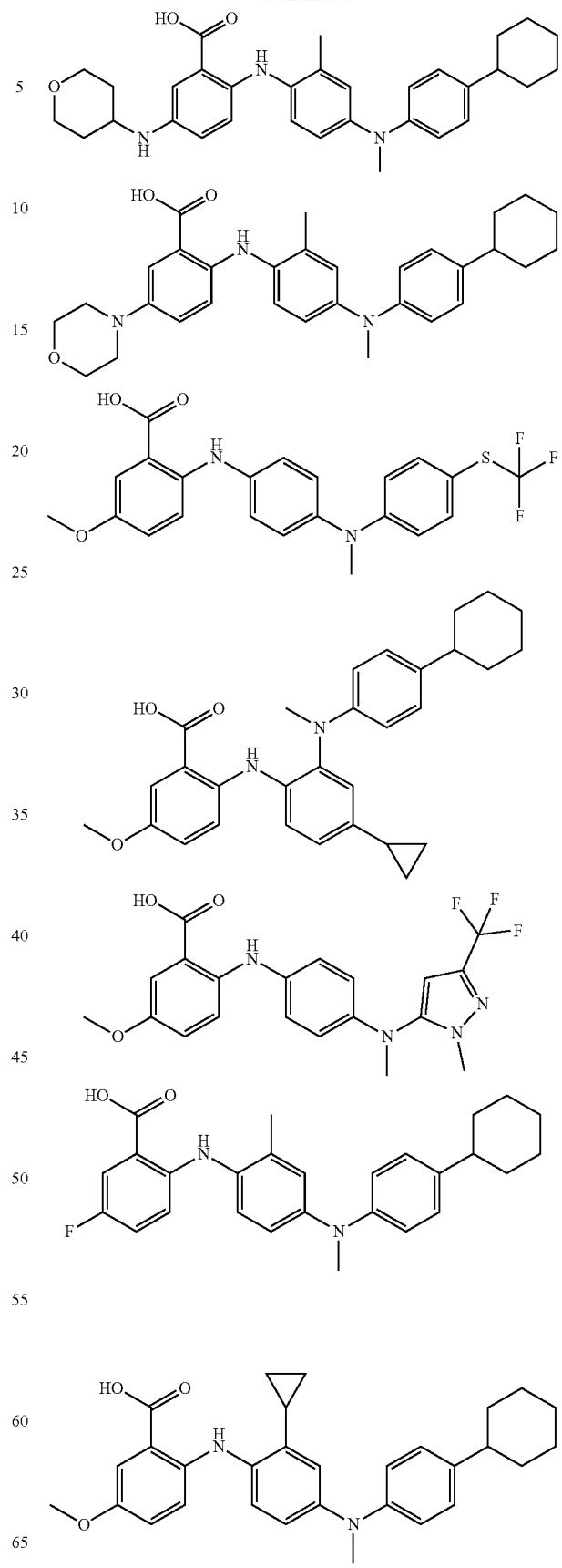

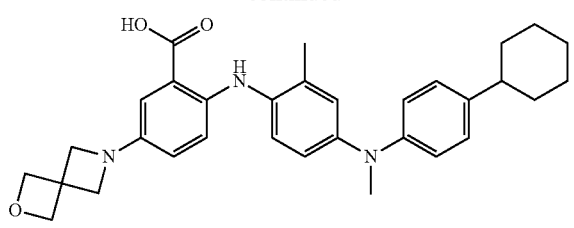
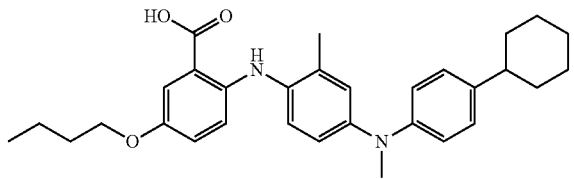
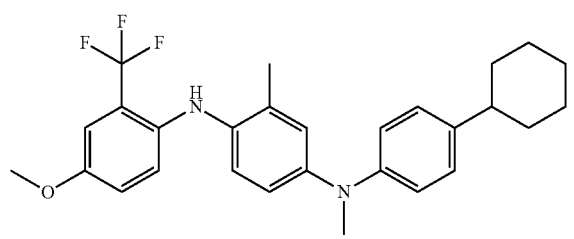
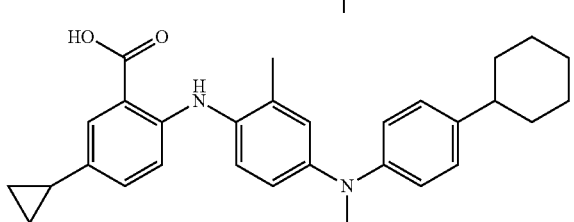
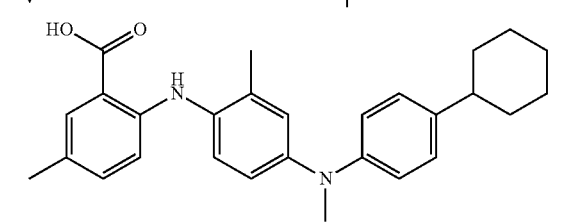
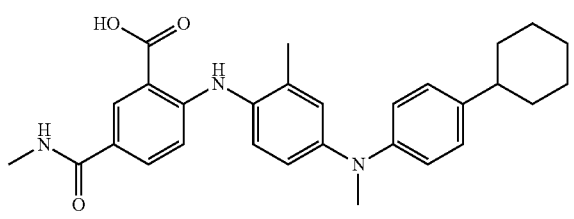
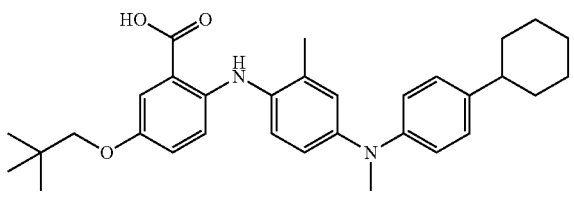
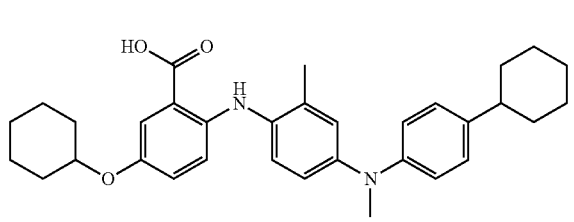
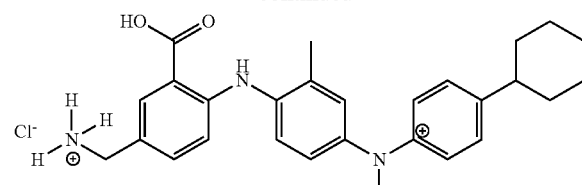
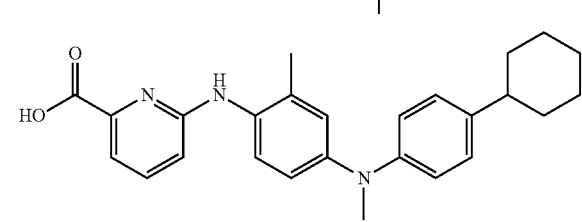
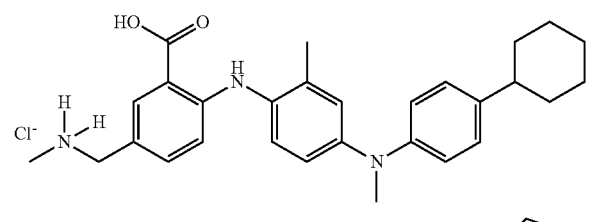
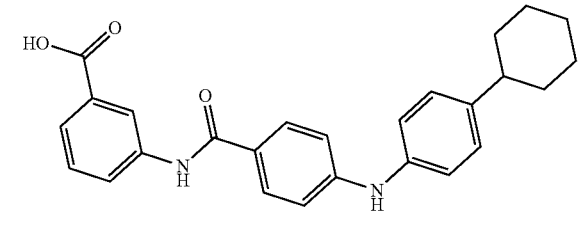
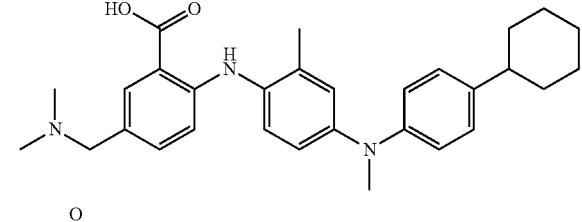
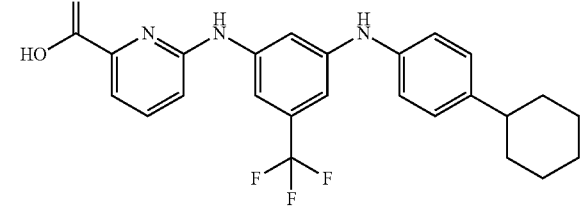
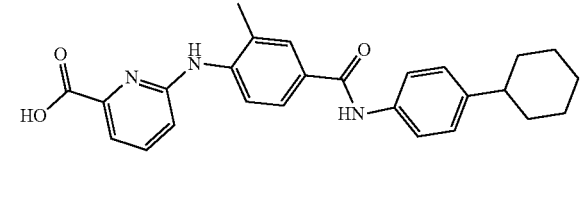
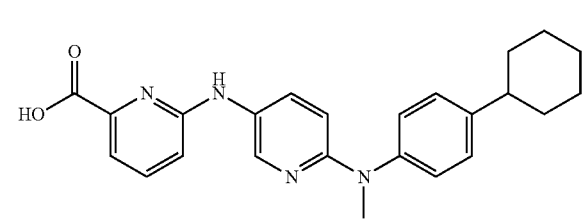

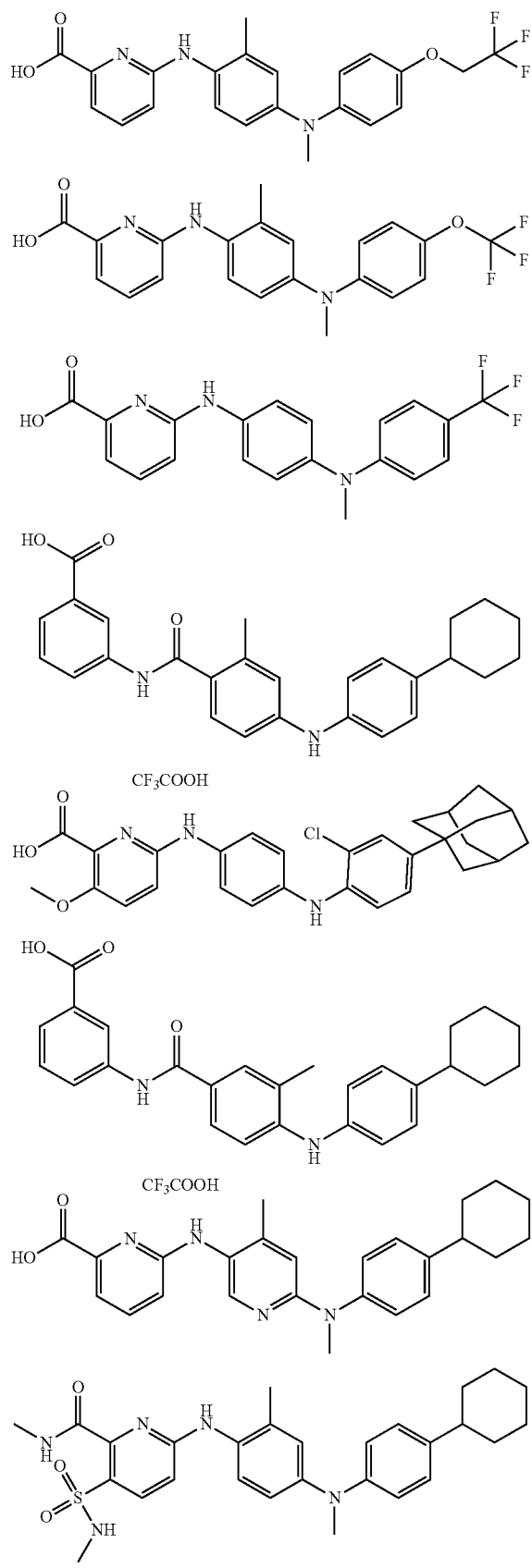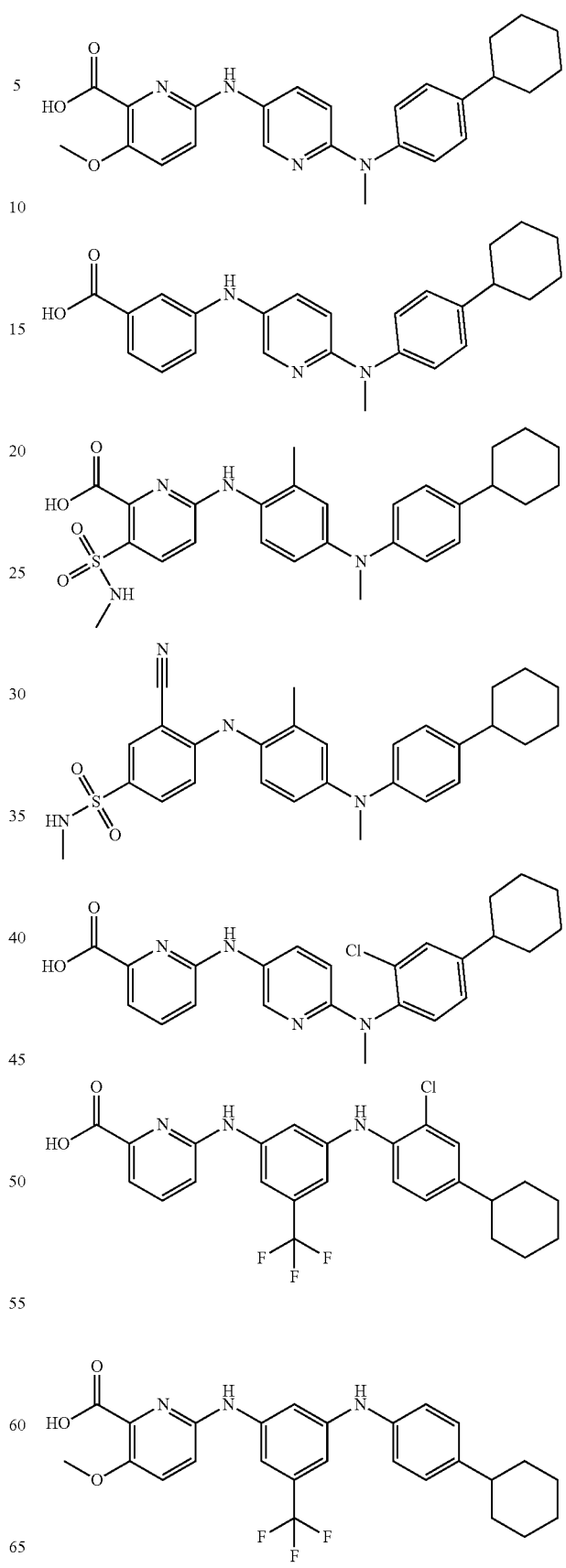

-continued
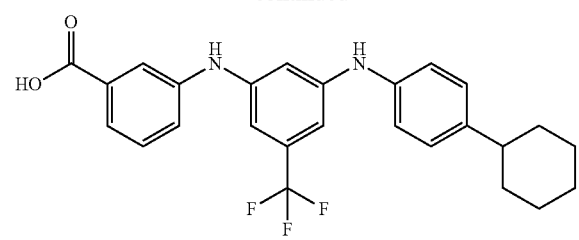
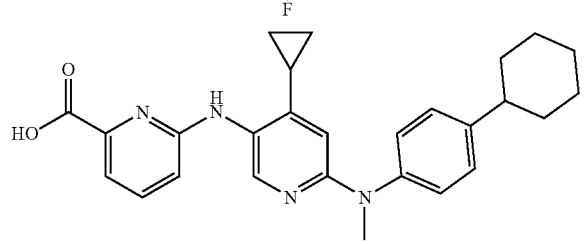
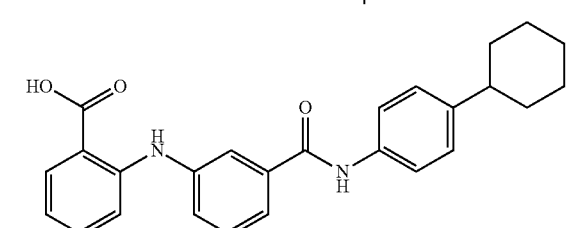
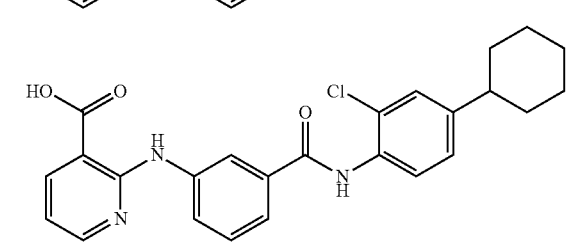
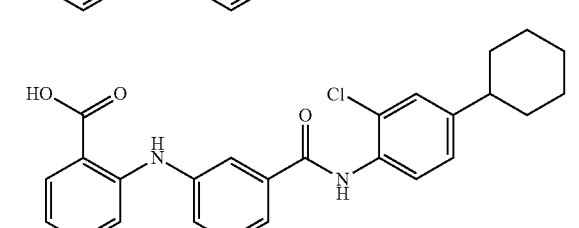
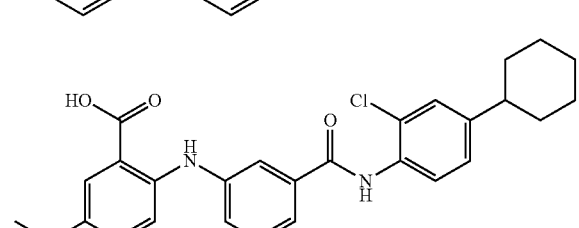
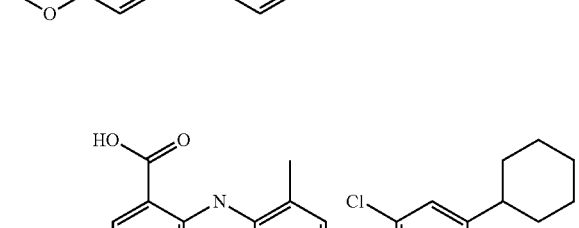
-continued
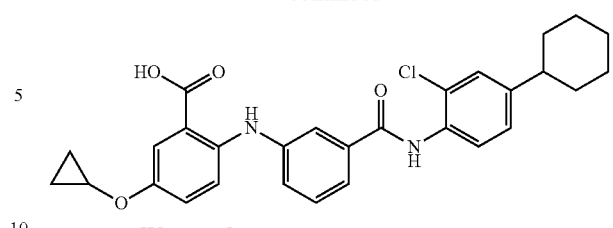
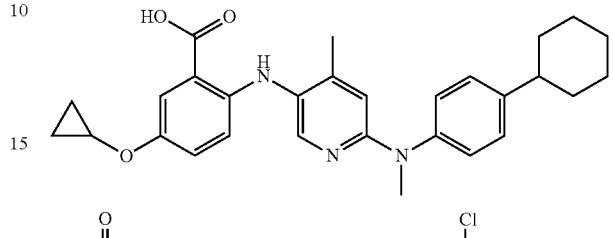
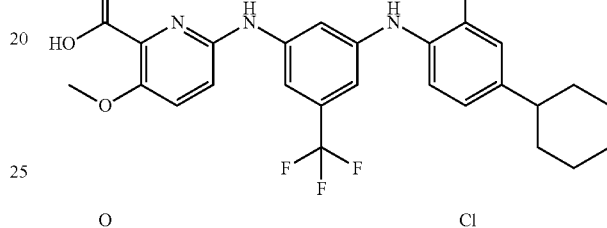
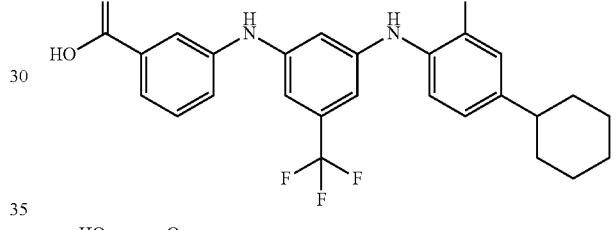
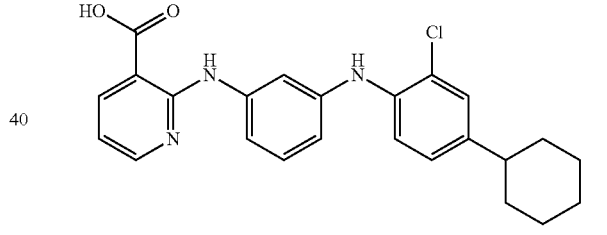
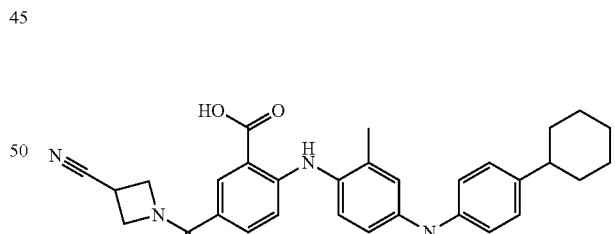
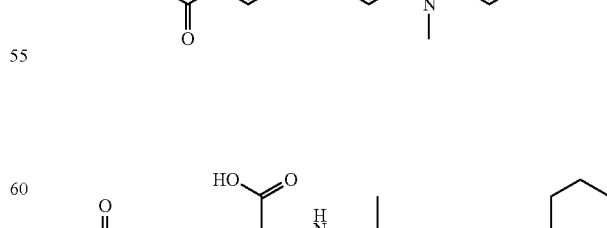

-continued

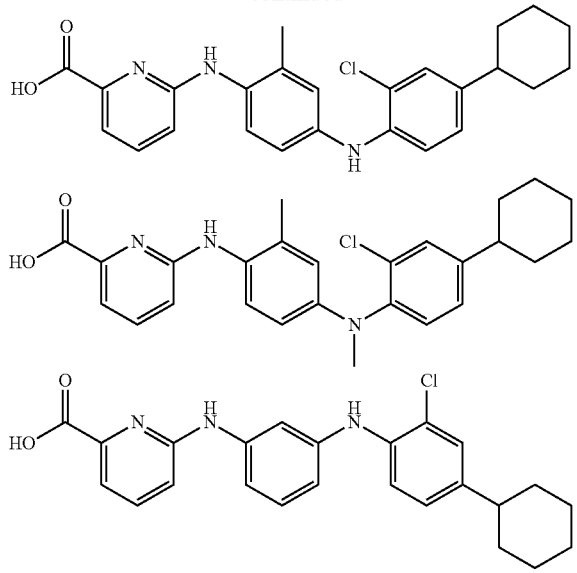

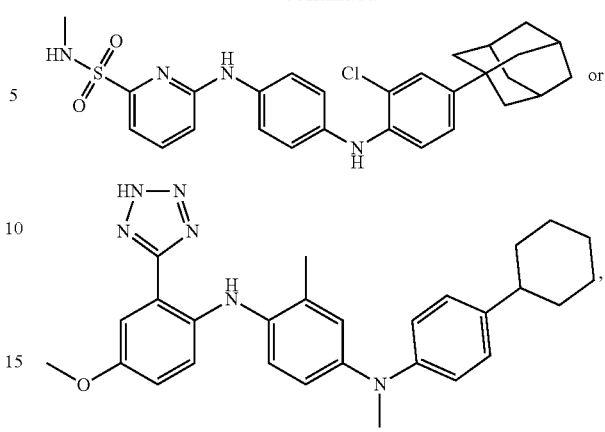

or a pharmaceutically acceptable salt of any of the foregoing.

21. A composition comprising a compound of claim 1, or a pharmaceutically acceptable salt thereof, and at least one pharmaceutically acceptable carrier.

22. A composition comprising a compound of claim 19, or a pharmaceutically acceptable salt thereof, and at least one pharmaceutically acceptable carrier.

23. A composition comprising a compound of claim 20, or a pharmaceutically acceptable salt thereof, and at least one pharmaceutically acceptable carrier.

* * * * *